(12) United States Patent
Shiau et al.

(10) Patent No.: US 12,162,870 B2
(45) Date of Patent: Dec. 10, 2024

(54) ANTICANCER COMPOUNDS

(71) Applicants: The Regents of the University of California, Oakland, CA (US); Poseidon Innovation, LLC, New York, NY (US)

(72) Inventors: Andrew K. Shiau, San Diego, CA (US); Mehmet Kahraman, La Jolla, CA (US); Michael J. Bishop, San Diego, CA (US)

(73) Assignees: The Regents of the University of California, Oakland, CA (US); Poseidon Innovation, LLC, New York, NY (US)

( * ) Notice: Subject to any disclaimer, the term of this patent is extended or adjusted under 35 U.S.C. 154(b) by 0 days.

(21) Appl. No.: 17/835,434

(22) Filed: Jun. 8, 2022

(65) Prior Publication Data
US 2023/0025178 A1    Jan. 26, 2023

Related U.S. Application Data

(60) Provisional application No. 63/208,191, filed on Jun. 8, 2021.

(51) Int. Cl.
| | | |
|---|---|---|
| *C07D 413/10* | (2006.01) | |
| *A61P 35/00* | (2006.01) | |
| *C07C 233/25* | (2006.01) | |
| *C07C 233/43* | (2006.01) | |
| *C07D 209/14* | (2006.01) | |
| *C07D 211/58* | (2006.01) | |
| *C07D 213/40* | (2006.01) | |
| *C07D 231/12* | (2006.01) | |
| *C07D 231/38* | (2006.01) | |
| *C07D 233/64* | (2006.01) | |
| *C07D 267/14* | (2006.01) | |
| *C07D 295/135* | (2006.01) | |
| *C07D 401/04* | (2006.01) | |
| *C07D 401/10* | (2006.01) | |
| *C07D 401/14* | (2006.01) | |
| *C07D 413/04* | (2006.01) | |
| *C07D 413/12* | (2006.01) | |
| *C07D 487/10* | (2006.01) | |

(52) U.S. Cl.
CPC ............ *C07D 413/10* (2013.01); *A61P 35/00* (2018.01); *C07C 233/25* (2013.01); *C07C 233/43* (2013.01); *C07D 209/14* (2013.01); *C07D 211/58* (2013.01); *C07D 213/40* (2013.01); *C07D 231/12* (2013.01); *C07D 231/38* (2013.01); *C07D 233/64* (2013.01); *C07D 267/14* (2013.01); *C07D 295/135* (2013.01); *C07D 401/04* (2013.01); *C07D 401/10* (2013.01); *C07D 401/14* (2013.01); *C07D 413/04* (2013.01); *C07D 413/12* (2013.01); *C07D 487/10* (2013.01)

(58) Field of Classification Search
CPC .. C07D 413/10; C07D 209/14; C07D 211/58; C07D 213/40; C07D 231/12; C07D 231/38; C07D 233/64; C07D 267/14; C07D 295/135; C07D 401/04; C07D 401/10; C07D 401/14; C07D 413/04; C07D 413/12; C07D 487/10
See application file for complete search history.

(56) References Cited

U.S. PATENT DOCUMENTS

| | | |
|---|---|---|
| 9,757,385 B2 | 9/2017 | Riveiro et al. |
| 9,795,612 B2 | 10/2017 | Dombret |
| 9,820,992 B2 | 11/2017 | Riveiro et al. |

(Continued)

FOREIGN PATENT DOCUMENTS

| | | |
|---|---|---|
| WO | WO-2003/077918 A1 | 9/2003 |
| WO | WO-2012/162254 A8 | 1/2014 |

OTHER PUBLICATIONS

Registry No. 322716-36-9, File Registry on STN, entered STN Feb. 21, 2001.*

(Continued)

*Primary Examiner* — Rebecca L Anderson
(74) *Attorney, Agent, or Firm* — Foley Hoag LLP; Dana M. Gordon; Laura A. Wzorek

(57) ABSTRACT

Disclosed are compounds of formula (I):

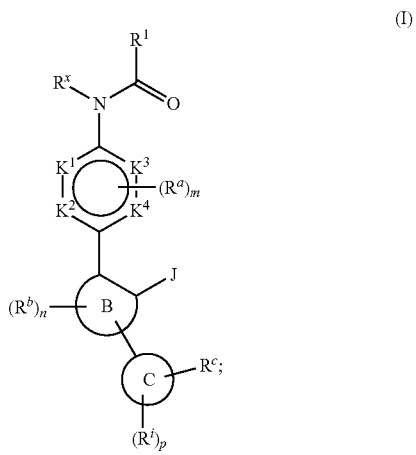

and pharmaceutically acceptable salts thereof. The compounds of the invention are BDII-selective inhibitors of BET proteins, and have therapeutic potential for treating cancer, acute kidney disease, and viral infections, among other diseases.

34 Claims, No Drawings

(56) References Cited

U.S. PATENT DOCUMENTS

| | | |
|---|---|---|
| 9,901,583 B2 | 2/2018 | Riveiro et al. |
| 9,956,228 B2 | 5/2018 | Noel et al. |
| 9,968,619 B2 | 5/2018 | Noel et al. |
| 9,968,620 B2 | 5/2018 | Bertoni |
| 2004/0087604 A1 | 5/2004 | Tsuri et al. |
| 2014/0187529 A1 | 7/2014 | Shetty et al. |
| 2016/0272588 A1 | 9/2016 | Blake et al. |
| 2022/0265617 A1 | 8/2022 | Aronchik et al. |

OTHER PUBLICATIONS

Registry No. 1431793-68-8, File Registry on STN, entered STN May 20, 2013.*

Registry No. 1642114-06-4, File Registry on STN, entered STN Jan. 9, 2015.*

Cancer and Metastasis Reviews (1998), 17(1), 91-106.*

Science (1999), vol. 286, 531-537.*

Cecil Textbook of Medicine, 20th edition (1996), vol. 2, pp. 2050-2057.*

Cecil Textbook of Medicine, 20th edition (1996), vol. 2, pp. 1992-1996.*

FDA mulls drug to slow late-stage Alzheimer's [online], [retrieved on Sep. 23, 2003]. Retrieved from the internet, URL;http;//www.cnn/com/2003/HEALTH/conditions/09/24/alzheimers.drug.ap/index.html>.*

Huff, Joel R., Journal of Medicinal Chemistry, vol. 34, No. 8, Aug. 1991, pp. 2305-2314.*

Invitation to Pay Additional Fees for Application No. PCT/US22/32669 dated Aug. 12, 2022.

PubChem CID 71477368., "N-[4-[3-(2,4-dimethoxyphenyl)-2-hydroxy-5-methoxyphenyl]-3,5-dimethoxyphenyl]acetamide," retrieved online <https://pubchem.ncbi.nlm.nih.gov/compound/71477368>: 8 pages (Create Date Jun. 10, 2013).

International Search Report and Written Opinion for International Application No. PCT/US22/32669 dated Oct. 6, 2022.

Faivre et al., "Selective inhibition of the BD2 bromodomain of BET proteins in prostate cancer", Nature 578.7794: 306-310 (2020).

Sheppard et al., "Discovery of N-Ethyl-4-[2-(4-fluoro-2, 6-dimethyl-phenoxy)-5-(1-hydroxy-1-methyl-ethyl) phenyl]-6-methyl-7-oxo-1 H-pyrrolo [2, 3-c] pyridine-2-carboxamide (ABBV-744), a BET Bromodomain Inhibitor with Selectivity for the Second Bromodomain", Journal of Medicinal Chemistry 63.10: 5585-5623 (2020).

International Preliminary Report on Patentability for Application No. PCT/US2022/032669 Issued Nov. 21, 2023.

Abdelrahman et al., "Revised assessment of response and long-term discontinuation rates among 111 patients with myelofibrosis treated with momelotinib or ruxolitinib," Leukemia 29(2): 498-500 (2015).

Al-Ali et al., "Safety and efficacy of ruxolitinib in an open-label, multicenter, single-arm phase 3b expanded-access study in patients with myelofibrosis: a snapshot of 1144 patients in the JUMP trial," Haematologica 101(9): 1065-1073 (2016).

Alqahtani et al., "Bromodomain and extra-terminal motif inhibitors: a review of preclinical and clinical advances in cancer therapy," Future. Sci. OA. 5(3), FSO372 (2019).

Ceribelli et al., "Blockade of oncogenic IkappaB kinase activity in diffuse large B-cell lymphoma by bromodomain and extraterminal domain protein inhibitors," Proc. Natl Acad. Sci. USA 111(31): 11365-11370 (2014).

Ding et al., "BRD4 is a novel therapeutic target for liver fibrosis," Proc. Natl Acad. Sci. USA 112(51): 15713-15718 (2015).

Gilan et al., Selective targeting of BD1 and BD2 of the BET proteins in cancer and immunoinflammation. Science. Apr. 24, 2020;368(6489):387-394.

Gupta et al., "Patterns of ruxolitinib therapy failure and its management in myelofibrosis: Perspectives of the Canadian Myeloproliferative Neoplasm Group," JCO. Oncol. Pract 16(7): 351-359 (2020).

Harrison et al., "Phase III MANIFEST-2: pelabresib + ruxolitinib vs placebo + ruxolitinib in JAK inhibitor treatment-naive myelofibrosis," Future Oncol. (Aug. 11, 2022).

International Search Report and Written Opinion for International Application No. PCT/US23/82872 dated Apr. 9, 2024.

International Search Report and Written Opinion for International Application No. PCT/US23/82888 dated Apr. 8, 2024.

International Search Report and Written Opinion for International Application No. PCT/US23/82892 dated Apr. 15, 2024.

Kleppe et al., "Dual targeting of oncogenic activation and inflammatory signaling increases therapeutic efficacy in myeloproliferative neoplasms," Cancer Cell. 33(1): 29-43 e27 (2018).

Kleppe et al., "Dual targeting of oncogenic activation and inflammatory signaling increases therapeutic efficacy in myeloproliferative neoplasms," Cancer. Cell. 33(4): 785-787 (2018).

Kuykendall et al., "Between a rux and a hard place: evaluating salvage treatment and outcomes in myelofibrosis after ruxolitinib discontinuation," Ann. Hematol. 97(3): 435-441 (2018).

Lucas et al., "Optimization of potent ATAD2 and CECR2 bromodomain inhibitors with an atypical binding mode." Journal of Medicinal Chemistry 63(10) (2020): 5212-5241.

Mascarenhas et al., "Patient characteristics and outcomes after ruxolitinib discontinuation in patients with myelofibrosis," J. Med. Econ. 23(7): 721-727 (2020).

Newberry et al., "Clonal evolution and outcomes in myelofibrosis after ruxolitinib discontinuation," Blood 130(9): 1125-1131 (2017).

Palandri et al., "Life after ruxolitinib: reasons for discontinuation, impact of disease phase, and outcomes in 218 patients with myelofibrosis," Cancer 126(6): 1243-1252 (2020).

Ross et al., "Persistence of myelofibrosis treated with ruxolitinib: biology and clinical implications," Haematologica 106(5): 1244-1253 (2021).

Stamford et al., U.S. Appl. No. 18/532,632, filed Dec. 7, 2023.

Stamford et al., U.S. Appl. No. 18/532,636, filed Dec. 7, 2023.

Stamford et al., U.S. Appl. No. 18/532,671, filed Dec. 7, 2023.

Stratton et al., "BRD4 inhibition for the treatment of pathological organ fibrosis," F1000Res 6(F 1000 Faculty Rev): 1015 (2017).

Tefferi, "Primary myelofibrosis: 2019 update on diagnosis, risk-stratification and management," Am. J. Hematol. 93(12): 1551-1560 (2018).

* cited by examiner

ANTICANCER COMPOUNDS

RELATED APPLICATIONS

This application claims the benefit of priority to U.S. Provisional Patent Application Ser. No. 63/208,191, filed Jun. 8, 2021.

BACKGROUND OF THE INVENTION

Proteins of the bromodomain and extra-terminal domain (BET) family are epigenetic readers that bind acetylated histones through their bromodomains to regulate gene transcription. As gene regulation is an important function to modulate for treatment of diseases such as cancer, the BET family proteins have received considerable attention as targets for drug discovery. BET proteins bind to acetylated histones through their tandem bromodomains, BDI and BDII. Pan-BET inhibitors that bind with similar affinities to the BDI and BDII bromodomains of BRD2, BRD3, BRD4 and BRDt have shown modest clinical activity in monotherapy cancer trials. Many pan-BET inhibitors are associated with dose-limiting adverse events, such as thrombocytopenia and signs of gastrointestinal toxicity.[1-5] These adverse events may represent on-target activities associated with pan-BET inhibition. The individual BET bromodomains may have distinct functions[7-9], and different cellular phenotypes after pharmacological inhibition of one or both bromodomains have been reported.[10-11] This observation suggests that selectively targeting one of the bromodomains may result in a different efficacy and tolerability profile compared with a pan-BET inhibitor. There remains a need to develop BET inhibitors that are selective for the BDII bromodomain. Such a selective inhibitor may maintain the therapeutic efficacy associated with a pan-BET inhibitor, while minimizing on-target adverse effects.

SUMMARY OF THE INVENTION

In some aspects, the present invention provides compounds having the structure of formula (I),

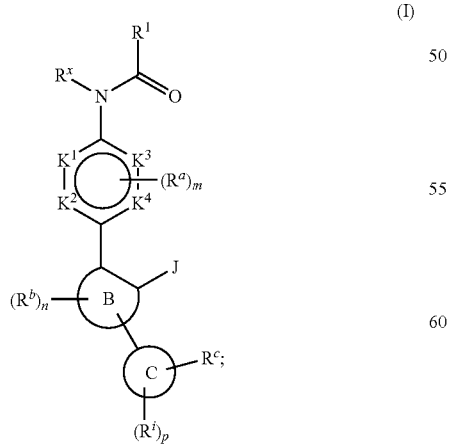

(I)

or a pharmaceutically acceptable salt thereof;

wherein:

each of $K^1$-$K^4$ is independently CH or N;
wherein at least one of $K^1$-$K^4$ is CH;

Ring B represents substituted or unsubstituted phenylene or 6-membered heteroarylene;

Ring C represents substituted or unsubstituted arylene or heteroarylene;

$R^1$ represents alkyl, alkenyl, haloalkyl, —O(alkyl), —S(alkyl), —NH(alkyl), or —N(alkyl)$_2$;

$R^x$ represents H, alkyl, or —C(O)alkyl;

or $R^1$ and $R^x$, taken together with the intervening atoms, form an optionally substituted heterocycloalkyl ring, heterocycloalkenyl ring, or heteroaryl ring;

each occurrence of $R^a$ is independently selected from the group consisting of halo, —NH$_2$, —NH(alkyl), —NH(cycloalkyl), —N(alkyl)$_2$, hydroxyl, alkyl, alkoxy, cycloalkyl, cycloalkoxy, haloalkoxy, heterocycloalkoxy, cyano, aryloxy, heteroaryloxy, and haloalkyl;

or $R^1$ and an occurrence of $R^a$, taken together with the intervening atoms, form an optionally substituted heterocycloalkyl ring;

or an occurrence of $R^a$ and $R^x$, taken together with the intervening atoms, form an optionally substituted heterocycloalkyl ring;

J represents —OH, —O(alkyl), —OC(O)(alkyl), —OC(O)O(alkyl), —OC(O)NH(alkyl), —OC(O)N(alkyl)$_2$, —OCH$_2$OC(O)O(alkyl), —NH$_2$, —NHR$^j$, or —CHF$_2$;

$R^j$ is alkyl, alkenyl, alkynyl, aryl, heteroaryl, arylalkyl, heteroarylalkyl, cycloalkyl, heterocycloalkyl, (cycloalkyl)alkyl, or (heterocycloalkyl)alkyl;

each occurrence of $R^b$ is independently selected from the group consisting of halo, oxo, alkyl, alkoxyl, haloalkyl, cyano, cycloalkyl, aryl, aryloxy, —OH, —NH(alkyl), —C(O)H, —CO$_2$(alkyl) and —CO$_2$H;

$R^c$ represents optionally substituted heterocycloalkyl, cycloalkyl, alkyl, aryl, heteroaryl, (heterocycloalkyl)alkyl, heterocycloalkenyl, alkoxyl, alkynyl, aryloxy, haloalkyl, haloalkoxy, cycloalkoxyl, or heterocycloalkoxyl, or represents halo, —S(alkyl), —NH$_2$, —CO$_2$H, —CO$_2$(alkyl), or —NHCO(alkyl);

each occurrence of $R^i$ is independently halo, oxo, —S(alkyl), —NH$_2$, —NH(alkyl), —N(alkyl)$_2$, —OH, or cyano, or is selected from the group consisting of optionally substituted alkyl, haloalkyl, haloalkoxyl, alkoxyl, heterocycloalkyl, and cycloalkoxyl;

or $R^c$ and an occurrence of $R^i$, taken together with the intervening atoms, form an optionally substituted aryl, heteroaryl, cycloalkyl, or heterocycloalkyl ring;

or two adjacent occurrences of $R^i$, taken together with the intervening atoms, form an optionally substituted aryl, heteroaryl, cycloalkyl, or heterocycloalkyl ring; and m, n, and p are each independently 0, 1, or 2.

In further aspects, the invention provides compounds having the structure of formula (II), (II)

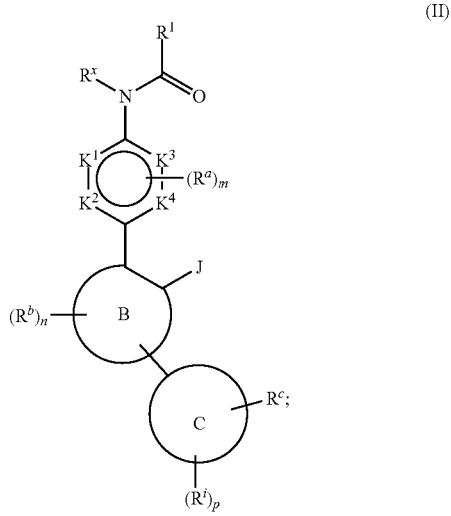

or a pharmaceutically acceptable salt thereof;
wherein:
each of $K^1$-$K^4$ is independently CH or N;
  wherein at least one of $K^1$-$K^4$ is CH;
Ring B represents substituted or unsubstituted phenylene or 6-membered heteroarylene;
Ring C represents substituted or unsubstituted arylene or heteroarylene;
$R^1$ represents alkyl, alkenyl, haloalkyl, —O(alkyl), —S(alkyl), —NH(alkyl), or —N(alkyl)$_2$;
$R^x$ represents H, alkyl, or —C(O)alkyl;
  or $R^1$ and $R^x$, taken together with the intervening atoms, form an optionally substituted heterocycloalkyl ring, heterocycloalkenyl ring, or heteroaryl ring;
each occurrence of $R^a$ is independently selected from the group consisting of halo, —NH$_2$, —NH(alkyl), —NH(cycloalkyl), —N(alkyl)$_2$, hydroxyl, alkyl, alkoxy, cycloalkyl, cycloalkoxy, haloalkoxy, heterocycloalkoxy, cyano, aryloxy, heteroaryloxy, and haloalkyl;
  or $R^1$ and an occurrence of $R^a$, taken together with the intervening atoms, form an optionally substituted heterocycloalkyl ring;
  or an occurrence of $R^a$ and $R^x$, taken together with the intervening atoms, form an optionally substituted heterocycloalkyl ring;
J represents —OH, —O(alkyl), —OC(O)(alkyl), —OC(O)O(alkyl), —OC(O)NH(alkyl), —OC(O)N(alkyl)$_2$, —OCH$_2$OC(O)O(alkyl), —NH$_2$, —NHR$^j$, or —CHF$_2$;
$R^j$ is alkyl, alkenyl, alkynyl, aryl, heteroaryl, arylalkyl, heteroarylalkyl, cycloalkyl, heterocycloalkyl, (cycloalkyl)alkyl, or (heterocycloalkyl)alkyl;
each occurrence of $R^b$ is independently selected from the group consisting of halo, oxo, alkyl, alkoxyl, haloalkyl, cyano, cycloalkyl, aryl, aryloxy, —OH, —NH(alkyl), —C(O)H, —CO$_2$(alkyl) and —CO$_2$H;
$R^c$ represents H;
each occurrence of $R^i$ is independently halo, oxo, —S(alkyl), —NH$_2$, —NH(alkyl), —N(alkyl)$_2$, —OH, or cyano, or is selected from the group consisting of optionally substituted alkyl, haloalkyl, haloalkoxyl, alkoxyl, heterocycloalkyl, and cycloalkoxyl;
  or two adjacent occurrences of $R^i$, taken together with the intervening atoms, form an optionally substituted aryl, heteroaryl, cycloalkyl, or heterocycloalkyl ring; and m, n, and p are each independently 0, 1, or 2.

The present invention also provides pharmaceutical compositions comprising a compound of the invention and a pharmaceutically acceptable excipient.

Also provided herein are methods of treating or preventing cancer, comprising administering to a subject in need thereof a therapeutically effective amount of a compound of the invention.

The present invention also provides methods of treating a disease or condition, comprising administering to a subject in need thereof a therapeutically effective amount of a compound of the invention, wherein the disease or condition is selected from the group consisting of Addison's disease, acute gout, ankylosing spondylitis, asthma, atherosclerosis, Behcet's disease, bullous skin diseases, chronic obstructive pulmonary disease (COPD), Crohn's disease, dermatitis, dermatomyositis, eczema, giant cell arteritis, glomerulonephritis, hepatitis, hypophysitis, inflammatory bowel disease, juvenile arthritis, Kawasaki disease, lupus nephritis, multiple sclerosis, myocarditis, myositis, nephritis, organ transplant rejection, osteoarthritis, pancreatitis, pediatric inflammatory multisystem syndrome, pericarditis, polyarteritis nodosa, pneumonitis, primary biliary cirrhosis, psoriasis, psoriatic arthritis, rheumatoid arthritis, scleritis, scleroderma, sclerosing cholangitis, sepsis, Sjögren syndrome, systemic lupus erythematosus, systemic sclerosis, Takayasu's arteritis, toxic shock syndrome, thyroiditis, type I diabetes, ulcerative colitis, uveitis, vasculitis, vitiligo and Wegener's granulomatosis.

Also provided herein are methods of treating an acquired immunodeficiency syndrome (AIDS), comprising administering to a subject in need thereof a therapeutically effective amount of a compound of the invention.

The present invention also provides methods of treating a disease or condition, comprising administering to a subject in need thereof a therapeutically effective amount of a compound of the invention, wherein the disease or condition is selected from the group consisting of obesity, dyslipidemia, hypercholesterolemia, Alzheimer's disease, metabolic syndrome, hepatic steatosis, type II diabetes, insulin resistance, diabetic retinopathy, and diabetic neuropathy.

The present invention also provides methods of treating an acute kidney disease, comprising administering to a subject in need thereof a therapeutically effective amount of a compound of the invention, wherein said acute kidney disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, drug toxicity induced kidney disease, diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease, and tubular interstitial nephritis.

Also provided herein are methods of treating fibrosis, comprising administering to a subject in need thereof a therapeutically effective amount of a compound of the invention.

In other aspects, the present invention provides methods of treating an epithelial wound, comprising administering to a subject in need thereof a therapeutically effective amount of a compound of the invention.

Also provided herein are methods of treating a viral infection, comprising administering to a subject in need thereof a therapeutically effective amount of a compound of the invention, wherein the viral infection is caused by a DNA virus or an RNA virus. For example, the viral infection may be caused by an RNA virus in the Coronaviridae viral family such as SARS-CoV or SARS-CoV-2.

In other aspects, the present invention provides methods of inhibiting a bromodomain and extra-terminal (BET) protein in a cell selectively at bromodomain II (BDII), comprising contacting the cell with an effective amount of a compound of the invention.

DETAILED DESCRIPTION

Definitions

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium, and alternatively oxygen, nitrogen or sulfur.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ alkyl group. In certain embodiments, the term "alkyl" refers to a $C_1$-$C_6$ alkyl group, for example a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged carbocyclic rings, each having from 3 to 12 carbon atoms, which can be completely saturated or which may can contain one or more units of unsaturation; but, for the avoidance of doubt, the degree of unsaturation does not result in an aromatic ring system. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[1.1.1]pentane, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocycloalkyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocycloalkyl, or a 5 or 6 membered monocyclic heteroaryl, wherein the fused bicyclic cycloalkyl is optionally substituted.

A "cycloalkenyl" group refers to a cycloalkyl group additionally having at least one unit of unsaturation, but for the avoidance of doubt, the degree of unsaturation does not result in an aromatic ring system.

The term "(cycloalkyl)alkyl" as used herein refers to an alkyl group substituted with one or more cycloalkyl groups. An example of (cycloalkyl)alkyl is cyclohexylmethyl group.

The term "heterocycloalkyl" as used herein refers to a radical of a non-aromatic ring system, including, but not limited to, monocyclic, bicyclic, and tricyclic rings, which can be completely saturated or which can contain one or more units of unsaturation; but, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocycloalkyl group is optionally substituted by one or more substituents as described below.

The term "(heterocycloalkyl)alkyl" as used herein refers to an alkyl group substituted with one or more heterocycloalkyl (i.e., heterocyclyl) groups.

A "heterocycloalkenyl" group refers to a heterocycloalkyl group additionally having at least one unit of unsaturation, but for the avoidance of doubt, the degree of unsaturation does not result in an aromatic ring system.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

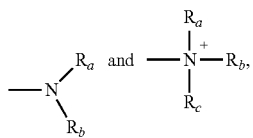

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$. In certain embodiments, the term "amino" refers to —$NH_2$.

In certain embodiments, the term "alkylamino" refers to —NH(alkyl).

In certain embodiments, the term "dialkylamino" refers to —N(alkyl)$_2$.

The term "amido", as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

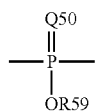

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

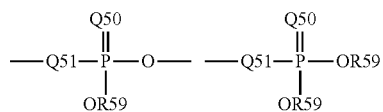

wherein Q50 and R59, each independently, are defined above, and Q51 represents O, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an —$N_3$ group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—.

The term "(alkylthio)alkyl" refers to an alkyl group substituted by an alkylthio group.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, and pyrene. Typically, an aryl group contains from 6-10 carbon ring atoms (i.e., ($C_6$-$C_{10}$)aryl). The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluoromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group.

The term "arylene" means a diradical obtained by removing two hydrogen atoms of an aryl group, as defined above. In certain embodiments an arylene refers to a disubstituted arene, i.e., an arene substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluoromethyl), cyano, or the like. That is, in certain embodiments, a "substituted aryl" is an "arylene".

The term "phenylene" means a diradical obtained by removing two hydrogen atoms of benzene. Exemplary phenylene groups include the following structures:

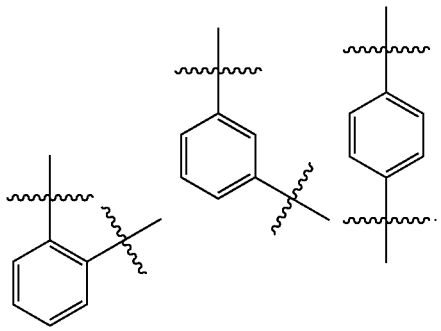 [SMILES: *c1ccccc1* ; *c1cccc(*)c1 ; *c1ccc(*)cc1]

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl (e.g., imidazo[4,5-c]pyridinyl, imidazo[1,2-a]pyridinyl, and imidazo[1,5-a]pyridinyl), indolyl, indolinyl, indolizinyl, indazolyl, isoindolinyl, isoxazolyl, isothiazolyl, isoquinolinyl, oxadiazolyl, oxazolyl, purinyl, pyranyl, pyrazinyl, pyrazolyl, pyridazinyl, pyridinyl, 2-pyridonyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. "Heteroaryl" also encompasses 2-pyridone, the tautomer of 2-hydroxypyridine.

The term "heteroarylene" means a diradical obtained by removing two hydrogen atoms of a heteroaryl group, as defined above. In certain embodiments an heteroarylene refers to a disubstituted heteroarene, i.e., a heteroarene substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluoromethyl), cyano, or the like. That is, in certain embodiments, a "substituted heteroaryl" is an "heteroarylene".

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" refers to an alkyl group substituted by an alkoxy group.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH-CH_2-O-$) and vinyloxy (i.e., $CH_2=CH-O-$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si$—) group (i.e., (hydrocarbyl)$_3Si$—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

"Substituted with deuterium" refers to the replacement of one or more hydrogen atoms with a corresponding number of deuterium atoms.

In certain embodiments, a compound of the invention is substituted by deuterium. For example, in an alkyl group, one or more hydrogen atoms may be replaced by a corresponding number of deuterium atoms.

It will be recognized that some variation of natural isotopic abundance occurs in a synthesized compound depending upon the origin of chemical materials used in the synthesis. Thus, a preparation of a compound of the invention will inherently contain small amounts of deuterated isotopologues. The concentration of naturally abundant stable hydrogen and carbon isotopes, notwithstanding this variation, is small and immaterial as compared to the degree of stable isotopic substitution of the deuterated compounds of this invention. See, for instance, Wada, E et al., Seikagaku, 1994, 66: 15; Gannes, L Z et al., Comp Biochem Physiol Mol Integr Physiol, 1998, 119:725.

In the compounds of this invention any atom not specifically designated as a particular isotope is meant to represent any stable isotope of that atom. The stable isotopes of hydrogen are $^1H$ (protium) and $^2H$ (deuterium). Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

In certain embodiments, the optional substituents can include, for example, halogen, haloalkyl (such as fluoroalkyl or trifluoromethyl), hydroxyl, carbonyl (such as carboxyl, alkoxycarbonyl, formyl, or acyl), thiocarbonyl (such as thioester, thioacetate, or thioformate), alkoxyl, alkenyloxy, alkynyloxy, phosphoryl, phosphate, phosphonate, phosphinate, amino (including alkyl- and dialkylamino), amido, amidine, imine, cyano, nitro, azido, sulfhydryl, alkylthio, sulfate, sulfonate, sulfamoyl, sulfonamido, sulfonyl, silyl, silyloxy, heterocycloalkyl, (heterocycloalkyl)alkyl, cycloalkyl, (cycloalkyl)alkyl, cycloalkoxy, heterocycloalkoxy, alkyl, alkenyl, alkynyl, hydroxyalkyl, alkoxyalkyl, haloalkoxy, haloalkoxyalkyl, aryl, heteroaryl, aryloxy, heteroaryloxy, aralkyl, or heteroaralkyl group.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2nd* ed.; Wiley: New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of formula (I). As another example, the salt may comprise less than one inorganic or organic acid molecule per molecule of base, such as two molecules of compound of formula (I) per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in Remington's Pharmaceutical Sciences by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In certain embodiments, a subject is a human.

Compounds

In certain embodiments, the invention provides a compound having the structure of formula (I),

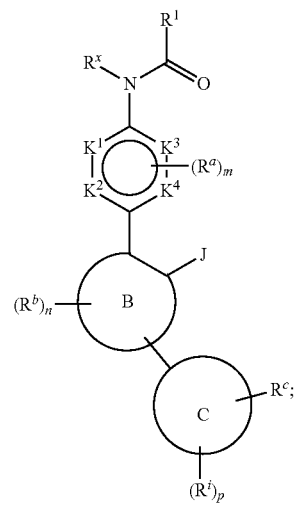

or a pharmaceutically acceptable salt thereof;
wherein:
each of $K^1$-$K^4$ is independently CH or N;
  wherein at least one of $K^1$-$K^4$ is CH;
Ring B represents substituted or unsubstituted phenylene or 6-membered heteroarylene;
Ring C represents substituted or unsubstituted arylene or heteroarylene;
$R^1$ represents alkyl, alkenyl, haloalkyl, —O(alkyl), —S(alkyl), —NH(alkyl), or —N(alkyl)$_2$;
$R^x$ represents H, alkyl, or —C(O)alkyl;
  or $R^1$ and $R^x$, taken together with the intervening atoms, form an optionally substituted heterocycloalkyl ring, heterocycloalkenyl ring, or heteroaryl ring;
each occurrence of $R^a$ is independently selected from the group consisting of halo, —NH$_2$, —NH(alkyl), —NH(cycloalkyl), —N(alkyl)$_2$, hydroxyl, alkyl, alkoxy, cycloalkyl, cycloalkoxy, haloalkoxy, heterocycloalkoxy, cyano, aryloxy, heteroaryloxy, and haloalkyl;
  or $R^1$ and an occurrence of $R^a$, taken together with the intervening atoms, form an optionally substituted heterocycloalkyl ring;
  or an occurrence of $R^a$ and $R^x$, taken together with the intervening atoms, form an optionally substituted heterocycloalkyl ring;
J represents —OH, —O(alkyl), —OC(O)(alkyl), —OC(O)O(alkyl), —OC(O)NH(alkyl), —OC(O)N(alkyl)$_2$, —OCH$_2$OC(O)O(alkyl), —NH$_2$, —NHR$^j$, or —CHF$_2$;
$R^j$ is alkyl, alkenyl, alkynyl, aryl, heteroaryl, arylalkyl, heteroarylalkyl, cycloalkyl, heterocycloalkyl, (cycloalkyl)alkyl, or (heterocycloalkyl)alkyl;
each occurrence of $R^b$ is independently selected from the group consisting of halo, oxo, alkyl, alkoxyl, haloalkyl, cyano, cycloalkyl, aryl, aryloxy, —OH, —NH(alkyl), —C(O)H, —CO$_2$(alkyl) and —CO$_2$H;
$R^c$ represents optionally substituted heterocycloalkyl, cycloalkyl, alkyl, aryl, heteroaryl, (heterocycloalkyl)alkyl, heterocycloalkenyl, alkoxyl, alkynyl, aryloxy, haloalkyl, haloalkoxyl, cycloalkoxyl, or heterocycloalkoxyl, or represents halo, S(alkyl), —NH$_2$, —CO$_2$H, —CO$_2$(alkyl), or —NHCO(alkyl);
each occurrence of $R^i$ is independently halo, oxo, —S(alkyl), —NH$_2$, —NH(alkyl), —N(alkyl)$_2$, —OH, or cyano, or is selected from the group consisting of optionally substituted alkyl, haloalkyl, haloalkoxyl, alkoxyl, heterocycloalkyl, and cycloalkoxyl;
or $R^c$ and an occurrence of $R^i$, taken together with the intervening atoms, form an optionally substituted aryl, heteroaryl, cycloalkyl, or heterocycloalkyl ring;
or two adjacent occurrences of $R^i$, taken together with the intervening atoms, form an optionally substituted aryl, heteroaryl, cycloalkyl, or heterocycloalkyl ring; and
m, n, and p are each independently 0, 1, or 2.

In certain embodiments of the compound of formula (I):
each of $K^1$-$K^4$ is independently CH or N;
wherein at least one of $K^1$-$K^4$ is CH;
Ring B represents substituted or unsubstituted phenylene or 6-membered heteroarylene;
Ring C represents substituted or unsubstituted arylene or heteroarylene;
$R^1$ represents alkyl, alkenyl, haloalkyl, —O(alkyl), —S(alkyl), —NH(alkyl), or —N(alkyl)$_2$;
$R^x$ represents H, alkyl, or —C(O)alkyl;
or $R^1$ and $R^x$, taken together with the intervening atoms, form an optionally substituted heterocycloalkyl ring, heterocycloalkenyl ring, or heteroaryl ring;
each occurrence of $R^a$ is independently selected from the group consisting of halo, —NH$_2$, —NH(alkyl), —NH(cycloalkyl), —N(alkyl)$_2$, alkyl, alkoxy, cycloalkoxy, haloalkoxy, heterocycloalkoxy, cyano, aryloxy, heteroaryloxy, and haloalkyl;
or $R^1$ and an occurrence of $R^a$, taken together with the intervening atoms, form an optionally substituted heterocycloalkyl ring;
or an occurrence of $R^a$ and $R^x$, taken together with the intervening atoms, form an optionally substituted heterocycloalkyl ring;
J represents —OH, —O(alkyl), —OC(O)(alkyl), —OC(O)O(alkyl), —OC(O)NH(alkyl), —OC(O)N(alkyl)$_2$, —OCH$_2$OC(O)O(alkyl), —NH$_2$, —NHR$^j$, or —CHF$_2$;
$R^j$ is alkyl, alkenyl, alkynyl, aryl, heteroaryl, arylalkyl, heteroarylalkyl, cycloalkyl, heterocycloalkyl, (cycloalkyl)alkyl, or (heterocycloalkyl)alkyl;
each occurrence of $R^b$ is independently selected from the group consisting of halo, alkyl, alkoxyl, cyano, cycloalkyl, aryl, aryloxy, —CO$_2$(alkyl) and —CO$_2$H;
$R^c$ represents optionally substituted heterocycloalkyl, cycloalkyl, alkyl, aryl, heteroaryl, alkoxyl, alkynyl, aryloxy, haloalkyl, haloalkoxy, cycloalkoxyl, or heterocycloalkoxyl, or represents halo, —S(alkyl), —NH$_2$, —CO$_2$H, —CO$_2$(alkyl), or —NHCO(alkyl);
each occurrence of $R^i$ is independently halo, oxo, —S(alkyl), or cyano, or is selected from the group consisting of optionally substituted alkyl, haloalkyl, haloalkoxyl, alkoxyl, heterocycloalkyl, and cycloalkoxyl;
or $R^c$ and an occurrence of $R^i$, taken together with the intervening atoms, form an optionally substituted aryl, heteroaryl, cycloalkyl, or heterocycloalkyl ring;
or two adjacent occurrences of $R^i$, taken together with the intervening atoms, form an optionally substituted aryl, heteroaryl, cycloalkyl, or heterocycloalkyl ring; and
m, n, and p are each independently 0, 1, or 2.

In certain embodiments, each of $K^1$-$K^4$ is CH. In such embodiments, any one or more of the hydrogen atoms of the CH groups of $K^1$-$K^4$ is optionally replaced by an occurrence of $R^a$.

For example, the compound of the invention may have the structure of formula (Ia):

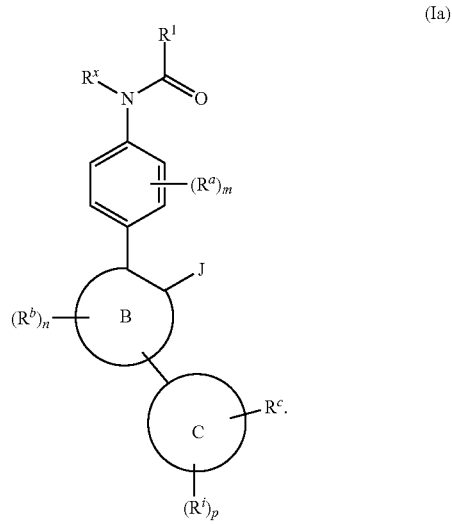

(Ia)

In certain embodiments, m is 0.
In certain embodiments, m is 1. For example, the compound of the invention may have the structure of formula (Iai):

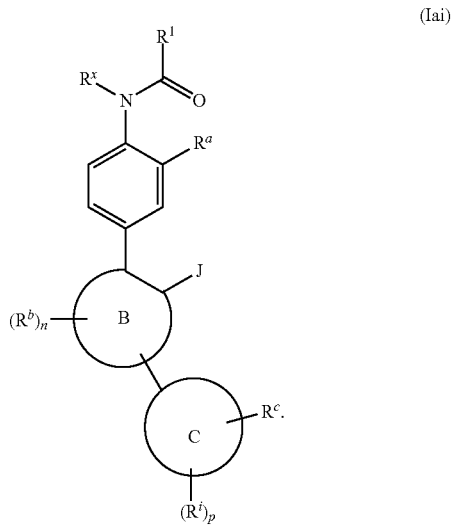

(Iai)

In certain embodiments, m is 2. For example, the compound of the invention may have the structure of formula (Iaii):

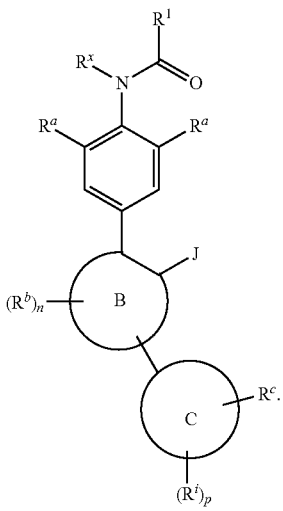

(Iaii)

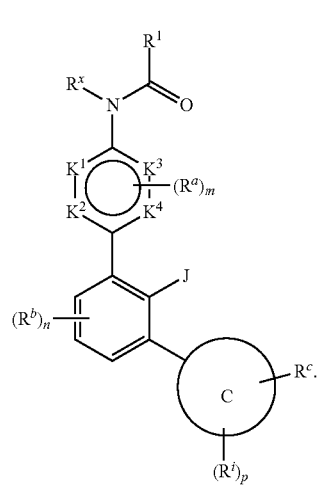

(Ibi)

In certain embodiments, one of $K^1$-$K^4$ is N, and the remaining of $K^1$-$K^4$ is CH. In such embodiments, any one or more of the hydrogen atoms of the CH groups of $K^1$-$K^4$ is optionally replaced by an occurrence of $R^a$.

For example, in certain such embodiments, $K^1$ is N. In alternative such embodiments, $K^2$ is N.

In certain embodiments, two of $K^1$-$K^4$ is N, and the remaining of $K^1$-$K^4$ is CH. In such embodiments, any one or more of the hydrogen atoms of the CH groups of $K^1$-$K^4$ is optionally replaced by an occurrence of $R^a$.

For example, in certain such embodiments, $K^1$ and $K^3$ are N. In alternative such embodiments, $K^1$ and $K^4$ are N. Alternatively still, $K^1$ and $K^2$ may be N.

In certain embodiments, Ring B represents substituted or unsubstituted phenylene (i.e., a 6-membered carbocyclic aromatic ring). For example, the compound of the invention may have the structure of formula (Ib):

In certain such embodiments, n is 1. For example, the compound of the invention may have the structure of formula (Ibii):

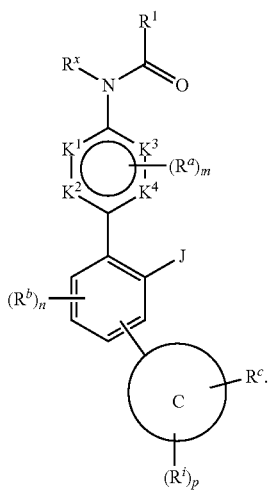

(Ib)

(Ibii)

In certain embodiments, Ring C occupies a position ortho to group J. For example, the compound of the invention may have the structure of formula (Ibi):

In other embodiments, n is 0. For example, the compound of the invention may have the structure of formula (Ibiii):

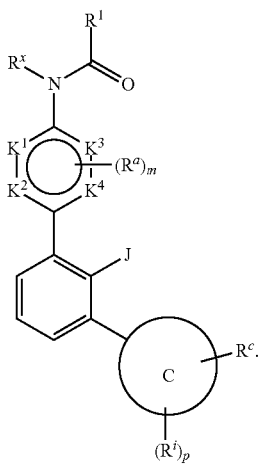
(Ibiii)

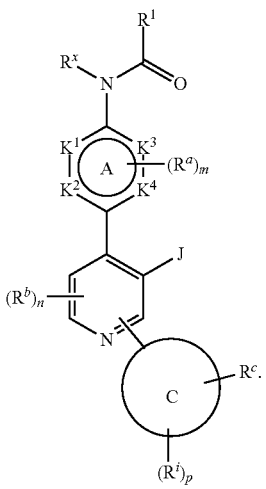
(Ibhi)

In certain embodiments, Ring B represents substituted or unsubstituted 6-membered heteroarylene. In certain such embodiments, the compound has the structure of formula (Ibh):

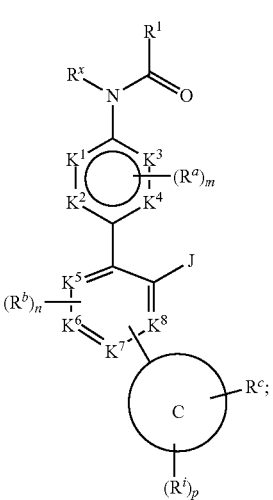
(Ibh)

wherein each of $K^5$-$K^8$ is independently selected from CH and N; and
at least one of $K^5$—$K^8$ is N.
For example, in some embodiments, $K^6$ is N.
In certain embodiments, one of $K^5$—$K^8$ is N. In alternative embodiments, two of $K^5$-$K^8$ are N.
In certain embodiments, Ring B represents substituted or unsubstituted pyridine. In certain such embodiments, the compound has the structure of formula (Ibhi):

In certain embodiments, Ring C occupies a position ortho to group J. For example, the compound of the invention may have the structure of formula (Ibhii):

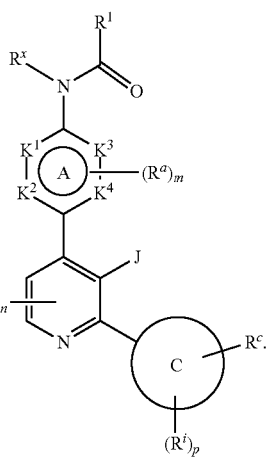
(Ibhii)

In certain such embodiments, n is 1. For example, the compound of the invention may have the structure of formula (Ibhiii):

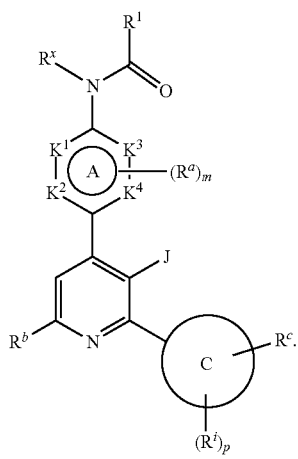
(Ibhiii)

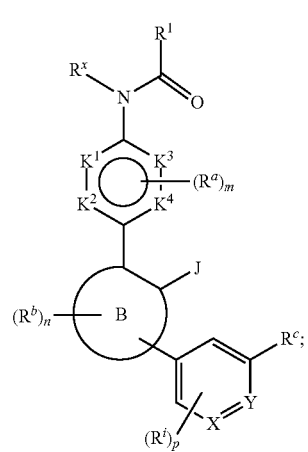
(Icm)

In other embodiments, n is 0. For example, the compound of the invention may have the structure of formula (Ibhiv):

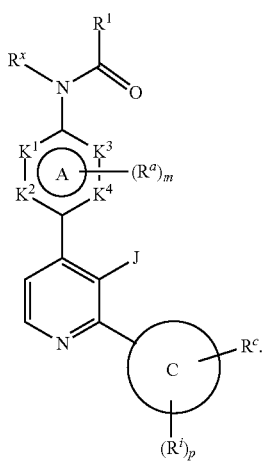
(Ibhiv)

In some embodiments, Ring C represents substituted or unsubstituted heteroarylene, for example, a substituted or unsubstituted 5-membered heteroarylene. For example, Ring C can be a substituted or unsubstituted 1,2-oxazole, 1,2-thiazole, 1,2-diazole, 1,3-oxazole, 1,3-thiazole, 1,3-diazole, or 1,3,4-triazole.

Alternatively, in some embodiments, Ring C is a substituted or unsubstituted bicyclic heteroarylene group.

Alternatively, in some embodiments, Ring C represents substituted or unsubstituted 6-membered arylene (i.e., phenylene) or 6-membered heteroarylene.

In certain such embodiments, the $R^c$ substituent on Ring C is in the meta position relative to Ring B.

Thus, in certain embodiments, the compound has the structure of formula (Icm):

wherein X and Y are each independently selected from CH and N; and
at least one of X and Y is CH.

In certain such embodiments, Ring C represents a substituted or unsubstituted phenylene (i.e., wherein both of X and Y are CH). Accordingly, in some embodiments, the compound of the invention has the structure of formula (Icmi):

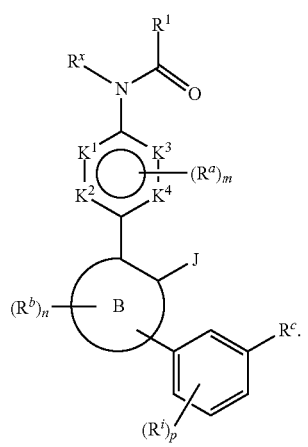
(Icmi)

In other such embodiments, Ring C represents a substituted or unsubstituted 6-membered heteroarylene (e.g., wherein one of X and Y is N). Accordingly, in some embodiments, the compound of the invention has the structure of formula (Icmii):

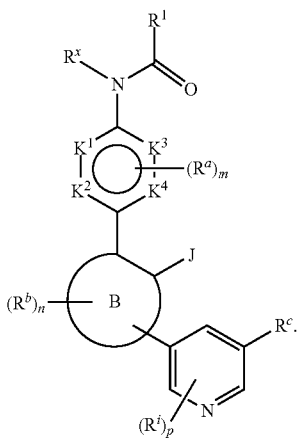

(Icmii)

In other embodiments, the compound of the invention has the structure of formula (Icmiii):

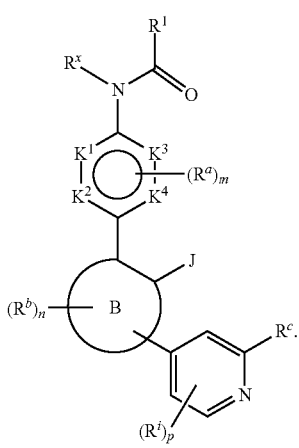

(Icmiii)

In other embodiments, the R$^c$ substituent on Ring C is in the para position relative to Ring B.

Thus, in certain embodiments, the compound has the structure of formula (Icp):

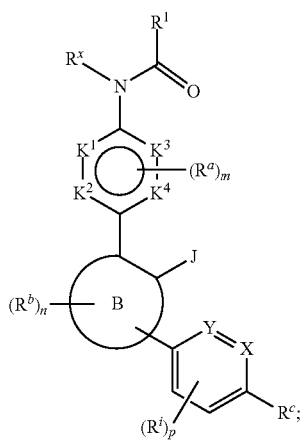

(Icp)

wherein X and Y are each independently selected from CH and N; and at least one of X and Y is CH.

In certain such embodiments, Ring C represents a substituted or unsubstituted phenylene (i.e., wherein both of X and Y are CH). Accordingly, in some embodiments, the compound of the invention has the structure of formula (Icpi):

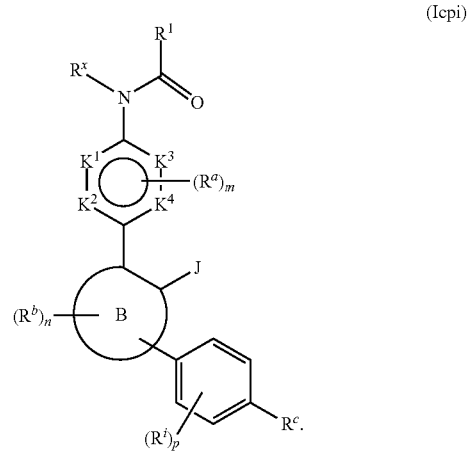

(Icpi)

In other such embodiments, Ring C represents a substituted or unsubstituted 6-membered heteroarylene (e.g., wherein one of X and Y is N). Accordingly, in some embodiments, the compound of the invention has the structure of formula (Icpii):

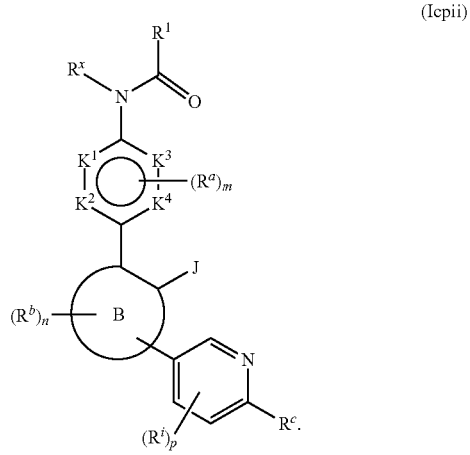

(Icpii)

In other embodiments, the compound of the invention has the structure of formula (Icpiii):

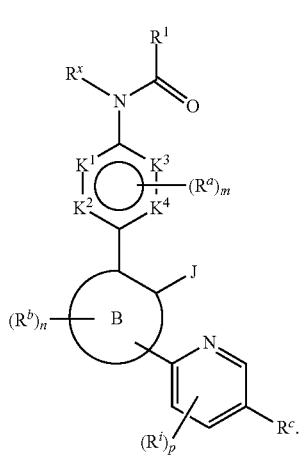

(Icpiii)

In other embodiments, the $R^c$ substituent on Ring C is in the ortho position relative to Ring B.

Thus, in certain embodiments, the compound has the structure of formula (Ico):

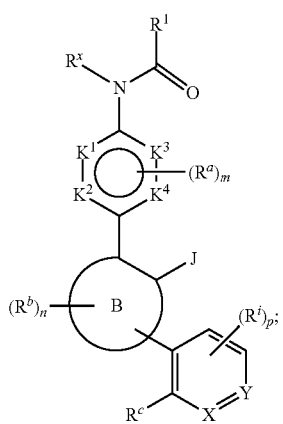

(Ico)

wherein X and Y are each independently selected from CH and N; and at least one of X and Y is CH.

In certain such embodiments, Ring C represents a substituted or unsubstituted phenylene (i.e., wherein both of X and Y are CH). Accordingly, in some embodiments, the compound of the invention has the structure of formula (Icoi):

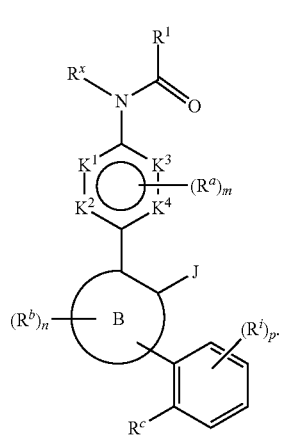

(Icoi)

In other such embodiments, Ring C represents a substituted or unsubstituted 6-membered heteroarylene (e.g., wherein one of X and Y is N). Accordingly, in some embodiments, the compound of the invention has the structure of formula (Icoii):

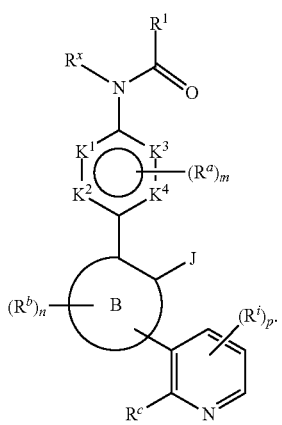

(Icoii)

In other embodiments, the compound of the invention has the structure of formula (Icoiii):

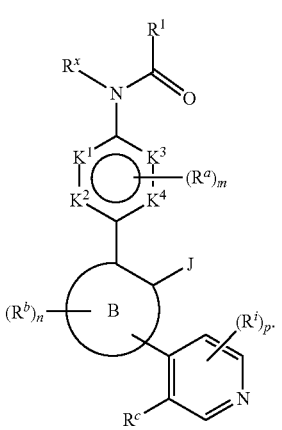

(Icoiii)

In certain embodiments, the compound of the invention has the structure of formula (Ie):

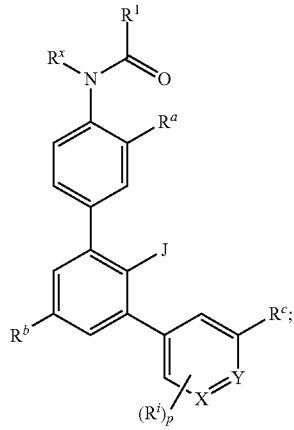

(Ie)

wherein X and Y are each independently selected from CH and N; and
at least one of X and Y is CH.

In certain such embodiments, the compound of the invention has the structure of formula (Iei):

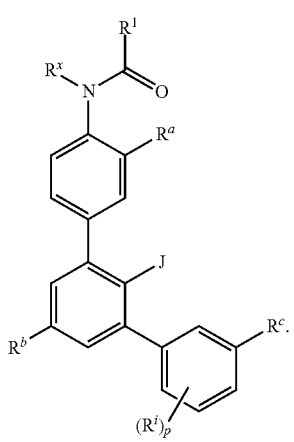

(Iei)

Alternatively, in some embodiments, the compound of the invention has the structure of formula (Ieii):

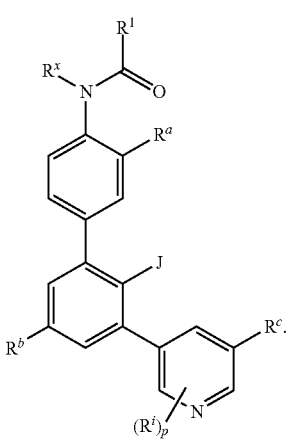

(Ieii)

In yet further embodiments, the compound of the invention has the structure of formula (Ieiii):

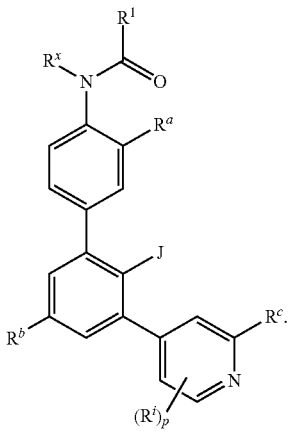

(Ieiii)

In yet further embodiments, the compound of the invention has the structure of formula (Ieu):

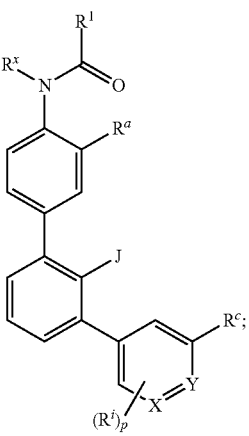

(Ieu)

wherein X and Y are each independently selected from CH and N; and
at least one of X and Y is CH.

In certain alternative embodiments wherein the B ring is pyridine, the compound of the invention has the structure of formula (If):

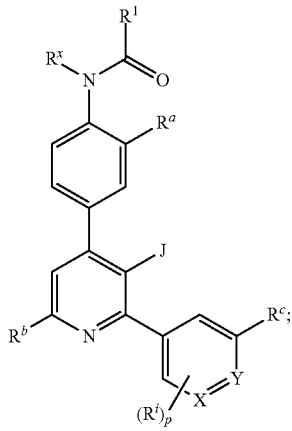

(If)

wherein X and Y are each independently selected from CH and N; and at least one of X and Y is CH.

In certain such embodiments, the compound of the invention has the structure of formula (Ifi):

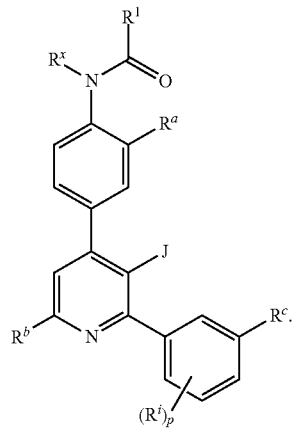
(Ifi)

Alternatively, the compound may have the structure of formula (Ifii):

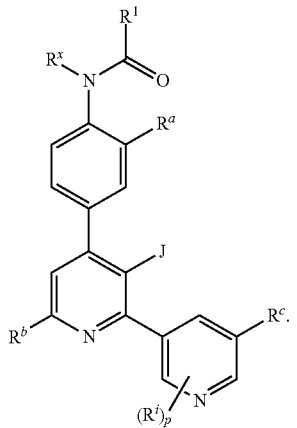
(Ifii)

In other alternative embodiments, the compound of the invention has the structure of formula (Ifiii):

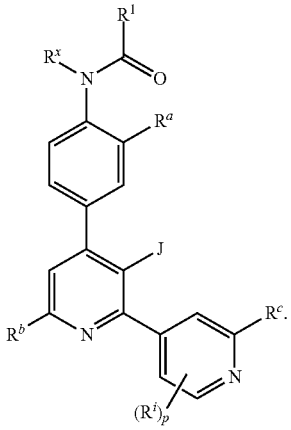
(Ifiii)

In certain alternative embodiments wherein the B ring is pyridine, the compound of the invention has the structure of formula (Ifu):

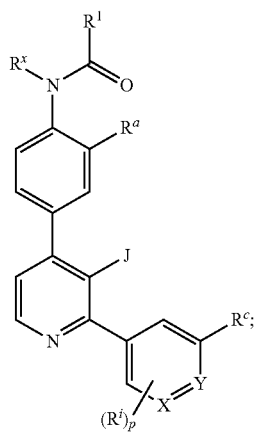
(Ifu)

wherein X and Y are each independently selected from CH and N; and at least one of X and Y is CH.

In certain embodiments, Ring C represents a substituted or unsubstituted 2-pyridone.

For example, in certain embodiments, the compound has the structure of formula (Igi):

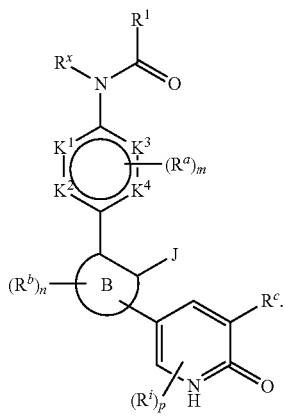

(Igi)

In certain such embodiments, the nitrogen of the pyridone is substituted with $R^1$. For example, the compound of the invention may have the structure of formula (Igia):

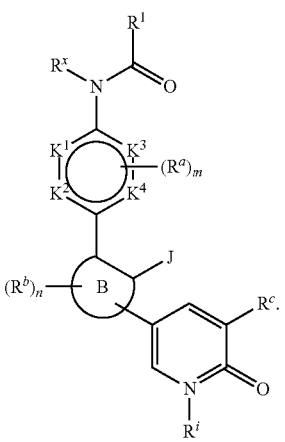

(Igia)

In certain such embodiments, Rings A and B are phenylene rings, and the compound of the invention has the structure of formula (Igib):

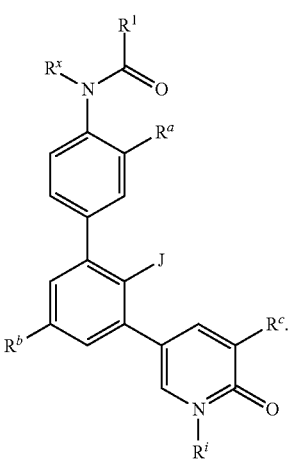

(Igib)

In alternative embodiments, the compound of the invention has the structure of formula (Igii):

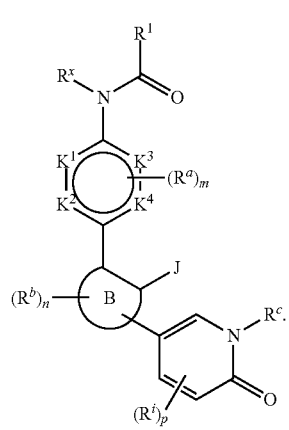

(Igii)

In certain such embodiments, Rings A and B are phenylene rings, and the compound of the invention has the structure of formula (Igiia):

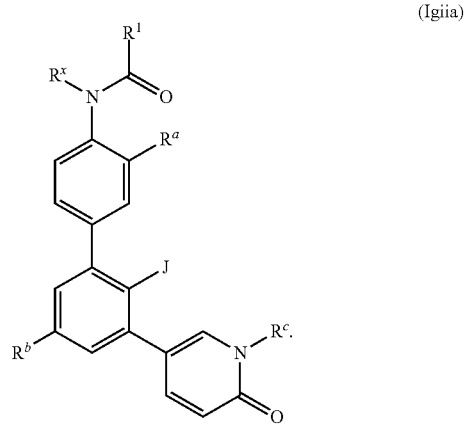

(Igiia)

In alternative embodiments, the compound of the invention has the structure of formula (Igiii):

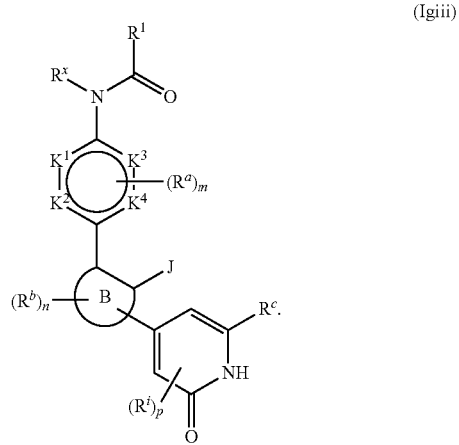

(Igiii)

In certain such embodiments, the nitrogen of the pyridone is substituted with $R^i$. For example, the compound of the invention may have the structure of formula (Igiiia):

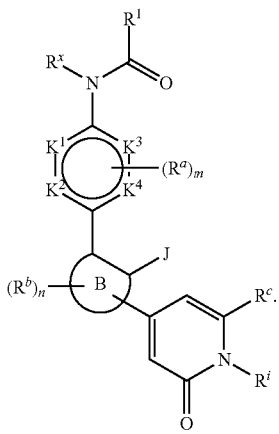
(Igiiia)

In certain such embodiments, Rings A and B are phenylene rings, and the compound of the invention has the structure of formula (Igiiib):

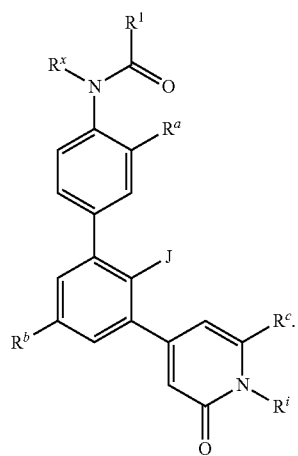
(Igiiib)

In certain embodiments, $R^1$ represents alkyl.

In certain embodiments, $R^1$ represents $(C_1\text{-}C_6)$alkyl, wherein at least one hydrogen atom ($^1H$) is replaced by a deuterium ($^2H$ or D).

In further embodiments, $R^1$ and $R^x$, taken together with the intervening atoms, form an optionally substituted heterocycloalkyl ring, heterocycloalkenyl ring, or heteroaryl ring.

In certain embodiments, $R^1$ and $R^x$, taken together with the intervening atoms, form an heterocycloalkyl ring, heterocycloalkenyl ring, or heteroaryl ring, wherein the ring is substituted by alkyl. In some embodiments, at least one hydrogen atom ($^1H$) of the alkyl substituent is replaced by a deuterium ($^2H$ or D).

In certain such embodiments,

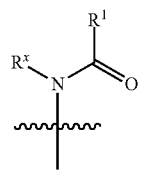

is selected from the group consisting of

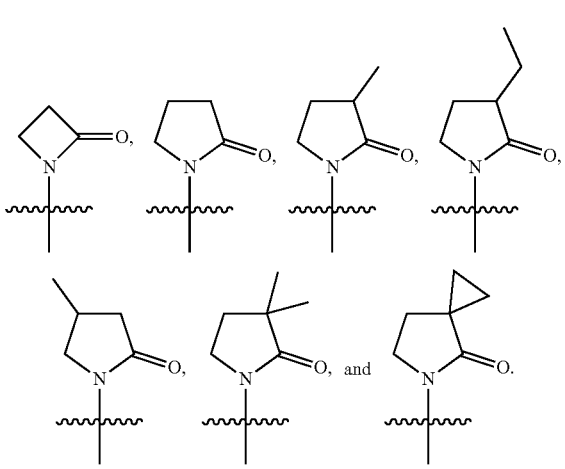

In further such embodiments,

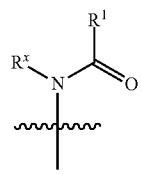

is selected from the group consisting of

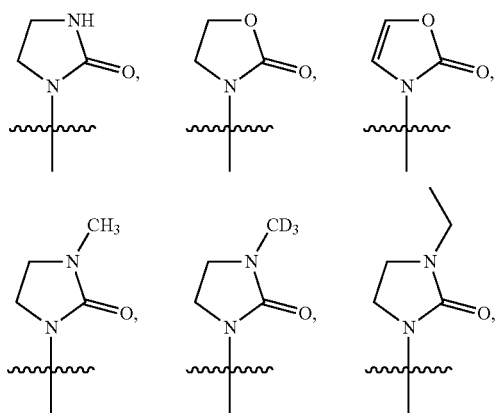

-continued

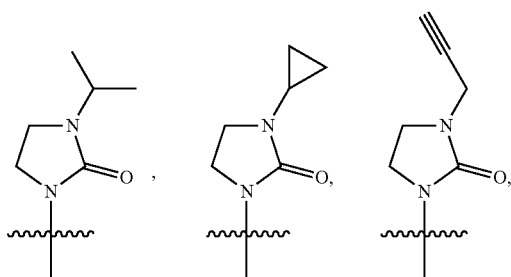

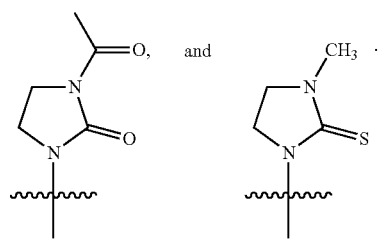

In still further embodiments,

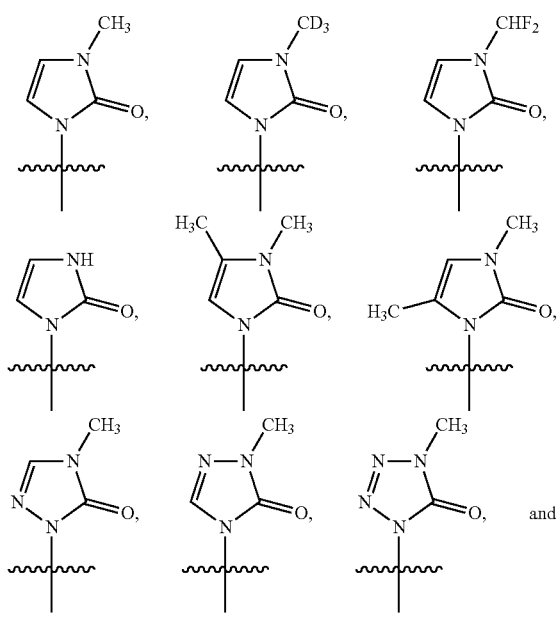

is selected from the group consisting of

-continued

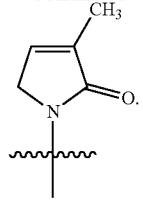

In yet further embodiments,

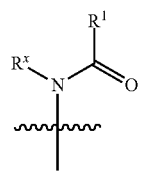

is selected from the group consisting of

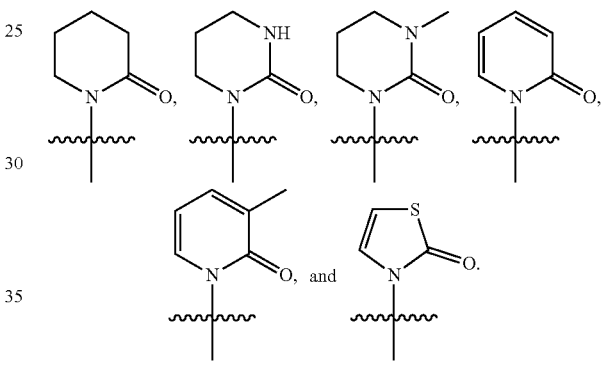

In some embodiments, m is 1.

In certain such embodiments, $R^a$ is halo, alkyl, alkoxy, or cycloalkoxy. For example, $R^a$ may be halo, e.g., fluoro or chloro.

In other embodiments, m is 2.

In certain such embodiments, $R^a$ is independently halo, alkyl, alkoxy, or cycloalkoxy. In some embodiments, at least one occurrence of $R^a$ is halo; e.g, at least one occurrence of $R^a$ is fluoro or chloro.

In certain embodiments, J represents —OH or —NH$_2$. For example, J may be —OH.

In other embodiments, J represents an —O— bound to a prodrug moiety. For example, J may be —OC(O)(alkyl), —OC(O)O(alkyl), —OC(O)NH(alkyl), —OC(O)N(alkyl)$_2$, or —OCH$_2$OC(O)O(alkyl).

In certain embodiments, n is 0.

Alternatively, n may be 1. In certain such embodiments, $R^b$ is halo or methyl. For example, $R^b$ may be halo, e.g. fluoro.

In certain embodiments, p is 0. Alternatively, p may be 1. In certain such embodiments, $R^t$ is alkyl or alkoxyl.

In certain embodiments, $R^c$ represents optionally substituted heterocycloalkyl. For example, in some embodiments, $R^c$ may represent optionally substituted piperazinyl, piperidinyl, morpholinyl, pyrrolidinyl, azepanyl, 3,8-diazabicyclo[3.2.1]octanyl, or 2,6-diazaspiro[3.3]heptanyl.

In further embodiments, $R^c$ represents piperazinyl, piperidinyl, or pyrrolidinyl, each optionally substituted by one or more substituents selected from the group consisting of amino, alkylamino, aminoalkyl, alkyl, alkoxyalkyl, halo, oxo, hydroxyl, heterocycloalkyl, (heterocycloalkyl)alkyl, cycloalkyl, (cycloalkyl)alkyl, amido, and alkoxyl.

For example, $R^c$ may represent piperazinyl substituted by alkyl.

Exemplary $R^c$ groups include, but are not limited to, the following:

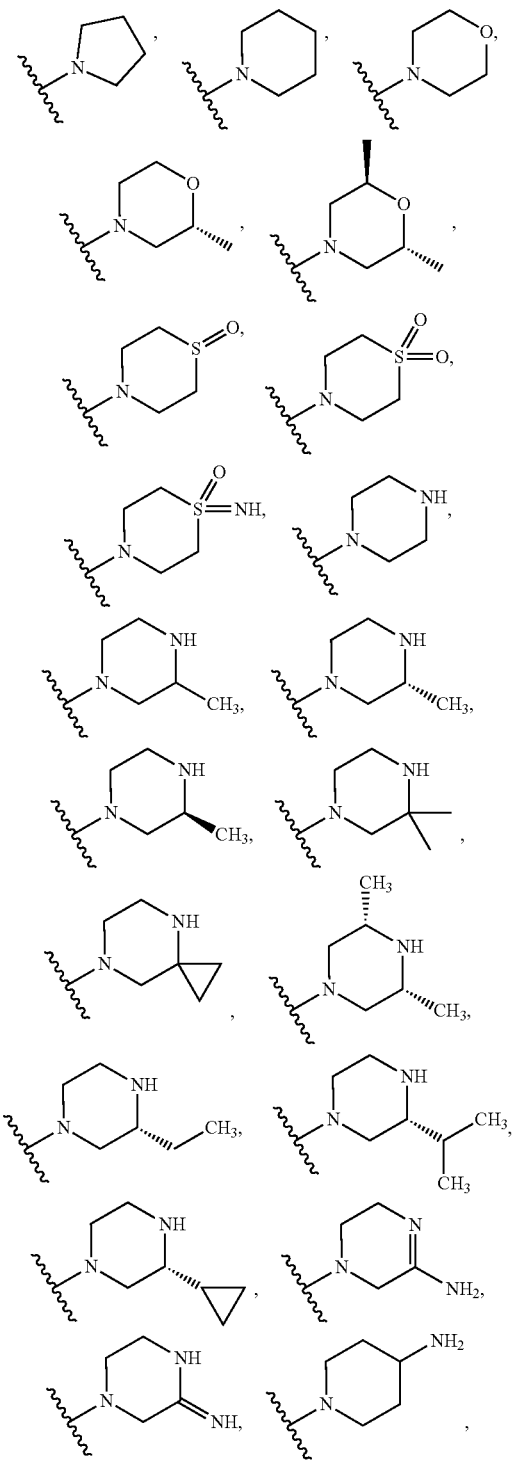

-continued

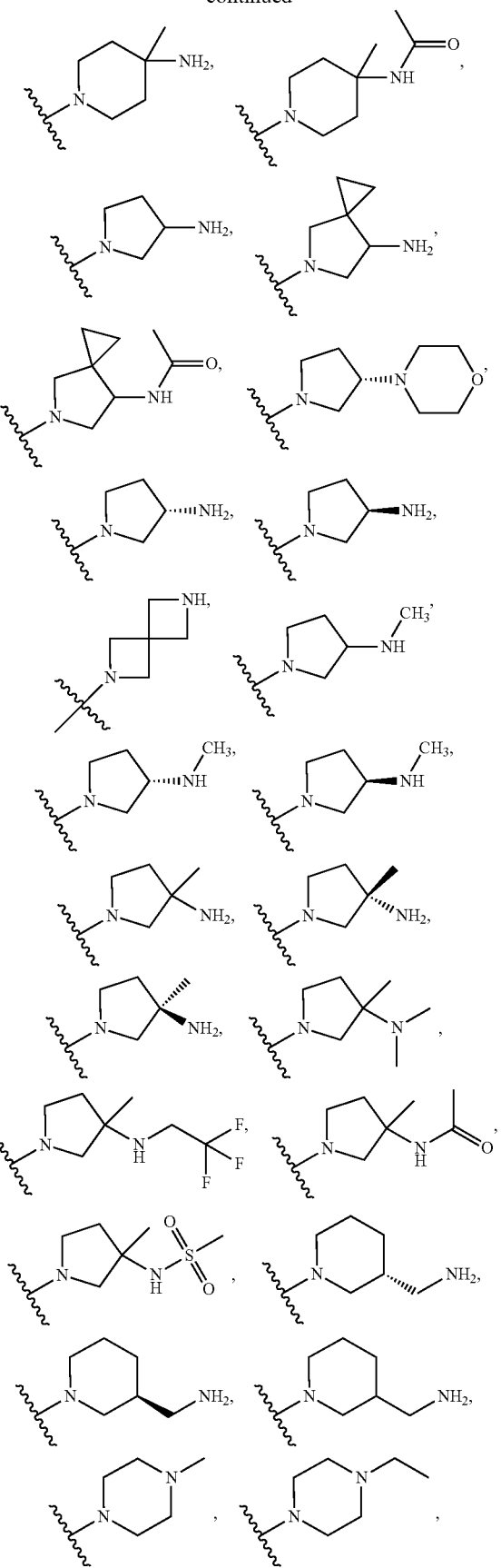

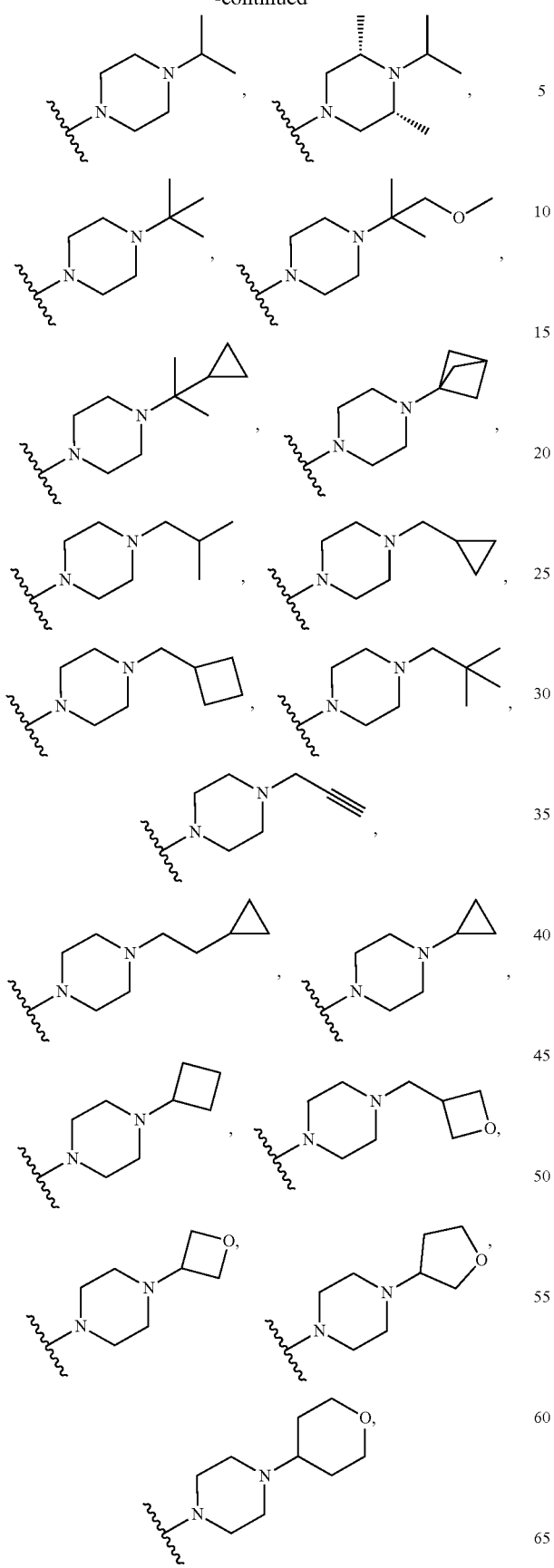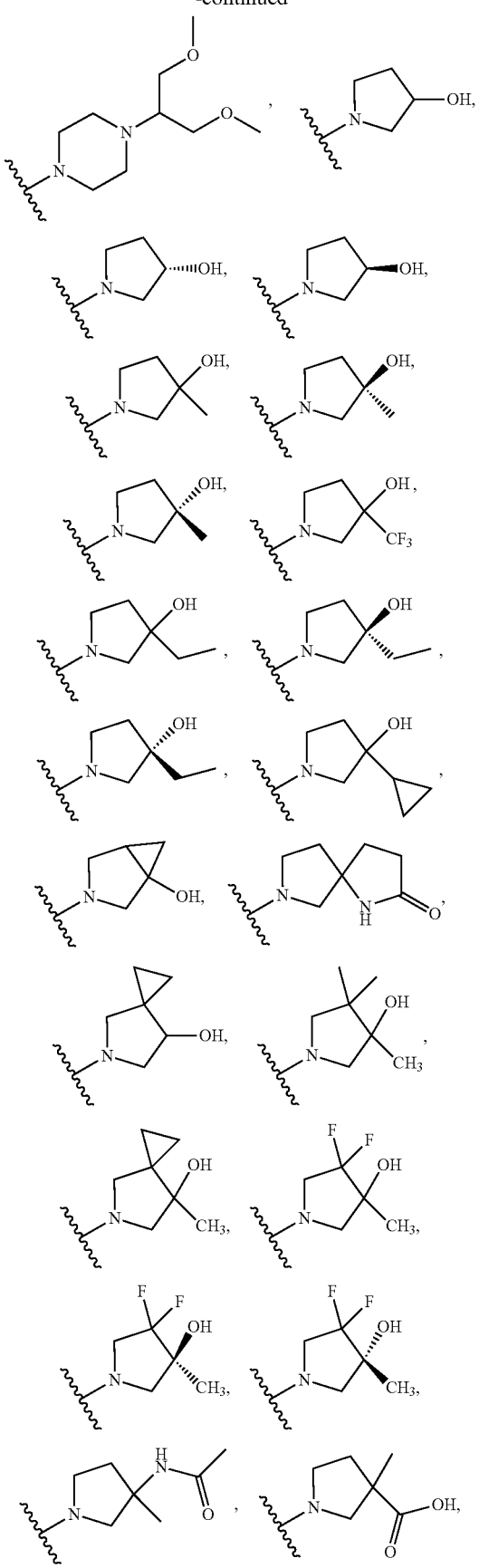

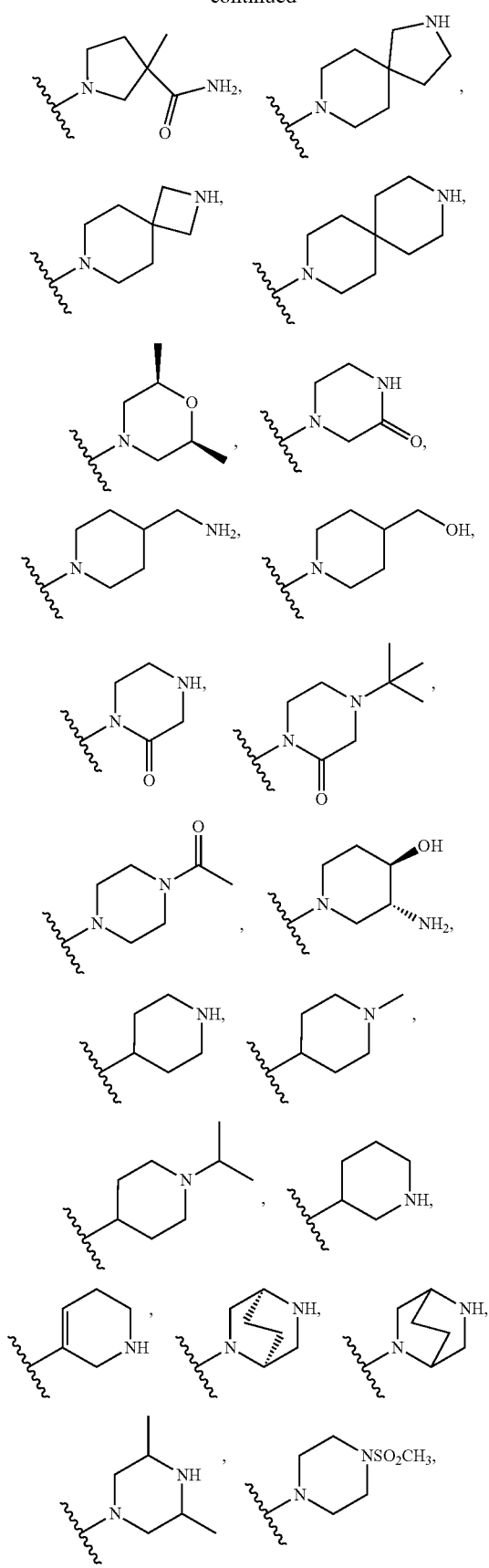
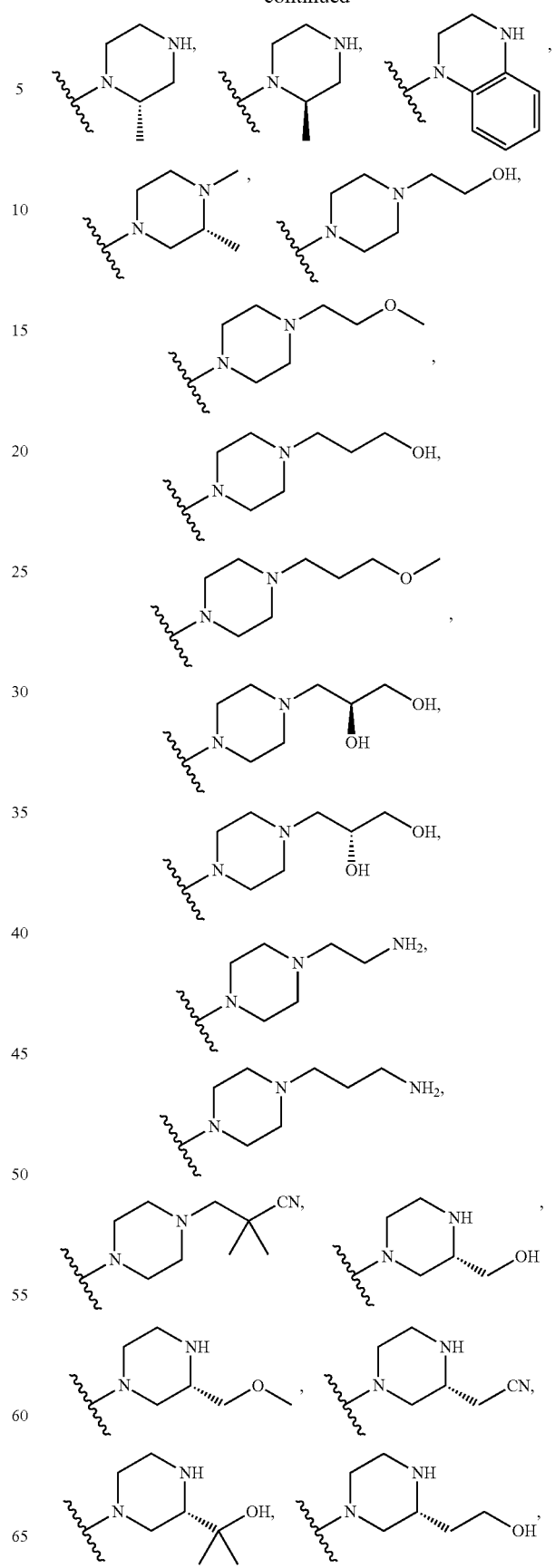

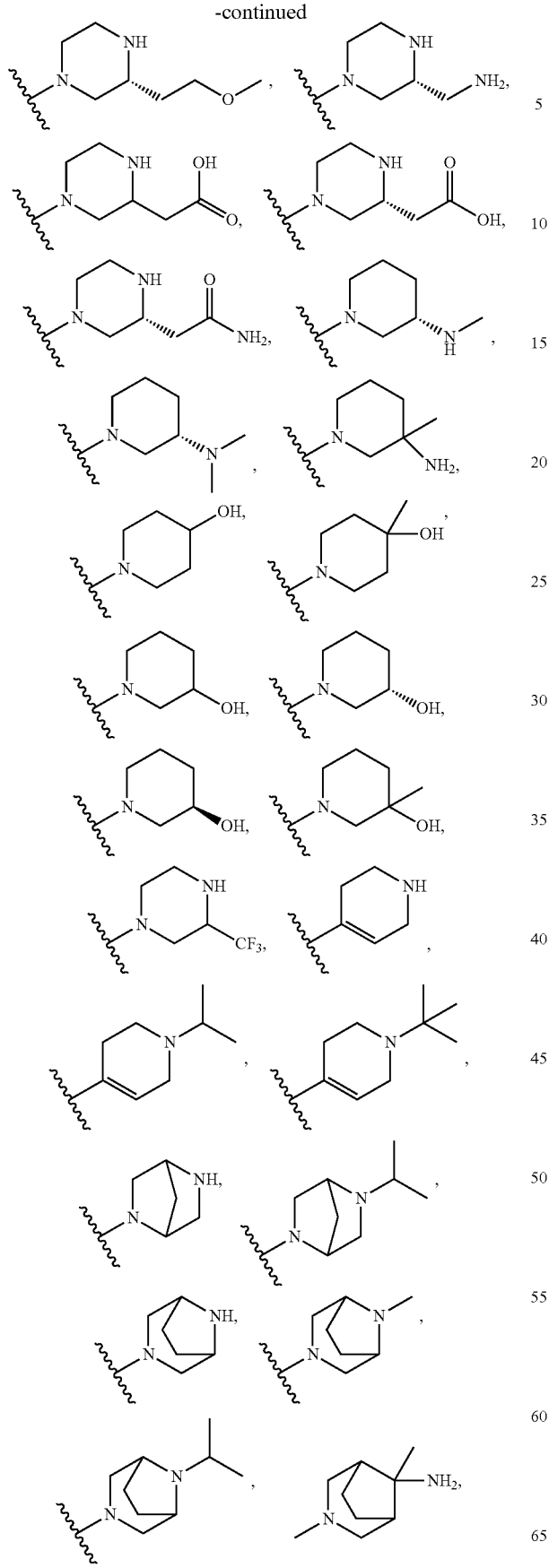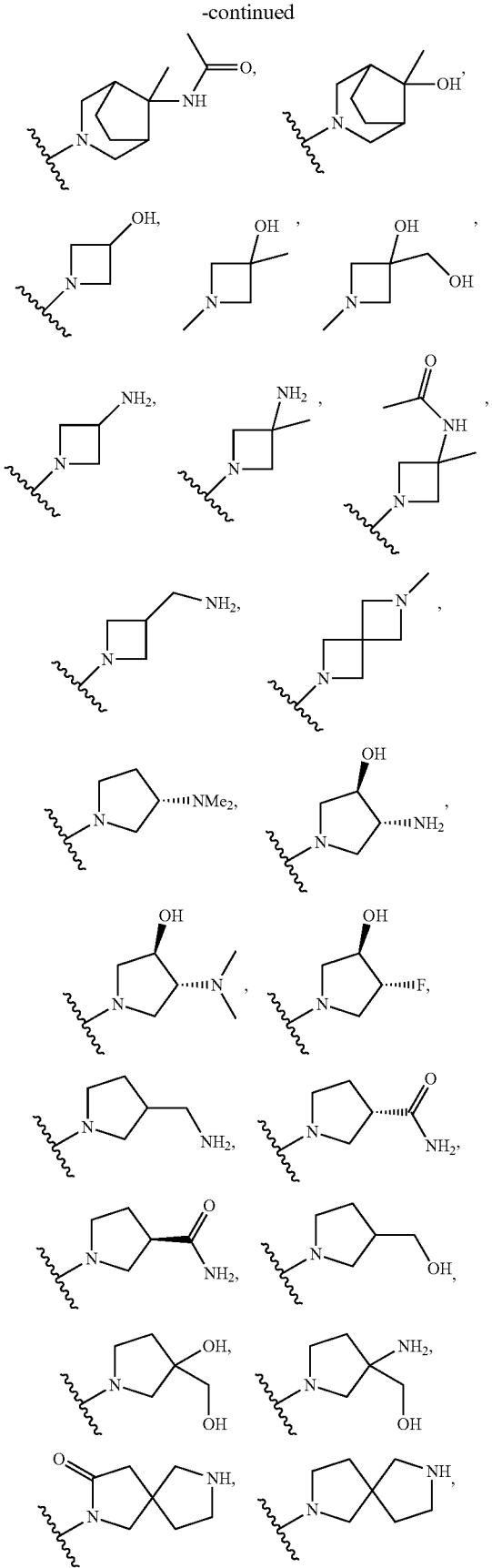

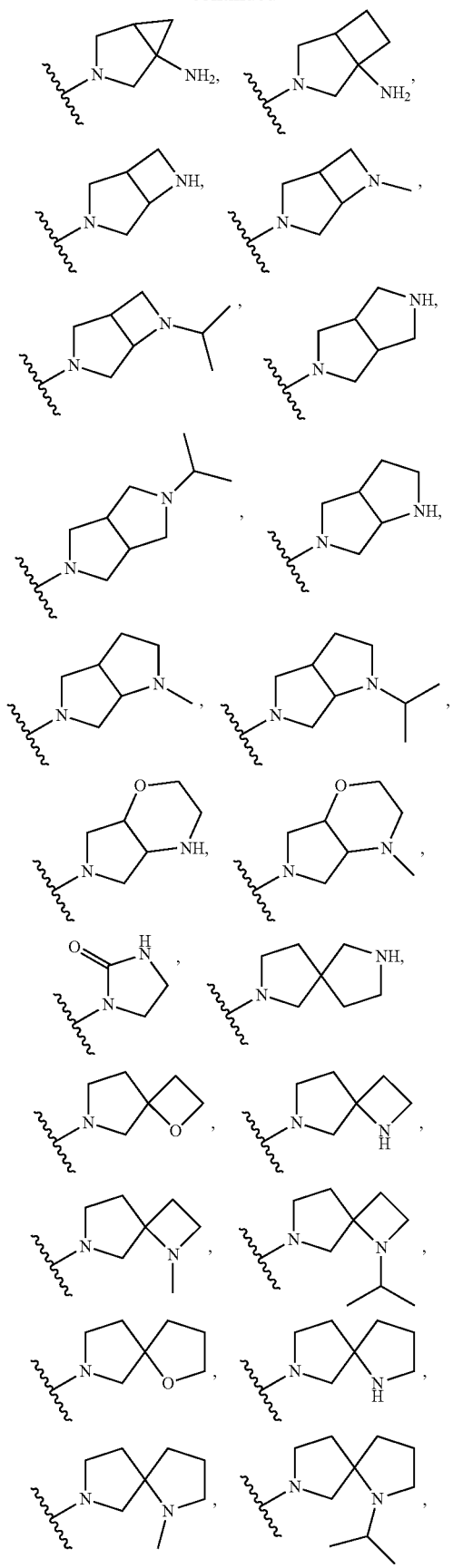
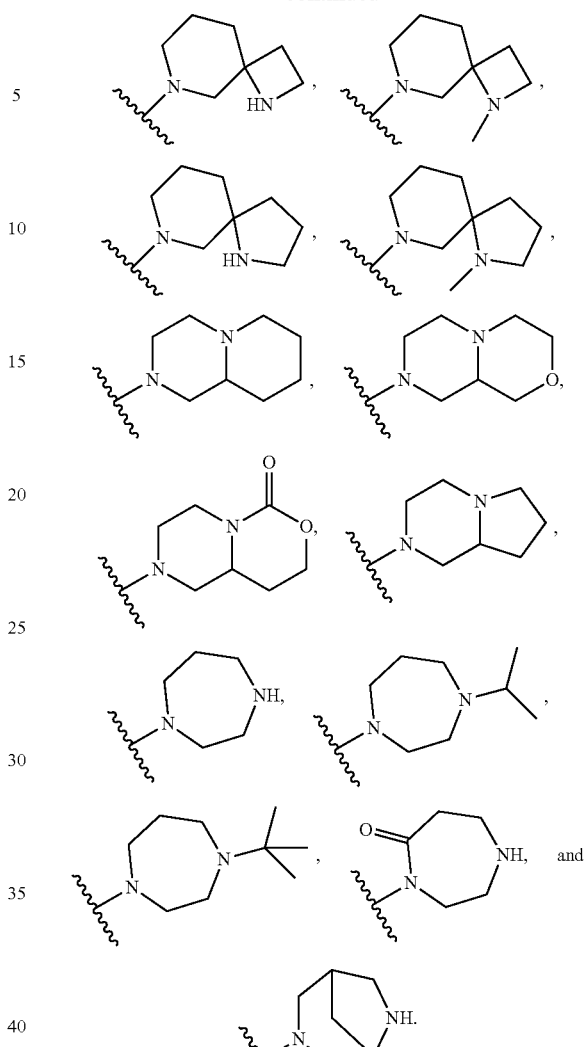
Exemplary compounds of the invention include:
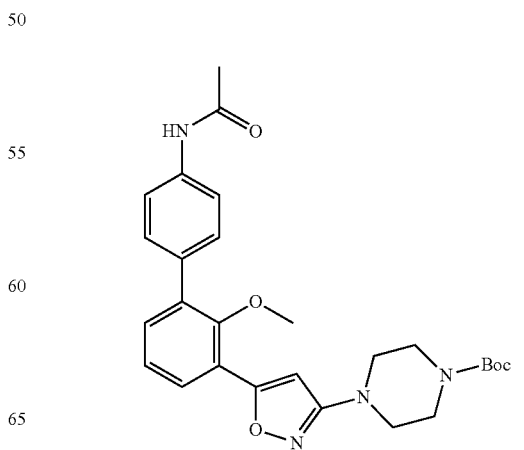

-continued
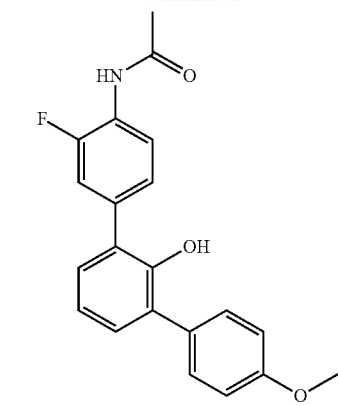
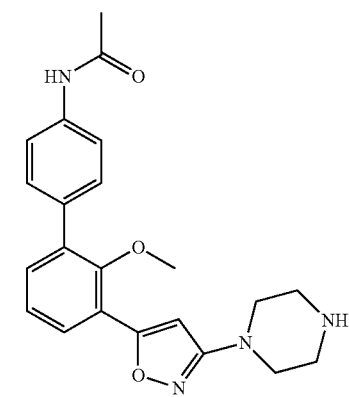
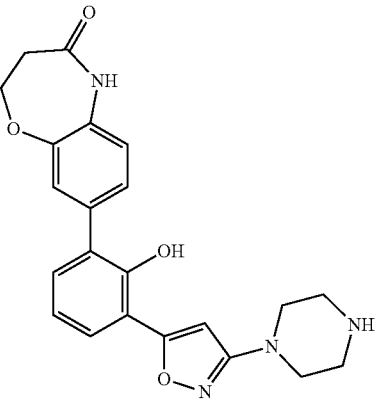
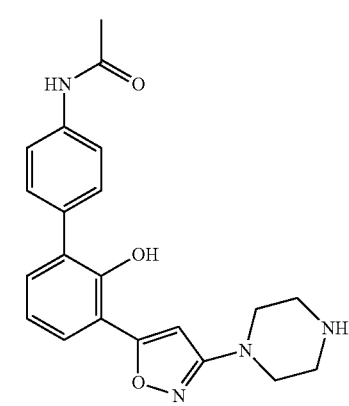
-continued
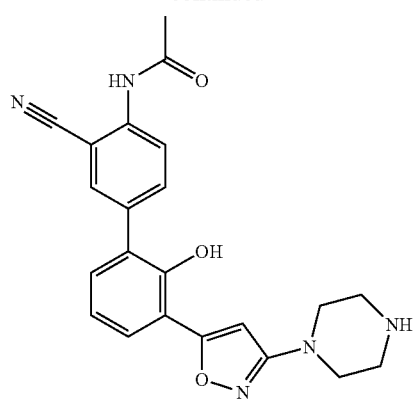
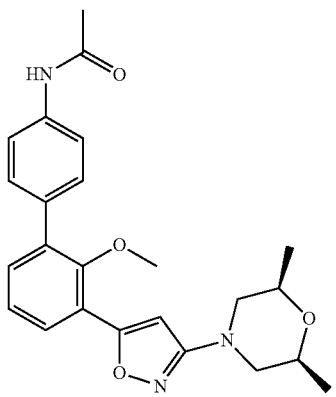
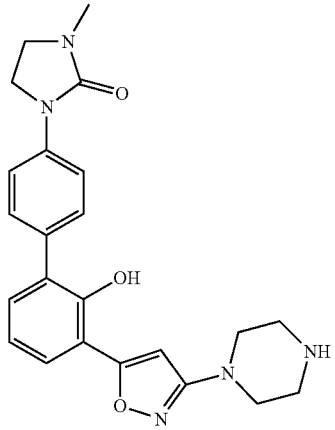
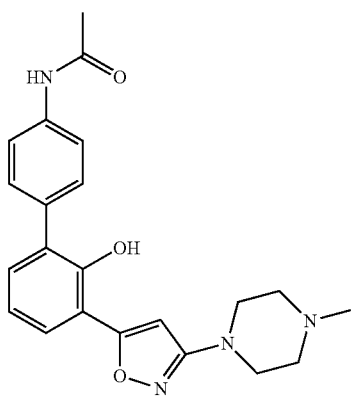

49
-continued
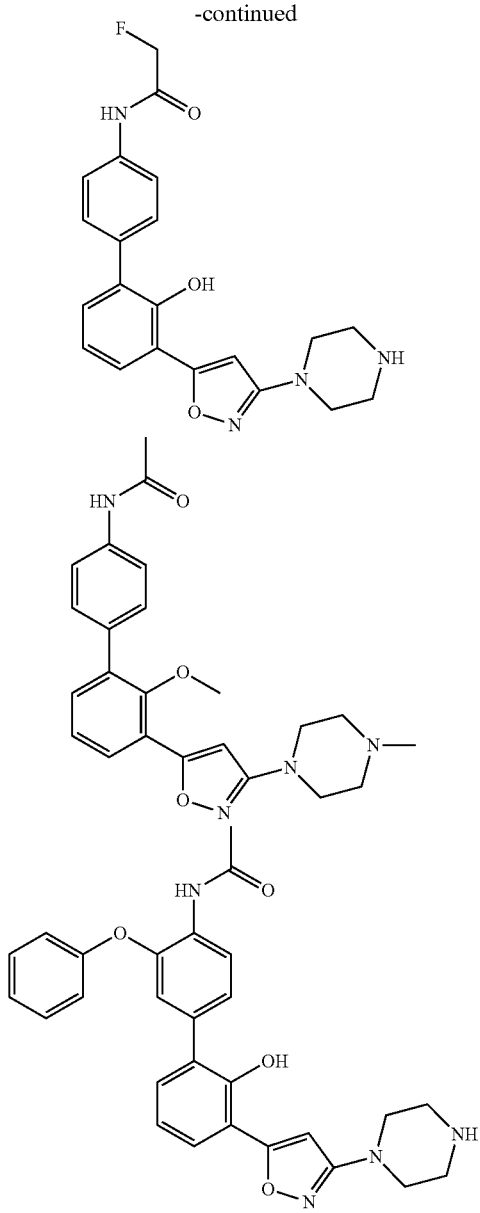
50
-continued
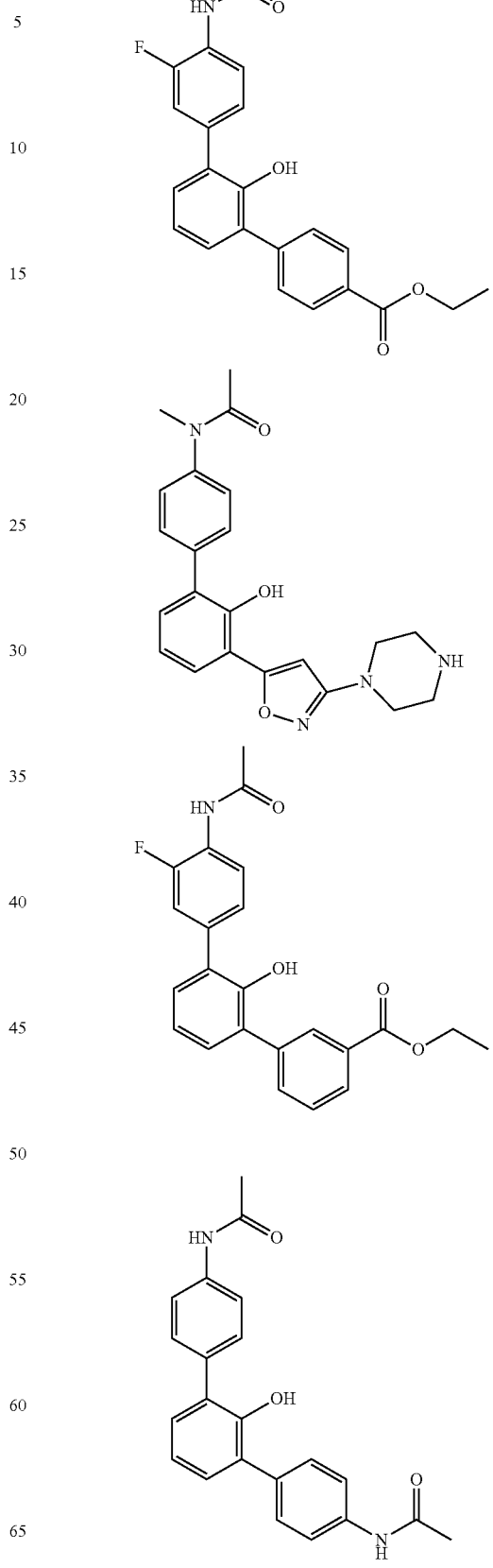

51
-continued
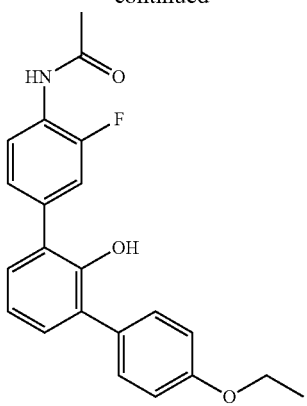
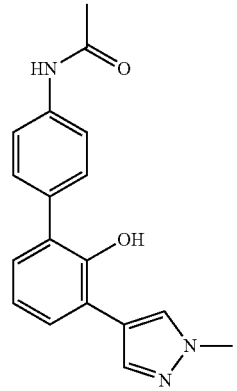
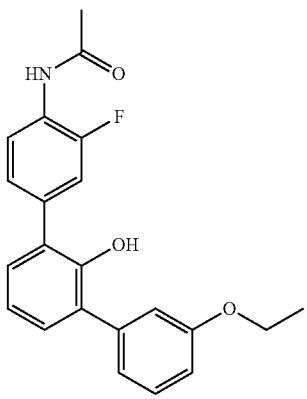
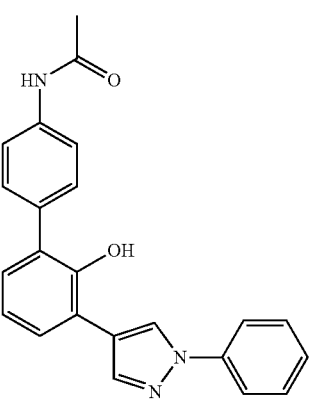
52
-continued
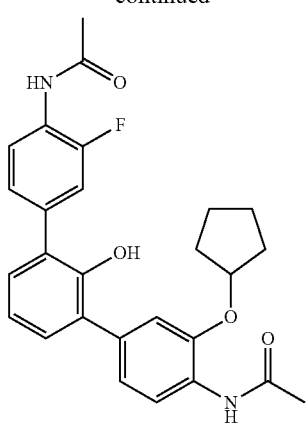
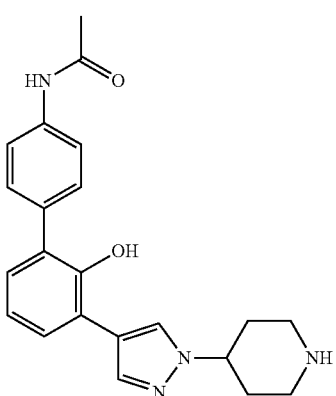
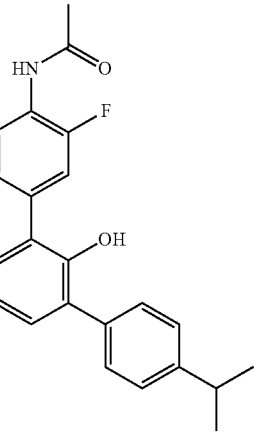
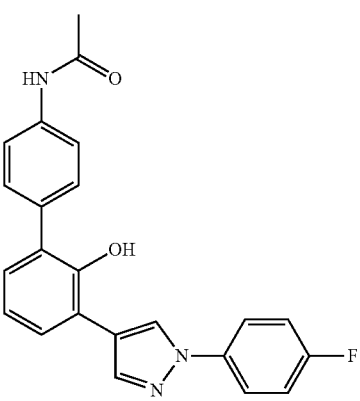

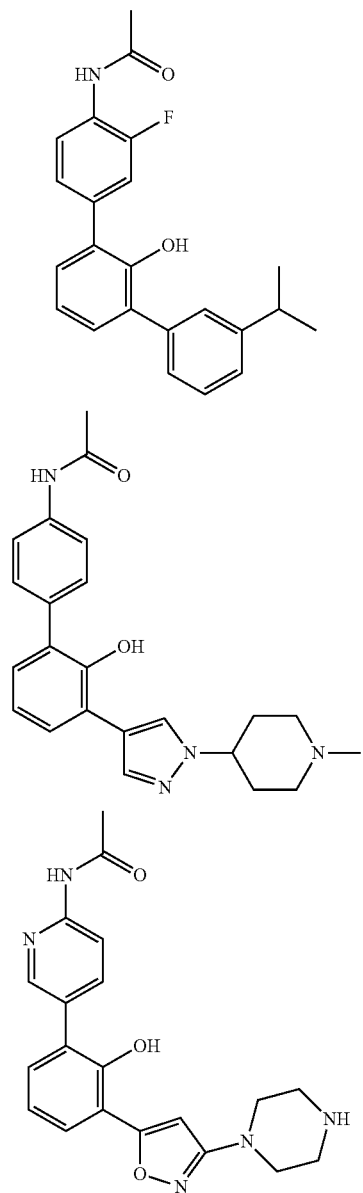
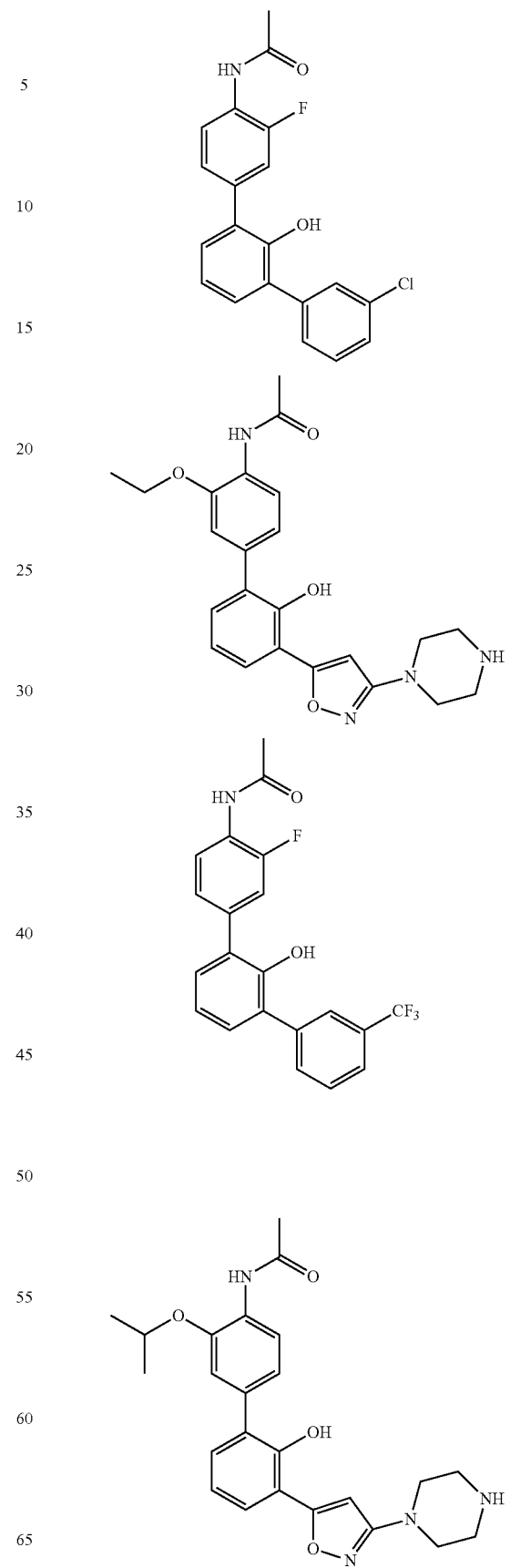

55
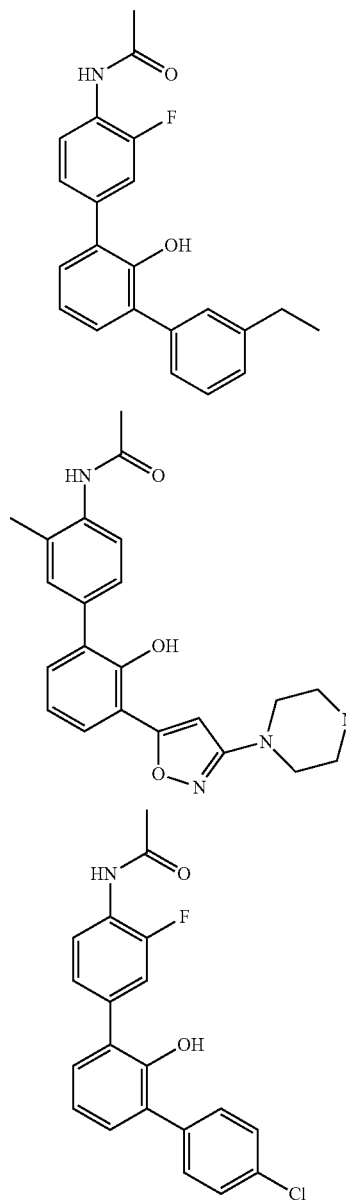
56
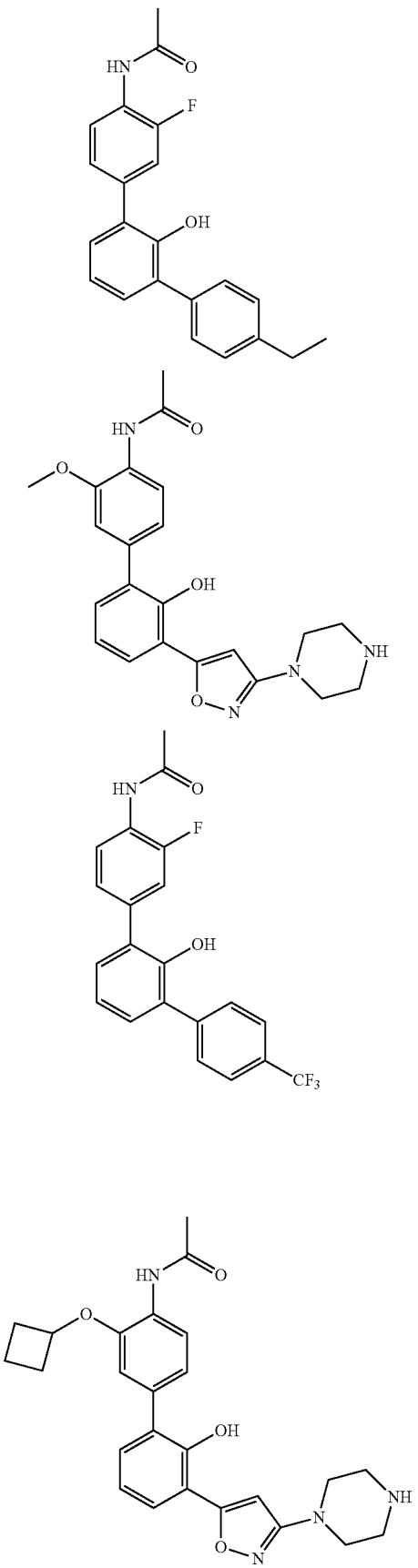

57
-continued
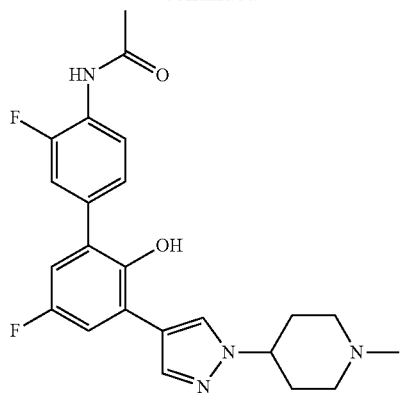
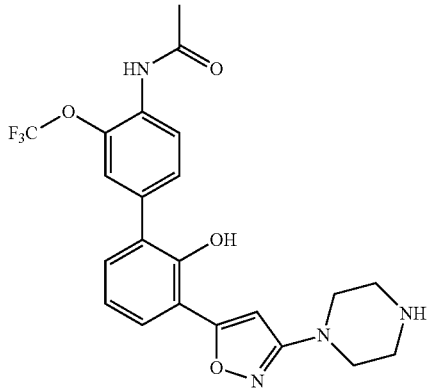
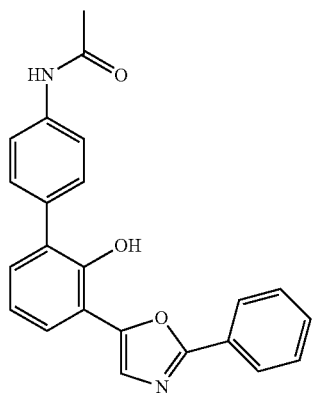
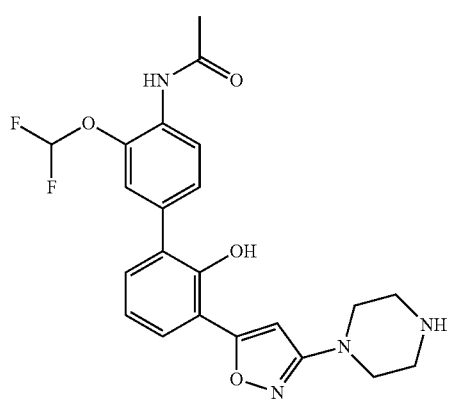
58
-continued
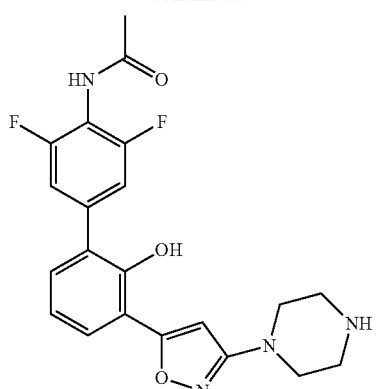
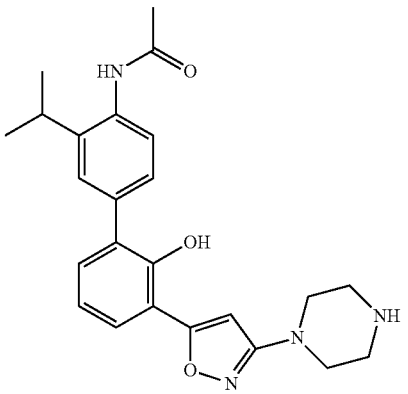
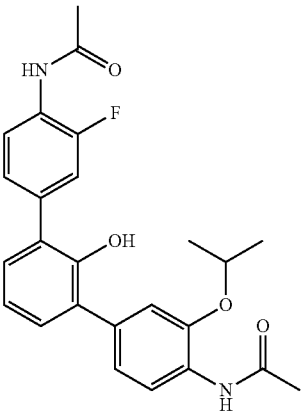
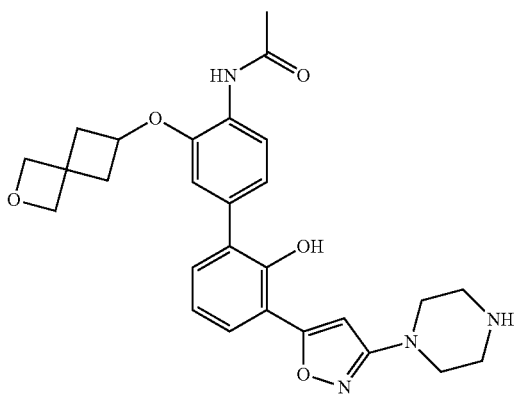

-continued
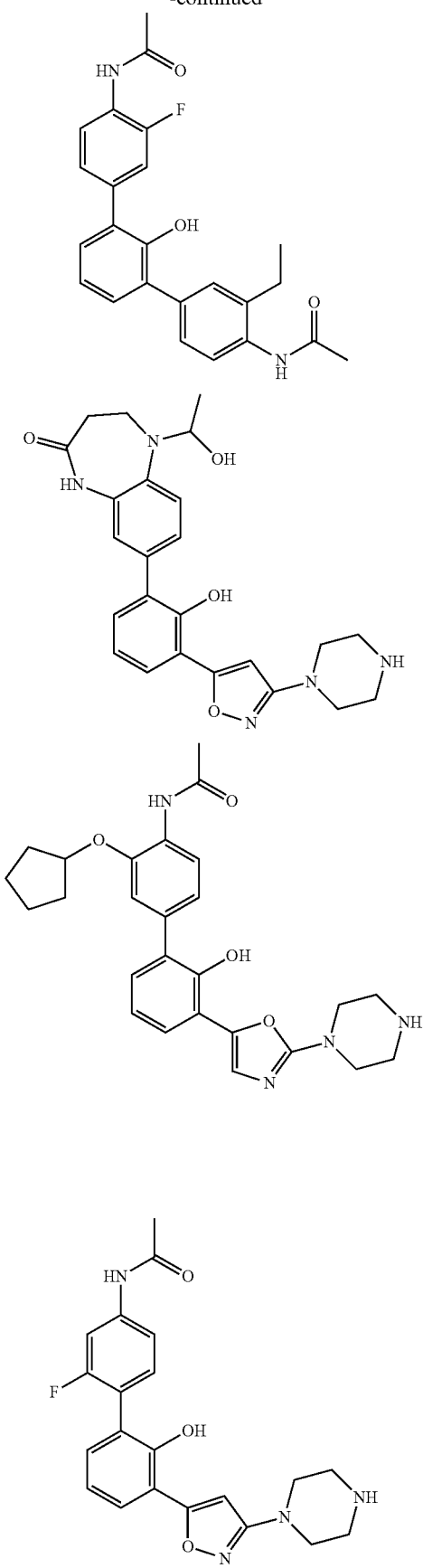
-continued
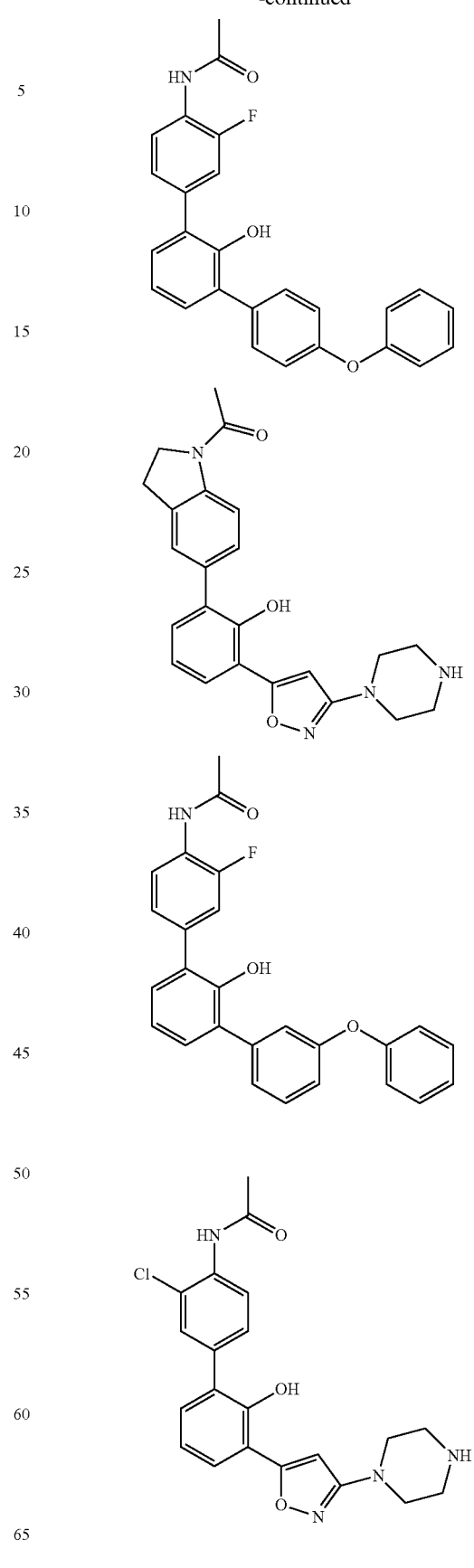

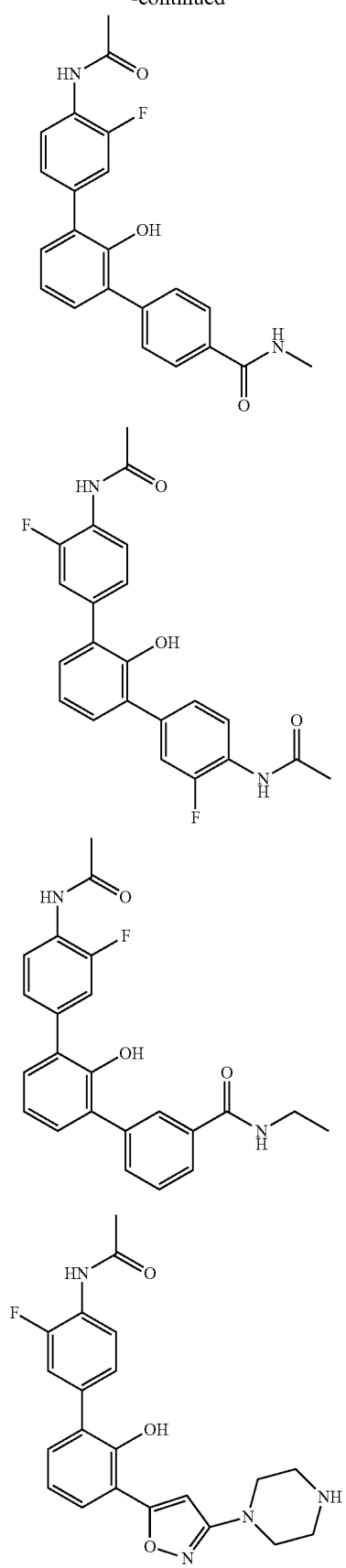
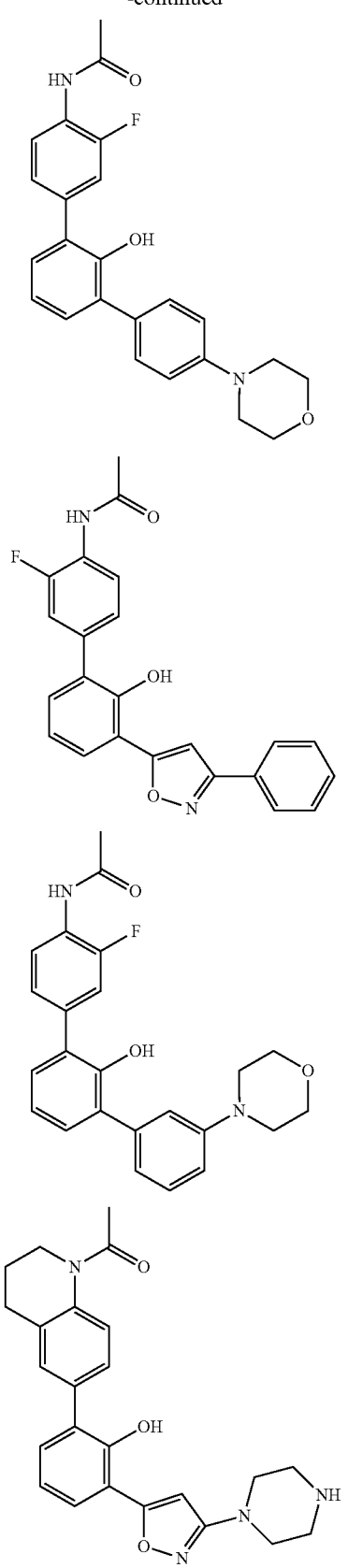

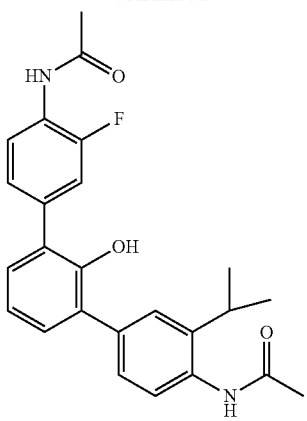
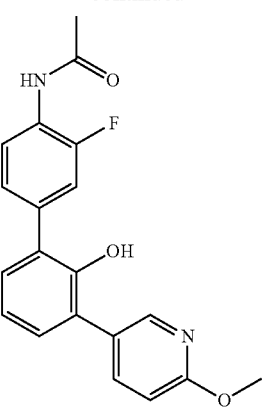
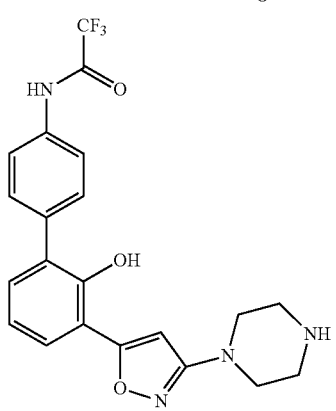
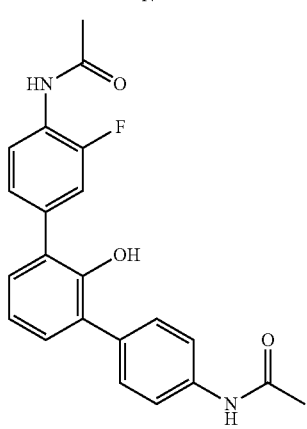
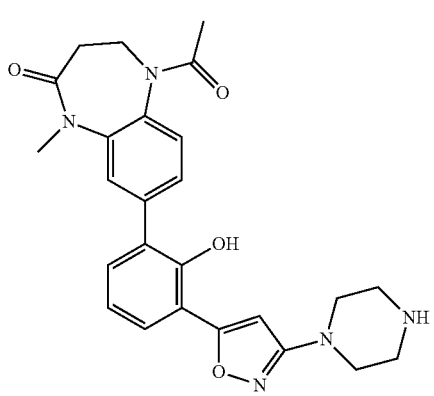
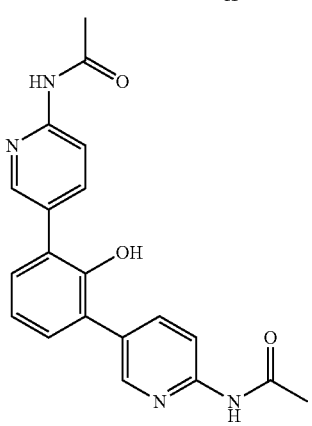

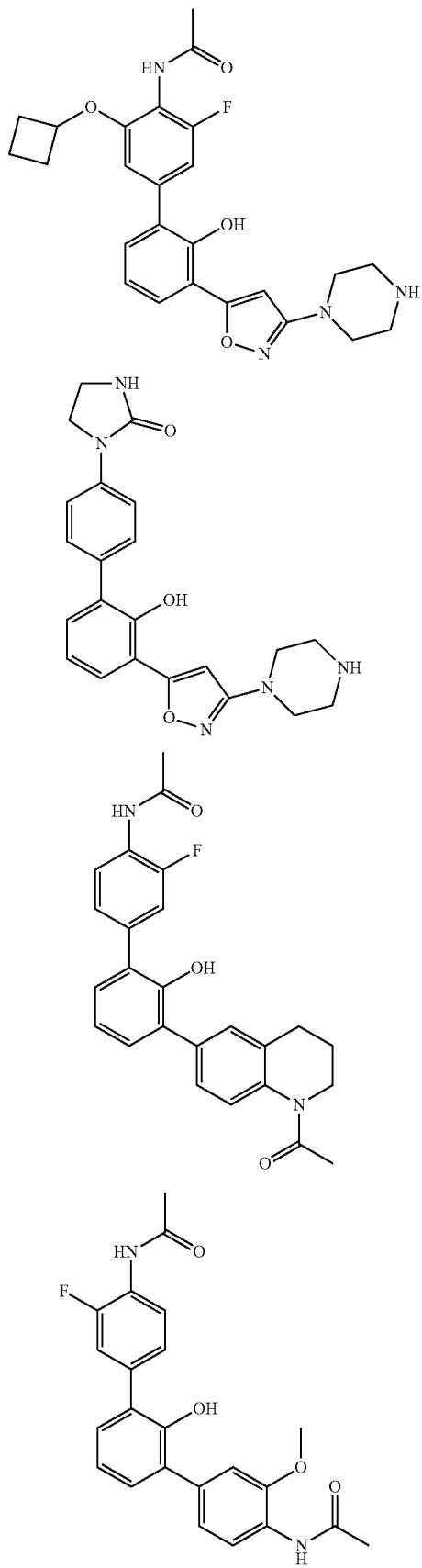
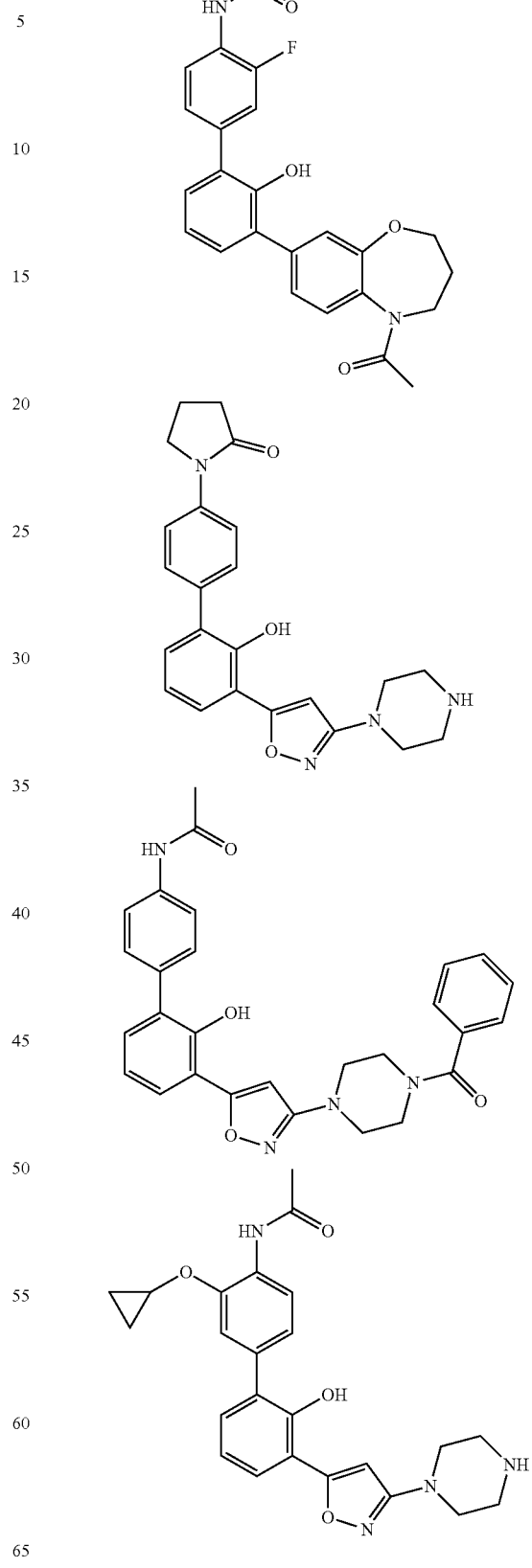

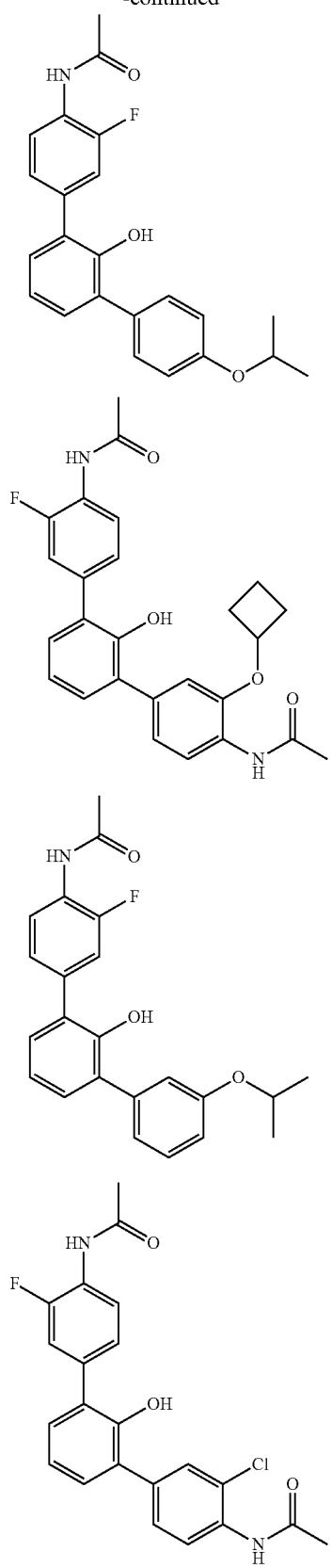
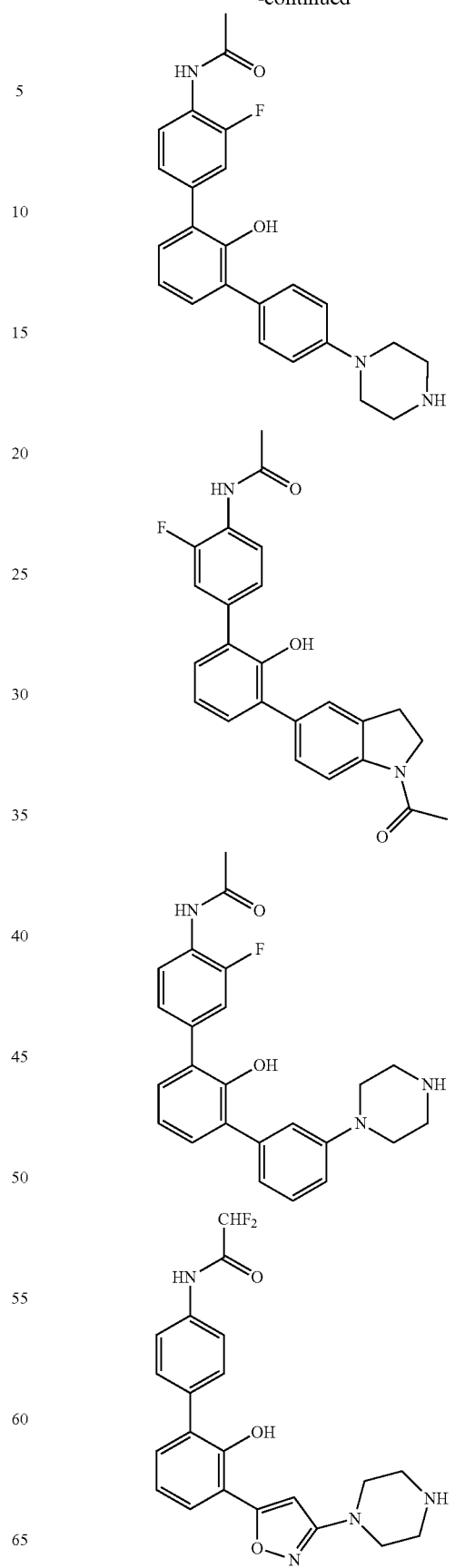

-continued
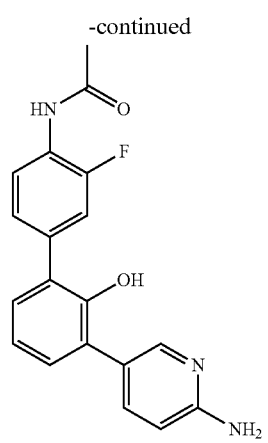
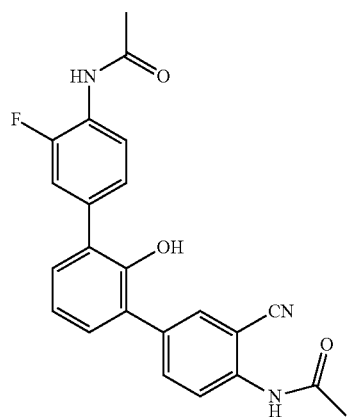
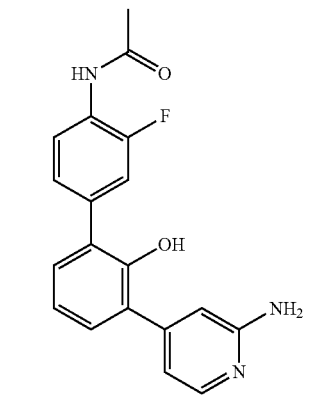
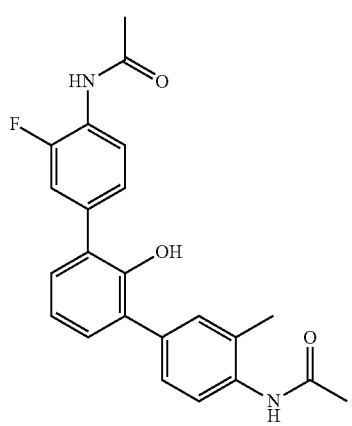
-continued
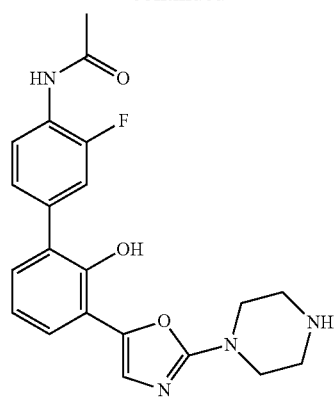
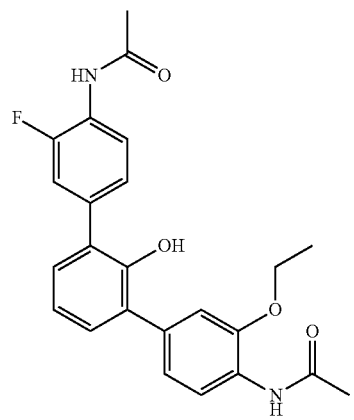
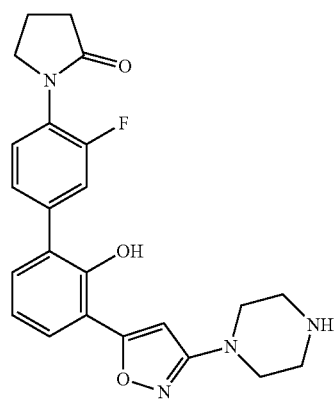
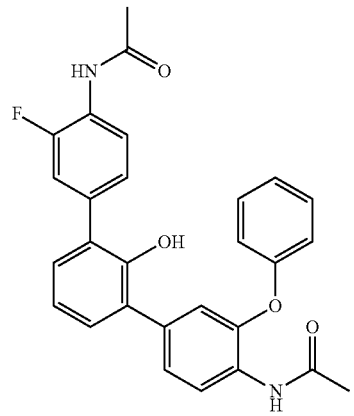

71
-continued
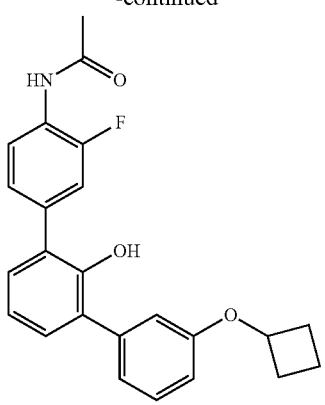
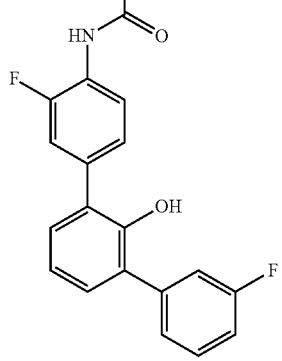
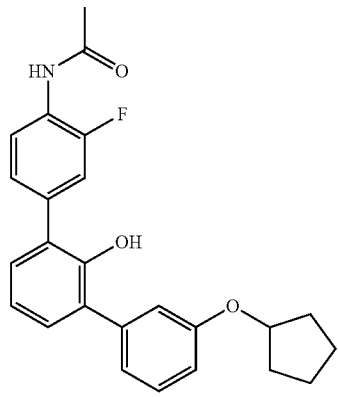
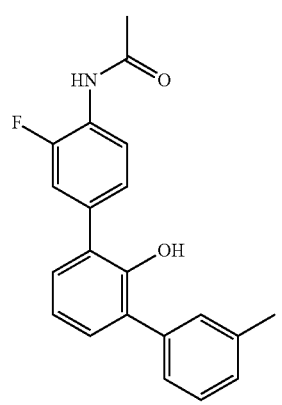
72
-continued
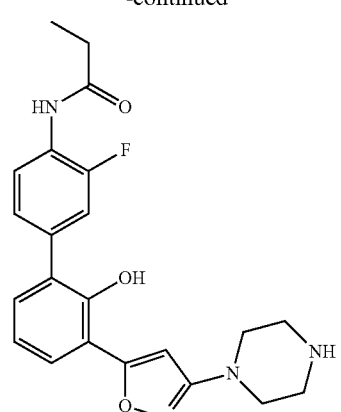
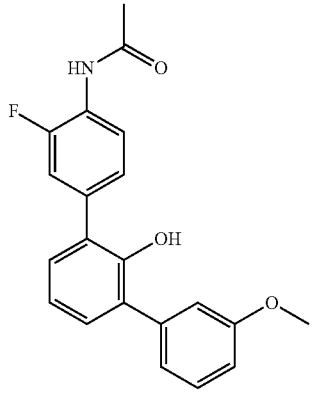
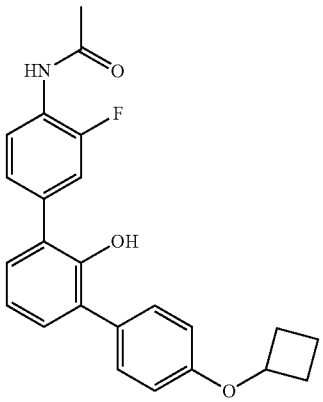
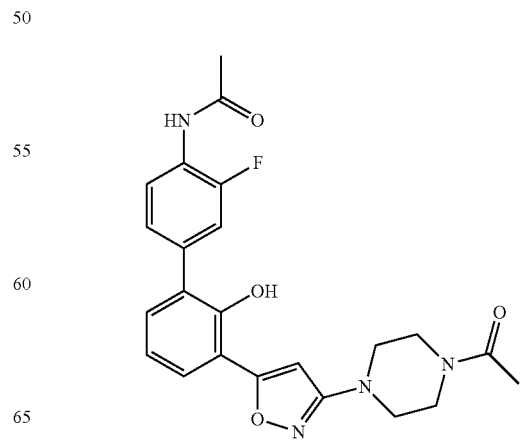

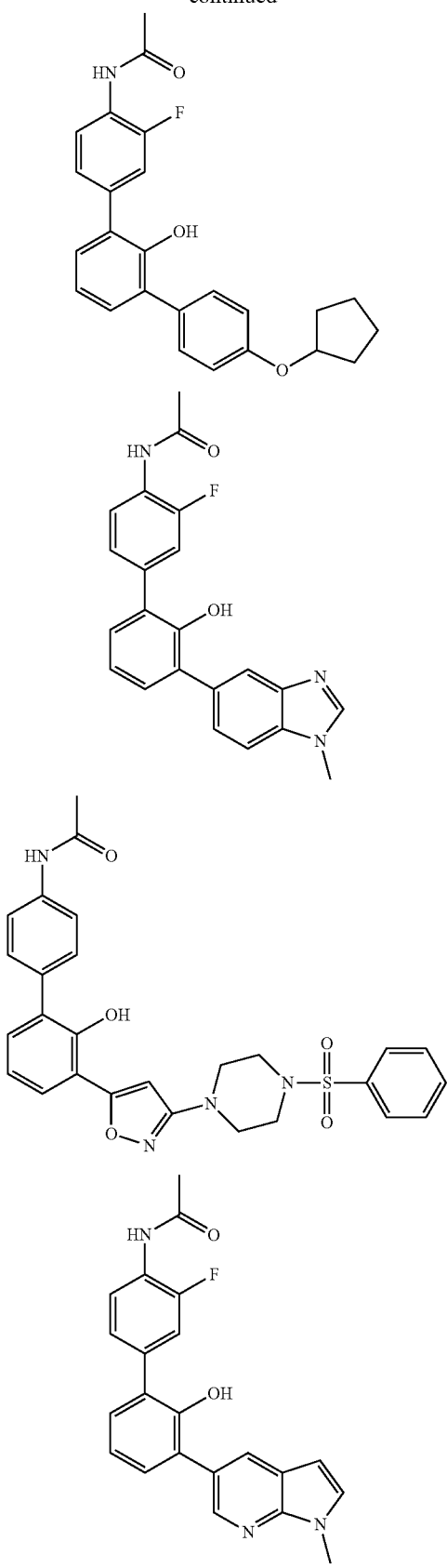
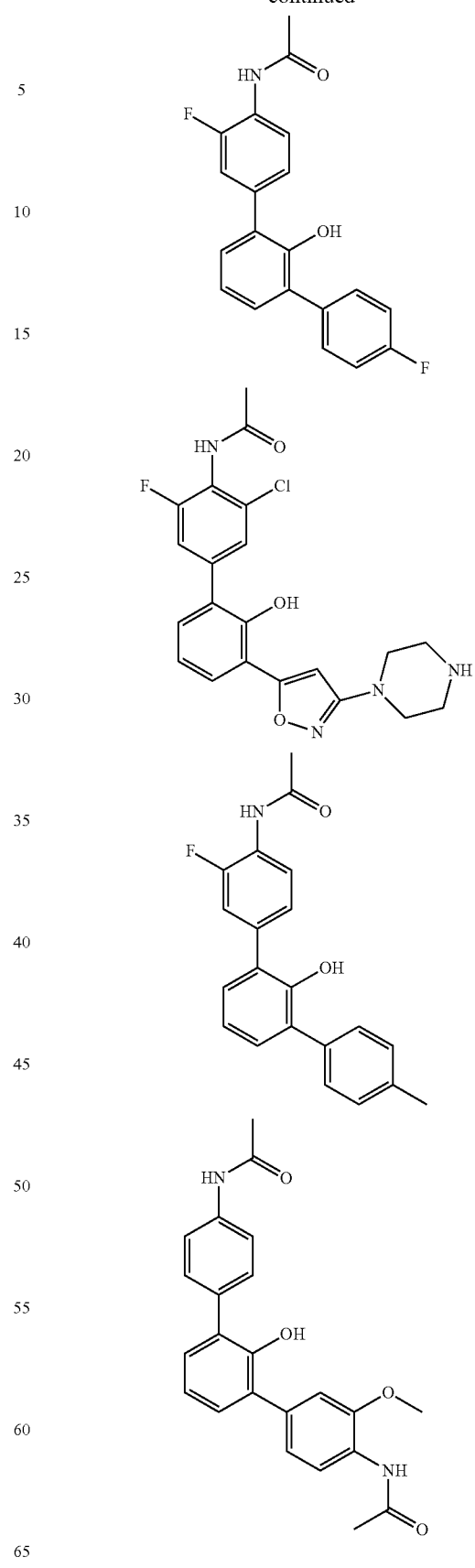

75
-continued
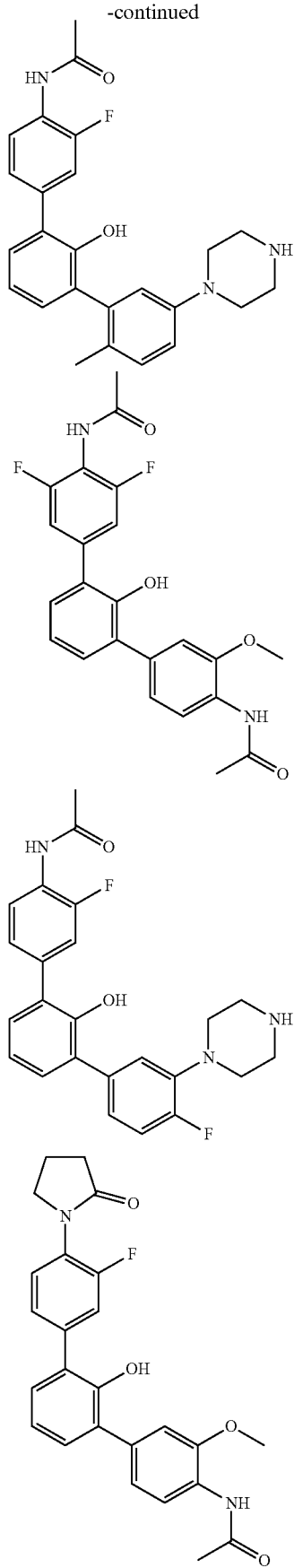
76
-continued
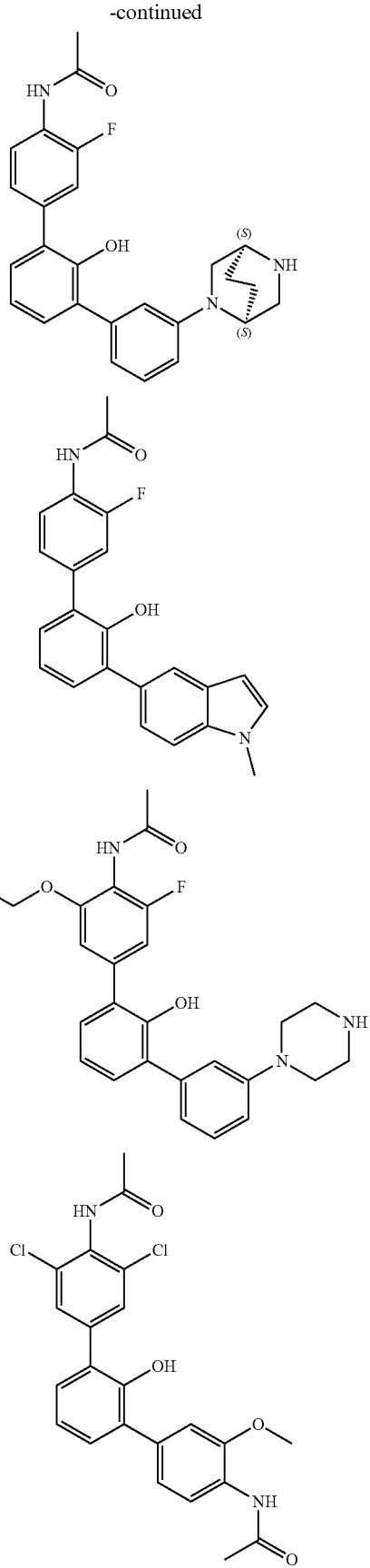

-continued
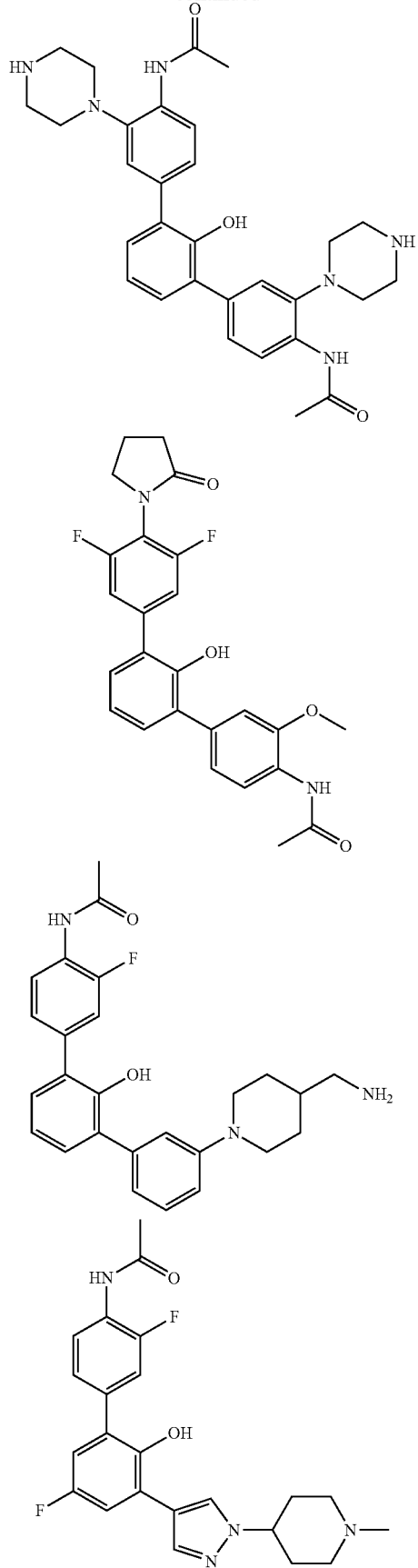
-continued
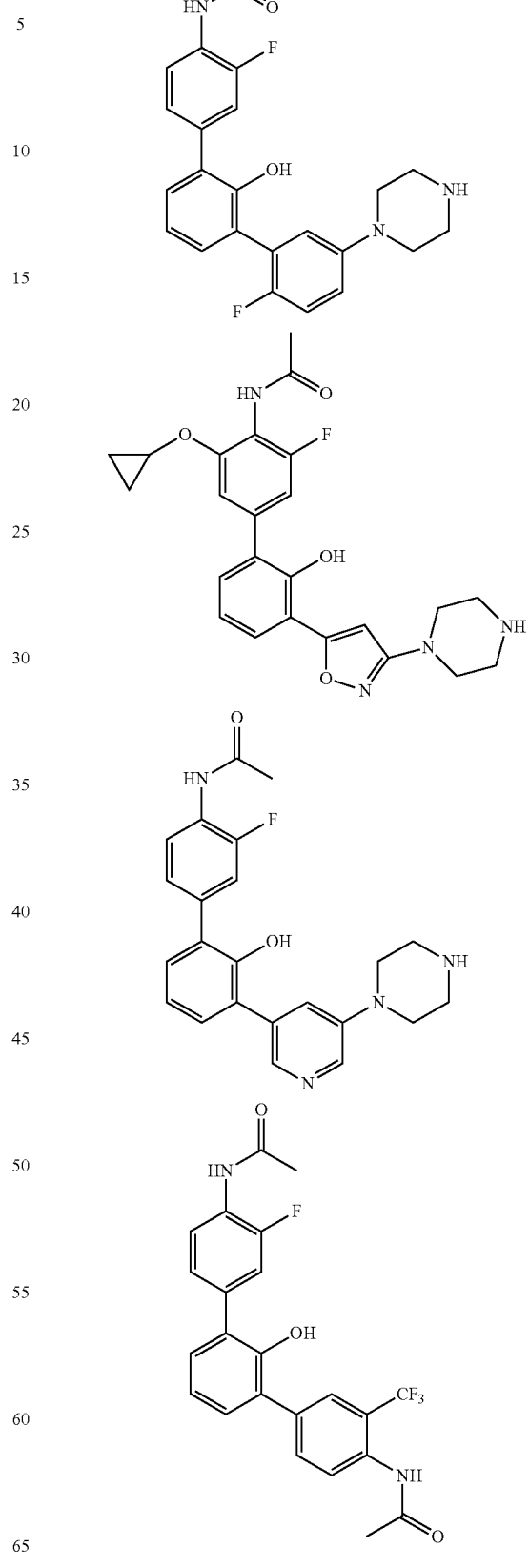

79
-continued
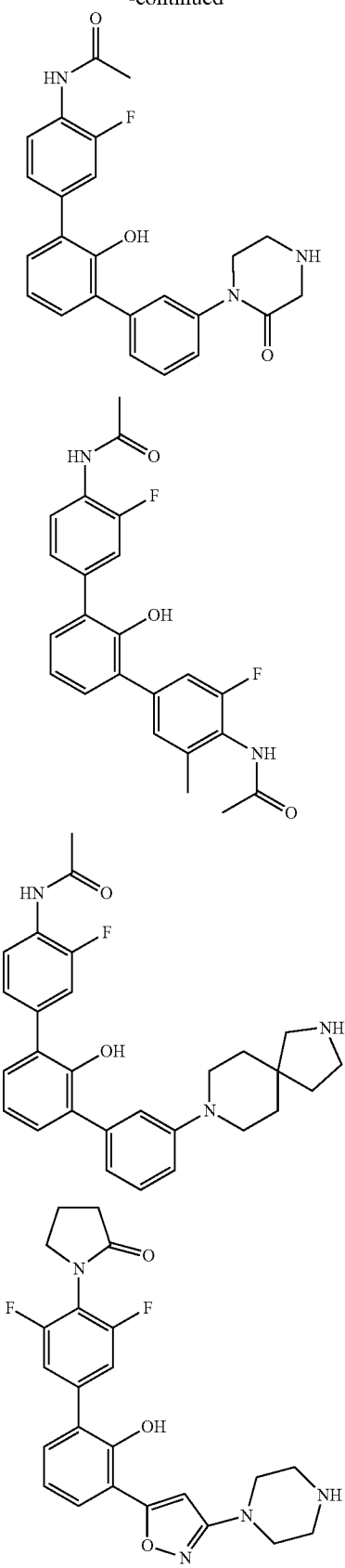
80
-continued
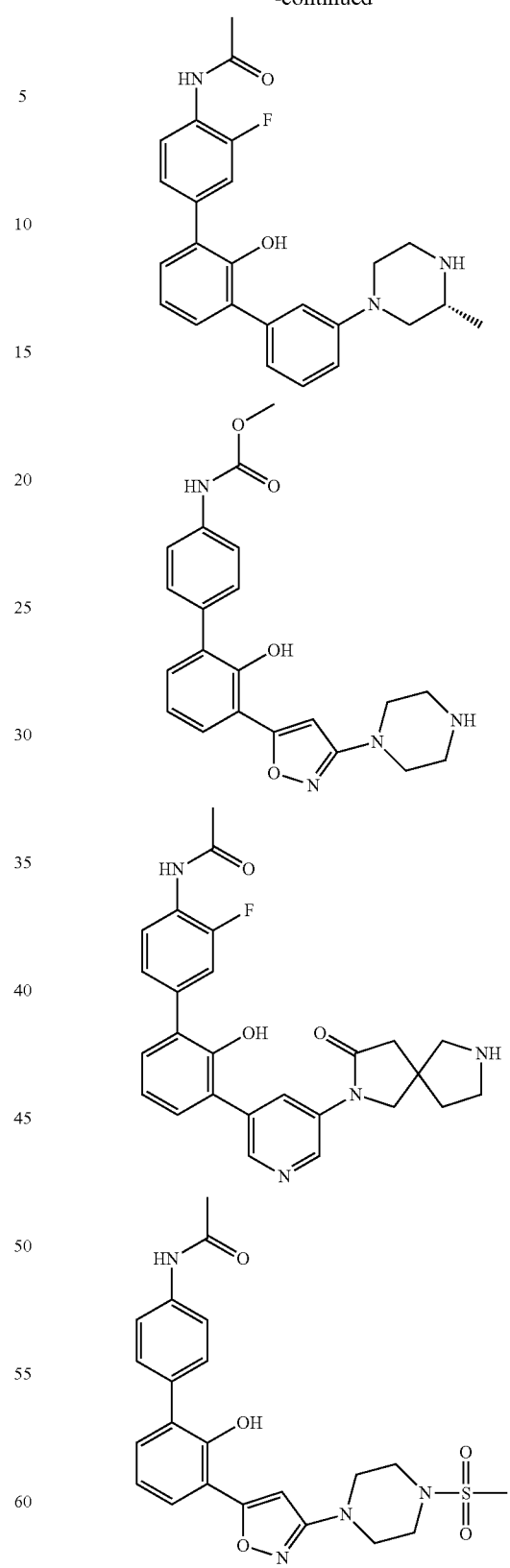

-continued
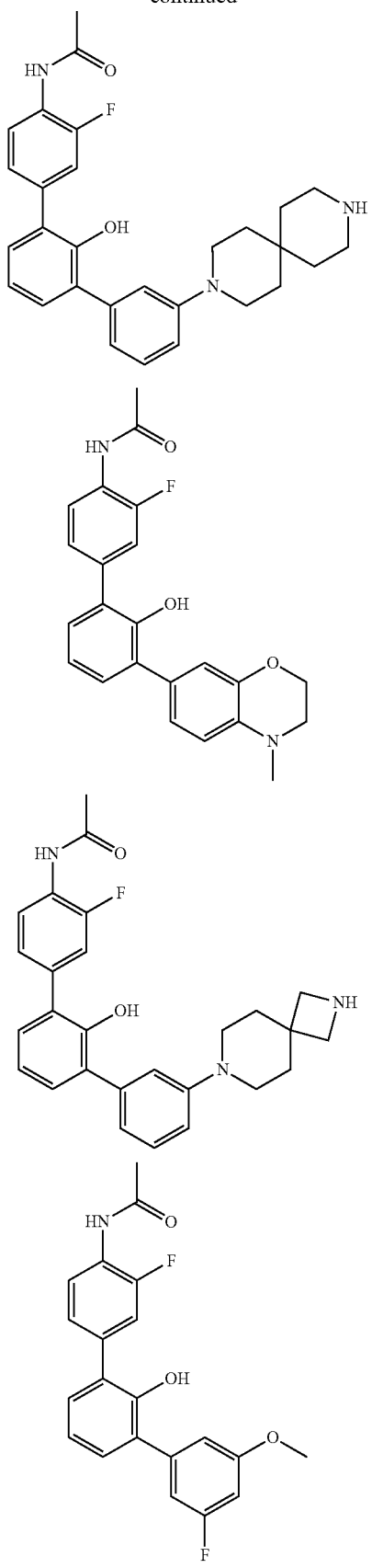
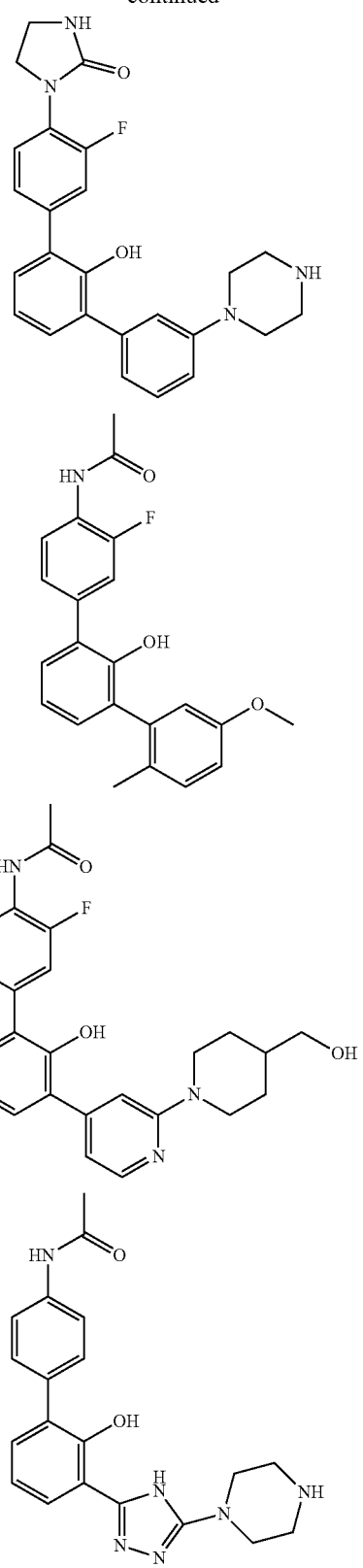

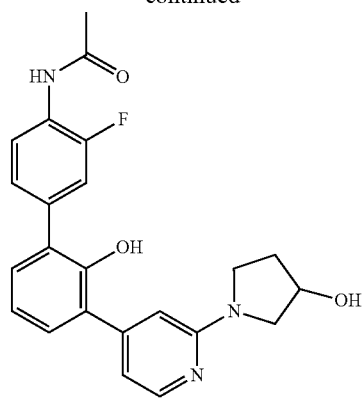
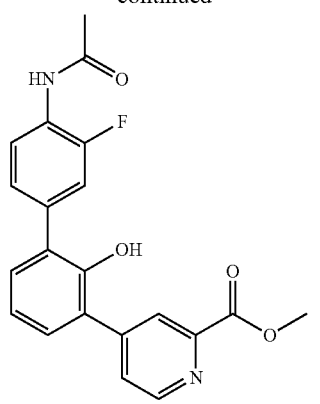
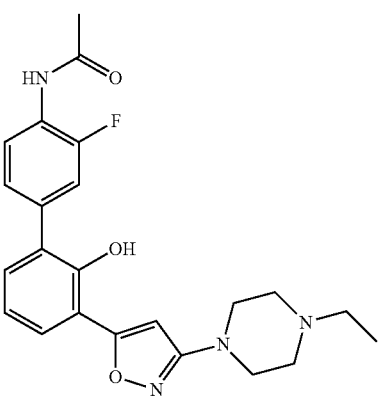
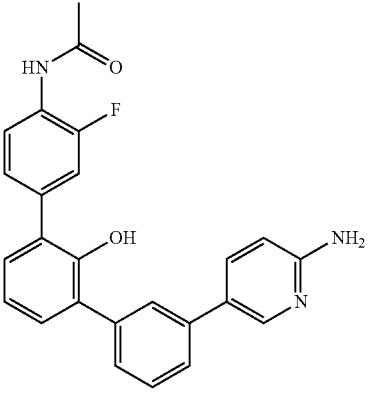
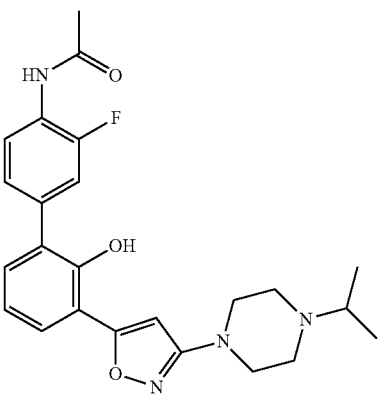

85
-continued
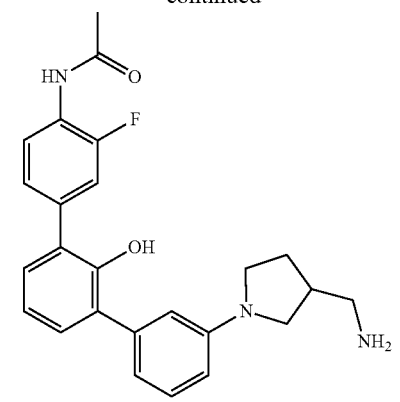
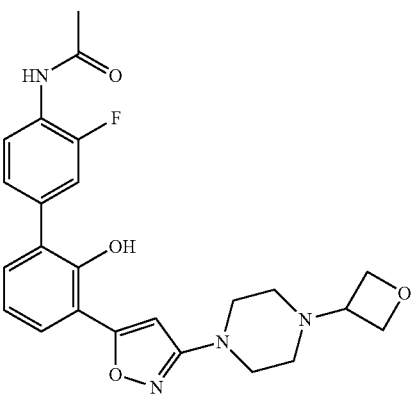
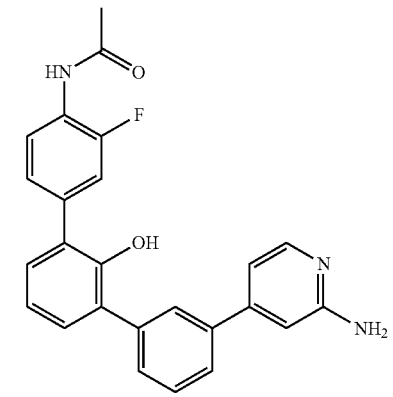
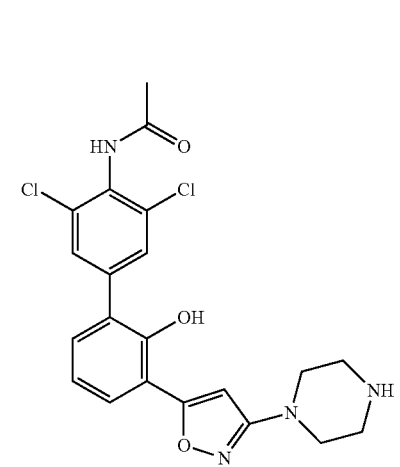
86
-continued
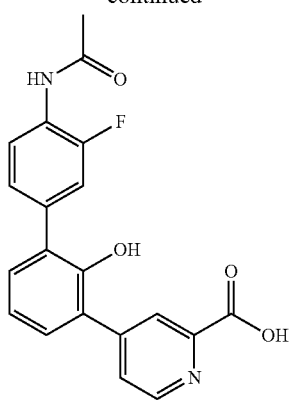
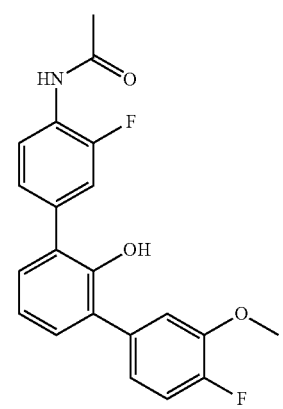
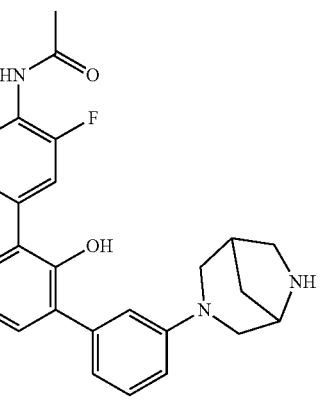
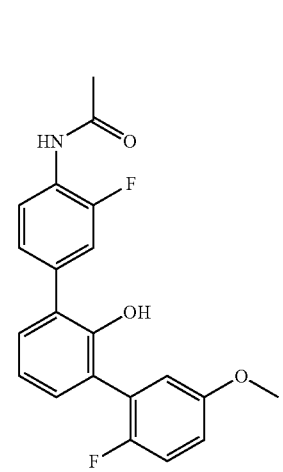

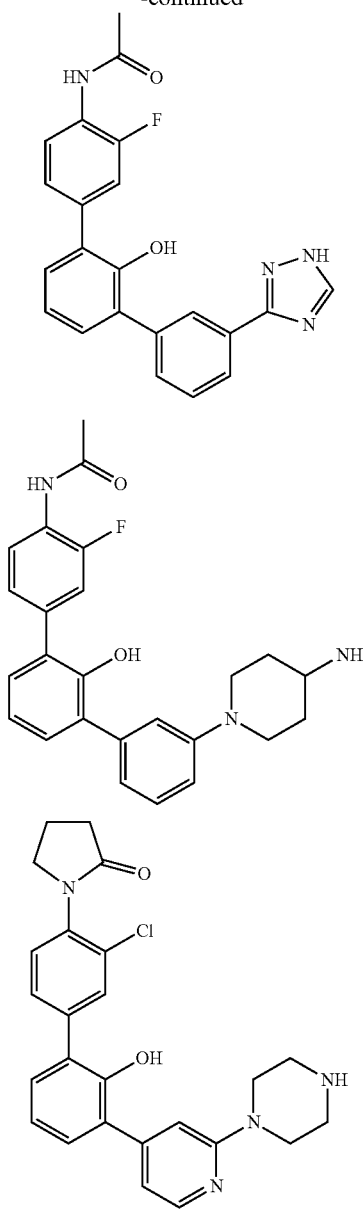
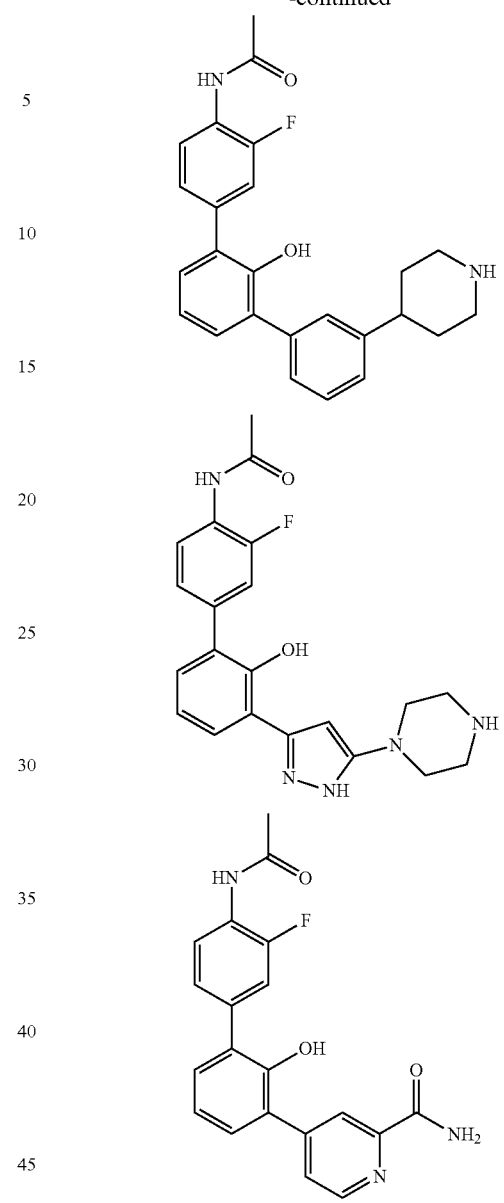
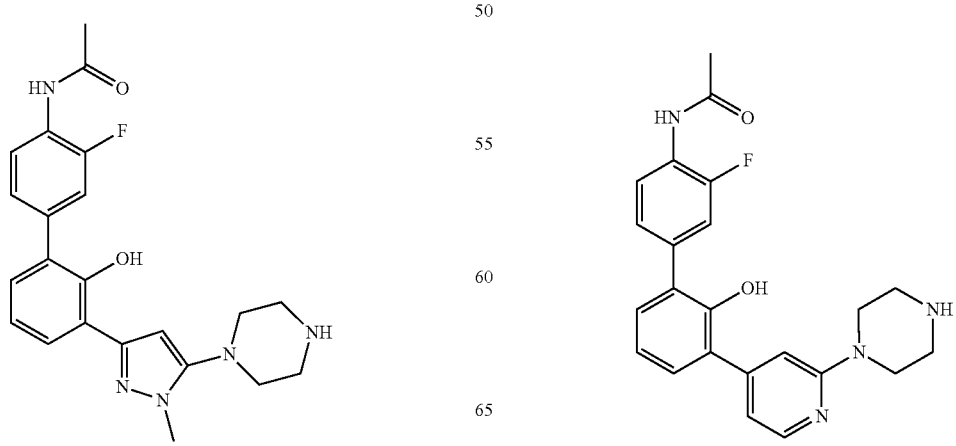

-continued
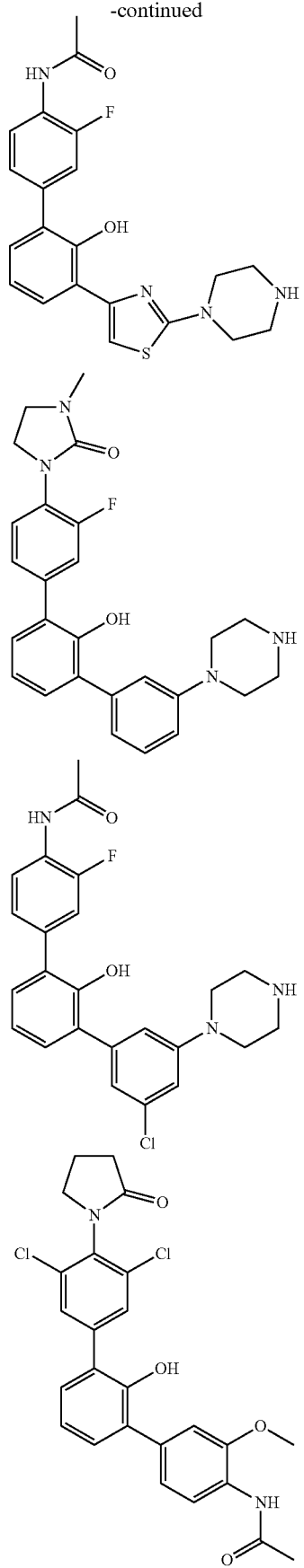
-continued
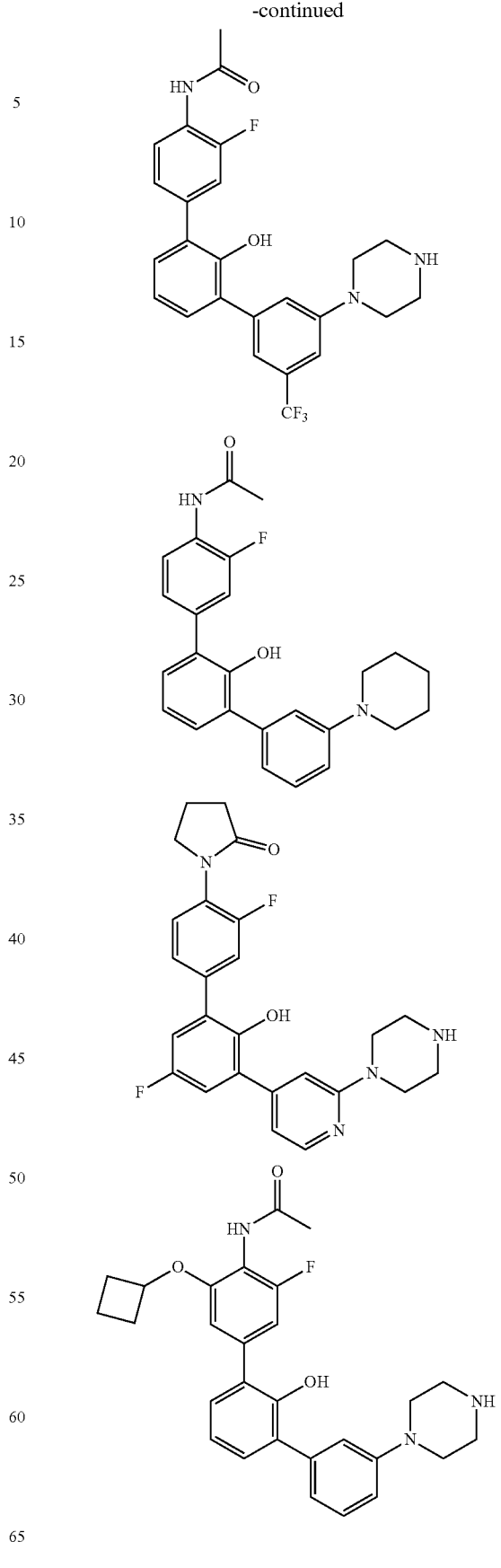

91
-continued
92
-continued
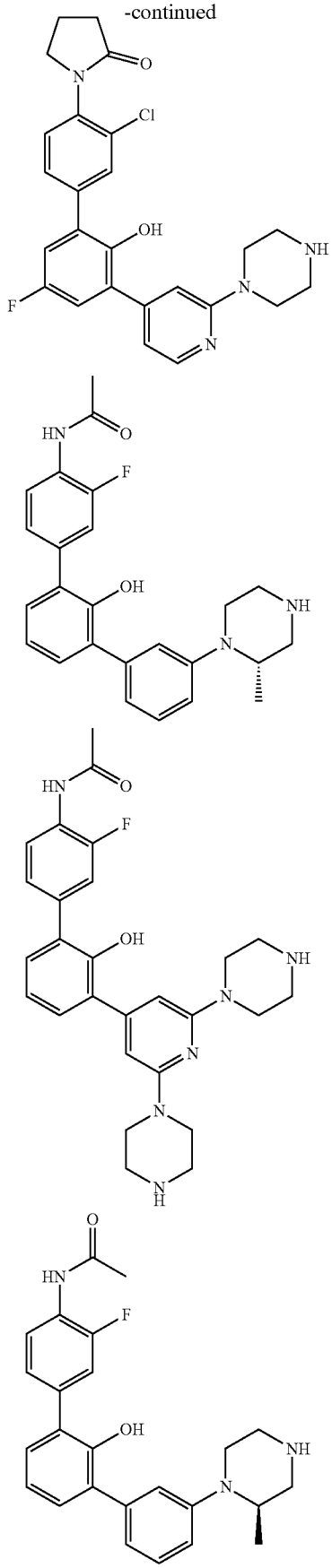
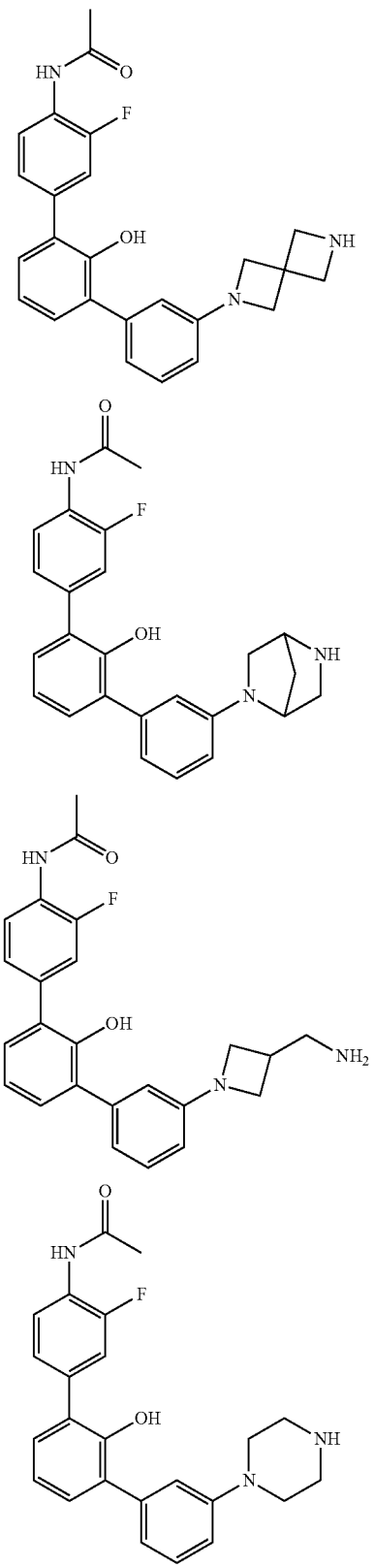

-continued
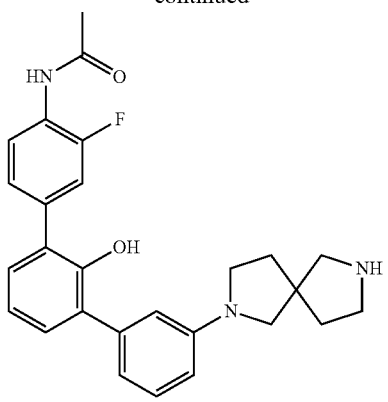
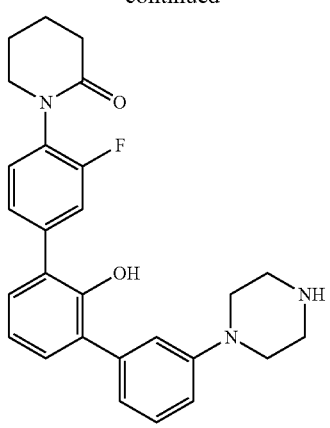
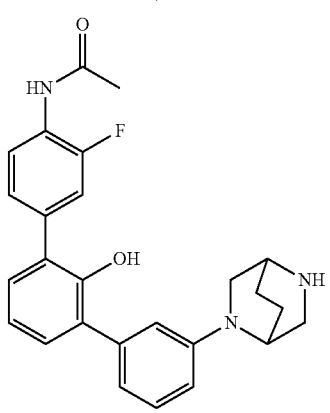
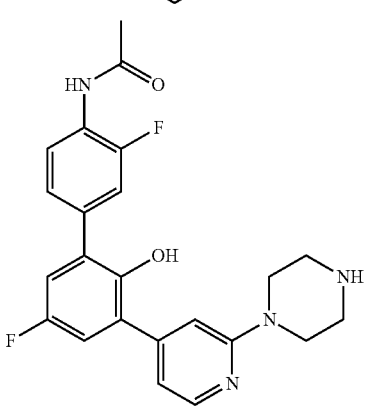
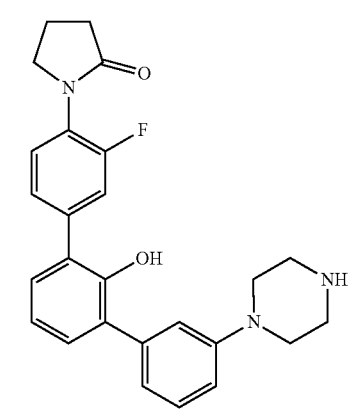
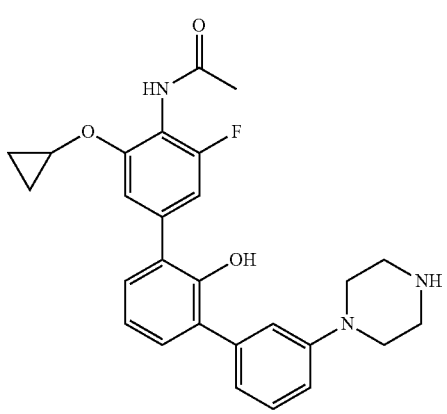

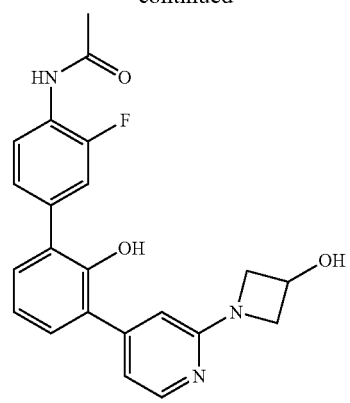
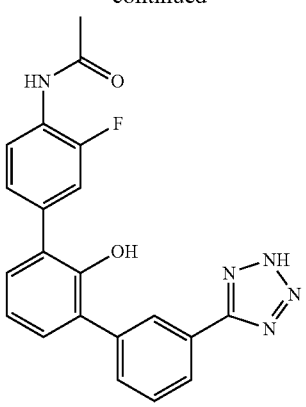
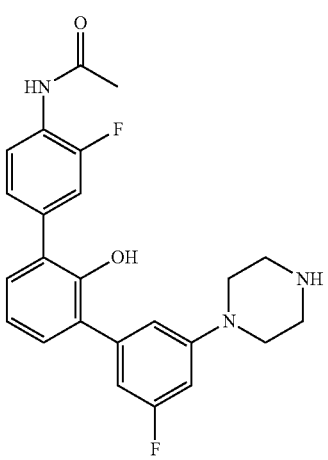
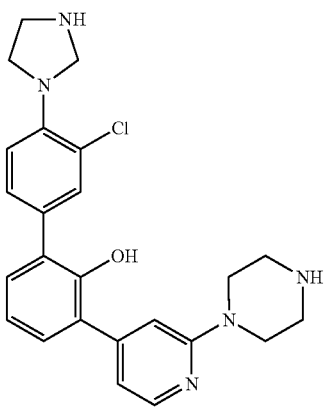
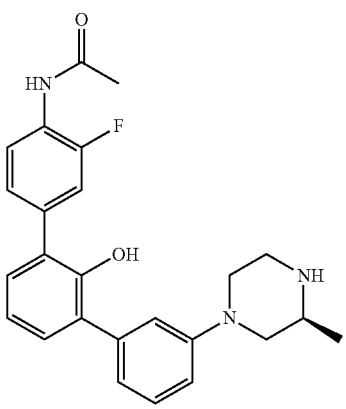

-continued
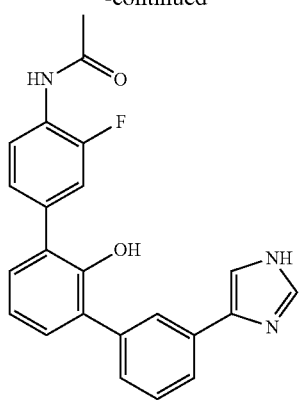
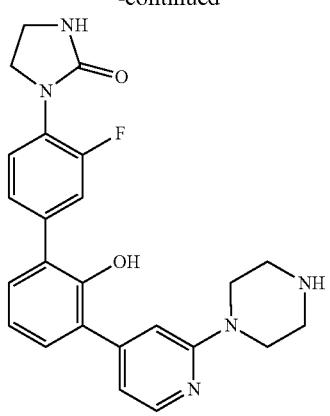
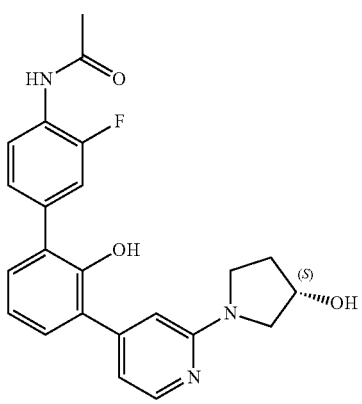
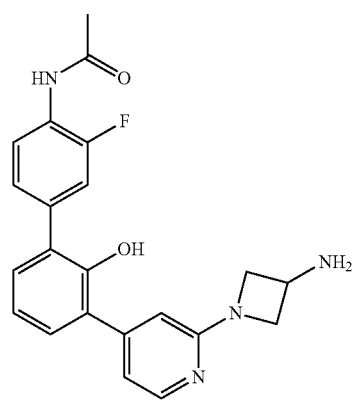
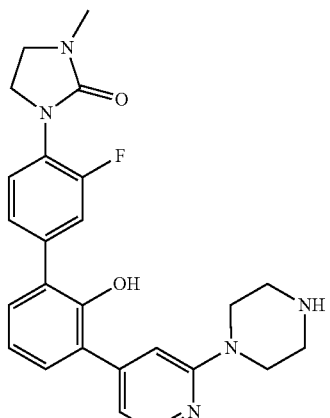

99                                                 100
-continued                                    -continued
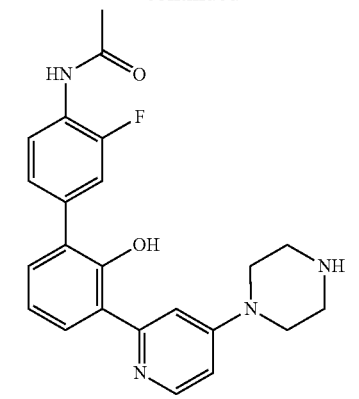
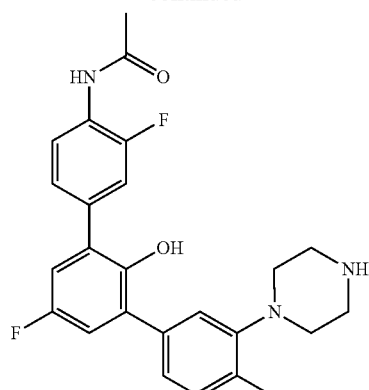
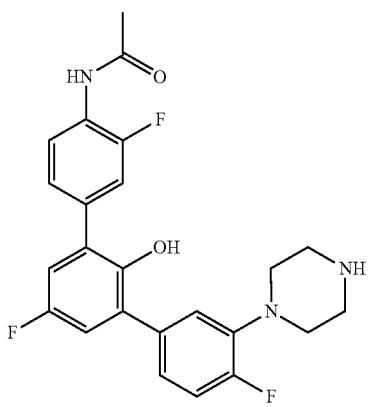
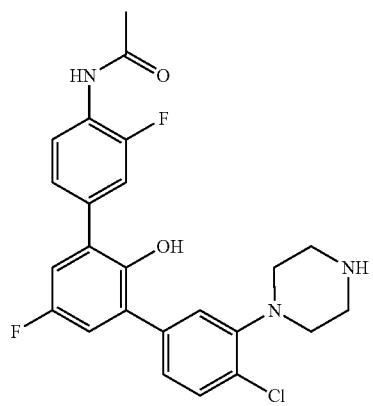
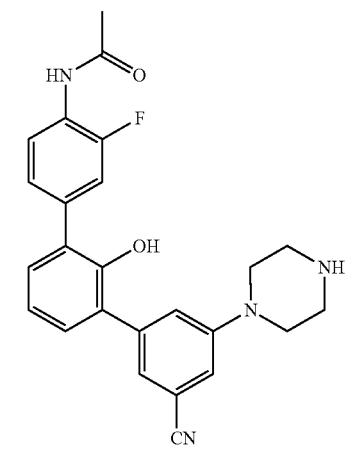
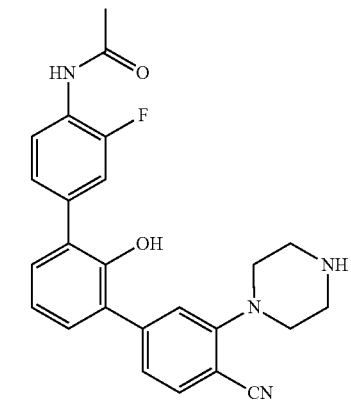
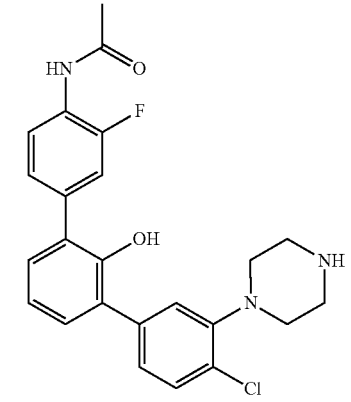
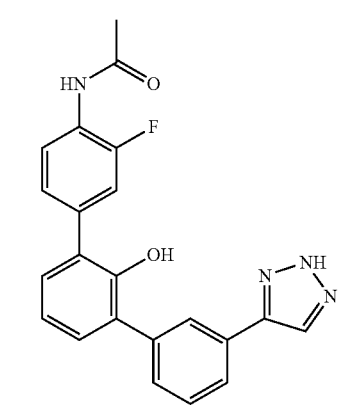

-continued
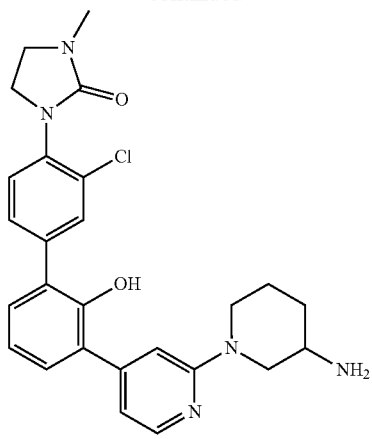
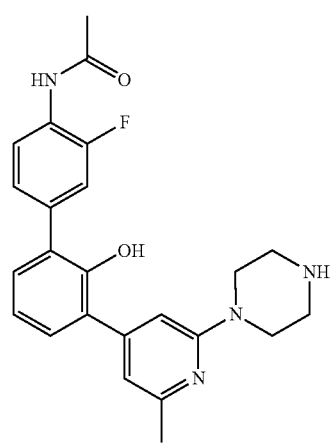
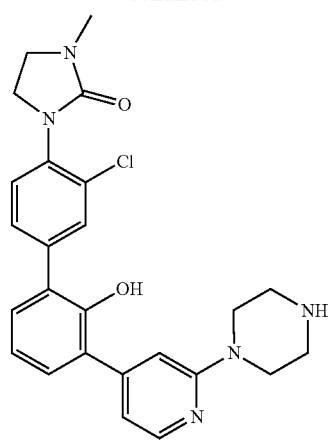
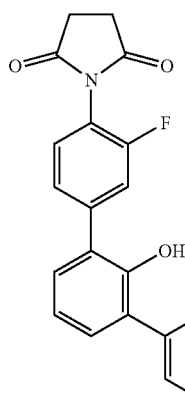
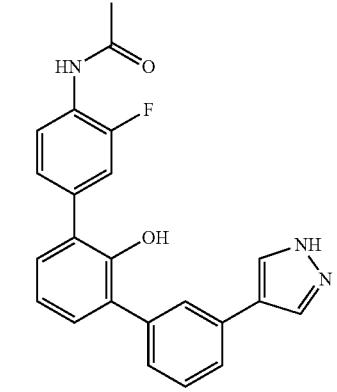
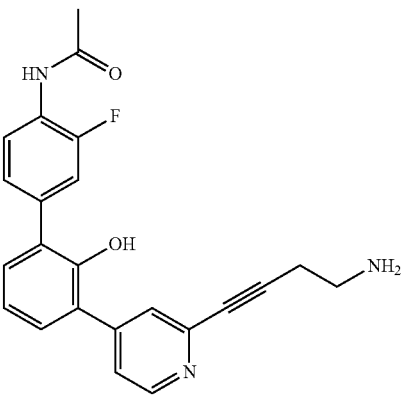

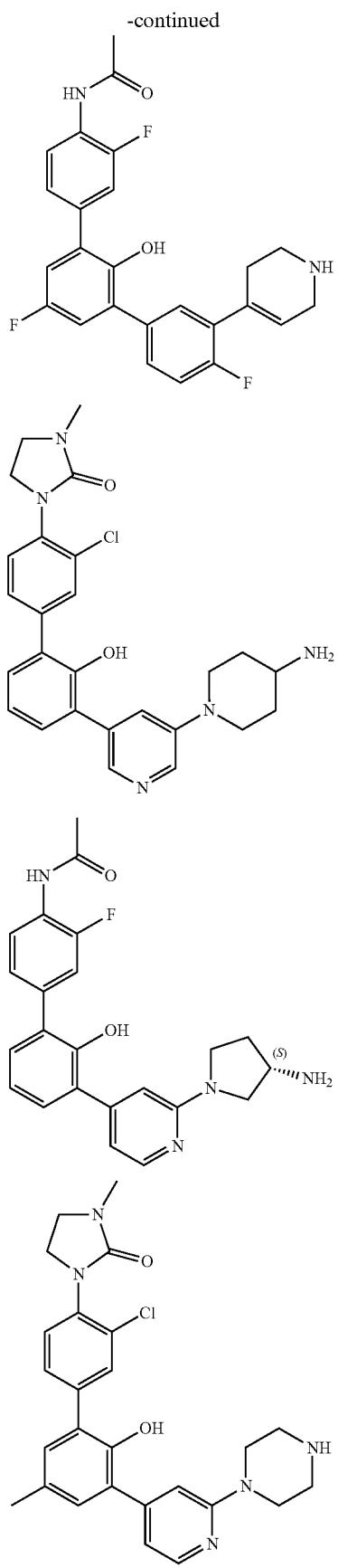
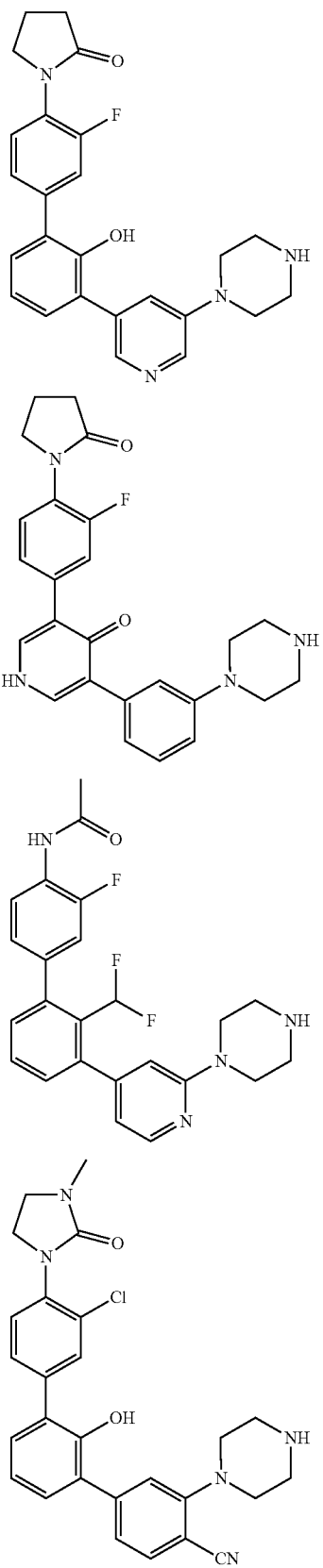

105
-continued
106
-continued
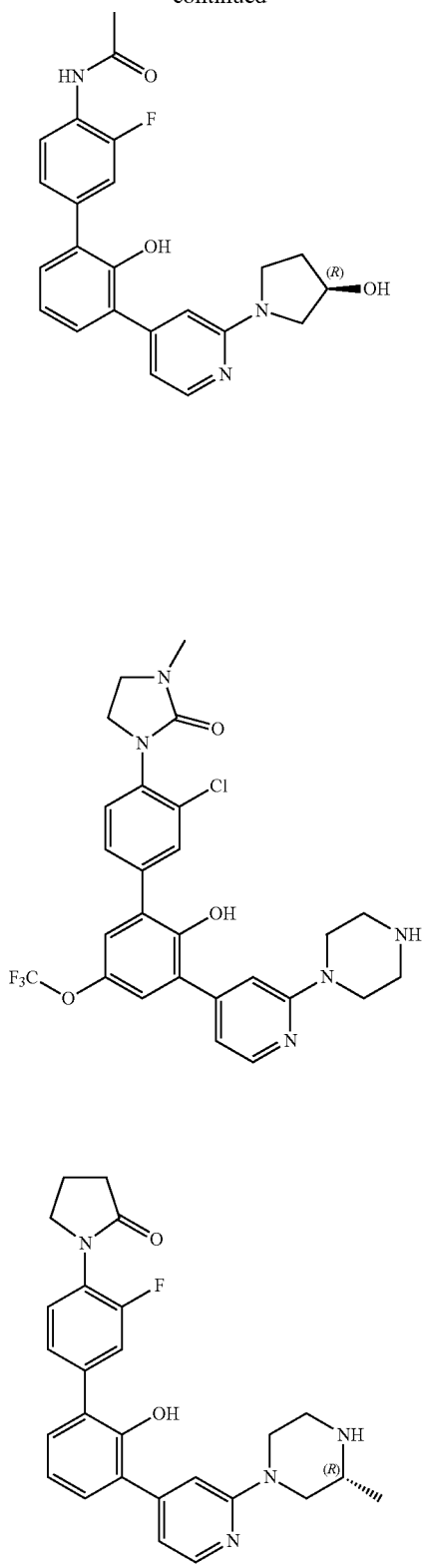
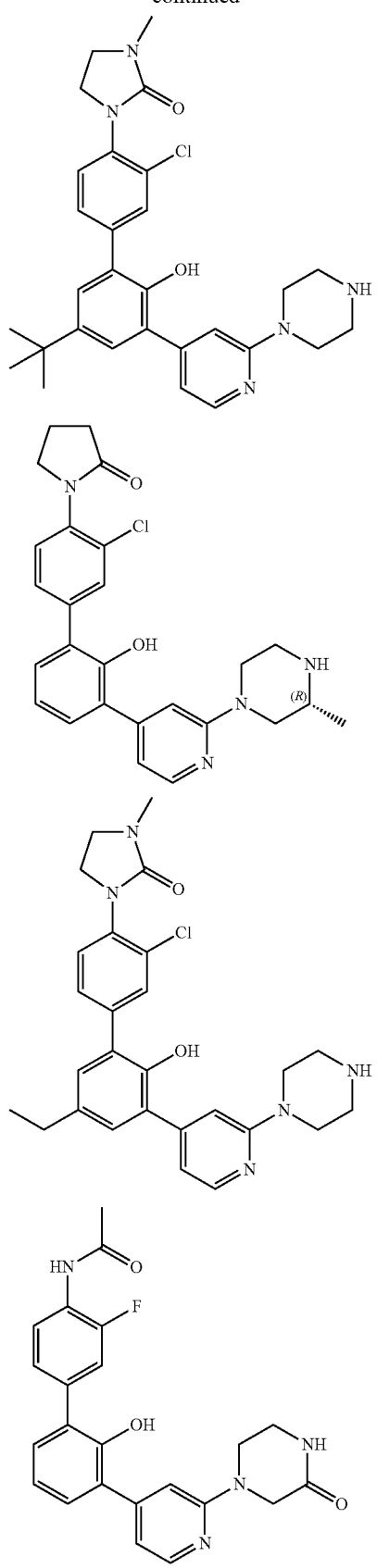

107
-continued
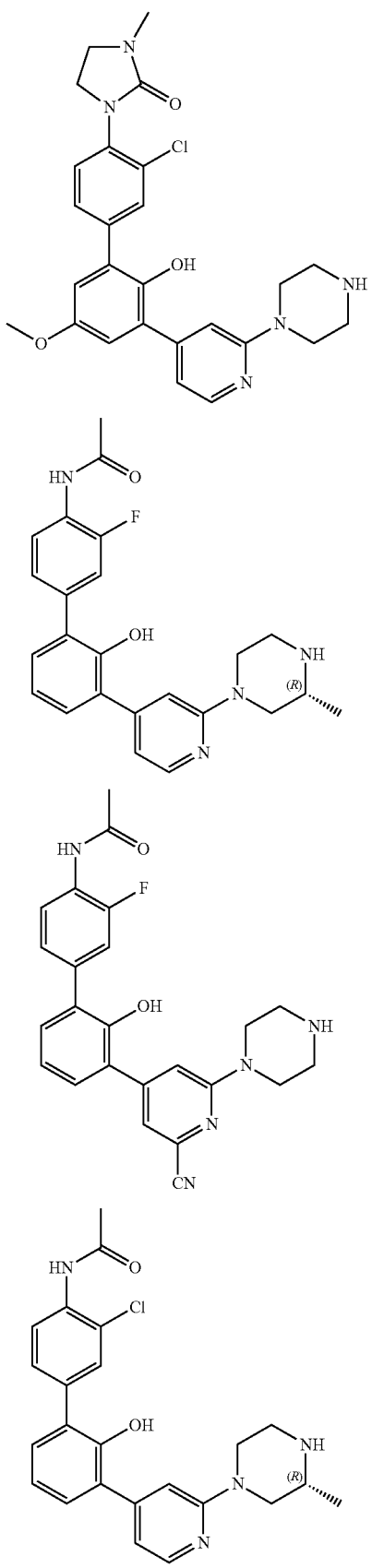
108
-continued
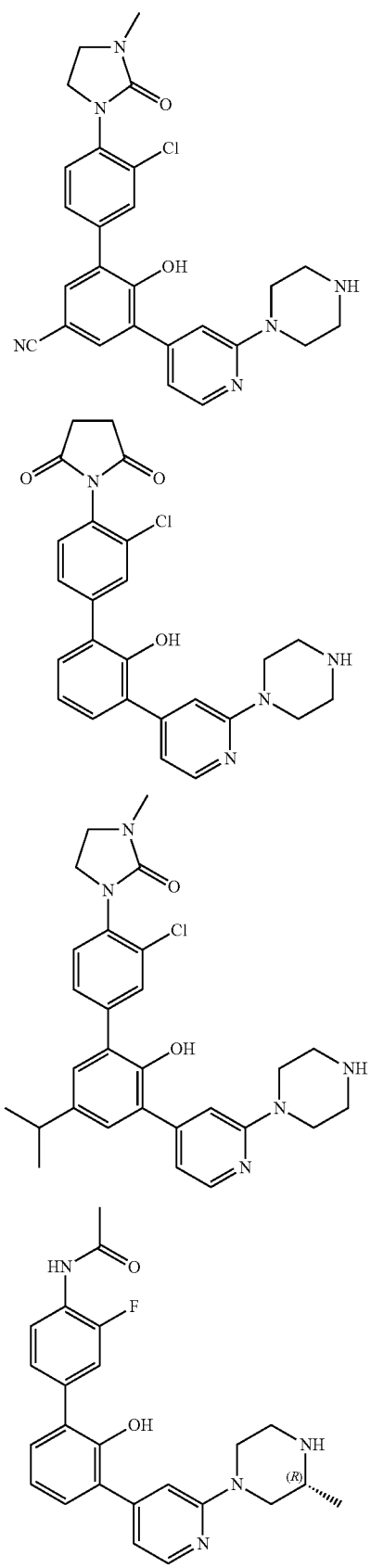

109
-continued
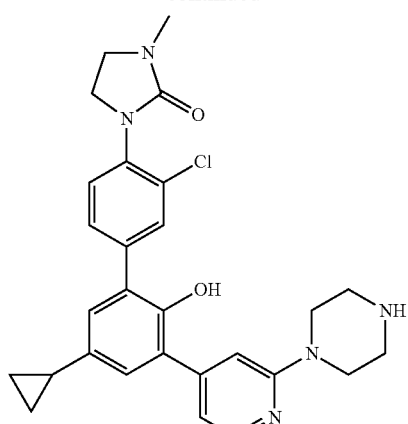
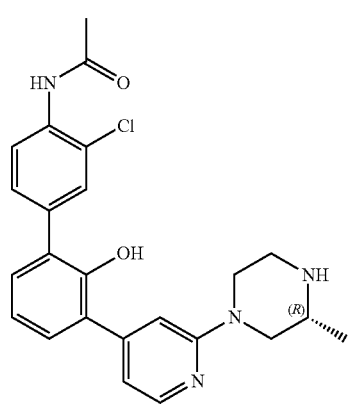
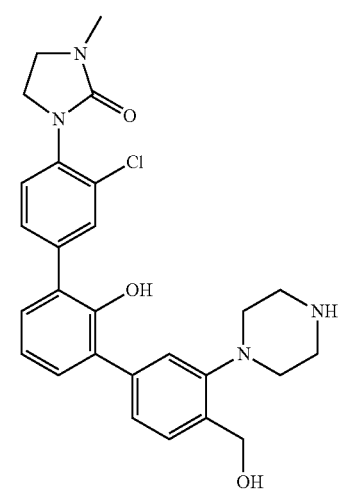
110
-continued
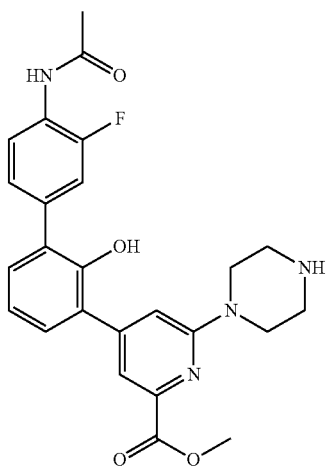
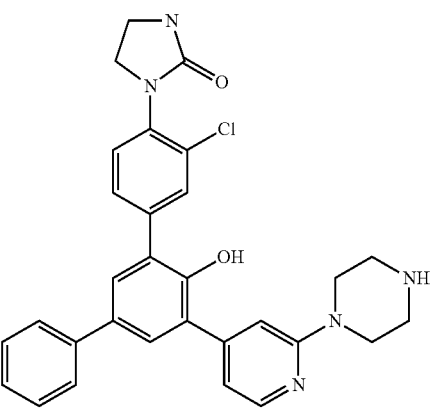
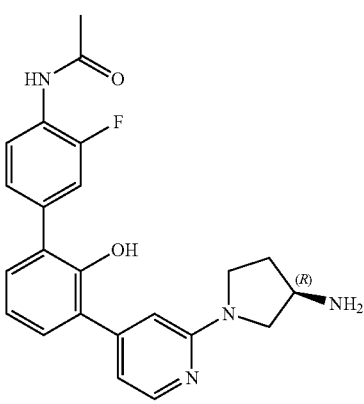

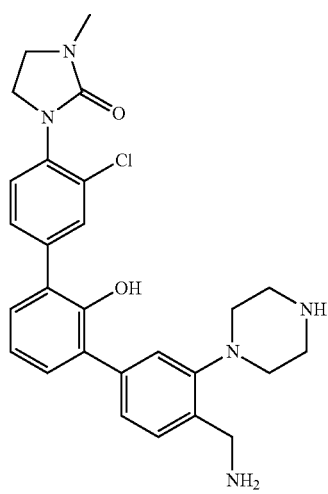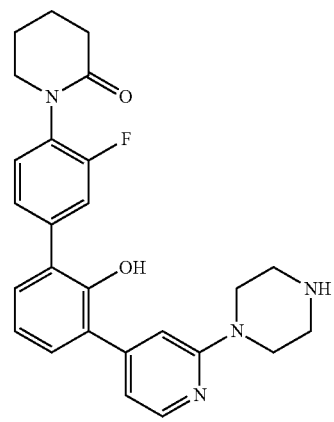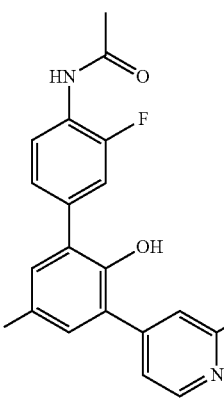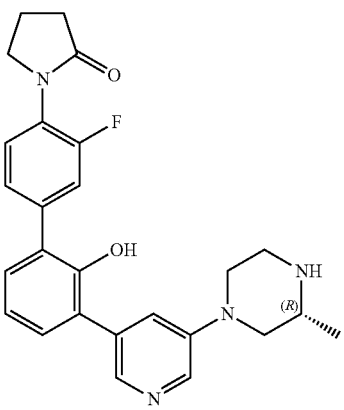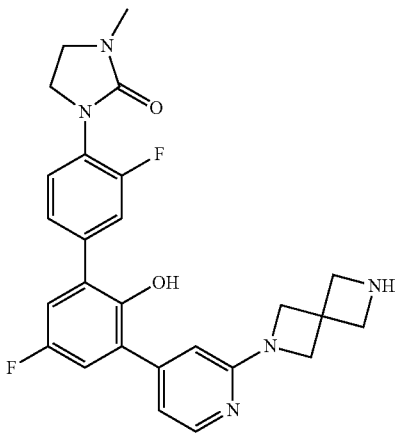

113
-continued
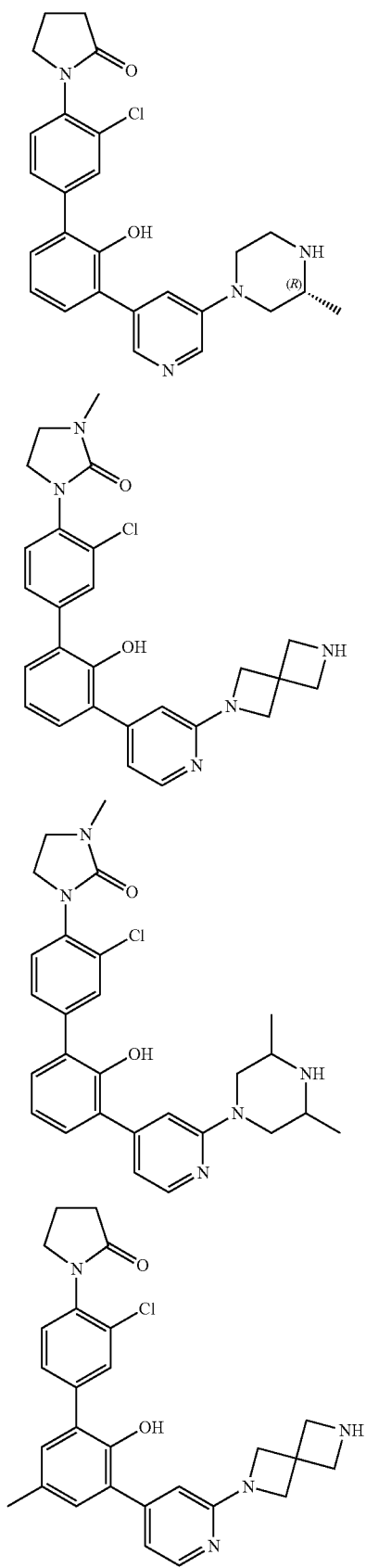
114
-continued
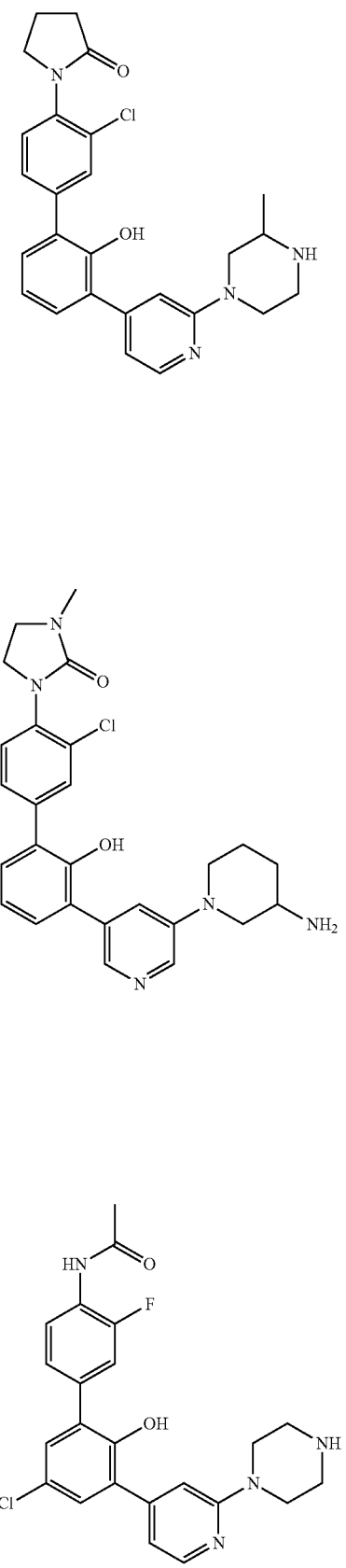

115
-continued
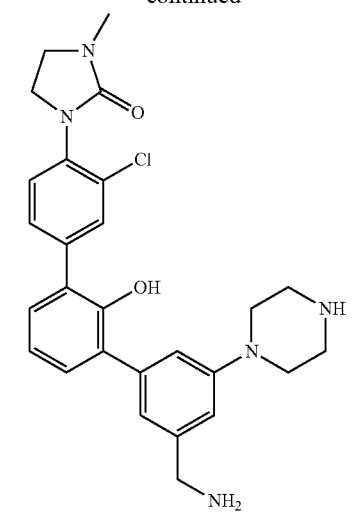
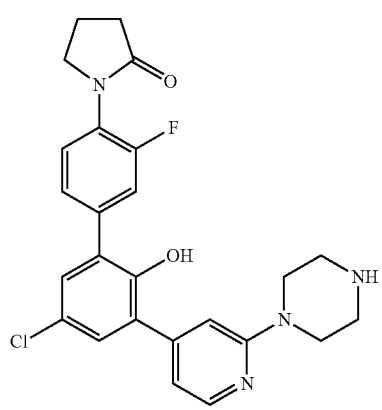
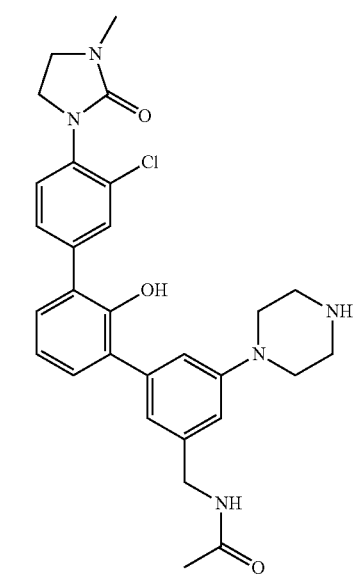
116
-continued
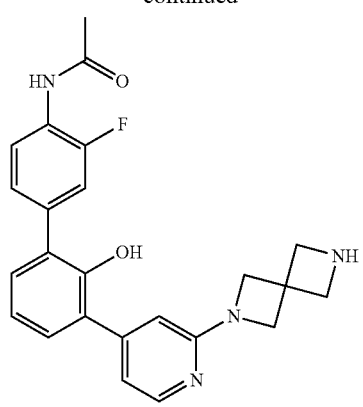
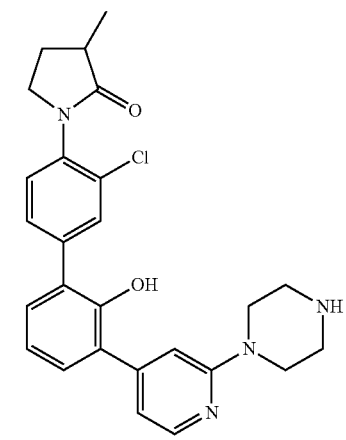
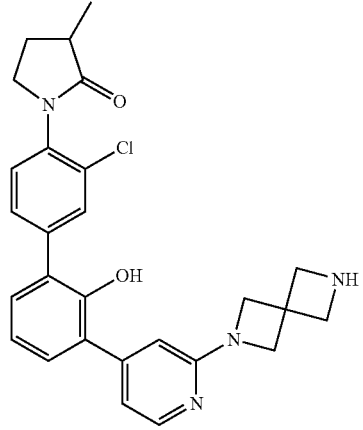
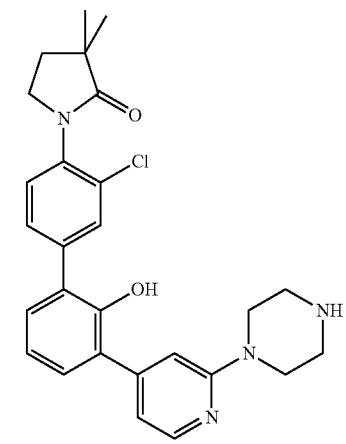

117
-continued
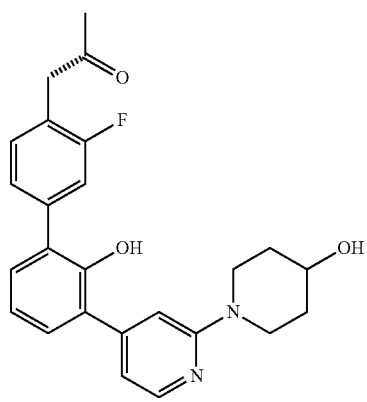
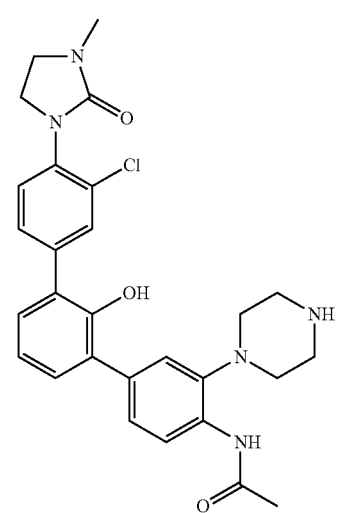
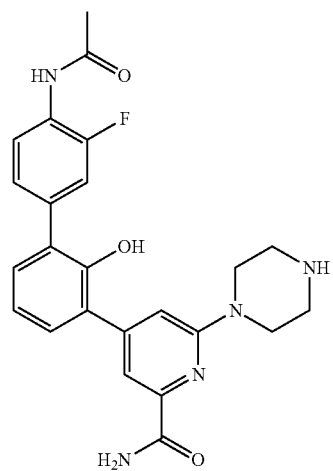
118
-continued
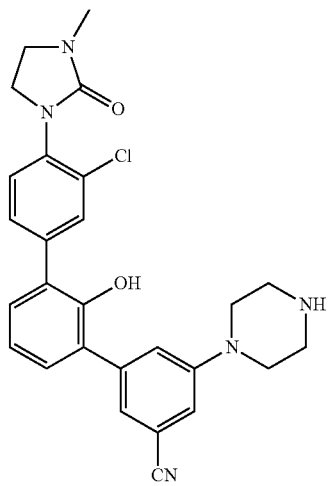
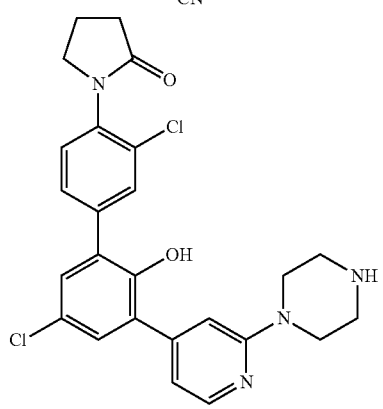
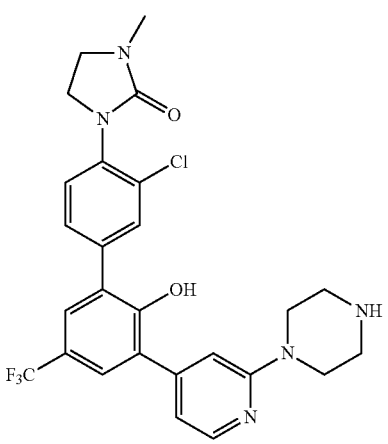
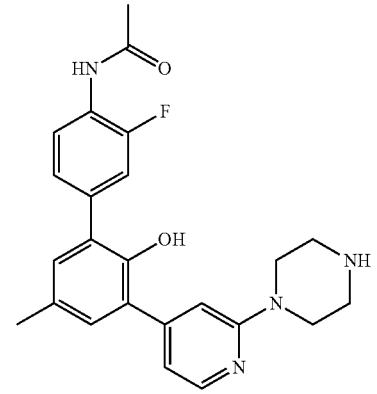

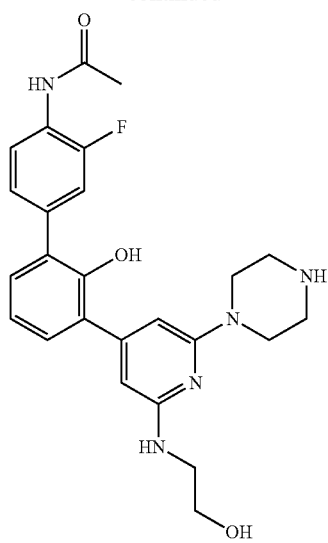
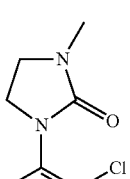
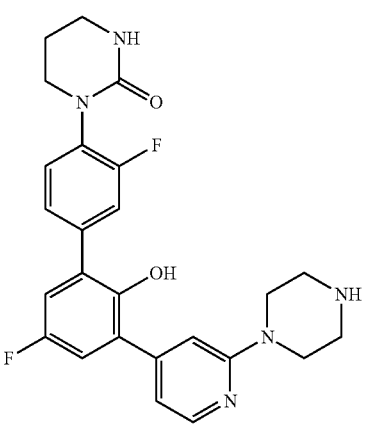

121
-continued
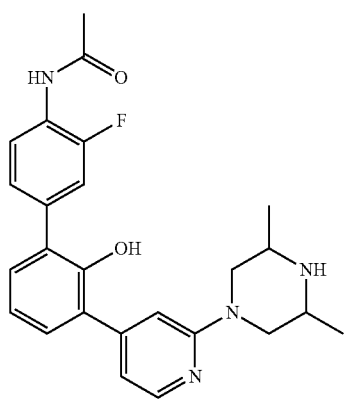
122
-continued
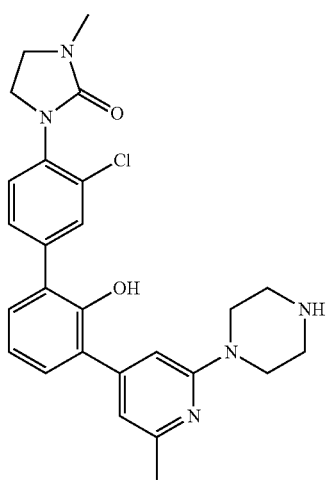
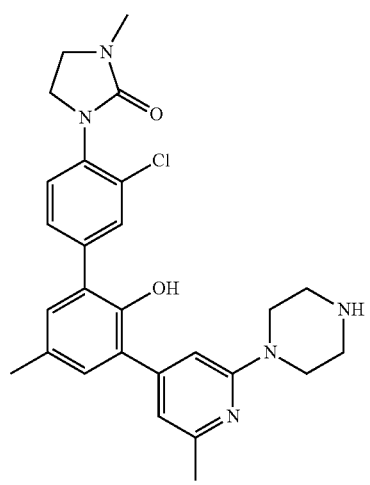
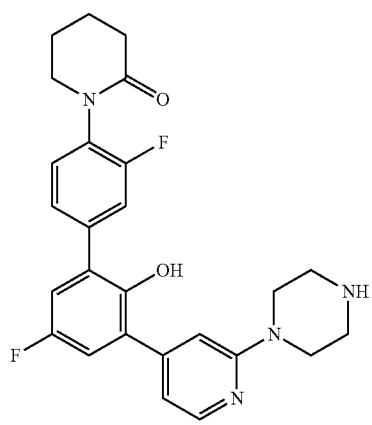
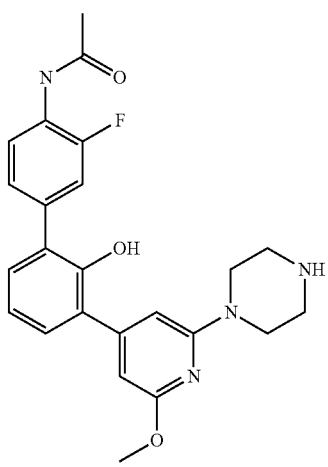

123
-continued
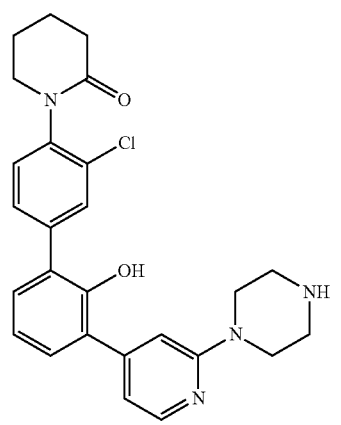
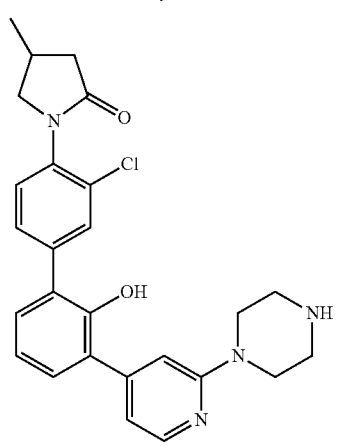
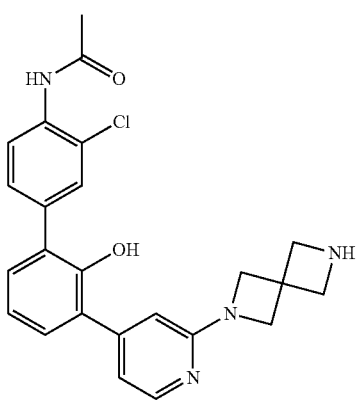
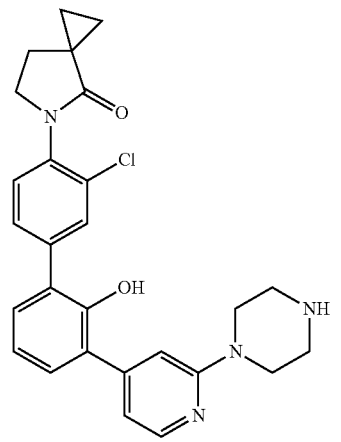
124
-continued
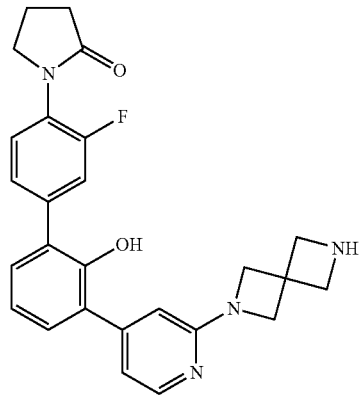
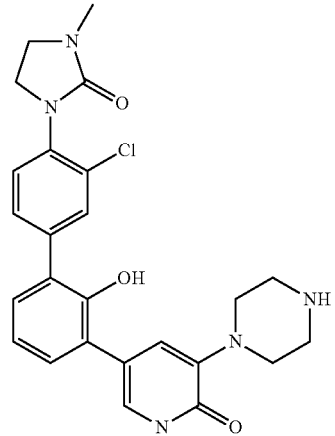
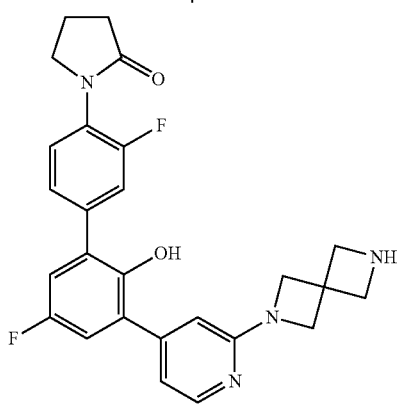
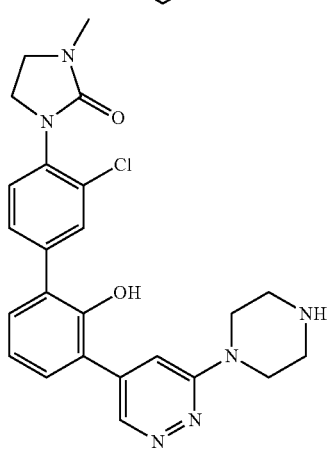

125
-continued
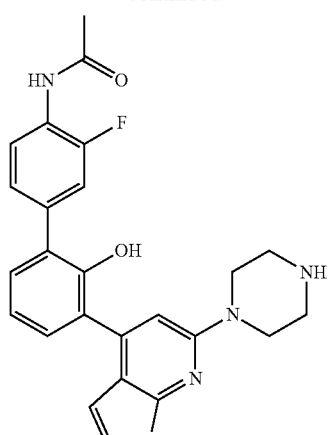
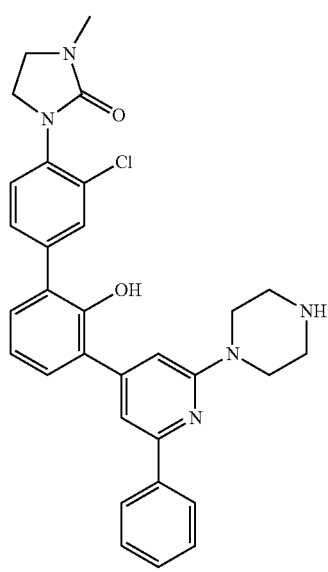
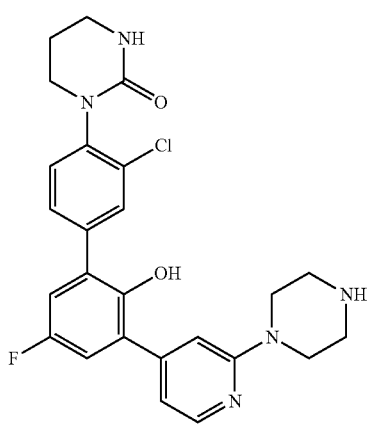
126
-continued
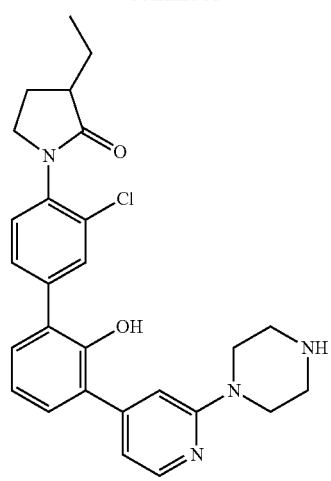
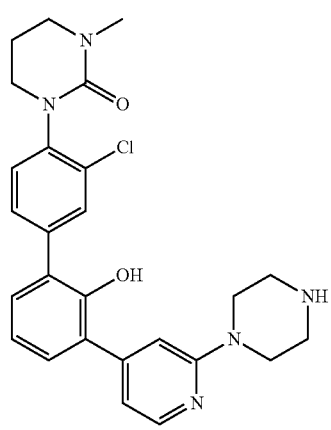
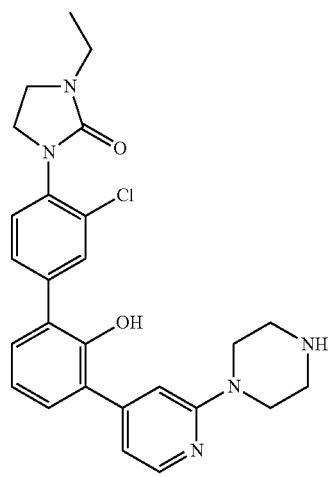

127
-continued
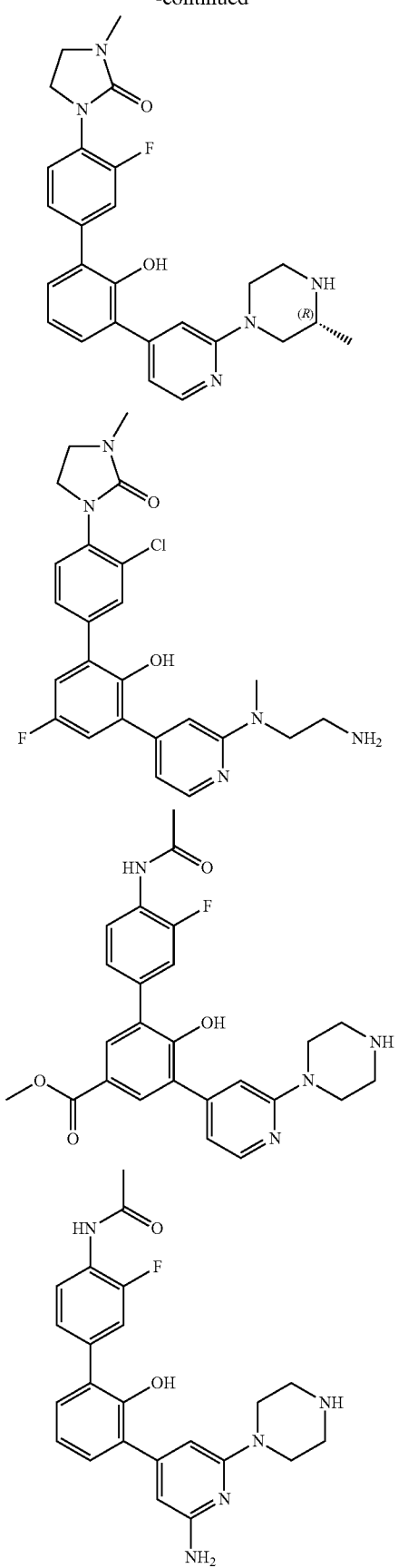
128
-continued
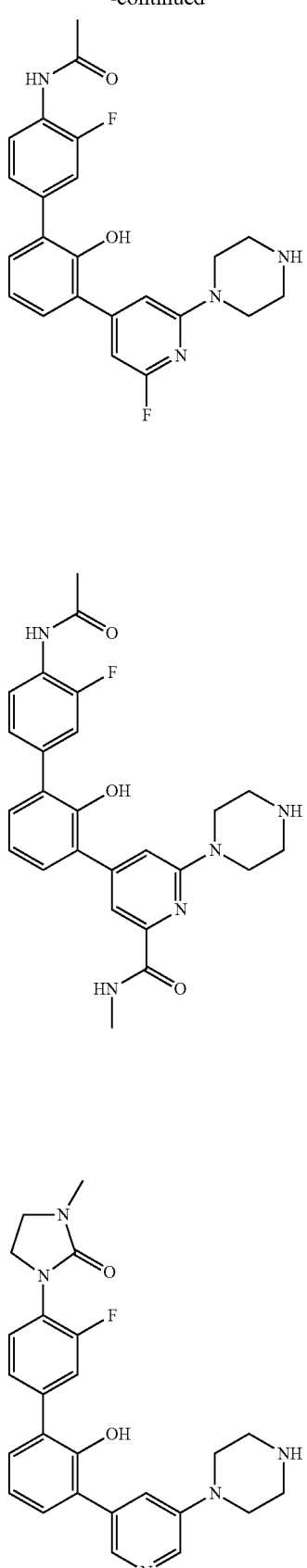

129
-continued
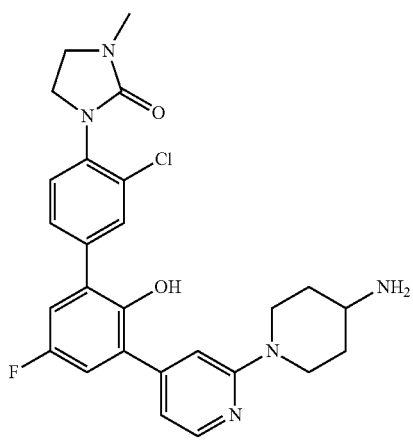
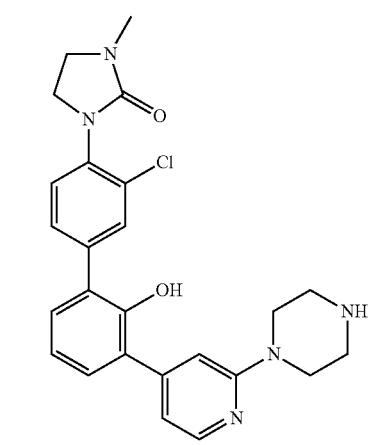
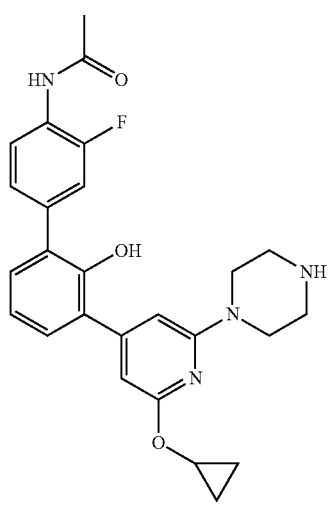
130
-continued
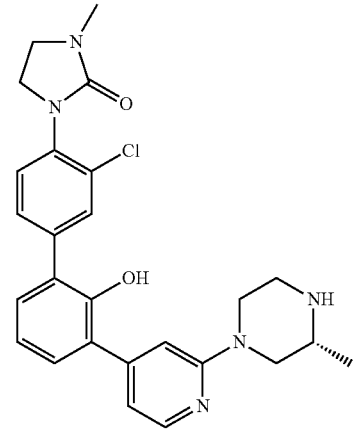
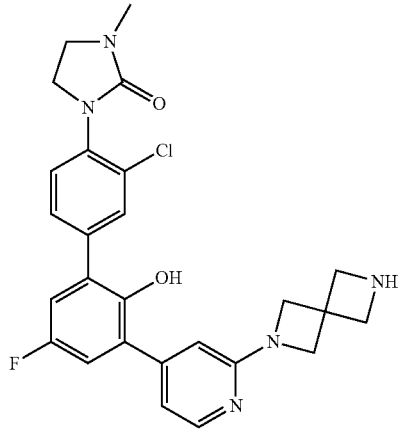
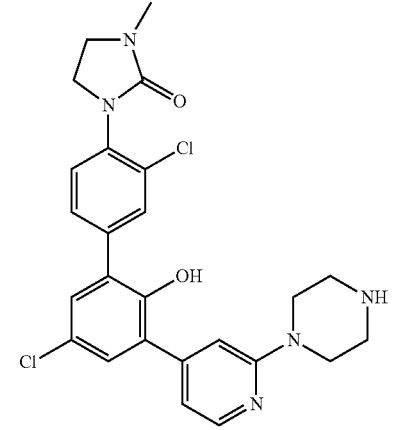
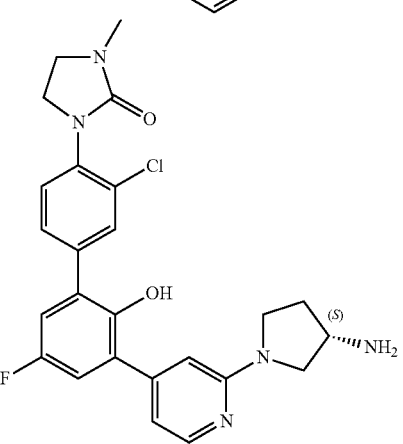

131
-continued
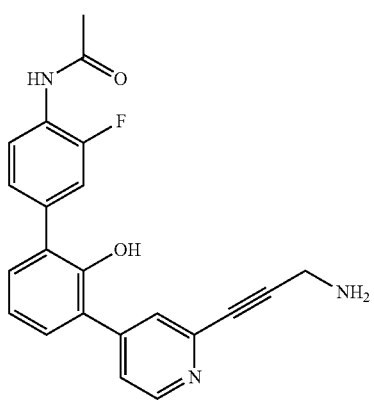
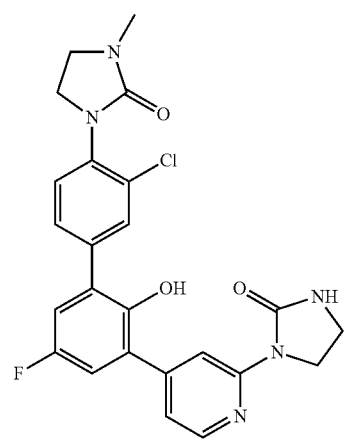
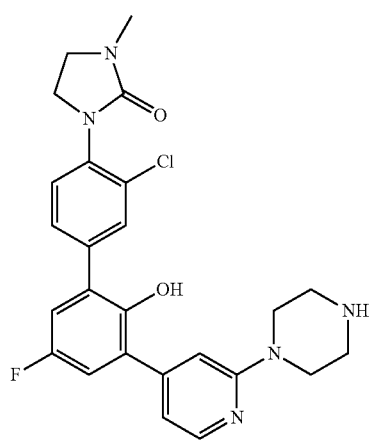
132
-continued
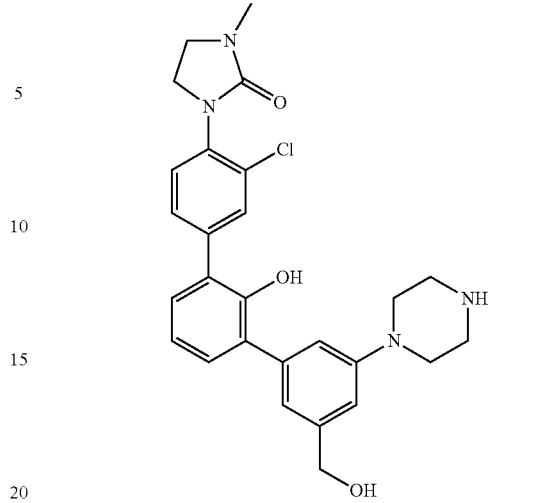
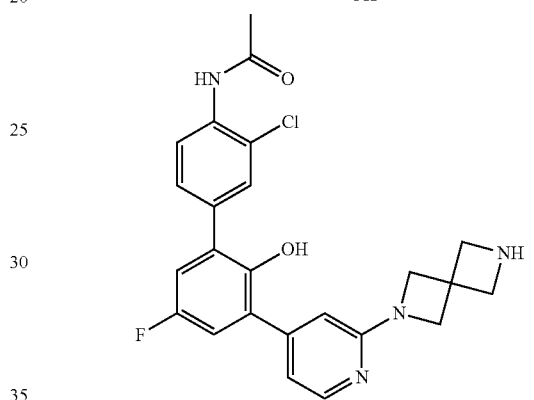
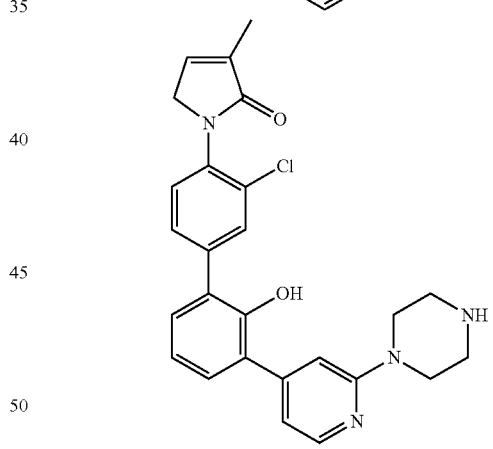
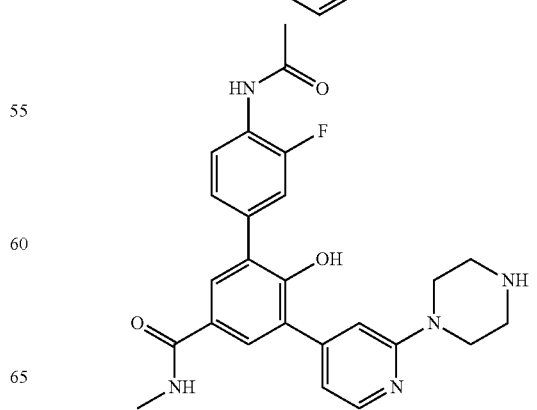

133
-continued
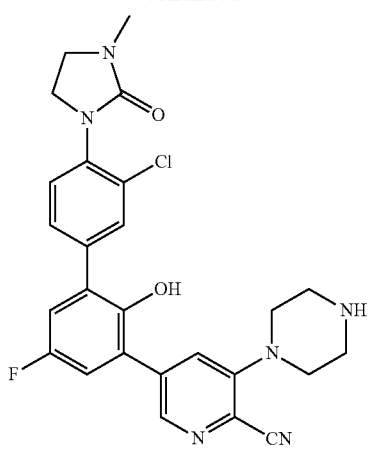
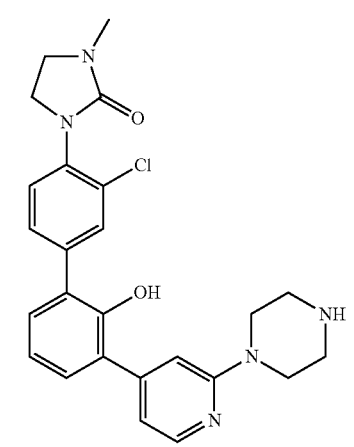
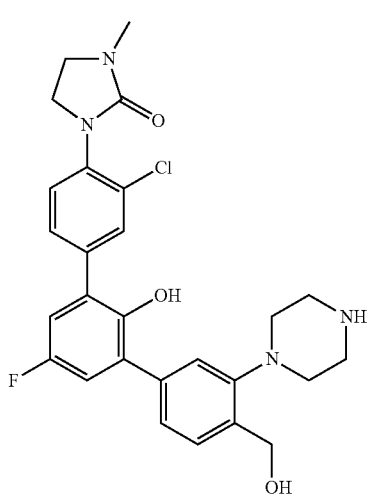
134
-continued
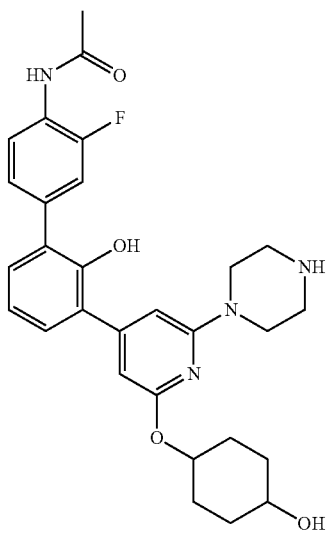
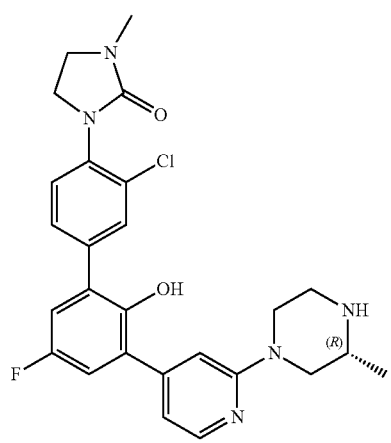
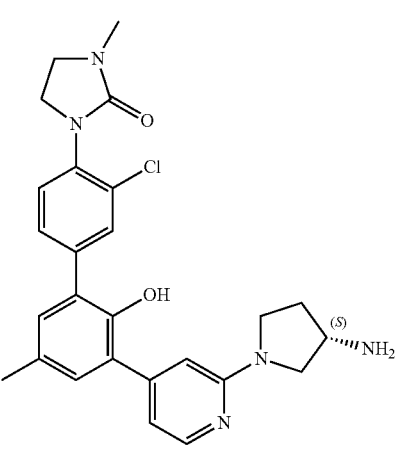

135
-continued
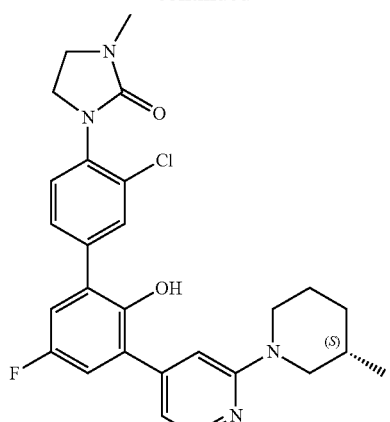
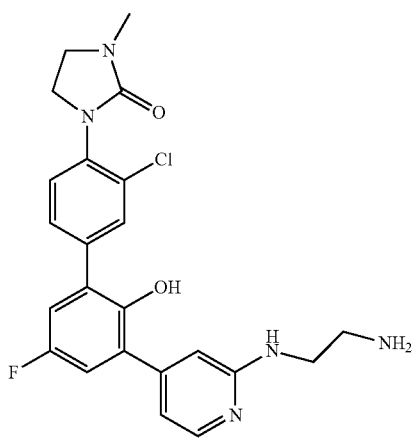
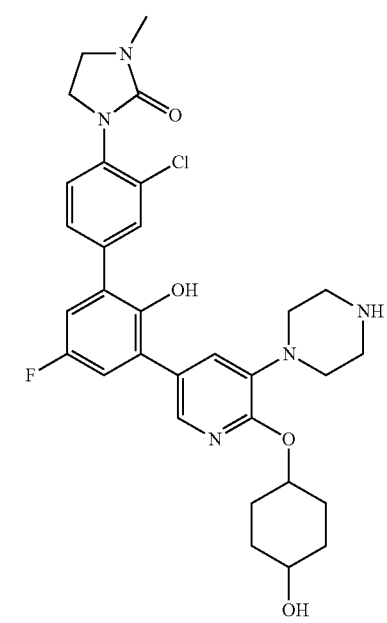
136
-continued
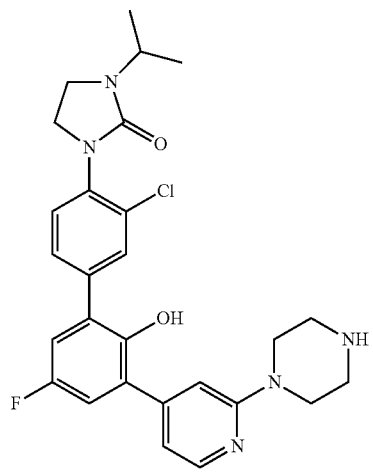
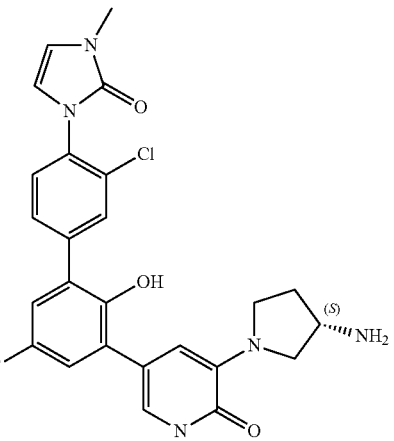
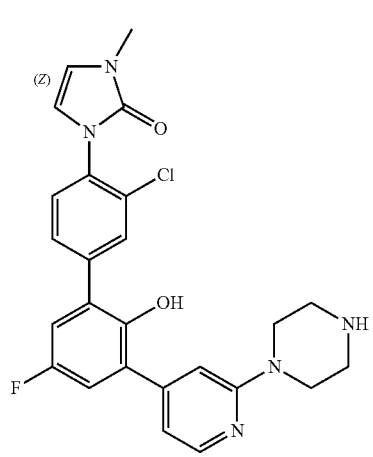

137
-continued
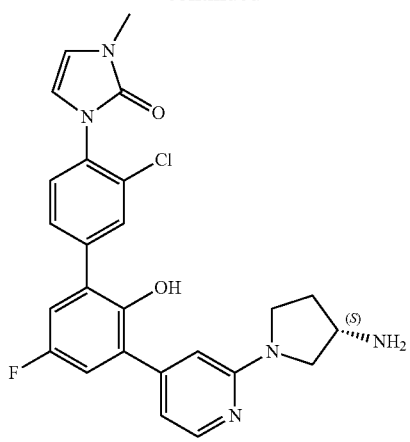
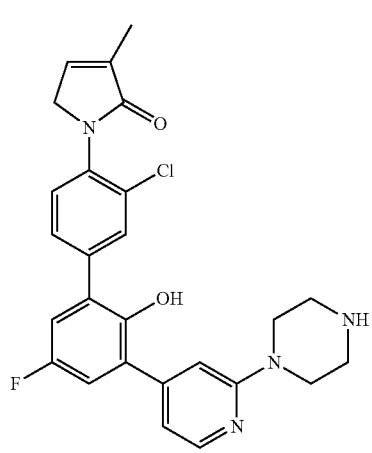
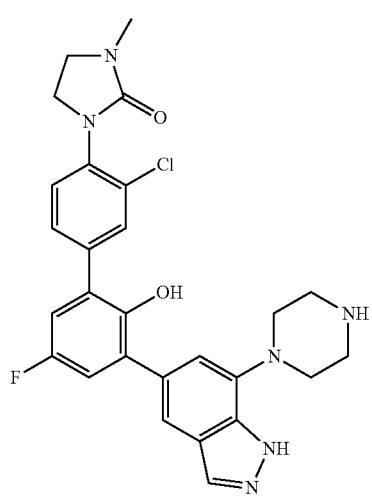
138
-continued
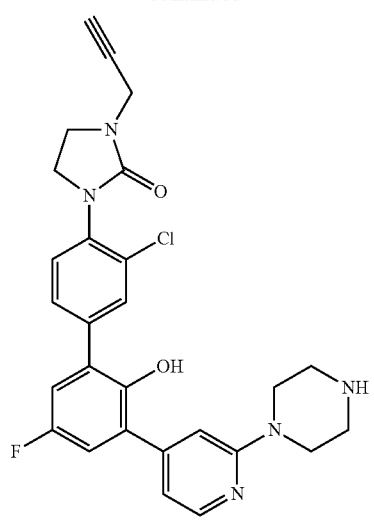
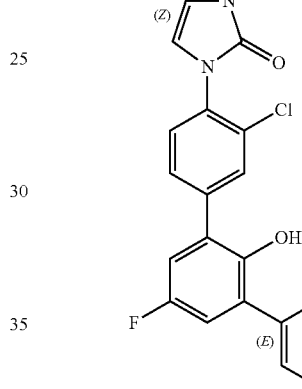
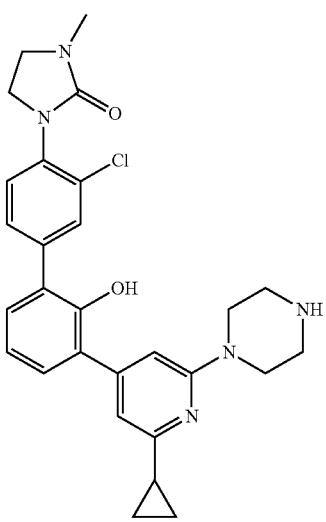

-continued
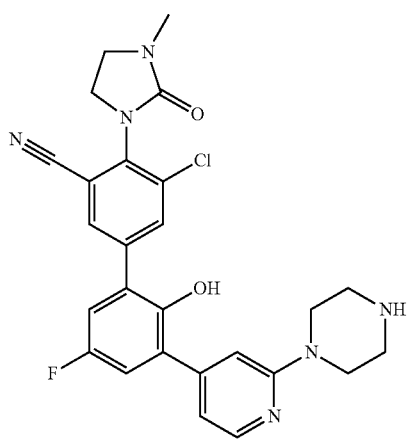
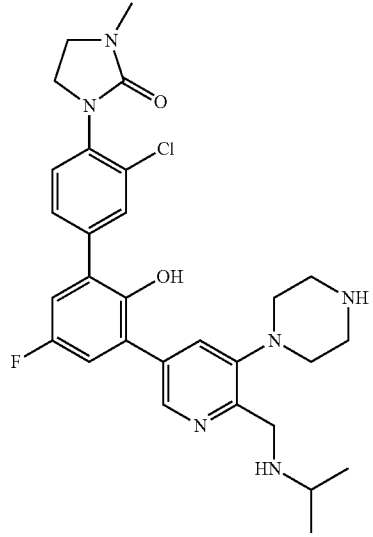
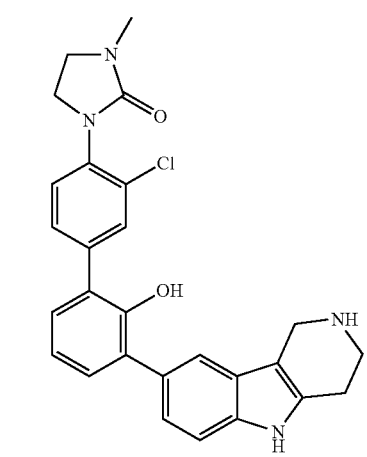
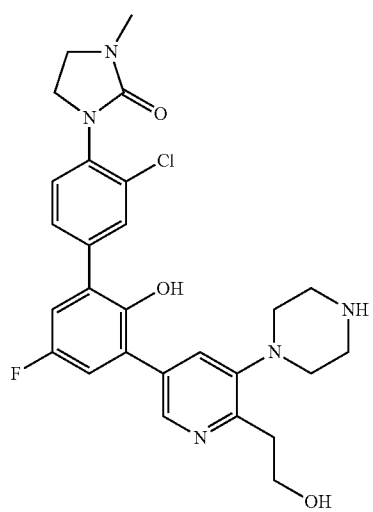
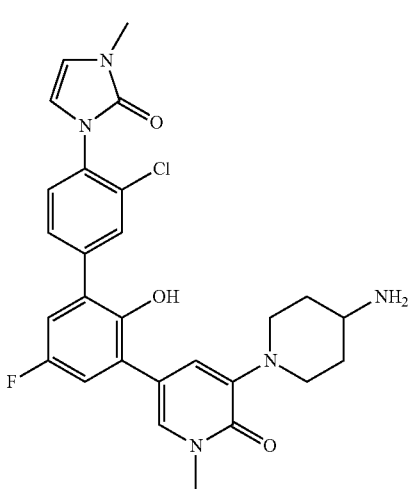
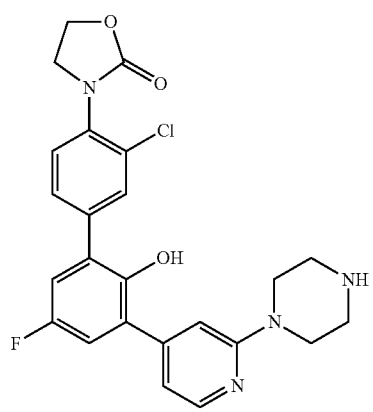

141
-continued
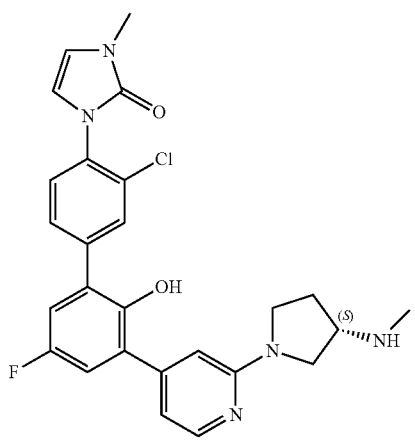
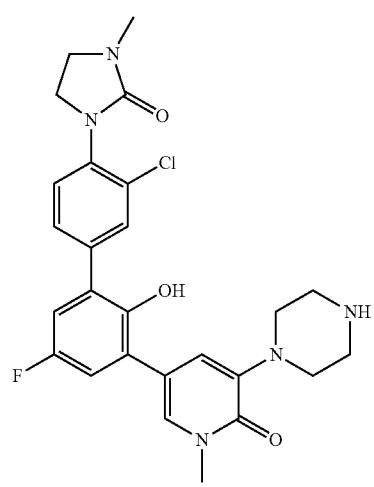
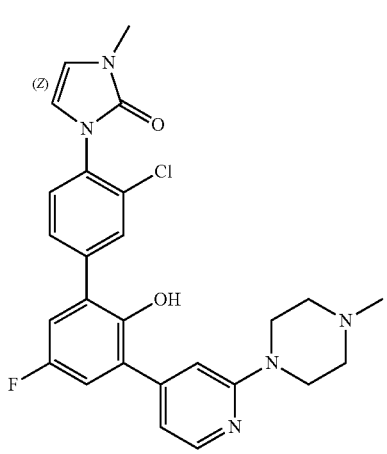
142
-continued
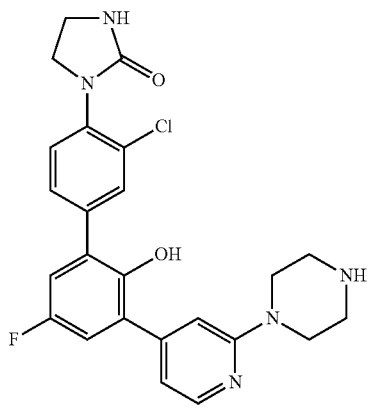
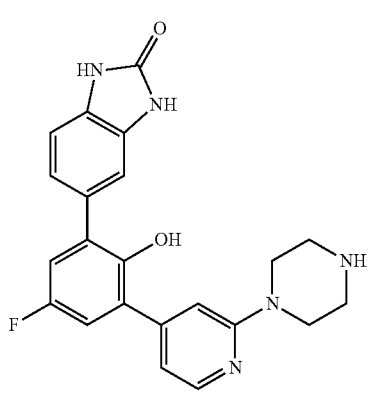
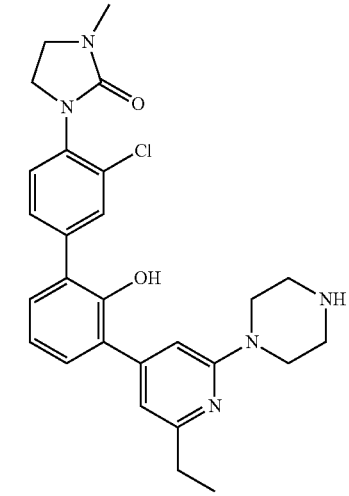

143
-continued
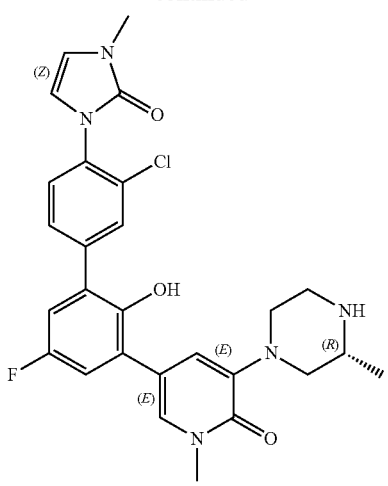
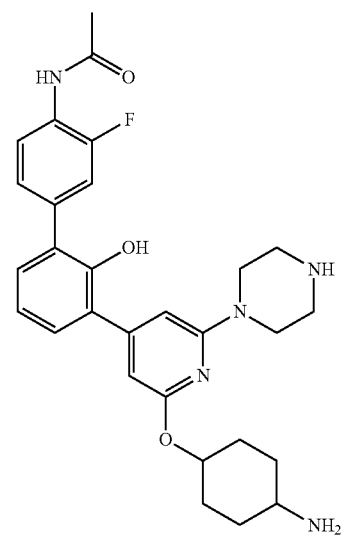
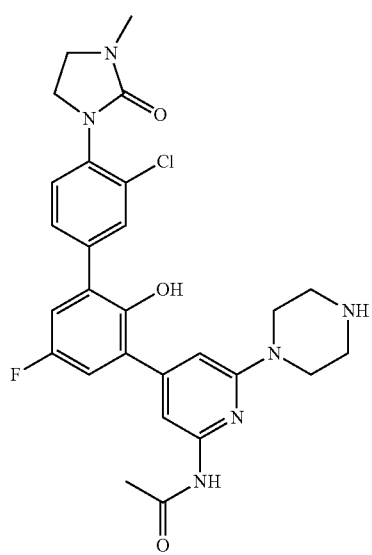
144
-continued
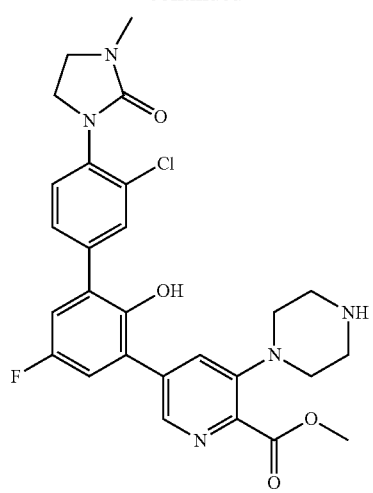
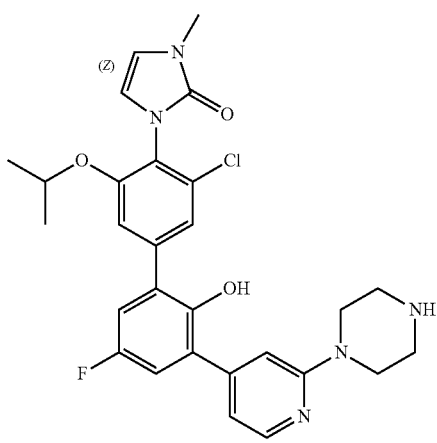
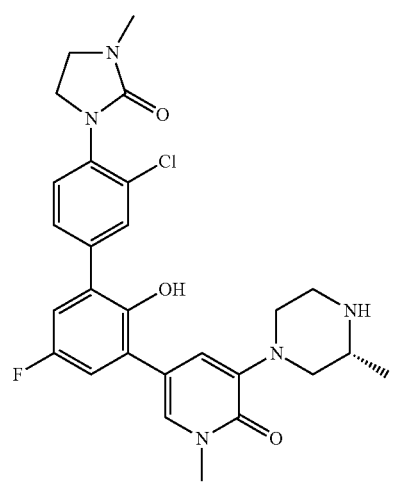

145
-continued
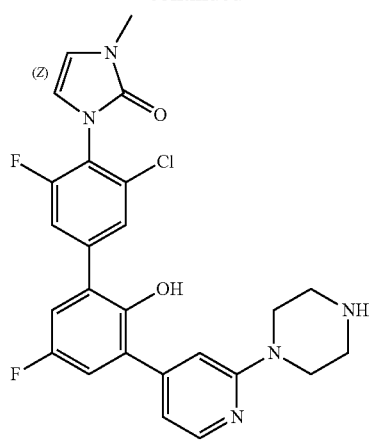
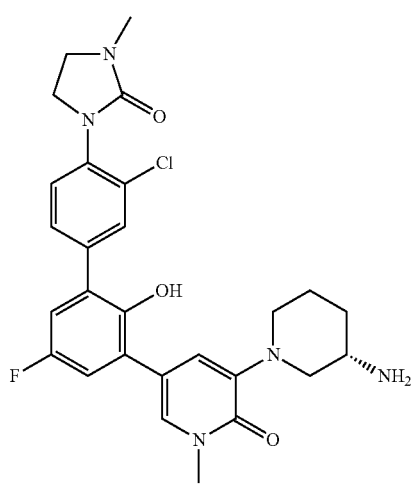
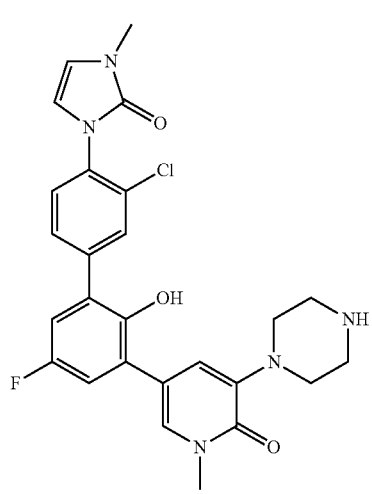
146
-continued
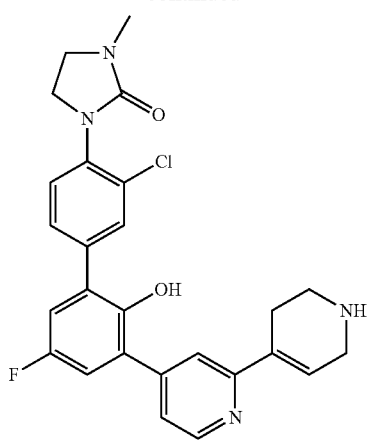
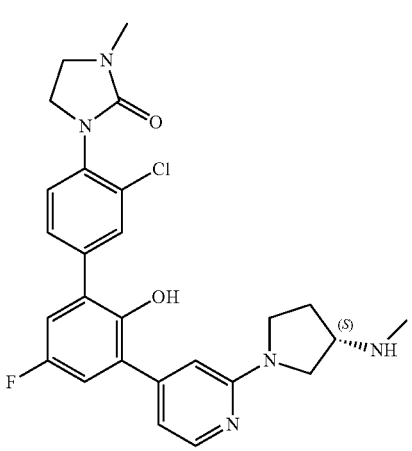
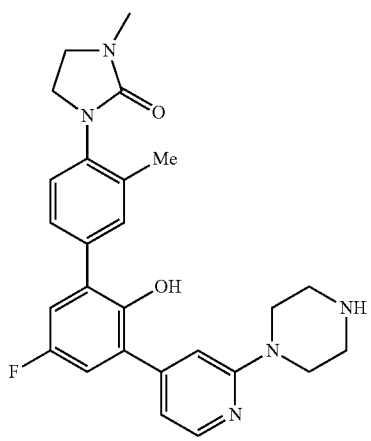

147
-continued
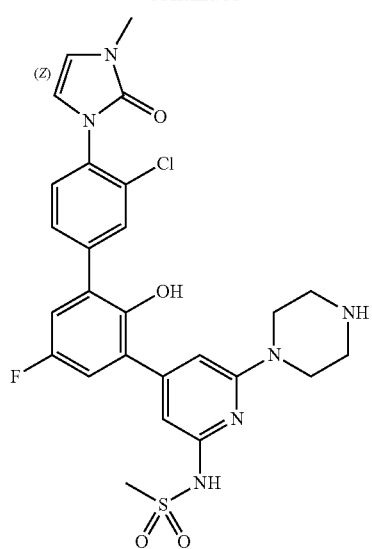
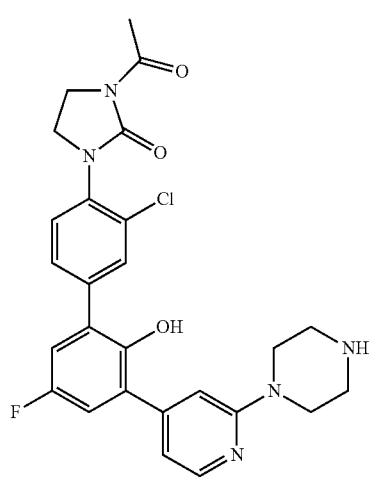
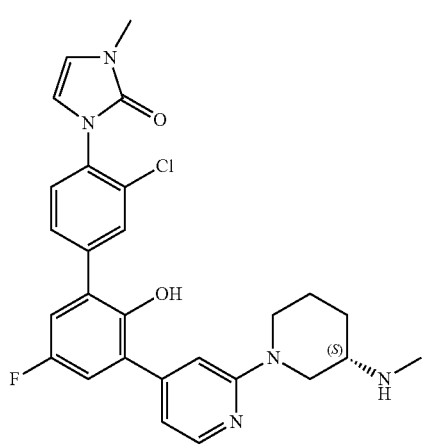
148
-continued
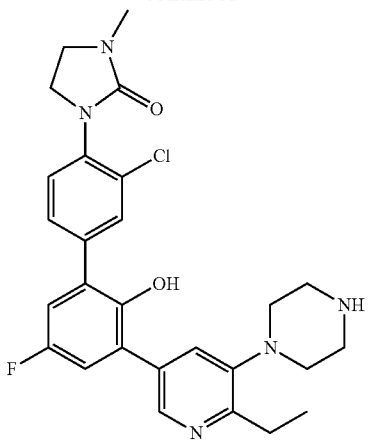
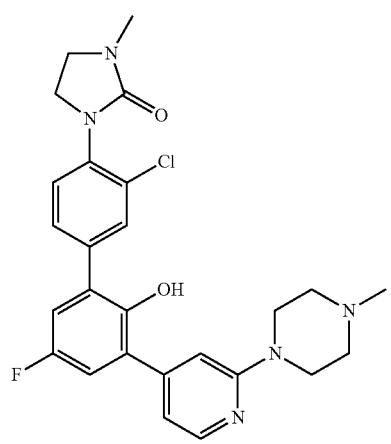
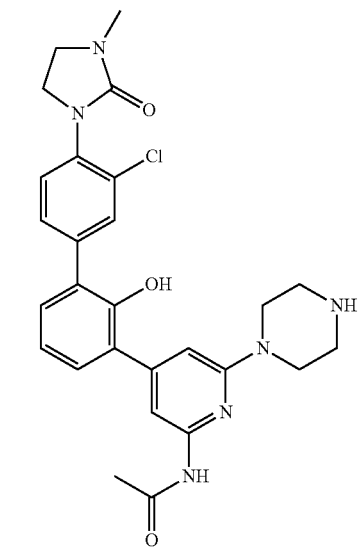

149
-continued
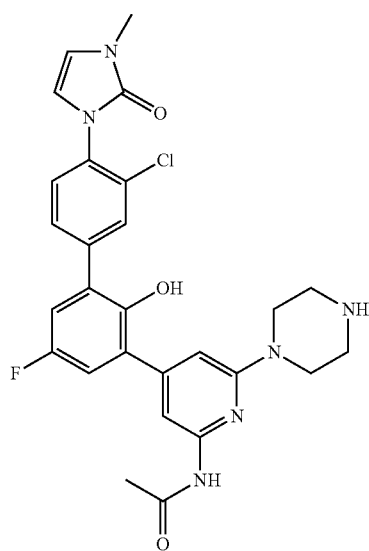
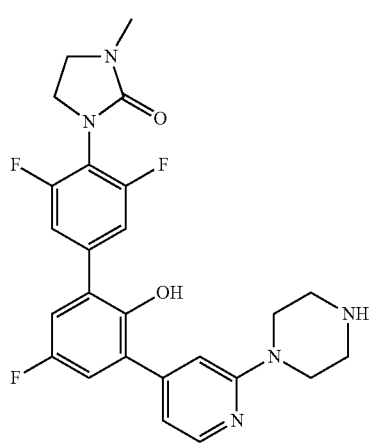
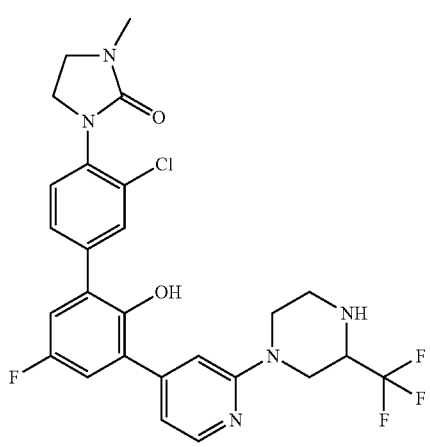
150
-continued
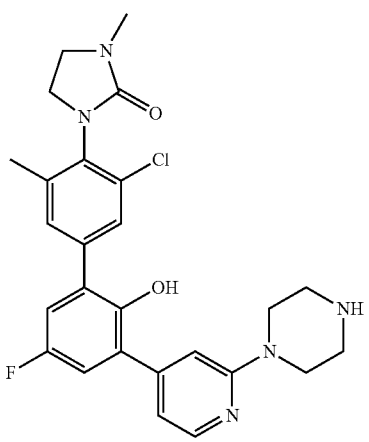
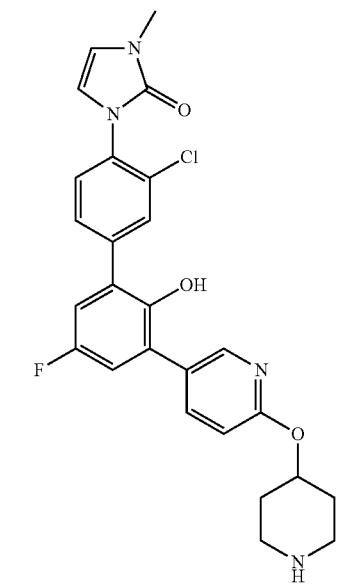
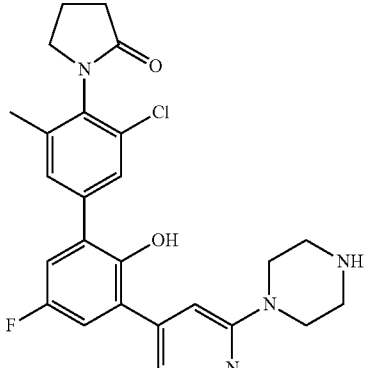

151
-continued
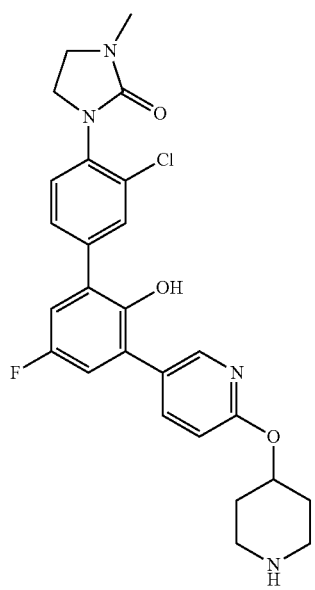
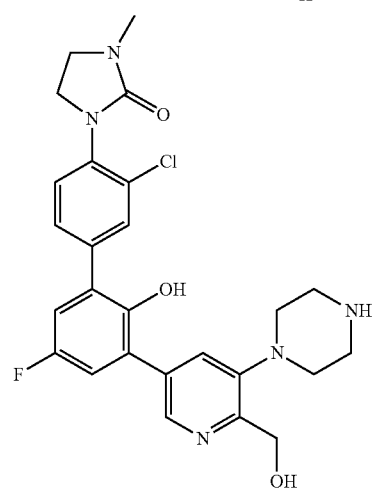
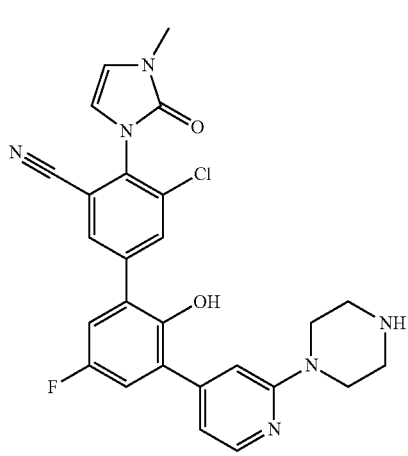
152
-continued
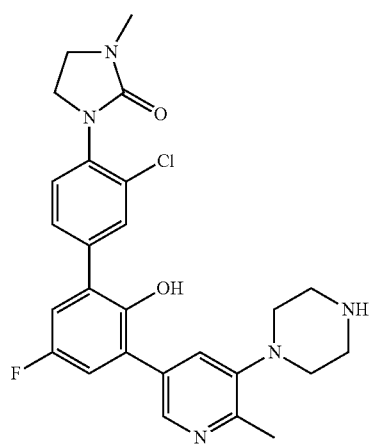
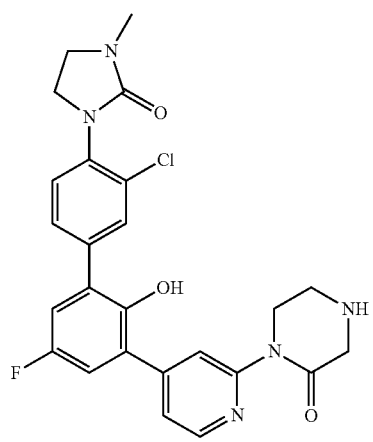
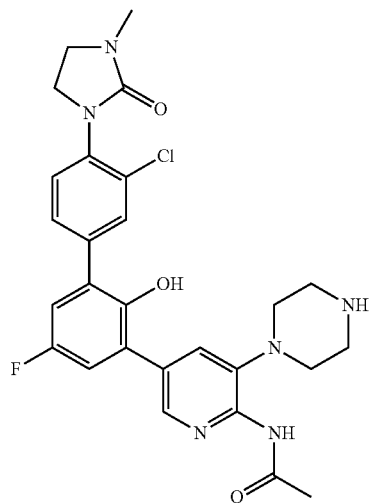

153
-continued
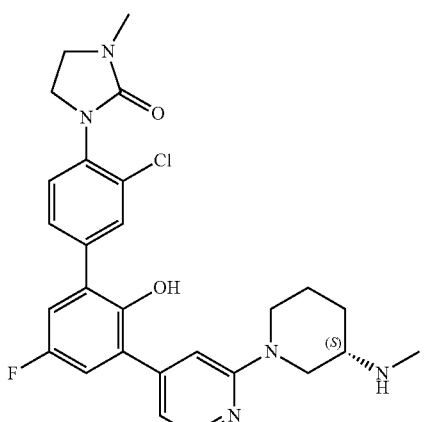
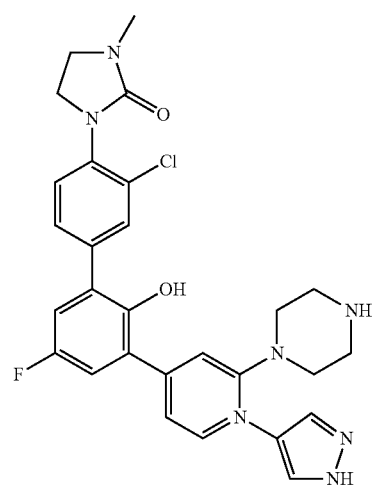
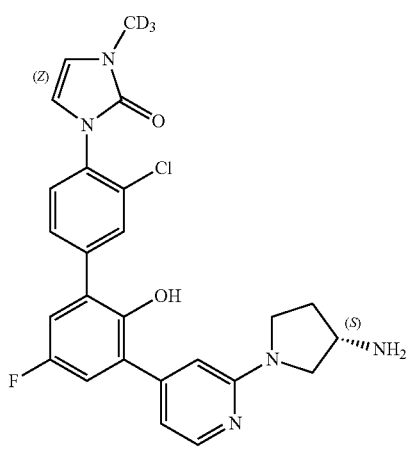
154
-continued
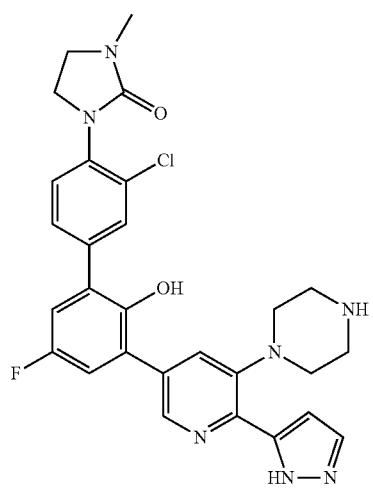
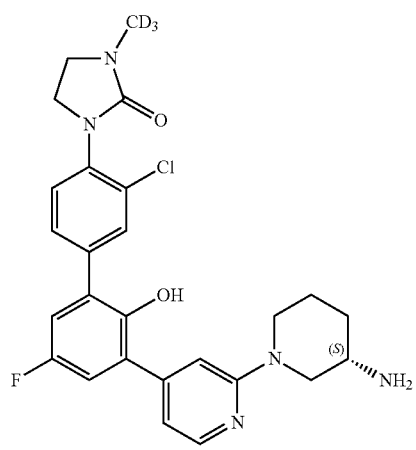
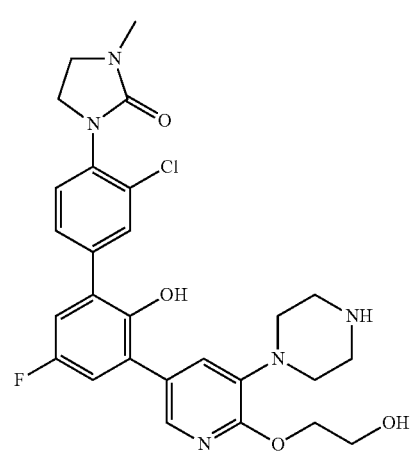

155
-continued
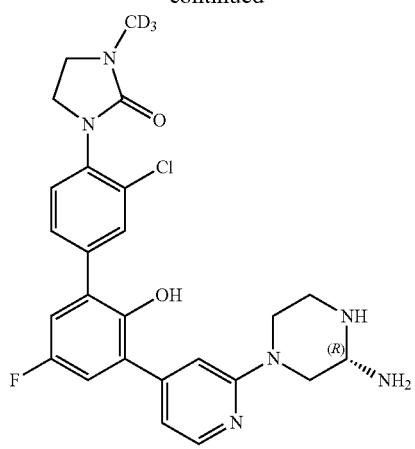
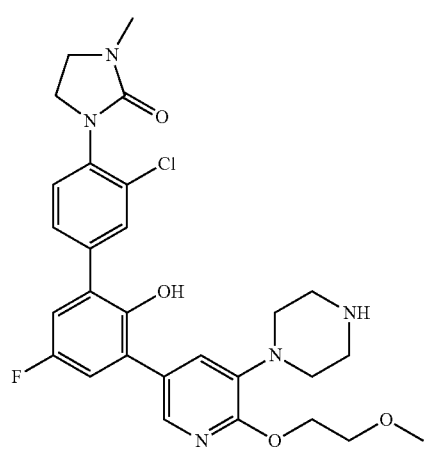
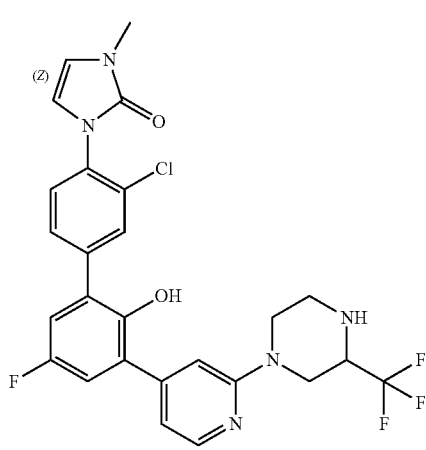
156
-continued
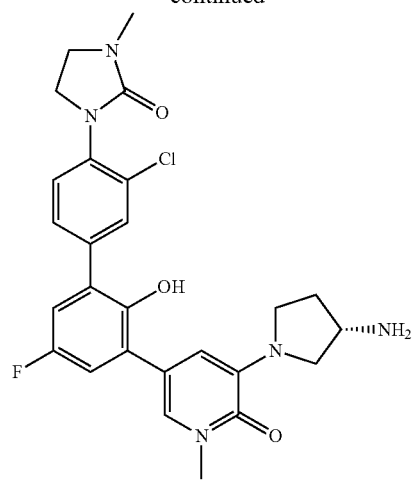
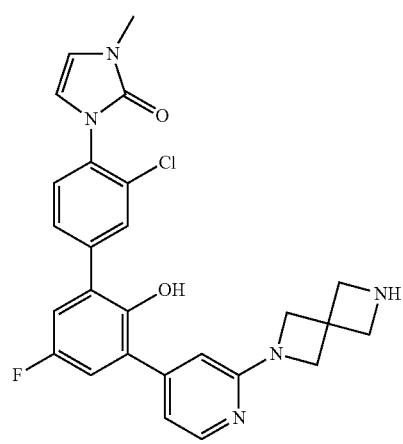
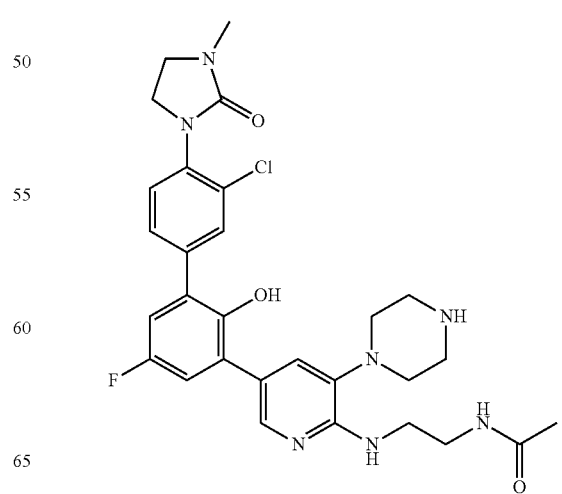

157
-continued
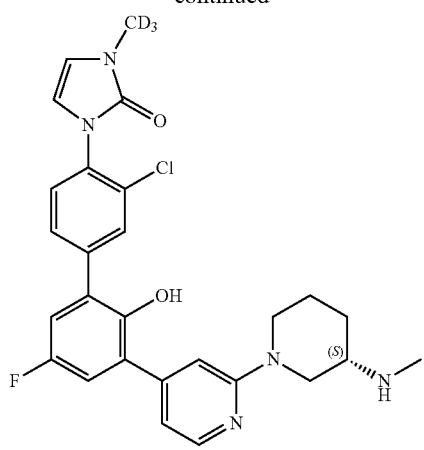
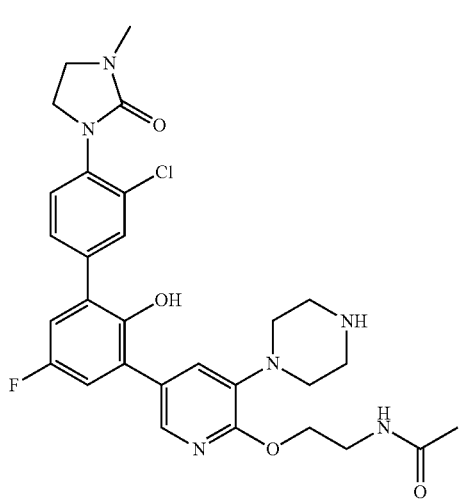
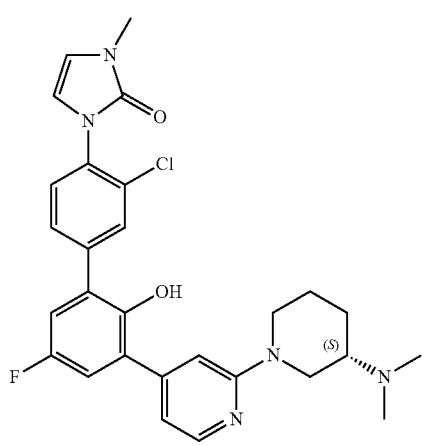
158
-continued
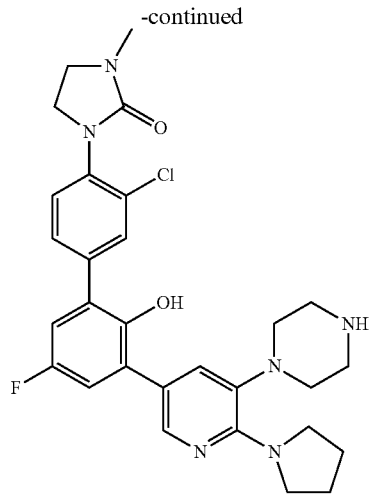
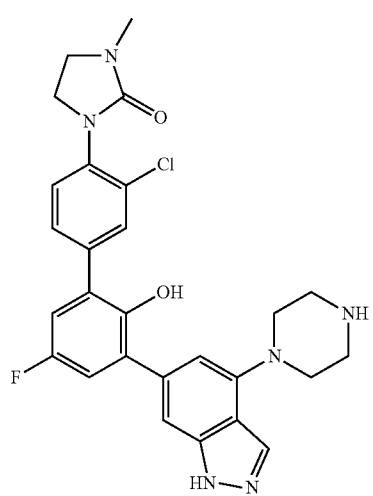
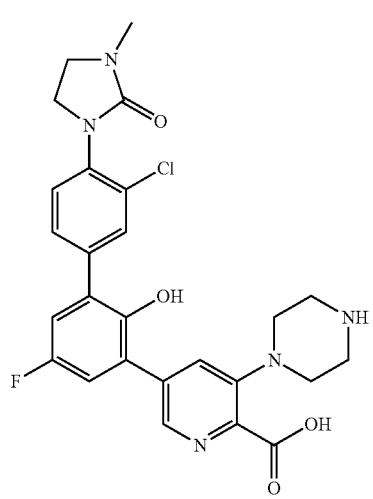

159
-continued
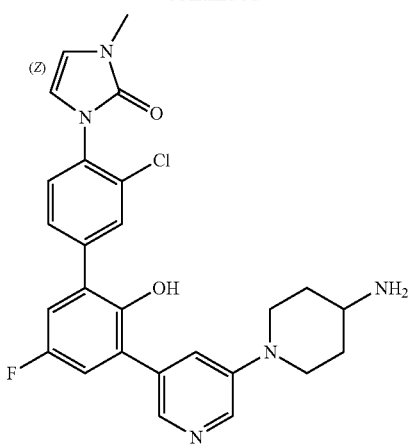
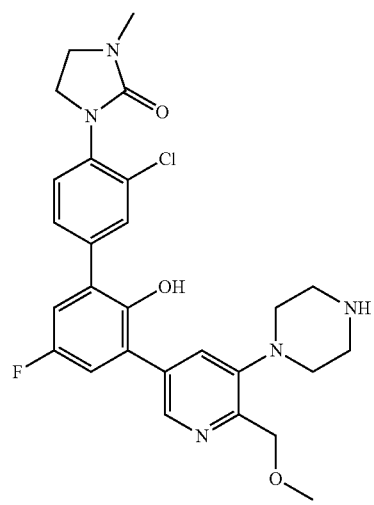
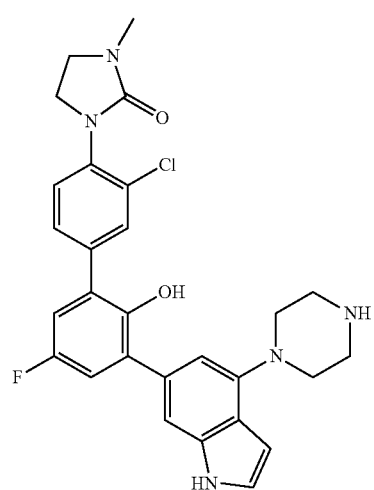
160
-continued
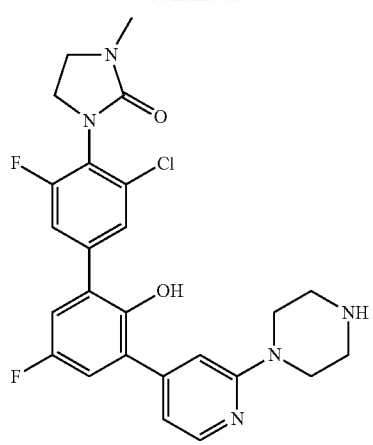
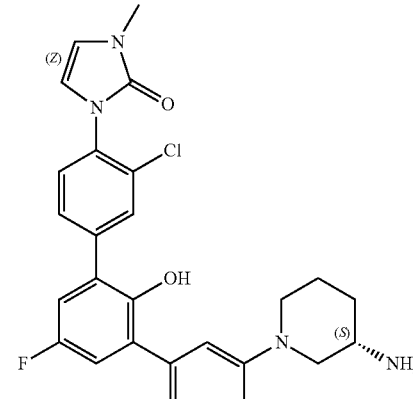
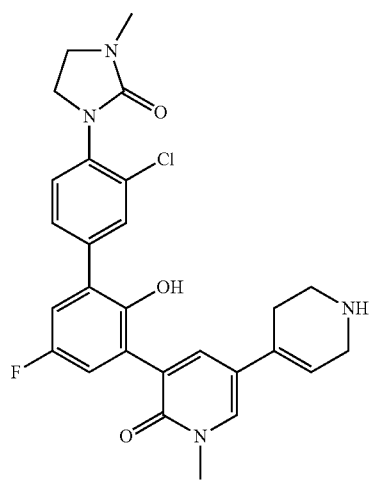

161
-continued
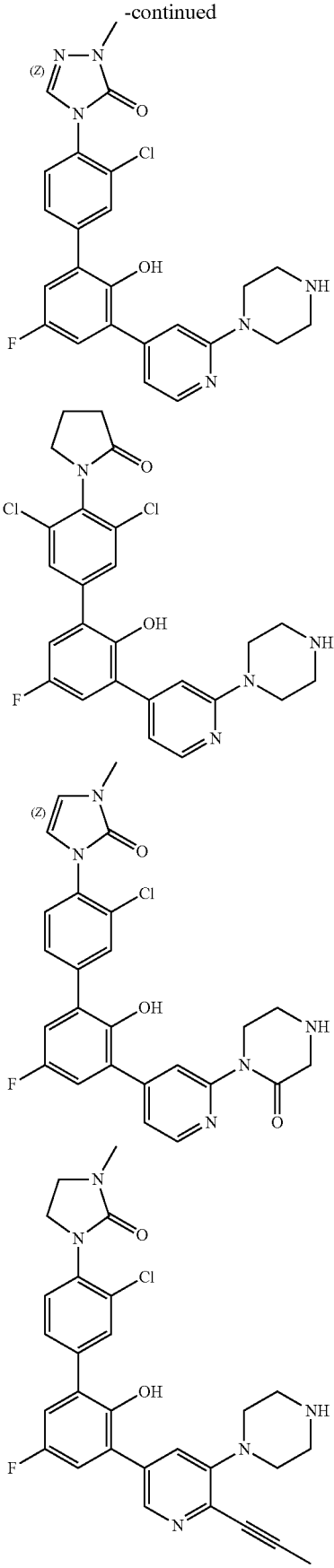
162
-continued
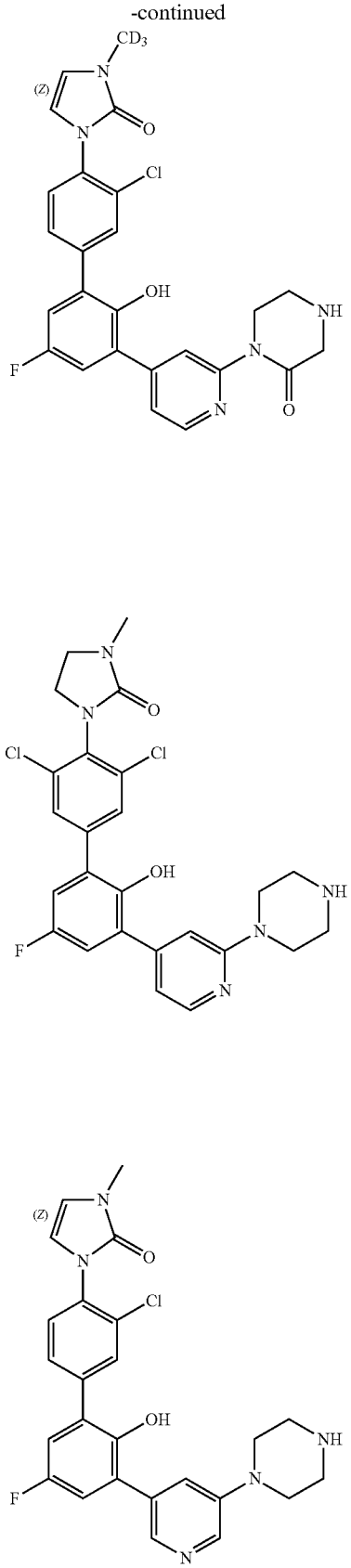

163
-continued
164
-continued
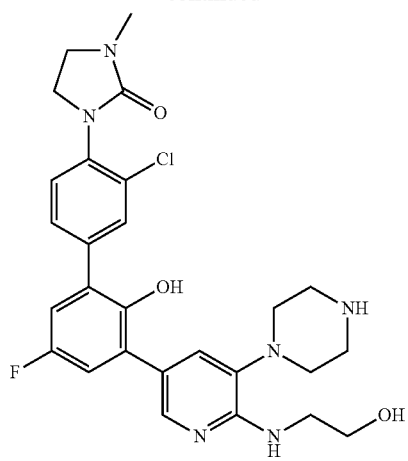
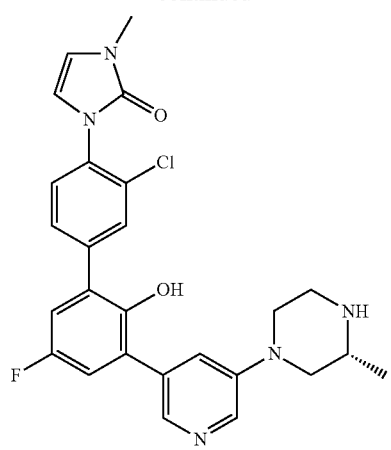
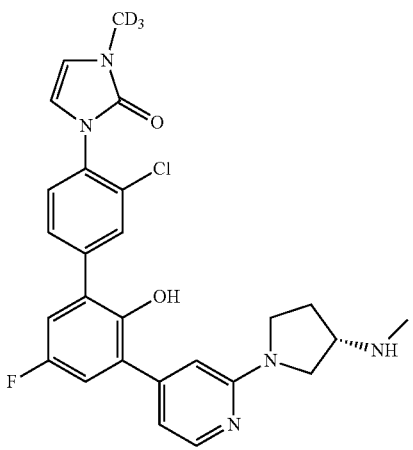
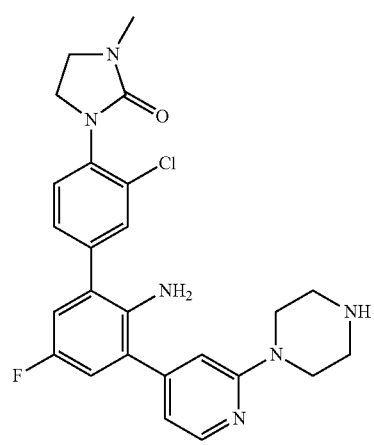
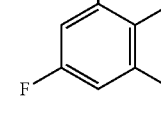

165
-continued
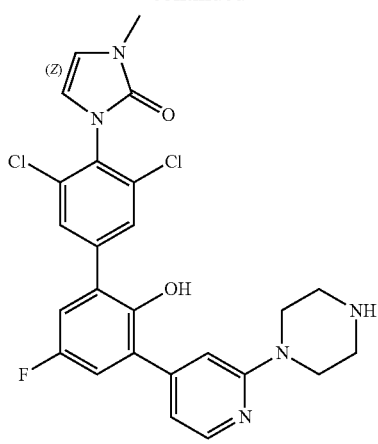
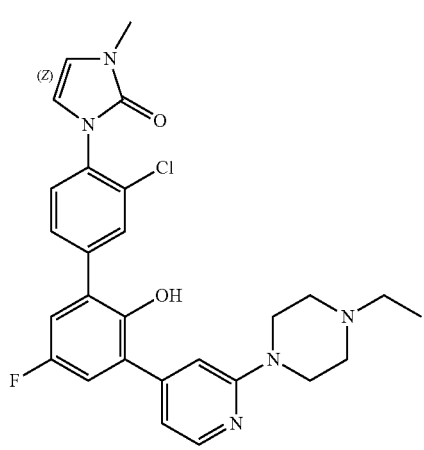
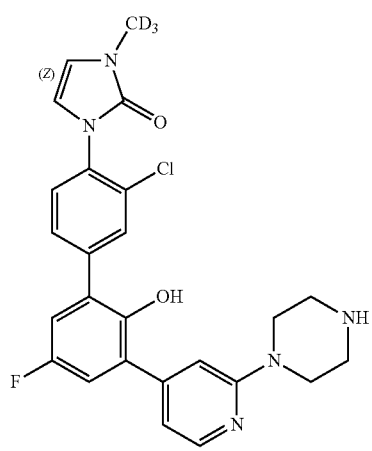
166
-continued
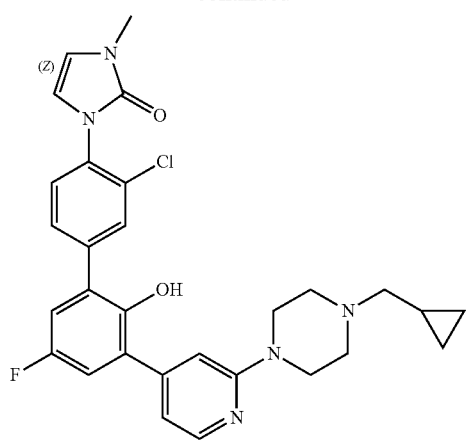
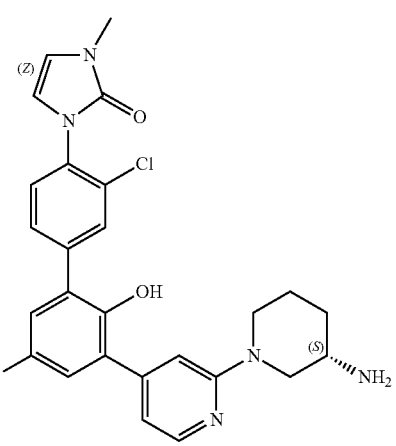
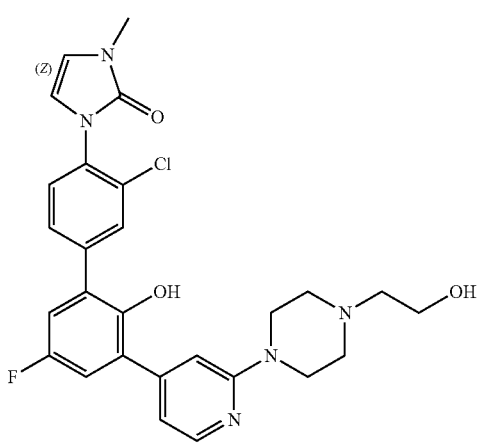

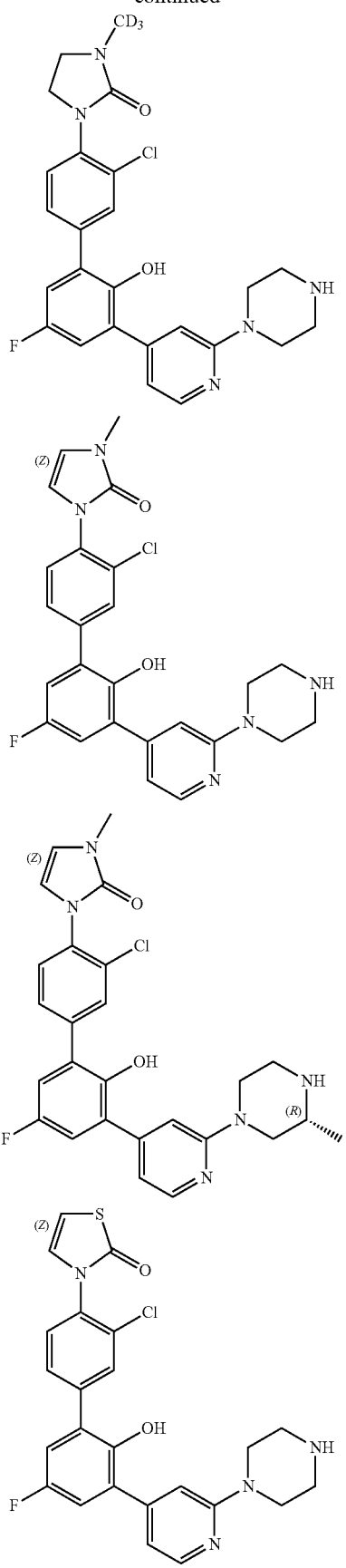
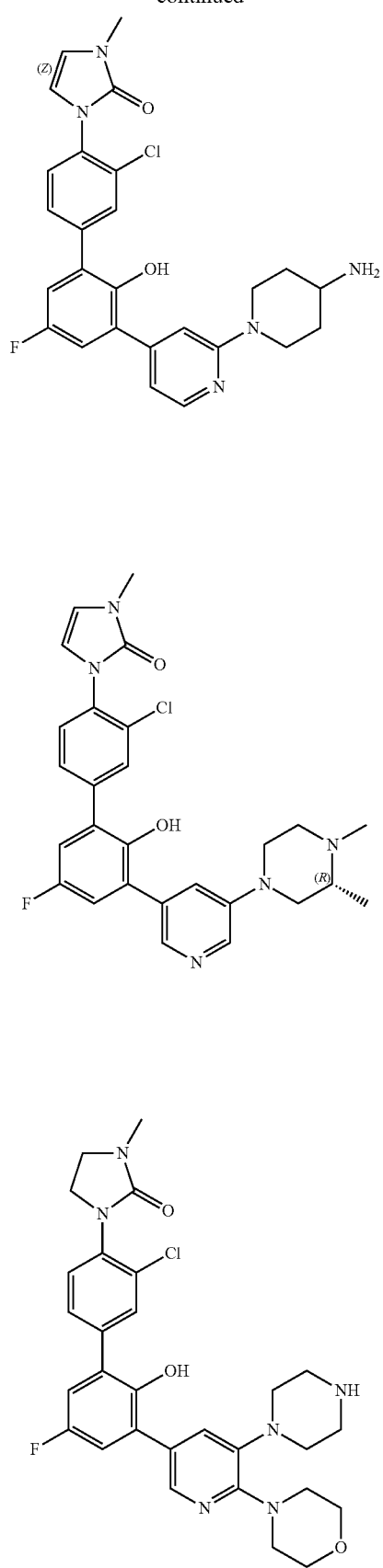

169
-continued
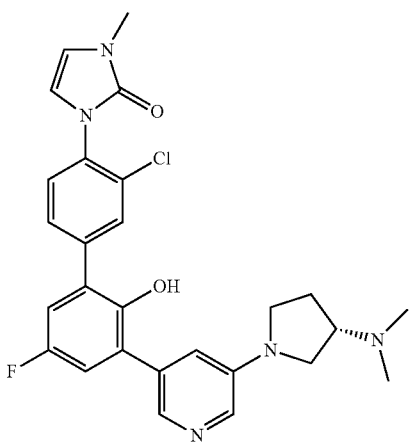
170
-continued
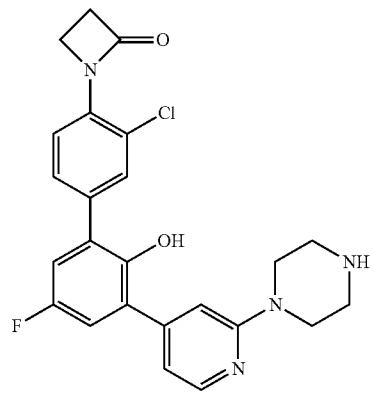
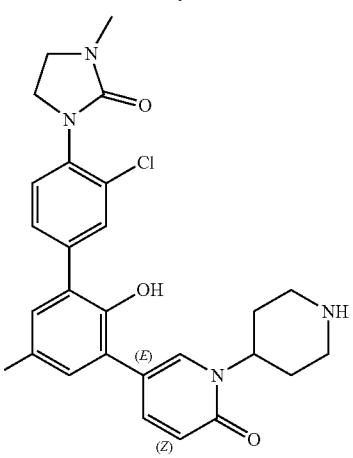
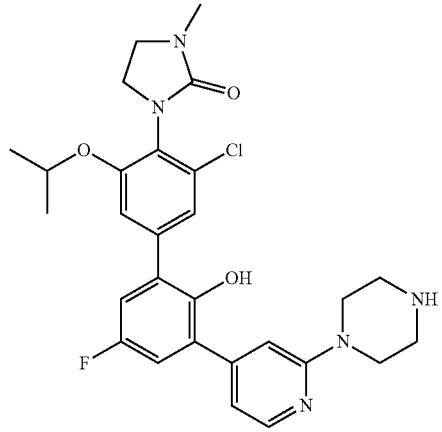
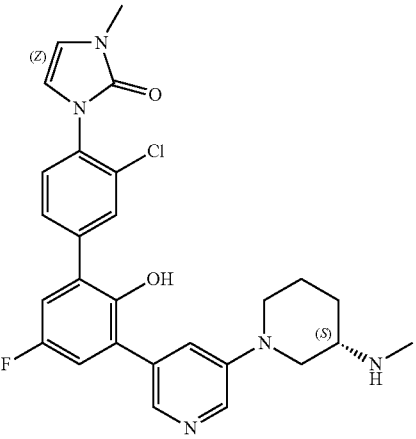

-continued
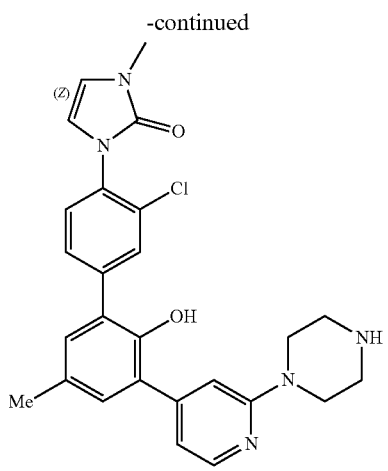
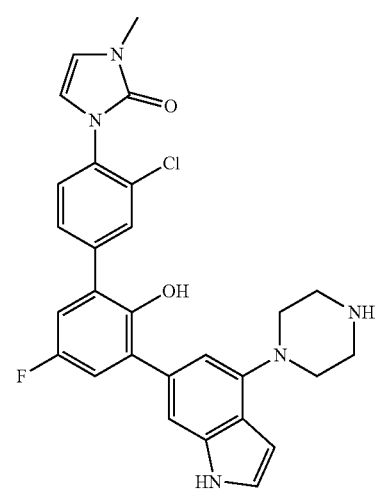
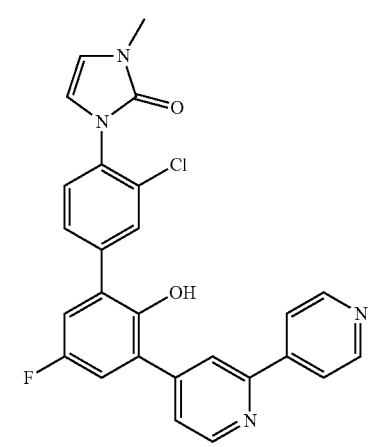
-continued
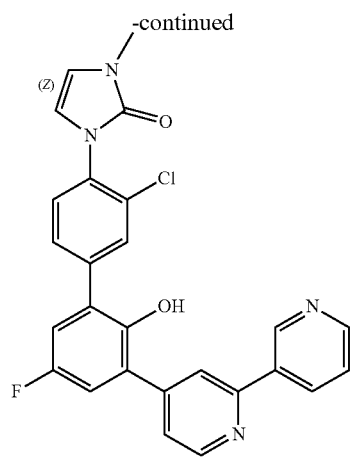
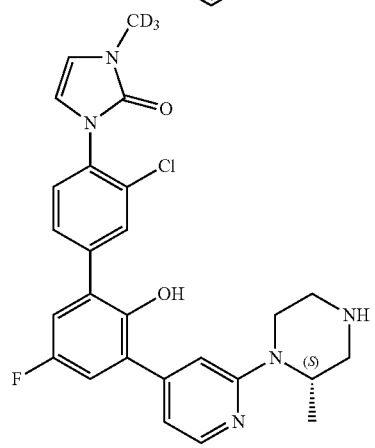
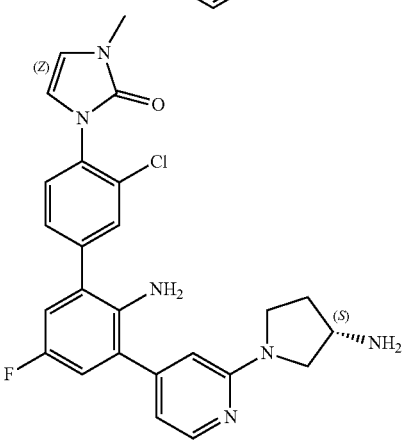
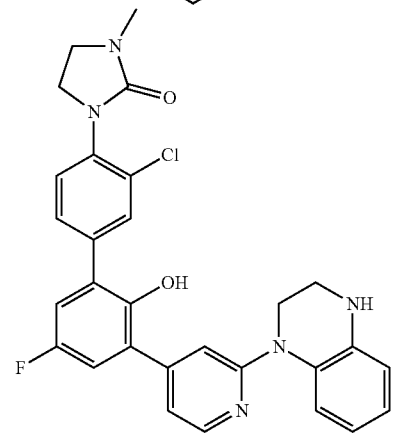

173
-continued
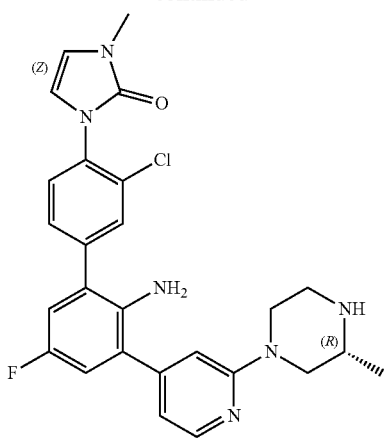
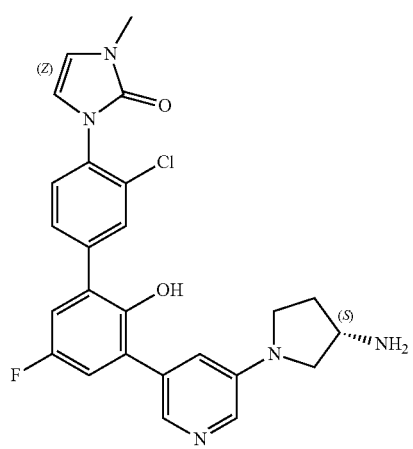
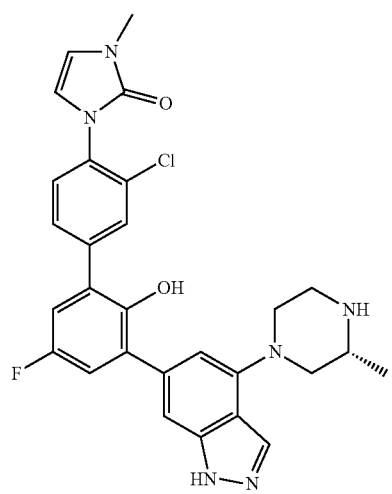
174
-continued
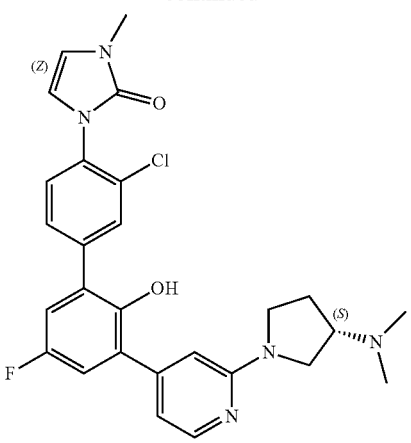
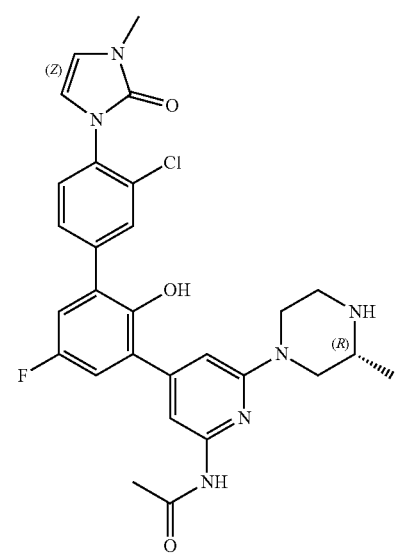
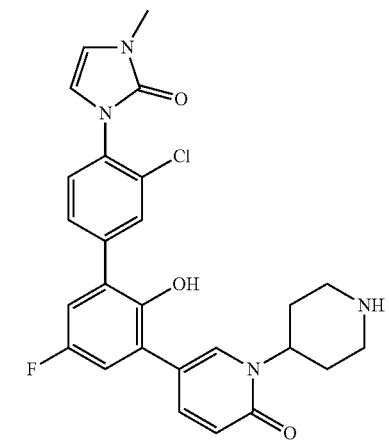

175
-continued
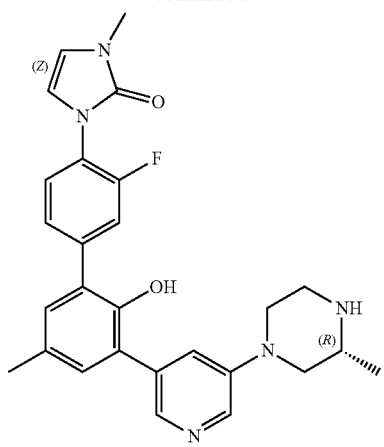
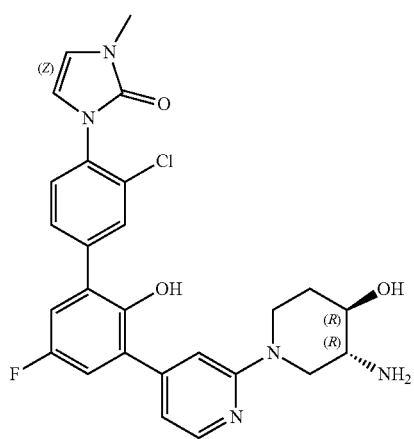
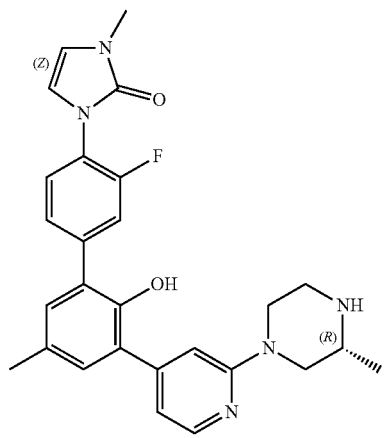
176
-continued
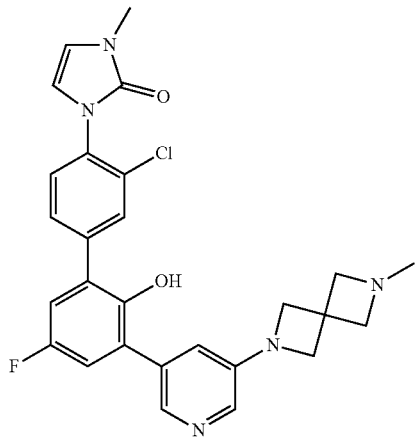
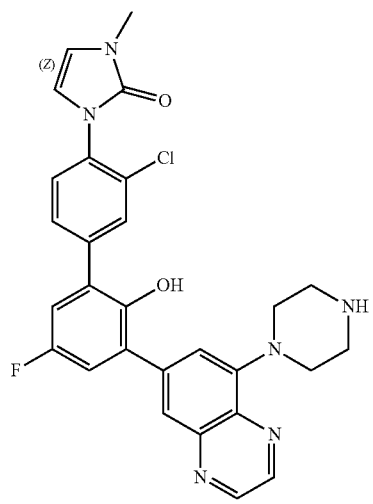
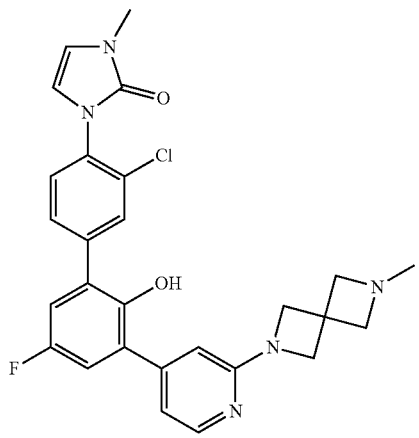

177
-continued
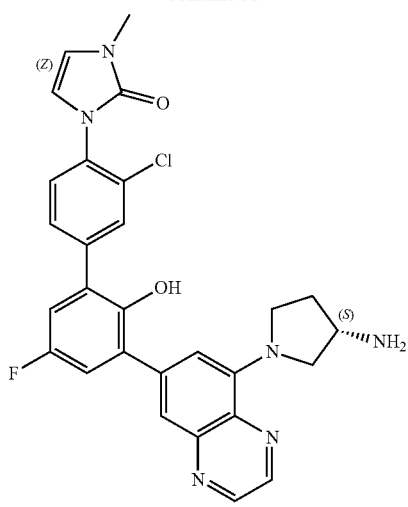
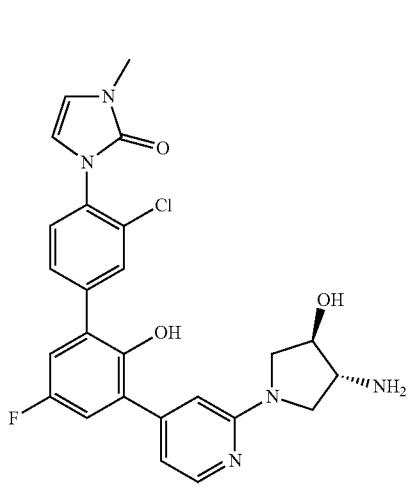
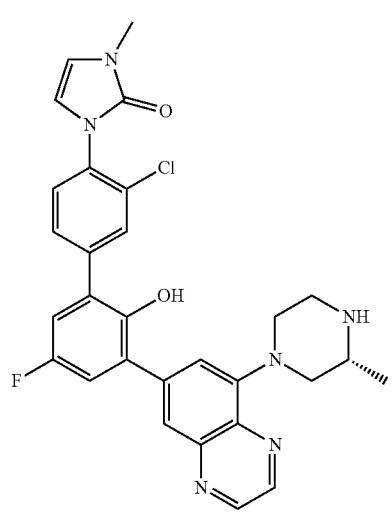
178
-continued
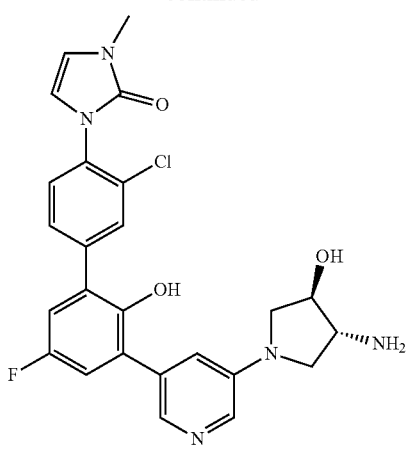
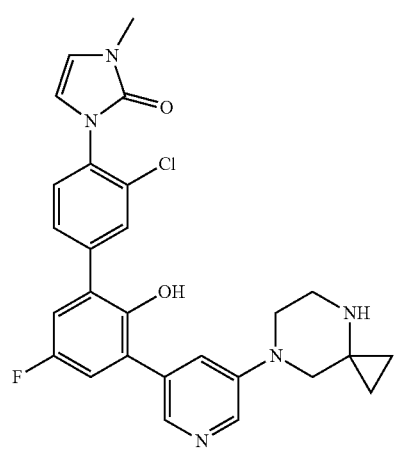
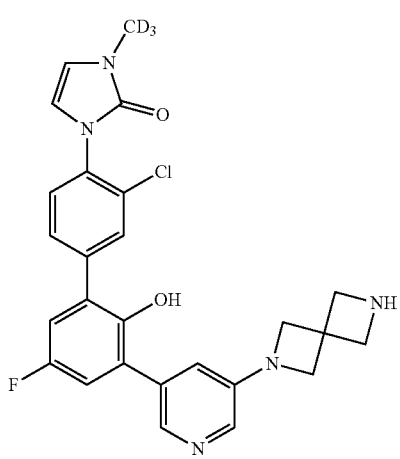

179
-continued
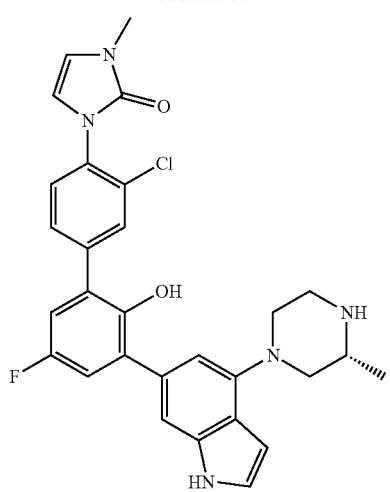
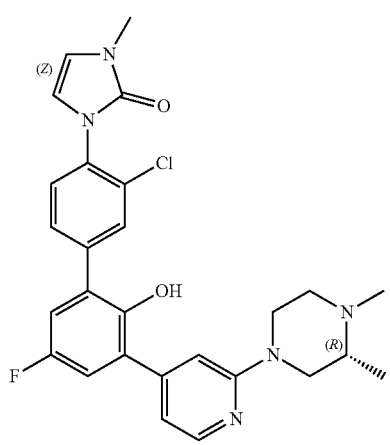
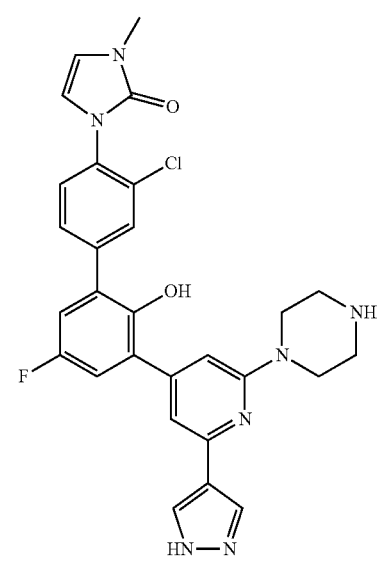
180
-continued
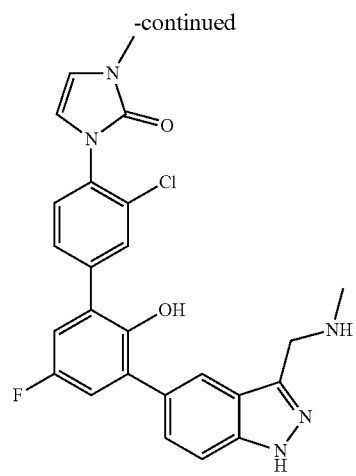
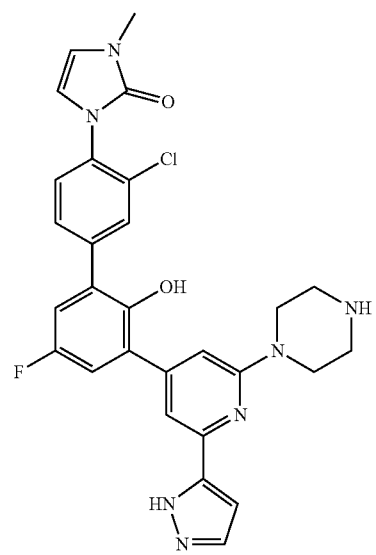
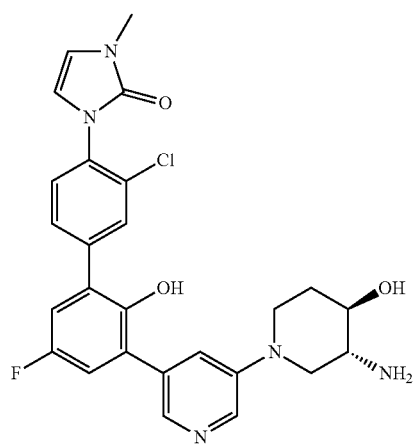

181
-continued
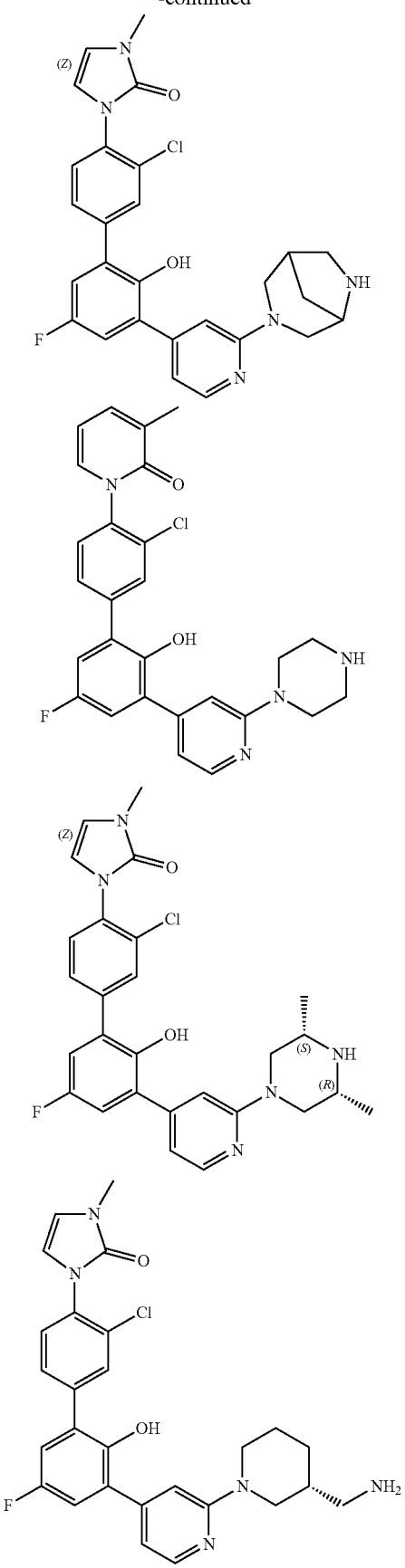
182
-continued
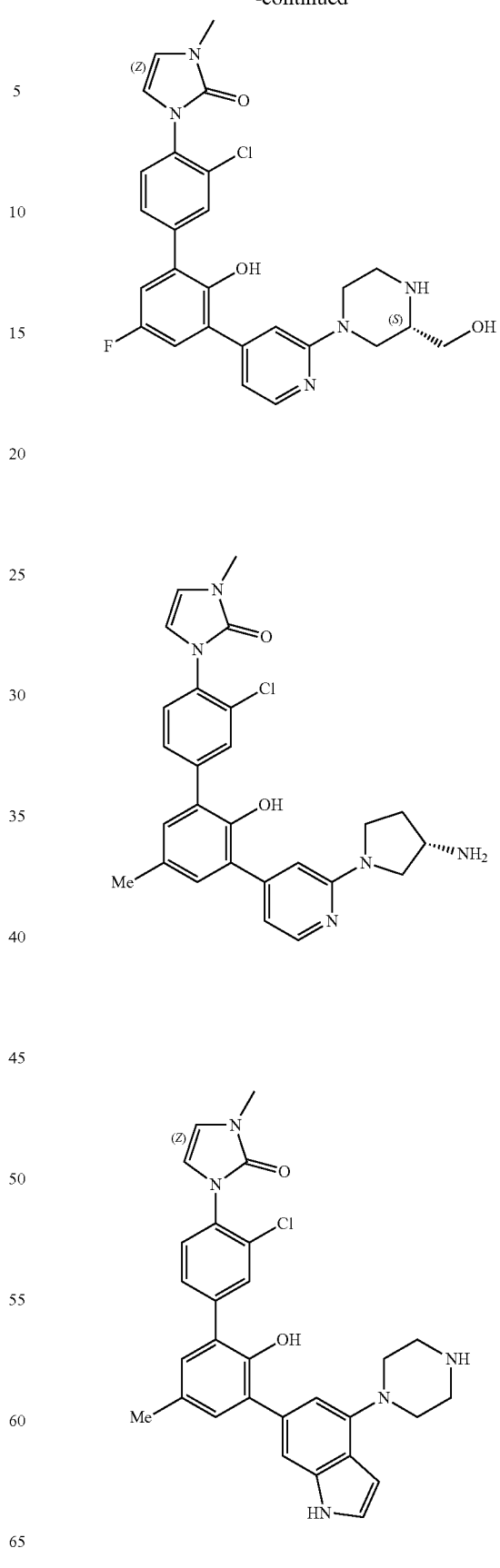

-continued
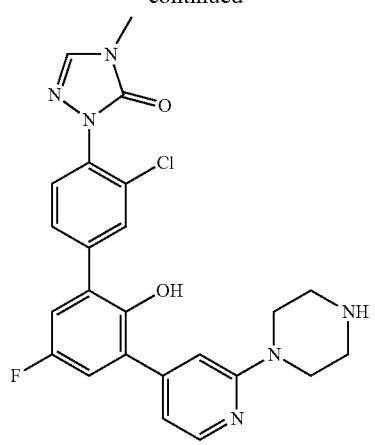
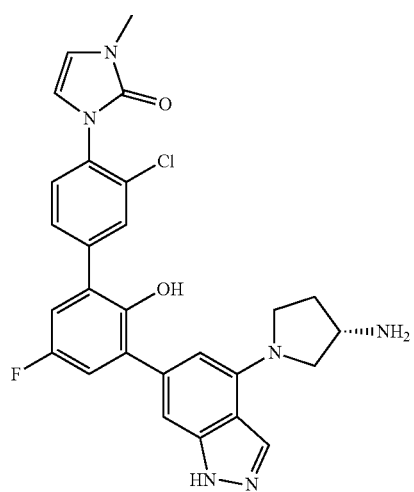
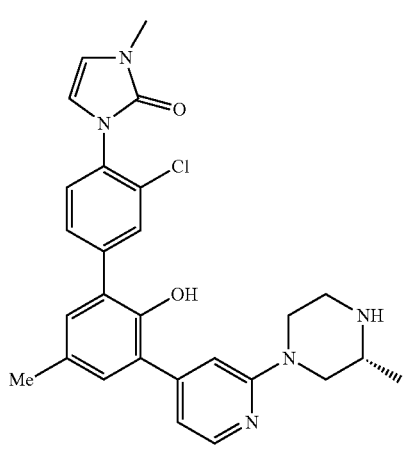
-continued
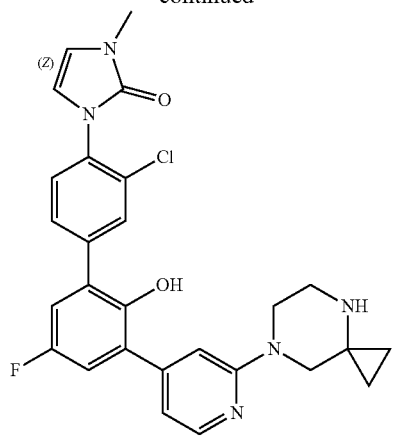
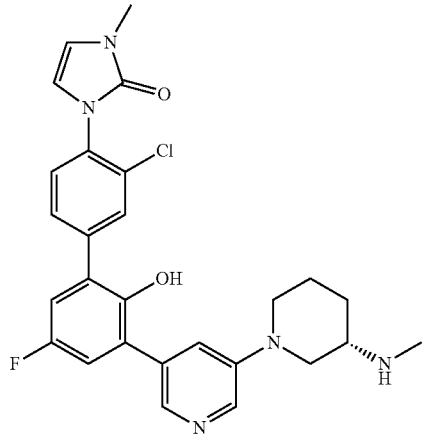
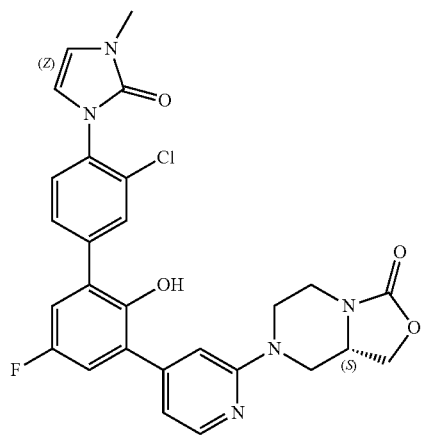
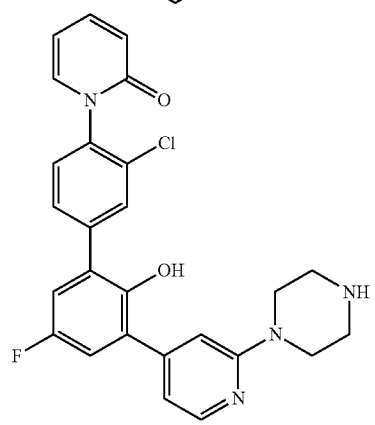

185
-continued
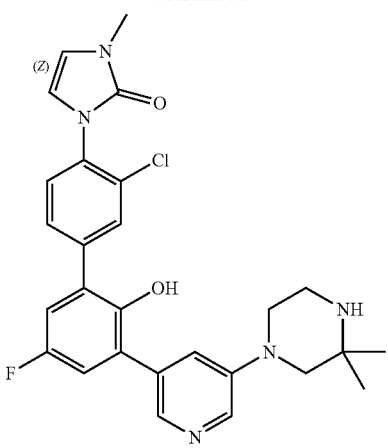
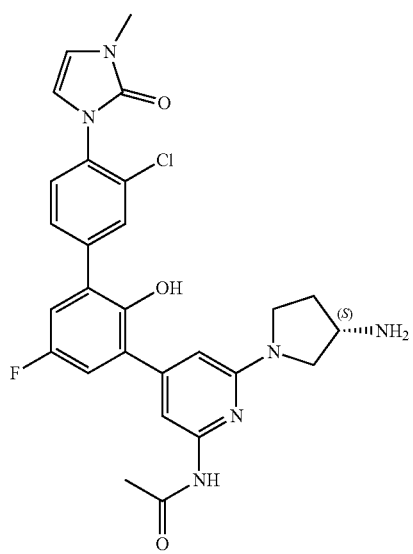
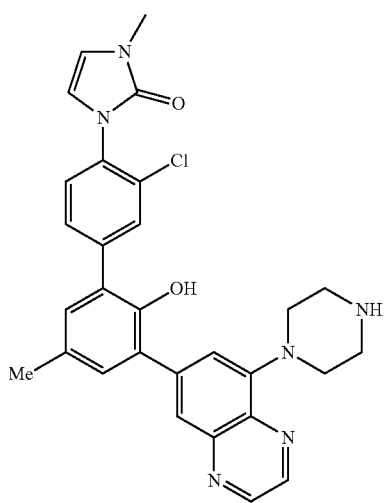
186
-continued
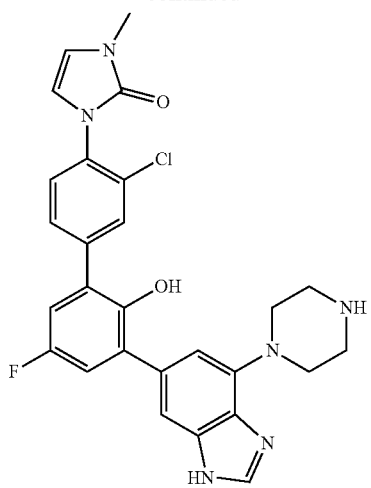
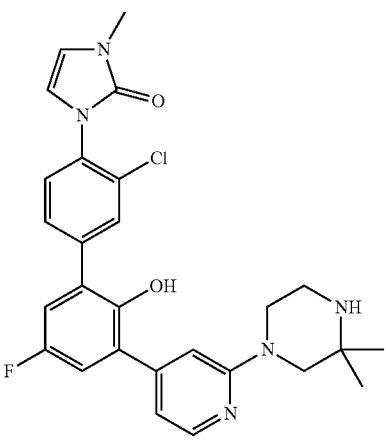
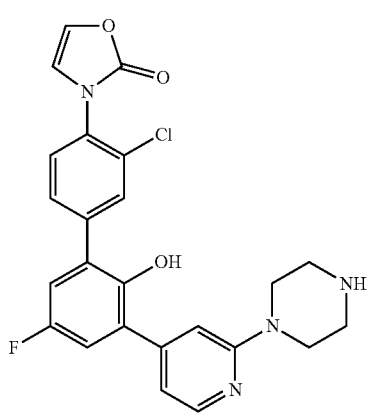

187
-continued
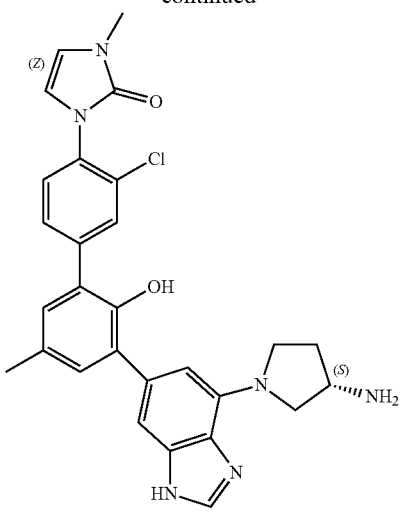
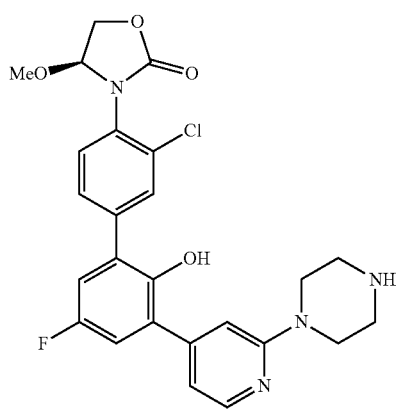
188
-continued
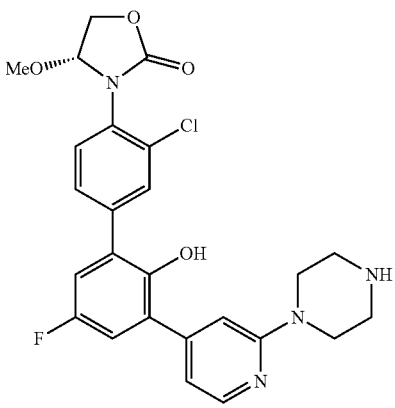
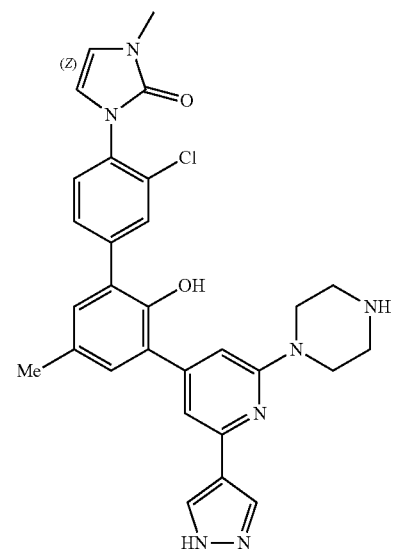
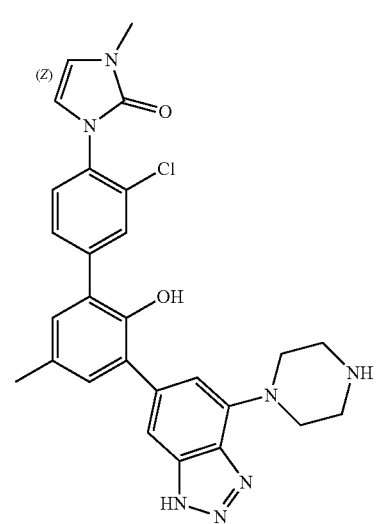
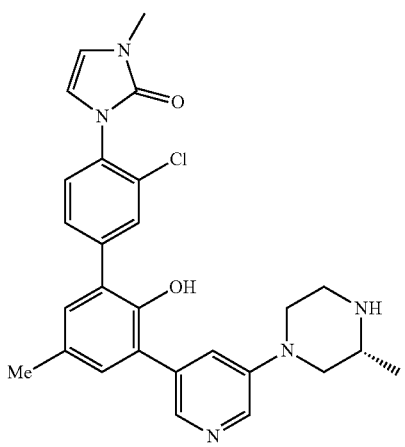

189
-continued
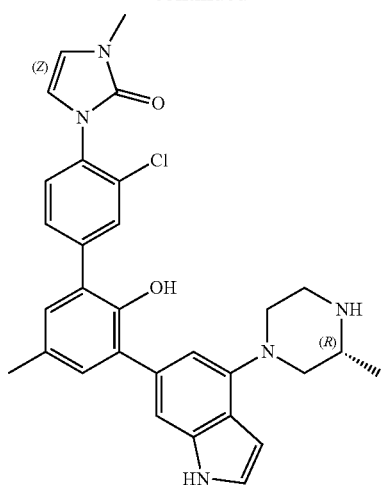
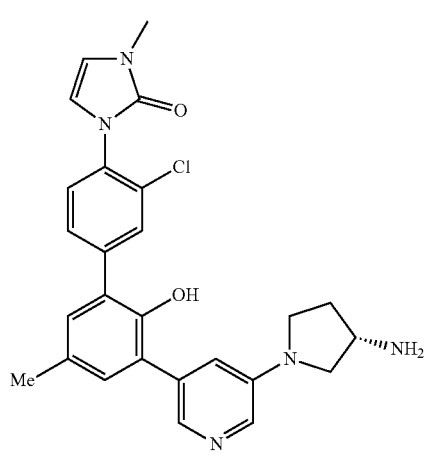
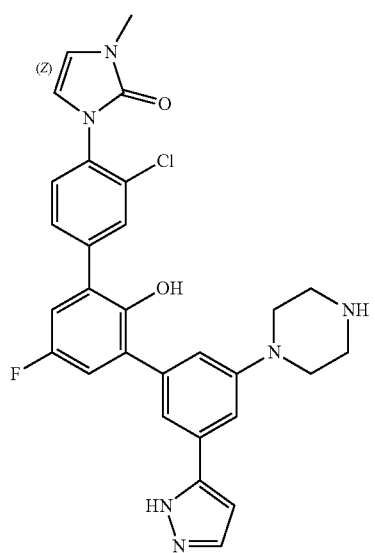
190
-continued
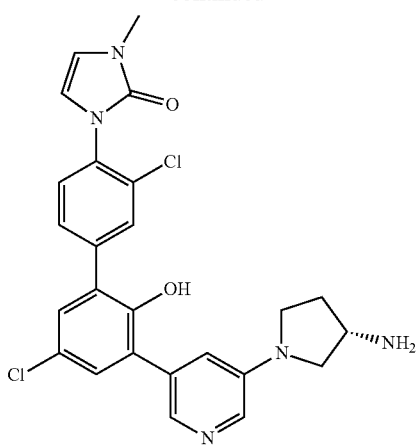
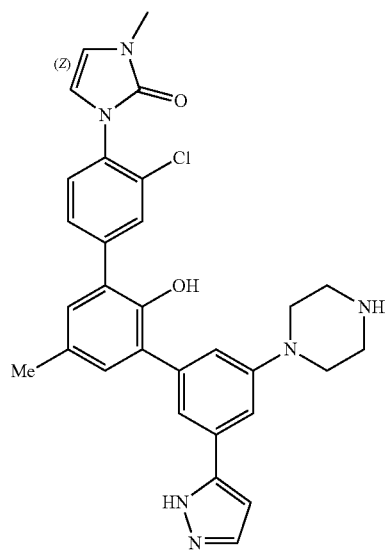
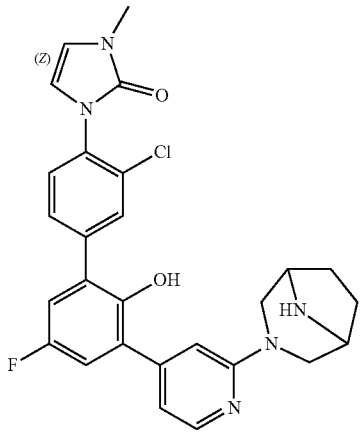

191
-continued
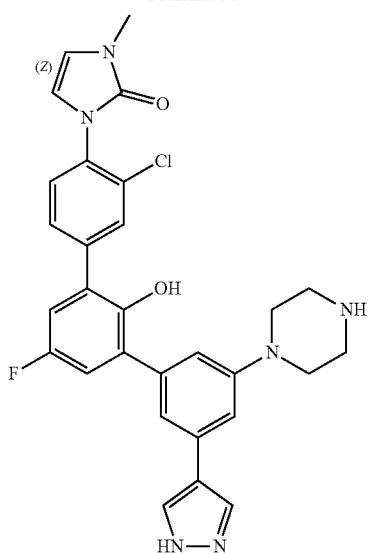
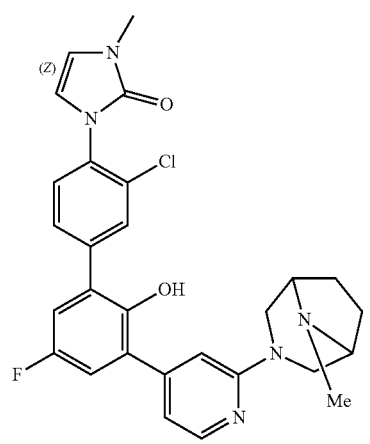
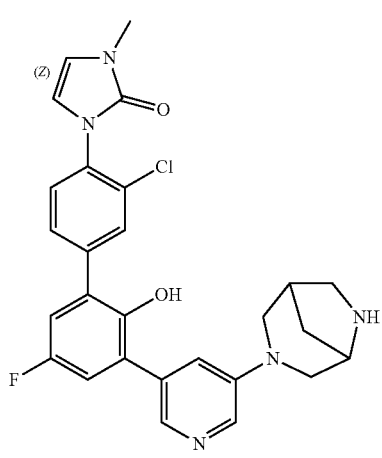
192
-continued
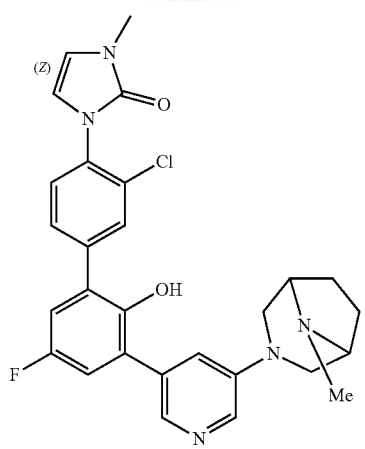
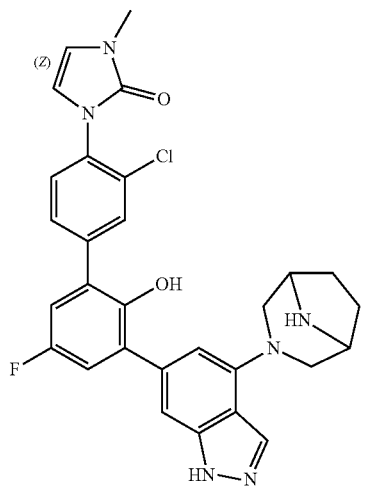
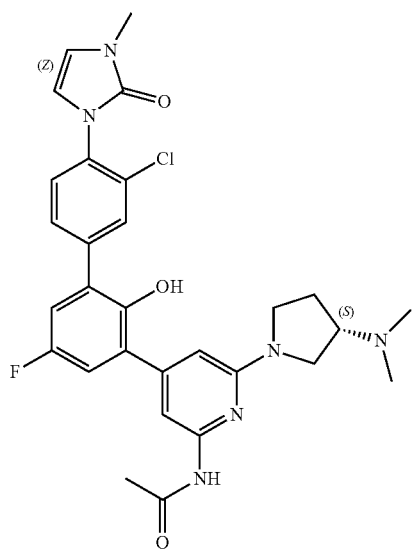

193
-continued
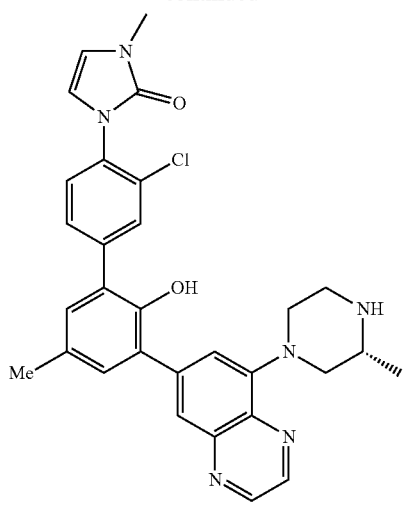
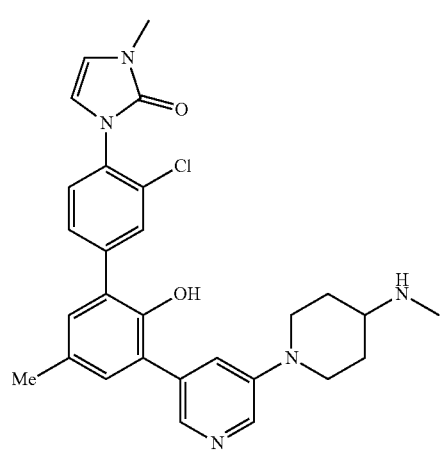
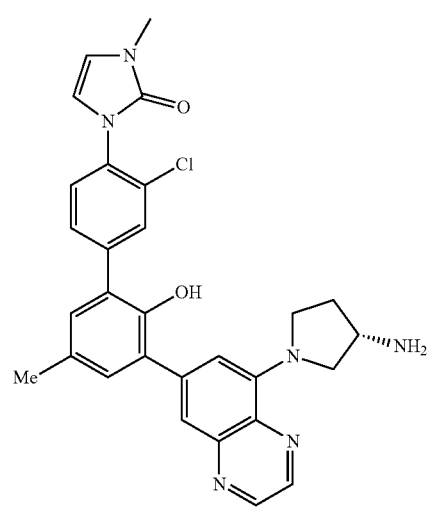
194
-continued
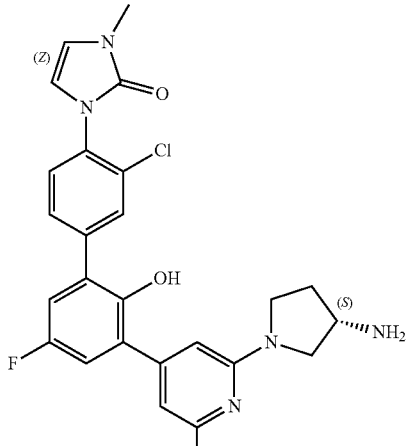
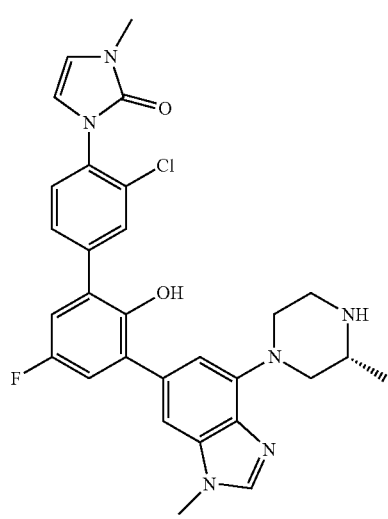
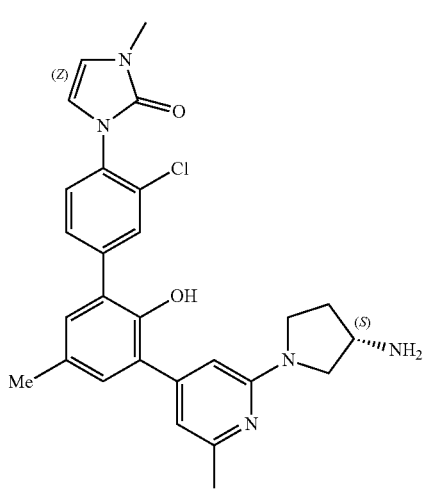

195
-continued
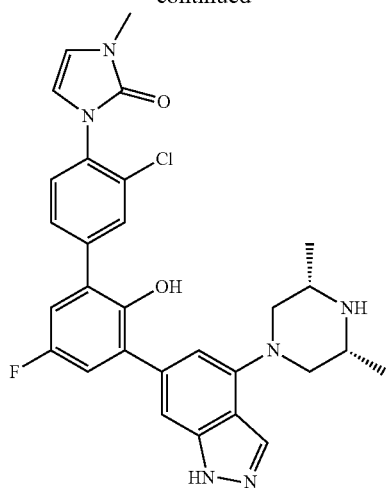
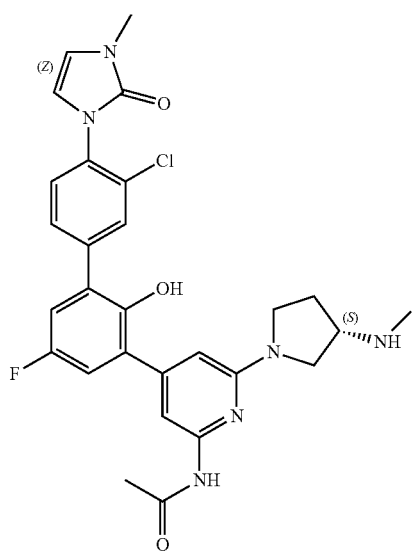
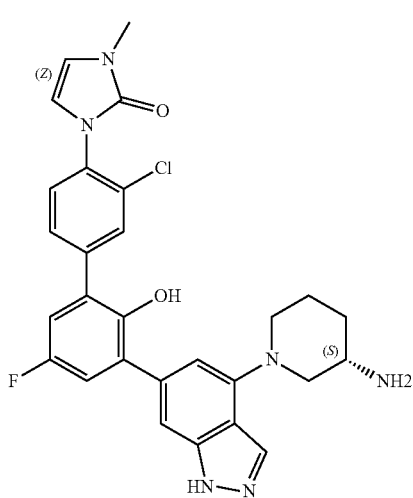
196
-continued
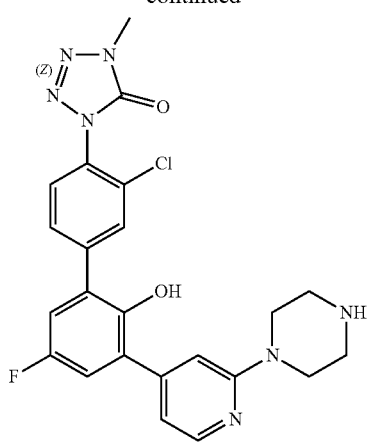
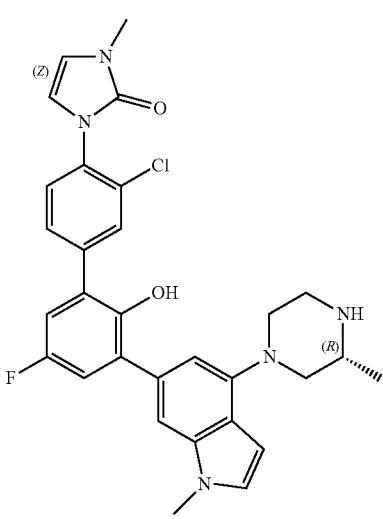
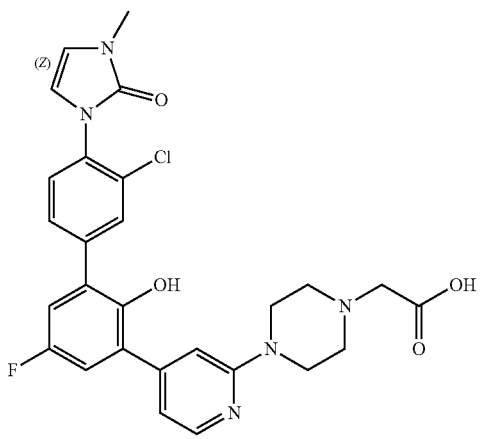

197
-continued
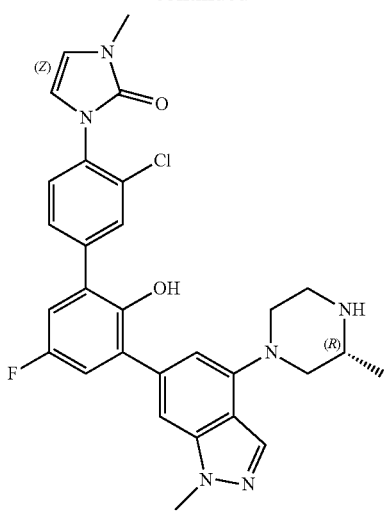
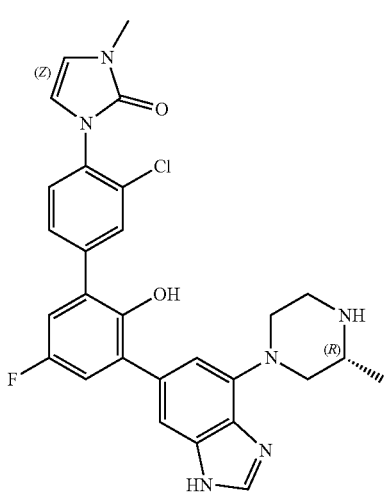
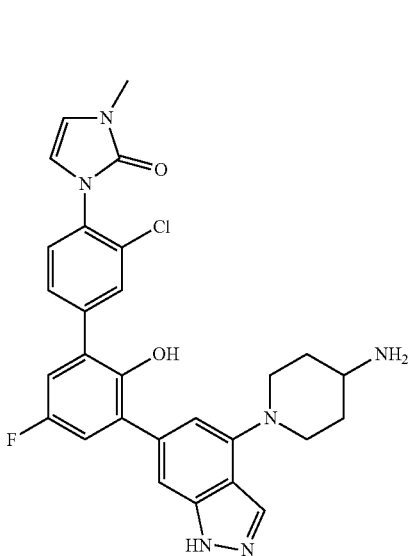
198
-continued
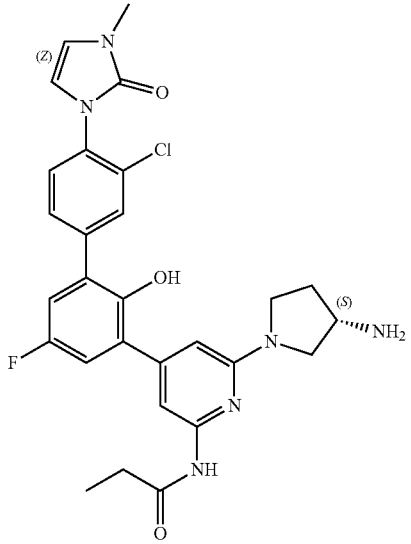
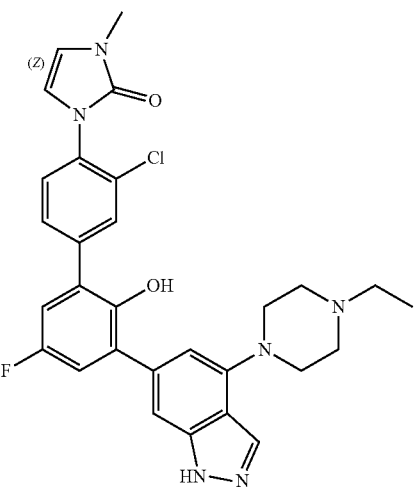
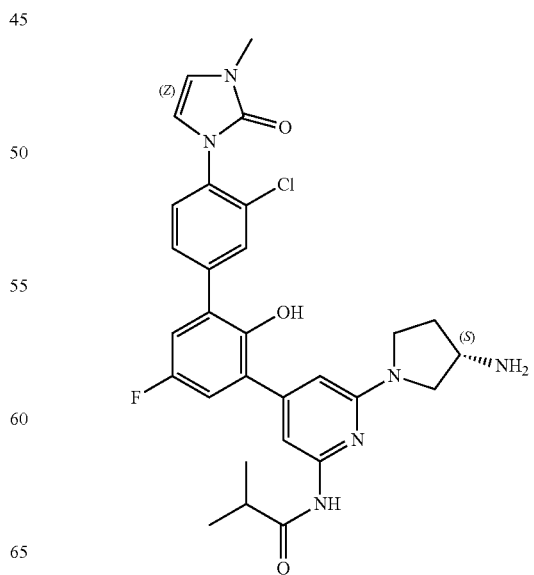

199
-continued
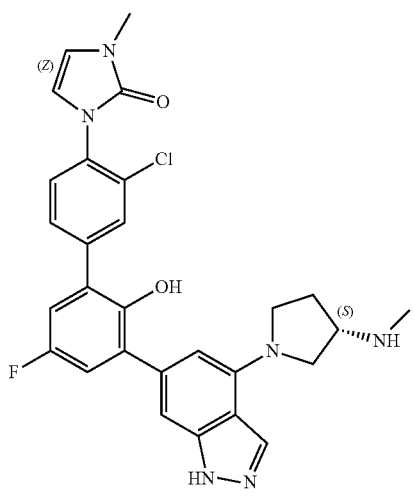
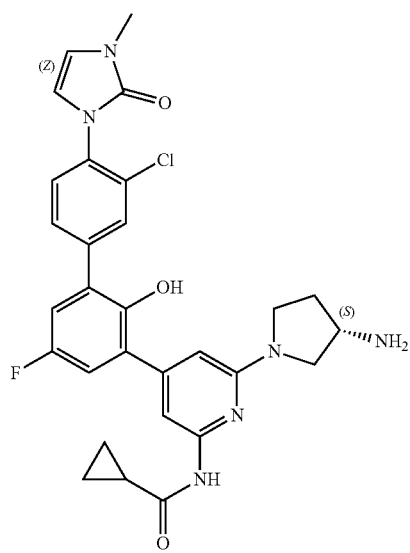
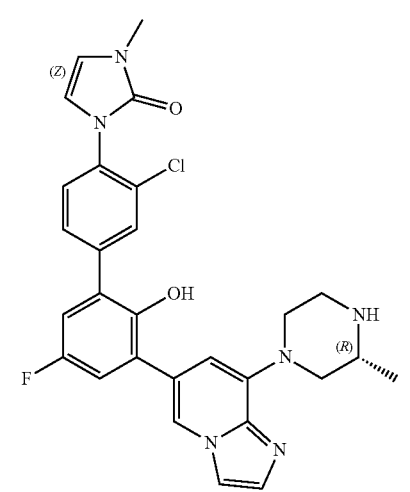
200
-continued
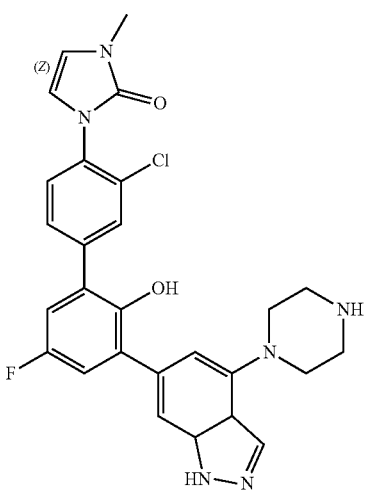
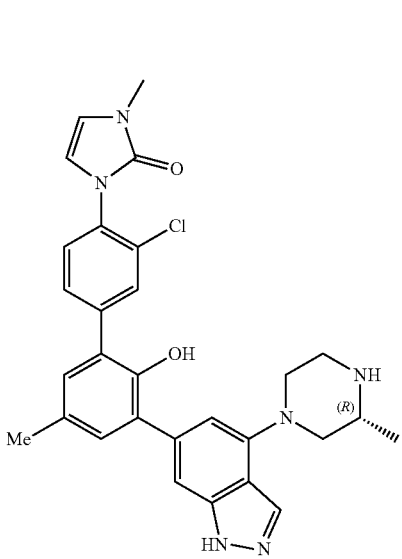
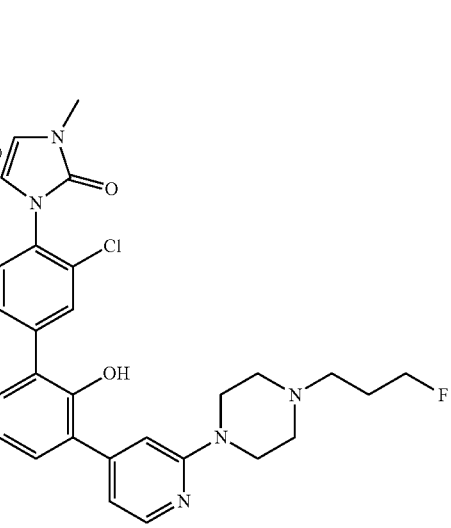

201
-continued
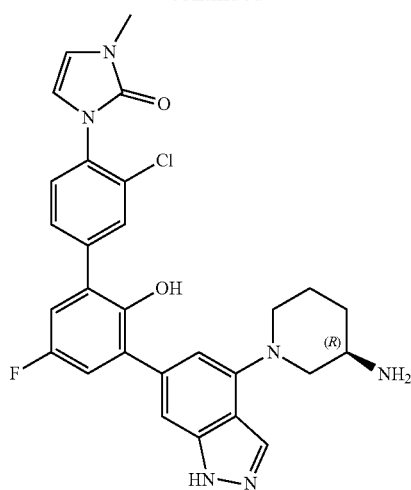
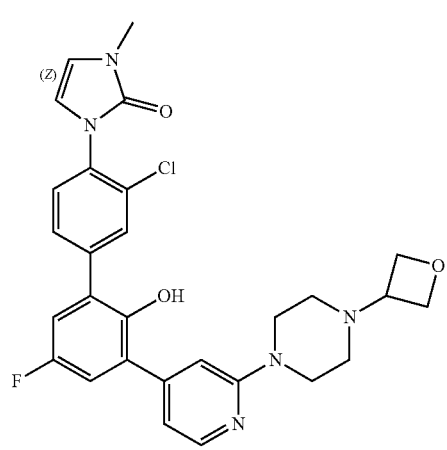
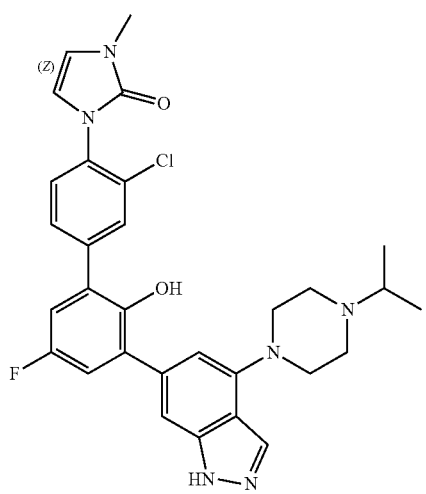
202
-continued
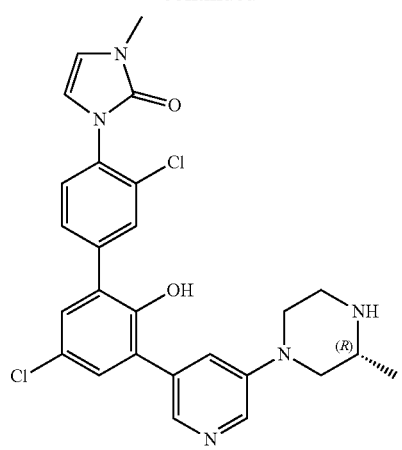
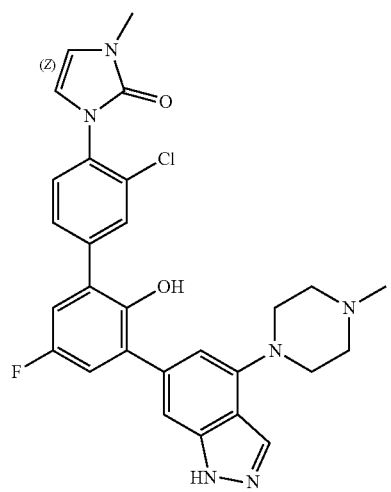
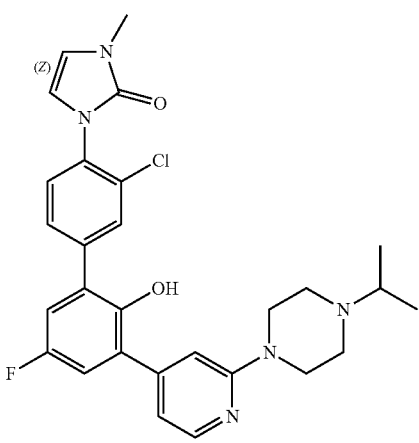

-continued
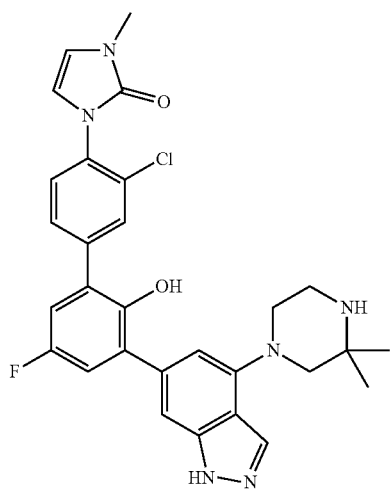
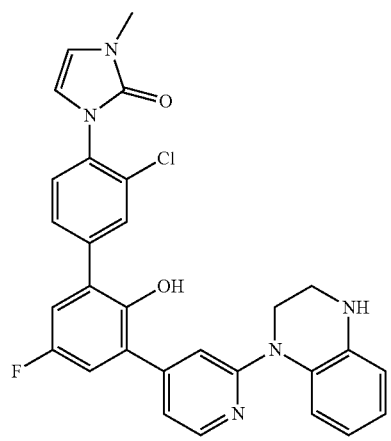
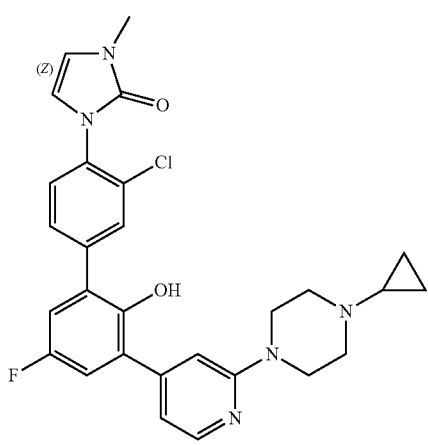
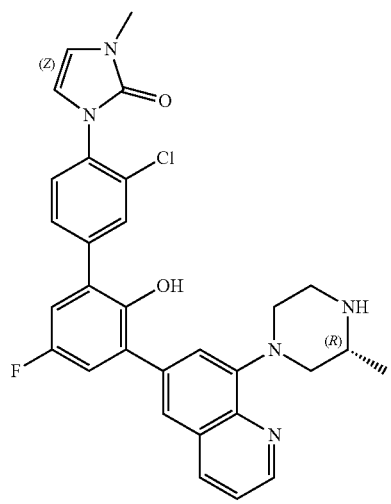
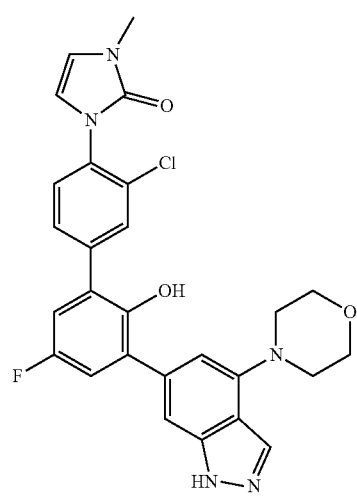
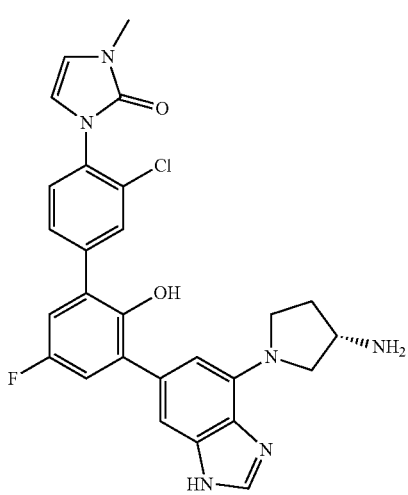

205
-continued
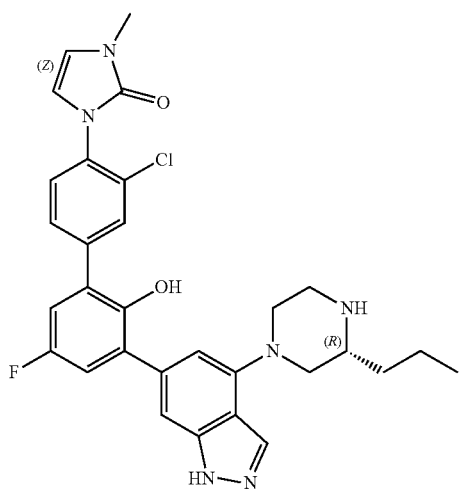
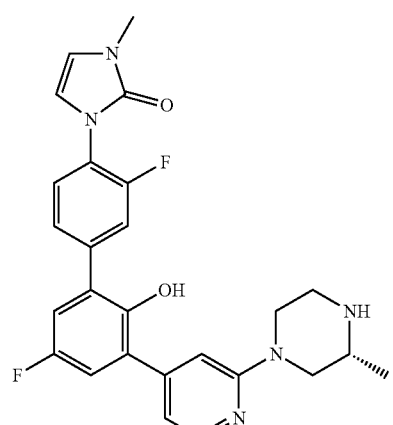
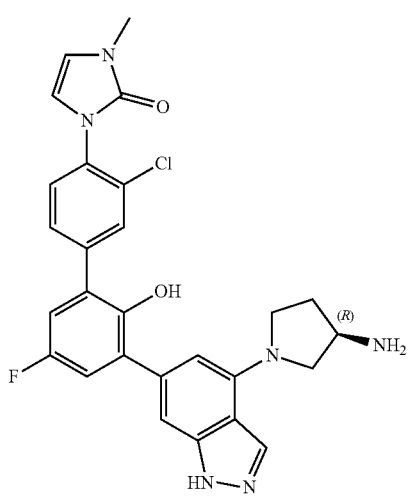
206
-continued
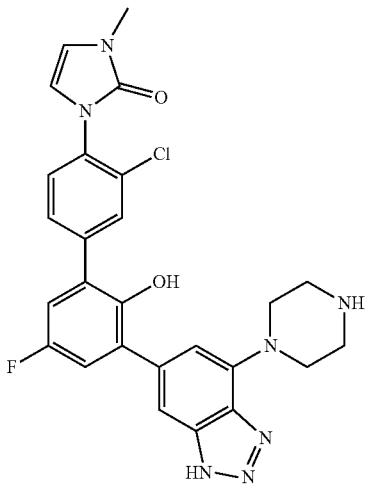
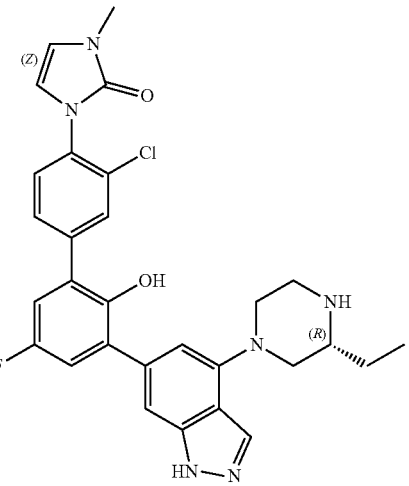
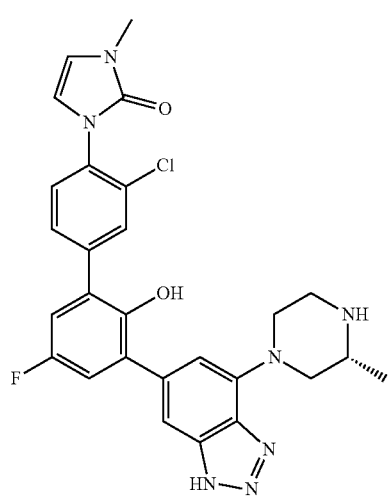

207
-continued
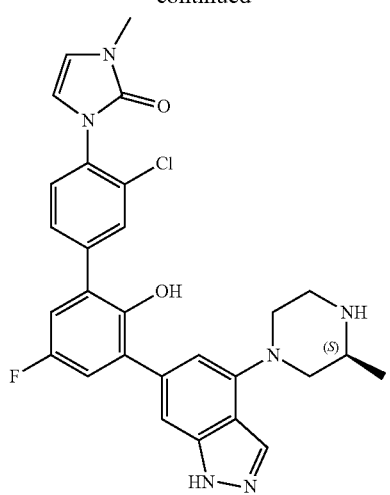
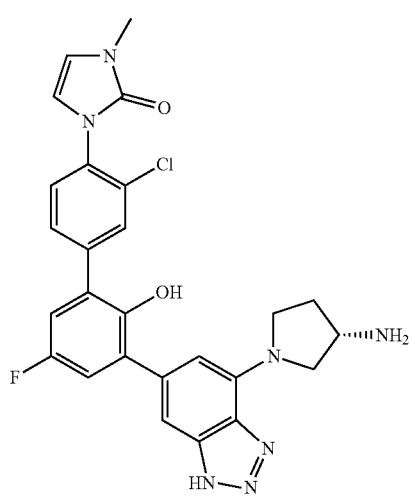
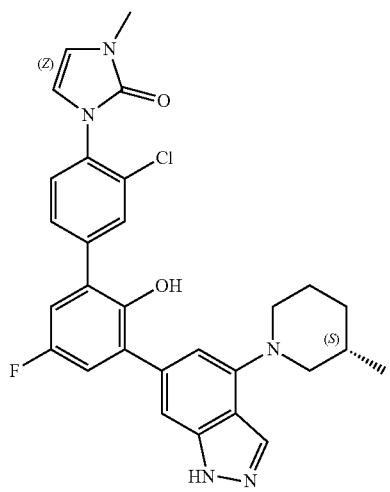
208
-continued
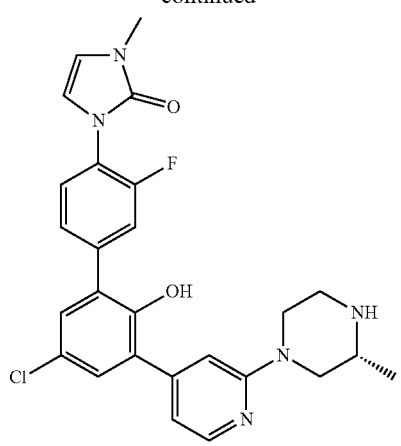
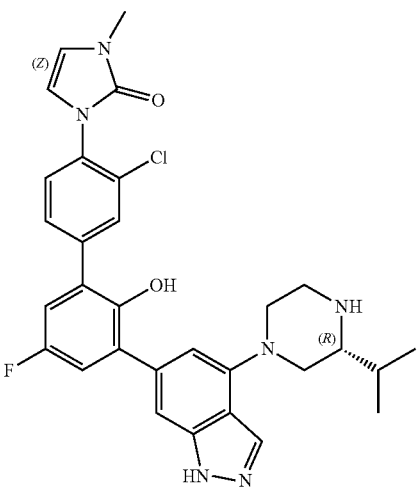
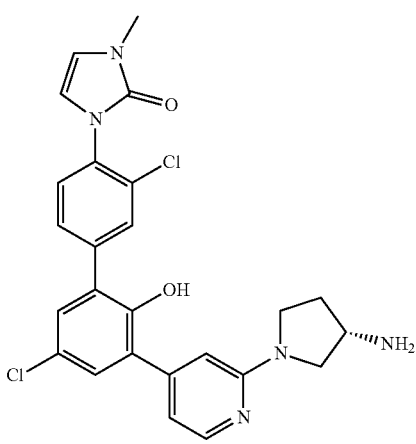

-continued
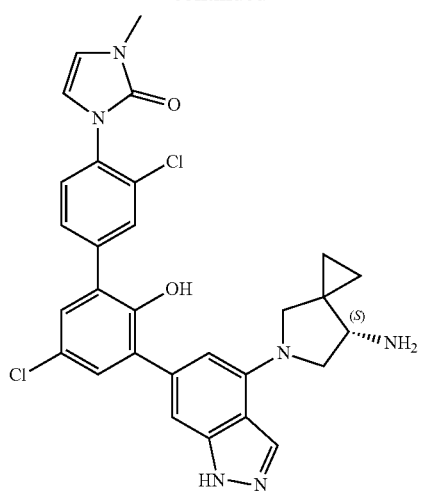
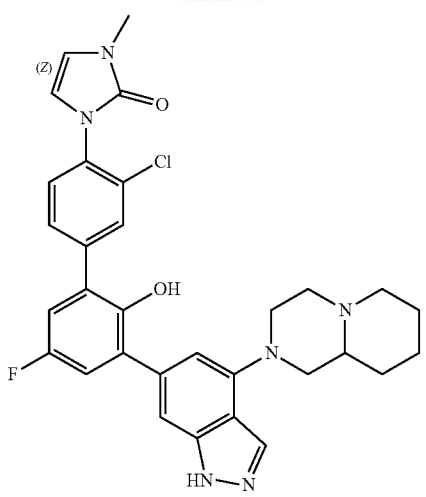
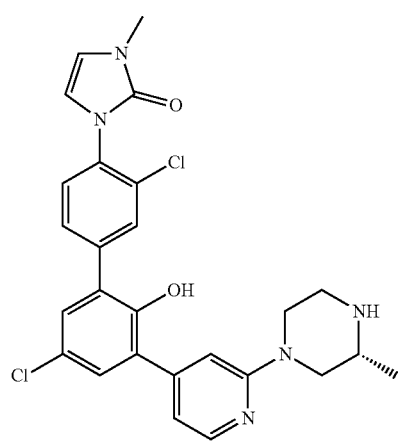
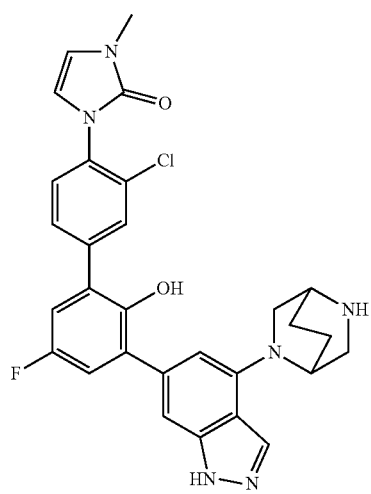
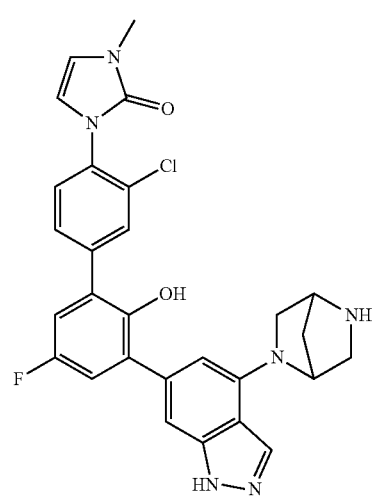
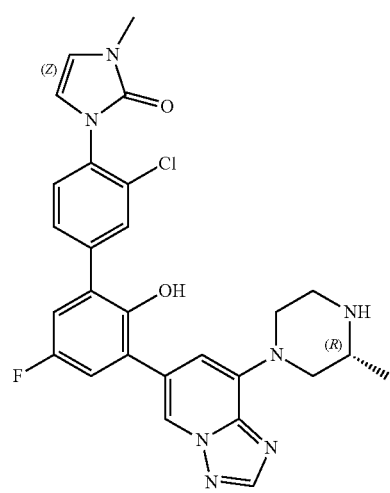

211
-continued
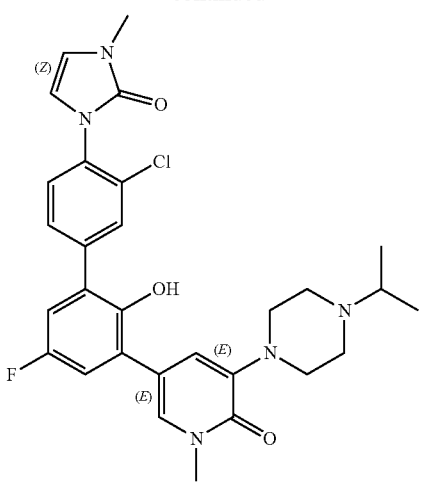
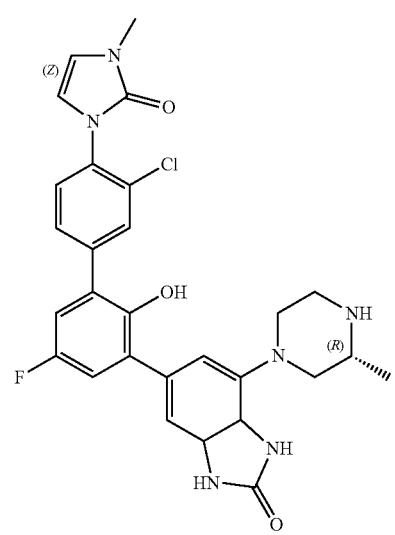
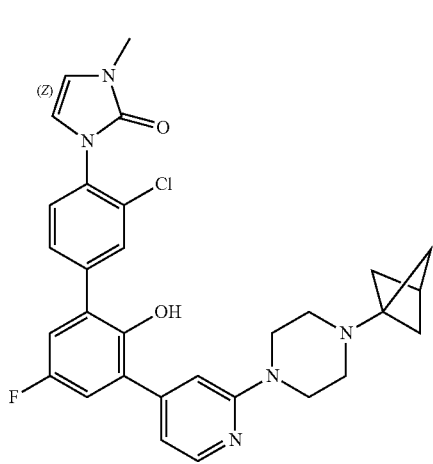
212
-continued
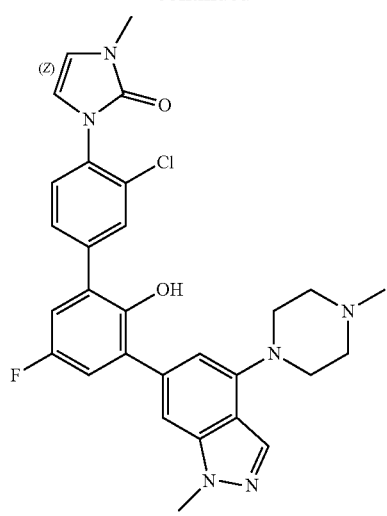
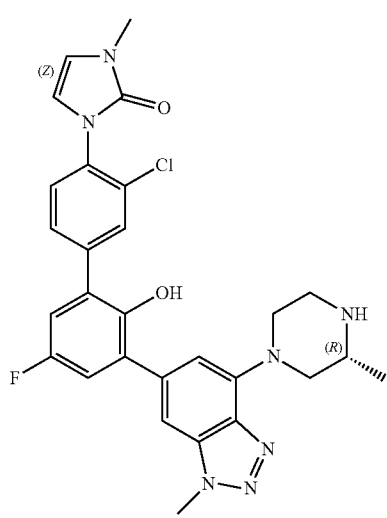

213
-continued
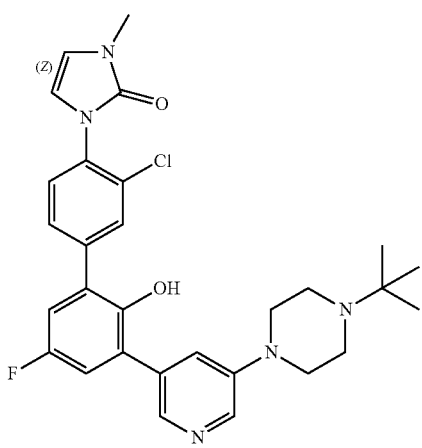
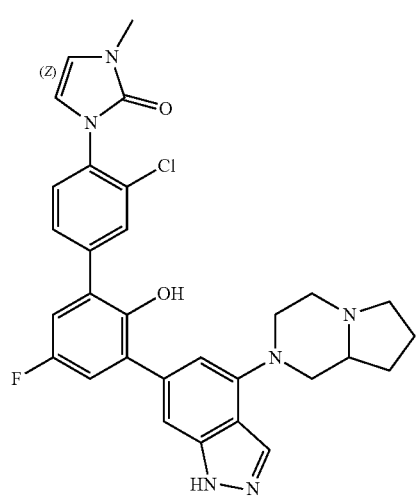
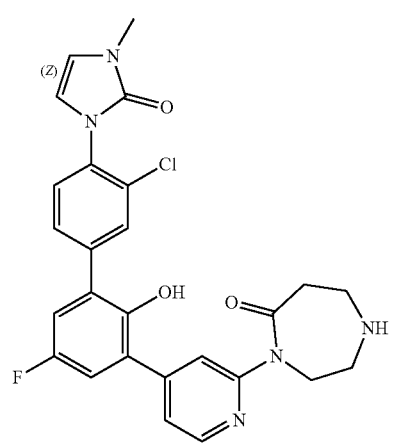
214
-continued
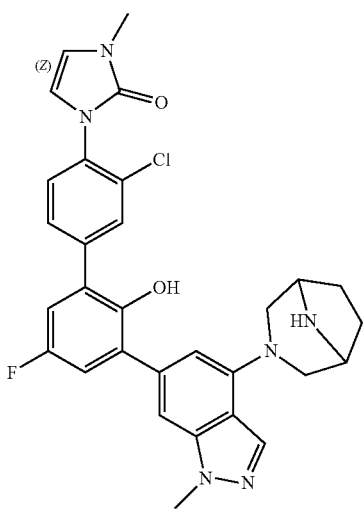
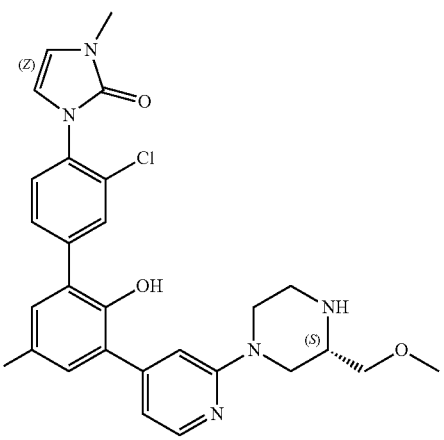
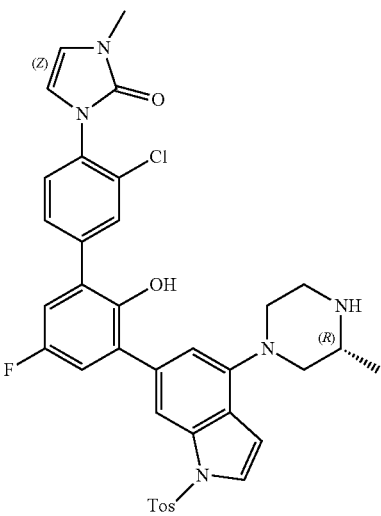

215
-continued
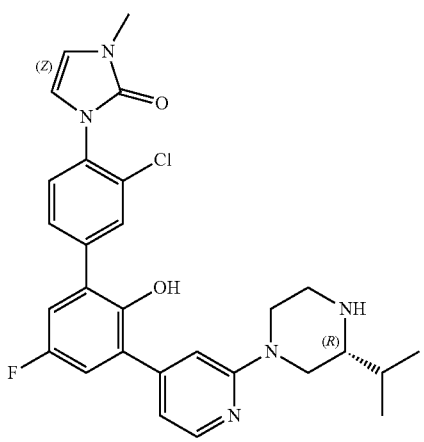
216
-continued
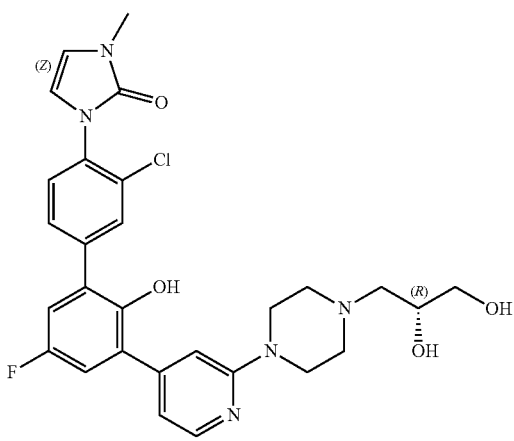
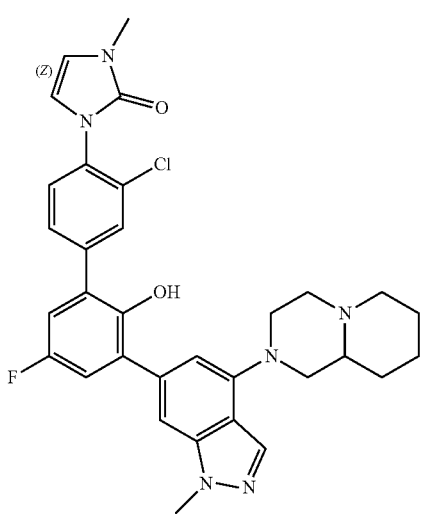
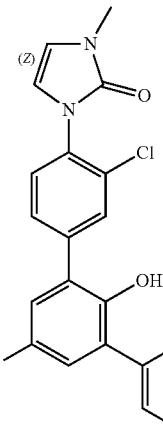
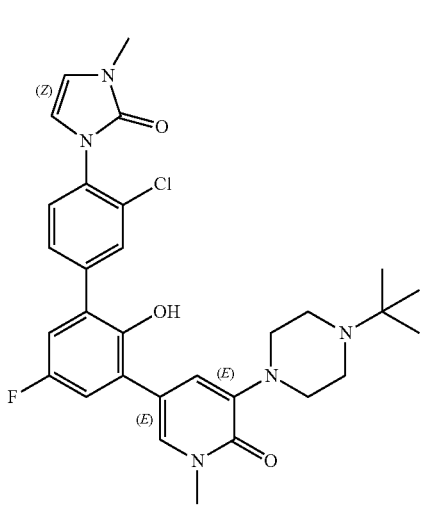
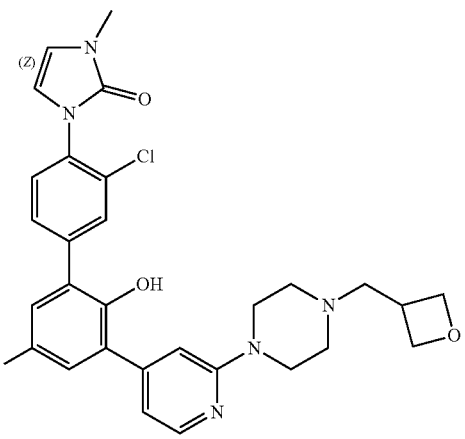

217
-continued
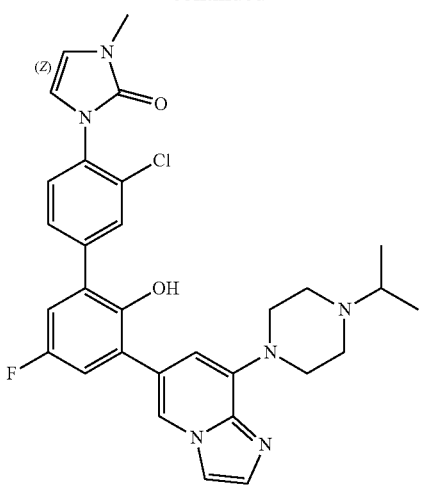
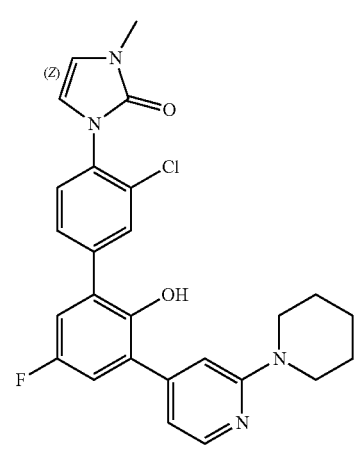
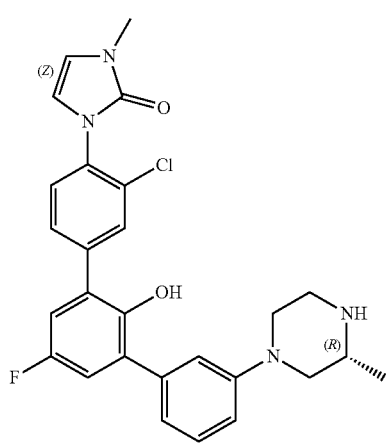
218
-continued
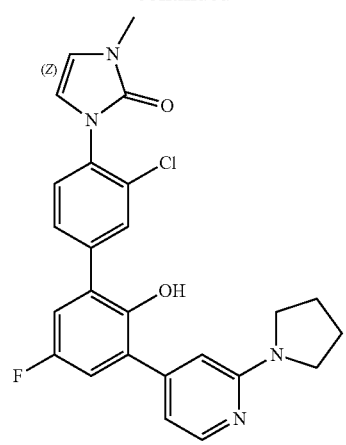
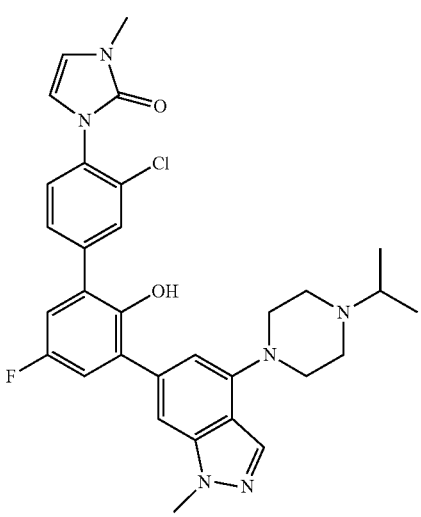
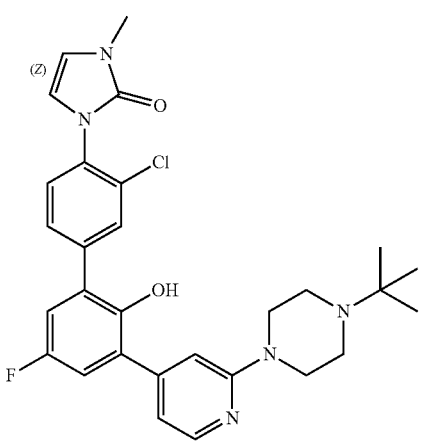

219
-continued
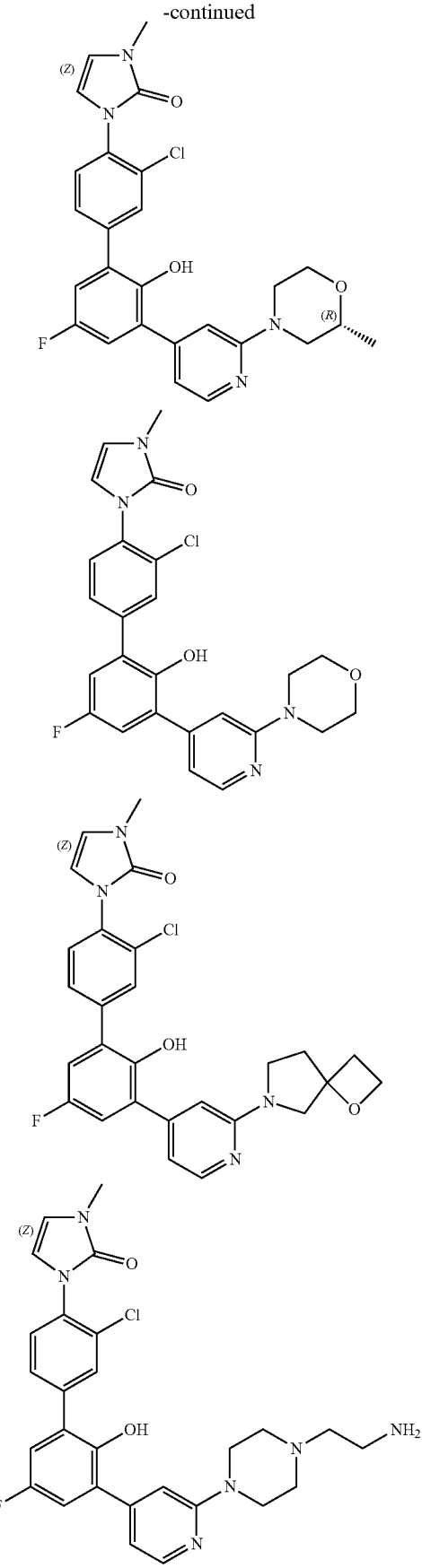
220
-continued
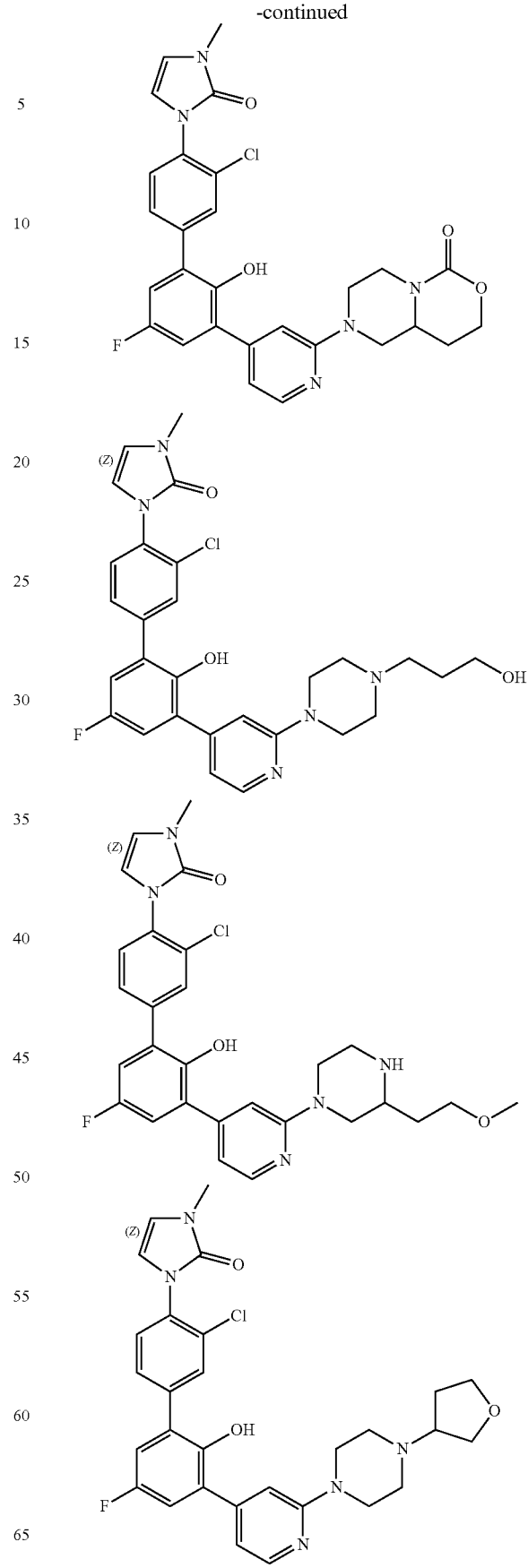

221
-continued
222
-continued
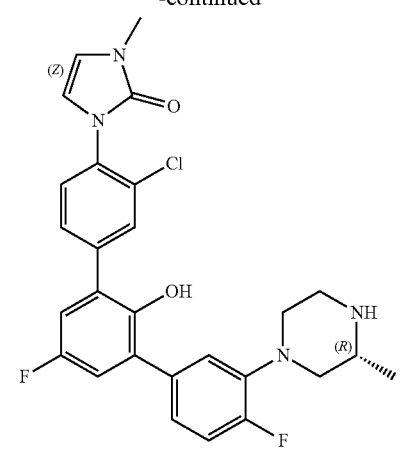
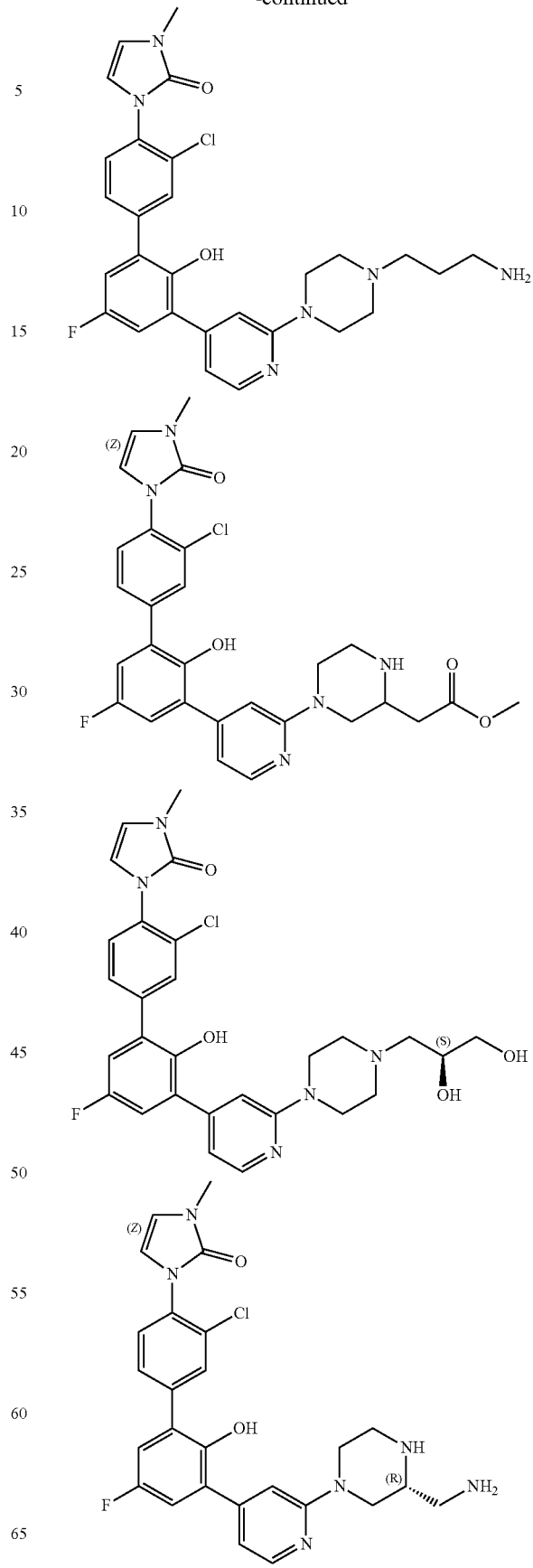

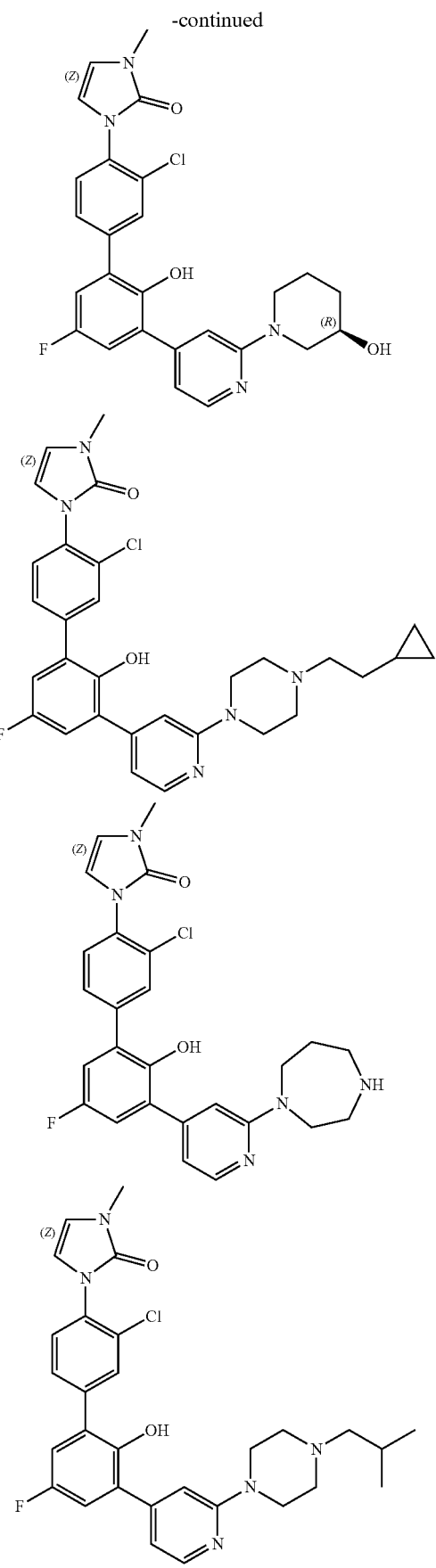
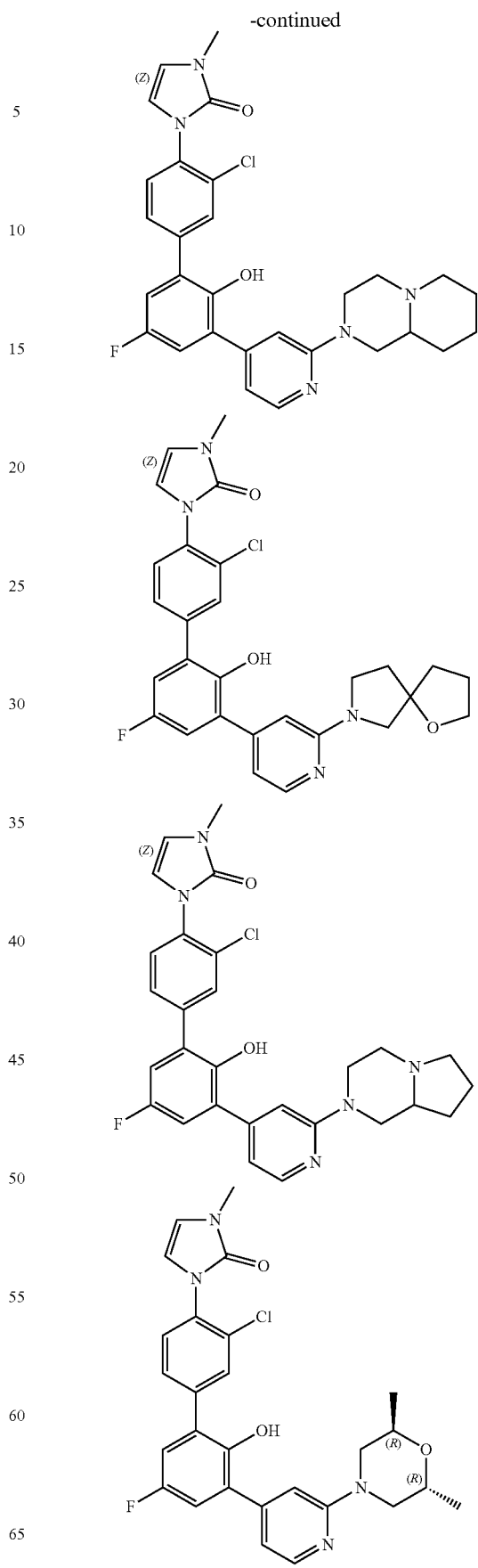

225
-continued
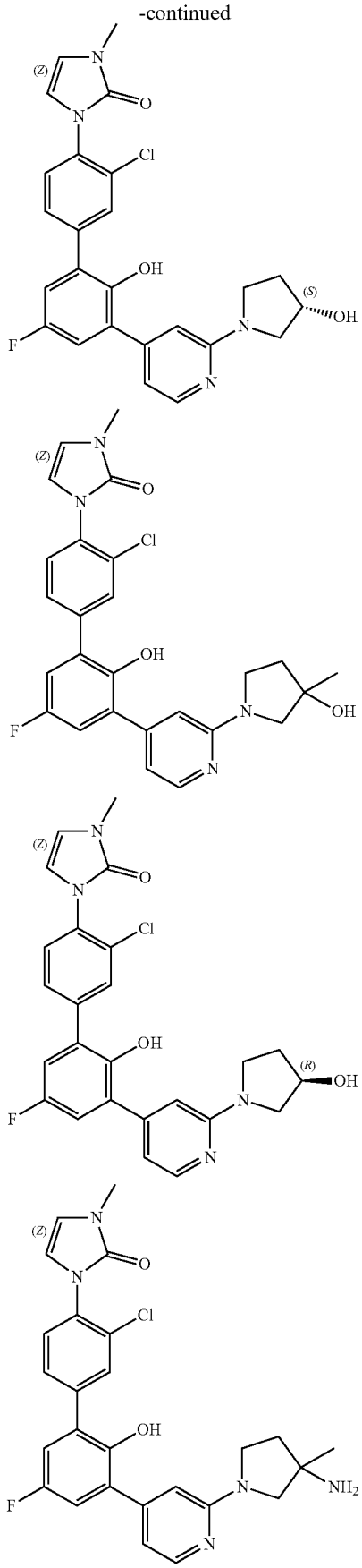
226
-continued
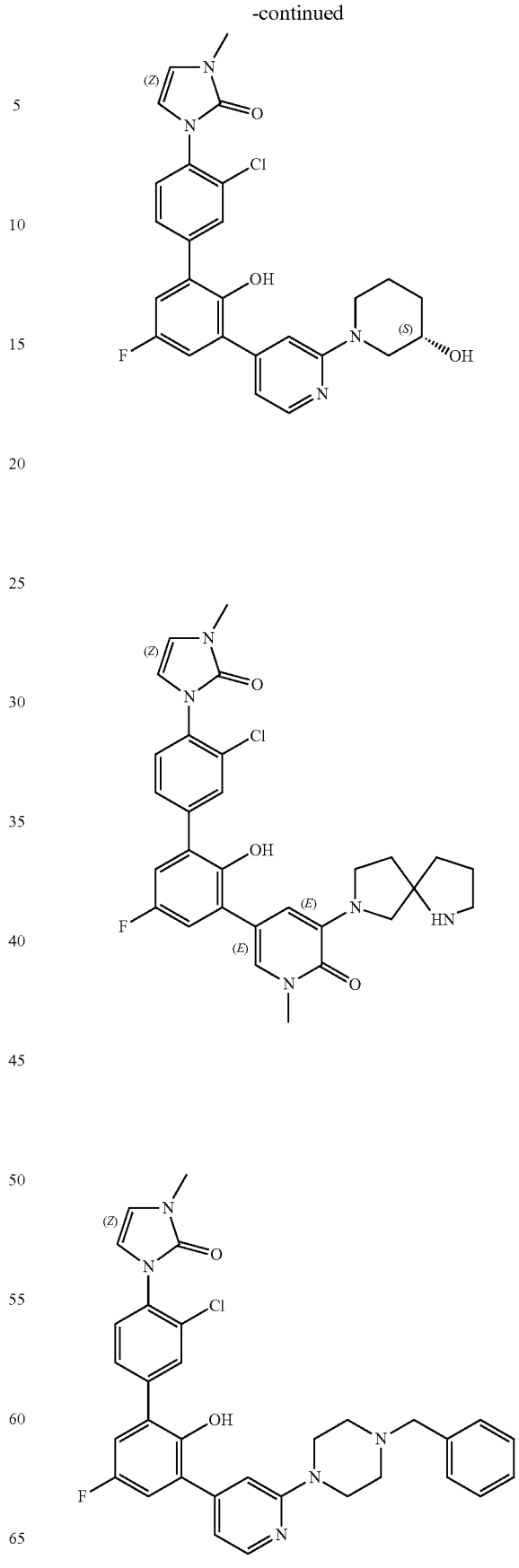

227
-continued
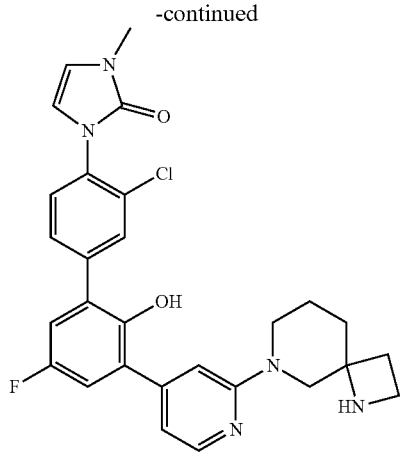
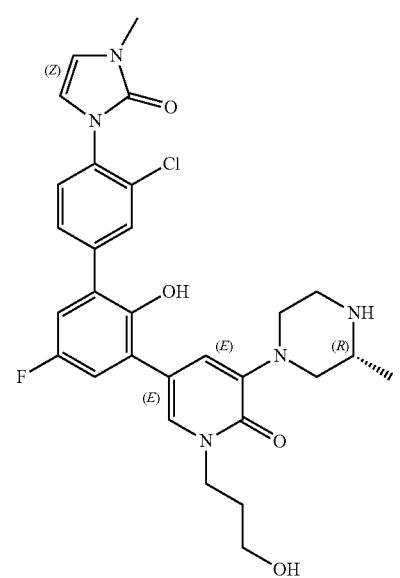
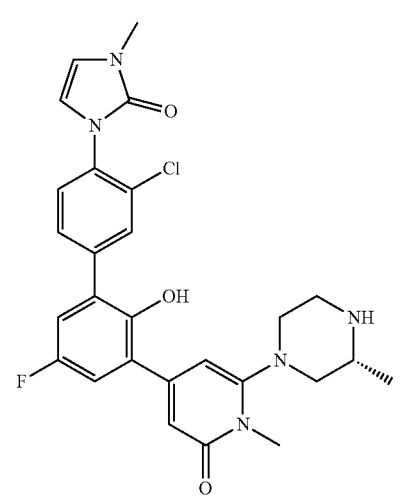
228
-continued
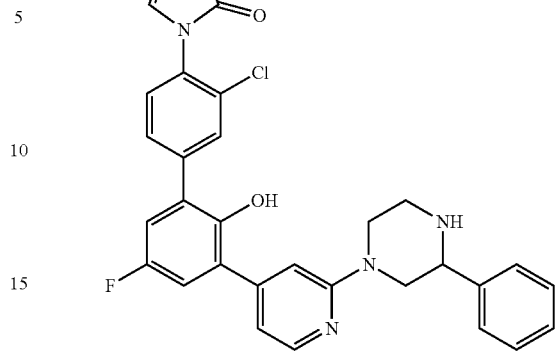
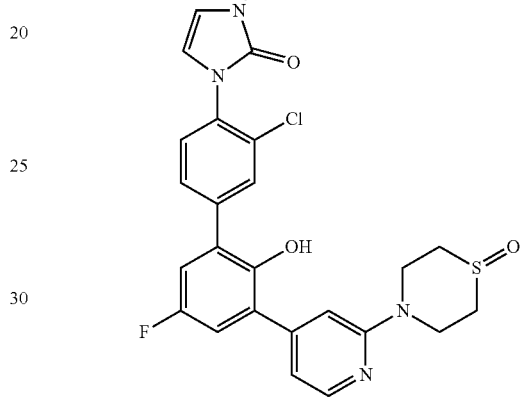
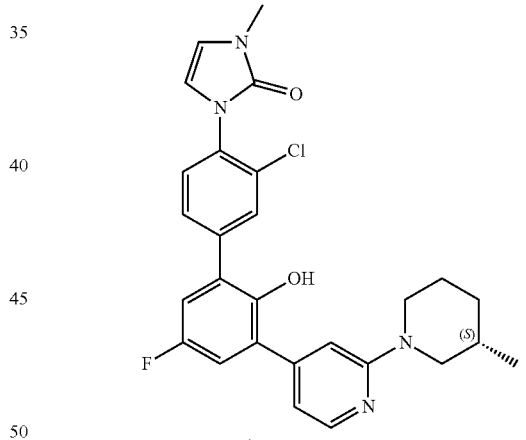
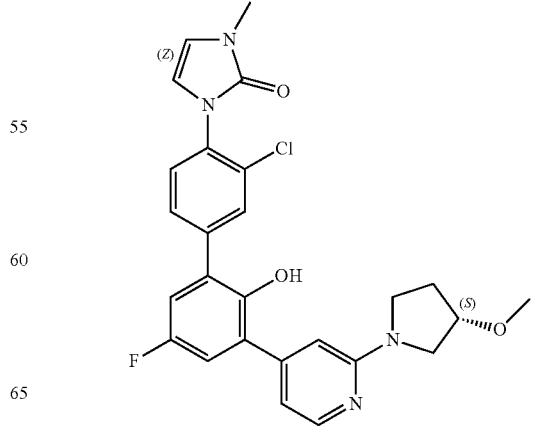

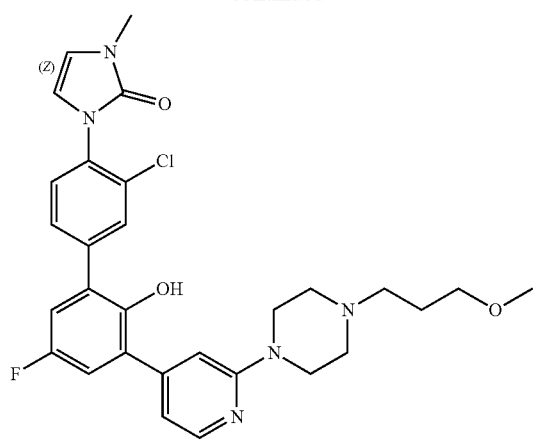
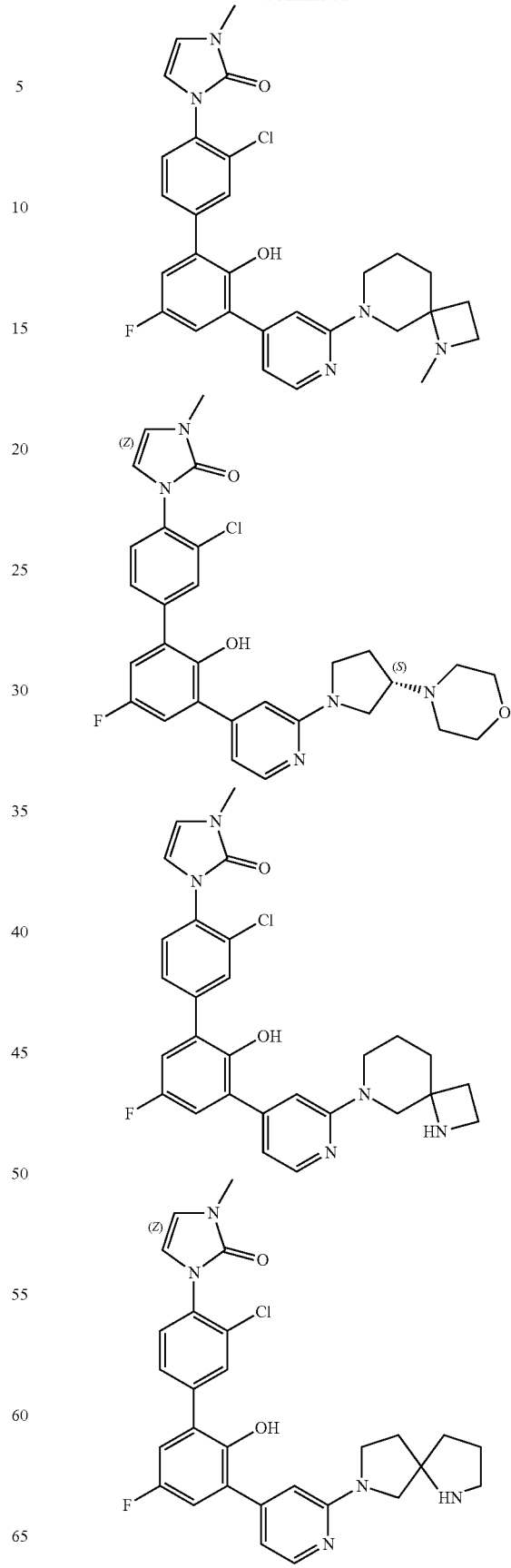

231
-continued
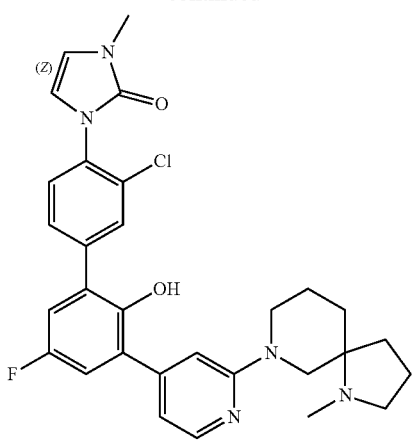 [SMILES: CN1CCCC12CCCN(c1cc(-c3cc(F)cc(-c4ccc(-n5ccn(C)c5=O)c(Cl)c4)c3O)ccn1)C2]
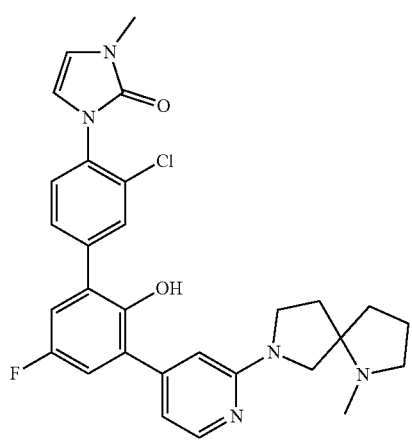
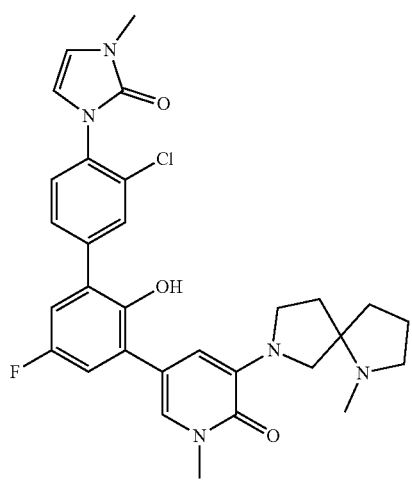
232
-continued
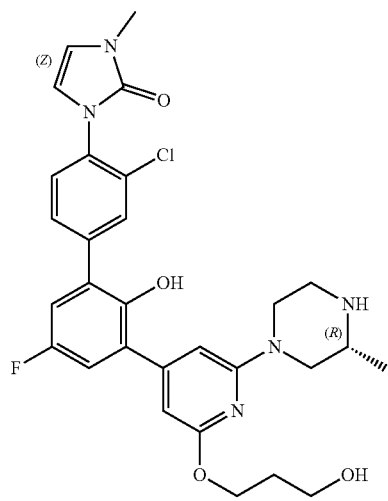
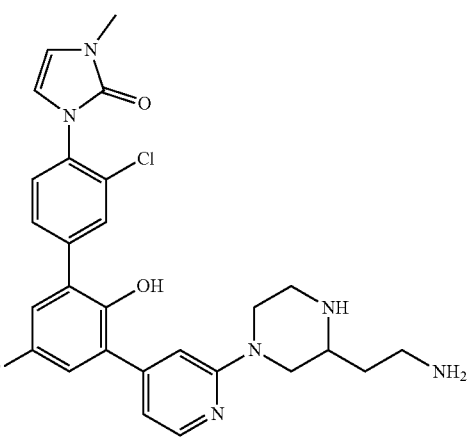
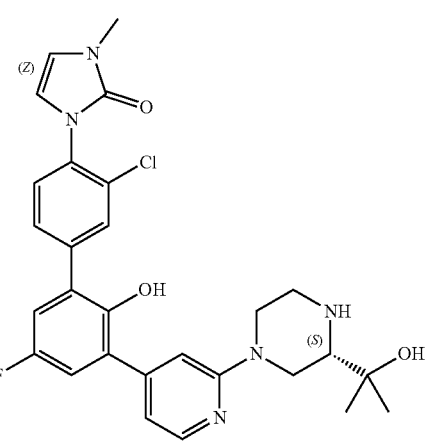

-continued
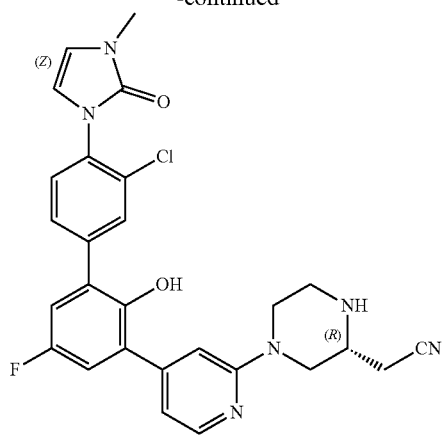
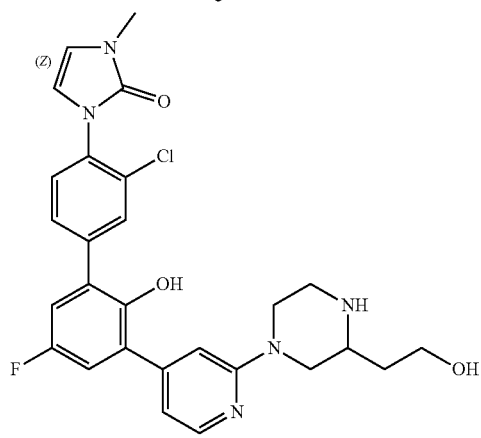
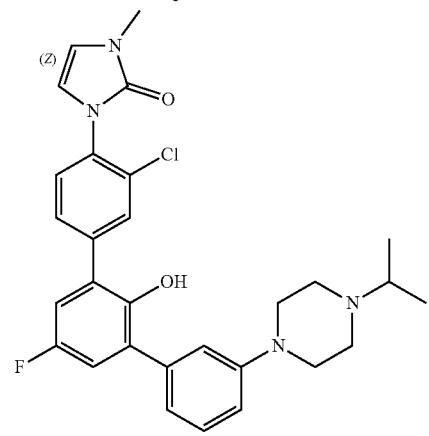
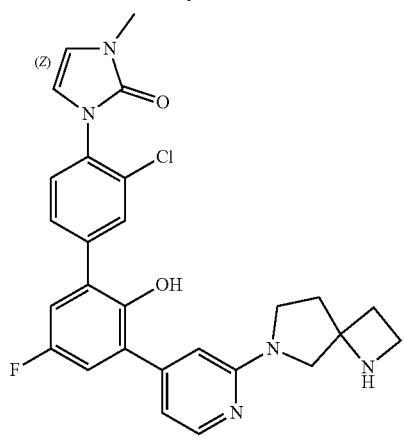
-continued
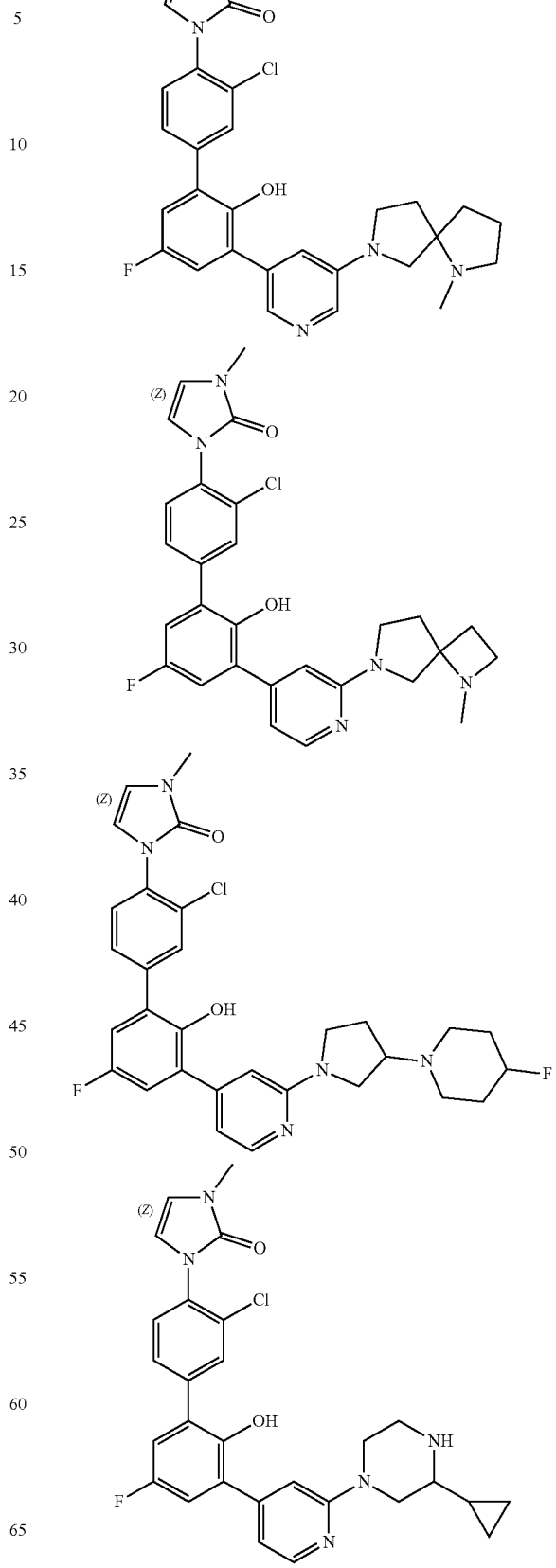

235
-continued
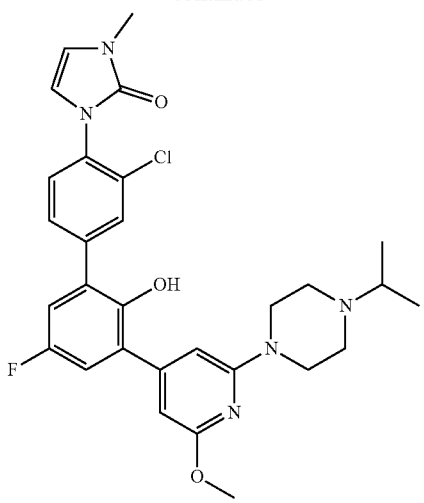
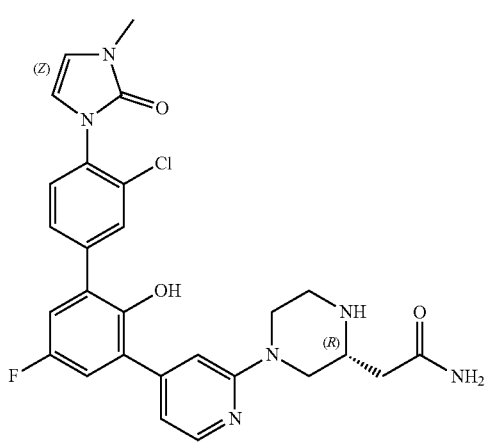
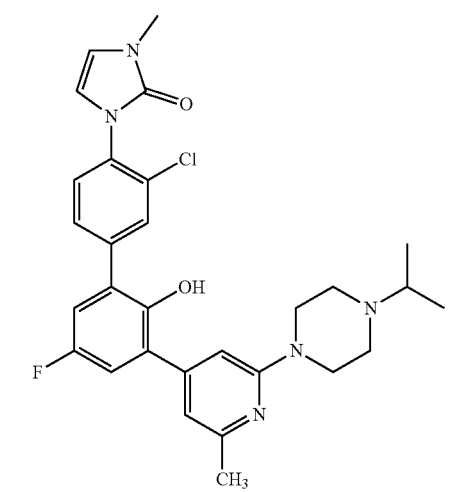
236
-continued
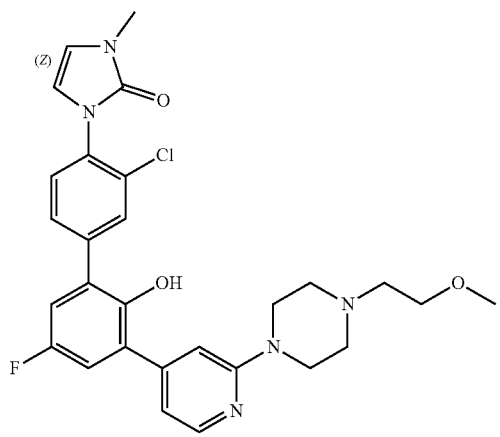
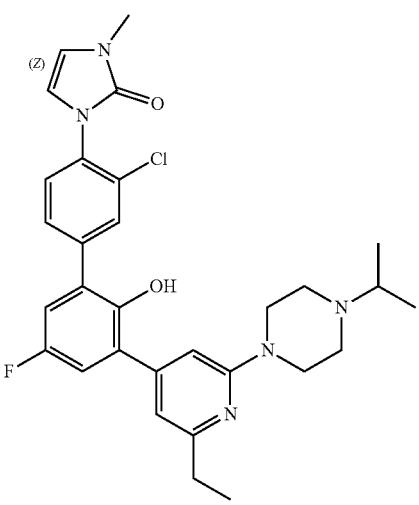
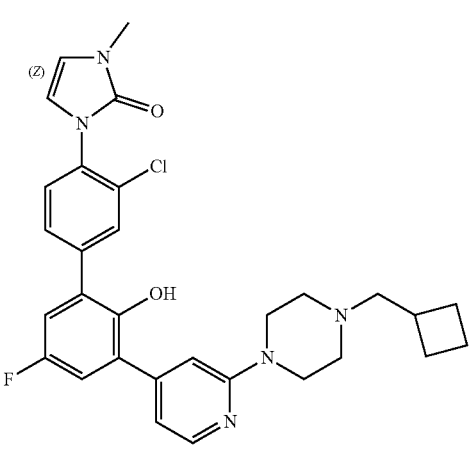

237
-continued
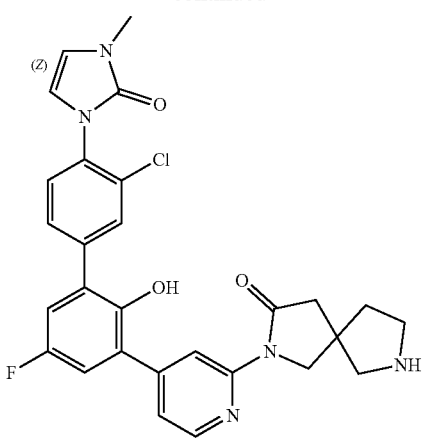
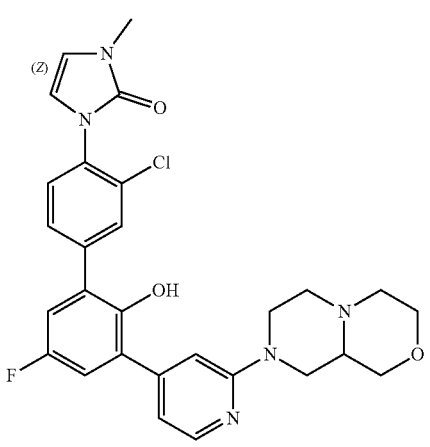
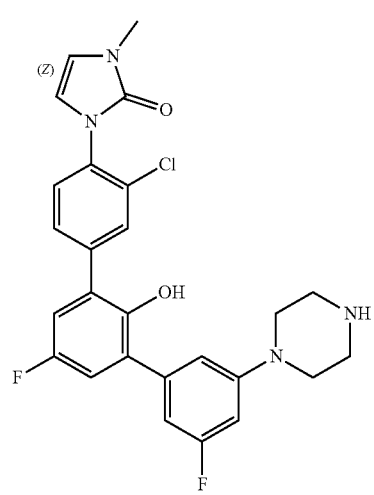
238
-continued
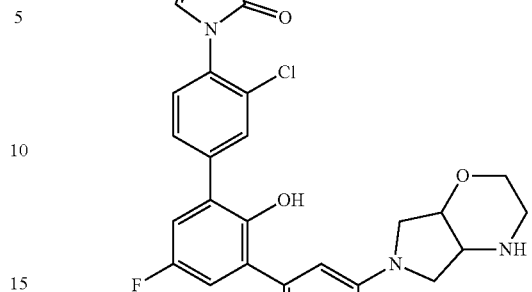
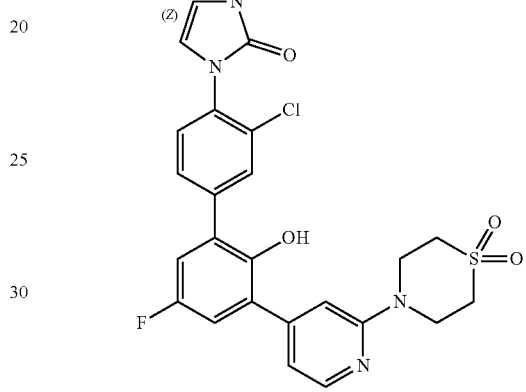
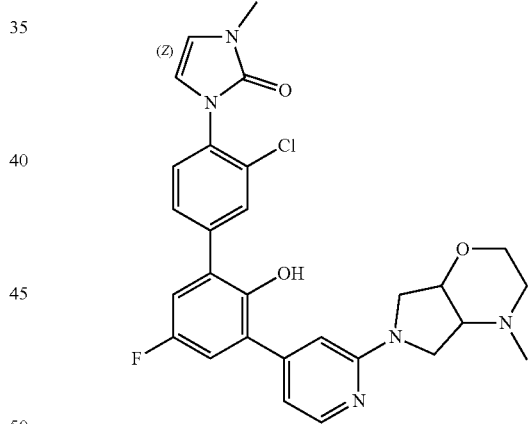
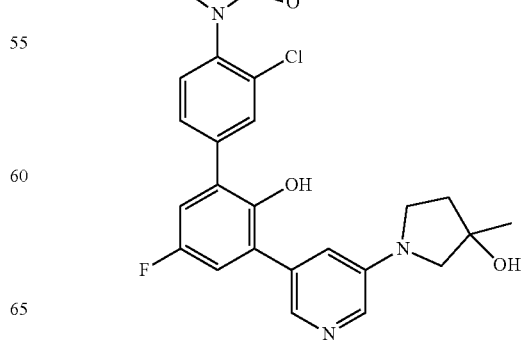

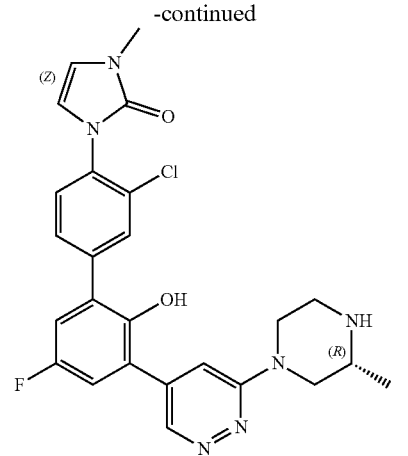
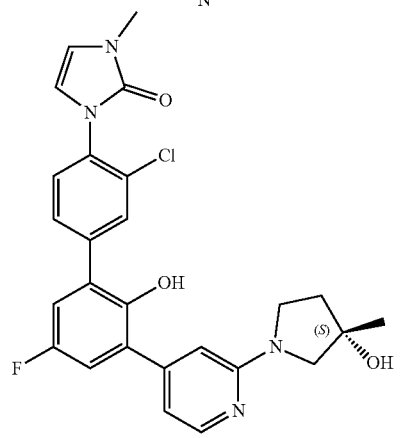
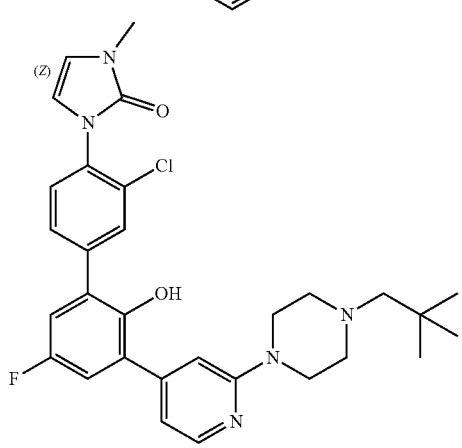
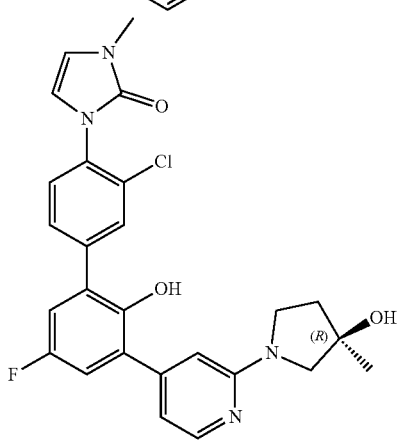
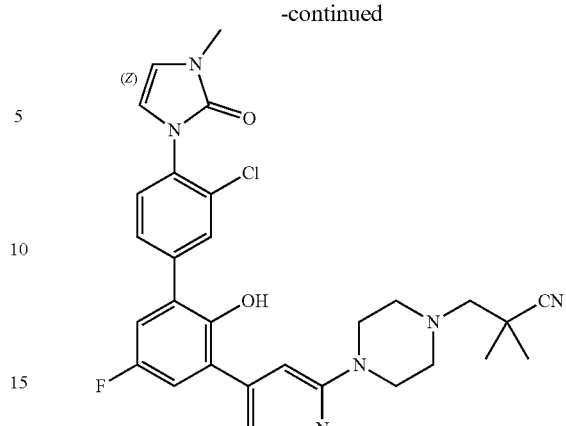
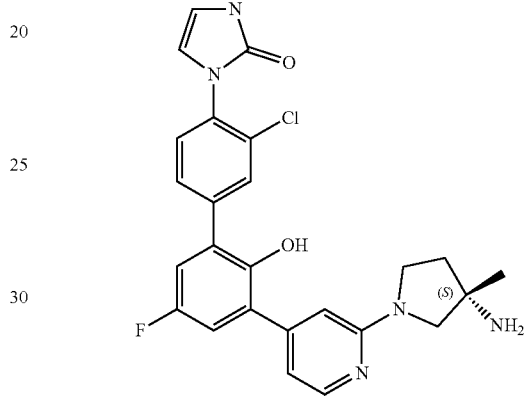
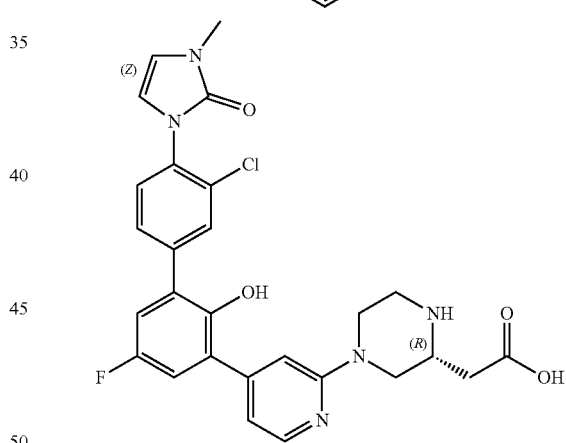
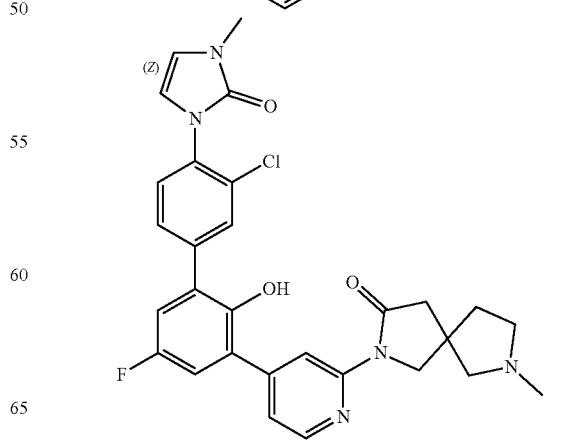

241
-continued
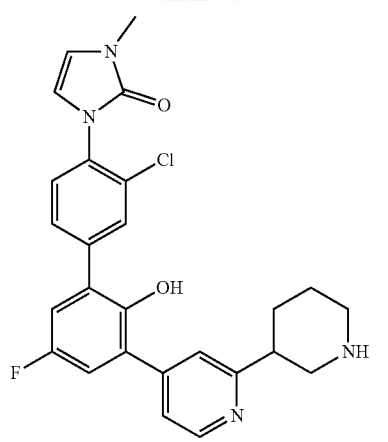
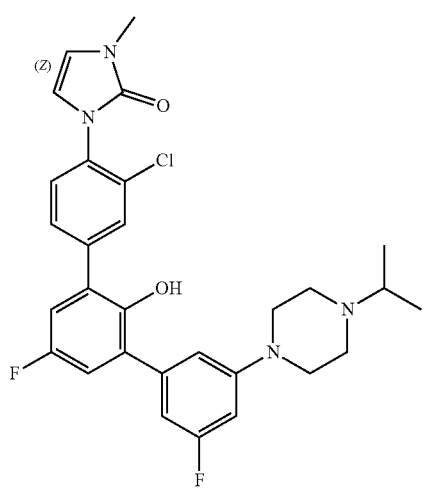
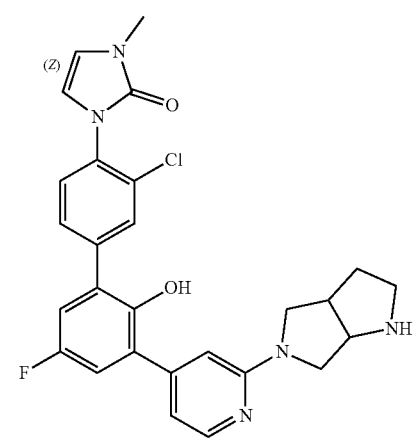
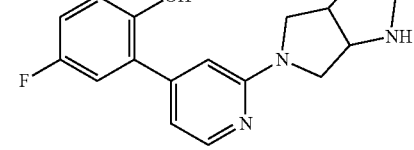
242
-continued
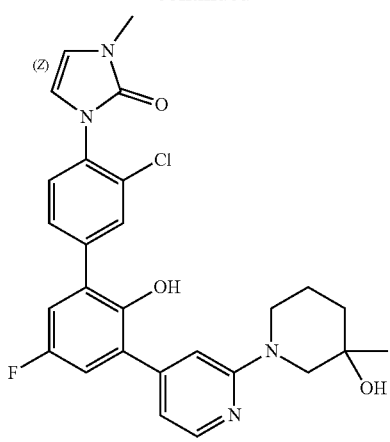
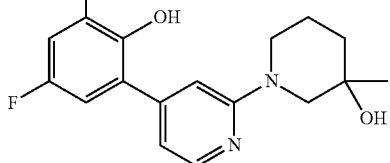
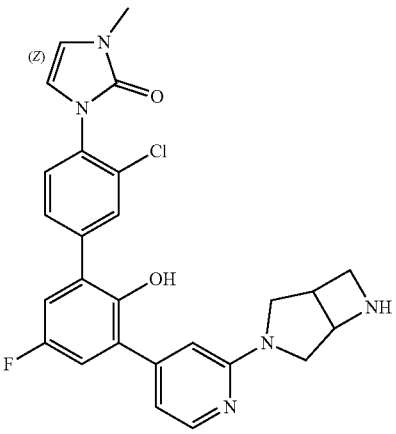
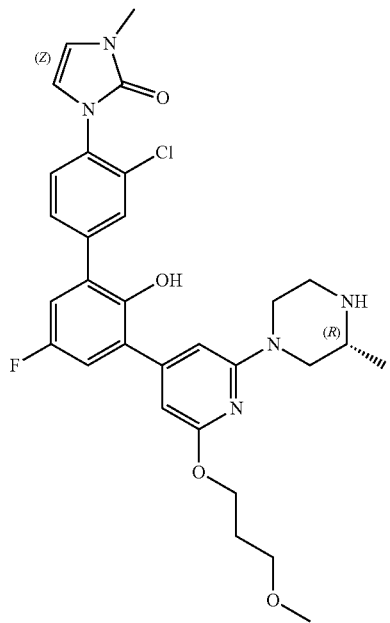

243
-continued
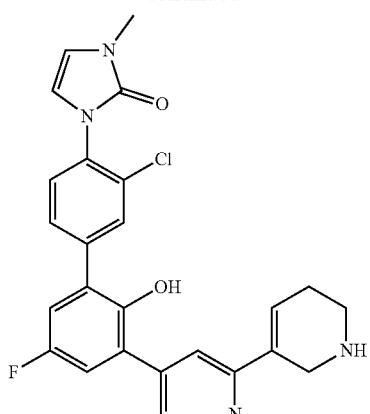
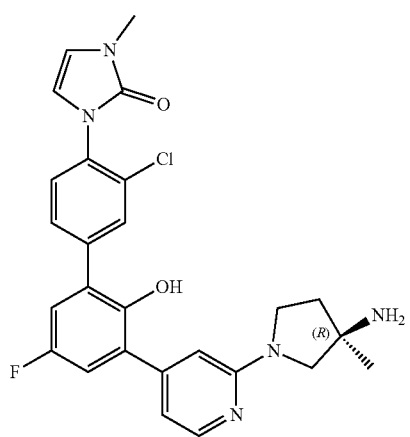
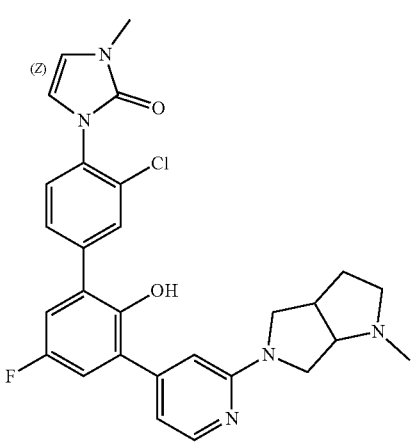
244
-continued
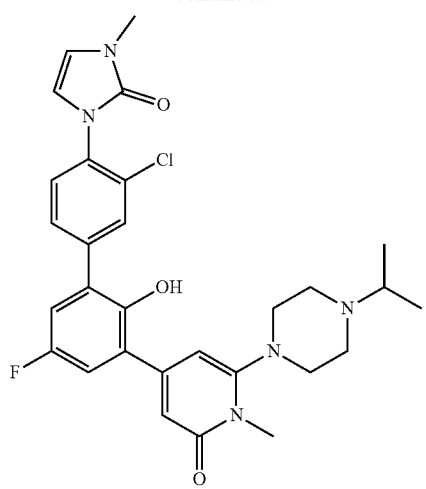
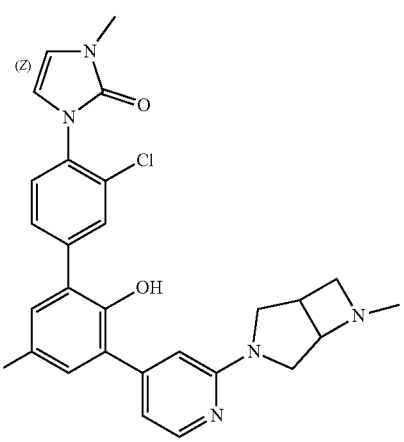
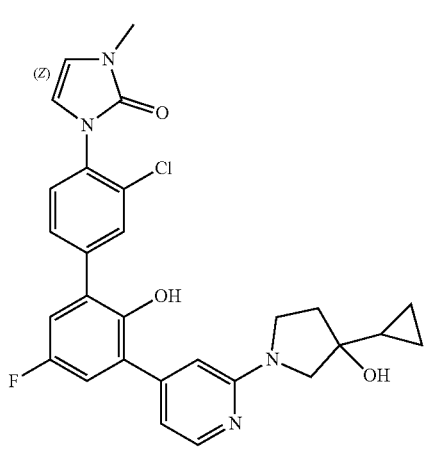

245
-continued
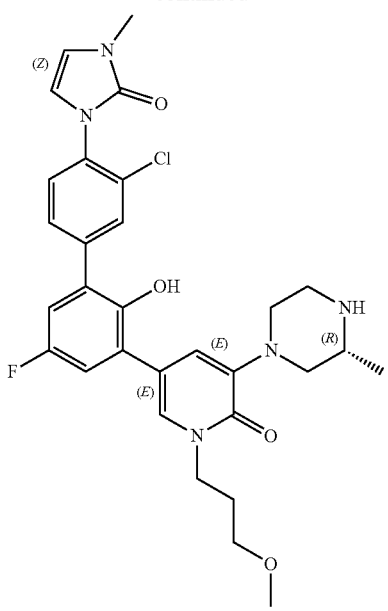
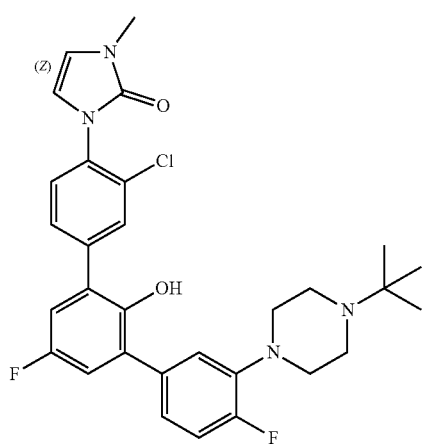
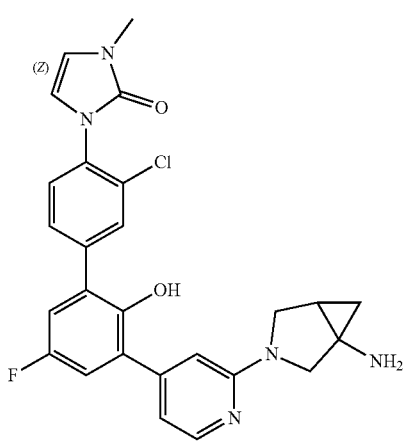
246
-continued
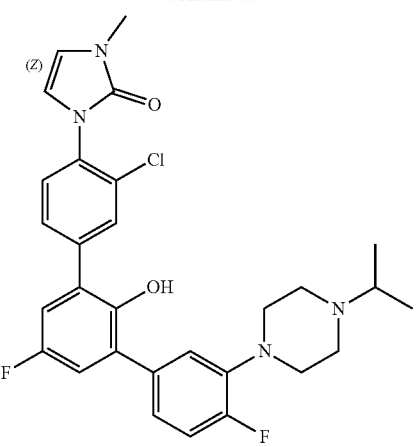
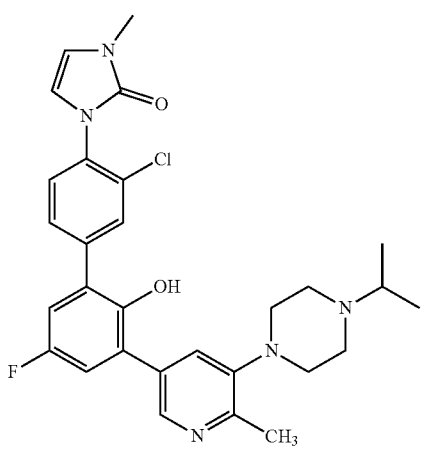
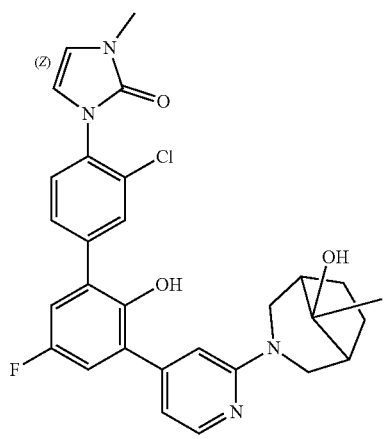

247
-continued
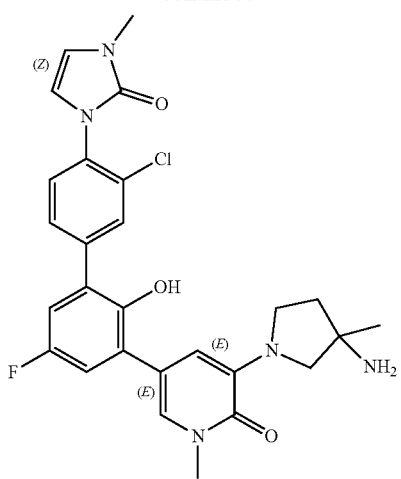
248
-continued
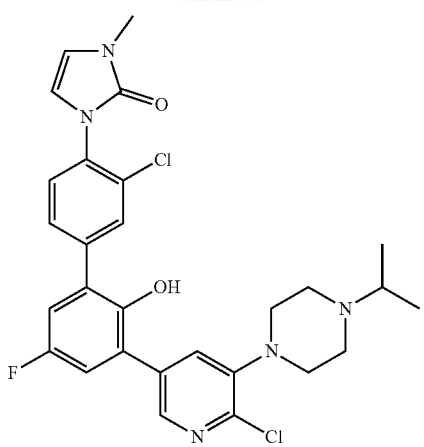
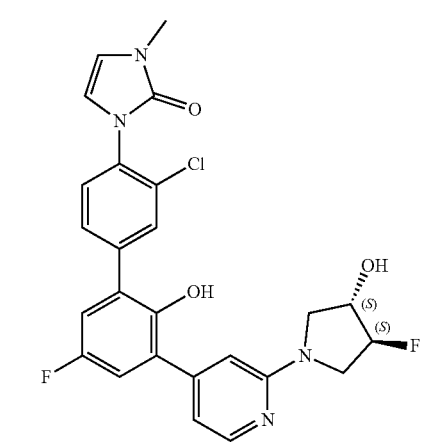
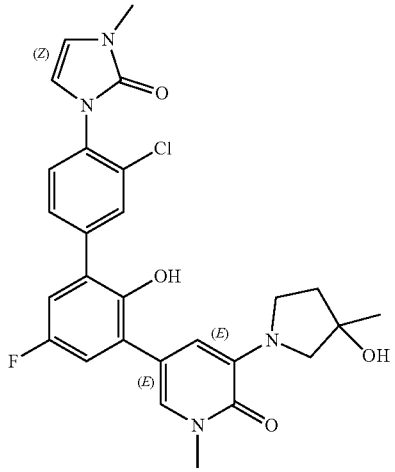
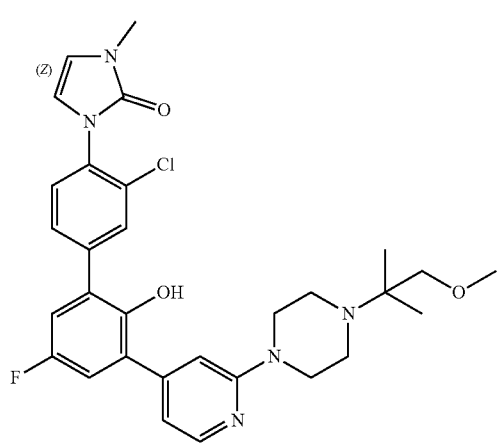
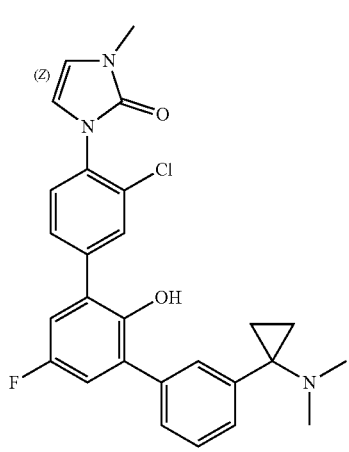

249
-continued
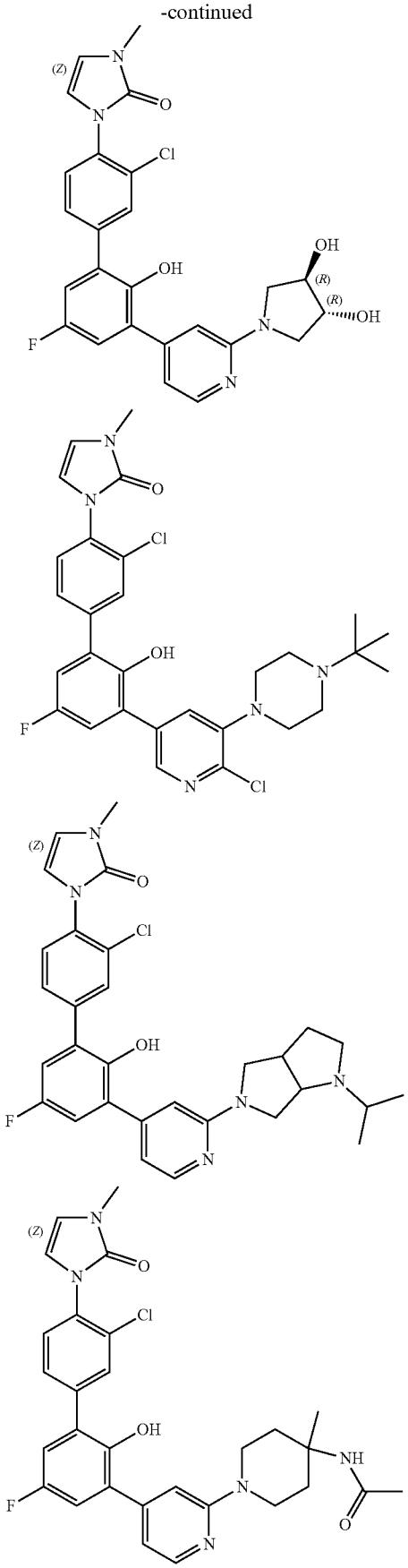
250
-continued
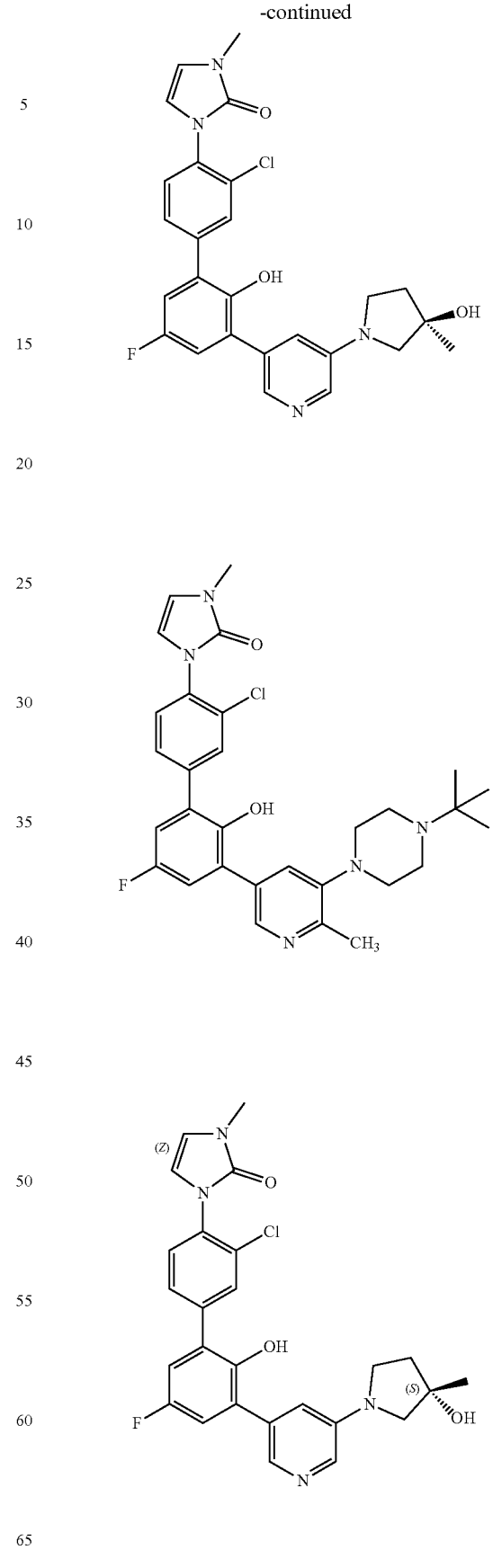

251
-continued
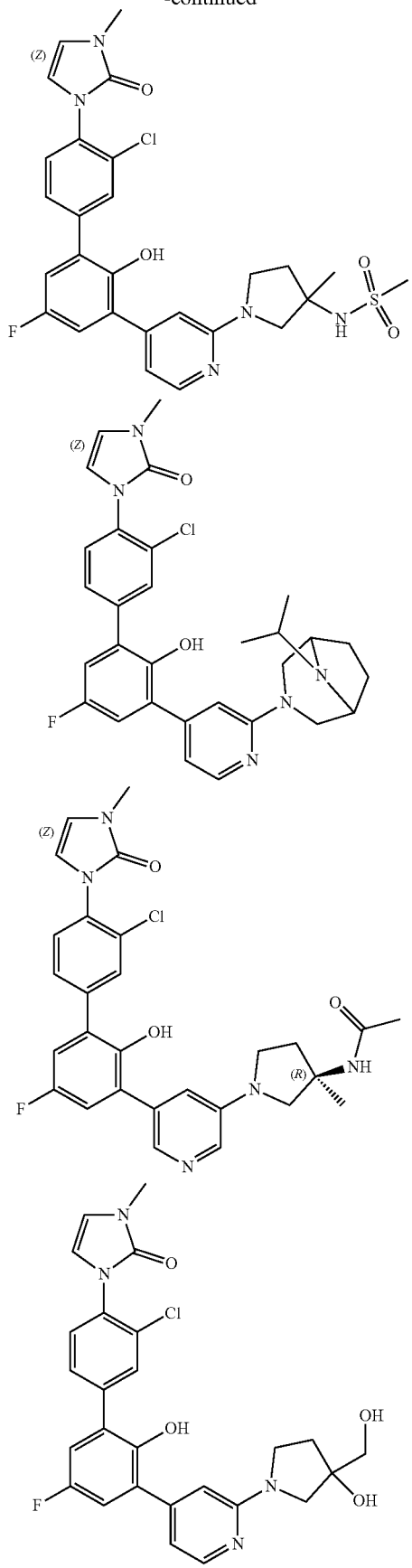
252
-continued
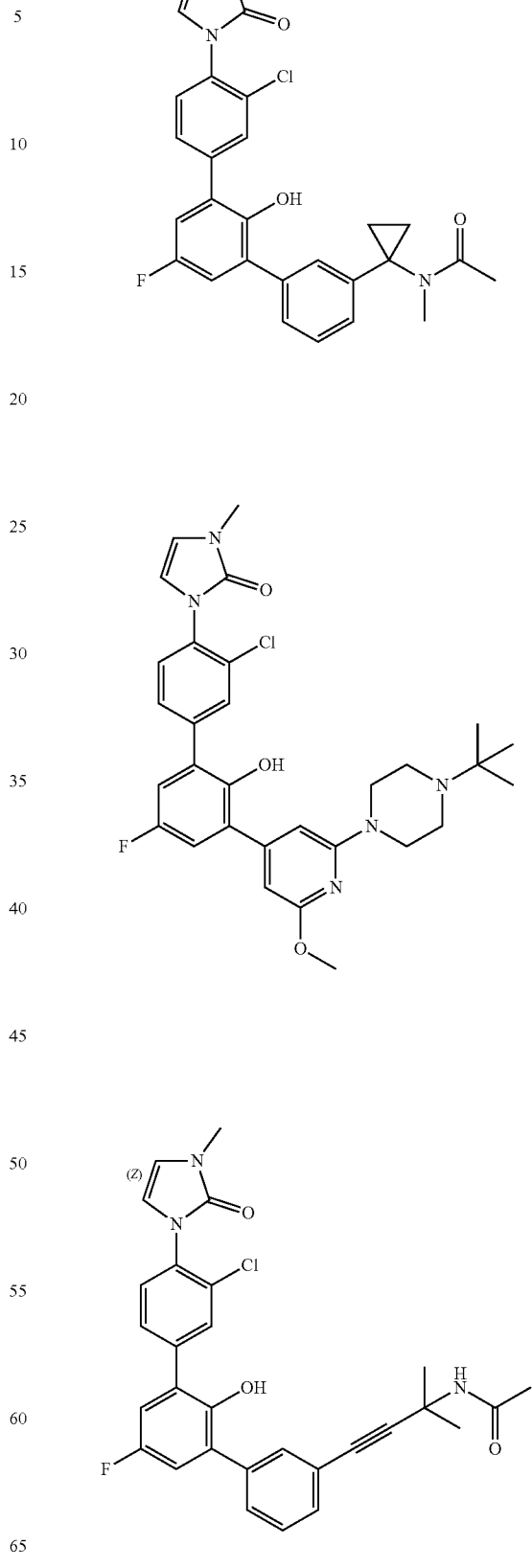

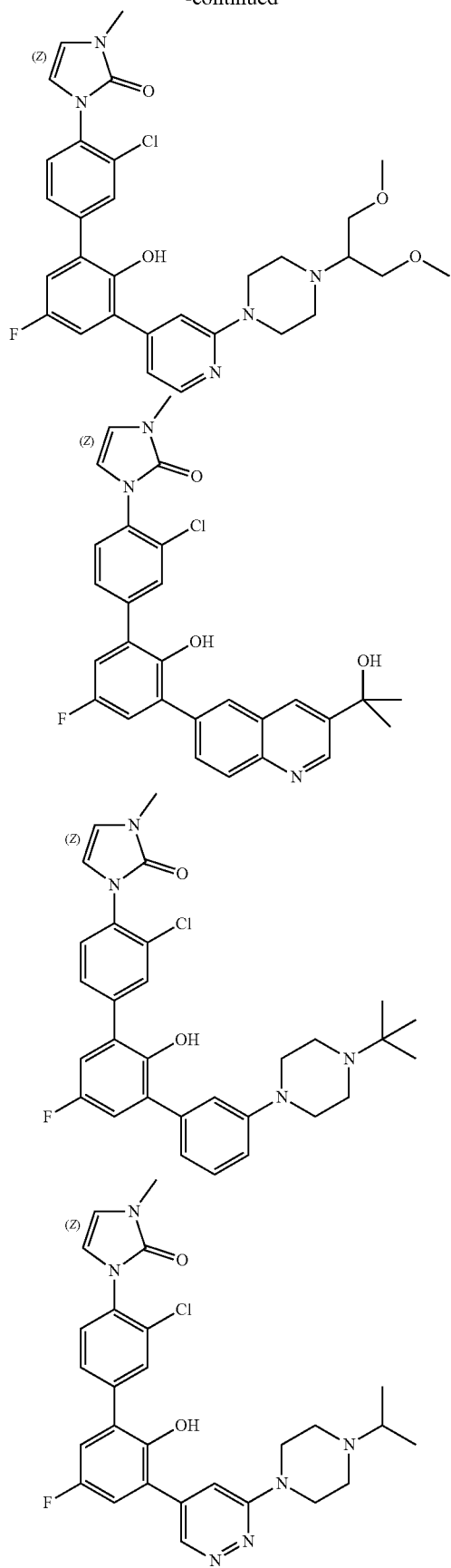
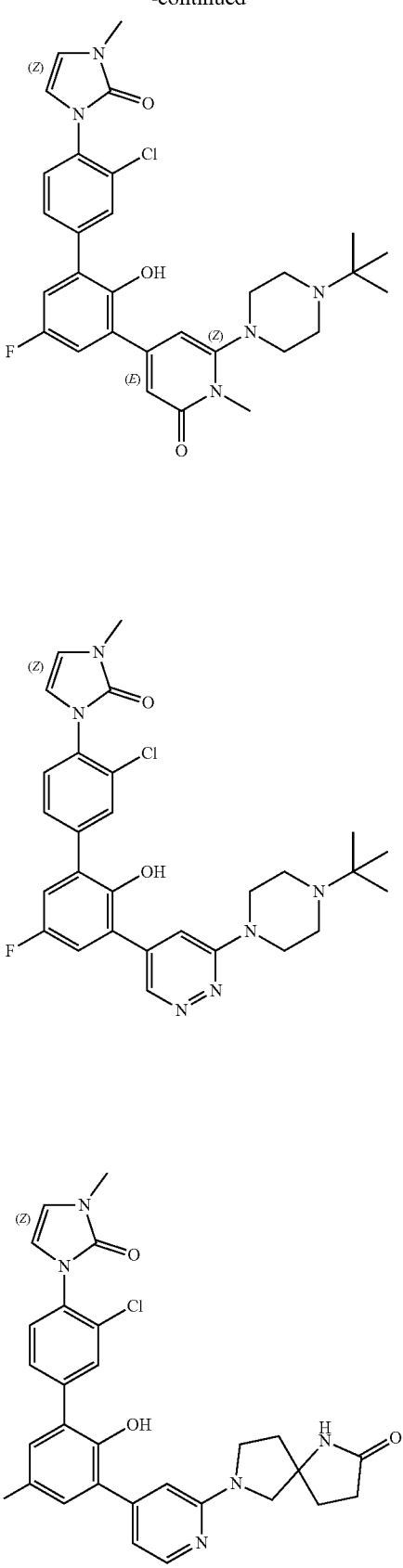

255
-continued
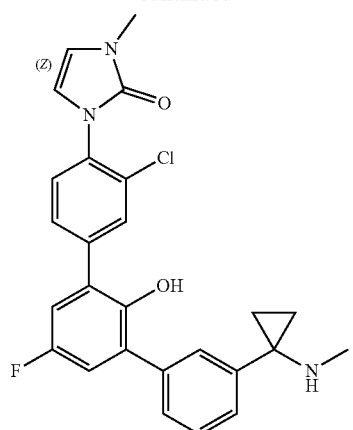
256
-continued
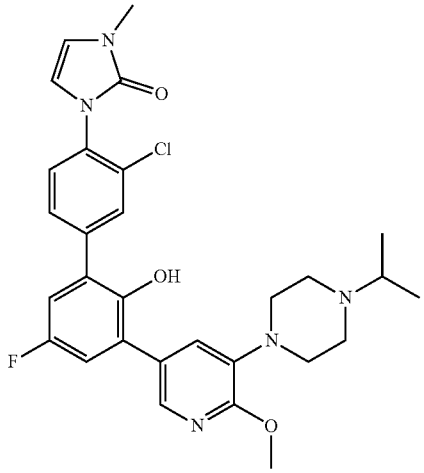
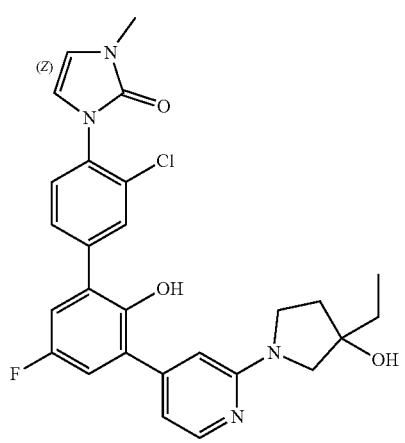
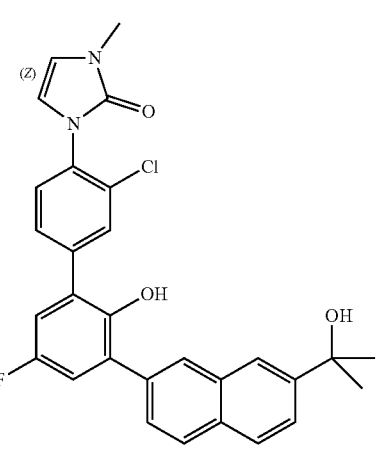
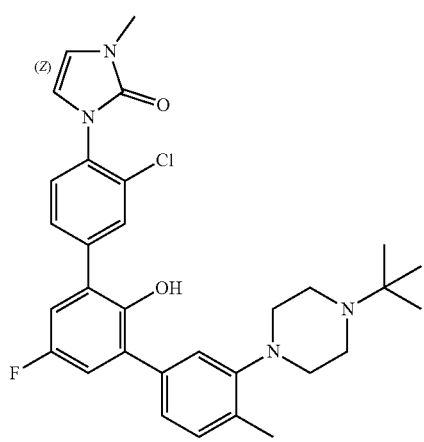
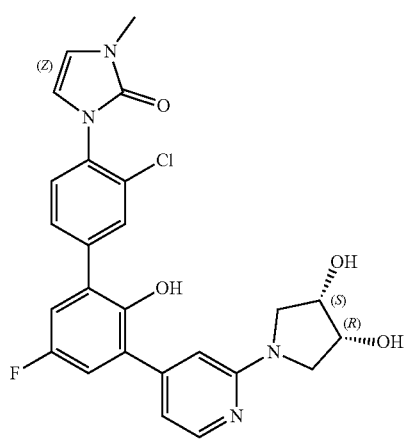

257
-continued
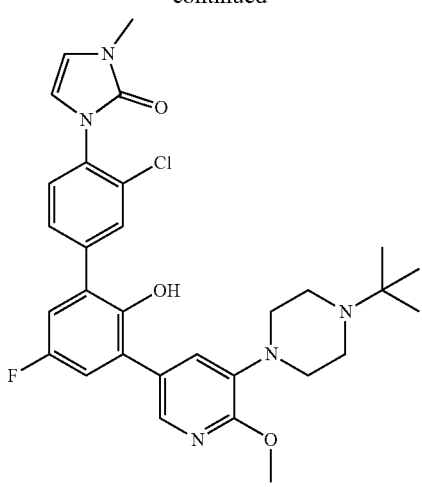
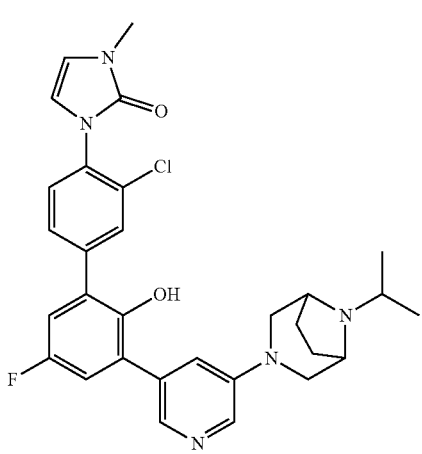
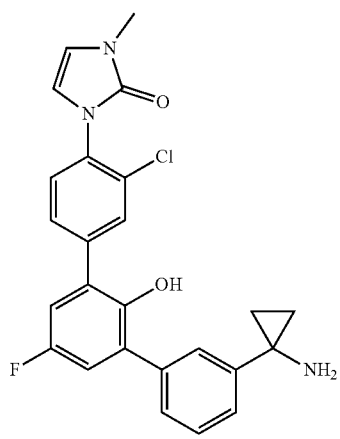
258
-continued
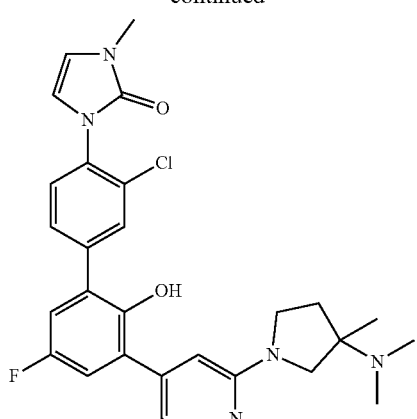
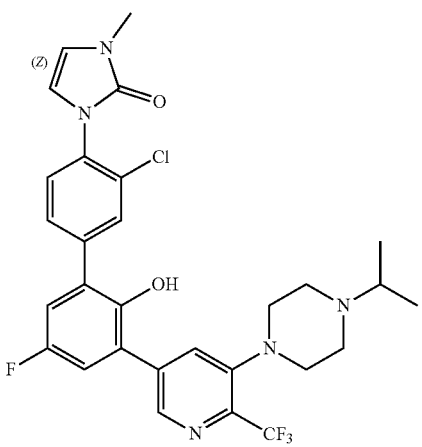
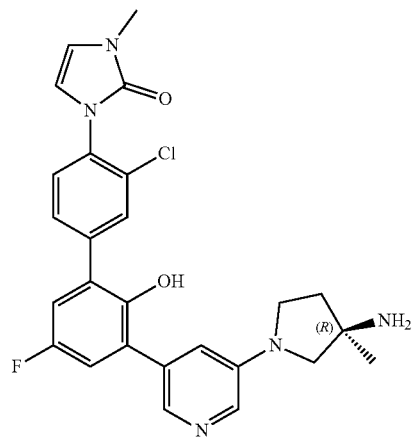

-continued
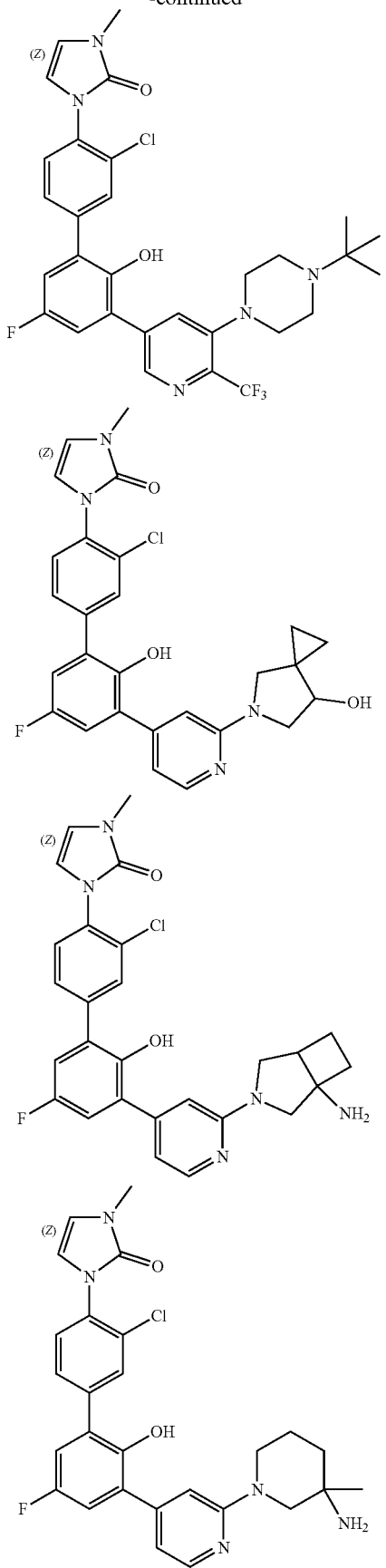
-continued
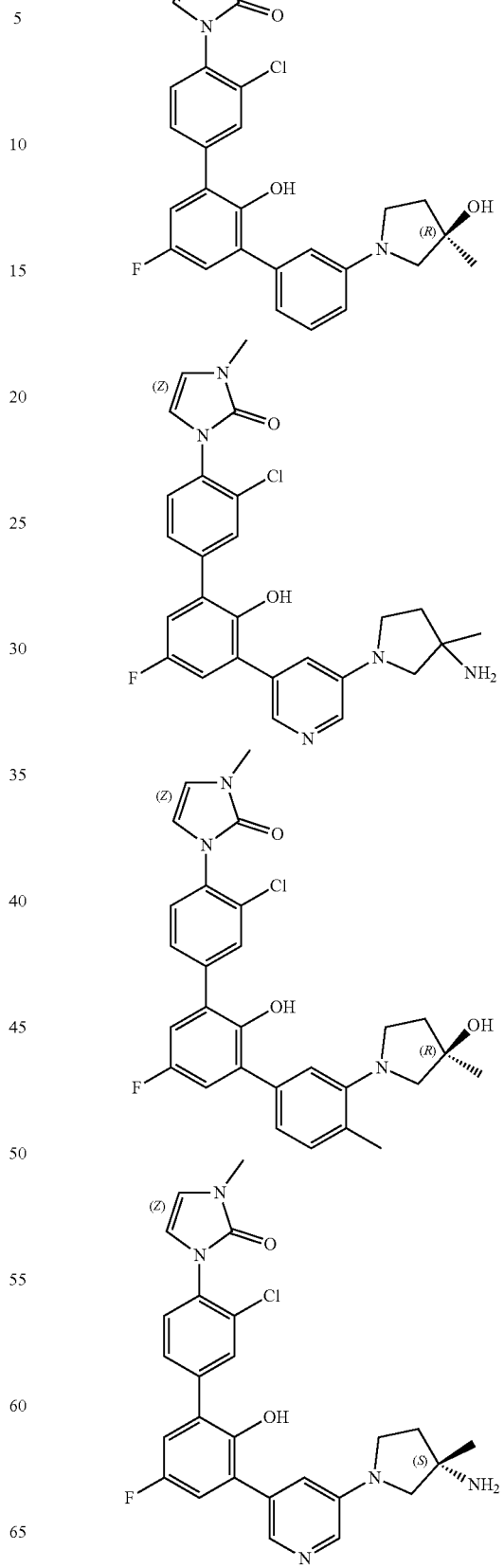

261
-continued
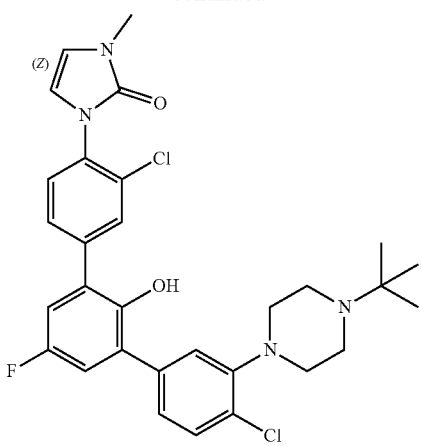
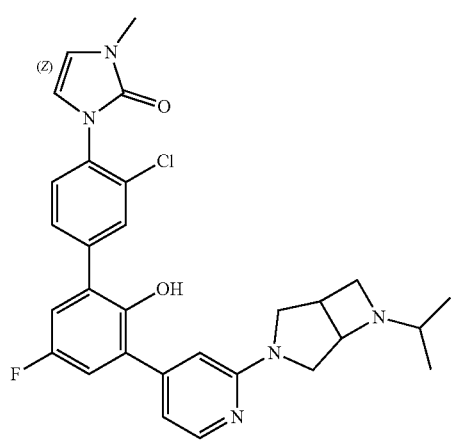
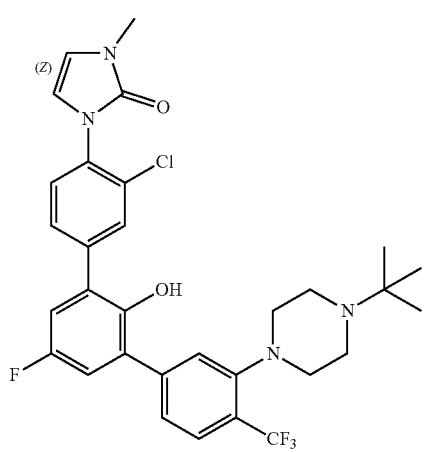
262
-continued
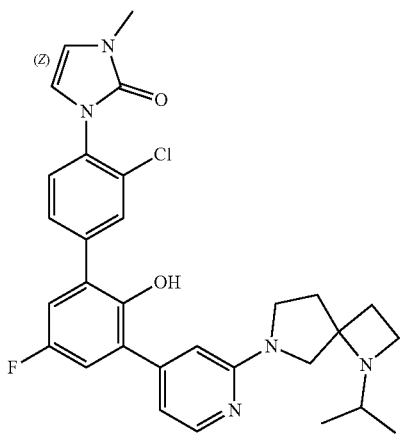
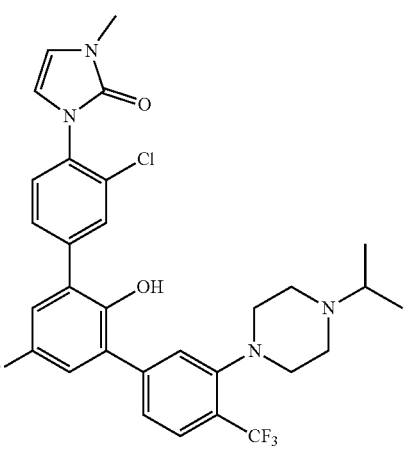
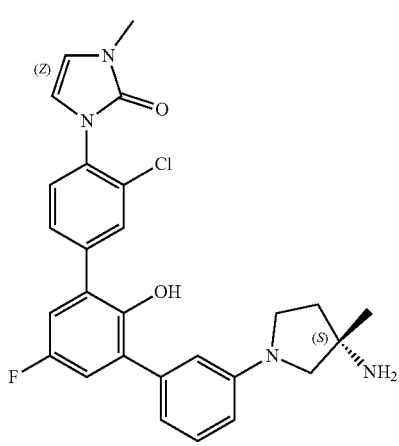

263
-continued
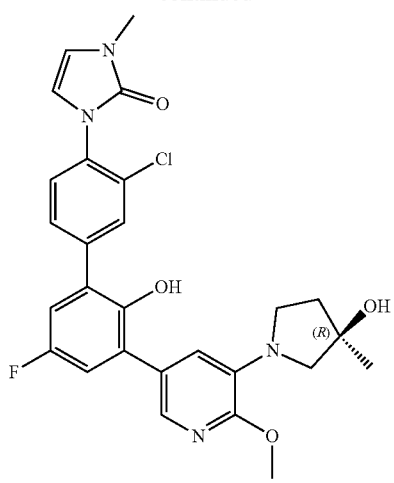
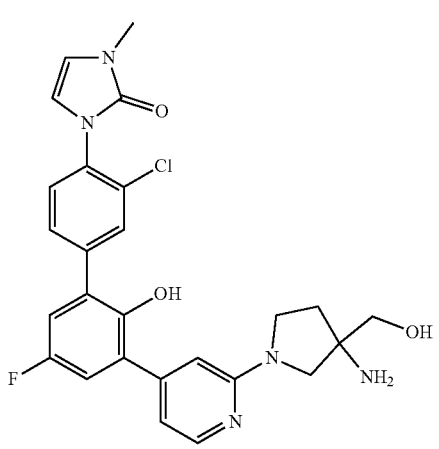
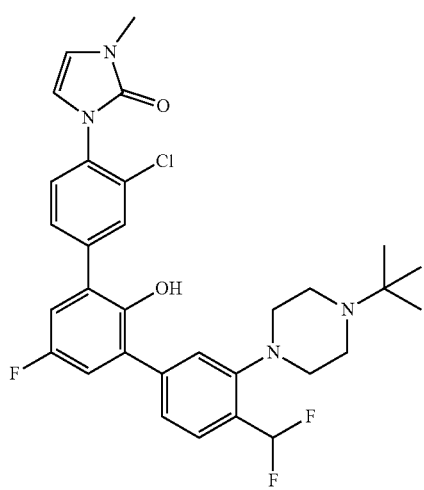
264
-continued
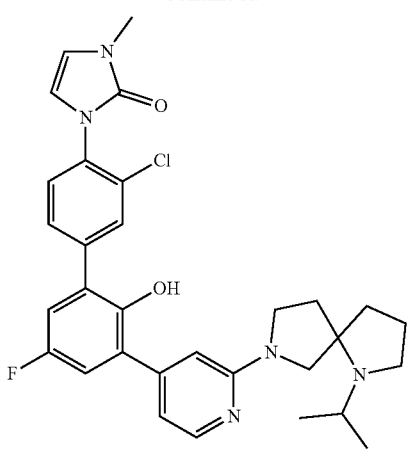
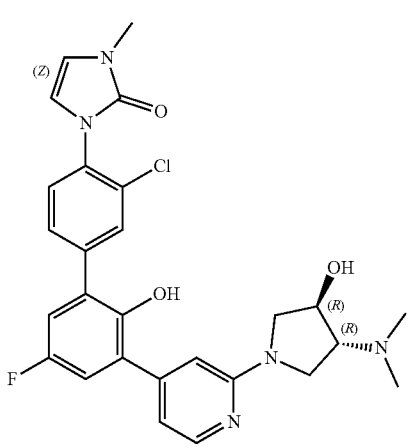

265
-continued
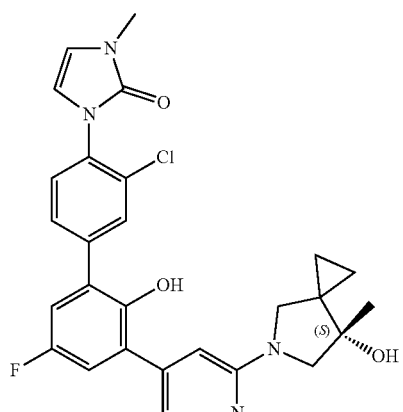
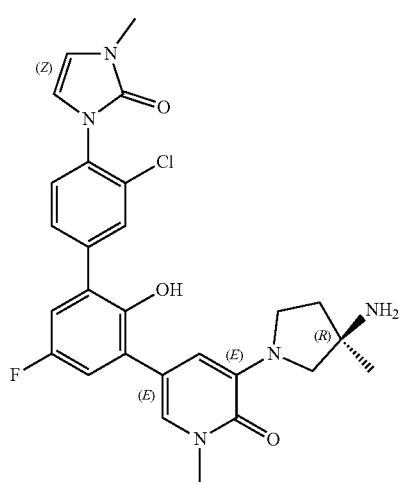
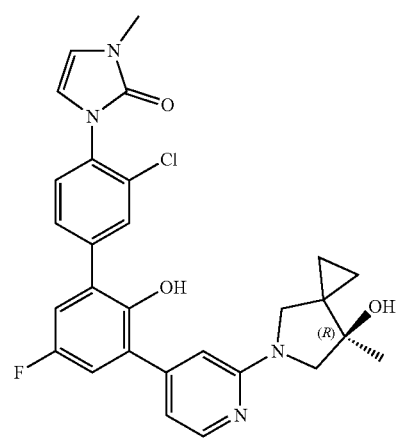
266
-continued
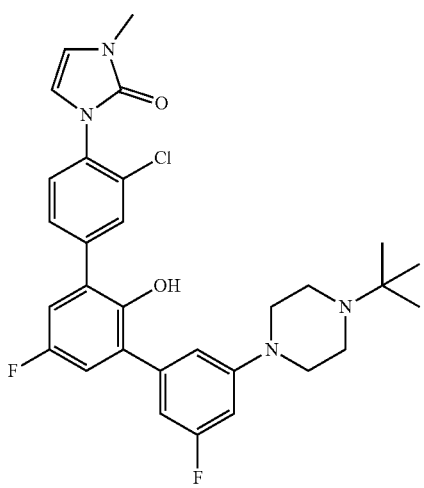
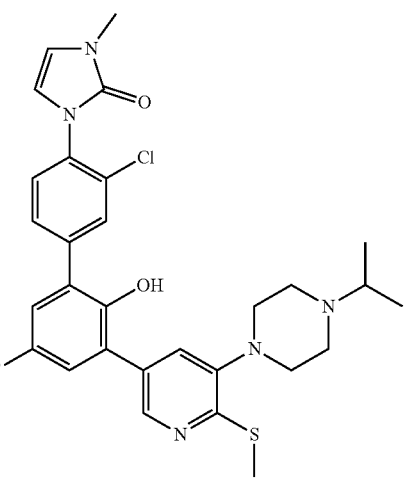
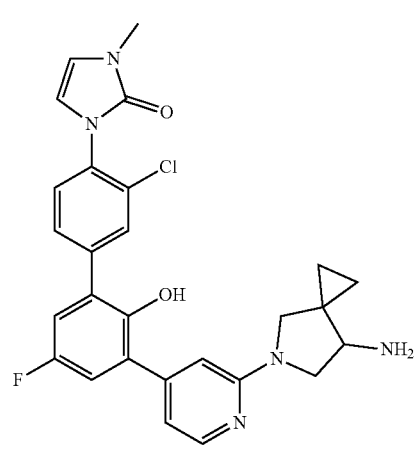

267
-continued
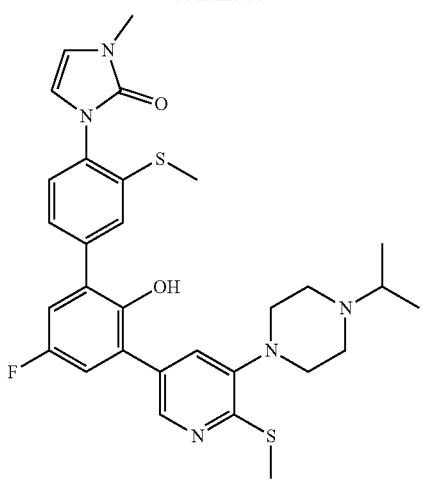
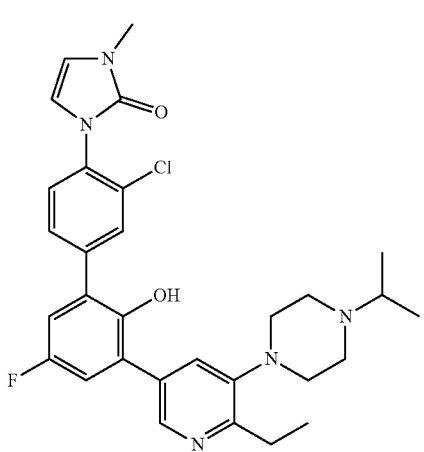
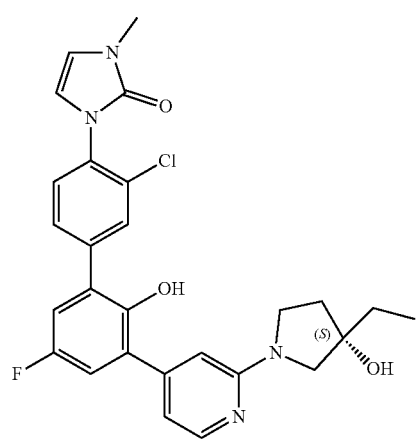
268
-continued
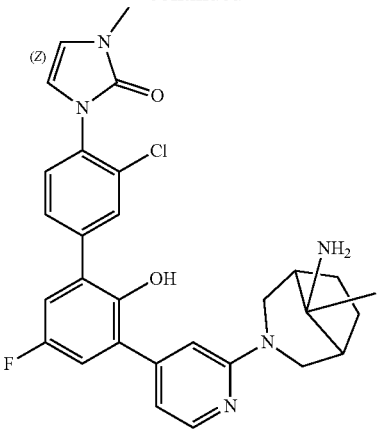
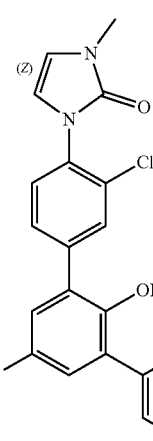
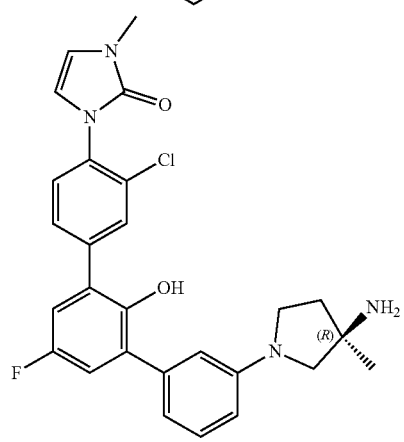
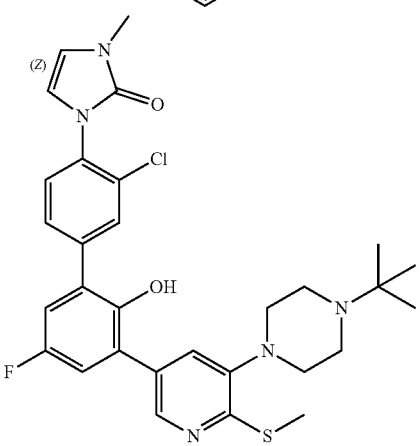

269
-continued
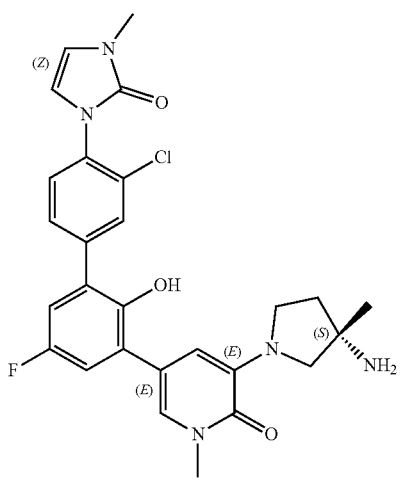
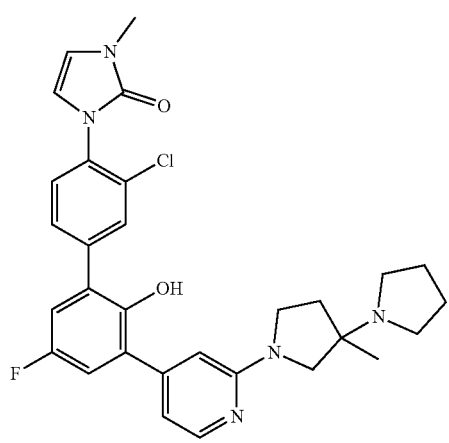
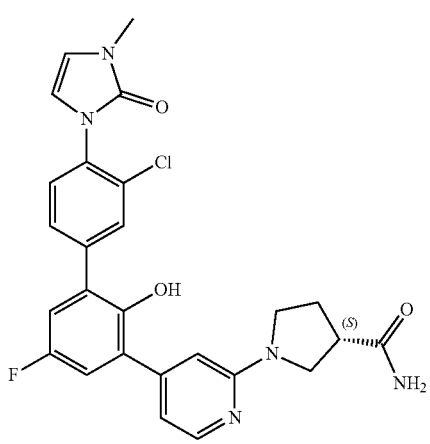
270
-continued
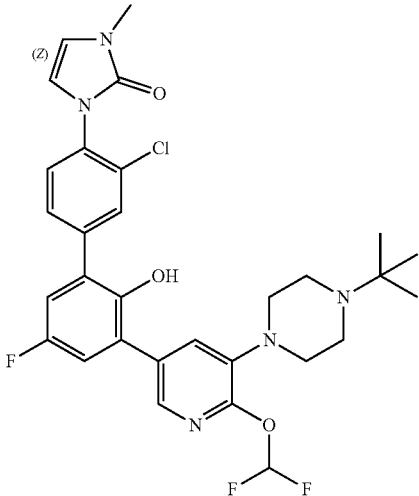
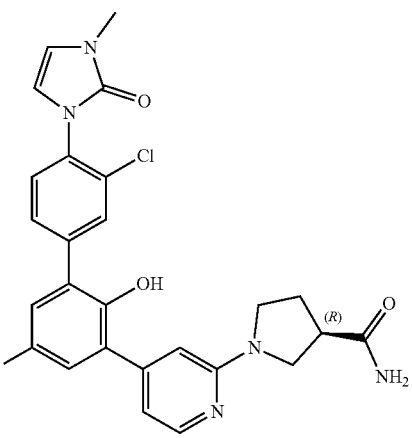
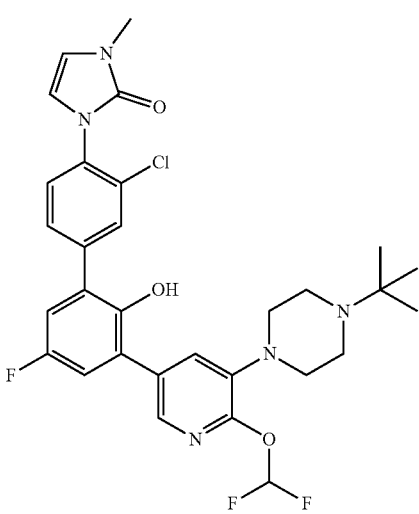

271
-continued
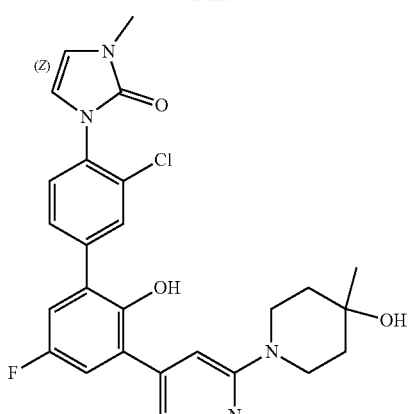
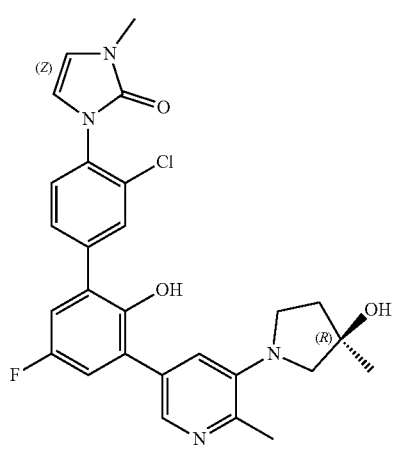
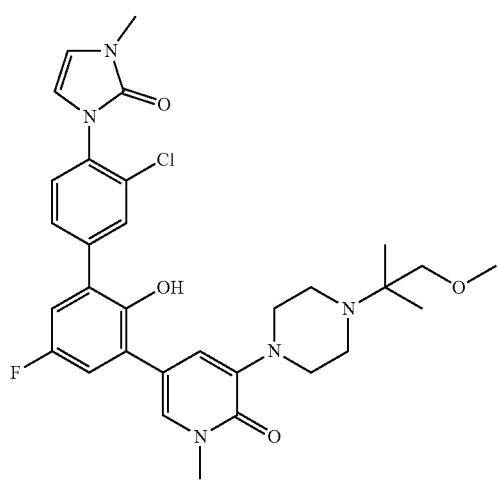
272
-continued
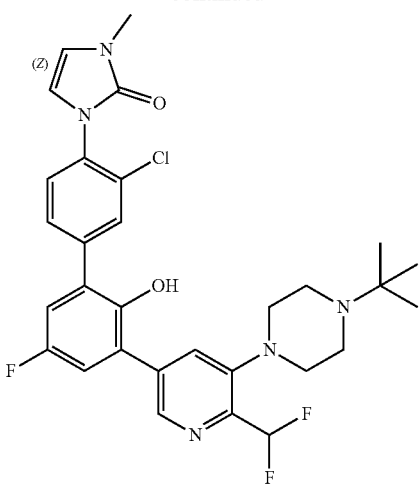
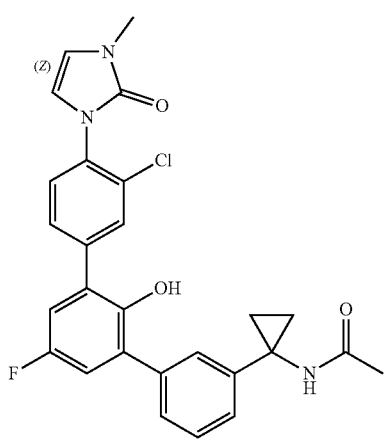
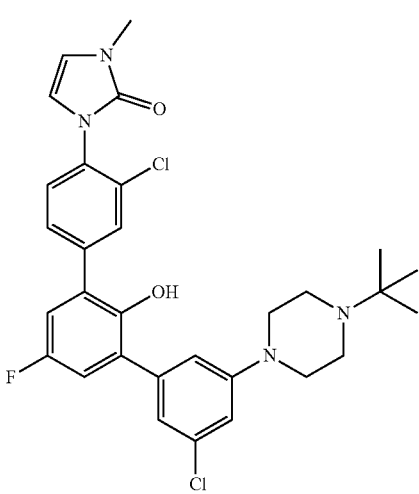

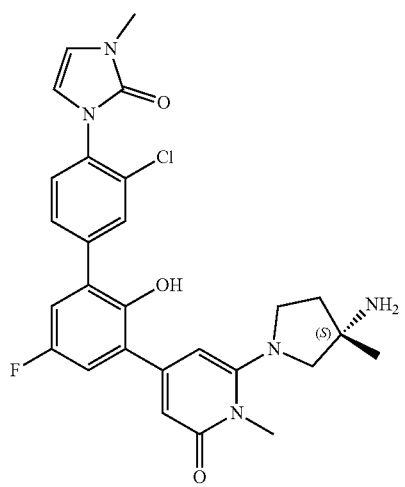
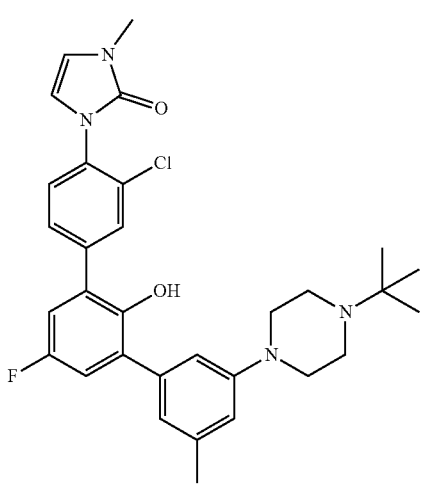
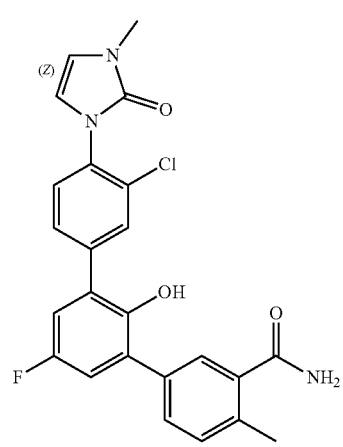
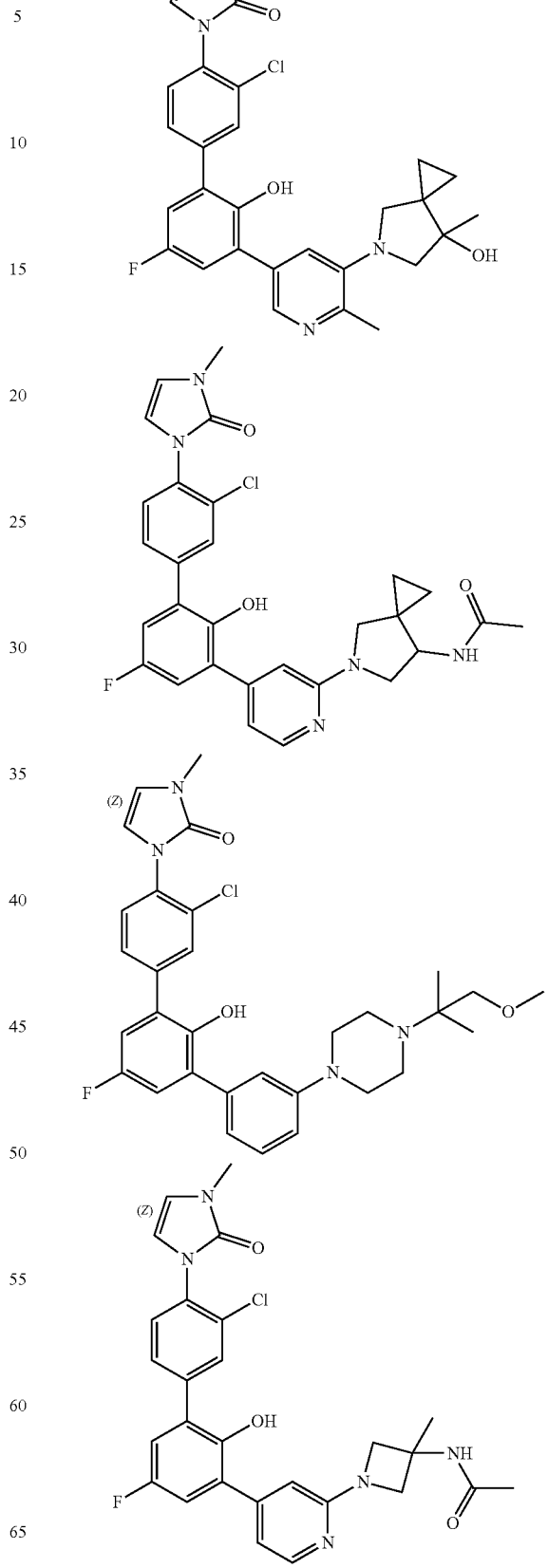

275
-continued
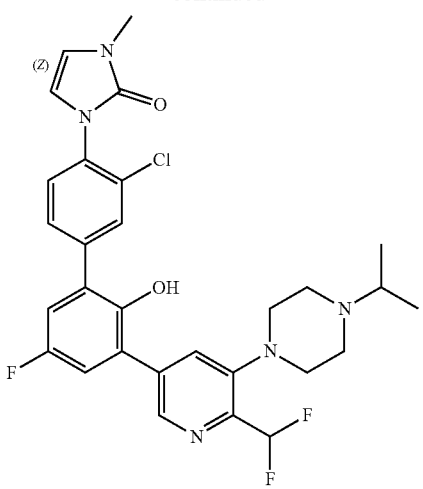
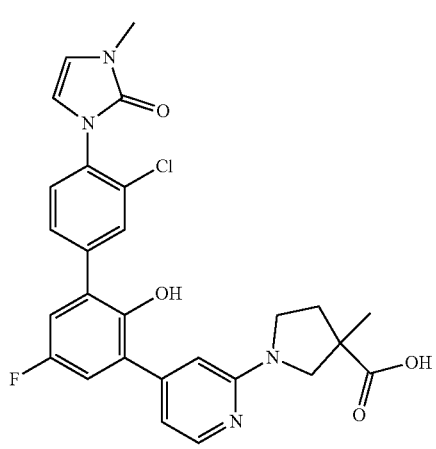
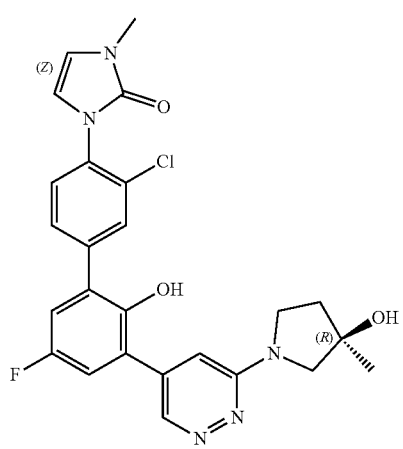
276
-continued
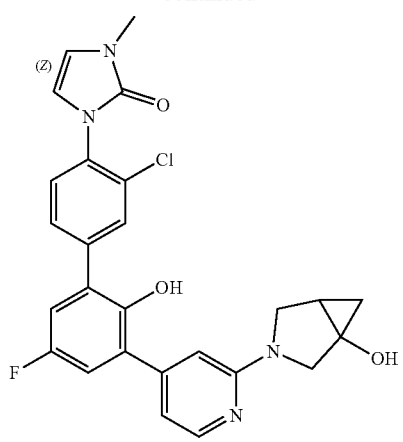
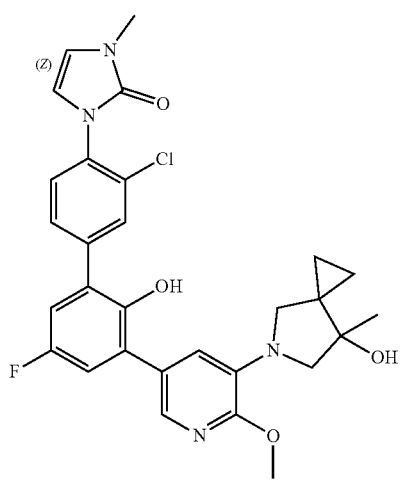
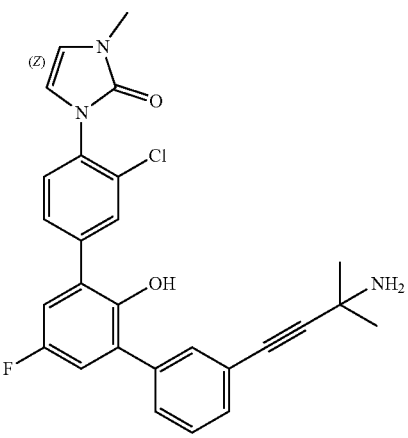

277
-continued
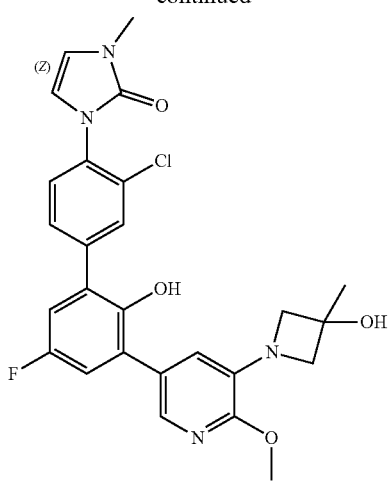
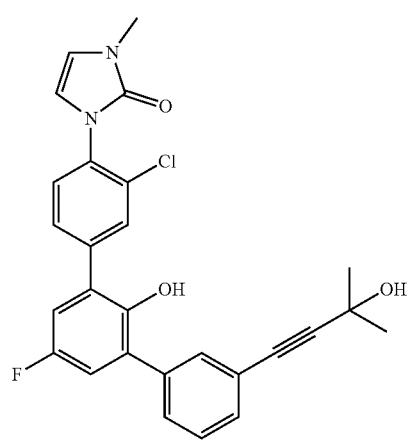
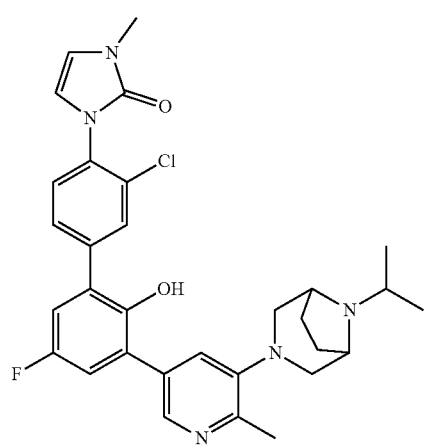
278
-continued
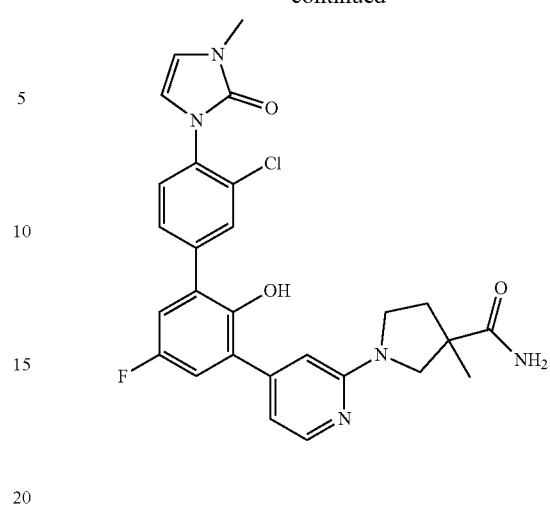
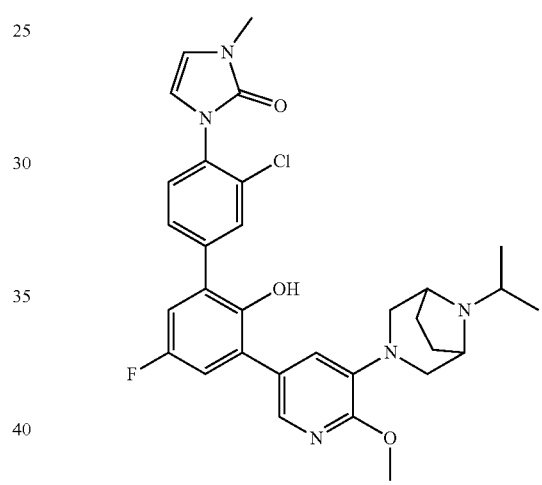
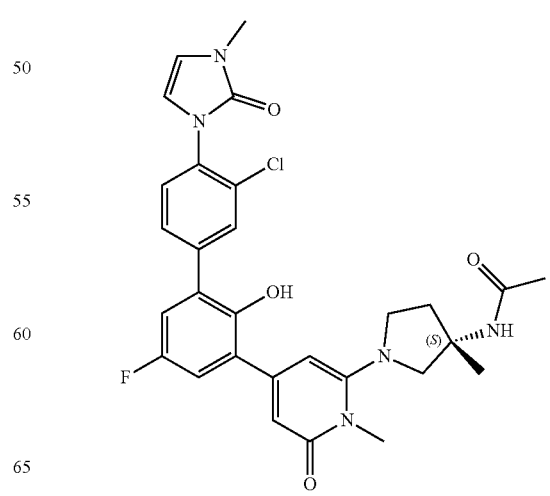

279
-continued
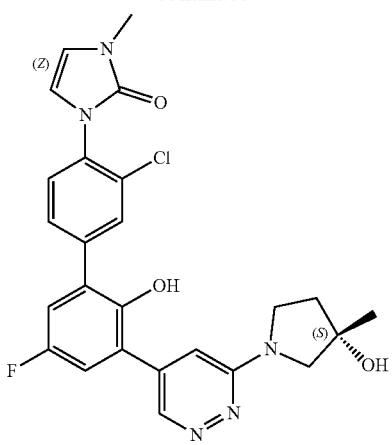
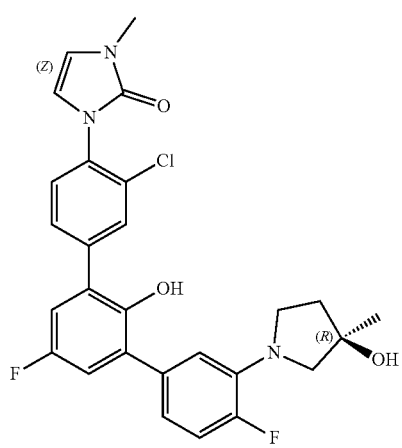
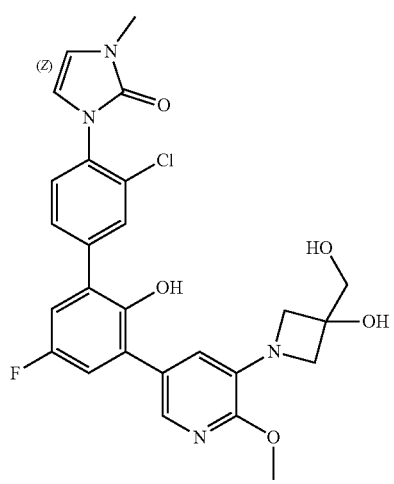
280
-continued
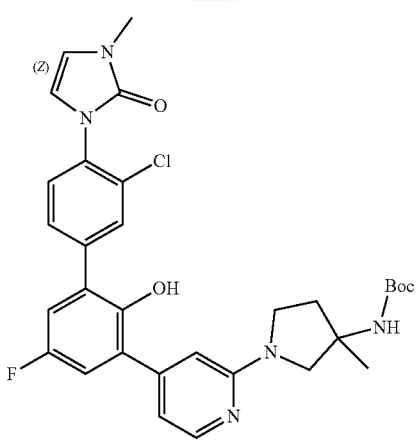
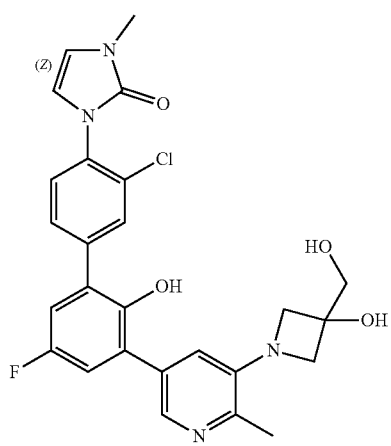
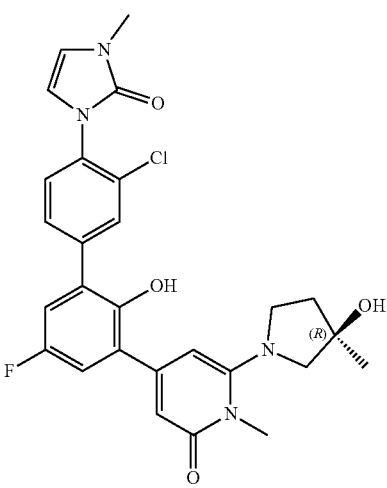

281
-continued
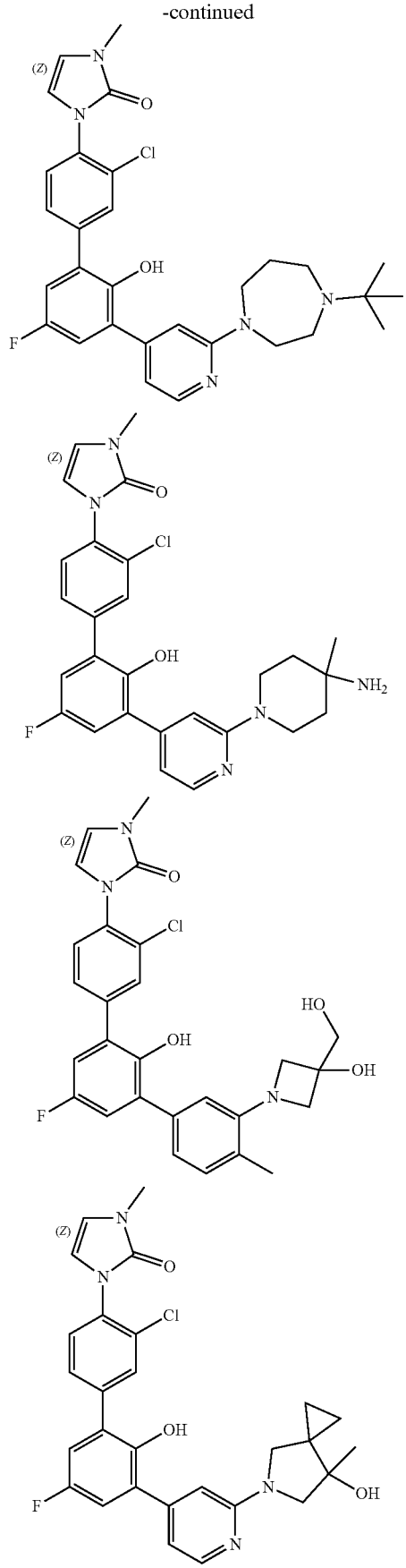
282
-continued
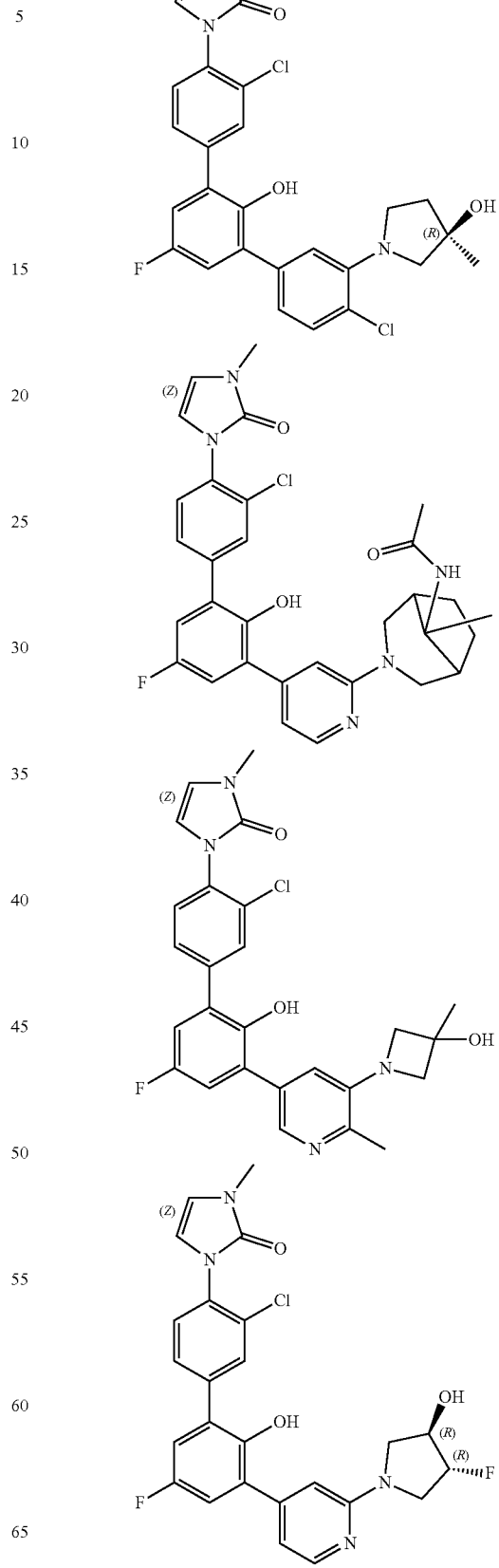

-continued
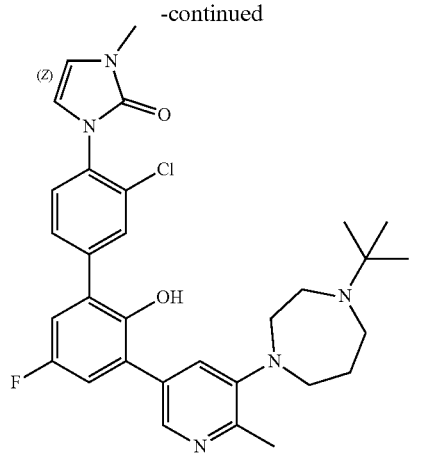
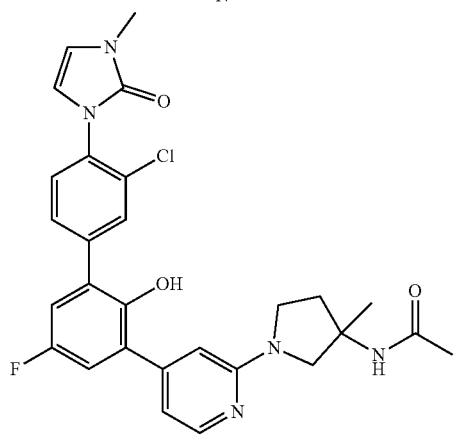
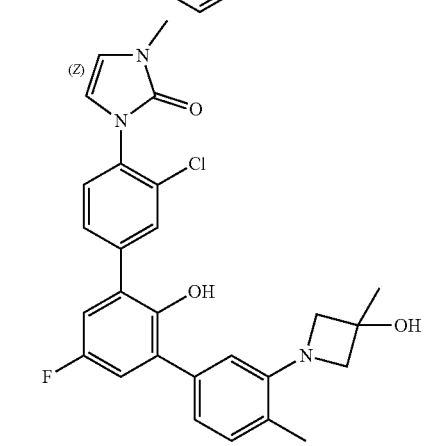
-continued
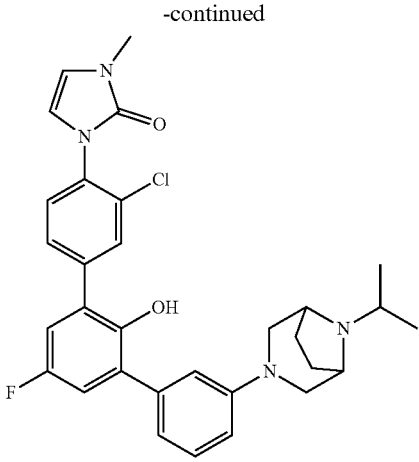
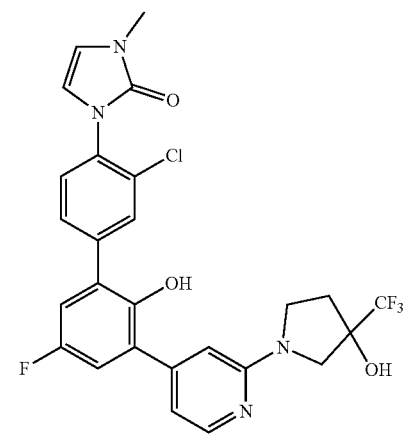
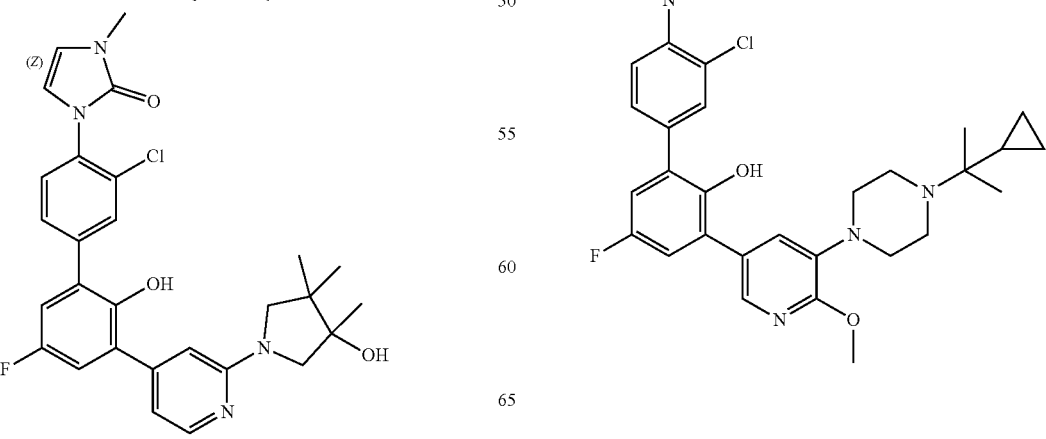

285
-continued
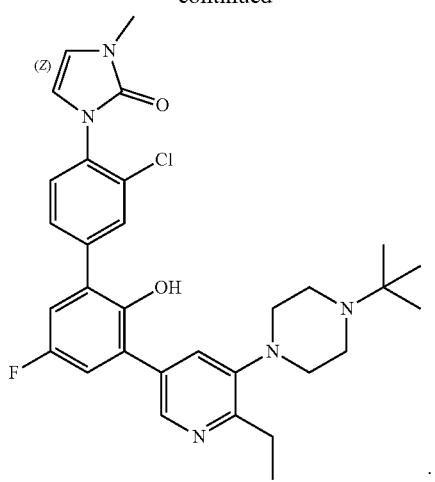
286
-continued
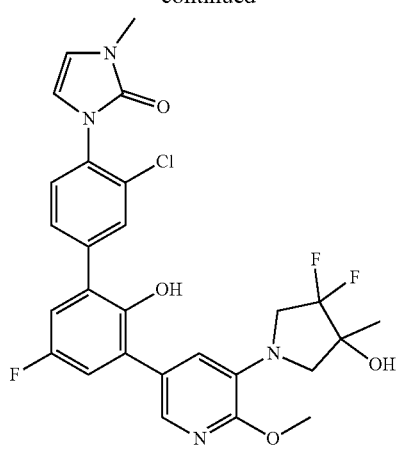
Further exemplary compounds of the invention include:
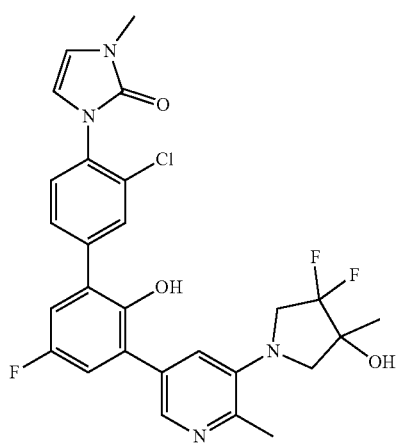
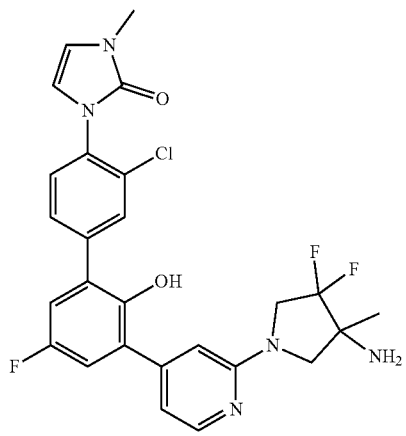
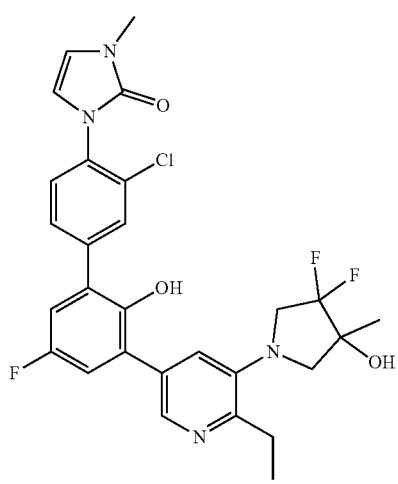
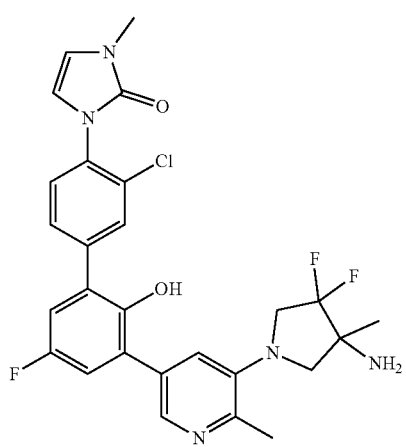

-continued
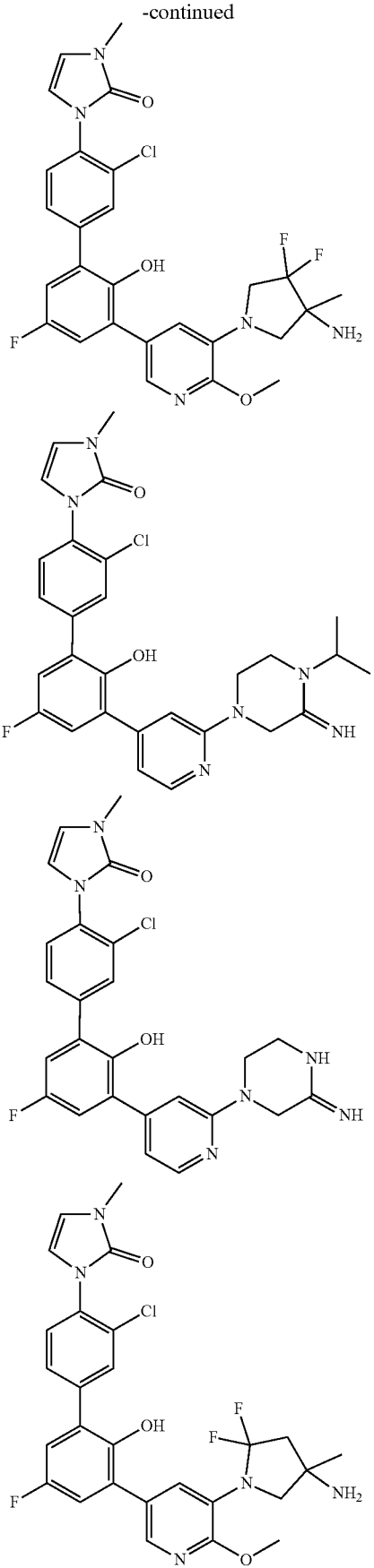
-continued
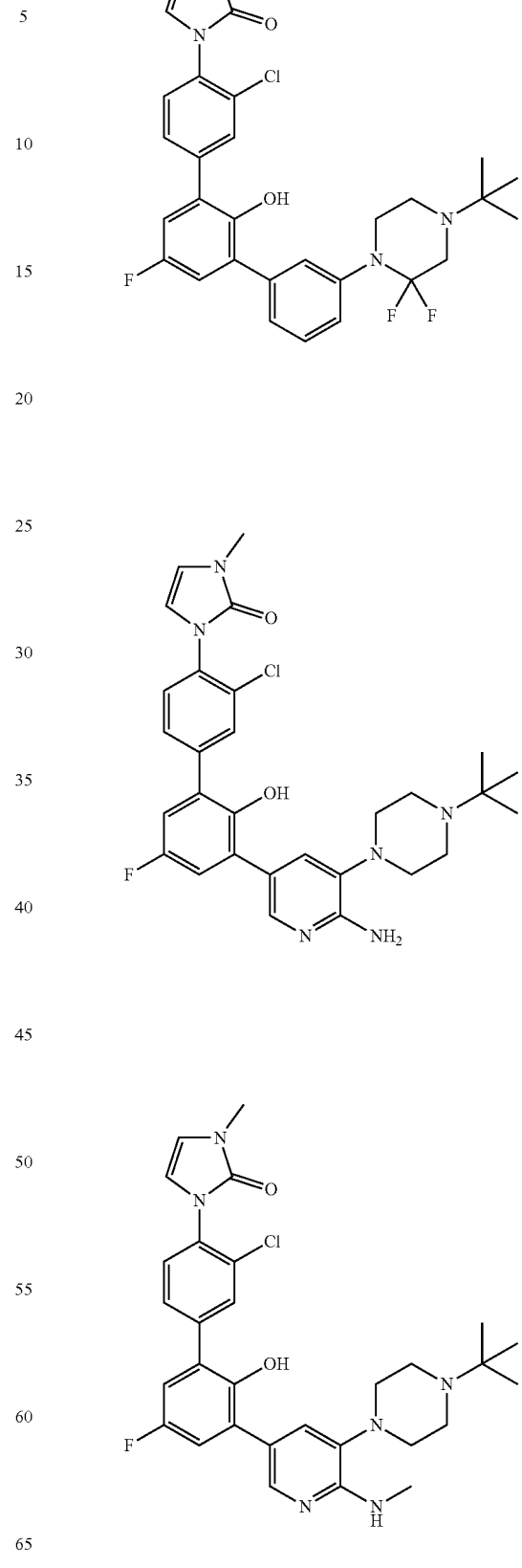

289
-continued
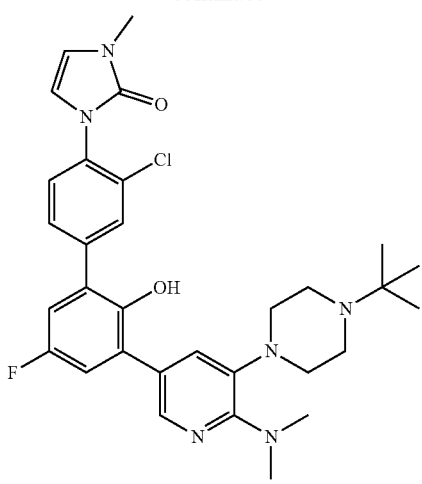
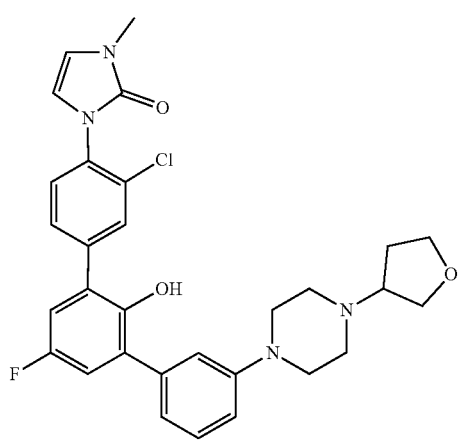
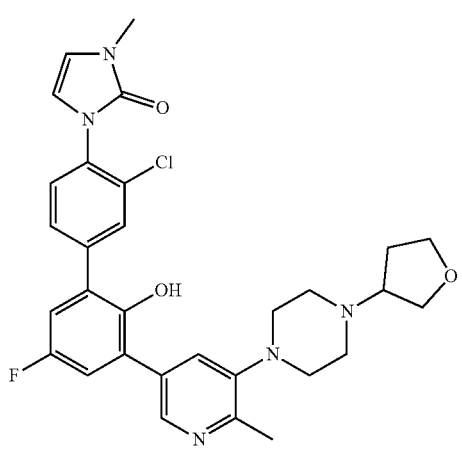
290
-continued
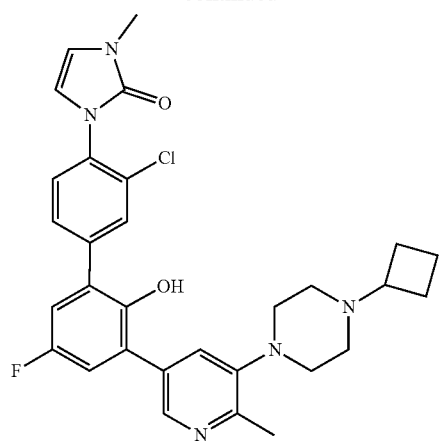
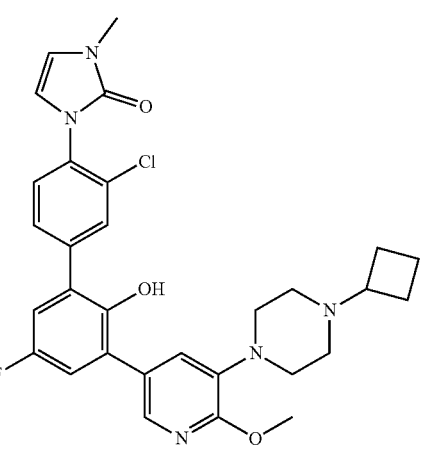
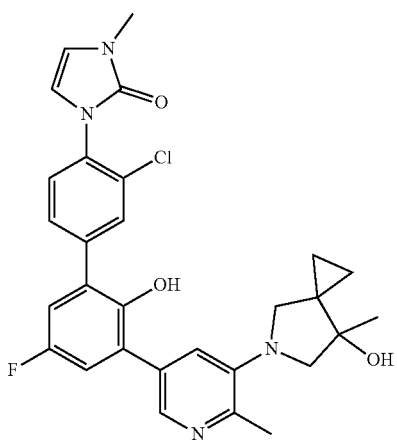

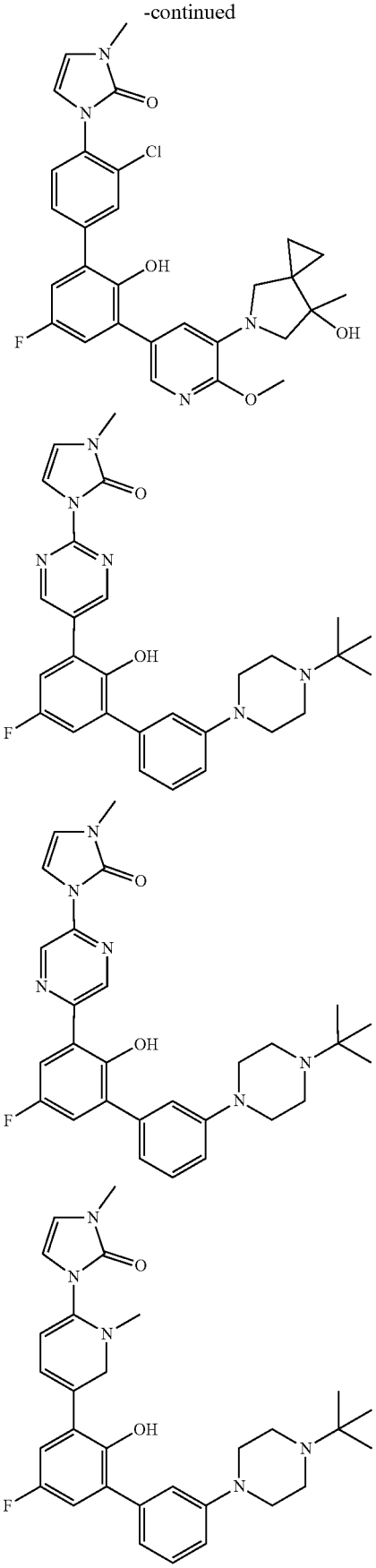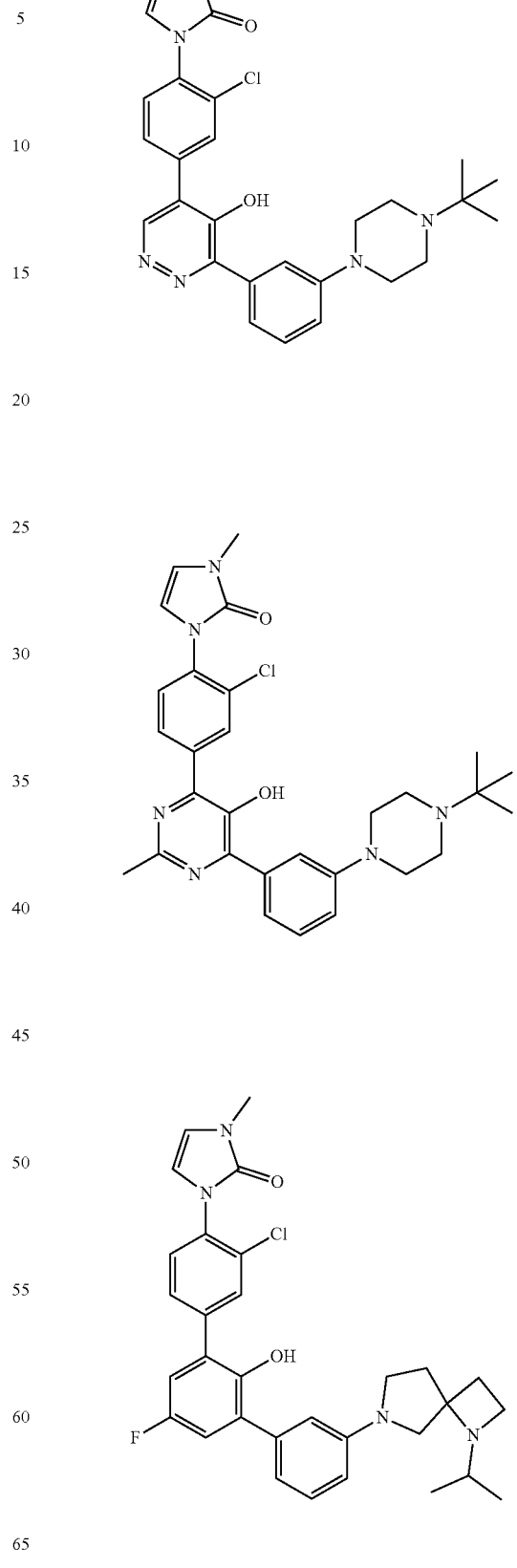

-continued
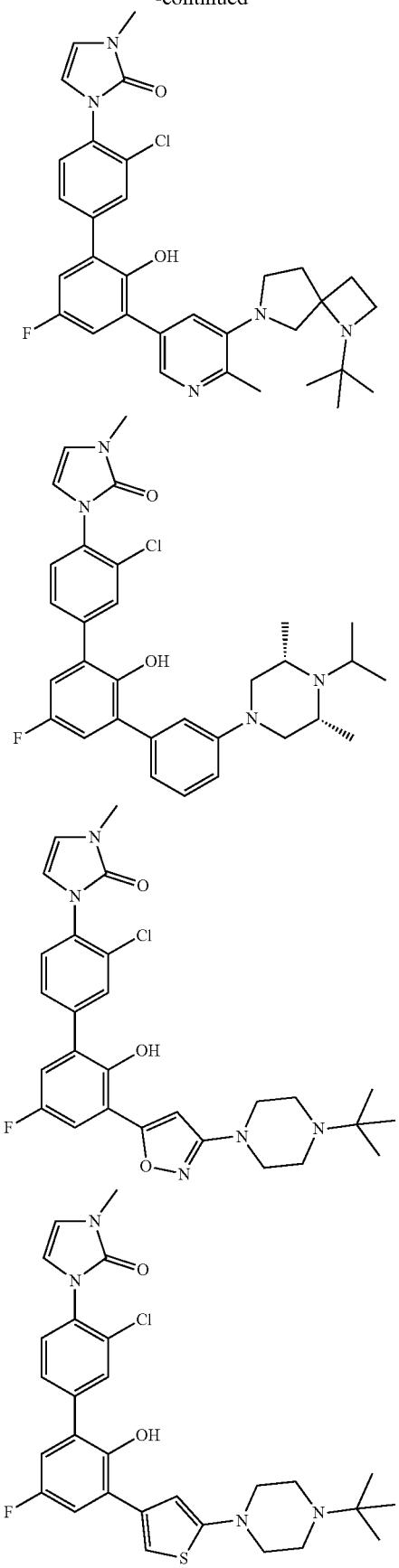
-continued
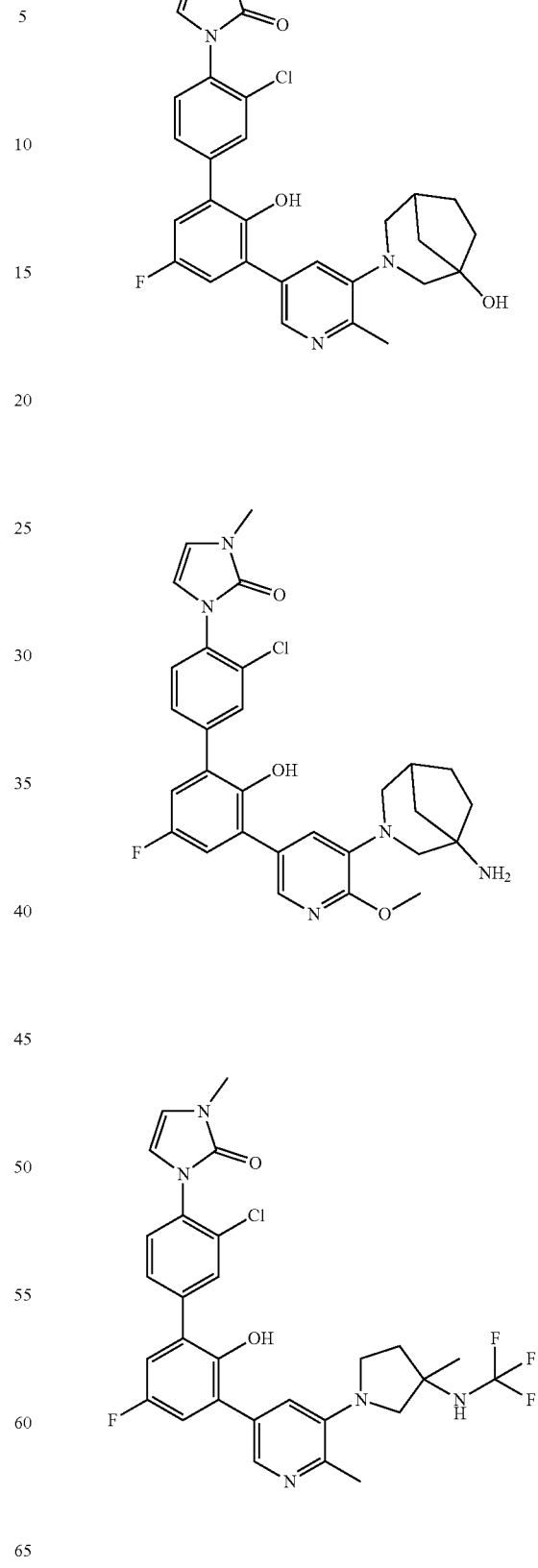

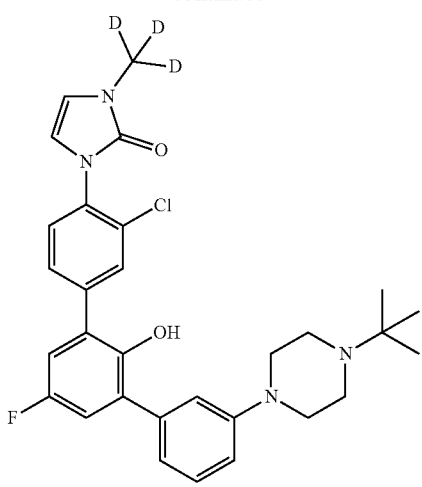
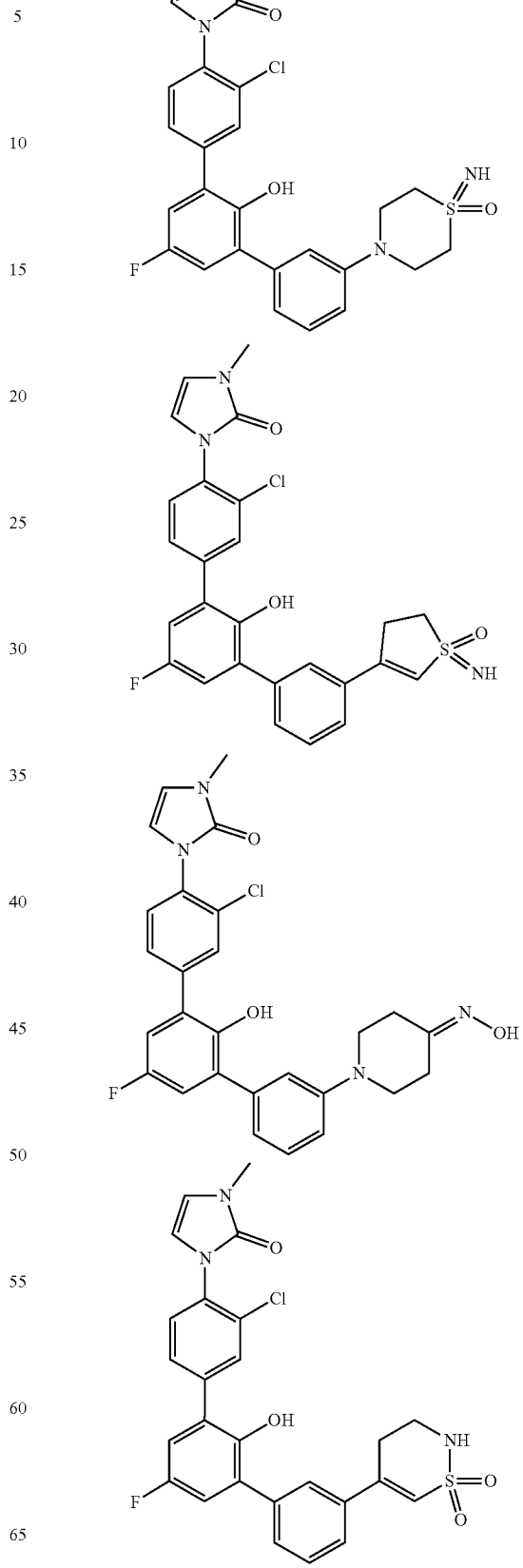

297
-continued
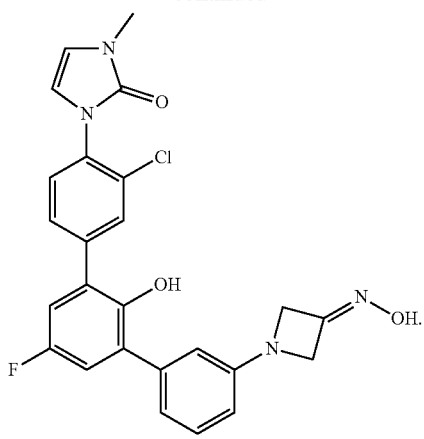
Further exemplary compounds of the invention include:
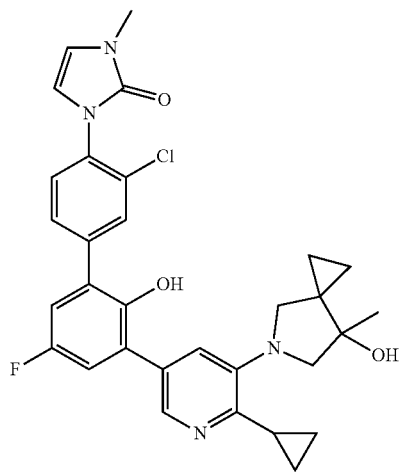
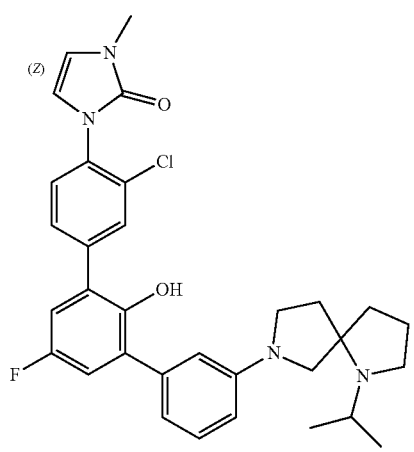
298
-continued
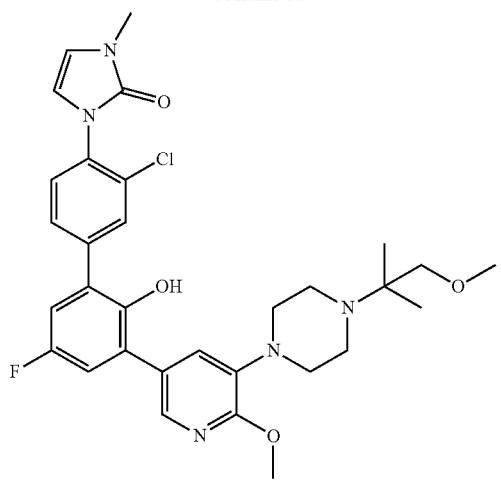
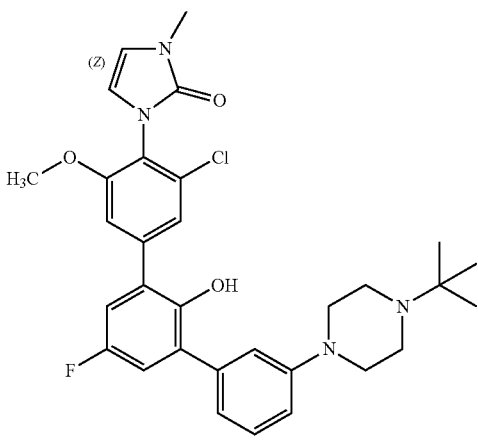
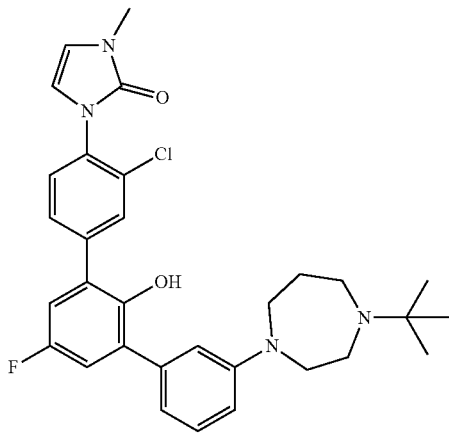

299
-continued
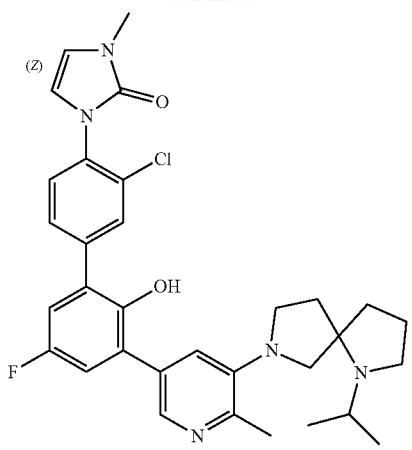
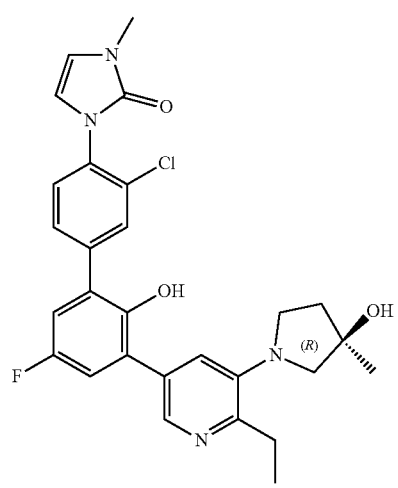
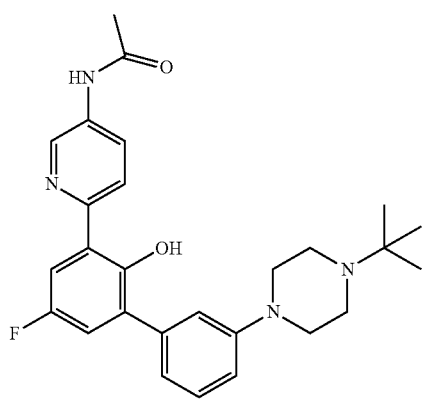
300
-continued
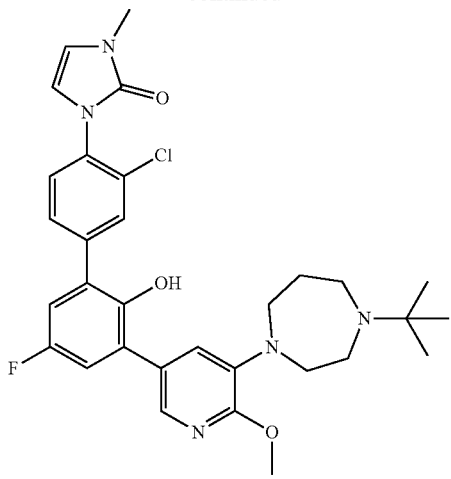
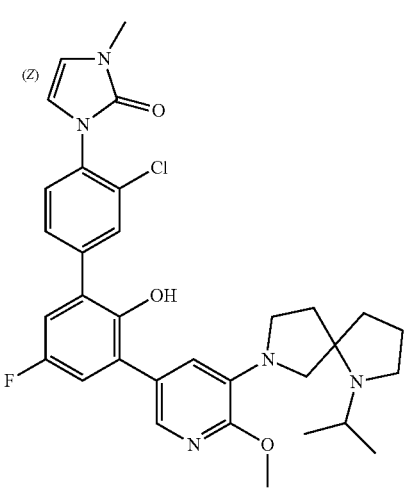
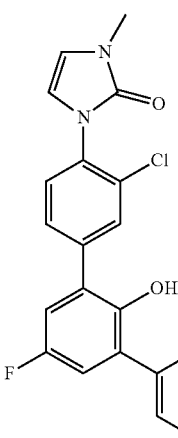

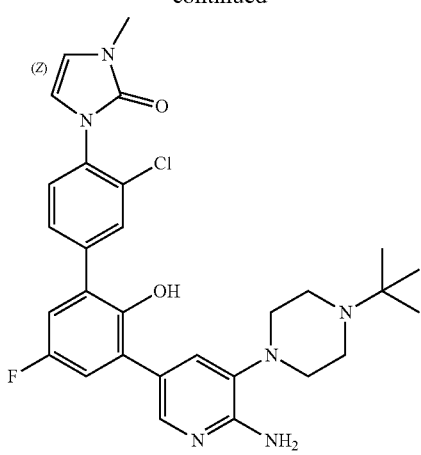
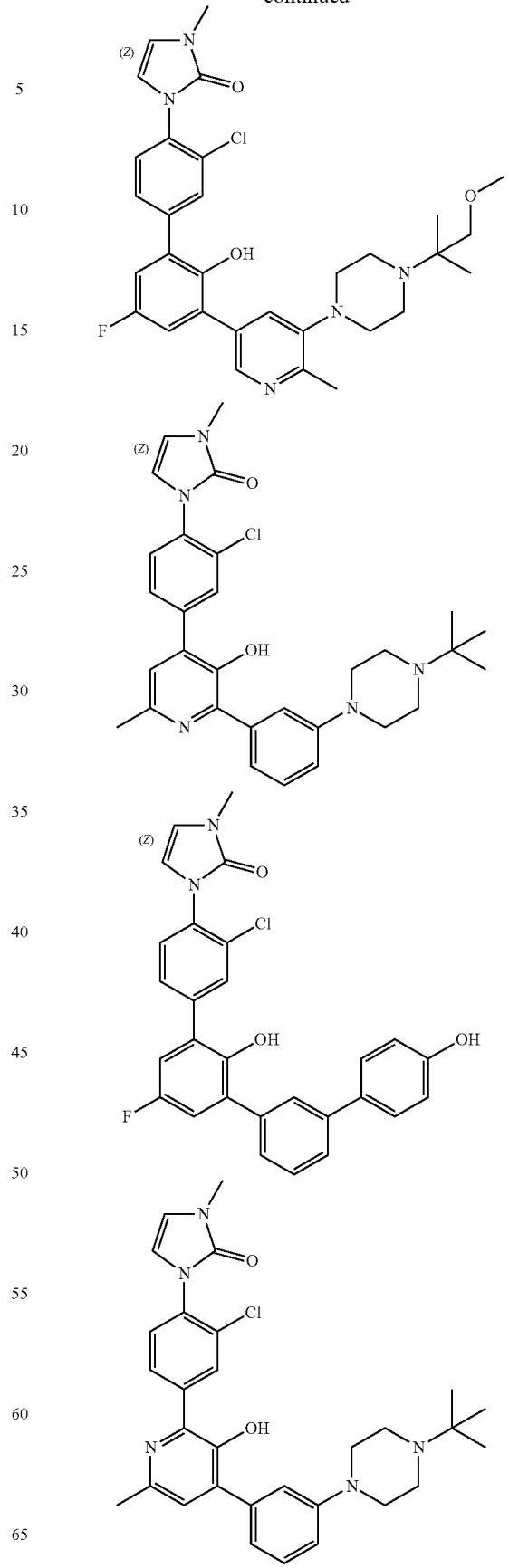

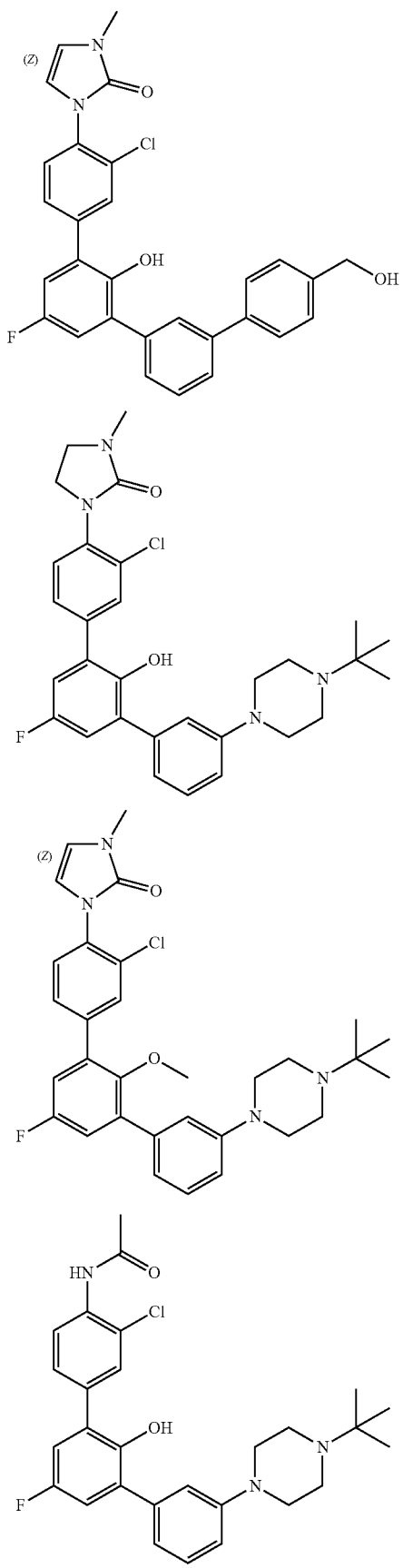
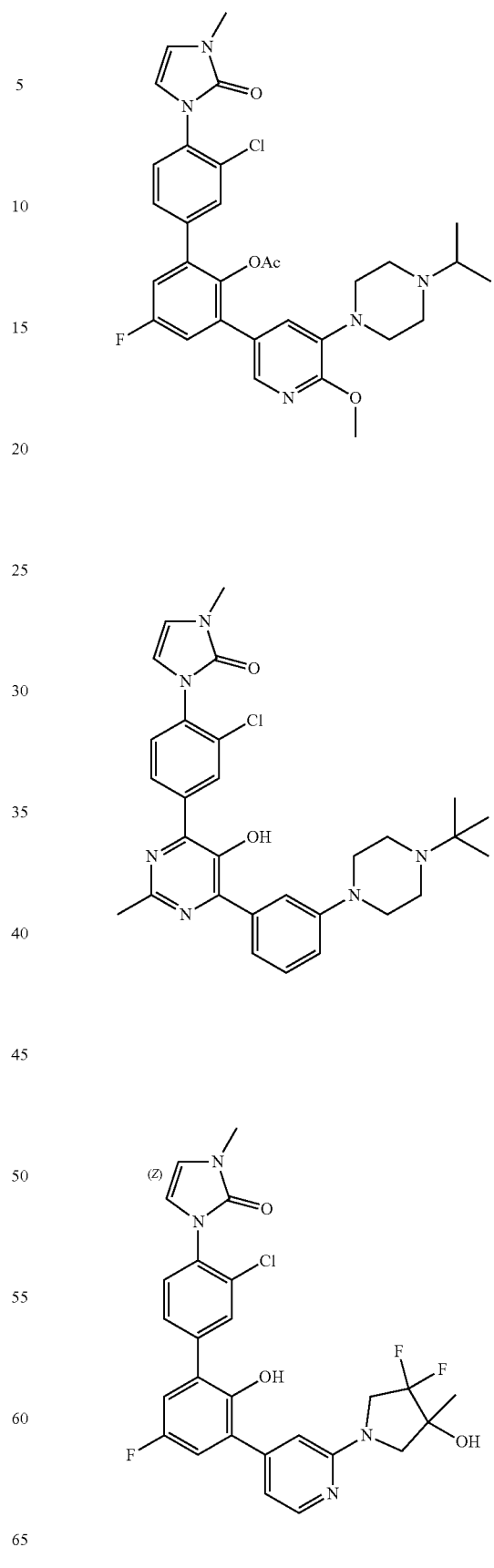

305
-continued
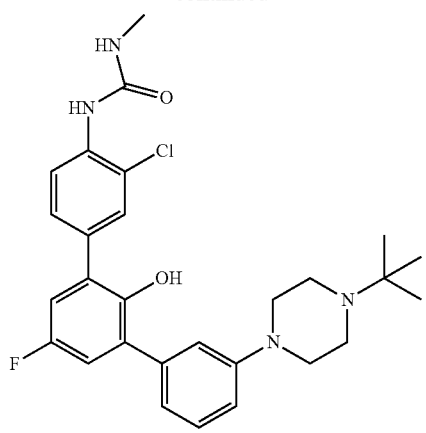
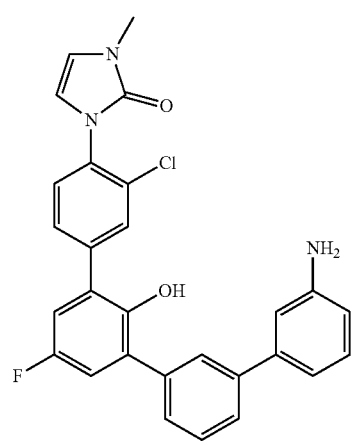
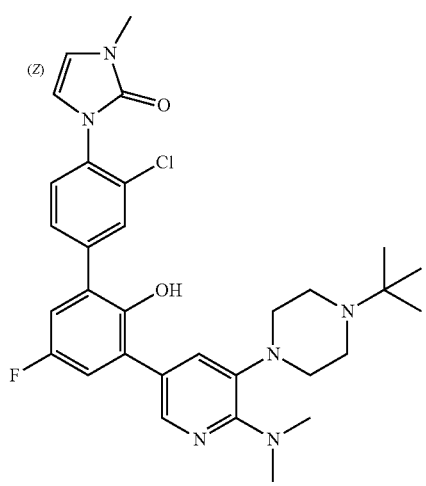
306
-continued
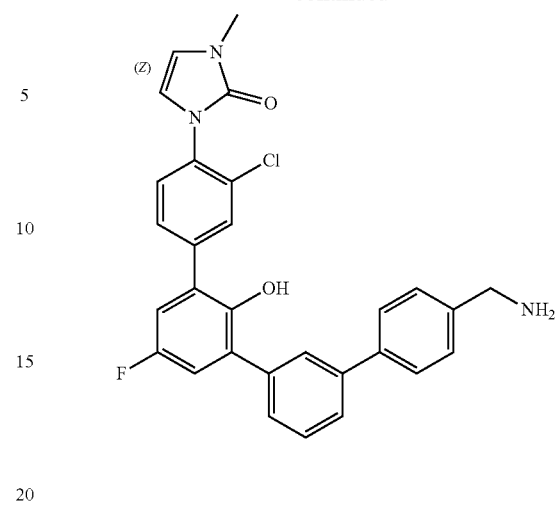
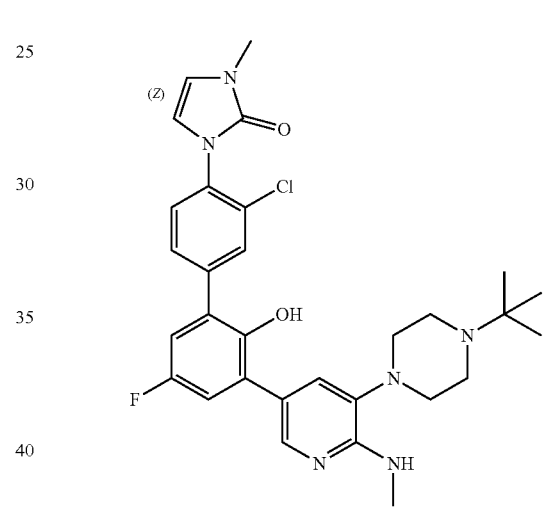
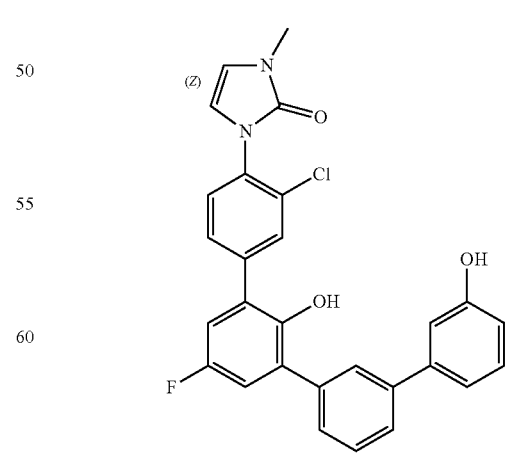

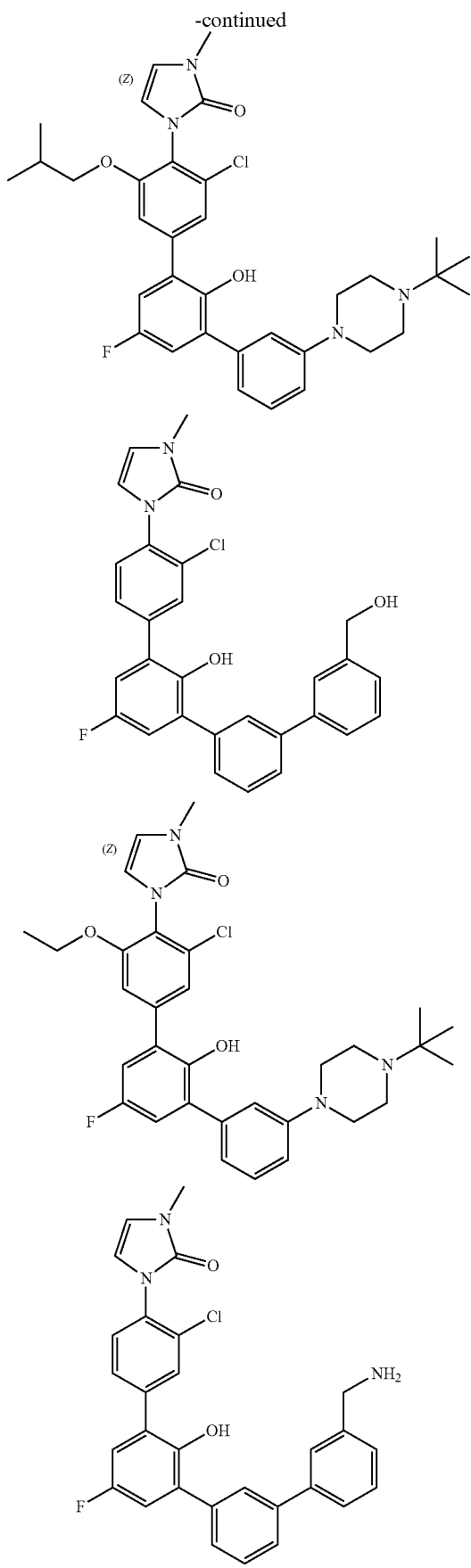

309
-continued
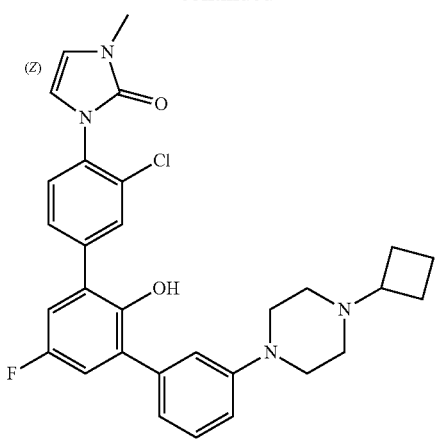
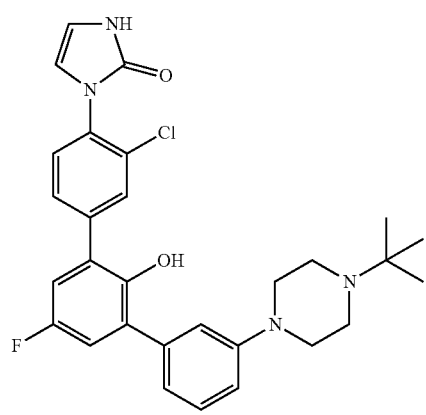
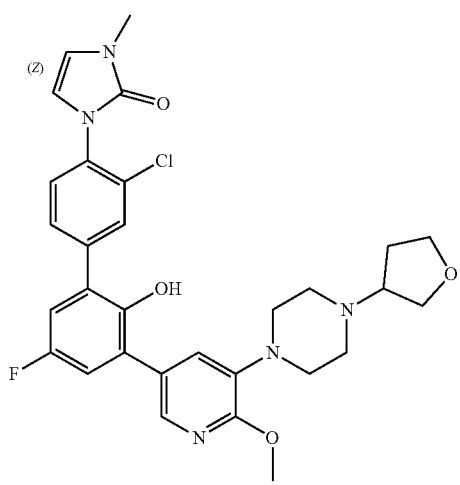
310
-continued
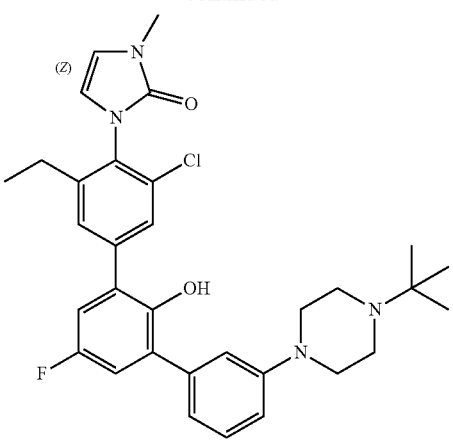
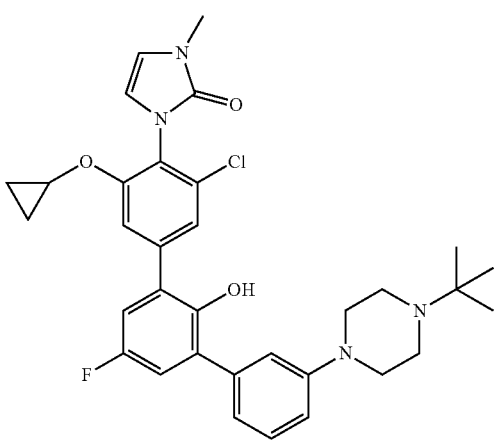

311
-continued
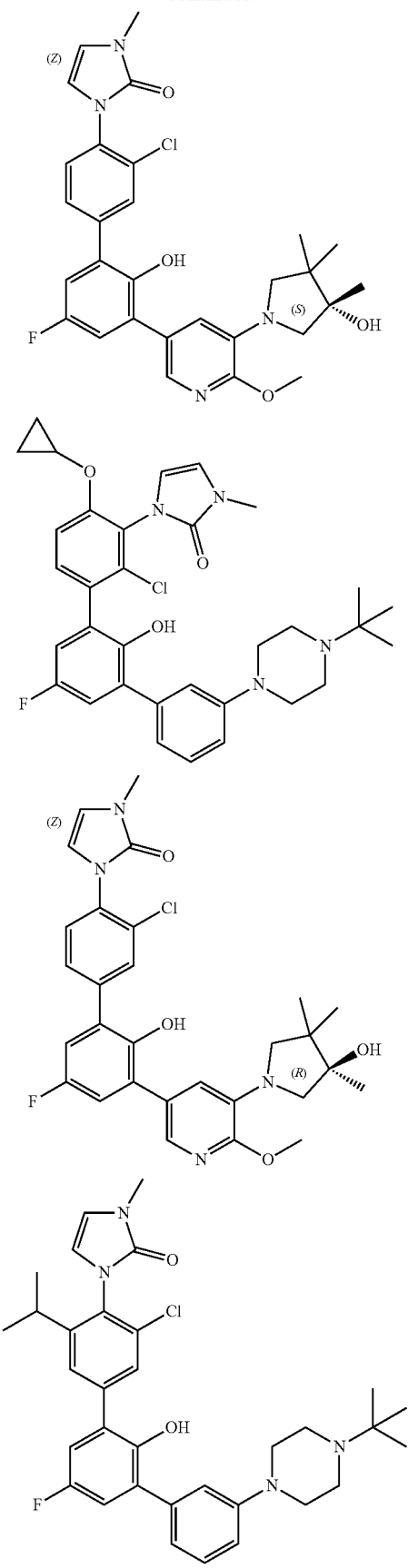
312
-continued
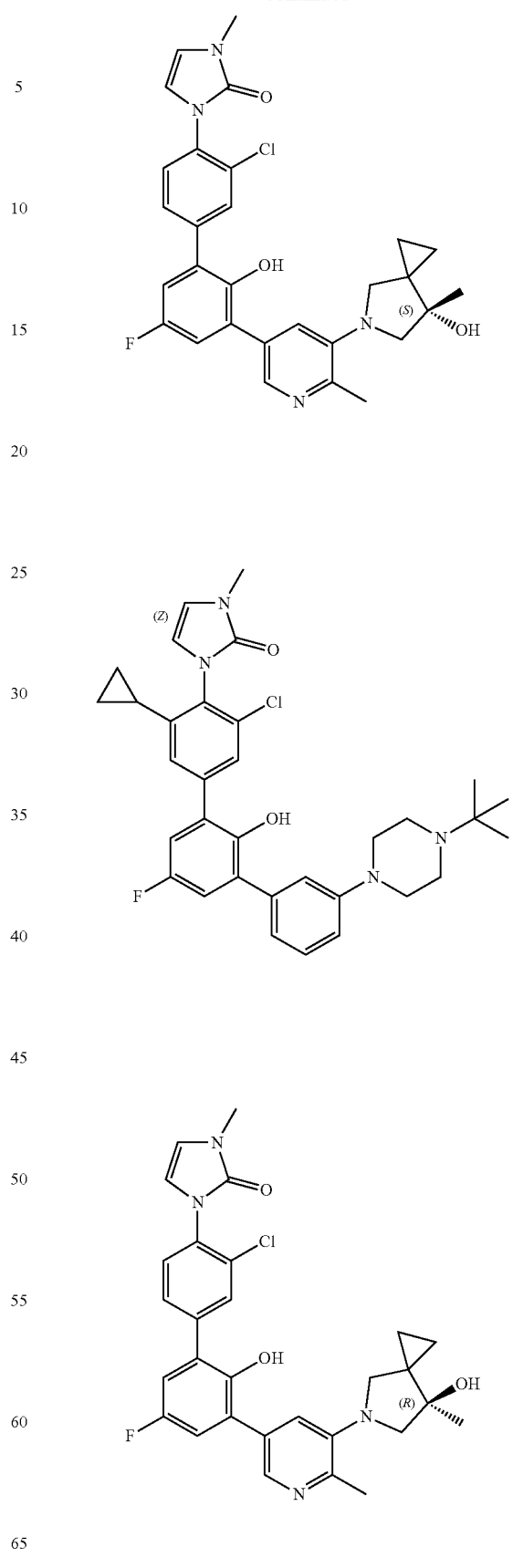

313
-continued
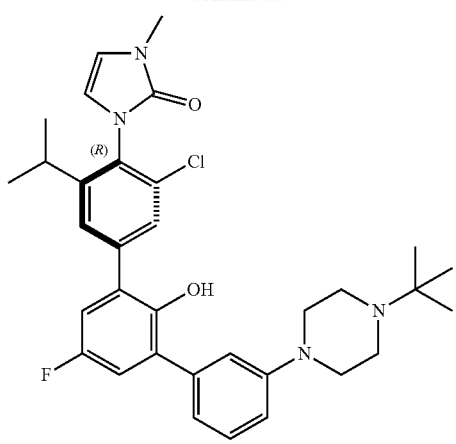
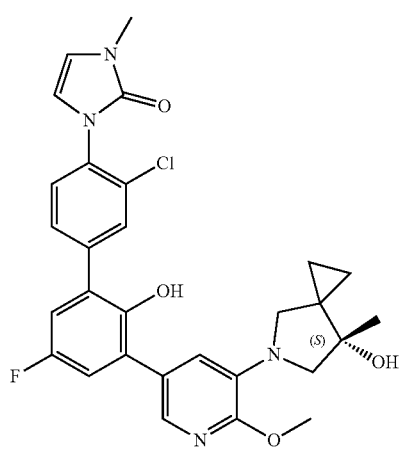
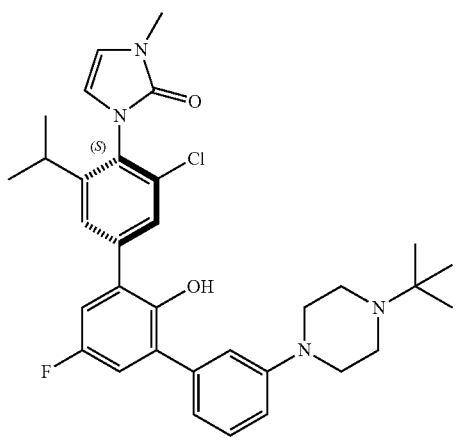
314
-continued
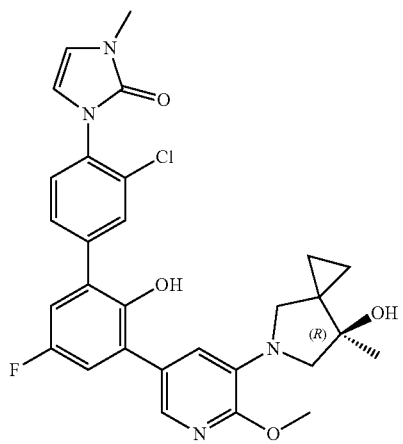
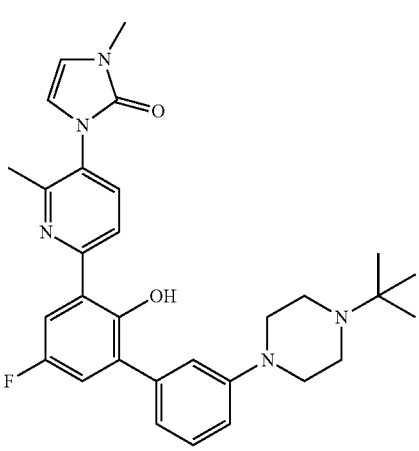
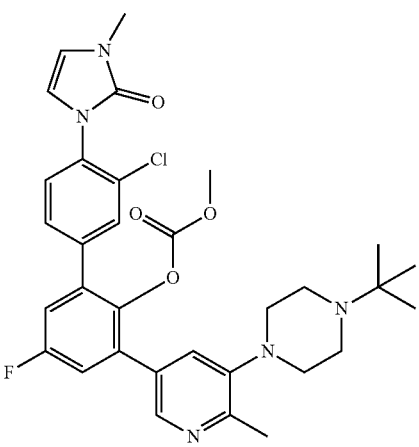

315
-continued
316
-continued
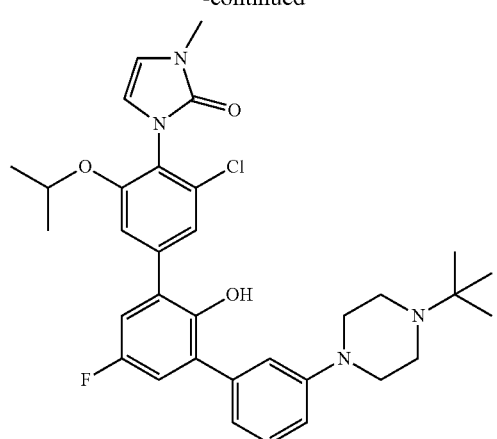
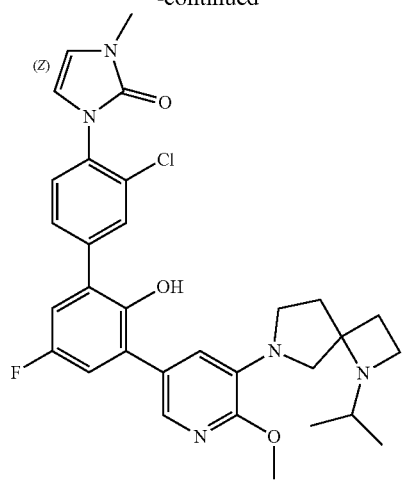
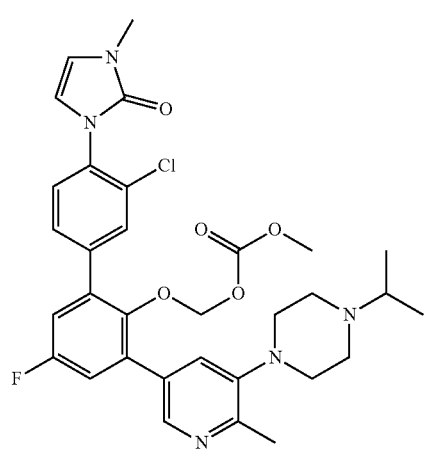
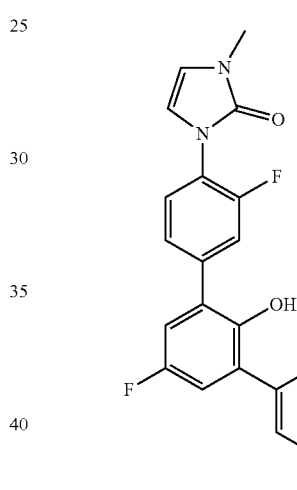
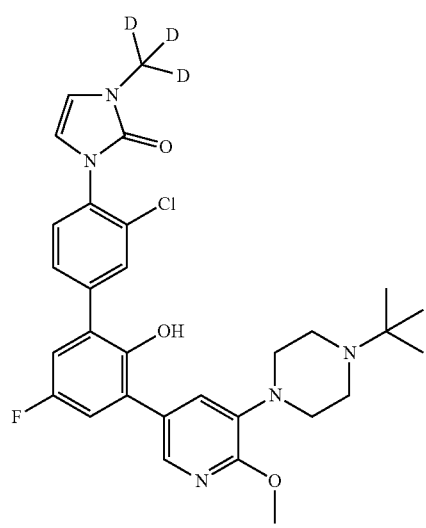
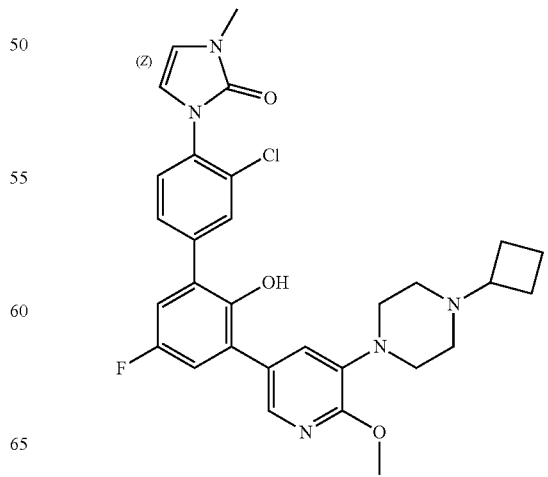

317
-continued
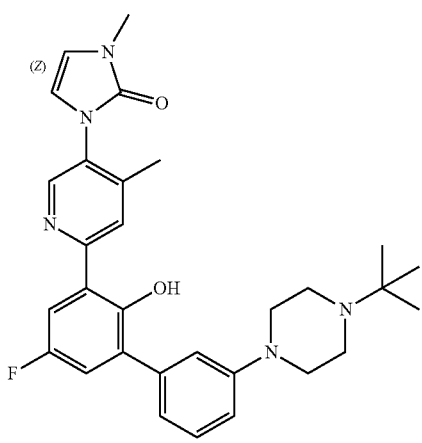
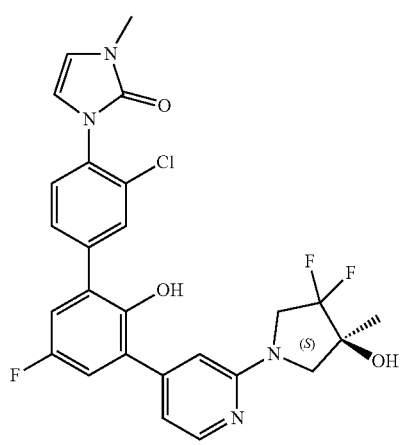
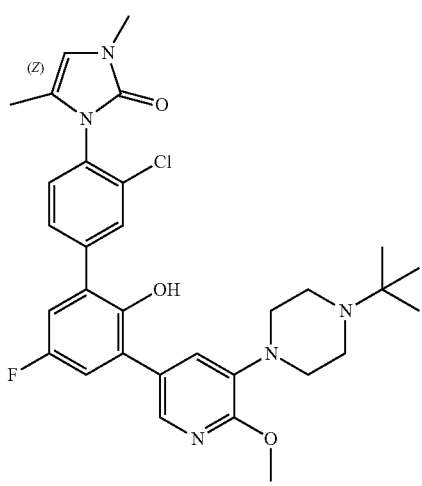
318
-continued
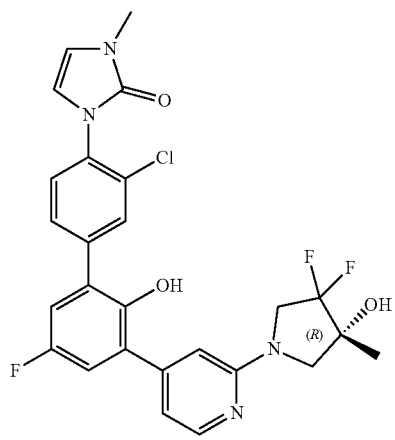
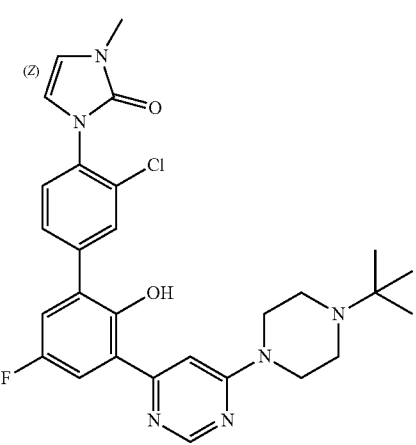
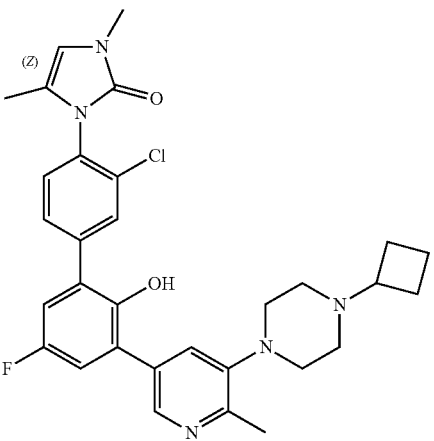

319
-continued
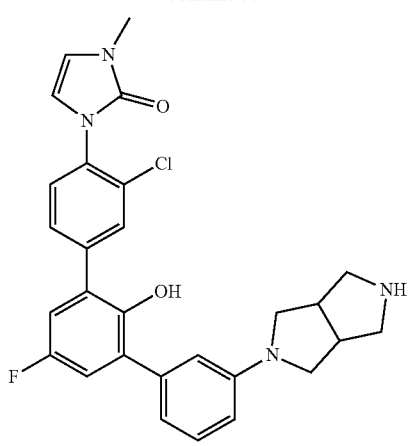
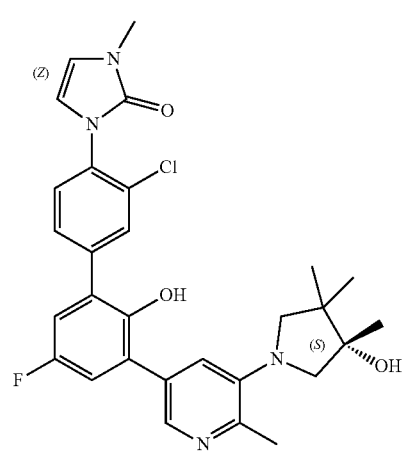
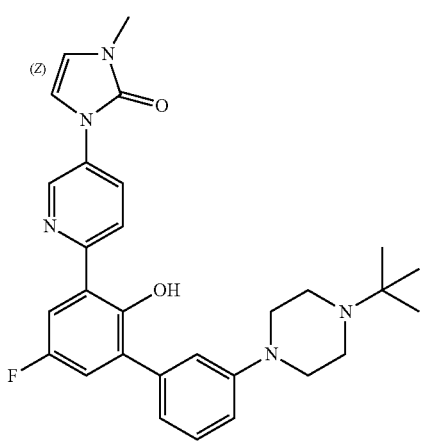
320
-continued
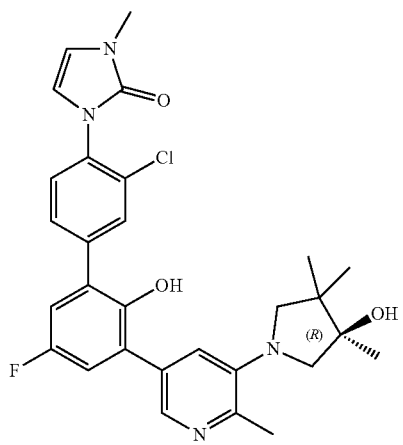
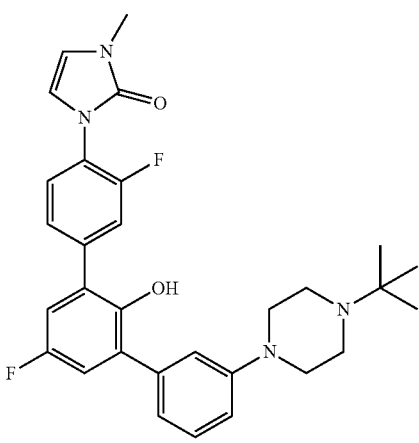

321
-continued
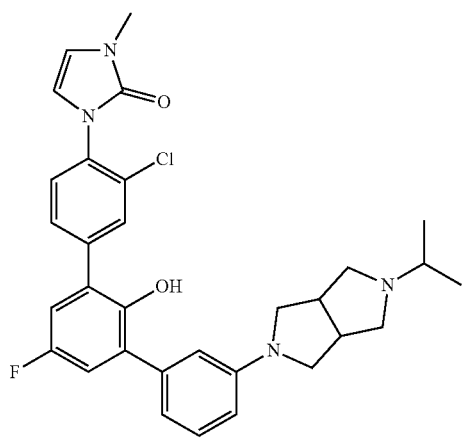
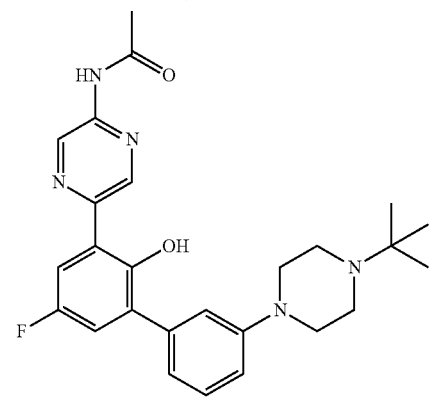
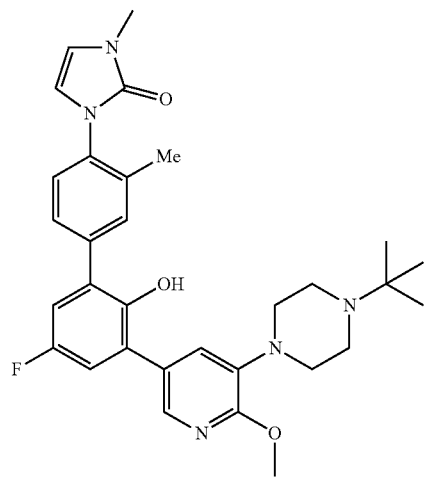
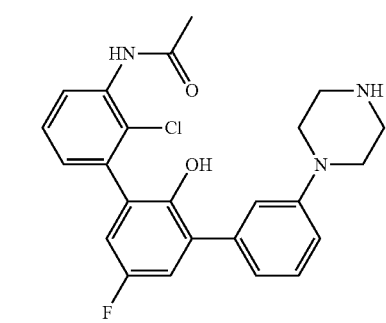
322
-continued
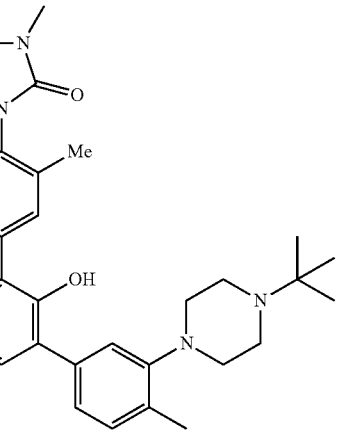
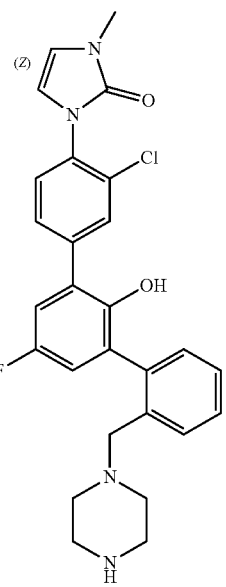
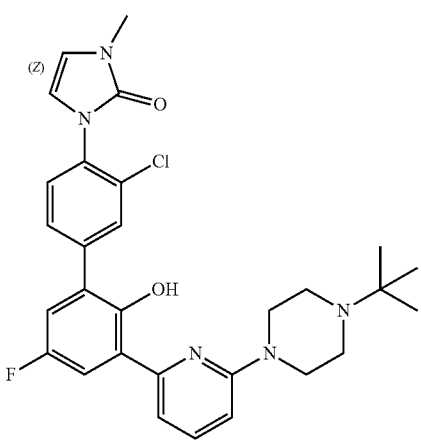

323
-continued
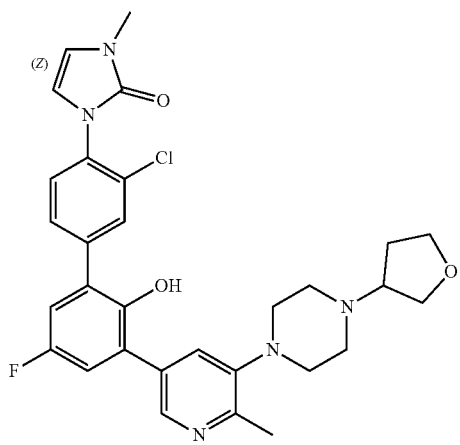
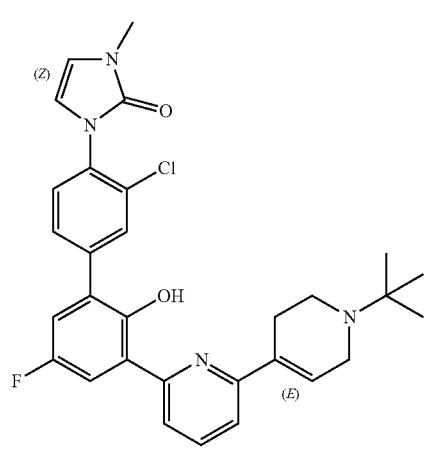
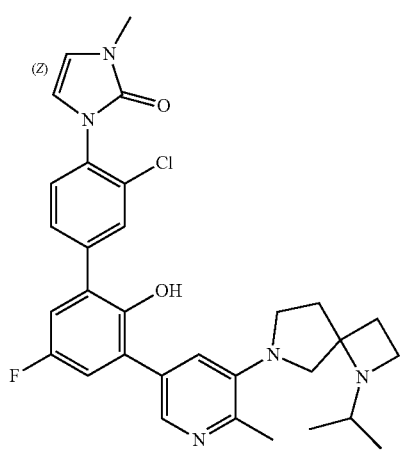
324
-continued
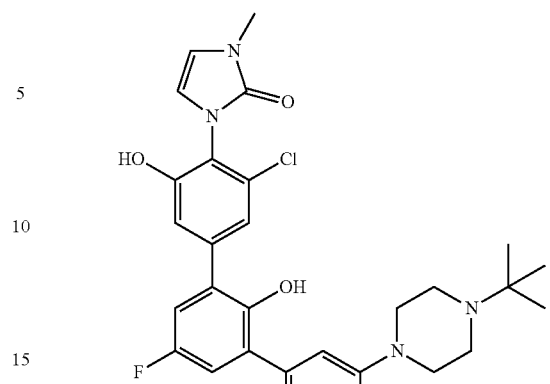
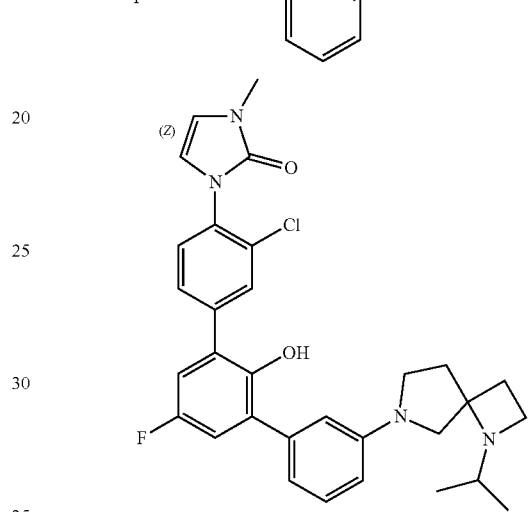
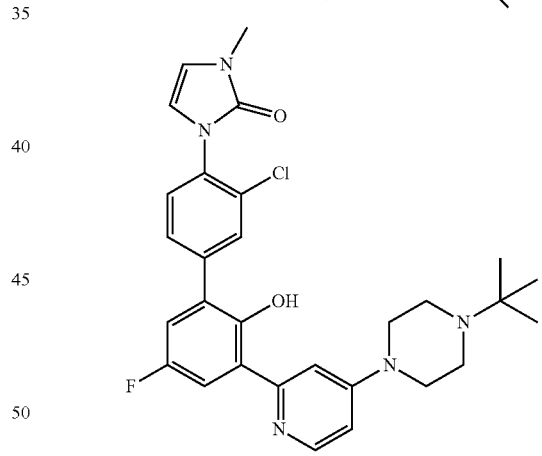
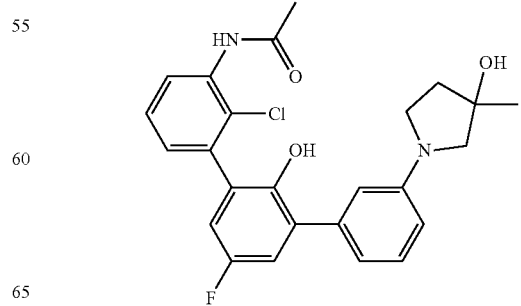

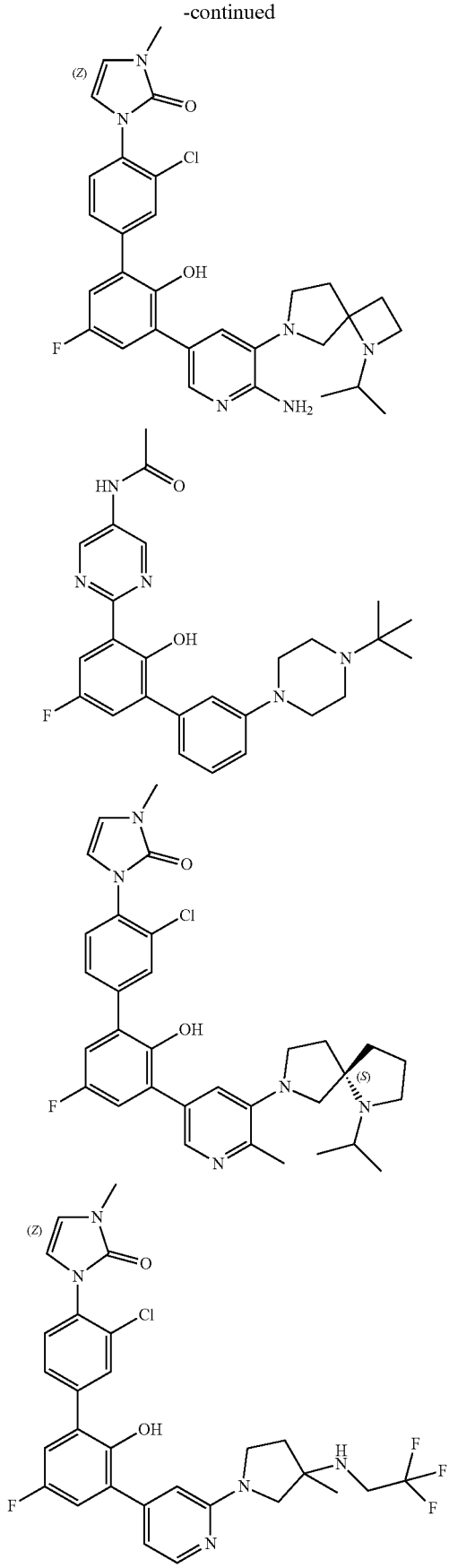

327
-continued
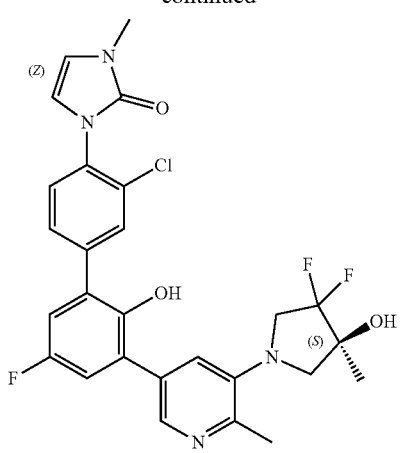
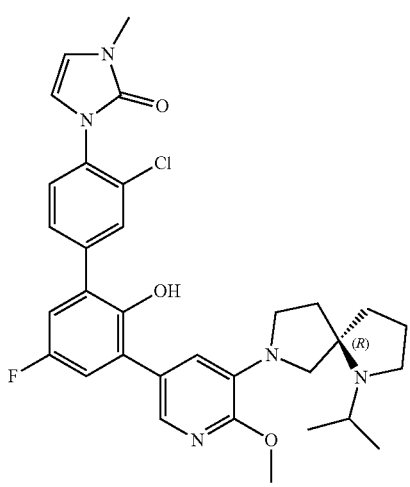
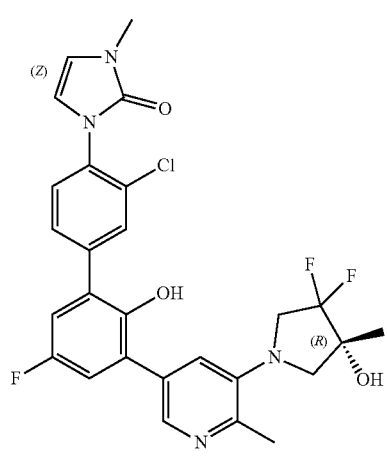
328
-continued
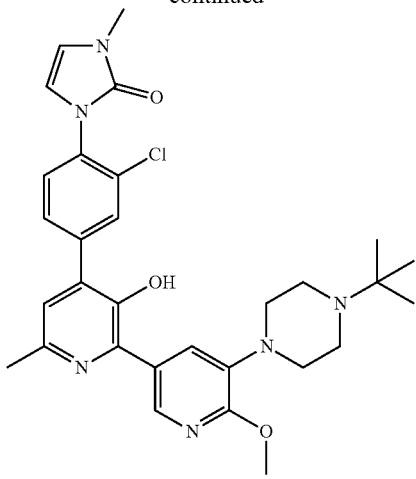
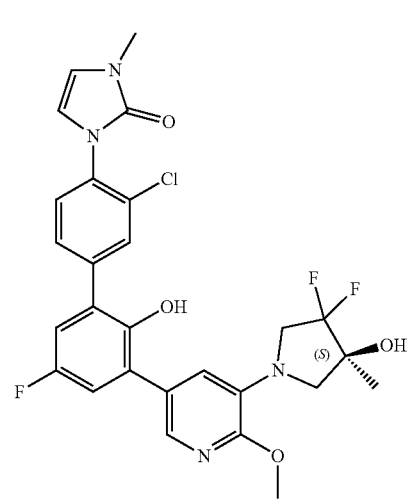
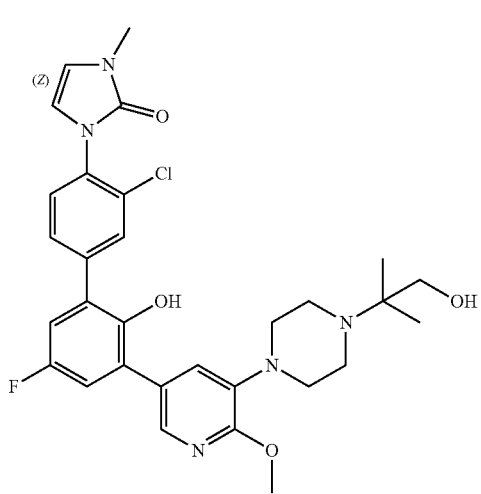

329
-continued
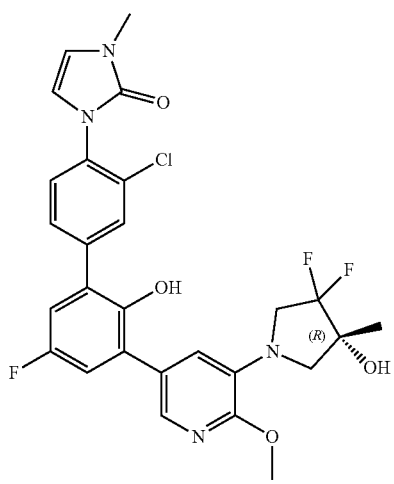
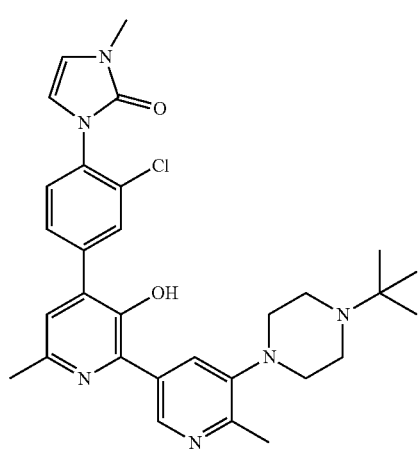
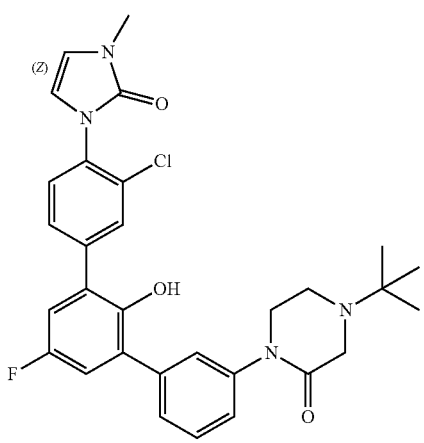
330
-continued
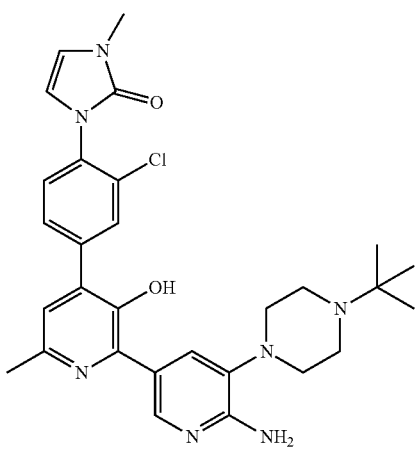
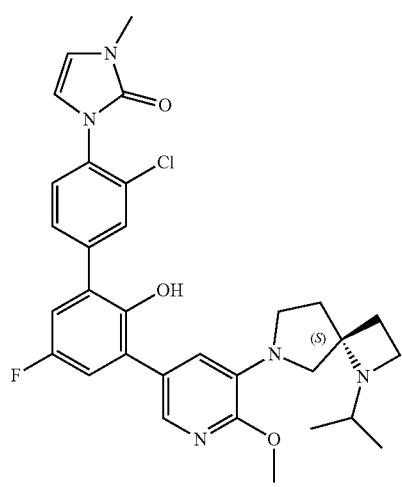
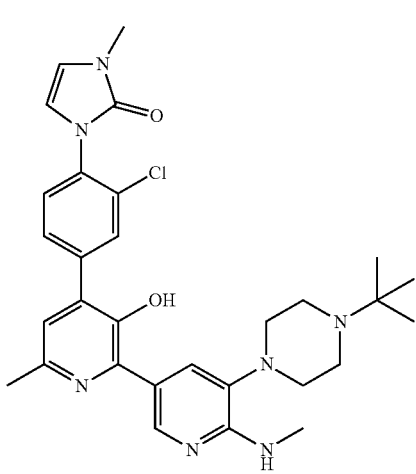

331
-continued
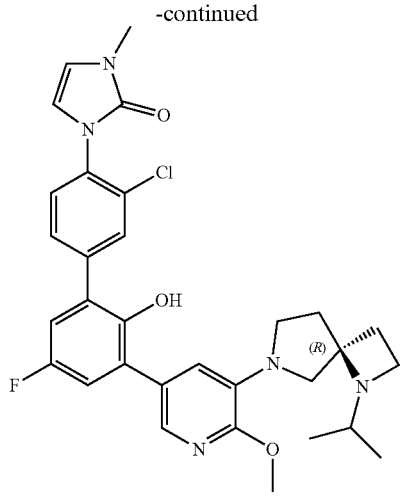
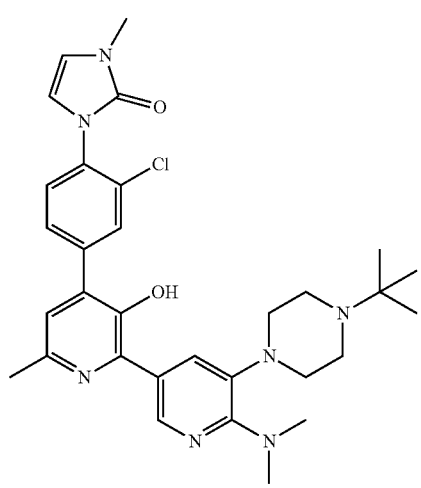
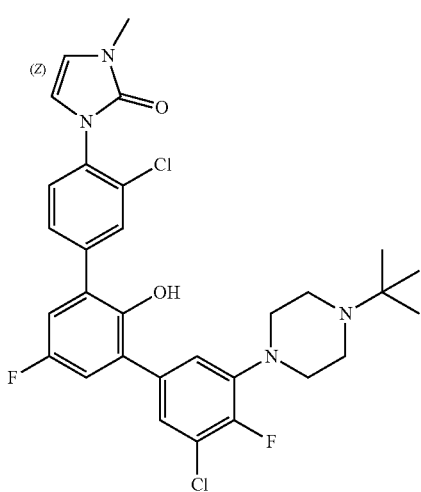
332
-continued
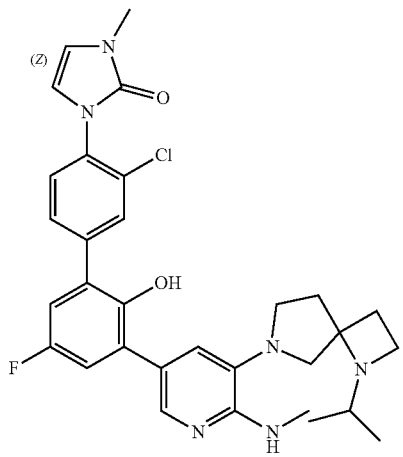
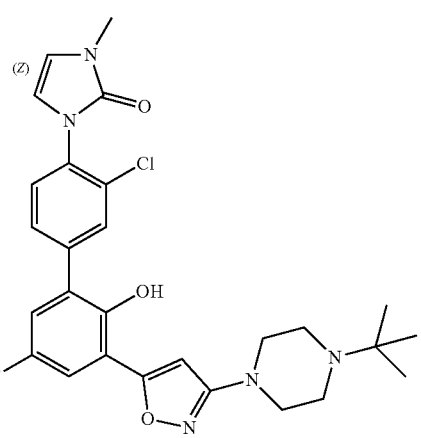
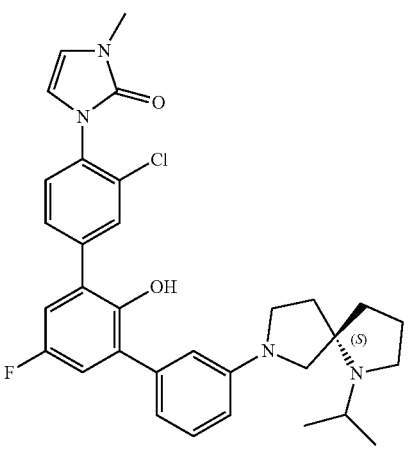

333
-continued
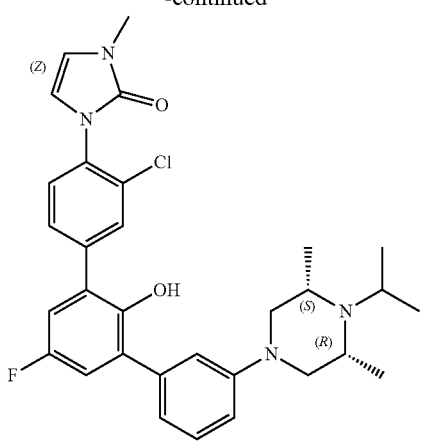
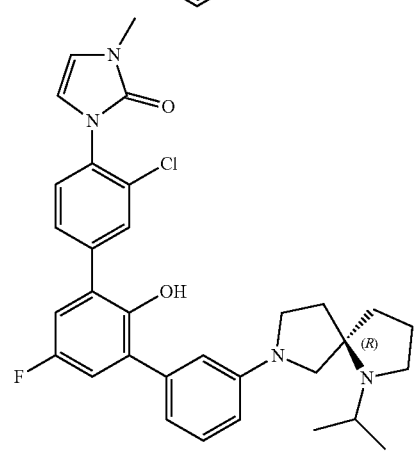
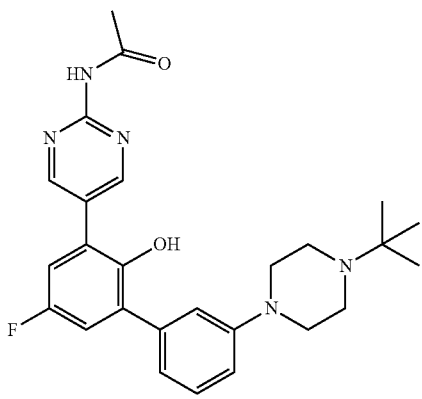
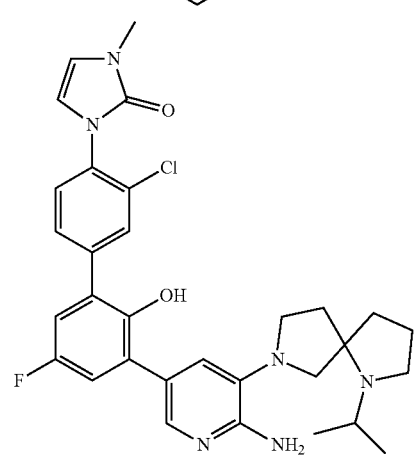
334
-continued
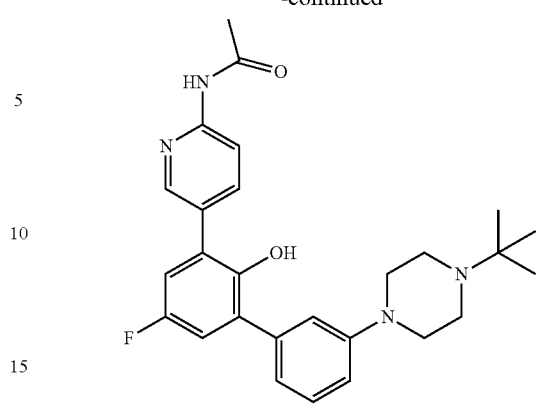
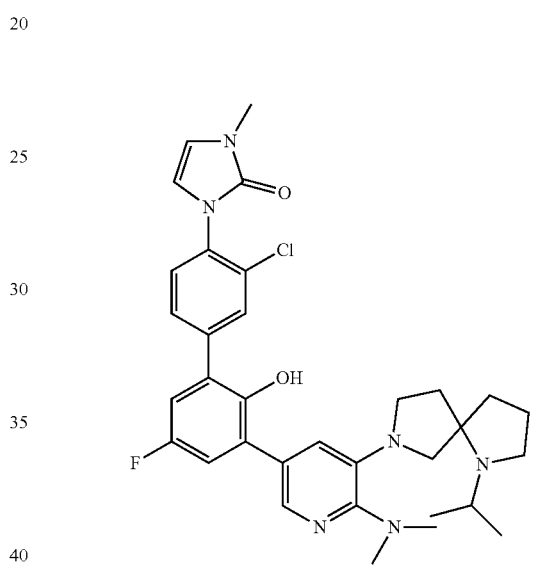
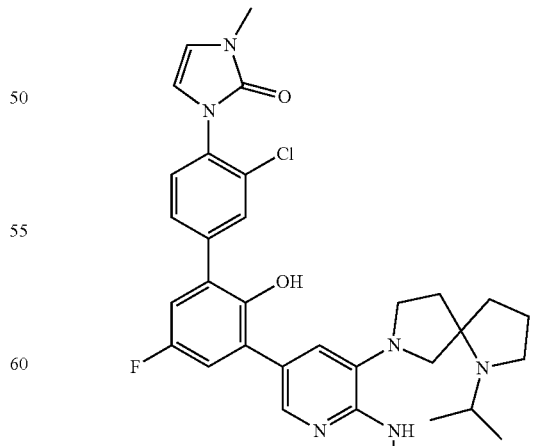

335
-continued
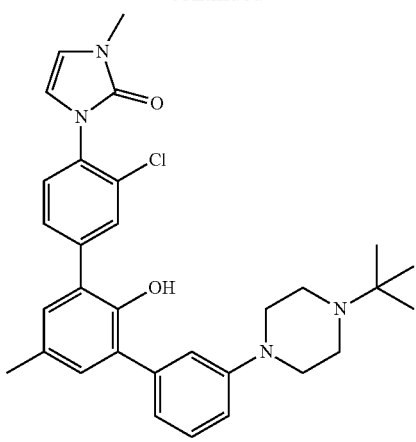
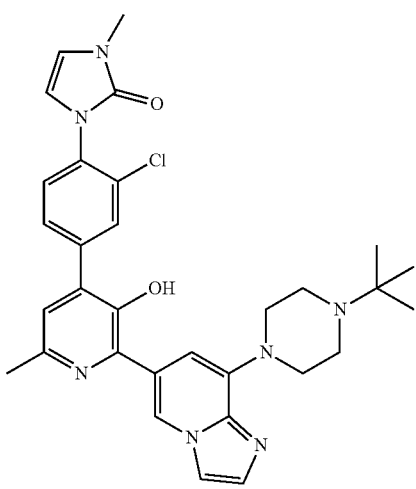
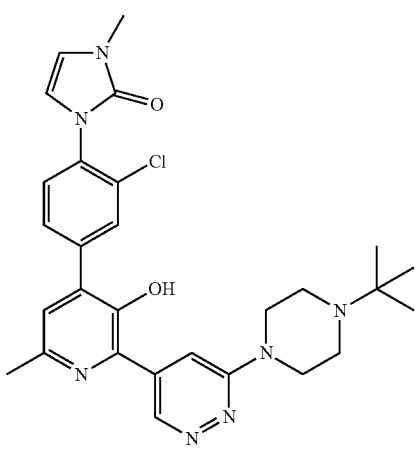
336
-continued
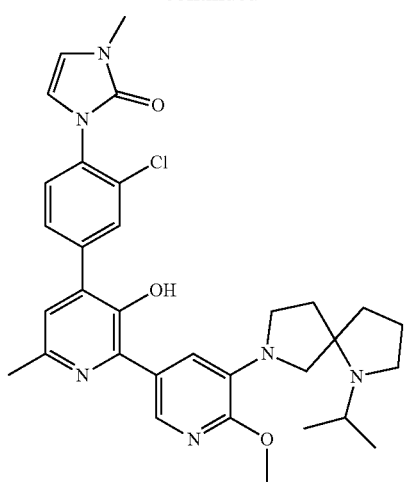
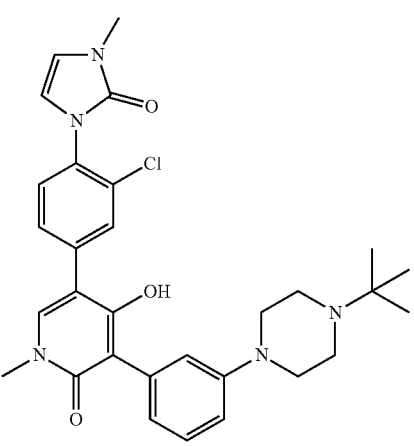
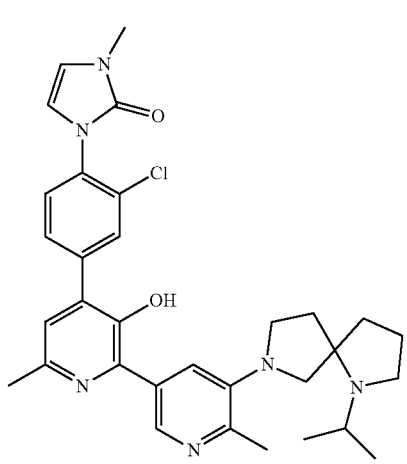

337
-continued
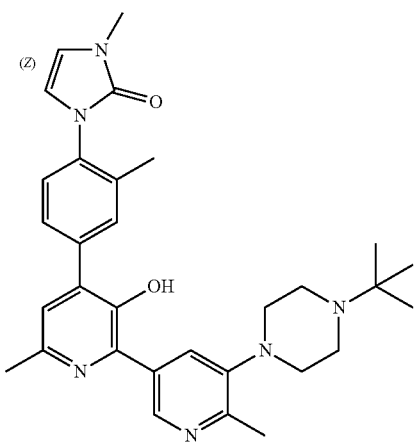
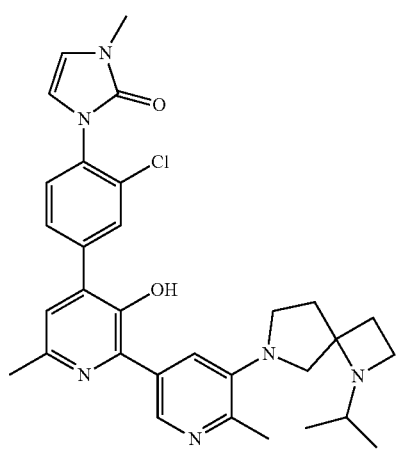
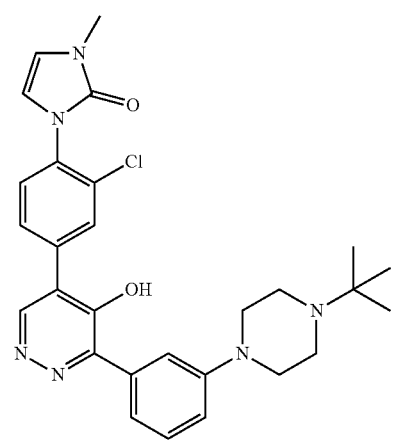
338
-continued
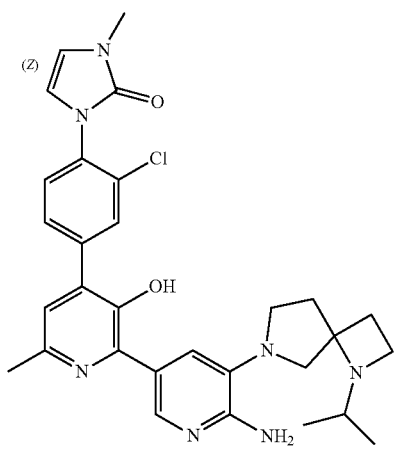
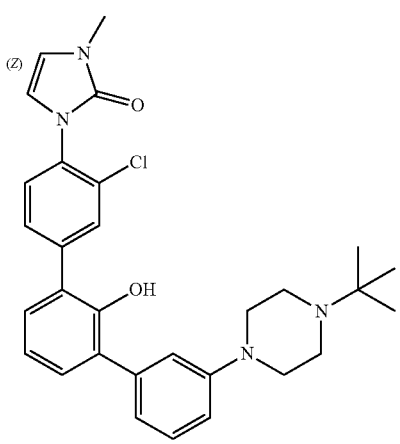
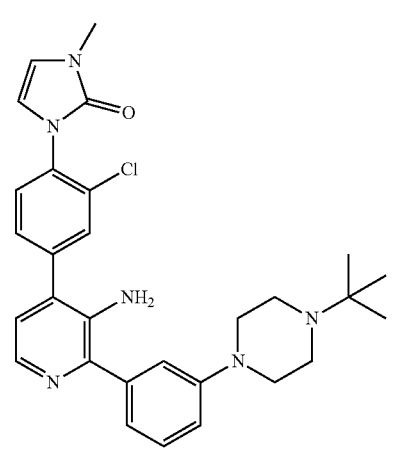

339
-continued
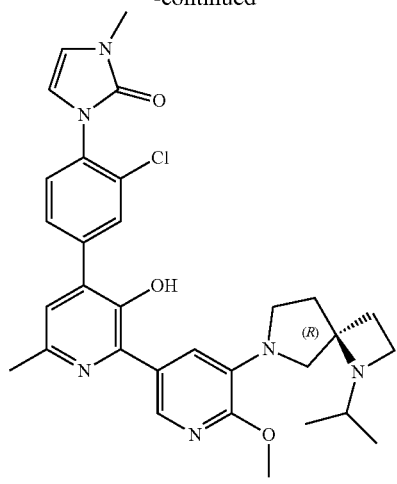
340
-continued
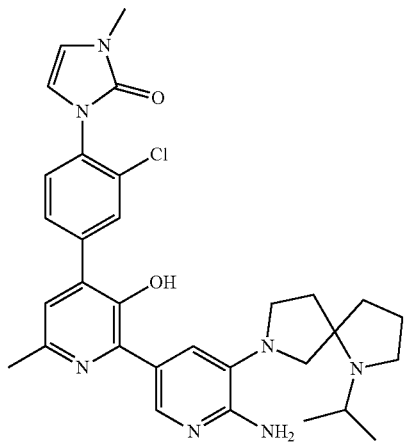
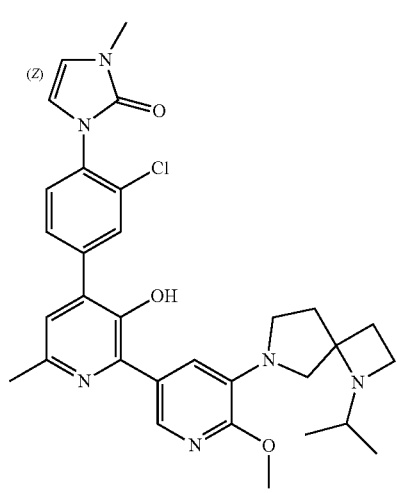
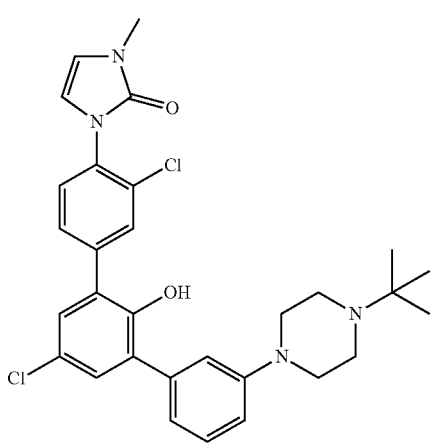
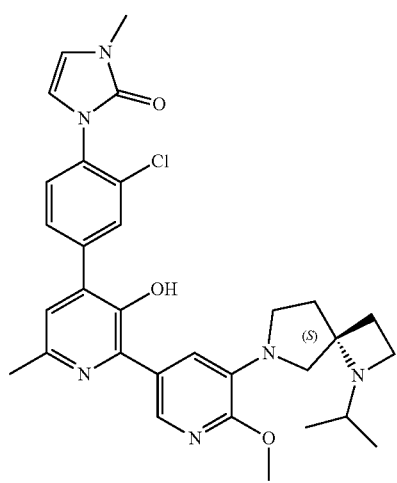
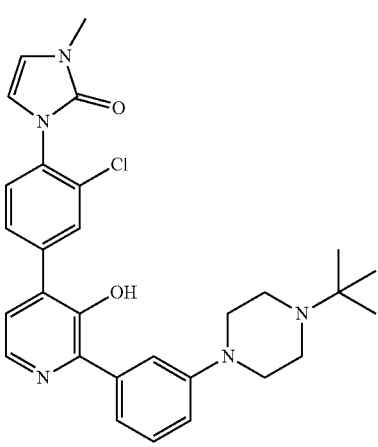

341
-continued
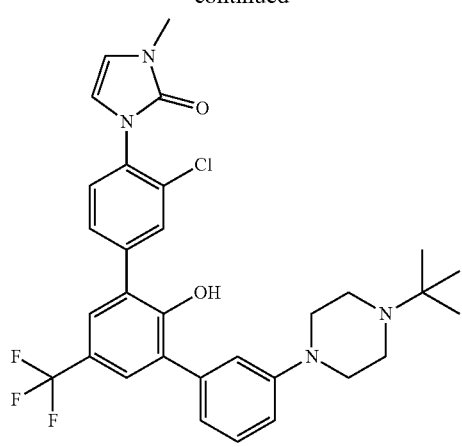
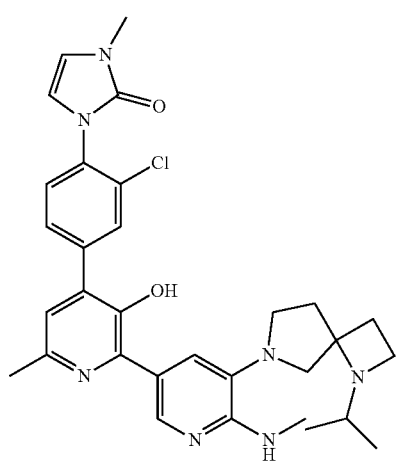
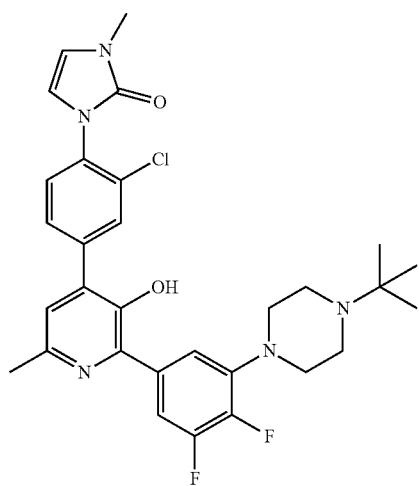
342
-continued
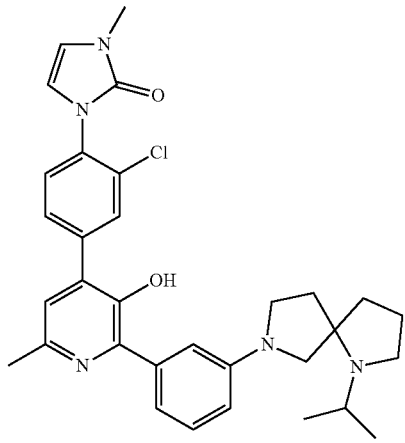
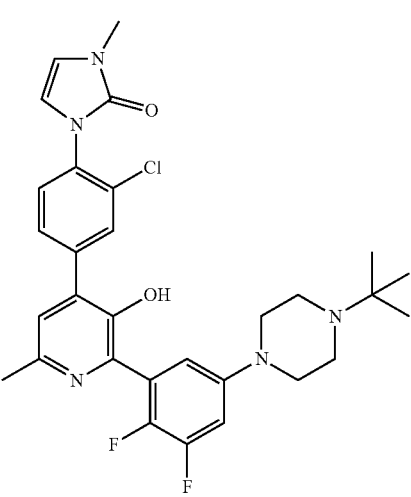
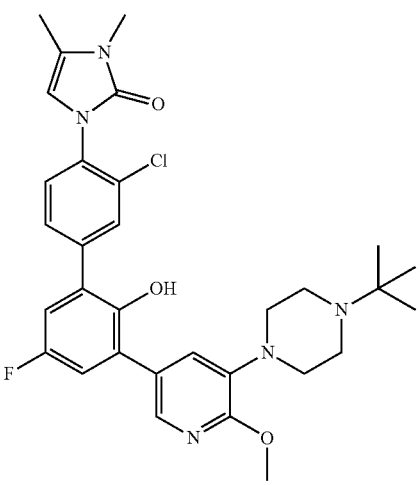

343
-continued
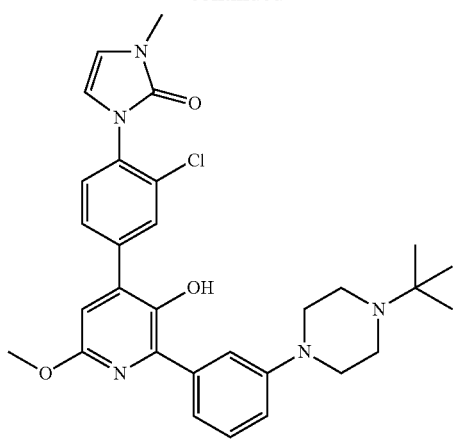
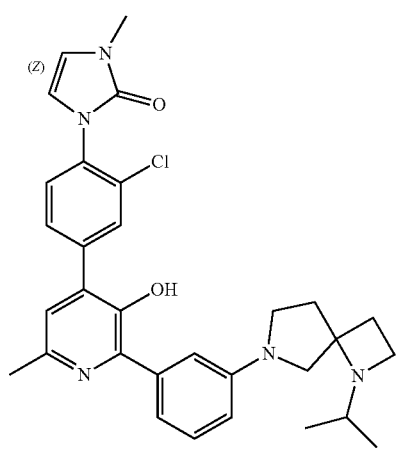
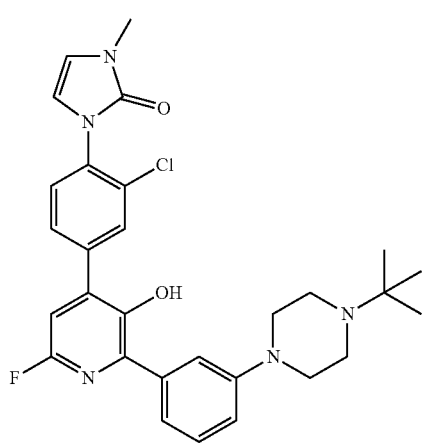
344
-continued
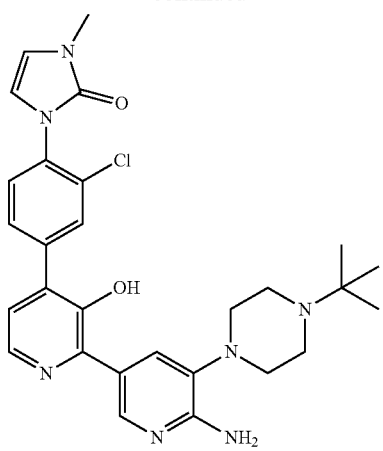
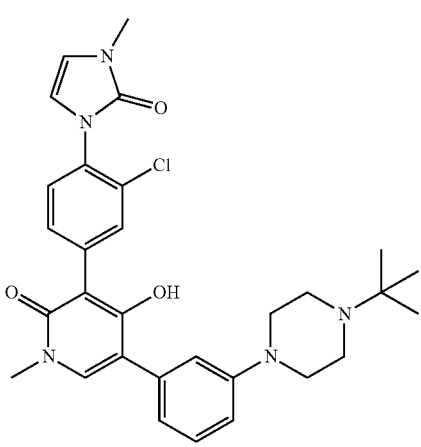
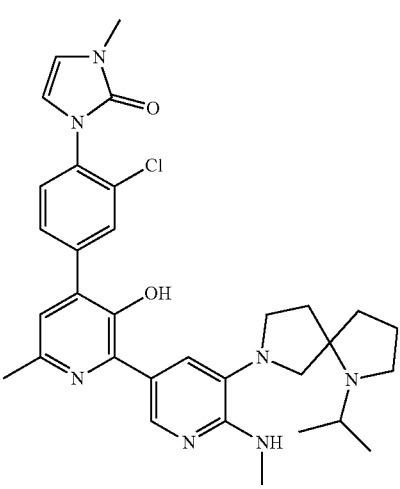

345
-continued
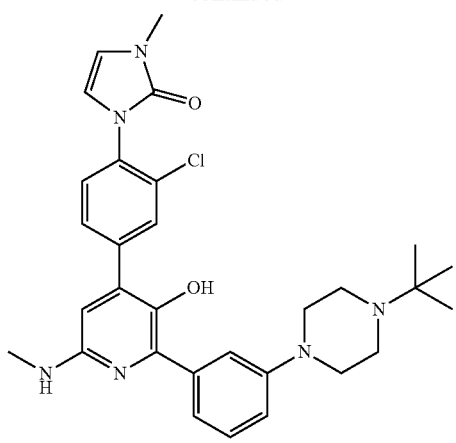
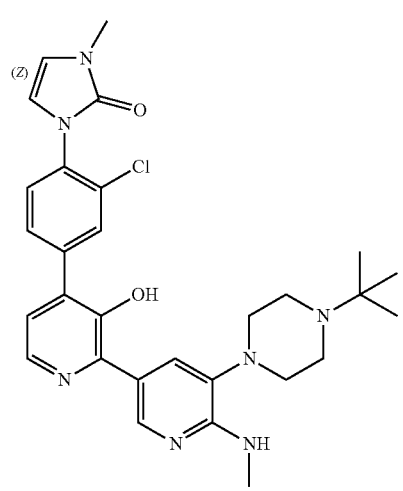
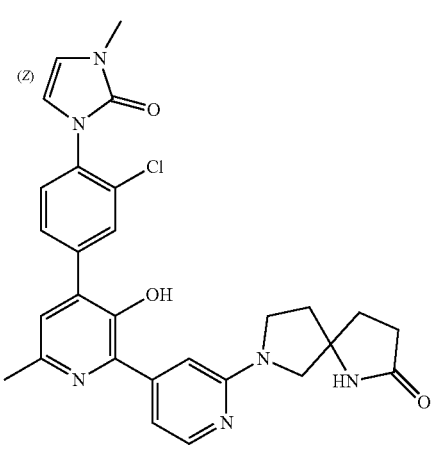
346
-continued
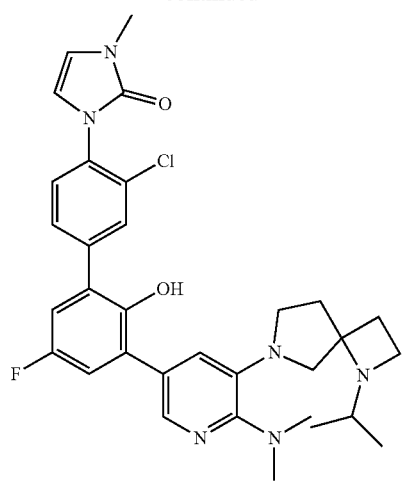
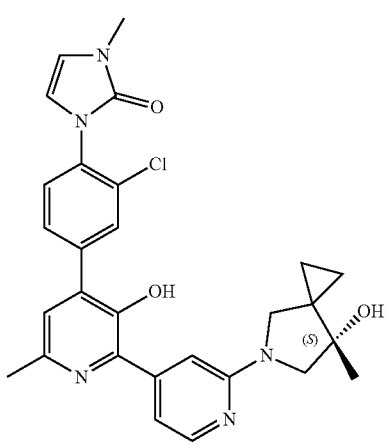
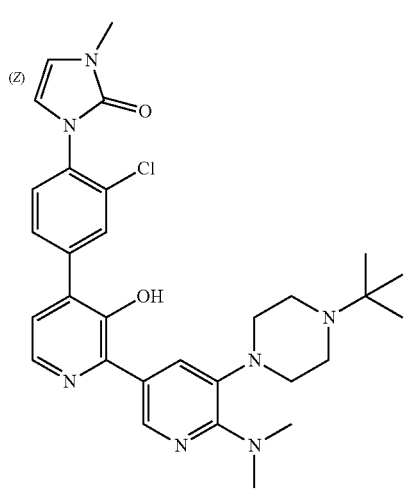

347
-continued
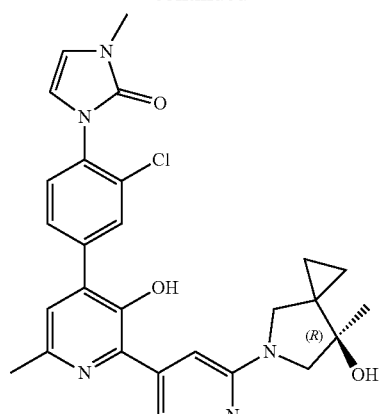
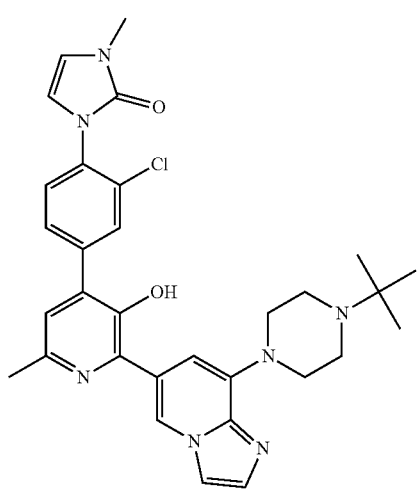
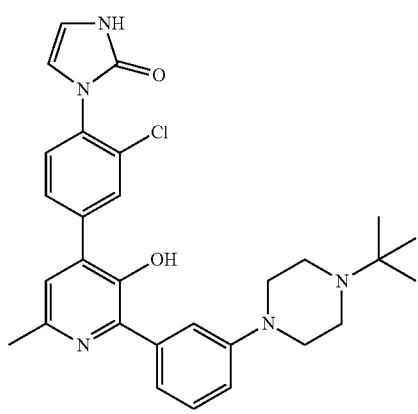
348
-continued
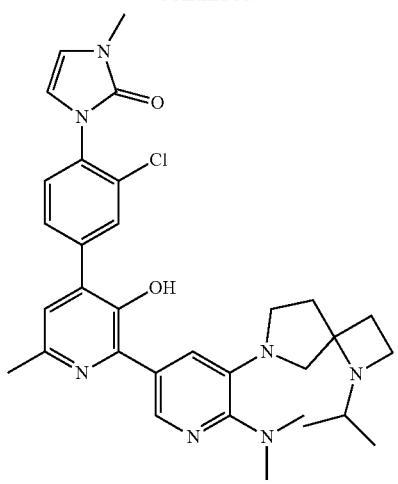
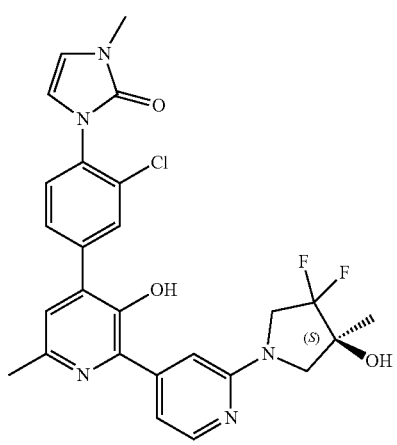
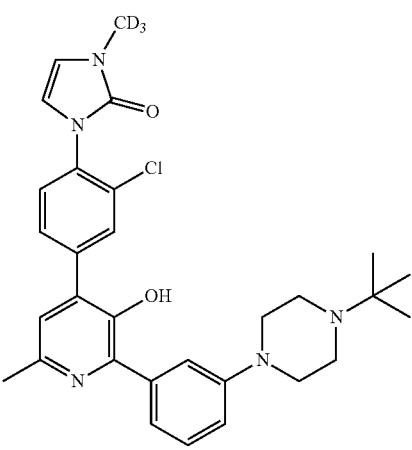

349
-continued
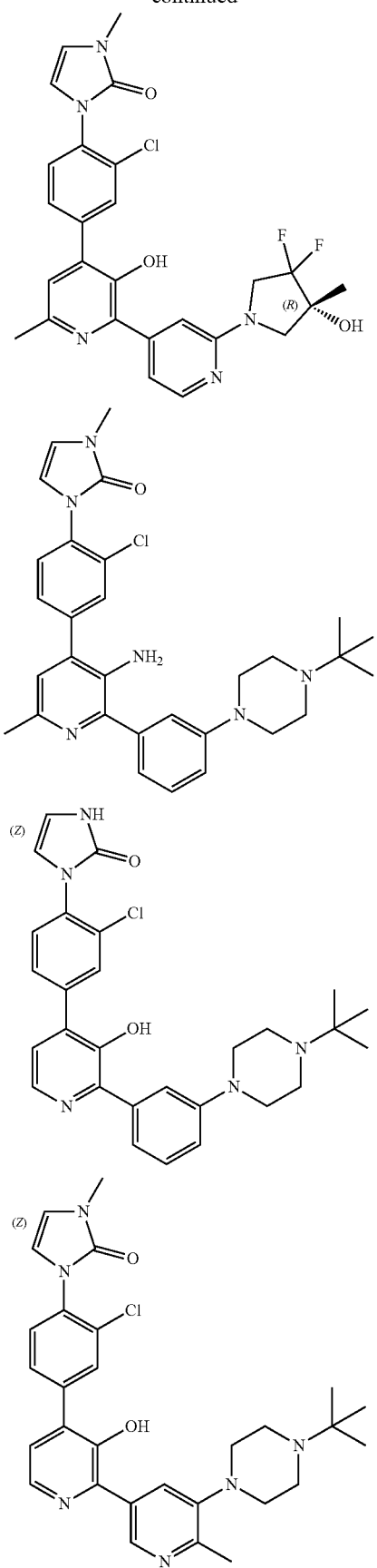
350
-continued
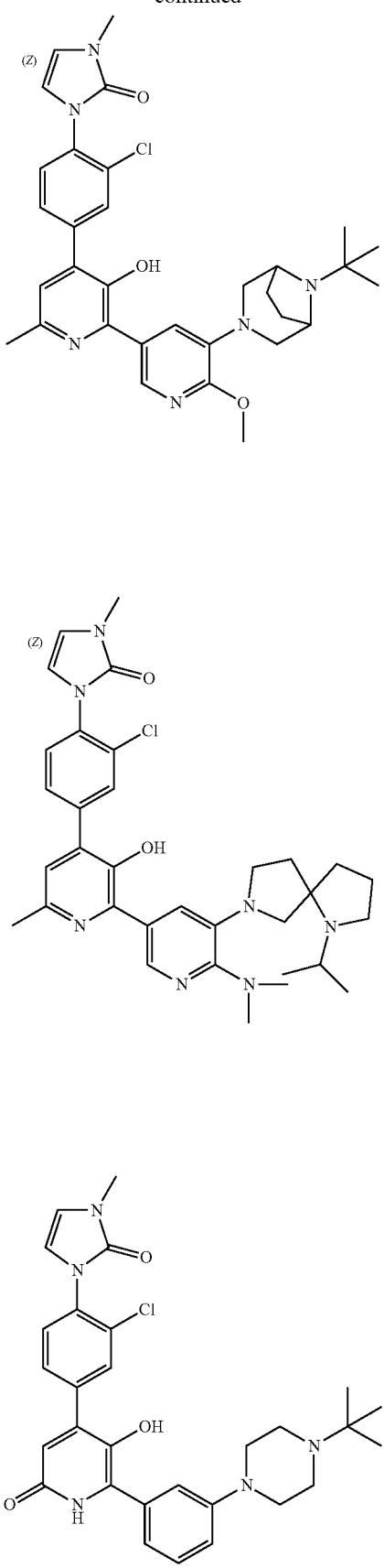

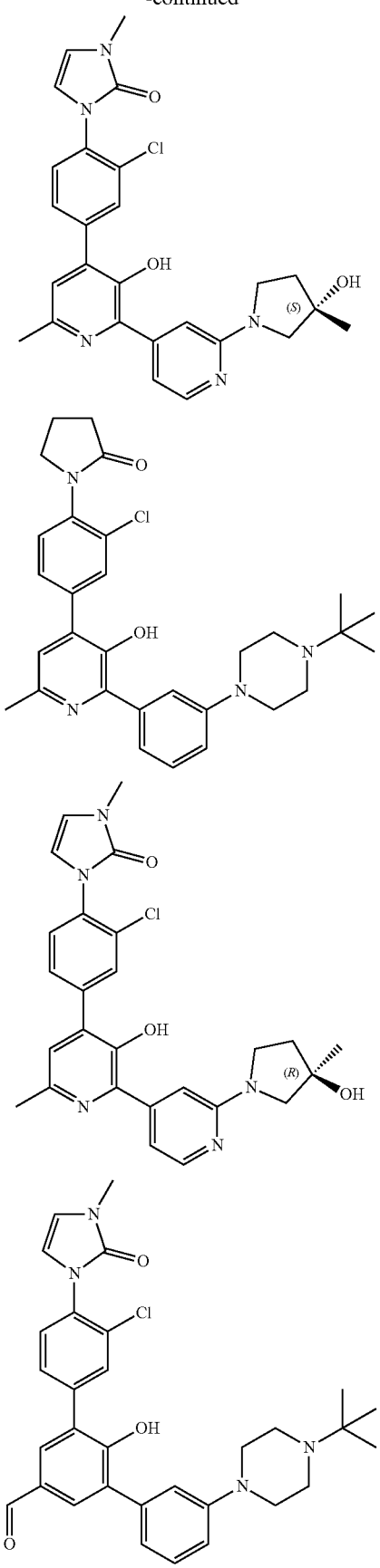
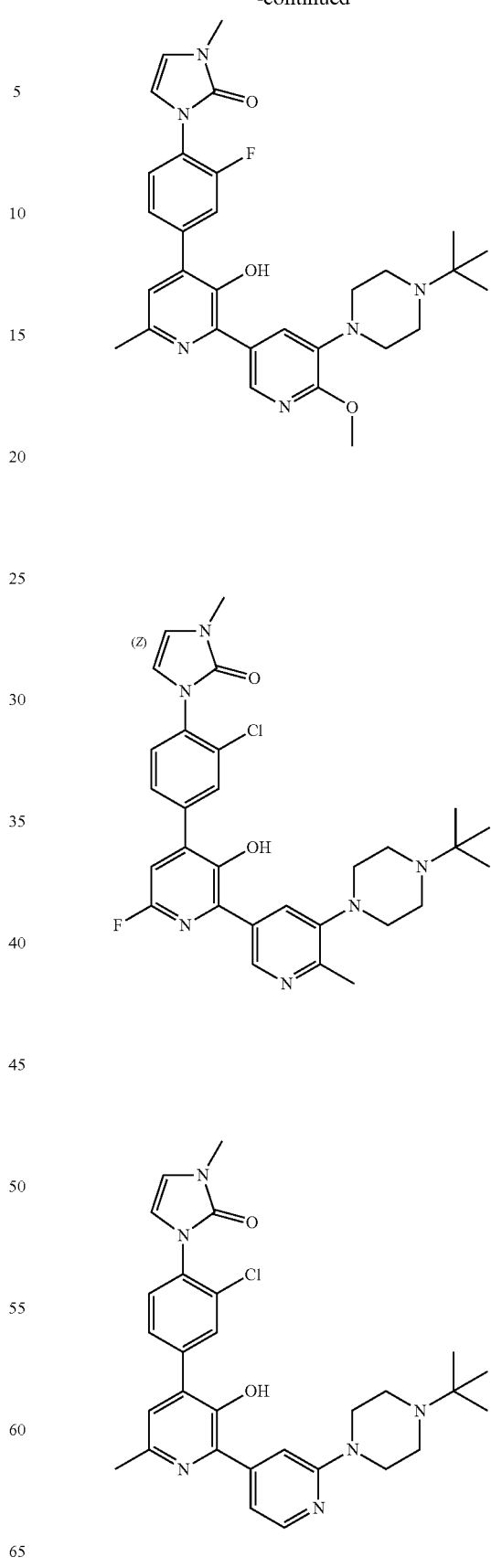

353
-continued
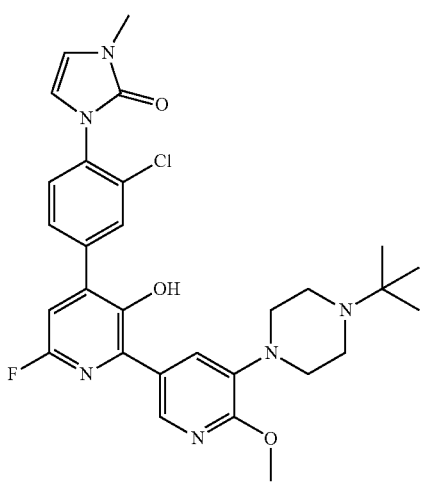
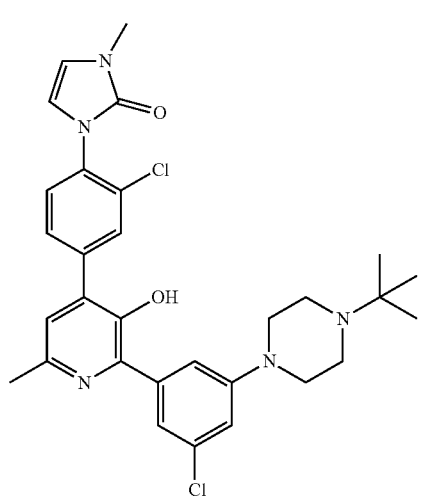
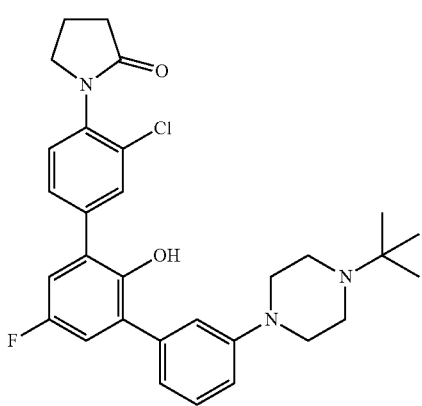
354
-continued
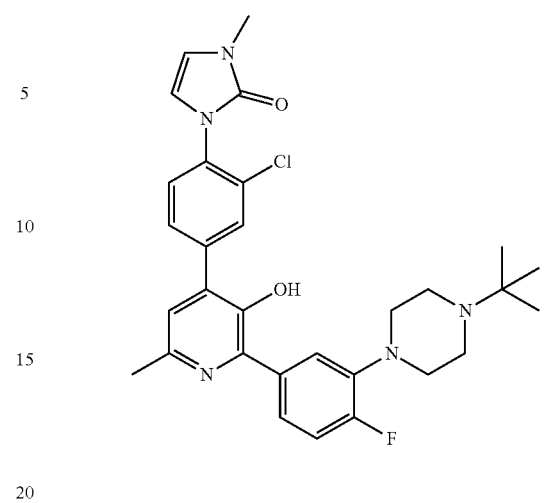
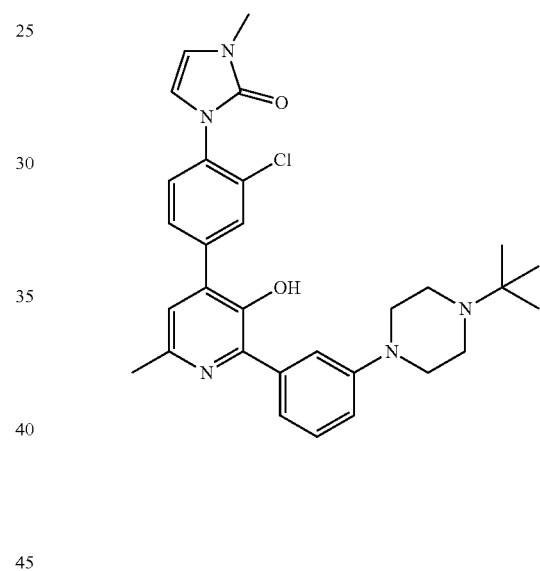
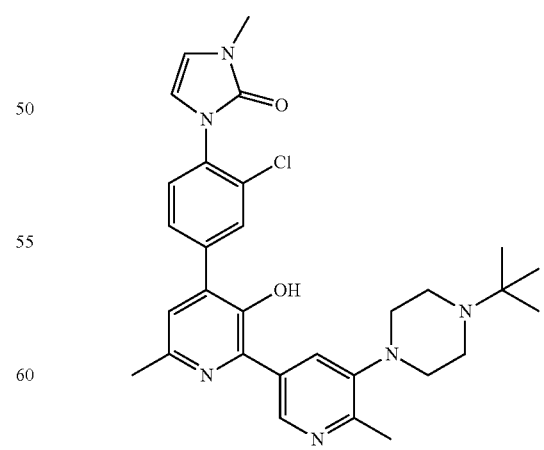

355
-continued
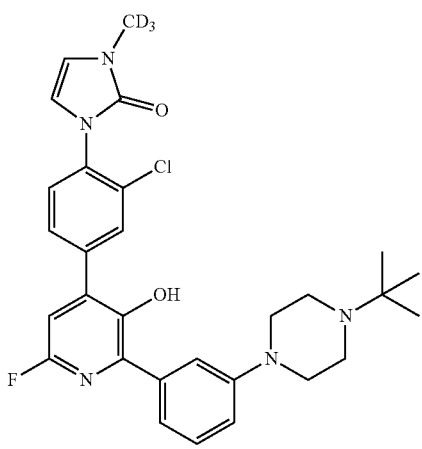
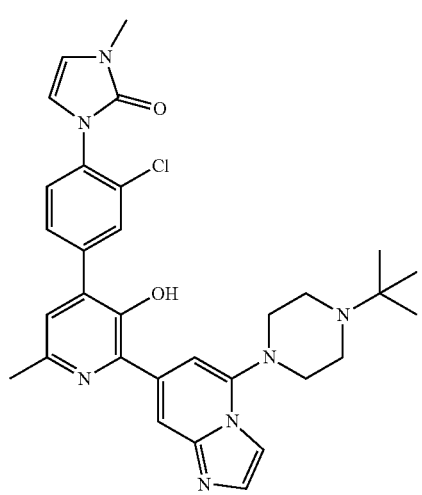
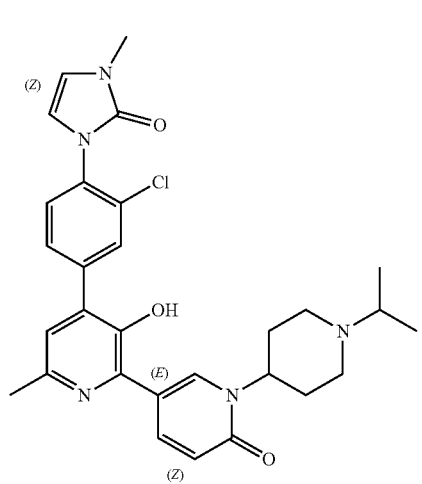
356
-continued
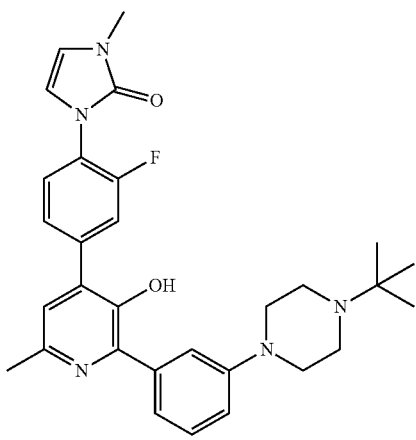
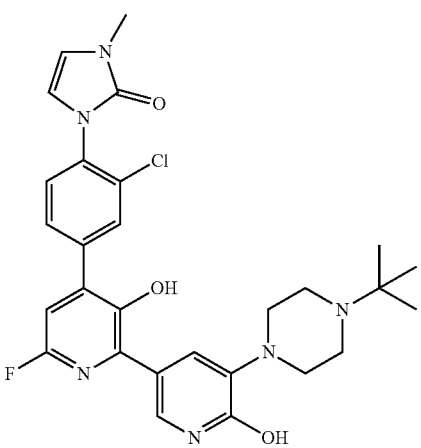
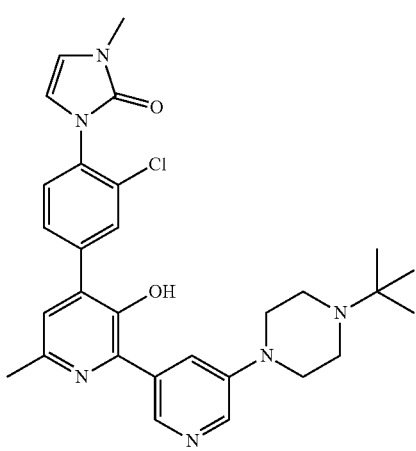

357
-continued
358
-continued
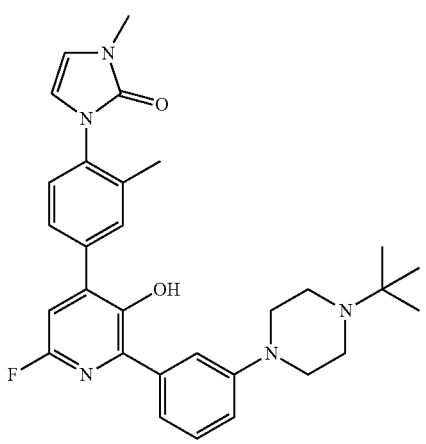
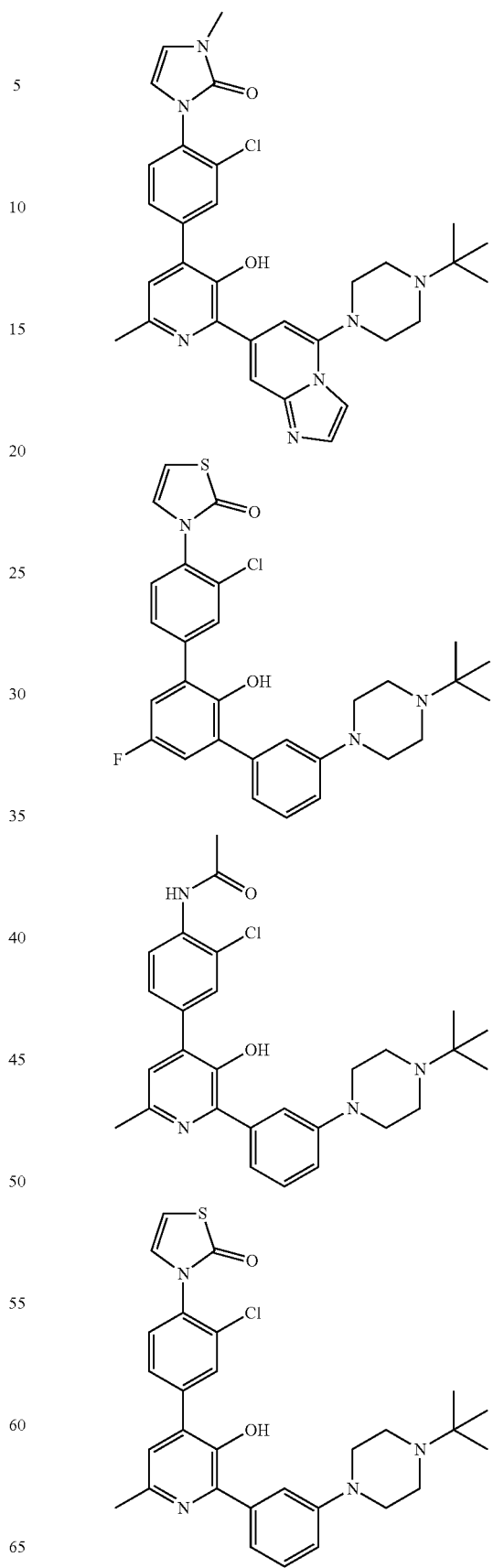

359
-continued
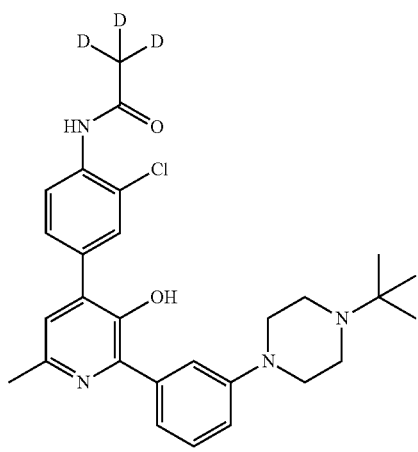
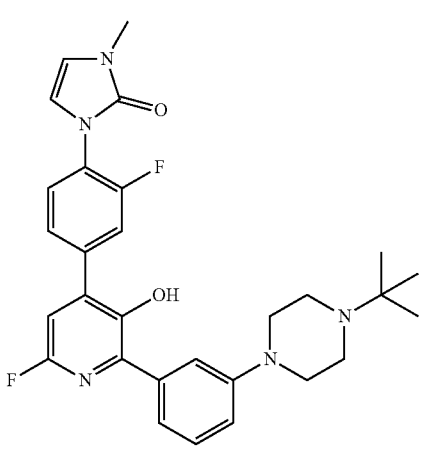
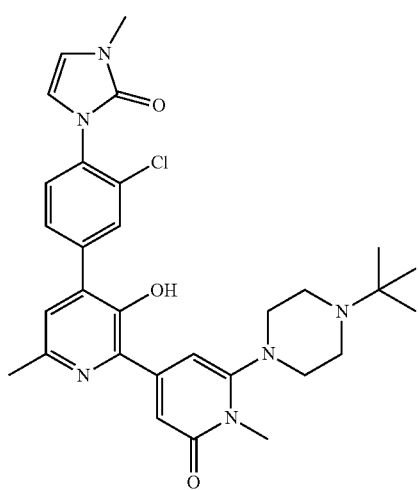
360
-continued
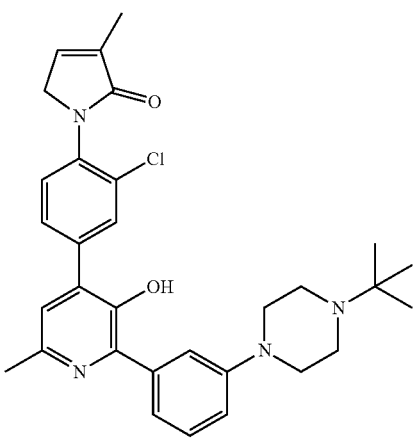
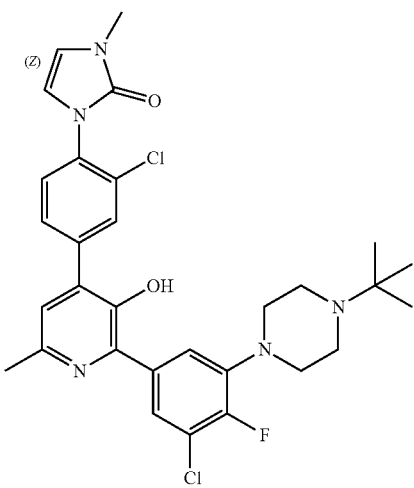
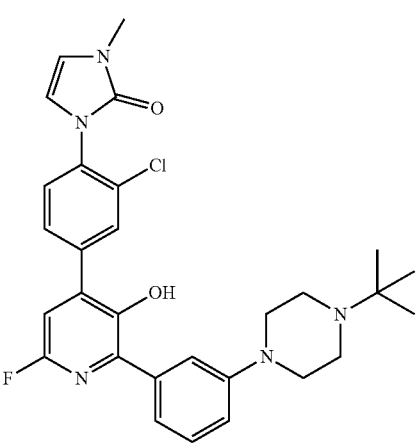

361
-continued
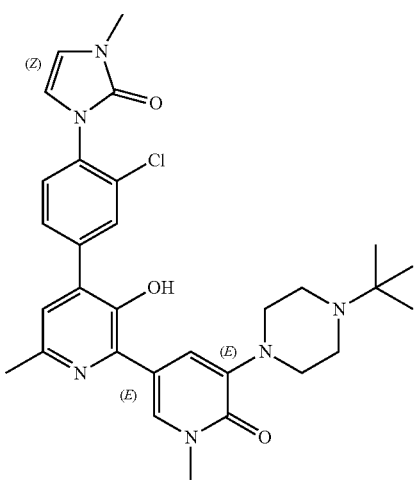
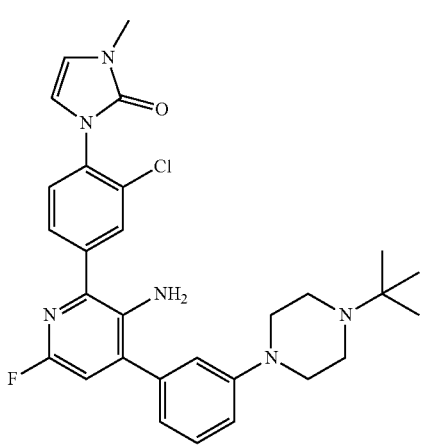
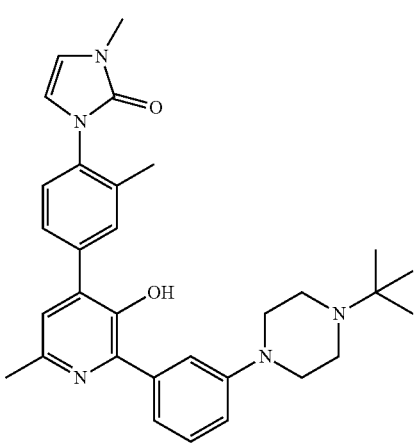
362
-continued
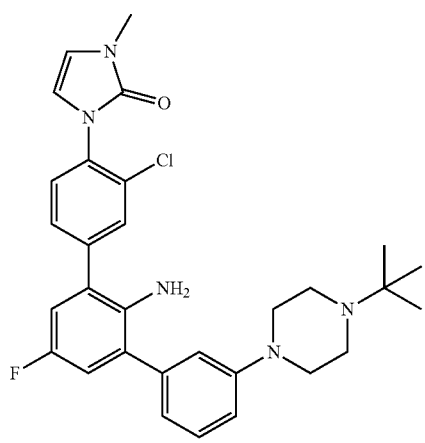
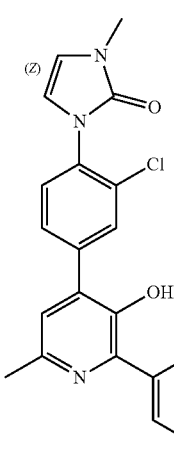
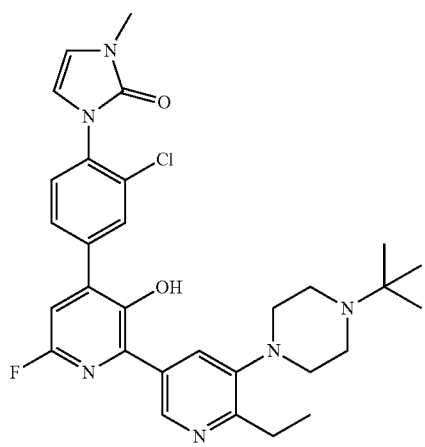

363
-continued
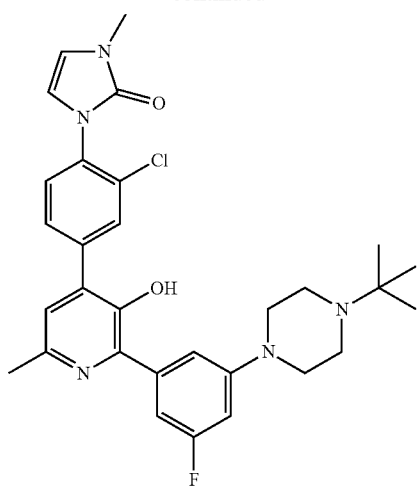
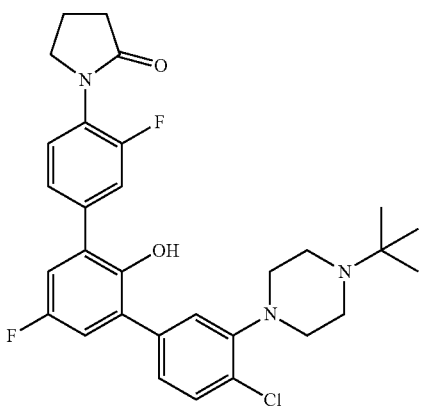
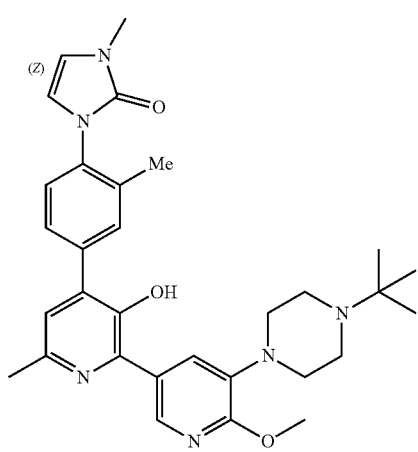
364
-continued
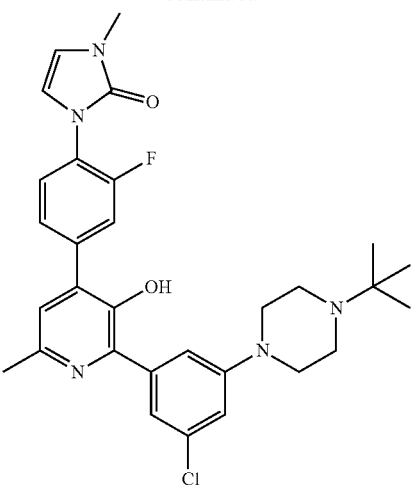
Further exemplary embodiments include the following, and may be synthesized according to the synthetic procedures described in detail in this application:
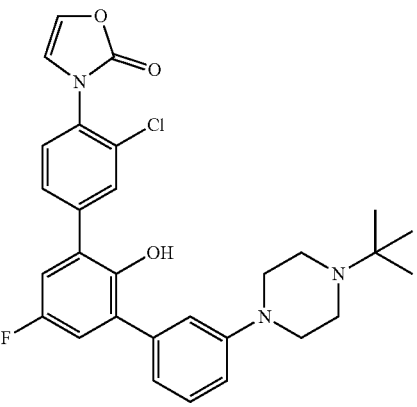
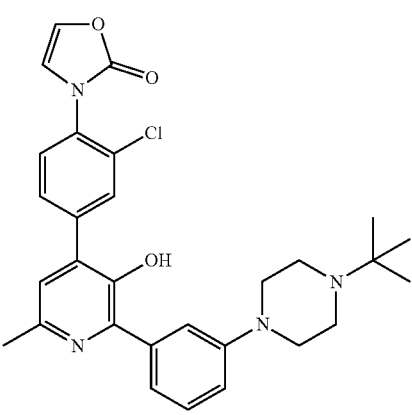

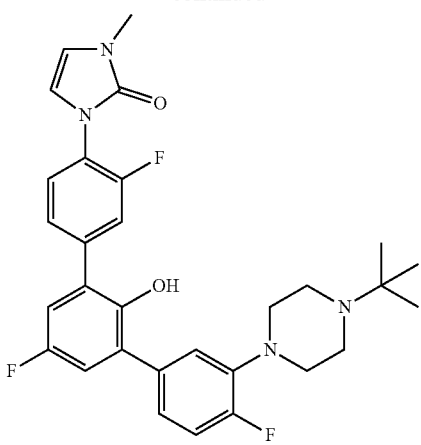

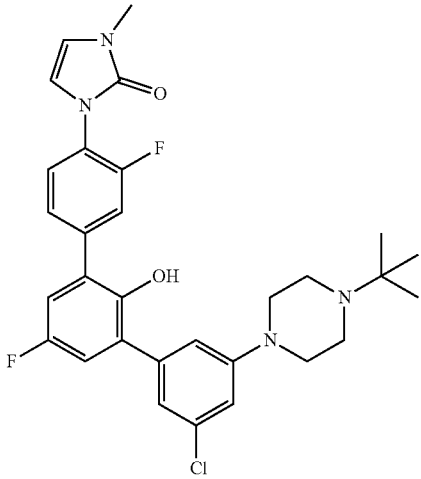

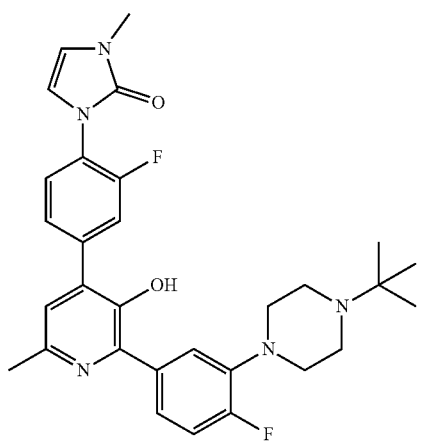

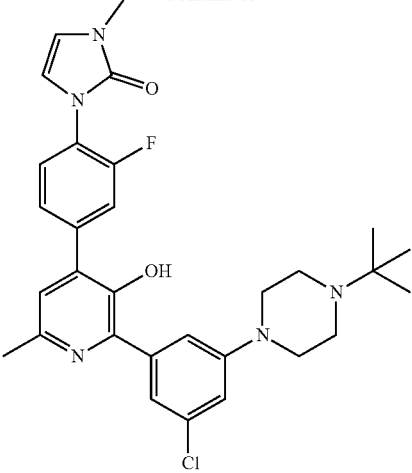

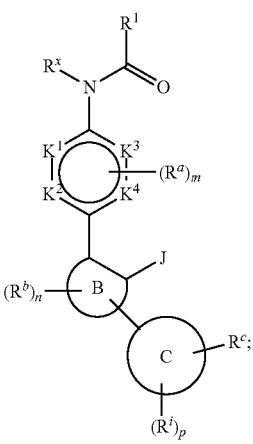

In other embodiments, the compound has the structure of formula (II), (II)

or a pharmaceutically acceptable salt thereof;
wherein:
each of $K^1$-$K^4$ is independently CH or N;
  wherein at least one of $K^1$-$K^4$ is CH;
Ring B represents substituted or unsubstituted phenylene or 6-membered heteroarylene;
Ring C represents substituted or unsubstituted arylene or heteroarylene;
$R^1$ represents alkyl, alkenyl, haloalkyl, —O(alkyl), —S(alkyl), —NH(alkyl), or —N(alkyl)$_2$;
$R^x$ represents H, alkyl, or —C(O)alkyl;
  or $R^1$ and $R^x$, taken together with the intervening atoms, form an optionally substituted heterocycloalkyl ring, heterocycloalkenyl ring, or heteroaryl ring;
each occurrence of $R^a$ is independently selected from the group consisting of halo, —NH$_2$, —NH(alkyl), —NH(cycloalkyl), —N(alkyl)$_2$, hydroxyl, alkyl, alkoxy, cycloalkyl, cycloalkoxy, haloalkoxy, heterocycloalkoxy, cyano, aryloxy, heteroaryloxy, and haloalkyl;
  or $R^1$ and an occurrence of $R^a$, taken together with the intervening atoms, form an optionally substituted heterocycloalkyl ring;

or an occurrence of $R^a$ and $R^x$, taken together with the intervening atoms, form an optionally substituted heterocycloalkyl ring;

J represents —OH, —O(alkyl), —OC(O)(alkyl), —OC(O)O(alkyl), —OC(O)NH(alkyl), —OC(O)N(alkyl)$_2$, —OCH$_2$OC(O)O(alkyl), —NH$_2$, —NHR$^j$, or —CHF$_2$;

R$^j$ is alkyl, alkenyl, alkynyl, aryl, heteroaryl, arylalkyl, heteroarylalkyl, cycloalkyl, heterocycloalkyl, (cycloalkyl)alkyl, or (heterocycloalkyl)alkyl;

each occurrence of R$^b$ is independently selected from the group consisting of halo, oxo, alkyl, alkoxyl, haloalkyl, cyano, cycloalkyl, aryl, aryloxy, —OH, —NH(alkyl), —C(O)H, —CO$_2$(alkyl) and —CO$_2$H;

R$^c$ represents H;

each occurrence of R$^i$ is independently halo, oxo, —S(alkyl), —NH$_2$, —NH(alkyl), —N(alkyl)$_2$, —OH, or cyano, or is selected from the group consisting of optionally substituted alkyl, haloalkyl, haloalkoxyl, alkoxyl, heterocycloalkyl, and cycloalkoxyl;

or two adjacent occurrences of R$^i$, taken together with the intervening atoms, form an optionally substituted aryl, heteroaryl, cycloalkyl, or heterocycloalkyl ring; and m, n, and p are each independently 0, 1, or 2.

In certain embodiments, each of $K^1$-$K^4$ is CH.

In certain embodiments, m is 1 and $R^a$ is halo.

In certain embodiments, Ring B represents substituted or unsubstituted phenylene.

In certain embodiments, n is 0.

In certain embodiments, J is OH.

In certain embodiments, $R^x$ represents H. In certain embodiments, $R^1$ is alkyl.

Alternatively, $R^1$ and $R^x$, taken together with the intervening atoms, may form an optionally substituted heterocycloalkyl ring, heterocycloalkenyl ring, or heteroaryl ring.

In certain embodiments, the compound of formula (II) is selected from the following table:

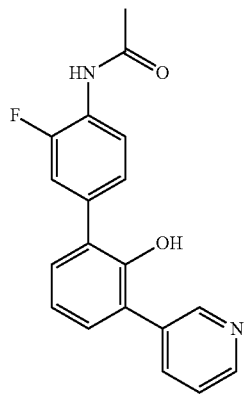 [SMILES: CC(=O)Nc1ccc(-c2cccc(-c3cccnc3)c2O)cc1F]
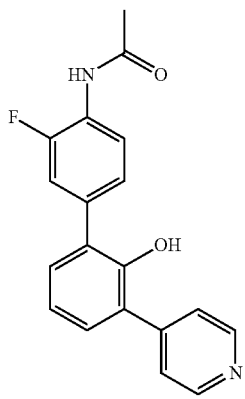 [SMILES: CC(=O)Nc1ccc(-c2cccc(-c3ccncc3)c2O)cc1F]
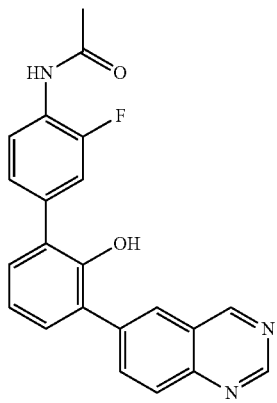 [SMILES: CC(=O)Nc1ccc(-c2cccc(-c3ccc4ncncc4c3)c2O)cc1F]
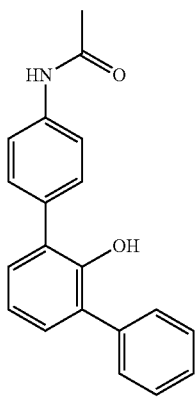 [SMILES: CC(=O)Nc1ccc(-c2cccc(-c3ccccc3)c2O)cc1]
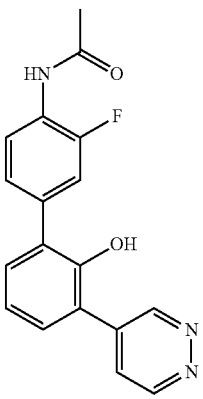 [SMILES: CC(=O)Nc1ccc(-c2cccc(-c3ccnnc3)c2O)cc1F]
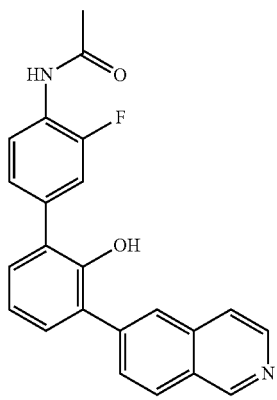 [SMILES: CC(=O)Nc1ccc(-c2cccc(-c3ccc4cnccc4c3)c2O)cc1F]

-continued
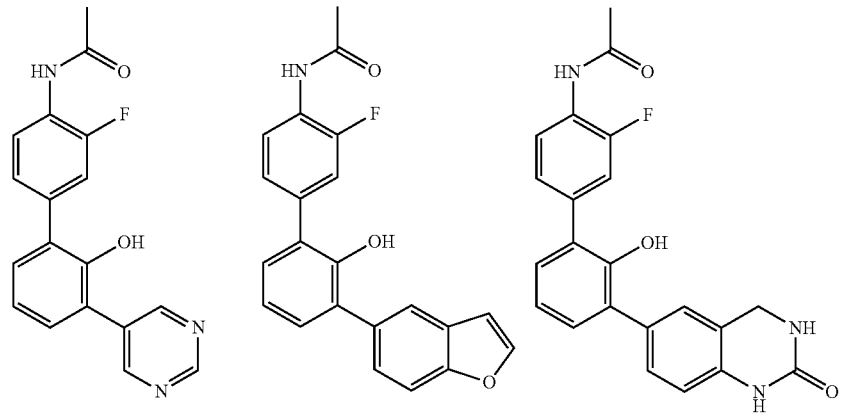
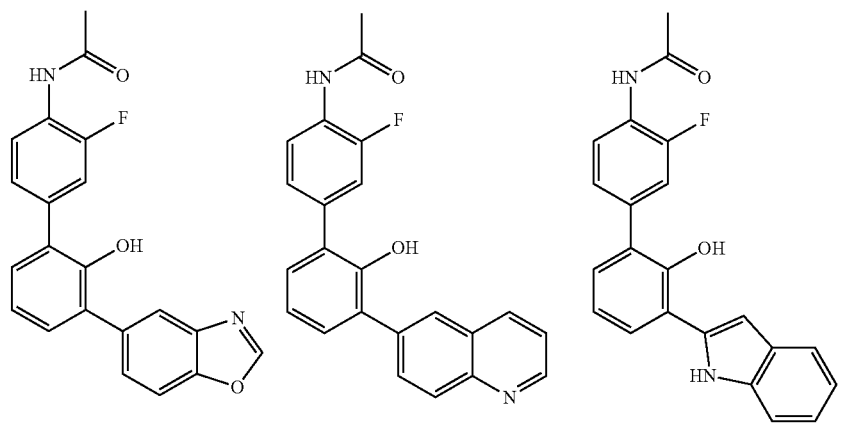
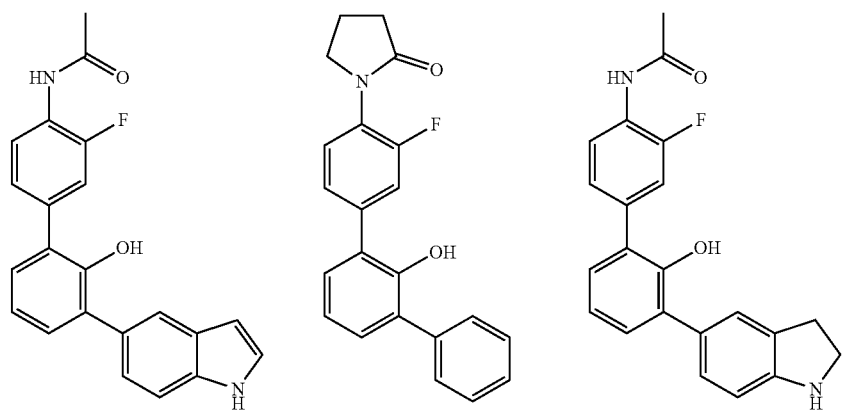
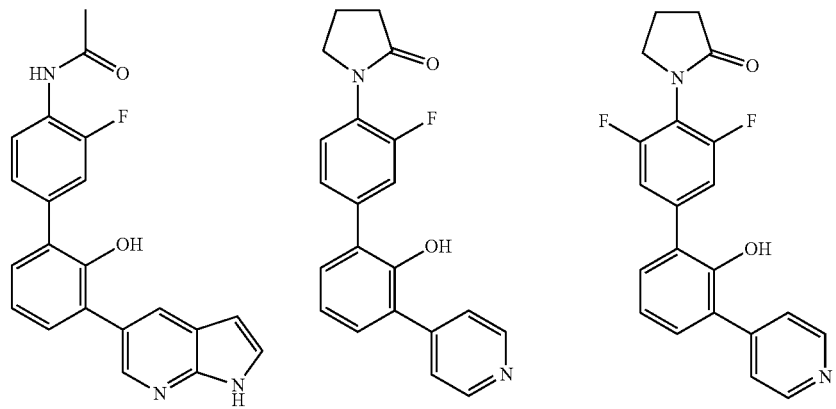

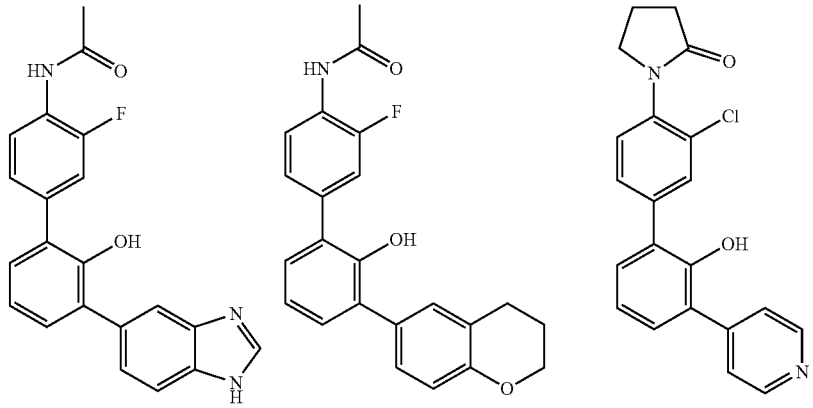

Pharmaceutical Compositions

The invention provides pharmaceutical compositions, each comprising one or more compounds of the invention, or pharmaceutically acceptable salts thereof, and a pharmaceutically acceptable excipient. In certain embodiments, the pharmaceutical composition comprises a compound of the invention and a pharmaceutically acceptable carrier. In certain embodiments, the pharmaceutical composition comprises a plurality of compounds of the invention, or pharmaceutically acceptable salts thereof, and a pharmaceutically acceptable carrier.

Pharmaceutical compositions of the invention can be prepared by combining one or more compounds of the invention, or pharmaceutically acceptable salts thereof, with a pharmaceutically acceptable carrier and, optionally, one or more additional pharmaceutically active agents.

Methods of Use

The present invention provides compounds, and pharmaceutically acceptable salts thereof, that are useful for treating or preventing a disease or condition whose treatment would benefit from BDII-selective inhibition.

Bromodomain and extra-terminal domain (BET) family proteins regulate gene transcription through their interaction with specific acetylated lysines in the tails of histones H3 and H4. At these sites, these BET proteins recruit key components of the transcriptional machinery, thereby enabling them to control a host of gene expression programs central to diseases such as cancer. These BET proteins bind to acetylated histone tails through their two tandem bromodomains, BDI and BDII. Unfortunately, pan-BET inhibitors have exhibited on-target toxicities, such as thrombocytopenia, anemia, neutropenia, and severe gastrointestinal events. Selective inhibition of the BDII bromodomain, however, provides therapeutic efficacy while minimizing undesired toxicities.

The compounds of the invention inhibit the binding of the second bromodomains (BDII) of BRD2, BRD3, BRD4, and BRDt to their cellular targets. This function effectively alters the expression of genes essential for the growth of certain cancers, such as acute myeloid leukemia and prostate cancer.

In certain embodiments, the invention provides a method of treating or preventing cancer, comprising administering to a subject in need thereof a therapeutically effective amount of a compound of the invention, e.g., a compound of formula (I).

In certain embodiments, the cancer is selected from the group consisting of: acoustic neuroma, acute leukemia, acute lymphocytic leukemia, acute myelocytic leukemia (monocytic, myeloblastic, myelomonocytic and promyelocytic), acute T-cell leukemia, adrenocortical carcinoma, anal cancers, angiosarcoma, astrocytoma, basal cell carcinoma, bile duct carcinoma, bladder cancer, brain cancer, breast cancer, bronchogenic carcinoma, carcinosarcomas, cervical cancer, chondrosarcoma, chordoma, choriocarcinoma, chronic leukemia, chronic lymphocytic leukemia, chronic myelocytic (granulocytic) leukemia, chronic myelogenous leukemia, chronic neutrophilic leukemia, chronic eosinophilic leukemia, clear cell carcinomas, colon cancer, colorectal cancer, craniopharyngioma, cystadenocarcinoma, desmoplastic small-round-cell tumor, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gall bladder cancer, gastric cancer, germ cell testicular cancer, glioma, glioblastoma, gliosarcoma, hairy cell leukemia, heavy chain disease, hemangioblastoma, hepatoma, hepatocellular cancer, hormone insensitive prostate cancer, leiomyosarcoma, leukemia, liposarcoma, lung cancer, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin, and uterus, lymphoid malignancies of T-cell or B-cell origin, lipogenic sarcoma, lymphoma, malignant peripheral nerve sheath tumor, medullary carcinoma, mantle cell lymphoma, medulloblastoma, melanoma, meningioma, mesothelioma, multiple myeloma, myelodysplastic syndrome, myeloproliferative disorders, myelofibrosis, mucoepidermoid carcinoma, myxoid tumors, myxosarcoma, neuroblastoma, NUT midline carcinoma, non-small cell lung cancer, oligodendroglioma, oral cancer, osteogenic sarcoma, ovarian cancer, pancreatic cancer, papillary adenocarcinomas, papillary carcinoma, pheochromocytoma, pinealoma, polycythemia vera, prostate cancer, rectal cancer, renal cell carcinoma, reticulum cell sarcomas, retinoblastoma, rhabdomyosarcoma, salivary duct carcinoma, sebaceous gland carcinoma, seminoma, skin cancer, small cell lung carcinoma, solid tumors (carcinomas and sarcomas), squamous cell carcinoma, synovial sarcoma, sweat gland carcinoma, thyroid cancer, Waldenstrom's macroglobulinemia, testicular tumors, uterine cancer, and Wilms' tumor.

In further embodiments, the invention provides a method of treating a disease or condition, comprising administering to a subject in need thereof a therapeutically effective amount of a compound of the invention, e.g., a compound of formula (I), wherein the disease or condition is selected from the group consisting of Addison's disease, acute gout, ankylosing spondylitis, asthma, atherosclerosis, Behcet's disease, bullous skin diseases, chronic obstructive pulmonary disease (COPD), Crohn's disease, dermatitis, dermatomyositis, eczema, giant cell arteritis, glomerulonephritis, hepatitis, hypophysitis, inflammatory bowel disease, juvenile arthritis, Kawasaki disease, lupus nephritis, multiple sclerosis, myocarditis, myositis, nephritis, organ transplant rejection, osteoarthritis, pancreatitis, pediatric inflammatory multisystem syndrome, pericarditis, polyarteritis nodosa, pneumonitis, primary biliary cirrhosis, psoriasis, psoriatic arthritis, rheumatoid arthritis, scleritis, scleroderma, sclerosing cholangitis, sepsis, Sjögren syndrome, systemic lupus erythematosus, systemic sclerosis, Takayasu's arteritis, toxic shock syndrome, thyroiditis, type I diabetes, ulcerative colitis, uveitis, vasculitis, vitiligo and Wegener's granulomatosis.

In further embodiments, the invention provides a method of treating an acquired immunodeficiency syndrome (AIDS), comprising administering to a subject in need thereof a therapeutically effective amount of a compound of the invention.

In further embodiments, the invention provides a method of treating a disease or condition, comprising administering to a subject in need thereof a therapeutically effective amount of a compound of the invention, wherein said disease or condition is selected from the group consisting of: obesity, dyslipidemia, hypercholesterolemia, Alzheimer's disease, metabolic syndrome, hepatic steatosis, type II diabetes, insulin resistance, diabetic retinopathy, and diabetic neuropathy.

In further embodiments, the invention provides a method of treating an acute kidney disease, comprising administering to a subject in need thereof a therapeutically effective amount of a compound of the invention, wherein said acute kidney disease or condition is selected from the group consisting of: ischemia-reperfusion induced kidney disease, cardiac and major surgery induced kidney disease, percutaneous coronary intervention induced kidney disease, radiocontrast agent induced kidney disease, sepsis induced kidney disease, pneumonia induced kidney disease, drug toxicity induced kidney disease, diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease, and tubular interstitial nephritis.

The present invention also provides methods of treating fibrosis, comprising administering to a subject in need thereof a therapeutically effective amount of a compound of the invention. The fibrosis may be, for example, pulmonary fibrosis, renal fibrosis, hepatic fibrosis, or cardiac fibrosis.

The present invention also provides methods of treating an epithelial wound, comprising administering to a subject in need thereof a therapeutically effective amount of a compound of the invention. The epithelial wound may be, for example, a surgical wound, a burn, an abrasion, an ulcer, or a diabetic wound, a wound caused by cancer, a wound caused by an infectious disease, or a wound caused by an inflammatory disease.

The present invention also provides methods of treating a viral infection, comprising administering to a subject in need thereof a therapeutically effective amount of a compound of the invention, wherein the viral infection is caused by a DNA virus or an RNA virus.

In certain embodiments, the DNA virus is selected from the group consisting of Adenoviridae, Papovaviridae, Parvoviridae, Herpesviridae, Poxviridae, Anelloviridae, and Pleolipoviridae viral families.

In certain embodiments, the RNA virus is selected from the group consisting of Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, and Hepeviridae viral families. Preferably, the viral infection is caused by an RNA virus in the Coronaviridae viral family. In such embodiments, the viral infection is SARS-CoV or SARS-CoV-2.

In further embodiments, the invention provides a method of inhibiting a bromodomain and extra-terminal (BET) protein in a cell selectively at bromodomain II (BDII), comprising contacting the cell with an effective amount of a compound of the invention. The cell may be in a mammalian body, e.g., a human body.

In certain aspects, the invention provides a compound of the invention, or a pharmaceutically acceptable salt thereof, for use as a medicament.

Formulations, Routes of Administration, and Dosing

The compounds of the invention, and pharmaceutically acceptable salts thereof, can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds or pharmaceutically acceptable salts thereof may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound (i.e., a compound of the invention or a pharmaceutically acceptable salt thereof) may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active compound which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active compound plus any additional desired ingredient present in the previously sterile-filtered solutions.

For topical administration, the present compounds or pharmaceutically acceptable salts thereof may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds or pharmaceutically acceptable salts thereof can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention, or pharmaceutically acceptable salts thereof, to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention, or pharmaceutically acceptable salts thereof, can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or pharmaceutically acceptable salt thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention, or pharmaceutically acceptable salts thereof, can be conveniently formulated in unit dosage form; for example, containing 5 to 1000 mg, 10 to 750 mg, or 50 to 500 mg of active compound per unit dosage form. In one embodiment, the invention provides a composition comprising a compound of the invention, or pharmaceutically acceptable salt thereof, formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention, or pharmaceutically acceptable salts thereof, can also be administered in combination with other therapeutic agents, for example, other agents that are useful for treating or preventing cancer, acute kidney disease, AIDS, or a viral infection.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active compound for at least 30 days, and preferably 60 days.

In certain embodiments, a compound of the invention, or pharmaceutically acceptable salt thereof, is formulated for intraocular administration, for example direct injection or insertion within or in association with an intraocular medical device.

The compounds of the invention, or pharmaceutically acceptable salts thereof, may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention, or pharmaceutically acceptable salts thereof, to the region of a body which has been treated by interventional technique.

In exemplary embodiments, a compound of the invention, or pharmaceutically acceptable salt thereof, may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the active compound is coated, adsorbed, placed, or otherwise incorporated into the device by methods known in the art. For example, the active compound may be embedded and released from within ("matrix type") or surrounded by and released through ("reservoir type") polymer materials that coat or span the medical device. In the latter example, the active compound may be entrapped within the polymer materials or coupled to the polymer materials using one or more the techniques for generating such materials known in the art. In other formulations, the active compound may be linked to the surface of the medical device without the need for a coating, for example by means of detachable bonds, and release with time or can be removed by active mechanical or chemical processes. In other formulations, the active compound may be in a permanently immobilized form that presents the active compound at the implantation site.

In certain embodiments, the active compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is suitable for this embodiment because, unlike a biostable polymer, it will typically not be present long after implantation to cause any adverse, chronic local response. Bioabsorbable polymers that could be used include, but are not limited to, poly(L-lactic acid), poly-caprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly (L-lactic acid), poly(D, L-lactic acid), poly(D, L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly (trimethylene carbonate), poly(iminocarbonate), copoly (ether-esters) (e.g., PEO/PLA), polyalkylene oxalates, polyphosphazenes and biomolecules such as fibrin, fibrinogen, cellulose, starch, collagen and hyaluronic acid, poly-epsilon caprolactone, polyhydroxy butyric acid, polyorthoesters, polyacetals, polydihydropyrans, polycyanoacrylates, cross linked or amphipathic block copolymers of hydrogels, and other suitable bioabsorbable copolymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspart-amide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention, or pharmaceutically acceptable salt thereof, is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound of the invention, or pharmaceutically acceptable salt thereof, is formulated for release from the polymer coating into the environment in which the medical device is placed. Preferably, the active compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the active compound from the polymer coating can be controlled. For example, the diffusion coefficient of the one or more polymer coatings can be modulated to control the release of the active compound from the polymer coating. In a variation on this theme, the diffusion coefficient of the one or more polymer coatings can be controlled to modulate the ability of an analyte that is present in the environment in which the medical device is placed (e.g., an analyte that facilitates the breakdown or hydrolysis of some portion of the polymer) to access one or more components within the polymer composition (and for example, thereby modulate the release of the active compound from the polymer coating). Yet another embodiment of the invention includes a device having a plurality of polymer coatings, each having a plurality of diffusion coefficients. In such embodiments of the invention, the release of the active compound from the polymer coating can be modulated by the plurality of polymer coatings.

In yet another embodiment of the invention, the release of the active compound from the polymer coating is controlled by modulating one or more of the properties of the polymer composition, such as the presence of one or more endogenous or exogenous compounds, or alternatively, the pH of the polymer composition. For example, certain polymer compositions can be designed to release an active compound in response to a decrease in the pH of the polymer composition.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

The following Synthetic Schemes represent synthetic routes to the compounds of the invention. Detailed experimental procedures follow the schemes.

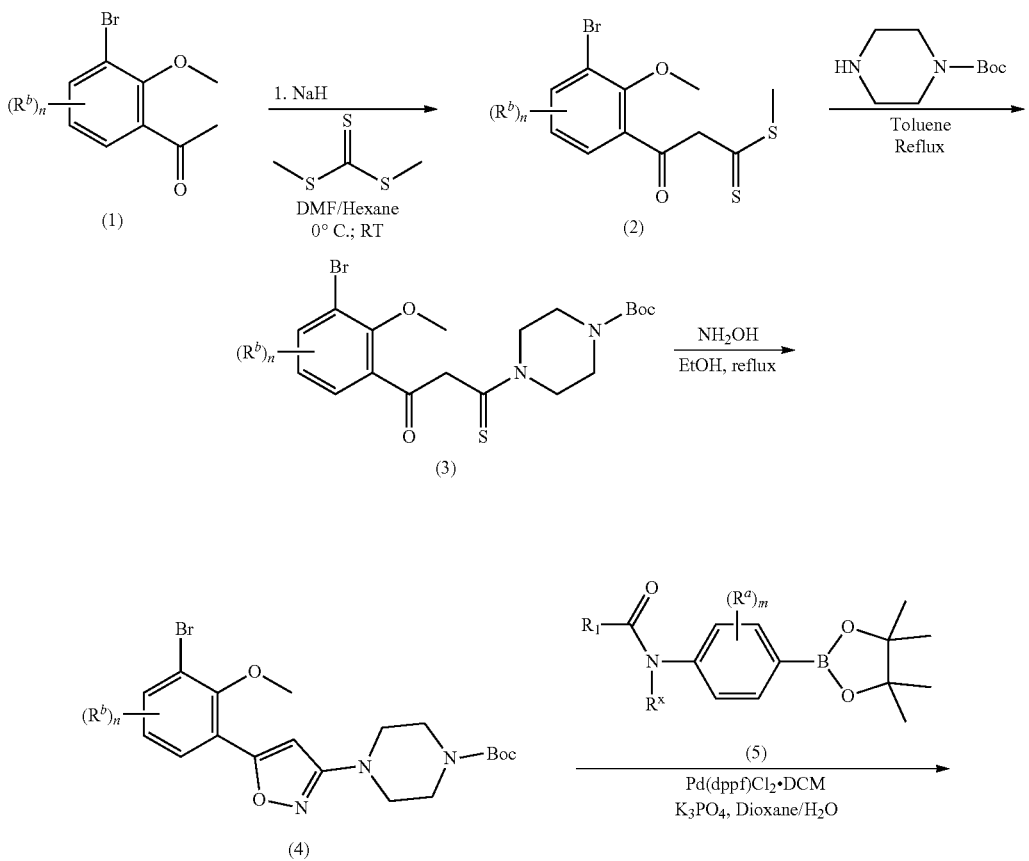

-continued
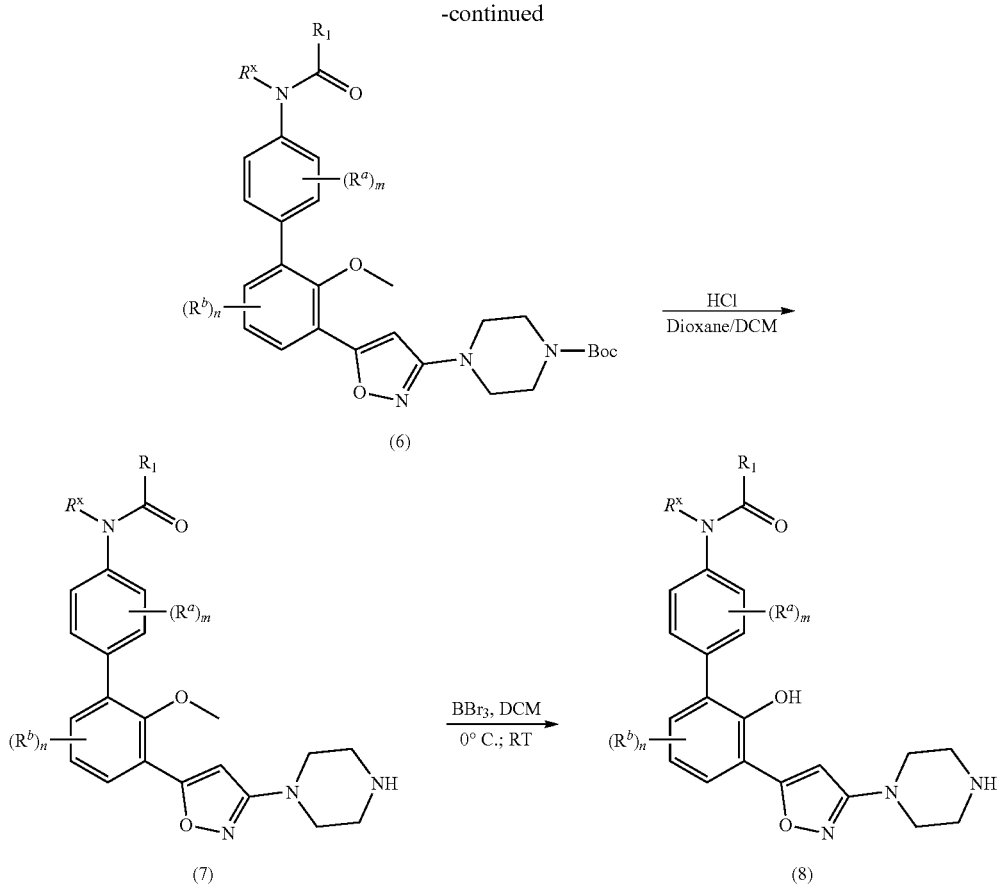
Scheme 2
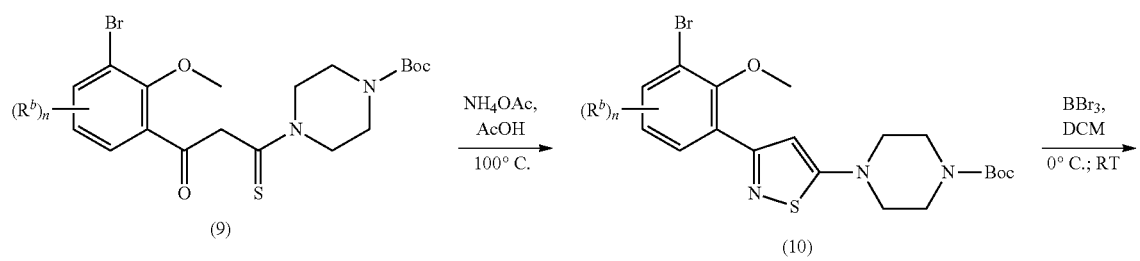
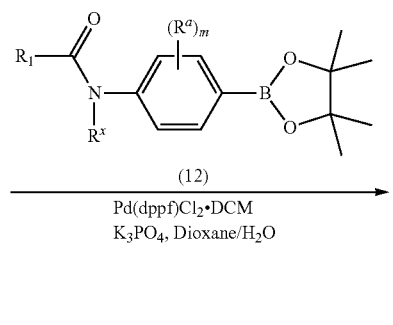

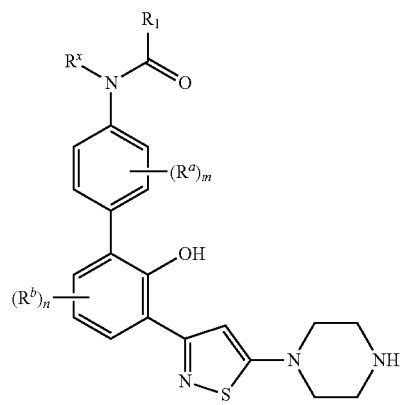
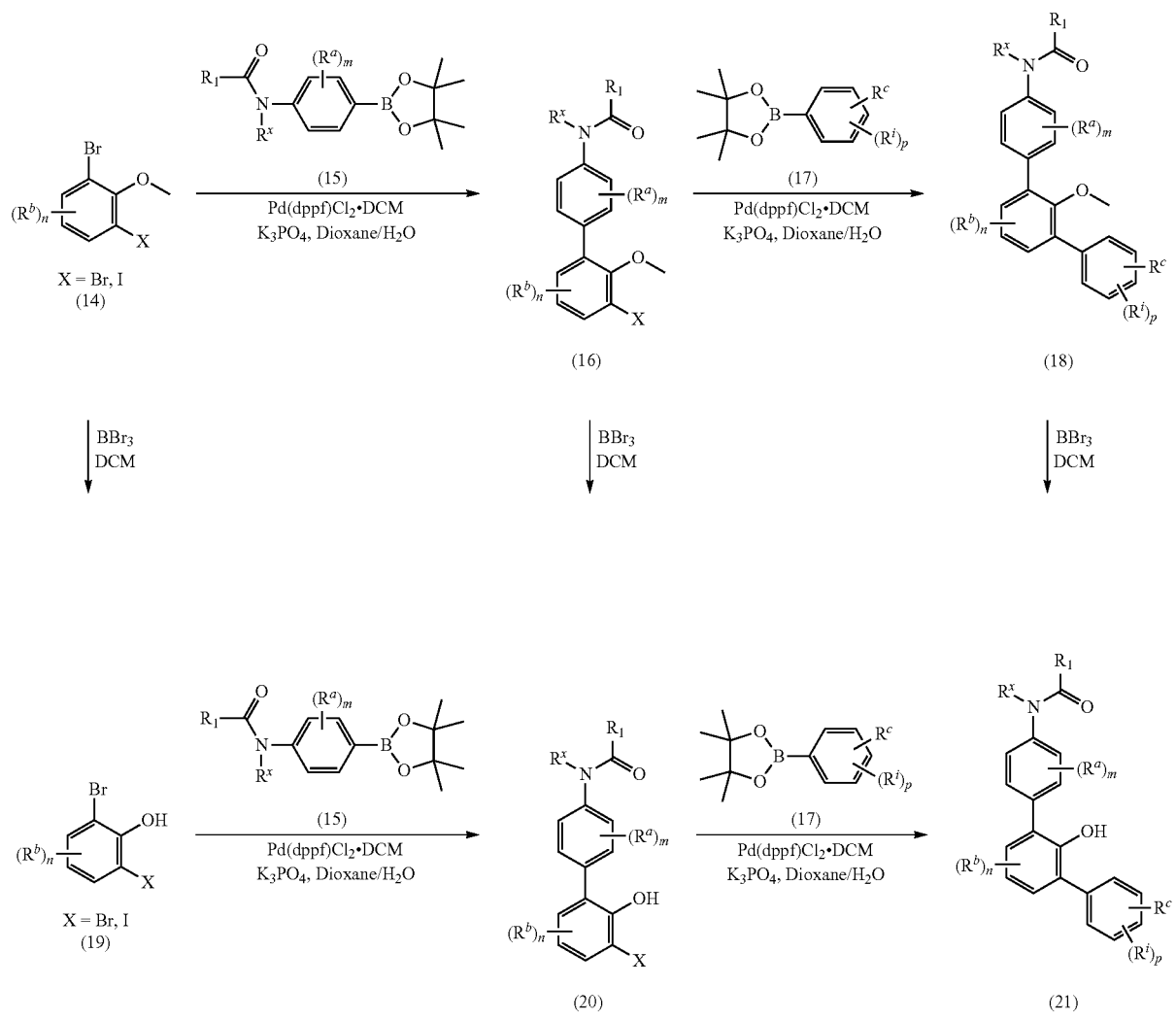
Scheme 3

Scheme 4
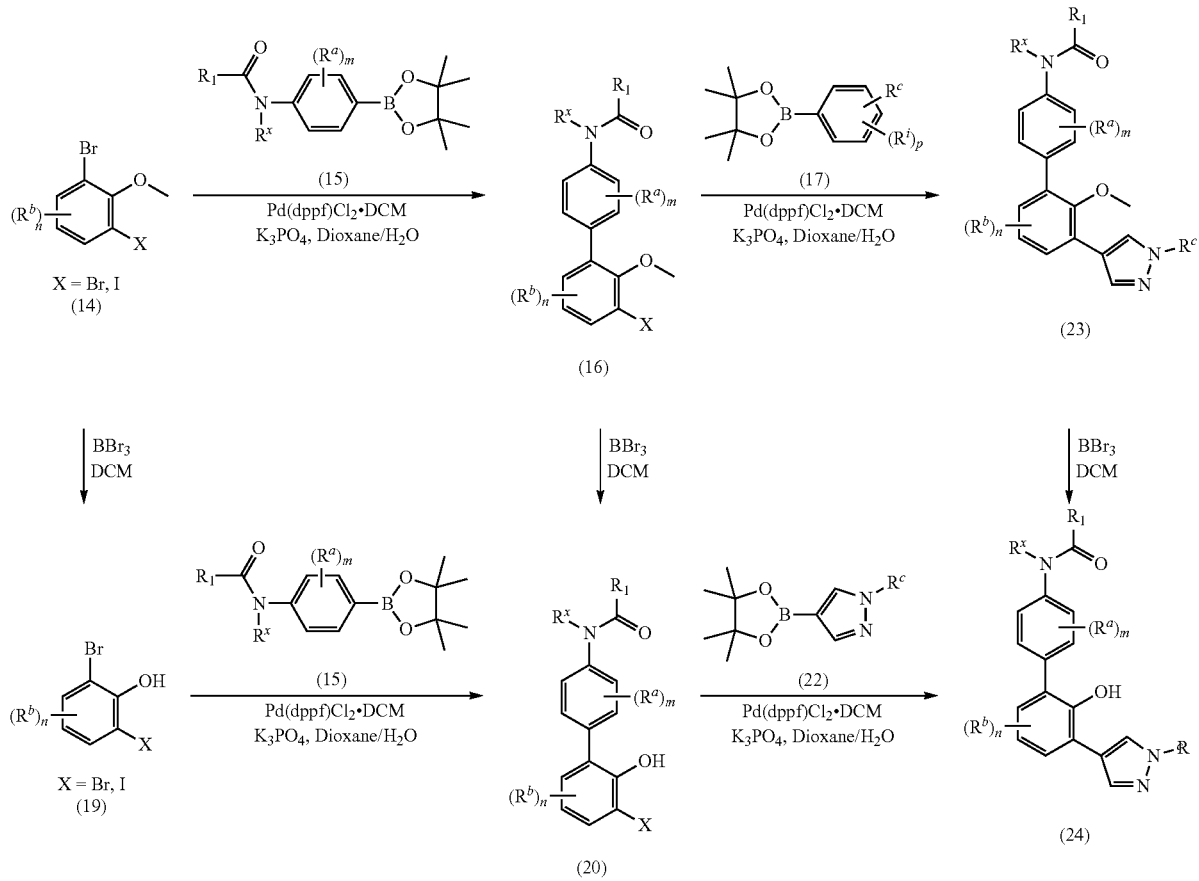
Scheme 5
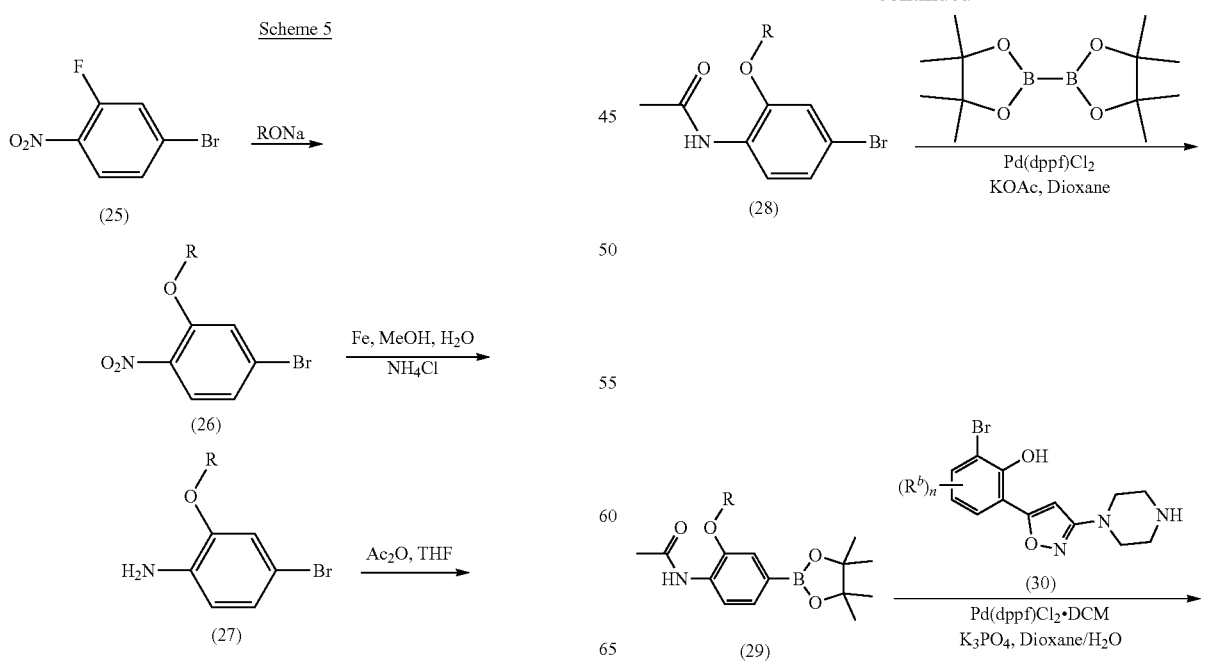

387
-continued
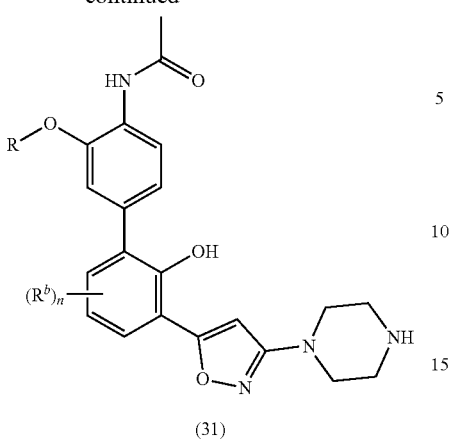
(31)
388
-continued
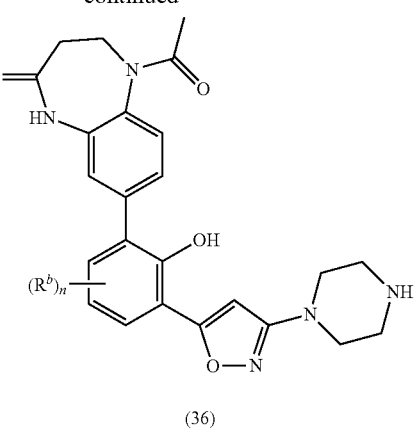
(36)
Scheme 6
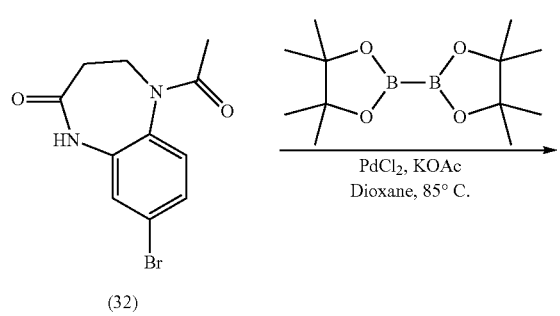
(32)
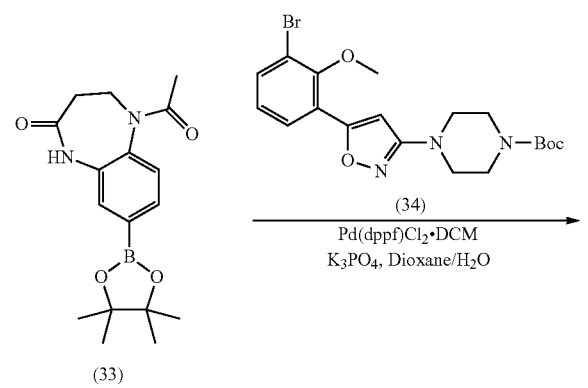
(33)
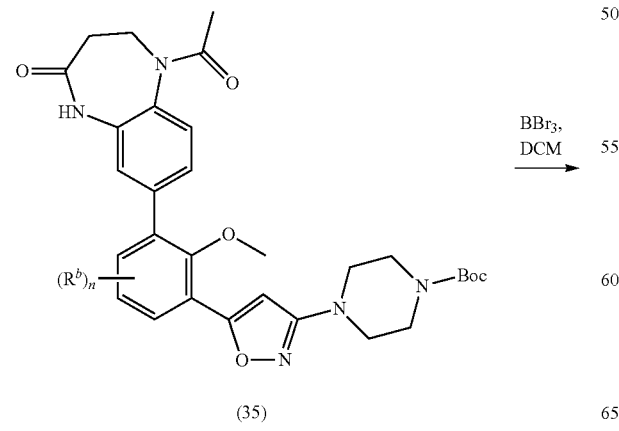
(35)
Scheme 7
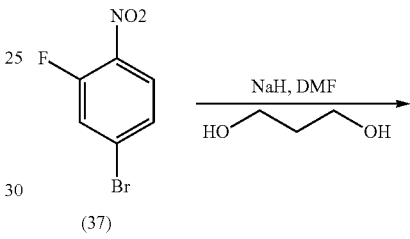
(37)
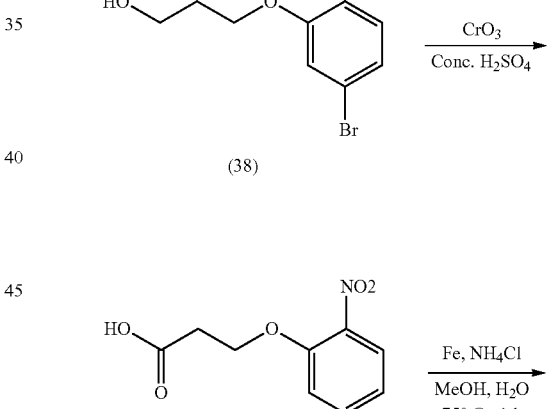
(38)
(39)
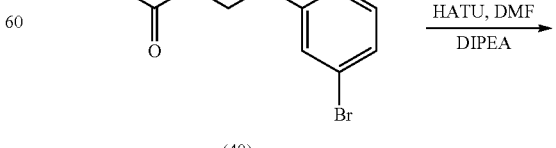
(40)

-continued
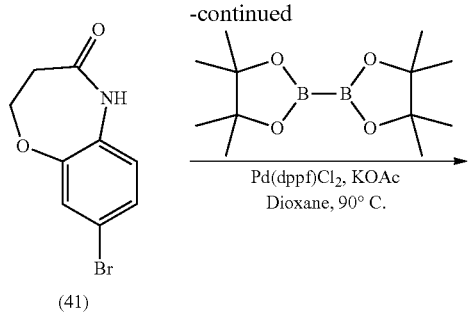
(41)
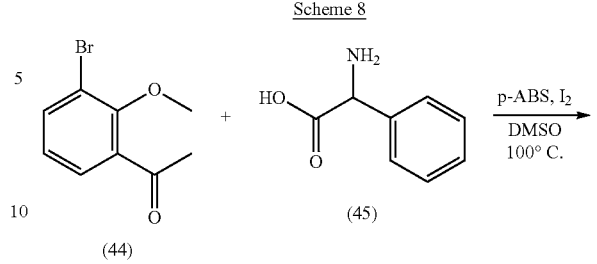
Scheme 8
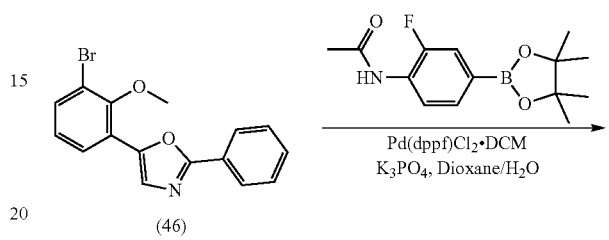
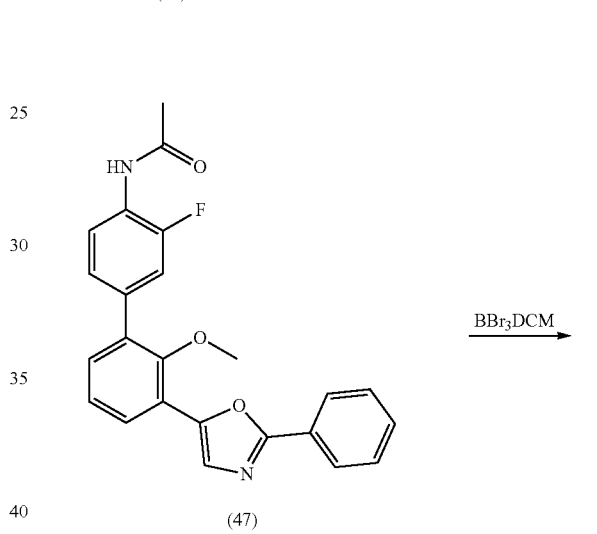
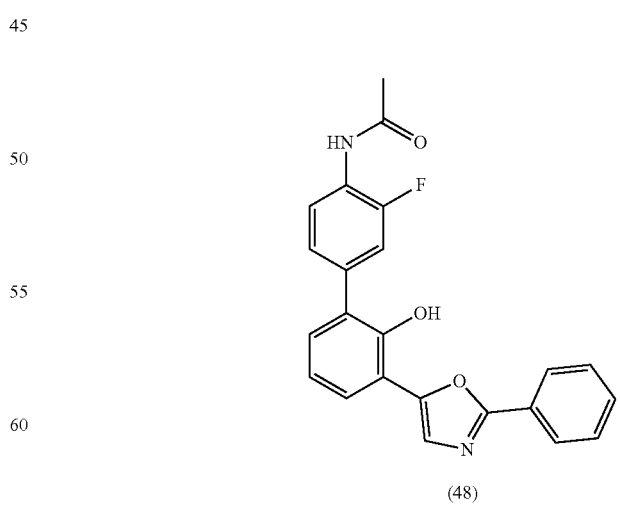

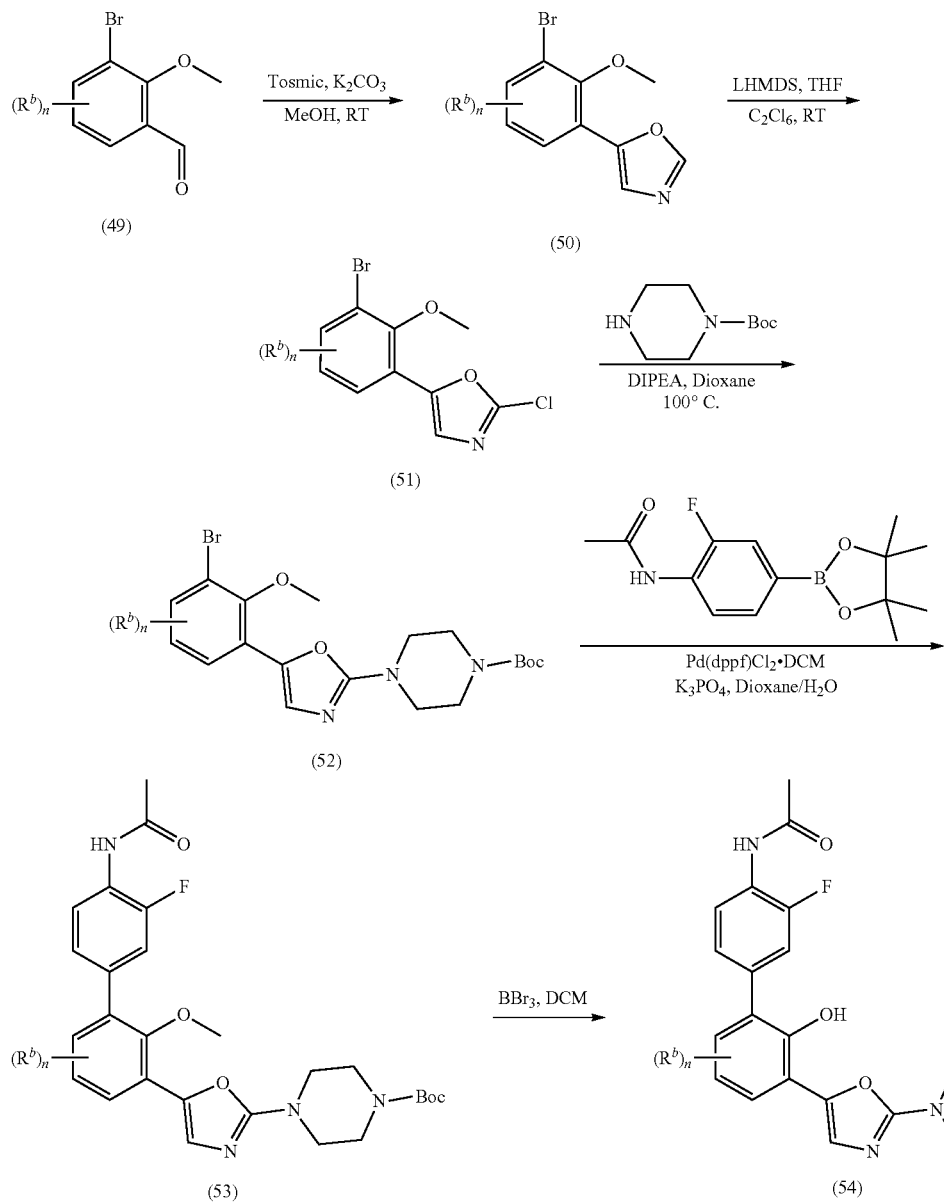
Scheme 9
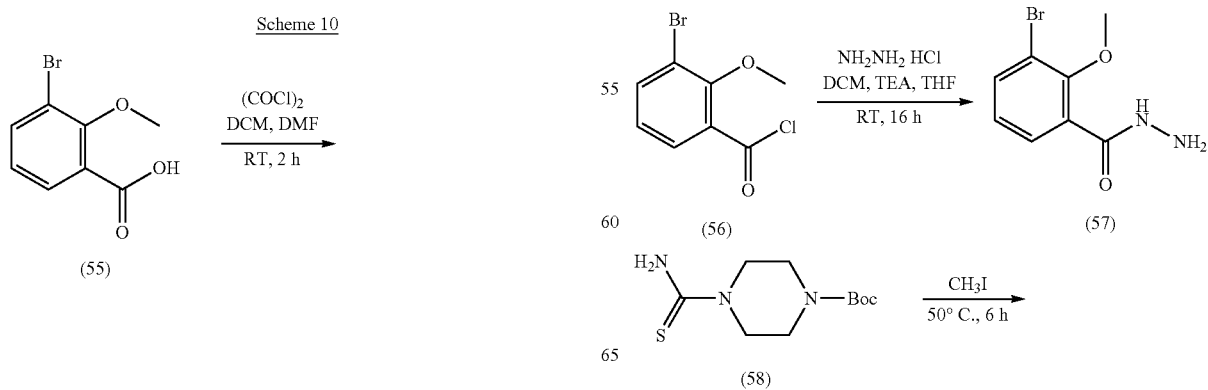
Scheme 10

Scheme 11
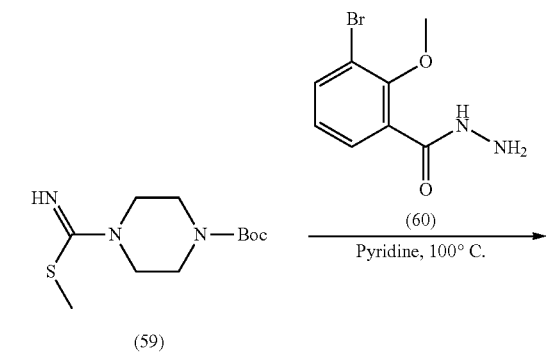
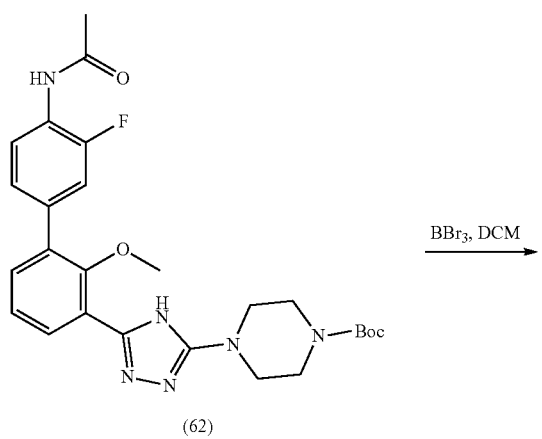
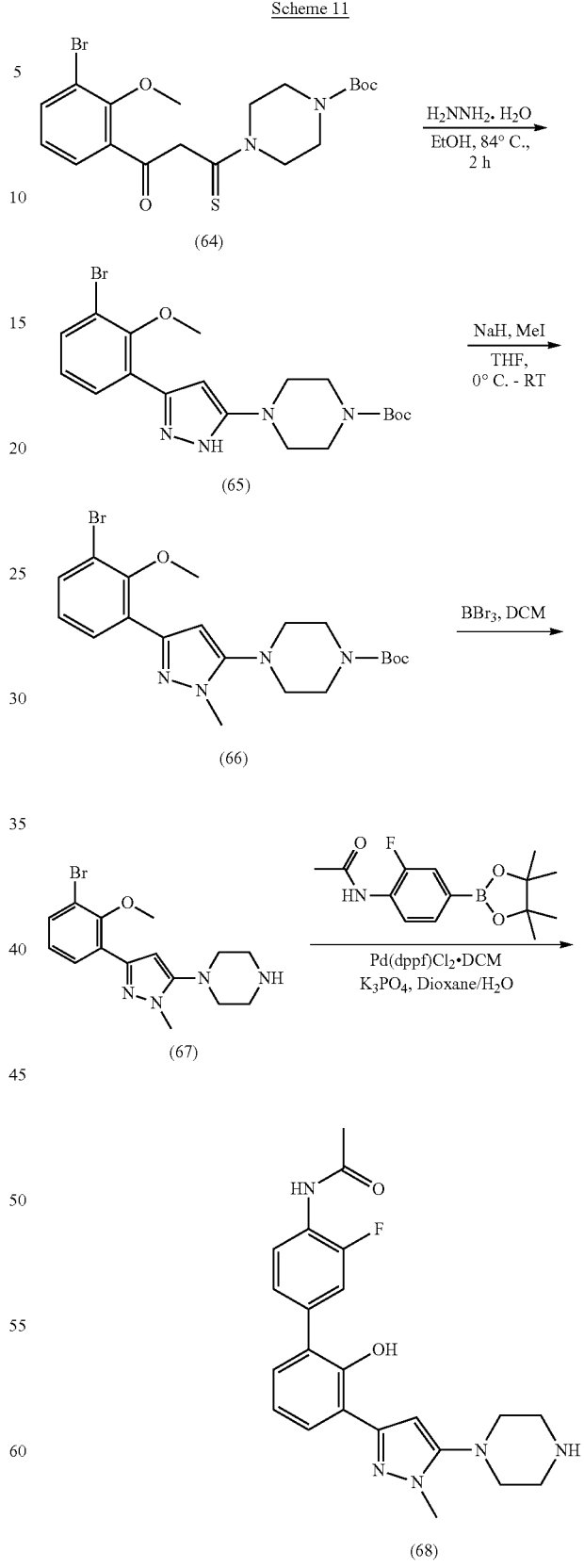
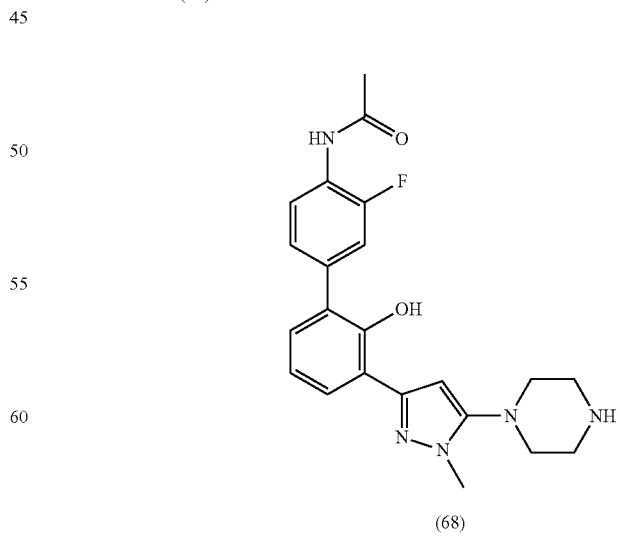

Scheme 12
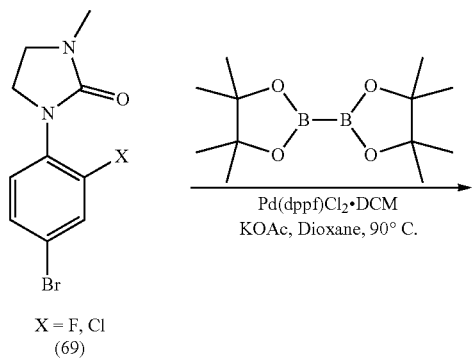
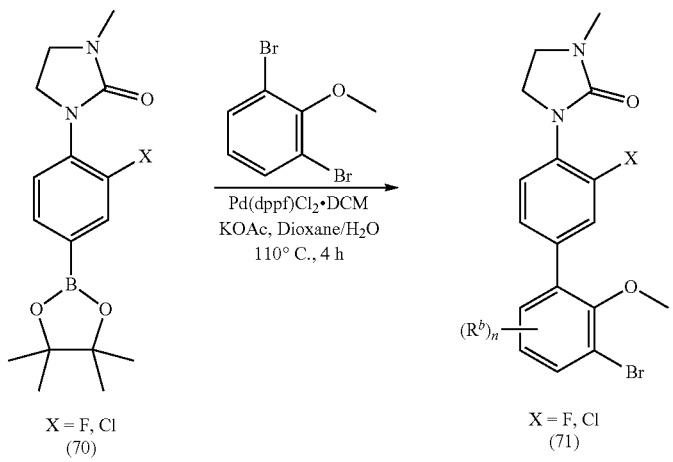
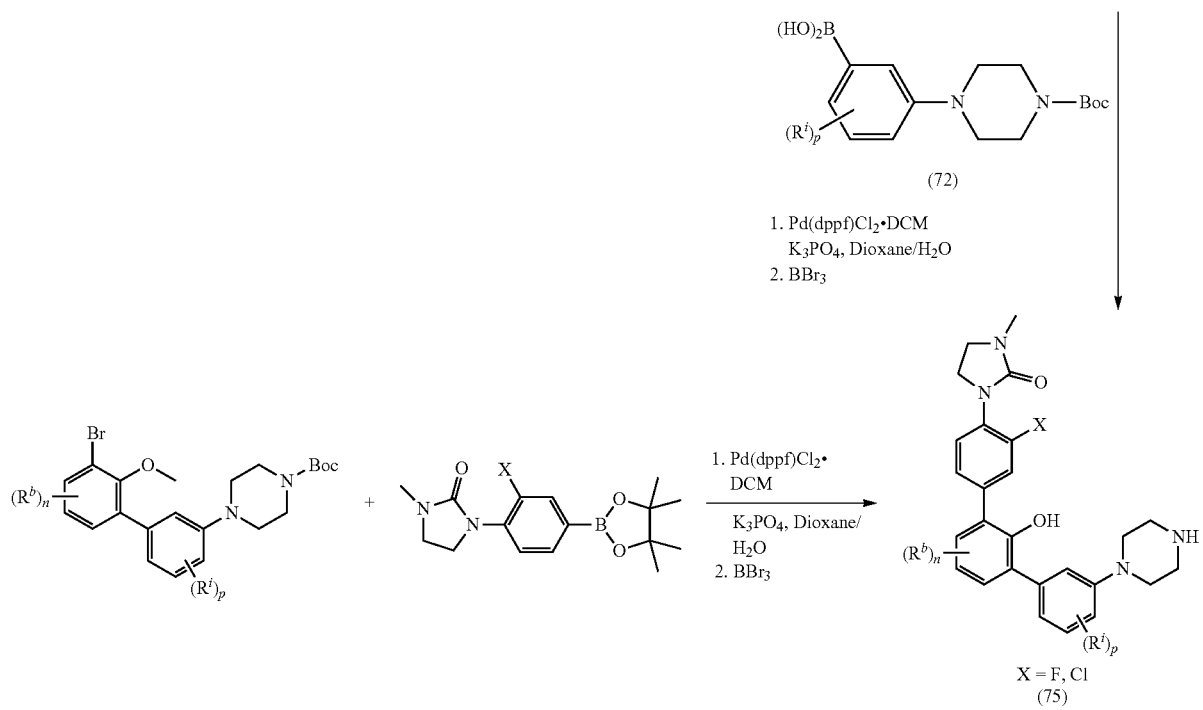
Scheme 13
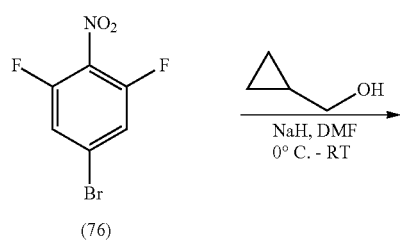
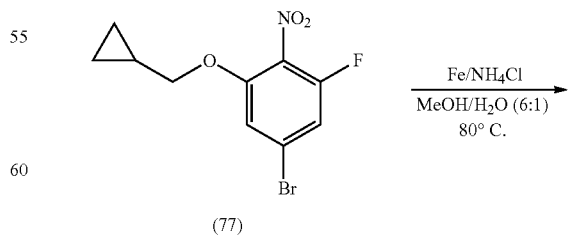

-continued
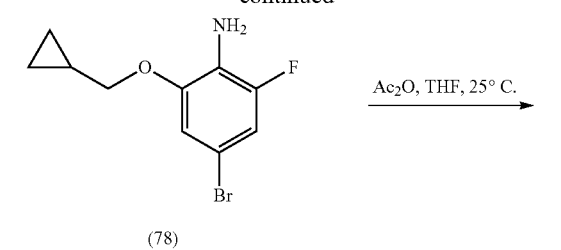
(78)
Ac₂O, THF, 25° C.
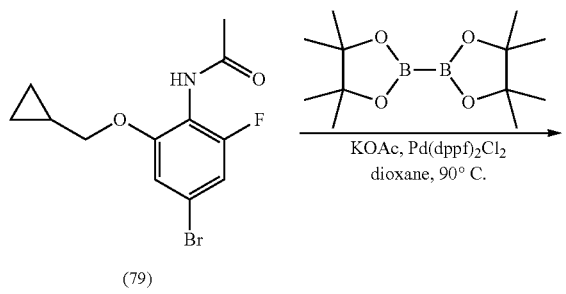
(79)
bis(pinacolato)diboron
KOAc, Pd(dppf)₂Cl₂
dioxane, 90° C.
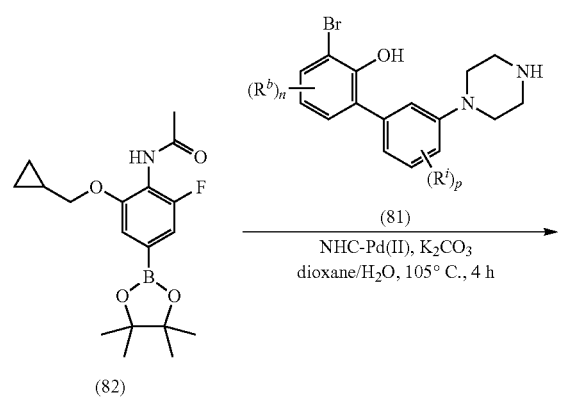
(82)
(81)
NHC-Pd(II), K₂CO₃
dioxane/H₂O, 105° C., 4 h
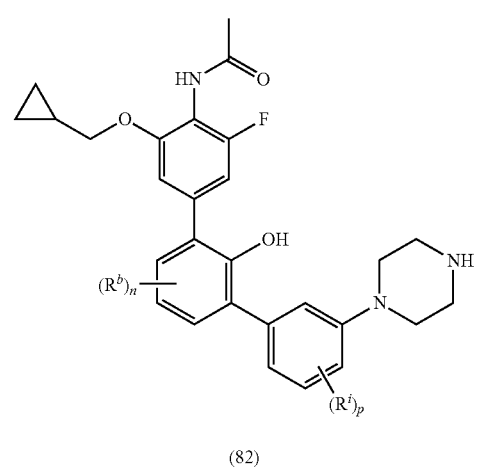
(82)
Scheme 14
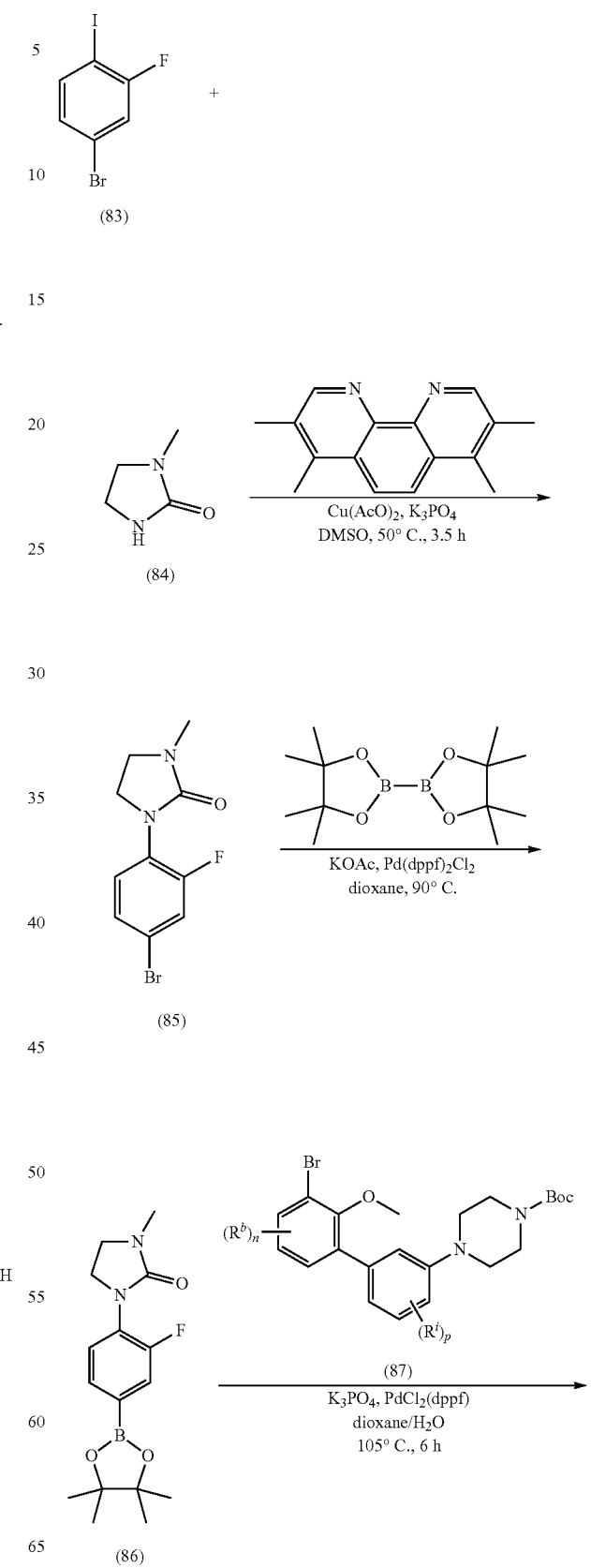

399
-continued
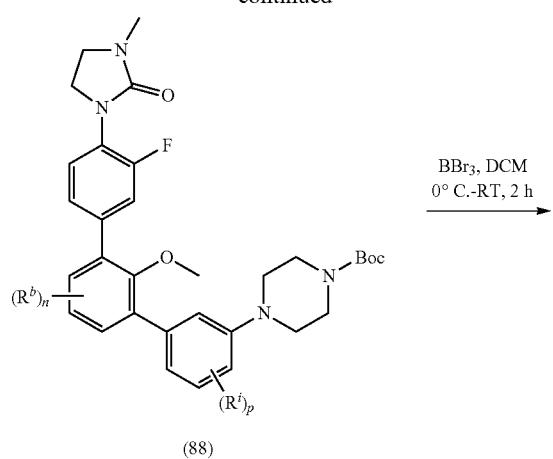
(88)
Scheme 15
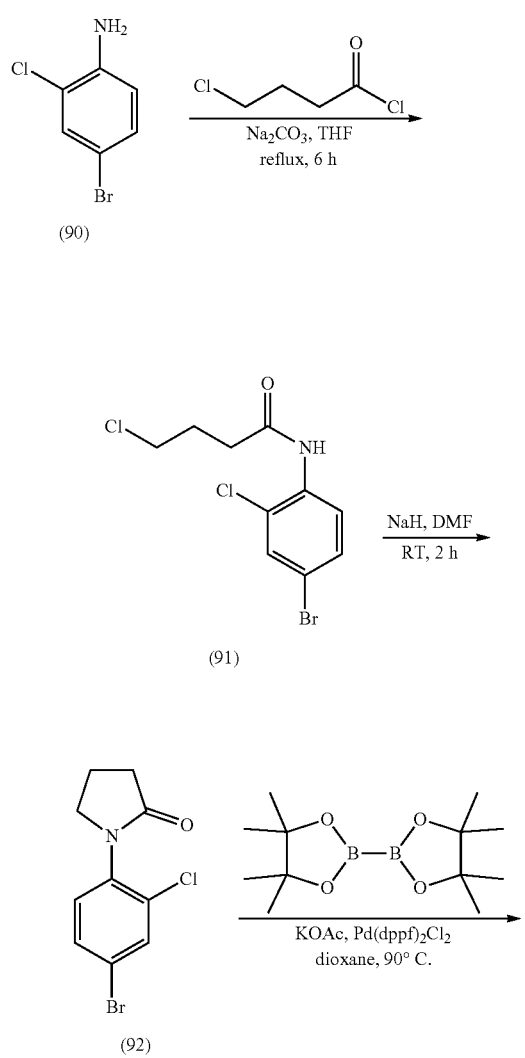
400
-continued
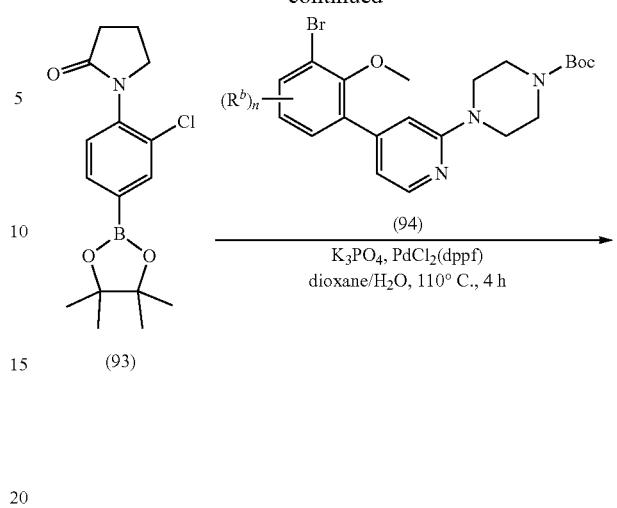
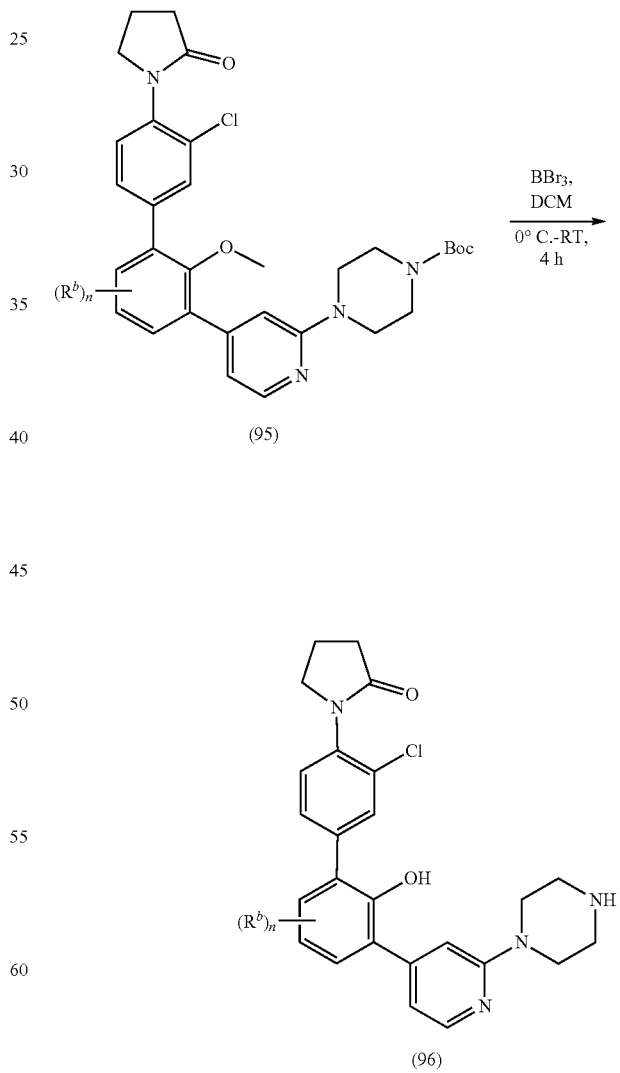

Scheme 16
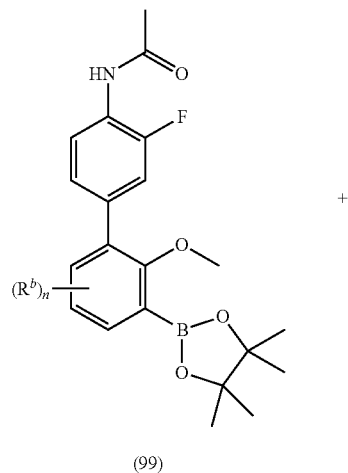
(99)
+
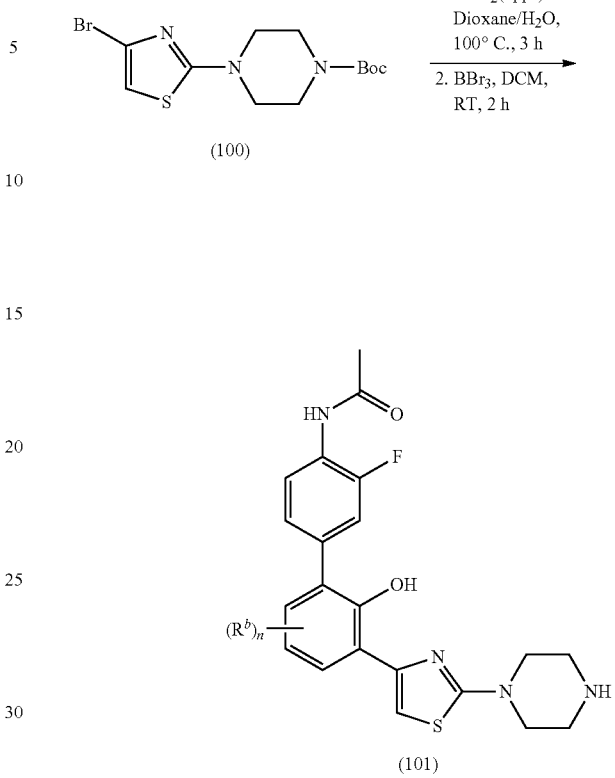
Scheme 17
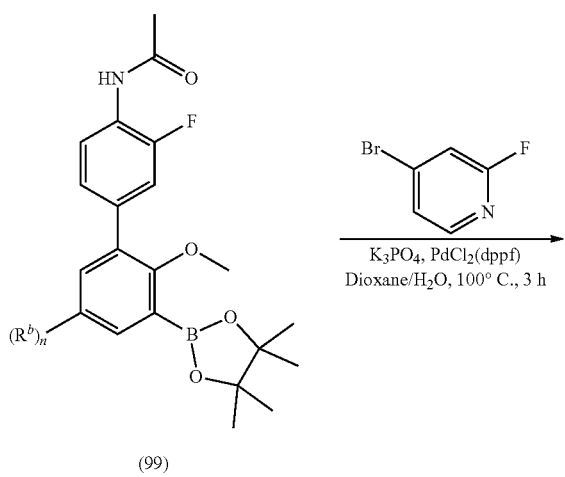
(99)

-continued
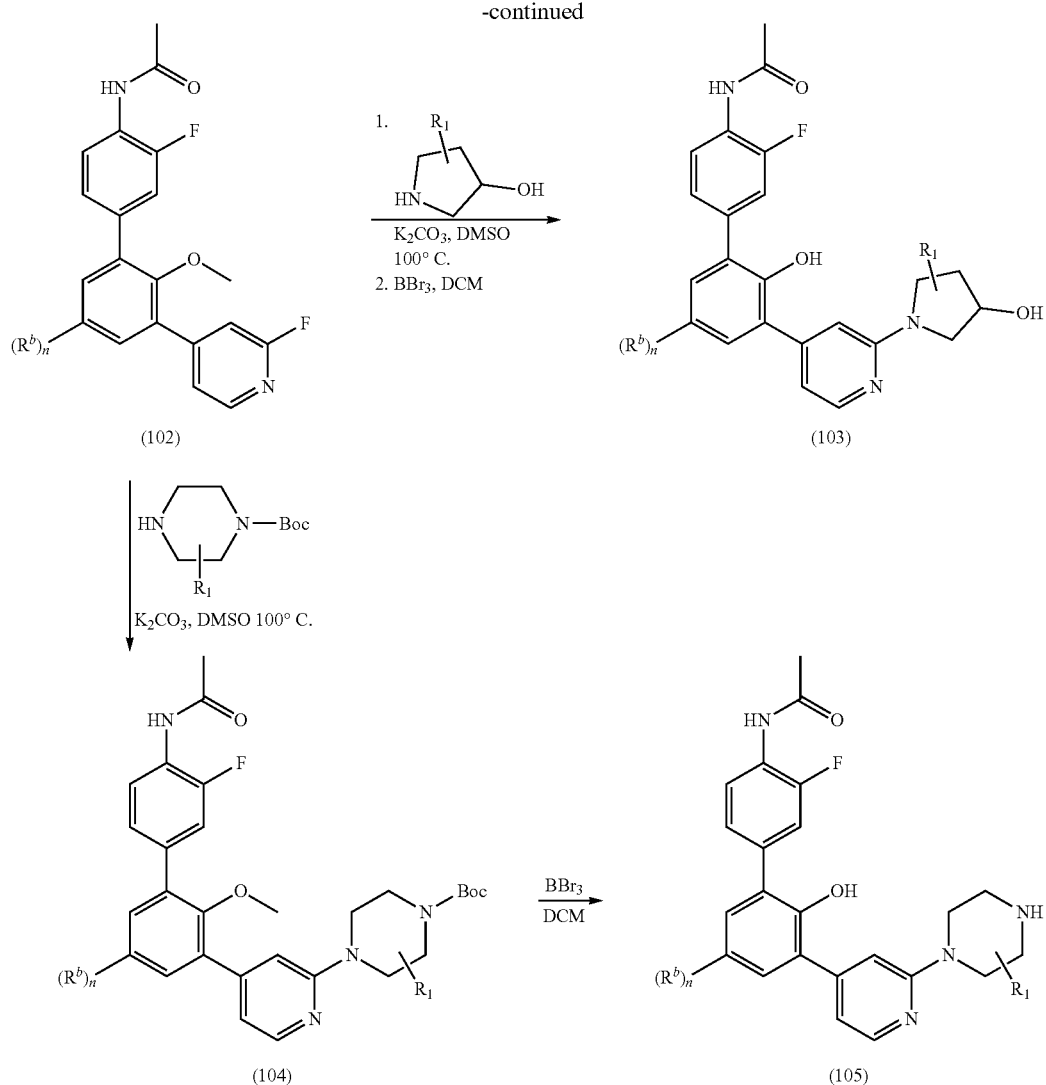
Scheme 18
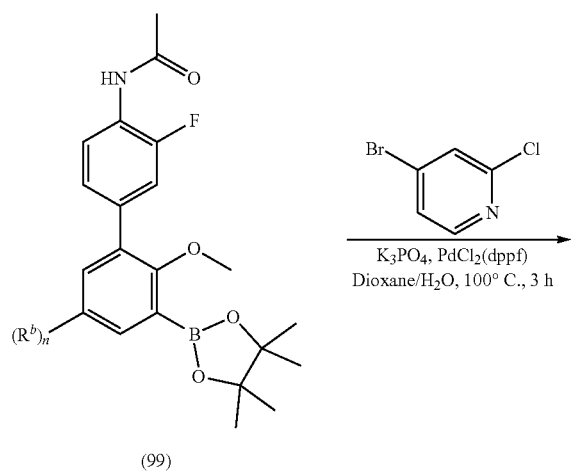

-continued
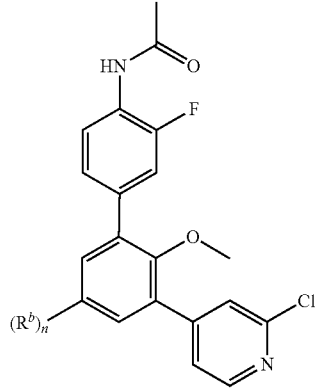
(106)
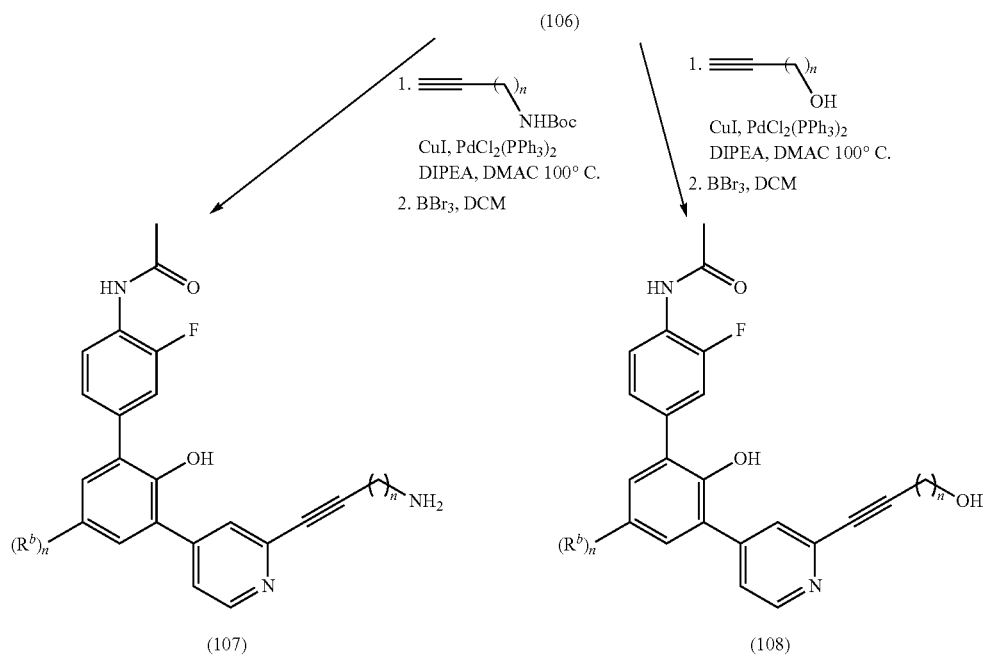
(107) (108)
Scheme 19
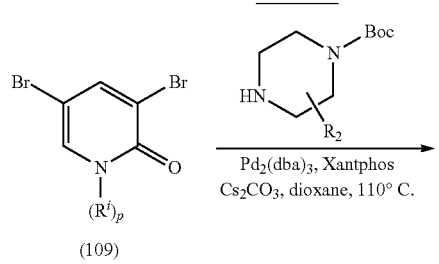
(109)
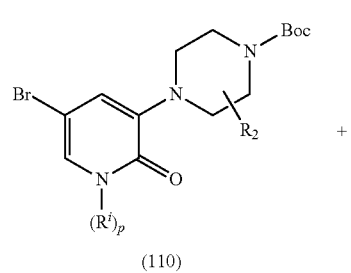
(110)
+
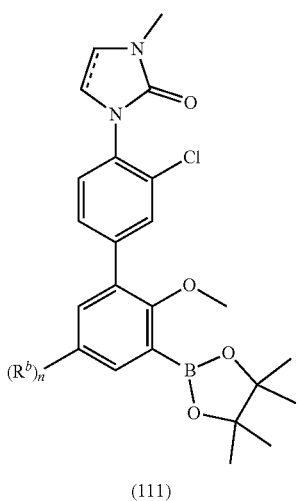
(111)

407
-continued
408
-continued
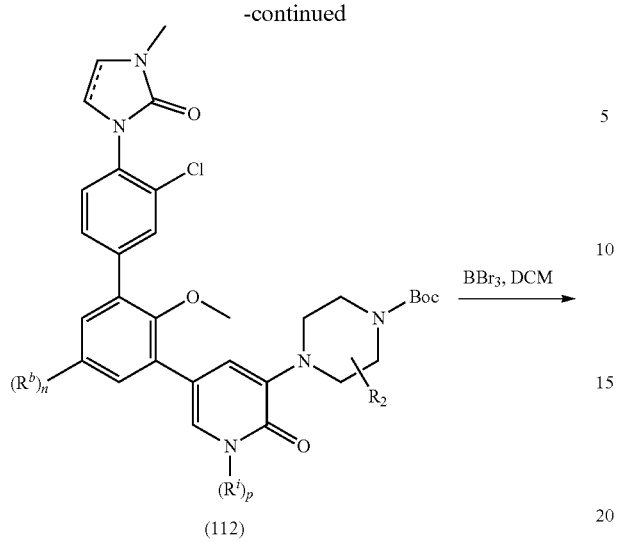
(112)
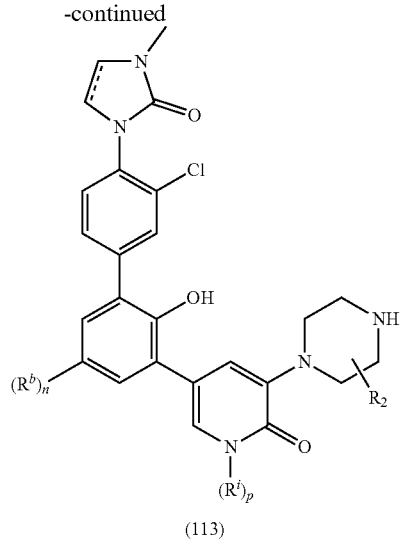
(113)
Scheme 20
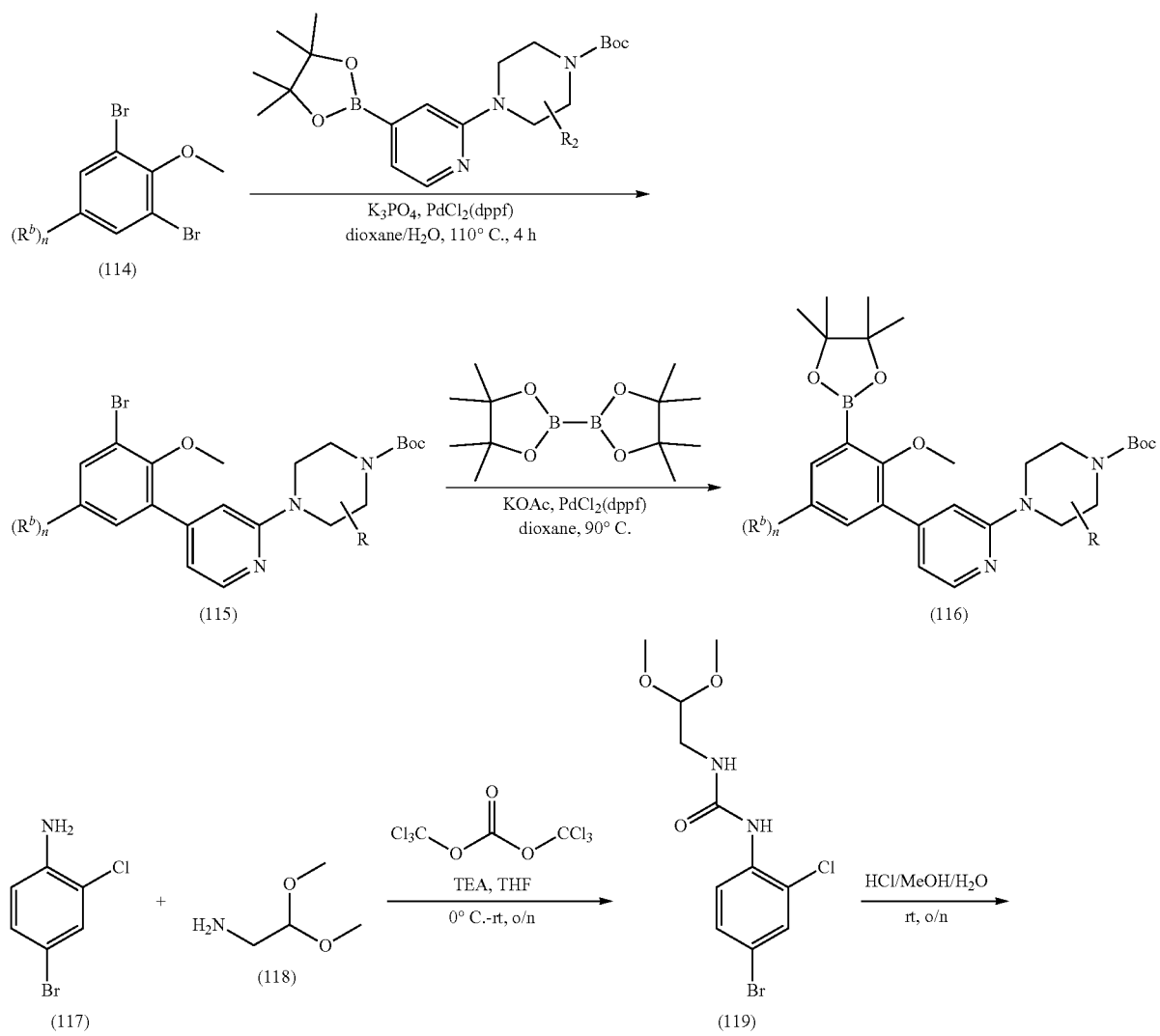

-continued
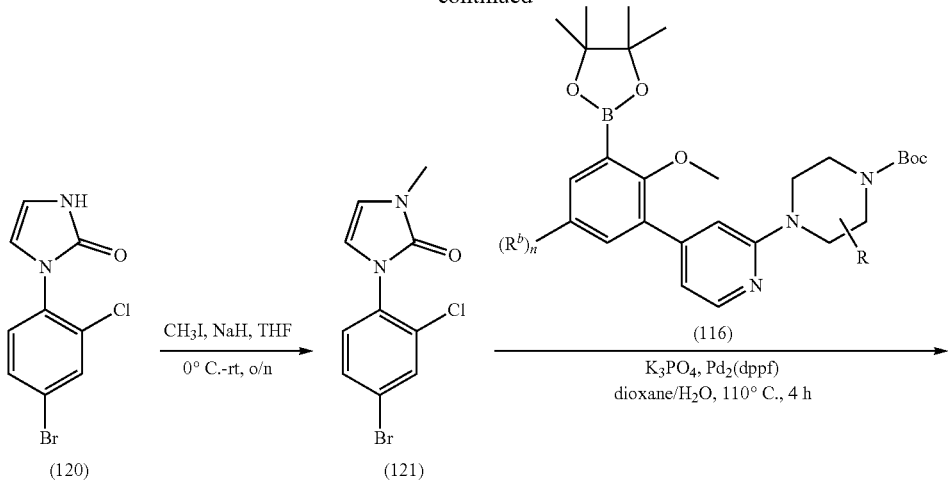
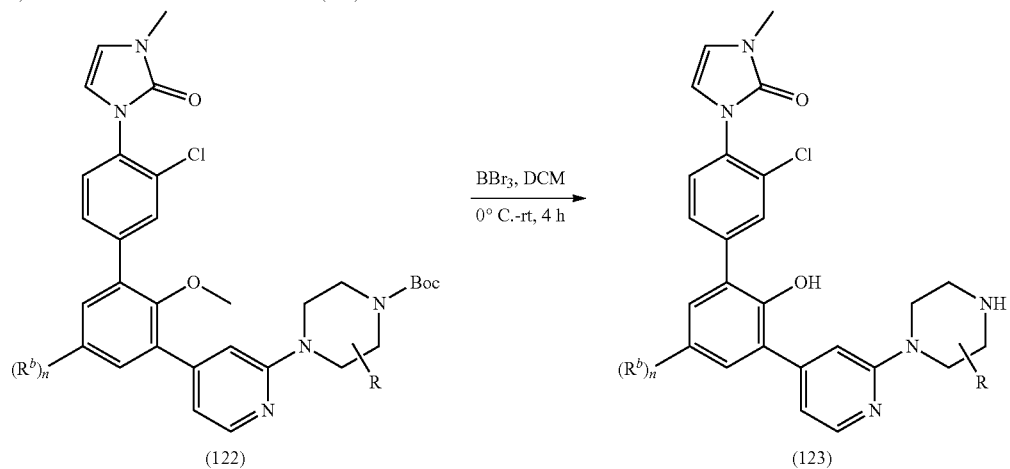
Scheme 21
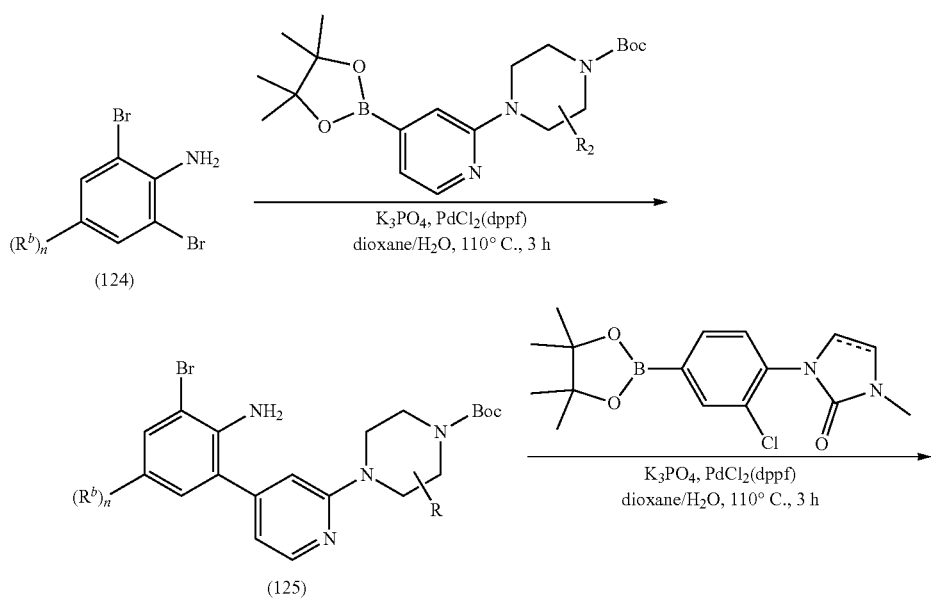

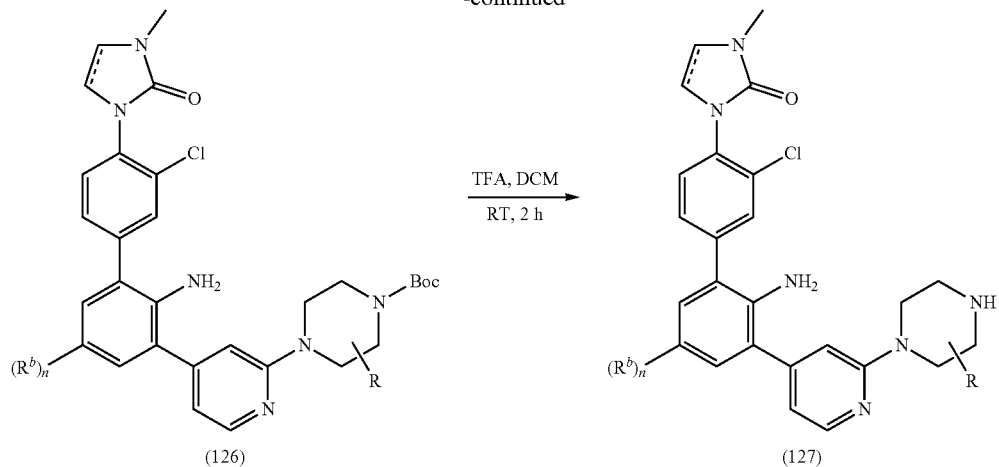
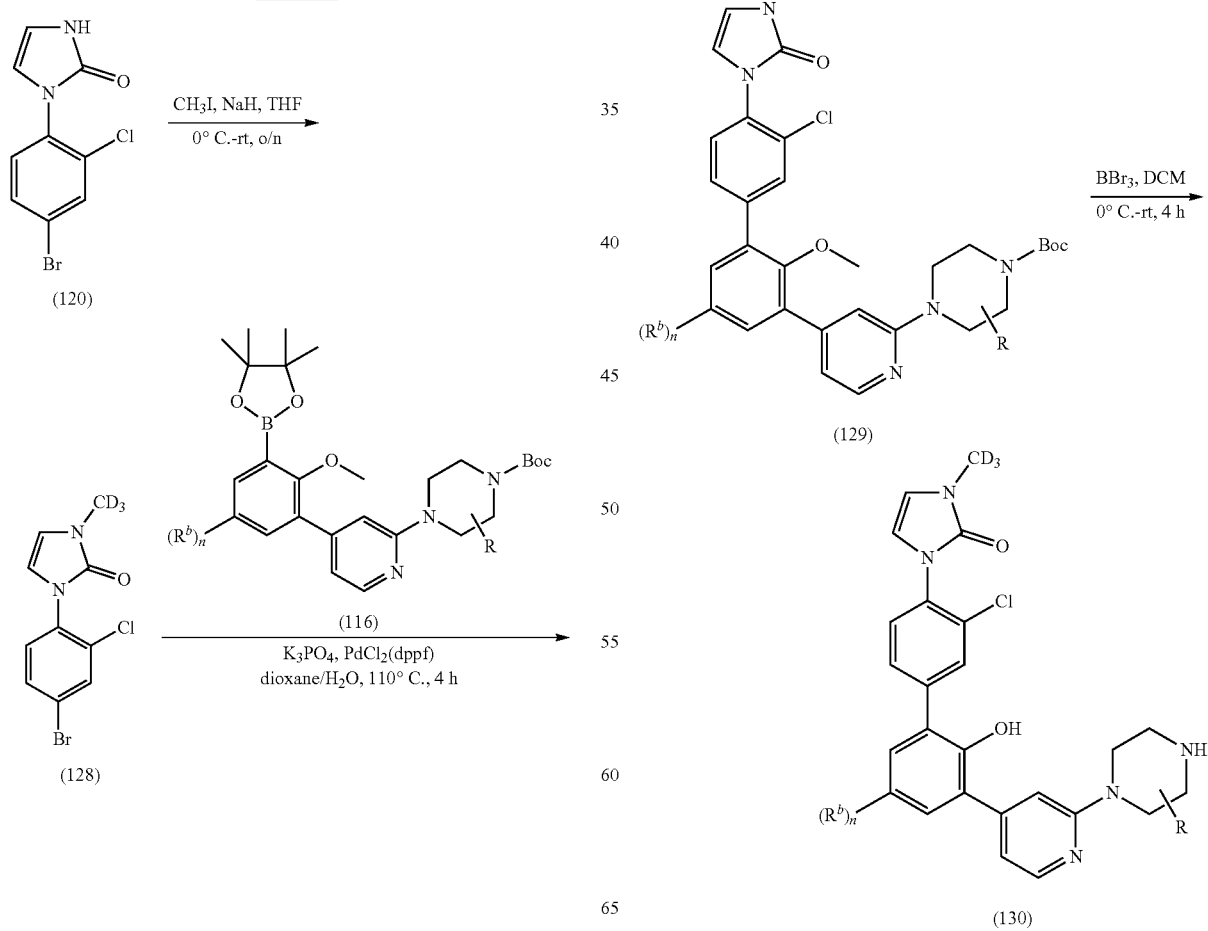

Scheme 23
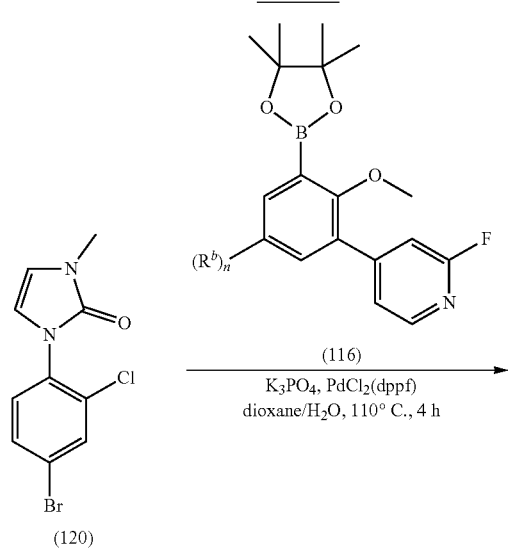
(120)
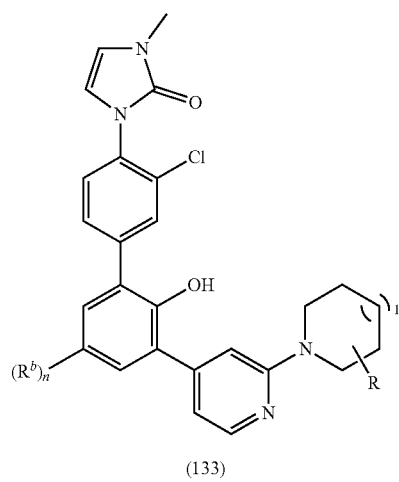
(133)
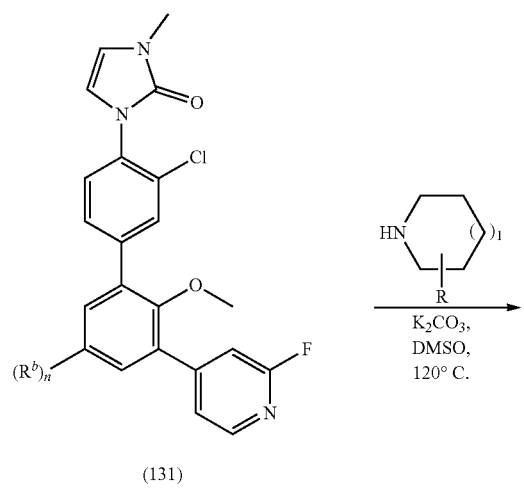
(131)
Scheme 24
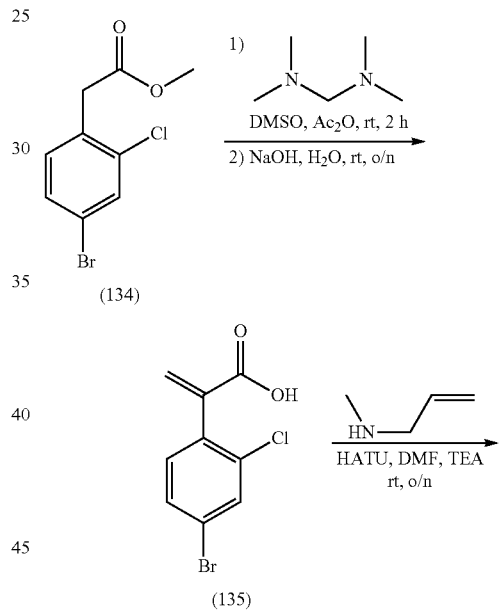
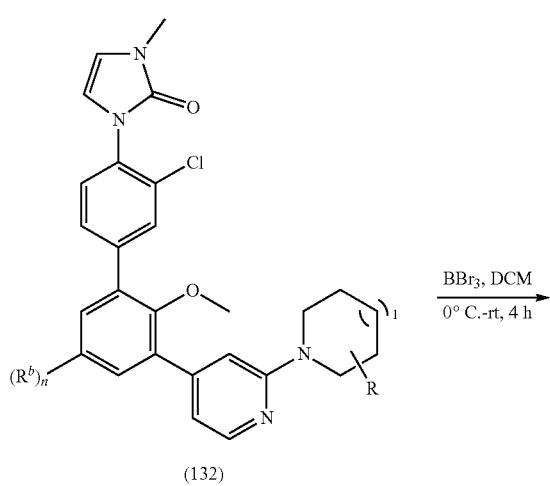
(132)
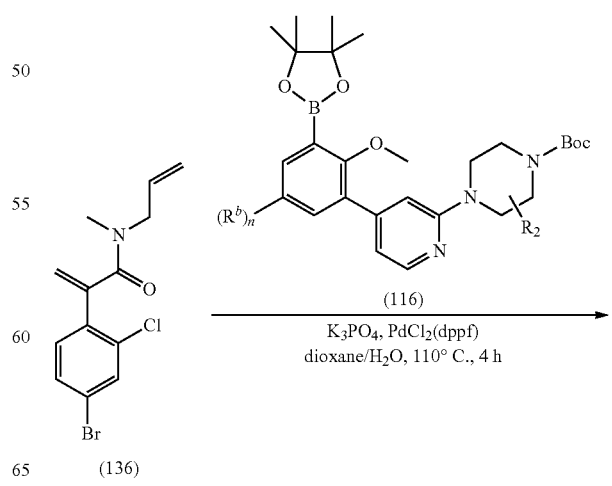

Scheme 25
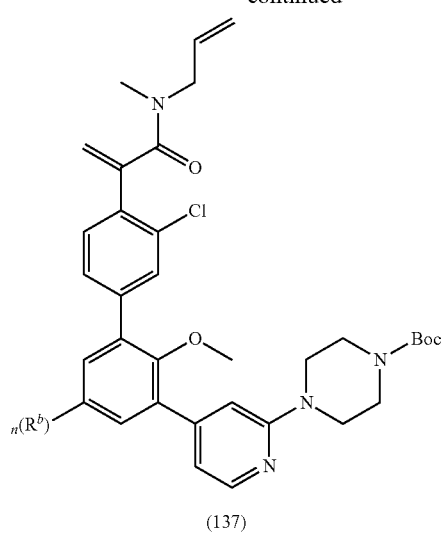
(137)
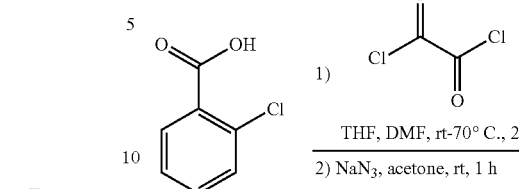
(140)
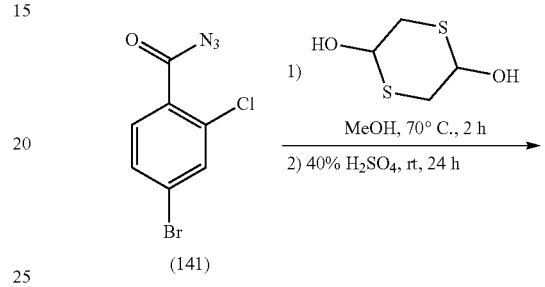
(141)
Tol., Umicore M51
110° C., 1 h
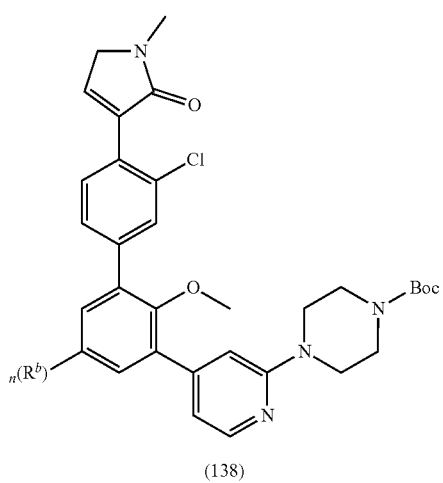
(138)
BBr$_3$, DCM
RT, 4 h
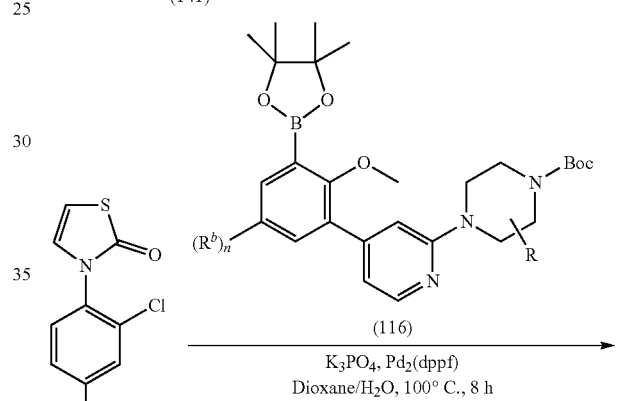
(142)
K$_3$PO$_4$, Pd$_2$(dppf)
Dioxane/H$_2$O, 100° C., 8 h
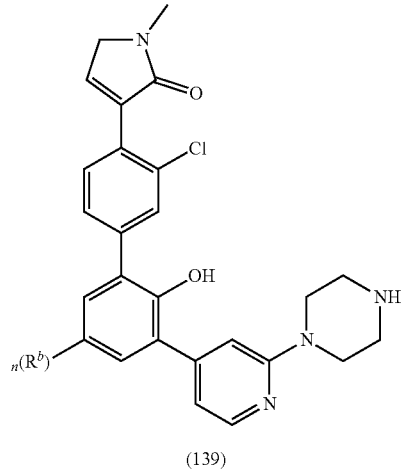
(139)
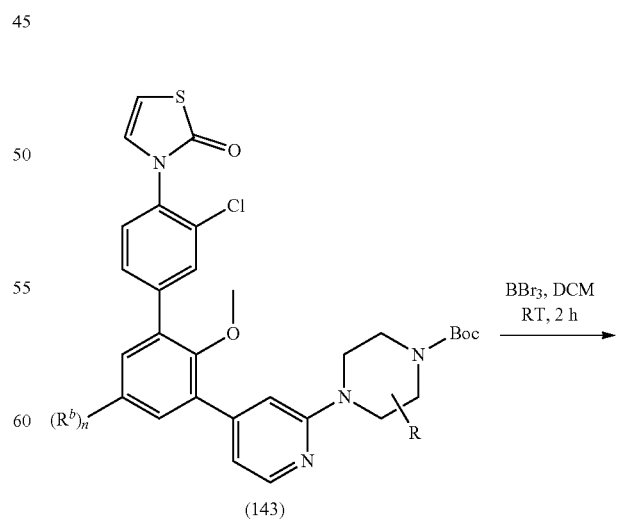
(143)
BBr$_3$, DCM
RT, 2 h

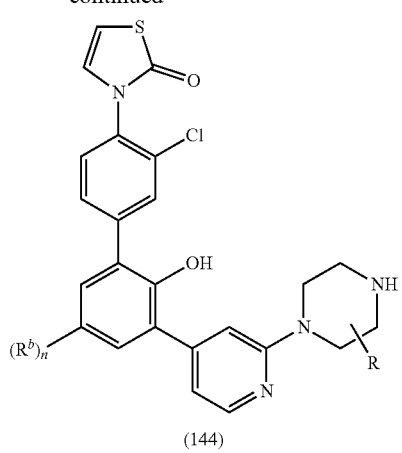
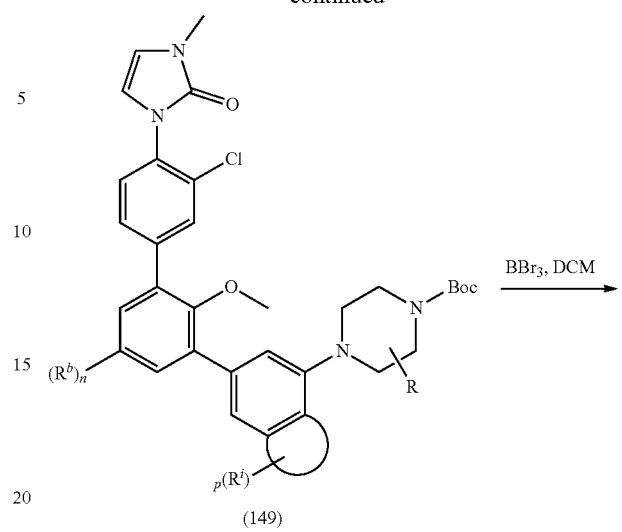
Scheme 26
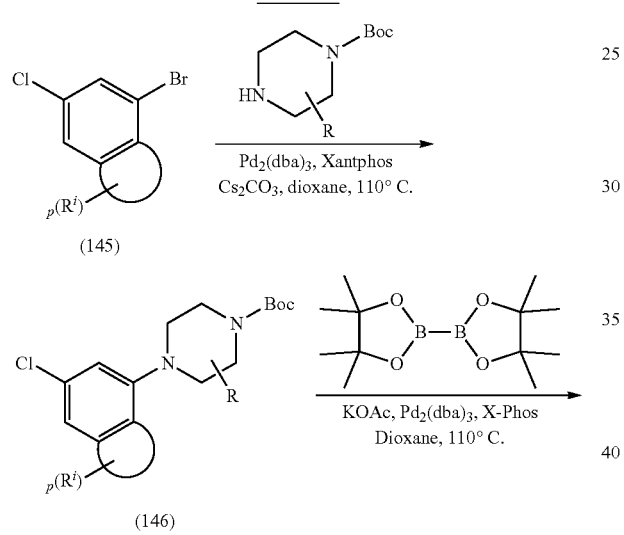
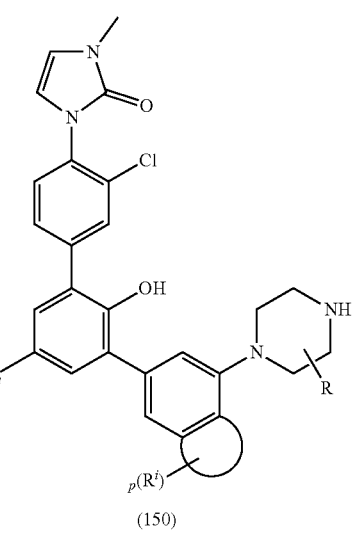
Scheme 27
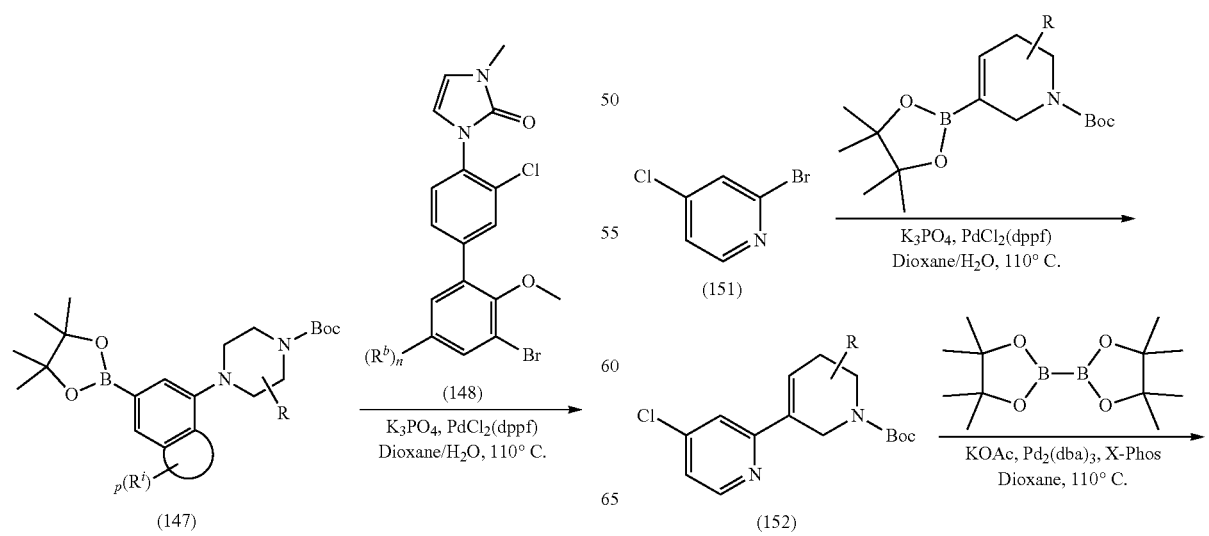

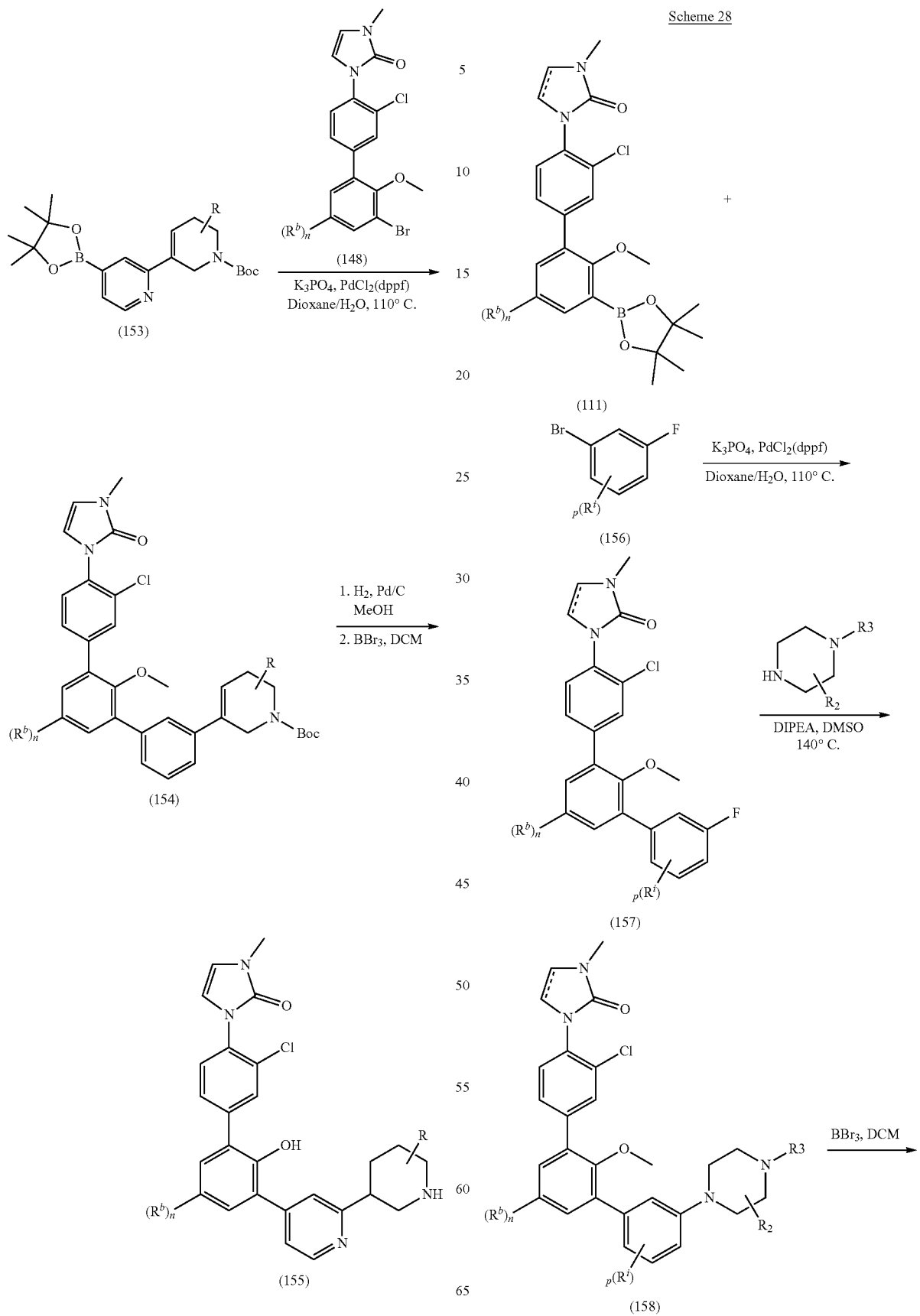

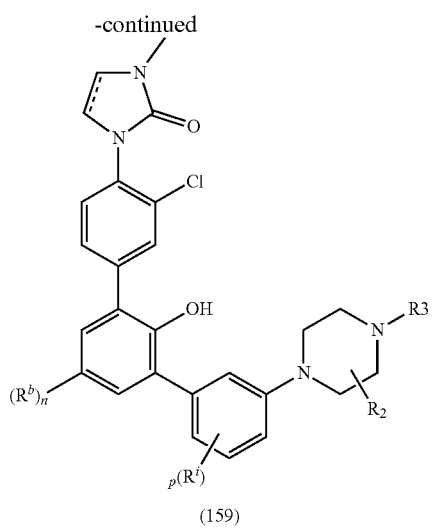
(159)
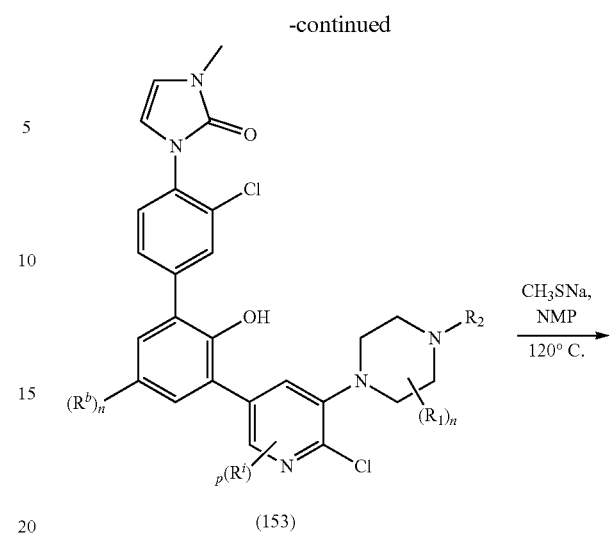
(153)
Scheme 29
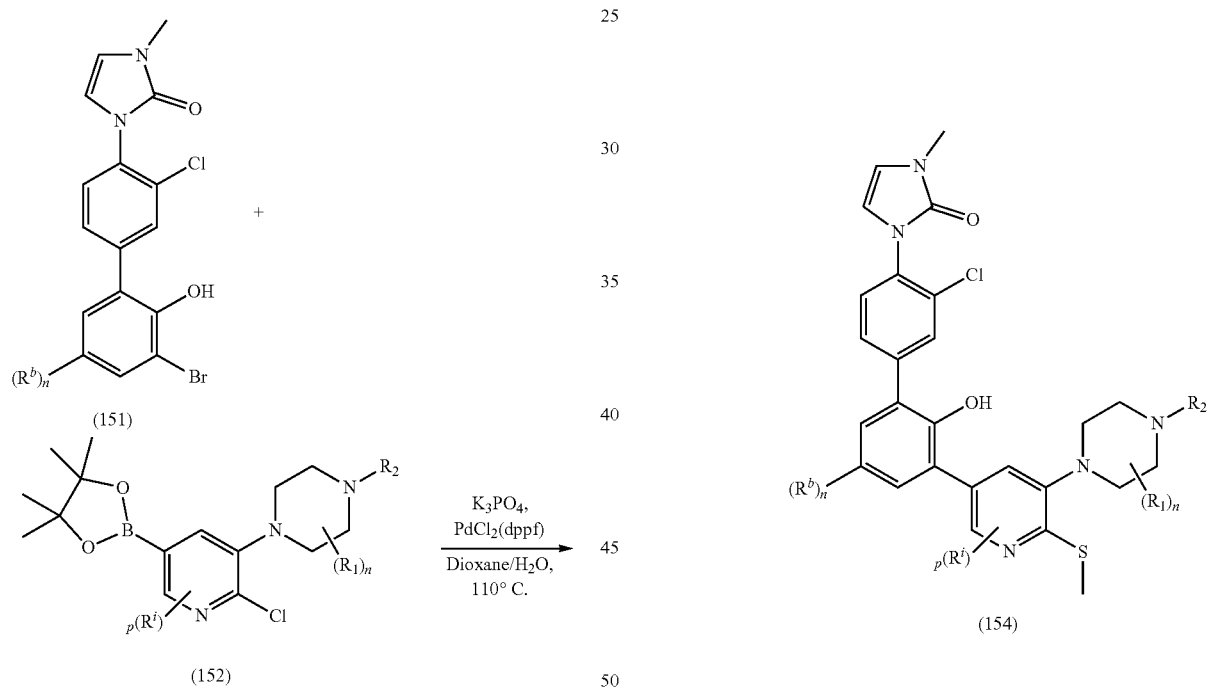
Scheme 30
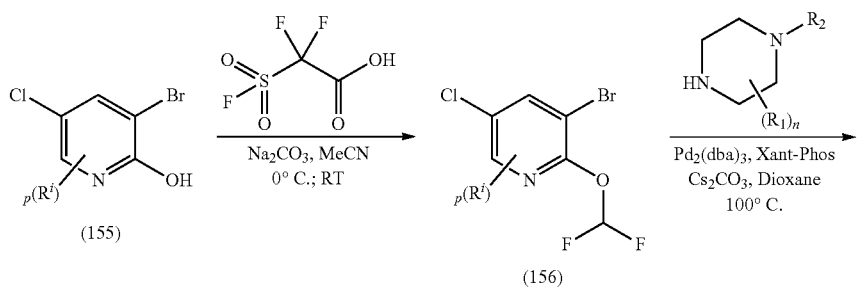

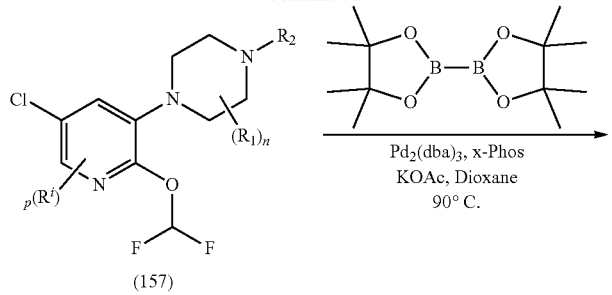
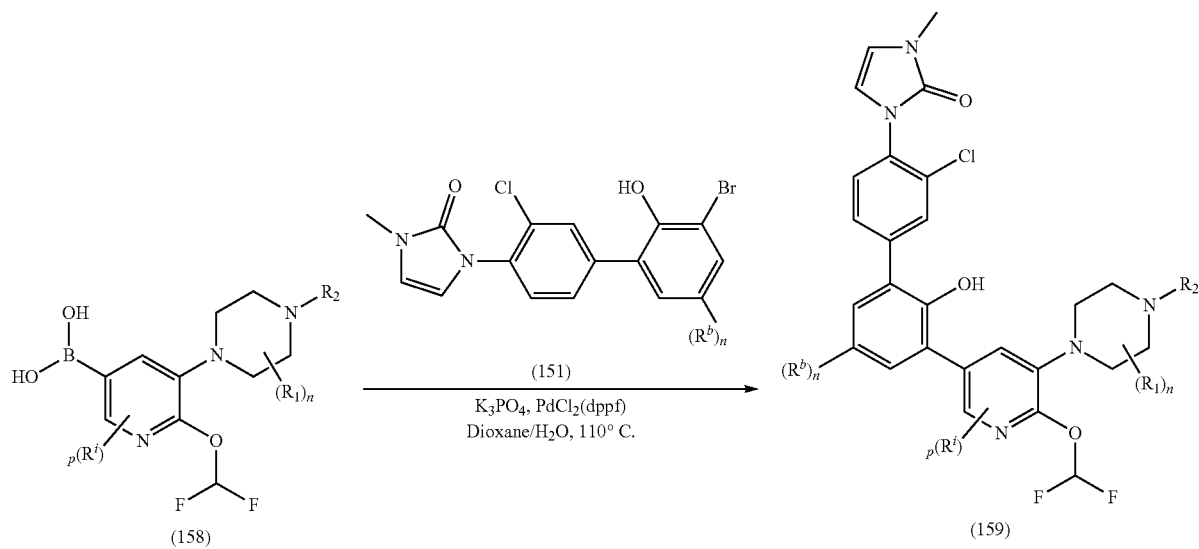
Scheme 31
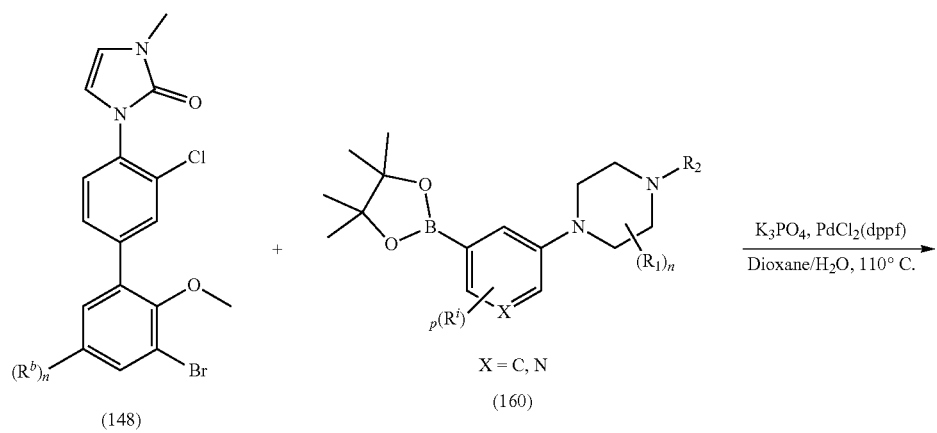

-continued
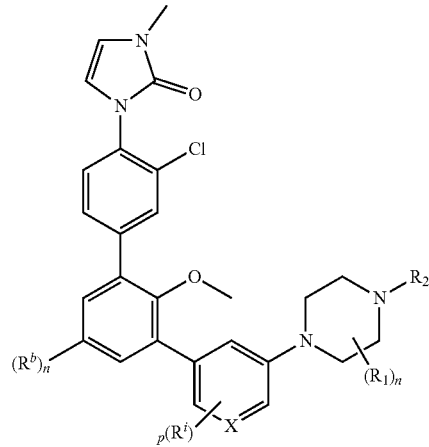
(161)
X = C, N
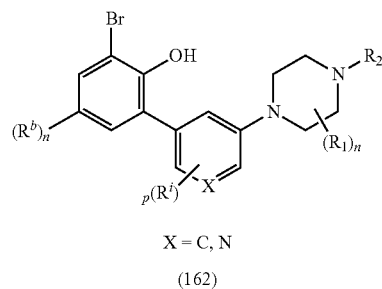
(162)
X = C, N
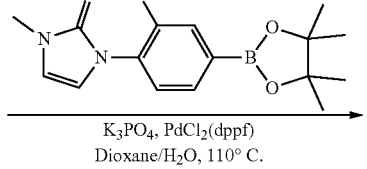
K₃PO₄, PdCl₂(dppf)
Dioxane/H₂O, 110° C.
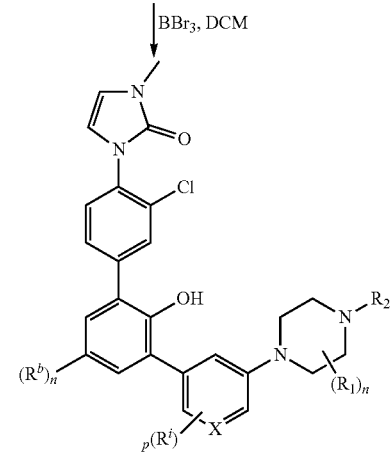
(163)
X = C, N
BBr₃, DCM
Scheme 32
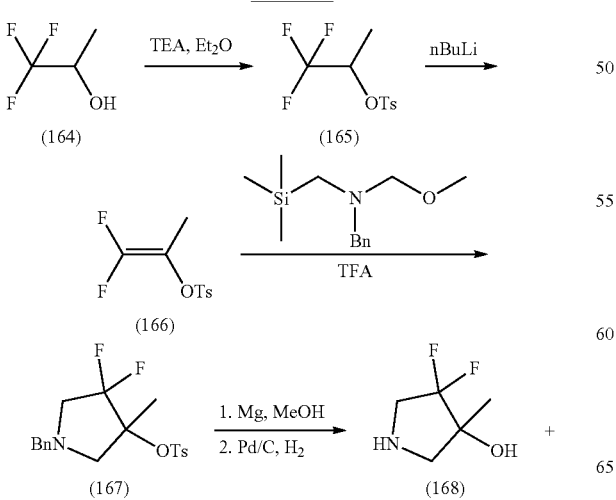
-continued
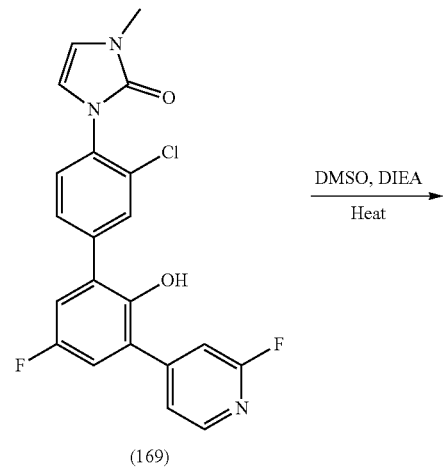
(169)
DMSO, DIEA
Heat Scheme 34
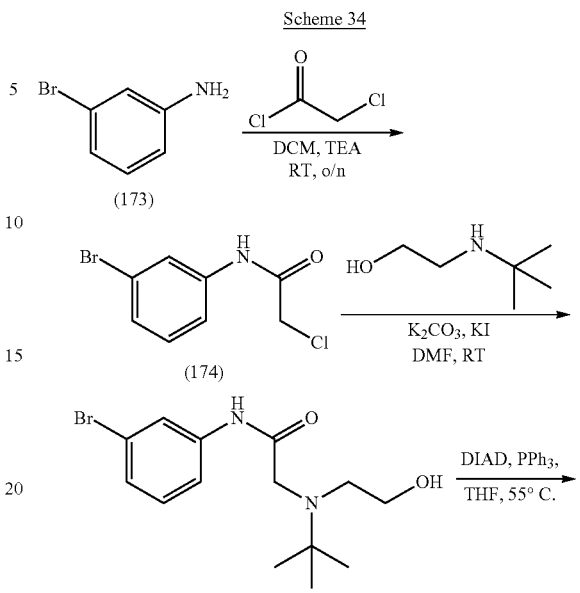
Scheme 33
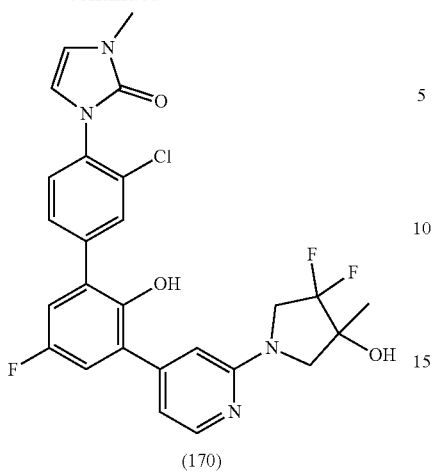
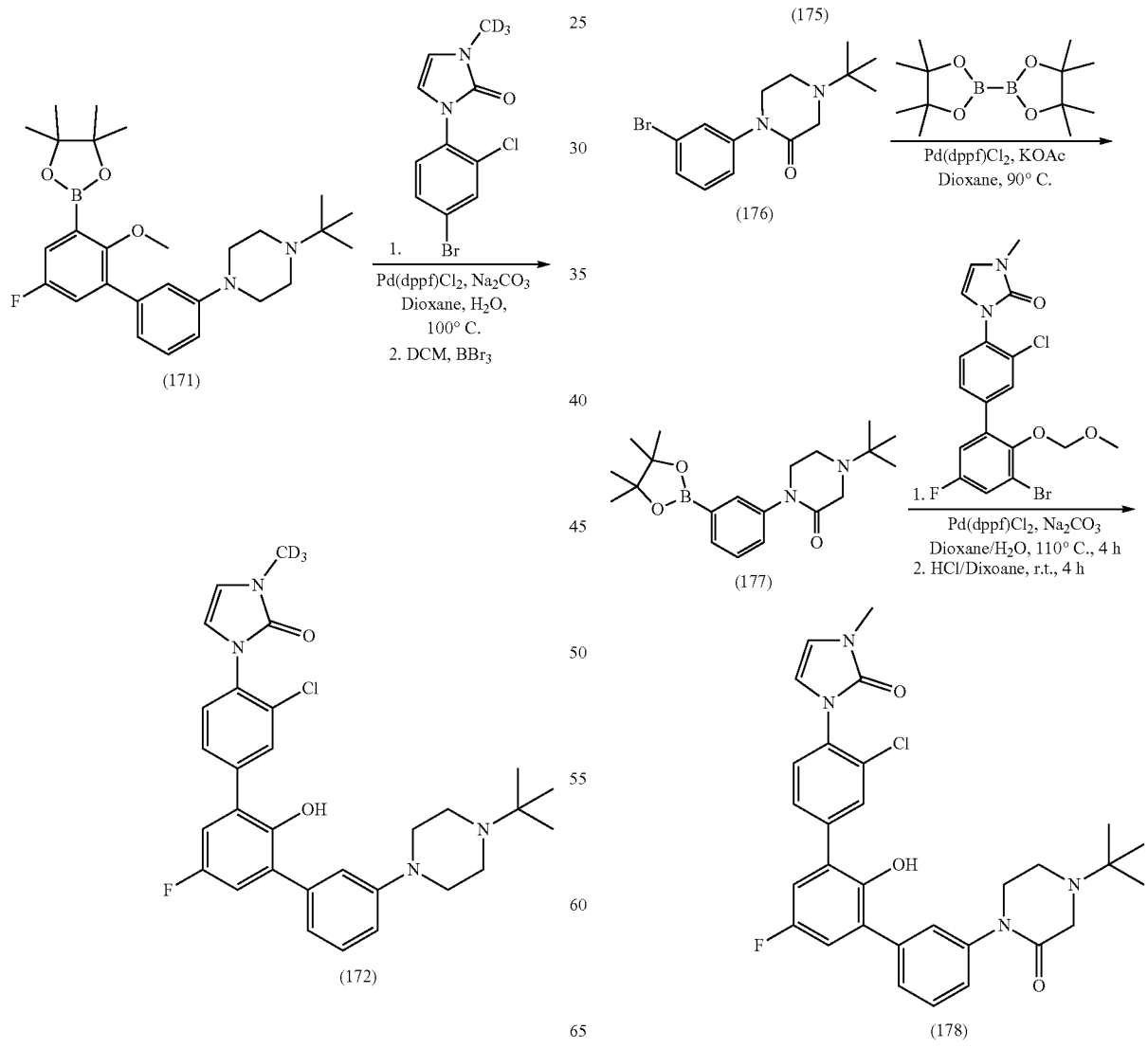

Scheme 35
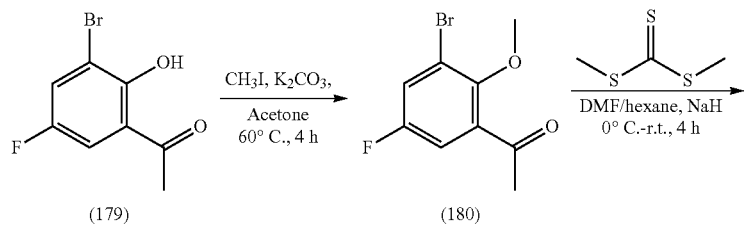
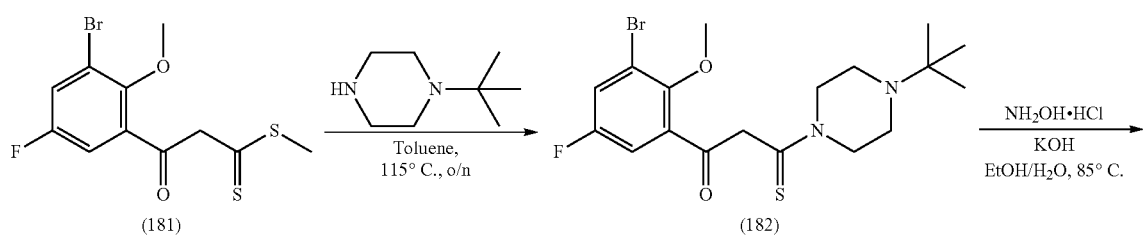
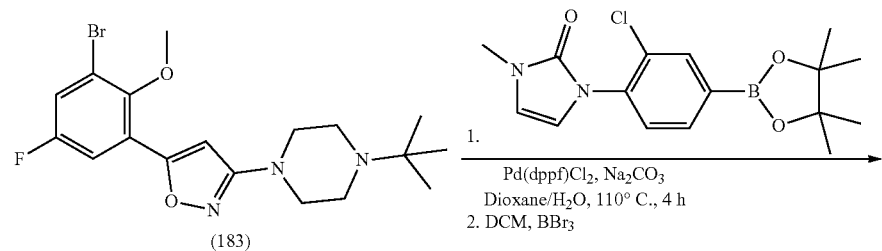
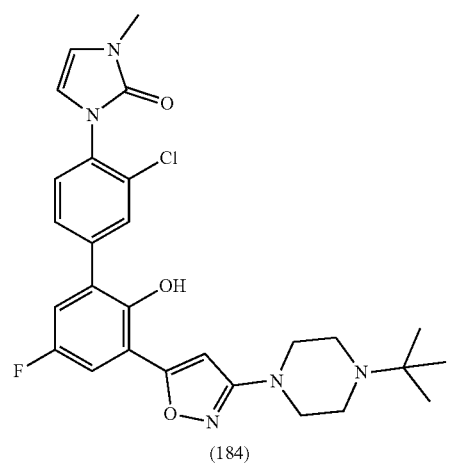

Scheme 36
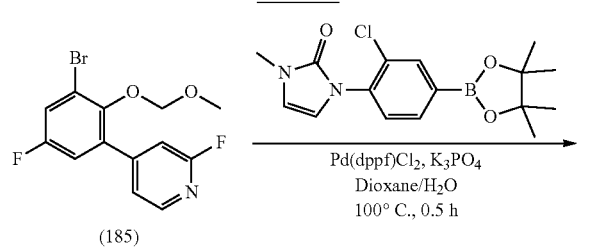
(185)
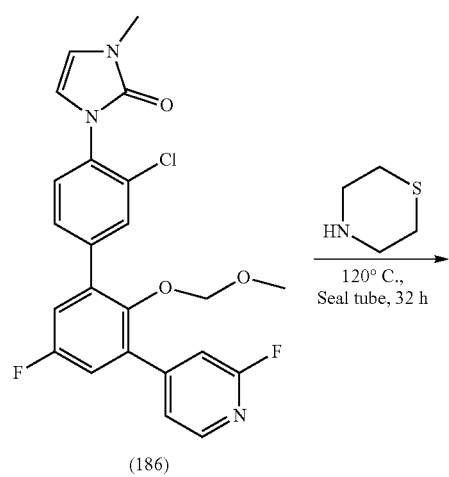
(186)
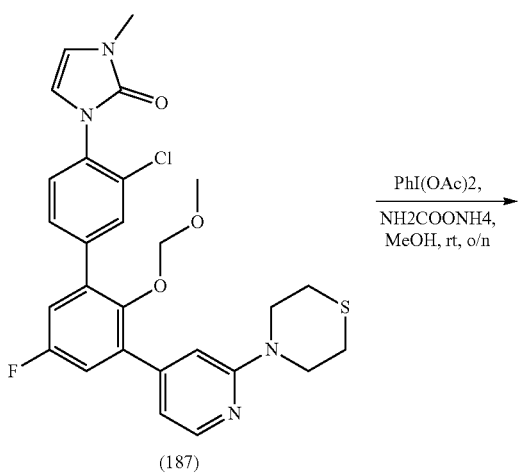
(187)
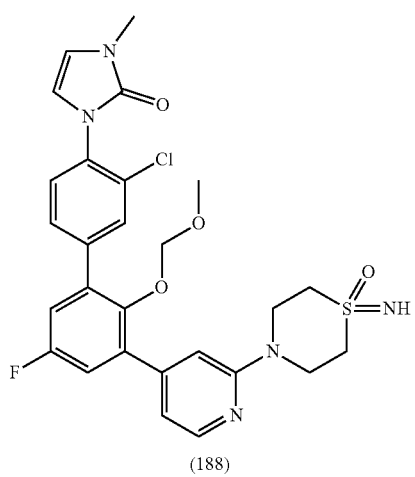
(188)
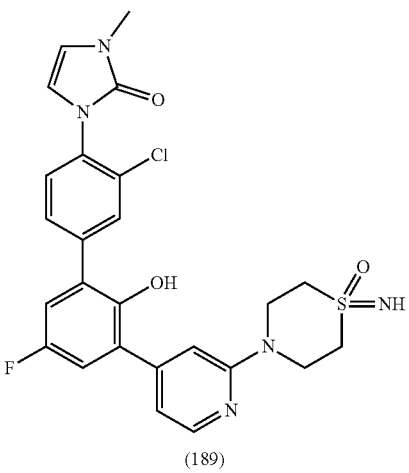 [SMILES: Cn1ccn(-c2ccc(-c3cc(F)cc(-c4ccnc(N5CCS(=N)(=O)CC5)c4)c3O)cc2Cl)c1=O]
(189)
Scheme 37
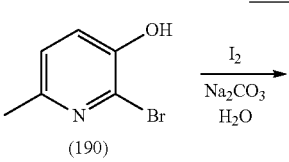
(190)
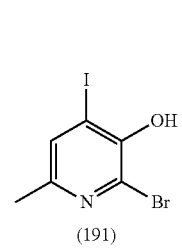
(191)
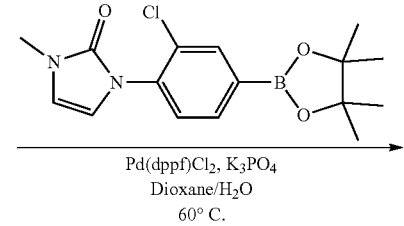
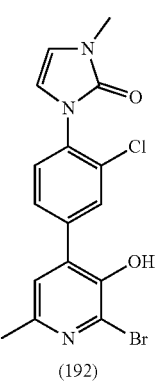
(192)
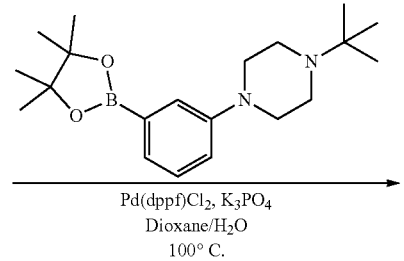

433
-continued
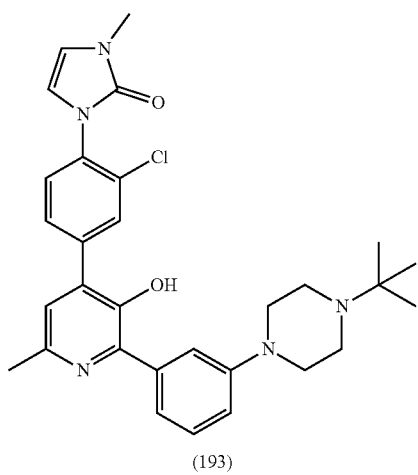
(193)
434
-continued
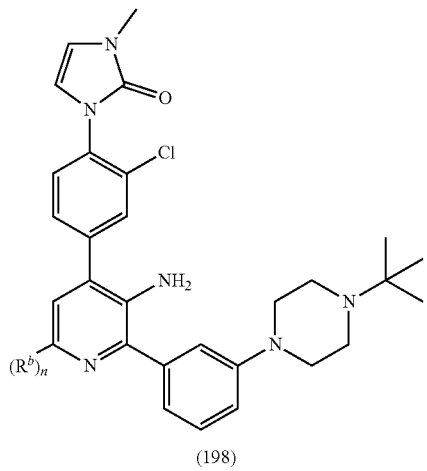
(198)
Scheme 38
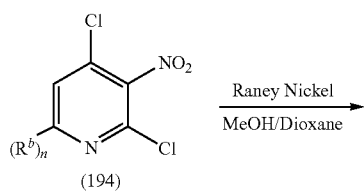
Scheme 39
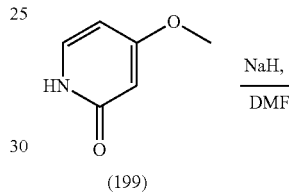
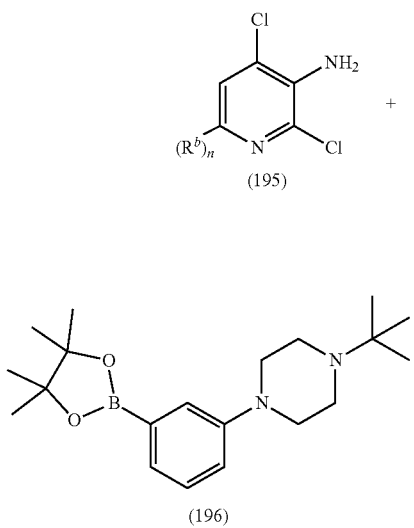
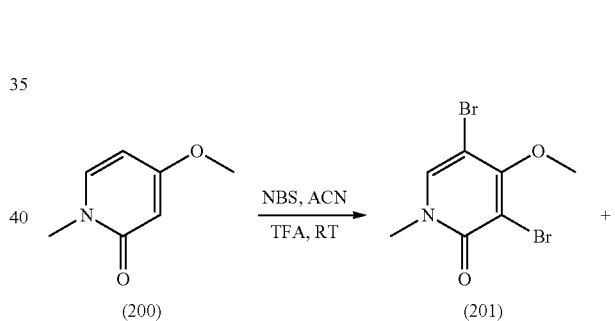
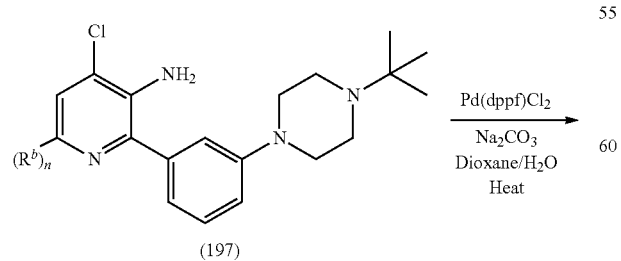
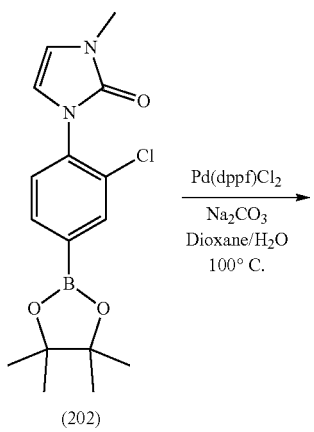

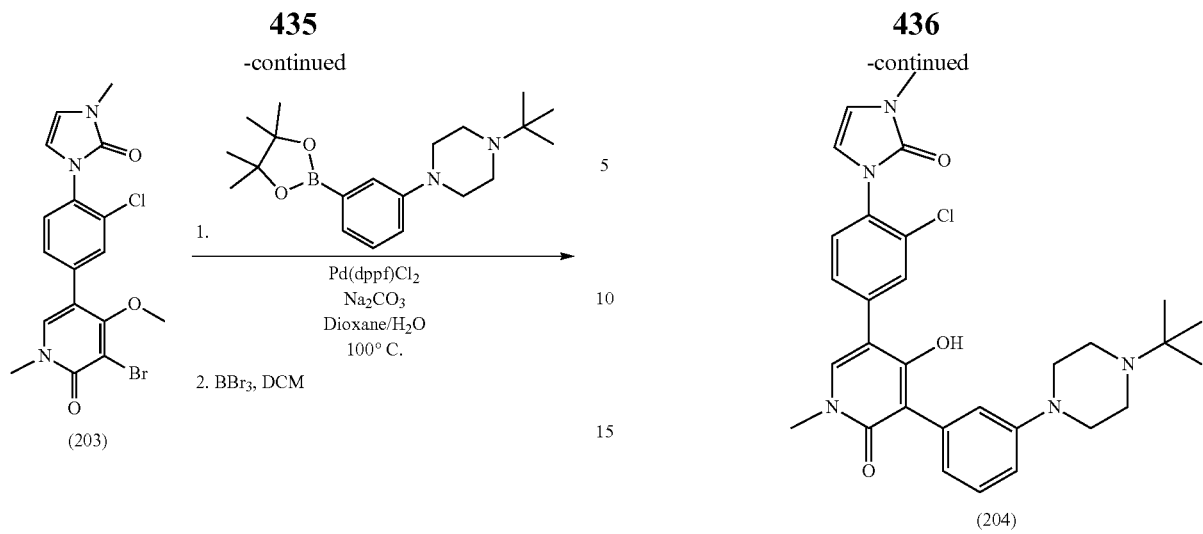
Scheme 40
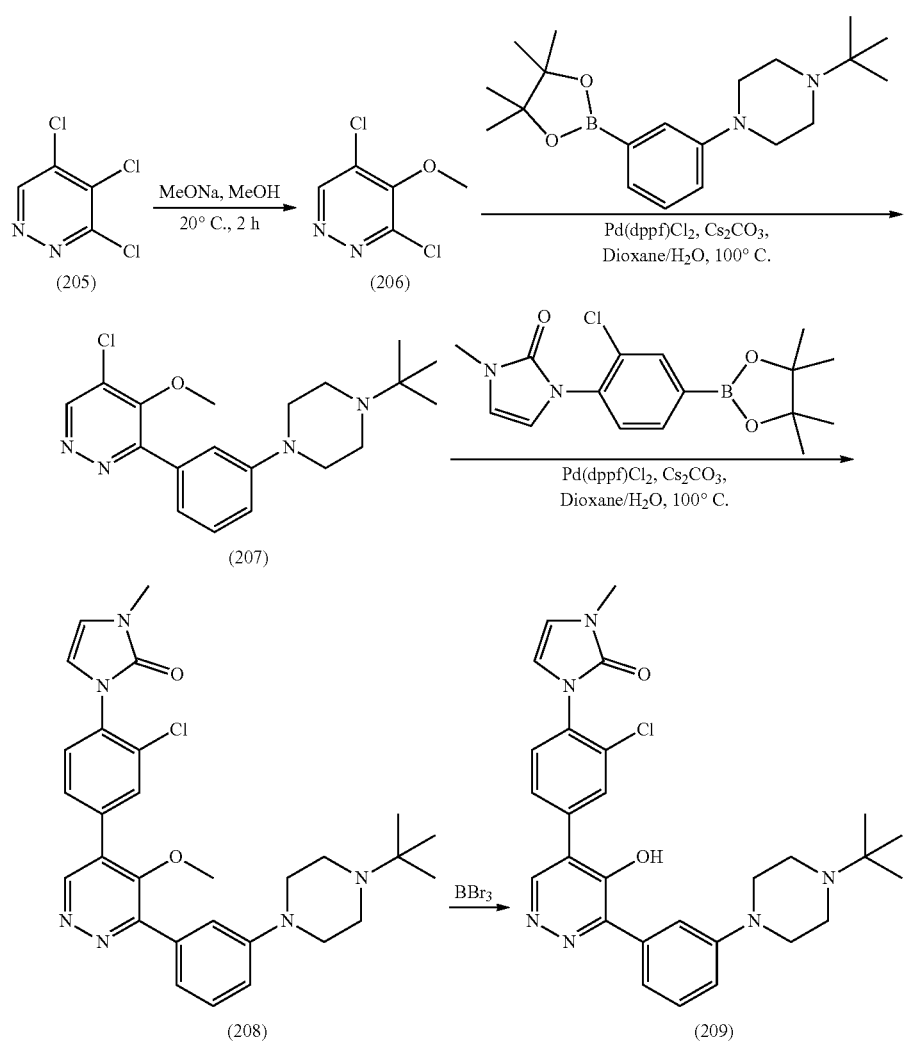

Scheme 41
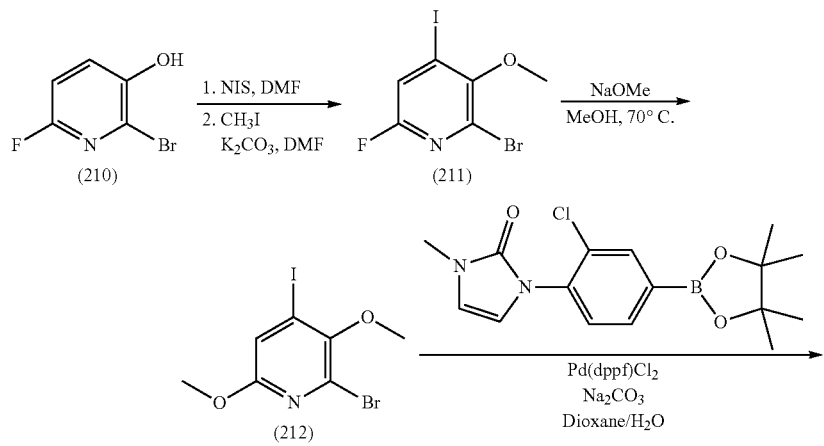
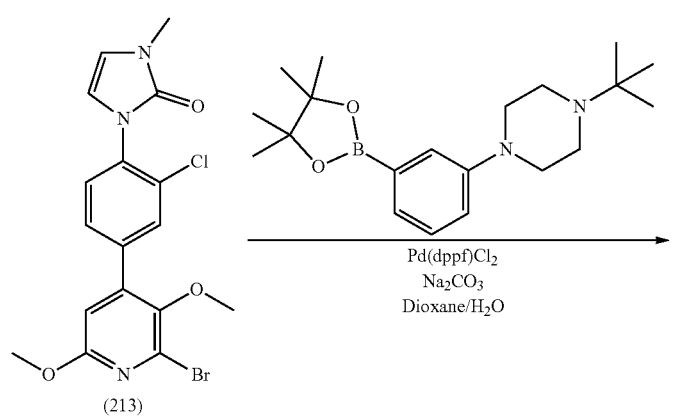
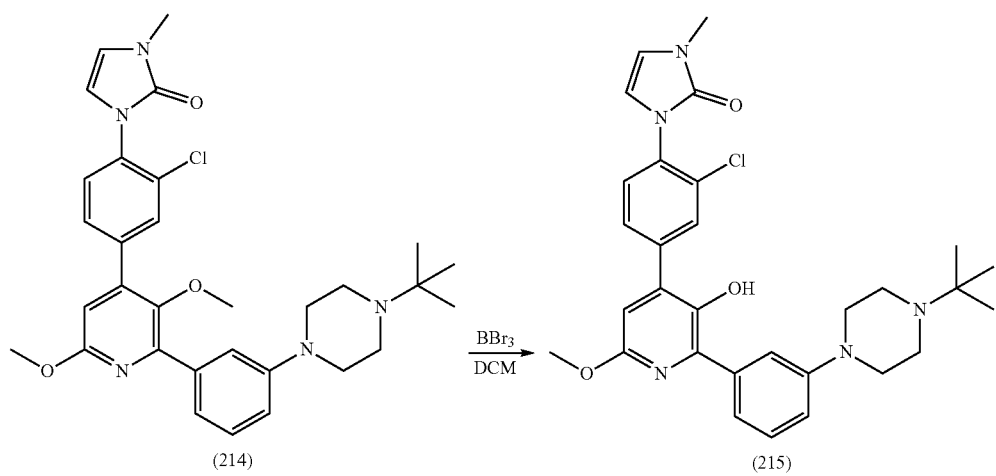

Scheme 42

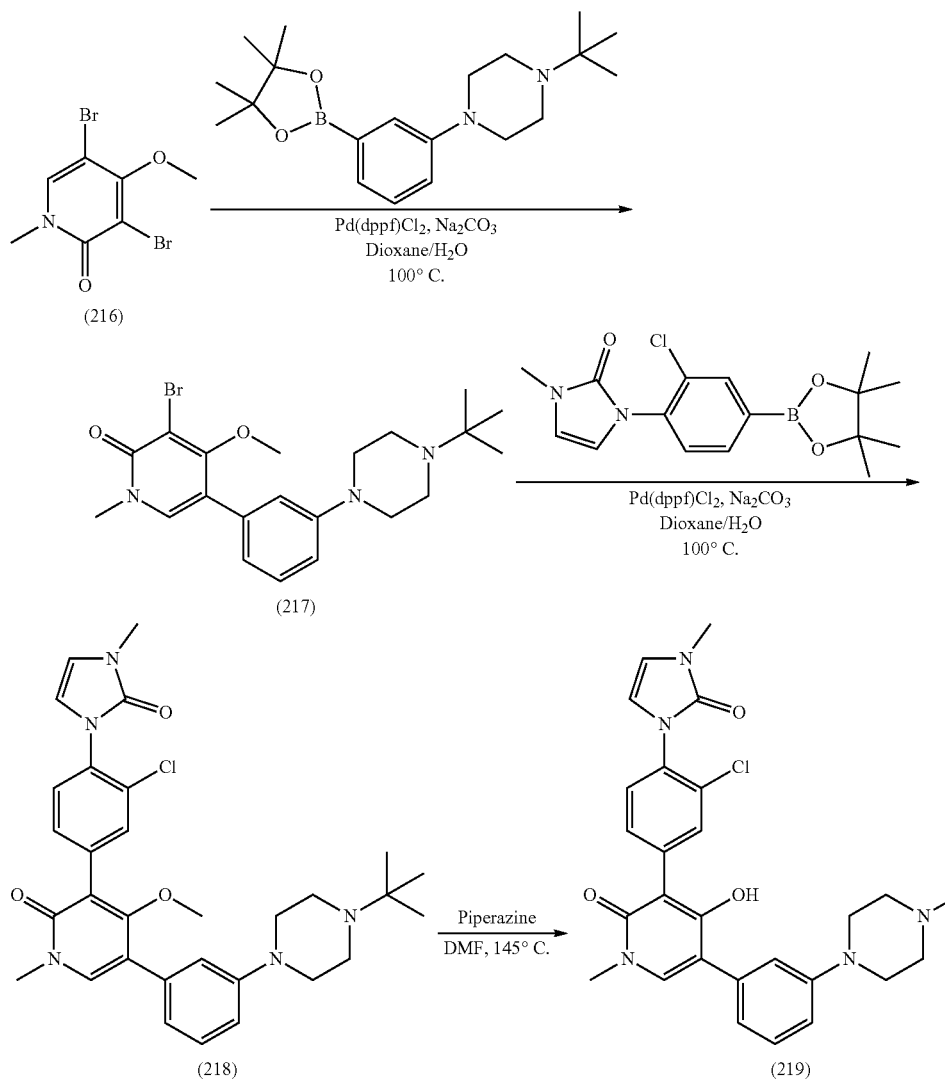

Abbreviations used in the preceding schemes or following examples, are listed in the Table below.

Table of Abbreviations.

| Abbreviation | Name |
|---|---|
| ACN or MeCN | acetonitrile |
| AcOH | glacial acetic acid |
| aq. | aqueous |
| conc. | concentrated |
| Cu(OAc)$_2$ | copper(II) acetate |
| DCM | dichloromethane |
| DIEA | diisopropyl-ethyl amine |
| DHP | 3,4-Dihydropyran |
| DMA | dimethylaniline |
| DMAP | 4-dimethylaminopyridine |
| DMF | N,N-dimethylformamide |
| DMSO | dimethylsulfoxide |
| Dppf or DPPF | 1,1'-Bis(diphenylphosphino)ferrocene |
| EtOAc or EA | ethyl acetate |
| EtOH | ethanol |
| h or hr(s) | hour or hours |

-continued

Table of Abbreviations.

| Abbreviation | Name |
|---|---|
| HPLC | high performance liquid chromatography |
| MeOH | methanol |
| MHz | megahertz |
| min | minute or minutes |
| LCMS | Liquid chromatography mass spectrometry |
| NBS | N-Bromosuccinimide |
| NIS | N-iodosuccinimide |
| NMR | nuclear magnetic resonance |
| Pd(PPh$_3$)$_4$ | tetrakis(triphenylphosphine)palladium |
| Pd(OAc)$_2$ | palladium (II) acetate |
| PE | petrolum ether |
| PPh$_3$ | triphenylphosphine |
| Pd(dppf)Cl$_2$ | 1,1'-bis(diphenylphosphino)ferrocene-palladium(II)dichloride |
| FCC | Flash column chromatography |
| rt or RT | room temperature |
| TBS | tert-Butyldimethylsilyl |
| TEA or Et$_3$N | triethylamine |
| TFA | trifluoroacetic acid |

-continued

| Table of Abbreviations. | |
|---|---|
| Abbreviation | Name |
| THF | tetrahydrofuran |
| TLC | thin layer chromatography |
| PTSA | p-Toluenesulfonic acid |

Example 1

4-(5-(4'-Acetamido-2-methoxy-[1,1'-biphenyl]-3-yl)isoxazol-3-yl)piperazine-1-carboxylate

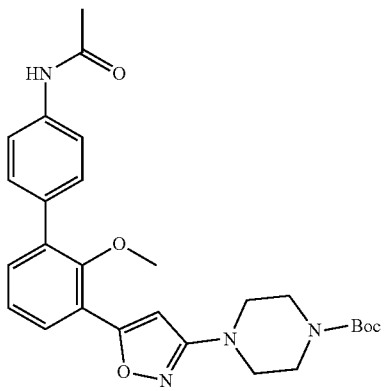 [SMILES: COc1c(-c2ccc(NC(C)=O)cc2)cccc1-c1cc(N2CCN(C(=O)OC(C)(C)C)CC2)no1]

Step 1: Methyl 3-(3-bromo-2-methoxyphenyl)-3-oxopropanedithioate

To a suspension of NaH (400 mg, 5.00 mmol, 60% suspension in mineral oil) in DMF/hexane (10:1, 11 mL) was added a solution of 1-(3-bromo-2-methoxyphenyl)ethanone (1.14 g, 5.00 mmol) in DMF/hexane (10:1, 1 mL) at rt under $N_2$. Then a solution of dimethyl carbonotrithioate (691.3 mg, 5.00 mmol) in DMF/hexane (10:1, 1 mL) was added to the above mixture. The reaction mixture was stirred at RT for 1 hour. The reaction mixture was quenched with 1 N aqueous HCl solution and extracted with DCM. The combined organic layer was dried over $Na_2SO_4$, filtered and concentrated. The residue was purified by chromatography on silica gel (PE/EA=8:1 to 6:1) to afford the title compound as a yellow solid (840 mg, 53% yield). LCMS: 318.9 $(M+H)^+$.

Step 2: tert-Butyl 4-(3-(3-bromo-2-methoxyphenyl)-3-oxopropanethioyl)piperazine-1-carboxylate A solution of methyl 3-(3-bromo-2-methoxyphenyl)-3-oxopropanedithioate (600 mg, 1.89 mmol), tert-butyl piperazine-1-carboxylate (386.9 mg, 2.08 mmol) in toluene (25 mL) was stirred at 115° C. for overnight under nitrogen atmosphere. After the reaction was complete by LCMS, the reaction mixture was cooled to RT and the solvent was removed under reduced pressure to afford the title compound as orange oil (864 mg, 100% yield). LCMS: 456.9 $(M+H)^+$.

Step 3: tert-butyl 4-(5-(3-bromo-2-methoxyphenyl)isoxazol-3-yl)piperazine-1-carboxylate A solution of tert-butyl 4-(3-(3-bromo-2-methoxyphenyl)-3-oxopropanethioyl)piperazine-1-carboxylate (775.2 mg, 1.70 mmol) and $NH_2OH$ (aq.) (prepared from 6.80 mmol of $NH_2OH \cdot HCl$ and 6.80 mmol of KOH in 4 mL of $H_2O$) in EtOH (40 mL) was stirred at 85° C. under nitrogen atmosphere overnight. After the reaction was complete by LCMS, the reaction mixture was cooled to RT and the solvent was removed under reduced pressure. The residue was washed with $H_2O$ and extracted with EA. The combined organic layer was dried over $Na_2SO_4$, filtered and concentrated. The residue was purified by chromatography on silica gel (DCM/MeOH=50:1 to PE/EA=6:1) to afford the title compound as a yellow solid (230.1 mg, 28% yield). LCMS: 437.9 $(M+H)^+$.

Step 4: tert-butyl 4-(5-(4'-acetamido-2-methoxy-[1,1'-biphenyl]-3-yl)isoxazol-3-yl)piperazine-1-carboxylate A solution of tert-butyl 4-(5-(3-bromo-2-methoxyphenyl)isoxazol-3-yl)piperazine-1-carboxylate (251.8 mg, 0.59 mmol), N-(4-(4,4,5,5-tetramethyl-1,3,2-dioxaborolan-2-yl)phenyl)acetamide (616.2 mg, 2.36 mmol), $K_3PO_4$ (375.7 mg, 1.77 mmol) and $Pd(dppf)Cl_2 \cdot DCM$ (87.8 mg, 0.2 mmol) in dioxane/water (4:1, 15 mL) was stirred at 110° C. for 20 hours in a microwave under nitrogen atmosphere. After the reaction was complete by LCMS, the reaction mixture was cooled to RT and the solvent was removed under reduced pressure. The residue was diluted with $H_2O$ and extracted with DCM. The combined organic layer was dried over $Na_2SO_4$, filtered and concentrated. The residue was purified by chromatography on silica gel (PE/EA=10:1 to PE/EA=2:1) to afford the title compound as a pale yellow solid (160.0 mg, 53% yield). $^1$H NMR (400 MHz, DMSO-$d_6$): δ 10.05 (s, 1H), 7.76-7.74 (m, 1H), 7.69 (d, J=8.4 Hz, 2H), 7.51 (d, J=8.4 Hz, 2H), 7.47-7.45 (m, 1H), 7.33 (t, J=7.6 Hz, 1H), 6.75 (s, 1H), 3.46-3.44 (m, 4H), 3.32 (s, 3H), 3.27-3.25 (m, 4H), 2.08 (s, 3H), 1.42 (s, 9H). LCMS: 493.2 $(M+H)^+$.

Example 2

N-(2'-Methoxy-3'-(3-(piperazin-1-yl)isoxazol-5-yl)-[1,1'-biphenyl]-4-yl)acetamide

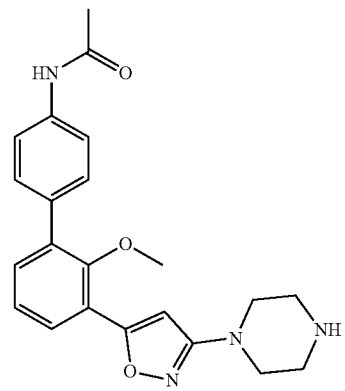 [SMILES: COc1c(-c2ccc(NC(C)=O)cc2)cccc1-c1cc(N2CCNCC2)no1]

A solution of tert-butyl 4-(5-(4'-acetamido-2-methoxy-[1,1'-biphenyl]-3-yl)isoxazol-3-yl)piperazine-1-carboxylate (15 mg, 0.03 mmol) in DCM (1 mL) and HCl in dioxane (4 M, 3 mL) was stirred at RT for 3 hours. After the reaction was complete by LCMS, the reaction mixture was concentrated. The residue was dissolved with $H_2O$ and lyophilized to afford the HCl salt of the title compound as a yellow solid (8.5 mg, 72% yield). ¹H NMR (400 MHz, DMSO-d₆): δ 10.12 (s, 1H), 9.16 (br s, 1H), 7.77-7.75 (m, 1H), 7.70 (d, J=8.8 Hz, 2H), 7.52-7.46 (m, 3H), 7.34 (t, J=8.0 Hz, 1H), 6.82 (s, 1H), 3.55-3.53 (m, 4H), 3.32 (s, 3H), 3.23-3.21 (m, 4H), 2.08 (s, 3H). LCMS: 393.2 (M+H)⁺.

Example 3

N-(2'-Hydroxy-3'-(3-(piperazin-1-yl)isoxazol-5-yl)-[1,1'-biphenyl]-4-yl)acetamide

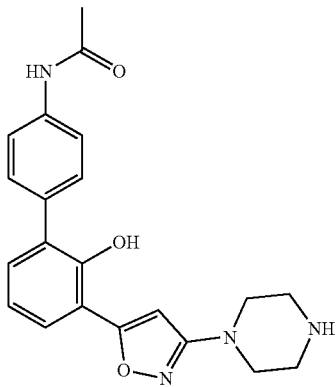 [SMILES: CC(=O)Nc1ccc(-c2cccc(-c3cc(N4CCNCC4)no3)c2O)cc1]

To a solution of tert-butyl 4-(5-(4'-acetamido-2-methoxy-[1,1'-biphenyl]-3-yl)isoxazol-3-yl)piperazine-1-carboxylate (50 mg, 0.10 mmol) in DCM (1 mL) was added BBr₃ (8 mL, 17% in DCM). The reaction mixture was stirred at 0° C.-5° C. under nitrogen atmosphere overnight. After the reaction was complete by LCMS, the reaction mixture was quenched with MeOH at 0° C. The mixture was concentrated, and the residue was purified by prep-HPLC (NH₄HCO₃) to afford the crude compound. The crude compound was dissolved in HCl/dioxane (4 M, 4 mL) and stirred at RT for 0.5 hour. Then, the reaction mixture was concentrated and lyophilized to afford the HCl salt of the title compound as an orange solid (21.3 mg, 29% yield). ¹H NMR (400 MHz, DMSO-d₆): δ 0.09 (s, 1H), 9.28 (br s, 1H), 9.20-9.16 (m, 2H), 7.68-7.64 (m, 3H), 7.43 (t, J=8.4 Hz, 2H), 7.31 (d, J=6.8 Hz, 1H), 7.08 (t, J=7.6 Hz, 1H), 6.74 (s, 1H), 3.54-3.42 (m, 4H), 3.30-3.21 (m, 4H), 2.07 (s, 3H). LCMS: 379.2 (M+H)⁺.

Example 5

N-(3'-(3-((2S,6R)-2,6-Dimethylmorpholino)isoxazol-5-yl)-2'-methoxy-[1,1'-biphenyl]-4-yl)acetamide

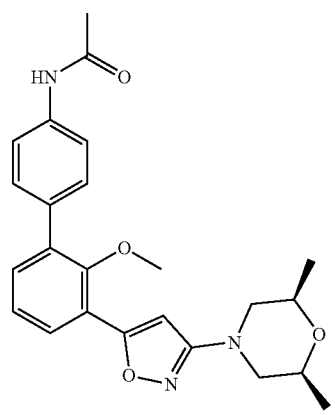 [SMILES: COc1c(-c2ccc(NC(C)=O)cc2)cccc1-c1cc(N2C[C@@H](C)O[C@@H](C)C2)no1]

The title compound was prepared following procedures described for Example 1, using methyl 3-(3-bromo-2-methoxyphenyl)-3-oxopropanedithioate and (2R,6S)-2,6-dimethylmorpholine to afford the title compound as a white solid (48.3 mg, 20% yield). ¹H NMR (400 MHz, DMSO-d₆): δ 10.07 (s, 1H), 7.76-7.74 (m, 1H), 7.69 (d, J=8.4 Hz, 2H), 7.51 (d, J=8.4 Hz, 2H), 7.47-7.45 (m, 1H), 7.33 (t, J=7.6 Hz, 1H), 6.77 (s, 1H), 3.71-3.63 (m, 4H), 3.31 (s, 3H), 2.50-2.46 (m, 2H), 2.07 (s, 3H), 1.14 (d, J=6.4 Hz, 6H). LCMS: 422.2 (M+H)⁺.

Example 6

N-(2'-Hydroxy-3'-(3-(4-methylpiperazin-1-yl)isoxazol-5-yl)-[1,1'-biphenyl]-4-yl)acetamide

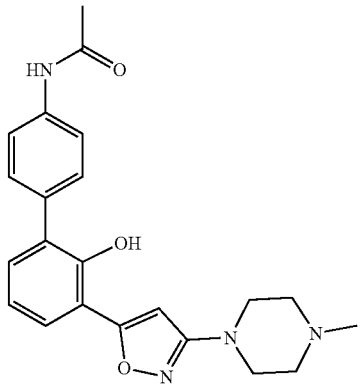 [SMILES: CC(=O)Nc1ccc(-c2cccc(-c3cc(N4CCN(C)CC4)no3)c2O)cc1]

A mixture of N-(2'-hydroxy-3'-(3-(piperazin-1-yl)isoxazol-5-yl)-[1,1'-biphenyl]-4-yl)acetamide hydrobromide (68.0 mg, 0.18 mmol), HCHO (5.4 mg, 0.18 mmol) and NaBH₃CN, (169.6 mg, 2.70 mmol) in MeOH (4 mL) was stirred at rt for 0.5 h. After the reaction was complete by LCMS, the reaction mixture was quenched with sat'd aqueous NaHCO₃ solution and extracted with DCM. The combined organic layer was dried over Na₂SO₄, filtered and concentrated. The residue was purified by prep-HPLC to afford the TFA salt of the title compound as a yellow solid (29.6 mg, 39% yield). This TFA salt was exchanged for HCl salt using HCl in dioxane to afford a yellow solid. ¹H NMR (400 MHz, DMSO-d₆): 10.04 (s, 1H), 9.18 (s, 1H), 7.68-7.65 (m, 3H), 7.44 (d, J=8.8 Hz, 2H), 7.32-7.30 (m, 1H), 7.08 (t, J=7.6 Hz, 1H), 6.76 (s, 1H), 3.88-3.61 (m, 4H), 3.35-3.18 (m, 4H), 2.86 (s, 3H), 2.07 (s, 3H). LCMS: 393.0 (M+H)⁺.

Example 7

N-(2'-Methoxy-3'-(3-(4-methylpiperazin-1-yl)isoxazol-5-yl)-[1,1'-biphenyl]-4-yl)acetamide

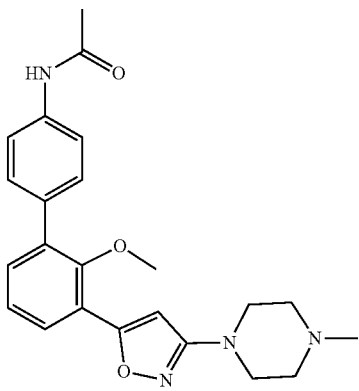 [SMILES: COc1c(-c2ccc(NC(C)=O)cc2)cccc1-c1cc(N2CCN(C)CC2)no1]

The title compound was prepared following procedures described for Example 6, using N-(2'-methoxy-3'-(3-(piperazin-1-yl)isoxazol-5-yl)-[1,1'-biphenyl]-4-yl)acetamide, HCHO, and NaBH$_3$CN affording the title compound as a white solid (3.7 mg, 5% yield). $^1$H NMR (400 MHz, DMSO-d$_6$): 10.08 (s, 1H), 9.86 (br s, 1H), 7.77-7.75 (m, 1H), 7.69 (d, J=8.8 Hz, 2H), 7.52-7.47 (m, 3H), 7.35 (t, J=7.6 Hz, 1H), 6.84 (s, 1H), 3.95-3.61 (m, 4H), 3.34-3.18 (m, 4H), 3.18 (s, 3H), 2.08 (s, 3H). LCMS: 407.0 (M+H)$^+$.

Example 8

N-(2'-Hydroxy-3'-(5-(piperazin-1-yl)isothiazol-3-yl)-[1,1'-biphenyl]-4-yl)acetamide

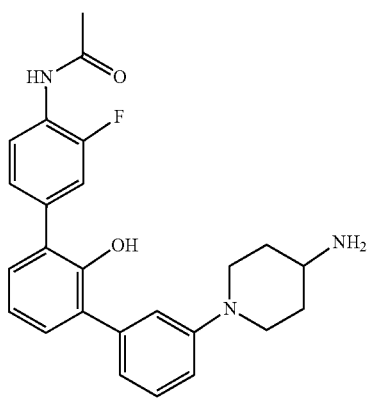 [SMILES: CC(=O)Nc1ccc(-c2cccc(-c3cccc(N4CCC(N)CC4)c3)c2O)cc1F]

Step 1: tert-butyl 4-(3-(3-bromo-2-methoxyphenyl)isothiazol-5-yl)piperazine-1-carboxylate To a solution of tert-butyl 4-(3-(3-bromo-2-methoxyphenyl)-3-oxopropanethioyl)piperazine-1-carboxylate (1.82 g, 4.00 mmol) in AcOH (10 mL) was added NH$_4$OAc (1.54 g, 20.00 mmol). The reaction mixture was stirred at 100° C. under nitrogen atmosphere for 16 hours. LCMS showed tert-butyl 4-(3-(3-bromo-2-methoxyphenyl)-3-oxopropanethioyl)piperazine-1-carboxylate was remained. Additional NH$_4$OAc (3.08 g, 40.0 mmol) was added. The reaction mixture was stirred at 100° C. under nitrogen atmosphere for 16 hours. After the reaction was complete by LCMS, the reaction mixture was concentrated and the residue was dissolved in H$_2$O (40 mL) and extracted with ethyl acetate (3×30 mL). The combined organic layers were dried over sodium sulfate, filtered and concentrated to afford a residue that was purified by silica gel chromatography using a mixture of 6:1 petroleum ether/ethyl acetate as the eluent to afford the title compound as a yellow solid (500 mg, 28% yield). LCMS: 456.1 (M+H)$^+$.

Step 2: 2-Bromo-6-(5-(piperazin-1-yl)isothiazol-3-yl)phenol

To a solution of tert-butyl 4-(3-(3-bromo-2-methoxyphenyl)isothiazol-5-yl)piperazine-1-carboxylate (400 mg, 0.88 mmol) in DCM (3 mL) was added BBr$_3$ (5 mL, 17% in DCM) at 0° C. The solution was stirred at room temperature under nitrogen atmosphere for 3 hours. After the reaction was complete by LCMS, the reaction mixture was quenched with MeOH (5 mL) at 0° C. The mixture was concentrated. The residue was adjusted pH to 8-10 with sat'd NaHCO$_3$ and extracted with DCM (3×20 mL). The combined organic layers were dried over sodium sulfate, filtered and concentrated to afford the title compound as a yellow solid (270 mg, 90% yield). LCMS: 340.0 (M+H)$^+$.

Step 3: N-(2'-Hydroxy-3'-(5-(piperazin-1-yl)isothiazol-3-yl)-[1,1'-biphenyl]-4-yl)acetamide The title compound was prepared following the procedure described for Example 1, Step 4, using 2-bromo-6-(5-(piperazin-1-yl)isothiazol-3-yl)phenol, N-(4-(4,4,5,5-tetramethyl-1,3,2-dioxaborolan-2-yl)phenyl) acetamide, K$_3$PO$_4$ and Pd(dppf)Cl$_2$·DCM to afford the crude product which was purified by prep-HPLC using acetonitrile in water in the presence of HCl to afford the title compound as HCl salt. $^1$H NMR (400 MHz, DMSO-d$_6$) (HCl salt): 12.42 (br s, 1H), 10.02 (s, 1H), 9.28 (br s, 2H), 7.84-7.81 (m, 1H), 7.62 (d, J=8.8 Hz, 2H), 7.51 (d, J=8.4 Hz, 2H), 7.35-7.31 (m, 1H), 7.18 (s, 1H), 7.06-6.98 (m, 1H), 3.61-3.59 (m, 4H), 3.33-3.31 (m, 4H), 2.07 (s, 3H). LCMS: 395.2 (M+H)$^+$.

Example 9

N-(2'-Hydroxy-3'-(3-(piperazin-1-yl)isoxazol-5-yl)-[1,1'-biphenyl]-4-yl)-N-methylacetamide

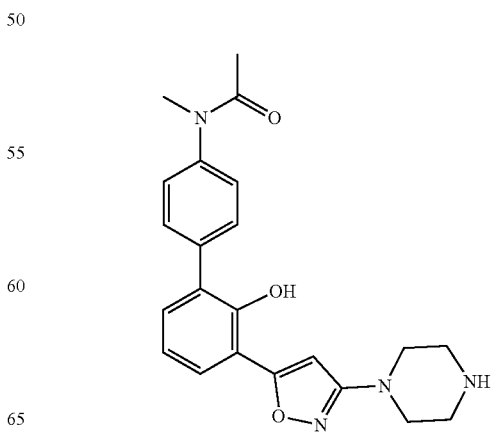

The title compound was prepared following procedures described for Example 1, Step 4, using 2-bromo-6-(3-(piperazin-1-yl)isoxazol-5-yl)phenol, N-methyl-N-(4-(4,4,5,5-tetramethyl-1,3,2-dioxaborolan-2-yl)phenyl)acetamide, K$_3$PO$_4$ and Pd(dppf)Cl$_2$·DCM to afford the crude product which was purified by prep-HPLC using acetonitrile in water in the presence of TFA to afford the title compound as TFA salt. $^1$H NMR (400 MHz, DMSO-d$_6$): 9.35 (s, 1H), 8.88 (br s, 2H), 7.71-7.69 (m, 1H), 7.58-7.56 (m, 2H), 7.42-7.26 (m, 3H), 7.13-7.09 (m, 1H), 6.76 (s, 1H), 3.50-3.47 (m, 8H), 3.24-3.20 (m, 3H), 1.86 (s, 3H). LCMS: 393.2 (M+H)$^+$.

Example 11

N,N'-(2'-hydroxy-[1,1':3',1''-terphenyl]-4,4''-diyl) diacetamide

The title compound was prepared following the procedures described for Example 1, Step 4 using 2,6-dibromophenol and N-(4-(4,4,5,5-tetramethyl-1,3,2-dioxaborolan-2-yl)phenyl)acetamide to afford the title compound. $^1$H NMR (400 MHz, DMSO-d$_6$): δ 9.99 (s, 2H), 8.16 (s, 1H), 7.62 (d, J=8.8 Hz, 4H), 7.45 (d, J=8.4 Hz, 4H), 7.15 (d, J=8.0 Hz, 2H), 6.99-6.96 (m, 1H), 2.06 (s, 6H). LCMS: 361.1 (M+H)$^+$.

Example 12

N-(2'-Hydroxy-[1,1':3',1''-terphenyl]-4-yl)acetamide

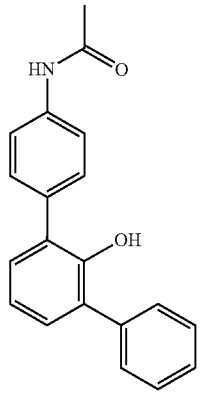 [SMILES: CC(=O)Nc1ccc(-c2cccc(-c3ccccc3)c2O)cc1]

Step 1: N-(3'-Bromo-2'-hydroxy-[1,1'-biphenyl]-4-yl)acetamide

A solution of 2-bromo-6-iodophenol (150.0 mg, 0.50 mmol), N-(4-(4,4,5,5-tetramethyl-1,3,2-dioxaborolan-2-yl)phenyl)acetamide (130.6 mg, 0.50 mmol), K$_3$PO$_4$ (318.3 mg, 1.50 mmol) and Pd(dppf)Cl$_2$·DCM (73.2 mg, 0.10 mmol) in dioxane:water (9:1, 5 mL) was stirred at rt for 2.5 hours under nitrogen atmosphere. After the reaction was complete by LCMS, the reaction mixture was used for the next step directly without further purification. LCMS: 306.0 (M+H)$^+$.

Step 2: N-(2'-Hydroxy-[1,1':3',1''-terphenyl]-4-yl) acetamide

To a solution of N-(3'-bromo-2'-hydroxy-[1,1'-biphenyl]-4-yl)acetamide (152.5 mg, 0.50 mmol) in dioxane:water (9:1, 5 mL) was added phenylboronic acid (122.0 mg, 1.00 mmol), K$_3$PO$_4$ (318.3 mg, 1.50 mmol) and Pd(dppf) Cl$_2$·DCM (73.2 mg, 0.10 mmol). The reaction mixture was stirred at 100° C. overnight under nitrogen atmosphere. The starting material was not completely reacted. Thus, 0.20 eq of Pd(dppf)$_2$Cl$_2$ and 3.00 eq of phenylboronic acid were added into the reaction mixture. The reaction mixture was continued heating to 110° C. for 10 hrs. The reaction mixture was cooled and concentrated. The residue was purified by chromatography on silica gel (PE to PE/EA=1:1) to afford the title compound (22.1 mg, 15% yield) as a white solid. $^1$H NMR (400 MHz, DMSO-d$_6$): δ 10.00 (s, 1H), 8.21 (s, 1H), 7.62 (d, J=7.2 Hz, 2H), 7.53 (d, J=6.8 Hz, 2H), 7.47-7.41 (m, 4H), 7.34 (d, J=6.4 Hz, 1H), 7.18 (s, 2H), 7.00 (t, J=6.8 Hz, 1H), 2.06 (s, 3H). LCMS: 304.2 (M+H)$^+$.

TABLE 1

Following compounds were prepared using N-(3'-bromo-2'-hydroxy-[1,1'-biphenyl]-4-yl)acetamide and a corresponding aryl or heteroaryl boronic ester or boronic acid as described for Example 12 (See preparation in Schemes 3-4).

| Ex. No. | Name/Structure | $^1$H NMR Data | LCMS (M + H)$^+$ |
|---|---|---|---|
| 13 | N-(2'-Hydroxy-3'-(1-methyl-1H-pyrazol-4-yl)-[1,1'-biphenyl]-4-yl)acetamide | $^1$H NMR (400 MHz, DMSO-d$_6$): δ 9.98 (s, 1H), 8.30 (s, 1H), 8.08 (s, 1H), 7.85 (s, 1H), 7.63 (d, J = 8.8 Hz, 2H), 7.45-7.42 (m, 3H), 7.04-7.02 (m, 1H), 6.95-6.93 (m, 1H), 3.87 (s, 3H), 2.06 (s, 3H) | 308.2 |
| 14 | N-(2'-Hydroxy-3'-(1-phenyl-1H-pyrazol-4-yl)-[1,1'-biphenyl]-4-yl)acetamide | $^1$H NMR (400 MHz, DMSO-d$_6$): δ 9.99 (s, 1H), 8.82 (s, 1H), 8.49 (s, 1H), 8.20 (s, 1H), 7.87 (d, J = 8.0 Hz, 2H), 7.64 (d, J = 8.8 Hz, 2H), 7.58-7.56 (m, 1H), 7.52-7.50 (m, 2H), 7.47-7.45 (m, 2H), 7.32 (t, J = 7.6 Hz, 1H), 7.13-7.11 (m, 1H), 7.00 (d, J = 7.6 Hz, 1H), 2.07 (s, 3H) | 370.2 |
| 15 | N-(2'-Hydroxy-3'-(1-(piperidin-4-yl)-1H-pyrazol-4-yl)-[1,1'-biphenyl]-4-yl)acetamide | $^1$H NMR (400 MHz, DMSO-d$_6$): δ 10.05 (s, 1H), 9.05 (br s, 1H), 8.83 (br s, 1H), 8.16 (s, 1H), 7.95 (s, 1H), 7.64 (d, J = 8.8 Hz, 2H), 7.49 (d, J = 2.0 Hz, 1H), 7.47-7.42 (m, 2H), 7.06-7.05 (m, 1H), 6.95 (t, J = 7.6 Hz, 1H), 4.58-4.54 (m, 1H), 3.42-3.39 (m, 2H), 3.09-3.03 (m, 2H), 2.22-2.16 (m, 4H), 2.07 (s, 3H) | 377.1 |

TABLE 1-continued

Following compounds were prepared using N-(3'-bromo-2'-hydroxy-[1,1'-biphenyl]-4-yl)acetamide and a corresponding aryl or heteroaryl boronic ester or boronic acid as described for Example 12 (See preparation in Schemes 3-4).

| Ex. No. | Name/Structure | $^1$H NMR Data | LCMS $(M + H)^+$ |
|---|---|---|---|
| 16 | N-(3'-(1-(4-Fluorophenyl)-1H-pyrazol-4-yl)-2'-hydroxy-[1,1'-biphenyl]-4-yl)acetamide | $^1$H NMR (400 MHz, DMSO-$d_6$): δ 9.99 (s, 1H), 8.81 (s, 1H), 8.48 (s, 1H), 8.20 (s, 1H), 7.93-7.89 (m, 2H), 7.64 (d, J = 8.8 Hz, 2H), 7.57-7.55 (m, 1H), 7.47-7.45 (m, 2H), 7.39-7.35 (m, 2H), 7.12 (d, J = 6.0 Hz, 1H), 7.11-6.99 (m, 1H), 2.07 (s, 3H) | 388.1 |
| 17 | N-(2'-Hydroxy-3'-(1-(1-methylpiperidin-4-yl)-1H-pyrazol-4-yl)-[1,1'-biphenyl]-4-yl)acetamide | $^1$H NMR (400 MHz, DMSO-$d_6$): δ 9.99 (s, 1H), 8.29 (s, 1H), 8.14 (s, 1H), 7.89 (s, 1H), 7.63 (d, J = 8.4 Hz, 2H), 7.46-7.42 (m, 3H), 7.05-7.03 (m, 1H), 6.96-6.92 (m, 1H), 4.20-4.12 (m, 1H), 2.90 (d, J = 11.2 Hz, 2H), 2.25 (s, 3H), 2.15-1.97 (m, 9H) | 391.2 |

Example 18

N-(3'-(4-(4-Fluorophenyl)-1H-imidazol-1-yl)-2'-hydroxy-[1,1'-biphenyl]-4-yl)acetamide

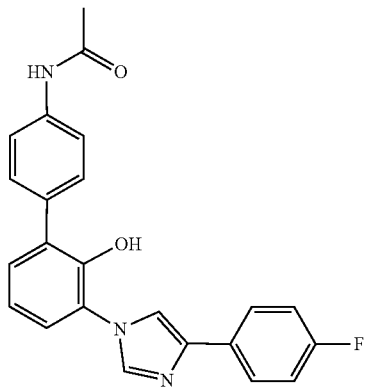 [SMILES: CC(=O)Nc1ccc(-c2cccc(-n3cnc(-c4ccc(F)cc4)c3)c2O)cc1]

A mixture of N-(3'-bromo-2'-hydroxy-[1,1'-biphenyl]-4-yl)acetamide (305 mg, 1.00 mmol), 4-(4-fluorophenyl)-1H-imidazole (324 mg, 2.20 mmol), L-proline (207 mg, 1.80 mmol), Cu$_2$O (129 mg, 0.9 mmol) and K$_2$CO$_3$ (276 mg, 2.0 mmol) in dioxane (10 mL) was heated at 105° C. for 4 days under nitrogen atmosphere. The reaction mixture was filtered, and the filtrate was concentrated under reduced pressure to afford a residue. The residue was purified by silica gel chromatography using petroleum ether/ethyl acetate/dichloromethane (1:1:1) and then using dichloromethane/methanol (20:1) to afford a crude product, which was further purified by prep-HPLC using acetonitrile in water in the presence of NH$_4$HCO$_3$ to afford the title compound (30.3 mg, 7% yield) as an off-white solid. $^1$H NMR (400 MHz, DMSO-d$_6$): 10.02 (s, 1H), 9.03 (s, 1H), 7.96-7.86 (m, 4H), 7.65 (d, J=8.4 Hz, 2H), 7.48 (d, J=8.4 Hz, 2H), 7.35-7.30 (m, 2H), 7.24-7.20 (m, 2H), 7.10-7.06 (m, 1H), 2.07 (s, 3H). LCMS: 388.1 (M+H)$^+$.

Example 19

N-(3-Ethoxy-2'-hydroxy-3'-(3-(piperazin-1-yl)isoxazol-5-yl)-[1,1'-biphenyl]-4-yl)acetamide 2,2,2-trifluoroacetate

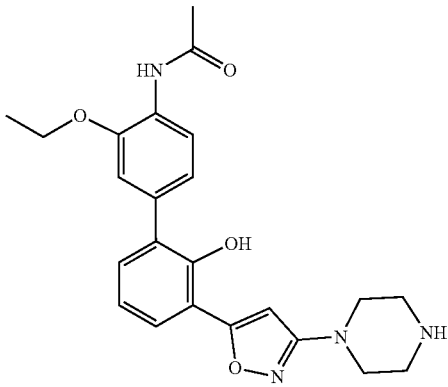 [SMILES: CCOc1cc(-c2cccc(-c3cc(N4CCNCC4)no3)c2O)ccc1NC(C)=O]

Step 1: 2-Bromo-6-(3-(piperazin-1-yl)isoxazol-5-yl)phenol

To a solution of tert-butyl 4-(5-(3-bromo-2-methoxyphenyl)isoxazol-3-yl)piperazine-1-carboxylate (50 mg, 0.11 mmol) in DCM (0.5 mL) was added BBr$_3$ (1 mL, 17% in DCM) at 0° C. The solution was stirred at room temperature under nitrogen atmosphere for 1 hour. After the reaction was complete by LCMS, the mixture was quenched with MeOH (1 mL) at 0° C. The mixture was concentrated to afford the title compound (37 mg, crude, 100% yield) as a gray solid. LCMS: 324.0 (M+H)$^+$.

Step 2: 4-Bromo-2-ethoxy-1-nitrobenzene

To a solution of 4-bromo-2-fluoro-1-nitrobenzene (2.0 g, 9.09 mmol) in EtOH (20 mL) was added EtONa (1.85 g, 27.27 mmol). The solution was stirred at room temperature for 2 hours under nitrogen atmosphere. After the reaction was complete by LCMS, the reaction mixture was concentrated. The residue was diluted with water (40 mL) and extracted with ethyl acetate (30 mL×3). The combined organic layers were washed with brine, dried over sodium sulfate, filtered, and concentrated to afford the title compound (2.28 g, crude, 100% yield) as a yellow solid. LCMS: 245.7 (M+H)$^+$.

Step 3: 4-Bromo-2-ethoxyaniline

To a mixture of 4-bromo-2-ethoxy-1-nitrobenzene (2.28 g, 9.27 mmol) in MeOH (45 mL) and H$_2$O (15 mL) was added Fe (5.19 g, 92.7 mmol) and NH$_4$Cl (4.96 g, 92.7 mmol). The reaction mixture was stirred at 50° C. for 3 hours. After the reaction was complete by LCMS, the reaction mixture was filtered and concentrated. The residue was diluted with water (50 mL) and extracted with ethyl acetate (40 mL×3). The combined organic layers were washed with brine, dried over sodium sulfate, filtered and concentrated to afford the title compound (1.75 g, crude, 88% yield) as brown oil. LCMS: 216.0 (M+H)$^+$.

Step 4: N-(4-Bromo-2-ethoxyphenyl)acetamide

To a solution of 4-bromo-2-ethoxyaniline (750 mg, 3.47 mmol) in THF (7 mL) was added acetic anhydride (0.5 mL) dropwise. The solution was stirred at room temperature for 2 hours under nitrogen atmosphere. After the reaction was indicated by LCMS, the reaction mixture was concentrated to afford the title compound (880 mg, 98% yield) as a grey solid.
LCMS: 258.0 (M+H)$^+$.

Step 5: N-(2-Ethoxy-4-(4,4,5,5-tetramethyl-1,3,2-dioxaborolan-2-yl)phenyl)acetamide A solution of N-(4-bromo-2-ethoxyphenyl)acetamide (516 mg, 2.00 mmol), 4,4,4',4',5,5,5',5'-octamethyl-2,2'-bi(1,3,2-dioxaborolane) (610 mg, 2.40 mmol). KOAc (589 mg, 6.01 mmol) and Pd(dppf)Cl$_2$·DCM (73 mg, 0.20 mmol) in dioxane (10 mL) was stirred at 90° C. for 2 hours under nitrogen atmosphere. After the reaction was complete by LCMS, the reaction mixture was cooled down to room temperature and filtered. The filtrate was concentrated to afford a residue that was purified by silica gel chromatography using petroleum ether and ethyl acetate (5:1) as the eluent to afford the title compound (550 mg, 90% yield) as a yellow solid.
LCMS: 306.2 (M+H)$^+$.

Step 6: N-(3-Ethoxy-2'-hydroxy-3'-(3-(piperazin-1-yl)isoxazol-5-yl)-[1,1'-biphenyl]-4-yl)acetamide 2,2,2-trifluoroacetate A mixture of 2-bromo-6-(3-(piperazin-1-yl)isoxazol-5-yl)phenol (37 mg, 0.11 mmol), N-(2-ethoxy-4-(4,4,5,5-tetramethyl-1,3,2-dioxaborolan-2-yl)phenyl)acetamide (139 mg, 0.45 mmol), $K_3PO_4$ (94 mg, 0.45 mmol) and Pd(dppf)Cl$_2$·DCM (16 mg, 0.022 mmol) in dioxane:water (8:1, 6 mL) was stirred at 110° C. for 2 hours under nitrogen atmosphere. After the reaction was indicated by LCMS, the reaction mixture was removed the solvent under reduced pressure. The residue was purified by silica gel chromatography using DCM/MeOH (10:1) to afford the crude product. The crude product was purified by prep-HPLC using acetonitrile in water in the presence of TFA to afford the title compound (9.3 mg, 16% yield) as pale-yellow oil. $^1$H NMR (400 MHz, DMSO-d$_6$) (TFA salt): δ (s, 1H), 9.04 (s, 1H), 8.82 (br s, 2H), 8.03 (d, J=8.4 Hz, 1H), 7.68-7.66 (m, 1H), 7.36-7.34 (m, 1H), 7.13 (s, 1H), 7.08 (t, J=8.0 Hz, 1H), 7.03-7.01 (m, 1H), 6.74 (s, 1H), 4.14 (q, J=6.8 Hz, 2H), 3.50-3.47 (m, 4H), 3.26-3.20 (m, 4H), 2.13 (s, 3H), 1.40 (t, J=6.8 Hz, 3H). LCMS: 423.2 (M+H)$^+$.

TABLE 2

Following compounds were prepared using 2-bromo-6-(3-(piperazin-1-yl)isoxazol-5-yl)phenol or tert-butyl 4-(5-(3-bromo-2-methoxyphenyl)isoxazol-3-yl)piperazine-1-carboxylate and a corresponding aryl boronic ester or aryl boronic acid as described for Example 19 (See preparation in Schemes 1-5).

| Ex. No. | Name/Structure | $^1$H NMR Data | LCMS (M + H)$^+$ |
|---|---|---|---|
| 20 | N-(2'-Hydroxy-3-isopropoxy-3'-(3-(piperazin-1-yl)isoxazol-5-yl)-[1,1'-biphenyl]-4-yl)acetamide | $^1$H NMR (400 MHz, DMSO-d$_6$): δ 8.89 (s, 1H), 8.02 (d, J = 8.4 Hz, 1H), 7.63 (d, J = 8.0 Hz, 1H), 7.31 (d, J = 7.2 Hz, 1H), 7.17 (s, 1H), 7.01 (d, J = 7.2 Hz, 2H), 6.65 (s, 1H), 4.67-4.61 (m, 1H), 3.20-3.14 (m, 4H), 2.80-2.78 (m, 4H), 2.13 (s, 3H), 1.33 (d, J = 6.0 Hz, 6H) | 437.2 |
| 21 | N-(2'-Hydroxy-3-methyl-3'-(3-(piperazin-1-yl)isoxazol-5-yl)-[1,1'-biphenyl]-4-yl)acetamide hydrochloride | $^1$H NMR (400 MHz, DMSO-d$_6$): δ 9.99 (s, 2H), 9.29 (br s, 2H), 7.66 (d, J = 6.8 Hz, 1H), 7.51 (d, J = 8.4 Hz, 1H), 7.35-7.27 (m, 3H), 7.08 (t, J = 7.6 Hz, 1H), 6.75 (s, 1H), 3.53-3.50 (m, 4H), 3.23-2.19 (m, 4H), 2.26 (s, 3H), 2.09 (s, 3H) | 393.2 |

TABLE 2-continued

Following compounds were prepared using 2-bromo-6-(3-(piperazin-1-yl)isoxazol-5-yl)phenol or tert-butyl 4-(5-(3-bromo-2-methoxyphenyl)isoxazol-3-yl)piperazine-1-carboxylate and a corresponding aryl boronic ester or aryl boronic acid as described for Example 19 (See preparation in Schemes 1-5).

| Ex. No. | Name/Structure | $^1$H NMR Data | LCMS (M + H)$^+$ |
|---|---|---|---|
| 22 | N-(3-Ethyl-2'-hydroxy-3'-(3-(piperazin-1-yl)isoxazol-5-yl)-[1,1'-biphenyl]-4-yl)acetamide 2,2,2-trifluoroacetate | $^1$H NMR (400 MHz, DMSO-d$_6$): δ 9.32 (s, 1H), 9.26 (s, 1H), 8.78 (br s, 2H), 7.68-7.48 (m, 1H), 7.46-7.36 (m, 1H), 7.34-7.30 (m, 2H), 7.08 (t, J = 7.6 Hz, 1H), 6.74 (s, 1H), 3.50-3.40 (m, 4H), 3.08-3.03 (m, 4H), 2.67-2.62 (m, 2H), 2.13 (s, 3H), 1.12 (t, J = 7.3 Hz, 3H) | 407.2 |
| 23 | N-(2'-Hydroxy-3-methoxy-3'-(3-(piperazin-1-yl)isoxazol-5-yl)-[1,1'-biphenyl]-4-yl)acetamide 2,2,2-trifluoroacetate | $^1$H NMR (400 MHz, DMSO-d$_6$): δ 9.22 (s, 1H), 8.94 (s, 1H), 8.83 (s, 2H), 8.03-8.01 (m, 1H), 7.54-7.51 (m, 1H), 7.29 (s, 1H), 7.11 (br s, 2H), 7.00 (d, J = 7.2 Hz, 2H), 3.87 (s, 3H), 3.83-3.72 (m, 8H), 2.11 (s, 3H) | 409.2 |
| 24 | N-(3-cyclobutoxy-2'-hydroxy-3'-(3-(piperazin-1-yl)isoxazol-5-yl)-[1,1'-biphenyl]-4-yl)acetamide 2,2,2-trifluoroacetate | $^1$H NMR (400 MHz, DMSO-d$_6$): δ 9.22 (s, 1H), 9.05 (s, 1H), 8.81 (br s, 2H), 8.04 (d, J = 8.0 Hz, 1H), 7.66 (dd, J = 8.0, 1.6 Hz, 1H), 7.33 (dd, J = 7.6, 1.6 Hz, 1H), 7.08 (t, J = 7.6 Hz, 1H), 7.04-7.00 (m, 1H), 6.97 (s, 1H), 6.73 (s, 1H), 4.81-4.77 (m, 1H), 3.50-3.43 (m, 4H), 3.24 (br s, 4H), 2.44-2.40 (m, 2H), 2.21-2.16 (m, 2H), 2.13 (s, 3H), 1.81-1.79 (m, 1H), 1.65-1.63 (m, 1H) | 449.2 |

TABLE 2-continued

Following compounds were prepared using 2-bromo-6-(3-(piperazin-1-yl)isoxazol-5-yl)phenol or tert-butyl 4-(5-(3-bromo-2-methoxyphenyl)isoxazol-3-yl)piperazine-1-carboxylate and a corresponding aryl boronic ester or aryl boronic acid as described for Example 19 (See preparation in Schemes 1-5).

| Ex. No. | Name/Structure | $^1$H NMR Data | LCMS $(M + H)^+$ |
|---|---|---|---|
| 25 | N-(2'-hydroxy-3'-(3-(piperazin-1-yl)isoxazol-5-yl)-3-(trifluoromethoxy)-[1,1'-biphenyl]-4-yl)acetamide | $^1$H NMR (400 MHz, DMSO-$d_6$): δ 9.82 (s, 1H), 9.46 (br s, 1H), 8.82 (br s, 2H), 7.99 (d, J = 8.8 Hz, 1H), 7.70 (d, J = 8.0 Hz, 1H), 7.49 (d, J = 7.6 Hz, 2H), 7.38 (d, J = 7.6 Hz, 1H), 7.12 (t, J = 7.6 Hz, 1H), 3.49-3.47 (m, 4H), 3.25-3.23 (m, 4H), 2.13 (s, 3H) | 463.2 |
| 26 | N-(3-(Difluoromethoxy)-2'-hydroxy-3'-(3-(piperazin-1-yl)isoxazol-5-yl)-[1,1'-biphenyl]-4-yl)acetamide 2,2,2-trifluoroacetate | $^1$H NMR (400 MHz, DMSO-$d_6$): δ 9.55 (s, 1H), 9.08 (s, 1H), 8.97 (br s, 2H), 7.94 (d, J = 8.0 Hz, 1H), 7.56-7.54 (m, 1H), 7.35-7.33, (m, 2H), 7.28 (d, J = 6.4 Hz, 1H), 7.16-7.13 (m, 2H), 7.06-6.98 (m, 1H), 3.73-3.71 (m, 4H), 3.26-3.25 (m, 4H), 2.15 (s, 3H) | 445.1 |
| 27 | N-(2'-Hydroxy-3-isopropyl-3'-(3-(piperazin-1-yl)isoxazol-5-yl)-[1,1'-biphenyl]-4-yl)acetamide 2,2,2-trifluoroacetate | $^1$H NMR (400 MHz, DMSO-$d_6$): δ 9.99 (s, 1H), 9.31 (s, 1H), 8.77 (br s, 1H), 7.69-7.66 (m, 1H), 7.43 (d, J = 1.2 Hz, 1H), 7.37-7.29 (m, 3H), 7.09 (t, J = 8.0 Hz, 1H), 6.75 (s, 1H), 3.50-3.47 (m, 4H), 3.23-3.20 (m, 5H), 2.08 (s, 3H), 1.18 (d, J = 6.8 Hz, 6H) | 421.3 |

TABLE 2-continued

Following compounds were prepared using 2-bromo-6-(3-(piperazin-1-yl)isoxazol-5-yl)phenol or tert-butyl 4-(5-(3-bromo-2-methoxyphenyl)isoxazol-3-yl)piperazine-1-carboxylate and a corresponding aryl boronic ester or aryl boronic acid as described for Example 19 (See preparation in Schemes 1-5).

| Ex. No. | Name/Structure | $^1$H NMR Data | LCMS (M + H)$^+$ |
|---|---|---|---|
| 28 | N-(3-(2-Oxaspiro[3.3]heptan-6-yloxy)-2'-hydroxy-3'-(3-(piperazin-1-yl)isoxazol-5-yl)-[1,1'-biphenyl]-4-yl)acetamide 2,2,2-trifluoroacetate | $^1$H NMR (400 MHz, DMSO-$d_6$): δ 9.22 (s, 1H), 9.03 (s, 1H), 8.85 (br s, 1H), 8.03 (d, J = 8.0 Hz, 1H), 7.68-7.66 (m, 1H), 7.34-7.32 (m, 1H), 7.08 (t, J = 8.0 Hz, 1H), 7.03-7.00 (m, 1H), 6.94 (s, 1H), 6.73 (t, J = 4.0 Hz, 1H), 4.70-4.67 (m, 1H), 4.62 (s, 2H), 4.56 (s, 2H), 3.50-3.45 (m, 4H), 3.35-3.21 (m, 4H), 2.82-2.77 (m, 2H), 2.39-2.34 (m, 2H), 2.12 (s, 3H) | 491.2 |

Example 29

5-Acetyl-8-(2-hydroxy-3-(3-(piperazin-1-yl)isoxazol-5-yl)phenyl)-4,5-dihydro-1H-benzo[b][1,4]diazepin-2(3H)-one 2,2,2-trifluoroacetate

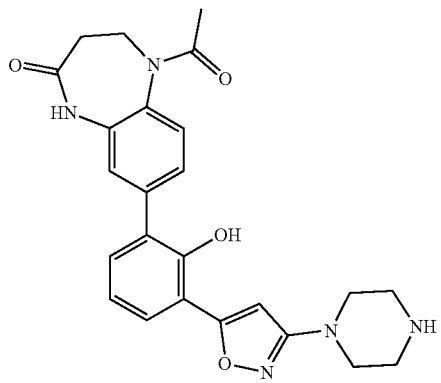 [SMILES: CC(=O)N1CCC(=O)Nc2cc(-c3cccc(-c4cc(N5CCNCC5)no4)c3O)ccc21]

Step 1: 5-Acetyl-8-(4,4,5,5-tetramethyl-1,3,2-dioxaborolan-2-yl)-4,5-dihydro-1H-benzo[b][1,4]diazepin-2(3H)-one A solution of 5-acetyl-8-bromo-4,5-dihydro-1H-benzo[b][1,4]diazepin-2(3H)-one (500 mg, 1.77 mmol), 4,4,4',4',5,5,5',5'-octamethyl-2,2'-bi(1,3,2-dioxaborolane) (675.5 mg, 2.66 mmol), KOAc (521 mg, 5.3 mmol) and PdCl$_2$ (124 mg, 0.17 mmol) in dioxane (12 mL) was stirred at 85° C. under nitrogen atmosphere for 16 hours. After the reaction was complete by LCMS, the reaction mixture was cooled and diluted with EA and filtered. The filtrated was concentrated. The residue was purified by silica gel chromatography using petroleum ether and ethyl acetate (10:1) as the eluent to afford the title compound (525.6 mg, 90% yield) as a white solid. LCMS: 331.1 (M+H)$^+$.

Step 2: Tert-butyl 4-(5-(3-(1-acetyl-4-oxo-2,3,4,5-tetrahydro-1H-benzo[b][1,4]diazepin-7-yl)-2-methoxyphenyl)isoxazol-3-yl)piperazine-1-carboxylate A solution of tert-butyl 4-(5-(3-bromo-2-methoxyphenyl)isoxazol-3-yl)piperazine-1-carboxylate (224.7 mg, 0.437 mmol, 85% purity), 5-acetyl-8-(4,4,5,5-tetramethyl-1,3,2-dioxaborolan-2-yl)-4,5-dihydro-1H-benzo[b][1,4]diazepin-2(3H)-one (360.2 mg, 1.09 mmol), K$_3$PO$_4$ (278.8 mg, 1.31 mmol) and Pd(dppf)Cl$_2$ (79.8 mg, 0.109 mmol) in dioxane:water (10:1, 9.9 mL) was stirred at 105° C. under nitrogen atmosphere for 2.5 hours. After the reaction was complete by LCMS, the reaction mixture was cooled and concentrated. The residue was purified by silica gel chromatography using petroleum ether, ethyl acetate and dichloromethane (1:1:1) as the eluent to afford the title compound (190 mg, 77% yield) as a yellow solid. LCMS: 562.3 (M+H)$^+$.

Step 3: 5-Acetyl-8-(2-hydroxy-3-(3-(piperazin-1-yl)isoxazol-5-yl)phenyl)-4,5-dihydro-1H-benzo[b][1,4]diazepin-2(3H)-one 2,2,2-trifluoroacetate A solution of tert-butyl 4-(5-(3-(1-acetyl-4-oxo-2,3,4,5-tetrahydro-1H-benzo[b][1,4]diazepin-7-yl)-2-methoxyphenyl)isoxazol-3-yl)piperazine-1-carboxylate (110 mg, 0.196 mmol) in DCM (0.5 mL) was added BBr$_3$ (4.5 mL, 17% in DCM) dropwise at 0° C., then it was stirred at room temperature under nitrogen atmosphere for 8 hours. The reaction mixture was quenched with H$_2$O (5 mL) and was added Na$_2$CO$_3$ (530 mg, 5.00 mmol) at 0° C. After stirring at 0° C. for 1 hour, the reaction mixture was extracted with DCM:MeOH (5 mL×10, 10:1). The combined organic layers dried over sodium sulfate, filtered and concentrated to afford a residue that was purified by prep-HPLC using acetonitrile in water in the presence of TFA to afford the title compound (17.1 mg, 16% yield) as a white solid. ¹H NMR (400 MHz, DMSO-d₆): δ 9.85 (s, 1H), 9.43 (s, 1H), 8.83 (br s, 2H), 7.72 (dd, J=8.0, 1.6 Hz, 1H), 7.45 (J=8.4 Hz, 1H), 7.36 (dd, J=9.2, 1.2 Hz, 1H), 7.32-7.30 (m, 1H), 7.23 (d, J=1.6 Hz, 1H), 7.11 (t, J=7.6 Hz, 1H), 6.77 (s, 1H), 4.75-4.67 (m, 1H), 3.50-3.47 (m, 4H), 3.24 (s, 5H), 2.72 (br s, 1H), 2.33 (s, 1H), 1.78 (s, 3H). LCMS: 448.2 (M+H)⁺.

TABLE 3

Following compounds were prepared using 2-bromo-6-(3-(piperazin-1-yl)isoxazol-5-yl)phenol or tert-butyl 4-(5-(3-bromo-2-methoxyphenyl)isoxazol-3-yl)piperazine-1-carboxylate and a corresponding aryl boronic ester or aryl boronic acid as described for Examples 19 and 29 (See preparation in Schemes 1-5).

| Ex. No. | Name/Structure | ¹H NMR Data | LCMS (M + H)⁺ |
|---|---|---|---|
| 30 | N-(2-Fluoro-2'-hydroxy-3'-(3-(piperazin-1-yl)isoxazol-5-yl)-[1,1'-biphenyl]-4-yl)acetamide 2,2,2-trifluoroacetate | ¹H NMR (400 MHz, DMSO-d₆): δ 10.23 (s, 1H), 9.31 (s, 1H), 8.83 (br s, 2H), 7.73-7.70 (m, 1H), 7.68-7.65 (m, 1H), 7.37-7.24 (m, 3H), 7.06 (t, J = 8.0 Hz, 1H), 6.73 (s, 1H), 3.50-3.47 (m, 4H), 3.26-3.21 (m, 4H), 2.09 (s, 3H) | 397.1 |
| 31 | 1-(5-(2-Hydroxy-3-(3-(piperazin-1-yl)isoxazol-5-yl)phenyl)indolin-1-yl)ethanone 2,2,2-trifluoroacetate | ¹H NMR (400 MHz, DMSO-d₆): δ 9.13 (br s, 1H), 9.84 (br s, 2H), 8.10 (d, J = 8.4 Hz, 1H), 7.67-7.64 (m, 1H), 7.36 (s, 1H), 7.32-7.27 (m, 2H), 7.07 (t, J = 7.6 Hz, 1H), 6.74 (s, 1H), 4.16-4.12 (m, 2H), 3.50-3.47 (m, 4H), 3.24-3.17 (m, 6H), 2.19 (s, 3H) | 405.2 |

TABLE 3-continued

Following compounds were prepared using 2-bromo-6-(3-(piperazin-1-yl)isoxazol-5-yl)phenol or tert-butyl 4-(5-(3-bromo-2-methoxyphenyl)isoxazol-3-yl)piperazine-1-carboxylate and a corresponding aryl boronic ester or aryl boronic acid as described for Examples 19 and 29 (See preparation in Schemes 1-5).

| Ex. No. | Name/Structure | $^1$H NMR Data | LCMS (M + H)$^+$ |
|---|---|---|---|
| 32 | N-(3-Chloro-2'-hydroxy-3'-(3-(piperazin-1-yl)isoxazol-5-yl)-[1,1'-biphenyl]-4-yl)acetamide 2,2,2-trifluoroacetate | $^1$H NMR (400 MHz, DMSO-d$_6$): δ 9.58 (s, 1H), 9.42 (s, 1H), 8.91 (br s, 2H), 7.82 (d, J = 8.4 Hz, 1H), 7.69 (dd, J = 8.0, 2.0 Hz, 1H), 7.60 (d, J = 2.0 Hz, 1H), 7.44 (d, J = 8.4, 1.6 Hz, 1H), 7.37 (dd, J = 7.6, 1.6 Hz, 1H), 7.10 (t, J = 7.6 Hz, 1H), 6.77 (s, 1H), 3.51-3.48 (m, 4H), 3.24 (s, 4H), 2.13 (s, 3H) | 413.1 |

Example 33

N,N'-(3,3''-Difluoro-2'-hydroxy-[1,1':3',1''-terphenyl]-4,4''-diyl)diacetamide

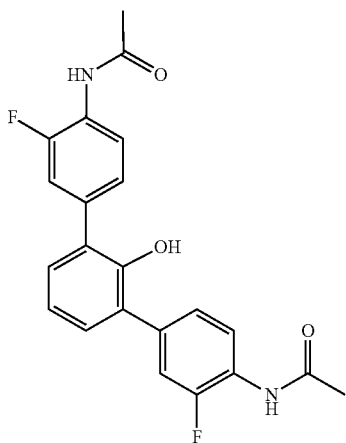 [SMILES: CC(=O)Nc1ccc(-c2cccc(-c3ccc(NC(C)=O)c(F)c3)c2O)cc1F]

A mixture of N-(2-fluoro-4-(4,4,5,5-tetramethyl-1,3,2-dioxaborolan-2-yl)phenyl)acetamide (200 mg, 0.72 mmol), 2,6-dibromophenol (91 mg, 0.36 mmol), K$_3$PO$_4$ (458 mg, 2.16 mmol) and Pd(dppf)Cl$_2$ (112 mg, 0.14 mmol) in dioxane:water (10:3, 13 mL) was stirred at 100° C. for 4 hours under N$_2$. After the reaction was indicated by LCMS, the reaction mixture was cooled down to room temperature and filtered. The filtrate was concentrated and the residue was purified by prep-HPLC using acetonitrile in water in the presence of NH$_4$HCO$_3$ to afford the title compound (28.0 mg, 10% yield) as a white solid. $^1$H NMR (400 MHz, DMSO-d$_6$): δ 9.77 (s, 2H), 8.53 (s, 1H), 7.93 (t, J=8.4 Hz, 2H), 7.43 (d, J=2.0, 2H), 7.40 (d, J=2.0 Hz, 2H), 7.30 (dd, J=8.4, 2.0 Hz, 2H), 7.02 (t, J=7.6, 1H), 2.11 (s, 6H). LCMS: 397.1 (M+H)$^+$.

Example 34

N-(3-Fluoro-2'-hydroxy-3'-(3-(piperazin-1-yl)isoxazol-5-yl)-[1,1'-biphenyl]-4-yl)acetamide trifluoroacetate The title compound was prepared following procedures described for Example 1, using N-(2-fluoro-4-(4,4,5,5-tetramethyl-1,3,2-dioxaborolan-2-yl)phenyl)acetamide [prepared from N-(4-bromo-2-fluorophenyl)acetamide and 4,4,4',4',5,5,5',5'-octamethyl-2,2'-bi(1,3,2-dioxaborolane)] and tert-butyl 4-(5-(3-bromo-2-methoxyphenyl)isoxazol-3-yl)piperazine-1-carboxylate followed by BBr$_3$ to afford TFA salt of the title compound (21% yield). $^1$H NMR (400 MHz, DMSO-d$_6$): δ 6 9.81 (s, 1H), 9.36 (s, 1H), 8.84 (br s, 2H), 7.98 (t, J=8.4, 1H), 7.68 (dd, J=8.0, 1.6 Hz, 1H), 7.40-7.29

(m, 2H), 7.29-7.27 (m, 1H), 7.11-7.08 (m, 1H), 6.76 (s, 1H), 3.56-3.47 (m, 4H), 3.42-3.24 (m, 4H), 2.11 (s, 3H). LCMS: 397.2 (M+H)+.

Example 35

N-(3-Fluoro-2'-hydroxy-3'-(1-phenyl-1H-pyrazol-4-yl)-[1,1'-biphenyl]-4-yl) acetamide

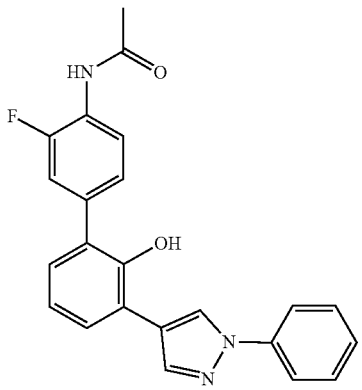 [SMILES: CC(=O)Nc1ccc(-c2cccc(-c3cnn(-c4ccccc4)c3)c2O)cc1F]

Step 1: N-(3'-Bromo-3-fluoro-2'-hydroxy-[1,1'-biphenyl]-4-yl)acetamide

A mixture of N-(2-fluoro-4-(4,4,5,5-tetramethyl-1,3,2-dioxaborolan-2-yl)phenyl)acetamide (200 mg, 0.72 mmol), 2,6-dibromophenol (910 mg, 3.6 mmol), $K_3PO_4$ (458 mg, 2.16 mmol) and Pd(dppf)Cl$_2$ (112 mg, 0.14 mmol) in dioxane:water (10:3, 13 mL) was stirred at 100° C. for 4 hours under $N_2$. After the reaction was complete by LCMS, the reaction mixture was cooled down to room temperature and filtered. The filtrate was concentrated and the residue was purified by prep-HPLC using acetonitrile in water in the presence of $NH_4HCO_3$ to afford the title compound (186.0 mg, 80% yield) as a white solid. LCMS: 324.0 (M+H)+.

Step 2: N-(3-Fluoro-2'-hydroxy-3'-(1-phenyl-1H-pyrazol-4-yl)-[1,1'-biphenyl]-4-yl) acetamide A solution of N-(3'-bromo-3-fluoro-2'-hydroxy-[1,1'-biphenyl]-4-yl)acetamide (100 mg, 0.32 mmol), 1-phenyl-4-(4,4,5,5-tetramethyl-1,3,2-dioxaborolan-2-yl)-1H-pyrazole (121 mg, 0.45 mmol), $K_3PO_4$ (191 mg, 0.9 mmol) and Pd(dppf)Cl$_2$ (43.8 mg, 0.06 mmol) in dioxane:water (10:3, 13 mL) was stirred at 110° C. under nitrogen atmosphere for 4 hours. After the reaction was complete by LCMS, the reaction mixture was cooled and concentrated. The residue was purified by prep-HPLC using acetonitrile in water in the presence of $NH_4HCO_3$ to afford the title compound (4.7 mg, 4% yield) as a white solid. $^1$H NMR (400 MHz, DMSO-d$_6$): 9.78 (s, 1H), 8.84 (s, 1H), 8.69 (s, 1H), 8.21 (s, 1H), 7.95 (t, J=8.4 Hz, 1H), 7.90-7.87 (m, 2H), 7.62-7.60 (m, 1H), 7.52 (t, J=7.6, 2H), 7.42 (d, J=1.6 Hz, 1H), 7.40-7.30 (m, 2H), 7.17 (dd, J=7.2, 1.6 Hz, 1H), 7.02 (t, J=8.0 Hz, 1H), 2.12 (s, 3H). LCMS: 388.1 (M+H)+.

TABLE 4

Following compounds were prepared using 2-bromo-6-(3-(piperazin-1-yl)isoxazol-5-yl)phenol or tert-butyl 4-(5-(3-bromo-2-methoxyphenyl)isoxazol-3-yl)piperazine-1-carboxylate and a corresponding aryl boronic ester or aryl boronic acid as described for Example 29 (See preparation in Schemes 1-5).

| Ex. No. | Name/Structure | $^1$H NMR Data | LCMS (M + H)+ |
|---|---|---|---|
| 36 | 1-(6-(2-Hydroxy-3-(3-(piperazin-1-yl)isoxazol-5-yl)phenyl)-3,4-dihydroquinolin-1(2H)-yl)ethanone 2,2,2-trifluoroacetate | 1H NMR (400 MHz, DMSO-d$_6$): δ 9.25 (s, 1H), 8.79 (br s, 2H), 7.68-7.66 (m, 2H), 7.35-7.29 (m, 3H), 7.08 (t, J = 7.6 Hz, 1H), 6.75 (s, 1H), 3.73-3.66 (m, 2H), 3.63-3.58 (m, 4H), 3.56-3.47 (m, 4H), 2.76 (t, J = 6.4 Hz, 2H), 2.22 (s, 3H), 1.91 (t, J = 6.4 Hz, 2H) | 419.2 |

TABLE 4-continued

Following compounds were prepared using 2-bromo-6-(3-(piperazin-1-yl)isoxazol-5-yl)phenol or tert-butyl 4-(5-(3-bromo-2-methoxyphenyl)isoxazol-3-yl)piperazine-1-carboxylate and a corresponding aryl boronic ester or aryl boronic acid as described for Example 29 (See preparation in Schemes 1-5).

| Ex. No. | Name/Structure | $^1$H NMR Data | LCMS $(M + H)^+$ |
|---|---|---|---|
| 37 | 3-(2'-Hydroxy-3'-(3-(piperazin-1-yl)isoxazol-5-yl)-[1,1'-biphenyl]-4-yl)oxazolidin-2-one 2,2,2-trifluoroacetate | $^1$H NMR (400 MHz, DMSO-d$_6$): δ 9.23 (s, 1H), 8.79 (br s, 2H), 7.68-7.65 (m, 3H), 7.55-7.53 (m, 2H), 7.35-7.32 (m, 1H), 7.10 (d, J = 8.0 Hz, 1H), 4.50-4.46 (m, 2H), 4.13-4.09 (m, 2H), 3.50-3.47 (m, 4H), 3.25-3.22 (m, 4H) | 407.2 |
| 38 | 5-Acetyl-8-(2-hydroxy-3-(3-(piperazin-1-yl)isoxazol-5-yl)phenyl)-1-methyl-1,3,4,5-tetrahydro-2H-benzo[b][1,4]diazepin-2-one | $^1$H NMR (400 MHz, DMSO-d$_6$): δ 9.48 (s, 1H), 8.83 (br s, 2H), 7.76-7.73 (m, 1H), 7.60 (d, J = 1.6 Hz, 1H), 7.48 (d, J = 8.0 Hz, 1H), 7.45-7.40 (m, 2H), 7.13 (d, J = 7.6 Hz, 1H), 76.79 (s, 1H), 4.75-4.67 (m, 1H), 3.50-3.45 (m, 4H), 3.43-3.40 (m, 1H), 3.37 (s, 3H), 3.26-3.24 (m, 4H), 2.67-2.58 (m, 1H), 2.35-2.31 (m, 1H), 21.81 (s, 3H) | 462.2 |
| 39 | 2,2,2-Trifluoro-N-(2'-hydroxy-3'-(3-(piperazin-1-yl)isoxazol-5-yl)-[1,1'-biphenyl]-4-yl)acetamide 2,2,2-trifluoroacetate | $^1$H NMR (400 MHz, DMSO-d$_6$): δ 11.37 (s, 1H), 9.28 (s, 1H). 8.82 (br s, 2H), 7.78-7.75 (m, 2H), 7.70-7.67 (m, 1H), 7.57-7.54 (m, 2H), 7.36-7.33 (m, 1H), 7.10 (t, J = 7.6 Hz, 1H), 6.75 (s, 1H), 3.54-3.47 (m, 4H), 3.24-3.22 (m, 4H) | 433.1 |

Example 40

N,N'-(5,5'-(2-Hydroxy-1,3-phenylene)bis(pyridine-5, 2-diyl))diacetamide

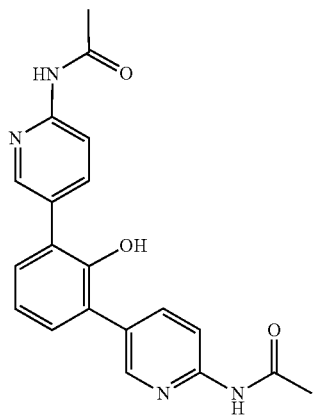 [SMILES: CC(=O)Nc1ccc(-c2cccc(-c3ccc(NC(C)=O)nc3)c2O)cn1]

A mixture of N-(5-(4,4,5,5-tetramethyl-1,3,2-dioxaborolan-2-yl)pyridin-2-yl)acetamide (230.6 mg, 0.88 mmol), 2,6-dibromophenol (100 mg, 0.40 mmol), $K_3PO_4$ (339.2 mg, 1.60 mmol) and Pd(dppf)$Cl_2$ (58.5 mg, 0.08 mmol) in dioxane:water (5:3, 8 mL) was stirred at 110° C. for 4 hours under $N_2$. After the reaction was complete by LCMS, the reaction mixture was cooled down to room temperature and filtered. The filtrate was concentrated, and the residue was purified by prep-HPLC using acetonitrile in water in the presence of $NH_4HCO_3$ to afford the title compound (5.7 mg, 4% yield) as a white solid. $^1$H NMR (400 MHz, DMSO-$d_6$): 10.54 (s, 2H), 8.64 (s, 1H), 8.46 (d, J=1.6 Hz, 2H), 8.13 (d, J=8.4 Hz, 2H), 7.92 (dd, J=8.4, 2.0 Hz, 2H), 7.28 (d, J=7.6 Hz, 2H), 7.06 (d, J=7.2 Hz, 1H), 2.12 (s, 6H). LCMS: 363.1 (M+H)$^+$.

Example 41

1-(2'-Hydroxy-3'-(3-(piperazin-1-yl)isoxazol-5-yl)-[1,1'-biphenyl]-4-yl)imidazolidin-2-one 2,2,2-trifluoroacetate

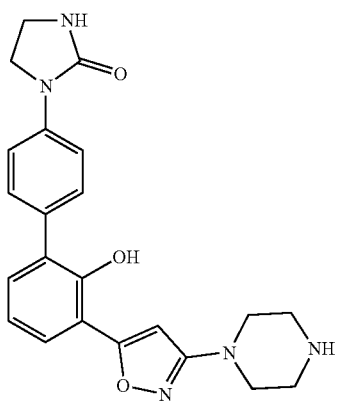 [SMILES: O=C1NCCN1c1ccc(-c2cccc(-c3cc(N4CCNCC4)no3)c2O)cc1]

The title compound was prepared following the procedures described for Example 29, using 1-(4-(4,4,5,5-tetramethyl-1,3,2-dioxaborolan-2-yl)phenyl)imidazolidin-2-one [prepared from 1-(4-bromophenyl)imidazolidin-2-one and 4,4,4',4',5,5,5',5'-octamethyl-2,2'-bi(1,3,2-dioxaborolane)] and tert-butyl 4-(5-(3-bromo-2-methoxyphenyl)isoxazol-3-yl)piperazine-1-carboxylate followed by $BBr_3$ to afford TFA salt of the title compound (29% yield). $^1$H NMR (400 MHz, DMSO-$d_6$): 9.18 (s, 1H), 8.78 (br s, 2H), 7.65 (d, J=8.8 Hz, 3H), 7.45 (d, J=8.8 Hz, 2H), 7.32 (dd, J=7.6, 1.2 Hz, 1H), 7.08 (t, J=8.0 Hz, 1H), 7.00 (s, 1H), 6.74 (s, 1H), 3.89 (t, J=8.4 Hz, 2H), 3.48-3.42 (m, 6H), 3.25-3.23 (m, 4H). LCMS: 406.2 (M+H)$^+$.

Example 42

N,N'-(3-Fluoro-2'-hydroxy-3''-methoxy-[1,1':3',1''-terphenyl]-4,4''-diyl)diacetamide

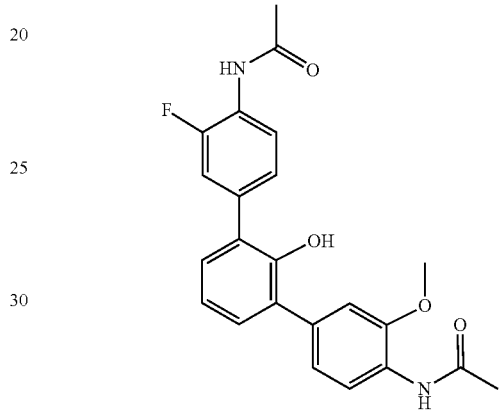

Step 1: N-(3'-bromo-3-fluoro-2'-hydroxy-[1,1'-biphenyl]-4-yl)acetamide

A mixture of N-(2-fluoro-4-(4,4,5,5-tetramethyl-1,3,2-dioxaborolan-2-yl)phenyl)acetamide (5.0 g, 17.9 mmol), 2,6-dibromophenol (22.6 g, 89.6 mmol), $K_3PO_4$ (22.8 g, 107.4 mmol) and Pd(dppf)$Cl_2$ (2.6 g, 3.58 mmol) in dioxane:water (10:3, 260 mL) was stirred at 100° C. for 4 hours under $N_2$. After the reaction was complete by LCMS, the reaction mixture was cooled down to room temperature and filtered. The filtrate was concentrated, and the residue was purified by silica gel chromatography using petroleum ether and ethyl acetate (2:1) as the eluent to get the title compound (2.3 g, 40% yield) as a green solid. LCMS: 324.0 (M+H)$^+$.

Step 2: N,N'-(3-fluoro-2'-hydroxy-3''-methoxy-[1,1':3',1''-terphenyl]-4,4''-diyl)diacetamide A solution of N-(3'-bromo-3-fluoro-2'-hydroxy-[1,1'-biphenyl]-4-yl)acetamide (150 mg, 0.46 mmol), N-(2-methoxy-4-(4,4,5,5-tetramethyl-1,3,2-dioxaborolan-2-yl)phenyl)acetamide (204 mg, 0.7 mmol), $K_3PO_4$ (293 mg, 1.38 mmol) and Pd(dppf)$_2Cl_2$ (65.8 mg, 0.09 mmol) in dioxane:water (10:3, 13 mL) was stirred at 110° C. for 4 hours under nitrogen atmosphere. After the reaction was complete by LCMS, the reaction mixture was cooled and filtered and the filtrated was concentrated. The residue was purified by prep-HPLC using acetonitrile in water in the presence of $NaHCO_3$ to afford the title compound (38.2 mg, 20% yield) as a white solid. $^1$H NMR (400 MHz, DMSO-$d_6$): 9.78 (s, 1H), 9.19 (s, 1H), 8.39 (s, 1H), 7.99 (d, J=8.4

Hz, 1H), 7.92 (t, J=8.4 Hz, 1H), 7.42 (dd, J=12.0, 1.6 Hz, 1H), 7.31 (d, J=8.4 Hz, 1H), 7.25-7.23 (m, 2H), 7.18 (d, J=2.0 Hz, 1H), 7.06-6.99 (m, 2H), 3.87 (s, 3H), 2.11 (s, 6H). LCMS: 409.1 (M+H)$^+$.

Example 43

1-(2'-Hydroxy-3'-(3-(piperazin-1-yl)isoxazol-5-yl)-[1,1'-biphenyl]-4-yl)pyrrolidin-2-one 2,2,2-trifluoroacetate

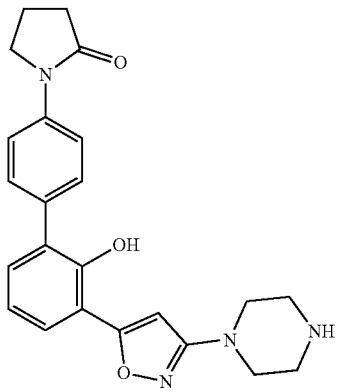 [SMILES: O=C1CCCN1c1ccc(-c2cccc(-c3cc(N4CCNCC4)no3)c2O)cc1]

The title compound was prepared following the procedures described for Example 29, using 1-(4-(4,4,5,5-tetramethyl-1,3,2-dioxaborolan-2-yl)phenyl)pyrrolidin-2-one [prepared from 1-(4-bromophenyl)pyrrolidin-2-one and 4,4,4',4',5,5,5',5'-octamethyl-2,2'-bi(1,3,2-dioxaborolane)] and tert-butyl 4-(5-(3-bromo-2-methoxyphenyl)isoxazol-3-yl)piperazine-1-carboxylate followed by BBr$_3$ to afford TFA salt of the title compound (5% yield). $^1$H NMR (400 MHz, DMSO-d$_6$): 9.24 (br s, 1H), 8.83 (br s, 2H), 7.74 (d, J=8.8 Hz, 2H), 7.68-7.66 (m, 1H), 7.52 (d, J=8.8 Hz, 2H), 7.33 (dd, J=7.6, 1.6 Hz, 1H), 7.09 (t, J=8.0 Hz, 1H), 6.75 (s, 1H), 3.88 (t, J=7.2 Hz, 2H), 3.49-3.47 (m, 4H), 3.25-3.22 (m, 4H), 2.55-2.50 (m, 2H), 2.13-2.06 (m, 2H). LCMS: 405.2 (M+H)$^+$.

Example 44

N-(3-Cyclopropoxy-2'-hydroxy-3'-(3-(piperazin-1-yl)isoxazol-5-yl)-[1,1'-biphenyl]-4-yl)acetamide 2,2,2-trifluoroacetate

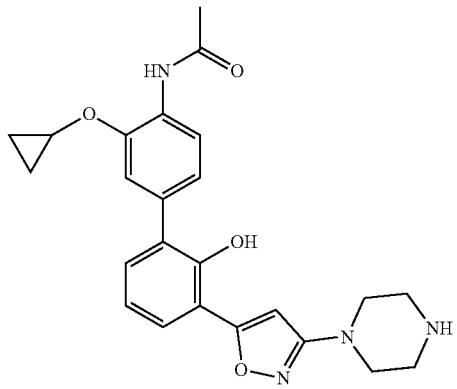 [SMILES: CC(=O)Nc1ccc(-c2cccc(-c3cc(N4CCNCC4)no3)c2O)cc1OC1CC1]

The title compound was prepared following the procedures described for Example 19, using N-(2-cyclopropoxy-4-(4,4,5,5-tetramethyl-1,3,2-dioxaborolan-2-yl)phenyl)acetamide [prepared from N-(4-bromo-2-cyclopropoxyphenyl)acetamide and 4,4,4',4',5,5,5',5'-octamethyl-2,2'-bi(1,3,2-dioxaborolane)] and 2-bromo-6-(3-(piperazin-1-yl)isoxazol-5-yl)phenol to afford TFA salt of the title compound (9.3 mg, 8% yield) as a white solid. $^1$H NMR (400 MHz, DMSO-d$_6$): 9.25 (s, 1H), 9.04 (s, 1H), 8.80 (br s, 2H), 8.01 (d, J=8.0 Hz, 1H), 7.68 (dd, J=8.0, 2.0 Hz, 1H), 7.42 (d, J=1.6 Hz, 1H), 7.35 (dd, J=7.6, 2.0 Hz, 1H), 7.11-7.04 (m, 2H), 6.74 (s, 1H), 3.94-3.91 (m, 1H), 3.49-3.47 (m, 4H), 3.27-3.23 (m, 4H), 2.10 (s, 3H), 0.81-0.78 (m, 4H). LCMS: 435.2 (M+H)$^+$.

Example 45

N,N'-(3-Cyclobutoxy-3''-fluoro-2'-hydroxy-[1,1':3',1''-terphenyl]-4,4''-diyl)diacetamide

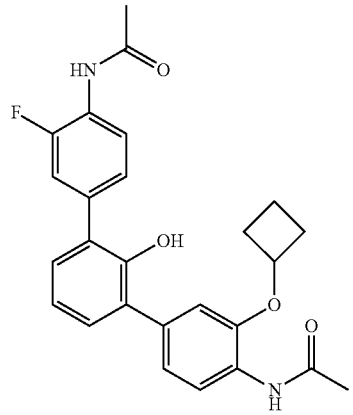 [SMILES: CC(=O)Nc1ccc(-c2cccc(-c3ccc(NC(C)=O)c(OC4CCC4)c3)c2O)cc1F]

The title compound was prepared following the procedures described for Example 42, using N-(2-cyclobutoxy-4-(4,4,5,5-tetramethyl-1,3,2-dioxaborolan-2-yl)phenyl)acetamide [prepared from N-(4-bromo-2-cyclobutoxyphenyl)acetamide and 4,4,4',4',5,5,5',5'-octamethyl-2,2'-bi(1,3,2-dioxaborolane)] and N-(3'-bromo-3-fluoro-2'-hydroxy-[1,1'-biphenyl]-4-yl)acetamide to afford the title compound (10.4 mg, 5% yield) as a white solid. $^1$H NMR (400 MHz, DMSO-d$_6$): 9.78 (s, 1H), 9.03 (s, 1H), 8.40 (s, 1H), 8.00 (d, J=7.6 Hz, 1H), 7.92 (t, J=8.4 Hz, 1H), 7.40 (dd, J=12.4, 1.6 Hz, 1H), 7.32-7.29 (m, 1H), 7.22 (d, J=7.2 Hz, 2H), 7.05-6.99 (m, 3H), 4.79-4.76 (m, 1H), 2.47-2.41 (m, 2H), 2.20-2.15 (m, 2H), 2.13 (s, 6H), 1.80-1.78 (m, 1H), 1.68-1.63 (m, 1H). LCMS: 449.2 (M+H)$^+$.

Example 46

N,N'-(3-Chloro-3"-fluoro-2'-hydroxy-[1,1':3',1"-terphenyl]-4,4"-diyl)diacetamide

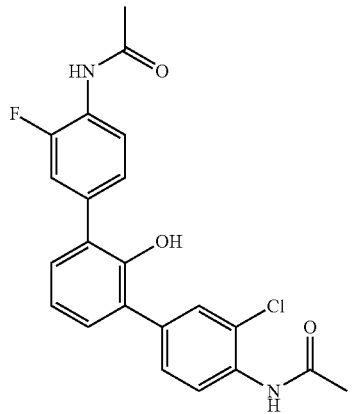

The title compound was prepared following the procedures described for Example 42, using N-(2-chloro-4-(4,4,5,5-tetramethyl-1,3,2-dioxaborolan-2-yl)phenyl)acetamide [prepared from N-(4-bromo-2-chlorophenyl)acetamide and 4,4,4',4',5,5,5',5'-octamethyl-2,2'-bi(1,3,2-dioxaborolane)] and N-(3'-bromo-3-fluoro-2'-hydroxy-[1,1'-biphenyl]-4-yl)acetamide to afford the title compound (34% yield) as a white solid. $^1$H NMR (400 MHz, DMSO-$d_6$): 9.77 (s, 1H), 9.55 (s, 1H), 8.58 (s, 1H), 7.93 (t, J=8.0 Hz, 1H), 7.77 (d, J=8.4 Hz, 1H), 7.64 (s, 1H), 7.47-7.40 (m, 2H), 7.32-7.30 (m, 1H), 7.27-7.24 (m, 2H), 7.03 (t, J=7.6 Hz, 1H), 2.11 (m, 6H). LCMS: 413.1 (M+H)$^+$.

Example 47

N-(3'-(1-Acetylindolin-5-yl)-3-fluoro-2'-hydroxy-[1,1'-biphenyl]-4-yl)acetamide

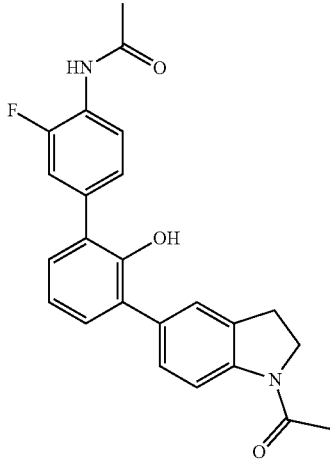 [SMILES: CC(=O)Nc1ccc(-c2cccc(-c3ccc4c(c3)CCN4C(C)=O)c2O)cc1F]

The title compound was prepared following the procedures described for Example 42, using 1-(5-(4,4,5,5-tetramethyl-1,3,2-dioxaborolan-2-yl)indolin-1-yl)ethanone and N-(3'-bromo-3-fluoro-2'-hydroxy-[1,1'-biphenyl]-4-yl)acetamide to afford the title compound (48.3 mg, 26% yield) as a white solid. $^1$H NMR (400 MHz, DMSO-$d_6$): 9.78 (s, 1H), 8.32 (s, 1H), 8.07 (d, J=8.4 Hz, 1H), 7.92 (t, J=8.4 Hz, 1H), 7.42 (d, J=1.6 Hz, 1H), 7.40 (s, 1H), 7.32-7.29 (m, 2H), 7.22-7.18 (m, 2H), 6.99 (t, J=7.6 Hz, 1H), 4.13 (t, J=7.6 Hz, 2H), 3.18 (t, J=8.0 Hz, 2H), 2.18 (s, 3H), 2.11 (s, 3H). LCMS: 405.1 (M+H)$^+$.

Example 48

2,2-Difluoro-N-(2'-hydroxy-3'-(3-(piperazin-1-yl)isoxazol-5-yl)-[1,1'-biphenyl]-4-yl)acetamide 2,2,2-trifluoroacetate

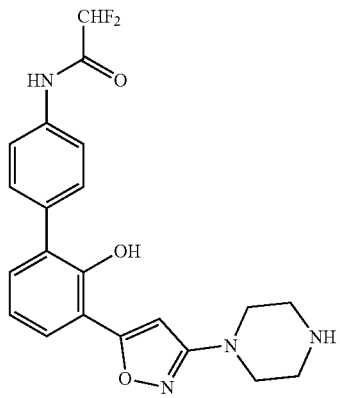

The title compound was prepared following the procedures described for Example 39, using tert-butyl 4-(5-(4'-amino-2-methoxy-[1,1'-biphenyl]-3-yl)isoxazol-3-yl)piperazine-1-carboxylate and 2,2-difluoroacetic anhydride to afford TFA salt of the title compound (23.5 mg, 43% yield) as a white solid. $^1$H NMR (400 MHz, DMSO-$d_6$): 10.87 (s, 1H), 9.26 (s, 1H), 8.87 (br s, 2H), 7.75 (d, J=8.4 Hz, 2H), 7.52 (d, J=8.8 Hz, 2H), 7.35-7.32 (m, 1H), 7.13-7.08 (m, 2H), 6.75 (s, 1H), 6.42 (t, J=53.6 Hz, 1H), 3.50-3.47 (m, 4H), 3.25-3.24 (m, 4H). LCMS: 415.2 (M+H)$^+$.

Example 49

N,N'-(3-Cyano-3"-fluoro-2'-hydroxy-[1,1':3',1"-terphenyl]-4,4"-diyl)diacetamide

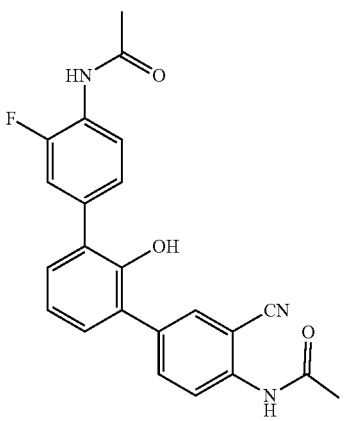 [SMILES: CC(=O)Nc1ccc(-c2cccc(-c3ccc(NC(C)=O)c(C#N)c3)c2O)cc1F]

The title compound was prepared following the procedures described for Example 42, using N-(2-cyano-4-(4,4,5,5-tetramethyl-1,3,2-dioxaborolan-2-yl)phenyl)acetamide and N-(3'-bromo-3-fluoro-2'-hydroxy-[1,1'-biphenyl]-4-yl)acetamide to afford the title compound (77.5 mg, 62% yield) as a white solid. $^1$H NMR (400 MHz, DMSO-$d_6$): 10.20 (s, 1H), 9.78 (s, 1H), 8.66 (s, 1H), 7.93 (t, J=2.0 Hz, 2H), 7.83-7.81 (m, 1H), 7.64 (d, J=8.4 Hz, 1H), 7.44-7.41 (m, 1H), 7.33-7.27 (m, 3H), 7.05 (t, J=8.0 Hz, 1H), 2.13 (s, 3H), 2.11 (s, 3H). LCMS: 404.1 (M+H)$^+$.

Example 50

N,N'-(3-Fluoro-2'-hydroxy-3"-methyl-[1,1':3',1"-terphenyl]-4,4"-diyl)diacetamide

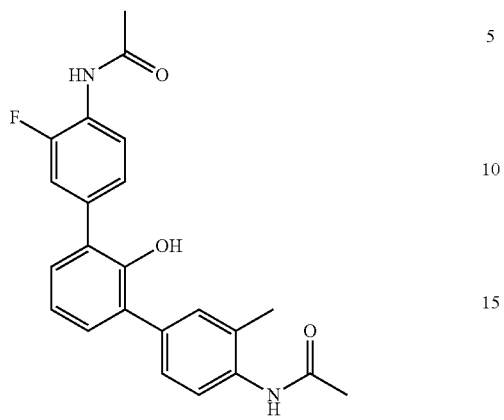

The title compound was prepared following the procedures described for Example 42, using N-(2-methyl-4-(4,4,5,5-tetramethyl-1,3,2-dioxaborolan-2-yl)phenyl)acetamide and N-(3'-bromo-3-fluoro-2'-hydroxy-[1,1'-biphenyl]-4-yl)acetamide to afford the title compound (33.5 mg, 28% yield) as an off-white solid. $^1$H NMR (400 MHz, DMSO-$d_6$): 9.76 (s, 1H), 9.31 (s, 1H), 8.37 (s, 1H), 7.92 (t, J=8.4 Hz, 1H), 7.48-7.37 (m, 3H), 7.30 (d, J=9.2 Hz, 2H), 7.23-7.19 (m, 2H), 7.00 (t, J=7.6 Hz, 1H), 2.25 (s, 3H), 2.11 (s, 3H), 2.08 (s, 3H). LCMS: 393.2 (M+H)$^+$.

TABLE 5

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 52 | N,N'-(3-Ethoxy-3"-fluoro-2'-hydroxy-[1,1':3',1"-terphenyl]-4,4"-diyl)diacetamide | $^1$H NMR (400 MHz, DMSO-$d_6$): δ 9.78 (s, 1H), 9.03 (s, 1H), 8.39 (s, 1H), 8.00-7.92 (m, 2H), 7.42 (dd, J = 12.4, 1.6 Hz, 1H), 7.32-7.29 (m, 1H), 7.23 (d, J = 7.6 Hz, 2H), 7.16 (d, J = 1.6 Hz, 1H), 7.05-6.99 (m, 2H), 4.16-4.11 (m, 2H), 2.12 (s, 3H), 2.11 (s, 3H), 1.39 (t, J = 7.2 Hz, 3H) | 423.2 |

TABLE 5-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 53 | N,N'-(3-Fluoro-2'-hydroxy-3''-phenoxy-[1,1':3',1''-terphenyl]-4,4''-diyl)diacetamide | $^1$H NMR (400 MHz, DMSO-d$_6$): δ 9.77 (s, 1H), 9.53 (s, 1H), 8.44 (d, J = 4.8 Hz, 1H), 8.04 (br s, 1H), 7.89 (d, J = 6.8 Hz, 1H), 7.38-7.34 (m, 3H), 7.29-7.25 (m, 2H), 7.21-7.16 (m, 2H), 7.13-6.98 (m, 4H), 6.96-6.95 (m, 1H), 2.10 (s, 3H), 2.03 (m, 3H) | 471.2 |
| 54 | N-(3,3''-Difluoro-2'-hydroxy-[1,1':3',1''-terphenyl]-4-yl)acetamide | 1H NMR (400 MHz, DMSO-d$_6$): δ 9.79 (s, 1H), 8.55 (s, 1H), 7.96-7.91 (m, 1H), 7.45-7.25 (m, 7H), 7.20-7.16 (m, 1H), 7.04 (t, J = 8.0 Hz, 1H), 2.11 (m, 3H) | 340.1 |
| 55 | N-(3-fluoro-2'-hydroxy-3''-methyl-[1,1':3',1''-terphenyl]-4-yl)acetamide | $^1$H NMR (400 MHz, DMSO-d$_6$): δ 9.76 (s, 1H), 8.33 (s, 1H), 7.94-7.91 (m, 1H), 7.43-7.30 (m, 5H), 7.25-7.15 (m, 3H), 7.01 (t, J = 8.0 Hz, 1H), 2.36 (s, 3H), 2.11 (m, 3H) | 336.1 |

TABLE 5-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | ¹H NMR Data | LCMS (M + H)⁺ |
|---|---|---|---|
| 56 | N-(3-fluoro-2'-hydroxy-3''-methoxy-[1,1':3',1''-terphenyl]-4-yl)acetamide | ¹H NMR (400 MHz, DMSO-d₆): δ 9.76 (s, 1H), 8.37 (s, 1H), 7.96-7.93 (m, 1H), 7.43-7.30 (m, 3H), 7.26-7.21 (m, 2H), 7.08 (t, J = 7.2 Hz, 2H), 7.07-6.92 (m, 1H), 6.91-6.90 (m, 1H), 3.79 (s, 3H), 2.11 (s, 3H) | 352.1 |

Example 57

N-(3'-(3-(4-Acetylpiperazin-1-yl)isoxazol-5-yl)-2'-hydroxy-[1,1'-biphenyl]-4-yl)acetamide

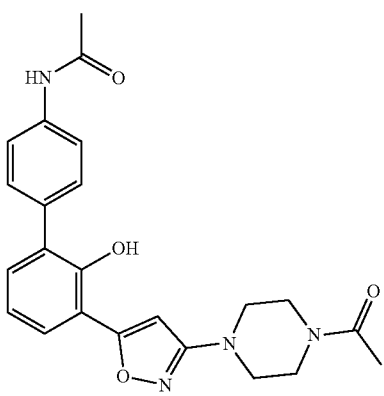 [SMILES: CC(=O)Nc1ccc(-c2cccc(-c3cc(N4CCN(C(C)=O)CC4)no3)c2O)cc1]

To a solution of N-(2'-hydroxy-3'-(3-(piperazin-1-yl)isoxazol-5-yl)-[1,1'-biphenyl]-4-yl)acetamide (40 mg, 0.1 mmol) in DCM (15 mL)) was added AC₂O (1.1 mL) and TEA (0.3 mmol) at 0° C. The reaction mixture was stirred at room temperature for 16 hours under nitrogen atmosphere. Sat NaHCO₃ aq (10 mL) and MeOH (10 mL) was added and then the mixture was heated to 60° C. for 16 hours. After the reaction was complete by LCMS, the reaction mixture was removed the solvent under reduced pressure to afford a residue which was added water (10 mL) and extracted with EA (6 mL×3). The combined organic layers were washed with brine, dried over sodium sulfate, filtered and concentrated under reduced pressure. The residue was purified by prep-HPLC using acetonitrile in water in the presence of NH₄HCO₃ to afford the title compound (5.0 mg, 12% yield) as a white solid. ¹H NMR (400 MHz, DMSO-d₆): 10.02 (s, 1H), 9.11 (br s, 1H), 7.67-7.63 (m, 3H), 7.43 (d, J=8.4 Hz, 2H), 7.31-7.29 (m, 1H), 7.17 (t, J=8.4 Hz, 1H), 6.70 (s, 1H), 3.57-3.55 (m, 4H), 3.31-3.29 (m, 2H), 3.23-3.20 (m, 2H), 2.08 (s, 3H), 2.04 (s, 3H). LCMS: 421.2 (M+H)⁺.

Example 58

N-(2'-Hydroxy-3'-(3-(4-(phenylsulfonyl)piperazin-1-yl)isoxazol-5-yl)-[1,1'-biphenyl]-4-yl)acetamide To a solution of N-(2'-hydroxy-3'-(3-(piperazin-1-yl)isoxazol-5-yl)-[1,1'-biphenyl]-4-yl)acetamide (70 mg, 0.1 mmol) in DCM (2 mL) was added benzenesulfonyl chloride (17.7 mg, 0.1 mmol) and TEA (30.3 mg, 0.30 mmol). The reaction mixture was stirred at room temperature for 16 hours under nitrogen atmosphere. Sat NaHCO₃ aq (10 mL) and MeOH (10 mL) was added and then the mixture was heated to 60° C. for 16 hours. After the reaction was complete by LCMS, the mixture was removed the solvent under reduced pressure to afford a residue which was added water (10 mL) and extracted with EA (6 mL×3). The combined organic layers were washed with brine, dried over sodium sulfate, filtered and concentrated under reduced pressure. The residue was purified by prep-HPLC using acetonitrile in water in the presence of $NH_4HCO_3$ to afford the title compound (10.9 mg, 21% yield) as a white solid. $^1H$ NMR (400 MHz, DMSO-$d_6$): 10.01 (s, 1H), 9.09 (br s, 1H), 7.78-7.73 (m, 3H), 7.69-7.60 (m, 5H), 7.41 (d, J=8.8 Hz, 2H), 7.29-7.27 (m, 1H), 7.04 (t, J=7.6 Hz, 1H), 6.63 (s, 1H), 3.37-3.31 (m, 4H), 3.03-3.01 (m, 4H), 2.08 (s, 3H). LCMS: 519.2 (M+H)$^+$.

TABLE 6

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Structure | $^1$H NMR Data | LCMS (M + H)$^+$ |
|---|---|---|---|
| 59 | N-(3,4''-Difluoro-2'-hydroxy-[1,1':3',1''-terphenyl]-4-yl)acetamide | $^1$H NMR (400 MHz, DMSO-$d_6$): δ 9.77 (s, 1H), 8.44 (s, 1H), 7.93 (t, J = 8.4 Hz, 1H), 7.58-7.54 (m, 2H), 7.41 (dd, J = 8.4, 1.6 Hz, 1H), 7.32-7.20 (m, 5H), 7.02 (t, J = 8.0 Hz, 1H), 2.11 (s, 3H) | 340.1 |
| 60 | N-(3-Fluoro-2'-hydroxy-4''-methyl-[1,1':3',1''-terphenyl]-4-yl)acetamide | $^1$H NMR (400 MHz, DMSO-$d_6$): δ 9.76 (s, 1H), 8.31 (s, 1H), 7.92 (t, J = 8.4 Hz, 1H), 7.43-7.39 (m, 3H), 7.31 (d, J = 8.4 Hz, 1H), 7.25-7.18 (m, 4H), 7.00 (t, J = 7.6 Hz, 1H), 2.35 (s, 3H), 2.11 (s, 3H) | 336.1 |
| 61 | N-(3-Fluoro-2'-hydroxy-4''-methoxy-[1,1':3',1''-terphenyl]-4-yl)acetamide | $^1$H NMR (400 MHz, DMSO-$d_6$): δ 9.76 (s, 1H), 8.29 (s, 1H), 7.92 (t, J = 8.4 Hz, 1H), 7.47-7.42 (m, 2H), 7.39 (d, J = 1.6 Hz, 1H), 7.32-7.29 (m, 1H), 7.21-7.17 (m, 2H), 7.01-6.98 (m, 3H), 3.79 (s, 3H), 2.11 (s, 3H) | 352.1 |

Example 62

8-(2-Hydroxy-3-(3-(piperazin-1-yl)isoxazol-5-yl)phenyl)-2,3-dihydrobenzo[b][1,4]oxazepin-4(5H)—one

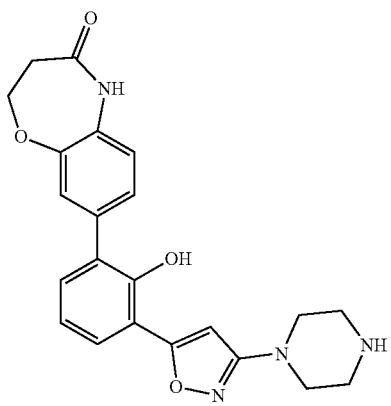 [SMILES: O=C1CCOc2cc(-c3cccc(-c4cc(N5CCNCC5)no4)c3O)ccc2N1]

Step 1: 3-(5-bromo-2-nitrophenoxy)propan-1-ol

To a solution of propane-1,3-diol (13.8 g, 181.8 mmol) in DMF (100 mL) was added NaH (2.2 g, 54.6 mmol, 60%) in one portion. The reaction mixture was stirred at 0° C. for 30 min. 4-bromo-2-fluoro-1-nitrobenzene (10.0 g, 45.5 mmol) was added. Then, the reaction mixture was stirred at 0° C. for 2 h. The reaction mixture was quenched with 1 N HCl. The mixture was filtered, and the filtrate was concentrated under reduced pressure to afford a residue which was added water (20 mL) and extracted with EA (5 mL×3). The combined organic layers were washed with brine, dried over sodium sulfate, filtered and concentrated under reduced pressure to afford the title compound (11.0 g, 88% yield) as yellow oil which was used to the next step without further purification.

Step 2: 3-(5-bromo-2-nitrophenoxy)propanoic acid

To a solution of 3-(5-bromo-2-nitrophenoxy)propan-1-ol (2.0 g, 43.6 mmol) in acetone (200 mL) at 0° C. was added slowly chromic acid solution which was prepared from $CrO_3$ (8.7 g, 87.2 mmol), water (30 mL) and con. $H_2SO_4$ (13.6 g, 139.5 mmol) at 0° C. Then, the reaction mixture was stirred for 2 hours at 0° C. The reaction mixture was added ice-cold water and extracted with EA (15 mL×3). The combined organic layers were washed with brine, dried over sodium sulfate, filtered and concentrated under reduced pressure to afford a residue which was purified by silica gel chromatography using petroleum ether and ethyl acetate (2:1) as the eluent to afford the title compound (8.0 g, 63% yield) as a yellow solid. LCMS: 290.2 (M+H)$^+$.

Step 3: 3-(2-amino-5-bromophenoxy)propanoic acid

To a solution of 3-(5-bromo-2-nitrophenoxy)propanoic acid (8.0 g, 27.7 mmol) in MeOH (100 mL) and $H_2O$ (20 mL) was added $NH_4Cl$ (11.8 g, 221.6 mmol) and Fe powder (7.7 g, 138.4 mmol). The reaction mixture was stirred at 75° C. for 1 hour under nitrogen atmosphere. The reaction mixture was filtered and the filtrate was concentrated to afford a residue which was purified by silica gel chromatography using petroleum ether and ethyl acetate (1:10) as the eluent to afford the title compound (1.5 g, 21% yield) as a brown solid. LCMS: 260.0 (M+H)$^+$.

Step 4: 8-bromo-2,3-dihydrobenzo[b][1,4]oxazepin-4(5H)-one

To a solution of 3-(2-amino-5-bromophenoxy)propanoic acid (1.5 g, 5.8 mmol) in DMF (20 mL) was added HATU (4.4 g, 11.6 mmol) and DIPEA (2.2 g, 17.4 mmol). The reaction mixture was stirred at room temperature under nitrogen atmosphere overnight. The reaction mixture was filtered, and the filtrate was concentrated to afford a residue which was added water and extracted with EA. The combined organic layers were washed with brine, dried over sodium sulfate, filtered and concentrated. The residue was purified by silica gel chromatography using petroleum ether and ethyl acetate (1:1) as the eluent to afford the title compound (600 mg, 43% yield) as a white solid. LCMS: 242.0 (M+H)$^+$.

Step 5: 8-(4,4,5,5-tetramethyl-1,3,2-dioxaborolan-2-yl)-2,3-dihydrobenzo[b][1,4]oxazepin-4(5H)-one The title compound was prepared following the procedure described for Example 29 using 8-bromo-2,3-dihydrobenzo[b][1,4]oxazepin-4(5H)-one and 4,4,4',4',5,5,5',5'-octamethyl-2,2'-bi(1,3,2-dioxaborolane) to afford the title compound (100% yield). LCMS: 290.1 (M+H)$^+$.

Step 6: 8-(2-hydroxy-3-(3-(piperazin-1-yl)isoxazol-5-yl)phenyl)-2,3 dihydrobenzo[b][1,4]oxazepin-4(5H)-one 2,2,2-trifluoroacetate The title compound was prepared following the procedure described for Example 29 using 8-(4,4,5,5-tetramethyl-1,3,2-dioxaborolan-2-yl)-2,3-dihydrobenzo[b][1,4]oxazepin-4(5H)-one and 2-bromo-6-(3-(piperazin-1-yl)isoxazol-5-yl)phenol to afford TFA salt of the title compound (1% yield). $^1$H NMR (400 MHz, DMSO-d$_6$): 9.86 (s, 1H), 9.25 (s, 1H), 8.81 (br s, 1H), 7.68-7.65 (m, 1H), 7.32 (dd, J=7.6, 1.6 Hz, 1H), 7.15 (s, 3H), 7.08 (d, J=7.6 Hz, 1H), 6.74 (s, 1H), 4.40 (t, J=6.0 Hz, 2H), 3.49-3.47 (m, 4H), 3.36-3.24 (m, 4H), 2.75 (t, J=5.6 Hz, 2H). LCMS: 407.2 (M+H)$^+$.

Example 63

N-(3-Fluoro-2'-hydroxy-3'-(pyridin-3-yl)-[1,1'-biphenyl]-4-yl)acetamide

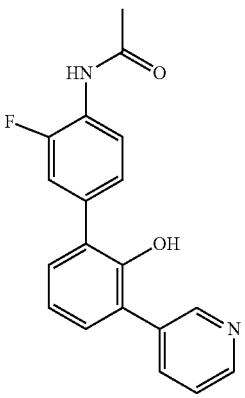

The title compound was prepared following the procedures described for Example 42, using pyridin-3-ylboronic acid and N-(3'-bromo-3-fluoro-2'-hydroxy-[1,1'-biphenyl]-4-yl)acetamide to afford the title compound (55 mg, 55% yield) as a white solid. $^1$H NMR (400 MHz, DMSO-d$_6$): 9.78 (s, 1H), 8.72 (d, J=1.6 Hz, 1H), 8.64 (s, 1H), 8.53 (t, J=2.0 Hz, 1H), 7.95-7.92 (m, 2H), 7.48-7.40 (m, 2H), 7.33-7.27 (m, 3H), 7.07 (t, J=7.6 Hz, 1H), 2.11 (s, 3H). LCMS: 323.1 (M+H)$^+$.

Example 64

N-(3-Cyano-2'-hydroxy-3'-(3-(piperazin-1-yl)isoxazol-5-yl)-[1,1'-biphenyl]-4-yl)acetamide 2,2,2-trifluoroacetate

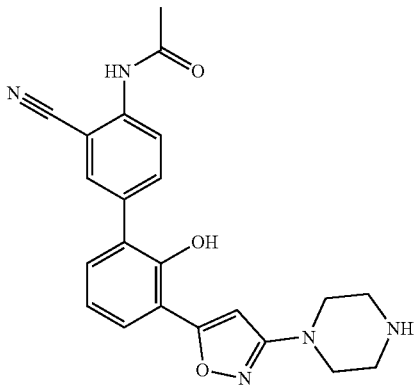 [SMILES: CC(=O)Nc1ccc(-c2cccc(-c3cc(N4CCNCC4)no3)c2O)cc1C#N]

The title compound was prepared following the procedure described for Example 19, using N-(2-cyano-4-(4,4,5,5-tetramethyl-1,3,2-dioxaborolan-2-yl)phenyl)acetamide and 2-bromo-6-(3-(piperazin-1-yl)isoxazol-5-yl)phenol to afford TFA salt of the title compound (9.4 mg, 7% yield) as a white solid. $^1$H NMR (400 MHz, DMSO-d$_6$): 10.25 (s, 1H), 9.49 (s, 1H), 8.80 (br s, 2H), 7.90 (d, J=2.4 Hz, 1H), 7.80-7.77 (m, 1H), 7.73-7.67 (m, 2H), 7.40 (dd, J=7.6, 1.6 Hz, 1H), 7.12 (t, J=7.6 Hz, 1H), 3.50-3.48 (m, 4H), 3.34-3.24 (m, 4H), 2.14 (s, 3H). LCMS: 404.2 (M+H)$^+$.

Example 65

1-(2'-Hydroxy-3'-(3-(piperazin-1-yl)isoxazol-5-yl)-[1,1'-biphenyl]-4-yl)-3-methylimidazolidin-2-one 2,2,2-trifluoroacetate

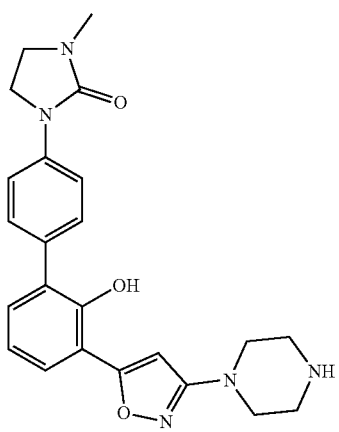 [SMILES: CN1CCN(c2ccc(-c3cccc(-c4cc(N5CCNCC5)no4)c3O)cc2)C1=O]

Step 1: tert-Butyl 4-(5-(2-methoxy-4'-(3-methyl-2-oxoimidazolidin-1-yl)-[1,1'-biphenyl]-3-yl)isoxazol-3-yl)piperazine-1-carboxylate A mixture of tert-butyl 4-(5-(3-bromo-2-methoxyphenyl)isoxazol-3-yl)piperazine-1-carboxylate (100 mg, 0.229 mmol), 1-methyl-3-(4-(4,4,5,5-tetramethyl-1,3,2-dioxaborolan-2-yl)phenyl)imidazolidin-2-one (173 mg, 0.573 mmol), K$_3$PO$_4$ (41 mg, 0.057 mmol) and Pd(dppf)Cl$_2$ (145 mg, 0.687 mmol) in dioxane:water (10:1, 4.95 mL) was stirred at 105° C. under N$_2$ overnight. After the reaction was complete by LCMS and TLC, the reaction mixture was diluted with DCM and filtrated to afford a residue which was purified by silica gel chromatography using petroleum ether and ethyl acetate (1:1) as the eluent to afford the title compound (70.0 mg, 57% yield) as a white solid. LCMS: 534.2 (M+H)$^+$.

Step 2: 1-(2'-Hydroxy-3'-(3-(piperazin-1-yl)isoxazol-5-yl)-[1,1'-biphenyl]-4-yl)-3-methylimidazolidin-2-one 2,2,2-trifluoroacetate To a solution of tert-butyl 4-(5-(2-hydroxy-4'-(3-methyl-2-oxoimidazolidin-1-yl)-[1,1'-biphenyl]-3-yl)isoxazol-3-yl)piperazine-1-carboxylate (65 mg, 0.12 mmol) in DCM (4 mL) was added BBr$_3$ in DCM (2 mL). The reaction mixture was stirred at 0° C. under nitrogen atmosphere overnight. After the reaction was indicated by LCMS, the reaction was quenched with MeOH and NaHCO$_3$ was added until no bubble was seen. The resulting mixture was filtrated. The solution was concentrated and purified by prep-HPLC using acetonitrile in water in the presence of TFA to afford TFA salt of the title compound (1.42 mg, 2% yield) as a white solid. $^1$H NMR (400 MHz, DMSO-d$_6$): 9.16 (br s, 1H), 8.80 (br s, 2H), 7.65 (br s, 3H), 7.46 (d, J=7.6 Hz, 2H), 7.32 (d, J=7.2 Hz, 1H), 7.08 (t, J=7.6 Hz, 1H), 6.74 (s, 1H), 3.85-3.82 (m, 2H), 3.48-3.35 (m, 6H), 3.33-3.24 (m, 4H), 2.79 (s, 3H). LCMS: 420.2 (M+H)$^+$.

Example 66

2-Fluoro-N-(2'-hydroxy-3'-(3-(piperazin-1-yl)isoxazol-5-yl)-[1,1'-biphenyl]-4-yl)acetamide 2,2,2-trifluoroacetate

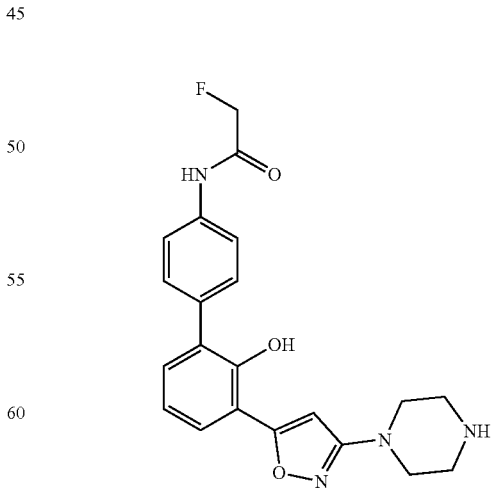

The title compound was prepared following the procedures described for Example 39, using tert-butyl 4-(5-(4'-amino-2-methoxy-[1,1'-biphenyl]-3-yl)isoxazol-3-yl)piperazine-1-carboxylate and 2-fluoroacetic acid in the presence of HATU and TEA to afford TFA salt of the title compound (23.5 mg, 43% yield) as a white solid. $^1$H NMR (400 MHz, DMSO-d$_6$): 10.20 (s, 1H), 9.22 (s, 1H), 8.80 (br s, 2H), 7.74 (d, J=8.8 Hz, 2H), 7.66 (dd, J=8.4, 2.0 Hz, 1H), 7.47 (d, J=8.4 Hz, 2H), 7.32 (dd, J=7.6, 1.6 Hz, 1H), 7.09 (t, J=7.6 Hz, 1H), 6.74 (s, 1H), 5.08 (s, 1H), 4.96 (s, 1H), 3.50-3.47 (m, 4H), 3.30-3.20 (m, 4H). LCMS: 397.2 (M+H)$^+$.

Example 67

N-(3-Fluoro-2'-hydroxy-3'-(pyridin-4-yl)-[1,1'-biphenyl]-4-yl)acetamide

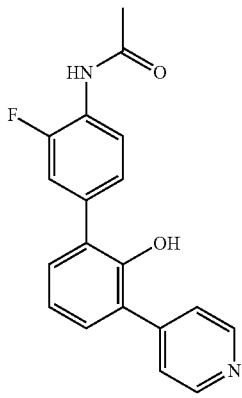 [SMILES: CC(=O)Nc1ccc(-c2cccc(-c3ccncc3)c2O)cc1F]

The title compound was prepared following the procedures described for Example 42, using pyridin-4-ylboronic acid and N-(3'-bromo-3-fluoro-2'-hydroxy-[1,1'-biphenyl]-4-yl)acetamide to afford the title compound (24% yield) as a white solid. $^1$H NMR (400 MHz, DMSO-d$_6$): 9.79 (s, 1H), 8.74 (s, 1H), 8.61 (d, J=6.4 Hz, 2H), 7.94 (t, J=8.4 Hz, 1H), 7.56 (d, J=6.0 Hz, 2H), 7.42 (dd, J=12.0, 1.6 Hz, 1H), 7.32-7.30 (m, 2H), 7.08 (t, J=7.6 Hz, 1H), 2.11 (s, 3H). LCMS: 323.1 (M+H)$^+$.

Example 68

N-(2'-Hydroxy-3-phenoxy-3'-(3-(piperazin-1-yl)isoxazol-5-yl)-[1,1'-biphenyl]-4-yl)acetamide 2,2,2-trifluoroacetate

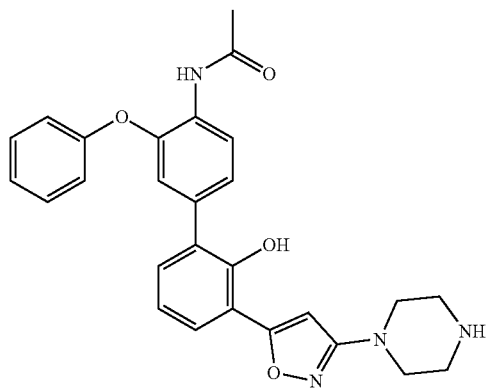 [SMILES: CC(=O)Nc1ccc(-c2cccc(-c3cc(N4CCNCC4)no3)c2O)cc1Oc1ccccc1]

The title compound was prepared following the procedures described for Example 19, using N-(2-phenoxy-4-(4,4,5,5-tetramethyl-1,3,2-dioxaborolan-2-yl)phenyl)acetamide (prepared from N-(4-bromo-2-phenoxyphenyl)acetamide and [4,4,4',4',5,5,5',5'-octamethyl-2,2'-bi(1,3,2-dioxaborolane)] and tert-butyl 4-(5-(3-bromo-2-methoxyphenyl)isoxazol-3-yl)piperazine-1-carboxylate followed by reaction with BBr$_3$ in DCM to afford the title compound (58% yield) as a white solid. $^1$H NMR (400 MHz, DMSO-d$_6$): 9.55 (s, 1H), 9.28 (s, 1H), 8.77 (br s, 2H), 8.10 (d, J=8.4 Hz, 1H), 7.64 (dd, J=8.0, 2.0 Hz, 1H), 7.40-7.36 (m, 2H), 7.30-7.24 (m, 2H), 7.14-7.10 (m, 1H), 7.10-7.02 (m, 4H), 6.71 (s, 1H), 3.48-3.46 (m, 4H), 3.30-3.20 (m, 4H), 2.05 (s, 3H). LCMS: 471.2 (M+H)$^+$.

TABLE 7

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 69 | Ethyl 4''-acetamido-3''-fluoro-2'-hydroxy-[1,1':3',1''-terphenyl]-4-carboxylate | $^1$H NMR (400 MHz, DMSO-d$_6$): 9.78 (s, 1H), 8.60 (s, 1H), 8.01 (d, J = 8.4 Hz, 2H), 7.94 (t, J = 8.0 | 394.1 |

TABLE 7-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| | 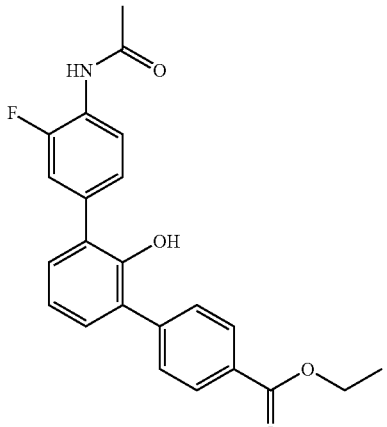 | Hz, 1H), 7.69 (d, J = 8.4 Hz, 2H), 7.42 (dd, J = 12.0, 2.0 Hz, 1H), 7.33-7.26 (m, 3H), 7.06 (t, J = 7.6 Hz, 1H), 4.35 (q, J = 7.2 Hz, 2H), 2.13 (s, 3H), 1.34 (t, J = 7.2 Hz, 3H) | |
| 70 | Ethyl 4''-acetamido-3''-fluoro-2'-hydroxy-[1,1':3',1''-terphenyl]-3-carboxylate | $^1$H NMR (400 MHz, DMSO-$d_6$): 9.78 (s, 1H), 8.56 (s, 1H), 8.12 (s, 1H), 7.96-7.93 (m, 2H), 7.79 (d, J = 7.6 Hz, 1H), 7.59 (t, J = 8.0 Hz, 1H), 7.42 (dd, J = 12.0, 1.6 Hz, 1H), 7.33-7.25 (m, 3H), 7.06 (t, J = 7.6 Hz, 1H), 4.35 (q, J = 7.2 Hz, 2H), 2.11 (s, 3H), 1.34 (t, J = 7.2 Hz, 3H) | 394.1 |
| 71 | N-(4''-ethoxy-3-fluoro-2'-hydroxy-[1,1':3',1''-terphenyl]-4-yl)acetamide | $^1$H NMR (400 MHz, DMSO-$d_6$): 9.76 (s, 1H), 8.28 (s, 1H), 7.92 (t, J = 8.4 Hz, 1H), 7.46-7.39 (m, 3H), 7.30 (d, J = 8.4 Hz, 1H), 7.21-7.17 (m, 2H), 7.01-6.97 (m, 3H), 4.06 (q, J = 7.2 Hz, 2H), 2.11 (s, 3H), 1.35 (t, J = 7.2 Hz, 3H) | 366.1 |

TABLE 7-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| 72 | N-(3''-Ethoxy-3-fluoro-2'-hydroxy-[1,1':3',1''-terphenyl]-4-yl)acetamide | $^1$H NMR (400 MHz, DMSO-d$_6$): 9.77 (s, 1H), 8.37 (s, 1H), 7.99-7.89 (m, 1H), 7.42 (dd, J = 12.0, 1.2 Hz, 1H), 7.35-7.30 (m, 2H), 7.23 (t, J = 7.2 Hz, 2H), 7.08-7.06 (m, 2H), 7.03-6.99 (m, 1H), 6.91-6.89 (m, 1H), 4.06 (q, J = 7.2 Hz, 2H), 2.10 (s, 3H), 1.34 (t, J = 7.2 Hz, 3H) | 366.1 |
| 73 | N,N'-(3-(Cyclopentyloxy)-3''-fluoro-2'-hydroxy-[1,1':3',1''-terphenyl]-4,4''-diyl)diacetamide | $^1$H NMR (400 MHz, DMSO-d$_6$): 9.77 (s, 1H), 8.84 (s, 1H), 8.38 (s, 1H), 87.97-7.90 (m, 2H), 7.42 (dd, J = 12.0, 1.6 Hz, 1H), 7.30 (dd, J = 8.4, 1.6 Hz, 1H), 7.24-7.22 (m, 2H), 7.15 (d, J = 1.2 Hz, 1H), 7.04-6.99 (m, 2H), 4.88-4.85 (m, 1H), 2.11 (s, 6H), 1.94-1.86 (m, 4H), 1.78-1.74 (m, 2H), 1.59-1.56 (m, 2H) | 463.2 |
| 74 | N-(3-Fluoro-2'-hydroxy-4''-isopropyl-[1,1':3',1''-terphenyl]-4-yl)acetamide | $^1$H NMR (400 MHz, DMSO-d$_6$): 9.77 (s, 1H), 8.35 (s, 1H), 7.92 (t, J = 8.0 Hz, 1H), 7.43-7.30 (m, 5H), 7.25-7.20 (m, 3H), 7.04-7.00 (m, 1H), 2.95-2.92 (m, 1H), 2.11 (s, 3H), 1.25 (d, J = 6.8 Hz, 6H) | 364.1 |

TABLE 7-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| 75 | N-(3-Fluoro-2'-hydroxy-3''-isopropyl-[1,1':3',1''-terphenyl]-4-yl)acetamide | $^1$H NMR (400 MHz, DMSO-$d_6$): 9.77 (s, 1H), 8.34 (s, 1H), 7.94-7.90 (m, 1H), 7.47-7.39 (m, 3H), 7.32-7.30 (m, 3H), 7.23-7.19 (m, 2H), 7.03-6.99 (m, 1H), 2.96-2.89 (m, 1H), 2.11 (s, 3H), 1.24 (d, J = 6.8 Hz, 6H) | 364.1 |

Example 76

N-(5-(2-Hydroxy-3-(3-(piperazin-1-yl)isoxazol-5-yl)phenyl)pyridin-2-yl)acetamide 2,2,2-trifluoroacetate The title compound was prepared following the procedures described for Example 1, using N-(5-(4,4,5,5-tetramethyl-1,3,2-dioxaborolan-2-yl)pyridin-2-yl)acetamide and tert-butyl 4-(5-(3-bromo-2-methoxyphenyl)isoxazol-3-yl)piperazine-1-carboxylate to afford TFA salt the title compound (20% yield). DH NMR (400 MHz, DMSO-$d_6$): 10.60 (s, 1H), 9.41 (br s, 1H), 8.85 (s, 2H), 8.42 (d, J=1.6 Hz, 1H), 8.16-8.14 (m, 1H), 7.91-7.89 (m, 1H), 7.72-7.70 (m, 1H), 7.39-7.37 (m, 1H), 7.14-7.10 (n, 1H), 6.77 (s, 1H), 3.50-3.48 (m, 3H), 3.24 (s, 4H), 2.13 (s, 3H). LCMS: 380.2 (M+H).

TABLE 8

Following compounds were prepared as described for Examples 42 using N-(4-bromo-2-fluorophenyl)acetamide or N-(3'-bromo-3-fluoro-2'-hydroxy-[1,1'-biphenyl]-4-yl)acetamide and a corresponding boronic ester or boronic acid (See preparation in Scheme 3).

| Ex. No. | Structure | $^1$H NMR Data | LCMS (M + H)$^+$ |
|---|---|---|---|
| 77 | N-(3''-Chloro-3-fluoro-2'-hydroxy-[1,1':3',1''-terphenyl]-4-yl)acetamide | $^1$H NMR (400 MHz, DMSO-d$_6$): 9.76 (s, 1H), 8.55-8.53 (m, 1H), 7.94-7.90 (m, 1H), 7.62 (s, 1H), 7.50-7.23 (m, 7H), 7.99-7.97 (m, 1H), 2.11 (s, 3H) | 356.1 |
| 78 | N-(3-Fluoro-2'-hydroxy-3''-(trifluoromethyl)-[1,1':3',1''-terphenyl]-4-yl)acetamide | $^1$H NMR (400 MHz, DMSO-d$_6$): 9.78 (s, 1H), 7.87-7.69 (m, 5H), 7.48-7.45 (m, 1H), 7.31-7.28 (m, 3H), 7.06 (s, 1H), 2.11 (s, 3H) | 390.1 |
| 79 | N-(3''-Ethyl-3-fluoro-2'-hydroxy-[1,1':3',1''-terphenyl]-4-yl)acetamide | $^1$H NMR (400 MHz, DMSO-d$_6$): 9.76 (s, 1H), 8.47 (s, 1H), 7.89-7.85 (m, 1H), 7.54-7.51 (m, 1H), 7.41-7.15 (m, 7H), 6.86-6.84 (m, 1H), 2.67-2.62 (m, 2H), 2.10 (s, 3H), 1.24-1.20 (m, 3H) | 350.1 |

TABLE 8-continued

Following compounds were prepared as described for Examples 42 using N-(4-bromo-2-fluorophenyl)acetamide or N-(3'-bromo-3-fluoro-2'-hydroxy-[1,1'-biphenyl]-4-yl)acetamide and a corresponding boronic ester or boronic acid (See preparation in Scheme 3).

| Ex. No. | Structure | $^1$H NMR Data | LCMS $(M + H)^+$ |
|---|---|---|---|
| 81 | N-(4''-Chloro-3-fluoro-2'-hydroxy-[1,1':3',1''-terphenyl]-4-yl)acetamide | $^1$H NMR (400 MHz, DMSO-d$_6$): 9.77 (s, 1H), 8.50 (s, 1H), 7.93 (t, J = 8.4 Hz, 1H), 7.57-7.54 (m, 2H), 7.50-7.48 (m, 2H), 7.42-7.39 (m, 1H), 7.32-7.21 (m, 3H), 7.03 (t, J = 7.6 Hz, 1H), 2.11 (s, 3H) | 356.1 |
| 82 | N-(4''-Ethyl-3-fluoro-2'-hydroxy-[1,1':3',1''-terphenyl]-4-yl)acetamide | $^1$H NMR (400 MHz, DMSO-d$_6$): 9.76 (s, 1H), 8.33 (s, 1H), 7.94-7.90 (m, 1H), 7.46-7.39 (m, 3H), 7.32-7.19 (m, 5H), 7.03-6.99 (m, 1H), 2.68-2.62 (m, 2H), 2.11 (s, 3H), 1.22 (t, J = 7.6 Hz, 3H) | 350.1 |
| 83 | N-(3-Fluoro-2'-hydroxy-4''-(trifluoromethyl)-[1,1':3',1''-terphenyl]-4-yl)acetamide | $^1$H NMR (400 MHz, DMSO-d$_6$): 9.80 (s, 1H), 8.64 (s, 1H), 7.79-7.77 (m, 5H), 7.31-7.27 (m, 4H), 7.06 (s, 1H), 2.11 (s, 3H) | 390.1 |

Example 84

N-(3,5'-Difluoro-2'-hydroxy-3'-(1-(1-methylpiperidin-4-yl)-1H-pyrazol-4-yl)-[1,1'-biphenyl]-4-yl)acetamide

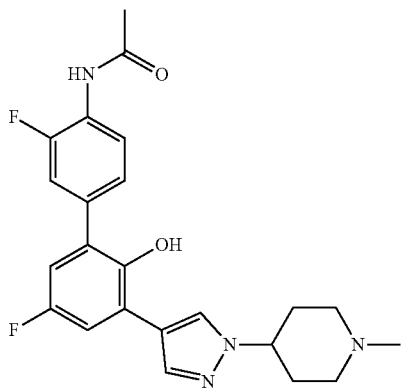 [SMILES: CC(=O)Nc1ccc(-c2cc(F)cc(-c3cnn(C4CCN(C)CC4)c3)c2O)cc1F]

The title compound was prepared following the procedures described for Example 35, using 1-methyl-4-(4-(4,4,5,5-tetramethyl-1,3,2-dioxaborolan-2-yl)-1H-pyrazol-1-yl)piperidine and N-(3'-bromo-3,5'-difluoro-2'-hydroxy-[1,1'-biphenyl]-4-yl)acetamide to afford the title compound. $^1$H NMR (400 MHz, DMSO-d$_6$): 9.75 (s, 1H), 8.31 (s, 2H), 7.95-7.88 (m, 2H), 7.36-7.30 (m, 3H), 6.93-6.90 (m, 1H), 4.12-4.08 (m, 1H), 2.87-2.84 (m, 2H), 2.20 (s, 3H), 2.10-1.93 (m, 9H). LCMS: 427.2 (M+H)$^+$.

Example 85

N-(3-Fluoro-2'-hydroxy-3'-(2-phenyloxazol-5-yl)-[1,1'-biphenyl]-4-yl)acetamide

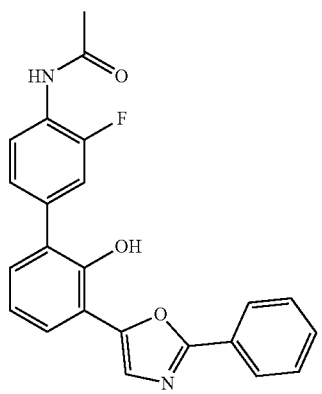 [SMILES: CC(=O)Nc1ccc(-c2cccc(-c3cnc(-c4ccccc4)o3)c2O)cc1F]

Step 1: 5-(3-Bromo-2-methoxyphenyl)-2-phenyloxazole

To a solution of 1-(3-bromo-2-methoxyphenyl)ethanone (1.6 g, 7.0 mmol) and 2-amino-2-phenylacetic acid (1.27 g, 8.4 mmol) in DMSO (40 mL) was added p-ABS (606 mg, 3.5 mmol) and I$_2$ (3.55 g, 14.0 mmol). The reaction mixture was stirred at 100° C. 5 hours under nitrogen atmosphere. After the reaction was indicated by LCMS, the reaction mixture was quenched with sat'd Na$_2$S$_2$O$_3$ and extracted with EA (80 mL×3). The combined organic layers were washed with brine, dried over sodium sulfate, filtered and concentrated under reduced pressure to afford a residue which was purified by silica gel chromatography using petroleum ether and ethyl acetate (6:1) as the eluent to afford the title compound (1.8 g, 78% yield) as a yellow solid. LCMS: 330.0 (M+H)$^+$.

Step 2: N-(3-Fluoro-2'-methoxy-3'-(2-phenyloxazol-5-yl)-[1,1'-biphenyl]-4-yl)acetamide The title compound was prepared following the procedure described for Example 54 using 5-(3-bromo-2-methoxyphenyl)-2-phenyloxazole and N-(2-fluoro-4-(4,4,5,5-tetramethyl-1,3,2-dioxaborolan-2-yl)phenyl)acetamide to afford the title compound (83% yield). LCMS: 403.1 (M+H)$^+$.

Step 3: N-(3-Fluoro-2'-hydroxy-3'-(2-phenyloxazol-5-yl)-[1,1'-biphenyl]-4-yl)acetamide The title compound was prepared following the procedure described for Example 65 using N-(3-fluoro-2'-methoxy-3'-(2-phenyloxazol-5-yl)-[1,1'-biphenyl]-4-yl)acetamide to afford the title compound (53.6% yield). $^1$H NMR (400 MHz, DMSO-d$_6$): 9.82 (s, 1H), 8.35 (s, 1H), 8.13 (d, J=1.6 Hz, 2H), 8.11 (t, J=0.8 Hz, 1H), 7.99-7.85 (m, 1H), 7.72 (s, 1H), 7.60-7.55 (m, 3H), 7.42-7.27 (m, 3H), 7.13 (t, J=7.2 Hz, 1H), 2.13 (s, 3H). LCMS: 389.1 (M+H)$^+$.

Example 86

N-(3,5-Difluoro-2'-hydroxy-3'-(3-(piperazin-1-yl)isoxazol-5-yl)-[1,1'-biphenyl]-4-yl)acetamide 2,2,2-trifluoroacetate

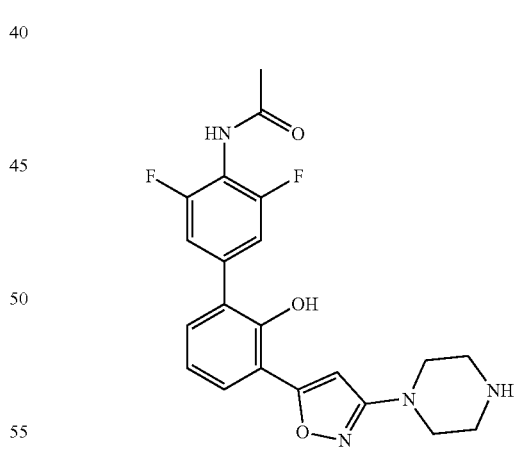

The title compound was prepared following the procedures described for Example 1 using tert-butyl 4-(5-(3-bromo-2-hydroxyphenyl)isoxazol-3-yl)piperazine-1-carboxylate and N-(2,6-difluoro-4-(4,4,5,5-tetramethyl-1,3,2-dioxaborolan-2-yl)phenyl)acetamide afford the title compound (50% yield). $^1$H NMR (400 MHz, DMSO-d$_6$): 9.75 (s, 1H), 9.56 (s, 1H), 8.84 (s, 2H), 7.72 (d, J=6.8 Hz, 1H), 7.42-7.40 (m, 1H), 7.28 (d, J=8.8 Hz, 2H), 7.12 (t, J=7.6 Hz, 1H), 6.77 (s, 1H), 3.50-3.47 (m, 4H), 3.24 (s, 4H), 2.09 (s, 3H). LCMS: 415.1 (M+H)$^+$.

Example 87

N,N'-(3-Fluoro-2'-hydroxy-3"-isopropoxy-[1,1':3',1"-terphenyl]-4,4"-diyl)diacetamide

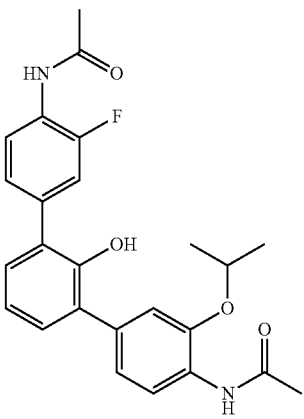 [SMILES: CC(=O)Nc1ccc(-c2cccc(-c3ccc(NC(C)=O)c(OC(C)C)c3)c2O)cc1F]

The title compound was prepared following the procedures described for Example 42 using N-(3'-bromo-3-fluoro-2'-hydroxy-[1,1'-biphenyl]-4-yl)acetamide and N-(2-isopropoxy-4-(4,4,5,5-tetramethyl-1,3,2-dioxaborolan-2-yl)phenyl)acetamide afford the title compound (29% yield). $^1$H NMR (400 MHz, DMSO-$d_6$): 9.76 (s, 1H), 8.88 (s, 1H), 8.38 (s, 1H), 8.01-7.89 (m, 2H), 7.42 (d, J=12.4 Hz, 1H), 7.32-7.29 (m, 1H), 7.24-7.18 (m, 3H), 7.04-6.98 (m, 2H), 4.66-4.60 (m, 1H), 2.12-2.07 (m, 6H), 1.33 (d, J=6.0 Hz, 6H). LCMS: 437.2 (M+H)$^+$.

Example 88

N,N'-(3-Ethyl-3"-fluoro-2'-hydroxy-[1,1':3',1"-terphenyl]-4,4"-diyl)diacetamide

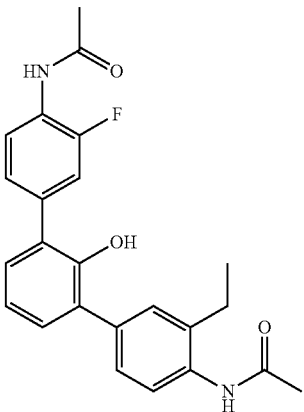 [SMILES: CCc1cc(-c2cccc(-c3ccc(NC(C)=O)c(F)c3)c2O)ccc1NC(C)=O]

The title compound was prepared following the procedures described for Example 42 using N-(2-ethyl-4-(4,4,5,5-tetramethyl-1,3,2-dioxaborolan-2-yl)phenyl)acetamide [prepared from N-(4-bromo-2-ethylphenyl)acetamide and 4,4,4',4',5,5,5',5'-octamethyl-2,2'-bi(1,3,2-dioxaborolane)] and N-(3'-bromo-3-fluoro-2'-hydroxy-[1,1'-biphenyl]-4-yl)acetamide afford the title compound (44% yield). $^1$H NMR (400 MHz, DMSO-$d_6$): 9.76 (s, 1H), 9.30 (s, 1H), 8.40 (s, 1H), 7.94-7.90 (m, 1H), 7.42-7.38 (m, 3H), 7.33-7.30 (m, 2H), 7.23-7.21 (m, 2H), 7.03-6.99 (m, 1H), 2.66-2.61 (m, 2H), 2.11-2.07 (m, 6H), 1.23-1.14 (m, 3H). LCMS: 407.1 (M+H)$^+$.

Example 89

N-(3-(Cyclopentyloxy)-2'-hydroxy-3'-(3-(piperazin-1-yl)isoxazol-5-yl)-[1,1'-biphenyl]-4-yl)acetamide 2,2,2-trifluoroacetate

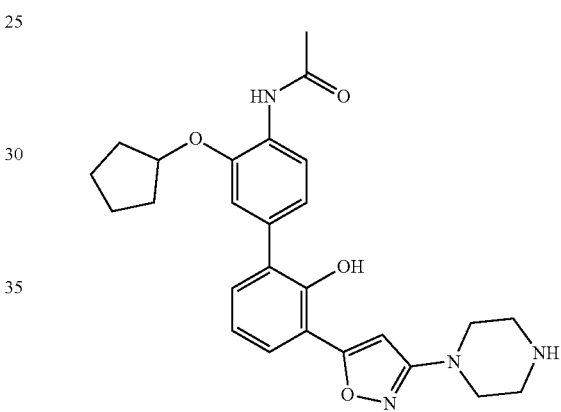

The title compound was prepared following the procedures described for Example 19, using N-(2-cyclopentyloxy-4-(4,4,5,5-tetramethyl-1,3,2-dioxaborolan-2-yl)phenyl) acetamide [prepared from 4-bromo-2-fluoro-1-nitrobenzene, cyclopentanol and 4,4,4',4',5,5,5',5'-octamethyl-2,2'-bi(1,3,2-dioxaborolane)] and 2-bromo-6-(3-(piperazin-1-yl)isoxazol-5-yl)phenol to afford the title compound (20% yield) as a white solid. $^1$H NMR (400 MHz, DMSO-$d_6$): 9.23 (s, 1H), 8.87-8.85 (m, 3H), 8.01 (d, J=8.4 Hz, 1H), 7.68-7.66 (m, 1H), 7.35-7.33 (m, 1H), 7.11-7.06 (m, 2H), 7.02-7.00 (m, 1H), 6.73 (s, 1H), 4.89-4.86 (m, 1H), 3.50-3.47 (m, 4H), 3.24 (s, 4H), 2.12 (s, 3H), 1.92-1.85 (m, 4H), 1.79-1.75 (m, 2H), 1.61-1.56 (m, 2H). LCMS: 463.2 (M+H)$^+$.

TABLE 9

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | ¹H NMR Data | LCMS (M + H)⁺ |
|---|---|---|---|
| 90 | N-(3-Fluoro-2'-hydroxy-4''-phenoxy-[1,1':3',1''-terphenyl]-4-yl)acetamide | ¹H NMR (400 MHz, DMSO-d₆): 9.77 (s, 1H), 8.41 (s, 1H), 7.95-7.91 (m, 1H), 7.54 (d, J = 8.8 Hz, 2H), 7.44-7.40 (m, 3H), 7.33-7.30 (m, 1H), 7.24-7.07 (m, 3H), 7.05-7.00 (m, 5H), 2.50 (s, 3H) | 414.1 |
| 91 | N-(3-Fluoro-2'-hydroxy-3''-phenoxy-[1,1':3',1''-terphenyl]-4-yl)acetamide | ¹H NMR (400 MHz, DMSO-d₆): 9.76 (s, 1H), 8.48 (s, 1H), 7.94-7.90 (m, 1H), 7.47-7.38 (m, 4H), 7.31-6.97 (m, 10H), 2.11 (s, 3H) | 414.1 |
| 92 | 4''-Acetamido-N-ethyl-3''-fluoro-2'-hydroxy-[1,1':3',1''-terphenyl]-4-carboxamide | ¹H NMR (400 MHz, DMSO-d₆): 9.78 (s, 1H), 8.52-8.47 (m, 2H), 7.95-7.89 (m, 3H), 7.63-7.61 (m, 2H), 7.44-7.41 (m, 1H), 7.33-7.25 (m, 3H), 7.06-7.02 (m, 1H), 3.34-3.28 (m, 2H), 2.11 (s, 3H), 1.16-1.12 (m, 3H) | 393.2 |

TABLE 9-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| 93 | 4"-Acetamido-N-ethyl-3"-fluoro-2'-hydroxy-[1,1':3',1"-terphenyl]-3-carboxamide | $^1$H NMR (400 MHz, DMSO-d$_6$): 9.79 (s, 1H), 8.49 (d, J = 6.8 Hz, 2H), 7.99-7.91 (m, 2H), 7.82-7.80 (m, 1H), 7.68-7.66 (m, 1H), 7.53-7.40 (m, 2H), 7.33-7.26 (m, 3H), 7.07-7.03 (m, 1H), 3.34-3.27 (m, 2H), 2.11 (s, 3H), 1.15-1.11 (m, 3H) | 393.1 |
| 94 | N-(3-Fluoro-2'-hydroxy-4"-morpholino-[1,1':3',1"-terphenyl]-4-yl)acetamide | $^1$H NMR (400 MHz, DMSO-d$_6$): 9.76 (s, 1H), 8.24 (s, 1H), 7.91 (s, 1H), 7.43-7.38 (m, 3H), 7.31-7.29 (m, 1H), 7.19-7.17 (m, 2H), 7.02-6.96 (m, 3H), 3.77-3.75 (m, 4H), 3.16-3.14 (m, 4H), 2.11 (s, 3H) | 407.2 |
| 95 | N-(3-Fluoro-2'-hydroxy-3"-morpholino-[1,1':3',1"-terphenyl]-4-yl)acetamide | $^1$H NMR (400 MHz, DMSO-d$_6$): 9.77 (s, 1H), 8.29 (s, 1H), 7.94-7.89 (m, 1H), 7.43-7.40 (m, 1H), 7.32-7.20 (m, 4H), 7.06-6.92 (m, 4H), 3.76-3.73 (m, 4H), 3.15-3.13 (m, 4H), 2.11 (s, 3H) | 407.2 |

TABLE 9-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 96 | N,N'-(3-Fluoro-2'-hydroxy-3''-isopropyl-[1,1':3',1''-terphenyl]-4,4'' diyl)diacetamide | $^1$H NMR (400 MHz, DMSO-d$_6$): 9.77 (s, 1H), 9.35 (s, 1H), 8.42 (s, 1H), 7.92 (t, J = 8.4 Hz, 1H), 7.44-7.39 (m, 2H), 7.34-7.21 (m, 5H), 7.04-7.00 (m, 1H), 3.22-3.18 (m, 1H), 2.09 (d, J = 15.2 Hz, 6H), 1.19-1.17 (m, 6H) | 421.2 |
| 97 | N-(3-Fluoro-2'-hydroxy-3'-(2-methoxypyridin-4-yl)-[1,1'-biphenyl]-4-yl)acetamide | $^1$H NMR (400 MHz, DMSO-d$_6$): 9.77 (s, 1H), 8.43 (s, 1H), 8.36 (s, 1H), 8.25 (d, J = 4.4 Hz, 1H), 7.93-7.89 (m, 1H), 7.41 (dd, J = 12.0, 1.6 Hz, 1H), 7.33-7.26 (m, 3H), 7.12-7.10 (m, 1H), 7.01-6.97 (m, 1H), 3.86 (s, 3H), 2.11 (s, 3H) | 353.1 |
| 98 | N-(3-Fluoro-2'-hydroxy-3'-(6-methoxypyridin-3-yl)-[1,1'-biphenyl]-4-yl)acetamide | $^1$H NMR (400 MHz, DMSO-d$_6$): 9.78 (s, 1H), 8.52 (s, 1H), 8.28 (d, J = 1.6 Hz, 1H), 7.95-7.85 (m, 2H), 7.43-7.40 (m, 1H), 7.32-7.23 (m, 3H), 7.05-7.01 (m, 1H), 6.88 (d, J = 8.4 Hz, 1H), 3.89 (s, 3H), 2.11 (s, 3H) | 353.1 |

TABLE 9-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | ¹H NMR Data | LCMS (M + H)⁺ |
|---|---|---|---|
| 99 | N,N'-(3-Fluoro-2'-hydroxy-[1,1':3',1''-terphenyl]-4,4''-diyl)diacetamide 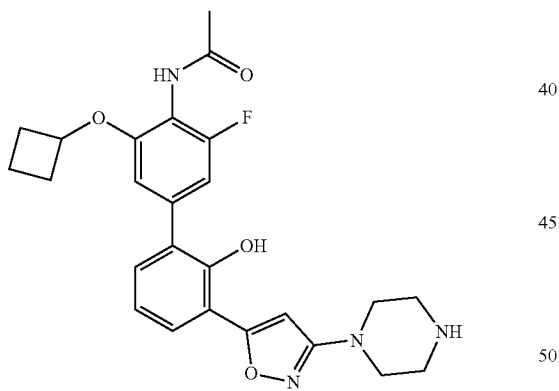 | ¹H NMR (400 MHz, DMSO-$d_6$): 9.98 (s, 1H), 9.76 (s, 1H), 8.33 (s, 1H), 7.94-7.90 (m, 1H), 7.63 (d, J = 8.8 Hz, 2H), 7.47-7.39 (m, 3H), 7.32-7.29 (m, 1H), 7.22-7.18 (m, 2H), 7.02-6.98 (m, 1H), 2.06 (s, 6H) | 379.1 |

Example 100

N-(3-Cyclobutoxy-5-fluoro-2'-hydroxy-3'-(3-(piperazin-1-yl)isoxazol-5-yl)-[1,1'-biphenyl]-4-yl)acetamide The title compound was prepared following the procedures described for Example 19, using N-(2-cyclobutoxy-6-fluoro-4-(4,4,5,5-tetramethyl-1,3,2-dioxaborolan-2-yl)phenyl)acetamide [prepared from N-(4-bromo-2-cyclobutoxy-6-fluorophenyl)acetamide and 4,4,4',4',5,5,5',5'-octamethyl-2,2'-bi(1,3,2-dioxaborolane)] and 2-bromo-6-(3-(piperazin-1-yl)isoxazol-5-yl)phenol to afford the title compound (12% yield) as a pale yellow solid. ¹H NMR (400 MHz, DMSO-$d_6$-TFA salt): 9.46 (s, 1H), 9.27 (s, 1H), 8.80 (s, 2H), 7.70 (dd, J=7.6, 1.6 Hz, 1H), 7.38 (dd, J=7.2, 1.2 Hz, 1H), 7.12-7.08 (m, 1H), 6.96-6.93 (m, 1H), 6.82 (s, 1H), 6.74 (s, 1H), 4.80-4.76 (m, 1H), 3.50-3.47 (m, 4H), 3.24 (s, 4H), 2.45-2.38 (m, 2H), 2.10-2.05 (m, 5H), 1.79-1.76 (m, 1H), 1.63-1.61 (m, 1H). LCMS: 467.2 (M+H)⁺.

TABLE 10

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | ¹H NMR Data | LCMS (M + H)⁺ |
|---|---|---|---|
| 101 | N-(3'-(1-Acetyl-1,2,3,4-tetrahydroquinolin-6-yl)-3-fluoro-2'-hydroxy-[1,1'-biphenyl]-4-yl)acetamide | ¹H NMR (400 MHz, DMSO-d₆): 9.77 (s, 1H), 9.39 (s, 1H), 7.92 (t, J = 8.4 Hz, 1H), 7.52-7.30 (m, 5H), 7.24-7.21 (m, 2H), 7.03-6.99 (m, 1H), 3.73-3.69 (m, 2H), 2.75 (t, J = 6.4 Hz, 2H), 2.21 (s, 3H), 2.11 (s, 3H), 1.94-1.87 (m, 2H) | 419.2 |
| 102 | N-(3-Fluoro-2'-hydroxy-3'-(pyridazin-4-yl)-[1,1'-biphenyl]-4-yl)acetamide | ¹H NMR (400 MHz, DMSO-d₆): 9.77 (s, 1H), 9.46 (d, J = 1.2 Hz, 1H), 9.25-9.24 (m, 2H), 7.97-7.87 (m, 2H), 7.46-7.31 (m, 4H), 7.10-7.06 (m, 1H), 2.11 (s, 3H) | 324.1 |
| 103 | N-(3-Fluoro-2'-hydroxy-3'-(pyrimidin-5-yl)-[1,1'-biphenyl]-4-yl)acetamide | ¹H NMR (400 MHz, DMSO-d₆): 9.79 (s, 1H), 9.15 (s, 1H), 8.96 (s, 2H), 8.90 (s, 1H), 7.95 (s, 1H), 7.45-7.31 (m, 4H), 7.12-7.10 (m, 1H), 2.11 (s, 3H) | 324.1 |

TABLE 10-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | ¹H NMR Data | LCMS (M + H)⁺ |
|---|---|---|---|
| 104 | N-(3'-(5-Acetyl-2,3,4,5-tetrahydrobenzo[b][1,4]oxazepin-8-yl)-3-fluoro-2'-hydroxy-[1,1'-biphenyl]-4-yl)acetamide 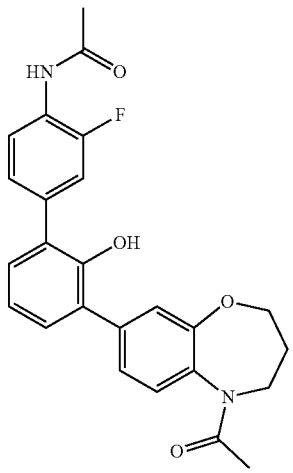 [SMILES: CC(=O)Nc1ccc(-c2cccc(-c3ccc4c(c3)OCCCN4C(C)=O)c2O)cc1F] | ¹H NMR (400 MHz, CD₃OD): 8.02-7.97 (m, 1H), 7.46-7.39 (m, 5H), 7.36-7.31 (m, 2H), 7.12-7.08 (m, 1H), 4.84-4.82 (m, 1H), 4.51-4.48 (m, 1H), 3.88-3.86 (m, 1H), 2.93-2.91 (m, 1H), 2.41 (s, 4H), 2.02 (s, 3H), 1.91-1.86 (m, 1H) | 435.2 |

Example 105

N-(3'-(3-(4-Benzoylpiperazin-1-yl)isoxazol-5-yl)-2'-hydroxy-[1,1'-biphenyl]-4-yl)acetamide

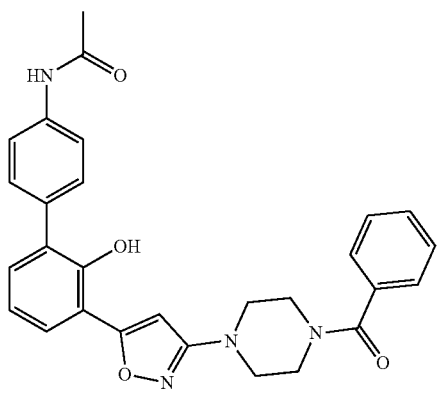 [SMILES: CC(=O)Nc1ccc(-c2cccc(-c3cc(N4CCN(C(=O)c5ccccc5)CC4)no3)c2O)cc1]

Step 1: N-(2'-Methoxy-3'-(3-(piperazin-1-yl)isoxazol-5-yl)-[1,1'-biphenyl]-4-yl)acetamide A solution of tert-butyl 4-(5-(4'-acetamido-2-methoxy-[1,1'-biphenyl]-3-yl)isoxazol-3-yl)piperazine-1-carboxylate (100 mg, 0.200 mmol) in 4 N HCl in Dioxane (6 mL) was stirred at room temperature for 3 hours under N₂. After the reaction mixture was complete by LCMS, the reaction mixture was concentrated under reduced pressure to afford the title compound (78 mg, 100%) as a white solid. LCMS: 393.2 (M+H)⁺.

Step 2: N-(3'-(3-(4-Benzoylpiperazin-1-yl)isoxazol-5-yl)-2'-methoxy-[1,1'-biphenyl]-4-yl)acetamide To a solution of N-(2'-methoxy-3'-(3-(piperazin-1-yl)isoxazol-5-yl)-[1,1'-biphenyl]-4-yl)acetamide (78 mg, 0.20 mmol) in DCM (2 mL) was TEA (64 mg, 0.60 mmol) and benzoyl chloride (28 mg, 0.20 mmol) at 0° C. The reaction mixture was stirred at room temperature for 16 hours under N₂. After the reaction mixture was complete by LCMS, the reaction mixture was concentrated under reduced pressure. The residue was purified by silica gel chromatography using petroleum ether and ethyl acetate (1:1) as the eluent to afford the title compound (40 mg, 40%) as a white solid. LCMS: 497.3 (M+H)⁺.

Step 3: N-(3'-(3-(4-Benzoylpiperazin-1-yl)isoxazol-5-yl)-2'-hydroxy-[1,1'-biphenyl]-4-yl)acetamide The title compound was prepared following the procedure described for Example 1 using N-(3'-(3-(4-benzoylpiperazin-1-yl)isoxazol-5-yl)-2'-methoxy-[1,1'-biphenyl]-4-yl)acetamide and BBr₃ to afford the title compound (13% yield). 8H NMR (400 MHz, DMSO-d₆): 10.01 (s, 1H), 9.13 (s, 1H), 7.66-7.64 (m, 3H), 7.48-7.43 (m, 7H), 7.30-7.28 (m, 1H), 7.05 (t, J=8.0 Hz, 1H), 6.70 (s, 1H), 3.74-3.47 (m, 4H), 3.31-3.29 (m, 4H), 2.07 (s, 3H). LCMS: 483.2 (M+H)⁺.

TABLE 11

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| 106 | N-(3-Fluoro-2'-hydroxy-4''-isopropoxy-[1,1':3',1''-terphenyl]-4-yl)acetamide | $^1$H NMR (400 MHz, DMSO-$d_6$): 9.77 (s, 1H), 8.29 (s, 1H), 7.94-7.90 (m, 1H), 7.45-7.39 (m, 3H), 7.32-7.30 (m, 1H), 7.21-7.17 (m, 2H), 7.01-6.96 (m, 3H), 4.68-4.62 (m, 1H), 2.11 (s, 3H), 1.29 (d, J = 6.0 Hz, 6H) | 380.2 |
| 107 | N-(3-Fluoro-2'-hydroxy-3''-isopropoxy-[1,1':3',1''-terphenyl]-4-yl)acetamide | $^1$H NMR (400 MHz, DMSO-$d_6$): 9.77 (s, 1H), 8.37 (s, 1H), 7.92 (t, J = 8.4 Hz, 1H), 7.41 (dd, J = 12.0, 1.6 Hz, 1H), 7.34-7.30 (m, 2H), 7.25-7.21 (m, 2H), 7.06-6.90 (m, 3H), 6.89-6.87 (m, 1H), 4.67-4.61 (m, 1H), 2.11 (s, 3H), 1.29 (d, J = 6.0 Hz, 6H) | 380.2 |
| 108 | N-(3-Fluoro-2'-hydroxy-4''-(piperazin-1-yl)-[1,1':3',1''-terphenyl]-4-yl)acetamide | $^1$H NMR (400 MHz, DMSO-$d_6$): 9.76 (s, 1H), 8.17 (br s, 1H), 7.93-7.89 (m, 1H), 7.42-7.38 (m, 3H), 7.31-7.29 (m, 1H), 7.17 (d, J = 7.2 Hz, 2H), 7.00-6.96 (m, 3H), 3.10-3.07 (m, 4H), 2.86-2.83 (m, 4H), 2.11 (s, 3H). One N—H or O—H proton not observed. | 406.2 |

TABLE 11-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| 109 | N-(3-Fluoro-2'-hydroxy-3"-(piperazin-1-yl)-[1,1':3',1"-terphenyl]-4-yl)acetamide | $^1$H NMR (400 MHz, DMSO-d$_6$): 9.77 (s, 1H), 7.91 (t, J = 8.8 Hz, 1H), 7.42 (dd, J = 12.4, 1.6 Hz, 1H), 7.32-7.19 (m, 4H), 7.03-6.89 (m, 4H), 3.09-3.06 (m, 4H), 2.85-2.82 (m, 4H), 2.11 (s, 3H). Two N—H or O—H proton not observed. | 406.2 |
| 110 | N-(3'-(6-Aminopyridin-3-yl)-3-fluoro-2'-hydroxy-[1,1'-biphenyl]-4-yl)acetamide | $^1$H NMR (400 MHz, DMSO-d$_6$): 9.76 (s, 1H), 8.33 (br s, 1H), 8.07 (d, J = 2.0 Hz, 1H), 7.92-7.87 (m, 1H), 7.58-7.55 (m, 1H), 7.43 (d, J = 12.0 Hz, 1H), 7.31-7.29 (m, 1H), 7.18-7.14 (m, 2H), 6.97 (s, 1H), 6.49 (d, J = 8.4 Hz, 1H), 5.93 (s, 2H), 2.10 (s, 3H) | 338.1 |
| 111 | N-(3'-(2-Aminopyridin-4-yl)-3-fluoro-2'-hydroxy-[1,1'-biphenyl]-4-yl)acetamide | $^1$H NMR (400 MHz, DMSO-d$_6$): 9.77 (s, 1H), 8.53 (s, 1H), 7.94-7.92 (m, 2H), 7.41-7.37 (m, 1H), 7.31-7.26 (m, 2H), 7.21-7.18 (m, 2H), 6.64-6.61 (m, 2H), 5.89 (s, 2H), 2.11 (s, 3H) | 338.1 |

Example 112

N-(3-Fluoro-2'-hydroxy-3'-(2-(piperazin-1-yl)oxazol-5-yl)-[1,1'-biphenyl]-4-yl)acetamide

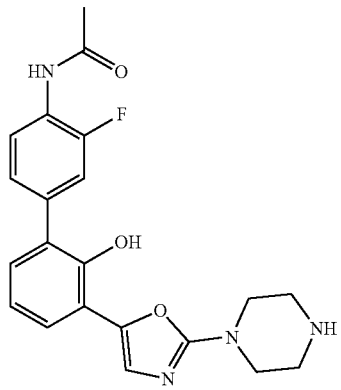 [SMILES: CC(=O)Nc1ccc(-c2cccc(-c3cnc(N4CCNCC4)o3)c2O)cc1F]

Step 1: 5-(3-Bromo-2-methoxyphenyl)oxazole

To a solution of 3-bromo-2-methoxybenzaldehyde (785 mg, 4.65 mmol) in MeOH (20 mL) was added $K_2CO_3$ (834 mg, 6.04 mmol) and Tosmic (785 mg, 5.12 mmol). The reaction mixture was stirred at room temperature for 16 hours under $N_2$. After the reaction was complete by LCMS, the reaction mixture was concentrated. The residue was diluted with $H_2O$ (50 mL) and extracted with EA (40 mL×3). The combined organic layers were washed with brine, dried over $Na_2SO_4$, filtered and concentrated to give the residue which was used for the next step without further purification (800 mg, 68% yield) as a pale yellow solid. LCMS: 254.0 (M+H)+.

Step 2: 5-(3-bromo-2-methoxyphenyl)-2-chlorooxazole

To a solution of 5-(3-bromo-2-methoxyphenyl)oxazole (800 mg, 3.15 mmol) in THF (20 mL) was added LiHMDS (3.46 mL, 3.46 mmol) at −78° C. dropwise. After the mixture was stirred for 30 min, $C_2Cl_6$ (1.49 g, 6.30 mmol) was added at −78° C. Then the reaction mixture was stirred at room temperature for 16 hours under $N_2$. After the reaction was complete by LCMS, the reaction mixture was quenched with sat $NH_4Cl$ solution and extracted with EA (40 mL×3). The combined organic layers were washed with brine, dried over $Na_2SO_4$, filtered and concentrated. The residue was purified by silica gel chromatography using petroleum ether and ethyl acetate (4:1) as the eluent to afford the title compound (590 mg, 65%) as a white solid. LCMS: 288.0 (M+H)+.

Step 3: tert-butyl 4-(5-(3-bromo-2-methoxyphenyl)oxazol-2-yl)piperazine-1-carboxylate To a solution of 5-(3-bromo-2-methoxyphenyl)-2-chlorooxazole (400 mg, 1.39 mmol) and tert-butyl piperazine-1-carboxylate (284 mg, 1.53 mmol) in dioxane (12 mL) was added DIPEA (358 mg, 2.78 mmol). The reaction mixture was stirred at 100° C. for 4 hours under $N_2$. After the reaction was complete by LCMS, the reaction mixture was concentrated. The residue was purified by silica gel chromatography using petroleum ether and ethyl acetate (4:1) as the eluent to afford the title compound (430 mg, 71%) as a pale yellow solid. LCMS: 438.1 (M+H)+.

Step 4: tert-butyl 4-(5-(4'-acetamido-3'-fluoro-2-methoxy-[1,1'-biphenyl]-3-yl)oxazol-2-yl)piperazine-1-carboxylate The title compound was prepared following the procedure described for Example 1 using tert-butyl 4-(5-(3-bromo-2-methoxyphenyl)oxazol-2-yl)piperazine-1-carboxylate and N-(2-fluoro-4-(4,4,5,5-tetramethyl-1,3,2-dioxaborolan-2-yl)phenyl)acetamide to afford the title compound (98% yield). LCMS: 511.3 (M+H)+.

Step 5: N-(3-fluoro-2'-hydroxy-3'-(2-(piperazin-1-yl)oxazol-5-yl)-[1,1'-biphenyl]-4-yl)acetamide The title compound was prepared following the procedure described for Example 1 using tert-butyl 4-(5-(4'-acetamido-3'-fluoro-2-methoxy-[1,1'-biphenyl]-3-yl)oxazol-2-yl)piperazine-1-carboxylate to afford the title compound (15% yield). $^1$H NMR (400 MHz, DMSO-$d_6$): δ 9.77 (s, 1H), 7.94 (t, J=8.0 Hz, 1H), 7.48 (d, J=7.6 Hz, 1H), 7.38 (d, J=12.0 Hz, 1H), 7.28-7.25 (m, 2H), 7.09 (d, J=6.4 Hz, 1H), 6.97 (d, J=6.4 Hz, 1H), 3.40 (t, J=4.4 Hz, 4H), 2.78 (t, J=4.8 Hz, 4H), 2.11 (s, 3H). N—H and O—H protons not observed. $^{19}$F NMR (376 MHz, DMSO-$d_6$): δ −125.33. LCMS: 397.2 (M+H)+.

Example 113

1-(3-Fluoro-2'-hydroxy-3'-(3-(piperazin-1-yl)isoxazol-5-yl)-[1,1'-biphenyl]-4-yl)pyrrolidin-2-one

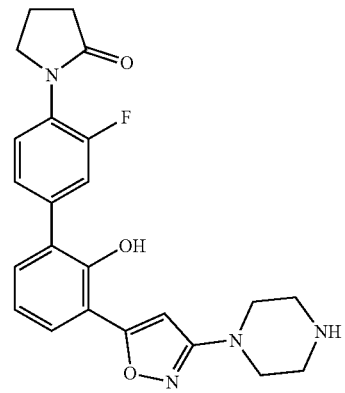 [SMILES: O=C1CCCN1c1ccc(-c2cccc(-c3cc(N4CCNCC4)no3)c2O)cc1F]

The title compound was prepared following the procedures described for Example 43 using tert-butyl 4-(5-(3-bromo-2-methoxyphenyl)isoxazol-3-yl)piperazine-1-carboxylate and 1-(2-fluoro-4-(4,4,5,5-tetramethyl-1,3,2-dioxaborolan-2-yl)phenyl)pyrrolidin-2-one to afford the title compound (22% yield). $^1$H NMR (400 MHz, DMSO-$d_6$): δ 7.66 (dd, J=7.6 Hz, 1.2 Hz, 1H), 7.52-7.45 (m, 2H), 7.39-7.34 (m, 2H), 7.03 (t, J=7.6 Hz, 1H), 6.67 (s, 1H), 3.79 (t, J=7.2 Hz, 2H), 3.16 (t, J=4.8 Hz, 4H), 2.80 (t, J=4.8 Hz, 4H), 2.47-2.43 (m, 2H), 2.16-2.12 (m, 2H). N—H and O—H proton not observed. $^{19}$F NMR (376 MHz, DMSO-$d_6$): δ −119.94. LCMS: 423.2 (M+H)+.

Example 114

N-(3"-Cyclobutoxy-3-fluoro-2'-hydroxy-[1,1':3',1"-terphenyl]-4-yl)acetamide

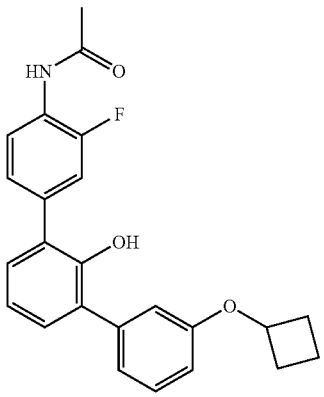 [SMILES: CC(=O)Nc1ccc(-c2cccc(-c3cccc(OC4CCC4)c3)c2O)cc1F]

The title compound was prepared following the procedures described for Example 42 using N-(3'-bromo-3-fluoro-2'-hydroxy-[1,1'-biphenyl]-4-yl)acetamide and 2-(3-cyclobutoxyphenyl)-4,4,5,5-tetramethyl-1,3,2-dioxaborolane [prepared from 1-bromo-3-cyclobutoxybenzene and 4,4,4',4',5,5,5',5'-octamethyl-2,2'-bi(1,3,2-dioxaborolane)] to afford the title compound (2% yield). $^1$H NMR (400 MHz, DMSO-$d_6$): δ 9.77 (s, 1H), 8.38 (s, 1H), 7.92 (t, J=8.0 Hz, 1H), 7.41 (dd, J=12.4 Hz, 1.2 Hz, 1H), 7.34-7.30 (m, 2H), 7.25-7.20 (m, 2H), 7.07 (d, J=7.6 Hz, 1H), 7.02-6.99 (m, 2H), 6.81 (dd, J=8.4 Hz, 2.0 Hz, 1H), 4.75-4.68 (m, 1H), 2.46-2.39 (m, 2H), 2.10 (s, 3H), 2.08-2.01 (m, 2H), 1.79-1.75 (m, 1H), 1.68-1.61 (m, 1H). N—H or O—H proton not observed. LCMS: 392.2 (M+H)$^+$.

Example 115

N-(3"-(Cyclopentyloxy)-3-fluoro-2'-hydroxy-[1,1':3',1"-terphenyl]-4-yl)acetamide

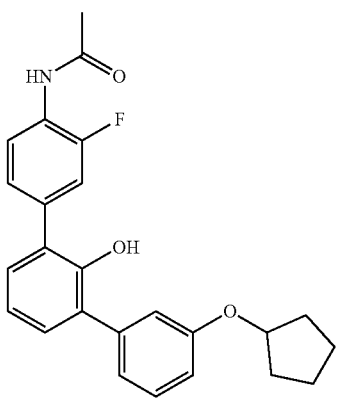 [SMILES: CC(=O)Nc1ccc(-c2cccc(-c3cccc(OC4CCCC4)c3)c2O)cc1F]

The title compound was prepared following the procedures described for Example 42 using N-(3'-bromo-3-fluoro-2'-hydroxy-[1,1'-biphenyl]-4-yl)acetamide and 1-bromo-3-(cyclopentyloxy)benzene, 4,4,4',4',5,5,5',5'-octamethyl-2,2'-bi(1,3,2-dioxaborolane) [prepared from 1-bromo-3-cyclopentyloxybenzene and 4,4,4',4',5,5,5',5'-octamethyl-2,2'-bi(1,3,2-dioxaborolane)] to afford the title compound. $^1$H NMR (400 MHz, DMSO-$d_6$): δ 9.76 (s, 1H), 8.36 (s, 1H), 7.91 (t, J=8.8 Hz, 1H), 7.41 (dd, J=12.0 Hz, 1.2 Hz, 1H), 7.34-7.30 (m, 2H), 7.22 (t, J=7.2 Hz, 2H), 7.05-6.99 (m, 3H), 6.87 (dd, J=8.0 Hz, 2.0 Hz, 1H), 4.86-4.83 (m, 1H), 2.10 (s, 3H), 1.96-1.87 (m, 2H), 1.75-1.66 (m, 4H), 1.63-1.56 (m, 2H). LCMS: 406.2 (M+H)$^+$.

Example 116

N-(2'-Hydroxy-3'-(3-(piperazin-1-yl)isoxazol-5-yl)-[1,1'-biphenyl]-4-yl)propionamide 2,2,2-trifluoroacetate

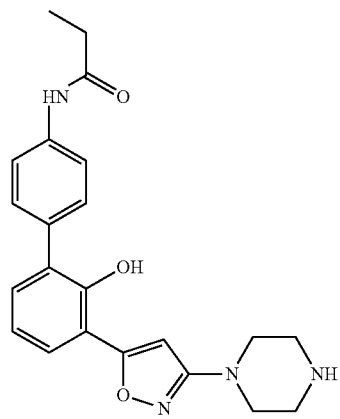 [SMILES: CCC(=O)Nc1ccc(-c2cccc(-c3cc(N4CCNCC4)no3)c2O)cc1]

The title compound was prepared following the procedures described for Example 42, using tert-butyl 4-(5-(4'-amino-2-methoxy-[1,1'-biphenyl]-3-yl)isoxazol-3-yl)piperazine-1-carboxylate and propionic acid to afford TFA salt of the title compound (32% yield) as a white solid. $^1$H NMR (400 MHz, DMSO-$d_6$): δ 9.96 (s, 1H), 9.16 (s, 1H), 8.81 (br s, 2H), 7.69-7.64 (m, 3H), 7.42 (d, J=8.4 Hz, 2H), 7.31 (dd, J=7.6 Hz, 1.6 Hz, 1H), 7.09-7.05 (m, 1H), 6.73 (s, 1H), 3.50-3.46 (m, 4H), 3.25-3.21 (m, 4H), 2.34 (q, J=7.2 Hz, 2H), 1.10 (t, J=7.6 Hz, 3H). LCMS: 393.3 (M+H)$^+$.

TABLE 12

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| 117 | N-(4''-Cyclobutoxy-3-fluoro-2'-hydroxy-[1,1':3',1''-terphenyl]-4-yl)acetamide | $^1$H NMR (400 MHz, DMSO-d$_6$): δ 9.76 (s, 1H), 8.29 (s, 1H), 7.91 (t, J = 8.4 Hz, 1H), 7.44-7.38 (m, 3H), 7.29 (d, J = 8.4 Hz, 2H), 7.20-7.16 (m, 2H), 6.98 (t, J = 7.2 Hz, 1H), 6.89 (d, J = 8.4 Hz, 1H), 4.75-4.68 (m, 1H), 2.46-2.41 (m, 2H), 2.10 (s, 3H), 2.08-2.01 (m, 2H), 1.83-1.76 (m, 1H), 1.69-1.62 (m, 1H) | 392.2 |
| 118 | N-(4''-(Cyclopentyloxy)-3-fluoro-2'-hydroxy-[1,1':3',1''-terphenyl]-4-yl)acetamide | $^1$H NMR (400 MHz, DMSO-d$_6$): δ 9.76 (s, 1H), 8.28 (s, 1H), 7.91 (t, J = 8.4 Hz, 1H), 7.44-7.38 (m, 3H), 7.30 (d, J = 8.0 Hz, 1H), 7.20-7.17 (m, 2H), 7.00-6.94 (m, 3H), 4.85 (t, J = 5.6 Hz, 1H), 2.10 (s, 3H), 1.97-1.89 (m, 2H), 1.75-1.63 (m, 4H), 1.60-1.26 (m, 2H) | 406.2 |
| 119 | N-(3'-(Benzofuran-5-yl)-3-fluoro-2'-hydroxy-[1,1'-biphenyl]-4-yl)acetamide | $^1$H NMR (400 MHz, DMSO-d$_6$): δ 9.76 (s, 1H), 8.34 (s, 1H), 8.01 (d, J = 2.0 Hz, 1H), 7.92 (t, J = 8.4 Hz, 1H), 7.77 (d, J = 1.6 Hz, 1H), 7.64 (d, J = 8.4 Hz, 1H), 7.46-7.41 (m, 2H), 7.34 (d, J = 1.6 Hz, 1H), 7.31-7.23 (m, 2H), 7.04-7.00 (m, 2H), 2.11 (s, 3H) | 362.1 |

TABLE 12-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 120 | N-(3-Fluoro-2'-hydroxy-3'-(quinolin-6-yl)-[1,1'-biphenyl]-4-yl)acetamide | $^1$H NMR (400 MHz, DMSO-d$_6$): δ 9.77 (s, 1H), 8.90 (dd, J = 4.4 Hz, 2.0 Hz, 1H), 8.60 (s, 1H), 8.41 (d, J = 7.6 Hz, 1H), 8.12 (d, J = 2.0 Hz, 1H), 8.06 (d, J = 8.4 Hz, 1H), 7.96-7.92 (m, 2H), 7.55 (dd, J = 8.4 Hz, 1.6 Hz, 1H), 7.47 (d, J = 1.6 Hz, 0.5H), 7.44 (d, J = 1.6 Hz, 0.5H), 7.37-7.30 (m, 3H), 7.08 (t, J = 7.6 Hz, 1H), 2.11 (s, 3H) | 373.1 |
| 121 | N-(3-Fluoro-2'-hydroxy-3'-(1-methyl-1H-benzo[d]imidazol-5-yl)-[1,1'-biphenyl]-4-yl)acetamide | $^1$H NMR (400 MHz, DMSO-d$_6$): δ 9.76 (s, 1H), 8.28 (s, 1H), 8.20 (s, 1H), 7.82 (t, J = 8.4 Hz, 1H), 7.75 (d, J = 0.8 Hz, 1H), 7.61 (d, J = 8.0 Hz, 1H), 7.45-7.41 (m, 2H), 7.33 (dd, J = 8.0 Hz, 1.2 Hz, 1H), 7.26-7.22 (m, 2H), 7.02 (t, J = 7.6 Hz, 1H), 3.87 (s, 3H), 2.10 (s, 3H) | 376.1 |
| 122 | N-(3'-(Benzo[d]oxazol-5-yl)-3-fluoro-2'-hydroxy-[1,1'-biphenyl]-4-yl)acetamide | $^1$H NMR (400 MHz, DMSO-d$_6$): δ 9.78 (s, 1H), 8.78 (s, 1H), 8.46 (s, 1H), 7.95-7.91 (m, 2H), 7.82 (d, J = 8.4 Hz, 1H), 7.58 (d, J = 8.0 Hz, 1H), 7.43 (d, J = 12.0 Hz, 1H), 7.33 (d, J = 8.4 Hz, 1H), 7.27 (d, J = 7.6 Hz, 2H), 7.06-7.02 (m, 1H), 2.11 (s, 3H) | 363.1 |

TABLE 12-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 123 | N-(3-Fluoro-2'-hydroxy-3'-(1H-indol-5-yl)-[1,1'-biphenyl]-4-yl)acetamide | $^1$H NMR (400 MHz, DMSO-d$_6$): δ 11.12 (s, 1H), 9.77 (s, 1H), 8.16 (s, 1H), 7.91 (t, J = 8.4 Hz, 1H), 7.67 (s, 1H), 7.45-7.42 (m, 2H), 7.37-7.32 (m, 2H), 7.25-7.19 (m, 3H), 7.01-6.97 (m, 1H), 6.46 (d, J = 1.6 Hz, 1H), 2.11 (s, 3H) | 361.1 |
| 124 | N-(3-fluoro-2'-hydroxy-3'-(1H-pyrrolo[2,3-b]pyridin-5-yl)-[1,1'-biphenyl]-4-yl)acetamide | $^1$H NMR (400 MHz, DMSO-d$_6$): δ 11.67 (s, 1H), 8.97 (s, 1H), 8.44 (s, 1H), 8.32 (d, J = 1.6 Hz, 1H), 8.05 (d, J = 2.0 Hz, 1H), 7.93 (t, J = 8.0 Hz, 1H), 7.50 (t, J = 2.8 Hz, 1H), 7.46 (d, J = 2.0 Hz, 0.5H), 7.43 (d, J = 1.6 Hz, 0.5H), 7.35 (d, J = 1.6 Hz, 0.5H), 7.32 (d, J = 1.6 Hz, 0.5H), 7.27-7.25 (m, 2H), 7.04 (t, J = 7.6 Hz, 1H), 6.49 (dd, J = 3.2 Hz, 2.0 Hz, 1H), 2.11 (s, 3H) | 362.1 |
| 125 | N-(3-Fluoro-2'-hydroxy-3'-(1-methyl-1H-pyrrolo[2,3-b]pyridin-5-yl)-[1,1'-biphenyl]-4-yl)acetamide | $^1$H NMR (400 MHz, DMSO-d$_6$): δ 9.77 (s, 1H), 8.44 (s, 1H), 8.38 (d, J = 2.0 Hz, 1H), 8.07 (d, J = 2.0 Hz, 1H), 7.95-7.90 (m, 1H), 7.55 (d, J = 3.6 Hz, 1H), 7.45 (d, J = 1.6 Hz, 1H), 7.42 (d, J = 1.6 Hz, 1H), 7.34-7.25 (m, 2H), 7.04 (t, J = 7.6 Hz, 1H), 6.50 (d, J = 3.6 Hz, 1H), 3.85 (s, 3H), 2.11 (s, 3H) | 376.1 |

Example 126

N-(3-Chloro-5-fluoro-2'-hydroxy-3'-(3-(piperazin-1-yl)isoxazol-5-yl)-[1,1'-biphenyl]-4-yl)acetamide 2,2,2-trifluoroacetate

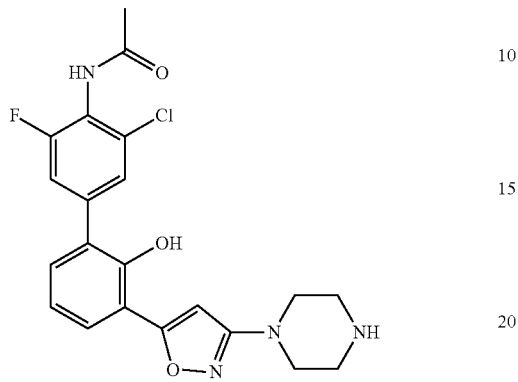

The title compound was prepared following the procedures described for Example 1 using tert-butyl 4-(5-(3-bromo-2-methoxyphenyl)isoxazol-3-yl)piperazine-1-carboxylate and N-(2-chloro-6-fluoro-4-(4,4,5,5-tetramethyl-1,3,2-dioxaborolan-2-yl)phenyl)acetamide [prepared from N-(4-bromo-2-chloro-6-fluorophenyl)acetamide and 4,4,4',4',5,5,5',5'-octamethyl-2,2'-bi(1,3,2-dioxaborolane)] followed by BBr$_3$ to afford the title compound (23% yield). $^1$H NMR (400 MHz, DMSO-d$_6$): δ 9.78 (s, 1H), 9.60 (s, 1H), 8.79 (br s, 2H), 7.73 (dd, J=8.0 Hz, 1.6 Hz, 1H), 7.50 (s, 1H), 7.43-7.40 (m, 2H), 7.12 (t, J=7.6 Hz, 1H), 6.78 (s, 1H), 3.51-3.46 (m, 4H), 3.24 (s, 4H), 2.09 (s, 3H). LCMS: 431.1 (M+H)$^+$.

TABLE 13

Following compounds were prepared similarly as described for Examples 42 using suitably substituted aryl halide and a corresponding boronic ester or boronic acid (See preparation in Scheme 3).

| Ex. No. | Name/Structure | $^1$H NMR Data | LCMS (M + H)$^+$ |
|---|---|---|---|
| 127 | N,N'-(2'-Hydroxy-3-methoxy-[1,1':3',1''-terphenyl]-4,4''-diyl)diacetamide | $^1$H NMR (400 MHz, DMSO-d$_6$): δ 9.97 (s, 1H), 9.16 (s, 1H), 8.17 (s, 1H), 7.98 (d, J = 8.4 Hz, 1H), 7.62 (d, J = 8.4 Hz, 2H), 7.46 (d, J = 8.4 Hz, 2H), 7.21-7.16 (m, 3H), 7.05-6.97 (m, 2H), 3.86 (s, 3H), 2.10 (s, 3H), 2.06 (s, 3H) | 391.2 |

TABLE 13-continued

*Following compounds were prepared similarly as described for Examples 42 using suitably substituted aryl halide and a corresponding boronic ester or boronic acid (See preparation in Scheme 3).*

| Ex. No. | Name/Structure | $^1$H NMR Data | LCMS $(M + H)^+$ |
|---|---|---|---|
| 128 | N,N'-(3,5-Difluoro-2'-hydroxy-3''-methoxy-[1,1':3',1''-terphenyl]-4,4''-diyl)diacetamide | $^1$H NMR (400 MHz, DMSO-d$_6$): δ 9.73 (s, 1H), 9.21 (s, 1H), 8.59 (s, 1H), 8.00 (d, J = 8.0 Hz, 1H), 7.32-7.27 (m, 4H), 7.18 (d, J = 1.6 Hz, 1H), 7.06-7.01 (m, 2H), 3.86 (s, 3H), 2.09 (d, J = 8.0 Hz, 6H) | 427.1 |
| 129 | N-(3''-Fluoro-2'-hydroxy-3-methoxy-4''-(2-oxopyrrolidin-1-yl)-[1,1':3',1''-terphenyl]-4-yl)acetamide | $^1$H NMR (400 MHz, DMSO-d$_6$): δ 9.17 (s, 1H), 8.46 (s, 1H), 7.99 (d, J = 8.0 Hz, 1H), 7.50-7.44 (m, 2H), 7.39 (dd, J = 8.0 Hz, 2.0 Hz, 1H), 7.27-7.25 (m, 2H), 7.18 (d, J = 2.0 Hz, 1H), 7.06-7.01 (m, 2H), 3.86 (s, 3H), 3.79 (t, J = 6.8 Hz, 2H), 2.46-2.43 (m, 2H), 2.18-2.14 (m, 2H), 2.10 (s, 3H) | 435.2 |

TABLE 13-continued

Following compounds were prepared similarly as described for Examples 42 using suitably substituted aryl halide and a corresponding boronic ester or boronic acid (See preparation in Scheme 3).

| Ex. No. | Name/Structure | $^1$H NMR Data | LCMS $(M + H)^+$ |
| --- | --- | --- | --- |
| 130 | N-(3-Fluoro-2'-hydroxy-3'-(1-methyl-1H-indol-5-yl)-[1,1'-biphenyl]-4-yl)acetamide | $^1$H NMR (400 MHz, DMSO-d$_6$): δ 9.75 (s, 1H), 8.16 (s, 1H), 7.91 (t, J = 8.4 Hz, 1H), 7.67 (d, J = 0.8 Hz, 1H), 7.49-7.41 (m, 2H), 7.35-7.29 (m, 3H), 7.23-7.20 (m, 2H), 7.02-6.98 (m, 1H), 6.46 (d, J = 3.2 Hz, 1H), 3.81 (s, 3H), 2.10 (s, 3H) | 375.1 |
| 131 | N-(3'-(1H-Benzo[d]imidazol-5-yl)-3-fluoro-2'-hydroxy-[1,1'-biphenyl]-4-yl)acetamide | $^1$H NMR (400 MHz, DMSO-d$_6$): δ 12.45 (s, 1H), 9.76 (s, 1H), 8.31-8.28 (m, 1H), 8.23 (s, 1H), 7.94-7.90 (m, 1H), 7.76-7.60 (m, 2H), 7.43 (dd, J = 12.4 Hz, 1.6 Hz, 1H), 7.34-7.32 (m, 2H), 7.26-7.23 (m, 2H), 7.02 (t, J = 7.6 Hz, 1H), 2.11 (s, 3H) | 362.1 |

TABLE 13-continued

Following compounds were prepared similarly as described for Examples 42 using suitably substituted aryl halide and a corresponding boronic ester or boronic acid (See preparation in Scheme 3).

| Ex. No. | Name/Structure | ¹H NMR Data | LCMS (M + H)⁺ |
|---|---|---|---|
| 132 | N,N'-(3,5-Dichloro-2'-hydroxy-3"-methoxy-[1,1':3',1"-terphenyl]-4,4"-diyl)diacetamide | ¹H NMR (400 MHz, DMSO-d₆): δ 9.84 (s, 1H), 9.18 (s, 1H), 8.62 (s, 1H), 8.00 (d, J = 8.4 Hz, 1H), 7.65 (s, 2H), 7.29 (d, J = 7.6 Hz, 2H), 7.18 (s, 1H), 7.06-7.02 (m, 2H), 3.87 (s, 3H), 2.09 (d, J = 8.4 Hz, 6H) | 459.1 |
| 133 | N-(3",5"-Difluoro-2'-hydroxy-3-methoxy-4"-(2-oxopyrrolidin-1-yl)-[1,1':3',1"-terphenyl]-4-yl)acetamide | ¹H NMR (400 MHz, DMSO-d₆): 9.18 (s, 1H), 8.62 (s, 1H), 8.02-7.99 (m, 1H), 7.41-7.37 (m, 2H), 7.30 (d, J = 7.6 Hz, 2H), 7.18 (d, J = 1.6 Hz, 1H), 7.07-7.02 (m, 2H), 3.87 (s, 3H), 3.74-3.70 (m, 2H), 2.51-2.45 (m, 2H), 2.23-2.16 (m, 2H), 2.11 (s, 3H) | 453.2 |

Example 134

N-(5'-fluoro-2'-hydroxy-3'-(1-(1-methylpiperidin-4-yl)-1H-pyrazol-4-yl)-[1,1'-biphenyl]-4-yl)acetamide

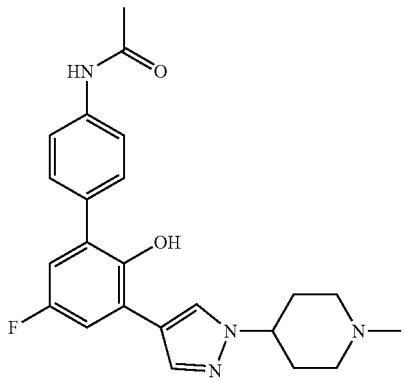 [SMILES: CC(=O)Nc1ccc(-c2cc(F)cc(-c3cnn(C4CCN(C)CC4)c3)c2O)cc1]

The title compound was prepared following the procedures described for Example 84 using N-(3'-bromo-5'-fluoro-2'-hydroxy-[1,1'-biphenyl]-4-yl)acetamide and 1-methyl-4-(4-(4,4,5,5-tetramethyl-1,3,2-dioxaborolan-2-yl)-1H-pyrazol-1-yl)piperidine to afford the title compound (13% yield). $^1$H NMR (400 MHz, DMSO-$d_6$): 10.01 (s, 1H), 8.33 (s, 1H), 8.23 (s, 1H), 7.97 (s, 1H), 7.65-7.63 (m, 2H), 7.47 (d, J=8.4 Hz, 2H), 7.33 (dd, J=10.0, 3.2 Hz, 1H), 6.87 (dd, J=9.6, 3.2 Hz, 1H), 4.15-4.11 (m, 1H), 2.87-2.84 (m, 2H), 2.21 (s, 3H), 2.07-1.94 (m, 9H). LCMS: 409.2 (M+H)$^+$.

Example 135

N-(3-cyclopropoxy-5-fluoro-2'-hydroxy-3'-(3-(piperazin-1-yl)isoxazol-5-yl)-[1,1'-biphenyl]-4-yl)acetamide 2,2,2-trifluoroacetate

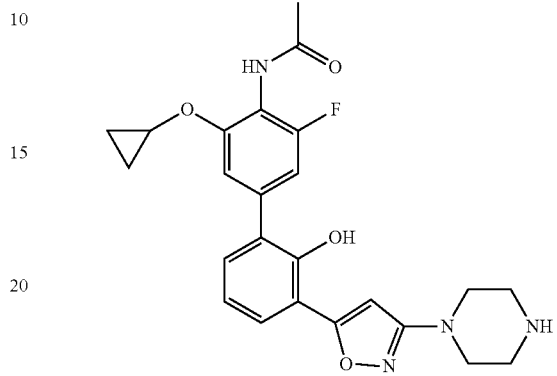

To a solution of 2-bromo-6-(3-(piperazin-1-yl)isoxazol-5-yl)phenol hydrobromide (100 mg, 0.249 mmol), N-(2-cyclopropoxy-6-fluoro-4-(4,4,5,5-tetramethyl-1,3,2-dioxaborolan-2-yl)phenyl) acetamide (250 mg, 0.747 mmol) and $K_2CO_3$ (206 mg, 1.49 mmol) in dioxane/water (10:1, 2.75 mL) in sealed tube was added NHC—Pd(II) (84 mg, 0.07 mmol). The reaction mixture was stirred at 120° C. for 4 hours under nitrogen atmosphere. After the reaction was complete by LCMS, the reaction mixture was cooled and diluted with DCM/MeOH (20:1, 5 mL) and filtered. The filtrate was concentrated under reduced pressure to afford a residue which was purified by silica gel chromatography using dichloromethane and methanol (15:1) as the eluent, then further purified by prep-HPLC using acetonitrile in water in the presence of TFA to afford the title compound (7.1 mg, 4% yield) as a white solid. $^1$H NMR (400 MHz, DMSO-$d_6$): 9.49 (s, 1H), 9.24 (s, 1H), 8.82 (s, 2H), 7.73-7.70 (m, 1H), 7.42-7.39 (m, 1H), 7.27 (s, 1H), 7.13-6.97 (m, 2H), 6.75 (s, 1H), 3.95-3.92 (m, 1H), 3.68-3.65 (m, 3H), 3.24 (s, 4H), 2.02 (s, 3H), 0.80-0.77 (m, 2H), 0.72-0.68 (m, 2H). N—H or OH proton not observed. LCMS: 453.2 (M+H)$^+$.

TABLE 14

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 136 | N-(3'-(chroman-6-yl)-3-fluoro-2'-hydroxy-[1,1'-biphenyl]-4-yl)acetamide | $^1$H NMR (400 MHz, DMSO-$d_6$): 9.76 (s, 1H), 8.24 (s, 1H), 7.91 (s, 1H), | 378.1 |

TABLE 14-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| | 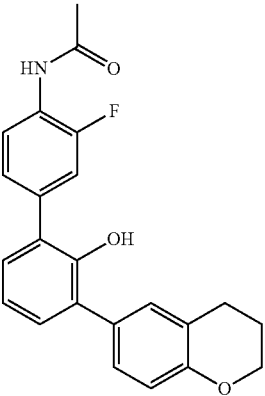 [SMILES: CC(=O)Nc1ccc(-c2cccc(-c3ccc4c(c3)CCCO4)c2O)cc1F] | 7.42-7.38 (m, 1H), 7.31-7.29 (m, 1H), 7.22-7.14 (m, 4H), 6.97 (t, J = 7.2 Hz, 1H), 6.78 (d, J = 8.8 Hz, 1H), 4.17-4.14 (m, 2H), 2.80-2.77 (m, 2H), 2.11 (s, 3H), 1.96-1.93 (m, 2H) | |
| 137 | N-(3-fluoro-2'-hydroxy-3'-(indolin-5-yl)-[1,1'-biphenyl]-4-yl)acetamide | $^1$H NMR (400 MHz, DMSO-d$_6$): 9.72 (s, 1H), 7.92-7.88 (m, 1H), 7.40 (dd, J = 12.0, 1.6 Hz, 1H), 7.31-7.20 (m, 2H), 7.15-7.05 (m, 3H), 6.96-6.93 (m, 1H), 6.55 (d, J = 7.6 Hz, 1H), 5.57 (s, 1H), 3.47-3.43 (m, 2H), 2.97-2.93 (m, 2H), 2.11 (s, 3H). N—H or O—H proton not observed. | 363.1 |
| 138 | N,N'-(3-fluoro-2'-hydroxy-3''-(trifluoromethyl)-[1,1':3',1''-terphenyl]-4,4''-diyl)diacetamide | $^1$H NMR (400 MHz, DMSO-d$_6$): 9.78 (s, 1H), 9.58 (s, 1H), 8.70 (s, 1H), 7.96-7.92 (m, 1H), 7.86 (d, J = 1.2 Hz, 1H), 7.81-7.79 (m, 1H), 7.55-7.53 (m, 1H), 7.44-7.40 (m, 1H), 7.33-7.28 (m, 3H), 7.08-7.04 (m, 1H), 2.11-2.08 (m, 6H). LCMS: 447.1 (M + H)$^+$. | 447.1 |

TABLE 14-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 139 | N,N'-(3,3''-difluoro-2'-hydroxy-5-methyl-[1,1':3',1''-terphenyl]-4,4''-diyl)diacetamide<br>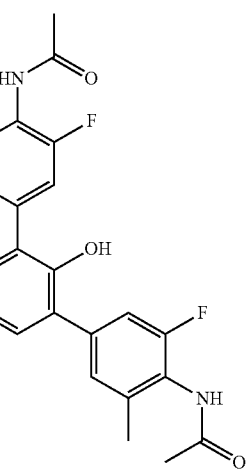 | $^1$H NMR (400 MHz, DMSO-d$_6$): 9.77 (s, 1H), 9.44 (s, 1H), 8.56 (s, 1H), 7.93 (s, 1H), 7.43-7.30 (m, 2H), 7.26-7.21 (m, 4H), 7.04-7.00 (m, 1H), 2.22 (s, 3H), 2.11-2.07 (m, 6H) | 411.2 |

Example 140

1-(3,5-difluoro-2'-hydroxy-3'-(3-(piperazin-1-yl)isoxazol-5-yl)-[1,1'-biphenyl]-4-yl)pyrrolidin-2-one

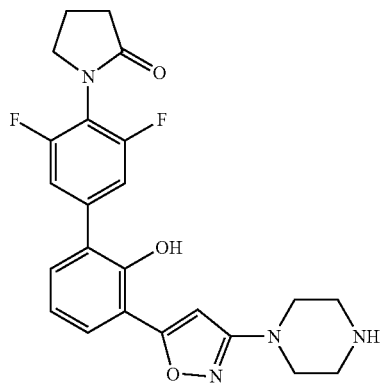 [SMILES: O=C1CCCN1c1c(F)cc(-c2cccc(-c3cc(N4CCNCC4)no3)c2O)cc1F]

Step 1: 1-(2,6-difluoro-4-(4,4,5,5-tetramethyl-1,3,2-dioxaborolan-2-yl)phenyl)pyrrolidin-2-one The title compound was prepared following the procedure described for Example 133 using 1-(4-bromo-2,6-difluorophenyl)pyrrolidin-2-one and 4,4,4',4',5,5,5',5'-octamethyl-2,2'-bi(1,3,2-dioxaborolane) to afford the title compound (100% yield). LCMS: 324.2 (M+H)$^+$.

Step 2: tert-butyl 4-(5-(3',5'-difluoro-2-methoxy-4'-(2-oxopyrrolidin-1-yl)-[1,1'-biphenyl]-3-yl)isoxazol-3-yl)piperazine-1-carboxylate The title compound was prepared following the procedure described for Example 1 using 1-(2,6-difluoro-4-(4,4,5,5-tetramethyl-1,3,2-dioxaborolan-2-yl)phenyl)pyrrolidin-2-one and tert-butyl 4-(5-(3-bromo-2-methoxyphenyl)isoxazol-3-yl)piperazine-1-carboxylate to afford the title compound (44% yield). LCMS: 555.0 (M+H)$^+$.

Step 3: 1-(3,5-difluoro-2'-hydroxy-3'-(3-(piperazin-1-yl)isoxazol-5-yl)-[1,1'-biphenyl]-4-yl)pyrrolidin-2-one The title compound was prepared following the procedure described for Example 1 using tert-butyl 4-(5-(3',5'-difluoro-2-methoxy-4'-(2-oxopyrrolidin-1-yl)-[1,1'-biphenyl]-3-yl)isoxazol-3-yl)piperazine-1-carboxylate to afford the title compound (13% yield). $^1$H NMR (400 MHz, DMSO-d$_6$): 7.68 (d, J=8.0 Hz, 1H), 7.43-7.37 (m, 3H), 7.02-6.98 (m, 1H), 6.71 (s, 1H), 3.73-3.69 (m, 2H), 3.20 (s, 4H), 2.85 (s, 4H), 2.50-2.45 (m, 2H), 2.22-2.18 (m, 2H). LCMS: 441.2 (M+H)$^+$.

Example 141

Methyl (2'-hydroxy-3'-(3-(piperazin-1-yl)isoxazol-5-yl)-[1,1'-biphenyl]-4-yl)carbamate 2,2,2-trifluoroacetate

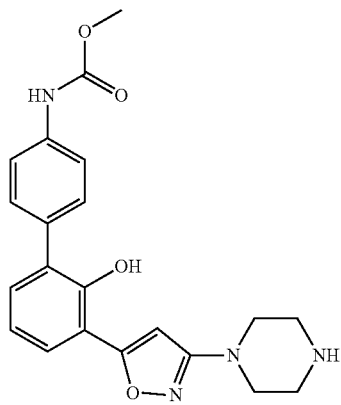 [SMILES: COC(=O)Nc1ccc(-c2cccc(-c3cc(N4CCNCC4)no3)c2O)cc1]

The title compound was prepared following the procedures described for Example 39 using tert-butyl 4-(5-(4'-amino-2-methoxy-[1,1'-biphenyl]-3-yl)isoxazol-3-yl)piperazine-1-carboxylate and methyl carbonochloridate to afford the title compound (44% yield). $^1$H NMR (400 MHz, DMSO-$d_6$): 9.77 (s, 1H), 9.18 (s, 1H), 8.80 (br s, 2H), 7.67-7.64 (m, 1H), 7.54 (d, J=8.4 Hz, 2H), 7.42 (d, J=8.4 Hz, 2H), 7.32-7.29 (m, 1H), 7.09-7.05 (m, 1H), 6.74 (s, 1H), 3.69 (s, 3H), 3.49-3.47 (m, 3H), 3.24 (s, 4H). N—H or O—H proton not observed. LCMS: 395.2 (M+H)$^+$.

Example 143

N-(2'-hydroxy-3'-(3-(4-(methylsulfonyl)piperazin-1-yl)isoxazol-5-yl)-[1,1'-biphenyl]-4-yl)acetamide

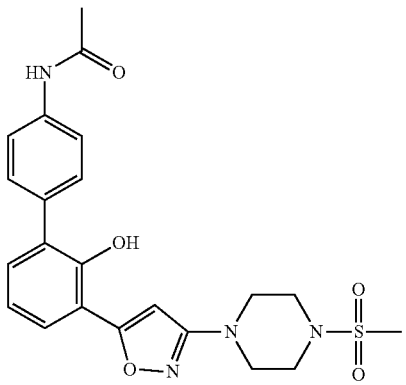 [SMILES: CC(=O)Nc1ccc(-c2cccc(-c3cc(N4CCN(S(C)(=O)=O)CC4)no3)c2O)cc1]

Step 1: N-(2'-methoxy-3'-(3-(4-(methylsulfonyl)piperazin-1-yl)isoxazol-5-yl)-[1,1'-biphenyl]-4-yl)acetamide To a solution of N-(2'-methoxy-3'-(3-(piperazin-1-yl)isoxazol-5-yl)-[1,1'-biphenyl]-4-yl)acetamide (78 mg, 0.2 mmol) in DCM (2 mL) was added MsCl (23 mg, 0.20 mmol) and TEA (60 mg, 0.60 mmol) at 0° C. The reaction mixture was stirred at room temperature under nitrogen atmosphere for 4 hours. After the reaction was complete by LCMS, the reaction mixture was concentrated, added water and extracted with EA. The combined organic layers were dried over sodium sulfate, filtered and concentrated to afford the title compound. LCMS: 471.2 (M+H)$^+$.

Step 2: N-(2'-hydroxy-3'-(3-(4-(methylsulfonyl)piperazin-1-yl)isoxazol-5-yl)-[1,1'-biphenyl]-4-yl)acetamide The title compound was prepared following the procedure described for Example 1 using N-(2'-methoxy-3'-(3-(4-(methylsulfonyl)piperazin-1-yl)isoxazol-5-yl)-[1,1'-biphenyl]-4-yl)acetamide and BBr$_3$ to afford the title compound (16% yield). $^1$H NMR (400 MHz, DMSO-$d_6$): 10.02 (s, 1H), 9.13 (s, 1H), 7.67-7.64 (m, 3H), 7.44 (d, J=8.8 Hz, 2H), 7.31-7.29 (m, 1H), 7.09-7.05 (m, 1H), 6.72 (s, 1H), 3.40-3.31 (m, 4H), 3.25-3.22 (m, 4H), 2.92 (s, 3H), 2.07 (s, 3H). LCMS: 457.2 (M+H)$^+$.

TABLE 15

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)$^+$ |
|---|---|---|---|
| 142 | N-(3-fluoro-2'-hydroxy-3'-(quinazolin-6-yl)-[1,1'-biphenyl]-4-yl)acetamide | $^1$H NMR (400 MHz, DMSO-$d_6$): 9.80 (s, 1H), 9.66 (s, 1H), 9.31 (s, 1H), 8.72 (s, 1H), 8.31 (s, 1H), 8.29-8.22 (m, 1H), 8.08-8.06 (m, 1H), 7.98-7.94 (m, 1H), 7.48-7.44 (m, 1H), 7.41-7.34 (m, 3H), 7.13-7.09 (m, 1H), 2.12 (s, 3H) | 374.2 |

TABLE 15-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS (M + H)+ |
|---|---|---|---|
| 144 | N-(3-fluoro-2'-hydroxy-3'-(4-methyl-3,4-dihydro-2H-benzo[b][1,4]oxazin-7-yl)-[1,1'-biphenyl]-4-yl)acetamide | $^1$H NMR (400 MHz, DMSO-d$_6$): 9.75 (s, 1H), 8.17 (s, 1H), 7.92 (s, 1H), 7.39 (d, J = 12.4 Hz, 1H), 7.16-7.13 (m, 3H), 6.97-6.86 (m, 3H), 6.76 (d, J = 8.4 Hz, 1H), 4.27-4.25 (m, 2H), 3.28-3.24 (m, 2H), 2.86 (s, 3H), 2.11 (s, 3H) | 393.2 |
| 145 | N-(3-fluoro-2'-hydroxy-3'-(isoquinolin-6-yl)-[1,1'-biphenyl]-4-yl)acetamide | $^1$H NMR (400 MHz, DMSO-d$_6$): 9.78 (s, 1H), 9.33 (s, 1H), 8.66 (s, 1H), 8.52 (d, J = 5.6 Hz, 1H), 8.18-8.10 (m, 2H), 7.95-7.86 (m, 3H), 7.47-743 (m, 1H), 7.38-7.32 (m, 3H), 7.12-7.10 (m, 1H), 2.11 (s, 3H) | 373.1 |
| 146 | N-(3,3''-difluoro-2'-hydroxy-5''-methoxy-[1,1':3',1''-terphenyl]-4-yl)acetamide | $^1$H NMR (400 MHz, DMSO-d$_6$): 9.77 (s, 1H), 8.52 (s, 1H), 7.95-7.90 (m, 1H), 7.41 (dd, J = 12.4, 2.0 Hz, 1H), 7.32-7.24 (m, 3H), 7.04-7.00 (m, 1H), 6.94-6.91 (m, 2H), 6.83-6.79 (m, 1H), 3.81 (s, 3H), 2.11 (s, 3H) | 370.1 |

TABLE 15-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | ¹H NMR Data | LCMS (M + H)⁺ |
|---|---|---|---|
| 147 | N-(3-fluoro-2'-hydroxy-5''-methoxy-2''-methyl-[1,1':3',1''-terphenyl]-4-yl)acetamide | ¹H NMR (400 MHz, DMSO-d₆): 9.78 (s, 1H), 8.21 (s, 1H), 7.91 (t, J = 8.8 Hz, 1H), 7.40 (dd, J = 12.4, 1.6 Hz, 1H), 7.33-7.17 (m, 3H), 7.04-6.96 (m, 2H), 6.86-6.74 (m, 1H), 6.73 (s, 1H), 3.74 (s, 3H), 2.11 (s, 3H), 2.07 (s, 3H) | 366.1 |

Example 148

N-(3-fluoro-2'-hydroxy-3'-(5-(piperazin-1-yl)-4H-1,2,4-triazol-3-yl)-[1,1'-biphenyl]-4-yl)acetamide

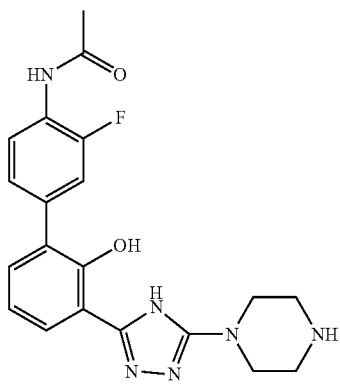

Step 1: 3-Bromo-2-methoxybenzoyl chloride

To a solution of 3-bromo-2-methoxybenzoic acid (900 mg, 3.90 mmol) and DMF (2 drops) in DCM (10 mL) was added a solution of oxalyl dichloride (742 mg, 580 mmol) in DCM (5 mL) dropwise. The solution was stirred at room temperature under nitrogen atmosphere for 2 hours. The reaction mixture was concentrated to afford the title compound (967 mg, 99% yield) as yellow oil.

Step 2: 3-Bromo-2-methoxybenzohydrazide

A solution of hydrazine hydrate (975 mg, 19.5 mmol) in a mixture of DCM (5 mL) and THF (7 mL) was added a solution of 3-bromo-2-methoxybenzoyl chloride (976 mg, 3.90 mmol) in DCM (2 mL) dropwise. The solution was stirred at room temperature under nitrogen atmosphere for 16 hours. After the reaction was complete by LCMS, the reaction mixture was quenched with MeOH (20 mL) and concentrated. The residue was purified by silica gel chromatography using dichloromethane and methanol (10:1) as the eluent to afford the title compound (300 mg, 32% yield) as a white solid. LCMS: 245.0 (M+H)⁺.

Step 3: tert-butyl 4-(imino(methylthio)methyl)piperazine-1-carboxylate hydroiodide A solution of tert-butyl 4-carbamimidoylpiperazine-1-carboxylate (900 mg, 3.70 mmol) and iodomethane (782 mg, 3.50 mmol) in MeOH (30 mL) was stirred at 50° C. under nitrogen atmosphere for 6 hours. The reaction mixture was cooled and concentrated to afford the title compound (1.40 g, 100% yield) as a yellow solid.

Step 4: Tert-butyl 4-(5-(3-bromo-2-methoxyphenyl)-4H-1,2,4-triazol-3-yl) piperazine-1-carboxylate A suspension of tert-butyl 4-(imino(methylthio)methyl)piperazine-1-carboxylate hydroiodide (1.40 g, 3.60 mmol) and 3-bromo-2-methoxybenzohydrazide (883 mg, 3.60 mmol) in pyridine (10 mL) was stirred at 100° C. under nitrogen atmosphere overnight. After the reaction was complete by LCMS, the reaction mixture was cooled and concentrated. The residue was purified by silica gel chromatography using petroleum ether and ethyl acetate (2:1) as the eluent to afford the title compound (300 mg, 19% yield) as a yellow solid. LCMS: 438.1 (M+H)⁺.

Step 5: Tert-butyl 4-(5-(4'-acetamido-3'-fluoro-2-methoxy-[1,1'-biphenyl]-3-yl)-4H-1,2,4-triazol-3-yl) piperazine-1-carboxylate The title compound was prepared following the procedure described for Example 1 using tert-butyl 4-(5-(3-bromo-2-methoxyphenyl)-4H-1,2,4-triazol-3-yl)piperazine-1-carboxylate and N-(2-fluoro-4-(4,4,5,5-tetramethyl-1,3,2-dioxaborolan-2-yl)phenyl)acetamide to afford the title compound (72% yield). LCMS: 511.2 (M+H)⁺.

551

Step 6: N-(3-fluoro-2'-hydroxy-3'-(5-(piperazin-1-yl)-4H-1,2,4-triazol-3-yl)-[1,1'-biphenyl]-4-yl)acetamide The title compound was prepared following the procedure described for Example 1 using tert-butyl 4-(5-(4'-acetamido-3'-fluoro-2-methoxy-[1,1'-biphenyl]-3-yl)-4H-1,2,4-triazol-3-yl)piperazine-1-carboxylate to afford the title compound (31% yield). $^1$H NMR (400 MHz, DMSO-d$_6$): 12.07 (br s, 1H), 9.77 (s, 1H), 7.94-7.87 (m, 2H), 7.52-7.48 (m, 1H), 7.39-7.36 (m, 2H), 7.01-6.97 (m, 1H), 3.33-3.31 (m, 4H), 2.81-2.79 (m, 4H), 2.11 (s, 3H). Two N—H or O—H proton not observed. LCMS: 397.2 (M+H)$^+$.

Example 149

1-(2'-hydroxy-3'-(3-(piperazin-1-yl)isoxazol-5-yl)-[1,1'-biphenyl]-4-yl)-3-methylurea

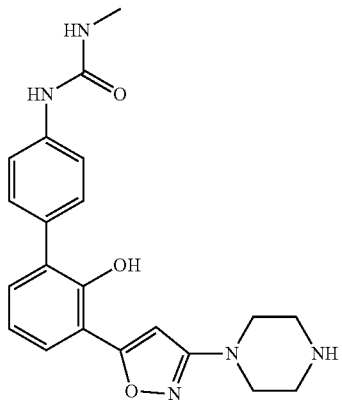 [SMILES: CNC(=O)Nc1ccc(-c2cccc(-c3cc(N4CCNCC4)no3)c2O)cc1]

Step 1: tert-butyl 4-(5-(2-methoxy-4'-(3-methylureido)-[1,1'-biphenyl]-3-yl)isoxazol-3-yl)piperazine-1-carboxylate The title compound was prepared following the procedure described for Example 1 using tert-butyl 4-(5-(3-bromo-2-methoxyphenyl)isoxazol-3-yl)piperazine-1-carboxylate and 1-methyl-3-(4-(4,4,5,5-tetramethyl-1,3,2-dioxaborolan-2-yl)phenyl)urea to afford the title compound (71% yield). LCMS: 508.2 (M+H)$^+$.

Step 2: 1-(2'-hydroxy-3'-(3-(piperazin-1-yl)isoxazol-5-yl)-[1,1'-biphenyl]-4-yl)-3-methylurea The title compound was prepared following the procedure described for Example 1-3 using tert-butyl 4-(5-(2-methoxy-4'-(3-methylureido)-[1,1'-biphenyl]-3-yl)isoxazol-3-yl)piperazine-1-carboxylate and BBr$_3$ to afford the title compound (12% yield). $^1$H NMR (400 MHz, DMSO-d$_6$): 8.61 (s, 1H), 7.61 (d, J=7.2 Hz, 1H), 7.49-7.46 (m, 2H), 7.38-7.36 (m, 2H), 7.28-7.26 (m, 1H), 7.04 (t, J=7.6 Hz, 1H), 6.63 (s, 1H), 6.04 (s, 1H), 3.16 (s, 4H), 2.81 (s, 4H), 2.66 (d, J=4.0 Hz, 3H). Two N—H or O—H proton not observed. LCMS: 394.2 (M+H)$^+$.

Example 150

N-(3-fluoro-2'-hydroxy-3'-(3-(4-methylpiperazin-1-yl)isoxazol-5-yl)-[1,1'-biphenyl]-4-yl)acetamide

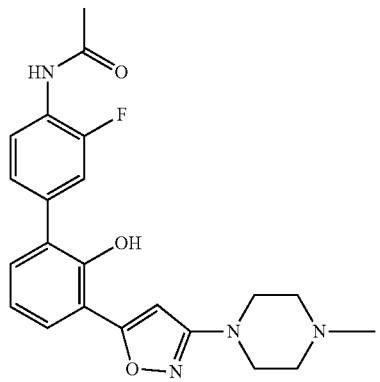 [SMILES: CC(=O)Nc1ccc(-c2cccc(-c3cc(N4CCN(C)CC4)no3)c2O)cc1F]

To a solution of N-(3-fluoro-2'-hydroxy-3'-(3-(piperazin-1-yl)isoxazol-5-yl)-[1,1'-biphenyl]-4-yl)acetamide hydrobromide (70 mg, 0.15 mmol) in MeOH (3 mL) was added NaBH$_3$(CN) (37.7 mg, 0.600 mmol), followed by the addition of HCHO (9.5 mg, 0.15 mmol). The reaction mixture was stirred at RT for 1.5 h. After the reaction was complete by LCMS, the reaction mixture was quenched with NH$_4$Cl aqueous solution and concentrated. The residue was purified by preparative-HPLC to afford the title compound (13 mg, 31% yield) as a white solid. $^1$H NMR (400 MHz, DMSO-d$_6$): 9.80 (s, 1H), 9.27 (br s, 1H), 7.99-7.95 (m, 1H), 7.66 (dd, J=7.6, 1.2 Hz, 1H), 7.40-7.27 (m, 3H), 7.10-7.06 (m, 1H), 6.67 (s, 1H), 3.26-3.23 (m, 4H), 2.44-2.41 (m, 4H), 2.22 (s, 3H), 2.12 (s, 3H). LCMS: 411.2 (M+H)$^+$.

Example 151

N-(3'-(3-(4-ethylpiperazin-1-yl)isoxazol-5-yl)-3-fluoro-2'-hydroxy-[1,1'-biphenyl]-4-yl)acetamide

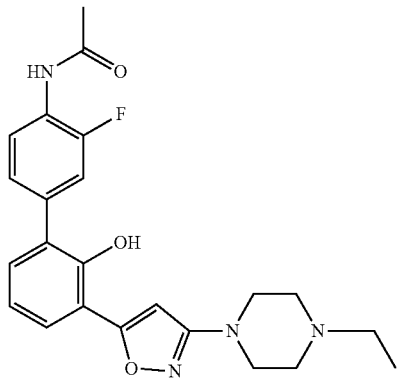 [SMILES: CCN1CCN(c2cc(-c3cccc(-c4ccc(NC(C)=O)c(F)c4)c3O)on2)CC1]

The title compound was prepared following the procedure described for Example 150 using N-(3-fluoro-2'-hydroxy-3'-(3-(piperazin-1-yl)isoxazol-5-yl)-[1,1'-biphenyl]-4-yl)acetamide hydrobromide and acetaldehyde to afford the title compound (37% yield). $^1$H NMR (400 MHz, DMSO-d$_6$): 9.80 (s, 1H), 9.27 (br s, 1H), 7.99-7.95 (m, 1H), 7.67 (dd, J=7.6, 1.6 Hz, 1H), 7.40-7.27 (m, 3H), 7.10-7.06 (m, 1H), 6.67 (s, 1H), 3.26-3.24 (m, 4H), 2.51-2.49 (m, 4H), 2.41-2.32 (m, 2H), 2.12 (s, 3H), 1.05-1.01 (m, 3H). LCMS: 425.2 (M+H)+.

Example 152

N-(3-fluoro-2'-hydroxy-3'-(3-(4-isopropylpiperazin-1-yl)isoxazol-5-yl)-[1,1'-biphenyl]-4-yl)acetamide 2,2,2-trifluoroacetate

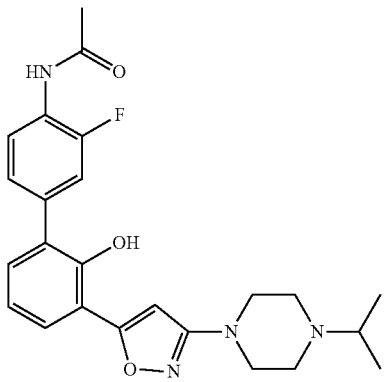 [SMILES: CC(=O)Nc1ccc(-c2cccc(-c3cc(N4CCN(C(C)C)CC4)no3)c2O)cc1F]

The title compound was prepared following the procedure described for Example 150 using N-(3-fluoro-2'-hydroxy-3'-(3-(piperazin-1-yl)isoxazol-5-yl)-[1,1'-biphenyl]-4-yl)acetamide hydrobromide and propan-2-one to afford the title compound (16% yield). $^1$H NMR (400 MHz, DMSO-d$_6$): 9.81 (s, 1H), 9.60 (br s, 1H), 9.36 (s, 1H), 8.00-7.96 (m, 1H), 7.69 (dd, J=8.0, 1.6 Hz, 1H), 7.40-7.28 (m, 3H), 7.12-7.08 (m, 1H), 6.79 (s, 1H), 3.94-3.91 (m, 2H), 3.56-3.50 (m, 3H), 3.22-3.15 (m, 4H), 2.12 (s, 3H), 1.30-1.28 (m, 6H). LCMS: 439.2 (M+H)+.

Example 153

N-(3-fluoro-2'-hydroxy-3'-(3-(4-(oxetan-3-yl)piperazin-1-yl)isoxazol-5-yl)-[1,1'-biphenyl]-4-yl)acetamide

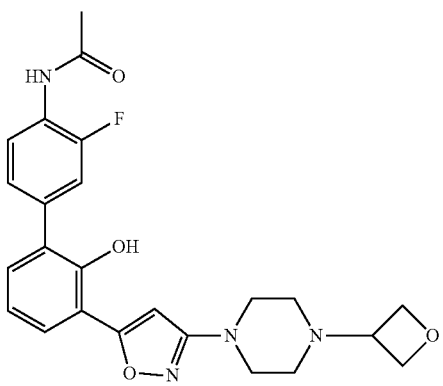 [SMILES: CC(=O)Nc1ccc(-c2cccc(-c3cc(N4CCN(C5COC5)CC4)no3)c2O)cc1F]

The title compound was prepared following the procedure described for Example 150 using N-(3-fluoro-2'-hydroxy-3'-(3-(piperazin-1-yl)isoxazol-5-yl)-[1,1'-biphenyl]-4-yl)acetamide hydrobromide and oxetan-3-one to afford the title compound (29% yield). $^1$H NMR (400 MHz, DMSO-d$_6$): 9.80 (s, 1H), 9.26 (br s, 1H), 7.97-7.95 (m, 1H), 7.67 (dd, J=8.0, 2.0 Hz, 1H), 7.40-7.27 (m, 3H), 7.08 (t, J=8.0 Hz, 1H), 6.69 (s, 1H), 4.58-4.54 (m, 2H), 4.48-4.45 (m, 2H), 3.47-3.44 (m, 1H), 3.29-3.26 (m, 4H), 2.51-2.49 (m, 4H), 2.11 (s, 3H). LCMS: 453.2 (M+H)+.

Example 154

N-(3,5-dichloro-2'-hydroxy-3'-(3-(piperazin-1-yl)isoxazol-5-yl)-[1,1'-biphenyl]-4-yl)acetamide

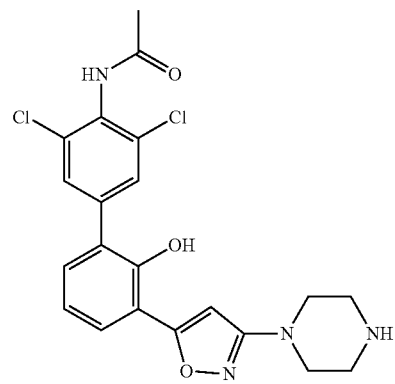 [SMILES: CC(=O)Nc1c(Cl)cc(-c2cccc(-c3cc(N4CCNCC4)no3)c2O)cc1Cl]

The title compound was prepared following the procedures described for Example 1 using tert-butyl 4-(5-(3-bromo-2-methoxyphenyl)isoxazol-3-yl)piperazine-1-carboxylate and N-(2,6-dichloro-4-(4,4,5,5-tetramethyl-1,3,2-dioxaborolan-2-yl)phenyl)acetamide followed by BBr$_3$ to afford the title compound (34% yield). $^1$H NMR (400 MHz, DMSO-d$_6$): 9.85 (s, 1H), 7.66 (s, 3H), 7.38-7.36 (m, 1H), 6.98 (t, J=7.6 Hz, 1H), 6.72 (s, 1H), 3.20-3.17 (m, 4H), 2.85-2.82 (m, 4H), 2.08 (s, 3H). Two N—H or O—H proton not observed. LCMS: 447.1 (M+H)+.

TABLE 16

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| 155 | N-(3-fluoro-2'-hydroxy-3'-(2-oxo-1,2,3,4-tetrahydroquinazolin-6-yl)-[1,1'-biphenyl]-4-yl)acetamide | $^1$H NMR (400 MHz, DMSO-d$_6$): 9.77 (s, 1H), 9.09 (s, 1H), 8.30 (s, 1H), 7.94-7.89 (m, 1H), 7.40 (dd, J = 12.4, 1.6 Hz, 1H), 7.31-7.26 (m, 3H), 7.21-7.15 (m, 2H), 7.00-6.96 (m, 1H), 6.84-6.82 (m, 2H), 4.36 (s, 2H), 2.09 (d, J = 9.2 Hz, 3H) | 392.1 |
| 156 | N-(3-fluoro-2'-hydroxy-3'-(1H-indol-2-yl)-[1,1'-biphenyl]-4-yl)acetamide | $^1$H NMR (400 MHz, DMSO-d$_6$): 11.24 (s, 1H), 9.79 (s, 1H), 8.88 (s, 1H), 7.99-7.94 (m, 1H), 7.69-7.67 (m, 1H), 7.55-7.41 (m, 3H), 7.34-7.32 (m, 1H), 7.24-7.21 (m, 1H), 7.10-6.93 (m, 4H), 2.12 (s, 3H) | 361.1 |
| 157 | N-(3,4''-difluoro-2'-hydroxy-3''-methoxy-[1,1':3',1''-terphenyl]-4-yl)acetamide | $^1$H NMR (400 MHz, DMSO-d$_6$): 9.77 (s, 1H), 8.41 (s, 1H), 7.92 (s, 1H), 7.44-7.32 (m, 1H), 7.30-7.23 (m, 5H), 7.08-7.00 (m, 2H), 3.87 (s, 3H), 2.11 (s, 3H) | 370.1 |

TABLE 16-continued

Following compounds were prepared as described for Examples 42 using N-(3'-bromo-3-fluoro-2'-hydroxy-[1,1'-biphenyl]-4-yl)acetamide and a corresponding boronic ester or boronic acid (See preparation in Scheme 3).

| Ex. No. | Name/Structure | $^1$H NMR Data | LCMS $(M + H)^+$ |
|---|---|---|---|
| 158 | N-(2'',3-difluoro-2'-hydroxy-5''-methoxy-[1,1':3',1''-terphenyl]-4-yl)acetamide | $^1$H NMR (400 MHz, DMSO-$d_6$): 9.77 (s, 1H), 8.51 (s, 1H), 7.92 (s, 1H), 7.42-7.38 (m, 1H), 7.32-7.28 (m, 2H), 7.18-7.16 (m, 2H), 7.03-6.92 (m, 3H), 3.77 (s, 3H), 2.11 (s, 3H). | 370.1 |

Example 159

N-(3''-(4-aminopiperidin-1-yl)-3-fluoro-2'-hydroxy-[1,1':3',1''-terphenyl]-4-yl)acetamide 2,2,2-trifluoroacetate

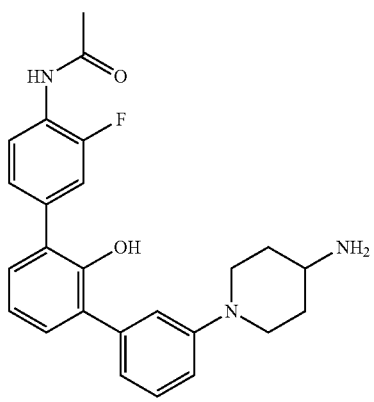 [SMILES: CC(=O)Nc1ccc(-c2cccc(-c3cccc(N4CCC(N)CC4)c3)c2O)cc1F]

Step 1: tert-butyl (1-(3-bromophenyl)piperidin-4-yl)carbamate

To a solution of 1-bromo-3-iodobenzene (0.60 mL, 5.0 mmol), and tert-butyl piperidin-4-ylcarbamate (1.0 g, 5.0 mmol) in toluene (10 mL) was added t-BuONa (1.37 g, 14.0 mmol), BINAP (156 mg, 0.250 mmol) and Pd$_2$(dba)$_3$ (229 mg, 0.250 mmol). The reaction mixture was stirred at 100° C. under nitrogen atmosphere overnight. After the reaction was indicated by LCMS, the reaction mixture was cooled and concentrated. The residue was purified by silica gel chromatography using petroleum ether and ethyl acetate (4:1) as the eluent to afford the title compound (800 mg, 45% yield) as a yellow solid. LCMS: 355.1 (M+H)$^+$.

Step 2: tert-butyl (1-(4''-acetamido-3''-fluoro-2'-methoxy-[1,1':3',1''-terphenyl]-3-yl)piperidin-4-yl) carbamate The title compound was prepared following the procedure described for Example 1 using tert-butyl (1-(3-bromophenyl)piperidin-4-yl)carbamate and N-(3-fluoro-2'-methoxy-3'-(4,4,5,5-tetramethyl-1,3,2-dioxaborolan-2-yl)-[1,1'-biphenyl]-4-yl)acetamide to afford the title compound (72% yield). LCMS: 534.2 (M+H)$^+$.

Step 3: tert-butyl N-(3''-(4-aminopiperidin-1-yl)-3-fluoro-2'-hydroxy-[1,1':3',1''-terphenyl]-4-yl)acetamide 2,2,2-trifluoroacetate The title compound was prepared following the procedure described for Example 3 using tert-butyl (1-(4''-acetamido-3''-fluoro-2'-methoxy-[1,1':3',1''-terphenyl]-3-yl)piperidin-4-yl)carbamate and BBr$_3$ to afford the title compound (55% yield). $^1$H NMR (400 MHz, DMSO-$d_6$): 9.87 (s, 1H), 8.36 (br s, 1H), 7.92-7.90 (m, 4H), 7.41 (dd, J=12.4, 2.0 Hz, 1H), 7.32-7.19 (m, 3H), 7.11 (s, 1H), 7.03-6.96 (m, 3H), 3.81-3.77 (m, 2H), 3.24-3.20 (m, 1H), 2.87-2.81 (m, 2H), 2.11 (s, 3H), 1.97-1.95 (m, 2H), 1.68-1.58 (m, 2H). N—H or O—H proton not observed. LCMS: 420.2 (M+H)$^+$.

Example 160

N-(3-fluoro-2'-hydroxy-3'-(1-methyl-5-(piperazin-1-yl)-1H-pyrazol-3-yl)-[1,1'-biphenyl]-4-yl)acetamide

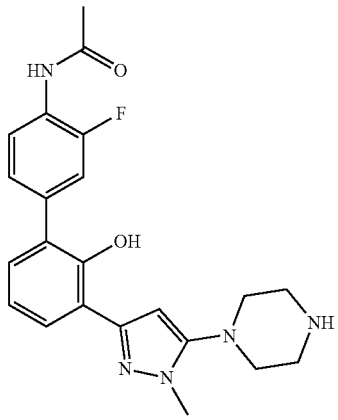 [SMILES: CC(=O)Nc1ccc(-c2cccc(-c3cc(N4CCNCC4)n(C)n3)c2O)cc1F]

Step 1: tert-butyl 4-(3-(3-bromo-2-methoxyphenyl)-1H-pyrazol-5-yl)piperazine-1-carboxylate To a solution of tert-butyl 4-(3-(3-bromo-2-methoxyphenyl)-3-oxopropanethioyl)piperazine-1-carboxylate (1.43 g, 3.14 mmol) in EtOH (5 mL) was added $NH_2NH_2·H_2O$ (5 mL). The reaction mixture was stirred at 84° C. under nitrogen atmosphere for 2 hours. After the reaction was complete by LCMS, the reaction mixture was cooled and removed the solvent under reduced pressure. The residue was purified by chromatography on silica gel (PE/EA=1:1) to afford the title compound (820 mg, 60% yield) as a yellow solid. LCMS: 437.1 $(M+H)^+$.

Step 2: tert-butyl 4-(3-(3-bromo-2-methoxyphenyl)-1-methyl-1H-pyrazol-5-yl)piperazine-1-carboxylate To a suspension of NaH (36 mg, 0.92 mmol, 60% wt. in mineral oil) in THF (8 mL) was added a solution of tert-butyl 4-(3-(3-bromo-2-methoxyphenyl)-1H-pyrazol-5-yl)piperazine-1-carboxylate (400 mg, 0.920 mmol) in THF (7 mL) at 0° C. After stirred at 0° C. for 30 minutes, $CH_3I$ (260 mg, 1.84 mmol) was added. The reaction mixture was stirred at room temperature for another 4 hours under $N_2$ atmosphere. The reaction mixture was quenched with water (10 mL) and extracted with EA (15 mL×3). The combined organic layers were washed with brine (20 mL), dried over sodium sulfate, filtered and concentrated. The residue was purified by chromatography on silica gel (PE/EA=2:1) to afford the title compound (250 mg, 60% yield) as colorless oil. LCMS: 451.1 $(M+H)^+$.

Step 3: 2-bromo-6-(1-methyl-5-(piperazin-1-yl)-1H-pyrazol-3-yl)phenol

The title compound was prepared following the procedure described for Example 3 using tert-butyl 4-(3-(3-bromo-2-methoxyphenyl)-1-methyl-1H-pyrazol-5-yl)piperazine-1-carboxylate and $BBr_3$ to afford the title compound (crude). LCMS: 337.0 $(M+H)^+$.

Step 4: N-(3-fluoro-2'-hydroxy-3'-(1-methyl-5-(piperazin-1-yl)-1H-pyrazol-3-yl)-[1,1'-biphenyl]-4-yl)acetamide The title compound was prepared following the procedure described for Example 1 using 2-bromo-6-(1-methyl-5-(piperazin-1-yl)-1H-pyrazol-3-yl)phenol and N-(2-fluoro-4-(4,4,5,5-tetramethyl-1,3,2-dioxaborolan-2-yl)phenyl)acetamide to afford the title compound (11% yield). $^1$H NMR (400 MHz, DMSO-$d_6$): 11.50 (br s, 1H), 9.78 (s, 1H), 7.94-7.90 (m, 1H), 7.68 (d, J=6.8 Hz, 1H), 7.52-7.48 (m, 1H), 7.39-7.26 (m, 2H), 6.99-6.95 (m, 1H), 6.51 (s, 1H), 3.73 (s, 3H), 3.05-2.88 (m, 8H), 2.12 (s, 3H). N—H or O—H proton not observed. LCMS: 410.3 $(M+H)^+$.

Example 162

N-(3-fluoro-2'-hydroxy-3'-(5-(piperazin-1-yl)-1H-pyrazol-3-yl)-[1,1'-biphenyl]-4-yl)acetamide ditrifluoroacetate

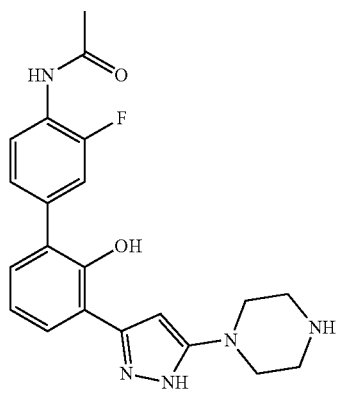 [SMILES: CC(=O)Nc1ccc(-c2cccc(-c3cc(N4CCNCC4)[nH]n3)c2O)cc1F]

The title compound was prepared following the procedures described for Example 160 using 2-bromo-6-(5-(piperazin-1-yl)-1H-pyrazol-3-yl)phenol and N-(2-fluoro-4-(4,4,5,5-tetramethyl-1,3,2-dioxaborolan-2-yl)phenyl)acetamide to afford the title compound (2% yield). $^1$H NMR (400 MHz, DMSO-$d_6$+$D_2O$): 7.86 (s, 1H), 7.66-7.63 (m, 1H), 7.47 (dd, J=12.4, 1.6 Hz, 1H), 7.39-7.28 (m, 2H), 7.05-7.01 (m, 1H), 6.32 (s, 1H), 3.44-3.41 (m, 4H), 3.29-3.26 (m, 4H), 2.12 (s, 3H). LCMS: 396.2 $(M+H)^+$.

Example 163

N-(3-fluoro-2'-hydroxy-3'-(2-(piperazin-1-yl)pyridin-4-yl)-[1,1'-biphenyl]-4-yl)acetamide

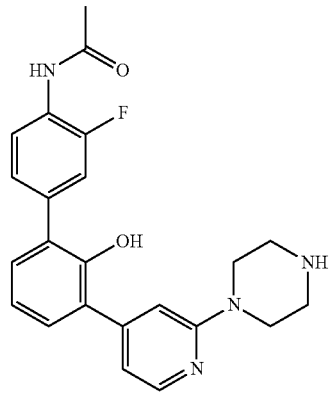 [SMILES: CC(=O)Nc1ccc(-c2cccc(-c3ccnc(N4CCNCC4)c3)c2O)cc1F]

Step 1: tert-butyl 4-(4-(4'-acetamido-3'-fluoro-2-methoxy-[1,1'-biphenyl]-3-yl)pyridin-2-yl)piperazine-1-carboxylate The title compound was prepared following the procedure described for Example 159 using N-(3-fluoro-2'-methoxy-3'-(4,4,5,5-tetramethyl-1,3,2-dioxaborolan-2-yl)-[1,1'-biphenyl]-4-yl)acetamide and tert-butyl 4-(4-bromopyridin-2-yl)piperazine-1-carboxylate to afford the title compound (26% yield). LCMS: 521.2 (M+H)+.

Step 2: N-(3-fluoro-2'-hydroxy-3'-(2-(piperazin-1-yl)pyridin-4-yl)-[1,1'-biphenyl]-4-yl)acetamide The title compound was prepared following the procedure described for Example 159 using tert-butyl 4-(4-(4'-acetamido-3'-fluoro-2-methoxy-[1,1'-biphenyl]-3-yl)pyridin-2-yl)piperazine-1-carboxylate and BBr₃ to afford the title compound (35% yield). ¹H NMR (400 MHz, DMSO-d₆): 9.79 (s, 1H), 8.13 (d, J=5.2 Hz, 1H), 7.92 (s, 1H), 7.43-7.40 (m, 1H), 7.32-7.24 (m, 3H), 7.05-6.89 (m, 1H), 6.79 (s, 1H), 6.77 (s, 1H), 3.44-3.42 (m, 4H), 2.80-2.77 (m, 4H), 2.11 (s, 3H). N—H and O—H protons not observed. LCMS: 407.2 (M+H)+.

Example 164

1-(3-Fluoro-2'-hydroxy-3''-(piperazin-1-yl)-[1,1':3',1''-terphenyl]-4-yl)-3-methylimidazolidin-2-one

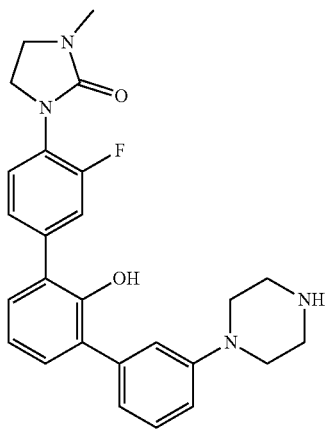 [SMILES: CN1CCN(c2ccc(-c3cccc(-c4cccc(N5CCNCC5)c4)c3O)cc2F)C1=O]

The title compound was prepared following the procedures described for Example 159 using tert-butyl 4-(3'-bromo-2'-methoxy-[1,1'-biphenyl]-3-yl)piperazine-1-carboxylate and 1-(2-fluoro-4-(4,4,5,5-tetramethyl-1,3,2-dioxaborolan-2-yl)phenyl)-3-methylimidazolidin-2-one followed by BBr₃ to afford the title compound. ¹H NMR (400 MHz, DMSO-d₆+D₂O): 7.50 (d, J=8.4 Hz, 1H), 7.42 (dd, J=12.8, 1.6 Hz, 1H), 7.37-7.33 (m, 2H), 7.28-7.22 (m, 2H), 7.12 (s, 1H), 7.07-7.03 (m, 2H), 7.01 (d, J=2.0 Hz, 1H), 3.79 (t, J=8.4 Hz, 2H), 3.51-3.47 (m, 2H), 3.41-3.38 (m, 4H), 3.26-3.24 (m, 4H), 2.78 (s, 3H). LCMS: 447.3 (M+H)+.

Example 165

N-(3'',5''-dichloro-2'-hydroxy-3-methoxy-4''-(2-oxopyrrolidin-1-yl)-[1,1':3',1''-terphenyl]-4-yl)acetamide

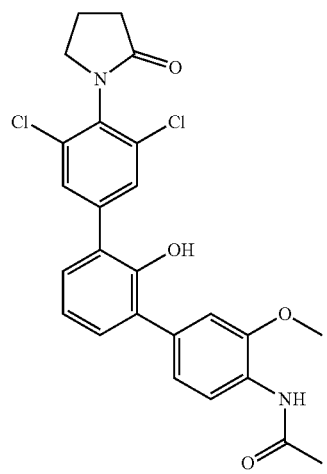 [SMILES: COc1cc(-c2cccc(-c3cc(Cl)c(N4CCCC4=O)c(Cl)c3)c2O)ccc1NC(C)=O]

The title compound was prepared following the procedures described for Example 42 using 1-(2,6-dichloro-4-(4,4,5,5-tetramethyl-1,3,2-dioxaborolan-2-yl)phenyl)pyrrolidin-2-one and N-(3'-bromo-2'-hydroxy-3-methoxy-[1,1'-biphenyl]-4-yl)acetamide to afford the title compound. ¹H NMR (400 MHz, DMSO-d₆): 9.20 (s, 1H), 8.69 (s, 1H), 8.07-7.99 (m, 1H), 7.73 (s, 2H), 7.32-7.29 (m, 2H), 7.18 (s, 1H), 7.07-7.03 (m, 2H), 3.87 (s, 3H), 3.66 (t, J=7.2 Hz, 2H), 2.50-2.45 (m, 2H), 2.26-2.21 (m, 2H), 2.11 (s, 3H). LCMS: 485.2 (M+H)+.

TABLE 17

Following compounds were prepared using similar procedures as described for Example 159 (See preparation in Scheme 3).

| Ex. No. | Name/Structure | ¹H NMR Data | LCMS (M + H)+ |
|---|---|---|---|
| 166 | N-(3-fluoro-2'-hydroxy-3''-(piperidin-1-yl)-[1,1':3',1''-terphenyl]-4-yl)acetamide | ¹H NMR (400 MHz, DMSO-d₆): 9.78 (s, 1H), | 405.2 |

TABLE 17-continued

Following compounds were prepared using similar procedures as described for Example 159 (See preparation in Scheme 3).

| Ex. No. | Name/Structure | ¹H NMR Data | LCMS (M + H)⁺ |
|---|---|---|---|
| | | 8.29 (s, 1H), 7.93-7.89 (m, 1H), 7.41 (dd, J = 12.4, 2.0 Hz, 1H), 7.32-7.19 (m, 4H), 7.04-6.89 (m, 4H), 3.17-3.15 (m, 4H), 2.11 (s, 3H), 1.66-1.62 (m, 4H), 1.56-1.53 (m, 2H) | |
| 167 | N-(3-cyclobutoxy-5-fluoro-2'-hydroxy-3''-(piperazin-1-yl)-[1,1':3',1''-terphenyl]-4-yl)acetamide | ¹H NMR (400 MHz, DMSO-d₆): 9.25 (s, 1H), 8.81 (s, 2H), 8.42 (s, 1H), 7.35-7.22 (m, 3H), 7.11 (s, 1H), 7.04-6.97 (m, 4H), 6.85 (s, 1H), 4.78-4.74 (m, 1H), 3.40-3.37 (m, 4H), 3.25 (s, 4H), 2.50-2.38 (m, 2H), 2.09-2.04 (m, 4H), 1.78-1.75 (m, 1H), 1.65-1.58 (m, 1H). One N—H or O—H proton not observed | 476.2 |
| 168 | (S)-N-(3-fluoro-2'-hydroxy-3''-(2-methylpiperazin-1-yl)-[1,1':3',1''-terphenyl]-4-yl)acetamide | ¹H NMR (400 MHz, DMSO-d₆): 9.76 (s, 1H), 8.26 (br s, 1H), 7.91 (t, J = 8.4 Hz, 1H), 7.41 (dd, J = 12.4, 1.6 Hz, 1H), 7.32-7.19 (m, 4H), 7.01-6.97 (m, 2H), 6.89-6.84 (m, 2H), 3.86 (s, 1H), 3.19-3.16 (m, 1H), 2.96-2.85 (m, 3H), 2.75-2.66 (m, 2H), 2.11 (s, 3H), 1.01 (d, J = 6.4 Hz, 3H). One N—H or O—H proton not observed | 420.2 |
| 169 | (R)-N-(3-fluoro-2'-hydroxy-3''-(2-methylpiperazin-1-yl)-[1,1':3',1''-terphenyl]-4-yl)acetamide | ¹H NMR (400 MHz, DMSO-d₆): δ 9.76 (s, 1H), 8.26 (br s, 1H), 7.91 (t, J = | 420.2 |

TABLE 17-continued

Following compounds were prepared using similar procedures as described for Example 159 (See preparation in Scheme 3).

| Ex. No. | Name/Structure | ¹H NMR Data | LCMS (M + H)⁺ |
|---|---|---|---|
| | | 8.4 Hz, 1H), 7.41 (dd, J = 12.4 Hz, 2.0 Hz, 1H), 7.31-7.19 (m, 4H), 6.99 (t, J = 7.6 Hz, 2H), 6.90-6.85 (m, 2H), 3.88-3.85 (m, 1H), 3.31-3.18 (m, 1H), 2.99-2.87 (m, 3H), 2.78-2.70 (m, 2H), 2.10 (s, 3H), 1.01 (d, J = 6.8 Hz, 3H). One N—H or O—H proton not observed | |
| 170 | N-(3"-(2,5-diazabicyclo[2.2.1]heptan-2-yl)-3-fluoro-2'-hydroxy-[1,1':3',1"-terphenyl]-4-yl)acetamide | ¹H NMR (400 MHz, DMSO-d₆): δ 9.76 (s, 1H), 7.90 (t, J = 8.4 Hz, 1H), 7.41 (dd, J = 12.4 Hz, 1.6 Hz, 1H), 7.30 (d, J = 8.4 Hz, 1H), 7.22-7.17 (m, 3H), 6.98 (t, J = 7.6 Hz, 1H), 6.71 (d, J = 7.6 Hz, 1H), 6.64 (s, 1H), 6.53 (d, J = 7.6 Hz, 1H), 4.33 (s, 1H), 3.60 (s, 1H), 3.51 (d, J = 7.2 Hz, 1H), 2.91-2.86 (m, 3H), 2.10 (s, 3H), 1.77 (d, J = 8.4 Hz, 1H), 1.64 (d, J = 8.4 Hz, 1H). Two N—H or O—H proton not observed | 418.1 |
| 171 | N-(3-chloro-2'-hydroxy-3"-(piperazin-1-yl)-[1,1':3',1"-terphenyl]-4-yl)acetamide | ¹H NMR (400 MHz, DMSO-d₆): δ 9.54 (s, 1H), 7.75 (d, J = 8.4 Hz, 1H), 7.64 (d, J = 1.6 Hz, 1H), 7.46 (dd, J = 8.4 Hz, 2.0 Hz, 1H), 7.28-7.19 (m, 3H), 7.03-6.97 (m, 2H), 6.92-6.89 (m, 2H), 3.07 (t, J = 4.4 Hz, 4H), 2.83 (t, J = 5.2 Hz, 4H), 2.11 (s, 3H). N—H or O—H protons not observed | 422.1 |

Example 172

1-(3,5-dichloro-2'-hydroxy-3'-(3-(piperazin-1-yl)isoxazol-5-yl)-[1,1'-biphenyl]-4-yl)pyrrolidin-2-one

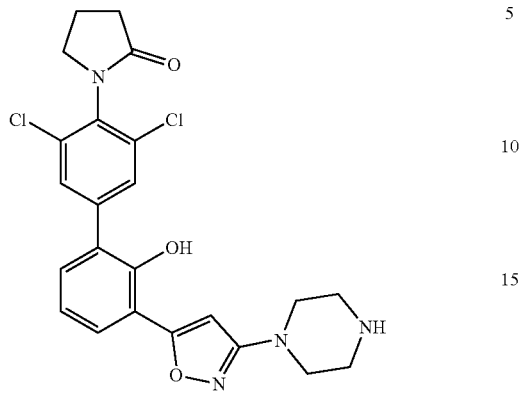

The title compound was prepared following the procedures described for Example 51 using 1-(2,6-dichloro-4-(4,4,5,5-tetramethyl-1,3,2-dioxaborolan-2-yl)phenyl)pyrrolidin-2-one and 2-bromo-6-(3-(piperazin-1-yl)isoxazol-5-yl)phenol to afford the title compound. $^1$H NMR (400 MHz, DMSO-$d_6$): δ 7.73 (s, 2H), 7.65 (dd, J=8.0 Hz, 1.6 Hz, 1H), 7.35 (dd, J=7.6 Hz, 1.6 Hz, 1H), 6.92 (t, J=7.6 Hz, 1H), 6.72 (s, 1H), 3.63 (t, J=6.8 Hz, 2H), 3.19 (t, J=4.8 Hz, 4H), 2.84 (t, J=4.8 Hz, 4H), 2.47-2.43 (m, 2H), 2.25-2.18 (m, 2H). N—H or O—H protons not observed. LCMS: 473.2 (M+H)$^+$.

TABLE 18

Following compounds were prepared using similar procedures as described for Example 159 (See preparation in Scheme 3, 12, 13, 14 and 15).

| Ex. No. | Name/Structure | $^1$H NMR Data | LCMS (M + H)$^+$ |
|---|---|---|---|
| 173 | 1-(3-fluoro-2'-hydroxy-3''-(piperazin-1-yl)-[1,1':3',1''-terphenyl]-4-yl)pyrrolidin-2-one | $^1$H NMR (400 MHz, DMSO-$d_6$): δ 8.81 (s, 1H), 8.44 (br s, 1H), 7.51-7.45 (m, 2H), 7.40-7.38 (m, 1H), 7.35-7.31 (m, 1H), 7.28-7.22 (m, 2H), 7.12 (s, 1H), 7.05-6.97 (m, 3H), 3.79 (t, J = 6.4 Hz, 2H), 3.40-3.37 (m, 4H), 3.27-3.24 (m, 4H), 2.47-2.43 (m, 2H), 2.18-2.10 (m, 2H). $^{19}$F NMR (376 MHz, DMSO-$d_6$): δ −74.16, −120.31 | 432.3 |
| 174 | N-(3''-(2,5-diazabicyclo[2.2.2]octan-2-yl)-3-fluoro-2'-hydroxy-[1,1':3',1''-terphenyl]-4-yl)acetamide | $^1$H NMR (400 MHz, DMSO-$d_6$ and D$_2$O): δ 7.88 (d, J = 8.4 Hz, 1H), 7.41 | 432.2 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | (structure) | (dd, J = 12.0 Hz, 1.2 Hz, 1H), 7.31 (dd, J = 8.4 Hz, 1.6 Hz, 1H), 7.25-7.19 (m, 3H), 7.01 (t, J = 7.2 Hz, 1H), 6.72-6.63 (m, 3H), 3.91 (s, 1H), 3.53-3.00 (m, 5H), 2.11 (s, 3H), 1.92-1.23 (m, 4H). N—H and O—H protons not observed. ¹⁹F NMR (376 MHz, DMSO-d₆): δ −125.57 | |
| 175 | N-(3-cyclopropoxy-5-fluoro-2'-hydroxy-3''-(piperazin-1-yl)-[1,1':3',1''-terphenyl]-4-yl)acetamide | ¹H NMR (400 MHz, DMSO-d₆): δ 9.21 (s, 1H), 7.29-7.21 (m, 4H), 7.03-7.00 (m, 3H), 6.93-6.90 (m, 2H), 3.92 (br s, 1H), 3.09-3.06 (m, 4H), 2.85-2.82 (m, 4H), 2.01 (s, 3H), 0.80-0.77 (m, 2H), 0.69-0.67 (m, 2H). N—H or O—H protons not observed. | 462.3 |
| 176 | N-(3''-((1R,5S)-3,8-diazabicyclo[3.2.1]octan-3-yl)-3-fluoro-2'-hydroxy-[1,1':3',1''-terphenyl]-4-yl)acetamide | ¹H NMR (400 MHz, DMSO-d₆): 9.79 (s, 1H), 8.96 (br s, 2H), 8.32 (s, 1H), 7.93-7.89 (m, 1H), 7.43-7.39 (m, 1H), 7.32-7.19 (m, 5H), 7.12 (s, 1H), 7.03-6.89 (m, 5H), 4.15 (s, 2H), 3.69 (d, J = 10.8 Hz, 2H), 3.08-3.05 (m, 2H), 2.11 (s, 3H). N—H or O—H protons not observed. | 432.2 |
| 177 | N-(3''-(3-aminopyrrolidin-1-yl)-3-fluoro-2'-hydroxy-[1,1':3',1''-terphenyl]-4-yl)acetamide | ¹H NMR (400 MHz, DMSO-d₆): 9.79 (s, 1H), 8.24 (s, 1H), 8.12 (s, 3H), | 406.2 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | | 7.94-7.90 (m, 1H), 7.41 (dd, J = 12.4, 2.0 Hz, 1H), 7.32-7.13 (m, 5H), 7.03-6.99 (m, 1H), 6.82-6.80 (m, 2H), 6.70-6.59 (m, 1H), 6.58 (s, 1H) 6.57-6.56 (m, 1H), 3.96 (s, 1H), 3.58-3.30 (m, 4H), 2.36-2.31 (m, 1H). N—H and O—H protons not observed. | |
| 178 | N-(3,3''-difluoro-2'-hydroxy-5''-(piperazin-1-yl)-[1,1':3',1''-terphenyl]-4-yl)acetamide | ¹H NMR (400 MHz, DMSO-d₆): 9.78 (s, 1H), 7.94-7.89 (m, 1H), 7.43-7.40 (m, 1H), 7.31-7.22 (m, 3H), 7.02-6.98 (m, 1H), 6.84 (s, 1H), 6.73-6.67 (m, 2H), 3.13-3.10 (m, 4H), 2.84-2.81 (m, 4H), 2.11 (s, 3H). N—H or O—H protons not observed. | 424.2 |
| 179 | (S)-N-(3-fluoro-2'-hydroxy-3''-(3-methylpiperazin-1-yl)-[1,1':3',1''-terphenyl]-4-yl)acetamide | ¹H NMR (400 MHz, DMSO-7₆): 9.79 (s, 1H), 8.96 (s, 1H), 8.60 (s, 1H), 8.33 (s, 1H), 7.92 (t, J = 8.8 Hz, 1H), 7.41 (dd, J = 12.0, 1.6 Hz, 1H), 7.35-7.20 (m, 4H), 7.12 (s, 1H), 7.03-6.98 (m, 3H), 3.85-3.76 (m, 2H), 3.42-3.36 (m, 2H), 3.18-3.15 (m, 1H), 2.98-2.89 (m, 1H), 2.76-2.67 (m, 1H), 2.11 (s, 3H), 1.27 (d, J = 6.4 Hz, 3H) | 420.2 |
| 180 | N-(3,5'-difluoro-2'-hydroxy-3''-(piperazin-1-yl)-[1,1':3',1''-terphenyl]-4-yl)acetamide | ¹H NMR (400 MHz, DMSO-d₆): 9.79 (s, 1H), 7.96-7.92 (m, 1H), 7.48- | 424.1 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | (structure shown) | 7.45 (m, 1H), 7.36-7.25 (m, 2H), 7.12-7.04 (m, 3H), 6.96-6.91 (m, 2H), 3.10-3.08 (m, 4H), 2.86-2.83 (m, 4H), 2.11 (s, 3H). N—H or O—H protons not observed | |
| 181 | N-(3-fluoro-2'-hydroxy-2''-methyl-5''-(piperazin-1-yl)-[1,1':3',1''-terphenyl]-4-yl)acetamide | ¹H NMR (400 MHz, DMSO-d₆): 9.77 (s, 1H), 7.93-7.89 (m, 1H), 7.40 (dd, J = 12.4, 1.6 Hz, 1H), 7.33-7.23 (m, 2H), 7.12-7.09 (m, 1H), 7.03-6.95 (m, 2H), 6.86-6.71 (m, 1H), 6.70 (s, 1H), 3.04-3.02 (m, 4H), 2.85-2.83 (m, 4H), 2.11 (s, 3H), 2.03 (s, 3H). N—H or O—H protons not observed | 420.2 |
| 182 | N-(3,4''-difluoro-2'-hydroxy-3(piperazin-1-yl)-[1,1':3',1''-terphenyl]-4-yl)acetamide | ¹H NMR (400 MHz, DMSO-d₆): 9.77 (s, 1H), 7.93-7.89 (m, 1H), 7.41 (dd, J = 12.0, 1.6 Hz, 1H), 7.32-7.29 (m, 1H), 7.25-7.06 (m, 5H), 7.02-6.98 (m, 1H), 2.96-2.95 (m, 4H), 2.84 (s, 4H), 2.11 (s, 3H). Two N—H or O—H proton not observed | 424.2 |
| 183 | N-(3''-((1S,4S)-2,5-diazabicyclo[2.2.2]octan-2-yl)-3-fluoro-2'-hydroxy-[1,1':3',1''-terphenyl]-4-yl)acetamide | ¹H NMR (400 MHz, DMSO-d₆): 9.76 (s, 1H), 7.93-7.88 (m, 1H), 7.41 (dd, J = 12.4, 1.6 Hz, 1H), | 432.3 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | | 7.32-7.29 (m, 1H), 7.23-7.18 (m, 3H), 7.00-6.96 (m, 1H), 6.73-6.61 (m, 3H), 3.90 (s, 1H), 3.51-3.48 (m, 1H), 3.34-3.32 (m, 1H), 3.14-3.01 (m, 3H), 2.11 (s, 3H), 1.89-1.65 (m, 4H). N—H or O—H protons not observed | |
| 184 | N-(3-(cyclopropylmethoxy)-5-fluoro-2'-hydroxy-3''-(piperazin-1-yl)-[1,1':3',1''-terphenyl]-4-yl)acetamide | ¹H NMR (400 MHz, DMSO-d₆ + D₂O): 7.36-7.27 (m, 1H), 7.24-7.22 (m, 2H), 7.10 (s, 1H), 7.05-6.98 (m, 5H), 3.91-3.90 (m, 2H), 3.40-3.38 (m, 4H), 3.26-3.25 (m, 4H), 2.06 (s, 3H), 1.25-1.20 (m, 1H), 0.58-0.54 (m, 2H), 0.36-0.32 (m, 2H) | 476.3 |
| 185 | N,N'-(2'-hydroxy-3,3''-di(piperazin-1-yl)-[1,1':3',1''-terphenyl]-4,4''-diyl)diacetamide | ¹H NMR (400 MHz, DMSO-d₆): 8.97 (s, 2H), 8.78 (s, 4H), 8.31 (s, 1H), 7.99-7.97 (m, 2H), 7.29-7.21 (m, 6H), 7.03-6.99 (m, 1H), 3.34 (s, 8H), 3.06-3.04 (m, 8H), 2.17 (s, 6H) | 529.3 |
| 186 | N-(3''-(4-(aminomethyl)piperidin-1-yl)-3-fluoro-2'-hydroxy-[1,1':3',1''-terphenyl]-4-yl)acetamide | ¹H NMR (400 MHz, DMSO-d₆ + D₂O): 7.92-7.88 (m, 1H), 7.48-7.25 (m, | 434.2 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | | 8H), 7.08-7.05 (m, 1H), 3.43 (s, 2H), 3.14-3.08 (m, 2H), 2.81-2.80 (m, 2H), 2.12 (s, 3H), 1.94-1.85 (m, 3H), 1.49-1.47 (m, 2H) | |
| 187 | N-(2'',3-difluoro-2'-hydroxy-5''-(piperazin-1-yl)-[1,1':3',1''-terphenyl]-4-yl)acetamide | ¹H NMR (400 MHz, DMSO-d₆): 9.76 (s, 1H), 7.92 (t, J = 8.4 Hz, 1H), 7.42-7.41 (m, 1H), 7.39-7.26 (m, 2H), 7.17-7.01 (m, 2H), 6.99-6.87 (m, 3H), 3.03-3.00 (m, 4H), 2.84-2.82 (m, 4H), 2.11 (s, 3H). N—H or O—H protons not observed | 424.1 |
| 188 | 1-(3-fluoro-2'-hydroxy-[1,1':3',1''-terphenyl]-4-yl)pyrrolidin-2-one | ¹H NMR (400 MHz, DMSO-d₆): 8.49 (s, 1H), 7.55-7.34 (m, 8H), 7.28-7.23 (m, 2H), 7.06-7.02 (m, 1H), 3.79 (t, J = 7.2 Hz, 2H), 2.50-2.43 (m, 2H), 2.16-2.13 (m, 2H) | 348.2 |
| 189 | N-(3-fluoro-2'-hydroxy-3'-(5-(piperazin-1-yl)pyridin-3-yl)-[1,1'-biphenyl]-4-yl)acetamide | ¹H NMR (400 MHz, DMSO-d₆): 9.78 (s, 1H), 8.25 (d, J = 2.4 Hz, 1H), | 407.1 |

TABLE 18-continued

Following compounds were prepared using similar procedures as described for Example 159
(See preparation in Scheme 3, 12, 13, 14 and 15).

| Ex. No. | Name/Structure | $^1$H NMR Data | LCMS (M + H)$^+$ |
|---|---|---|---|
| | | 8.12 (d, J = 1.2 Hz, 1H), 7.92 (t, J = 8.4 Hz, 1H), 7.44-7.25 (m, 5H), 7.06-7.02 (m, 1H), 3.18-3.16 (m, 4H), 2.90-2.87 (m, 4H), 2.11 (s, 3H). N—H or O—H protons not observed | |
| 190 | 1-(3-fluoro-2'-hydroxy-3'-(pyridin-4-yl)-[1,1'-biphenyl]-4-yl)pyrrolidin-2-one | $^1$H NMR (400 MHz, DMSO-d$_6$): 8.70 (s, 1H), 8.60 (d, J = 6.0 Hz, 2H), 7.59 (d, J = 5.6 Hz, 2H), 7.51-7.47 (m, 2H), 7.42-7.32 (m, 3H), 7.11 (s, 1H), 3.81-3.78 (m, 2H), 2.47-2.43 (m, 2H), 2.16-2.13 (m, 2H) | 349.1 |
| 191 | N-(3-fluoro-2'-hydroxy-3''-(2-oxopiperazin-1-yl)-[1,1':3',1''-terphenyl]-4-yl)acetamide | $^1$H NMR (400 MHz, DMSO-d$_6$): 9.77 (s, 1H), 8.49 (s, 1H), 7.95-7.90 (m, 1H), 7.49-7.40 (m, 4H), 7.32-7.22 (m, 4H), 7.05-7.01 (m, 1H), 3.65 (t, J = 5.2 Hz, 2H), 3.40 (s, 2H), 3.03 (t, J = 5.2 Hz, 2H), 2.11 (s, 3H). N—H or O—H proton not observed | 420.1 |
| 192 | N-(3-fluoro-2'-hydroxy-3''-(2,8-diazaspiro[4.5]decan-8-yl)-[1,1':3',1''-terphenyl]-4-yl)acetamide | $^1$H NMR (400 MHz, DMSO-d$_6$): 9.76 (s, 1H), 7.91 (s, 1H), 7.43-7.19 (m, | 460.2 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | | 5H), 7.06-6.89 (m, 4H), 3.25-3.13 (m, 6H), 2.73 (s, 2H), 2.11 (s, 3H), 1.74-1.61 (m, 6H). N—H and O—H protons not observed | |
| 193 | (R)-N-(3-fluoro-2'-hydroxy-3''-(3-methylpiperazin-1-yl)-[1,1':3',1''-terphenyl]-4-yl)acetamide | ¹H NMR (400 MHz, DMSO-d₆): 9.76 (s, 1H), 7.91 (s, 1H), 7.43-7.40 (m, 1H), 7.32-7.19 (m, 4H), 7.03-6.89 (m, 4H), 3.56-3.51 (m, 2H), 2.94 (s, 1H), 2.80-2.76 (m, 2H), 2.57-2.51 (m, 1H), 2.24-2.19 (m, 1H), 2.11 (s, 3H), 1.02 (d, J = 6.0 Hz, 3H). N—H and O—H protons not observed. | 420.2 |
| 194 | N-(3-fluoro-2'-hydroxy-3''-(3-oxo-2,7-diazaspiro[4.4]nonan-2-yl)-[1,1':3',1''-terphenyl]-4-yl)acetamide | ¹H NMR (400 MHz, DMSO-d₆): 9.77 (s, 1H), 7.92 (s, 1H), 7.69-7.67 (m, 2H), 7.43-7.39 (m, 2H), 7.32-7.21 (m, 4H), 7.05-7.01 (m, 1H), 3.79 (d, J = 2.4 Hz, 2H), 3.39-3.36 (m, 2H), 2.90-2.59 (m, 4H), 2.33 (s, 3H), 2.11-1.79 (m, 2H). N—H and O—H protons not observed | 460.2 |
| 195 | N-(3-fluoro-2'-hydroxy-3''-(3,9-diazaspiro[5.5]undecan-3-yl)-[1,1':3',1''-terphenyl]-4-yl)acetamide | ¹H NMR (400 MHz, DMSO-d₆): 9.77 (s, 1H), 8.39 (s, 3H), 7.94-7.90 (m, | 474.2 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | | 1H), 7.43-7.39 (m, 1H), 7.36-7.21 (m, 5H), 7.11-7.00 (m, 3H), 3.27 (s, 4H), 3.08 (s, 4H), 2.11 (s, 3H), 1.67 (s, 8H) | |
| 196 | N-(3-fluoro-2'-hydroxy-3"-(2,7-diazaspiro[3.5]nonan-7-yl)-[1,1':3',1"-terphenyl]-4-yl)acetamide | ¹H NMR (400 MHz, DMSO-d₆): 9.77 (s, 1H), 7.91 (t, J = 8.4 Hz, 1H), 7.41 (dd, J = 12.4, 1.6 Hz, 1H), 7.32-7.18 (m, 4H), 7.05-6.89 (m, 4H), 3.56-3.47 (m, 4H), 3.26-3.12 (m, 4H), 2.11 (s, 3H), 1.83-1.78 (m, 4H). N—H and O—H protons not observed | 446.2 |
| 197 | 1-(3-fluoro-2'-hydroxy-3"-(piperazin-1-yl)-[1,1':3',1"-terphenyl]-4-yl)imidazolidin-2-one | ¹H NMR (400 MHz, DMSO-d₆): 7.52 (t, J = 8.4 Hz, 1H), 7.43-7.40 (m, 2H), 7.35-7.20 (m, 3H), 7.03-7.00 (m, 2H), 6.99-6.89 (m, 3H), 3.86 (t, J = 7.2 Hz, 2H), 3.46-3.42 (m, 2H), 3.09-3.06 (m, 4H), 2.85-2.82 (m, 4H). N—H and O—H protons not observed | 433.2 |
| 198 | N-(3-fluoro-2'-hydroxy-3'-(2-(4-(hydroxymethyl)piperidin-1-yl)pyridin-4-yl)-[1,1'-biphenyl]-4-yl)acetamide | ¹H NMR (400 MHz, DMSO-d₆): 9.78 (s, 1H), 8.52 (s, 1H), 8.11 (d, J = | 436.2 |

TABLE 18-continued

Following compounds were prepared using similar procedures as described for Example 159
(See preparation in Scheme 3, 12, 13, 14 and 15).

| Ex. No. | Name/Structure | $^1$H NMR Data | LCMS (M + H)$^+$ |
|---|---|---|---|
| | | 4.8 Hz, 1H), 7.94-7.90 (m, 1H), 7.43-7.40 (m, 1H), 7.31-7.24 (m, 3H), 7.05-7.01 (m, 1H), 6.90 (s, 1H), 6.75-6.73 (m, 1H), 4.48-4.45 (m, 1H), 4.34 (d, J = 13.2 Hz, 2H), 3.30-3.26 (m, 2H), 2.81-2.76 (m, 2H), 2.11 (s, 3H), 1.73-1.60 (m, 3H), 1.18-1.11 (m, 2H) | |
| 199 | N-(3-fluoro-2'-hydroxy-3'-(2-(3-hydroxypyrrolidin-1-yl)pyridin-4-yl)-[1,1'-biphenyl]-4-yl)acetamide | $^1$H NMR (400 MHz, DMSO-d$_6$): δ 9.78 (s, 1H), 8.53 (s, 1H), 8.08 (d, J = 5.2 Hz, 1H), 7.92 (t, J = 8.4 Hz, 1H), 7.41 (dd, J = 12.4 Hz, 1.6 Hz, 1H), 7.31-7.24 (m, 3H), 7.02 (t, J = 7.2 Hz, 1H), 6.68 (d, J = 5.2 Hz, 1H), 6.52 (s, 1H), 4.94 (d, J = 3.2 Hz, 1H), 4.39 (s, 1H), 3.53-3.45 (m, 4H), 2.10 (s, 3H), 2.03-1.99 (m, 1H), 1.91-1.89 (m, 1H) | 408.2 |
| 200 | N-(3''-(3,5-dimethylpiperazin-1-yl)-3-fluoro-2'-hydroxy-[1,1':3',1''-terphenyl]-4-yl)acetamide | $^1$H NMR (400 MHz, DMSO-d$_6$): δ 9.76 (s, 1H), 8.26 (br s, 1H), 7.91 (t, J = 8.0 Hz, 1H), 7.41 (d, J = 12.4 Hz, 1H), 7.31-7.18 (m, 4H), 7.01-6.97 (m, 2H), 6.90 (t, J = 5.2 Hz, 2H), 3.57 (d, J = 10.8 Hz, 2H), 2.87-2.85 (m, 2H), 2.18-2.10 (m, 5H), 1.03 (d, J = 6.0 Hz, 6H). N—H or O—H proton not observed | 434.2 |
| 201 | Methyl 4-(4'-acetamido-3'-fluoro-2-hydroxy-[1,1'-biphenyl]-3-yl)picolinate | $^1$H NMR (400 MHz, DMSO-d$_6$): δ 9.78 (s, 1H), | 381.1 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | | 8.89 (s, 1H), 8.76 (d, J = 4.8 Hz, 1H), 8.25 (s, 1H), 7.95 (t, J = 7.6 Hz, 1H), 7.81 (d, J = 4.8 Hz, 1H), 7.44-7.31 (m, 4H), 7.10 (t, J = 7.6 Hz, 1H), 3.90 (s, 3H), 2.11 (s, 3H) | |
| 202 | N-(3''-(6-aminopyridin-3-yl)-3-fluoro-2'-hydroxy-[1,1':3',1''-terphenyl]-4-yl)acetamide | ¹H NMR (400 MHz, DMSO-d₆): δ 9.76 (s, 1H), 8.43 (s, 1H), 8.28 (d, J = 2.4 Hz, 1H), 7.92 (t, J = 8.4 Hz, 1H), 7.74 (dd, J = 8.8 Hz, 2.8 Hz, 1H), 7.68 (s, 1H), 7.54-7.51 (m, 1H), 7.48-7.41 (m, 3H), 7.33-7.24 (m, 3H), 7.03 (t, J = 7.6 Hz, 1H), 6.53 (d, J = 8.4 Hz, 1H), 6.04 (s, 2H), 2.11 (s, 3H) | 414.1 |
| 203 | N-(3''-(3-(aminomethyl)pyrrolidin-1-yl)-3-fluoro-2'-hydroxy-[1,1':3',1''-terphenyl]-4-yl)acetamide | ¹H NMR (400 MHz, DMSO-d₆): δ 9.75 (s, 1H), 7.90 (t, J = 8.0 Hz, 1H), 7.40 (d, J = 12.0 Hz, 1H), 7.30 (d, J = 8.0 Hz, 1H), 7.22-7.20 (m, 3H), 6.98 (t, J = 7.2 Hz, 1H), 6.71 (d, J = 7.2 Hz, 1H), 6.63 (s, 1H), 6.50 (d, J = 7.2 Hz, 1H), 4.30 (br s, 2H), 3.39-3.23 (m, 4H), 3.02-2.99 (m, 1H), 2.66-2.61 (m, 2H), 2.32-2.28 (m, 1H), 2.10 (s, 3H), 1.72-1.68 (m, 1H). N—H or O—H proton not observed | 420.2 |
| 204 | N-(3''-(2-aminopyridin-4-yl)-3-fluoro-2'-hydroxy-[1,1':3',1''-terphenyl]-4-yl)acetamide | ¹H NMR (400 MHz, DMSO-d₆): δ 9.77 (s, 1H), 8.52 (s, 1H), 7.98-7.91 (m, | 414.1 |

TABLE 18-continued

Following compounds were prepared using similar procedures as described for Example 159
(See preparation in Scheme 3, 12, 13, 14 and 15).

| Ex. No. | Name/Structure | $^1$H NMR Data | LCMS $(M + H)^+$ |
|---|---|---|---|
| | 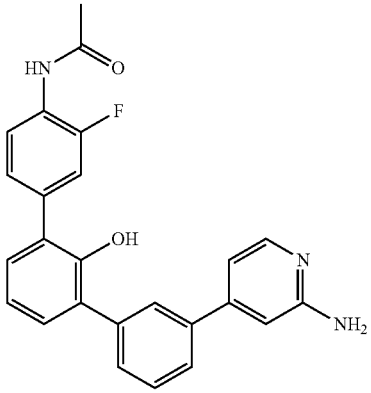 [SMILES: CC(=O)Nc1ccc(-c2cccc(-c3cccc(-c4ccnc(N)c4)c3)c2O)cc1F] | 2H), 7.78 (s, 1H), 7.61-7.53 (m, 3H), 7.43 (d, J = 12.0 Hz, 1H), 7.34-7.27 (m, 3H), 7.05 (t, J = 7.2 Hz, 1H), 6.83 (d, J = 4.0 Hz, 1H), 6.76 (s, 1H), 5.95 (s, 2H), 2.11 (s, 3H) | |
| 205 | 4-(4'-acetamido-3'-fluoro-2-hydroxy-[1,1'-biphenyl]-3-yl)picolinic acid | $^1$H NMR (400 MHz, DMSO-d$_6$): δ 9.78 (s, 1H), 8.69 (s, 1H), 8.20 (s, 1H), 7.94 (br s, 1H), 7.71 (s, 1H), 7.44-7.33 (m, 4H), 7.10-7.08 (m, 1H), 2.11 (s, 3H). N—H and O—H protons not observed | 367.1 |
| 206 | N-(3''-(3,6-diazabicyclo[3.2.1]octan-3-yl)-3-fluoro-2'-hydroxy-[1,1':3',1''-terphenyl]-4-yl)acetamide | $^1$H NMR (400 MHz, DMSO-d$_6$ with D$_2$O): δ 7.90 (t, J = 8.4 Hz, 1H), 7.41 (d, J = 12.0 Hz, 1H), 7.32-7.18 (m, 4H), 7.03-6.97 (m, 2H), 6.90-6.83 (m, 1H), 3.80-3.62 (m, 2H), 3.05 (s, 2H), 2.89-2.81 (m, 2H), 2.61 (s, 1H), 2.11 (s, 3H), 1.79-1.74 (m, 3H) | 432.2 |
| 207 | 1-(3,5-difluoro-2'-hydroxy-3'-(pyridin-4-yl)-[1,1'-biphenyl]-4-yl)pyrrolidin-2-one | $^1$H NMR (400 MHz, DMSO-d$_6$): δ 8.99 (s, 1H), | 367.1 |

TABLE 18-continued

Following compounds were prepared using similar procedures as described for Example 159
(See preparation in Scheme 3, 12, 13, 14 and 15).

| Ex. No. | Name/Structure | $^1$H NMR Data | LCMS (M + H)$^+$ |
|---|---|---|---|
| | | 8.62 (d, J = 5.6 Hz, 2H), 7.57 (d, J = 6.0 Hz, 2H), 7.40-7.35 (m, 4H), 7.10 (t, J = 7.6 Hz, 1H), 3.72 (t, J = 6.8 Hz, 2H), 2.47-2.45 (m, 2H), 2.23-2.18 (m, 2H) | |
| 208 | N-(3-fluoro-2'-hydroxy-3''-(1H-1,2,4-triazol-3-yl)-[1,1':3',1''-terphenyl]-4-yl)acetamide | $^1$H NMR (400 MHz, DMSO-d$_6$): δ 14.17 (br s, 1H), 9.77 (s, 1H), 8.50 (br s, 1H), 8.20 (s, 1H), 7.99-7.91 (m, 2H), 7.58-7.55 (m, 2H), 7.43 (d, J = 12.0 Hz, 1H), 7.34-7.27 (m, 3H), 7.05 (t, J = 7.6 Hz, 1H), 2.11 (s, 3H). N—H or O—H proton not observed | 389.1 |
| 209 | 1-(3-chloro-2'-hydroxy-3'-(2-(piperazin-1-yl)pyridin-4-yl)-[1,1'-biphenyl]-4-yl)pyrrolidin-2-one | $^1$H NMR (400 MHz, DMSO-d$_6$): δ 8.88 (br s, 3H), 8.20 (d, J = 5.6 Hz, 1H), 7.71 (d, J = 1.6 Hz, 1H), 7.55-7.46 (m, 2H), 7.34 (d, J = 8.4 Hz, 2H), 7.13-7.06 (m, 2H), 6.97 (s, 1H), 3.78-3.71 (m, 6H), 3.24-3.21 (m, 4H), 2.47-2.43 (m, 2H), 2.18-2.15 (m, 2H). $^{19}$F NMR (376 MHz, DMSO-d$_6$): δ −74.53 | 449.2 |
| 210 | N-(3-fluoro-2'-hydroxy-3''-(piperidin-4-yl)-[1,1':3',1''-terphenyl]-4-yl)acetamide | $^1$H NMR (400 MHz, DMSO-d$_6$): δ 9.78 (s, 1H), | 405.2 |

TABLE 18-continued

Following compounds were prepared using similar procedures as described for Example 159
(See preparation in Scheme 3, 12, 13, 14 and 15).

| Ex. No. | Name/Structure | ¹H NMR Data | LCMS (M + H)⁺ |
|---|---|---|---|
| | 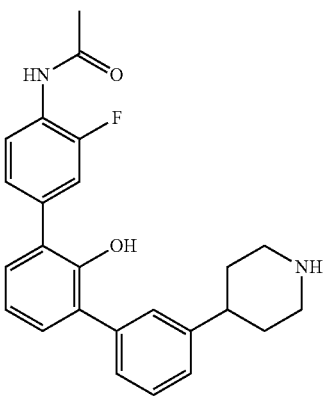 [SMILES: CC(=O)Nc1ccc(-c2cccc(-c3cccc(C4CCNCC4)c3)c2O)cc1F] | 8.62 (br s, 1H), 8.42 (s, 1H), 8.32 (t, J = 5.2 Hz, 1H), 7.92 (t, J = 8.0 Hz, 1H), 7.42-7.40 (m, 4H), 7.31 (d, J = 8.0 Hz, 1H), 7.26-7.21 (m, 3H), 7.03 (t, J = 7.2 Hz, 1H), 3.41-3.38 (m, 2H), 3.06-2.98 (m, 2H), 2.93-2.87 (m, 1H), 2.11 (s, 3H), 2.00-1.97 (m, 2H), 1.88-1.79 (m, 2H) | |
| 211 | 4-(4'-acetamido-3'-fluoro-2-hydroxy-[1,1'-biphenyl]-3-yl)picolinamide 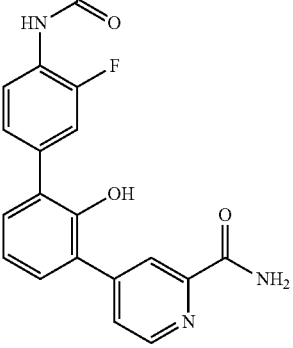 | ¹H NMR (400 MHz, DMSO-d₆): δ 9.78 (s, 1H), 8.71-8.66 (m, 2H), 8.24 (s, 1H), 8.15 (s, 1H), 7.95 (t, J = 8.4 Hz, 1H), 7.75 (d, J = 4.0 Hz, 1H), 7.66 (s, 1H), 7.42 (d, J = 12.0 Hz, 1H), 7.36-7.31 (m, 3H), 7.11-7.07 (m, 1H), 2.11 (s, 3H) | 366.1 |

Example 212

N-(3-Fluoro-2'-hydroxy-3'-(2-(piperazin-1-yl)thiazol-4-yl)-[1,1'-biphenyl]-4-yl)acetamide

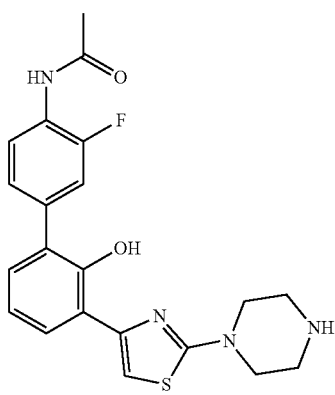 [SMILES: CC(=O)Nc1ccc(-c2cccc(-c3csc(N4CCNCC4)n3)c2O)cc1F]

Step 1: tert-Butyl 4-(4-(4'-acetamido-3'-fluoro-2-methoxy-[1,1'-biphenyl]-3-yl)thiazol-2-yl)piperazine-1-carboxylate The title compound was prepared following the procedure described for Example 1 using tert-butyl 4-(4-bromothiazol-2-yl)piperazine-1-carboxylate and N-(3-fluoro-2'-methoxy-3'-(4,4,5,5-tetramethyl-1,3,2-dioxaborolan-2-yl)-[1,1'-biphenyl]-4-yl)acetamide to afford the title compound (75% yield). LCMS: 527.2 (M+H)⁺.

Step 2: N-(3-fluoro-2'-hydroxy-3'-(2-(piperazin-1-yl)thiazol-4-yl)-[1,1'-biphenyl]-4-yl)acetamide The title compound was prepared following the procedure described for Example 1 using tert-butyl 4-(4-(4'-acetamido-3'-fluoro-2-methoxy-[1,1'-biphenyl]-3-yl)thiazol-2-yl)piperazine-1-carboxylate and BBr₃ to afford the title compound. ¹H NMR (400 MHz, DMSO-d₆): δ 12.56 (s, 1H), 9.75 (s, 1H), 7.88 (t, J=8.4 Hz, 2H), 7.73 (dd, J=8.0 Hz, 1.2 Hz, 1H), 7.46 (dd, J=12.4 Hz, 1.2 Hz, 1H), 7.39 (s, 1H), 7.33 (d, J=8.4 Hz, 1H), 7.27 (dd, J=7.6 Hz, 1.2 Hz, 1H), 6.92 (t, J=7.6 Hz, 1H), 3.37 (t, J=4.4 Hz, 4H), 2.83 (t, J=5.2 Hz, 4H), 2.10 (s, 3H). LCMS: 413.1 (M+H)⁺.

Example 213

1-(3-Chloro-2'-hydroxy-3'-(pyridin-4-yl)-[1,1'-biphenyl]-4-yl)pyrrolidin-2-one 2,2,2-trifluoroacetate

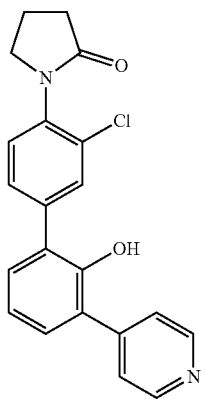

Step 1:
N-(4-bromo-2-chlorophenyl)-4-chlorobutanamide

To a solution of 4-bromo-2-chloroaniline (2.60 g, 12.6 mmol) in THF (30 mL) was added 4-chlorobutanoyl chloride (2.66 g, 18.9 mmol, 2.22 mL) and $Na_2CO_3$ (2.00 g, 18.9 mmol). After the addition, the reaction mixture was stirred at 84° C. under nitrogen atmosphere for 6 hours. After the reaction was indicated by LCMS, the reaction mixture was filtered and concentrated, dilute with $H_2O$ (50 mL) and extracted with EA (30 mL×3). The combined organic layers were washed with brine, dried over sodium sulfate, filtered and concentrated to afford the title compound (3.9 g, 99% yield) as a brown solid. LCMS: 309.9 (M+H)$^+$.

Step 2:
1-(4-Bromo-2-chlorophenyl)pyrrolidin-2-one

To a solution of N-(4-bromo-2-chlorophenyl)-4-chlorobutanamide (2.00 g, 6.40 mmol) in THF (30 mL) was added NaH (282 mg, 7.04 mmol, 60% wt in mineral oil). After the addition, the reaction mixture was stirred at room temperature under nitrogen atmosphere for 2 hours. After the reaction was indicated by LCMS and TLC, the reaction mixture was quenched with $H_2O$ (80 mL) and extracted with EA (30 mL×3). The combined organic layers were washed with brine, dried over sodium sulfate, filtered and concentrated to afford the title compound (1.3 g, 74% yield) as brown oil. LCMS: 273.9 (M+H)$^+$.

Step 3: 1-(2-Chloro-4-(4,4,5,5-tetramethyl-1,3,2-dioxaborolan-2-yl)phenyl)pyrrolidin-2-one A mixture of 1-(4-bromo-2-chlorophenyl)pyrrolidin-2-one (1.30 g, 4.74 mmol), 4,4,4',4',5,5,5',5'-octamethyl-2,2'-bi(1,3,2-dioxaborolane) (2.41 g, 9.47 mmol), KOAc (1.39 g, 14.2 mmol) and Pd(dppf)Cl$_2$ (347 mg, 0.474 mmol) in dioxane (30 mL) was stirred at 90° C. overnight under nitrogen atmosphere. After the reaction was indicated by LCMS, the reaction mixture was removed the solvent under reduced pressure. The residue was purified by silica gel chromatography using petroleum ether and ethyl acetate as the eluent: petroleum ether:ethyl acetate=2:1 to afford the title compound (1.4 g, 93% yield) as brown oil. LCMS: 322.1 (M+H)$^+$.

Step 4: 1-(3'-Bromo-3-chloro-2'-hydroxy-[1,1'-biphenyl]-4-yl)pyrrolidin-2-one A mixture of 1-(2-chloro-4-(4,4,5,5-tetramethyl-1,3,2-dioxaborolan-2-yl)phenyl)pyrrolidin-2-one (500 mg, 1.55 mmol), 2-bromo-6-iodophenol (466 mg, 1.55 mmol), K$_3$PO$_4$ (989 mg, 4.66 mmol) and Pd(dppf)Cl$_2$ (228 mg, 0.310 mmol) in dioxane:water (8:1, 15 mL) was stirred at 40° C. overnight under nitrogen atmosphere. After the reaction was indicated by LCMS, the reaction mixture was removed the solvent under reduced pressure. The residue was purified by silica gel chromatography using petroleum ether and ethyl acetate as the eluent: petroleum ether:ethyl acetate=1:1 to afford the title compound (200 mg, 35% yield) as a brown solid. LCMS: 365.9 (M+H)$^+$.

Step 5: 1-(3-Chloro-2'-hydroxy-3'-(pyridin-4-yl)-[1,1'-biphenyl]-4-yl)pyrrolidin-2-one 2,2,2-trifluoroacetate A mixture of 1-(3'-bromo-3-chloro-2'-hydroxy-[1,1'-biphenyl]-4-yl)pyrrolidin-2-one (150 mg, 0.410 mmol), pyridin-4-ylboronic acid (201 mg, 1.64 mmol), K$_3$PO$_4$ (261 mg, 1.23 mmol) and Pd(dppf)Cl$_2$ (60 mg, 0.080 mmol) in dioxane:water (8:1, 10 mL) was stirred at 110° C. for 4 hours under nitrogen atmosphere. After the reaction was indicated by LCMS, the reaction mixture was removed the solvent under reduced pressure. The residue was purified by silica gel chromatography using dichloromethane and methanol as the eluent: DCM:MeOH=15:1 to afford the crude product. The crude product was purified by prep-HPLC using acetonitrile in water in the presence of TFA to afford the title compound (31.5 mg, 16% yield) as a white solid. $^1$H NMR (400 MHz, DMSO-d$_6$) (TFA salt): δ 9.39 (1H), 8.87 (d, J=3.2 Hz, 2H), 8.10 (s, 2H), 7.74 (d, J=1.6 Hz, 1H), 7.57 (dd, J=8.0, 1.6 Hz, 1H), 7.51-7.45 (m, 3H), 7.20-7.16 (m, 1H), 3.75-3.72 (m, 2H), 2.48-2.41 (m, 2H), 2.21-2.14 (m, 2H). LCMS: 365.2 (M+H)$^+$.

Example 214

N-(3"-chloro-3-fluoro-2'-hydroxy-5"-(piperazin-1-yl)-[1,1':3',1"-terphenyl]-4-yl)acetamide

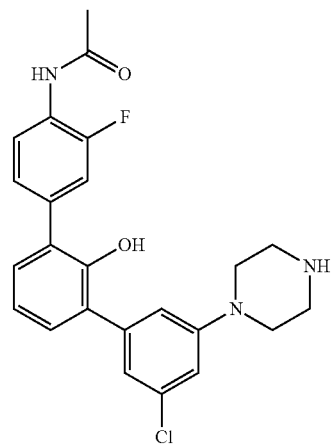 [SMILES: CC(=O)Nc1ccc(-c2cccc(-c3cc(Cl)cc(N4CCNCC4)c3)c2O)cc1F]

Step 1: Tert-butyl 4-(3-bromo-5-chlorophenyl)piperazine-1-carboxylate

To a solution of 1,3-dibromo-5-chlorobenzene (2.00 g, 7.40 mmol) and tert-butyl piperazine-1-carboxylate (459 mg, 2.47 mmol) in DMSO (25 mL) was added $K_2CO_3$ (1.02 g, 7.40 mmol), CuI (281 mg, 1.41 mmol) and (L)-Proline (340 mg, 2.96 mmol). The reaction mixture was stirred at 70° C. under nitrogen atmosphere overnight. After the reaction was indicated by LCMS, the reaction mixture was cooled, $H_2O$ (100 mL) was added and extracted with ethyl acetate (30 mL×3). The combined organic layers were washed with brine (30 mL), dried over sodium sulfate, filtered and concentrated to afford a residue which was purified by silica gel chromatography using petroleum ether and ethyl acetate as the eluent: petroleum ether:ethyl acetate=5:1 to afford the title compound (200 mg, 22% yield) as a white solid. LCMS: 318.9 (M−56+H)$^+$.

Step 2: Tert-butyl 4-(4"-acetamido-5-chloro-3"-fluoro-2'-methoxy-[1,1':3',1"-terphenyl]-3-yl)piperazine-1-carboxylate A mixture of tert-butyl 4-(3-bromo-5-chlorophenyl)piperazine-1-carboxylate (200 mg, 0.530 mmol), N-(3-fluoro-2'-methoxy-3'-(4,4,5,5-tetramethyl-1,3,2-dioxaborolan-2-yl)-[1,1'-biphenyl]-4-yl)acetamide (205 mg, 0.530 mmol), $K_3PO_4$ (337 mg, 1.59 mmol) and Pd(dppf)Cl$_2$ (78 mg, 0.11 mmol) in dioxane:water (8:1, 10 mL) was stirred at 110° C. for 4 hours under nitrogen atmosphere. After the reaction was indicated by LCMS, the reaction mixture was removed the solvent under reduced pressure. The residue was purified by silica gel chromatography using petroleum ether and ethyl acetate as the eluent: petroleum ether:ethyl acetate=4:1 to afford the title compound (200 mg, 68% yield) as a yellow solid. LCMS: 554.2 (M+H)$^+$.

Step 3: N-(3"-chloro-3-fluoro-2'-hydroxy-5"-(piperazin-1-yl)-[1,1':3',1"-terphenyl]-4-yl)acetamide To a solution of tert-butyl 4-(4"-acetamido-5-chloro-3"-fluoro-2'-methoxy-[1,1':3',1"-terphenyl]-3-yl)piperazine-1-carboxylate (200 mg, 0.360 mmol) in DCM (1 mL) was added BBr$_3$ (5 mL, 17% in DCM) dropwise at 0° C. Then the reaction mixture was stirred at room temperature under nitrogen atmosphere for 4 hours. After the reaction was indicated by LCMS, the reaction mixture was quenched with MeOH (5 mL) at 0° C. The mixture was concentrated and the residue was purified by prep-HPLC using acetonitrile in water in the presence of NH$_4$HCO$_3$ to afford the title compound (25.6 mg, 16% yield) as a white solid. $^1$H NMR (400 MHz, DMSO-d$_6$): 9.78 (s, 1H), 7.94-7.90 (m, 1H), 7.42 (dd, J=12.4, 1.2 Hz, 1H), 7.32-7.30 (m, 1H), 7.26-7.22 (m, 2H), 7.02-6.90 (m, 4H), 3.11 (d, J=4.4 Hz, 4H), 2.82 (d, J=4.4 Hz, 4H), 2.11 (s, 3H). N—H or O—H proton not observed. LCMS: 440.2 (M+H)$^+$.

TABLE 19

Following compounds were prepared using similar procedures as described for Examples 159, 163, 213 or 214.

| Ex. No. | Name/Structure | $^1$H NMR Data | LCMS (M + H)$^+$ |
|---|---|---|---|
| 215 | N-(3-fluoro-2'-hydroxy-3"-(piperazin-1-yl)-5"-(trifluoromethyl)-[1,1':3',1"-terphenyl]-4-yl)acetamide | $^1$H NMR (400 MHz, DMSO-d$_6$): δ 9.77 (s, 1H), 7.92 (t, J = 8.4 Hz, 1H), 7.42 (dd, J = 12.0 Hz, 1.6 Hz, 1H), 7.31 (dd, J = 8.4 Hz, 1.6 Hz, 1H), 7.28-7.25 (m, 4H), 7.19 (s, 1H), 7.12 (s, 1H), 7.02 (d, J = 7.6 Hz, 1H), 3.16 (t, J = 4.4 Hz, 4H), 2.83 (t, J = 5.2 Hz, 4H), 2.10 (s, 3H). N—H or O—H proton not observed | 474.1 |
| 216 | 1-(3,5'-Difluoro-2'-hydroxy-3'-(2-(piperazin-1-yl)pyridin-4-yl)-[1,1'-biphenyl]-4-yl)pyrrolidin-2-one | $^1$H NMR (400 MHz, DMSO-d$_6$): δ 8.92-8.75 (m, 3H), 8.22 (d, J = 5.2 Hz, | 451.2 |

TABLE 19-continued

Following compounds were prepared using similar procedures as described for Examples 159, 163, 213 or 214.

| Ex. No. | Name/Structure | $^1$H NMR Data | LCMS (M + H)$^+$ |
|---|---|---|---|
| | | 1H), 7.54-7.50 (m, 2H), 7.43 (dd, J = 8.0, 1.6 Hz, 1H), 7.27-7.21 (m, 2H), 7.12 (s, 1H), 7.00 (d, J = 5.2 Hz, 1H), 3.82-3.78 (m, 6H), 3.22-3.17 (m, 4H), 2.47-2.43 (m, 2H), 2.19-2.09 (m, 2H) | |
| 217 | 1-(3-chloro-5'-fluoro-2'-hydroxy-3'-(2-(piperazin-1-yl)pyridin-4-yl)-[1,1'-biphenyl]-4-yl)pyrrolidin-2-one | $^1$H NMR (400 MHz, DMSO-d$_6$): δ 8.92 (br s, 3H), 8.21 (d, J = 5.6 Hz, 1H), 7.75 (d, J = 1.6 Hz, 1H), 7.58 (dd, J = 8.0 Hz, 1.6 Hz, 1H), 7.49 (d, J = 8.0 Hz, 1H), 7.27-7.21 (m, 2H), 7.11 (s, 1H), 6.99 (d, J = 5.2 Hz, 1H), 3.78-3.71 (m, 6H), 3.23-3.20 (m, 4H), 2.47-2.43 (m, 2H), 2.20-2.15 (m, 2H) | 467.1 |
| 218 | N-(3'-(2,6-di(piperazin-1-yl)pyridin-4-yl)-3-fluoro-2'-hydroxy-[1,1'-biphenyl]-4-yl)acetamide | $^1$H NMR (400 MHz, DMSO-d$_6$): δ 9.79 (s, 1H), 8.84 (s, 4H), 8.40 (s, 1H), 7.93-7.90 (m, 1H), 7.41 (d, J = 11.6 Hz, 1H), 7.29 (d, J = 7.2 Hz, 2H), 7.23 (d, J = 7.2 Hz, 1H), 7.01 (t, J = 7.6 Hz, 1H), 6.37 (s, 2H), 3.73-3.69 (m, 8H), 3.22-3.18 (m, 8H), 2.10 (s, 3H) | 491.2 |

TABLE 19-continued

Following compounds were prepared using similar procedures as described for Examples 159, 163, 213 or 214.

| Ex. No. | Name/Structure | $^1$H NMR Data | LCMS (M + H)$^+$ |
|---|---|---|---|
| 219 | N-(3-fluoro-2'-hydroxy-3''-(2,6-diazaspiro[3.3]heptan-2-yl)-[1,1':3',1''-terphenyl]-4-yl)acetamide | $^1$H NMR (400 MHz, DMSO-d$_6$): δ 9.76 (s, 1H), 7.91 (t, J = 8.4 Hz, 1H), 7.41 (dd, J = 12.4 Hz, 1.6 Hz, 1H), 7.30 (dd, J = 8.8 Hz, 1.6 Hz, 1H), 7.23-7.16 (m, 3H), 6.98 (t, J = 7.6 Hz, 1H), 6.81 (d, J = 7.6 Hz, 1H), 6.54 (s, 1H), 6.40 (dd, J = 7.6 Hz, 1.6 Hz, 1H), 3.89 (s, 5H), 3.61 (s, 4H), 2.10 (s, 3H). N—H or O—H proton not observed | 418.2 |
| 220 | N-(3''-(3-(aminomethyl)azetidin-1-yl)-3-fluoro-2'-hydroxy-[1,1':3',1''-terphenyl]-4-yl)acetamide | $^1$H NMR (400 MHz, DMSO-d$_6$): δ 9.76 (s, 1H), 7.90 (t, J = 8.4 Hz, 1H), 7.41 (dd, J = 12.0 Hz, 1.6 Hz, 1H), 7.30 (dd, J = 8.4 Hz, 1.6 Hz, 1H), 7.23-7.16 (m, 3H), 6.98 (t, J = 7.2 Hz, 1H), 6.79 (d, J = 7.6 Hz, 1H), 6.52 (s, 1H), 6.38 (dd, J = 8.0 Hz, 1.2 Hz, 1H), 3.84 (t, J = 7.6 Hz, 2H), 3.53-3.50 (m, 2H), 3.32 (br s, 2H), 2.76 (d, J = 7.2 Hz, 2H), 2.66-2.63 (m, 1H), 2.10 (s, 3H). N—H or O—H proton not observed | 406.2 |
| 221 | N-(3-fluoro-2'-hydroxy-3''-(2,7-diazaspiro[4.4]nonan-2-yl)-[1,1':3',1''-terphenyl]-4-yl)acetamide | $^1$H NMR (400 MHz, DMSO-d$_6$): δ 9.77 (s, 1H), 8.89 (br s, 1H), 8.21 (s, 1H), 7.90 (t, J = 8.4 Hz, 1H), 7.41 (dd, J = 12.4 Hz, 2.0 Hz, 1H), 7.30 (dd, J = 8.4 Hz, 1.6 Hz, 1H), 7.26-7.18 (m, 3H), 6.99 (t, J = 7.2 Hz, 1H), 6.76 (d, J = 8.0 Hz, 1H), 6.65 (s, 1H), 6.51 (dd, J = 8.4 Hz, 2.0 Hz, 1H), 3.38-3.25 (m, 6H), 3.17 (t, J = 5.6 Hz, 2H), 2.10 (s, 3H), 2.08-1.93 (m, 4H). N—H or O—H proton not observed | 446.2 |
| 222 | N-(3-chloro-5'-fluoro-2'-hydroxy-3'-(2-(piperazin-1-yl)pyridin-4-yl)-[1,1'-biphenyl]-4-yl)acetamide | $^1$H NMR (400 MHz, DMSO-d$_6$): δ 9.58 (s, 1H), 8.14 (d, J = 4.4 Hz, 1H), | 441.1 |

TABLE 19-continued

Following compounds were prepared using similar procedures as described for Examples 159, 163, 213 or 214.

| Ex. No. | Name/Structure | ¹H NMR Data | LCMS (M + H)⁺ |
|---|---|---|---|
|  | 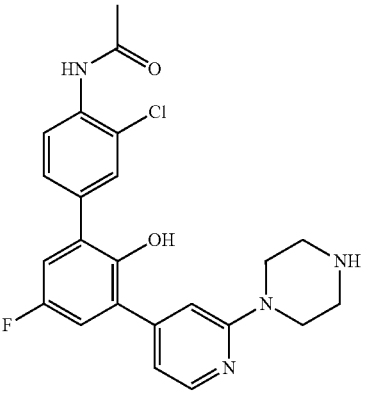 [SMILES: CC(=O)Nc1ccc(-c2cc(F)cc(-c3ccnc(N4CCNCC4)c3)c2O)cc1Cl] | 7.78 (d, J = 7.6 Hz, 1H), 7.69 (s, 1H), 7.49 (d, J = 8.0 Hz, 1H), 7.16 (t, J = 10.0 Hz, 2H), 6.91 (s, 1H), 6.80 (d, J = 4.4 Hz, 1H), 3.45-3.42 (m, 4H), 2.79-2.76 (m, 4H), 2.12 (s, 3H). N—H or O—H protons not observed |  |
| 223 | 1-(3-fluoro-2'-hydroxy-3"-(piperazin-1-yl)-[1,1':3',1"-terphenyl]-4-yl)piperidin-2-one 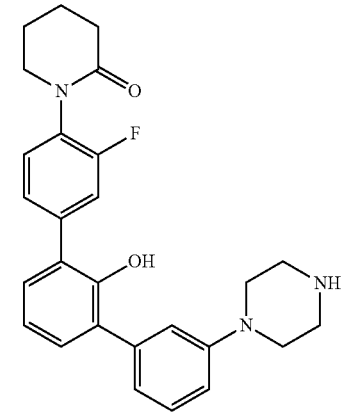 [SMILES: O=C1CCCCN1c1ccc(-c2cccc(-c3cccc(N4CCNCC4)c3)c2O)cc1F] | ¹H NMR (400 MHz, DMSO-d₆): δ 7.45-7.38 (m, 3H), 7.29-7.21 (m, 3H), 7.03-6.99 (m, 2H), 6.93-6.91 (m, 2H), 3.57 (t, J = 5.2 Hz, 2H), 3.07 (t, J = 4.4 Hz, 4H), 2.83 (t, J = 4.8 Hz, 4H), 2.43-2.40 (m, 2H), 1.88-1.85 (m, 4H). N—H or O—H protons not observed | 446.3 |
| 224 | N-(3,5'-difluoro-2'-hydroxy-3'-(2-(piperazin-1-yl)pyridin-4-yl)-[1,1'-biphenyl]-4-yl)acetamide 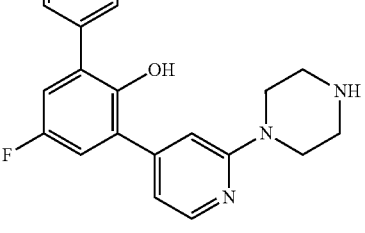 | ¹H NMR (400 MHz, DMSO-d₆): 9.79 (s, 1H), 8.14 (d, J = 5.2 Hz, 1H), 7.95 (t, J = 8.0 Hz, 1H), 7.48-7.45 (m, 1H), 7.36-7.33 (m, 1H), 7.19-7.12 (m, 2H), 6.91 (s, 1H), 6.80 (d, J = 5.2 Hz, 1H), 3.45-3.43 (m, 4H), 2.80-2.77 (m, 4H), 2.11 (s, 3H). N—H and O—H protons not observed | 425.2 |
| 225 | N-(3-fluoro-2'-hydroxy-3'-(2-(3-hydroxyazetidin-1-yl)pyridin-4-yl)-[1,1'-biphenyl]-4-yl)acetamide | ¹H NMR (400 MHz, DMSO-d₆): δ 8.52 (br s, 1H), 7.85 (d, J = 13.2 Hz, | 394.2 |

TABLE 19-continued

Following compounds were prepared using similar procedures as described for Examples 159, 163, 213 or 214.

| Ex. No. | Name/Structure | $^1$H NMR Data | LCMS (M + H)$^+$ |
|---|---|---|---|
| | | 1H), 7.73-7.70 (m, 1H), 7.67-7.65 (m, 1H), 7.40 (d, J = 8.4 Hz, 1H), 7.33 (dd, J = 8.0, 1.6 Hz, 1H), 7.24 (d, J = 6.8 Hz, 1H), 7.18 (d, J = 6.0 Hz, 1H), 6.26-6.24 (m, 1H), 4.31 (s, 1H), 4.24-4.21 (m, 1H), 4.08-4.04 (m, 1H), 3.60-3.51 (m, 3H), 2.08 (s, 3H). N—H and O—H protons not observed | |
| 226 | N-(3'-(2-chloro-6-(piperazin-1-yl)pyridin-4-yl)-3-fluoro-2'-hydroxy-[1,1'-biphenyl]-4-yl)acetamide | $^1$H NMR (400 MHz, DMSO-d$_6$): 9.77 (s, 1H), 7.92 (t, J = 8.4 Hz, 1H), 7.44-7.40 (m, 1H), 7.31-7.26 (m, 3H), 7.02 (t, J = 7.6 Hz, 1H), 6.83 (s, 1H), 6.79 (s, 1H), 3.45-3.43 (m, 4H), 2.78-2.76 (m, 4H), 2.11 (s, 3H). N—H or O—H protons not observed | 441.1 |
| 227 | N-(3-fluoro-2'-hydroxy-3''-(2H-tetrazol-5-yl)-[1,1':3',1''-terphenyl]-4-yl)acetamide | $^1$H NMR (400 MHz, DMSO-d$_6$): 9.78 (s, 1H), 8.60 (br s, 1H), 8.22 (s, 1H), 8.02-7.93 (m, 2H), 7.72-7.62 (m, 2H), 7.46-7.42 (m, 1H), 7.35-7.30 (m, 3H), 7.07 (t, J = 7.6 Hz, 1H), 2.12 (s, 3H). N—H or O—H proton not observed | 390.1 |
| 228 | 1-(3-chloro-2'-hydroxy-3'-(2-(piperazin-1-yl)pyridin-4-yl)-[1,1'-biphenyl]-4-yl)imidazolidin-2-one | $^1$H NMR (400 MHz, DMSO-d$_6$): 8.14 (d, J = 4.8 Hz, 1H), 7.66 (d, J = 1.6 | 450.2 |

TABLE 19-continued

Following compounds were prepared using similar procedures as described for Examples 159, 163, 213 or 214.

| Ex. No. | Name/Structure | ¹H NMR Data | LCMS (M + H)⁺ |
|---|---|---|---|
| | (structure: 1-[4-(chloro)-phenyl with imidazolidin-2-one, biphenyl-OH, piperazinyl pyridine) | Hz, 1H), 7.51-7.44 (m, 2H), 7.31-7.26 (m, 2H), 7.06-7.02 (m, 1H), 6.88 (s, 1H), 6.82-6.77 (m, 2H), 3.82-3.78 (m, 2H), 3.48-3.42 (m, 6H), 2.80-2.77 (m, 4H). N—H and O—H protons not observed | |
| 229 | N-(3-fluoro-2'-hydroxy-3''-(1H-imidazol-4-yl)-[1,1':3',1''-terphenyl]-4-yl)acetamide | ¹H NMR (400 MHz, DMSO-d₆): 12.18 (s, 1H), 9.80 (s, 1H), 8.44 (s, 1H), 7.95-7.91 (m, 2H), 7.76-7.64 (m, 3H), 7.45-7.25 (m, 6H), 7.24-7.02 (m, 1H), 2.11 (s, 3H) | 388.1 |
| 230 | N-(3-fluoro-2'-hydroxy-3'-(2-(3-(hydroxymethyl)pyrrolidin-1-yl)pyridin-4-yl)-[1,1'-biphenyl]-4-yl)acetamide | ¹H NMR (400 MHz, DMSO-d₆): 9.77 (s, 1H), 8.51 (s, 1H), 8.08 (d, J = 5.2 Hz, 1H), 7.92 (t, J = 7.6 Hz, 1H), 7.42-7.39 (m, 1H), 7.31-7.25 (m, 3H), 7.04-7.01 (m, 1H), 6.88 (d, J = 5.2 Hz, 1H), 6.54 (s, 1H), 4.70-4.67 (m, 1H), 3.55-3.37 (m, 5H), 3.21-3.17 (m, 1H), 2.43-2.40 (m, 1H), 2.11 (s, 3H), 2.07-2.00 (m, 1H), 1.77-1.72 (m, 1H) | 422.2 |
| 231 | 1-(3-fluoro-2'-hydroxy-3'-(2-(piperazin-1-yl)pyridin-4-yl)-[1,1'-biphenyl]-4-yl)imidazolidin-2-one | ¹H NMR (400 MHz, DMSO-d₆): 8.13 (d, J = 5.2 Hz, 1H), 7.55-7.51 (m, | 434.2 |

TABLE 19-continued

Following compounds were prepared using similar procedures as described for Examples 159, 163, 213 or 214.

| Ex. No. | Name/Structure | ¹H NMR Data | LCMS (M + H)⁺ |
|---|---|---|---|
| | | 1H), 7.44-7.25 (m, 4H), 7.03 (t, J = 7.6 Hz, 1H), 6.89 (s, 2H), 6.78 (d, J = 5.2 Hz, 1H), 3.87-3.84 (m, 2H), 3.46-3.42 (m, 6H), 2.79-2.77 (m, 4H). N—H and O—H protons not observed | |
| 232 | N-(3'-(2-(3-aminoazetidin-1-yl)pyridin-4-yl)-3-fluoro-2'-hydroxy-[1,1'-biphenyl]-4-yl)acetamide | ¹H NMR (400 MHz, DMSO-d₆): 9.78 (s, 1H), 7.93-7.89 (m, 1H), 7.40 (dd, J = 12.4, 1.6 Hz, 1H), 7.31-7.11 (m, 4H), 7.00-6.96 (m, 1H), 6.76 (s, 1H), 6.68-6.60 (m, 2H), 5.71-5.70 (m, 1H), 3.31 (s, 3H), 3.09-2.95 (m, 2H), 2.08 (s, 3H). N—H and O—H protons not observed | 392.1 |
| 233 | N-(3-fluoro-2'-hydroxy-3'-(4-(piperazin-1-yl)pyridin-2-yl)-[1,1'-biphenyl]-4-yl)acetamide | ¹H NMR (400 MHz, DMSO-d₆): 9.77 (s, 1H), 8.16 (d, J = 6.4 Hz, 1H), 8.10-8.08 (m, 1H), 7.89 (s, 1H), 7.53-7.48 (m, 2H), 7.39-7.35 (m, 2H), 6.94-6.88 (m, 2H), 3.44-3.42 (m, 4H), 2.84-2.81 (m, 4H), 2.11 (s, 3H). N—H and O—H protons not observed | 407.1 |
| 234 | N-(3''-cyano-3-fluoro-2'-hydroxy-5''-(piperazin-1-yl)-[1,1':3',1''-terphenyl]-4-yl)acetamide | ¹H NMR (400 MHz, DMSO-d₆): 9.77 (s, 1H), 7.95-7.90 (m, 1H), 7.45- | 431.1 |

TABLE 19-continued

Following compounds were prepared using similar procedures as described for Examples 159, 163, 213 or 214.

| Ex. No. | Name/Structure | ¹H NMR Data | LCMS (M + H)⁺ |
|---|---|---|---|
| | | 7.41 (m, 1H), 7.32-7.25 (m, 6H), 7.02 (t, J = 7.6 Hz, 1H), 3.17-3.15 (m, 4H), 2.83-2.81 (m, 4H), 2.11 (s, 3H). N—H and O—H protons not observed | |
| 235 | N-(4''-cyano-3,5'-difluoro-2'-hydroxy-3''-(piperazin-1-yl)-[1,1':3',1''-terphenyl]-4-yl)acetamide | ¹H NMR (400 MHz, DMSO-d₆): 9.80 (s, 1H), 7.95 (t, J = 8.0 Hz, 1H), 7.75-7.73 (m, 1H), 7.47 (dd, J = 12.0, 1.6 Hz, 1H), 7.36-7.34 (m, 1H), 7.27-7.18 (m, 4H), 3.13-3.11 (m, 4H), 2.89-2.87 (m, 4H), 2.11 (s, 3H). N—H and O—H protons not observed | 449.2 |
| 236 | N-(4''-cyano-3-fluoro-2'-hydroxy-3''-(piperazin-1-yl)-[1,1':3',1''-terphenyl]-4-yl)acetamide | ¹H NMR (400 MHz, DMSO-d₆): 9.78 (s, 1H), 7.95 (t, J = 8.0 Hz, 1H), 7.73 (d, J = 8.0 Hz, 1H), 7.42 (dd, J = 12.4, 2.0 Hz, 1H), 7.32-7.22 (m, 5H), 7.07-7.03 (m, 1H), 3.13-3.10 (m, 4H), 2.89-2.87 (m, 4H), 2.11 (s, 3H). N—H and O—H protons not observed | 431.2 |
| 237 | N-(3,4'',5'-trifluoro-2'-hydroxy-3''-(piperazin-1-yl)-[1,1':3',1''-terphenyl]-4-yl)acetamide | ¹H NMR (400 MHz, DMSO-d₆): 9.79 (s, 1H), 7.94 (t, J = 8.4 Hz, 1H), | 442.1 |

TABLE 19-continued

Following compounds were prepared using similar procedures as described for Examples 159, 163, 213 or 214.

| Ex. No. | Name/Structure | $^1$H NMR Data | LCMS (M + H)$^+$ |
|---|---|---|---|
| | | 7.46 (dd, J = 12.0, 1.6 Hz, 1H), 7.36-7.33 (m, 1H), 7.21-7.08 (m, 5H), 2.98-2.97 (m, 4H), 2.87-2.86 (m, 4H), 2.11 (s, 3H). N—H and O—H protons not observed | |
| 238 | 1-(3-fluoro-2'-hydroxy-3'-(2-(piperazin-1-yl)pyridin-4-yl)-[1,1'-biphenyl]-4-yl)pyrrolidin-2-one | $^1$H NMR (400 MHz, DMSO-d$_6$): 8.14 (d, J = 5.2 Hz, 1H), 7.51-7.37 (m, 3H), 7.32-7.26 (m, 2H), 7.06-7.02 (m, 1H), 6.89 (s, 1H), 6.78 (d, J = 5.2 Hz, 1H), 3.81-3.77 (m, 2H), 3.44-3.42 (m, 4H), 2.79-2.77 (m, 4H), 2.47-2.43 (m, 2H), 2.18-2.12 (m, 2H). N—H and O—H protons not observed | 433.2 |
| 239 | (S)-N-(3-fluoro-2'-hydroxy-3'-(2-(3-hydroxypyrrolidin-1-yl)pyridin-4-yl)-[1,1'-biphenyl]-4-yl)acetamide | $^1$H NMR (400 MHz, DMSO-d$_6$): 9.79 (s, 1H), 8.54 (s, 1H), 8.08 (d, J = 4.8 Hz, 1H), 7.92 (t, J = 8.4 Hz, 1H), 7.41 (dd, J = 12.4, 1.2 Hz, 1H), 7.32-7.24 (m, 3H), 7.04-7.01 (m, 1H), 6.67 (dd, J = 5.6, 1.2 Hz, 1H), 6.53 (s, 1H), 4.94 (d, J = 3.6 Hz, 1H), 4.39 (s, 1H), 3.53-3.45 (m, 3H), 3.33-3.31 (m, 1H), 2.11 (s, 3H), 2.04-1.90 (m, 2H) | 408.2 |
| 240 | 1-(3-fluoro-2'-hydroxy-3'-(2-(piperazin-1-yl)pyridin-4-yl)-[1,1'-biphenyl]-4-yl)-3-methylimidazolidin-2-one | $^1$H NMR (400 MHz, DMSO-d$_6$): 8.13 (d, J = 5.4 Hz, 1H), 7.55-7.51 (m, | 448.3 |

TABLE 19-continued

Following compounds were prepared using similar procedures as described for Examples 159, 163, 213 or 214.

| Ex. No. | Name/Structure | ¹H NMR Data | LCMS (M + H)⁺ |
|---|---|---|---|
| | (structure) | 1H), 7.44-7.25 (m, 4H), 7.03 (t, J = 7.6 Hz, 1H), 6.88 (s, 1H), 6.78 (d, J = 5.2 Hz, 1H), 3.80-3.77 (m, 2H), 3.50-3.42 (m, 6H), 2.79 (s, 7H). N—H and O—H protons not observed | |
| 241 | N-(4"-chloro-3-fluoro-2'-hydroxy-3"-(piperazin-1-yl)-[1,1':3',1"-terphenyl]-4-yl)acetamide | ¹H NMR (400 MHz, DMSO-d₆): 9.77 (s, 1H), 7.92 (t, J = 8.4 Hz, 1H), 7.45-7.40 (m, 2H), 7.32-7.16 (m, 5H), 7.04-7.00 (m, 1H), 2.94-2.93 (m, 4H), 2.87-2.86 (m, 4H), 2.11 (s, 3H). N—H and O—H protons not observed | 440.2 |
| 242 | N-(4"-chloro-3,5'-difluoro-2'-hydroxy-3"-(piperazin-1-yl)-[1,1'-terphenyl]-4-yl)acetamide | ¹H NMR (400 MHz, DMSO-d₆): 9.79 (s, 1H), 7.94 (t, J = 8.0 Hz, 1H), 7.48-7.45 (m, 2H), 7.36-7.34 (m, 1H), 7.27 (s, 1H), 7.22-7.11 (m, 3H), 2.95-2.94 (m, 4H), 2.88-2.87 (m, 4H), 2.11 (s, 3H). N—H and O—H protons not observed | 458.2 |
| 243 | N-(3-fluoro-2'-hydroxy-3"-(2H-1,2,3-triazol-4-yl)-[1,1':3',1"-terphenyl]-4-yl)acetamide | ¹H NMR (400 MHz, DMSO-d₆): 9.77 (s, 1H), 8.37 (s, 1H), 8.01 (m, 1H), | 389.2 |

TABLE 19-continued

Following compounds were prepared using similar procedures as described for Examples 159, 163, 213 or 214.

| Ex. No. | Name/Structure | ¹H NMR Data | LCMS (M + H)⁺ |
|---|---|---|---|
| | | 7.95-7.91 (m, 1H), 7.85-7.83 (m, 1H), 7.54-7.50 (m, 2H), 7.43 (dd, J = 12.4, 1.6 Hz, 1H), 7.34-7.27 (m, 3H), 7.07-7.03 (m, 1H), 2.11 (s, 3H). N—H and O—H protons not observed | |
| 244 | N-(3-fluoro-2'-hydroxy-3'-(2-methyl-6-(piperazin-1-yl)pyridin-4-yl)-[1,1'-biphenyl]-4-yl)acetamide | ¹H NMR (400 MHz, DMSO-d₆): 9.78 (s, 1H), 8.84 (s, 2H), 8.58 (s, 1H), 7.93 (t, J = 8.4 Hz, 1H), 7.43-7.39 (m, 1H), 7.32-7.25 (m, 3H), 7.04 (t, J = 7.6 Hz, 1H), 6.88 (s, 1H), 6.83 (s, 1H), 3.77-3.74 (m, 4H), 3.21 (s, 4H), 2.40 (s, 3H), 2.11 (s, 3H) | 421.2 |
| 245 | 1-(3-Chloro-2'-hydroxy-3'-(2-(piperazin-1-yl)pyridin-4-yl)-[1,1'-biphenyl]-4-yl)-3-methylimidazolidin-2-one | ¹H NMR (TFA salt - 400 MHz, DMSO-d₆): 8.88-8.77 (m, 3H), 8.20 (d, J = 5.2 Hz, 1H), 7.67 (d, J = 2.0 Hz, 1H), 7.52-7.45 (m, 2H), 7.35-7.30 (m, 2H), 7.10-7.06 (m, 2H), 6.96 (d, J = 5.6 Hz, 1H), 3.79-3.71 (m, 6H), 3.51-3.47 (m, 2H), 3.22 (s, 4H), 2.77 (s, 3H) | 464.2 |
| 246 | N-(3-fluoro-2'-hydroxy-3"-(1H-pyrazol-4-yl)-[1,1':3',1"-terphenyl]-4-yl)acetamide | ¹H NMR (400 MHz, DMSO-d₆): 12.90 (s, 1H), 9.77 (s, 1H), 8.39 (s, 1H), | 388.1 |

TABLE 19-continued

Following compounds were prepared using similar procedures as described for Examples 159, 163, 213 or 214.

| Ex. No. | Name/Structure | $^1$H NMR Data | LCMS (M + H)$^+$ |
|---|---|---|---|
| | 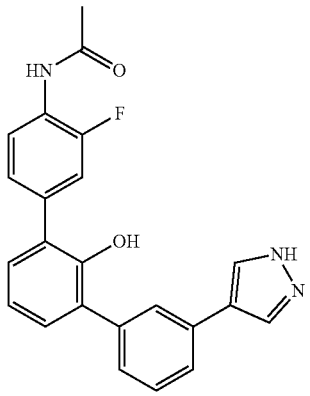 | 8.18-7.91 (m, 2H), 7.73 (s, 1H), 7.59-7.57 (m, 1H), 7.45-7.25 (m, 6H), 7.05-7.02 (m, 1H), 2.11 (s, 3H). N—H and O—H protons not observed | |
| 247 | N-(3,4'',5'-trifluoro-2'-hydroxy-3''-(1,2,3,6-tetrahydropyridin-4-yl)-[1,1':3',1''-terphenyl]-4-yl)acetamide 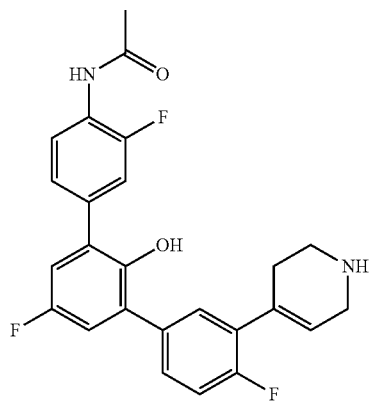 | $^1$H NMR (TFA salt - 400 MHz, DMSO-d$_6$): 9.83 (s, 1H), 8.90 (s, 2H), 8.50 (s, 1H), 7.95 (t, J = 8.4 Hz, 1H), 7.57-7.54 (m, 2H), 7.47 (dd, J = 12.4, 1.6 Hz, 1H), 7.37-7.30 (m, 2H), 7.17-7.12 (m, 2H), 6.10 (s, 1H), 3.79 (s, 2H), 3.34-3.33 (m, 2H), 2.70 (s, 2H), 2.11 (s, 3H) | 439.2 |
| 248 | (S)-N-(3'-(2-(3-aminopyrrolidin-1-yl)pyridin-4-yl)-3-fluoro-2'-hydroxy-[1,1'-biphenyl]-4-yl)acetamide 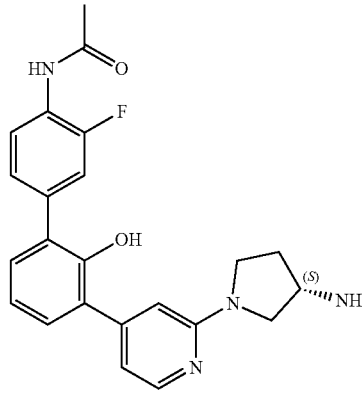 | $^1$H NMR (TFA salt - 400 MHz, DMSO-d$_6$): δ 9.78 (s, 1H), 8.08 (d, J = 4.8 Hz, 1H), 7.92 (t, J = 8.4 Hz, 1H), 7.41 (dd, J = 12.4 Hz, 1.6 Hz, 1H), 7.31-7.23 (m, 3H), 7.02 (t, J = 7.6 Hz, 1H), 6.67 (d, J = 5.2 Hz, 1H), 6.51 (s, 1H), 3.59-3.50 (m, 3H), 3.43-3.41 (m, 1H), 3.11-3.09 (m, 1H), 2.10 (s, 3H), 2.07-2.04 (m, 1H), 1.73-1.70 (m, 1H). N—H and O—H protons not observed. $^{19}$F NMR (376 MHz, DMSO-d$_6$): δ −125.50. LCMS: 407.2 (M + H)$^+$. | 407.2 |
| 249 | 1-(3-fluoro-2'-hydroxy-3'-(5-(piperazin-1-yl)pyridin-3-yl)-[1,1'-biphenyl]-4-yl)pyrrolidin-2-one | $^1$H NMR (400 MHz, DMSO-d$_6$): δ 8.25 (d, J = 2.8 Hz, 1H), 8.12 (d, J = | 433.2 |

TABLE 19-continued

Following compounds were prepared using similar procedures as described for Examples 159, 163, 213 or 214.

| Ex. No. | Name/Structure | $^1$H NMR Data | LCMS (M + H)$^+$ |
|---|---|---|---|
| | (pyrrolidinone-phenyl-OH-biphenyl-pyridine-piperazine structure) | 1.2 Hz, 1H), 7.51-7.45 (m, 2H), 7.41-7.38 (m, 2H), 7.31-7.26 (m, 2H), 7.05 (t, J = 7.6 Hz, 1H), 3.79 (t, J = 6.8 Hz, 2H), 3.14 (t, J = 4.8 Hz, 4H), 2.84 (t, J = 4.8 Hz, 4H), 2.45 (t, J = 7.6 Hz, 2H), 2.16-2.12 (m, 2H). N—H and O—H protons not observed. $^{19}$F NMR (376 MHz, DMSO-d$_6$): δ −120.3. | |

Example 250

N-(2'-(difluoromethyl)-3-fluoro-3'-(2-(piperazin-1-yl)pyridin-4-yl)-[1,1'-biphenyl]-4-yl)acetamide

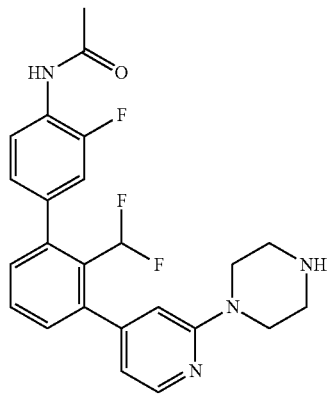 [SMILES: CC(=O)Nc1ccc(-c2cccc(-c3ccnc(N4CCNCC4)c3)c2C(F)F)cc1F]

Step 1: 1,3-dibromo-2-(difluoromethyl)benzene

To a solution of 2,6-dibromobenzaldehyde (1.00 g, 3.80 mmol) in DCM (40 mL) was added BAST (1.68 g, 7.60 mmol) slowly. After the addition, the reaction mixture was stirred at room temperature under nitrogen atmosphere overnight. After the reaction was indicated by LCMS, the reaction mixture was slowly added to vigorously stirring sat. NaHCO$_3$ aqueous solution was added to the mixture at 0° C. After stirring for 1 h, the phases were separated and the aqueous layer was extracted with DCM (30 mL×3). The combined organic layers were washed with brine, dried over sodium sulfate, filtered and concentrated to afford a residue which was purified by silica gel chromatography using Petroleum ether and ethyl acetate as the eluent: Petroleum ether:ethyl acetate=10:1 to afford the title compound (860 mg, 80% yield) as colorless oil. LCMS: 285.1 (M+H)$^+$.

Step 2: N-(3'-bromo-2'-(difluoromethyl)-3-fluoro-[1,1'-biphenyl]-4-yl)acetamide The title compound was prepared following the procedure described for Example 1 using 1,3-dibromo-2-(difluoromethyl)benzene and N-(2-fluoro-4-(4,4,5,5-tetramethyl-1,3,2-dioxaborolan-2-yl)phenyl)acetamide to afford the title compound. LCMS: 358.1 (M+H)$^+$.

Step 3: tert-Butyl 4-(4-(4'-acetamido-2-(difluoromethyl)-3'-fluoro-[1,1'-biphenyl]-3-yl)pyridin-2-yl)piperazine-1-carboxylate The title compound was prepared following the procedure described for Example 1 using N-(3'-bromo-2'-(difluoromethyl)-3-fluoro-[1,1'-biphenyl]-4-yl)acetamide and tert-butyl 4-(4-(4,4,5,5-tetramethyl-1,3,2-dioxaborolan-2-yl)pyridin-2-yl)piperazine-1-carboxylate to afford the title compound. LCMS: 541.2 (M+H)$^+$.

Step 4: N-(2'-(difluoromethyl)-3-fluoro-3'-(2-(piperazin-1-yl)pyridin-4-yl)-[1,1'-biphenyl]-4-yl)acetamide To a solution of tert-butyl 4-(4-(4'-acetamido-2-(difluoromethyl)-3'-fluoro-[1,1'-biphenyl]-3-yl)pyridin-2-yl)piperazine-1-carboxylate (100 mg, 0.185 mmol) in HCl/Dioxane (5 mL). The reaction mixture was stirred at room temperature for 4 hours under nitrogen atmosphere. The reaction mixture was filtered, and the filtrate was concentrated under reduced pressure to afford a residue that was purified by prep-HPLC using acetonitrile in water in the presence of NH$_4$HCO$_3$ to afford the title compound (27.8 mg, 34% yield) as a white solid. $^1$H NMR (400 MHz, DMSO-d$_6$): δ 9.83 (s, 1H), 8.16 (d, J=4.8 Hz, 1H), 7.99 (t, J=7.6 Hz, 1H), 7.65-7.63 (m, 1H), 7.42 (t, J=8.0 Hz, 2H), 7.27 (d, J=11.2 Hz, 1H), 7.16 (d, J=8.4 Hz, 1H), 6.73-6.59 (m, 3H), 3.45-3.43 (m, 4H), 2.79-2.77 (m, 4H), 2.12 (s, 3H). N—H or O—H proton not observed. $^{19}$F NMR (376 MHz, DMSO-d$_6$): δ −101.03, −125.17. LCMS: 441.2 (M+H)$^+$.

Example 251

(R)—N-(3-fluoro-2'-hydroxy-3'-(2-(3-hydroxypyrrolidin-1-yl)pyridin-4-yl)-[1,1'-biphenyl]-4-yl)acetamide

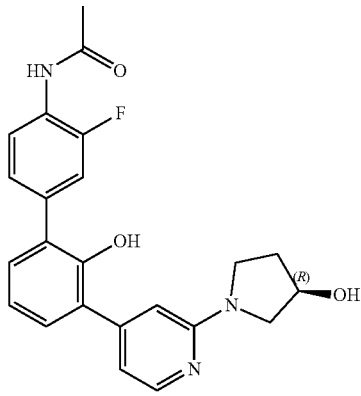

The title compound was prepared following the procedure described for Example 163 (Scheme 17) using N-(3-fluoro-3'-(2-fluoropyridin-4-yl)-2'-methoxy-[1,1'-biphenyl]-4-yl)acetamide, (R)-pyrrolidin-3-ol and BBr$_3$. $^1$H NMR (400 MHz, DMSO-d$_6$): δ 9.76 (s, 1H), 8.51 (s, 1H), 8.08 (d, J=5.2 Hz, 1H), 7.92 (t, J=8.4 Hz, 1H), 7.41 (dd, J=12.4 Hz, 2.0 Hz, 1H), 7.31-7.24 (m, 3H), 7.02 (t, J=7.6 Hz, 1H), 6.67 (dd, J=5.2 Hz, 0.8 Hz, 1H), 6.52 (s, 1H), 4.93 (d, J=3.6 Hz, 1H), 4.39 (s, 1H), 3.53-3.45 (m, 3H), 3.34-3.31 (m, 1H), 2.10 (s, 3H), 2.07-1.99 (m, 1H), 1.91-1.87 (m, 1H). LCMS: 408.2 (M+H)$^+$.

Example 252

(R)-1-(3-fluoro-2'-hydroxy-3'-(2-(3-methylpiperazin-1-yl)pyridin-4-yl)-[1,1'-biphenyl]-4-yl)pyrrolidin-2-one

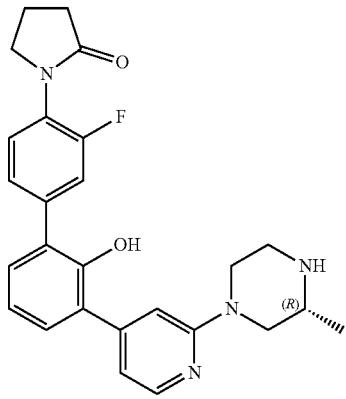

Step 1: (R)-tert-butyl 4-(4-bromopyridin-2-yl)-2-methylpiperazine-1-carboxylate To a solution of (R)-tert-butyl 2-methylpiperazine-1-carboxylate (1.76 g, 10.0 mmol) and 4-bromo-2-fluoropyridine (2.0 g, 10 mmol) in DMSO (50 mL) was added K$_2$CO$_3$ (4.0 g, 30 mmol). After the addition, the reaction mixture was stirred at 100° C. under nitrogen atmosphere for 16 hours. After the reaction was indicated by LCMS, the reaction mixture was filtered and concentrated, dilute with H$_2$O (150 mL) and extracted with EA (30 mL×3). The combined organic layers were washed with brine, dried over sodium sulfate, filtered and concentrated to afford the title compound (2.1 g, 59% yield) as colorless oil. LCMS: 356.1 (M+H)$^+$.

Step 2: (R)-(2-(4-(tert-butoxycarbonyl)-3-methylpiperazin-1-yl)pyridin-4-yl)boronic acid The title compound was prepared following the procedure described for Example 1 using (R)-tert-butyl 4-(4-bromopyridin-2-yl)-2-methylpiperazine-1-carboxylate and 4,4,4',4',5,5,5',5'-octamethyl-2,2'-bi(1,3,2-dioxaborolane) to afford the title compound (44% yield). LCMS: 322.2 (M+H)$^+$.

Step 3: (R)-tert-butyl 4-(4-(3-bromo-2-methoxyphenyl)pyridin-2-yl)-2-methylpiperazine-1-carboxylate The title compound was prepared following the procedure described for Example 1 using (R)-(2-(4-(tert-butoxycarbonyl)-3-methylpiperazin-1-yl)pyridin-4-yl)boronic acid and 1,3-dibromo-2-methoxybenzene to afford the title compound (37% yield). LCMS: 462.1 (M+H)$^+$.

Step 4: (R)-tert-butyl 4-(4-(3'-fluoro-2-methoxy-4'-(2-oxopyrrolidin-1-yl)-[1,1'-biphenyl]-3-yl)pyridin-2-yl)-2-methylpiperazine-1-carboxylate The title compound was prepared following the procedure described for Example 1 using (R)-tert-butyl 4-(4-(3-bromo-2-methoxyphenyl)pyridin-2-yl)-2-methylpiperazine-1-carboxylate and 1-(2-fluoro-4-(4,4,5,5-tetramethyl-1,3,2-dioxaborolan-2-yl)phenyl)pyrrolidin-2-one to afford the title compound (69% yield). LCMS: 561.2 (M+H)$^+$.

Step 5: (R)-1-(3-fluoro-2'-hydroxy-3'-(2-(3-methylpiperazin-1-yl)pyridin-4-yl)-[1,1'-biphenyl]-4-yl)pyrrolidin-2-one The title compound was prepared following the procedure described for Example 214 using (R)-tert-butyl 4-(4-(3'-fluoro-2-methoxy-4'-(2-oxopyrrolidin-1-yl)-[1,1'-biphenyl]-3-yl)pyridin-2-yl)-2-methylpiperazine-1-carboxylate and BBr$_3$ to afford the title compound. $^1$H NMR (400 MHz, DMSO-d$_6$): δ 8.13 (d, J=4.8 Hz, 1H), 7.50-7.44 (m, 2H), 7.39 (dd, J=8.0 Hz, 1.6 Hz, 1H), 7.32-7.26 (m, 2H), 7.04 (t, J=8.0 Hz, 1H), 6.89 (s, 1H), 6.77 (d, J=5.2 Hz, 1H), 4.16-4.11 (m, 2H), 3.79 (t, J=6.8 Hz, 2H), 2.95-2.92 (m, 1H), 2.71-2.66 (m, 3H), 2.45 (t, J=8.0 Hz, 2H), 2.35-2.29 (m, 1H), 2.18-2.10 (m, 2H), 1.02 (d, J=6.0 Hz, 3H). N—H and O—H protons not observed. $^{19}$F NMR (376 MHz, DMSO-d$_6$): δ −120.24. LCMS: 447.3 (M+H)$^+$.

Example 253

(R)-1-(3-chloro-2'-hydroxy-3'-(2-(3-methylpiperazin-1-yl)pyridin-4-yl)-[1,1'-biphenyl]-4-yl)pyrrolidin-2-one

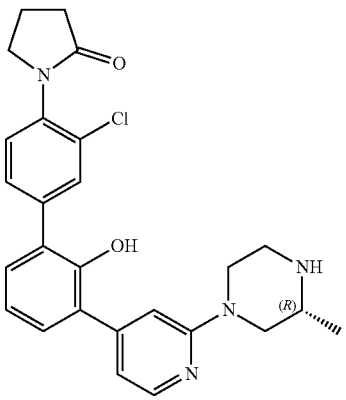

The title compound was prepared following the procedure described for Example 252 using (R)-tert-butyl 4-(4-(3'-chloro-2-methoxy-4'-(2-oxopyrrolidin-1-yl)-[1,1'-biphenyl]-3-yl)pyridin-2-yl)-2-methylpiperazine-1-carboxylate and BBr$_3$ to afford the title compound (61% yield). $^1$H NMR (2 TFA salt—400 MHz, DMSO-d$_6$): δ 9.05 (br s, 1H), 8.75 (br s, 2H), 8.20 (d, J=5.2 Hz, 1H), 7.71 (d, J=1.6 Hz, 1H), 7.55-7.53 (m, 1H), 7.48-7.46 (m, 1H), 7.36-7.31 (m, 2H), 7.12-7.07 (m, 2H), 6.96 (d, J=5.2 Hz, 1H), 4.41-4.36 (m, 2H), 3.73 (t, J=6.8 Hz, 2H), 3.42-3.32 (m, 2H), 3.16-3.07 (m, 2H), 2.97-2.91 (m, 1H), 2.45 (t, J=8.0 Hz, 2H), 2.20-2.13 (m, 2H), 1.27 (d, J=6.8 Hz, 3H). N—H or O—H proton not observed. $^{19}$F NMR (376 MHz, DMSO-d$_6$): δ −74.39. LCMS: 463.3 (M+H)$^+$.

TABLE 20

Following compounds were prepared using similar procedures as described for Examples 163, 214, 251, 252 or 253.

| Ex. No. | Name/Structure | $^1$H NMR Data | LCMS (M + H)$^+$ |
|---|---|---|---|
| 254 | N-(3-fluoro-2'-hydroxy-3''-(3-oxopiperazin-1-yl)-[1,1':3',1''-terphenyl]-4-yl)acetamide | $^1$H NMR (400 MHz, DMSO-d$_6$): δ 9.78 (s, 1H), 8.32 (s, 1H), 8.06 (s, 1H), 7.91 (t, J=8.0 Hz, 1H), 7.42 (dd, J= 12.4 Hz, 1.6 Hz, 1H), 7.32-7.28 (m, 2H), 7.24-7.21 (m, 2H), 7.04-7.00 (m, 2H), 6.98-6.90 (m, 2H), 3.75 (s, 2H), 3.45-3.42 (m, 2H), 3.33-3.31 (m, 2H), 2.10 (s, 3H). $^{19}$F NMR (376 MHz, DMSO-d$_6$): δ −125.53 | 420.2 |
| 255 | (R)-N-(3-fluoro-2'-hydroxy-3'-(2-(3-methylpiperazin-1-yl)pyridin-4-yl)-[1,1'-biphenyl]-4-yl)acetamide | $^1$H NMR (400 MHz, DMSO-d$_6$): δ 9.77 (s, 1H), 8.12 (d, J = 5.2 Hz, 1H), | 421.2 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | [Structure] | 7.92 (t, J = 8.0 Hz, 1H), 7.41 (dd, J = 12.0 Hz, 1.6 Hz, 1H), 7.31-7.23 (m, 3H), 7.02 (t, J = 7.6 Hz, 1H), 6.88 (s, 1H), 6.76 (d, J = 5.2 Hz, 1H), 4.16-4.11 (m, 2H), 2.95-2.93 (m, 1H), 2.73-2.66 (m, 3H), 2.36-2.31 (m, 1H), 2.11 (s, 3H), 1.03 (d, J = 6.0 Hz, 3H). N-H and O-H protons not observed. ¹⁹F NMR (376 MHz, DMSO-d₆): δ −125.46 | |
| 256 | (R)-N-(3-chloro-2'-hydroxy-3'-(2-(3-methylpiperazin-1-yl)pyridin-4-yl)-[1,1'-biphenyl]-4-yl)acetamide [Structure] | 1H NMR (400 MHz, DMSO-d₆): δ 9.55 (s, 1H), 8.12 (d, 7= 5.2 Hz, 1H), 7.76 (d, J = 8.0 Hz, 1H), 7.63 (d, J = 1.6 Hz, 1H), 7.45 (dd, J = 8.4 Hz, 2.0 Hz, 1H), 7.29-7.24 (m, 2H), 7.03 (t, J = 7.6 Hz, 1H), 6.88 (s, 1H), 6.77 (d, J = 5.2 Hz, 1H), 4.17-4.11 (m, 2H), 2.96-2.94 (m, 1H), 2.71-2.66 (m, 3H), 2.37-2.32 (m, 1H), 2.11 (s, 3H), 1.03 (d, J = 6.4 Hz, 3H). N-H and O-H protons not observed | 437.2 |
| 257 | 1-(3-fluoro-2'-hydroxy-3'-(5-(piperazin-1-yl)pyridin-3-yl)-[1,1'-biphenyl]-4-yl)pyrrolidine-2,5-dione [Structure] | ¹H NMR (400 MHz, DMSO-d₆): δ 8.26 (d, J = 2.4 Hz, 1H), 8.13 (s, 1H), 7.56 (dd, J = 11.2 Hz, 1.6 Hz, 1H), 7.49 (dd, J = 8.0 Hz, 1.6 Hz, 1H), 7.41-7.38 (m, 2H), 7.35-7.29 (m, 2H), 7.07 (t, J = 7.6 Hz, 1H), 3.18-3.16 (m, 4H), 2.89-2.87 (m, 8H). N-H and O-H protons not observed | 447.1 |
| 258 | ((R)-N-(3-fluoro-2'-hydroxy-3'-(5-(3-methylpiperazin-1-yl)pyridin-3-yl)-[1,1'-biphenyl]-4-yl)acetamide | ¹H NMR (400 MHz, DMSO-d₆): δ 9.77 (s, 1H), 8.25 (d, J = 2.4 Hz, 1H), | 421.2 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | | 8.10 (d, J = 1.6 Hz, 1H), 7.92 (t, J = 8.4 Hz, 1H), 7.43-7.37 (m, 2H), 7.32-7.24 (m, 3H), 7.03 (t, J = 7.6 Hz, 1H), 3.62 (t, J = 9.2 Hz, 2H), 2.97 (d, J = 12.0 Hz, 1H), 2.83-2.78 (m, 2H), 2.65-2.59 (m, 1H), 2.29-2.24 (m, 1H), 2.10 (s, 3H), 1.02 (d, J = 6.4 Hz, 3H). N-H and O-H protons not observed | |
| 259 | (R)-N-(3-chloro-2'-hydroxy-3'-(5-(3-methylpiperazin-1-yl)pyridin-3-yl)-[1,1'-biphenyl]-4-yl)acetamide | ¹H NMR (400 MHz, DMSO-d₆): δ 9.75 (s, 1H), 8.25 (d, 7=2.4 Hz, 1H), 8.10 (d, J = 1.6 Hz, 1H), 7.76 (d, J = 8.4 Hz, 1H), 7.64 (d, J = 1.6 Hz, 1H), 7.46 (dd, J = 28.4 Hz, 1.6 Hz, 1H), 7.38 (t, J = 2.0 Hz, 1H), 7.29-7.25 (m, 2H), 7.04 (d, J = 7.6 Hz, 1H), 3.62 (t, J = 10.4 Hz, 2H), 2.97 (d, J = 11.6 Hz, 1H), 2.83-2.78 (m, 2H), 2.65-2.59 (m, 1H), 2.29-2.24 (m, 1H), 2.11 (s, 3H), 1.02 (d, J = 6.4 Hz, 3H). N-H and O-H protons not observed | 437.2 |
| 260 | Methyl 4-(4'-acetamido-3'-fluoro-2-hydroxy-[1,1'-biphenyl]-3-yl)-6-(piperazin-1-yl)picolinate | ¹H NMR (400 MHz, DMSO-d₆): δ 9.77 (s, 1H), 7.93 (t, J = 8.4 Hz, 1H), 7.41 (dd, J = 12.0 Hz, 1.6 Hz, 1H), 7.33-7.31 (m, 4H), 7.08-7.03 (m, 2H), 3.89 (s, 3H), 3.61-3.59 (m, 2H), 3.46-3.44 (m, 2H), 2.82-2.75 (m, 4H), 2.10 (s, 3H). N-H and O-H protons not observed | 465.1 |
| 261 | (R)-N-(3'(2-(3-aminopyrrolidin-1-yl)pyridin-4-yl)-3-fluoro-2'-hydroxy-[1,1'-biphenyl]-4-yl)acetamide | ¹H NMR (400 MHz, DMSO-d₆): δ 9.76 (s, 1H), 8.07 (d, J = 5.2 Hz, 1H), | 407.1 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | (structure) | 7.92 (t, J = 8.4 Hz, 1H), 7.41 (dd, J = 12.0 Hz, 1.6 Hz, 1H), 7.31-7.23 (m, 3H), 7.02 (t, J = 7.6 Hz, 1H), 6.67 (d, J = 5.2 Hz, 1H), 6.51 (s, 1H), 3.56-3.50 (m, 3H), 3.43-3.37 (m, 1H), 3.11-3.08 (m, 1H), 2.10 (s, 3H), 2.07-2.02 (m, 1H), 1.73-1.69 (m, 1H). N-H and O-H protons not observed | |
| 262 | 1-(3-chloro-2'-hydroxy-3'-(5-(piperazin-1-yl)pyridin-3-yl)-[1,1'-biphenyl]-4-yl)pyrrolidin-2-one | ¹H NMR (400 MHz, DMSO-d₆): δ 8.25 (d, J = 2.8 Hz, 1H), 8.12 (d, J = 1.6 Hz, 1H), 7.72 (d, J = 2.0 Hz, 1H), 7.55 (dd, J = 8.4 Hz, 2.0 Hz, 1H), 7.46 (d, J = 8.0 Hz, 1H), 7.39 (s, 1H), 7.31-7.27 (m, 2H), 7.06 (t, J = 7.2 Hz, 1H), 3.72 (t, J = 6.8 Hz, 2H), 3.14 (t, J = 4.8 Hz, 4H), 2.84 (t, J = 5.2 Hz, 4H), 2.46-2.42 (m, 2H), 2.20-2.12 (m, 2H). N-H and O-H protons not observed | 449.1 |
| 263 | 1-(3-fluoro-2'-hydroxy-3'-(2-(piperazin-1-yl)pyridin-4-yl)-[1,1'-biphenyl]-4-yl)piperidin-2-one | ¹H NMR (400 MHz, DMSO-d₆): δ 8.15 (d, J = 5.2 Hz, 1H), 7.44-7.36 (m, 3H), 7.33-7.30 (m, 2H), 7.07 (t, J = 8.0 Hz, 1H), 7.01 (s, 1H), 6.91 (dd, J = 5.6 Hz, 1.2 Hz, 1H), 3.69 (t, J = 4.8 Hz, 2H), 3.55 (t, J = 5.2 Hz, 4H), 2.97 (t, J = 5.2 Hz, 4H), 2.57 (t, J = 6.0 Hz, 2H), 2.06-2.00 (m, 4H). N-H or O-H proton not observed | 447.2 |
| 264 | (R)-1-(3-fluoro-2'-hydroxy-3'-(5-(3-methylpiperazin-1-yl)pyridin-3-yl)-[1,1'-biphenyl]-4-yl)pyrrolidin-2-one | ¹H NMR (400 MHz, DMSO-d₆): δ 8.24 (d, J = 2.8 Hz, 1H), 8.10 (d, J = | 447.3 |

TABLE 20-continued

Following compounds were prepared using similar procedures as described for Examples 163, 214, 251, 252 or 253.

| Ex. No. | Name/Structure | $^1$H NMR Data | LCMS (M + H)$^+$ |
|---|---|---|---|
| | | 1.6 Hz, 1H), 7.51-7.45 (m, 2H), 7.41-7.37 (m, 2H), 7.31-7.26 (m, 2H), 7.05 (t, J = 7.6 Hz, 1H), 3.79 (t, J = 6.8 Hz, 2H), 3.62 (t, J = 8.8 Hz, 2H), 2.96 (d, J = 12.0 Hz, 1H), 2.83-2.76 (m, 2H), 2.65-2.59 (m, 1H), 2.45 (t, 7= 7.6 Hz, 2H), 2.28-2.10 (m, 3H), 1.02 (d, J =6.4 Hz, 3H). N-H and O-H protons not observed | |
| 265 | (R)-1-(3-chloro-2'-hydroxy-3'-(5-(3-methylpiperazin-1-yl)pyridin-3-yl)-[1,1'-biphenyl]-4-yl)pyrrolidin-2-one | $^1$H NMR (400 MHz, DMSO-d$_6$): δ 8.25 (d, J= 2.8 Hz, 1H), 8.10 (d, J = 1.6 Hz, 1H), 7.71 (d, J = 1.6 Hz, 1H), 7.56-7.53 (m, 1H), 7.46 (d, J= 8.0 Hz, 1H), 7.38 (t, J = 2.0 Hz, 1H), 7.31-7.27 (m, 2H), 7.05 (t, J = 8.0 Hz, 1H), 3.73 (t, J = 6.8 Hz, 2H), 3.62 (t, J= 10.8 Hz, 2H), 2.97 (d, J = 11.6 Hz, 1H), 2.83-2.76 (m, 2H), 2.65-2.61 (m, 1H), 2.44 (t,J = 7.6 Hz, 2H), 2.29-2.14 (m, 3H), 1.02 (d,J = 6.4 Hz, 3H). N-H or O-H proton not observed | 463.3 |
| 266 | 1-(3'-(2-(3,5-dimethylpiperazin-1-yl)pyridin-4-yl)-3-fluoro-2'-hydroxy-[1,1'-biphenyl]-4-yl)pyrrolidin-2-one | $^1$H NMR (400 MHz, DMSO-d$_6$): δ 8.11 (d, J = 4.8 Hz, 1H), 7.50-7.37 (m, 3H), 7.31-7.26 (m, 2H), 7.04 (t, J = 7.6 Hz, 1H), 6.89 (s, 1H), 6.75 (d, J = 5.2 Hz, 1H), 4.18 (d, J = 11.2 Hz, 2H), 3.79 (t, J = 7.2 Hz, 2H), 2.77-2.72 (m, 2H), 2.45 (t, J = 8.0 Hz, 2H), 2.28-2.07 (m, 4H), 1.03 (d, J = 6.4 Hz, 6H). N-H and O-H protons not observed | 461.3 |
| 267 | 1-(3-chloro-3'-(2-(3,5-dimethylpiperazin-1-yl)pyridin-4-yl)-2'-hydroxy-[1,1'-biphenyl]-4-yl)pyrrolidin-2-one | $^1$H NMR (400 MHz, DMSO-d$_6$): δ 8.11 (d, J = 4.8 Hz, 1H), 7.7 (d, J = 1.6 Hz, 1H), 7.54 (dd, J = 8.0 | 477.3 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | 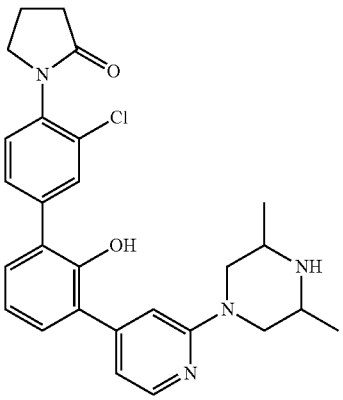 | Hz, 1.6 Hz, 1H), 7.45 (d, J = 8.4 Hz, 1H), 7.32-7.27 (m, 2H), 7.05 (d, J = 7.6 Hz, 1H), 6.88 (s, 1H), 6.76 (d, J = 5.2 Hz, 1H), 4.17 (d, J = 11.6 Hz, 2H), 3.72 (t, J = 6.8 Hz, 2H), 2.77-2.72 (m, 2H), 2.44 (t, J = 8.0 Hz, 2H), 2.26-2.14 (m, 4H), 1.02 (d, J = 6.4 Hz, 6H). N-H and O-H protons not observed | |
| 268 | N-(5'-chloro-3-fluoro-2'-hydroxy-3'-(2-(piperazin-1-yl)pyridin-4-yl)-[1,1'-biphenyl]-4-yl)acetamide 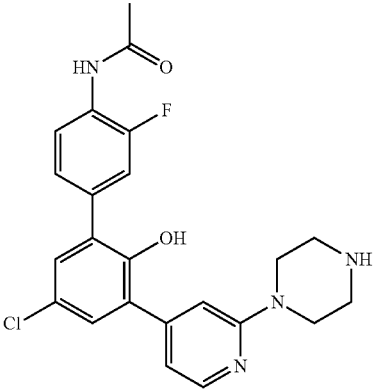 [SMILES: CC(=O)Nc1ccc(-c2cc(Cl)cc(-c3ccnc(N4CCNCC4)c3)c2O)cc1F] | ¹H NMR (400 MHz, CD₃OD): δ 8.17 (d, 7 = 5.2Hz, 1H), 7.98 (d, 7 = 8.8 Hz, 1H), 7.41 (dd, J = 12.0 Hz, 1.6 Hz, 1H), 7.33 (d, J = 8.0 Hz, 1H), 7.30-7.28 (m, 2H), 7.00 (s, 1H), 6.89 (dd, J = 5.2 Hz, 1.2 Hz, 1H), 3.58 (t, J = 5.2 Hz, 4H), 2.99 (t, J = 5.2 Hz, 4H), 2.21 (s, 3H) | 441.2 |
| 269 | 1-(5'-chloro-3-fluoro-2'-hydroxy-3'-(2-(piperazin-1-yl)pyridin-4-yl)-[1,1'-biphenyl]-4-yl)pyrrolidin-2-one 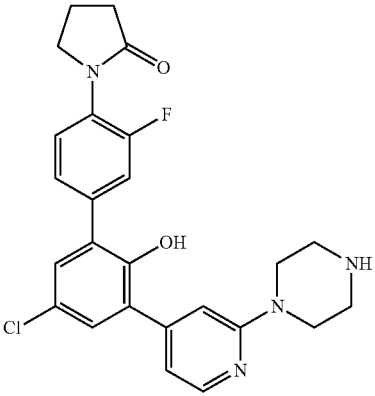 [SMILES: O=C1CCCN1c1ccc(-c2cc(Cl)cc(-c3ccnc(N4CCNCC4)c3)c2O)cc1F] | ¹H NMR (400 MHz, CD₃OD): δ 8.04 (d, J = 5.6 Hz, 1H), 7.38-7.34 (m, 2H), 7.30-7.28 (m, 1H), 7.17 (dd, J = 4.4 Hz, 2.4 Hz, 2H), 6.89 (s, 1H), 6.77 (d, J = 5.6 Hz, 1H), 3.79 (t, J = 7.2 Hz, 2H), 3.44 (t, J = 4.8 Hz, 4H), 2.85 (t, J = 5.2 Hz, 4H), 2.48 (t, J = 8.0 Hz, 2H), 2.20-2.12 (m, 2H) | 467.2 |
| 270 | N-(3'-(2-(2,6-diazaspiro[3.3]heptan-2-yl)pyridin-4-yl)-3-fluoro-2'-hydroxy-[1,1'-biphenyl]-4-yl)acetamide | ¹H NMR (TFA salt - 400 MHz, DMSO-d₆): δ 9.80 (s, 1H), 8.96 (br s, 1H), | 419.1 |

TABLE 20-continued

Following compounds were prepared using similar procedures as described for Examples 163, 214, 251, 252 or 253.

| Ex. No. | Name/Structure | $^1$H NMR Data | LCMS (M + H)$^+$ |
|---|---|---|---|
|  | *(structure shown)* | 8.67 (brs, 2H), 8.08 (d, J = 6.4 Hz, 1H), 7.95 (t, J = 8.0 Hz, 1H), 7.42-7.29 (m, 4H), 7.11-7.05 (m, 2H), 6.88 (s, 1H), 4.36 (s, 4H), 4.20 (t, J= 5.6 Hz, 4H), 2.11 (s, 3H) |  |
| 271 | 1-(3'-(2-(2,6-diazaspiro[3.3]heptan-2-yl)pyridin-4-yl)-3-chloro-2'-hydroxy-[1,1'-biphenyl]-4-yl)pyrrolidin-2-one | $^1$H NMR (TFA salt - 400 MHz, DMSO-d$_6$): δ 9.10 (br s, 1H), 8.64 (br s, 2H), 8.08 (d, J = 6.4 Hz, 1H), 7.71 (d, J = 1.6 Hz, 1H), 7.55-7.53 (m, 2H), 7.41-7.37 (m, 2H), 7.12 (t, J = 8.0 Hz, 1H), 7.07 (d, J = 6.0 Hz, 1H), 6.89 (s, 1H), 4.37 (s, 4H), 4.27 (s, 4H), 3.73 (t, J = 7.2 Hz, 2H), 2.45 (t, J = 8.0 Hz, 2H), 2.20-2.13 (m, 2H) | 461.1 |
| 272 | N-(3-fluoro-2'-hydroxy-3'-(2-(4-hydroxypiperidin-1-yl)pyridin-4-yl)-[1,1'-biphenyl]-4-yl)acetamide | $^1$H NMR (400 MHz, DMSO-d$_6$): 9.77 (s, 1H), 8.54 (s, 1H), 8.12 (d, J = 5.2 Hz, 1H), 7.92-7.90 (m, 1H), 7.41 (dd, J= 12.0, 1.6 Hz, 1H), 7.31-7.24 (m, 3H), 7.05-7.01 (m, 1H), 6.92 (s, 1H), 6.74 (d, J = 5.2 Hz, 1H), 4.67 (d, J = 4.4 Hz, 1H), 4.05 (dd, J = 8.8, 4.0 Hz, 2H), 3.71-3.69 (m, 1H), 3.12-3.06 (m, 2H), 2.11 (s, 3H), 1.81-1.76 (m, 2H), 1.39-1.34 (m, 2H) | 422.1 |
| 273 | 4-(4'-acetamido-3'-fluoro-2-hydroxy-[1,1'-biphenyl]-3-yl)-6-(piperazin-1-yl)picolinamide | $^1$H NMR (400 MHz, DMSO-d$_6$): 9.77 (s, 1H), 7.93-7.90 (m, 2H), 7.46- | 450.2 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
|  |  | 7.41 (m, 3H), 7.33-7.27 (m, 3H), 7.06-7.02 (m, 2H), 3.54-3.51 (m, 4H), 2.81-2.78 (m, 4H), 2.11 (s, 3H). N-H or O-H proton not observed |  |
| 274 | 1-(3,5'-dichloro-2'-hydroxy-3'-(2-(piperazin-1-yl)pyridin-4-yl)-[1,1'-biphenyl]-4-yl)pyrrolidin-2-one | ¹H NMR (400 MHz, DMSO-d₆): 8.14 (d, J = 5.2 Hz, 1H), 7.74 (d, J = 1.6 Hz, 1H), 7.57-7.54 (m, 1H), 7.48-7.46 (m, 1H), 7.36 (d, J = 2.4 Hz, 1H), 7.32 (d, J = 2.4 Hz, 1H), 6.91 (d, J = 2.4 Hz, 1H), 6.80 (d, J = 5.2 Hz, 1H), 3.73 (t, J = 6.8 Hz, 2H), 3.53-3.46 (m, 4H), 3.19-3.15 (m, 4H), 2.50-2.43 (m, 2H), 2.33-1.99 (m, 2H). N-H and O-H protons not observed | 483.2 |
| 275 | N-(3-fluoro-2'-hydroxy-5'-methyl-3'-(2-(piperazin-1-yl)pyridin-4-yl)-[1,1'-biphenyl]-4-yl)acetamide | ¹H NMR (400 MHz, DMSO-d₆): 9.76 (s, 1H), 8.12 (d, J = 5.2 Hz, 1H), 7.91 (t, J = 8.0 Hz, 1H), 7.39 (dd, J = 12.0, 1.6 Hz, 1H), 7.29 (dd, J = 8.4, 1.2 Hz, 1H), 7.09 (dd, J = 9.2, 1.6 Hz, 2H), 6.87 (s, 1H), 6.77 (d, J = 5.2 Hz, 1H), 3.45-3.37 (m, 4H), 2.81-2.78 (m, 4H), 2.29 (s, 3H), 2.11 (s, 3H). N-H and O-H protons not observed | 321.2 |
| 276 | 1-(3-chloro-2'-hydroxy-3'-(2-(piperazin-1-yl)pyridin-4-yl)-[1,1'-biphenyl]-4-yl)tetrahydropyrimidin-2(1H)-one | ¹H NMR (400 MHz, DMSO-d₆): 8.14 (d, J = 5.2 Hz, 1H), 7.65 (d, J = 2.0 | 464.2 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | | Hz, 1H), 7.48 (dd, J = 8.4, 2.0 Hz, 1H), 7.39 (d, J = 8.4 Hz, 1H), 7.31-7.26 (m, 2H), 7.05 (t, J = 8.0 Hz, 1H), 6.89 (s, 1H), 6.78 (d, J = 5.2 Hz, 1H), 6.61 (s, 1H), 3.50-3.43 (m, 6H), 3.31-3.27 (m, 2H), 2.81-2.77 (m, 4H), 2.01-1.98 (m, 2H). N-H and O-H protons not observed | |
| 277 | 1-(3-fluoro-2'-hydroxy-3'-(2-(piperazin-1-yl)pyridin-4-yl)-[1,1'-biphenyl]-4-yl)tetrahydropyrimidin-2(1H)-one | ¹H NMR (400 MHz, DMSO-d₆): 8.14 (d, J = 5.2 Hz, 1H), 7.40-7.25 (m, 5H), 7.06-7.02 (m, 1H), 6.89 (s, 1H), 6.78 (d, J = 5.2 Hz, 1H), 6.65 (s, 1H), 3.57-3.54 (m, 2H), 3.45-3.42 (m, 4H), 3.28-3.25 (m, 2H), 2.80-2.77 (m, 4H), 1.99-1.96 (m, 2H). N-H and O-H protons not observed | 448.2 |
| 278 | 1-(3,5'-difluoro-2'-hydroxy-3'-(2-(piperazin-1-yl)pyridin-4-yl)-[1,1'-biphenyl]-4-yl)tetrahydropyrimidin-2(1H)-one | ¹H NMR (400 MHz, DMSO-d₆): 8.14 (d, J = 5.6 Hz, 1H), 7.45-7.36 (m, 3H), 7.20-7.14 (m, 2H), 6.92 (s, 1H), 6.81 (d, J = 5.2 Hz, 1H), 6.66 (s, 1H), 3.57-3.54 (m, 2H), 3.45-3.43 (m, 4H), 3.28-3.25 (m, 2H), 2.79-2.76 (m, 4H), 2.00-1.94 (m, 2H). N-H or O-H proton not observed | 466.2 |
| 279 | N-(3'-(2-(3,5-dimethylpiperazin-1-yl)pyridin-4-yl)-3-fluoro-2'-hydroxy-[1,1'-biphenyl]-4-yl)acetamide | ¹H NMR (400 MHz, DMSO-d₆): 9.79 (s, 1H), 8.12 (d, J = 5.2 Hz, 1H), | |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
|  |  | 7.92 (t, J = 8.4 Hz, 1H), 7.41 (dd, J = 12.0, 1.2 Hz, 1H), 7.32-7.24 (m, 3H), 7.03 (t, J = 7.6 Hz, 1H), 6.89 (s, 1H), 6.75 (d, J = 5.2 Hz, 1H), 4.18 (d, J = 10.0 Hz, 2H), 2.77-2.74 (m, 2H), 2.24 (t, J = 11.6 Hz, 2H), 2.11 (s, 3H), 1.03 (s, 3H), 1.02 (s,3H). N-H or O-H proton not observed | 435.2 |
| 280 | 1-(3,5'-difluoro-2'-hydroxy-3'-(2-(piperazin-1-yl)pyridin-4-yl)-[1,1'-biphenyl]-4-yl)piperidin-2-one | ¹H NMR (400 MHz, DMSO-d): 8.15 (d,J=4.8 Hz, 1H), 7.49 (d, J= 12.4 Hz, 1H), 7.42 (d, J = 4.8 Hz, 2H), 7.23-7.15 (m, 2H), 6.92 (s, 1H), 6.81 (d, J = 4.8 Hz, 1H), 3.59-3.56 (m, 2H), 3.46-3.44 (m, 4H), 2.80-2.79 (m, 4H), 2.44-2.40 (m, 2H), 1.90-1.86 (m, 4H). N-H and O-H protons not observed | 465.3 |
| 281 | 1-(3-chloro-5'-fluoro-2'-hydroxy-3'-(2-(piperazin-1-yl)pyridin-4-yl)-[1,1'-biphenyl]-4-yl)piperidin-2-one | ¹H NMR (400 MHz, DMSO-d₆): 8.14 (d, J = 5.2 Hz, 1H), 7.74 (d,J = 1.6 Hz, 1H), 7.57 (dd, J = 8.4, 2.0 Hz, 1H), 7.43 (d, J = 8.0 Hz, 1H), 7.23-7.16 (m, 2H), 6.92 (s, 1H), 6.81 (d, J = 5.2 Hz, 1H), 3.56-3.54 (m, 1H), 3.45-3.42 (m, 6H), 2.79-2.76 (m, 4H), 2.43-2.39 (m, 2H), 1.91-1.84 (m, 4H). N-H or O-H proton not observed | 481.2 |
| 282 | 1-(3-chloro-2'-hydroxy-3'-(2-(piperazin-1-yl)pyridin-4-yl)-[1,1'-biphenyl]-4-yl)piperidin-2-one | ¹H NMR (400 MHz, DMSO-d₆): 8.14 (d, J = 4.8 Hz, 1H), 7.70 (d, J = 2.0 | 463.3 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | | Hz, 1H), 7.53 (dd, J = 8.0, 2.0 Hz, 1H), 7.42 (d, J = 8.0 Hz, 1H), 7.33-7.27 (m, 2H), 7.05 (d, J = 7.6 Hz, 1H), 6.89 (s, 1H), 6.78 (d, J = 5.2 Hz, 1H), 3.57-3.52 (m, 6H), 2.80-2.77 (m, 4H), 2.43-2.40 (m, 2H), 1.94-1.84 (m, 4H). N-H and O-H protons not observed | |
| 283 | N-(3'-(2-(2,6-diazaspiro[3.3]heptan-2-yl)pyridin-4-yl)-3-chloro-2'-hydroxy-[1,1'-biphenyl]-4-yl)acetamide | ¹H NMR (400 MHz, DMSO-d₆): 9.61 (s, 1H), 8.09 (d, J = 5.6 Hz, 1H), 7.76 (d, J = 8.4 Hz, 1H), 7.63 (d, J = 2.0 Hz, 1H), 7.45 (dd, J = 8.4, 2.0 Hz, 1H), 7.30-7.24 (m, 2H), 7.04 (t, J = 7.2 Hz, 1H), 6.80 (d, J = 4.8 Hz, 1H), 6.50 (s, 1H), 4.04-4.03 (m, 4H), 3.73-3.72 (m, 4H), 2.12 (s, 3H). N-H or O-H proton not observed | 435.1 |
| 284 | 1-(3'-(2-(2,6-diazaspiro[3.3]heptan-2-yl)pyridin-4-yl)-3-fluoro-2'-hydroxy-[1,1'-biphenyl]-4-yl)pyrrolidin-2-one | ¹H NMR (400 MHz, DMSO-d₆): 8.09 (d, J = 5.2 Hz, 1H), 7.51-7.44 (m, 2H), 7.38 (dd, J = 8.0, 1.2 Hz, 1H), 7.30 (dd, J = 7.6, 1.6 Hz, 1H), 7.26 (dd, J = 7.6, 1.6 Hz, 1H), 7.03 (t, J = 7.6 Hz, 1H), 6.79 (d, J = 5.2 Hz, 1H), 6.50 (s, 1H), 4.02-4.01 (m, 4H), 3.79 (t, J = 6.8 Hz, 2H), 3.49-3.48 (m, 4H), 2.45 (t, J = 8.0 Hz, 2H), 2.18-2.11 (m, 2H). N-H and O-H protons not observed | 445.3 |
| 285 | 1-(3'-(2-(2,6-diazaspiro[3.3]heptan-2-yl)pyridin-4-yl)-3,5'-difluoro-2'-hydroxy-[1,1'-biphenyl]-4-yl)pyrrolidin-2-one | ¹H NMR (400 MHz, DMSO-d₆): 8.10 (d, J = 5.2 Hz, 1H), 7.52-7.48 (m, 2H), 7.42 (dd, J = 8.0, 1.6 | 463.3 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | 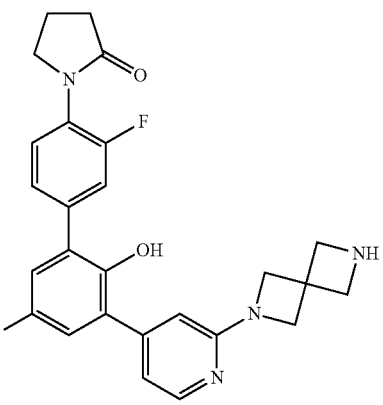 | Hz, 1H), 7.20 (d, J = 9.2 Hz, 1H), 7.14 (d, J = 9.2 Hz, 1H), 6.82 (d, J = 4.8 Hz, 1H), 6.54 (s, 1H), 4.03-4.02 (m, 4H), 3.79 (t, J = 7.2 Hz, 2H), 3.67-3.66 (m, 4H), 2.47-2.43 (m, 2H), 2.16-2.12 (m, 2H). N-H and O-H protons not observed | |
| 286 | N-(3-fluoro-2'-hydroxy-3'-(6-(piperazin-1-yl)-1H-pyrrolo[2,3-b]pyridin-4-yl)-[1,1'-biphenyl]-4-yl)acetamide<br>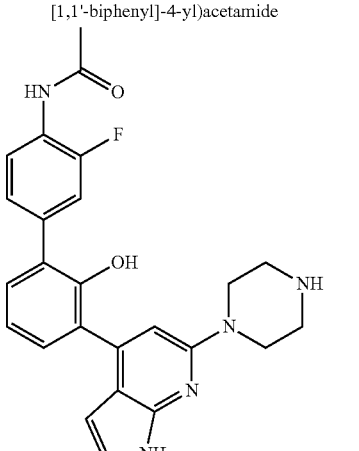 | ¹H NMR (400 MHz, DMSO-d₆): 11.09 (s, 1H), 9.78 (s, 1H), 7.92 (t, J = 8.8 Hz, 1H), 7.46 (dd, J = 12.4, 1.6 Hz, 1H), 7.36-7.30 (m, 3H), 7.07-7.02 (m, 2H), 6.67 (s, 1H), 6.13 (t, J = 1.2 Hz, 1H), 3.42-3.40 (m, 4H), 2.83-2.81 (m, 4H), 2.11 (s, 3H). N-H and O-H protons not observed | 446.1 |
| 287 | 1-(3-chloro-5'-fluoro-2'-hydroxy-3'-(2-(piperazin-1-yl)pyridin-4-yl)-[1,1'-biphenyl]-4-yl)tetrahydropyrimidin-2(1H)-one<br>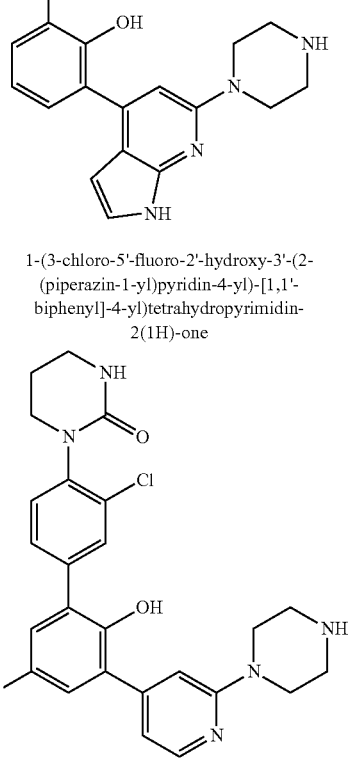 | ¹H NMR (400 MHz, DMSO-d): 8.14 (d, J = 5.2 Hz, 1H), 7.70 (d, J = 2.0 Hz, 1H), 7.52 (dd, J = 8.0, 1.6 Hz, 1H), 7.41 (d, J = 8.0 Hz, 1H), 7.22-7.15 (m, 2H), 6.92 (s, 1H), 6.81 (d, J = 5.2 Hz, 1H), 6.64 (s, 1H), 3.46-3.43 (m, 6H), 3.33-3.27 (m, 2H), 2.80-2.77 (m, 4H), 2.02-1.98 (m, 2H). N-H and O-H protons not observed | 482.1 |
| 288 | 1-(3-fluoro-2'-hydroxy-3'-(2-(piperazin-1-yl)pyridin-4-yl)-[1,1'-biphenyl]-4-yl)-3-methyltetrahydropyrimidin-2(1H)-one | ¹H NMR (400 MHz, DMSO-d₆): 8.14 (d, J = 5.2 Hz, 1H), 7.40-7.25 (m, | 462.3 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | | 5H), 7.04 (t, J = 7.6 Hz, 1H), 6.89 (s, 1H), 6.78 (d, J = 5.2 Hz, 1H), 3.60-3.57 (m, 2H), 3.45-3.43 (m, 4H), 3.38-3.35 (m, 2H), 2.86 (s, 3H), 2.80-2.78 (m, 4H), 2.08-2.02 (m, 2H). N-H and O-H protons not observed | |
| 289 | (R)-1-(3-fluoro-2'-hydroxy-3'-(2-(3-methylpiperazin-1-yl)pyridin-4-yl)-[1,1'-biphenyl]-4-yl)-3-methylimidazolidin-2-one | ¹H NMR (400 MHz, DMSO-$d_6$): 8.13 (d, J = 5.2 Hz, 1H), 7.53 (t, J = 8.4 Hz, 1H), 7.42 (dd, J = 12.8, 2.0 Hz, 1H), 7.36-7.25 (m, 3H), 7.04 (t, J = 7.6 Hz, 1H), 6.89 (s, 1H), 6.77 (d, J = 4.8 Hz, 1H), 4.17-4.11 (m, 2H), 3.81-3.77 (m, 2H), 3.50-3.46 (m, 2H), 2.96-2.94 (m, 1H), 2.77 (s, 3H), 2.71-2.67 (m, 3H), 2.37-2.31 (m, 1H), 1.02 (d, J = 6.4 Hz, 3H). N-H and O-H protons not observed | 462.3 |
| 290 | Methyl 4'-acetamido-3'-fluoro-6-hydroxy-5-(2-(piperazin-1-yl)pyridin-4-yl)-[1,1'-biphenyl]-3-carboxylate | ¹H NMR (400 MHz, DMSO-$d_6$): 9.77 (s, 1H), 8.15 (d, J = 5.2 Hz, 1H), 7.93-7.89 (m, 1H), 7.79 (d, J = 2.0 Hz, 2H), 7.57-7.53 (m, 1H), 7.33 (d, J = 7.6 Hz, 1H), 7.16 (s, 1H), 6.89 (d, J = 5.2 Hz, 1H), 3.79 (s, 3H), 3.62-3.59 (m, 4H), 3.03-3.02 (m, 4H), 2.11 (s, 3H). N-H and O-H protons not observed | 465.1 |
| 291 | N-(3-fluoro-3'-(2-fluoro-6-(piperazin-1-yl)pyridin-4-yl)-2'-hydroxy-[1,1'-biphenyl]-4-yl)acetamide | ¹H NMR (400 MHz, DMSO-$d_6$): 9.79 (s, 1H), 7.93 (t, J = 8.4 Hz, 1H), | 425.1 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| | | 7.42 (dd, J = 12.0, 1.2 Hz, 1H), 7.32-7.28 (m, 3H), 7.03 (d, J = 7.6 Hz, 1H), 6.75 (s, 1H), 6.40 (s, 1H), 3.44-3.42 (m, 4H), 2.78-2.76 (m, 4H), 2.11 (s, 3H). N-H and O-H protons not observed | |
| 292 | 1-(3-fluoro-2'-hydroxy-3'-(5-(piperazin-1-yl)pyridin-3-yl)-[1,1'-biphenyl]-4-yl)-3-methylimidazolidin-2-one | ¹H NMR (400 MHz, DMSO-d₆): 8.25 (s, 1H), 8.12 (s, 1H), 7.53 (t, J = 8.4 Hz, 1H), 7.43 (dd, J = 12.4 Hz, 1.6 Hz, 1H), 7.39-7.34 (m, 2H), 7.30-7.26 (m, 2H), 7.05 (t, J = 7.6 Hz, 1H), 3.79 (t, J = 8.0 Hz, 2H), 3.48 (t, J = 7.6 Hz, 2H), 3.14 (t, J = 4.8 Hz, 4H), 2.85 (t, J = 5.2 Hz, 4H), 2.77 (s, 3H). N-H or O-H proton not observed | 448.3 |
| 293 | 1-(3-chloro-2'-hydroxy-3'-(5-(piperazin-1-yl)pyridin-3-yl)-[1,1'-biphenyl]-4-yl)-3-methylimidazolidin-2-one | ¹H NMR (400 MHz, DMSO-d₆): 8.15-8.13 (m, 2H), 7.58 (d, J = 2.0 Hz, 1H), 7.52 (d, J = 2.0 Hz, 1H), 7.43-7.41 (m, 1H), 7.33 (d, J = 8.4 Hz, 1H), 7.19 (t, J= 6.4 Hz, 2H), 6.98 (t, J = 7.6 Hz, 1H), 3.75-3.71 (m, 2H), 3.50 (t, J = 8.0 Hz, 2H), 3.32 (t, J = 4.8Hz, 4H), 3.14 (t, J = 4.8 Hz, 4H), 2.79 (s, 3H). N-H and O-H protons not observed | 464.3 |

TABLE 20-continued

Following compounds were prepared using similar procedures as described for Examples 163, 214, 251, 252 or 253.

| Ex. No. | Name/Structure | ¹H NMR Data | LCMS (M + H)⁺ |
|---|---|---|---|
| 294 | (R)-1-(3-chloro-2'-hydroxy-3'-(2-(3-methylpiperazin-1-yl)pyridin-4-yl)-[1,1'-biphenyl]-4-yl)-3-methylimidazolidin-2-one | ¹H NMR (400 MHz, DMSO-d₆): 8.13 (d, J = 5.2 Hz, 1H), 7.67 (s, 1H), 7.52-7.50 (m, 1H), 7.44 (d, J = 8.0 Hz, 1H), 7.32-7.27 (m, 2H), 7.05 (t, J = 7.6 Hz, 1H), 6.89 (s, 1H), 6.77 (d, J = 5.2 Hz, 1H), 4.14 (t, J = 13.0 Hz, 2H), 3.72 (t, J = 7.6 Hz, 2H), 3.49 (t, J = 7.6 Hz, 2H), 2.95 (d, J = 8.4 Hz, 1H), 2.70 (t, J = 8.8 Hz, 6H), 2.34 (t, J = 11.2 Hz, 1H), 1.03 (d, J = 6.4 Hz, 3H). N-H and O-H protons not observed | 478.3 |
| 295 | 1-(3,5'-dichloro-2'-hydroxy-3'-(2-(piperazin-1-yl)pyridin-4-yl)-[1,1'-biphenyl]-4-yl)-3-methylimidazolidin-2-one | ¹H NMR (400 MHz, DMSO-d₆): 8.14 (d, J = 5.2 Hz, 1H), 7.72 (s, 1H), 7.53 (dd, J = 8.4, 1.6 Hz, 1H), 7.45 (d, J = 8.4 Hz, 1H), 7.35 (d, J = 2.4 Hz, 1H), 7.32 (d, J = 2.4 Hz, 1H), 6.92 (s, 1H), 6.80 (d, J = 5.2 Hz, 1H), 3.74-3.71 (m, 2H), 3.51-3.44 (m, 6H), 2.81-2.77 (m, 7H). N-H and O-H protons not observed | 498.2 |

Example 296

N-(3'-(2-(3-aminoprop-1-yn-1-yl)pyridin-4-yl)-3-fluoro-2'-hydroxy-[1,1'-biphenyl]-4-yl)acetamide

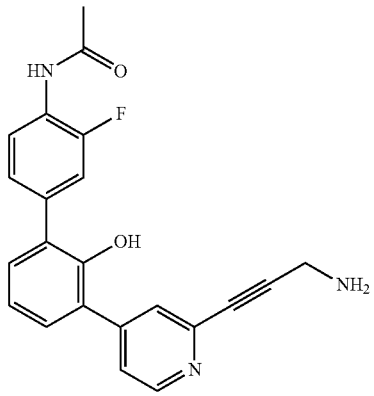 [SMILES: CC(=O)Nc1ccc(-c2cccc(-c3ccnc(C#CCN)c3)c2O)cc1F]

Step 1: N-(3'-(2-chloropyridin-4-yl)-3-fluoro-2'-methoxy-[1,1'-biphenyl]-4-yl)acetamide The title compound was prepared following the procedure described for Example 214 using N-(3-fluoro-2'-methoxy-3'-(4,4,5,5-tetramethyl-1,3,2-dioxaborolan-2-yl)-[1,1'-biphenyl]-4-yl)acetamide and 4-bromo-2-chloropyridine to afford the title compound (65% yield). LCMS: 371.2 (M+H)$^+$.

Step 2: tert-butyl (3-(4-(4'-acetamido-3'-fluoro-2-methoxy-[1,1'-biphenyl]-3-yl)pyridin-2-yl)prop-2-yn-1-yl)carbamate A solution of N-(3'-(2-chloropyridin-4-yl)-3-fluoro-2'-methoxy-[1,1'-biphenyl]-4-yl)acetamide (100 mg, 0.270 mmol), tert-butyl prop-2-yn-1-ylcarbamate (49.6 mg, 0.320 mmol), CuI (5.1 mg, 0.027 mmol), DIPEA (70 mg, 0.54 mmol) and PdCl$_2$(PPh3)$_2$ (19 mg, 0.027 mmol) in DMAC (5 mL) was stirred at 100° C. for 4 hours under microwave. After the reaction was complete by LCMS, the reaction mixture was cooled and poured into H$_2$O (20 mL), extracted with DCM (20 mL×3). The combined organic layers were washed with water (20 mL) and brine (20 mL). The organic layer was dried over sodium sulfate, filtered and concentrated under reduced pressure to afford a residue, which was purified by silica gel chromatography using petroleum ether and ethyl acetate as the eluent (4:1) to afford the title compound (65 mg, 49% yield) as black oil. LCMS: 490.1 (M+H)$^+$.

Step 3: N-(3'-(2-(3-aminoprop-1-yn-1-yl)pyridin-4-yl)-3-fluoro-2'-hydroxy-[1,1'-biphenyl]-4-yl)acetamide The title compound was prepared following the procedure described for Example 214 using tert-butyl (3-(4-(4'-acetamido-3'-fluoro-2-methoxy-[1,1'-biphenyl]-3-yl)pyridin-2-yl)prop-2-yn-1-yl)carbamate and BBr$_3$ to afford the title compound (9% yield). $^1$H NMR (400 MHz, DMSO-d$_6$): 9.80 (s, 1H), 8.57 (d, J=5.2 Hz, 1H), 7.96-7.92 (m, 1H), 7.65 (s, 1H), 7.52 (dd, J=5.2, 2.0 Hz, 1H), 7.42 (dd, J=5.2, 1.6 Hz, 1H), 7.34-7.31 (m, 3H), 7.07 (t, J=7.6 Hz, 1H), 3.55 (s, 2H), 2.11 (s, 3H). N—H or O—H protons not observed. LCMS: 376.2 (M+H)$^+$.

Example 297

1-(3-chloro-5'-fluoro-2'-hydroxy-3'-(2-(piperazin-1-yl)pyridin-4-yl)-[1,1'-biphenyl]-4-yl)-3-methylimidazolidin-2-one

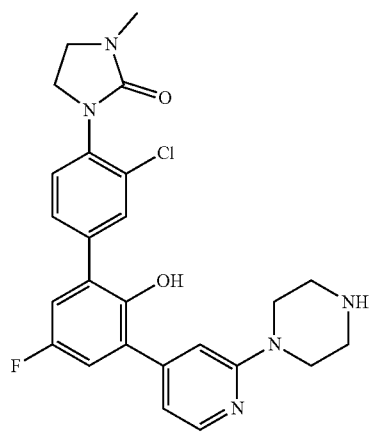 [SMILES: CN1CCN(c2ccc(-c3cc(F)cc(-c4ccnc(N5CCNCC5)c4)c3O)cc2Cl)C1=O]

Step 1: tert-butyl 4-(4-(3'-chloro-5-fluoro-2-methoxy-4'-(3-methyl-2-oxoimidazolidin-1-yl)-[1,1'-biphenyl]-3-yl)pyridin-2-yl)piperazine-1-carboxylate The title compound was prepared following the procedure described for Example 1 using tert-butyl 4-(4-(3-bromo-5-fluoro-2-methoxyphenyl)pyridin-2-yl)piperazine-1-carboxylate and 1-(2-chloro-4-(4,4,5,5-tetramethyl-1,3,2-dioxaborolan-2-yl)phenyl)-3-methylimidazolidin-2-one to afford the title compound (57% yield). LCMS: 596.2 (M+H)$^+$.

Step 2: 1-(3-chloro-5'-fluoro-2'-hydroxy-3'-(2-(piperazin-1-yl)pyridin-4-yl)-[1,1'-biphenyl]-4-yl)-3-methylimidazolidin-2-one The title compound was prepared following the procedure described for Example 214 using tert-butyl 4-(4-(3'-chloro-5-fluoro-2-methoxy-4'-(3-methyl-2-oxoimidazolidin-1-yl)-[1,1'-biphenyl]-3-yl)pyridin-2-yl)piperazine-1-carboxylate and BBr$_3$ to afford the title compound (48% yield). $^1$H NMR (400 MHz, DMSO-d$_6$): 8.14 (d, J=5.2 Hz, 1H), 7.71 (d, J=1.6 Hz, 1H), 7.56-7.53 (m, 1H), 7.46 (d, J=8.4 Hz, 1H), 7.22-7.16 (m, 2H), 6.92 (s, 1H), 6.81 (d, J=5.2 Hz, 1H), 3.75-3.71 (m, 2H), 3.51-3.47 (m, 2H), 3.46-3.43 (m, 4H), 2.80-2.77 (m, 7H). N—H and O—H protons not observed. LCMS: 482.2 (M+H)$^+$.

Example 298

N-(3'-(2-(2,6-diazaspiro[3.3]heptan-2-yl)pyridin-4-yl)-3-chloro-5'-fluoro-2'-hydroxy-[1,1'-biphenyl]-4-yl)acetamide

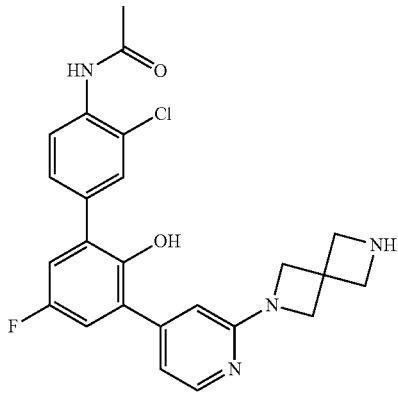 [SMILES: CC(=O)Nc1ccc(-c2cc(F)cc(-c3ccnc(N4CC5(CNC5)C4)c3)c2O)cc1Cl]

Step 1: tert-butyl 6-(4-(4'-acetamido-3'-chloro-5-fluoro-2-methoxy-[1,1'-biphenyl]-3-yl)pyridin-2-yl)-2,6-diazaspiro[3.3]heptane-2-carboxylate The title compound was prepared following the procedure described for Example 1 using tert-butyl 6-(4-(3-bromo-5-fluoro-2-methoxyphenyl)pyridin-2-yl)-2,6-diazaspiro[3.3]heptane-2-carboxylate and N-(2-chloro-4-(4,4,5,5-tetramethyl-1,3,2-dioxaborolan-2-yl)phenyl)acetamide to afford the title compound. LCMS: 567.1 (M+H)$^+$.

Step 2: N-(3'-(2-(2,6-diazaspiro[3.3]heptan-2-yl)pyridin-4-yl)-3-chloro-5'-fluoro-2'-hydroxy-[1,1'-biphenyl]-4-yl)acetamide The title compound was prepared following the procedure described for Example 214 using tert-butyl 6-(4-(4'-acetamido-3'-chloro-5-fluoro-2-methoxy-[1,1'-biphenyl]-3-yl)pyridin-2-yl)-2,6-diazaspiro[3.3]heptane-2-carboxylate and BBr$_3$ to afford the title compound. $^1$H NMR (400 MHz, DMSO-d$_6$): 9.58 (s, 1H), 8.09 (d, J=5.2 Hz, 1H), 7.78 (d, J=8.0 Hz, 1H), 7.69 (d, J=1.6 Hz, 1H), 7.49 (dd, J=8.0, 1.6 Hz, 1H), 7.20-7.12 (m, 2H), 6.82 (d, J=5.2 Hz, 1H), 6.54 (s, 1H), 4.03-4.02 (m, 4H), 3.66-3.64 (m, 4H), 2.12 (s, 3H). N—H and O—H protons not observed. LCMS: 453.1 (M+H)$^+$.

Example 299

4'-Acetamido-3'-fluoro-6-hydroxy-N-methyl-5-(2-(piperazin-1-yl)pyridin-4-yl)-[1,1'-biphenyl]-3-carboxamide

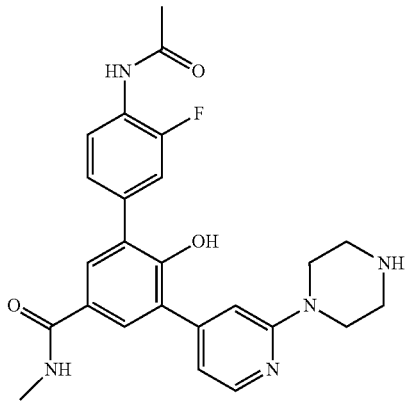 [SMILES: CNC(=O)c1cc(-c2ccnc(N3CCNCC3)c2)c(O)c(-c2ccc(NC(C)=O)c(F)c2)c1]

Step 1: tert-butyl 4-(4-(3-bromo-2-methoxy-5-(methoxycarbonyl)phenyl)pyridin-2-yl)piperazine-1-carboxylate A solution of tert-butyl 4-(4-(3-bromo-2-hydroxy-5-(methoxycarbonyl)phenyl)pyridin-2-yl)piperazine-1-carboxylate (100 mg, 0.203 mmol), CH$_3$I (32.0 mg, 0.223 mmol) and K$_2$CO$_3$ (42.0 mg, 0.304 mmol) in acetone (10 mL) was stirred at 60° C. for 3 hours. The reaction mixture was cooled and concentrated. The residue was purified by silica gel chromatography using petroleum ether and ethyl acetate as the eluent: petroleum ether:ethyl acetate (4:1 to 1:1) to afford the title compound (77 mg, 75% yield) as a white solid. LCMS: 506.0 (M+H)$^+$.

Step 2: tert-butyl 4-(4-(4'-acetamido-3'-fluoro-2-methoxy-5-(methoxycarbonyl)-[1,1'-biphenyl]-3-yl)pyridin-2-yl)piperazine-1-carboxylate The title compound was prepared following the procedure described for Example 1 using tert-butyl 4-(4-(3-bromo-2-methoxy-5-(methoxycarbonyl)phenyl)pyridin-2-yl)piperazine-1-carboxylate and N-(2-fluoro-4-(4,4,5,5-tetramethyl-1,3,2-dioxaborolan-2-yl)phenyl)acetamide to afford the title compound (83% yield). LCMS: 579.2 (M+H)$^+$.

Step 3: tert-butyl 4-(4-(4'-acetamido-3'-fluoro-2-methoxy-5-(methylcarbamoyl)-[1,1'-biphenyl]-3-yl)pyridin-2-yl)piperazine-1-carboxylate A solution of tert-butyl 4-(4-(4'-acetamido-3'-fluoro-2-methoxy-5-(methoxycarbonyl)-[1,1'-biphenyl]-3-yl)pyridin-2-yl)piperazine-1-carboxylate (62 mg, 0.12 mmol) in CH$_3$NH$_2$/EtOH (5 mL, 3 M) was stirred at 150° C. in microwave for 3 hours. The reaction mixture was cooled and concentrated. The residue was purified by silica gel chromatography using petroleum ether and ethyl acetate as the eluent (2:1) to afford the title compound as a white solid. LCMS: 578.0 (M+H).

Step 4: 4'-acetamido-3'-fluoro-6-hydroxy-N-methyl-5-(2-(piperazin-1-yl)pyridin-4-yl)-[1,1'-biphenyl]-3-carboxamide The title compound was prepared following the procedure described for Example 214 using tert-butyl 4-(4-(4'-acetamido-3'-fluoro-2-methoxy-5-(methylcarbamoyl)-[1,1'-biphenyl]-3-yl)pyridin-2-yl)piperazine-H-carboxylate and BBr₃ to afford the title compound. ¹H NMR (400 MHz, DMSO-d₆): 9.80 (s, 1H), 8.34 (d, J=4.4 Hz, 1H), 8.15 (d, J=5.2 Hz, 1H), 7.95-7.94 (m, 1H), 7.75 (dd, J=16.8, 2.4 Hz, 2H), 7.49 (d, J=12.4 Hz, 1H), 7.36 (d, J=8.4 Hz, 1H), 6.96 (s, 1H), 6.82 (d, J=5.2 Hz, 1H), 3.47-3.43 (m, 4H), 2.83-2.80 (m, 4H), 2.77 (d, J=4.0 Hz, 3H), 2.11 (s, 3H). N—H and O—H protons not observed. LCMS: 464.2 (M+H)⁺.

TABLE 21

Following compounds were prepared using similar procedures as described for Examples 163, 214, 251, 252, 253 or 296.

| Ex. No. | Name/Structure | ¹H NMR Data | LCMS (M + H)⁺ |
|---|---|---|---|
| 300 | 1-(3'-(2-(4-aminopiperidin-1-yl)pyridin-4-yl)-3-chloro-2'-hydroxy-[1,1'-biphenyl]-4-yl)-3-methylimidazolidin-2-one 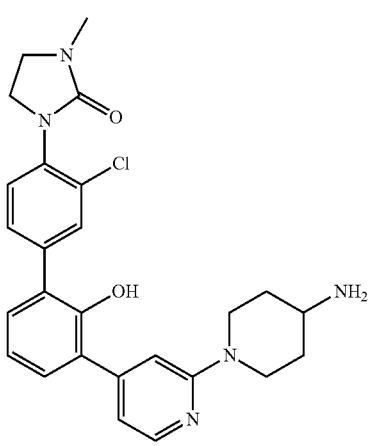 [SMILES: CN1CCN(c2ccc(-c3cccc(-c4ccnc(N5CCC(N)CC5)c4)c3O)cc2Cl)C1=O] | ¹H NMR (400 MHz, DMSO-d₆): 8.11 (d, J =5.2 Hz, 1H), 7.69 (d, J = 1.6 Hz, 1H), 7.51 (dd, J = 8.0, 1.6 Hz, 1H), 7.43 (d, J = 8.4 Hz, 1H), 7.30-7.26 (m, 2H), 7.00 (t, J = 7.6 Hz, 1H), 6.94 (s, 1H), 6.76 (d, J = 5.2 Hz, 1H), 4.24-4.21 (m, 2H), 3.72 (t, J = 7.6 Hz, 2H), 3.48 (t, J = 7.6 Hz, 2H), 2.91-2.77 (m, 2H), 2.74-2.72 (m, 4H), 1.76-1.73 (m, 2H), 1.26-1.16 (m, 2H). N-H and O-H protons not observed | 478.2 |
| 301 | 1-(3'-(2-(3-aminopiperidin-1-yl)pyridin-4-yl)-3-chloro-2'-hydroxy-[1,1'-biphenyl]-4-yl)-3-methylimidazolidin-2-one 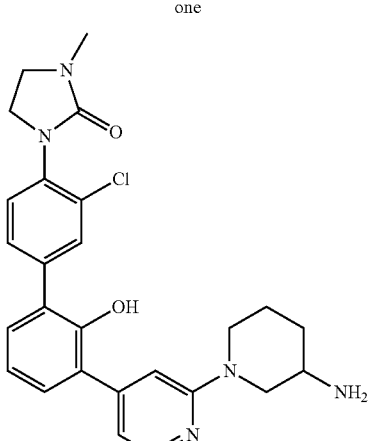 | ¹H NMR (400 MHz, DMSO-d₆): 8.11 (d, J = 5.2 Hz, 1H), 7.67 (d, J = 1.6 Hz, 1H), 7.53-7.49 (m, 1H), 7.44 (d, J = 8.0 Hz, 1H), 7.32-7.26 (m, 2H), 7.05 (t, J = 7.2 Hz, 1H), 6.90 (s, 1H), 6.74 (d, J = 5.2 Hz, 1H), 4.26-4.23 (m, 1H), 4.18-4.13 (m, 1H), 3.73 (t, J = 7.6 Hz, 2H), 3.49 (t, J = 7.6 Hz, 2H), 2.84-2.81 (m, 1H), 2.77 (s, 3H), 2.74-2.67 (m, 1H), 2.62-2.56 (m, 1H), 1.90-1.87 (m, 1H), 1.72-1.66 (m, 1H), 1.51-1.41 (m, 1H), 1.30-1.20 (m, 1H). N-H and O-H protons not observed | 478.2 |
| 302 | N-(3'-(2-(2-aminoethoxy)-6-(piperazin-1-yl)pyridin-4-yl)-3-fluoro-2'-hydroxy-[1,1'-biphenyl]-4-yl)acetamide | ¹H NMR (TFA salt - 400 MHz, DMSO-dg): 9.79 (s, 1H), 8.99-8.92 (m, 2H), | 466.3 |

TABLE 21-continued

Following compounds were prepared using similar procedures as described for Examples 163, 214, 251, 252, 253 or 296.

| Ex. No. | Name/Structure | ¹H NMR Data | LCMS (M + H)⁺ |
|---|---|---|---|
|  |  | 8.54 (s, 1H), 8.01-7.91 (m, 4H), 7.40 (dd, J = 12.0, 1.2 Hz, 1H), 7.31-7.23 (m, 3H), 7.04 (t, J = 7.6 Hz, 1H), 6.59 (s, 1H), 6.35 (s, 1H), 4.42 (t, J = 4.8 Hz, 2H), 3.73-3.72 (m, 4H), 3.22-3.19 (m, 6H), 2.11 (s, 3H) |  |
| 303 | 1-(3-fluoro-2'-hydroxy-3'-(2-(piperazin-1-yl)pyridin-4-yl)-[1,1'-biphenyl]-4-yl)pyrrolidine-2,5-dione | ¹H NMR (400 MHz, DMSO-$d_6$): 9.79 (s, 1H), 8.99-8.92 (m, 2H), 8.54 (s, 1H), 8.01-7.91 (m, 4H), 7.40 (dd, J = 12.0, 1.2 Hz, 1H), 7.31-7.23 (m, 3H), 7.04 (t, J = 7.6 Hz, 1H), 6.59 (s, 1H), 6.35 (s, 1H), 4.42 (t, J = 4.8 Hz, 2H), 3.73-3.72 (m, 4H), 3.22-3.19 (m, 6H), 2.11 (s, 3H) | 466.3 |
| 304 | N-(3'-(2-(4-aminobut-1-yn-1-yl)pyridin-4-yl)-3-fluoro-2'-hydroxy-[1,1'-biphenyl]-4-yl)acetamide | ¹H NMR (TFA salt - 400 MHz, DMSO-$d_6$): 9.79 (s, 1H), 8.82 (s, 1H), 8.58 (d, J = 5.2 Hz, 1H), 7.97-7.93 (m, 3H), 7.74 (s, 1H), 7.56 (dd, J = 5.2, 1.6 Hz, 1H), 7.41 (dd, J = 12.0, 1.6 Hz, 1H), 7.36-7.31 (m, 3H), 7.09 (t, J = 7.6 Hz, 1H), 3.10-3.07 (m, 2H), 2.83 (t, J = 7.2 Hz, 2H), 2.11 (s, 3H). N-H or O-H proton not observed | 390.2 |
| 305 | 1-(3'-(5-(4-aminopiperidin-1-yl)pyridin-3-yl)-3-chloro-2'-hydroxy-[1,1'-biphenyl]-4-yl)-3-methylimidazolidin-2- | ¹H NMR (400 MHz, DMSO-$d_6$): 8.25 (d, J = 2.4 Hz, 1H), 8.09 (d, J = 1.2 | 478.2 |

TABLE 21-continued

Following compounds were prepared using similar procedures as described for Examples 163, 214, 251, 252, 253 or 296.

| Ex. No. | Name/Structure | $^1$H NMR Data | LCMS (M + H)$^+$ |
|---|---|---|---|
|  | one | Hz, 1H), 7.68 (d, J = 1.6 Hz, 1H), 7.52 (dd, J = 8.0, 1.6 Hz, 1H), 7.46-7.40 (m, 2H), 7.28 (t, J = 6.0 Hz, 2H), 7.06-7.03 (m, 1H), 3.74-3.71 (m, 4H), 3.51-3.47 (m, 2H), 2.84-2.74 (m, 6H), 1.81-1.78 (m, 2H), 1.36-1.33 (m, 2H). N-H and O-H protons not observed |  |
| 306 | 1-(3-chloro-2'-hydroxy-5'-methyl-3'-(2-(piperazin-1-yl)pyridin-4-yl)-[1,1'-biphenyl]-4-yl)-3-methylimidazolidin-2-one | $^1$H NMR (400 MHz, DMSO-d): 8.12 (d, J = 5.2 Hz, 1H), 7.65 (d, J = 1.6 Hz, 1H), 7.51-7.42 (m, 2H), 7.10 (d, J = 8.8 Hz, 2H), 6.87 (s, 1H), 6.78 (d, J = 4.8 Hz, 1H), 3.74-3.70 (m, 2H), 3.50-3.46 (m, 2H), 3.44-3.42 (m, 4H), 2.80-2.77 (m, 7H), 2.29 (s, 3H). N-H or O-H proton not observed | 478.2 |
| 307 | 3-(3-fluoro-4-(2-oxopyrrolidin-1-yl)phenyl)-5-(3-(piperazin-1-yl)phenyl)pyridin-4(1H)-one | $^1$H NMR (400 MHz, DMSO-d$_6$): 7.84 (d, J = 1.6 Hz, 1H), 7.75 (d, J = 1.6 Hz, 1H), 7.53-7.50 (m, 1H), 7.39-7.34 (m, 2H), 7.23-7.17 (m, 2H), 6.95 (d, J = 7.6 Hz, 1H), 6.88 (dd, J = 8.4, 2.0 Hz, 1H), 3.78 (t, J = 7.2 Hz, 2H), 3.13-3.11 (m, 4H), 2.96-2.94 (m, 4H), 2.50-2.46 (m, 2H), 2.18-2.14 (m, 2H). N-H and O-H protons not observed | 433.3 |
| 308 | 3''-chloro-2'-hydroxy-4''-(3-methyl-2-oxoimidazolidin-1-yl)-3-(piperazin-1-yl)-[1,1':3',1''-terphenyl]-4-carbonitrile | $^1$H NMR (400 MHz, DMSO-d$_6$): 7.74 (d, J = 8.0 Hz, 1H), 7.67 (d, J = 1.6 | 488.3 |

TABLE 21-continued

Following compounds were prepared using similar procedures as described for Examples 163, 214, 251, 252, 253 or 296.

| Ex. No. | Name/Structure | ¹H NMR Data | LCMS (M + H)⁺ |
|---|---|---|---|
| | | Hz, 1H), 7.51 (dd, J = 8.0, 1.6 Hz, 1H), 7.45 (d, J = 8.4 Hz, 1H), 7.31 (dd, J = 8.0, 2.4 Hz, 2H), 7.25-7.23 (m, 2H), 7.09-7.05 (m, 1H), 3.74-3.70 (m, 2H), 3.51-3.47 (m, 2H), 3.13-3.10 (m, 4H), 2.89-2.87 (m, 4H), 2.77 (s, 3H). N-H and O-H protons not observed | |
| 309 | 1-(3-chloro-2'-hydroxy-3'-(2-(piperazin-1-yl)pyridin-4-yl)-5'-(trifluoromethoxy)-[1,1'-biphenyl]-4-yl)-3-methylimidazolidin-2-one | ¹H NMR (400 MHz, DMSO-d₆): 8.15 (d, J = 4.8 Hz, 1H), 7.73 (d, J = 2.0 Hz, 1H), 7.54 (dd, J = 8.4, 1.6 Hz, 1H), 7.46 (d, J = 8.4 Hz, 1H), 7.30 (d, J = 12.8 Hz, 2H), 6.95 (s, 1H), 6.81 (d, J = 5.6 Hz, 1H), 3.75-3.71 (m, 2H), 3.51-3.45 (m, 6H), 2.82-2.77 (m, 7H). N-H and O-H protons not observed | 548.2 |
| 310 | 1-(5'-(tert-butyl)-3-chloro-2'-hydroxy-3'-(2-(piperazin-1-yl)pyridin-4-yl)-[1,1'-biphenyl]-4-yl)-3-methylimidazolidin-2-one | ¹H NMR (400 MHz, DMSO-d₆): 8.14 (d, J =5.2 Hz, 1H), 7.67 (d, J = 1.6 Hz, 1H), 7.50 (dd, J = 8.4, 2.0 Hz, 1H), 7.44 (d, J = 8.4 Hz, 1H), 7.26 (d, J = 2.8 Hz, 1H), 7.22 (d, J = 2.0 Hz, 1H), 6.90 (s, 1H), 6.78 (d, J = 4.8 Hz, 1H), 3.74-3.70 (m, 2H), 3.51-3.47 (m, 6H), 2.83-2.77 (m, 7H), 1.31 (s, 9H). N-H and O-H protons not observed | 520.3 |

TABLE 21-continued

Following compounds were prepared using similar procedures as described for Examples 163, 214, 251, 252, 253 or 296.

| Ex. No. | Name/Structure | $^1$H NMR Data | LCMS (M + H)$^+$ |
|---|---|---|---|
| 311 | 1-(3-chloro-5'-ethyl-2'-hydroxy-3'-(2-(piperazin-1-yl)pyridin-4-yl)-[1,1'-biphenyl]-4-yl)-3-methylimidazolidin-2-one | $^1$H NMR (400 MHz, DMSO-d$_6$): 8.13 (d, J = 4.8 Hz, 1H), 7.67 (s, 1H), 7.51 (d, J = 7.6 Hz, 1H), 7.44 (d, J = 8.0 Hz, 1H), 7.12 (d, J = 11.2 Hz, 2H), 6.89 (s, 1H), 6.79 (d, J = 5.2 Hz, 1H), 3.74-3.70 (m, 2H), 3.51-3.45 (m, 6H), 2.81-2.77 (m, 7H), 2.61-2.57 (m, 2H), 1.20 (t, J = 7.6 Hz, 3H). N-H and O-H protons not observed | 492.2 |
| 312 | 1-(3-chloro-2'-hydroxy-5'-methoxy-3'-(2-(piperazin-1-yl)pyridin-4-yl)-[1,1'-biphenyl]-4-yl)-3-methylimidazolidin-2-one | $^1$H NMR (400 MHz, DMSO-d$_6$): 8.16 (d, J = 5.2 Hz, 1H), 7.70 (d, J = 1.2 Hz, 1H), 7.55-7.52 (m, 1H), 7.44 (d, J = 8.4 Hz, 1H), 6.96 (s, 1H), 6.90 (d, J = 3.2 Hz, 1H), 6.86 (d, J = 3.2 Hz, 2H), 3.78 (s, 3H), 3.74-3.70 (m, 2H), 3.58-3.56 (m, 4H), 3.51-3.47 (m, 2H), 2.96-2.94 (m, 4H), 2.77 (s, 3H). N-H and O-H protons not observed | 494.2 |
| 313 | N-(3'-(2-cyano-6-(piperazin-1-yl)pyridin-4-yl)-3-fluoro-2'-hydroxy-[1,1'-biphenyl]-4-yl)acetamide | $^1$H NMR (400 MHz, CD$_3$OD): 7.84 (d, J = 5.2 Hz, 1H), 7.34 (s, 1H), 7.26-7.20 (m, 5H), 7.00-6.96 (m, 1H), 3.84-3.81 (m, 4H), 3.25-3.21 (m, 4H), 2.10 (s, 3H). N-H and O-H protons not observed | 432.2 |

TABLE 21-continued

Following compounds were prepared using similar procedures as described for Examples 163, 214, 251, 252, 253 or 296.

| Ex. No. | Name/Structure | ¹H NMR Data | LCMS (M + H)⁺ |
|---|---|---|---|
| 314 | 3'-chloro-6-hydroxy-4'-(3-methyl-2-oxoimidazolidin-1-yl)-5-(2-(piperazin-1-yl)pyridin-4-yl)-[1,1'-biphenyl]-3-carbonitrile | ¹H NMR (TFA salt - 400 MHz, DMSO-$d_6$): 9.97 (brs, 1H), 8.80 (brs, 2H), 8.22 (d, J = 5.2 Hz, 1H), 7.82-7.79 (m, 2H), 7.72 (d, J = 1.6 Hz, 1H), 7.56-7.48 (m, 2H), 7.10 (s, 1H), 6.97 (d, J = 5.2 Hz, 1H), 3.78-3.72 (m, 6H), 3.52-3.48 (m, 2H), 3.22-3.20 (m, 4H), 2.77 (s, 3H) | 489.1 |
| 315 | 1-(3-chloro-2'-hydroxy-5'-isopropyl-3'-(2-(piperazin-1-yl)pyridin-4-yl)-[1,1'-biphenyl]-4-yl)-3-methylimidazolidin-2-one | ¹H NMR (400 MHz, DMSO-$d_6$): 8.13 (d, J = 4.8 Hz, 1H), 7.67 (s, 1H), 7.51 (d, J = 8.4 Hz, 1H), 7.44 (d, J = 8.0 Hz, 1H), 7.13 (d, J = 13.2 Hz, 2H), 6.88 (s, 1H), 6.78 (d, J = 4.8 Hz, 1H), 3.74-3.70 (m, 2H), 3.51-3.44 (m, 6H), 2.92-2.88 (m, 1H), 2.79-2.77 (m, 7H), 1.22 (d, J = 6.4 Hz, 6H). N-H and O-H protons not observed | 506.2 |
| 316 | 1-(3-chloro-5'-cyclopropyl-2'-hydroxy-3'-(2-(piperazin-1-yl)pyridin-4-yl)-[1,1'-biphenyl]-4-yl)-3-methylimidazolidin-2-one | ¹H NMR (400 MHz, DMSO-$d_6$): 8.12 (d, J = 5.6 Hz, 1H), 7.66 (d, J = 1.6 Hz, 1H), 7.50 (dd, J = 8.4, | 504.2 |

TABLE 21-continued

Following compounds were prepared using similar procedures as described for Examples 163, 214, 251, 252, 253 or 296.

| Ex. No. | Name/Structure | ¹H NMR Data | LCMS (M + H)⁺ |
|---|---|---|---|
| | 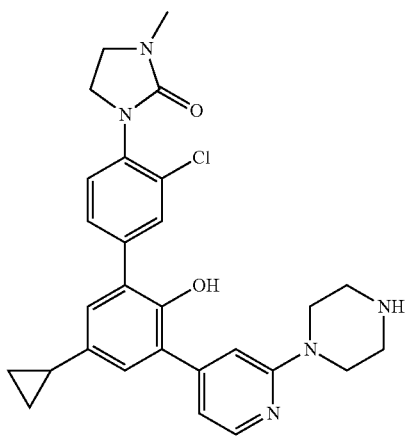 [SMILES: CN1CCN(c2ccc(-c3cc(C4CC4)cc(-c4ccnc(N5CCNCC5)c4)c3O)cc2Cl)C1=O] | 2.0 Hz, 1H), 7.43 (d, J = 8.4 Hz, 1H), 6.98 (s, 2H), 6.88 (s, 1H), 6.78 (d, J = 5.2 Hz, 1H), 3.74-3.70 (m, 2H), 3.50-3.45 (m, 6H), 2.81-2.77 (m, 7H), 1.96-1.89 (m, 1H), 0.91-0.87 (m, 2H), 0.71-0.68 (m, 2H). N-H and O-H protons not observed | |

Example 317

1-(3-chloro-2'-hydroxy-4"-hydroxymethyl)-3"-(piperazin-1-yl)-[1,1':3',1"-terphenyl]-4-yl)-3-methylimidazolidin-2-one

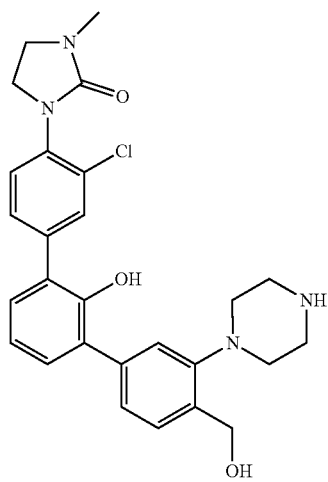 [SMILES: CN1CCN(c2ccc(-c3cccc(-c4ccc(CO)c(N5CCNCC5)c4)c3O)cc2Cl)C1=O]

Step 1: tert-Butyl 4-(3"-chloro-4-formyl-2'-methoxy-4"-(3-methyl-2-oxoimidazolidin-1-yl)-[1,1':3',1"-terphenyl]-3-yl)piperazine-1-carboxylate The title compound was prepared following the procedure described for Example 1 using tert-butyl 4-(5-bromo-2-formylphenyl)piperazine-1-carboxylate and 1-(3-chloro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (77% yield). LCMS: 605.2 (M+H)⁺.

Step 2: tert-butyl 4-(3"-chloro-4-(hydroxymethyl)-2'-methoxy-4"-(3-methyl-2-oxoimidazolidin-1-yl)-[1,1':3',1"-terphenyl]-3-yl)piperazine-1-carboxylate To a solution of tert-butyl 4-(3"-chloro-4-formyl-2'-methoxy-4"-(3-methyl-2-oxoimidazolidin-1-yl)-[1,1':3',1"-terphenyl]-3-yl)piperazine-1-carboxylate (100 mg, 0.166 mmol) in MeOH (3 mL) was added NaBH₄ (12.6 mg, 0.330 mmol) at 0° C. The reaction mixture was stirred at rt for 3 h under N₂. After the reaction was indicated by LCMS, H₂O was added to this reaction and extracted with DCM (10 mL×3). The combined organic layers were washed with brine (50 mL), dried over sodium sulfate, filtered and concentrated. The residue was purified by flash column chromatography (PE:EA=1:2) to afford the title compound (80 mg, 80% yield) as a white solid. LCMS: 607.6 (M+H)⁺.

Step 3: 1-(3-chloro-2'-hydroxy-4"-(hydroxymethyl)-3"-(piperazin-1-yl)-[1,1':3',1"-terphenyl]-4-yl)-3-methylimidazolidin-2-one The title compound was prepared following the procedures described for Example 3 using tert-butyl 4-(3"-chloro-4-(hydroxymethyl)-2'-methoxy-4"-(3-methyl-2-oxoimidazolidin-1-yl)-[1,1':3',1"-terphenyl]-3-yl)piperazine-1-carboxylate and BBr₃ to afford the title compound (11% yield). ¹H NMR (400 MHz, DMSO-d₆): 7.67 (d, J=1.6 Hz, 1H), 7.53-7.50 (m, 2H), 7.44 (d, J=8.4 Hz, 1H), 7.26-7.19 (m, 4H), 7.04 (d, J=7.6 Hz, 1H), 5.14-5.13 (m, 1H), 4.58 (s, 2H), 3.74-3.70 (m, 2H), 3.51-3.47 (m, 2H), 3.19-2.91 (m, 8H), 2.77 (s, 3H). N—H and O—H protons not observed. LCMS: 493.2 (M+H)⁺.

Example 318

1-(3-chloro-6'-hydroxy-5'-(2-(piperazin-1-yl)pyridin-4-yl)-[1,1':3',1''-terphenyl]-4-yl)-3-methylimidazolidin-2-one

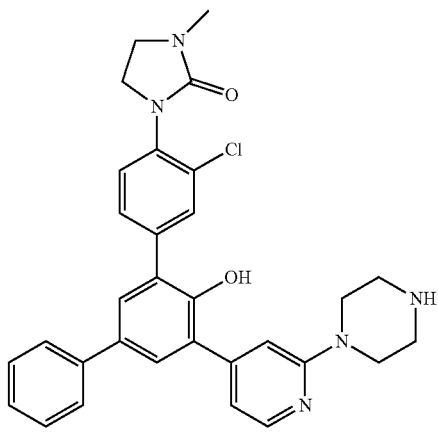 [SMILES: CN1CCN(c2ccc(-c3cc(-c4ccccc4)cc(-c4ccnc(N5CCNCC5)c4)c3O)cc2Cl)C1=O]

The title compound was prepared following the procedures described for Example 298 using [1,1'-biphenyl]-4-ol, 1-(2-chloro-4-(4,4,5,5-tetramethyl-1,3,2-dioxaborolan-2-yl)phenyl)-3-methylimidazolidin-2-one and (2-(4-(tert-butoxycarbonyl)piperazin-1-yl)pyridin-4-yl)boronic acid to afford the title compound (34% yield). $^1$H NMR (400 MHz, DMSO-$d_6$): 8.16 (d, J=5.2 Hz, 1H), 7.78 (d, J=1.6 Hz, 1H), 7.73 (d, J=7.6 Hz, 2H), 7.62 (dd, J=8.0, 1.6 Hz, 1H), 7.55 (dd, J=15.2, 2.4 Hz, 2H), 7.47-7.41 (m, 3H), 7.32 (t, J=7.2 Hz, 1H), 6.98 (s, 1H), 6.88 (d, J=5.2 Hz, 1H), 3.75-3.72 (m, 2H), 3.51-3.46 (m, 6H), 2.79-2.78 (m, 7H). N—H and O—H protons not observed. LCMS: 540.3 (M+H)$^+$.

Example 319

1-(4''-(aminomethyl)-3-chloro-2'-hydroxy-3''-(piperazin-1-yl)-[1,1':3',1''-terphenyl]-4-yl)-3-methylimidazolidin-2-one

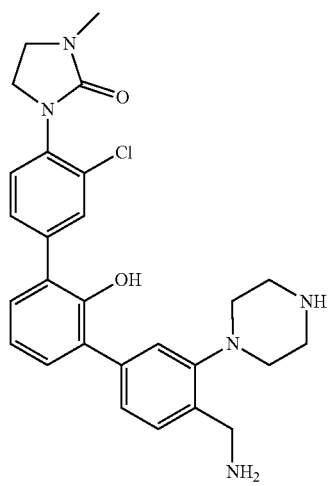 [SMILES: CN1CCN(c2ccc(-c3cccc(-c4ccc(CN)c(N5CCNCC5)c4)c3O)cc2Cl)C1=O]

Step 1: tert-Butyl 4-(3''-chloro-4-((hydroxyimino)methyl)-2'-methoxy-4''-(3-methyl-2-oxoimidazolidin-1-yl)-[1,1':3',1''-terphenyl]-3-yl)piperazine-1-carboxylate To a solution of tert-butyl 4-(3''-chloro-4-formyl-2'-methoxy-4''-(3-methyl-2-oxoimidazolidin-1-yl)-[1,1':3',1''-terphenyl]-3-yl)piperazine-1-carboxylate (130 mg, 0.220 mmol) in EtOH (6 mL) was added NH$_2$—OH·HCl (45 mg, 0.65 mmol) and NaOAc (53 mg, 0.65 mmol). The reaction mixture was stirred at rt for 6 h under N$_2$. After the reaction was complete by LCMS, H$_2$O (50 mL) was added to this reaction and extracted with DCM (15 mL×3). The combined organic layers were washed with brine, dried over sodium sulfate, filtered and concentrated to afford the title compound (130 mg, 96% yield) as a white solid which was used to the next step without further purification. LCMS: 620.6 (M+H)$^+$.

Step 2: tert-Butyl 4-(4-(aminomethyl)-3''-chloro-2'-methoxy-4''-(3-methyl-2-oxoimidazolidin-1-yl)-[1,1':3',1''-terphenyl]-3-yl)piperazine-1-carboxylate To a solution of tert-butyl 4-(3''-chloro-4-((hydroxyimino)methyl)-2'-methoxy-4''-(3-methyl-2-oxoimidazolidin-1-yl)-[1,1':3',1''-terphenyl]-3-yl)piperazine-1-carboxylate (130 mg, 0.210 mmol) in acetic acid (4 mL) was added Zn (134 mg, 2.10 mmol). The reaction mixture was stirred at 70° C. for 16 h under N$_2$. After the reaction was complete by LCMS, the reaction mixture was filtered and concentrated. The residue was adjusted pH=9-11 with sat. NaHCO$_3$ and extracted with DCM (10 mL×3). The combined organic layers were washed with brine, dried over sodium sulfate, filtered and concentrated to afford the title compound (110 mg, 87% yield) as a pale-yellow solid which was used to the next step without further purification. LCMS: 606.6 (M+H)$^+$.

Step 3: 1-(4''-(aminomethyl)-3-chloro-2'-hydroxy-3''-(piperazin-1-yl)-[1,1':3',1''-terphenyl]-4-yl)-3-methylimidazolidin-2-one 2,2,2-trifluoroacetate The title compound was prepared following the procedure described for Example 214 using tert-butyl 4-(4-(aminomethyl)-3''-chloro-2'-methoxy-4''-(3-methyl-2-oxoimidazolidin-1-yl)-[1,1':3',1''-terphenyl]-3-yl)piperazine-1-carboxylate and BBr$_3$ to afford the title compound (35% yield). $^1$H NMR (400 MHz, DMSO-$d_6$): 8.90 (br s, 2H), 8.65 (s, 1H), 8.16-8.15 (m, 3H), 7.68 (d, J=1.6 Hz, 1H), 7.53-7.41 (m, 5H), 7.30-7.27 (m, 2H), 7.09-7.07 (m, 1H), 4.16-4.14 (m, 2H), 3.75-3.71 (m, 2H), 3.51-3.47 (m, 2H), 3.32-3.30 (m, 4H), 3.10-3.08 (m, 4H), 2.77 (s, 3H). LCMS: 492.2 (M+H)$^+$.

Example 320

N-((3"-chloro-2'-hydroxy-4"-(3-methyl-2-oxoimidazolidin-1-yl)-3-(piperazin-1-yl)-[1,1':3',1"-terphenyl]-4-yl)methyl)acetamide

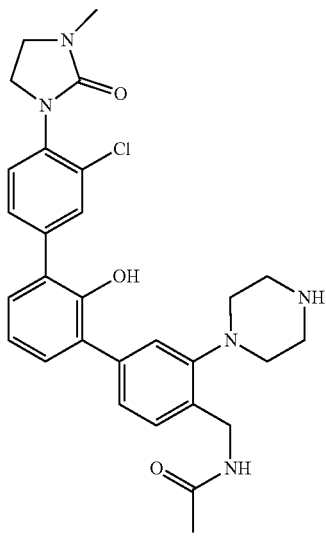 [SMILES: CC(=O)NCc1ccc(-c2cccc(-c3ccc(N4CCN(C)C4=O)c(Cl)c3)c2O)cc1N1CCNCC1]

Step 1: tert-butyl 4-(4-(acetamidomethyl)-3"-chloro-2'-methoxy-4"-(3-methyl-2-oxoimidazolidin-1-yl)-[1,1':3',1"-terphenyl]-3-yl)piperazine-1-carboxylate To a solution of tert-butyl 4-(4-(aminomethyl)-3"-chloro-2'-methoxy-4"-(3-methyl-2-oxoimidazolidin-1-yl)-[1,1':3',1"-terphenyl]-3-yl)piperazine-1-carboxylate (40 mg, 0.066 mmol) in DCM (1 mL) was added TEA (20.0 mg, 0.198 mmol) and CH$_3$COCl (8.0 mg, 0.099 mmol) at 0° C. The reaction mixture was stirred at rt for 2 h under N$_2$. After the reaction was complete by LCMS, the reaction mixture was diluted with H$_2$O (15 mL) and extracted with DCM (5 mL×3). The combined organic layers were washed with brine, dried over sodium sulfate, filtered and concentrated to afford the title compound (40 mg, 94% yield) as a pale-yellow solid which was used to the next step without further purification. LCMS: 648.7 (M+H)$^+$.

Step 2: N-((3"-chloro-2'-hydroxy-4"-(3-methyl-2-oxoimidazolidin-1-yl)-3-(piperazin-1-yl)-[1,1':3',1"-terphenyl]-4-yl)methyl)acetamide The title compound was prepared following the procedure described for Example 214 using tert-butyl 4-(4-(acetamidomethyl)-3"-chloro-2'-methoxy-4"-(3-methyl-2-oxoimidazolidin-1-yl)-[1,1':3',1"-terphenyl]-3-yl)piperazine-1-carboxylate and BBr$_3$ to afford the title compound. $^1$H NMR (400 MHz, DMSO-d$_6$): 8.23 (d, J=5.6 Hz, 1H), 7.66 (d, J=1.6 Hz, 1H), 7.51 (dd, J=8.0, 1.2 Hz, 1H), 7.44 (d, J=8.0 Hz, 1H), 7.29-7.21 (m, 5H), 7.03 (t, J=7.6 Hz, 1H), 4.36 (d, J=5.2 Hz, 2H), 3.74-3.70 (m, 2H), 3.51-3.47 (m, 2H), 2.88-2.77 (m, 11H), 1.91 (s, 3H). N—H and O—H protons not observed. LCMS: 534.2 (M+H)$^+$.

TABLE 22

Following compounds were prepared using similar procedures as described for Examples 163, 214, 251, 252, 253 or 296.

| Ex. No. | Name/Structure | $^1$H NMR Data | LCMS (M + H)$^+$ |
|---|---|---|---|
| 321 | N-(3'-(2-(2,6-diazaspiro[3.3]heptan-2-yl)pyridin-4-yl)-3,5'-difluoro-2'-hydroxy-[1,1'-biphenyl]-4-yl)acetamide | $^1$H NMR (400 MHz, DMSO-d$_6$): 9.83 (s, 1H), 8.88-8.84 (m, 2H), 8.10 (d, J = 6.0 Hz, 1H), 7.97 (t, J = 8.0 Hz, 1H), 7.46 (dd, J = 12.4, 1.6 Hz, 1H), 7.35 (d, J = 8.4 Hz, 1H), 7.27-7.23 (m, 2H), 7.04 (d, J = 4.4 Hz, 1H), 6.87-6.85 (m, 1H), 4.33-4.32 (m, 4H), 4.21-4.19 (m, 4H), 2.11 (s, 3H). N—H or O—H proton not observed | 437.1 |
| 322 | 1-(3'-(2-(2,6-diazaspiro[3.3]heptan-2-yl)pyridin-4-yl)-3-fluoro-2'-hydroxy-[1,1'-biphenyl]-4-yl)-3-methylimidazolidin-2-one | $^1$H NMR (400 MHz, DMSO-d$_6$): 8.08 (d, J = 6.0 Hz, 1H), 7.53 (t, J = 8.4 Hz, 1H), 7.41 (dd, J = 12.8, 1.6 Hz, 1H), 7.35- | 460.2 |

TABLE 22-continued

Following compounds were prepared using similar procedures as described for Examples 163, 214, 251, 252, 253 or 296.

| Ex. No. | Name/Structure | ¹H NMR Data | LCMS (M + H)⁺ |
|---|---|---|---|
| | 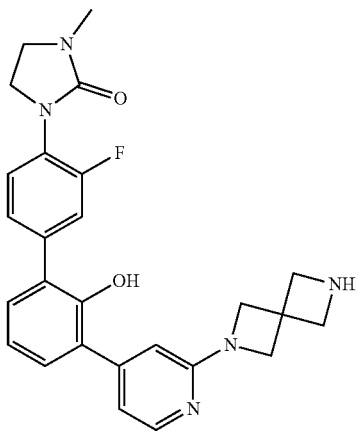 [SMILES: CN1CCN(c2ccc(-c3cccc(-c4ccnc(N5CC6(CNC6)C5)c4)c3O)cc2F)C1=O] | 7.29 (m, 2H), 7.26-7.24 (m, 1H), 7.03 (t, J = 7.6 Hz, 1H), 6.80 (d, J = 4.8 Hz, 1H), 6.50 (s, 1H), 4.03-4.02 (m, 4H), 3.81-3.77 (m, 2H), 3.64-3.63 (m, 4H), 3.50-3.46 (m, 2H), 2.77 (s, 3H). N—H and O—H protons not observed. | |
| 323 | 1-(3'-(2-(2,6-diazaspiro[3.3]heptan-2-yl)pyridin-4-yl)-3-chloro-2'-hydroxy-[1,1'-biphenyl]-4-yl)-3-methylimidazolidin-2-one 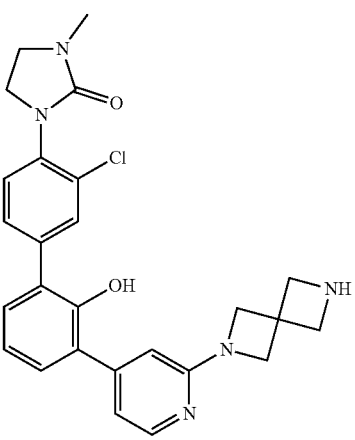 [SMILES: CN1CCN(c2ccc(-c3cccc(-c4ccnc(N5CC6(CNC6)C5)c4)c3O)cc2Cl)C1=O] | ¹H NMR (400 MHz, DMSO-d₆): 8.09 (d, J = 5.2 Hz, 1H), 7.66 (d, J = 1.6 Hz, 1H), 7.49 (d, J = 1.6 Hz, 1H), 7.45 (d, J = 8.4 Hz, 1H), 7.31-7.26 (m, 2H), 7.05-7.03 (m, 1H), 6.80 (d, J = 5.2 Hz, 1H), 6.51 (s, 1H), 4.04-4.03 (m, 4H), 3.74-3.70 (m, 6H), 3.51-3.47 (m, 2H), 2.77 (s, 3H). N—H and O—H protons not observed | 476.1 |
| 324 | 1-(3'-(2-(2,6-diazaspiro[3.3]heptan-2-yl)pyridin-4-yl)-3-chloro-5'-fluoro-2'-hydroxy-[1,1'-biphenyl]-4-yl)pyrrolidin-2-one | ¹H NMR (400 MHz, DMSO-d₆): 8.09 (d, J = 5.2 Hz, 1H), 7.76 (s, 1H), 7.57 (d, J = 8.0 Hz, 1H), 7.47 (d, J = 8.0 Hz, 1H), 7.21 (dd, J = 8.8, 3.2 Hz, 1H), 7.15 (dd, J = 8.8, 3.2 Hz, 1H), 6.83 (d, J = 5.2 Hz, 1H), 6.55 (s, 1H), 4.03-4.02 (m, 4H), 3.74-3.71 (m, 2H), 3.65-3.64 (m, 4H), 2.47-2.43 (m, 2H), 2.18-2.15 (m, 2H). N—H and O—H protons not observed | 479.1 |

TABLE 22-continued

Following compounds were prepared using similar procedures as described for Examples 163, 214, 251, 252, 253 or 296.

| Ex. No. | Name/Structure | $^1$H NMR Data | LCMS (M + H)$^+$ |
|---|---|---|---|
| 325 | 1-(3'-(5-(3-aminopiperidin-1-yl)pyridin-3-yl)-3-chloro-2'-hydroxy-[1,1'-biphenyl]-4-yl)-3-methylimidazolidin-2-one | $^1$H NMR (400 MHz, DMSO-d$_6$): 8.25 (d, J = 2.4 Hz, 1H), 8.09 (s, 1H), 7.68 (d, J = 1.6 Hz, 1H), 7.52 (dd, J = 8.4, 2.0 Hz, 1H), 7.45 (d, J = 8.4, 1H), 7.39 (s, 1H), 7.29 (t, J = 7.2 Hz, 2H), 7.06 (t, J = 7.6 Hz, 1H), 3.75-3.62 (m, 5H), 3.51-3.47 (m, 2H), 2.82-2.81 (m, 5H), 1.88-1.84 (m, 1H), 1.77-1.73 (m, 1H), 1.61-1.52 (m, 1H), 1.24-1.17 (m, 1H). N—H and O—H protons not observed | 478.2 |
| 326 | 1-(3''-(aminomethyl)-3-chloro-2'-hydroxy-5''-(piperazin-1-yl)-[1,1':3',1''-terphenyl]-4-yl)-3-methylimidazolidin-2-one | $^1$H NMR (TFA salt - 400 MHz, DMSO-d$_6$): 8.84 (s, 2H), 8.47 (s, 1H), 8.17 (s, 3H), 7.68 (d, J = 1.6 Hz, 1H), 7.50-7.45 (m, 2H), 7.30-7.16 (m, 2H), 7.11-7.06 (m, 4H), 4.05-4.04 (m, 2H), 7.20-7.12 (m, 2H), 3.74-3.71 (m, 2H), 3.51-3.47 (m, 2H), 3.42-3.40 (m, 4H), 3.27-3.25 (m, 4H), 2.77 (s, 3H). | 492.3 |
| 327 | N-((3''-chloro-2'-hydroxy-4''-(3-methyl-2-oxoimidazolidin-1-yl)-5-(piperazin-1-yl)-[1,1':3',1''-terphenyl]-3-yl)methyl)acetamide | $^1$H NMR (400 MHz, DMSO-d$_6$): 8.26 (d, J = 5.6 Hz, 1H), 7.66 (d, J = 1.6 Hz, 1H), 7.50 (dd, J = 8.4, 2.0 Hz, 1H), 7.44 (d, J = | 534.3 |

TABLE 22-continued

Following compounds were prepared using similar procedures as described for Examples 163, 214, 251, 252, 253 or 296.

| Ex. No. | Name/Structure | ¹H NMR Data | LCMS (M + H)⁺ |
|---|---|---|---|
|  |  | 8.4 Hz, 1H), 7.22 (dd, J = 16.0, 7.6 Hz, 2H), 7.02 (t, J = 7.6 Hz, 1H), 6.91 (s, 1H), 6.82 (s, 2H), 5.24 (d, J = 6.4 Hz, 2H), 3.74-3.70 (m, 2H), 3.51-3.47 (m, 2H), 3.08-3.07 (m, 4H), 2.85-2.84 (m, 4H), 2.77 (s, 3H), 1.86 (s, 3H). N—H and O—H protons not observed |  |

Example 328

1-(3-chloro-2'-hydroxy-3'-(2-(piperazin-1-yl)pyridin-4-yl)-[1,1'-biphenyl]-4-yl)-3-methylpyrrolidin-2-one

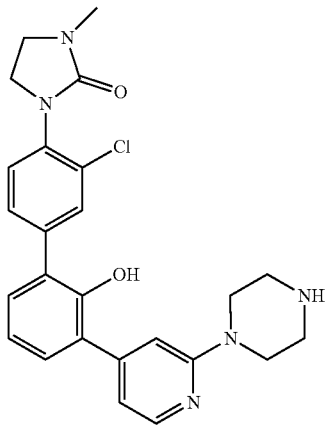 [SMILES: CN1CCN(c2ccc(-c3cccc(-c4ccnc(N5CCNCC5)c4)c3O)cc2Cl)C1=O]

Step 1: 1-(4-bromo-2-chlorophenyl)-3-methylpyrrolidin-2-one

To a solution of 1-(4-bromo-2-chlorophenyl)pyrrolidin-2-one (500 mg, 1.82 mmol) in THF (9 mL) was added LiHMDS (2 mL, 2 mmol, 1 M in THF) at −78° C. under N₂. Then the reaction mixture was stirred at −78° C. for 1 h under N₂. CH₃I (312 mg, 2.20 mmol) was added at −78° C. under N₂. The reaction mixture was stirred at rt under nitrogen atmosphere for 2 h. After the reaction was complete by LCMS, the reaction mixture was quenched with aqueous NH₄Cl, extracted with EA (20 mL×3). The combined organic layers were washed with brine, dried over Na₂SO₄, filtered and concentrated to afford the title compound (500 mg, 95% yield) as brown oil. LCMS: 288.0 (M+H)⁺.

Step 2: 1-(2-chloro-4-(4,4,5,5-tetramethyl-1,3,2-dioxaborolan-2-yl)phenyl)-3-methylpyrrolidin-2-one The title compound was prepared following the procedure described for Example 1 using 1-(4-bromo-2-chlorophenyl)-3-methylpyrrolidin-2-one and 4,4,4',4',5,5,5',5'-octamethyl-2,2'-bi(1,3,2-dioxaborolane) to afford the title compound (60% yield). LCMS: 336.3 (M+H)⁺.

Step 3: tert-butyl 4-(4-(3'-chloro-2-hydroxy-4'-(3-methyl-2-oxopyrrolidin-1-yl)-[1,1'-biphenyl]-3-yl)pyridin-2-yl)piperazine-1-carboxylate The title compound was prepared following the procedure described for Example 1 using 1-(2-chloro-4-(4,4,5,5-tetramethyl-1,3,2-dioxaborolan-2-yl)phenyl)-3-methylpyrrolidin-2-one and tert-butyl 4-(4-(3-bromo-2-hydroxyphenyl)pyridin-2-yl)piperazine-1-carboxylate to afford the title compound (59% yield). LCMS: 563.3 (M+H)⁺.

Step 4: 1-(3-chloro-2'-hydroxy-3'-(2-(piperazin-1-yl)pyridin-4-yl)-[1,1'-biphenyl]-4-yl)-3-methylpyrrolidin-2-one To a solution of tert-butyl 4-(4-(3'-chloro-2-hydroxy-4'-(3-methyl-2-oxopyrrolidin-1-yl)-[1,1'-biphenyl]-3-yl)pyridin-2-yl)piperazine-1-carboxylate (150 mg, 0.266 mmol) in DCM (2 mL) was added TFA (2 mL). Then the reaction mixture was stirred at rt for 4 h under N₂. After the reaction was complete by LCMS, the reaction mixture was concentrated. The residue was purified by prep-HPLC to afford the title compound (23.7 mg, 19% yield) as pale-yellow solid. ¹H NMR (400 MHz, DMSO-d₆): 8.14 (d, J=4.8 Hz, 1H), 7.70 (d, J=1.6 Hz, 1H), 7.54 (dd, J=8.4, 1.6 Hz, 1H), 7.45 (d, J=8.4 Hz, 1H), 7.30 (dd, J=10.4, 7.6 Hz, 2H), 7.05 (t, J=7.6 Hz, 1H), 6.89 (s, 1H), 6.78 (d, J=5.2 Hz, 1H), 3.70-3.61 (m, 2H), 3.45-3.43 (m, 4H), 2.80-2.78 (m, 4H), 2.63-2.57 (m, 1H), 2.43-2.35 (m, 1H), 1.83-1.78 (m, 1H), 1.18 (d, J=7.2 Hz, 3H). N—H or O—H protons not observed. LCMS: 463.2 (M+H)+.

Example 329

1-(3-chloro-2'-hydroxy-3'-(2-(piperazin-1-yl)pyridin-4-yl)-[1,1'-biphenyl]-4-yl)-3,3-dimethylpyrrolidin-2-one

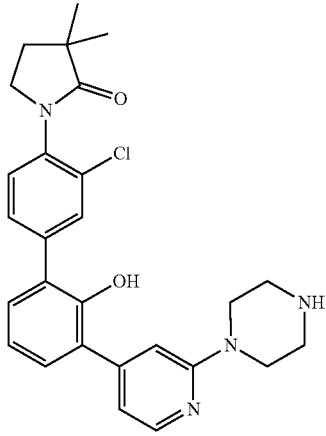 [SMILES: CC1(C)CCN(c2ccc(-c3cccc(-c4ccnc(N5CCNCC5)c4)c3O)cc2Cl)C1=O]

The title compound was prepared following the procedures described for Example 328 using tert-butyl 4-(4-(3'-chloro-4'-(3,3-dimethyl-2-oxopyrrolidin-1-yl)-2-hydroxy-[1,1'-biphenyl]-3-yl)pyridin-2-yl)piperazine-1-carboxylate to afford the title compound. $^1$H NMR (400 MHz, DMSO-$d_6$): 8.13 (d, J=5.2 Hz, 1H), 7.70 (d, J=1.2 Hz, 1H), 7.54 (dd, J=8.0, 1.6 Hz, 1H), 7.45 (d, J=8.4 Hz, 1H), 7.30 (dd, J=11.2, 7.2 Hz, 2H), 7.05 (t, J=7.6 Hz, 1H), 6.89 (s, 1H), 6.78 (d, J=4.8 Hz, 1H), 3.66 (t, J=7.2 Hz, 2H), 3.45-3.43 (m, 4H), 2.80-2.78 (m, 4H), 2.05 (d, J=6.4 Hz, 2H), 1.18 (s, 6H). N—H and O—H protons not observed. LCMS: 477.1 (M+H)+.

Example 330

N-(3"-chloro-2'-hydroxy-4"-(3-methyl-2-oxoimidazolidin-1-yl)-3-(piperazin-1-yl)-[1,1':3',1"-terphenyl]-4-yl)acetamide

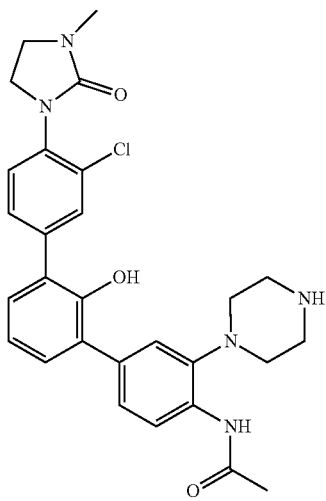 [SMILES: CC(=O)Nc1ccc(-c2cccc(-c3ccc(N4CCN(C)C4=O)c(Cl)c3)c2O)cc1N1CCNCC1]

Step 1: tert-butyl 4-(4-acetamido-3"-chloro-2'-methoxy-4"-(3-methyl-2-oxoimidazolidin-1-yl)-[1,1':3',1"-terphenyl]-3-yl)piperazine-1-carboxylate The title compound was prepared following the procedure described for Example 1 using tert-butyl 4-(2-acetamido-5-bromophenyl)piperazine-1-carboxylate and 1-(3-chloro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (82% yield). LCMS: 634.0 (M+H)+.

Step 2: N-(3"-chloro-2'-hydroxy-4"-(3-methyl-2-oxoimidazolidin-1-yl)-3-(piperazin-1-yl)-[1,1':3',1"-terphenyl]-4-yl)acetamide The title compound was prepared following the procedures described for Example 3 using tert-butyl 4-(4-acetamido-3"-chloro-2'-methoxy-4"-(3-methyl-2-oxoimidazolidin-1-yl)-[1,1':3',1"-terphenyl]-3-yl)piperazine-1-carboxylate and BBr$_3$ to afford the title compound. $^1$H NMR (400 MHz, DMSO-$d_6$): 8.83 (s, 1H), 7.96 (d, J=8.4 Hz, 1H), 7.67 (d, J=1.6 Hz, 1H), 7.51 (dd, J=8.4 Hz, 1.6 Hz, 1H), 7.44 (d, J=8.0 Hz, 1H), 7.27-7.20 (m, 4H), 7.03 (t, J=8.0 Hz, 1H), 3.73 (t, J=7.2 Hz, 2H), 3.49 (t, J=8.4 Hz, 2H) 2.91-2.89 (m, 4H), 2.78-2.76 (m, 7H), 2.14 (s, 3H). N—H or O—H protons not observed. LCMS: 520.2 (M+H)+.

Example 331

3"-chloro-2'-hydroxy-4"-(3-methyl-2-oxoimidazolidin-1-yl)-5-(piperazin-1-yl)-[1,1':3',1"-terphenyl]-3-carbonitrile

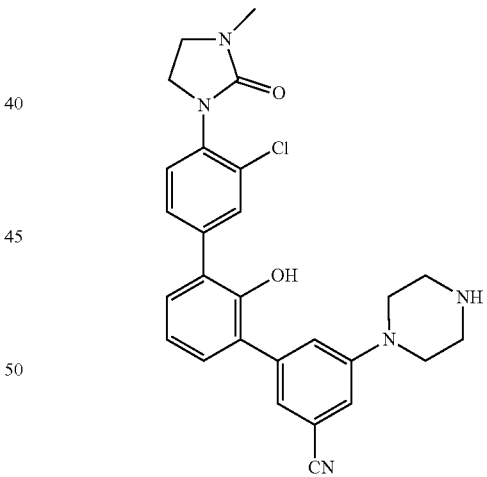

Step 1: tert-butyl 4-(3"-chloro-5-cyano-2'-methoxy-4"-(3-methyl-2-oxoimidazolidin-1-yl)-[1,1':3',1"-terphenyl]-3-yl)piperazine-1-carboxylate The title compound was prepared following the procedures described for Example 1 using 1-(3-chloro-2'-methoxy-3'-(4,4,5,5-tetramethyl-1,3,2-dioxaborolan-2-yl)-[1,1'-biphenyl]-4-yl)-3-methylimidazolidin-2-one and tert-butyl 4-(3-bromo-5-cyanophenyl)piperazine-1-carboxylate to afford the title compound (45% yield). LCMS: 602.2 (M+H)+.

Step 2: 3"-chloro-2'-hydroxy-4"-(3-methyl-2-oxo-imidazolidin-1-yl)-5-(piperazin-1-yl)-[1,1':3',1"-terphenyl]-3-carbonitrile The title compound was prepared following the procedures described for Example 3 using tert-butyl 4-(3"-chloro-5-cyano-2'-methoxy-4"-(3-methyl-2-oxoimidazolidin-1-yl)-[1,1':3',1"-terphenyl]-3-yl)piperazine-1-carboxylate and BBr$_3$ to afford the title compound (18% yield). $^1$H NMR (400 MHz, DMSO-d$_6$): 7.68 (d, J=2.0 Hz, 1H), 7.52 (dd, J=8.4, 2.0 Hz, 1H), 7.45 (d, J=8.4 Hz, 1H), 7.32-7.28 (m, 5H), 7.05 (t, J=7 Hz, 1H), 3.73 (t, J=7.2 Hz, 2H), 3.49 (t, J=7.6 Hz, 2H), 3.18-3.16 (m, 4H), 2.84-2.82 (m, 4H), 2.77 (s, 3H). N—H or O—H protons not observed. LCMS: 488.2 (M+H)$^+$.

Example 332

1-(3-chloro-2'-hydroxy-3'-(2-(piperazin-1-yl)pyridin-4-yl)-5'-(trifluoromethyl)-[1,1'-biphenyl]-4-yl)-3-methylimidazolidin-2-one

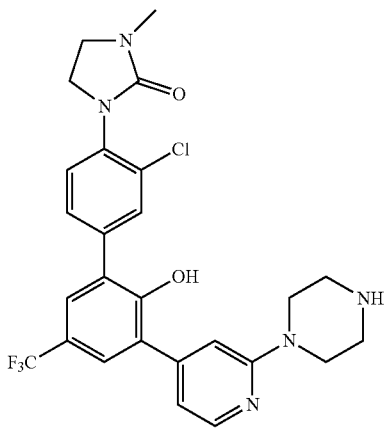 [SMILES: CN1CCN(c2ccc(-c3cc(C(F)(F)F)cc(-c4ccnc(N5CCNCC5)c4)c3O)cc2Cl)C1=O]

Step 1: 1-(3'-bromo-3-chloro-2'-methoxy-5'-(trifluoromethyl)-[1,1'-biphenyl]-4-yl)-3-methylimidazolidin-2-one The title compound was prepared following the procedures described for Example 1 using 1,3-dibromo-2-methoxy-5-(trifluoromethyl)benzene and 1-(2-chloro-4-(4,4,5,5-tetramethyl-1,3,2-dioxaborolan-2-yl)phenyl)-3-methylimidazolidin-2-one. LCMS: 463.0 (M+H)$^+$.

Step 2: tert-butyl 4-(4-(3'-chloro-2-methoxy-4'-(3-methyl-2-oxoimidazolidin-1-yl)-5-(trifluoromethyl)-[1,1'-biphenyl]-3-yl)pyridin-2-yl)piperazine-1-carboxylate The title compound was prepared following the procedures described for Example 1 using 1-(3'-bromo-3-chloro-2'-methoxy-5'-(trifluoromethyl)-[1,1'-biphenyl]-4-yl)-3-methylimidazolidin-2-one and tert-butyl 4-(4-(4,4,5,5-tetramethyl-1,3,2-dioxaborolan-2-yl)pyridin-2-yl)piperazine-1-carboxylate. LCMS: 646.2 (M+H)$^+$.

Step 3: 1-(3-chloro-2'-hydroxy-3'-(2-(piperazin-1-yl)pyridin-4-yl)-5'-(trifluoromethyl)-[1,1'-biphenyl]-4-yl)-3-methylimidazolidin-2-one The title compound was prepared following the procedures described for Example 3 using tert-butyl 4-(4-(3'-chloro-2-methoxy-4'-(3-methyl-2-oxoimidazolidin-1-yl)-5-(trifluoromethyl)-[1,1'-biphenyl]-3-yl)pyridin-2-yl)piperazine-1-carboxylate and BBr$_3$ to afford the title compound. $^1$H NMR (400 MHz, DMSO-d$_6$): 9.65 (s, 1H), 8.79 (br s, 2H), 8.23 (d, J=5.2 Hz, 1H), 7.73 (d, J=1.6 Hz, 1H), 7.64-7.59 (m, 2H), 7.57-7.54 (m, 1H), 7.50-7.48 (m, 1H), 7.09 (s, 1H), 6.96 (d, J=4.8 Hz, 1H), 3.78-3.72 (m, 6H), 3.52-3.48 (m, 2H), 3.21-3.20 (m, 4H), 2.78 (s, 3H). LCMS: 532.2 (M+H)$^+$.

Example 333

N-(3-fluoro-2'-hydroxy-3'-(2-((2-hydroxyethyl)amino)-6-(piperazin-1-yl)pyridin-4-yl)-[1,1'-biphenyl]-4-yl)acetamide

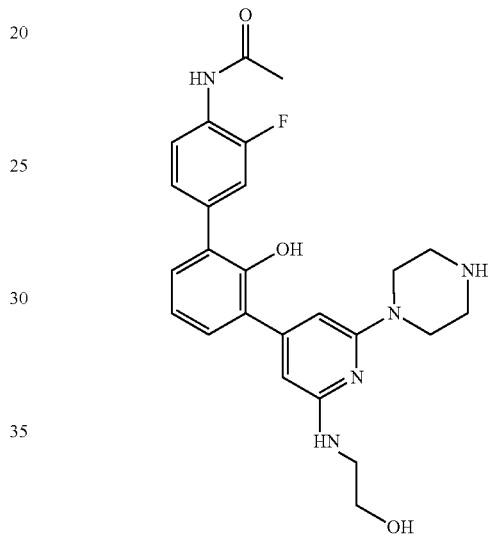

Step 1: tert-butyl 4-(6-((2-hydroxyethyl)amino)-4-iodopyridin-2-yl)piperazine-1-carboxylate A solution of tert-butyl 4-(6-fluoro-4-iodopyridin-2-yl)piperazine-1-carboxylate (407 mg, 1.00 mmol), 2-aminoethanol (610 mg, 10.0 mmol)) in EtOH (2 mL) was stirred at 90° C. for 2 days under nitrogen. After the reaction was complete by LCMS, the reaction mixture was cooled down to room temperature and concentrated. The residue was diluted with water (6 mL) and extracted with ethyl acetate (3 mL×4). The combined organic layers were washed with brine (5 mL), dried over sodium sulfate, filtered and concentrated to afford a residue which was purified by silica gel chromatography using petroleum ether and ethyl acetate as the eluent: (10:1 to 2:1) to afford the title compound as an orange solid. LCMS: 449.0 (M+H)$^+$.

Step 2: tert-butyl 4-(4-(4'-acetamido-3'-fluoro-2-methoxy-[1,1'-biphenyl]-3-yl)-6-((2-hydroxyethyl)amino)pyridin-2-yl)piperazine-1-carboxylate The title compound was prepared following the procedures described for Example 1 using tert-butyl 4-(6-((2-hydroxyethyl)amino)-4-iodopyridin-2-yl)piperazine-1-carboxylate and N-(3-fluoro-2'-methoxy-3'-(4,4,5,5- tetramethyl-1,3,2-dioxaborolan-2-yl)-[1,1'-biphenyl]-4-yl) acetamide (67% yield). LCMS: 580.2 (M+H)⁺.

Step 3: N-(3-fluoro-2'-hydroxy-3'-(2-((2-hydroxyethyl)amino)-6-(piperazin-1-yl)pyridin-4-yl)-[1,1'-biphenyl]-4-yl)acetamide The title compound was prepared following the procedure described for Example 3 using tert-butyl 4-(4-(4'-acetamido-3'-fluoro-2-methoxy-[1,1'-biphenyl]-3-yl)-6-((2-hydroxyethyl)amino)pyridin-2-yl)piperazine-1-carboxylate and BBr₃ to afford the title compound (3% yield). ¹H NMR (400 MHz, DMSO-d₆): 9.76 (s, 1H), 7.91 (t, J=8.4 Hz, 1H), 7.39 (d, J=12.4 Hz, 1H), 7.30-7.23 (m, 2H), 7.16 (d, J=7.2 Hz, 1H), 6.97 (t, J=7.6 Hz, 1H), 6.16 (t, J=6.4 Hz, 1H), 5.95 (d, J=16.0 Hz, 2H), 4.64 (t, J=6.4 Hz, 1H), 3.53 (t, J=5.2 Hz, 2H), 3.40-3.39 (m, 4H), 3.31-3.30 (m, 2H), 2.82-2.81 (m, 4H), 2.11 (s, 3H). N—H and O—H protons not observed. LCMS: 466.2 (M+H)⁺.

TABLE 23

Following compounds were prepared using similar procedures as described for Examples 163 or 328-333.

| Ex. No. | Name/Structure | ¹H NMR Data | LCMS (M + H)⁺ |
|---|---|---|---|
| 334 | 1-(3'-(5-(2,6-diazaspiro[3.3]heptan-2-yl)pyridin-3-yl)-3-fluoro-2'-hydroxy-[1,1'-biphenyl]-4-yl)-3-methylimidazolidin-2-one 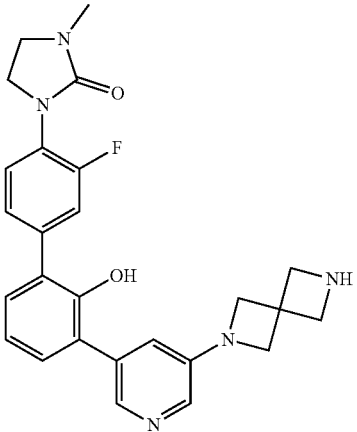 [SMILES: CN1CCN(c2ccc(-c3cccc(-c4cncc(N5CC6(CNC6)C5)c4)c3O)cc2F)C1=O] | ¹H NMR (400 MHz, DMSO-d₆): 8.05 (s, 1H), 7.78 (d, J = 2.4 Hz, 1H), 7.55-7.51 (m, 1H), 7.43 (d, J = 12.8 Hz, 1H), 7.35 (d, J = 8.4 Hz, 1H), 7.29 (d, J = 6.8 Hz, 1H), 7.24 (d, J = 7.6 Hz, 1H), 7.04 (t, J = 7.6 Hz, 1H), 6.93 (s, 1H), 4.02-3.97 (m, 4.5H), 3.81-3.77 (m, 2H), 3.64-3.63 (m, 3.5H), 3.50-3.46 (m, 2H), 2.77 (s, 3H). N—H and O—H protons not observed | 460.2 |
| 335 | 1-(3'-(5-(2,6-diazaspiro[3.3]heptan-2-yl)pyridin-3-yl)-3-chloro-2'-hydroxy-[1,1'-biphenyl]-4-yl)-3-methylimidazolidin-2-one 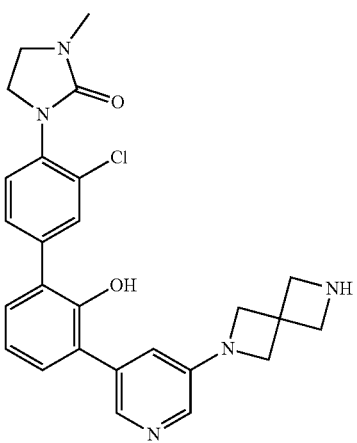 [SMILES: CN1CCN(c2ccc(-c3cccc(-c4cncc(N5CC6(CNC6)C5)c4)c3O)cc2Cl)C1=O] | ¹H NMR (400 MHz, DMSO-d₆): 8.05 (s, 1H), 7.78 (d, J = 2.0 Hz, 1H), 7.68 (s, 1H), 7.51 (d, J = 8.0 Hz, 1H), 7.44 (d, J = 8.0 Hz, 1H), 7.30-7.24 (m, 2H), 7.04 (t, J = 7.2 Hz, 1H), 6.93 (s, 1H), 4.00-3.97 (m, 4.5H), 3.74-3.70 (m, 2H), 3.63-3.62 (m, 3.5H), 3.51-3.47 (m, 2H), 2.77 (s, 3H). N—H and O—H protons not observed | 476.1 |
| 336 | N-(3-fluoro-2'-hydroxy-3''-(piperazin-1-yl)-4''-(trifluoromethyl)-[1,1':3',1''-terphenyl]-4-yl)acetamide acetate | ¹H NMR (TFA salt - 400 MHz, DMSO-d₆): 9.78 (s, 1H), 7.94-7.93 (m, 1H), 7.70 (d, J = 8.4 Hz, 1H), | 474.2 |

TABLE 23-continued

Following compounds were prepared using similar procedures as described for Examples 163 or 328-333.

| Ex. No. | Name/Structure | ¹H NMR Data | LCMS (M + H)⁺ |
|---|---|---|---|
| | | 7.62 (s, 1H), 7.48-7.41 (m, 2H), 7.33-7.28 (m, 3H), 7.08-7.04 (m, 1H), 2.84-2.83 (m, 8H), 2.11 (s, 3H), 1.90 (s, 3H). N—H and O—H protons not observed. | |
| 337 | 1-(3-chloro-2'-hydroxy-5'-methyl-3'-(2-methyl-6-(piperazin-1-yl)pyridin-4-yl)-[1,1'-biphenyl]-4-yl)-3-methylimidazolidin-2-one | ¹H NMR (400 MHz, DMSO-d₆): 7.65 (d, J = 2.0 Hz, 1H), 7.50 (dd, J = 8.4, 2.0 Hz, 1H), 7.42 (d, J = 8.0 Hz, 1H), 7.10 (d, J = 2.0 Hz, 1H), 7.06 (d, J = 2.0 Hz, 1H), 6.65 (s, 2H), 3.74-3.70 (m, 2H), 3.50-3.47 (m, 2H), 3.43-3.41 (m, 4H), 2.80-2.77 (m, 7H), 2.34 (s, 3H), 2.29 (s, 3H). N—H and O—H protons not observed | 492.2 |
| 338 | 1-(3-chloro-2'-hydroxy-3'-(2-methyl-6-(piperazin-1-yl)pyridin-4-yl)-[1,1'-biphenyl]-4-yl)-3-methylimidazolidin-2-one | ¹H NMR (400 MHz, DMSO-d₆): 7.66 (d, J = 1.6 Hz, 1H), 7.50 (dd, J = 8.0, 2.0 Hz, 1H), 7.44 (d, J = 8.0 Hz, 1H), 7.29 (dd, J = | 478.2 |

TABLE 23-continued

Following compounds were prepared using similar procedures as described for Examples 163 or 328-333.

| Ex. No. | Name/Structure | $^1$H NMR Data | LCMS $(M + H)^+$ |
|---|---|---|---|
| | | 7.6, 2.0 Hz, 1H), 7.24 (dd, J = 7.6, 2.0 Hz, 1H), 7.03 (t, J = 7.6 Hz, 1H), 6.65 (d, J = 2.8 Hz, 2H), 3.74-3.70 (m, 2H), 3.51-3.47 (m, 2H), 3.43-3.41 (m, 4H), 2.79-2.77 (m, 7H), 2.35 (s, 3H). N—H and O—H proton not observed | |
| 339 | N-(3-fluoro-2'-hydroxy-3'-(2-methoxy-6-(piperazin-1-yl)pyridin-4-yl)-[1,1'-biphenyl]-4-yl)acetamide | $^1$H NMR (400 MHz, DMSO-d$_6$): 9.77 (s, 1H), 7.91 (t, J = 8.4 Hz, 1H), 7.41 (dd, J = 12.0, 1.2 Hz, 1H), 7.31-7.26 (m, 2H), 7.22 (d, J = 7.6 Hz, 1H), 7.00 (t, J = 7.6 Hz, 1H), 6.38 (s, 1H), 6.15 (s, 1H), 3.81 (s, 3H), 3.43-3.41 (m, 4H), 2.80-2.77 (m, 4H), 2.11 (s, 3H). N—H and O—H protons not observed | 437.2 |
| 340 | 1-(3-chloro-2'-hydroxy-3'-(2-(piperazin-1-yl)pyridin-4-yl)-[1,1'-biphenyl]-4-yl)-4-methylpyrrolidin-2-one | $^1$H NMR (400 MHz, DMSO-d$_6$): 8.14 (d, J = 5.2 Hz, 1H), 7.70 (d, J = 1.6 Hz, 1H), 7.54 (dd, J = 8.0, 1.6 Hz, 1H), 7.45 (d, J = 8.0 Hz, 1H), 7.32-7.27 (m, 2H), 7.05 (t, J = 7.6 Hz, 1H), 6.89 (s, 1H), 6.79 (d, J = 4.8 Hz, 1H), 3.87-3.83 (m, 1H), 3.45-3.43 (m, 4H), 3.35-3.31 (m, 1H), 2.80-2.78 (m, 4H), 2.66-2.57 (m, 2H), 2.14-2.07 (m, 1H), 1.18 (d, J = 6.4 Hz, 3H). N—H and O—H protons not observed | 463.2 |

TABLE 23-continued

Following compounds were prepared using similar procedures as described for Examples 163 or 328-333.

| Ex. No. | Name/Structure | $^1$H NMR Data | LCMS (M + H)$^+$ |
|---|---|---|---|
| 341 | 5-(3-chloro-2'-hydroxy-3'-(2-(piperazin-1-yl)pyridin-4-yl)-[1,1'-biphenyl]-4-yl)-5-azaspiro[2.4]heptan-4-one | $^1$H NMR (400 MHz, DMSO-d$_6$): 8.14 (d, J = 5.2 Hz, 1H), 7.71 (d, J = 2.0 Hz, 1H), 7.54 (dd, J = 8.4, 2.0 Hz, 1H), 7.48 (d, J = 8.4 Hz, 1H), 7.33-7.27 (m, 2H), 7.07-7.03 (m, 1H), 6.89 (s, 1H), 6.79 (d, J = 5.2 Hz, 1H), 3.82 (t, J = 7.2 Hz, 2H), 3.45-3.43 (m, 4H), 2.80-2.77 (m, 4H), 2.30-2.27 (m, 2H), 0.98-0.87 (m, 4H). Two N—H or O—H proton not observed | 475.2 |

Example 342

5-(3'-chloro-2-hydroxy-4'-(3-methyl-2-oxoimidazolidin-1-yl)-[1,1'-biphenyl]-3-yl)-1-methyl-3-(piperazin-1-yl)pyridin-2(1H)-one

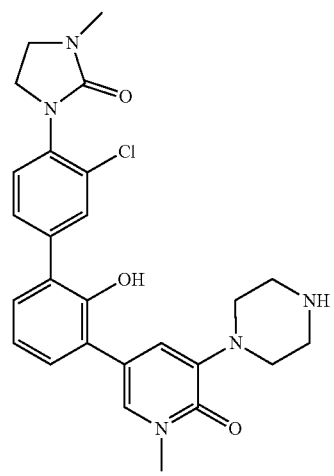

Step 1: tert-butyl 4-(5-bromo-1-methyl-2-oxo-1,2-dihydropyridin-3-yl)piperazine-1-carboxylate To a solution of 3,5-dibromo-1-methylpyridin-2(1H)-one (267 mg, 1.00 mmol) and tert-butyl piperazine-1-carboxylate (186 mg, 1.00 mmol) in dioxane (10 mL) was added Pd$_2$(dba)$_3$ (91.6 mg, 0.10 mmol), xantphos (116 mg, 0.20 mmol) and Cs$_2$CO$_3$ (652 mg, 2.00 mmol). After the addition, the reaction mixture was stirred at 110° C. under nitrogen atmosphere overnight. After the reaction was complete by LCMS, the reaction mixture was cooled, added DCM (100 mL) and filtered. The filtrate was concentrated to give a residue which was purified by silica gel chromatography using petroleum ether and ethyl acetate as the eluent (4:1) to afford the title compound (110 mg, 30% yield) as a yellow solid. LCMS: 372.1 (M+H)$^+$.

Step 2: tert-butyl 4-(5-(3'-chloro-2-methoxy-4'-(3-methyl-2-oxoimidazolidin-1-yl)-[1,1'-biphenyl]-3-yl)-1-methyl-2-oxo-1,2-dihydropyridin-3-yl)piperazine-1-carboxylate The title compound was prepared following the procedures described for Example 1 using (tert-butyl 4-(5-bromo-1-methyl-2-oxo-1,2-dihydropyridin-3-yl)piperazine-1-carboxylate and 1-(3-chloro-2'-methoxy-3'-(4,4,5,5-tetramethyl-1,3,2-dioxaborolan-2-yl)-[1,1'-biphenyl]-4-yl)-3-methylimidazolidin-2-one to afford the title compound. LCMS: 608.7 (M+H)$^+$.

Step 3: 5-(3'-chloro-2-hydroxy-4'-(3-methyl-2-oxoimidazolidin-1-yl)-[1,1'-biphenyl]-3-yl)-1-methyl-3-(piperazin-1-yl)pyridin-2(1H)-one The title compound was prepared following the procedures described for Example 3 using tert-butyl 4-(5-(3'-chloro-2-methoxy-4'-(3-methyl-2-oxoimidazolidin-1-yl)-[1,1'-biphenyl]-3-yl)-1-methyl-2-oxo-1,2-dihydropyridin-3-yl)piperazine-1-carboxylate and BBr$_3$ to afford the title compound (37% yield). $^1$H NMR (400 MHz, DMSO-d$_6$): 7.66 (d, J=2.0 Hz, 1H), 7.51-7.48 (m, 2H), 7.43 (d, J=8.4 Hz, 1H), 7.23 (d, J=7.6 Hz, 2H), 7.00 (t, J=7.6 Hz, 1H), 6.81 (d, J=2.0 Hz, 1H), 3.74-3.70 (m, 2H), 3.51-3.47 (m, 5H), 3.02-3.01 (m, 4H), 2.82-2.77 (m, 7H). Two N—H or O—H proton not observed. LCMS: 494.2 (M+H)$^+$

Example 343

1-(3-chloro-2'-hydroxy-3'-(6-(piperazin-1-yl)pyridazin-4-yl)-[1,1'-biphenyl]-4-yl)-3-methylimidazolidin-2-one

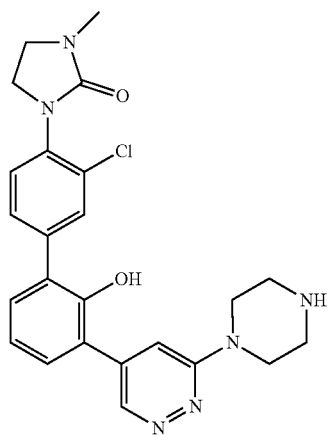 [SMILES: CN1CCN(c2ccc(-c3cccc(-c4cnnc(N5CCNCC5)c4)c3O)cc2Cl)C1=O]

Step 1: 1-(3-chloro-3'-(6-chloropyridazin-4-yl)-2'-methoxy-[1,1'-biphenyl]-4-yl)-3-methylimidazolidin-2-one The title compound was prepared following the procedures described for Example 1 using 5-bromo-3-chloropyridazine and 1-(3-chloro-2'-methoxy-3'-(4,4,5,5-tetramethyl-1,3,2-dioxaborolan-2-yl)-[1,1'-biphenyl]-4-yl)-3-methylimidazolidin-2-one to afford the title compound. LCMS: 429.3 (M+H)$^+$.

Step 2: tert-butyl 4-(5-(3'-chloro-2-methoxy-4'-(3-methyl-2-oxoimidazolidin-1-yl)-[1,1'-biphenyl]-3-yl)pyridazin-3-yl)piperazine-1-carboxylate The title compound was prepared following the procedures described for Example 163 using 1-(3-chloro-3'-(6-chloropyridazin-4-yl)-2'-methoxy-[1,1'-biphenyl]-4-yl)-3-methylimidazolidin-2-one and tert-butyl piperazine-1-carboxylate to afford the title compound. LCMS: 579.6 (M+H)$^+$.

Step 3: 1-(3-chloro-2'-hydroxy-3'-(6-(piperazin-1-yl)pyridazin-4-yl)-[1,1'-biphenyl]-4-yl)-3-methylimidazolidin-2-one The title compound was prepared following the procedures described for Example 3 using tert-butyl 4-(5-(3'-chloro-2-methoxy-4'-(3-methyl-2-oxoimidazolidin-1-yl)-[1,1'-biphenyl]-3-yl)pyridazin-3-yl)piperazine-1-carboxylate and BBr$_3$ to afford the title compound. $^1$H NMR (400 MHz, DMSO-d$_6$): 8.71 (d, J=2.0 Hz, 1H), 7.69 (d, J=1.6 Hz, 1H), 7.53-7.51 (m, 1H), 7.46-7.44 (m, 1H), 7.38-7.34 (m, 2H), 7.31 (s, 1H), 7.09-7.05 (m, 1H), 3.74-3.71 (m, 2H), 3.56-3.47 (m, 6H), 2.83-2.81 (m, 4H), 2.77 (m, 3H). N—H and O—H protons not observed. LCMS: 465.1 (M+H)$^+$.

TABLE 24

Following compounds were prepared using similar procedures as described for Examples 163 or 328-333.

| Ex. No. | Name/Structure | $^1$H NMR Data | LCMS (M + H)$^+$ |
|---|---|---|---|
| 344 | 1-(3-chloro-2'-hydroxy-3'-(2-phenyl-6-(piperazin-1-yl)pyridin-4-yl)-[1,1'-biphenyl]-4-yl)-3-methylimidazolidin-2-one | $^1$H NMR (400 MHz, DMSO-d$_6$): 8.07 (d, J = 7.6 Hz, 2H), 7.70 (d, J = 2.0 Hz, 1H), 7.55-7.52 (m, 1H), 7.48-7.44 (m, 3H), 7.41-7.32 (m, 4H), 7.07 (d, J = 7.2 Hz, 1H), 6.88 (s, 1H), 3.75-3.71 (m, 2H), 3.55-3.51 (m, 4H), 3.49-3.47 (m, 2H), 2.84-2.82 (m, 4H), 2.77 (m, 3H). N—H or O—H proton not observed | 540.2 |

TABLE 24-continued

Following compounds were prepared using similar procedures as described for Examples 163 or 328-333.

| Ex. No. | Name/Structure | $^1$H NMR Data | LCMS $(M + H)^+$ |
|---|---|---|---|
| 345 | 1-(3-chloro-2'-hydroxy-3'-(2-(piperazin-1-yl)pyridin-4-yl)-[1,1'-biphenyl]-4-yl)-3-ethylpyrrolidin-2-one | $^1$H NMR (400 MHz, DMSO-d$_6$): 8.14 (d, J = 4.4 Hz, 1H), 7.71-7.70 (m, 1H), 7.55-7.53 (m, 1H), 7.46-7.44 (m, 1H), 7.32-7.28 (m, 2H), 7.07-7.04 (m, 1H), 6.90 (s, 1H), 6.80-6.78 (m, 1H), 3.73-3.64 (m, 2H), 3.46-3.44 (m, 4H), 2.81-2.80 (m, 4H), 2.35-2.32 (m, 2H), 1.89-1.75 (m, 2H), 1.51-1.45 (m, 1H), 0.98 (t, J = 7.6 Hz, 3H). N—H or O—H proton not observed | 477.1 |
| 346 | 1-(3-chloro-2'-hydroxy-3'-(2-(piperazin-1-yl)pyridin-4-yl)-[1,1'-biphenyl]-4-yl)-3-ethylimidazolidin-2-one | $^1$H NMR (400 MHz, DMSO-d$_6$): 8.14 (d, J = 5.2 Hz, 1H), 7.67 (d, J = 2.0 Hz, 1H), 7.52-7.49 (m, 1H), 7.45 (d, J = 8.4 Hz, 1H), 7.31-7.27 (m, 2H), 7.07-7.03 (m, 1H), 6.89 (s, 1H), 6.79-6.78 (m, 1H), 3.75-3.71 (m, 2H), 3.52-3.50 (m, 2H), 3.48-3.43 (m, 4H), 3.25-3.19 (m, 2H), 2.80-2.79 (m, 4H), 1.10 (t, J = 7.2 Hz, 3H). N—H and O—H protons not observed | 478.2 |
| 347 | 1-(3'-(2-((2-aminoethyl)(methyl)amino)pyridin-4-yl)-3-chloro-5'-fluoro-2'-hydroxy-[1,1'-biphenyl]-4-yl)-3-methylimidazolidin-2-one | $^1$H NMR (400 MHz, DMSO-d$_6$): 8.09 (d, J = 4.8 Hz, 1H), 7.72 (d, J = 2.0 Hz, 1H), 7.56-7.53 (m, 1H), 7.45 (d, J = 8.4 Hz, 1H), 7.21-7.13 (m, 2H), | 470.1 |

TABLE 24-continued

Following compounds were prepared using similar procedures as described for Examples 163 or 328-333.

| Ex. No. | Name/Structure | ¹H NMR Data | LCMS (M + H)⁺ |
|---|---|---|---|
| | (structure) | 6.76-6.71 (m, 2H), 3.74-3.70 (m, 2H), 3.54-3.47 (m, 4H), 3.05 (s, 3H), 2.77-2.72 (m, 5H). N—H and O—H protons not observed | |
| 348 | N-(3'-(2-amino-6-(piperazin-1-yl)pyridin-4-yl)-3-fluoro-2'-hydroxy-[1,1'-biphenyl]-4-yl)acetamide | ¹H NMR (400 MHz, DMSO-d₆): 9.76 (s, 1H), 7.91 (d, J = 8.4 Hz, 1H), 7.41-7.37 (m, 1H), 7.30-7.28 (m, 1H), 7.25-7.23 (m, 1H), 7.17-7.15 (m, 1H), 6.99-6.95 (m, 1H), 6.95 (s, 1H), 5.98 (s, 1H), 5.57-5.56 (m, 2H), 3.34-3.31 (m, 4H), 2.76-2.75 (m, 4H), 2.11 (s, 3H). N—H and O—H protons not observed | 422.2 |
| 349 | 4-(4'-acetamido-3'-fluoro-2-hydroxy-[1,1'-biphenyl]-3-yl)-N-methyl-6-(piperazin-1-yl)picolinamide | ¹H NMR (400 MHz, DMSO-d₆): 9.78 (s, 1H), 8.48 (d, J = 4.8 Hz, 1H), 7.93 (t, J = 8.4 Hz, 1H), | 464.2 |

TABLE 24-continued

Following compounds were prepared using similar procedures as described for Examples 163 or 328-333.

| Ex. No. | Name/Structure | ¹H NMR Data | LCMS (M + H)⁺ |
|---|---|---|---|
| | | 7.45-7.41 (m, 2H), 7.32-7.28 (m, 3H), 7.04 (t, J = 7.6 Hz, 2H), 3.49-3.47 (m, 4H), 2.83-2.82 (m, 7H), 2.11 (s, 3H). N—H and O—H protons not observed | |
| 350 | 1-(3'-(2-(4-aminopiperidin-1-yl)pyridin-4-yl)-3-chloro-5'-fluoro-2'-hydroxy-[1,1'-biphenyl]-4-yl)-3-methylimidazolidin-2-one | ¹H NMR (400 MHz, DMSO-d₆): 8.12 (d, J = 4.2 Hz, 1H), 7.74 (d, J = 1.2 Hz, 1H), 7.54 (dd, J = 8.4, 2.0 Hz, 1H), 7.45 (d, J = 8.4 Hz, 1H), 7.20-7.14 (m, 2H), 6.98 (s, 1H), 6.78 (d, J = 5.2 Hz, 1H), 4.25-4.21 (m, 2H), 3.74-3.70 (m, 2H), 3.51-3.47 (m, 2H), 2.92-2.86 (m, 2H), 2.83-2.77 (m, 4H), 1.77-1.74 (m, 2H), 1.25-1.18 (m, 2H). N—H and O—H protons not observed | 496.2 |
| 351 | N-(3'-(2-cyclopropoxy-6-(piperazin-1-yl)pyridin-4-yl)-3-fluoro-2'-hydroxy-[1,1'-biphenyl]-4-yl)acetamide | ¹H NMR (400 MHz, DMSO-d₆): 9.78 (s, 1H), 7.93-7.91 (m, 1H), 7.43-7.40 (m, 1H), 7.31-7.22 | 463.3 |

TABLE 24-continued

Following compounds were prepared using similar procedures as described for Examples 163 or 328-333.

| Ex. No. | Name/Structure | $^1$H NMR Data | LCMS $(M + H)^+$ |
|---|---|---|---|
| | 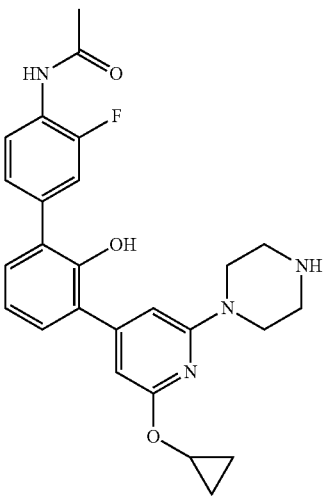 [SMILES: CC(=O)Nc1ccc(-c2cccc(-c3cc(OC4CC4)nc(N4CCNCC4)c3)c2O)cc1F] | (m, 3H), 7.02-7.01 (m, 1H), 6.45 (s, 1H), 6.24 (d, J = 4.8 Hz, 1H), 4.12-4.11 (m, 1H), 3.43-3.39 (m, 4H), 2.79-2.78 (m, 4H), 2.11 (s, 3H), 0.74-0.66 (m, 4H). N—H and O—H protons not observed | |
| 352 | 1-(3'-(2-(2,6-diazaspiro[3.3]heptan-2-yl)pyridin-4-yl)-3-chloro-5'-fluoro-2'-hydroxy-[1,1'-biphenyl]-4-yl)-3-methylimidazolidin-2-one | $^1$H NMR (400 MHz, DMSO-$d_6$): 8.09 (d, J = 4.8 Hz, 1H), 7.72 (d, J = 2.0 Hz, 1H), 7.54 (dd, J = 8.4, 2.0 Hz, 1H), 7.45 (d, J = 8.4 Hz, 1H), 7.22-7.13 (m, 2H), 6.83 (d, J = 5.2 Hz, 1H), 6.55 (s, 1H), 4.03-4.01 (m, 4H), 3.74-3.71 (m, 2H), 3.65-3.64 (m, 4H), 3.51-3.47 (m, 2H), 2.77 (s, 3H). N—H and O—H proton not observed | 494.2 |
| 353 | (S)-1-(3'-(2-(3-aminopyrrolidin-1-yl)pyridin-4-yl)-3-chloro-5'-fluoro-2'-hydroxy-[1,1'-biphenyl]-4-yl)-3-methylimidazolidin-2-one | $^1$H NMR (400 MHz, DMSO-$d_6$): 8.09 (d, J = 5.2 Hz, 1H), 7.71 (d, J = 1.2 Hz, 1H), 7.54 (dd, J = 8.4, 2.0 Hz, 1H), 7.46 (d, J = | 482.2 |

TABLE 24-continued

Following compounds were prepared using similar procedures as described for Examples 163 or 328-333.

| Ex. No. | Name/Structure | ¹H NMR Data | LCMS (M + H)⁺ |
|---|---|---|---|
| | | 8.0 Hz, 1H), 7.22-7.14 (m, 2H), 6.70 (d, J = 5.2 Hz, 1H), 6.55 (s, 1H), 3.75-3.71 (m, 2H), 3.57-3.41 (m, 6H), 3.10-3.09 (m, 1H), 2.77 (s, 3H), 2.07-2.03 (m, 1H), 1.73-1.69 (m, 1H). N—H and O—H protons not observed | |
| 354 | 1-(3-chloro-5'-fluoro-2'-hydroxy-3'-(2-(2-oxoimidazolidin-1-yl)pyridin-4-yl)-[1,1'-biphenyl]-4-yl)-3-methylimidazolidin-2-one | ¹H NMR (400 MHz, DMSO-d₆): 8.42-8.40 (m, 2H), 8.09-8.08 (m, 1H), 7.84-7.83 (m, 1H), 7.66 (d, J = 8.0 Hz, 1H), 7.25-7.23 (s, 1H), 7.05 (s, 1H), 6.98-6.88 (m, 2H), 4.00 (t, J = 8.0 Hz, 2H), 3.70-3.66 (m, 2H), 3.48-3.37 (m, 4H), 2.76 (s, 3H). N—H or O—H proton not observed | 482.2 |
| 355 | 1-(3-chloro-2'-hydroxy-3''-(hydroxymethyl)-5''-(piperazin-1-yl)-[1,1':3',1''-terphenyl]-4-yl)-3-methylimidazolidin-2-one | ¹H NMR (400 MHz, DMSO-d₆): 7.67 (d, J = 2.0 Hz, 1H), 7.51 (dd, J = 8.0, 1.6 Hz, 1H), 7.43 (d, J = 8.4 Hz, 1H), 7.25-7.20 (m, | 493.2 |

TABLE 24-continued

Following compounds were prepared using similar procedures as described for Examples 163 or 328-333.

| Ex. No. | Name/Structure | ¹H NMR Data | LCMS (M + H)⁺ |
|---|---|---|---|
| | 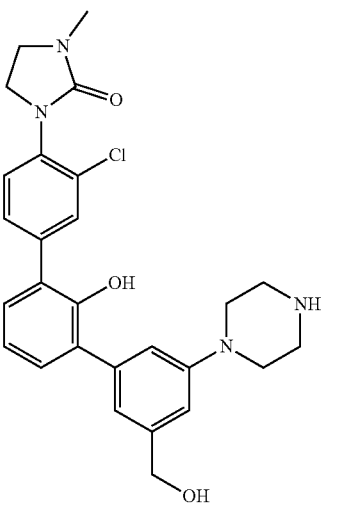 [SMILES: CN1CCN(c2ccc(-c3cccc(-c4cc(CO)cc(N5CCNCC5)c4)c3O)cc2Cl)C1=O] | 2H), 7.03-6.99 (m, 1H), 6.90-6.88 (m, 3H), 5.10 (brs, 1H), 4.49 (s, 2H), 3.74-3.70 (m, 2H), 3.50-3.47 (m, 2H), 3.09-3.06 (m, 4H), 2.85-2.83 (m, 4H), 2.77 (s, 3H). N—H and O—H protons not observed | |

Example 356

1-(3-chloro-2'-hydroxy-3'-(2-(piperazin-1-yl)pyridin-4-yl)-[1,1'-biphenyl]-4-yl)-3-methyl-1H-pyrrol-2(5H)-one

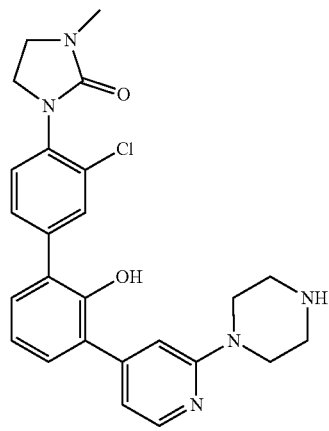 [SMILES: CN1CCN(c2ccc(-c3cccc(-c4ccnc(N5CCNCC5)c4)c3O)cc2Cl)C1=O]

Step 1: tert-butyl 4-(4-(3-bromo-2-methoxyphenyl)pyridin-2-yl)piperazine-1-carboxylate The title compound was prepared following the procedures described for Example 159 using tert-butyl 4-(4-(4,4,5,5-tetramethyl-1,3,2-dioxaborolan-2-yl)pyridin-2-yl)piperazine-1-carboxylate and 1,3-dibromo-2-methoxybenzene to afford the title compound. LCMS: 448.3 (M+H)⁺.

Step 2: tert-butyl 4-(4-(2-methoxy-3-(4,4,5,5-tetramethyl-1,3,2-dioxaborolan-2-yl)phenyl)pyridin-2-yl)piperazine-1-carboxylate The title compound was prepared following the procedures described for Example 159 using tert-butyl 4-(4-(3-bromo-2-methoxyphenyl)pyridin-2-yl)piperazine-1-carboxylate and 4,4,4',4',5,5,5',5'-octamethyl-2,2'-bi(1,3,2-dioxaborolane) to afford the title compound. LCMS: 496.6 (M+H)⁺.

Step 3: N-allyl-4-bromo-2-chloroaniline

To a solution of 4-bromo-2-chloroaniline (7.5 g, 36 mmol) and Na₂CO₃ (7.7 g, 72 mmol) in DMF (80 mL) was added 3-bromoprop-1-ene (6.60 g, 54.5 mmol). The reaction mixture was stirred at 80° C. for 16 h under N₂. After the reaction was complete by LCMS, the reaction was cooled to rt, filtered, water (400 mL) was added and extracted with PE (100 mL×3). The combined organic layers were washed with brine, dried over Na₂SO₄, filtered and concentrated. The residue was purified by silica gel chromatography using dichloromethane and methanol as the eluent: PE to afford the title compound (5.0 g, 56% yield, 50% purity) as colorless oil, which were used in the next step without further purification.

Step 4: N-allyl-N-(4-bromo-2-chlorophenyl)methacrylamide

To a solution of N-allyl-4-bromo-2-chloroaniline (1.0 g, 4.0 mmol) in DCM (20 mL) was added TEA (1.24 g, 12.3 mmol) and methacryloyl chloride (637 mg, 6.10 mmol) at 0° C. The reaction mixture was stirred at rt for 16 h under N₂. After the reaction was complete by LCMS, the reaction mixture was concentrated. The residue was purified by silica gel chromatography using dichloromethane and methanol as the eluent (5:1) to afford the title compound (750 mg, 59% yield) as colorless oil. LCMS: 314.1 (M+H)⁺.

Step 5: 1-(4-bromo-2-chlorophenyl)-3-methyl-1H-pyrrol-2(5H)-one

To a solution of N-allyl-N-(4-bromo-2-chlorophenyl)methacrylamide (750 mg, 2.4 mmol) in toluene (24 mL) was added 2$^{nd}$ generation Grubbs catalyst (101 mg, 0.120 mmol). The reaction mixture was stirred at 80° C. for 3 h under N$_2$. After the reaction was complete by LCMS, the reaction mixture was cooled and concentrated. The residue was purified by silica gel chromatography using dichloromethane and methanol as the eluent (3:1) to afford the title compound (630 mg, 92% yield) as a brown solid. LCMS: 286.1 (M+H)$^+$.

Step 6: tert-butyl 4-(4-(3'-chloro-2-methoxy-4'-(3-methyl-2-oxo-2,5-dihydro-1H-pyrrol-1-yl)-[1,1'-biphenyl]-3-yl)pyridin-2-yl)piperazine-1-carboxylate The title compound was prepared following the procedure described for Example 1 using 1-(4-bromo-2-chlorophenyl)-3-methyl-1H-pyrrol-2(5H)-one and tert-butyl 4-(4-(2-methoxy-3-(4,4,5,5-tetramethyl-1,3,2-dioxaborolan-2-yl) phenyl)pyridin-2-yl)piperazine-1-carboxylate to afford the title compound (20% yield). LCMS: 575.6 (M+H)$^+$.

Step 7: 1-(3-chloro-2'-hydroxy-3'-(2-(piperazin-1-yl)pyridin-4-yl)-[1,1'-biphenyl]-4-yl)-3-methyl-1H-pyrrol-2(5H)-one The title compound was prepared following the procedure described for Example 3 using tert-butyl 4-(4-(3'-chloro-2-methoxy-4'-(3-methyl-2-oxo-2,5-dihydro-1H-pyrrol-1-yl)-[1,1'-biphenyl]-3-yl)pyridin-2-yl)piperazine-1-carboxylate and BBr$_3$ to afford the title compound. $^1$H NMR (TFA salt—400 MHz, DMSO-d$_6$): 8.92-8.89 (m, 3H), 8.20 (d, J=5.6 Hz, 1H), 7.73 (d, J=1.6 Hz, 1H), 7.55-7.51 (m, 2H), 7.38-7.34 (m, 2H), 7.17-7.01 (m, 4H), 4.32-4.31 (m, 2H), 3.81-3.80 (m, 4H), 3.23-3.22 (m, 4H), 1.87 (d, J=1.2 Hz, 3H). LCMS: 461.2 (M+H)$^+$.

TABLE 25

Following compounds were prepared using similar procedures as described for Examples 163 or 328-333.

| Ex. No. | Name/Structure | $^1$H NMR Data | LCMS (M + H)$^+$ |
|---|---|---|---|
| 357 | 5-(3'-chloro-5-fluoro-2-hydroxy-4'-(3-methyl-2-oxoimidazolidin-1-yl)-[1,1'-biphenyl]-3-yl)-3-(piperazin-1-yl)picolinonitrile 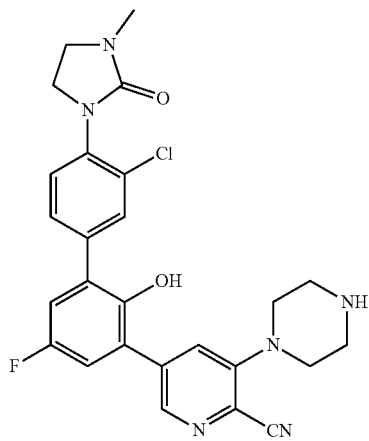 | $^1$H NMR (400 MHz, DMSO-d$_6$): 8.45 (d, J = 1.6 Hz, 1H), 7.74 (dd, J = 8.0, 1.6 Hz, 2H), 7.56 (dd, J = 8.4, 2.0 Hz, 1H), 7.47 (d, J = 8.4 Hz, 1H), 7.36-7.26 (m, 2H), 3.75-3.71 (m, 2H), 3.51-3.47 (m, 2H), 3.22-3.19 (m, 4H), 2.91-2.89 (m, 4H), 2.77 (s, 3H). N—H and O—H protons not observed | 507.2 |
| 358 | 1-(3-chloro-5'-fluoro-2'-hydroxy-4''-(hydroxymethyl)-3''-(piperazin-1-yl)-[1,1':3',1''-terphenyl]-4-yl)-3-methylimidazolidin-2-one | $^1$H NMR (400 MHz, DMSO-d$_6$): 7.71 (d, J = 1.6 Hz, 1H), 7.56-7.50 (m, 2H), 7.45 (d, J = 8.4 Hz, 1H), 7.26 (dd, J = 8.0, 1.6 | 511.2 |

TABLE 25-continued

Following compounds were prepared using similar procedures as described for Examples 163 or 328-333.

| Ex. No. | Name/Structure | ¹H NMR Data | LCMS (M + H)⁺ |
|---|---|---|---|
| | 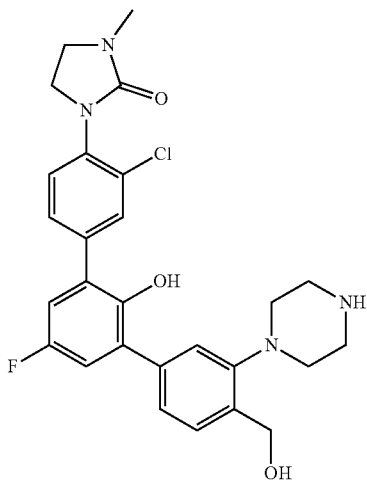 | Hz, 1H), 7.21-7.20 (m, 1H), 7.16-7.09 (m, 2H), 5.13 (s, 1H), 4.59-4.58 (m, 2H), 3.75-3.71 (m, 2H), 3.51-3.47 (m, 2H), 2.92-2.86 (m, 8H), 2.77 (s, 3H). N—H and O—H protons not observed | |
| 359 | (R)-1-(3-chloro-5'-fluoro-2'-hydroxy-3'-(2-(3-methylpiperazin-1-yl)pyridin-4-yl)-[1,1'-biphenyl]-4-yl)-3-methylimidazolidin-2-one 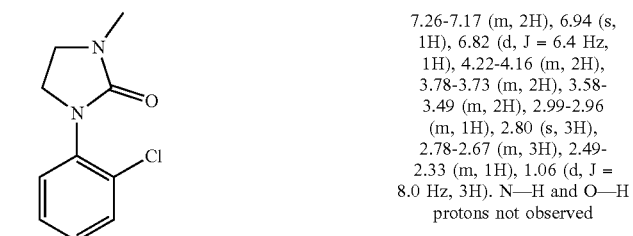 | ¹H NMR (400 MHz, DMSO-d₆): 8.16 (d, J = 6.8 Hz, 1H), 7.74 (d, J = 2.0 Hz, 1H), 7.59-7.55 (m, 1H), 7.50-7.47 (m, 1H), 7.26-7.17 (m, 2H), 6.94 (s, 1H), 6.82 (d, J = 6.4 Hz, 1H), 4.22-4.16 (m, 2H), 3.78-3.73 (m, 2H), 3.58-3.49 (m, 2H), 2.99-2.96 (m, 1H), 2.80 (s, 3H), 2.78-2.67 (m, 3H), 2.49-2.33 (m, 1H), 1.06 (d, J = 8.0 Hz, 3H). N—H and O—H protons not observed | 496.2 |
| 360 | (S)-1-(3'-(2-(3-aminopiperidin-1-yl)pyridin-4-yl)-3-chloro-5'-fluoro-2'-hydroxy-[1,1'-biphenyl]-4-yl)-3-methylimidazolidin-2-one | ¹H NMR (400 MHz, DMSO-d₆): 8.11 (d, J = 4.8 Hz, 1H), 7.72 (d, J = 2.0 Hz, 1H), 7.54 (dd, J = 8.0, 1.6 Hz, 1H), 7.45 (d, J = | 496.2 |

TABLE 25-continued

Following compounds were prepared using similar procedures as described for Examples 163 or 328-333.

| Ex. No. | Name/Structure | $^1$H NMR Data | LCMS (M + H)$^+$ |
|---|---|---|---|
| | 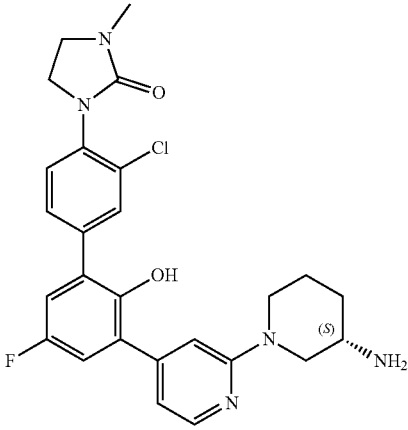 | 8.4 Hz, 1H), 7.22-7.14 (m, 2H), 6.93 (s, 1H), 6.76 (d, J = 5.2 Hz, 1H), 4.26-4.16 (m, 2H), 3.74-3.71 (m, 2H), 3.51-3.47 (m, 2H), 2.82-2.57 (m, 6H), 1.88-1.85 (m, 1H), 1.70-1.67 (m, 1H), 1.46-1.43 (m, 1H), 1.27-1.20 (m, 1H). N—H and O—H protons not observed | |
| 361 | N-(3-fluoro-2'-hydroxy-3'-(2-((4-hydroxycyclohexyl)oxy)-6-(piperazin-1-yl)pyridin-4-yl)-[1,1'-biphenyl]-4-yl)acetamide 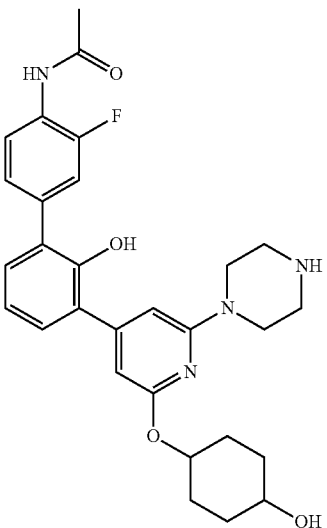 [SMILES: CC(=O)Nc1ccc(-c2cccc(-c3cc(OC4CCC(O)CC4)nc(N4CCNCC4)c3)c2O)cc1F] | $^1$H NMR (TFA salt - 400 MHz, DMSO-d$_6$): 9.80 (s, 1H), 8.92 (brs, 2H), 8.51 (s, 1H), 7.92 (t, J = 8.4 Hz, 1H), 7.43-7.24 (m, 4H), 7.17-7.00 (m, 1H), 6.50 (s, 1H), 6.26 (s, 1H), 4.99-4.97 (m, 1H), 3.72-3.69 (m, 4H), 3.63-3.61 (m, 2H), 3.20-3.19 (m, 4H), 2.11 (s, 3H), 1.91-1.87 (m, 2H), 1.67-1.60 (m, 6H) | 521.2 |
| 362 | (S)-1-(3'-(2-(3-aminopyrrolidin-1-yl)pyridin-4-yl)-3-chloro-2'-hydroxy-5'-methyl-[1,1'-biphenyl]-4-yl)-3-methylimidazolidin-2-one | $^1$H NMR (400 MHz, DMSO-d$_6$): 8.06 (d, J = 5.2 Hz, 1H), 7.65 (d, J = 2.0 Hz, 1H), 7.51-7.48 (m, 1H), 7.44-7.42 (m, 1H), | 478.2 |

TABLE 25-continued

Following compounds were prepared using similar procedures as described for Examples 163 or 328-333.

| Ex. No. | Name/Structure | $^1$H NMR Data | LCMS $(M + H)^+$ |
|---|---|---|---|
| | 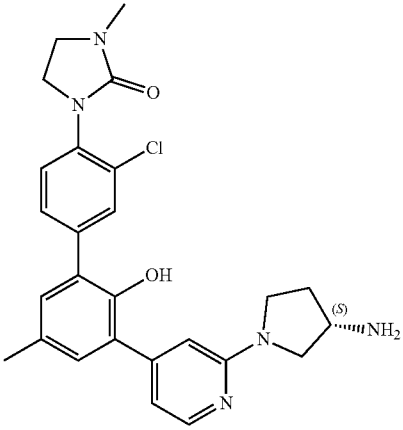 | 7.11-7.08 (m, 2H), 6.66 (dd, J = 1.2, 5.2 Hz, 1H), 6.50 (s, 1H), 3.74-3.70 (m, 2H), 3.58-3.46 (m, 5H), 3.43-3.37 (m, 1H), 3.11-3.06 (m, 1H), 2.77 (s, 3H), 2.29 (s, 3H), 2.07-2.03 (m, 1H), 1.73-1.68 (m, 1H). N—H and O—H protons not observed | |
| 363 | 1-(3'-(2-((2-aminoethyl)amino)pyridin-4-yl)-3-chloro-5'-fluoro-2'-hydroxy-[1,1'-biphenyl]-4-yl)-3-methylimidazolidin-2-one | $^1$H NMR (400 MHz, DMSO-d$_6$ + D$_2$O): 7.99 (d, J = 5.2 Hz, 1H), 7.72 (d, J = 2.0 Hz, 1H), 7.56-7.53 (m, 1H), 7.46-7.44 (m, 1H), 7.17 (dd, J = 3.2, 8.8 Hz, 1H), 7.10 (dd, J = 3.6, 9.2 Hz, 1H), 6.74-6.72 (m, 2H), 3.76-3.72 (m, 2H), 3.53-3.49 (m, 2H), 3.35-3.33 (m, 2H), 2.78 (s, 5H). N—H and O—H protons not observed | 456.1 |
| 364 | 1-(3-chloro-5'-fluoro-2'-hydroxy-3'-(2-(piperazin-1-yl)pyridin-4-yl)-[1,1'-biphenyl]-4-yl)-3-isopropylimidazolidin-2-one | $^1$H NMR (TFA salt - 400 MHz, DMSO-d$_6$): 8.14 (d, J = 5.2 Hz, 1H), 7.71 (d, J = 2.0 Hz, 1H), 7.54-7.52 (m, 1H), 7.47-7.44 (m, | 510.3 |

TABLE 25-continued

Following compounds were prepared using similar procedures as described for Examples 163 or 328-333.

| Ex. No. | Name/Structure | ¹H NMR Data | LCMS (M + H)⁺ |
|---|---|---|---|
| | 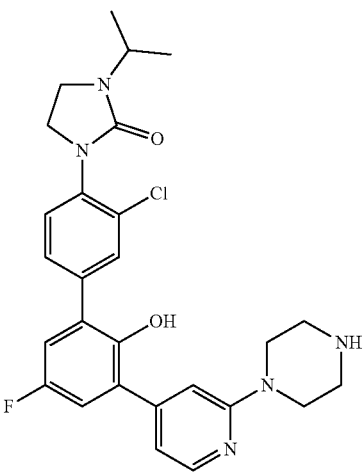 | 1H), 7.22-7.15 (m, 2H), 6.91 (s, 1H), 6.81 (dd, J = 0.8, 5.2 Hz, 1H), 4.04-3.97 (m, 1H), 3.74-3.70 (m, 2H), 3.46-3.40 (m, 6H), 2.80-2.78 (m, 4H), 1.13 (d, J = 6.8 Hz, 6H). N—H and O—H protons not observed | |

Example 365

1-(3-chloro-5'-fluoro-2'-hydroxy-3'-(2-(piperazin-1-yl)pyridin-4-yl)-[1,1'-biphenyl]-4-yl)-3-methyl-1H-imidazol-2(3H)-one

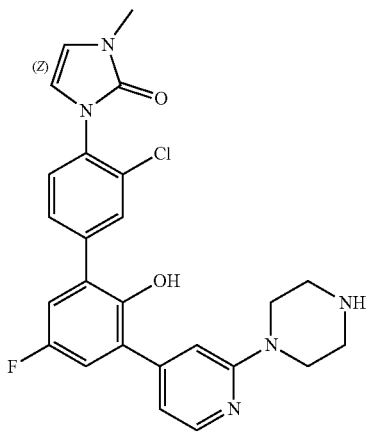

Step 1: 1-(4-bromo-2-chlorophenyl)-3-(2,2-dimethoxyethyl)urea

To a solution of 4-bromo-2-chloroaniline (10.0 g, 48.4 mmol) in THF (400 mL) was added TEA (40 mL, 0.29 mol) and bis(trichloromethyl) carbonate (7.20 g, 24.7 mmol) slowly at 0° C. under $N_2$. The reaction mixture was stirred at 0° C. for 3 hours. Then 2,2-dimethoxyethanamine (6.10 g, 0.0581 mol) was added at 0° C. The reaction mixture was stirred at r.t. overnight. Another four batches of parallel reactions were completed. The five batches were combined and concentrated together to afford the title compound (81.4 g, 100%) as a white solid. ¹H NMR (400 MHz, CDCl₃): 8.06 (d, J=8.8 Hz, 1H), 7.46 (d, J=2.4 Hz, 1H), 7.33 (dd, J=8.8, 2.4 Hz, 1H), 7.13 (br s, 1H), 5.18 (br s, 1H), 4.43 (t, J=4.8 Hz, 1H), 3.44-3.41 (m, 8H).

Step 2: 1-(4-bromo-2-chlorophenyl)-1H-imidazol-2(3H)-one

To a solution of 1-(4-bromo-2-chlorophenyl)-3-(2,2-dimethoxyethyl)urea (75 g, 0.222 mol) in MeOH (250 mL) was added H₂O (250 mL) and conc. aqueous HCl solution (1 L) subsequently. Then the mixture was stirred at r.t. for 16 h. The residue was adjusted to pH~9-11 by addition of aqueous NaOH solution, methanol was evaporated, and the residue was extracted with ethyl acetate (200 mL×3). The combined organic layers were washed with brine, dried over Na₂SO₄, filtered and concentrated to afford the title compound (56 g, 92.2% yield) as a pale-yellow solid. ¹H NMR (400 MHz, CDCl₃): 10.14 (br s, 1H), 7.69 (d, J=2.4 Hz, 1H), 7.50 (dd, J=8.4, 2.4 Hz, 1H), 7.35 (d, J=8.4 Hz, 1H), 6.42 (s, 1H), 6.38 (s, 1H).

Step 3: 1-(4-bromo-2-chlorophenyl)-3-methyl-1H-imidazol-2(3H)-one

To a solution of 1-(4-bromo-2-chlorophenyl)-1H-imidazol-2(3H)-one (69.4 g, 0.254 mol) in THF (650 mL) was added NaH (60%, 25.5 g, 0.638 mol) in portions at 0° C. under N₂. The reaction mixture was stirred at 0° C. for 1 hour. Then CH₃I (47.6 mL, 0.765 mol) was added at 0° C. The reaction mixture was stirred at r.t. overnight. H₂O (200 mL) was added and the mixture was extracted with ethyl acetate (200 mL×3). The combined organic layers were washed with brine and concentrated to afford the title compound (72.9 g, 99% yield) as a white solid. ¹H NMR (400 MHz, CDCl₃): 7.66 (d, J=2.4 Hz, 1H), 7.47 (dd, J=8.4, 2.4 Hz, 1H), 7.34 (d, J=8.4 Hz, 1H), 6.39 (d, J=3.2 Hz, 1H), 6.32 (d, J=3.2 Hz, 1H), 1.63 (s, 3H).

Step 4: tert-butyl 4-(4-(3-bromo-5-fluoro-2-methoxyphenyl)pyridin-2-yl) piperazine-1-carboxylate To a solution of tert-butyl 4-(4-(4,4,5,5-tetramethyl-1,3,2-dioxaborolan-2-yl)pyridin-2-yl)piperazine-1-carboxylate (3 g, 7.7 mmol, commercial) and 1,3-dibromo-5-fluoro-2-methoxybenzene (11 g, 38.6 mmol, commercial) in dioxane/$H_2O$ (8:1, 50 mL) was added $K_3PO_4$ (4.91 g, 23.2 mmol) and Pd(dppf)$Cl_2$ (1.13 g, 1.54 mmol) at rt under $N_2$. The reaction mixture was stirred at 110° C. for 4 hours under $N_2$. The reaction mixture was cooled and concentrated. The residue was purified by flash column chromatography using (PE:EA=5:1) on silica gel to afford the title compound (1.6 g, 45%) as a pale yellow solid. LCMS: 466/468 $(M+H)^+$.

Step 5: tert-butyl 4-(4-(3-bromo-5-fluoro-2-methoxyphenyl)pyridin-2-yl) piperazine-1-carboxylate A solution of tert-butyl 4-(4-(3-bromo-5-fluoro-2-methoxyphenyl)pyridin-2-yl) piperazine-1-carboxylate (1.6 g, 3.43 mmol), 4,4,4',4',5,5,5',5'-octamethyl-2,2'-bi (1,3,2-dioxaborolane) (1.29 g, 5.1 mmol), KOAc (1.01 g, 10.3 mmol) and Pd(dppf)$Cl_2$ (251 mg, 0.34 mmol) in dioxane (20 mL) was stirred at 90° C. under nitrogen atmosphere for 16 hours. The reaction mixture was concentrated and purified by silica gel chromatography using petroleum ether and ethyl acetate (5:1) as the eluent to afford the title compound (1.6 g, 91% yield) as a yellow solid. LCMS: 514 $(M+H)^+$.

Step 6: tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperazine-1-carboxylate To a solution of tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate (179 mg, 0.35 mmol) and 1-(4-bromo-2-chlorophenyl)-3-methyl-1H-imidazol-2(3H)-one (100 mg, 0.35 mmol) in dioxane/$H_2O$ (4:1, 10 mL) was added $K_3PO_4$ (221 mg, 1.04 mmol) and Pd(dppf)$Cl_2$ (51 mg, 0.07 mmol) at rt under $N_2$. The reaction mixture was stirred at 110° C. for 4 hours under $N_2$. The reaction mixture was cooled and concentrated. The residue was purified by flash column chromatography (100% EA) to afford the title compound (208 mg, 53%) as a pale-yellow solid. LCMS: 594.6 $(M+H)^+$.

Step 7: 1-(3-chloro-5'-fluoro-2'-hydroxy-3'-(2-(piperazin-1-yl)pyridin-4-yl)-[1,1'-biphenyl]-4-yl)-3-methyl-1H-imidazol-2(3H)-one To a solution of tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperazine-1-carboxylate (110 mg, 0.185 mol) in DCM (1 mL) was added $BBr_3$ (1M solution in DCM, 5 mL) at 0° C. under $N_2$. The reaction mixture was stirred at r.t. for 4 hours. Then, MeOH (5 mL) was added to quench the reaction. Then the mixture was concentrated under reduced pressure. The residue was purified by prep-HPLC to afford the title compound (88.9 mg, 30% yield) as a green solid. $^1$H NMR (400 MHz, DMSO-$d_6$): 8.14 (d, J=4.8 Hz, 1H), 7.81 (d, J=2.0 Hz, 1H), 7.62 (dd, J=8.4, 2.0 Hz, 1H), 7.52 (d, J=8.0 Hz 1H), 7.25-7.17 (m, 2H), 6.93 (s, 1H), 6.82 (dd, J=0.8, 5.2 Hz, 1H), 6.71 (d, J=2.8 Hz, 1H), 6.68 (d, J=2.8 Hz, 1H), 3.46-3.43 (m, 4H), 3.21 (s, 3H), 2.79-2.77 (m, 4H). LCMS: 480.2 $(M+H)^+$.

Example 366

1-(3-chloro-5'-fluoro-2'-hydroxy-3'-(2-(piperazin-1-yl)pyridin-4-yl)-[1,1'-biphenyl]-4-yl)-3-methyl-1,5-dihydro-2H-pyrrol-2-one

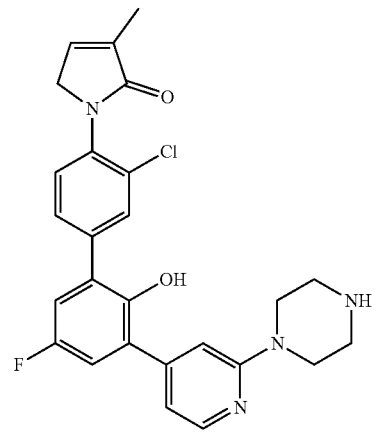

Step 1: tert-butyl 4-(4-(3'-chloro-5-fluoro-2-methoxy-4'-(3-methyl-2-oxo-2,5-dihydro-1H-pyrrol-1-yl)-[1,1'-biphenyl]-3-yl)pyridin-2-yl)piperazine-1-carboxylate The title compound was prepared following the procedures described for Example 365 using 1-(4-bromo-2-chlorophenyl)-3-methyl-1H-pyrrol-2(5H)-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (58% yield). LCMS: 593.6 $(M+H)^+$.

Step 2: 1-(3-chloro-5'-fluoro-2'-hydroxy-3'-(2-(piperazin-1-yl)pyridin-4-yl)-[1,1'-biphenyl]-4-yl)-3-methyl-1H-pyrrol-2(5H)-one 2,2,2-trifluoroacetate The title compound was prepared following the procedures described for Example 365 using tert-butyl 4-(4-(3'-chloro-5-fluoro-2-methoxy-4'-(3-methyl-2-oxo-2,5-dihydro-1H-pyrrol-1-yl)-[1,1'-biphenyl]-3-yl)pyridin-2-yl)piperazine-1-carboxylate and $BBr_3$ to afford the title compound (21% yield). $^1$H NMR (400 MHz, DMSO-$d_6$-TFA salt): 8.83-8.75 (m, 3H), 8.21 (d, J=5.2 Hz, 1H), 7.77 (d, J=2.0 Hz, 1H), 7.60-7.53 (m, 2H), 7.29-7.21 (m, 2H), 7.21-7.10 (m, 2H), 6.98 (d, J=5.2 Hz, 1H), 4.32-4.31 (m, 2H), 3.77-3.76 (m, 4H), 3.21 (s, 4H), 1.87-1.86 (m, 3H). LCMS: 479.2 $(M+H)^+$.

Example 367

1-(3-chloro-5'-fluoro-2'-hydroxy-3'-(2-(piperazin-1-yl)pyridin-4-yl)-[1,1'-biphenyl]-4-yl)-3-(prop-2-yn-1-yl)imidazolidin-2-one

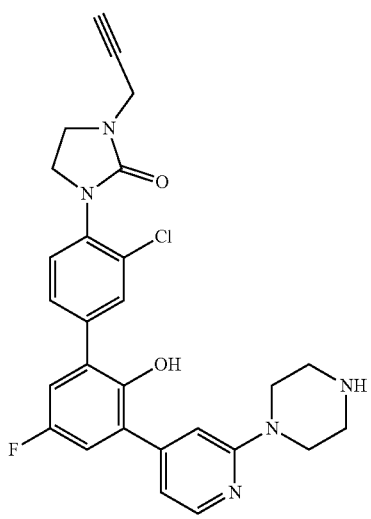 [SMILES: C#CCN1CCN(c2ccc(-c3cc(F)cc(-c4ccnc(N5CCNCC5)c4)c3O)cc2Cl)C1=O]

Step 1: tert-butyl 4-(4-(3'-chloro-5-fluoro-2-methoxy-4'-(2-oxoimidazolidin-1-yl)-[1,1'-biphenyl]-3-yl)pyridin-2-yl)piperazine-1-carboxylate The title compound was prepared following the procedures described for Example 365 using tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate and 1-(4-bromo-2-chlorophenyl)imidazolidin-2-one to afford the title compound (47% yield). LCMS: 582.6 (M+H)$^+$.

Step 2: tert-butyl 4-(4-(3'-chloro-5-fluoro-2-methoxy-4'-(2-oxo-3-(prop-2-yn-1-yl)imidazolidin-1-yl)-[1,1'-biphenyl]-3-yl)pyridin-2-yl)piperazine-1-carboxylate To a solution of tert-butyl 4-(4-(3'-chloro-5-fluoro-2-methoxy-4'-(2-oxoimidazolidin-1-yl)-[1,1'-biphenyl]-3-yl)pyridin-2-yl)piperazine-1-carboxylate (100 mg, 0.170 mmol) in THF (4 mL) was added NaH (17 mg, 0.43 mmol, 60% wt in mineral oil). After the reaction mixture was stirred at 0° C. under nitrogen atmosphere for 1 hour, the mixture was added 3-bromoprop-1-yne (61 mg, 0.52 mmol). After the addition complete, the reaction mixture was stirred at room temperature under nitrogen atmosphere overnight. After the reaction was indicated by LCMS, the reaction mixture was quenched with H$_2$O (10 mL) and extracted with EA (10 mL×3). The combined organic layers were washed with brine, dried over sodium sulfate, filtered and concentrated to afford the title compound (100 mg, 95% yield) as a brown solid. LCMS: 620.7 (M+H)$^+$.

Step 3: 1-(3-chloro-5'-fluoro-2'-hydroxy-3'-(2-(piperazin-1-yl)pyridin-4-yl)-[1,1'-biphenyl]-4-yl)-3-(prop-2-yn-1-yl)imidazolidin-2-one The title compound was prepared following the procedures described for Example 365 using tert-butyl 4-(4-(3'-chloro-5-fluoro-2-methoxy-4'-(2-oxo-3-(prop-2-yn-1-yl)imidazolidin-1-yl)-[1,1'-biphenyl]-3-yl)pyridin-2-yl)piperazine-1-carboxylate and BBr$_3$ to afford the title compound (11% yield). $^1$H NMR (400 MHz, DMSO-d$_6$-TFA salt): 8.85-8.72 (m, 3H), 8.21 (d, J=5.2 Hz, 1H), 7.73 (d, J=2.0 Hz, 1H), 7.57-7.54 (m, 1H), 7.51-7.48 (m, 1H), 7.26-7.20 (m, 2H), 7.09 (s, 1H), 6.98 (d, J=5.2 Hz, 1H), 4.04 (d, J=2.4 Hz, 2H), 3.77-3.75 (m, 6H), 3.57-3.53 (m, 2H), 3.30 (t, J=2.0 Hz, 1H), 3.20 (s, 4H). LCMS: 506.2 (M+H)$^+$.

Example 368

1-(3-chloro-3'-(2-cyclopropyl-6-(piperazin-1-yl)pyridin-4-yl)-2'-hydroxy-[1,1'-biphenyl]-4-yl)-3-methylimidazolidin-2-one

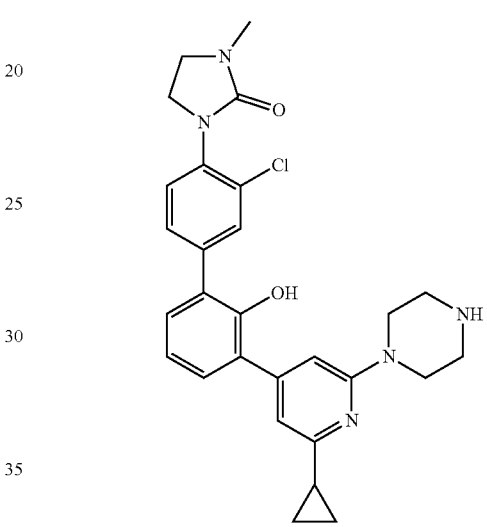

Step 1: tert-butyl 4-(6-chloro-4-(3'-chloro-2-methoxy-4'-(3-methyl-2-oxoimidazolidin-1-yl)-[1,1'-biphenyl]-3-yl)pyridin-2-yl)piperazine-1-carboxylate A solution of 1-(3-chloro-3'-(2,6-dichloropyridin-4-yl)-2'-methoxy-[1,1'-biphenyl]-4-yl)-3-methylimidazolidin-2-one (400 mg, 0.738 mmol) and tert-butyl piperazine-1-carboxylate (242 mg, 1.30 mmol) in DMSO (8 mL) in a sealed tube was degassed using a stream of nitrogen. Then the reaction mixture was stirred at 150° C. under microwave irradiation for 4 hours. After the reaction was complete by LCMS, the reaction mixture was cooled down to room temperature and filtered. The filtrate was concentrated to give a residue which was diluted with H$_2$O (16 mL), extracted with EA (5 mL×3). The combined organic layers were washed with brine, dried over sodium sulfate, filtered and concentrated. The residue was purified by silica gel chromatography using (10:1 to 2:1) petroleum ether and ethyl acetate as the eluent to afford the title compound (161 mg, 36% yield) as an earthy yellow solid. LCMS: 612.3 (M+H)$^+$.

Step 2: tert-butyl 4-(4-(3'-chloro-2-methoxy-4'-(3-methyl-2-oxoimidazolidin-1-yl)-[1,1'-biphenyl]-3-yl)-6-cyclopropylpyridin-2-yl)piperazine-1-carboxylate The title compound was prepared following the procedures described for Example 365 using tert-butyl 4-(6- chloro-4-(3'-chloro-2-methoxy-4'-(3-methyl-2-oxoimidazolidin-1-yl)-[1,1'-biphenyl]-3-yl)pyridin-2-yl)piperazine-1-carboxylate and cyclopropylboronic acid to afford the title compound (70% yield). LCMS: 618.2 (M+H)+.

Step 3: 1-(3-chloro-3'-(2-cyclopropyl-6-(piperazin-1-yl)pyridin-4-yl)-2'-hydroxy-[1,1'-biphenyl]-4-yl)-3-methylimidazolidin-2-one The title compound was prepared following the procedures described for Example 365 using tert-butyl 4-(4-(3'-chloro-2-methoxy-4'-(3-methyl-2-oxoimidazolidin-1-yl)-[1,1'-biphenyl]-3-yl)-6-cyclopropylpyridin-2-yl)piperazine-1-carboxylate and BBr$_3$ to afford the title compound (35% yield). $^1$H NMR (400 MHz, DMSO-d$_6$-TFA salt): 8.78 (s, 2H), 8.62 (s, 1H), 7.67 (d, J=1.6 Hz, 1H), 7.52-7.44 (m, 2H), 7.31 (dd, J=2.0, 7.6 Hz, 1H), 7.26 (dd, J=1.2, 7.2 Hz, 1H), 7.05 (t, J=7.6 Hz, 1H), 6.83 (s, 1H), 6.76 (s, 1H), 3.74-7.68 (m, 6H), 3.48 (t, J=8.0 Hz, 2H), 3.17 (s, 4H), 2.77 (s, 3H), 2.05-1.99 (m, 1H), 0.93-0.89 (m, 4H). LCMS: 504.2 (M+H)+.

Example 369

1-(3-chloro-2'-hydroxy-3'-(2,3,4,5-tetrahydro-1H-pyrido[4,3-b]indol-8-yl)-[1,1'-biphenyl]-4-yl)-3-methylimidazolidin-2-one

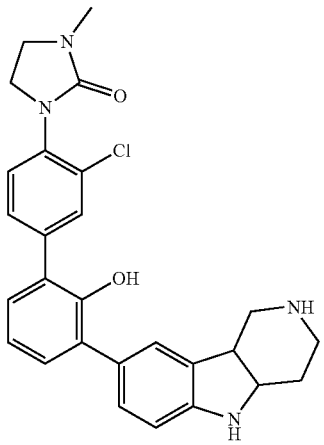 [SMILES: CN1CCN(c2ccc(-c3cccc(-c4ccc5c(c4)C4CNCCC4N5)c3O)cc2Cl)C1=O]

Step 1: tert-butyl 8-(3'-chloro-2-methoxy-4'-(3-methyl-2-oxoimidazolidin-1-yl)-[1,1'-biphenyl]-3-yl)-3,4-dihydro-1H-pyrido[4,3-b]indole-2(5H)-carboxylate The title compound was prepared following the procedure described for Example 342 using 1-(3-chloro-2'-methoxy-3'-(4,4,5,5-tetramethyl-1,3,2-dioxaborolan-2-yl)-[1,1'-biphenyl]-4-yl)-3-methylimidazolidin-2-one and tert-butyl 8-bromo-3,4-dihydro-1H-pyrido[4,3-b]indole-2(5H)— carboxylate to afford the title compound (60% yield). LCMS: 587.3 (M+H)+.

Step 2: 1-(3-chloro-2'-hydroxy-3'-(2,3,4,5-tetrahydro-1H-pyrido[4,3-b]indol-8-yl)-[1,1'-biphenyl]-4-yl)-3-methylimidazolidin-2-one The title compound was prepared following the procedure described for Example 342 using tert-butyl 8-(3'-chloro-2-methoxy-4'-(3-methyl-2-oxoimidazolidin-1-yl)-[1,1'-biphenyl]-3-yl)-3,4-dihydro-1H-pyrido[4,3-b]indole-2(5H)-carboxylate and BBr$_3$ to afford the title compound (3% yield). $^1$H NMR (400 MHz, DMSO-d$_6$): 10.76 (s, 1H), 7.68 (d, J=2.0 Hz, 1H), 7.54-7.51 (m, 1H), 7.44-7.42 (m, 2H), 7.32 (d, J=8.4 Hz, 1H), 7.22 (t, J=7.6 Hz, 2H), 7.15 (dd, J=1.2, 8.4 Hz, 1H), 7.00 (t, J=7.6 Hz, 1H), 3.89 (s, 2H), 3.74-3.70 (m, 2H), 3.48 (t, J=8.0 Hz, 2H), 3.05 (t, J=5.6 Hz, 2H), 2.77 (s, 3H), 2.72-2.67 (m, 2H). N—H and O—H protons not observed. LCMS: 473.3 (M+H)+.

Example 370

N-((5-(3'-chloro-5-fluoro-2-hydroxy-4'-(3-methyl-2-oxoimidazolidin-1-yl)-[1,1'-biphenyl]-3-yl)-3-(piperazin-1-yl)pyridin-2-yl)methyl)acetamide

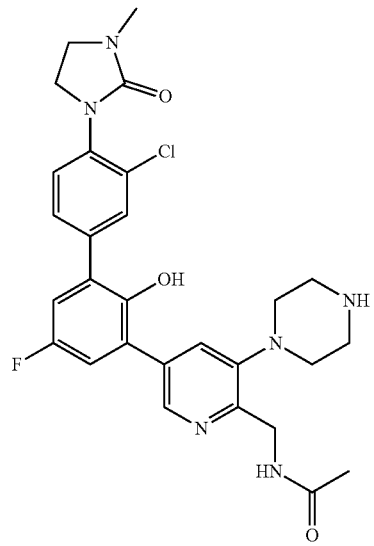 [SMILES: CC(=O)NCc1ncc(-c2cc(F)cc(-c3ccc(N4CCN(C)C4=O)c(Cl)c3)c2O)cc1N1CCNCC1]

Step 1: tert-butyl 4-(5-bromo-2-cyanopyridin-3-yl)piperazine-1-carboxylate

A mixture of 5-bromo-3-fluoropicolinonitrile (500 mg, 2.49 mmol), tert-butyl piperazine-1-carboxylate (1.39 g, 7.46 mmol) and K$_2$CO$_3$ (860 mg, 6.22 mmol) in Tol (30 mL) was stirred at 125° C. under nitrogen atmosphere for 12 hours. After the reaction was indicated by LCMS, the reaction mixture was cooled, added water (30 mL) and extracted with EA (20 mL×3). The combined organic layers were dried over sodium sulfate and filtered. The filtrate was concentrated, and the residue was purified by silica gel chromatography using (4:1) petroleum ether and ethyl acetate as the eluent to afford the title compound (630 mg, 69% yield) as a white solid. LCMS: 369.1 (M+H)+.

Step 2: tert-butyl 4-(2-cyano-5-(4,4,5,5-tetramethyl-1,3,2-dioxaborolan-2-yl)pyridin-3-yl)piperazine-1-carboxylate The title compound was prepared following the procedures described for Example 368 using tert-butyl 4-(5-bromo-2-cyanopyridin-3-yl)piperazine-1-carboxylate and 4,4,4',4',5,5,5',5'-octamethyl-2,2'-bi(1,3,2-dioxaborolane) to afford the title compound (86% yield). LCMS: 415.3 (M+H)+.

Step 3: tert-butyl 4-(5-(3'-chloro-5-fluoro-2-hydroxy-4'-(3-methyl-2-oxoimidazolidin-1-yl)-[1,1'-biphenyl]-3-yl)-2-cyanopyridin-3-yl)piperazine-1-carboxylate The title compound was prepared following the procedures described for Example 368 using tert-butyl 4-(2-cyano-5-(4,4,5,5-tetramethyl-1,3,2-dioxaborolan-2-yl)pyridin-3-yl)piperazine-1-carboxylate and 1-(3'-bromo-3-chloro-5'-fluoro-2'-hydroxy-[1,1'-biphenyl]-4-yl)-3-methylimidazolidin-2-one to afford the title compound (57% yield). LCMS: 607.3 (M+H)+.

Step 4: tert-butyl 4-(2-amino-5-(3'-chloro-5-fluoro-2-hydroxy-4'-(3-methyl-2-oxoimidazolidin-1-yl)-[1,1'-biphenyl]-3-yl)pyridin-3-yl)piperazine-1-carboxylate To a solution of tert-butyl 4-(5-(3'-chloro-5-fluoro-2-hydroxy-4'-(3-methyl-2-oxoimidazolidin-1-yl)-[1,1'-biphenyl]-3-yl)-2-cyanopyridin-3-yl)piperazine-1-carboxylate (500 mg, 2.49 mmol) in EtOH (30 mL) was added Raney-Ni (860 mg, 6.22 mmol). The reaction mixture was stirred at room temperature under H₂ atmosphere for 4 hours. After the reaction was complete by LCMS, the reaction mixture was filtered. The filtrate was concentrated to afford the title compound (60 mg, 50% yield) as a white solid. LCMS: 611.3 (M+H)+.

Step 5: tert-butyl 4-(2-(acetamidomethyl)-5-(3'-chloro-5-fluoro-2-hydroxy-4'-(3-methyl-2-oxoimidazolidin-1-yl)-[1,1'-biphenyl]-3-yl)pyridin-3-yl)piperazine-1-carboxylate To a solution of tert-butyl 4-(2-amino-5-(3'-chloro-5-fluoro-2-hydroxy-4'-(3-methyl-2-oxoimidazolidin-1-yl)-[1,1'-biphenyl]-3-yl)pyridin-3-yl)piperazine-1-carboxylate (60 mg, 0.098 mmol) in DCM (2 mL) was added TEA (15 mg, 0.15 mmol) and AcCl (7.7 mg, 0.098 mmol) dropwise. The reaction mixture was stirred at −78° C. for 30 min. After the reaction was complete by LCMS, the reaction mixture was added water (10 mL) and extracted with DCM (10 mL×3). The combined organic layers were dried over sodium sulfate and filtered. The filtrate was concentrated to afford a residue which was diluted with 3 mL of a mixture of THF:MeOH:H₂O (1:1:1) and added NaOH (40 mg, 1.0 mmol). After the mixture was stirred at room temperature for 1 hour, the mixture was adjusted pH to 7 with 1 M HCl. The mixture was extracted with EA (10 mL×3). The combined organic layers were dried over sodium sulfate and filtered. The filtrate was concentrated to afford the title compound (50 mg, 78% yield) as colorless oil. LCMS: 653.3 (M+H)+.

Step 6: N-((5-(3'-chloro-5-fluoro-2-hydroxy-4'-(3-methyl-2-oxoimidazolidin-1-yl)-[1,1'-biphenyl]-3-yl)-3-(piperazin-1-yl)pyridin-2-yl)methyl)acetamide The title compound was prepared following the procedure described for Example 368 using tert-butyl 4-(2-(acetamidomethyl)-5-(3'-chloro-5-fluoro-2-hydroxy-4'-(3-methyl-2-oxoimidazolidin-1-yl)-[1,1'-biphenyl]-3-yl)pyridin-3-yl)piperazine-1-carboxylate and TFA to afford the title compound (6% yield). ¹H NMR (400 MHz, DMSO-d₆): 8.42 (d, J=1.6 Hz, 1H), 8.15-8.13 (m, 1H), 7.72 (d, J=2.0 Hz, 1H), 7.62 (d, J=1.6 Hz, 1H), 7.56-7.54 (m, 1H), 7.47-7.45 (m, 1H), 7.24-7.19 (m, 2H), 4.47 (d, J=5.2 Hz, 2H), 3.72 (t, J=7.6 Hz, 2H), 3.49 (t, J=8.0 Hz, 2H), 2.88-2.86 (m, 8H), 2.77 (s, 3H), 1.89 (s, 3H). N—H and O—H protons not observed. LCMS: 553.3 (M+H)+.

Example 371

3-(3-chloro-5'-fluoro-2'-hydroxy-3'-(2-(piperazin-1-yl)pyridin-4-yl)-[1,1'-biphenyl]-4-yl)oxazolidin-2-one

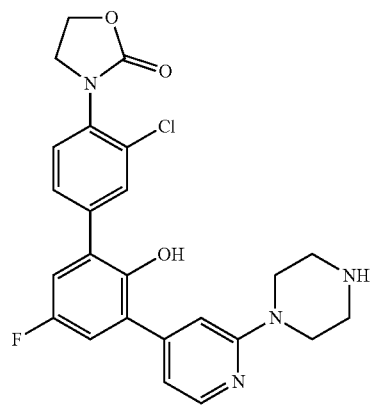

Step 1: 3-(4-bromo-2-chlorophenyl)oxazolidin-2-one

To a solution of 4-bromo-2-chloroaniline (1.00 g, 4.84 mmol) in MeOH (20 mL) was added 2-chloroethyl carbonochloridate (692 mg, 4.84 mmol) and KOH (679 mg, 12.1 mmol). After the addition, the reaction mixture was stirred at room temperature under nitrogen atmosphere for 12 hours. After the reaction was complete by LCMS, the reaction mixture was filtered and concentrated, dilute with H₂O (50 mL) and extracted with EA (10 mL×3). The combined organic layers were washed with brine, dried over sodium sulfate and filtered. The filtrate was concentrated, and the residue was purified by silica gel chromatography using (3:1) petroleum ether and ethyl acetate as the eluent to afford the title compound (1.0 g, 76% yield) as a white solid. LCMS: 275.9 (M+H)+.

Step 2: tert-butyl 4-(4-(3'-chloro-5-fluoro-2-methoxy-4'-(2-oxooxazolidin-3-yl)-[1,1'-biphenyl]-3-yl)pyridin-2-yl)piperazine-1-carboxylate The title compound was prepared following the procedure described for Example 365 using 3-(4-bromo-2-chlorophenyl)oxazolidin-2-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (66% yield). LCMS: 583.2 (M+H)+.

Step 3: 3-(3-chloro-5'-fluoro-2'-hydroxy-3'-(2-(piperazin-1-yl)pyridin-4-yl)-[1,1'-biphenyl]-4-yl)oxazolidin-2-one The title compound was prepared following the procedures described for Example 368 using tert-butyl 4-(4-(3'- chloro-5-fluoro-2-methoxy-4'-(2-oxooxazolidin-3-yl)-[1,1'-biphenyl]-3-yl)pyridin-2-yl)piperazine-1-carboxylate and BBr$_3$ to afford the title compound (32% yield). $^1$H NMR (400 MHz, DMSO-d$_6$): 8.18 (d, J=6.8 Hz, 1H), 7.81 (s, 1H), 7.67-7.61 (m, 2H), 7.28-7.19 (m, 2H), 6.95 (s, 1H), 6.85 (d, J=6.8 Hz, 1H), 4.55 (t, J=9.6 Hz, 2H), 4.02 (t, J=10.8 Hz, 2H), 3.50-3.46 (m, 4H), 2.84-2.81 (m, 4H). N—H and O—H protons not observed. LCMS: 469.2 (M+H)$^+$.

Example 372

5-(3'-chloro-5-fluoro-2-hydroxy-4'-(3-methyl-2-oxo-imidazolidin-1-yl)-[1,1'-biphenyl]-3-yl)-1-methyl-3-(piperazin-1-yl)pyridin-2(1H)-one

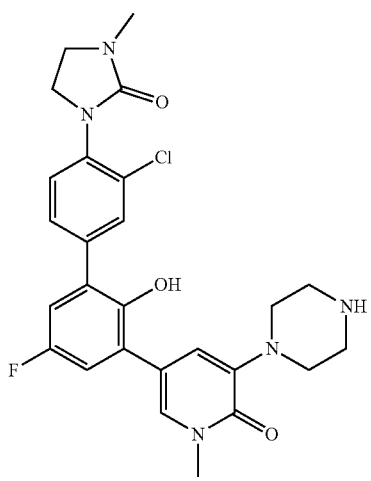

Step 1: tert-butyl 4-(5-bromo-1-methyl-2-oxo-1,2-dihydropyridin-3-yl)piperazine-1-carboxylate To a solution of 3,5-dibromo-1-methylpyridin-2(1H)-one (267 mg, 1.00 mmol) and tert-butyl piperazine-1-carboxylate (186 mg, 1.0.0 mmol) in dioxane (10 mL) was added Cs$_2$CO$_3$ (652 mg, 2.00 mmol), Pd$_2$(dba)$_3$ (91.6 mg, 0.100 mmol) and xantphos (116 mg, 0.200 mmol). After the addition, the reaction mixture was stirred at 110° C. in a steal tube under nitrogen atmosphere overnight. After the reaction was complete by LCMS, the reaction mixture was cooled and filtered. The filtrate was concentrated to give a residue which was purified by silica gel chromatography using (4:1) petroleum ether and ethyl acetate as the eluent to afford the title compound afford the title compound (110 mg, 29% yield) as a yellow solid. LCMS: 316.2 (M−56+H)$^+$.

Step 2: tert-butyl 4-(5-(3'-chloro-5-fluoro-2-methoxy-4'-(3-methyl-2-oxoimidazolidin-1-yl)-[1,1'-biphenyl]-3-yl)-1-methyl-2-oxo-1,2-dihydropyridin-3-yl)piperazine-1-carboxylate The title compound was prepared following the procedure described for Example 342 using tert-butyl 4-(5-bromo-1-methyl-2-oxo-1,2-dihydropyridin-3-yl)piperazine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (59% yield). LCMS: 626.7 (M+H)$^+$.

Step 3: 5-(3'-chloro-5-fluoro-2-hydroxy-4'-(3-methyl-2-oxoimidazolidin-1-yl)-[1,1'-biphenyl]-3-yl)-1-methyl-3-(piperazin-1-yl)pyridin-2(1H)-one The title compound was prepared following the procedure described for Example 342 using tert-butyl 4-(5-(3'-chloro-5-fluoro-2-methoxy-4'-(3-methyl-2-oxoimidazolidin-1-yl)-[1,1'-biphenyl]-3-yl)-1-methyl-2-oxo-1,2-dihydropyridin-3-yl)piperazine-1-carboxylate and BBr$_3$ to afford the title compound (49% yield). $^1$H NMR (400 MHz, DMSO-d$_6$): 7.71 (d, J=2.0 Hz, 1H), 7.56-7.51 (m, 2H), 7.44 (d, J=8.0 Hz, 1H), 7.14-7.10 (m, 2H), 6.85 (d, J=2.0 Hz, 1H), 3.74-3.70 (m, 2H), 3.50-3.47 (m, 5H), 3.01 (s, 4H), 2.81-2.78 (m, 7H). N—H and O—H protons not observed. LCMS: 512.3 (M+H)$^+$.

Example 373

1-(3-chloro-5'-fluoro-2'-hydroxy-3'-(2-(piperazin-1-yl)pyridin-4-yl)-[1,1'-biphenyl]-4-yl)imidazolidin-2-one

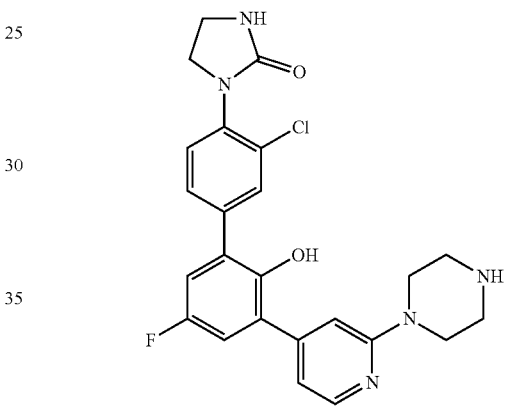

Step 1: 1-(4-bromo-2-chlorophenyl)-3-(2-chloroethyl)urea

A mixture of 4-bromo-2-chloroaniline (8.26 g, 40.1 mmol), 1-chloro-2-isocyanatoethane (5.49 g, 52.0 mmol) in DCM (200 mL) was stirred at room temperature under nitrogen atmosphere overnight. After the reaction was complete by LCMS, the solvent was removed to give a residue, which was treated with toluene (50 mL), filtered, the cake was dried to afford the title compound (11.0 g, 88% yield) as a gray solid. LCMS: 311.1 (M+H)$^+$.

Step 2: 1-(4-bromo-2-chlorophenyl)imidazolidin-2-one

To a solution of 1-(4-bromo-2-chlorophenyl)-3-(2-chloroethyl)urea (5.00 g, 16.0 mmol) in THF (75 mL) was added NaH (961 mg, 24.0 mmol, 60% wt in mineral oil). After the addition, the reaction mixture was stirred at room temperature under nitrogen atmosphere for 2 hours. After the reaction was indicated by LCMS, the reaction mixture was quenched with H$_2$O (110 mL) and extracted with DCM (30 mL×3). The combined organic layers were washed with brine, dried over sodium sulfate, filtered and concentrated to afford the title compound (4.2 g, 95% yield) as a pink solid. LCMS: 275.0 (M+H)$^+$.

Step 3: 1-acetyl-3-(4-bromo-2-chlorophenyl)imidazolidin-2-one

To a solution of 1-(4-bromo-2-chlorophenyl)imidazolidin-2-one (500 mg, 1.81 mmol) in Ac$_2$O (10 mL). The reaction mixture was stirred at 130° C. overnight. The reaction mixture was cooled, the solvent was removed, and the residue was diluted with H$_2$O (30 mL), adjusted pH to 9-11 with sat. K$_2$CO$_3$ aqueous and extracted with EA (30 mL×3), the combined organic layers were washed with brine, dried over sodium sulfate, filtered and concentrated to afford the title compound (550 mg, 96% yield) as a brown solid. LCMS: 317.1 (M+H)$^+$.

Step 4: tert-butyl 4-(4-(4'-(3-acetyl-2-oxoimidazolidin-1-yl)-3'-chloro-5-fluoro-2-methoxy-[1,1'-biphenyl]-3-yl)pyridin-2-yl)piperazine-1-carboxylate The title compound was prepared following the procedures described for Example 365 using 1-acetyl-3-(4-bromo-2-chlorophenyl)imidazolidin-2-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (42% yield). LCMS: 624.6 (M+H)$^+$.

Step 5: 1-(3-chloro-5'-fluoro-2'-hydroxy-3'-(2-(piperazin-1-yl)pyridin-4-yl)-[1,1'-biphenyl]-4-yl)imidazolidin-2-one The title compound was prepared following the procedures described for Example 365 using tert-butyl 4-(4-(4'-(3-acetyl-2-oxoimidazolidin-1-yl)-3'-chloro-5-fluoro-2-methoxy-[1,1'-biphenyl]-3-yl)pyridin-2-yl)piperazine-1-carboxylate and BBr$_3$ to afford the title compound (30% yield). $^1$H NMR (400 MHz, DMSO-d$_6$): 8.14 (d, J=5.2 Hz, 1H), 7.71 (d, J=2.0 Hz, 1H), 7.53 (dd, J=2.0, 8.0 Hz, 1H), 7.46 (d, J=8.4 Hz, 1H), 7.21-7.15 (m, 2H), 6.91 (s, 1H), 6.84 (s, 1H), 6.81 (d, J=5.2 Hz, 1H), 3.80 (t, J=7.2 Hz, 2H), 3.48-3.43 (m, 6H), 2.79-2.77 (m, 4H). N—H and O—H protons not observed. LCMS: 468.2 (M+H)$^+$.

Example 374

1-(3-chloro-3'-(2-ethyl-6-(piperazin-1-yl)pyridin-4-yl)-2'-hydroxy-[1,1'-biphenyl]-4-yl)-3-methylimidazolidin-2-one

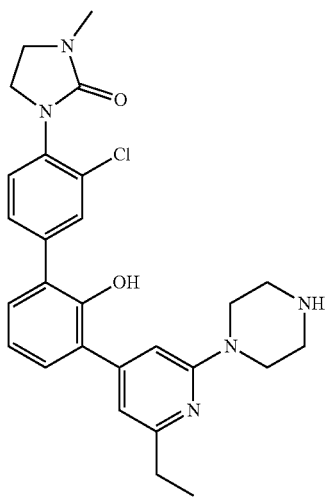 [SMILES: CCc1cc(-c2cccc(-c3ccc(N4CCN(C)C4=O)c(Cl)c3)c2O)cc(N2CCNCC2)n1]

The title compound was prepared following the procedures described for Example 368 using tert-butyl 4-(6-chloro-4-(3'-chloro-2-methoxy-4'-(3-methyl-2-oxoimidazolidin-1-yl)-[1,1'-biphenyl]-3-yl)pyridin-2-yl)piperazine-1-carboxylate and ethylboronic acid to afford the title compound. $^1$H NMR (400 MHz, DMSO-d$_6$): 8.79-8.64 (m, 3H), 7.67 (d, J=2.0 Hz, 1H), 7.51-7.44 (m, 2H), 7.33-7.26 (m, 2H), 7.05 (t, J=7.6 Hz, 1H), 6.86 (s, 1H), 6.80 (s, 1H), 3.75-3.70 (m, 6H), 3.49 (t, J=6.0 Hz, 2H), 3.20 (s, 4H), 2.77 (s, 3H), 2.70-2.64 (m, 2H), 1.24 (t, J=7.6 Hz, 3H). LCMS: 492.2 (M+H)$^+$.

Example 375

N-(3'-(2-((4-aminocyclohexyl)oxy)-6-(piperazin-1-yl)pyridin-4-yl)-3-fluoro-2'-hydroxy-[1,1'-biphenyl]-4-yl)acetamide

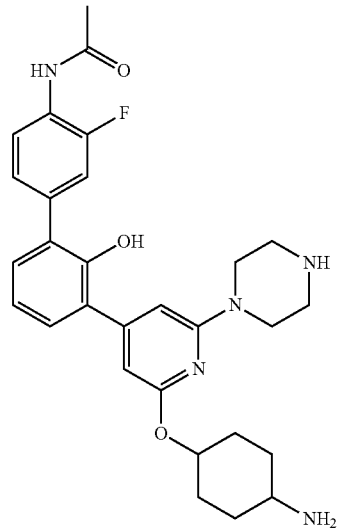 [SMILES: CC(=O)Nc1ccc(-c2cccc(-c3cc(OC4CCC(N)CC4)nc(N4CCNCC4)c3)c2O)cc1F]

Step 1: tert-butyl 4-(6-((4-((tert-butoxycarbonyl)amino)cyclohexyl)oxy)-4-iodopyridin-2-yl)piperazine-1-carboxylate To a suspension of tert-butyl (4-hydroxycyclohexyl)carbamate (951 mg, 4.42 mmol) in dioxane (20 mL) was added NaH (183 mg, 4.57 mmol, 60% in mineral oil) in portion. Then the reaction mixture was stirred at rt for 15 min under nitrogen. Then, a solution of tert-butyl 4-(6-fluoro-4-iodopyridin-2-yl)piperazine-1-carboxylate (600 mg, 1.47 mmol) was added in dioxane (5 mL). The reaction mixture was stirred at 100° C. for 6 hours under nitrogen. After the reaction was complete by LCMS, the reaction mixture was cooled, added water (40 mL) and extracted with ethyl acetate (10 mL×3). The combined organic layers were dried over sodium sulfate, filtered and concentrated. The residue was purified by silica gel chromatography using (50:1) petroleum ether/ethyl acetate and (1:1) dichloromethane/methanol as the eluent to afford the title compound (55 mg, 5% yield) as a white solid. LCMS: 603.2 (M+H)$^+$.

Step 2: tert-butyl 4-(4-(4'-acetamido-3'-fluoro-2-methoxy-[1,1'-biphenyl]-3-yl)-6-((4-((tert-butoxycarbonyl)amino)cyclohexyl)oxy)pyridin-2-yl)piperazine-1-carboxylate The title compound was prepared following the procedure described for Example 163 using tert-butyl 4-(6-((4-((tert-butoxycarbonyl)amino)cyclohexyl)oxy)-4-iodopyridin-2-yl)piperazine-1-carboxylate and N-(3-fluoro-2'-methoxy-3'-(4,4,5,5-tetramethyl-1,3,2-dioxaborolan-2-yl)-[1,1'-biphenyl]-4-yl)acetamide to afford the title compound (89% yield). LCMS: 734.3 (M+H)⁺.

Step 3: tert-butyl 4-(4-(4'-acetamido-3'-fluoro-2-hydroxy-[1,1'-biphenyl]-3-yl)-6-((4-((tert-butoxycarbonyl)amino)cyclohexyl)oxy)pyridin-2-yl)piperazine-1-carboxylate The title compound was prepared following the procedure described for Example 163 using tert-butyl 4-(4-(4'-acetamido-3'-fluoro-2-methoxy-[1,1'-biphenyl]-3-yl)-6-((4-((tert-butoxycarbonyl)amino)cyclohexyl)oxy)pyridin-2-yl)piperazine-1-carboxylate and piperazine to afford the title compound (28% yield). LCMS: 720.3 (M+H)⁺.

Step 4: N-(3'-(2-((4-aminocyclohexyl)oxy)-6-(piperazin-1-yl)pyridin-4-yl)-3-fluoro-2'-hydroxy-[1,1'-biphenyl]-4-yl)acetamide The title compound was prepared following the procedure described for Example 163 using tert-butyl 4-(4-(4'-acetamido-3'-fluoro-2-hydroxy-[1,1'-biphenyl]-3-yl)-6-((4-((tert-butoxycarbonyl)amino)cyclohexyl)oxy)pyridin-2-yl)piperazine-1-carboxylate and TFA to afford the title compound (80% yield). $^1$H NMR (400 MHz, CD3OD-bis TFA): 7.92 (t, J=8.4 Hz, 1H), 7.39-7.24 (m, 4H), 7.03 (t, J=7.6 Hz, 1H), 6.56 (s, 1H), 6.32 (s, 1H), 4.98-4.95 (m, 1H), 3.84-3.81 (m, 4H), 3.36-3.32 (m, 4H), 3.21-3.18 (m, 1H), 2.30-2.28 (m, 2H), 2.20 (s, 3H), 2.17-2.14 (m, 2H), 1.68-1.54 (m, 4H). N—H and O—H protons not observed. LCMS: 520.3 (M+H)⁺.

Example 376

Methyl 5-(3'-chloro-5-fluoro-2-hydroxy-4'-(3-methyl-2-oxoimidazolidin-1-yl)-[1,1'-biphenyl]-3-yl)-3-(piperazin-1-yl)picolinate

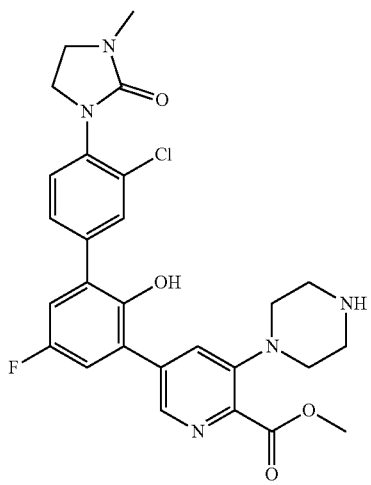

Step 1: tert-butyl 4-(5-(3'-chloro-5-fluoro-2-methoxy-4'-(3-methyl-2-oxoimidazolidin-1-yl)-[1,1'-biphenyl]-3-yl)-2-(methoxycarbonyl)pyridin-3-yl)piperazine-1-carboxylate The title compound was prepared following the procedures described for Example 368 using tert-butyl 4-(5-bromo-2-(methoxycarbonyl)pyridin-3-yl)piperazine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (59% yield). LCMS: 653.2 (M+H)⁺.

Step 2: Methyl 5-(3'-chloro-5-fluoro-2-hydroxy-4'-(3-methyl-2-oxoimidazolidin-1-yl)-[1,1'-biphenyl]-3-yl)-3-(piperazin-1-yl)picolinate The title compound was prepared following the procedures described for Example 368 using tert-butyl 4-(5-(3'-chloro-5-fluoro-2-methoxy-4'-(3-methyl-2-oxoimidazolidin-1-yl)-[1,1'-biphenyl]-3-yl)-2-(methoxycarbonyl)pyridin-3-yl)piperazine-1-carboxylate and BBr₃ to afford the title compound (35% yield). $^1$H NMR (400 MHz, DMSO-d₆): 8.35 (s, 1H), 7.77 (d, J=1.6 Hz, 1H), 7.71 (s, 1H), 7.62 (dd, J=2.0, 8.4 Hz, 1H), 7.50 (d, J=8.4 Hz, 1H), 7.40-7.33 (m, 2H), 3.77-3.73 (m, 2H), 3.51-3.44 (m, 2H), 3.17-3.09 (m, 11H), 2.77 (s, 3H). N—H and O—H protons not observed. LCMS: 540.0 (M+H)⁺.

Example 377

(R)-5-(3'-chloro-5-fluoro-2-hydroxy-4'-(3-methyl-2-oxoimidazolidin-1-yl)-[1,1'-biphenyl]-3-yl)-1-methyl-3-(3-methylpiperazin-1-yl)pyridin-2(1H)-one

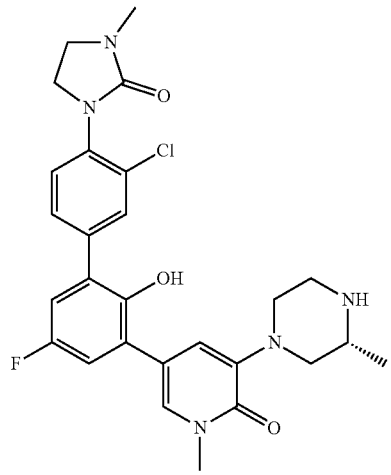 [SMILES: C[C@@H]1CN(c2cc(-c3cc(F)cc(-c4ccc(N5CCN(C)C5=O)c(Cl)c4)c3O)cn(C)c2=O)CCN1]

The title compound was prepared following the procedures described for Example 372 using 3,5-dibromo-1-methylpyridin-2(1H)-one, (R)-tert-butyl 2-methylpiperazine-1-carboxylate, 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one and BBr₃ to afford the title compound (15% yield). $^1$H NMR (400 MHz, DMSO-d₆): 7.70 (d, J=2.0 Hz, 1H), 7.55-7.51 (m, 2H), 7.44 (d, J=8.0 Hz, 1H), 7.15-7.10 (m, 2H), 6.83 (d, J=2.0 Hz, 1H), 3.74-3.70 (m, 2H), 3.58 (d, J=11.2 Hz, 2H), 3.51-3.47 (m, 5H), 2.90-2.77 (m, 6H), 2.41-2.35 (m, 1H), 2.04 (t, J=10.0 Hz, 1H), 0.97 (d, J=6.4 Hz, 3H). N—H and O—H protons not observed. LCMS: 526.3 (M+H)⁺.

Example 378

(S)-3-(3-aminopiperidin-1-yl)-5-(3'-chloro-5-fluoro-2-hydroxy-4'-(3-methyl-2-oxoimidazolidin-1-yl)-[1,1'-biphenyl]-3-yl)-1-methylpyridin-2(1H)-one

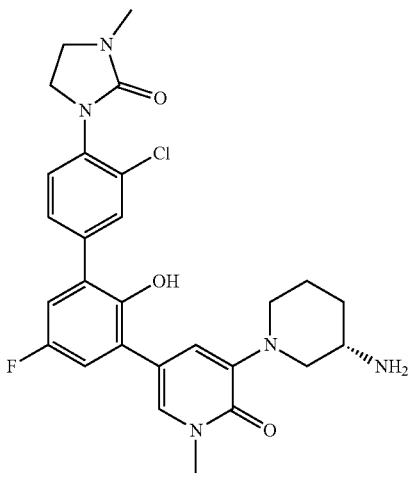 [SMILES: CN1CCN(c2ccc(-c3cc(F)cc(-c4cc(N5CCC[C@H](N)C5)c(=O)n(C)c4)c3O)cc2Cl)C1=O]

The title compound was prepared following the procedures described for Example 372 using 3,5-dibromo-1-methylpyridin-2(1H)-one, (S)-tert-butyl piperidin-3-ylcarbamate, 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one and $BBr_3$ to afford the title compound (13% yield). $^1$H NMR (400 MHz, DMSO-$d_6$): 8.78 (s, 2H), 8.62 (s, 1H), 7.67 (d, J=1.6 Hz, 1H), 7.52-7.44 (m, 2H), 7.31 (dd, J=2.0, 7.6 Hz, 1H), 7.26 (dd, J=1.2, 7.2 Hz, 1H), 7.05 (t, J=7.6 Hz, 1H), 6.83 (s, 1H), 6.76 (s, 1H), 3.74-7.68 (m, 6H), 3.48 (t, J=8.0 Hz, 2H), 3.17 (s, 4H), 2.77 (s, 3H), 2.05-1.99 (m, 1H), 0.93-0.89 (m, 4H). LCMS: 504.2 (M+H)$^+$.

Example 379

1-(3-chloro-5'-fluoro-2'-hydroxy-3'-(1',2',3',6'-tetrahydro-[2,4'-bipyridin]-4-yl)-[1,1'-biphenyl]-4-yl)-3-methylimidazolidin-2-one

Step 1: tert-butyl 4-chloro-5',6'-dihydro-[2,4'-bipyridine]-1'(2'H)-carboxylate The title compound was prepared following the procedures described for Example 368 using 2-bromo-4-chloropyridine and tert-butyl 4-(4,4,5,5-tetramethyl-1,3,2-dioxaborolan-2-yl)-5,6-dihydropyridine-1(2H)-carboxylate to afford the title compound (91% yield). LCMS: 239.1 (M−56+H)$^+$.

Step 2: tert-butyl 4-(3'-chloro-5-fluoro-2-methoxy-4'-(3-methyl-2-oxoimidazolidin-1-yl)-[1,1'-biphenyl]-3-yl)-5',6'-dihydro-[2,4'-bipyridine]-1'(2'H)-carboxylate The title compound was prepared following the procedures described for Example 368 using tert-butyl 4-chloro-5',6'-dihydro-[2,4'-bipyridine]-1'(2'H)-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (45% yield). LCMS: 593.6 (M+H)$^+$.

Step 3: 1-(3-chloro-5'-fluoro-2'-hydroxy-3'-(1',2',3',6'-tetrahydro-[2,4'-bipyridin]-4-yl)-[1,1'-biphenyl]-4-yl)-3-methylimidazolidin-2-one The title compound was prepared following the procedures described for Example 368 using tert-butyl 4-(3'-chloro-5-fluoro-2-methoxy-4'-(3-methyl-2-oxoimidazolidin-1-yl)-[1,1'-biphenyl]-3-yl)-5',6'-dihydro-[2,4'-bipyridine]-1'(2'H)-carboxylate and $BBr_3$ to afford the title compound (26% yield). $^1$H NMR (400 MHz, DMSO-$d_6$): 10.76 (s, 1H), 7.68 (d, J=2.0 Hz, 1H), 7.54-7.51 (m, 1H), 7.44-7.42 (m, 2H), 7.32 (d, J=8.4 Hz, 1H), 7.22 (t, J=7.6 Hz, 2H), 7.15 (dd, J=1.2, 8.4 Hz, 1H), 7.00 (t, J=7.6 Hz, 1H), 3.89 (s, 2H), 3.74-3.70 (m, 2H), 3.48 (t, J=8.0 Hz, 2H), 3.05 (t, J=5.6 Hz, 2H), 2.77 (s, 3H), 2.72-2.67 (m, 2H). N—H and O—H protons not observed. LCMS: 473.3 (M+H)$^+$.

Example 380

1-(5'-fluoro-2'-hydroxy-3-methyl-3'-(2-(piperazin-1-yl)pyridin-4-yl)-[1,1'-biphenyl]-4-yl)-3-methylimidazolidin-2-one

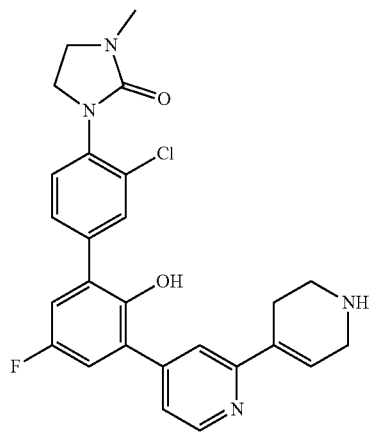

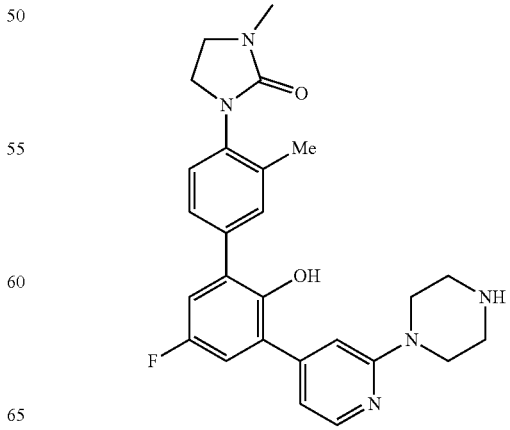

Step 1: tert-butyl 4-(4-(5-fluoro-2-methoxy-3'-methyl-4'-(3-methyl-2-oxoimidazolidin-1-yl)-[1,1'-biphenyl]-3-yl)pyridin-2-yl)piperazine-1-carboxylate The title compound was prepared following the procedures described for Example 379 using 1-(4-bromo-2-methylphenyl)-3-methylimidazolidin-2-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (62% yield). LCMS: 576.7 (M+H)+.

Step 2: 1-(5'-fluoro-2'-hydroxy-3-methyl-3'-(2-(piperazin-1-yl)pyridin-4-yl)-[1,1'-biphenyl]-4-yl)-3-methylimidazolidin-2-one The title compound was prepared following the procedures described for Example 379 using tert-butyl 4-(4-(5-fluoro-2-methoxy-3'-methyl-4'-(3-methyl-2-oxoimidazolidin-1-yl)-[1,1'-biphenyl]-3-yl)pyridin-2-yl)piperazine-1-carboxylate and BBr$_3$ to afford the title compound (22% yield). $^1$H NMR (400 MHz, DMSO-d$_6$): 8.42 (d, J=1.6 Hz, 1H), 8.15-8.13 (m, 1H), 7.72 (d, J=2.0 Hz, 1H), 7.62 (d, J=1.6 Hz, 1H), 7.56-7.54 (m, 1H), 7.47-7.45 (m, 1H), 7.24-7.19 (m, 2H), 4.47 (d, J=5.2 Hz, 2H), 3.72 (t, J=7.6 Hz, 2H), 3.49 (t, J=8.0 Hz, 2H), 2.88-2.86 (m, 8H), 2.77 (s, 3H), 1.89 (s, 3H). N—H and O—H proton not observed. LCMS: 553.3 (M+H)+.

Example 381

1-acetyl-3-(3-chloro-5'-fluoro-2'-hydroxy-3'-(2-(piperazin-1-yl)pyridin-4-yl)-[1,1'-biphenyl]-4-yl)imidazolidin-2-one

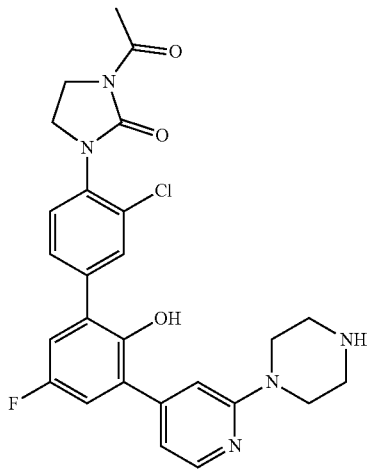

Step 1: tert-butyl 4-(4-(4'-(3-acetyl-2-oxoimidazolidin-1-yl)-3'-chloro-5-fluoro-2-hydroxy-[1,1'-biphenyl]-3-yl)pyridin-2-yl)piperazine-1-carboxylate The title compound was prepared following the procedures described for Example 380 using 1-acetyl-3-(2-chloro-4-(4,4,5,5-tetramethyl-1,3,2-dioxaborolan-2-yl)phenyl)imidazolidin-2-one and tert-butyl 4-(4-(3-bromo-5-fluoro-2-hydroxyphenyl)pyridin-2-yl)piperazine-1-carboxylate to afford the title compound (78% yield). LCMS: 610.2 (M+H)+.

Step 2: 1-acetyl-3-(3-chloro-5'-fluoro-2'-hydroxy-3'-(2-(piperazin-1-yl)pyridin-4-yl)-[1,1'-biphenyl]-4-yl)imidazolidin-2-one The title compound was prepared following the procedures described for Example 380 using tert-butyl 4-(4-(4'-(3-acetyl-2-oxoimidazolidin-1-yl)-3'-chloro-5-fluoro-2-hydroxy-[1,1'-biphenyl]-3-yl)pyridin-2-yl)piperazine-1-carboxylate and TFA to afford the title compound (62% yield). $^1$H NMR (400 MHz, DMSO-d$_6$): 8.18 (d, J=6.8 Hz, 1H), 7.81 (s, 1H), 7.67-7.61 (m, 2H), 7.28-7.19 (m, 2H), 6.95 (s, 1H), 6.85 (d, J=6.8 Hz, 1H), 4.55 (t, J=9.6 Hz, 2H), 4.02 (t, J=10.8 Hz, 2H), 3.50-3.46 (m, 4H), 2.84-2.81 (m, 4H). N—H and O—H protons not observed. LCMS: 469.2 (M+H)+.

Example 382

1-(3-chloro-3'-(6-ethyl-5-(piperazin-1-yl)pyridin-3-yl)-5'-fluoro-2'-hydroxy-[1,1'-biphenyl]-4-yl)-3-methylimidazolidin-2-one

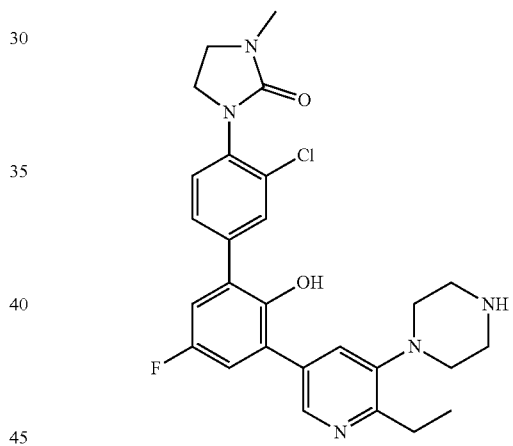

Step 1: tert-butyl 4-(2-chloro-5-(3'-chloro-5-fluoro-2-methoxy-4'-(3-methyl-2-oxoimidazolidin-1-yl)-[1,1'-biphenyl]-3-yl)pyridin-3-yl)piperazine-1-carboxylate The title compound was prepared following the procedure described for Example 374 using tert-butyl 4-(5-bromo-2-chloropyridin-3-yl)piperazine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (61% yield). LCMS: 630.2 (M+H)+.

Step 3: tert-butyl 4-(5-(3'-chloro-5-fluoro-2-methoxy-4'-(3-methyl-2-oxoimidazolidin-1-yl)-[1,1'-biphenyl]-3-yl)-2-ethylpyridin-3-yl)piperazine-1-carboxylate The title compound was prepared following the procedures described for Example 374 using tert-butyl 4-(2- chloro-5-(3'-chloro-5-fluoro-2-methoxy-4'-(3-methyl-2-oxoimidazolidin-1-yl)-[1,1'-biphenyl]-3-yl)pyridin-3-yl)piperazine-1-carboxylate and ethylboronic acid to afford the title compound (31% yield). LCMS: 624.7 (M+H)+.

Step 4: 1-(3-chloro-3'-(6-ethyl-5-(piperazin-1-yl)pyridin-3-yl)-5'-fluoro-2'-hydroxy-[1,1'-biphenyl]-4-yl)-3-methylimidazolidin-2-one The title compound was prepared following the procedures described for Example 374 using tert-butyl 4-(5-(3'-chloro-5-fluoro-2-methoxy-4'-(3-methyl-2-oxoimidazolidin-1-yl)-[1,1'-biphenyl]-3-yl)-2-ethylpyridin-3-yl)piperazine-1-carboxylate and $BBr_3$ to afford the title compound (29% yield). $^1$H NMR (400 MHz, DMSO-$d_6$): 8.39 (d, J=1.6 Hz, 1H), 7.72 (d, J=2.0 Hz, 1H), 7.56-7.54 (m, 2H), 7.46 (d, J=8.4 Hz, 1H), 7.23-7.17 (m, 2H), 3.75-7.30 (m, 2H), 3.51-3.47 (m, 2H), 2.93-2.92 (m, 4H), 2.86-2.80 (m, 6H), 2.77 (s, 3H), 1.27 (t, J=7.6 Hz, 3H). N—H and O—H protons not observed. LCMS: 510.3 (M+H)+.

Example 383

N-(4-(3'-chloro-2-hydroxy-4'-(3-methyl-2-oxoimidazolidin-1-yl)-[1,1'-biphenyl]-3-yl)-6-(piperazin-1-yl)pyridin-2-yl)acetamide

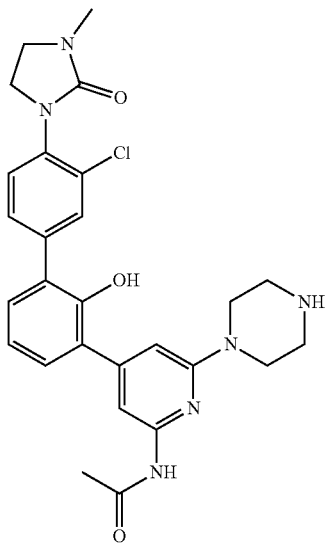 [SMILES: CC(=O)Nc1cc(-c2cccc(-c3ccc(N4CCN(C)C4=O)c(Cl)c3)c2O)cc(N2CCNCC2)n1]

Step 1: tert-butyl 4-(6-acetamido-4-(3'-chloro-2-methoxy-4'-(3-methyl-2-oxoimidazolidin-1-yl)-[1,1'-biphenyl]-3-yl)pyridin-2-yl)piperazine-1-carboxylate A suspension of tert-butyl 4-(6-chloro-4-(3'-chloro-2-methoxy-4'-(3-methyl-2-oxoimidazolidin-1-yl)-[1,1'-biphenyl]-3-yl)pyridin-2-yl)piperazine-1-carboxylate (110 mg, 0.180 mmol), acetamide (32 mg, 0.54 mmol), xantphos (13 mg, 0.022 mmol), $K_3PO_4$ (115 mg, 0.540 mmol) and $Pd_2(dba)_3$ (6.4 mg, 0.0070 mmol) in dioxane (2 mL) was stirred at 140° C. in MW under nitrogen atmosphere for 4 h. After the reaction was complete by LCMS, the reaction mixture was cooled and filtered. The filtrate was concentrated. The residue was purified by silica gel chromatography using (10:1 to 1:3) petroleum ether and ethyl acetate as the eluent to afford the title compound (80 mg, 70% yield) as a yellow solid.

LCMS: 635.2 (M+H)+.

Step 3: N-(4-(3'-chloro-2-hydroxy-4'-(3-methyl-2-oxoimidazolidin-1-yl)-[1,1'-biphenyl]-3-yl)-6-(piperazin-1-yl)pyridin-2-yl)acetamide The title compound was prepared following the procedures described for Example 374 using tert-butyl 4-(6-acetamido-4-(3'-chloro-2-hydroxy-4'-(3-methyl-2-oxoimidazolidin-1-yl)-[1,1'-biphenyl]-3-yl)pyridin-2-yl)piperazine-1-carboxylate to afford the title compound (49% yield). $^1$H NMR (400 MHz, DMSO-$d_6$+D2O): 7.66 (d, J=1.6 Hz, 1H), 7.57 (s, 1H), 7.51 (dd, J=1.6, 8.0 Hz, 1H), 7.45 (d, J=8.4 Hz, 1H), 7.32 (dd, J=2.0, 7.6 Hz, 1H), 7.24 (dd, J=1.6, 7.6 Hz, 1H), 7.07 (t, J=7.2 Hz, 1H), 6.71 (s, 1H), 3.76-3.71 (m, 6H), 3.48-3.47 (m, 2H), 3.20-3.18 (m, 4H), 2.77 (s, 3H), 2.09 (s, 3H). N—H and O—H protons not observed. LCMS: 521.2 (M+H)+.

Example 384

1-methyl-3-(3,5,5'-trifluoro-2'-hydroxy-3'-(2-(piperazin-1-yl)pyridin-4-yl)-[1,1'-biphenyl]-4-yl)imidazolidin-2-one

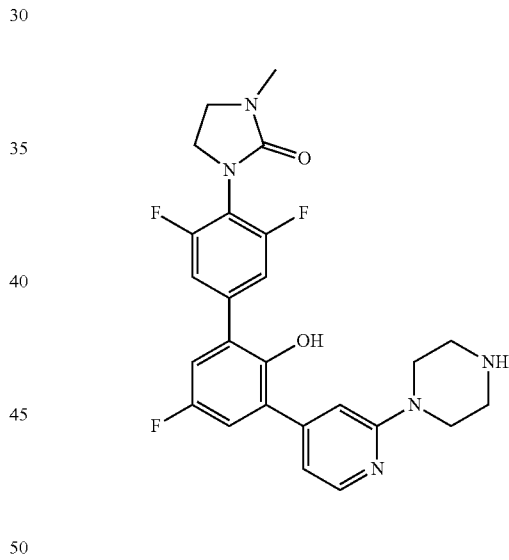

Step 1: tert-butyl 4-(4-(3',5,5'-trifluoro-2-methoxy-4'-(3-methyl-2-oxoimidazolidin-1-yl)-[1,1'-biphenyl]-3-yl)pyridin-2-yl)piperazine-1-carboxylate The title compound was prepared following the procedures described for Example 380 using 1-(4-bromo-2,6-difluorophenyl)-3-methylimidazolidin-2-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (51% yield). LCMS: 598.3 (M+H)+

Step 2: 1-methyl-3-(3,5,5'-trifluoro-2'-hydroxy-3'-(2-(piperazin-1-yl)pyridin-4-yl)-[1,1'-biphenyl]-4-yl)imidazolidin-2-one The title compound was prepared following the procedures described for Example 380 using tert-butyl 4-(4-(3',5,5'-trifluoro-2-methoxy-4'-(3-methyl-2-oxoimidazolidin-1-yl)-[1,1'-biphenyl]-3-yl)pyridin-2-yl)piperazine-1-carboxylate and BBr₃ to afford the title compound (35% yield). ¹H NMR (400 MHz, DMSO-d): 8.13 (d, J=5.2 Hz, 1H), 7.42 (d, J=9.2 Hz, 2H), 7.23 (dd, J=3.2, 9.2 Hz, 1H), 7.18 (dd, J=3.2, 9.2 Hz, 1H), 6.95 (s, 1H), 6.81 (dd, J=1.2, 5.2 Hz, 1H), 3.69-3.65 (m, 2H), 3.54-3.50 (m, 2H), 3.44-3.42 (m, 4H), 2.79-2.76 (m, 7H). N—H and O—H protons not observed. LCMS: 484.2 (M+H)⁺.

Example 385

1-(3-chloro-5'-fluoro-2'-hydroxy-5-methyl-3'-(2-(piperazin-1-yl)pyridin-4-yl)-[1,1'-biphenyl]-4-yl)-3-methylimidazolidin-2-one

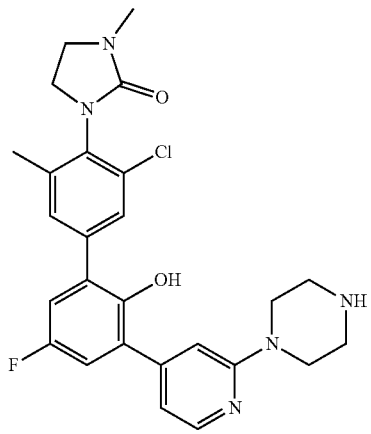

The title compound was prepared following the procedures described for Example 384 using 4-bromo-2-chloro-6-methylaniline and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (9% yield).

¹H NMR (400 MHz, DMSO-d₆): 8.15 (d, J=5.2 Hz, 1H), 7.55 (d, J=1.6 Hz, 1H), 7.44 (d, J=1.6 Hz, 1H), 7.20-7.15 (m, 2H), 6.91 (s, 1H), 6.82 (d, J=5.2 Hz, 1H), 3.71-3.65 (m, 4H), 3.58-3.53 (m, 4H), 2.82-2.79 (m, 4H), 2.75 (s, 3H), 2.69 (s, 3H). N—H and O—H protons not observed. LCMS: 496.2 (M+H)⁺.

Example 386

1-(3-chloro-5'-fluoro-2'-hydroxy-5-methyl-3'-(2-(piperazin-1-yl)pyridin-4-yl)-[1,1'-biphenyl]-4-yl)pyrrolidin-2-one

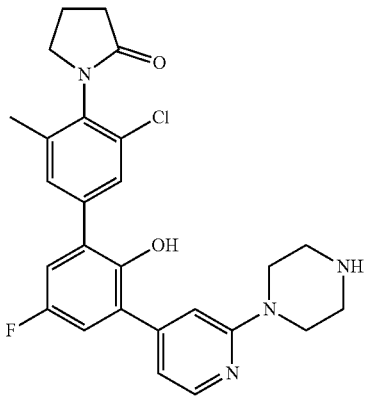

The title compound was prepared following the procedures described for Example 252 using 1-(4-bromo-2-chloro-6-methylphenyl)pyrrolidin-2-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (12% yield). ¹H NMR (400 MHz, DMSO-d₆): 8.14 (d, J=5.2 Hz, 1H), 7.58 (d, J=1.2 Hz, 1H), 7.46 (d, J=1.2 Hz, 1H), 7.21-7.15 (m, 2H), 6.91 (s, 1H), 6.81 (dd, J=0.8, 5.2 Hz, 1H), 3.69-3.65 (m, 1H), 3.61-3.55 (m, 1H), 3.45-3.43 (m, 4H), 2.80-2.77 (m, 4H), 2.49-2.42 (m, 2H), 2.23 (s, 3H), 2.22-2.17 (m, 2H). Two N—H or O—H proton not observed. LCMS: 481.1 (M+H)⁺.

Example 387

1-(3-chloro-5'-fluoro-2'-hydroxy-3'-(6-(hydroxymethyl)-5-(piperazin-1-yl)pyridin-3-yl)-[1,1'-biphenyl]-4-yl)-3-methylimidazolidin-2-one

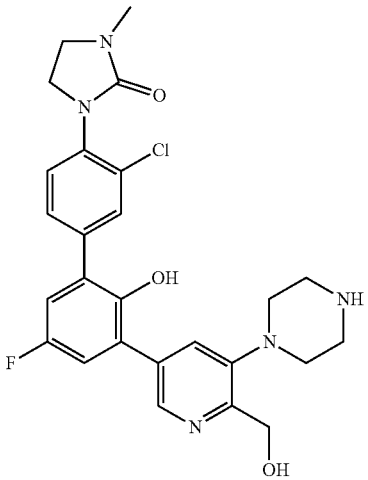

Step 1: tert-butyl 4-(5-(3'-chloro-5-fluoro-2-methoxy-4'-(3-methyl-2-oxoimidazolidin-1-yl)-[1,1'-biphenyl]-3-yl)-2-(hydroxymethyl)pyridin-3-yl)piperazine-1-carboxylate The title compound was prepared following the procedures described for Example 376 using tert-butyl 4-(5-bromo-2-(hydroxymethyl)pyridin-3-yl)piperazine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (34% yield). LCMS: 626.2 (M+H)$^+$.

Step 2: 1-(3-chloro-5'-fluoro-2'-hydroxy-3'-(6-(hydroxymethyl)-5-(piperazin-1-yl)pyridin-3-yl)-[1,1'-biphenyl]-4-yl)-3-methylimidazolidin-2-one The title compound was prepared following the procedure described for Example 376 using tert-butyl 4-(5-(3'-chloro-5-fluoro-2-methoxy-4'-(3-methyl-2-oxoimidazolidin-1-yl)-[1,1'-biphenyl]-3-yl)-2-(hydroxymethyl)pyridin-3-yl)piperazine-1-carboxylate and BBr$_3$ to afford the title compound (34% yield). $^1$H NMR (400 MHz, DMSO-d$_6$): 8.41 (d, J=1.6 Hz, 1H), 7.72 (d, J=2.0 Hz, 1H), 7.58-7.54 (m, 2H), 7.46 (d, J=8.4 Hz, 1H), 7.25-7.19 (m, 2H), 5.03-5.01 (m, 1H), 4.61 (d, J=4.8 Hz, 2H), 3.74-3.70 (m, 2H), 3.51-3.47 (m, 2H), 2.89-2.88 (m, 8H), 2.77 (s, 3H). N—H and O—H protons not observed. LCMS: 512.3 (M+H)$^+$.

Example 388

1-(3-chloro-5'-fluoro-2'-hydroxy-3'-(6-methyl-5-(piperazin-1-yl)pyridin-3-yl)-[1,1'-biphenyl]-4-yl)-3-methylimidazolidin-2-one

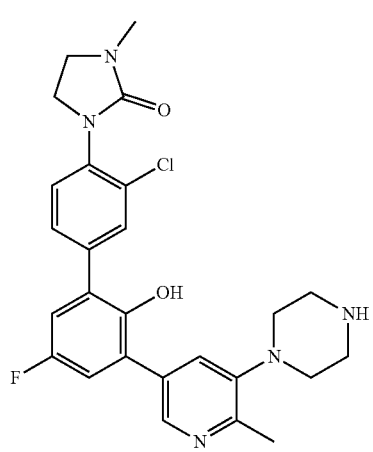

The title compound was prepared following the procedures described for Example 382 using tert-butyl 4-(2-chloro-5-(3'-chloro-5-fluoro-2-methoxy-4'-(3-methyl-2-oxoimidazolidin-1-yl)-[1,1'-biphenyl]-3-yl)pyridin-3-yl)piperazine-1-carboxylate and methylboronic acid to afford the title compound (5% yield). $^1$H NMR (400 MHz, DMSO-d): 8.29 (d, J=1.6 Hz, 1H), 7.72 (d, J=1.6 Hz, 1H), 7.55 (dd, J=2.0, 8.0 Hz, 1H), 7.51 (d, J=2.0 Hz, 1H), 7.46 (d, J=8.4 Hz, 1H), 7.20-7.17 (m, 2H), 3.74-3.70 (m, 2H), 3.51-3.47 (m, 2H), 2.86-2.84 (m, 8H), 2.77 (s, 3H), 2.47 (s, 3H). N—H or O—H protons not observed. LCMS: 496.2 (M+H)$^+$.

Example 389

N-(5-(3'-chloro-5-fluoro-2-hydroxy-4'-(3-methyl-2-oxoimidazolidin-1-yl)-[1,1'-biphenyl]-3-yl)-3-(piperazin-1-yl)pyridin-2-yl)acetamide

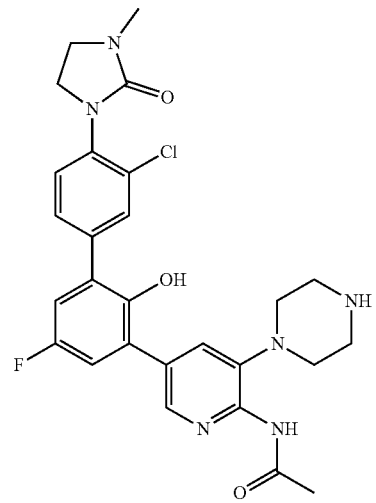 [SMILES: CC(=O)Nc1ncc(-c2cc(F)cc(-c3ccc(N4CCN(C)C4=O)c(Cl)c3)c2O)cc1N1CCNCC1]

The title compound was prepared following the procedures described for Example 383 using tert-butyl 4-(2-chloro-5-(3'-chloro-5-fluoro-2-methoxy-4'-(3-methyl-2-oxoimidazolidin-1-yl)-[1,1'-biphenyl]-3-yl)pyridin-3-yl)piperazine-1-carboxylate and acetamide to afford the title compound (76% yield). $^1$H NMR (400 MHz, DMSO-d): 9.20 (s, 1H), 8.22 (d, J=2.0 Hz, 1H), 7.72 (d, J=2.4 Hz, 1H), 7.73 (d, J=2.4 Hz, 1H), 7.55 (dd, J=2.0, 8.0 Hz, 1H), 7.46 (d, J=8.0 Hz, 1H), 7.25-7.17 (m, 2H), 3.74-3.70 (m, 2H), 3.51-3.47 (m, 2H), 2.86-2.84 (m, 8H), 2.77 (s, 3H), 2.17 (s, 3H). N—H or O—H protons not observed. LCMS: 539.1 (M+H)$^+$.

Example 390

1-(3-chloro-5'-fluoro-2'-hydroxy-3'-(5-(piperazin-1-yl)-6-(1H-pyrazol-4-yl)pyridin-3-yl)-[1,1'-biphenyl]-4-yl)-3-methylimidazolidin-2-one

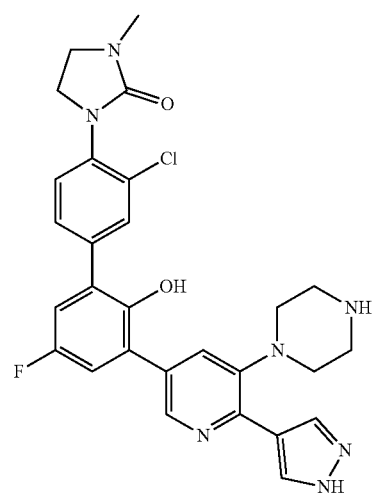 [SMILES: CN1CCN(c2ccc(-c3cc(F)cc(-c4cnc(-c5cn[nH]c5)c(N5CCNCC5)c4)c3O)cc2Cl)C1=O]

The title compound was prepared following the procedures described for Example 388 using tert-butyl 4-(2- chloro-5-(3'-chloro-5-fluoro-2-methoxy-4'-(3-methyl-2-oxoimidazolidin-1-yl)-[1,1'-biphenyl]-3-yl)pyridin-3-yl)piperazine-1-carboxylate, tert-butyl 4-(4,4,5,5-tetramethyl-1,3,2-dioxaborolan-2-yl)-1H-pyrazole-1-carboxylate and BBr$_3$ to afford the title compound. $^1$H NMR (400 MHz, DMSO-d$_6$-TFA salt): 8.86-8.75 (m, 3H), 8.51 (s, 1H), 8.41 (s, 2H), 7.79-7.73 (m, 2H), 7.56 (dd, J=2.0, 8.4 Hz, 1H), 7.48 (d, J=8.4 Hz, 1H), 7.32-7.22 (m, 2H), 3.75-3.71 (m, 2H), 3.51-3.47 (m, 2H), 3.34 (s, 4H), 3.10 (s, 4H), 2.77 (s, 3H). N—H or O—H proton not observed. LCMS: 548.3 (M+H)$^+$.

Example 391

1-(3-chloro-5'-fluoro-2'-hydroxy-3'-(5-(piperazin-1-yl)-6-(1H-pyrazol-5-yl)pyridin-3-yl)-[1,1'-biphenyl]-4-yl)-3-methylimidazolidin-2-one

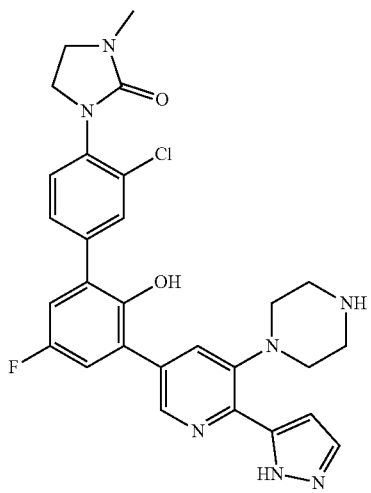 [SMILES: CN1CCN(c2ccc(-c3cc(F)cc(-c4cnc(-c5ccn[nH]5)c(N5CCNCC5)c4)c3O)cc2Cl)C1=O]

The title compound was prepared following the procedures described for Example 388 using tert-butyl 4-(2-chloro-5-(3'-chloro-5-fluoro-2-methoxy-4'-(3-methyl-2-oxoimidazolidin-1-yl)-[1,1'-biphenyl]-3-yl)pyridin-3-yl)piperazine-1-carboxylate, 1-(tetrahydro-2H-pyran-2-yl)-5-(4,4,5,5-tetramethyl-1,3,2-dioxaborolan-2-yl)-1H-pyrazole and BBr$_3$ to afford the title compound (14% yield). $^1$H NMR (400 MHz, DMSO-d$_6$): 8.84-8.75 (m, 3H), 8.56 (d, J=1.6 Hz 1H), 7.80 (s, 1H), 7.74 (d, J=1.6 Hz, 1H), 7.69 (s, 1H), 7.57 (dd, J=2.0, 8.4 Hz, 1H), 7.48 (d, J=8.4 Hz, 1H), 7.35 (dd, J=3.2, 8.8 Hz, 1H), 7.25 (dd, J=2.8, 8.8 Hz, 1H), 7.07 (s, 1H), 3.96-3.94 (m, 2H), 3.75-3.71 (m, 2H), 3.33 (s, 4H), 3.13 (s, 4H), 2.77 (s, 3H). N—H or O—H proton not observed. LCMS: 548.3 (M+H)$^+$.

Example 392

1-(3-chloro-5'-fluoro-2'-hydroxy-3'-(6-(2-hydroxyethoxy)-5-(piperazin-1-yl)pyridin-3-yl)-[1,1'-biphenyl]-4-yl)-3-methylimidazolidin-2-one

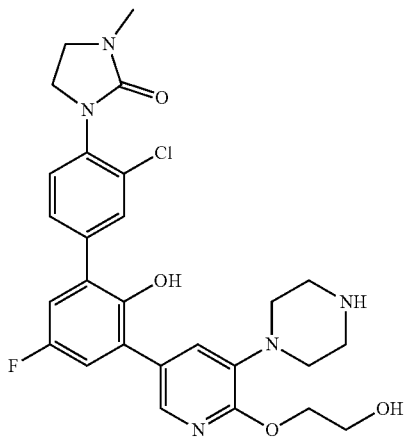 [SMILES: CN1CCN(c2ccc(-c3cc(F)cc(-c4cnc(OCCO)c(N5CCNCC5)c4)c3O)cc2Cl)C1=O]

Step 1: tert-butyl 4-(5-(3'-chloro-5-fluoro-2-methoxy-4'-(3-methyl-2-oxoimidazolidin-1-yl)-[1,1'-biphenyl]-3-yl)-2-(2-methoxyethoxy)pyridin-3-yl)piperazine-1-carboxylate To a solution of tert-butyl 4-(2-chloro-5-(3'-chloro-5-fluoro-2-methoxy-4'-(3-methyl-2-oxoimidazolidin-1-yl)-[1,1'-biphenyl]-3-yl)pyridin-3-yl)piperazine-1-carboxylate (200 mg, 0.317 mmol) in dioxane (10 mL) was added 2-methoxyethanol (121 mg, 1.59 mmol) and NaH (76.1 mg, 3.17 mmol, 60% in mineral oil). After stirring at 100° C. for 12 hours, the reaction mixture was cooled, 20 mL water was added and extracted with ethyl acetate (15 mL×3). The combined organic layers were dried over sodium sulfate, filtered and concentrated to afford a residue which was purified by silica gel chromatography using (1:1) petroleum ether and ethyl acetate as the eluent to afford the title compound (160 mg, 79% yield) as a yellow solid. LCMS: 670.7 (M+H)$^+$.

Step 2: 1-(3-chloro-5'-fluoro-2'-hydroxy-3'-(6-(2-hydroxyethoxy)-5-(piperazin-1-yl)pyridin-3-yl)-[1,1'-biphenyl]-4-yl)-3-methylimidazolidin-2-one The title compound was prepared following the procedures described for Example 388 using tert-butyl 4-(5-(3'-chloro-5-fluoro-2-methoxy-4'-(3-methyl-2-oxoimidazolidin-1-yl)-[1,1'-biphenyl]-3-yl)-2-(2-methoxyethoxy)pyridin-3-yl)piperazine-1-carboxylate and BBr$_3$ (12% yield). $^1$H NMR (400 MHz, DMSO-d$_6$): 7.86 (d, J=2.4 Hz 1H), 7.71 (d, J=2.0 Hz, 1H), 7.54 (dd, J=2.0, 8.0 Hz, 1H), 7.45 (d, J=8.4 Hz, 1H), 7.31 (d, J=2.0 Hz, 1H), 7.18-7.13 (m, 2H), 4.79-4.76 (m, 1H), 4.36 (t, J=4.8 Hz, 2H), 3.76-3.70 (m, 4H), 3.50-3.46 (m, 2H), 3.02-2.97 (m, 4H), 2.84-2.83 (m, 4H), 2.77 (s, 3H). N—H and O—H protons not observed. LCMS: 542.3 (M+H)$^+$.

Example 393

1-(3-chloro-5'-fluoro-2'-hydroxy-3'-(6-(2-methoxy-ethoxy)-5-(piperazin-1-yl)pyridin-3-yl)-[1,1'-biphenyl]-4-yl)-3-methylimidazolidin-2-one

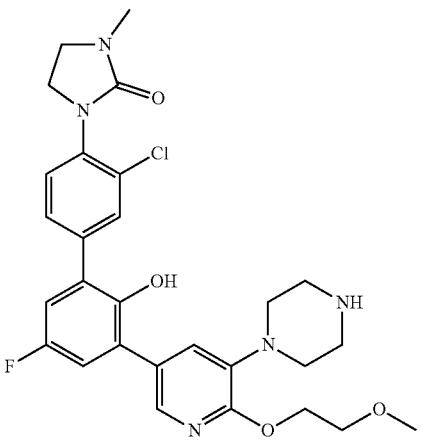 [SMILES: COCCOc1ncc(-c2cc(F)cc(-c3ccc(N4CCN(C)C4=O)c(Cl)c3)c2O)cc1N1CCNCC1]

The title compound was prepared following the procedures described for Example 392 using tert-butyl 4-(5-(3'-chloro-5-fluoro-2-hydroxy-4'-(3-methyl-2-oxoimidazolidin-1-yl)-[1,1'-biphenyl]-3-yl)-2-(2-methoxyethoxy) pyridin-3-yl)piperazine-1-carboxylate and TFA (25% yield). $^1$H NMR (400 MHz, DMSO-$d_6$): 7.86 (d, J=2.0 Hz 1H), 7.71 (d, J=2.0 Hz, 1H), 7.54 (dd, J=1.6, 8.0 Hz, 1H), 7.45 (d, J=8.4 Hz, 1H), 7.31 (d, J=1.6 Hz, 1H), 7.18-7.13 (m, 2H), 4.44 (t, J=4.8 Hz, 2H), 3.74-3.69 (m, 4H), 3.50-3.46 (m, 2H), 3.33 (s, 3H), 3.02-2.97 (m, 4H), 2.84-2.83 (m, 4H), 2.77 (s, 3H). N—H and O—H protons not observed. LCMS: 556.3 (M+H)$^+$.

Example 394

(S)-3-(3-aminopyrrolidin-1-yl)-5-(3'-chloro-5-fluoro-2-hydroxy-4'-(3-methyl-2-oxoimidazolidin-1-yl)-[1,1'-biphenyl]-3-yl)-1-methylpyridin-2(1H)-one

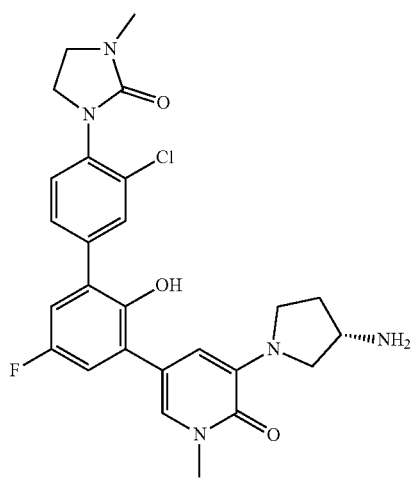 [SMILES: CN1CCN(c2ccc(-c3cc(F)cc(-c4cc(N5CC[C@H](N)C5)c(=O)n(C)c4)c3O)cc2Cl)C1=O]

The title compound was prepared following the procedures described for Example 378 using (S)-tert-butyl (1-(5-bromo-1-methyl-2-oxo-1,2-dihydropyridin-3-yl)pyrrolidin-3-yl)carbamate, 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one and BBr$_3$ to afford the title compound. $^1$H NMR (400 MHz, DMSO-$d_6$+D$_2$O): 7.71 (d, J=1.6 Hz, 1H), 7.54 (dd, J=2.0, 8.4 Hz, 1H), 7.46 (d, J=8.4 Hz, 1H), 7.42 (d, J=2.0 Hz, 1H), 7.14 (s, 1H), 7.12 (s, 1H), 6.69 (d, J=2.0 Hz, 1H), 3.84-3.81 (m, 1H), 3.76-3.72 (m, 2H), 3.63-3.50 (m, 8H), 3.24-3.21 (m, 1H), 2.78 (s, 3H), 2.32-2.28 (m, 1H), 1.96-1.90 (m, 1H). N—H and O-H protons not observed. LCMS: 512.2 (M+H)$^+$.

Example 395

N-(2-((5-(3'-chloro-5-fluoro-2-hydroxy-4'-(3-methyl-2-oxoimidazolidin-1-yl)-[1,1'-biphenyl]-3-yl)-3-(piperazin-1-yl)pyridin-2-yl)amino)ethyl)acetamide

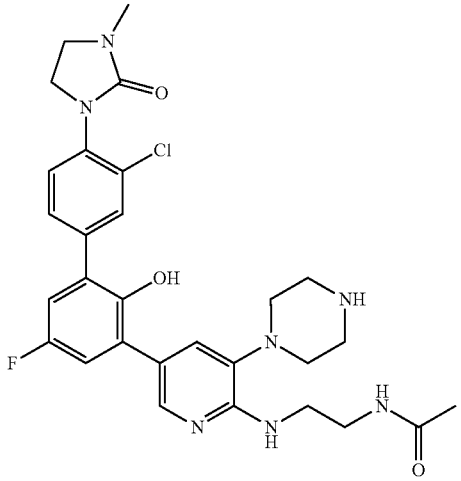 [SMILES: CC(=O)NCCNc1ncc(-c2cc(F)cc(-c3ccc(N4CCN(C)C4=O)c(Cl)c3)c2O)cc1N1CCNCC1]

The title compound was prepared following the procedures described for Example 393 using tert-butyl 4-(2-chloro-5-(3'-chloro-5-fluoro-2-methoxy-4'-(3-methyl-2-oxoimidazolidin-1-yl)-[1,1'-biphenyl]-3-yl)pyridin-3-yl) piperazine-1-carboxylate, N-(2-aminoethyl)acetamide and BBr$_3$ to afford the title compound (32% yield). $^1$H NMR (400 MHz, DMSO-$d_6$): 8.00 (t, J=5.2 Hz, 1H), 7.94 (d, J=2.0 Hz, 1H), 7.70 (d, J=2.0 Hz, 1H), 7.53 (dd, J=2.0, 8.4 Hz, 1H), 7.44 (d, J=8.0 Hz, 1H), 7.34 (d, J=1.6 Hz, 1H), 7.11-7.06 (m, 2H), 6.00 (t, J=5.6 Hz, 1H), 3.74-3.70 (m, 2H), 3.51-3.42 (m, 4H), 3.31-3.28 (m, 2H), 2.88-2.87 (m, 4H), 2.77 (s, 3H), 2.73 (s, 4H), 1.82 (s, 3H). N—H and O—H protons not observed. LCMS: 582.1 (M+H)$^+$.

Example 396

N-(2-((5-(3'-chloro-5-fluoro-2-hydroxy-4'-(3-methyl-2-oxoimidazolidin-1-yl)-[1,1'-biphenyl]-3-yl)-3-(piperazin-1-yl)pyridin-2-yl)oxy)ethyl)acetamide

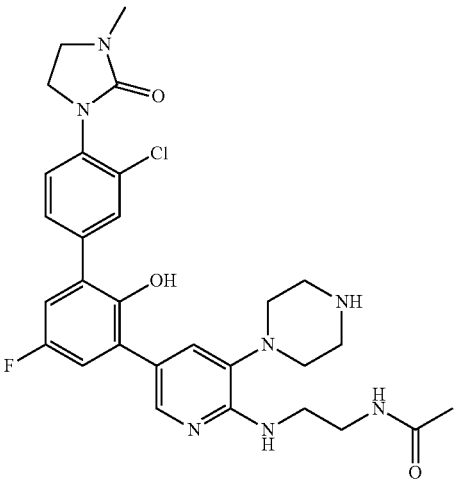 [SMILES: CC(=O)NCCNc1ncc(-c2cc(F)cc(-c3ccc(N4CCN(C)C4=O)c(Cl)c3)c2O)cc1N1CCNCC1]

The title compound was prepared following the procedures described for Example 395 using tert-butyl 4-(2-chloro-5-(3'-chloro-5-fluoro-2-methoxy-4'-(3-methyl-2-oxoimidazolidin-1-yl)-[1,1'-biphenyl]-3-yl)pyridin-3-yl) piperazine-1-carboxylate, N-(2-hydroxyethyl)acetamide, piperazine and TFA afford the title compound (35% yield). $^1$H NMR (400 MHz, DMSO-$d_6$+$D_2$O): 7.96 (d, J=2.0 Hz, 1H), 7.72 (d, J=2.0 Hz, 1H), 7.54 (dd, J=1.6, 8.4 Hz, 1H), 7.48-7.45 (m, 2H), 7.19-7.15 (m, 2H), 4.35-4.28 (m, 2H), 3.79-3.75 (m, 2H), 3.59-3.53 (m, 4H), 3.30 (s, 8H), 2.80 (s, 3H), 1.92 (s, 3H). N—H and O—H protons not observed. LCMS: 583.1 (M+H)$^+$.

Example 397

1-(3-chloro-5'-fluoro-2'-hydroxy-3'-(5-(piperazin-1-yl)-6-(pyrrolidin-1-yl)pyridin-3-yl)-[1,1'-biphenyl]-4-yl)-3-methylimidazolidin-2-one

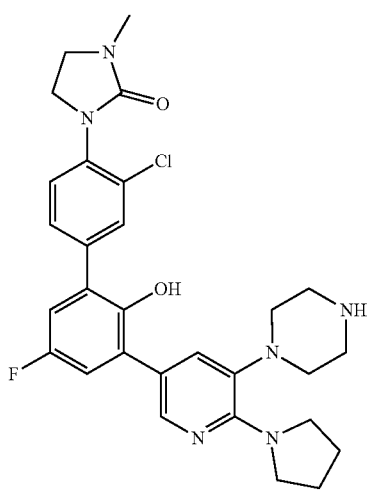 [SMILES: CN1CCN(c2ccc(-c3cc(F)cc(-c4cnc(N5CCCC5)c(N5CCNCC5)c4)c3O)cc2Cl)C1=O]

The title compound was prepared following the procedures described for Example 395 using tert-butyl 4-(2-chloro-5-(3'-chloro-5-fluoro-2-methoxy-4'-(3-methyl-2-oxoimidazolidin-1-yl)-[1,1'-biphenyl]-3-yl)pyridin-3-yl) piperazine-1-carboxylate, pyrrolidine and BBr$_3$ to afford the title compound. $^1$H NMR (400 MHz, DMSO-$d_6$+$D_2$O): 7.95 (s, 1H), 7.86 (d, J=1.6 Hz, 1H), 7.72 (d, J=1.2 Hz, 1H), 7.54 (dd, J=1.2, 8.4 Hz, 1H), 7.48 (d, J=8.0 Hz, 1H), 7.28-7.21 (m, 2H), 3.80-3.73 (m, 6H), 3.54-3.50 (m, 2H), 3.31 (s, 4H), 3.13 (s, 4H), 2.78 (s, 3H), 1.99 (s, 4H). N—H and O—H protons not observed. LCMS: 551.3 (M+H)$^+$.

Example 398

5-(3'-chloro-5-fluoro-2-hydroxy-4'-(3-methyl-2-oxoimidazolidin-1-yl)-[1,1'-biphenyl]-3-yl)-3-(piperazin-1-yl)picolinic acid

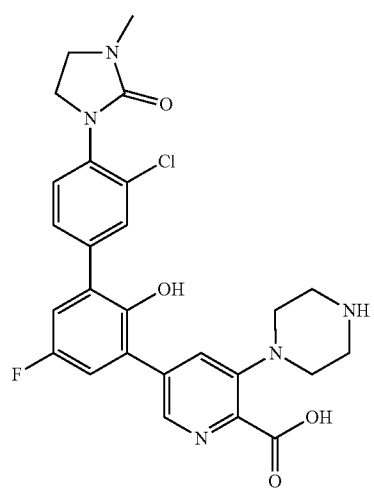 [SMILES: CN1CCN(c2ccc(-c3cc(F)cc(-c4cnc(C(=O)O)c(N5CCNCC5)c4)c3O)cc2Cl)C1=O]

Step 1: methyl 5-(3'-chloro-5-fluoro-2-hydroxy-4'-(3-methyl-2-oxoimidazolidin-1-yl)-[1,1'-biphenyl]-3-yl)-3-(piperazin-1-yl)picolinate The title compound was prepared following the procedures described for Example 376 using tert-butyl 4-(5-(3'-chloro-5-fluoro-2-methoxy-4'-(3-methyl-2-oxoimidazolidin-1-yl)-[1,1'-biphenyl]-3-yl)-2-(methoxycarbonyl) pyridin-3-yl)piperazine-1-carboxylate and BBr$_3$ to afford the title compound (quant). LCMS: 540.1 (M+H)$^+$ Step 2: 5-(3'-chloro-5-fluoro-2-hydroxy-4'-(3-methyl-2-oxoimidazolidin-1-yl)-[1,1'-biphenyl]-3-yl)-3-(piperazin-1-yl)picolinic acid A mixture of methyl 5-(3'-chloro-5-fluoro-2-hydroxy-4'-(3-methyl-2-oxoimidazolidin-1-yl)-[1,1'-biphenyl]-3-yl)-3-(piperazin-1-yl)picolinate (18 mg, 0.033 mmol) and LiOH—H$_2$O (5.5 mg, 0.13 mmol) in 3 mL THF/MeOH/H$_2$O (1:1:1) was stirred at room temperature for 4 hours. The reaction mixture was dried under reduced pressure. The product was purified by prep-HPLC to afford the title compound (0.92 mg, 5% yield) as a yellow solid. $^1$H NMR (400 MHz, CD$_3$OD): 7.70 (s, 1H), 7.12 (s, 1H), 6.91 (d, J=4.0 Hz, 1H), 6.73 (dd, J=2.0, 7.6 Hz, 1H), 6.66 (d, J=8.0 Hz, 1H), 6.42-6.32 (m, 2H), 3.05-3.01 (m, 2H), 2.80 (t, J=8.8 Hz, 2H), 2.56 (s, 8H), 2.09 (s, 3H). N—H and O—H protons not observed. LCMS: 526.2 (M+H)⁺.

Example 399

1-(3-chloro-5'-fluoro-2'-hydroxy-3'-(6-(methoxymethyl)-5-(piperazin-1-yl)pyridin-3-yl)-[1,1'-biphenyl]-4-yl)-3-methylimidazolidin-2-one

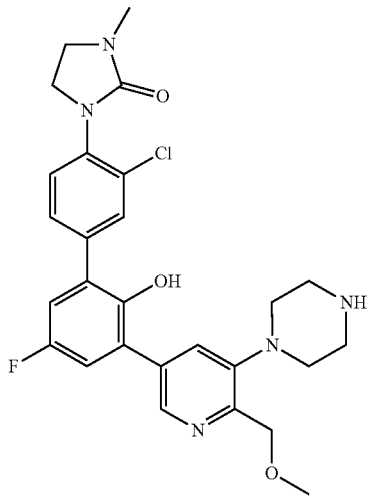

Step 1: tert-butyl 4-(5-bromo-2-(hydroxymethyl)pyridin-3-yl)piperazine-1-carboxylate A mixture of tert-butyl 4-(5-bromo-2-(methoxycarbonyl)pyridin-3-yl)piperazine-1-carboxylate (800 mg, 2.00 mmol), CaCl₂ (1.11 g, 10.0 mmol) and NaBH₄ (371 mg, 10.0 mmol) in a 20 mL mixture of 1:1 CH₃OH/THF was stirred at 0° C. for 4 hours. After the reaction was complete by LCMS, the reaction mixture was concentrated to give residue which was purified by silica gel chromatography using petroleum ether and ethyl acetate as the eluent to afford the title compound (464 mg, 63% yield) as a white solid. LCMS: 374.1 (M+H)⁺.

Step 2: tert-butyl 4-(5-bromo-2-(methoxymethyl)pyridin-3-yl)piperazine-1-carboxylate To a solution of tert-butyl 4-(5-bromo-2-(hydroxymethyl)pyridin-3-yl)piperazine-1-carboxylate (300 mg, 0.809 mmol) in DMF (10 mL) was added NaH (58.2 mg, 2.43 mmol, 60% wt. in mineral oil) at 0° C. After stirred at 0° C. for 30 minutes, CH₃I (230 mg, 1.62 mmol) was added. The reaction mixture was stirred at room temperature for another 2.5 hours under N₂ atmosphere. The reaction mixture was quenched with water (10 mL) and extracted with EA (15 mL×3). The combined organic layers were dried over sodium sulfate, filtered and concentrated. The residue was purified by chromatography on silica gel using petroleum ether and ethyl acetate as the eluent to afford the title compound (212 mg, 68% yield) as a yellow solid. LCMS: 388.1 (M+H)⁺.

Step 3: tert-butyl 4-(2-(methoxymethyl)-5-(4,4,5,5-tetramethyl-1,3,2-dioxaborolan-2-yl)pyridin-3-yl)piperazine-1-carboxylate The title compound was prepared following the procedure described for Example 398 using tert-butyl 4-(5-bromo-2-(methoxymethyl)pyridin-3-yl)piperazine-1-carboxylate and 4,4,4',4',5,5,5',5'-octamethyl-2,2'-bi(1,3,2-dioxaborolane) to afford the title compound (quant). LCMS: 434.2 (M+H)⁺.

Step 4: tert-butyl 4-(5-(3'-chloro-5-fluoro-2-hydroxy-4'-(3-methyl-2-oxoimidazolidin-1-yl)-[1,1'-biphenyl]-3-yl)-2-(methoxymethyl)pyridin-3-yl)piperazine-1-carboxylate The title compound was prepared following the procedure described for Example 398 using tert-butyl 4-(2-(methoxymethyl)-5-(4,4,5,5-tetramethyl-1,3,2-dioxaborolan-2-yl)pyridin-3-yl)piperazine-1-carboxylate and 1-(3'-bromo-3-chloro-5'-fluoro-2'-hydroxy-[1,1'-biphenyl]-4-yl)-3-methylimidazolidin-2-one to afford the title compound (58% yield). LCMS: 626.2 (M+H)⁺.

Step 5: 1-(3-chloro-5'-fluoro-2'-hydroxy-3'-(6-(methoxymethyl)-5-(piperazin-1-yl)pyridin-3-yl)-[1,1'-biphenyl]-4-yl)-3-methylimidazolidin-2-one The title compound was prepared following the procedure described for Example 398 using tert-butyl 4-(5-(3'-chloro-5-fluoro-2-hydroxy-4'-(3-methyl-2-oxoimidazolidin-1-yl)-[1,1'-biphenyl]-3-yl)-2-(methoxymethyl)pyridin-3-yl)piperazine-1-carboxylate and TFA to afford the title compound (49% yield) ¹H NMR (400 MHz, DMSO-d₆): 8.40 (d, J=2.0 Hz, 1H), 7.72 (d, J=2.0 Hz, 1H), 7.61 (d, J=2.0 Hz, 1H), 7.55 (dd, J=2.0, 8.4 Hz, 1H), 7.46 (d, J=8.0 Hz, 1H), 7.25-7.19 (m, 2H), 4.52 (m, 2H), 3.75-3.71 (m, 2H), 3.51-3.47 (m, 2H), 3.38 (s, 3H), 2.91-2.89 (m, 8H), 2.77 (s, 3H). N—H and O—H protons not observed. LCMS: 526.1 (M+H)⁺.

Example 400

1-(3-chloro-5,5'-difluoro-2'-hydroxy-3'-(2-(piperazin-1-yl)pyridin-4-yl)-[1,1'-biphenyl]-4-yl)-3-methylimidazolidin-2-one

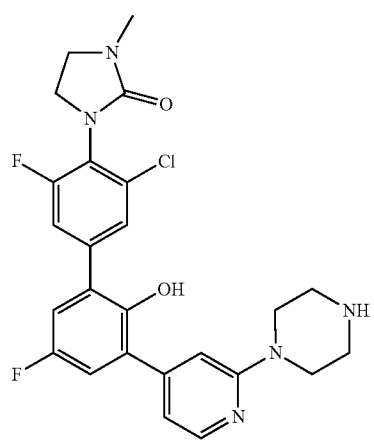 [SMILES: CN1CCN(c2c(F)cc(-c3cc(F)cc(-c4ccnc(N5CCNCC5)c4)c3O)cc2Cl)C1=O]

The title compound was prepared following the procedures described for Example 384 using 1-(4-bromo-2-chloro-6-fluorophenyl)-3-methylimidazolidin-2-one, tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate and BBr₃ to afford the title compound (41% yield). ¹H NMR (400 MHz, DMSO-d₆): 8.15 (d, J=5.2 Hz, 1H), 7.62-7.61 (m, 1H), 7.53 (dd, J=2.0, 10.8 Hz, 1H), 7.26

(dd, J=3.2, 8.8 Hz, 1H), 7.20 (dd, J=3.2, 8.8 Hz, 1H), 6.92 (s, 1H), 6.81 (dd, J=0.8, 4.8 Hz, 1H), 3.77-3.73 (m, 1H), 3.58-3.44 (m, 7H), 2.81-2.78 (m, 4H), 2.77 (s, 3H). N—H and O—H protons not observed. LCMS: 500.2 (M+H)+.

TABLE 26

Following compounds were prepared using similar procedures as described for Examples 163-400.

| Ex. No. | Name/Structure | $^1$H NMR Data | LCMS (M + H)+ |
|---|---|---|---|
| 401 | 5-(3'-chloro-5-fluoro-2-hydroxy-4'-(3-methyl-2-oxoimidazolidin-1-yl)-[1,1'-biphenyl]-3-yl)-1-methyl-1',2',3',6'-tetrahydro-[3,4'-bipyridin]-6(1H)-one | $^1$H NMR (400 MHz, DMSO-d$_6$ + D$_2$O): 8.11 (d, J = 2.0 Hz, 1H), 8.06 (d, J = 2.4 Hz, 1H), 7.72 (d, J = 2.0 Hz, 1H), 7.56 (dd, J = 2.0, 8.4 Hz, 1H), 7.45 (d, J = 8.4 Hz, 1H), 7.30-7.28 (m, 2H), 6.29 (s, 1H), 3.76-3.69 (m, 7H), 3.52-3.48 (m, 2H), 3.34 (t, J = 6.0 Hz, 2H), 2.77 (s, 3H), 2.66 (s, 2H). N—H and O—H protons not observed. | 509.3 |
| 402 | 1-(3,5-dichloro-5'-fluoro-2'-hydroxy-3'-(2-(piperazin-1-yl)pyridin-4-yl)-[1,1'-biphenyl]-4-yl)pyrrolidin-2-one | $^1$H NMR (400 MHz, DMSO-d$_6$): 8.14 (d, J = 5.6 Hz, 1H), 7.77 (s, 2H), 7.26 (dd, J = 2.8, 8.8 Hz, 1H), 7.21 (dd, J = 3.2, 8.8 Hz, 1H), 6.93 (s, 1H), 6.82 (dd, J = 1.2, 5.2 Hz, 1H), 3.65 (t, J = 6.8 Hz, 2H), 3.46-3.44 (m, 4H), 2.80-2.78 (m, 4H), 2.49-2.44 (m, 2H), 2.26-2.21 (m, 2H). N—H and O—H protons not observed. | 501.1 |
| 403 | 1-(3-chloro-5'-fluoro-2'-hydroxy-3'-(5-(piperazin-1-yl)-6-(prop-1-yn-1-yl)pyridin-3-yl)-[1,1'-biphenyl]-4-yl)-3-methylimidazolidin-2-one | $^1$H NMR (400 MHz, DMSO-d$_6$): 8.41 (d, J = 1.6 Hz, 1H), 7.79 (d, J = 1.6 Hz, 1H), 7.70 (d, J = 2.0 Hz, 1H), 7.52 (dd, J = 2.0, | 519.9 |

TABLE 26-continued

Following compounds were prepared using similar procedures as described for Examples 163-400.

| Ex. No. | Name/Structure | ¹H NMR Data | LCMS (M + H)⁺ |
|---|---|---|---|
| 404 | 1-(3,5-dichloro-5'-fluoro-2'-hydroxy-3'-(2-(piperazin-1-yl)pyridin-4-yl)-[1,1'-biphenyl]-4-yl)-3-methylimidazolidin-2-one 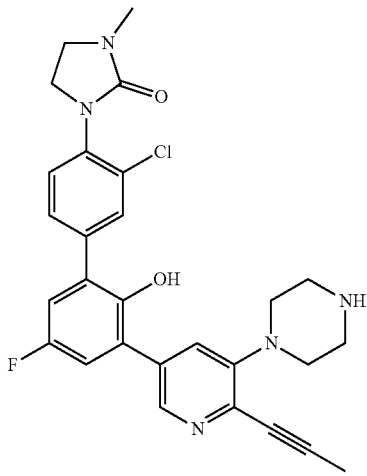 [SMILES: CC#Cc1ncc(-c2cc(F)cc(-c3ccc(N4CCN(C)C4=O)c(Cl)c3)c2O)cc1N1CCNCC1] | 8.4 Hz, 1H), 7.45 (d, J = 8.4 Hz, 1H), 7.19 (dd, J = 3.2, 8.4 Hz, 1H), 7.11 (dd, J = 3.2, 8.8 Hz, 1H), 3.85-3.81 (m, 2H), 3.62-3.60 (m, 2H), 3.54-3.43 (m, 8H), 2.89 (s, 3H), 2.22 (s, 3H). N—H and O—H protons not observed. ¹H NMR (400 MHz, DMSO-d₆): 8.89-8.87 (m, 3H), 8.21 (d, J = 5.2 Hz, 1H), 7.74 (s, 2H), 7.32 (dd, J = 2.8, 8.8 Hz, 1H), 7.27-7.24 (m, 1H), 7.10 (s, 1H), 6.98 (d, J = 4.8 Hz, 1H), 3.78 (s, 4H), 3.67-3.63 (m, 2H), 3.57-3.53 (m, 2H), 3.21 (s, 4H), 2.77 (s, 3H) | 516.2 |
| 405 | 1-(3-chloro-5'-fluoro-2'-hydroxy-3'-(6-((2-hydroxyethyl)amino)-5-(piperazin-1-yl)pyridin-3-yl)-[1,1'-biphenyl]-4-yl)-3-methylimidazolidin-2-one | ¹H NMR (400 MHz, DMSO-d₆): 7.94 (d, J = 2.0 Hz, 1H), 7.70 (d, J = 1.6 Hz, 1H), 7.53 (dd, J = 2.0, 8.0 Hz, 1H), 7.44 (d, J = | 541.2 |

TABLE 26-continued

Following compounds were prepared using similar procedures as described for Examples 163-400.

| Ex. No. | Name/Structure | $^1$H NMR Data | LCMS (M + H)$^+$ |
|---|---|---|---|
| | | 2.0 Hz, 1H), 7.35 (d, J = 2.0 Hz, 1H), 7.12-7.07 (m, 2H), 5.90 (t, J = 5.6 Hz, 1H), 4.80 (s, 1H), 3.72 (t, J = 7.6 Hz, 2H), 3.58-3.45 (m, 6H), 2.90-2.88 (m, 4H), 2.77 (s, 7H). N—H and O—H protons not observed | |
| 406 | 1-(2'-amino-3-chloro-5'-fluoro-3'-(2-(piperazin-1-yl)pyridin-4-yl)-[1,1'-biphenyl]-4-yl)-3-methylimidazolidin-2-one | $^1$H NMR (400 MHz, DMSO-d$_6$): 8.52-8.48 (br, 1H), 8.24 (d, J = 5.2 Hz, 1H), 7.62 (d, J = 1.6 Hz, 1H), 7.52-7.45 (m, 2H), 7.03-6.97 (m, 3H), 6.84 (dd, J = 0.8, 5.2 Hz, 1H), 4.36 (s, 2H), 3.77-3.71 (m, 6H), 3.51-3.47 (m, 2H), 3.17 (t, J = 4.8 Hz, 4H), 2.77 (s, 3H) | 481.2 |
| 407 | 1-(3-chloro-3'-(6-chloro-5-(piperazin-1-yl)pyridin-3-yl)-5'-fluoro-2'-hydroxy-[1,1'-biphenyl]-4-yl)-3-methylimidazolidin-2-one | $^1$H NMR (400 MHz, DMSO-d$_6$): 8.21 (d, J = 2.0 Hz, 1H), 7.72 (d, J = 2.0 Hz, 1H), 7.67 (d, J = 2.4 Hz, 1H), 7.55 (dd, J = 2.0, 8.0 Hz, 1H), 7.46 (d, J = 8.4 Hz, 1H), 7.29-7.22 (m, 2H), 3.75-3.71 (m, 2H), 3.51-3.47 (m, 2H), 3.01-2.99 (m, 4H), 2.90-2.88 (m, 4H), 2.77 (s, 3H). N—H and O—H protons not observed | 516.2 |

TABLE 26-continued

Following compounds were prepared using similar procedures as described for Examples 163-400.

| Ex. No. | Name/Structure | ¹H NMR Data | LCMS (M + H)⁺ |
|---|---|---|---|
| 408 | 1-(3,5-dichloro-5'-fluoro-2'-hydroxy-3'-(2-(piperazin-1-yl)pyridin-4-yl)-[1,1'-biphenyl]-4-yl)-3-methyl-1H-imidazol-2(3H)-one | ¹H NMR (400 MHz, DMSO-d₆): 8.15 (d, J = 5.2 Hz, 1H), 7.82 (s, 2H), 7.31 (dd, J = 3.2, 8.8 Hz, 1H), 7.23 (dd, J = 3.2, 8.8 Hz, 1H), 6.94 (s, 1H), 6.83 (d, J = 4.8 Hz, 1H), 6.75 (d, J = 3.2 Hz, 1H), 6.62 (d, J = 3.2 Hz, 1H), 3.48-3.46 (m, 4H), 3.22 (s, 3H), 2.82-2.80 (m, 4H). N—H and O—H protons not observed | 514.2 |

Example 409

1-(3-chloro-5'-fluoro-2'-hydroxy-3'-(2-(piperazin-1-yl)pyridin-4-yl)-[1,1'-biphenyl]-4-yl)-3-(trideuteromethyl)-1H-imidazol-2(3H)-one

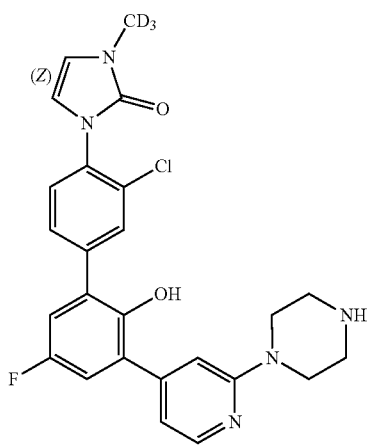 [SMILES: [2H]C([2H])([2H])n1ccn(-c2ccc(-c3cc(F)cc(-c4ccnc(N5CCNCC5)c4)c3O)cc2Cl)c1=O]

The title compound was prepared following the procedures described for Example 365 using 1-(4-bromo-2-chlorophenyl)-1H-imidazol-2(3H)-one, CD₃I, tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate and BBr₃ to afford the title compound (2.9% yield). ¹H NMR (400 MHz, DMSO-d₆): 8.15 (d, J=5.2 Hz, 1H), 7.80 (d, J=1.6 Hz, 1H), 7.61 (dd, J=2.0, 8.4 Hz, 1H), 7.52 (d, J=8.0 Hz, 1H), 7.25-7.18 (m, 2H), 6.93 (s, 1H), 6.82 (dd, J=1.2, 7.6 Hz, 1H), 6.71 (d, J=3.2 Hz, 1H), 6.68 (d, J=2.8 Hz, 1H), 3.47-3.45 (m, 4H), 2.82-2.79 (m, 4H). N—H and O—H protons not observed. LCMS: 483.2 (M+H)⁺.

Example 411

(S)-1-(3'-(2-(3-aminopiperidin-1-yl)pyridin-4-yl)-3-chloro-5'-fluoro-2'-hydroxy-[1,1'-biphenyl]-4-yl)-3-methyl-1H-imidazol-2(3H)-one

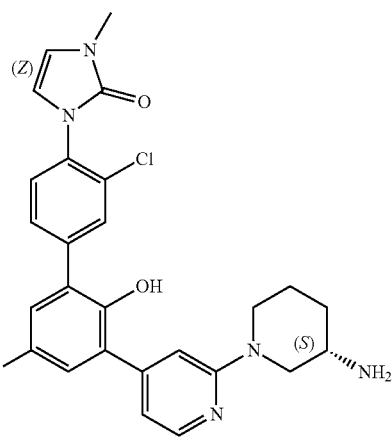

The title compound was prepared following the procedure described for Example 365 using 1-(3-chloro-5'-fluoro-3'-(2-fluoropyridin-4-yl)-2'-methoxy-[1,1'-biphenyl]-4-yl)-3-methyl-1H-imidazol-2(3H)-one and (S)-tert-butyl piperidin-3-ylcarbamate and BBr₃ to afford the title compound (26% yield). ¹H NMR (400 MHz, DMSO-d₆): 8.11 (d, J=5.2 Hz, 1H), 7.81 (d, J=1.6 Hz, 1H), 7.62 (dd, J=2.0, 8.0 Hz, 1H), 7.51 (d, J=8.4 Hz, 1H), 7.25-7.16 (m, 2H), 6.94 (s, 1H), 6.77-6.68 (m, 3H), 4.25 (d, J=12.0 Hz, 1H), 4.17 (d, J=12.8 Hz, 1H), 3.21 (s, 3H), 2.80 (t, J=11.6 Hz, 1H), 2.68-2.66 (m, 1H), 2.59-2.53 (m, 1H), 1.88-1.85 (m, 1H), 1.71-1.67 (m, 1H), 1.49-1.40 (m, 1H), 1.27-1.94 (m, 1H). N—H and O—H protons not observed. LCMS: 494.2 (M+H)+.

Example 412

1-(3-chloro-5'-fluoro-2'-hydroxy-3'-(2-(piperazin-1-yl)pyridin-4-yl)-[1,1'-biphenyl]-4-yl)-3-deuteromethylimidazolidin-2-one

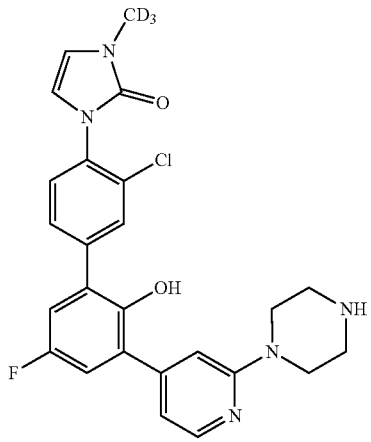 [SMILES: [2H]C([2H])([2H])n1ccn(-c2ccc(-c3cc(F)cc(-c4ccnc(N5CCNCC5)c4)c3O)cc2Cl)c1=O]

The title compound was prepared following the procedure described for Example 379 using tert-butyl 4-(4-(3'-chloro-5-fluoro-2-methoxy-4'-(2-oxoimidazolidin-1-yl)-[1,1'-biphenyl]-3-yl)pyridin-2-yl)piperazine-1-carboxylate and CD₃I to BBr₃ to afford the title compound (15% yield). ¹H NMR (400 MHz, DMSO-d₆): 8.15 (d, J=5.2 Hz, 1H), 7.71 (d, J=2.0 Hz, 1H), 7.54 (dd, J=2.0, 8.4 Hz, 1H), 7.45 (d, J=8.4 Hz, 1H), 7.22-7.15 (m, 2H), 6.92 (s, 1H), 6.81 (dd, J=0.8, 5.2 Hz, 1H), 3.75-3.71 (m, 2H), 3.50-3.44 (m, 6H), 2.80 (t, J=4.8 Hz, 4H). N—H and O—H protons not observed. LCMS: 485.2 (M+H)+.

Example 413

(R)-1-(3-chloro-5'-fluoro-2'-hydroxy-3'-(2-(3-methylpiperazin-1-yl)pyridin-4-yl)-[1,1'-biphenyl]-4-yl)-3-methyl-1H-imidazol-2(3H)-one

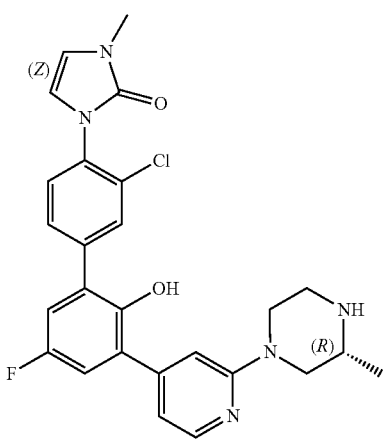

The title compound was prepared following the procedure described for Example 365 using 1-(3-chloro-5'-fluoro-3'-(2-fluoropyridin-4-yl)-2'-methoxy-[1,1'-biphenyl]-4-yl)-3-methyl-1H-imidazol-2(3H)-one, (R)-tert-butyl 2-methylpiperazine-1-carboxylate and BBr₃ to afford the title compound (33% yield).
¹H NMR (400 MHz, DMSO-d₆): 8.14 (d, J=5.2 Hz, 1H), 7.80 (d, J=2.0 Hz, 1H), 7.61 (dd, J=2.0, 8.4 Hz, 1H), 7.52 (d, J=8.0 Hz, 1H), 7.26-7.17 (m, 2H), 6.93 (s, 1H), 6.81 (dd, J=0.8, 4.8 Hz, 1H), 6.72 (d, J=3.2 Hz, 1H), 6.68 (d, J=2.8 Hz, 1H), 4.19-4.14 (m, 2H), 3.21 (s, 3H), 2.97-2.95 (m, 1H), 2.74-2.67 (m, 3H), 2.36 (t, J=12.0 Hz, 1H), 1.03 (d, J=6.4 Hz, 3H). N—H and O—H protons not observed. LCMS: 494.2 (M+H)+.

Example 414

1-(3'-(2-(4-aminopiperidin-1-yl)pyridin-4-yl)-3-chloro-5'-fluoro-2'-hydroxy-[1,1'-biphenyl]-4-yl)-3-methyl-1H-imidazol-2(3H)-one

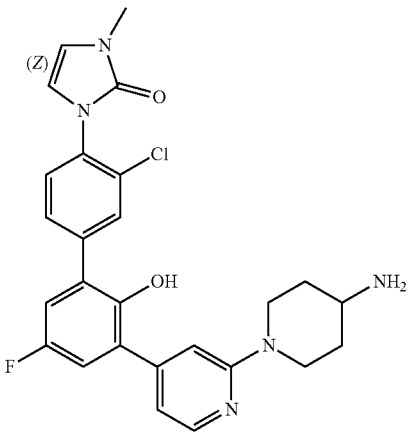 [SMILES: Cn1ccn(-c2ccc(-c3cc(F)cc(-c4ccnc(N5CCC(N)CC5)c4)c3O)cc2Cl)c1=O]

Step 1: 1,3-dibromo-5-fluoro-2-methoxybenzene

A solution of 2,6-dibromo-4-fluorophenol (30.0 g, 111 mmol), CH₃I (19.0 g, 133 mmol) and K₂CO₃ (30.0 g, 222 mmol) in acetone (150 mL) was stirred at 60° C. for 3 hours. After the reaction was complete by LCMS, the reaction mixture was cooled and concentrated. The residue was diluted with water (100 mL) and extracted with EA ((100 mL×3). The combined organic layer was washed with brine, dried over Na₂SO₄, filtered and concentrated to afford the title compound (32 g, 98% yield) as a brown solid. LCMS: 283.1 (M+H)+.

Step 2: 1-(2-chloro-4-(4,4,5,5-tetramethyl-1,3,2-dioxaborolan-2-yl)phenyl)-3-methyl-1H-imidazol-2(3H)-one The title compound was prepared following the procedure described for Example 365 using 1-(4-bromo-2-chlorophenyl)-3-methyl-1H-imidazol-2(3H)-one and 4,4,4',4',5,5,5',5'-octamethyl-2,2'-bi(1,3,2-dioxaborolane) to afford the title compound (76% yield). LCMS: 335.1 (M+H)+.

Step 3: 1-(3'-bromo-3-chloro-5'-fluoro-2'-methoxy-[1,1'-biphenyl]-4-yl)-3-methyl-1H-imidazol-2(3H)-one The title compound was prepared following the procedure described for Example 365 using 1-(2-chloro-4-(4,4,5,5- tetramethyl-1,3,2-dioxaborolan-2-yl)phenyl)-3-methyl-1H-imidazol-2(3H)-one and 1,3-dibromo-5-fluoro-2-methoxybenzene to afford the title compound (52% yield). LCMS: 411.0 (M+H)+.

Step 4: 1-(3-chloro-5'-fluoro-3'-(2-fluoropyridin-4-yl)-2'-methoxy-[1,1'-biphenyl]-4-yl)-3-methyl-1H-imidazol-2(3H)-one The title compound was prepared following the procedure described for Example 365 using 1-(3'-bromo-3-chloro-5'-fluoro-2'-methoxy-[1,1'-biphenyl]-4-yl)-3-methyl-1H-imidazol-2(3H)-one and (2-fluoropyridin-4-yl)boronic acid to afford the title compound (76% yield). LCMS: 428.1 (M+H)+.

Step 5: tert-butyl (1-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperidin-4-yl)carbamate The title compound was prepared following the procedure described for Example 163 using 1-(3-chloro-5'-fluoro-3'-(2-fluoropyridin-4-yl)-2'-methoxy-[1,1'-biphenyl]-4-yl)-3-methyl-1H-imidazol-2(3H)-one and tert-butyl piperidin-4-ylcarbamate to afford the title compound (68% yield). LCMS: 608.3 (M+H)+.

Step 6: 1-(3'-(2-(4-aminopiperidin-1-yl)pyridin-4-yl)-3-chloro-5'-fluoro-2'-hydroxy-[1,1'-biphenyl]-4-yl)-3-methyl-1H-imidazol-2(3H)-one The title compound was prepared following the procedure described for Example 365 using tert-butyl (1-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperidin-4-yl)carbamate and BBr₃ to afford the title compound (31% yield). ¹H NMR (400 MHz, DMSO-d): 8.12 (d, J=4.8 Hz, 1H), 7.84 (d, J=1.6 Hz, 1H), 7.62 (dd, J=2.0, 8.4 Hz, 1H), 7.50 (d, J=8.0 Hz, 1H), 7.23-7.16 (m, 2H), 7.00 (s, 1H), 6.79 (dd, J=1.2, 5.2 Hz, 1H), 6.70 (d, J=3.2 Hz, 1H), 6.68 (d, J=3.2 Hz, 1H), 4.25-4.22 (m, 2H), 3.21 (s, 3H), 2.92-2.82 (m, 3H), 1.76 (d, J=10.0 Hz, 2H), 1.24-1.20 (m, 2H). N—H and O—H protons not observed. LCMS: 494.2 (M+H)+.

TABLE 27

Following compounds were prepared using similar procedures as described for Examples 163-414.

| Ex. No. | Name/Structure | ¹H NMR Data | LCMS (M + H)+ |
|---|---|---|---|
| 415 | 1-(3-chloro-5'-fluoro-2'-hydroxy-3'-(6-morpholino-5-(piperazin-1-yl)pyridin-3-yl)-[1,1'-biphenyl]-4-yl)-3-methylimidazolidin-2-one | ¹H NMR (400 MHz, CD₃OD): 8.18 (d, J = 2.0 Hz, 1H), 7.72 (d, J = 2.0 Hz, 1H), 7.60 (d, J = 2.0 Hz, 1H), 7.54 (dd, J = 2.0, 8.0 Hz, 1H), 7.46 (d, J = 8.0 Hz, 1H), 7.12-7.05 (m, 2H), 3.89-3.83 (m, 6H), 3.64-3.60 (m, 2H), 3.52-3.50 (m, 4H), 3.44 (s, 8H), 2.91 (s, 3H). N—H and O—H protons not observed | 567.3 |
| 416 | 1-(3-chloro-5'-fluoro-2'-hydroxy-3'-(5-morpholino-3-(piperazin-1-yl)pyridin-2-yl)-[1,1'-biphenyl]-4-yl)-3-methylimidazolidin-2-on | ¹H NMR (400 MHz, CD₃OD): 8.29 (s, 1H), 8.10 (d, J = 1.6 Hz, 1H), 7.71 (d, J = 2.0 Hz, 1H), | 567.3 |

TABLE 27-continued

Following compounds were prepared using similar procedures as described for Examples 163-414.

| Ex. No. | Name/Structure | ¹H NMR Data | LCMS (M + H)⁺ |
|---|---|---|---|
|  | 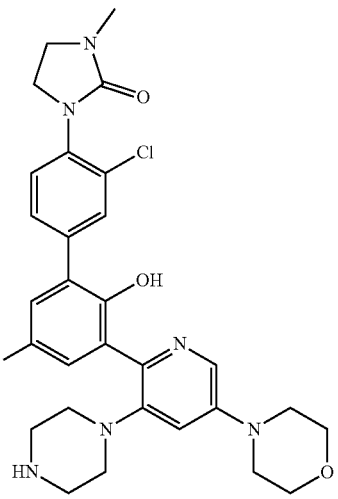 | 7.52-7.48 (m, 2H), 7.22 (dd, J = 2.8, 8.4 Hz, 1H), 7.14 (dd, J = 2.8, 8.4 Hz, 1H), 4.82-4.76 (m, 3H), 4.18-4.13 (m, 4H), 3.91-3.84 (m, 5H), 3.65-3.61 (m, 3H), 3.51-3.47 (m, 5H), 2.92 (s, 3H). N—H and O—H protons not observed |  |
| 417 | 1-(3-chloro-5'-fluoro-2'-hydroxy-3'-(2-(piperazin-1-yl)pyridin-4-yl)-[1,1'-biphenyl]-4-yl)azetidin-2-one 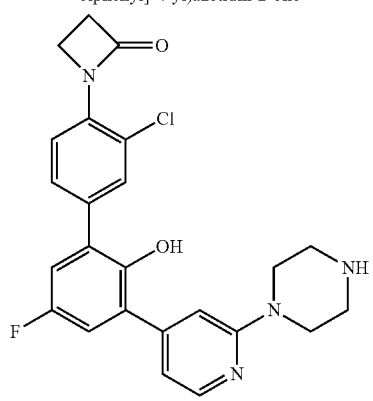 | ¹H NMR (400 MHz, DMSO-d₆): 8.14 (d, J = 5.2 Hz, 1H), 7.90 (d, J = 8.4 Hz, 1H), 7.68 (d, J = 2.0 Hz, 1H), 7.53 (dd, J = 1.6, 8.4 Hz, 1H), 7.20-7.14 (m, 2H), 6.91 (s, 1H), 6.81 (d, J = 5.2 Hz, 1H), 3.99 (t, J = 4.4 Hz, 2H), 3.47-3.45 (m, 4H), 3.16 (t, J = 4.4 Hz, 2H), 2.81 (t, J = 4.8 Hz, 4H). N—H and O—H protons not observed | 453.2 |
| 418 | 1-(3-chloro-5'-fluoro-2'-hydroxy-5-isopropoxy-3'-(2-(piperazin-1-yl)pyridin-4-yl)-[1,1'-biphenyl]-4-yl)-3-methylimidazolidin-2-one 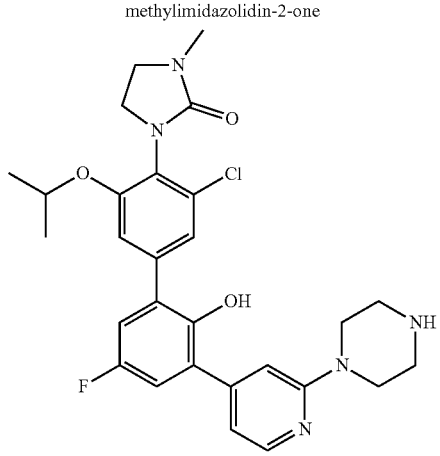 | ¹H NMR (400 MHz, DMSO-d₆): 8.92 (s, 2H), 8.90 (brs, 1H), 8.21 (d, J = 5.2 Hz, 1H), 7.28-7.18 (m, 4H), 7.09 (s, 1H), 6.99 (dd, J = 0.8, 5.2 Hz, 1H), 4.72-4.66 (m, 1H), 3.78 (t, J = 4.8 Hz, 4H), 3.64-3.58 (m, 1H), 3.53-3.44 (m, 3H), 3.21 (s, 4H), 2.74 (s, 3H), 1.27 (dd, J = 6.0, 8.8 Hz, 6H) | 540.3 |

TABLE 27-continued

Following compounds were prepared using similar procedures as described for Examples 163-414.

| Ex. No. | Name/Structure | ¹H NMR Data | LCMS (M + H)⁺ |
|---|---|---|---|
| 420 | 1-(3-chloro-2'-hydroxy-5'-methyl-3'-(2-(piperazin-1-yl)pyridin-4-yl)-[1,1'-biphenyl]-4-yl)-3-methyl-1H-imidazol-2(3H)-one 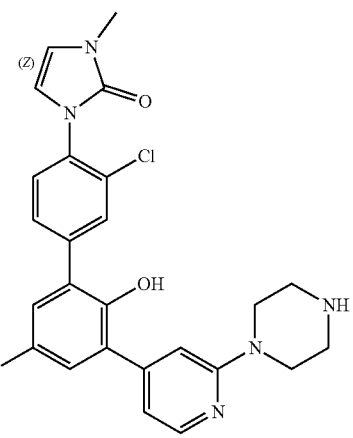 | ¹H NMR (400 MHz, DMSO-d₆): 8.12 (d, J = 5.2 Hz, 1H), 7.74 (d, J = 2.0 Hz, 1H), 7.58-7.56 (m, 1H), 7.49 (d, J = 8.0 Hz, 1H), 7.15 (d, J = 1.6 Hz, 1H), 7.11 (d, J = 1.6 Hz, 1H), 6.87 (s, 1H), 6.78 (d, J = 5.2 Hz, 1H), 6.71 (d, J = 2.8 Hz, 1H), 6.68 (d, J = 3.2 Hz, 1H), 3.44-3.41 (m, 4H), 3.21 (s, 3H), 2.78 (s, 4H), 2.30 (s, 3H). N—H and O—H protons not observed | 476.2 |
| 421 | 1-(3-chloro-5'-fluoro-2'-hydroxy-3'-(6-((4-hydroxycyclohexyl)oxy)-5-(piperazin-1-yl)pyridin-3-yl)-[1,1'-biphenyl]-4-yl)-3-methylimidazolidin-2-one 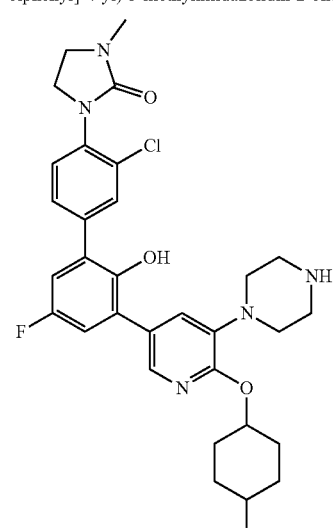 | ¹H NMR (400 MHz, DMSO-d₆): 7.84 (d, J = 2.0 Hz, 1H), 7.71 (d, J = 2.0 Hz, 1H), 7.54 (dd, J = 2.0, 8.4 Hz, 1H), 7.45 (d, J = 8.4 Hz, 1H), 7.29 (s, 1H), 7.16 (s, 1H), 7.13 (s, 1H), 5.21 (s, 1H), 4.55 (d, J = 4.0 Hz, 1H), 3.74-3.71 (m, 2H), 3.60-3.58 (m, 1H), 3.51-3.46 (m, 2H), 3.02 (s, 4H), 2.88 (s, 4H), 2.77 (s, 3H), 1.92-1.90 (m, 2H), 1.66-1.56 (m, 6H). N—H and O—H protons not observed | 596.3 |
| 422 | (S)-3-(3-aminopyrrolidin-1-yl)-5-(3'-chloro-5'-fluoro-2-hydroxy-4'-(3-methyl 2-oxo-2,3-dihydro-1H-imidazol-1-yl)-[1,1'-biphenyl]-3-yl)-1-methylpyridin-2(1H)-one | ¹H NMR (400 MHz, DMSO-d₆ + D₂O): 7.80 (d, J = 1.6 Hz, 1H), 7.61 (dd, J = 2.4, 8.4 Hz, 1H), 7.52 (d, J = 8.4 Hz, 1H), 7.43 (d, | 510.2 |

TABLE 27-continued

Following compounds were prepared using similar procedures as described for Examples 163-414.

| Ex. No. | Name/Structure | ¹H NMR Data | LCMS (M + H)⁺ |
|---|---|---|---|
| | 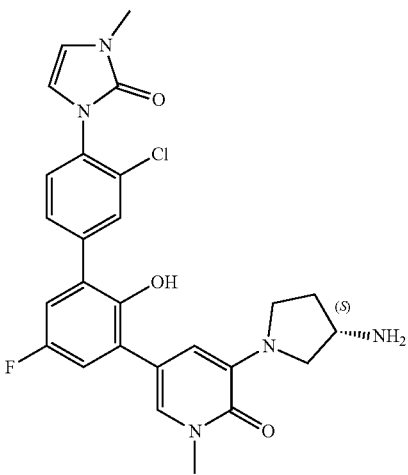 | J = 2.4 Hz, 1H), 7.18-7.13 (m, 2H), 7.72 (d, J = 3.2 Hz, 1H), 6.68 (d, J = 2.8 Hz, 1H), 6.66 (d, J = 2.0 Hz, 1H), 3.83-3.81 (m, 1H), 3.65-3.55 (m, 3H), 3.50 (s, 3H), 3.26-3.22 (m, 4H), 2.33-2.24 (m, 1H), 1.97-1.88 (m, 1H). N—H and O—H protons not observed | |
| 423 | (S)-1-(3'-(2-(3-aminopyrrolidin-1-yl)pyridin-4-yl)-3-chloro-5'-fluoro-2'-hydroxy-[1,1'-biphenyl]-4-yl)-3-methyl-1H-imidazol-2(3H)-one<br>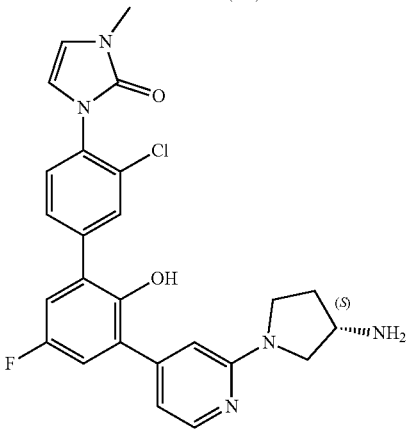 | ¹H NMR (400 MHz, DMSO-d₆ + D₂O): 8.12 (d, J = 5.2 Hz, 1H), 7.80 (d, J = 1.6 Hz, 1H), 7.62 (dd, J = 1.6, 8.0 Hz, 1H), 7.53 (d, J = 8.4 Hz, 1H), 7.25 (dd, J = 3.2, 9.2 Hz, 1H), 7.18 (dd, J = 3.2, 8.8 Hz, 1H), 6.80 (dd, J = 1.2, 5.2 Hz, 1H), 6.72 (d, J = 2.8 Hz, 1H), 6.68 (d, J = 3.2 Hz, 1H), 6.63 (s, 1H), 3.85-3.80 (m, 1H), 3.71-3.67 (m, 2H), 3.51-3.40 (m, 2H), 3.22 (s, 3H), 2.31-2.24 (m, 1H), 2.02-1.95 (m, 1H). N—H and O—H protons not observed | 480.2 |
| 424 | 1-(3-chloro-5'-fluoro-2'-hydroxy-3'-(7-(piperazin-1-yl)-1H-indazol-5-yl)-[1,1'-biphenyl]-4-yl)-3-methylimidazolidin-2-one | ¹H NMR (400 MHz, DMSO-d₆): 13.25 (s, 1H), 8.73-8.71 (m, 2H), 8.41 (s, 1H), 8.15 (s, 1H), 7.74 (d, J = 1.6 Hz, 1H), 7.60-7.55 (m, 2H), 7.46 (d, J = 8.0 Hz, 1H), 7.18-7.14 (m, 2H), 7.00 (s, 1H), 3.75-3.71 (m, 2H), 3.60-3.49 (m, 10H), 2.77 (s, 3H). N—H and O—H protons not observed | 521.3 |

TABLE 27-continued

Following compounds were prepared using similar procedures as described for Examples 163-414.

| Ex. No. | Name/Structure | ¹H NMR Data | LCMS (M + H)⁺ |
|---|---|---|---|
| 425 | (S)-3-(3-aminopiperidin-1-yl)-5-(3'-chloro-5-fluoro-2-hydroxy-4'-(3-methyl-2-oxo-2,3-dihydro-1H-imidazol-1-yl)-[1,1'-biphenyl]-3-yl)-1-methylpyridin-2(1H)-one 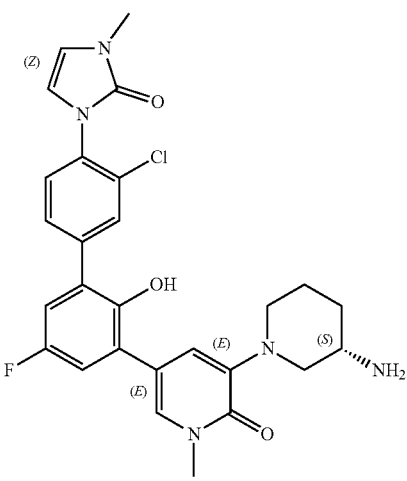 | ¹H NMR (400 MHz, DMSO-d₆): 7.80 (d, J = 2.0 Hz, 1H), 7.62-7.57 (m, 2H), 7.51 (d, J = 8.4 Hz, 1H), 7.17-7.14 (m, 2H), 6.89 (d, J = 2.0 Hz, 1H), 6.71 (d, J = 3.2 Hz, 1H), 6.68 (d, J = 3.2 Hz, 1H), 3.56-3.48 (m, 6H), 3.32 (s, 3H), 2.87-2.84 (m, 1H), 2.33-2.30 (m, 1H), 1.85-1.83 (m, 1H), 1.73-1.70 (m, 1H), 1.58-1.54 (m, 1H), 1.18-1.15 (m, 1H). N—H and O—H protons not observed | 524.2 |
| 426 | 5-chloro-5'-fluoro-2'-hydroxy-4-(3-methyl-2-oxoimidazolidin-1-yl)-3'-(2-(piperazin-1-yl)pyridin-4-yl)-[1,1'-biphenyl]-3-carbonitrile 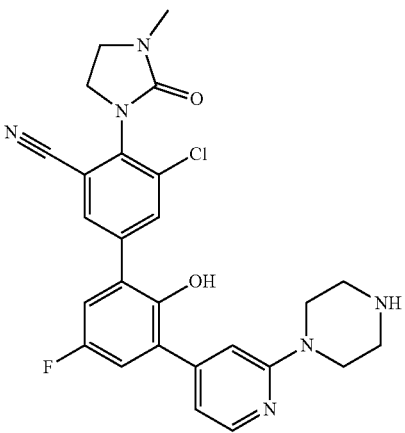 [SMILES: CN1CCN(c2c(Cl)cc(-c3cc(F)cc(-c4ccnc(N5CCNCC5)c4)c3O)cc2C#N)C1=O] | ¹H NMR (400 MHz, DMSO-d₆): 8.15-8.08 (m, 3H), 7.32 (dd, J = 3.2, 8.8 Hz, 1H), 7.22 (dd, J = 3.2, 9.2 Hz, 1H), 6.95 (s, 1H), 6.82 (dd, J = 0.8, 5.2 Hz, 1H), 3.83-3.79 (m, 1H), 3.69-3.65 (m, 1H), 3.60-3.55 (m, 2H), 3.46-3.43 (m, 4H), 2.79-2.78 (m, 7H). N—H and O—H protons not observed | 507.2 |
| 427 | 3-(4-aminopiperidin-1-yl)-5-(3'-chloro-5-fluoro-2-hydroxy-4'-(3-methyl-2-oxo-2,3-dihydro-1H-imidazol-1-yl)-[1,1'-biphenyl]-3-yl)-1-methylpyridin-2(1H)-one | ¹H NMR (400 MHz, DMSO-d₆ + D₂O): 7.80 (d, J = 2.0 Hz, 1H), 7.62-7.59 (m, 2H), 7.52 (d, J = 8.4 | 524.2 |

TABLE 27-continued

Following compounds were prepared using similar procedures as described for Examples 163-414.

| Ex. No. | Name/Structure | $^1$H NMR Data | LCMS (M + H)$^+$ |
|---|---|---|---|
| | 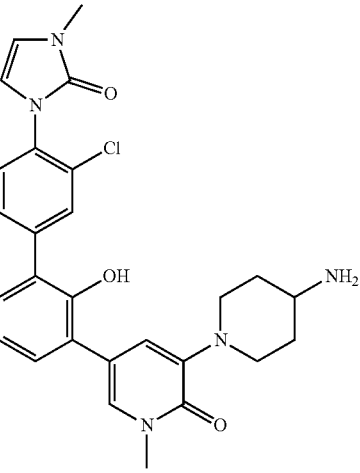 | Hz, 1H), 7.18-7.15 (m, 2H), 6.96 (d, J = 2.0 Hz, 1H), 6.72 (d, J = 3.2 Hz, 1H), 6.68 (d, J = 2.8 Hz, 1H), 3.76 (s, 1H), 3.72 (s, 1H), 3.49 (s, 3H), 3.24-3.13 (m, 4H), 2.58-2.55 (m, 2H), 1.97-1.95 (m, 2H), 1.69-1.61 (m, 2H). N—H and O—H protons not observed | |
| 428 | 1-(3-chloro-5'-fluoro-2'-hydroxy-3'-(6-(2-hydroxyethyl)-5-(piperazin-1-yl)pyridin-3-yl)-[1,1'-biphenyl]-4-yl)-3-methylimidazolidin-2-one 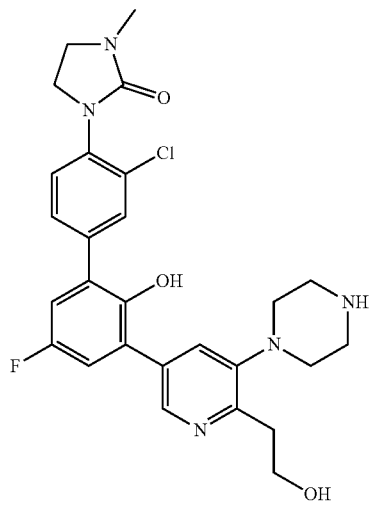 [SMILES: CN1CCN(c2ccc(-c3cc(F)cc(-c4cnc(CCO)c(N5CCNCC5)c4)c3O)cc2Cl)C1=O] | $^1$H NMR (400 MHz, CD$_3$OD): 8.30 (d, J = 2.0 Hz, 1H), 7.67 (d, J = 2.0 Hz, 1H), 7.61 (d, J = 2.0 2H), 3.88 (t, J = 6.8 Hz, 2H), 3.75-3.71 (m, 2H), 3.52-3.48 (m, 2H), 3.07-3.03 (m, 2H), 2.97-2.89 (m, 8H), 2.79 (s, 3H). N—H and O—H protons not observed | 525.9 |
| 429 | S)-1-(3-chloro-5'-fluoro-2'-hydroxy-3'-(2-(3-(methylamino)pyrrolidin-1-yl)pyridin-4-yl)-[1,1'-biphenyl]-4-yl)-3-methyl-1H-imidazol-2(3H)-one | $^1$H NMR (400 MHz, DMSO-d$_6$ +D$_2$O): 8.11 (d, J = 6.4 Hz, 1H), 7.82 (d, J = 2.0 Hz, 1H), 7.63 (dd, J = | 494.2 |

TABLE 27-continued

Following compounds were prepared using similar procedures as described for Examples 163-414.

| Ex. No. | Name/Structure | $^1$H NMR Data | LCMS $(M + H)^+$ |
|---|---|---|---|
| | 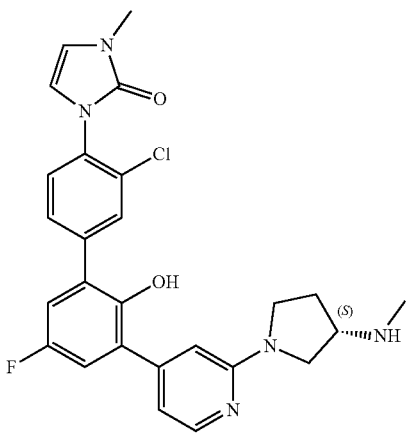 | 2.0, 8.4 Hz, 1H), 7.55 (d, J = 8.0 Hz, 1H), 7.38-7.32 (m, 2H), 7.13-7.09 (m, 2H), 6.73 (d, J = 3.2 Hz, 1H), 6.68 (d, J = 2.8 Hz, 1H), 3.40-3.96 (m, 1H), 3.91-3.87 (m, 1H), 3.80-3.76 (m, 1H), 3.74-3.69 (m, 1H), 3.77-3.51 (m, 1H), 3.22 (s, 3H), 2.68 (s, 3H), 2.48-2.41 (m, 1H), 2.31-2.25 (m, 1H). N—H and O—H protons not observed | |
| 430 | 1-(3-chloro-5'-fluoro-2'-hydroxy-3'-(2-(4-methylpiperazin-1-yl)pyridin-4-yl)-[1,1'-biphenyl]-4-yl)-3-methyl-1H-imidazol-2(3H)-one<br>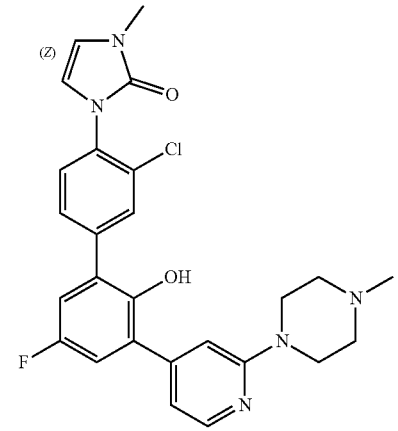 [SMILES: CN1CCN(c2cc(-c3cc(F)cc(-c4ccc(-n5ccn(C)c5=O)c(Cl)c4)c3O)ccn2)CC1] | $^1$H NMR (400 MHz, DMSO-d$_6$ + D$_2$O): 8.16 (d, J = 5.2 Hz, 1H), 7.81 (d, J = 2.0 Hz, 1H), 7.62 (dd, J = 1.6, 8.4 Hz, 1H), 7.53-7.51 (m, 1H), 7.25-7.18 (m, 2H), 6.95 (s, 1H), 6.85 (d, J = 5.2 Hz, 1H), 6.70 (dd, J = 6.8, 13.2 Hz, 2H), 3.53-3.51 (m, 4H), 3.22 (s, 3H), 2.43-2.41 (m, 4H), 2.22 (s, 3H). N—H and O—H protons not observed | 494.2 |
| 431 | 5-(5-fluoro-2-hydroxy-3-(2-(piperazin-1-yl)pyridin-4-yl)phenyl)-1H-benzo[d]imidazol-2(3H)-one<br>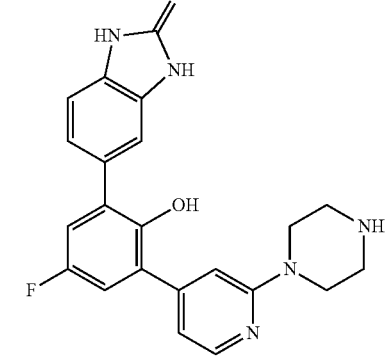 | $^1$H NMR (400 MHz, D$_2$O): 7.99 (d, J = 6.8 Hz, 1H), 7.34 (d, J = 6.0 Hz, 1H), 7.21-7.06 (m, 6H), 3.90-3.88 (m, 4H), 3.44-3.42 (m, 4H). N—H and O—H protons not observed | 406.2 |
| 432 | (R)-5-(3'-chloro-5-fluoro-2-hydroxy-4'-(3-methyl-2-oxo-2,3-dihydro-1H-imidazol-1-yl)-[1,1'-biphenyl]-3-yl)-1-methyl-3-(3-methylpiperazin-1-yl)pyridin-2(1H)-one | $^1$H NMR (400 MHz, CD$_3$OD): 7.70 (d, J = 2.0 Hz, 1H), 7.51-7.39 (m, 3H), 7.02-6.94 (m, 3H), 6.57-6.53 (m, 2H), 3.54- | 524.2 |

TABLE 27-continued

Following compounds were prepared using similar procedures as described for Examples 163-414.

| Ex. No. | Name/Structure | $^1$H NMR Data | LCMS $(M + H)^+$ |
|---|---|---|---|
| | 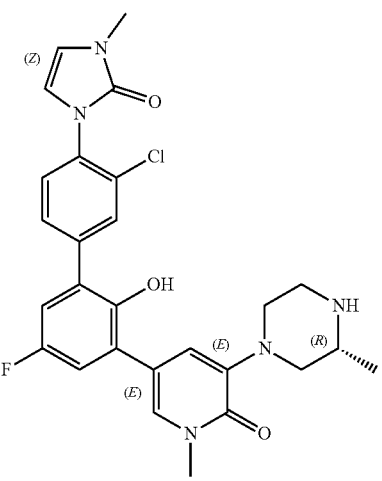 | 3.51 (m, 5H), 3.25 (s, 3H), 2.99-2.95 (m, 3H), 2.58-2.47 (m, 1H), 2.17-2.14 (m, 1H), 1.03 (d, J = 6.8 Hz, 3H). N—H and O—H protons not observed | |
| 433 | N-(4-(3'-chloro-5-fluoro-2-hydroxy-4'-(3-methyl-2-oxoimidazolidin-1-yl)-[1,1'-biphenyl]-3-yl)-6-(piperazin-1-yl)pyridin-2-yl)acetamide<br>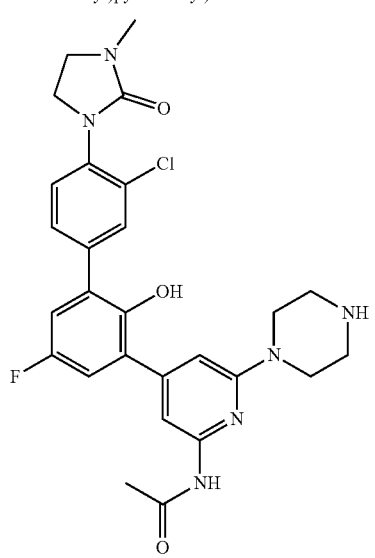 | $^1$H NMR (400 MHz, DMSO-d$_6$ + D$_2$O): 7.71 (d, J = 1.2 Hz, 1H), 7.57-7.53 (m, 2H), 7.48-7.46 (m, 1H), 7.21 (dd, J = 3.2, 9.2 Hz, 1H), 7.12 (dd, J = 3.2, 8.4 Hz, 1H), 6.72 (s, 1H), 3.81-3.69 (m, 6H), 3.53-3.49 (m, 2H), 3.20-3.16 (m, 4H), 2.78 (s, 3H), 2.07 (s, 3H). N—H and O—H protons not observed | 539.3 |
| 434 | 1-(3-chloro-5'-fluoro-2'-hydroxy-5-isopropoxy-3'-(2-(piperazin-1-yl)pyridin-4-yl)-[1,1'-biphenyl]-4-yl)-3-methyl-1H-imidazol-2(3H)-one | $^1$H NMR (400 MHz, DMSO-d$_6$): 8.15 (d, J = 4.8 Hz, 1H), 7.33 (d, J = 1.2 Hz, 1H), 7.27-7.24 (m, | 538.3 |

TABLE 27-continued

Following compounds were prepared using similar procedures as described for Examples 163-414.

| Ex. No. | Name/Structure | ¹H NMR Data | LCMS (M + H)⁺ |
|---|---|---|---|
| | | 2H), 7.19 (dd, J = 3.6, 9.2 Hz, 1H), 6.92 (s, 1H), 6.84-6.82 (m, 1H), 6.65 (d, J = 2.8 Hz, 1H), 6.45-6.43 (m, 1H), 4.69-4.63 (m, 1H), 3.51-3.45 (m, 4H), 3.19 (s, 3H), 2.81-2.77 (m, 4H), 1.23-1.16 (m, 6H). N—H and O—H protons not observed | |

Example 436

1-(3-chloro-5,5'-difluoro-2'-hydroxy-3'-(2-(piperazin-1-yl)pyridin-4-yl)-[1,1'-biphenyl]-4-yl)-3-methyl-1H-imidazol-2(3H)-one

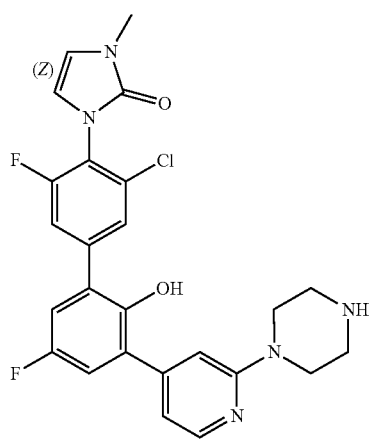 [SMILES: Cn1ccn(-c2c(F)cc(-c3cc(F)cc(-c4ccnc(N5CCNCC5)c4)c3O)cc2Cl)c1=O]

The title compound was prepared following the procedures described for Example 365 using 4-bromo-2-chloro-6-fluoroaniline, 2,2-dimethoxy-N-methylethanamine, tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate and BBr₃ (33% yield). ¹H NMR (400 MHz, DMSO-d₆): 8.15 (d, J=5.2 Hz, 1H), 7.71 (d, J=1.6 Hz, 1H), 7.63 (dd, J=1.6, 10.4 Hz, 1H), 7.30 (dd, J=3.2, 9.2 Hz, 1H), 7.22 (dd, J=3.2, 9.2 Hz, 1H), 6.94 (s, 1H), 6.83-6.81 (m, 1H), 6.76 (d, J=3.2 Hz, 1H), 6.69 (d, J=2.8 Hz, 1H), 3.47-3.44 (m, 4H), 3.22 (s, 3H), 2.81-2.78 (m, 4H). N—H and O—H proton not observed. LCMS: 498.2 (M+H)⁺.

Example 437

5-(3'-chloro-5-fluoro-2-hydroxy-4'-(3-methyl-2-oxo-2,3-dihydro-1H-imidazol-1-yl)-[1,1'-biphenyl]-3-yl)-1-methyl-3-(piperazin-1-yl)pyridin-2(1H)-one

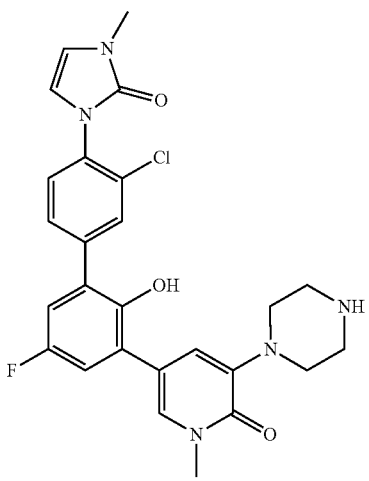 [SMILES: Cn1cc(-c2cc(F)cc(-c3ccc(-n4ccn(C)c4=O)c(Cl)c3)c2O)cc(N2CCNCC2)c1=O]

The title compound was prepared following the procedures described for Example 372 using tert-butyl 4-(5-bromo-1-methyl-2-oxo-1,2-dihydropyridin-3-yl)piperazine-1-carboxylate, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr₃ (16% yield). ¹H NMR (400 MHz, DMSO-d₆): 8.71 (br s, 2H), 8.67 (s, 1H), 7.81 (d, J=2.0 Hz, 1H), 7.68 (d, J=2.4 Hz, 1H), 7.60 (dd, J=8.0, 1.6 Hz, 1H), 7.52 (d, J=8.4 Hz, 1H), 7.18 (d, J=9.2 Hz, 2H), 7.02 (d, J=1.6 Hz, 1H), 6.72 (d, J=3.2 Hz, 1H), 6.68 (d, J=3.2 Hz, 1H), 3.51 (s, 3H), 3.42-3.3.38 (m, 4H), 3.35-3.24 (m, 4H), 3.21 (s, 3H). LCMS: 510.2 (M+H)⁺.

Example 438

(S)-1-(3-chloro-5'-fluoro-2'-hydroxy-3'-(2-(3-(methylamino)pyrrolidin-1-yl)pyridin-4-yl)-[1,1'-biphenyl]-4-yl)-3-methylimidazolidin-2-one

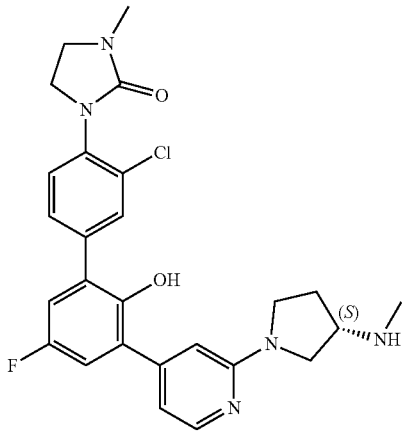

The title compound was prepared following the procedure described for Example 414 using 1-(3-chloro-5'-fluoro-3'-(2-fluoropyridin-4-yl)-2'-methoxy-[1,1'-biphenyl]-4-yl)-3-methylimidazolidin-2-one, (S)-tert-butyl methyl(pyrrolidin-3-yl)carbamate and BBr$_3$ (52% yield). $^1$H NMR (400 MHz, DMSO-d$_6$+D$_2$O): 8.09 (d, J=6.4 Hz, 1H), 7.73 (d, J=1.6 Hz, 1H), 7.56 (dd, J=8.4, 2.0 Hz, 1H), 7.49 (d, J=8.0 Hz, 1H), 7.34-7.30 (m, 2H), 7.12 (d, J=6.0 Hz, 1H), 7.09 (s, 1H), 4.00-3.96 (m, 1H), 3.91-3.87 (m, 1H), 3.80-3.69 (m, 4H), 3.67-3.64 (m, 1H), 3.52-3.48 (m, 2H), 2.78 (s, 3H), 2.68 (s, 3H), 2.51-2.41 (m, 1H), 2.32-2.25 (m, 1H). N—H and O—H protons not observed. LCMS: 496.2 (M+H)$^+$.

Example 439

N-(4-(3'-chloro-5-fluoro-2-hydroxy-4'-(3-methyl-2-oxo-2,3-dihydro-1H-imidazol-1-yl)-[1,1'-biphenyl]-3-yl)-6-(piperazin-1-yl)pyridin-2-yl)methanesulfonamide

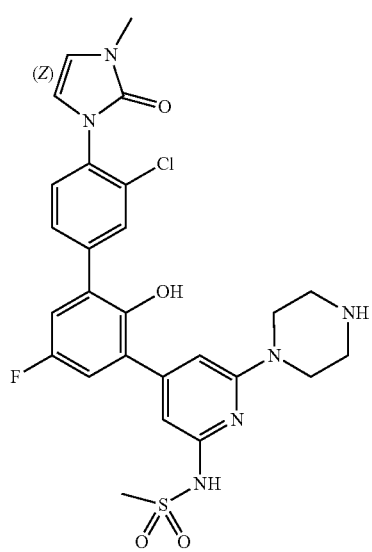 [SMILES: Cn1ccn(-c2ccc(-c3cc(F)cc(-c4cc(NS(C)(=O)=O)nc(N5CCNCC5)c4)c3O)cc2Cl)c1=O]

Step 1: tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)-6-(methylsulfonamido)pyridin-2-yl)piperazine-1-carboxylate The title compound was prepared following the procedure described for Example 365 using tert-butyl 4-(4-bromo-6-(N-(methylsulfonyl)methylsulfonamido)pyridin-2-yl)piperazine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one (44% yield). LCMS: 687.4 (M+H)$^+$.

Step 2: N-(4-(3'-chloro-5-fluoro-2-hydroxy-4'-(3-methyl-2-oxo-2,3-dihydro-1H-imidazol-1-yl)-[1,1'-biphenyl]-3-yl)-6-(piperazin-1-yl)pyridin-2-yl)methanesulfonamide The title compound was prepared following the procedure described for Example 365 using tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)-6-(methylsulfonamido)pyridin-2-yl)piperazine-1-carboxylate and BBr$_3$ (21% yield). $^1$H NMR (400 MHz, DMSO-d$_6$): 7.79 (d, J=2.0 Hz, 1H), 7.61-7.59 (m, 1H), 7.52 (d, J=8.4 Hz, 1H), 7.25 (dd, J=8.4, 3.2 Hz, 1H), 7.13 (dd, J=8.8, 2.8 Hz, 1H), 6.72 (d, J=2.8 Hz, 1H), 6.69 (d, J=3.2 Hz, 1H), 6.52 (s, 1H), 6.33 (s, 1H), 3.45-3.38 (m, 4H), 3.33 (s, 3H), 3.21 (s, 3H), 2.81-2.62 (m, 4H). N—H and O—H protons not observed. LCMS: 573.2 (M+H)$^+$.

Example 440

(S)-1-(3-chloro-5'-fluoro-2'-hydroxy-3'-(2-(3-(methylamino)piperidin-1-yl)pyridin-4-yl)-[1,1'-biphenyl]-4-yl)-3-methyl-1H-imidazol-2(3H)-one

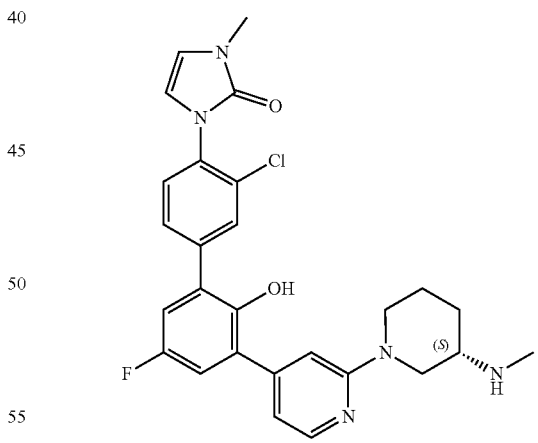

The title compound was prepared following the procedures described for Example 414 using 1-(3-chloro-5'-fluoro-3'-(2-fluoropyridin-4-yl)-2'-methoxy-[1,1'-biphenyl]-4-yl)-3-methyl-1H-imidazol-2(3H)-one, (S)-tert-butyl methyl(piperidin-3-yl)carbamate and BBr$_3$ (39% yield). $^1$H NMR (400 MHz, DMSO-d$_6$): 8.82 (s, 1H), 8.62 (s, 2H), 8.18 (d, J=5.2 Hz, 1H), 7.81 (d, J=2.0 Hz, 1H), 7.62 (dd, J=8.4, 2.0 Hz, 1H), 7.54 (d, J=8.4 Hz, 1H), 7.27 (dd, J=8.8, 3.2 Hz, 1H), 7.22 (dd, J=8.8, 3.2 Hz, 1H), 7.10 (s, 1H), 6.95-6.94 (m, 1H), 6.73 (d, J=2.8 Hz, 1H), 6.68 (d, J=3.2 Hz, 1H), 4.31-4.27 (m, 1H), 3.92-3.89 (m, 1H), 3.35-3.30 (m, 1H), 3.21-3.17 (m, 5H), 2.65 (t, J=5.2 Hz, 3H), 2.09-2.04 (m, 1H), 1.84-1.80 (m, 1H), 1.67-1.52 (m, 2H). LCMS: 508.2 (M+H)$^+$.

Example 441

1-(3-chloro-5'-fluoro-2'-hydroxy-3'-(2-(4-methylpiperazin-1-yl)pyridin-4-yl)-[1,1'-biphenyl]-4-yl)-3-methylimidazolidin-2-one

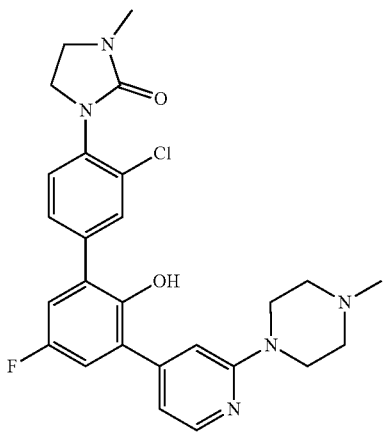 [SMILES: CN1CCN(c2cc(-c3cc(F)cc(-c4ccc(N5CCN(C)C5=O)c(Cl)c4)c3O)ccn2)CC1]

The title compound was prepared following the procedure described for Example 414 using 1-(3-chloro-5'-fluoro-3'-(2-fluoropyridin-4-yl)-2'-methoxy-[1,1'-biphenyl]-4-yl)-3-methylimidazolidin-2-one, 1-methylpiperazine and BBr$_3$ (46% yield). $^1$H NMR (400 MHz, DMSO-d$_6$): 8.63 (s, 1H), 8.15 (d, J=4.4 Hz, 1H), 7.71 (d, J=1.6 Hz, 1H), 7.54 (dd, J=8.4, 2.0 Hz, 1H), 7.45 (d, J=8.4 Hz, 1H), 7.22-7.16 (m, 2H), 6.95 (s, 1H), 6.83 (dd, J=5.2, 0.8 Hz, 1H), 3.75-3.71 (m, 2H), 3.53-3.47 (m, 6H), 2.77 (s, 3H), 2.41 (t, J=4.4 Hz, 4H), 2.22 (s, 3H). LCMS: 496.2 (M+H)$^+$.

Example 442

N-(4-(3'-chloro-5-fluoro-2-hydroxy-4'-(3-methyl-2-oxo-2,3-dihydro-1H-imidazol-1-yl)-[1,1'-biphenyl]-3-yl)-6-(piperazin-1-yl)pyridin-2-yl)acetamide

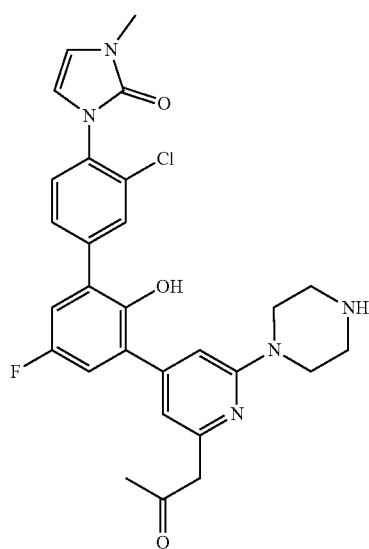

Step 1: tert-butyl 4-(6-acetamido-4-bromopyridin-2-yl)piperazine-1-carboxylate

To a solution of tert-butyl 4-(6-amino-4-bromopyridin-2-yl)piperazine-1-carboxylate (230 mg, 0.643 mmol) in DCM (5 mL) was added TEA (195 mg, 1.93 mmol), DMAP (7.9 mg, 0.064 mmol) and acetyl chloride (76 mg, 0.97 mmol). The mixture was stirred at room temperature for 8 hours. After the reaction was complete by LCMS, the reaction mixture was added water (10 mL), extracted with DCM (10 mL×3). The combined organic layers were dried over sodium sulfate and filtered. The filtrate was concentrated to afford a residue, which was purified by silica gel chromatography using a mixture of 3:1 petroleum ether and ethyl acetate as the eluent to afford the title compound (220 mg, 86% yield) as a white solid. LCMS: 401.1 (M+H)$^+$.

Step 2: tert-butyl 4-(6-acetamido-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperazine-1-carboxylate The title compound was prepared following the procedures described for Example 439 using 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and tert-butyl 4-(6-acetamido-4-bromopyridin-2-yl)piperazine-1-carboxylate (49% yield). LCMS: 651.3 (M+H)$^+$.

Step 3: N-(4-(3'-chloro-5-fluoro-2-hydroxy-4'-(3-methyl-2-oxo-2,3-dihydro-1H-imidazol-1-yl)-[1,1'-biphenyl]-3-yl)-6-(piperazin-1-yl)pyridin-2-yl)acetamide 2,2,2-trifluoroacetate The title compound was prepared following the procedure described for Example 439 using tert-butyl 4-(6-acetamido-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperazine-1-carboxylate and BBr$_3$ to afford the title compound (19% yield). $^1$H NMR (400 MHz, DMSO-d$_6$): δ 10.09 (d, J=5.6 Hz, 1H), 8.80-8.76 (m, 2H), 8.69 (s, 1H), 7.80 (d, J=2.0 Hz, 1H), 7.62-7.57 (m, 2H), 7.52 (d, J=8.4 Hz, 1H), 7.26 (dd, J=3.2, 8.8 Hz, 1H), 7.13 (dd, J=3.2, 8.8 Hz, 1H), 6.73-6.71 (m, 2H), 6.68 (d, J=2.8 Hz, 1H), 3.82-3.76 (m, 4H), 3.22-3.18 (m, 7H), 2.09 (s, 3H). LCMS: 537.2 (M+H)$^+$.

Example 444

1-(3-chloro-5'-fluoro-2'-hydroxy-3'-(2-(3-(trifluoromethyl)piperazin-1-yl)pyridin-4-yl)-[1,1'-biphenyl]-4-yl)-3-methylimidazolidin-2-one

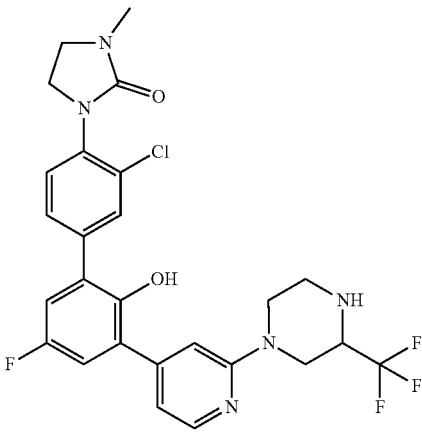 [SMILES: CN1CCN(c2ccc(-c3cc(F)cc(-c4ccnc(N5CCNC(C(F)(F)F)C5)c4)c3O)cc2Cl)C1=O]

The title compound was prepared following the procedure described for 414 using 1-(3-chloro-5'-fluoro-3'-(2-fluoropyridin-4-yl)-2'-methoxy-[1,1'-biphenyl]-4-yl)-3-methylimidazolidin-2-one, 2-(trifluoromethyl)piperazine and BBr$_3$ (10% yield). $^1$H NMR (400 MHz, DMSO-d$_6$): δ 8.65 (s, 1H), 8.18 (d, J=5.2 Hz, 1H), 7.71 (d, J=2.0 Hz, 1H), 7.54 (dd, J=2.0, 8.0 Hz, 1H), 7.46 (d, J=8.4 Hz, 1H), 7.23-7.17 (m, 2H), 6.99 (s, 1H), 6.88 (dd, J=0.8, 5.2 Hz, 1H), 4.40 (dd, J=2.8, 12.4 Hz, 1H), 3.97-3.94 (m, 1H), 3.75-3.70 (m, 2H), 3.50-3.38 (m, 3H), 3.01-2.90 (m, 4H), 2.77-2.73 (m, 4H). LCMS: 550.2 (M+H)$^+$.

Example 445

1-(3-chloro-5'-fluoro-2'-hydroxy-3'-(6-(piperidin-4-yloxy)pyridin-3-yl)-[1,1'-biphenyl]-4-yl)-3-methyl-1H-imidazol-2(3H)-one

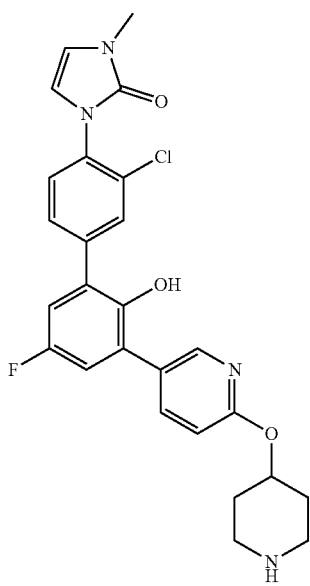 [SMILES: Cn1ccn(-c2ccc(-c3cc(F)cc(-c4ccc(OC5CCNCC5)nc4)c3O)cc2Cl)c1=O]

The title compound was prepared following the procedures described for Example 365 using tert-butyl 4-((5-bromopyridin-2-yl)oxy)piperidine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr$_3$ (21% yield). $^1$H NMR (400 MHz, DMSO-d$_6$): δ 8.70-8.53 (m, 3H), 8.33 (d, J=2.0 Hz, 1H), 7.94 (dd, J=2.4, 8.4 Hz, 1H), 7.81 (d, J=1.6 Hz, 1H), 7.62 (dd, J=2.0, 8.4 Hz, 1H), 7.53 (d, J=8.4 Hz, 1H), 7.23-7.17 (m, 2H), 6.92 (d, J=8.4 Hz, 1H), 6.71 (d, J=3.2 Hz, 1H), 6.68 (d, J=2.8 Hz, 1H), 5.31-5.29 (m, 1H), 3.31-3.27 (m, 2H), 3.20 (s, 3H), 3.19-3.15 (m, 2H), 2.19-2.14 (m, 2H), 1.90-1.87 (m, 2H). LCMS: 495.2 (M+H)$^+$.

Example 446

1-(3-chloro-5'-fluoro-2'-hydroxy-3'-(6-(piperidin-4-yloxy)pyridin-3-yl)-[1,1'-biphenyl]-4-yl)-3-methyl-imidazolidin-2-one

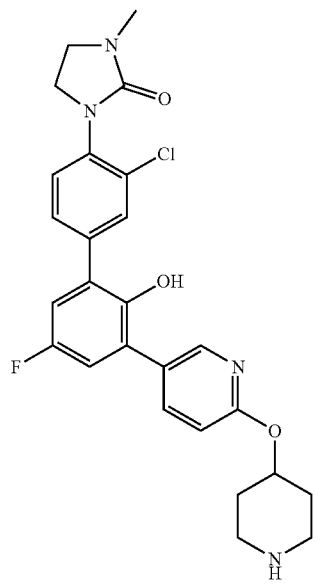 [SMILES: CN1CCN(c2ccc(-c3cc(F)cc(-c4ccc(OC5CCNCC5)nc4)c3O)cc2Cl)C1=O]

The title compound was prepared following the procedure described for Example 445 using 1-(3-chloro-5'-fluoro-2'-methoxy-3'-(4,4,5,5-tetramethyl-1,3,2-dioxaborolan-2-yl)-[1,1-biphenyl]-4-yl)-3-methylimidazolidin-2-one, tert-butyl 4-((5-bromopyridin-2-yl)oxy)piperidine-1-carboxylate and BBr$_3$ (40% yield). $^1$H NMR (400 MHz, DMSO-d$_6$): δ 8.63-8.56 (m, 3H), 8.32 (d, J=2.4 Hz, 1H), 7.93 (dd, J=2.8, 8.8 Hz, 1H), 7.71 (d, J=1.6 Hz, 1H), 7.54 (dd, J=1.6, 8.0 Hz, 6H), 7.47 (d, J=8.4 Hz, H), 7.19-7.15 (m, 2H), 6.91 (d, J=8.8 Hz, 1H), 5.32-5.28 (m, 1H), 3.74-3.70 (m, 2H), 3.51-3.47 (m, 2H), 3.30-3.26 (m, 2H), 3.17-3.14 (m, 2H), 2.77 (s, 3H), 2.19-2.14 (m, 2H), 1.92-1.85 (s, 2H). LCMS: 497.2 (M+H)$^+$.

TABLE 28

Following compounds were prepared using similar procedures as described for Examples 163-414.

| Ex. No. | Name/Structure | $^1$H NMR Data | LCMS (M + H)$^+$ |
|---|---|---|---|
| 448 | 5-chloro-5'-fluoro-2'-hydroxy-4-(3-methyl-2-oxo-2,3-dihydro-1H-imidazol-1-yl)-3'-(2-(piperazin-1-yl)pyridin-4-yl)-[1,1'-biphenyl]-3-carbonitrile | $^1$H NMR (400 MHz, DMSO-d$_6$): δ 8.21-8.14 (m, 3H), 7.36 (dd, J = 2.8, 8.8 Hz, 1H), 7.24 (dd, J = 3.2, 9.2 Hz, 1H), 6.91 (s, 1H), 6.84-6.80 (m, 3H), 3.48-3.44 (m, 4H), 3.24 (s, 3H), 2.82-2.78 (m, 4H). N—H and O—H protons not observed | 505.2 |
| 449 | 1-(4-(3'-chloro-5-fluoro-2-hydroxy-4'-(3-methyl-2-oxoimidazolidin-1-yl)-[1,1'-biphenyl]-3-yl)pyridin-2-yl)piperazin-2-one | $^1$H NMR (400 MHz, DMSO-d$_6$): δ 8.49 (d, J = 4.4 Hz, 1H), 8.03 (s, 1H), 7.72 (s, 1H), 7.56-7.42 (m, 3H), 7.26-7.18 (m, 2H), 3.89-3.87 (m, 2H), 3.74-3.71 (m, 2H), 3.50-3.48 (m, 4H), 3.07-3.05 (m, 2H), 2.77 (s, 3H). N—H and O—H protons not observed | 496.2 |
| 450 | ((S)-1-(3-chloro-5'-fluoro-2'-hydroxy-3'-(2-(3-(methylamino)piperidin-1-yl)pyridin-4-yl)-[1,1'-biphenyl]-4-yl)-3-methylimidazolidin-2-one | $^1$H NMR (400 MHz, CD$_3$OD): δ 8.05 (d, J = 5.6 Hz, 1H), 7.60 (d, J = 1.6 Hz, 1H), 7.42 (dd, J = 2.0, 8.0 Hz, 1H), 7.35 (d, J = 8.4 Hz, 1H), 7.19(s, 1H), 7.09-7.00 (m, 3H), 7.06 (d, J = 12.4 Hz, 1H), 3.75-3.66 (m, 3H), 3.60-3.48 (m, 3H), 3.41-3.21 (m, 2H), 2.79 (s, 3H), 2.70 (s, 3H), 2.13-2.09 (m, 1H), 1.88-1.65 (m, 3H). N—H and O—H protons not observed | 510.2 |

TABLE 28-continued

Following compounds were prepared using similar procedures as described for Examples 163-414.

| Ex. No. | Name/Structure | ¹H NMR Data | LCMS (M + H)⁺ |
|---|---|---|---|
| 451 | (S)-1-(3'-(2-(3-aminopyrrolidin-1-yl)pyridin-4-yl)-3-chloro-5'-fluoro-2'-hydroxy-[1,1'-biphenyl]-4-yl)-3-deuteromethyl-1H-imidazol-2(3H)-one | ¹H NMR (400 MHz, DMSO-d₆): δ 8.09 (d, J = 5.6 Hz, 1H), 7.80 (d, J = 1.6 Hz, 1H), 7.61 (dd, J = 2.0, 8.0 Hz, 1H), 7.52 (d, J = 8.4 Hz, 1H), 7.23 (dd, J = 3.2, 9.2 Hz, 1H), 7.17 (dd, J = 3.2, 9.2 Hz, 1H), 6.71-6.67 (m, 3H), 6.55 (s, 1H), 3.64-3.50 (m, 3H), 3.44-3.38 (m, 1H), 3.14-3.11 (m, 1H), 2.08-2.04 (m, 1H), 1.75-1.70 (m, 1H). N—H and O—H protons not observed | 483.2 |
| 452 | (S)-1-(3'-(2-(3-aminopiperidin-1-yl)pyridin-4-yl)-3-chloro-5'-fluoro-2'-hydroxy-[1,1'-biphenyl]-4-yl)-3-deuteromethyl-1H-imidazol-2(3H)-one | ¹H NMR (400 MHz, DMSO-d₆): δ 8.77 (s, 1H), 8.18 (d, J = 5.2 Hz, 1H), 7.94-7.93 (m, 3H), 7.81 (d, J = 1.6 Hz, 1H), 7.62 (dd, J = 1.6, 8.0 Hz, 1H), 7.53 (d, J = 8.0 Hz, 1H), 7.29-7.20 (m, 2H), 7.06-7.04 (m, 1H), 6.93-6.91 (m, 1H), 6.72 (d, J = 2.8 Hz, 1H), 6.68 (d, J = 2.8 Hz, 1H), 4.33 (d, J = 12.0 Hz, 1H), 3.95 (d, J = 12.4 Hz, 1H), 3.20-3.12 (m, 3H), 2.03-2.00 (m, 1H), 1.81-1.77 (m, 1H), 1.64-1.54 (m, 2H) | 497.2 |
| 453 | (R)-1-(3-chloro-5'-fluoro-2'-hydroxy-3'-(2-(3-methylpiperazin-1-yl)pyridin-4-yl)-[1,1'-biphenyl]-4-yl)-3-deuteromethyl-1H-imidazol-2(3H)-one | ¹H NMR (400 MHz, DMSO-d₆): δ 9.08-9.07 (m, 1H), 8.77-8.75 (m, 2H), 8.21 (d, J = 4.8 Hz, 1H), 7.81 (d, J = 1.2 Hz, 1H), 7.62 (dd, J = 1.6, 8.0 Hz, 1H), 7.54 (d, J = 8.0 Hz, 1H), 7.29-7.21 (m, 2H), 7.12(s, 1H), 6.98 (d, J = 5.2 Hz, 1H), 6.73-6.68 (m, 2H), 4.43-4.30 (m, 2H), 3.42-3.33 (m, 1H), 3.19-3.12 (m, 1H), 3.10-3.07 (m, 2H), 2.97-2.91 (m, 1H), 1.28 (d, J = 6.4 Hz, 3H) | 497.2 |

TABLE 28-continued

Following compounds were prepared using similar procedures as described for Examples 163-414.

| Ex. No. | Name/Structure | $^1$H NMR Data | LCMS (M + H)$^+$ |
|---|---|---|---|
| 454 | 1-(3-chloro-5'-fluoro-2'-hydroxy-3'-(2-(3-(trifluoromethyl)piperazin-1-yl)pyridin-4-yl)-[1,1'-biphenyl]-4-yl)-3-methyl-1H-imidazol-2(3H)-one | $^1$H NMR (400 MHz, CD$_3$OD): δ 8.18 (d, J = 6.4 Hz, 1H), 7.82 (d, J = 2.0 Hz, 1H), 7.63 (dd, J = 2.0, 4.4 Hz, 1H), 7.56 (d, J = 8.0 Hz, 1H), 7.44 (d, J = 1.2 Hz, 1H), 7.27-7.20 (m, 3H), 6.71 (d, J = 2.8 Hz, 1H), 6.66 (d, J = 2.8 Hz, 1H), 4.61-4.58 (m, 1H), 4.26-4.23 (m, 1H), 4.07-4.04 (m, 1H), 3.43-3.38 (m, 5H), 3.27-3.15 (m, 2H). N—H and O—H protons not observed | 548.2 |
| 455 | 1-(3'-(2-(2,6-diazaspiro[3.3]heptan-2-yl)pyridin-4-yl)-3-chloro-5'-fluoro-2'-hydroxy-[1,1'-biphenyl]-4-yl)-3-methyl-1H-imidazol-2(3H)-one | $^1$H NMR (400 MHz, CD$_3$OD): δ 7.99-7.97 (m, 1H), 7.80 (d, J = 1.6 Hz, 1H), 7.62-7.55 (m, 2H), 7.30-7.23 (m, 3H), 7.06 (d, J = 7.6 Hz, 1H), 6.71 (d, J = 3.2 Hz, 1H), 6.65 (d, J = 2.8 Hz, 1H), 4.57-4.55 (m, 4H), 4.39 (br s, 4H), 3.33 (s, 3H). N—H and O—H protons not observed | 492.2 |
| 456 | (S)-1-(3-chloro-5'-fluoro-2'-hydroxy-3'-(2-(3-(methylamrno)piperidin-1-yl)pyridin-4-yl)-[1,1'-biphenyl]-4-yl)-3-deuteromethyl-1H-imidazol-2(3H)-one | $^1$H NMR (400 MHz, DMSO-d$_6$ + D$_2$O): δ 8.15 (d, J = 5.6 Hz, 1H), 7.82 (d, J = 2.0 Hz, 1H), 7.64- | 511.2 |

TABLE 28-continued

Following compounds were prepared using similar procedures as described for Examples 163-414.

| Ex. No. | Name/Structure | ¹H NMR Data | LCMS (M + H)⁺ |
|---|---|---|---|
| | *(structure)* | 7.62 (m, 1H), 7.56-7.54 (m, 1H), 7.33-7.25 (m, 3H), 7.06 (d, J = 5.4 Hz, 1H), 6.73 (d, J = 3.2 Hz, 1H), 6.68 (d, J = 3.2 Hz, 1H), 4.25-4.22 (m, 1H), 3.90-3.87 (m, 1H), 3.46-3.41 (m, 1H), 3.33-3.24 (m, 2H), 1.53 (s, 3H), 2.10-2.06 (m, 1H), 1.87-1.85 (m, 1H), 1.74-1.57 (m, 2H). N—H and O—H protons not observed | |
| 457 | (S)-1-(3-chloro-3'-(2-(3-(dimethylamino)piperidin-1-yl)pyridin-4-yl)-5'-fluoro-2'-hydroxy-[1,1'-biphenyl]-4-yl)-3-methyl-1H-imidazol-2(3H)-one | ¹H NMR (400 MHz, CD₃OD): δ 8.08 (d, J = 5.2 Hz, 1H), 7.69 (d, J = 2.0 Hz, 1H), 7.52-7.49 (m, 1H), 7.42 (d, J = 8.0 Hz, 1H), 7.18 (s, 1H), 7.11-7.06 (m, 2H), 7.00 (d, J = 5.2 Hz, 1H), 6.58 (d, J = 3.2 Hz, 1H), 6.53 (d, J = 2.8 Hz, 1H), 4.27-4.25 (m, 1H), 3.85-3.81 (m, 1H), 3.61-3.56 (m, 1H), 3.39-3.33 (m, 1H), 3.25 (s, 3H), 2.90-2.89 (m, 7H), 2.15-2.12 (m, 1H), 1.94-1.82 (m, 2H), 1.71-1.68 (m, 1H). N—H and O—H protons not observed | 522.2 |
| 458 | 1-(3-chloro-5'-fluoro-2'-hydroxy-3'-(4-(piperazin-1-yl)-1H-indazol-6-yl)-[1,1'-biphenyl]-4-yl)-3-methylimidazolidin-2-one | ¹H NMR (400 MHz, DMSO-d₆): δ 13.14 (brs, 1H), 8.76 (br s, 2H), 8.48 (s, 1H), 8.23 (s, 1H), 7.74 (d, J = 2.0 Hz, 1H), 7.56 (dd, J = 2.0, 8.4 Hz, 1H), 7.48-7.46 (m, 1H), 7.31 (s, 1H), 7.22-7.17 (m, 2H), 6.64 (s, 1H), 3.75-3.71 (m, 2H), 3.57-3.28 (m, 10H), 2.77 (s, 3H) | 521.2 |

TABLE 28-continued

Following compounds were prepared using similar procedures as described for Examples 163-414.

| Ex. No. | Name/Structure | $^1$H NMR Data | LCMS (M + H)$^+$ |
|---|---|---|---|
| 459 | 1-(3'-(5-(4-aminopiperidin-1-yl)pyridin-3-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$ + D$_2$O): δ 8.24 (d, J = 2.8 Hz, 1H), 8.12 (d, J = 1.6 Hz, 1H), 7.85 (d, J = 2.0 Hz, 1H), 7.64 (dd, J = 2.0, 8.0 Hz, 1H), 7.52-7.49 (m, 2H), 7.22-7.17 (m, 2H), 6.71 (d, J = 3.2 Hz, 1H), 6.68 (d, J = 3.2 Hz, 1H), 3.78-3.74 (m, 2H), 3.22 (s, 3H), 2.84-2.74 (m, 3H), 1.84-1.81 (m, 2H), 1.43-1.33 (m, 2H). N—H and O—H protons not observed | 494.2 |
| 460 | 1-(3-chloro-5'-fluoro-2'-hydroxy-3'-(4-(piperazin-1-yl)-1H-indol-6-yl)-[1,1'-biphenyl]-4-yl)-3-methylimidazolidin-2-one | $^1$H NMR (400 MHz, DMSO-d$_6$ + D$_2$O): δ 7.73 (d, J = 1.6 Hz, 1H), 7.56 (dd, J = 2.0, 8.0 Hz, 1H), 7.46 (d, J = 8.4 Hz, 1H), 7.37-7.33 (m, 2H), 7.16-7.11 (m, 2H), 6.53 (s, 1H), 6.52 (s, 1H), 3.76-3.72 (m, 2H), 3.52-3.49 (m, 2H), 3.38-3.36 (m, 8H), 2.78 (s, 3H). N—H and O—H protons not observed | 520.2 |
| 461 | (S)-1-(3'-(5-(3-aminopiperidin-1-yl)pyridin-3-yl)-3-chloro-5'-fluoro-2'-hydroxy-[1,1'-biphenyl]-4-yl)-3-methyl-1,3-dihydro-2H-imidazol-2-one | $^1$H NMR (400 MHz, DMSO-d$_6$ + D$_2$O): δ 8.23 (d, J = 2.4 Hz, 1H), 8.11 (d, J = 1.6 Hz, 1H), 7.83 | 494.1 |

TABLE 28-continued

Following compounds were prepared using similar procedures as described for Examples 163-414.

| Ex. No. | Name/Structure | ¹H NMR Data | LCMS (M + H)⁺ |
|---|---|---|---|
| | (structure shown) | (d, J = 1.6 Hz, 1H), 7.65-7.63 (m, 1H), 7.53-7.51 (m, 1H), 7.47 (t, J = 2.0 Hz, 1H), 7.23-7.17 (m, 2H), 6.72-6.68 (m, 2H), 3.72-3.61 (m, 2H), 3.23 (s, 3H), 2.83-2.75 (m, 2H), 2.61-2.58 (m, 1H), 1.90-1.86 (m, 1H), 1.77-1.73 (m, 1H), 1.58-1.54 (m, 1H), 1.26-1.22 (m, 1H). N—H and O—H protons not observed. ¹⁹F NMR (376 MHz, DMSO-d₆): δ -123.44 | |

Example 462

4-(3-chloro-5'-fluoro-2'-hydroxy-3'-(2-(piperazin-1-yl)pyridin-4-yl)-[1,1'-biphenyl]-4-yl)-1-methyl-1H-1,2,4-triazol-5(4H)-one

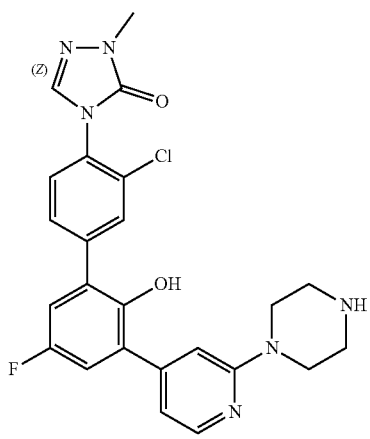

Step 1: 4-(4-bromo-2-chlorophenyl)-1-methyl-1H-1,2,4-triazol-5(4H)-one

A mixture of (4-bromo-2-chlorophenyl)boronic acid (318 mg, 1.35 mmol), 1-methyl-1H-1,2,4-triazol-5(4H)-one (200 mg, 2.02 mmol), several molecular sieves Cu(OAc)₂ (367 mg, 2.02 mmol) and Py (214 mg, 2.70 mmol) in DCM (5 mL) was stirred at 25° C. overnight under O₂. After the reaction was indicated by LCMS, the reaction mixture was filtered and concentrated to afford a residue, which was purified by flash column using petroleum ether and ethyl acetate as the eluent: petroleum ether:ethyl acetate=10:1 to 2:1 to afford the title compound (18 mg, 3% yield) as an off-white solid. LCMS: 288.0 (M+H)⁺.

Step 2: tert-butyl 4-(4-(3'-chloro-5-fluoro-2-methoxy-4'-(1-methyl-5-oxo-1H-1,2,4-triazol-4(5H)—yl)-[1,1'-biphenyl]-3-yl)pyridin-2-yl)piperazine-1-carboxylate The title compound was prepared following the procedures described for Example 365 using 4-(4-bromo-2-chlorophenyl)-1-methyl-1H-1,2,4-triazol-5(4H)-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (46% yield). LCMS: 595.2 (M+H)⁺.

Step 3: 4-(3-chloro-5'-fluoro-2'-hydroxy-3'-(2-(piperazin-1-yl)pyridin-4-yl)-[1,1'-biphenyl]-4-yl)-1-methyl-1H-1,2,4-triazol-5(4H)-one The title compound was prepared following the procedures described for Example 365 using tert-butyl 4-(4-(3'-chloro-5-fluoro-2-methoxy-4'-(1-methyl-5-oxo-1H-1,2,4-triazol-4(5H)-yl)-[1,1'-biphenyl]-3-yl)pyridin-2-yl)piperazine-1-carboxylate and BBr₃ to afford the title compound (22% yield). ¹H NMR (400 MHz, DMSO-d): δ 8.24 (s, 1H), 8.15 (d, J=5.2 Hz, 1H), 7.88 (d, J=2.0 Hz, 1H), 7.70-7.63 (m, 2H), 7.27-7.19 (m, 2H), 6.93 (s, 1H), 6.82 (d, J=5.2 Hz, 1H), 3.46-3.42 (m, 4H), 3.31 (s, 3H), 2.80-2.78 (m, 4H). N—H and O—H protons not observed. LCMS: 481.2 (M+H)⁺.

Example 463

1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)piperazin-2-one

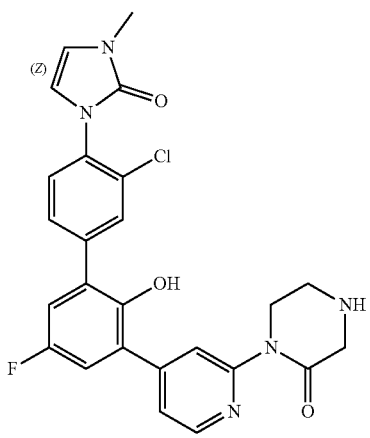

Step 1: (2-(4-(tert-butoxycarbonyl)-2-oxopiperazin-1-yl)pyridin-4-yl)boronic acid The title compound was prepared following the procedure described for Example 365 using tert-butyl 4-(4-bromopyridin-2-yl)-3-oxopiperazine-1-carboxylate and 4,4,4',4',5,5,5',5'-octamethyl-2,2'-bi(1,3,2-dioxaborolane) (100% yield). LCMS: 322.2 (M+H)$^+$.

Step 2: tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-3-oxopiperazine-1-carboxylate The title compound was prepared following the procedures described for Example 365 using (2-(4-(tert-butoxycarbonyl)-2-oxopiperazin-1-yl)pyridin-4-yl)boronic acid and 1-(3'-bromo-3-chloro-5'-fluoro-2'-methoxy-[1,1'-biphenyl]-4-yl)-3-methyl-1H-imidazol-2(3H)-one (58% yield). LCMS: 608.3 (M+H)$^+$.

Step 5: 1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)piperazin-2-one The title compound was prepared following the procedure described for Example 365 using tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-3-oxopiperazine-1-carboxylate and BBr$_3$ (39% yield). $^1$H NMR (400 MHz, DMSO-d$_6$): δ 8.49 (d, J=4.8 Hz, 1H), 7.95 (s, 1H), 7.81 (d, J=1.6 Hz, 1H), 7.63 (dd, J=8.4, 2.0 Hz, 1H), 7.53 (d, J=8.0 Hz, 1H), 7.43 (d, J=4.0 Hz, 1H), 7.30-7.20 (m, 1H), 6.70 (dd, J=14.0, 3.2 Hz, 2H), 3.89-3.86 (m, 2H), 3.47 (s, 2H), 3.21 (s, 3H), 3.06-3.03 (m, 2H). N—H and O—H proton not observed. LCMS: 494.2 (M+H)$^+$.

Example 464

1-(4-(3'-chloro-5-fluoro-2-hydroxy-4'-(3-deuteromethyl-2-oxo-2,3-dihydro-1H-imidazol-1-yl)-[1,1'-biphenyl]-3-yl)pyridin-2-yl)piperazin-2-one

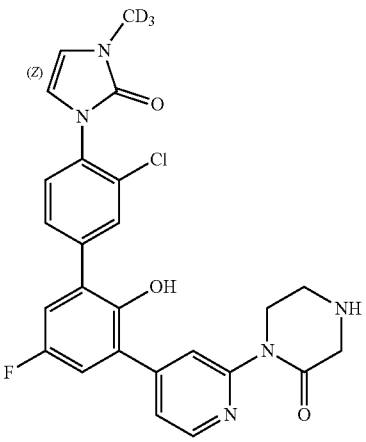 [SMILES: [2H]C([2H])([2H])n1ccn(-c2ccc(-c3cc(F)cc(-c4ccnc(N5CCNCC5=O)c4)c3O)cc2Cl)c1=O]

The title compound was prepared following the procedure described for Example 463 using (2-(4-(tert-butoxycarbonyl)-2-oxopiperazin-1-yl)pyridin-4-yl)boronic acid, 1-(3'-bromo-3-chloro-5'-fluoro-2'-methoxy-[1,1'-biphenyl]-4-yl)-3-deuteromethyl-1H-imidazol-2(3H)-one and BBr$_3$ (14% yield). $^1$H NMR (400 MHz, DMSO-d$_6$): δ 8.49 (d, J=5.2 Hz, 1H), 8.01 (s, 1H), 7.81 (d, J=2.0 Hz, 1H), 7.62 (dd, J=8.0, 2.0 Hz, 1H), 7.53 (d, J=8.0 Hz, 1H), 7.43 (dd, J=4.8, 1.2 Hz, 1H), 7.31-7.28 (m, 1H), 7.23-7.20 (m, 1H), 6.70 (dd, J=13.2, 3.2 Hz, 2H), 3.89-3.86 (m, 2H), 3.47 (s, 2H), 3.06-3.03 (m, 2H). N—H and O—H protons not observed. LCMS: 497.2 (M+H)$^+$.

Example 465

1-(3-chloro-5'-fluoro-2'-hydroxy-3'-(5-(4-methylpiperazin-1-yl)pyridin-3-yl)-[1,1'-biphenyl]-4-yl)-3-methyl-1H-imidazol-2(3H)-one

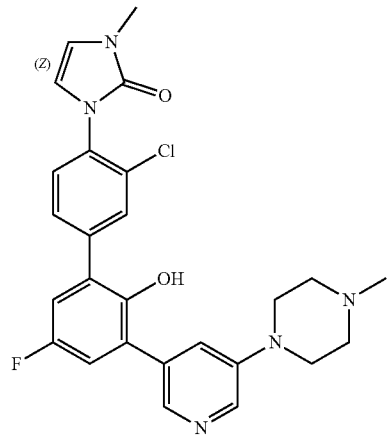

799

Step 1: 1-(3-chloro-5'-fluoro-2'-methoxy-3'-(5-(4-methylpiperazin-1-yl)pyridin-3-yl)-[1,1'-biphenyl]-4-yl)-3-methyl-1H-imidazol-2(3H)-one The title compound was prepared following the procedures described for Example 365 using 1-(5-bromopyridin-3-yl)-4-methylpiperazine and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one (43% yield). LCMS: 508.2 (M+H)+.

Step 3: 1-(3-chloro-5'-fluoro-2'-hydroxy-3'-(5-(4-methylpiperazin-1-yl)pyridin-3-yl)-[1,1'-biphenyl]-4-yl)-3-methyl-1H-imidazol-2(3H)-one The title compound was prepared following the procedure described for Example 365 using 1-(3-chloro-5'-fluoro-2'-methoxy-3'-(5-(4-methylpiperazin-1-yl)pyridin-3-yl)-[1,1'-biphenyl]-4-yl)-3-methyl-1H-imidazol-2(3H)-one and BBr$_3$ (7% yield). $^1$H NMR (400 MHz, DMSO-d$_6$): δ 8.69 (s, 1H), 8.29 (d, J=2.4 Hz, 1H), 8.17 (s, 1H), 7.82 (d, J=1.6 Hz, 1H), 7.62 (dd, J=8.0, 2.0 Hz, 1H), 7.52 (d, J=8.4 Hz, 1H), 7.45 (s, 1H), 7.24-7.20 (m, 2H), 6.70 (dd, J=12.8, 3.2 Hz, 2H), 3.31 (br s, 4H), 3.26-3.24 (m, 3H), 2.50-2.46 (m, 4H), 2.23 (s, 3H). LCMS: 494.2 (M+H)+.

Example 466

(S)-1-(3-chloro-5'-fluoro-2'-hydroxy-3'-(2-(3-(methylamino)pyrrolidin-1-yl)pyridin-4-yl)-[1,1'-biphenyl]-4-yl)-3-(deuteromethyl)-1H-imidazol-2(3H)-one

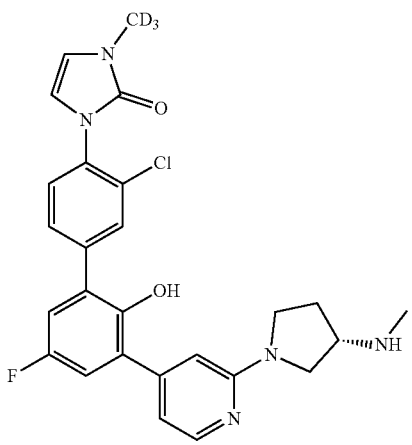 [SMILES: [2H]C([2H])([2H])n1ccn(-c2ccc(-c3cc(F)cc(-c4ccnc(N5CC[C@H](NC)C5)c4)c3O)cc2Cl)c1=O]

The title compound was prepared following the procedure described for Example 365 using 1-(3-chloro-5'-fluoro-3'-(2-fluoropyridin-4-yl)-2'-methoxy-[1,1'-biphenyl]-4-yl)-3-(deuteromethyl)-1H-imidazol-2(3H)-one, (S)-tert-butyl methyl(pyrrolidin-3-yl)carbamate and BBr$_3$ to afford the title compound (21% yield). $^1$H NMR (400 MHz, DMSO-d$_6$): δ 8.09 (d, J=5.2 Hz, 1H), 7.80 (d, J=2.0 Hz, 1H), 7.61 (dd, J=8.4, 2.4 Hz, 1H), 7.51 (d, J=8.4 Hz, 1H), 7.25-7.16 (m, 2H), 6.72-6.70 (m, 3H), 6.56 (s, 1H), 3.59-3.50 (m, 1H), 3.49-3.44 (m, 1H), 3.42-3.38 (m, 1H), 3.26-3.19 (m, 3H), 2.33 (s, 3H), 2.10-2.05 (m, 1H), 1.82-1.77 (m, 1H). N—H or O—H proton not observed. LCMS: 497.2 (M+H)+.

800

Example 467

(R)-1-(3-chloro-5'-fluoro-2'-hydroxy-3'-(5-(3-methylpiperazin-1-yl)pyridin-3-yl)-[1,1'-biphenyl]-4-yl)-3-methyl-1H-imidazol-2(3H)-one

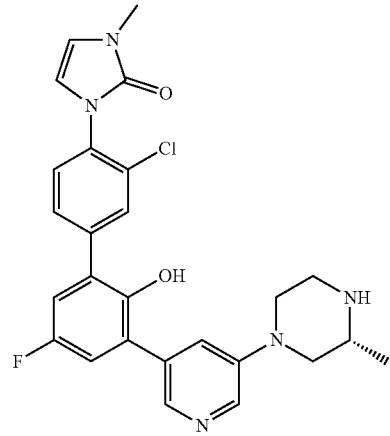 [SMILES: C[C@@H]1CN(c2cncc(-c3cc(F)cc(-c4ccc(-n5ccn(C)c5=O)c(Cl)c4)c3O)c2)CCN1]

Step 1: (R)-tert-butyl 4-(5-(3'-chloro-5-fluoro-2-methoxy-4'-(3-methyl-2-oxo-2,3-dihydro-1H-imidazol-1-yl)-[1,1'-biphenyl]-3-yl)pyridin-3-yl)-2-methylpiperazine-1-carboxylate The title compound was prepared following the procedure described for Example 365 using (R)-tert-butyl 4-(5-bromopyridin-3-yl)-2-methylpiperazine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (37% yield). LCMS: 608.3 (M+H)+.

Step 2: (R)-1-(3-chloro-5'-fluoro-2'-hydroxy-3'-(5-(3-methylpiperazin-1-yl)pyridin-3-yl)-[1,1'-biphenyl]-4-yl)-3-methyl-1H-imidazol-2(3H)-one The title compound was prepared following the procedure described for Example 365 using (R)-tert-butyl 4-(5-(3'-chloro-5-fluoro-2-methoxy-4'-(3-methyl-2-oxo-2,3-dihydro-1H-imidazol-1-yl)-[1,1'-biphenyl]-3-yl)pyridin-3-yl)-2-methylpiperazine-1-carboxylate and BBr$_3$ to afford the title compound (14% yield). $^1$H NMR (400 MHz, DMSO-d$_6$): δ 8.27 (d, J=2.8 Hz, 1H), 8.14 (d, J=1.6 Hz, 1H), 7.81 (d, J=1.6 Hz, 1H), 7.62 (dd, J=8.0, 1.6 Hz, 1H), 7.52 (d, J=8.4 Hz, 1H), 7.42 (dd, J=8.4, 2.4 Hz, 1H), 7.24-7.19 (m, 2H), 6.72-6.68 (m, 2H), 3.68-3.38 (m, 2H), 3.21 (s, 3H), 3.03-2.93 (m, 1H), 2.83-2.77 (m, 2H), 2.67-2.51 (m, 1H), 2.42-2.37 (m, 1H), 1.05-0.97 (m, 3H). N—H and O—H protons not observed. LCMS: 494.2 (M+H)+.

Example 468

1-(3-chloro-5'-fluoro-2'-hydroxy-3'-(2-(piperazin-1-yl)pyridin-4-yl)-[1,1'-biphenyl]-4-yl)-3-(difluoromethyl)-1H-imidazol-2(3H)-one

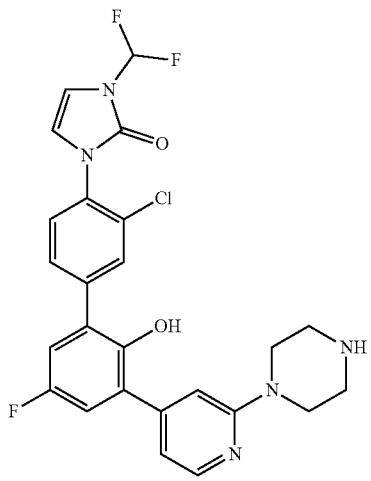 [SMILES: O=c1n(-c2ccc(-c3cc(F)cc(-c4ccnc(N5CCNCC5)c4)c3O)cc2Cl)ccn1C(F)F]

Step 1: 1-(4-bromo-2-chlorophenyl)-3-(difluoromethyl)-1H-imidazol-2(3H)-one

To a solution of 1-(4-bromo-2-chlorophenyl)-1H-imidazol-2(3H)-one (1.00 g, 3.66 mmol) in DMA (25 mL) was added $Cs_2CO_3$ (2.98 g, 9.14 mmol) and chlorodifluoromethane. The reaction mixture was stirred at rt for 12 h. After the reaction was indicated by LCMS, water was added and extracted with EtOAc (20 mL×3). The combined organic layers were, dried over sodium sulfate, filtered and concentrated. The residue was purified by prep-HPLC to afford the title compound (300 mg, 25% yield) as a white solid. LCMS: 325.1 $(M+H)^+$.

Step 2: tert-butyl 4-(4-(3'-chloro-4'-(3-(difluoromethyl)-2-oxo-2,3-dihydro-1H-imidazol-1-yl)-5-fluoro-2-methoxy-[1,1'-biphenyl]-3-yl)pyridin-2-yl)piperazine-1-carboxylate The title compound was prepared following the procedure described for Example 1 using 1-(4-bromo-2-chlorophenyl)-3-(difluoromethyl)-1H-imidazol-2(3H)-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (13% yield). LCMS: 630.6 $(M+H)^+$.

Step 3: 1-(3-chloro-5'-fluoro-2'-hydroxy-3'-(2-(piperazin-1-yl)pyridin-4-yl)-[1,1'-biphenyl]-4-yl)-3-(difluoromethyl)-1H-imidazol-2(3H)-one The title compound was prepared following the procedure described for Example 365 using tert-butyl 4-(4-(3'-chloro-4'-(3-(difluoromethyl)-2-oxo-2,3-dihydro-1H-imidazol-1-yl)-5-fluoro-2-methoxy-[1,1'-biphenyl]-3-yl)pyridin-2-yl)piperazine-1-carboxylate and $BBr_3$ to afford the title compound (32% yield). $^1H$ NMR (400 MHz, DMSO-$d_6$): δ 8.16 (d, J=5.2 Hz, 1H), 7.85 (d, J=1.6 Hz, 1H), 7.68-7.62 (m, 2.3H), 7.49 (s, 0.5H), 7.34 (s, 0.2H), 7.26 (dd, J=8.8, 3.2 Hz, 1H), 7.21 (dd, J=9.2, 3.2 Hz, 1H), 7.20 (d, J=3.2 Hz, 1H), 7.11 (d, J=3.6 Hz, 1H), 7.00 (d, J=3.2 Hz, 1H), 6.83 (dd, J=5.2, 1.2 Hz, 1H), 3.48-3.45 (m, 4H), 2.82-2.80 (m, 4H). N—H and O—H proton not observed. LCMS: 516.1 $(M+H)^+$.

Example 469

1-(3-chloro-3'-(2-(4-ethylpiperazin-1-yl)pyridin-4-yl)-5'-fluoro-2'-hydroxy-[1,1'-biphenyl]-4-yl)-3-methyl-1H-imidazol-2(3H)-one

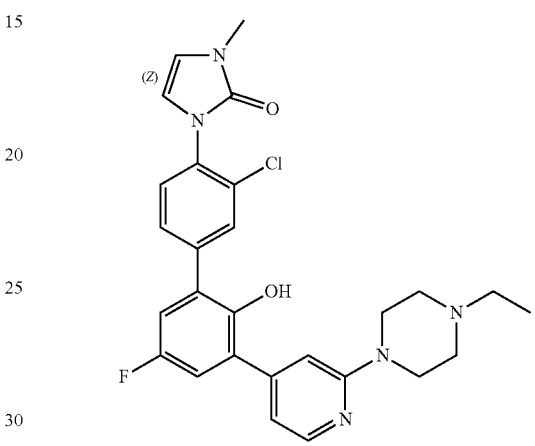

Step 1: 1-(3-chloro-3'-(2-(4-ethylpiperazin-1-yl)pyridin-4-yl)-5'-fluoro-2'-methoxy-[1,1'-biphenyl]-4-yl)-3-methyl-1H-imidazol-2(3H)-one To a solution of tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperazine-1-carboxylate (150 mg, 0.253 mmol) in DCM (2 mL) was added TFA (2 mL). The reaction mixture was stirred at room temperature for 3 hours. After the reaction was complete by LCMS, the reaction mixture was concentrated to give a residue, the residue was diluted with $CH_3OH$ (5 mL), the mixture was added acetaldehyde (0.15 mL, 0.76 mmol) and AcOH (1 drop), after stirred at room temperature for 30 min, $NaBH_3CN$ (48 mg, 0.76 mmol) was added at 0° C. The reaction mixture was stirred at room temperature for 16 hours under nitrogen atmosphere. After the reaction was complete by LCMS, the reaction mixture was diluted with $H_2O$ (30 mL), extracted with EA (10 mL×3), the combined organic layers were washed with brine (30 mL), dried over sodium sulfate, filtered and the filtrated was concentrated to afford the title compound (110 mg, 83% yield) as a brown solid. LCMS: 522.5 $(M+H)^+$.

Step 2: 1-(3-chloro-3'-(2-(4-ethylpiperazin-1-yl)pyridin-4-yl)-5'-fluoro-2'-hydroxy-[1,1'-biphenyl]-4-yl)-3-methyl-1H-imidazol-2(3H)-one The title compound was prepared following the procedure described for Example 365 using 1-(3-chloro-3'-(2-(4-ethylpiperazin-1-yl)pyridin-4-yl)-5'-fluoro-2'-methoxy-[1,1'-biphenyl]-4-yl)-3-methyl-1H-imidazol-2(3H)-one and $BBr_3$ (20% yield). $^1H$ NMR (400 MHz, DMSO-$d_6$): δ 8.71 (brs, 1H), 8.16 (d, J=4.8 Hz, 1H), 7.81 (s, 1H), 7.63-7.61 (m, 1H), 7.53-7.51 (m, 1H), 7.25-7.19 (m, 2H), 6.96 (s, 1H), 6.84 (d, J=4.8 Hz, 1H), 6.71-6.69 (m, 2H), 3.53-3.51 (m, 4H), 3.21 (s, 3H), 2.45-2.39 (m, 4H), 2.37-2.34 (m, 2H), 1.04 (t, J=7.2 Hz, 3H). LCMS: 508.2 (M+H)+.

Example 470

1-(3-chloro-3'-(2-(4-(cyclopropylmethyl)piperazin-1-yl)pyridin-4-yl)-5'-fluoro-2'-hydroxy-[1,1'-biphenyl]-4-yl)-3-methyl-1H-imidazol-2(3H)-one

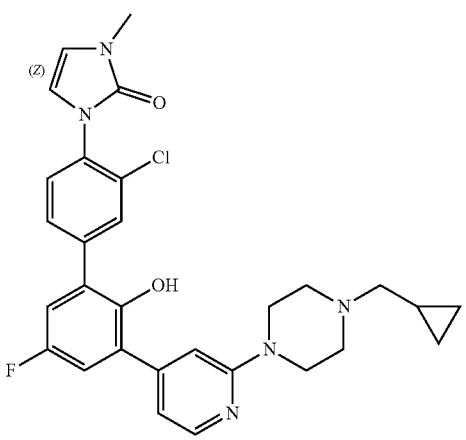 [SMILES: Cn1ccn(-c2ccc(-c3cc(F)cc(-c4ccnc(N5CCN(CC6CC6)CC5)c4)c3O)cc2Cl)c1=O]

Step 1: 1-(3-chloro-3'-(2-(4-(cyclopropylmethyl)piperazin-1-yl)pyridin-4-yl)-5'-fluoro-2'-methoxy-[1,1'-biphenyl]-4-yl)-3-methyl-1H-imidazol-2(3H)-one A mixture of 1-(3-chloro-5'-fluoro-2'-methoxy-3'-(2-(piperazin-1-yl)pyridin-4-yl)-[1,1'-biphenyl]-4-yl)-3-methyl-1H-imidazol-2(3H)-one (97 mg, 0.20 mmol), (bromomethyl)cyclopropane (81 mg, 0.60 mmol) and K$_2$CO$_3$ (83 mg, 0.60 mmol) in MeCN (5 mL) was stirred at 80° C. under nitrogen atmosphere overnight. After the reaction was complete by LCMS, the reaction mixture was cooled and concentrated to give a residue, which was purified by silica gel chromatography using a mixture of (10:1) dichloromethane and methanol as the eluent to afford the title compound (60 mg, 55% yield) as a brown solid. LCMS: 548.6 (M+H)+.

Step 2: 1-(3-chloro-3'-(2-(4-(cyclopropylmethyl)piperazin-1-yl)pyridin-4-yl)-5'-fluoro-2'-hydroxy-[1,1'-biphenyl]-4-yl)-3-methyl-1H-imidazol-2(3H)-one The title compound was prepared following the procedure described for Example 365 using 1-(3-chloro-3'-(2-(4-(cyclopropylmethyl)piperazin-1-yl)pyridin-4-yl)-5'-fluoro-2'-methoxy-[1,1'-biphenyl]-4-yl)-3-methyl-1H-imidazol-2(3H)-one and piperazine, instead of BBr$_3$. (35% yield). $^1$H NMR (400 MHz, DMSO-d$_6$): δ 8.70 (brs, 1H), 8.16 (d, J=5.2 Hz, 1H), 7.80 (d, J=2.0 Hz, 1H), 7.63-7.60 (m, 1H), 7.53-7.51 (m, 1H), 7.26-7.18 (m, 2H), 6.96 (s, 1H), 6.84-6.83 (m, 1H), 6.71 (d, J=2.8 Hz, 1H), 6.68 (d, J=2.8 Hz, 1H), 3.54-3.52 (m, 4H), 3.21 (s, 3H), 2.54-2.49 (m, 4H), 2.24-2.22 (m, 2H), 0.87-0.85 (m, 1H), 0.50-0.46 (m, 2H), 0.12-0.08 (m, 2H). LCMS: 534.2 (M+H)+.

Example 471

1-(3-chloro-5'-fluoro-2'-hydroxy-3'-(2-(4-(2-hydroxyethyl)piperazin-1-yl)pyridin-4-yl)-[1,1'-biphenyl]-4-yl)-3-methyl-1H-imidazol-2(3H)-one

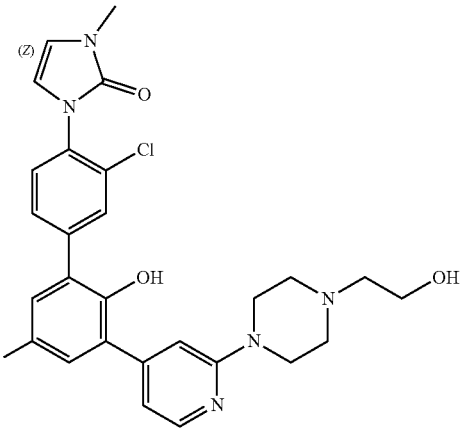

The title compound was prepared following the procedure described for Example 470 using 1-(3-chloro-5'-fluoro-2'-methoxy-3'-(2-(piperazin-1-yl)pyridin-4-yl)-[1,1'-biphenyl]-4-yl)-3-methyl-1H-imidazol-2(3H)-one, 2-bromoethanol and piperazine (10 yield). $^1$H NMR (400 MHz, DMSO-d$_6$): δ 8.70 (br s, 1H), 8.16 (d, J=5.2 Hz, 1H), 7.80 (d, J=2.0 Hz, 1H), 7.62 (dd, J=8.4, 2.0 Hz, 1H), 7.52 (d, J=8.4 Hz, 1H), 7.26-7.18 (m, 2H), 6.95 (s, 1H), 6.84-6.83 (m, 1H), 6.71 (d, J=2.8 Hz, 1H), 6.68 (d, J=2.8 Hz, 1H), 4.44 (br s, 1H), 3.57-3.52 (m, 6H), 3.21 (s, 3H), 2.57-2.51 (m, 4H), 2.46-2.44 (m, 2H). LCMS: 524.2 (M+H)+.

Example 472

1-(3-chloro-5'-fluoro-2'-hydroxy-3'-(5-(piperazin-1-yl)pyridin-3-yl)-[1,1'-biphenyl]-4-yl)-3-methyl-1H-imidazol-2(3H)-one

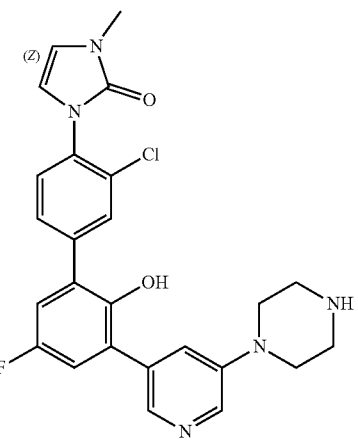

The title compound was prepared following the procedure described for Example B-365 using tert-butyl 4-(5-bromopyridin-3-yl)piperazine-1-carboxylate, 1-(3-chloro-5'- fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr$_3$ to afford the title compound (21% yield). $^1$H NMR (400 MHz, DMSO-d$_6$): δ 8.28 (d, J=2.8 Hz, 1H), 8.16 (d, J=1.2 Hz, 1H), 7.82 (d, J=2.0 Hz, 1H), 7.62 (dd, J=8.0, 2.0 Hz, 1H), 7.52 (d, J=8.4 Hz, 1H), 7.43-7.42 (m, 1H), 7.24-7.21 (m, 2H), 6.72-6.68 (m, 2H), 3.21 (s, 3H), 3.18-3.15 (m, 4H), 2.87-2.85 (m, 4H). N—H and O—H proton not observed. LCMS: 480.2 (M+H)$^+$.

Example 473

3-(3-chloro-5'-fluoro-2'-hydroxy-3'-(2-(piperazin-1-yl)pyridin-4-yl)-[1,1'-biphenyl]-4-yl)thiazol-2(3H)-one

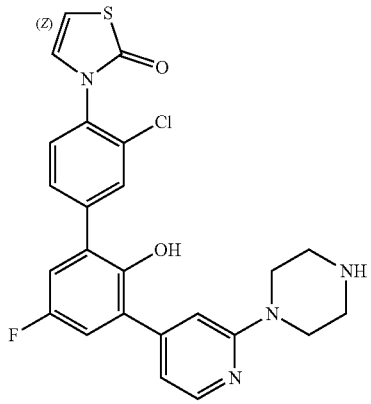

Step 1: 4-bromo-2-chlorobenzoyl azide

To a solution of 4-bromo-2-chlorobenzoic acid (1.00 g, 4.25 mmol) in THF (12 mL) was added DMF (1 drop), after stirred at room temperature for 20 min under N$_2$, the mixture was added oxalyl dichloride (674 mg, 5.31 mmol) dropwise, The mixture was stirred at room temperature to 70° C. for 2 hours. The reaction mixture was cooled down to room temperature and concentrated to remove THF to give a residue. The residue was diluted with acetone (15 mL) and NaN$_3$ (282 mg, 4.33 mmol) was added. The mixture was stirred at room temperature for 1 hour. The mixture was concentrated to remove acetone and solid was formed, filtered to give the title compound (900 mg, 90% yield) as crude product.

Step 2: 3-(4-bromo-2-chlorophenyl)thiazol-2(3H)-one

To a solution of 1,4-dithiane-2,5-diol (100 mg, 0.657 mmol) in MeOH (10 mL) was added 4-bromo-2-chlorobenzoyl azide (409 mg, 1.19 mmol), the mixture was stirred at 70° C. for 2 hours, the reaction mixture was cooled and 40% H$_2$SO$_4$ was added, the mixture was stirred at room temperature for 24 hours. After the reaction was complete by LCMS, the reaction mixture was diluted with H$_2$O (30 mL), extracted with EA (20 mL×3), the combined organic layers were dried over sodium sulfate, filtered and the filtrate was concentrated to give a residue, which was purified by silica gel chromatography using a mixture of (4:1) petroleum ether and ethyl acetate as the eluent to afford the title compound (160 mg, 94% yield) as a white solid. LCMS: 289.9 (M+1)$^+$.

Step 3: tert-butyl 4-(4-(3'-chloro-5-fluoro-2-methoxy-4'-(2-oxothiazol-3(2H)-yl)-[1,1'-biphenyl]-3-yl)pyridin-2-yl)piperazine-1-carboxylate The title compound was prepared following the procedure described for Example 1 using 3-(4-bromo-2-chlorophenyl)thiazol-2(3H)-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate (55% yield). LCMS: 597.2 (M)$^+$.

Step 4: 3-(3-chloro-5'-fluoro-2'-hydroxy-3'-(2-(piperazin-1-yl)pyridin-4-yl)-[1,1'-biphenyl]-4-yl)thiazol-2(3H)-one The title compound was prepared following the procedure described for Example 365 using tert-butyl 4-(4-(3'-chloro-5-fluoro-2-methoxy-4'-(2-oxothiazol-3(2H)-yl)-[1,1'-biphenyl]-3-yl)pyridin-2-yl)piperazine-1-carboxylate and BBr$_3$ (29% yield). $^1$H NMR (400 MHz, DMSO-d$_6$): δ 8.15 (d, J=4.8 Hz, 1H), 7.88 (d, J=1.6 Hz, 1H), 7.69-7.66 (m, 1H), 7.62 (d, J=8.4 Hz, 1H), 7.26 (dd, J=9.2, 3.2 Hz, 1H), 7.21 (dd, J=9.2, 3.2 Hz, 1H), 7.13 (d, J=5.2 Hz, 1H), 6.93 (s, 1H), 6.83-6.81 (m, 1H), 6.68 (d, J=5.6 Hz, 1H), 3.46-3.38 (m, 4H), 2.80-2.76 (m, 4H). N—H and O—H proton not observed. LCMS: 483.1 (M+H)$^+$.

Example 474

(R)-1-(3-chloro-3'-(5-(3,4-dimethylpiperazin-1-yl)pyridin-3-yl)-5'-fluoro-2'-hydroxy-[1,1'-biphenyl]-4-yl)-3-methyl-1H-imidazol-2(3H)-one

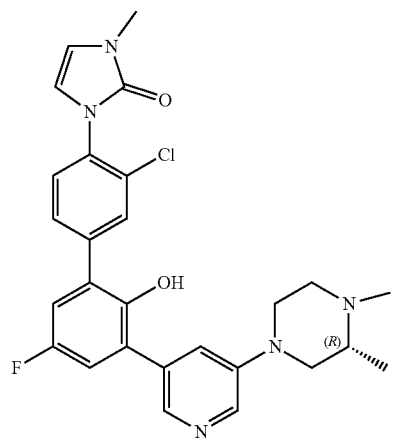

The title compound was prepared following the procedure described for Example 467 using (R)-1-(3-chloro-5'-fluoro-2'-hydroxy-3'-(5-(3-methylpiperazin-1-yl)pyridin-3-yl)-[1,1'-biphenyl]-4-yl)-3-methyl-1H-imidazol-2(3H)-one and formaldehyde (42% yield). $^1$H NMR (400 MHz, CD$_3$OD): δ 8.52 (s, 1H), 8.47 (s, 1H), 8.21 (s, 1H), 7.82 (d, J=1.2 Hz, 1H), 7.62 (dd, J=8.0, 1.6 Hz, 1H), 7.55 (d, J=8.0 Hz, 1H), 7.34-7.31 (m, 1H), 7.25-7.22 (m, 1H), 6.70 (d, J=2.8 Hz, 1H), 6.65 (d, J=2.8 Hz, 1H), 4.20-4.18 (m, 2H), 3.72-3.71 (m, 1H), 3.54-3.50 (m, 1H), 3.42-3.41 (m, 2H), 3.37 (s, 3H), 3.35-3.32 (m, 1H), 3.03 (s, 3H), 1.51 (d, J=6.4 Hz, 3H). LCMS: 508.2 (M+H)$^+$.

Example 475

(S)-1-(3-chloro-3'-(5-(3-(dimethylamino)pyrrolidin-1-yl)pyridin-3-yl)-5'-fluoro-2'-hydroxy-[1,1'-biphenyl]-4-yl)-3-methyl-1H-imidazol-2(3H)-one

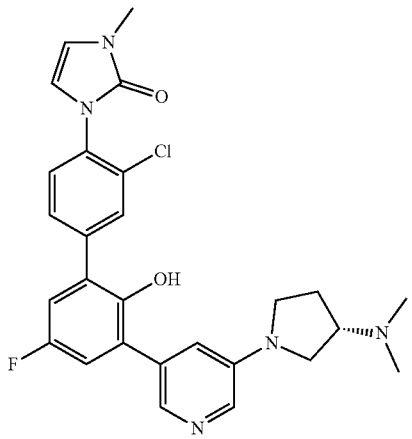

A solution of (S)-1-(3-chloro-5'-fluoro-2'-hydroxy-3'-(5-(3-(methylamino)pyrrolidin-1-yl)pyridin-3-yl)-[1,1'-biphenyl]-4-yl)-3-methyl-1H-imidazol-2(3H)-one (80 mg, 0.14 mmol), a solution of HCHO—H$_2$O (31.5 mg, 0.42 mmol) and AcOH (1 drop) in MeOH (3 mL) was stirred at rt overnight under N$_2$. After the reaction was complete by LCMS, The reaction mixture was concentrated and purified by prep-HPLC to afford the title compound (20.8 mg, 29% yield) as a light yellow solid. $^1$H NMR (400 MHz, DMSO-d$_6$): δ 8.65 (s, 1H), 8.00 (d, J=1.6 Hz, 1H), 7.93 (d, J=2.4 Hz, 1H), 7.81 (d, J=2.0 Hz, 1H), 7.62 (dd, J=8.0, 1.6 Hz, 1H), 7.52 (d, J=8.0 Hz, 1H), 7.24-7.18 (m, 2H), 7.04 (t, J=2.0 Hz, 1H), 6.72-6.68 (m, 2H), 3.55-3.51 (m, 1H), 3.49-3.44 (m, 1H), 3.34-3.27 (m, 1H), 3.21 (s, 3H), 3.12-3.08 (m, 1H), 2.83-2.79 (m, 1H), 2.22-2.16 (m, 7H), 1.85-1.79 (m, 1H). LCMS: 508.2 (M+H)$^+$.

Example 476

(S)-1-(3-chloro-5'-fluoro-2'-hydroxy-3'-(5-(3-(methylamino)pyrrolidin-1-yl)pyridin-3-yl)-[1,1'-biphenyl]-4-yl)-3-methyl-1H-imidazol-2(3H)-one

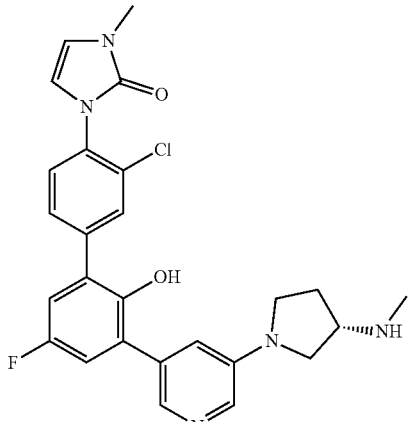

Step 1: (S)-tert-butyl (1-(5-(3'-chloro-5-fluoro-2-methoxy-4'-(3-methyl-2-oxo-2,3-dihydro-1H-imidazol-1-yl)-[1,1'-biphenyl]-3-yl)pyridin-3-yl)pyrrolidin-3-yl)(methyl)carbamate The title compound was prepared following the procedure described for Example 1 using (S)-(5-(3-((tert-butoxycarbonyl)(methyl)amino)pyrrolidin-1-yl)pyridin-3-yl)boronic acid and 1-(3'-bromo-3-chloro-5'-fluoro-2'-methoxy-[1,1'-biphenyl]-4-yl)-3-methyl-1H-imidazol-2(3H)-one to afford the title compound (92% yield). LCMS: 608.3 (M+H)$^+$.

Step 2: (S)-1-(3-chloro-5'-fluoro-2'-hydroxy-3'-(5-(3-(methylamino)pyrrolidin-1-yl)pyridin-3-yl)-[1,1'-biphenyl]-4-yl)-3-methyl-1H-imidazol-2(3H)-one The title compound was prepared following the procedure described for Example 365 using (S)-tert-butyl (1-(5-(3'-chloro-5-fluoro-2-methoxy-4'-(3-methyl-2-oxo-2,3-dihydro-1H-imidazol-1-yl)-[1,1'-biphenyl]-3-yl)pyridin-3-yl)pyrrolidin-3-yl)(methyl)carbamate and BBr$_3$ to afford the title compound (34% yield). LCMS: 494.2 (M+H)$^+$. $^1$H NMR (400 MHz, DMSO-d$_6$): δ 7.99 (d, J=1.2 Hz, 1H), 7.90 (d, J=2.8 Hz, 1H), 7.81 (d, J=2.0 Hz, 1H), 7.62 (dd, J=8.0, 2.0 Hz, 1H), 7.52 (d, J=8.4 Hz, 1H), 7.23-7.18 (m, 2H), 7.01 (t, J=2.0 Hz, 1H), 6.72-6.68 (m, 2H), 3.49-3.42 (m, 1H), 3.39-3.36 (m, 1H), 3.31-3.27 (m, 2H), 3.21 (s, 3H), 3.09-3.06 (m, 1H), 2.31 (s, 3H), 2.15-2.07 (m, 1H), 1.86-1.75 (m, 1H). N—H and O—H protons not observed. LCMS: 494.2 (M+H)$^+$.

Example 477

5-(3'-chloro-5-fluoro-2-hydroxy-4'-(3-methyl-2-oxo-imidazolidin-1-yl)-[1,1'-biphenyl]-3-yl)-1-(piperidin-4-yl)pyridin-2(1H)-one

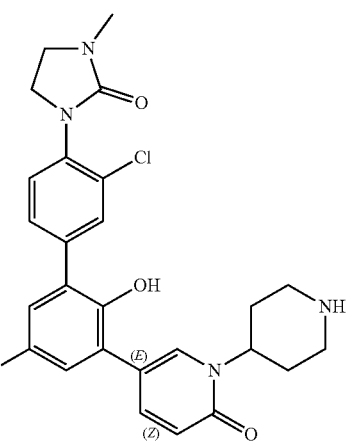

Step 1: tert-butyl 4-(5-bromo-2-oxopyridin-1(2H)-yl)piperidine-1-carboxylate

The title compound was prepared using tert-butyl 4-(tosyloxy)piperidine-1-carboxylate and 5-bromopyridin-2(1H)-one to afford the title compound (48%7 yield). LCMS: 357.0 (M+H)$^+$.

Step 2: tert-butyl 4-(5-(3'-chloro-5-fluoro-2-methoxy-4'-(3-methyl-2-oxoimidazolidin-1-yl)-[1,1'-biphenyl]-3-yl)-2-oxopyridin-1(2H)-yl)piperidine-1-carboxylate The title compound was prepared following the procedure described for Example 365 using tert-butyl 4-(5-bromo-2-oxopyridin-1(2H)-yl)piperidine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one to afford the title compound (35% yield). LCMS: 611.1 (M+H)$^+$.

Step 3: 5-(3'-chloro-5-fluoro-2-hydroxy-4'-(3-methyl-2-oxoimidazolidin-1-yl)-[1,1'-biphenyl]-3-yl)-1-(piperidin-4-yl)pyridin-2(1H)-one The title compound was prepared following the procedure described for Example 365 using tert-butyl 4-(5-(3'-chloro-5-fluoro-2-methoxy-4'-(3-methyl-2-oxoimidazolidin-1-yl)-[1,1'-biphenyl]-3-yl)-2-oxopyridin-1(2H)-yl)piperidine-1-carboxylate and BBr$_3$ to afford the title compound (27% yield). $^1$H NMR (400 MHz, DMSO-d$_6$): δ 8.74-8.55 (m, 1H), 8.21 (br s, 1H), 7.72-7.67 (m, 3H), 7.53 (dd, J=8.4, 2.0 Hz, 1H), 7.46 (d, J=8.0 Hz, 1H), 7.22-7.14 (m, 2H), 6.52 (d, J=9.2 Hz, 1H), 5.03-4.99 (m, 1H), 3.83-3.73 (m, 2H), 3.52-3.42 (m, 4H), 3.16-3.12 (m, 2H), 2.77 (s, 3H), 2.15-2.12 (m, 2H), 1.99-1.96 (m, 2H). LCMS: 497.1 (M+H)$^+$.

Example 478

(S)-1-(3-chloro-5'-fluoro-2'-hydroxy-3'-(5-(3-(methylamino)piperidin-1-yl)pyridin-3-yl)-[1,1'-biphenyl]-4-yl)-3-methyl-1H-imidazol-2(3H)-one

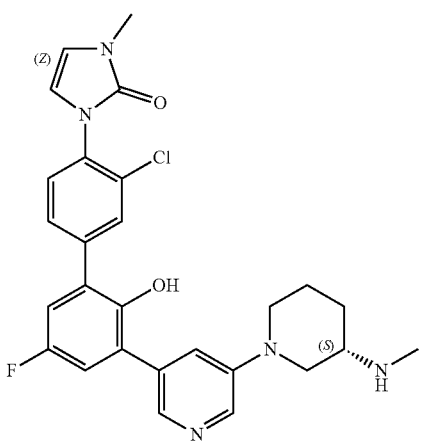

The title compound was prepared following the procedure described for Example 465 using (S)-tert-butyl methyl(piperidin-3-yl)carbamate, 3,5-dibromopyridine and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one to afford the title compound (7% yield). $^1$H NMR (400 MHz, DMSO-d$_6$): δ 8.27 (d, J=2.8 Hz, 1H), 8.12 (d, J=1.6 Hz, 1H), 7.81 (d, J=2.0 Hz, 1H), 7.63 (dd, J=2.0, 8.4 Hz, 1H), 7.52 (d, J=8.0 Hz, 1H), 7.44-7.42 (m, 1H), 7.24-7.19 (m, 2H), 6.70 (dd, J=3.2, 13.2 Hz, 2H), 3.78 (d, J=8.8 Hz, 1H), 3.65-3.62 (m, 1H), 3.21 (s, 3H), 2.82-2.76 (m, 1H), 2.56-2.50 (m, 2H), 2.34 (s, 3H), 1.94-1.91 (m, 1H), 1.76-1.73 (m, 1H), 1.57-1.54 (m, 1H), 1.23-1.19 (m, 1H). N—H and O—H protons not observed. LCMS: 508.2 (M+H)$^+$.

Example 479

1-(3-chloro-5'-fluoro-2'-hydroxy-3'-(4-(piperazin-1-yl)-1H-indol-6-yl)-[1,1'-biphenyl]-4-yl)-3-methyl-1H-imidazol-2(3H)-one

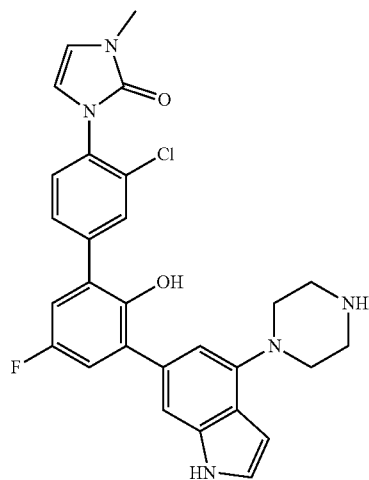

The title compound was prepared following the procedure described for Example 465 using tert-butyl 4-(6-bromo-1H-indol-4-yl)piperazine-1-carboxylate, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr$_3$ to afford the title compound (19% yield). $^1$H NMR (400 MHz, DMSO-d$_6$): δ 11.24 (s, 1H), 8.77 (brs, 1H), 8.40 (s, 1H), 7.82 (d, J=1.6 Hz, 1H), 7.63 (dd, J=2.0, 8.4 Hz, 1H), 7.52 (d, J=8.0 Hz, 1H), 7.36 (t, J=2.4 Hz, 1H), 7.31 (s, 1H), 7.16 (d, J=9.2 Hz, 2H), 6.72-6.67 (m, 3H), 6.52 (s, 1H), 3.50-3.36 (m, 8H), 3.21 (s, 3H). LCMS: 518.2 (M+H)$^+$.

Example 480

1-(3'-([2,3'-bipyridin]-4-yl)-3-chloro-5'-fluoro-2'-hydroxy-[1,1'-biphenyl]-4-yl)-3-methyl-1H-imidazol-2(3H)-one

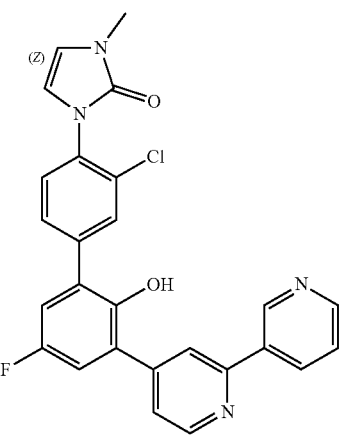 [SMILES: Cn1ccn(-c2ccc(-c3cc(F)cc(-c4ccnc(-c5cccnc5)c4)c3O)cc2Cl)c1=O]

Step 1: 1-(3-chloro-3'-(2-chloropyridin-4-yl)-5'-fluoro-2'-methoxy-[1,1'-biphenyl]-4-yl)-3-methyl-1H-imidazol-2(3H)-one The title compound was prepared using 1-(3'-bromo-3-chloro-5'-fluoro-2'-methoxy-[1,1'-biphenyl]-4-yl)-3-methyl-1H-imidazol-2(3H)-one and (2-chloropyridin-4-yl)boronic acid to afford the title compound (46% yield). LCMS: 444.0 (M+H)+.

Step 2: 1-(3'-([2,3'-bipyridin]-4-yl)-3-chloro-5'-fluoro-2'-methoxy-[1,1'-biphenyl]-4-yl)-3-methyl-1H-imidazol-2(3H)-one The title compound was prepared using 1-(3-chloro-3'-(2-chloropyridin-4-yl)-5'-fluoro-2'-methoxy-[1,1'-biphenyl]-4-yl)-3-methyl-1H-imidazol-2(3H)-one and pyridin-3-ylboronic acid to afford the title compound (53% yield). LCMS: 487.1 (M+H)+.

Step 3: 1-(3'-([2,3'-bipyridin]-4-yl)-3-chloro-5'-fluoro-2'-hydroxy-[1,1'-biphenyl]-4-yl)-3-methyl-1H-imidazol-2(3H)-one The title compound was prepared following the procedure described for Example 365 using 1-(3'-([2,3'-bipyridin]-4-yl)-3-chloro-5'-fluoro-2'-methoxy-[1,1'-biphenyl]-4-yl)-3-methyl-1H-imidazol-2(3H)-one and BBr3 to afford the title compound (16% yield). 1H NMR (400 MHz, DMSO-d6): δ 9.33 (d, J=1.6 Hz, 1H), 8.96 (s, 1H), 8.77 (d, J=4.8 Hz, 1H), 8.65 (dd, J=1.6, 4.8 Hz, 1H), 8.52-8.49 (m, 1H), 8.22 (d, J=0.8 Hz, 1H), 7.85 (d, J=2.0 Hz, 1H), 7.66-7.64 (m, 2H), 7.55-7.52 (m, 2H), 7.42 (dd, J=3.2, 8.8 Hz, 1H), 8.32 (dd, J=3.2, 8.8 Hz, 1H), 6.72 (d, J=3.2 Hz, 1H), 6.69 (d, J=3.2 Hz, 1H), 3.21 (s, 3H). LCMS: 473.1 (M+H)+.

Example 481

1-(3'-([2,4'-bipyridin]-4-yl)-3-chloro-5'-fluoro-2'-hydroxy-[1,1'-biphenyl]-4-yl)-3-methyl-1H-imidazol-2(3H)-one

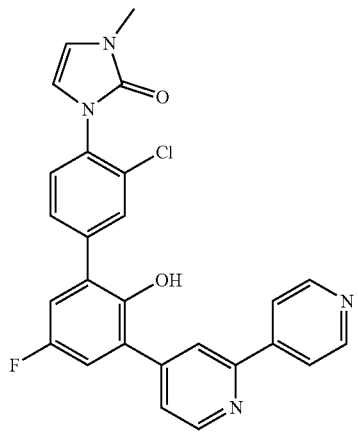 [SMILES: Cn1ccn(-c2ccc(-c3cc(F)cc(-c4ccnc(-c5ccncc5)c4)c3O)cc2Cl)c1=O]

The title compound was prepared following the procedure described for Example 480 using 1-(3-chloro-3'-(2-chloropyridin-4-yl)-5'-fluoro-2'-methoxy-[1,1'-biphenyl]-4-yl)-3-methyl-1H-imidazol-2(3H)-one, pyridin-4-ylboronic acid and BBr3 to afford the title compound (38% yield). 1H NMR (400 MHz, DMSO-d6): δ 9.03 (brs, 1H), 8.88-8.85 (m, 3H), 8.44-8.42 (m, 3H), 7.85 (d, J=2.0 Hz, 1H), 7.80 (dd, J=1.6, 4.8 Hz, 1H), 7.66 (dd, J=2.0, 8.0 Hz, 1H), 7.55 (d, J=9.2 Hz, 1H), 7.45 (dd, J=2.8, 8.8 Hz, 1H), 7.35 (dd, J=3.2, 9.2 Hz, 1H), 6.72 (d, J=3.2 Hz, 1H), 6.69 (d, J=3.2 Hz, 1H), 3.21 (s, 3H). LCMS: 473.1 (M+H)+.

Example 482

(S)-1-(3-chloro-5'-fluoro-2'-hydroxy-3'-(2-(2-methylpiperazin-1-yl)pyridin-4-yl)-[1,1'-biphenyl]-4-yl)-3-deuteromethyl-1H-imidazol-2(3H)-one

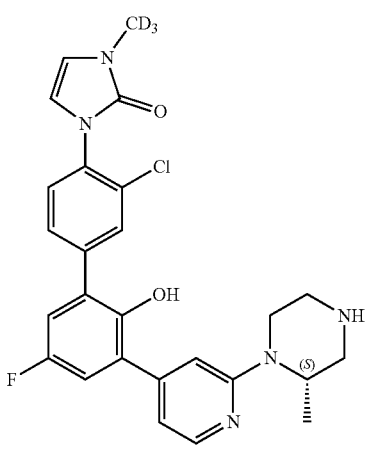

Step 1: (S)-tert-butyl 4-(4-bromopyridin-2-yl)-3-methylpiperazine-1-carboxylate A mixture of 4-bromo-2-fluoropyridine (100 mg, 0.568 mmol), (S)-tert-butyl 3-methylpiperazine-1-carboxylate (369 mg, 2.82 mmol) and Cs2CO3 (553 mg, 1.70 mmol) in DMSO (10 mL) in seal tube was stirred at 120° C. under nitrogen atmosphere for 12 hours. After the reaction was complete by LCMS, the reaction mixture was cooled and added water (15 mL), extracted with EA (15 mL×3). The combined organic layers were washed with brine (10 mL×3), dried over sodium sulfate and filtered. The filtrate was concentrated to give a residue, which was purified by silica gel chromatography using petroleum ether and ethyl acetate (4:1) as the eluent to afford the title compound (50 mg, 25% yield) as colorless oil. LCMS: 358.3 (M+H)+.

Step 2: (S)-tert-butyl 4-(4-(3'-chloro-5-fluoro-2-methoxy-4'-(3-deuteromethyl-2-oxo-2,3-dihydro-1H-imidazol-1-yl)-[1,1'-biphenyl]-3-yl)pyridin-2-yl)-3-methylpiperazine-1-carboxylate The title compound was prepared following the procedures described for Example 480 using (S)-tert-butyl 4-(4-bromopyridin-2-yl)-3-methylpiperazine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-deuteromethyl-1H-imidazol-2(3H)-one to afford the title compound (58% yield). LCMS: 611.3 (M+H)+.

Step 3: (S)-1-(3-chloro-5'-fluoro-2'-hydroxy-3'-(2-(2-methylpiperazin-1-yl)pyridin-4-yl)-[1,1'-biphenyl]-4-yl)-3-deuteromethyl-1H-imidazol-2(3H)-one The title compound was prepared following the procedure described for Example 480 using (S)-tert-butyl 4-(4-(3'- chloro-5-fluoro-2-methoxy-4'-(3-deuteromethyl-2-oxo-2,3-dihydro-1H-imidazol-1-yl)-[1,1'-biphenyl]-3-yl)pyridin-2-yl)-3-methylpiperazine-1-carboxylate and BBr₃ to afford the title compound (18% yield). ¹H NMR (400 MHz, DMSO-d₆): δ 9.04-9.01 (m, 1H), 8.76 (brs, 1H), 8.60-8.56 (m, 1H), 8.21 (d, J=5.2 Hz, 1H), 7.81 (d, J=2.0 Hz, 1H), 7.61 (dd, J=2.0, 8.0 Hz, 1H), 7.53 (d, J=8.0 Hz, 1H), 7.28-7.20 (m, 2H), 7.01 (s, 1H), 6.94 (dd, J=1.2, 4.8 Hz, 1H), 6.72 (d, J=3.2 Hz, 1H), 6.68 (d, J=3.2 Hz, 1H), 4.82-4.79 (m, 1H), 4.34-4.30 (m, 1H), 3.36-3.29 (m, 2H), 3.21-3.14 (m, 2H), 3.03-2.99 (m, 1H), 1.23 (d, J=6.8 Hz, 3H). LCMS: 497.2 (M+H)⁺.

Example 483

1-(3-chloro-3'-(2-(3,4-dihydroquinoxalin-1(2H)-yl)pyridin-4-yl)-5'-fluoro-2'-hydroxy-[1,1'-biphenyl]-4-yl)-3-methylimidazolidin-2-one

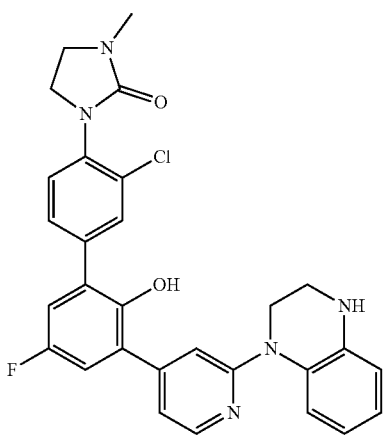 [SMILES: CN1CCN(c2ccc(-c3cc(F)cc(-c4ccnc(N5CCNc6ccccc65)c4)c3O)cc2Cl)C1=O]

Step 1: tert-butyl 4-(4-(3'-chloro-5-fluoro-2-methoxy-4'-(3-methyl-2-oxoimidazolidin-1-yl)-[1,1'-biphenyl]-3-yl)pyridin-2-yl)-3,4-dihydroquinoxaline-1(2H)-carboxylate The title compound was prepared following the procedure described for Example 482 using 1-(3-chloro-5'-fluoro-2'-methoxy-3'-(4,4,5,5-tetramethyl-1,3,2-dioxaborolan-2-yl)-[1,1'-biphenyl]-4-yl)-3-methylimidazolidin-2-one and tert-butyl 4-(4-chloropyridin-2-yl)-3,4-dihydroquinoxaline-1(2H)—carboxylate to afford the title compound (43% yield). LCMS: 644.2 (M+H)⁺.

Step 2: 1-(3-chloro-3'-(2-(3,4-dihydroquinoxalin-1(2H)-yl)pyridin-4-yl)-5'-fluoro-2'-hydroxy-[1,1'-biphenyl]-4-yl)-3-methylimidazolidin-2-one The title compound was prepared following the procedure described for Example 482 using tert-butyl 4-(4-(3'-chloro-5-fluoro-2-methoxy-4'-(3-methyl-2-oxoimidazolidin-1-yl)-[1,1'-biphenyl]-3-yl)pyridin-2-yl)-3,4-dihydroquinoxaline-1(2H)-carboxylate and BBr₃ to afford the title compound (19% yield). ¹H NMR (400 MHz, CD₃OD): δ 8.13 (dd, J=0.8, 5.2 Hz, 1H), 7.57 (d, J=1.6 Hz, 1H), 7.40 (dd, J=2.0, 8.4 Hz, 1H), 7.32 (d, J=8.0 Hz, 1H), 7.24 (s, 1H), 7.08 (dd, J=1.2, 8.0 Hz, 1H), 6.95-6.90 (m, 2H), 6.88 (dd, J=1.6, 5.2 Hz, 1H), 6.75-6.70 (m, 1H), 6.57 (dd, J=1.2, 8.0 Hz, 1H), 6.49-6.44 (m, 1H), 3.89-3.87 (m, 2H), 3.74-3.70 (m, 2H), 3.51-3.47 (m, 2H), 3.27-3.24 (m, 2H), 2.78 (s, 3H). N—H and O—H proton not observed. LCMS: 530.2 (M+H)⁺.

Example 484

(S)-1-(3'-(5-(3-aminopyrrolidin-1-yl)pyridin-3-yl)-3-chloro-5'-fluoro-2'-hydroxy-[1,1'-biphenyl]-4-yl)-3-methyl-1H-imidazol-2(3H)-one

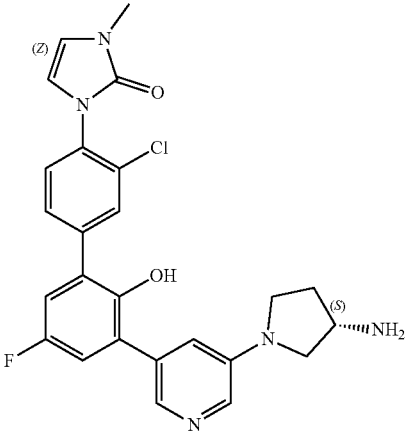

The title compound was prepared following the procedures described for Example 480 using 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one, (S)-tert-butyl (1-(5-bromopyridin-3-yl)pyrrolidin-3-yl)carbamate and BBr₃ to afford the title compound (10% yield). ¹H NMR (400 MHz, DMSO-d₆): δ 7.98 (d, J=1.6 Hz, 1H), 7.88 (d, J=2.8 Hz, 1H), 7.81 (d, J=2.0 Hz, 1H), 7.62 (dd, J=2.0, 8.4 Hz, 1H), 7.52 (d, J=8.0 Hz, 1H), 7.23-7.16 (m, 2H), 6.99 (t, J=2.0 Hz, 1H), 6.72 (d, J=3.2 Hz, 1H), 6.68 (d, J=2.8 Hz, 1H), 3.62-3.59 (m, 1H), 3.48-3.40 (m, 3H), 3.20 (s, 3H), 2.98-2.95 (m, 1H), 2.11-2.06 (m, 1H), 1.76-1.71 (m, 1H). N—H and O—H proton not observed. LCMS: 480.1 (M+H)⁺.

Example 485

(S)-1-(3-chloro-3'-(2-(3-(dimethylamino)pyrrolidin-1-yl)pyridin-4-yl)-5'-fluoro-2'-hydroxy-[1,1'-biphenyl]-4-yl)-3-methyl-1,3-dihydro-2H-imidazol-2-one

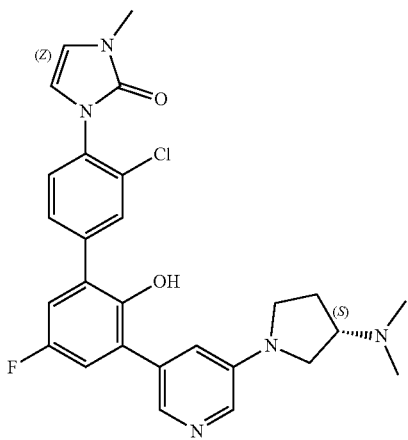

The title compound was prepared using (S)-1-(3-chloro-5'-fluoro-2'-hydroxy-3'-(2-(3-(methylamino)pyrrolidin-1-yl)pyridin-4-yl)-[1,1'-biphenyl]-4-yl)-3-methyl-1H-imidazol-2(3H)-one dihydrochloride, formaldehyde and NaCNBH₄ in the presence of acetic acid to afford the title compound (40% yield). ¹H NMR (400 MHz, DMSO-d₆): δ 8.67 (s, 1H), 8.10 (d, J=5.2 Hz, 1H), 7.80 (d, J=2.0 Hz, 1H), 7.61 (dd, J=2.0, 8.0 Hz, 1H), 7.52 (d, J=8.4 Hz, 1H), 7.25-7.17 (m, 2H), 6.74-6.68 (m, 3H), 6.59 (s, 1H), 3.73-3.69 (m, 1H), 3.64-3.59 (m, 1H), 3.39-3.34 (m, 1H), 3.20 (s, 3H), 3.15 (t, J=8.8 Hz, 1H), 2.80-2.77 (m, 1H), 2.22 (s, 6H), 2.18-2.14 (m, 1H), 1.83-1.78 (m, 1H). LCMS: 508.2 (M+H)⁺.

Example 486

5-(3'-chloro-5-fluoro-2-hydroxy-4'-(3-methyl-2-oxo-2,3-dihydro-1H-imidazol-1-yl)-[1,1'-biphenyl]-3-yl)-1-(piperidin-4-yl)pyridin-2(1H)-one

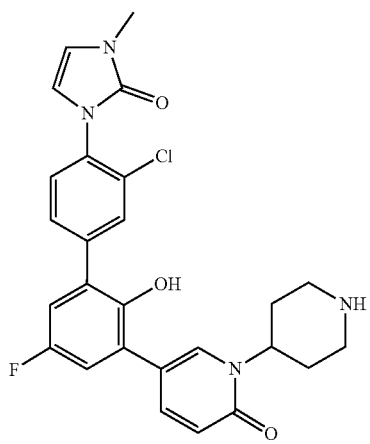

Step 1: tert-butyl 4-(5-(3'-chloro-5-fluoro-2-methoxy-4'-(3-methyl-2-oxo-2,3-dihydro-1H-imidazol-1-yl)-[1,1'-biphenyl]-3-yl)-2-oxopyridin-1(2H)-yl)piperidine-1-carboxylate The title compound was prepared following the procedure described for Example 477 using 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and tert-butyl 4-(5-bromo-2-oxopyridin-1(2H)-yl)piperidine-1-carboxylate to afford the title compound (47% yield). LCMS: 609.2 (M+H)⁺.

Step 2: 5-(3'-chloro-5-fluoro-2-hydroxy-4'-(3-methyl-2-oxo-2,3-dihydro-1H-imidazol-1-yl)-[1,1'-biphenyl]-3-yl)-1-(piperidin-4-yl)pyridin-2(1H)-one 2,2,2-trifluoroacetate The title compound was prepared following the procedure described for Example 477 using tert-butyl 4-(5-(3'-chloro-5-fluoro-2-methoxy-4'-(3-methyl-2-oxo-2,3-dihydro-1H-imidazol-1-yl)-[1,1'-biphenyl]-3-yl)-2-oxopyridin-1(2H)-yl)piperidine-1-carboxylate and BBr₃ to afford the title compound (9% yield). ¹H NMR (400 MHz, CD₃OD): δ 7.77 (d, J=2.4 Hz, 1H), 7.71-7.68 (m, 2H), 7.48 (dd, J=2.0, 8.4 Hz, 1H), 7.41 (d, J=8.4 Hz, 1H), 7.04-6.96 (m, 2H), 6.58- 6.52 (m, 3H), 5.00-4.92 (m, 1H), 3.51-3.48 (m, 2H), 3.25 (s, 3H), 3.16-3.12 (m, 2H), 2.20-2.08 (m, 4H). N—H and O—H proton not observed. LCMS: 495.2 (M+H)⁺.

Example 487

1-(3'-(2-((3R,4R)-3-amino-4-hydroxypiperidin-1-yl)pyridin-4-yl)-3-chloro-5'-fluoro-2'-hydroxy-[1,1'-biphenyl]-4-yl)-3-methyl-1H-imidazol-2(3H)-one

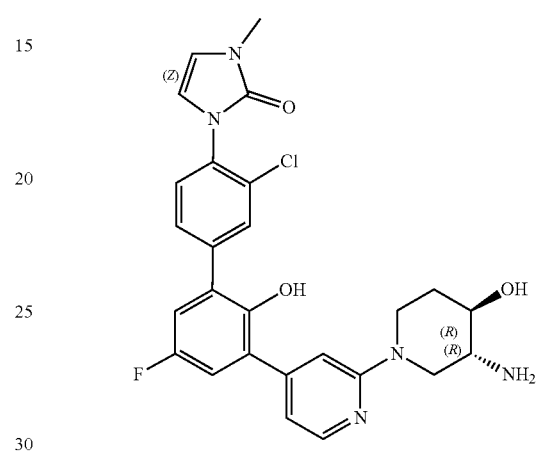

Step 1: tert-butyl ((3R,4R)-1-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-4-hydroxypiperidin-3-yl)carbamate The title compound was prepared following the procedure described for Example 365 using tert-butyl ((3R,4R)-1-(4-(3-bromo-5-fluoro-2-methoxyphenyl)pyridin-2-yl)-4-hydroxypiperidin-3-yl)carbamate and 1-(2-chloro-4-(4,4,5,5-tetramethyl-1,3,2-dioxaborolan-2-yl)phenyl)-3-methyl-1H-imidazol-2(3H)-one to afford the title compound (48% yield). LCMS: 624.6 (M+H)⁺.

Step 4: 1-(3'-(2-((3R,4R)-3-amino-4-hydroxypiperidin-1-yl)pyridin-4-yl)-3-chloro-5'-fluoro-2'-hydroxy-[1,1'-biphenyl]-4-yl)-3-methyl-1H-imidazol-2(3H)-one The title compound was prepared following the procedure described for Example 365 using tert-butyl ((3R,4R)-1-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-4-hydroxypiperidin-3-yl)carbamate and BBr₃ to afford the title compound (11% yield). ¹H NMR (400 MHz, DMSO-d₆+D₂O): δ 8.14 (d, J=5.2 Hz, 1H), 7.80 (d, J=1.6 Hz, 1H), 7.62 (dd, J=2.0, 8.0 Hz, 1H), 7.52 (d, J=8.4 Hz, 1H), 7.26-7.18 (m, 2H), 6.97 (s, 1H), 6.82 (d, J=5.6 Hz, 1H), 6.71 (d, J=3.2 Hz, 1H), 6.68 (d, J=3.2 Hz, 1H), 4.38-4.35 (m, 1H), 4.28-4.25 (m, 1H), 3.45-3.42 (m, 1H), 3.21 (s, 3H), 2.90-2.84 (m, 1H), 2.80-2.77 (m, 2H), 1.89-1.85 (m, 1H), 1.39-1.36 (m, 1H). N—H and O—H proton not observed. LCMS: 510.1 (M+H)⁺.

Example 488

1-(3-chloro-5'-fluoro-2'-hydroxy-3'-(5-(6-methyl-2,6-diazaspiro[3.3]heptan-2-yl)pyridin-3-yl)-[1,1'-biphenyl]-4-yl)-3-methyl-1H-imidazol-2(3H)-one

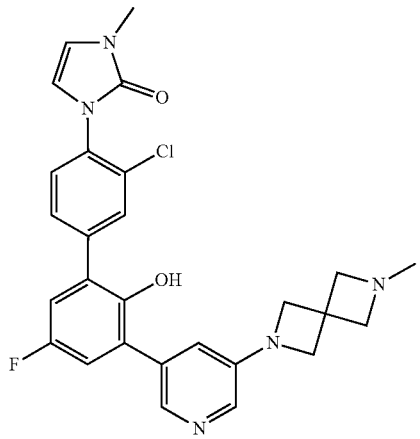

Step 1: 1-(3-chloro-5'-fluoro-2'-methoxy-3'-(5-(6-methyl-2,6-diazaspiro[3.3]heptan-2-yl)pyridin-3-yl)-[1,1'-biphenyl]-4-yl)-3-methyl-1H-imidazol-2(3H)-one The title compound was prepared using 2-(5-bromopyridin-3-yl)-6-methyl-2,6-diazaspiro[3.3]heptane and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one to afford the title compound (47% yield). LCMS: 520.2 (M+H)+.

Step 2: 1-(3-chloro-5'-fluoro-2'-hydroxy-3'-(5-(6-methyl-2,6-diazaspiro[3.3]heptan-2-yl)pyridin-3-yl)-[1,1'-biphenyl]-4-yl)-3-methyl-1H-imidazol-2(3H)-one To a solution of 1-(3-chloro-5'-fluoro-2'-methoxy-3'-(5-(6-methyl-2,6-diazaspiro[3.3]heptan-2-yl)pyridin-3-yl)-[1,1'-biphenyl]-4-yl)-3-methyl-1H-imidazol-2(3H)-one (54 mg, 0.10 mmol) in DMF (0.5 mL) was added piperazine (1.70 g, 20.8 mmol). The reaction mixture was stirred at 150° C. under microwave for 4 h. After the reaction was complete by LCMS, the reaction mixture was cooled to rt, added water (15 mL) and extracted with DCM/MeOH (20:1, 20 mL×3). The combined organic layers were washed with brine, dried over sodium sulfate, filtered and concentrated. The residue was purified by prep-HPLC to afford the title compound (5.1 mg, 8% yield) as a white solid. LCMS: 506.3 (M+H)+. 1H NMR (400 MHz, DMSO-d6): δ 9.91 (br s, 1H), 8.97 (brs, 1H), 8.26 (s, 1H), 7.98 (s, 1H), 7.82 (d, J=2.0 Hz, 1H), 7.63 (dd, J=2.0, 8.4 Hz, 1H), 7.55 (d, J=8.4 Hz, 1H), 7.37-7.27 (m, 3H), 6.78 (d, J=2.8 Hz, 1H), 6.68 (d, J=2.8 Hz, 1H), 4.67-4.51 (m, 3H), 4.28-4.21 (m, 5H), 4.14 (s, 3H), 2.83 (d, J=4.8 Hz, 3H).

Example 489

1-(3-chloro-5'-fluoro-2'-hydroxy-3'-(2-(6-methyl-2,6-diazaspiro[3.3]heptan-2-yl)pyridin-4-yl)-[1,1'-biphenyl]-4-yl)-3-methyl-1H-imidazol-2(3H)-one

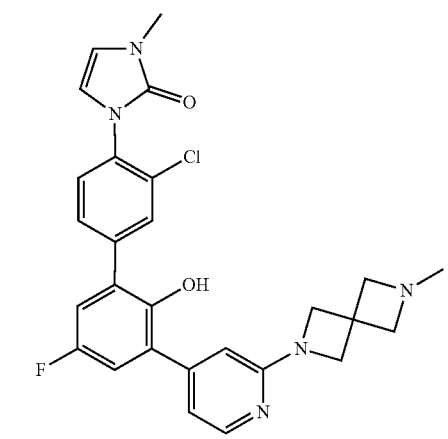 [SMILES: CN1CC2(C1)CN(c1cc(-c3cc(F)cc(-c4ccc(-n5ccn(C)c5=O)c(Cl)c4)c3O)ccn1)C2]

Step 1: 1-(3'-(2-(2,6-diazaspiro[3.3]heptan-2-yl)pyridin-4-yl)-3-chloro-5'-fluoro-2'-hydroxy-[1,1'-biphenyl]-4-yl)-3-methyl-1H-imidazol-2(3H)-one The title compound was prepared following the procedure described for Example 485 using tert-butyl 6-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-2,6-diazaspiro[3.3]heptane-2-carboxylate and TFA to afford the title compound (20% yield). LCMS: 492.1 (M+H)+.

Step 2: 1-(3-chloro-5'-fluoro-2'-hydroxy-3'-(2-(6-methyl-2,6-diazaspiro[3.3]heptan-2-yl)pyridin-4-yl)-[1,1'-biphenyl]-4-yl)-3-methyl-1H-imidazol-2(3H)-one 2,2,2-trifluoroacetate The title compound was prepared following the procedure described for Example 485 using 1-(3'-(2-(2,6-diazaspiro[3.3]heptan-2-yl)pyridin-4-yl)-3-chloro-5'-fluoro-2'-hydroxy-[1,1'-biphenyl]-4-yl)-3-methyl-1H-imidazol-2(3H)-one to afford the title compound (41% yield). 1H NMR (400 MHz, DMSO-d6): δ 9.91 (brs, 1H), 9.07 (brs, 1H), 8.10 (d, J=6.0 Hz, 1H), 7.81 (d, J=2.0 Hz, 1H), 7.62 (dd, J=2.0, 8.4 Hz, 1H), 7.55 (d, J=8.0 Hz, 1H), 7.35-7.27 (m, 2H), 7.06 (d, J=6.0 Hz, 1H), 6.89 (s, 1H), 6.72 (d, J=2.8 Hz, 1H), 6.68 (d, J=2.8 Hz, 1H), 4.44-4.38 (m, 5H), 4.31 (s, 3H), 4.24-4.19 (m, 3H), 2.82 (d, J=4.4 Hz, 3H). LCMS: 506.2 (M+H)+.

Example 490

1-(3'-(2-((3R,4R)-3-amino-4-hydroxypyrrolidin-1-yl)pyridin-4-yl)-3-chloro-5'-fluoro-2'-hydroxy-[1,1'-biphenyl]-4-yl)-3-methyl-1H-imidazol-2(3H)-one

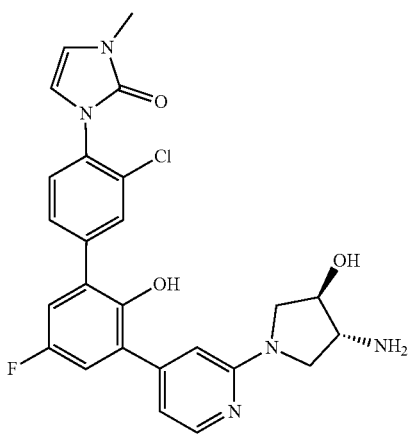 [SMILES: Cn1ccn(-c2ccc(-c3cc(F)cc(-c4ccnc(N5C[C@@H](N)[C@H](O)C5)c4)c3O)cc2Cl)c1=O]

Step 1: tert-butyl ((3R,4R)-1-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-4-hydroxypyrrolidin-3-yl)carbamate A mixture of tert-butyl ((3R,4R)-4-hydroxypyrrolidin-3-yl)carbamate (113.6 mg, 0.5617 mmol), 1-(3-chloro-5'-fluoro-3'-(2-fluoropyridin-4-yl)-2'-methoxy-[1,1'-biphenyl]-4-yl)-3-methyl-1H-imidazol-2(3H)-one (80.0 mg, 0.187 mmol) and DIEA (120.8 mg, 0.9347 mmol) in DMSO (2 mL) was stirred at 100° C. under N₂ overnight. After the reaction was complete by LCMS, the reaction mixture was cooled to rt, added H₂O (5 mL) and sat. NH₄Cl solution (1 mL) and extracted with EA (3 mL×3). The combined organic layer was washed with H₂O (4 mL×2) and brine, dried over Na₂SO₄, filtered and concentrated. The residue was purified by silica gel chromatography using DCM and MeOH (20:1) as the eluent to afford the title compound (84 mg, 74% yield) as an orange solid. LCMS: 610.3 (M+H)$^+$

Step 2: 1-(3'-(2-((3R,4R)-3-amino-4-hydroxypyrrolidin-1-yl)pyridin-4-yl)-3-chloro-5'-fluoro-2'-hydroxy-[1,1'-biphenyl]-4-yl)-3-methyl-1H-imidazol-2(3H)-one The title compound was prepared following the procedure described for Example 487 using tert-butyl ((3R,4R)-1-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-4-hydroxypyrrolidin-3-yl)carbamate and BBr₃ to afford the title compound (40% yield). $^1$H NMR (400 MHz, DMSO-d₆+D₂O): δ 8.08 (d, J=5.6 Hz, 1H), 7.80 (d, J=2.0 Hz, 1H), 7.62 (dd, J=2.0, 8.4 Hz, 1H), 7.52 (d, J=8.0 Hz, 1H), 7.25-7.16 (m, 2H), 6.73-6.68 (m, 3H), 6.55 (s, 1H), 3.98-3.95 (m, 1H), 3.71-3.60 (m, 2H), 3.31-3.26 (m, 2H), 3.22 (s, 3H), 3.20-3.18 (m, 1H). N—H and O—H proton not observed. LCMS: 496.1 (M+H)$^+$.

Example 491

1-(3'-(5-((3R,4R)-3-amino-4-hydroxypyrrolidin-1-yl)pyridin-3-yl)-3-chloro-5'-fluoro-2'-hydroxy-[1,1'-biphenyl]-4-yl)-3-methyl-1H-imidazol-2(3H)-one

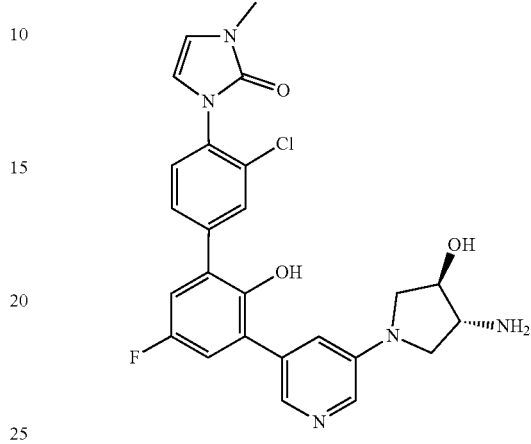

The title compound was prepared following the procedure described for Example 490 using tert-butyl ((3R,4R)-1-(5-bromopyridin-3-yl)-4-hydroxypyrrolidin-3-yl)carbamate and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr₃ to afford the title compound (28% yield). $^1$H NMR (400 MHz, DMSO-d₆+D₂O): δ 7.96 (d, J=1.6 Hz, 1H), 7.86 (d, J=2.8 Hz, 1H), 7.81 (d, J=2.0 Hz, 1H), 7.63 (dd, J=2.0, 8.4 Hz, 1H), 7.52 (d, J=8.0 Hz, 1H), 7.23-7.17 (m, 2H), 6.99 (t, J=2.0 Hz, 1H), 6.72 (d, J=3.2 Hz, 1H), 6.68 (d, J=3.2 Hz, 1H), 3.99-3.96 (m, 1H), 3.64-3.52 (m, 2H), 3.31-3.28 (m, 1H), 3.22 (s, 3H), 3.14-3.11 (m, 1H), 3.05-3.02 (m, 1H). N—H and O—H protons not observed. LCMS: 496.1 (M+H)$^+$.

Example 492

1-(3'-(2-(2,6-diazaspiro[3.3]heptan-2-yl)pyridin-4-yl)-3-chloro-5'-fluoro-2'-hydroxy-[1,1'-biphenyl]-4-yl)-3-deuteromethyl-1H-imidazol-2(3H)-one

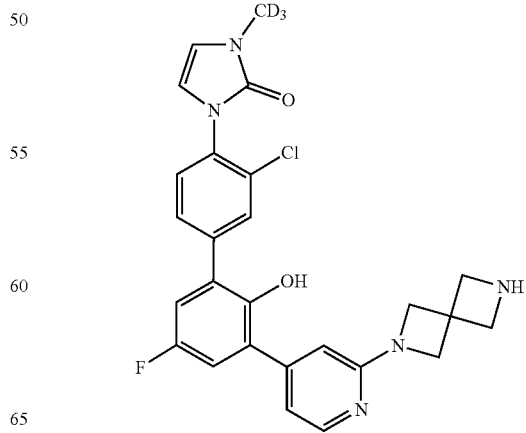

Step 1: tert-butyl 6-(4-(3'-chloro-5-fluoro-2-hydroxy-4'-(2-oxo-3-(trideuteromethylmethyl)-2,3-dihydro-1H-imidazol-1-yl)-[1,1'-biphenyl]-3-yl)pyridin-2-yl)-2,6-diazaspiro[3.3]heptane-2-carboxylate The title compound was prepared following the procedure described for Example 489 using tert-butyl 6-(4-(4,4,5,5-tetramethyl-1,3,2-dioxaborolan-2-yl)pyridin-2-yl)-2,6-diazaspiro[3.3]heptane-2-carboxylate and 1-(3'-bromo-3-chloro-5'-fluoro-2'-hydroxy-[1,1'-biphenyl]-4-yl)-3-(trideuteromethylmethyl)-1H-imidazol-2(3H)-one to afford the title compound (36% yield). LCMS: 595.2 (M+H)$^+$.

Step 2: 1-(3'-(2-(2,6-diazaspiro[3.3]heptan-2-yl)pyridin-4-yl)-3-chloro-5'-fluoro-2'-hydroxy-[1,1'-biphenyl]-4-yl)-3-trideuteromethyl-1H-imidazol-2(3H)-one The title compound was prepared following the procedure described for Example 489 using tert-butyl 6-(4-(3'-chloro-5-fluoro-2-hydroxy-4'-(2-oxo-3-(trideuteromethylmethyl)-2,3-dihydro-1H-imidazol-1-yl)-[1,1'-biphenyl]-3-yl)pyridin-2-yl)-2,6-diazaspiro[3.3]heptane-2-carboxylate and BBr$_3$ to afford the title compound (16% yield). $^1$H NMR (400 MHz, DMSO-d$_6$): δ 9.05 (br s, 1H), 8.67 (br s, 2H), 8.10 (d, J=6.0 Hz, 1H), 7.81 (d, J=1.6 Hz, 1H), 7.62 (dd, J=8.0, 1.6 Hz, 1H), 7.55 (d, J=8.0 Hz, 1H), 7.35-7.27 (m, 2H), 7.05 (d, J=5.6 Hz, 1H), 6.87 (s, 1H), 6.72 (d, J=3.2 Hz, 1H), 6.67 (d, J=2.8 Hz, 1H), 4.49-4.33 (m, 4H), 4.27-4.15 (m, 4H). LCMS: 495.2 (M+H)$^+$.

Example 493

(R)-1-(3-chloro-3'-(2-(3,4-dimethylpiperazin-1-yl)pyridin-4-yl)-5'-fluoro-2'-hydroxy-[1,1'-biphenyl]-4-yl)-3-methyl-1H-imidazol-2(3H)-one

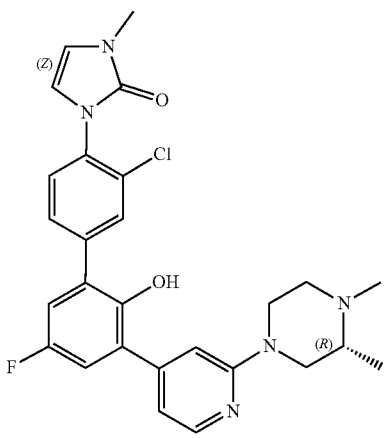

The title compound was prepared following the procedure described for Example 414 using (R)-1,2-dimethylpiperazine, 1-(3-chloro-5'-fluoro-3'-(2-fluoropyridin-4-yl)-2'-methoxy-[1,1'-biphenyl]-4-yl)-3-methyl-1H-imidazol-2(3H)-one and BBr$_3$ to afford the title compound (9% yield). $^1$H NMR (400 MHz, DMSO-d$_6$): δ 8.68 (br s, 1H), 8.14 (d, J=5.2 Hz, 1H), 7.80 (d, J=1.6 Hz, 1H), 7.63-7.51 (m, 2H), 7.26-7.18 (m, 2H), 6.95 (s, 1H), 6.82 (dd, J=5.2, 0.8 Hz, 1H), 6.72 (d, J=3.2 Hz, 1H), 6.69 (d, J=3.2 Hz, 1H), 4.13 (t, J=10.8 Hz, 2H), 3.24 (s, 3H), 2.95-2.91 (m, 1H), 2.89-2.79 (m, 1H), 2.33 (s, 3H), 2.32-2.21 (m, 1H), 2.18-2.06 (m, 1H), 1.03 (d, J=6.8 Hz, 3H). N—H or O—H proton not observed. LCMS: 508.2 (M+H)$^+$.

Example 494

1-(3-chloro-5'-fluoro-2'-hydroxy-3'-(3-((methylamino)methyl)-1H-indazol-5-yl)-[1,1'-biphenyl]-4-yl)-3-methyl-1H-imidazol-2(3H)-one

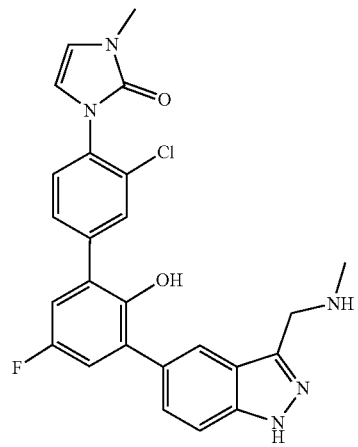

Step 1: 5-bromo-1-(tetrahydro-2H-pyran-2-yl)-1H-indazole-3-carbaldehyde

To a solution of 5-bromo-1H-indazole-3-carbaldehyde (3.00 g, 12.5 mmol) in DCM/THF (1:1, 67 mL) was added DHP (3.14 g, 37.4 mmol) and PTSA (429 mg, 2.494 mmol). The reaction mixture was stirred at rt under N$_2$ for 16 h. After the reaction was complete by LCMS, the reaction mixture was concentrated. The residue was purified by silica gel chromatography using PE and EtOAc (5:1) as the eluent to afford the title compound (1.3 g, 32% yield) as a yellow solid. LCMS: 309.0 (M+H)$^+$.

Step 2: 1-(tetrahydro-2H-pyran-2-yl)-5-(4,4,5,5-tetramethyl-1,3,2-dioxaborolan-2-yl)-1H-indazole-3-carbaldehyde The title compound was prepared using 5-bromo-1-(tetrahydro-2H-pyran-2-yl)-1H-indazole-3-carbaldehyde and 4,4,4',4',5,5,5',5'-octamethyl-2,2'-bi(1,3,2-dioxaborolane) to afford the title compound (70% yield). LCMS: 357.2 (M+H)$^+$.

Step 3: 5-(3'-chloro-5-fluoro-2-methoxy-4'-(3-methyl-2-oxo-2,3-dihydro-1H-imidazol-1-yl)-[1,1'-biphenyl]-3-yl)-1-(tetrahydro-2H-pyran-2-yl)-1H-indazole-3-carbaldehyde The title compound was prepared following the procedure described for Example 492 using 1-(tetrahydro-2H-pyran-2-yl)-5-(4,4,5,5-tetramethyl-1,3,2-dioxaborolan-2-yl)-1H-indazole-3-carbaldehyde and 1-(3'-bromo-3-chloro-5'-fluoro-2'-methoxy-[1,1'-biphenyl]-4-yl)-3-methyl-1H-imidazol-2(3H)-one to afford the title compound (69% yield). LCMS: 561.0 (M+H)$^+$.

Step 4: 1-(3-chloro-5'-fluoro-2'-methoxy-3'-(3-((methylamino)methyl)-1-(tetrahydro-2H-pyran-2-yl)-1H-indazol-5-yl)-[1,1'-biphenyl]-4-yl)-3-methyl-1H-imidazol-2(3H)-one To a solution of 5-(3'-chloro-5-fluoro-2-methoxy-4'-(3-methyl-2-oxo-2,3-dihydro-1H-imidazol-1-yl)-[1,1'-biphenyl]-3-yl)-1-(tetrahydro-2H-pyran-2-yl)-1H-indazole-3-carbaldehyde (100 mg, 0.180 mmol) in MeOH (5 mL) was added methanamine (5 mL) and AcOH (1 drop). The reaction mixture was stirred at rt under $N_2$ for 16 h. NaBH$_4$ (20 mg, 0.53 mmol) was added. Then the mixture was stirred at rt for 2 h under $N_2$. After the reaction was complete by LCMS, H$_2$O (20 mL) was added to quenched the reaction. The mixture was concentrated and extracted with DCM (8 mL×3). The combined organic layer was washed with brine, dried over Na$_2$SO$_4$, filtered and concentrated. The residue was purified by silica gel chromatography using DCM and MeOH (10:1) as the eluent to afford the title compound (50 mg, 48% yield) as a brown solid. LCMS: 576.0 (M+H)$^+$.

Step 5: 1-(3-chloro-5'-fluoro-2'-hydroxy-3'-(3-((methylamino)methyl)-1-(tetrahydro-2H-pyran-2-yl)-1H-indazol-5-yl)-[1,1'-biphenyl]-4-yl)-3-methyl-1H-imidazol-2(3H)-one To a solution of 1-(3-chloro-5'-fluoro-2'-methoxy-3'-(3-((methylamino)methyl)-1-(tetrahydro-2H-pyran-2-yl)-1H-indazol-5-yl)-[1,1'-biphenyl]-4-yl)-3-methyl-1H-imidazol-2(3H)-one (45 mg, 0.078 mmol) in DMF (2 mL) was added piperazine (1.00 g, 11.7 mmol). The reaction mixture was stirred at 150° C. under MW for 6 h. After the reaction was complete by LCMS, the reaction mixture was cooled to rt, H$_2$O was added to quench the reaction and extracted with DCM (5 mL×3). The combined organic layer was washed with brine, dried over Na$_2$SO$_4$, filtered and concentrated. The residue was purified by prep-TLC using DCM:MeOH (10:1) to afford the title compound (20 mg, 45% yield) as a pale yellow solid. LCMS: 562.0 (M+H)$^+$.

Step 6: 1-(3-chloro-5'-fluoro-2'-hydroxy-3'-(3-((methylamino)methyl)-1H-indazol-5-yl)-[1,1'-biphenyl]-4-yl)-3-methyl-1H-imidazol-2(3H)-one The title compound was prepared using 1-(3-chloro-5'-fluoro-2'-hydroxy-3'-(3-((methylamino)methyl)-1-(tetrahydro-2H-pyran-2-yl)-1H-indazol-5-yl)-[1,1'-biphenyl]-4-yl)-3-methyl-1H-imidazol-2(3H)-one and TFA to afford the title compound (20% yield). $^1$H NMR (400 MHz, DMSO-d$_6$): δ 13.46 (s, 1H), 8.97 (s, 2H), 8.58 (s, 1H), 8.12 (s, 1H), 7.83 (d, J=2.0 Hz, 1H), 7.67-7.63 (m, 3H), 7.54 (d, J=8.4 Hz, 1H), 7.24-7.18 (m, 2H), 6.73 (d, J=2.4 Hz, 1H), 6.69 (d, J=3.2 Hz, 1H), 4.58 (d, J=5.6 Hz, 2H), 3.21 (s, 3H), 2.68-2.67 (m, 3H). LCMS: 478.2 (M+H)$^+$.

Example 495

1-(3'-(5-((3R,4R)-3-amino-4-hydroxypiperidin-1-yl)pyridin-3-yl)-3-chloro-5'-fluoro-2'-hydroxy-[1,1'-biphenyl]-4-yl)-3-methyl-1H-imidazol-2(3H)-one

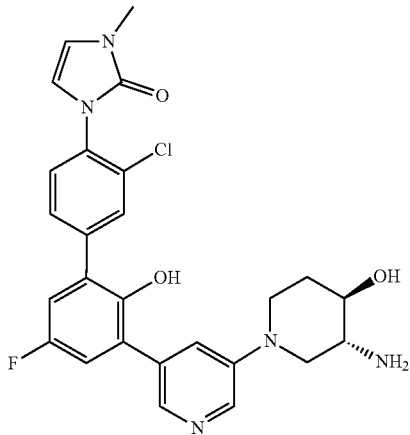 [SMILES: Cn1ccn(-c2ccc(-c3cc(F)cc(-c4cncc(N5CC[C@@H](O)[C@H](N)C5)c4)c3O)cc2Cl)c1=O]

The title compound was prepared following the procedure described for Example 491 using tert-butyl ((3R,4R)-1-(5-bromopyridin-3-yl)-4-hydroxypiperidin-3-yl) carbamate, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr$_3$ afford the title compound (15% yield). $^1$H NMR (400 MHz, CD$_3$OD): δ 8.45 (s, 1H), 8.42 (s, 1H), 8.15 (s, 1H), 7.82 (d, J=2.0 Hz, 1H), 7.62 (dd, J=8.4, 2.0 Hz, 1H), 7.55 (d, J=8.0 Hz, 1H), 7.30 (dd, J=8.4, 2.8 Hz, 1H), 7.23 (dd, J=8.4, 2.8 Hz, 1H), 6.70 (d, J=2.8 Hz, 1H), 6.65 (d, J=3.2 Hz, 1H), 4.19-4.16 (m, 1H), 4.02-3.99 (m, 1H), 3.81-3.75 (m, 1H), 3.37 (s, 3H), 3.25-3.11 (m, 3H), 2.21-2.17 (m, 1H), 1.82-1.77 (m, 1H). N—H and O—H protons not observed. LCMS: 510.2 (M+H)$^+$.

Example 496

1-(3-chloro-5'-fluoro-2'-hydroxy-3'-(2-(piperazin-1-yl)pyridin-4-yl)-[1,1'-biphenyl]-4-yl)-3-methylpyridin-2(1H)-one

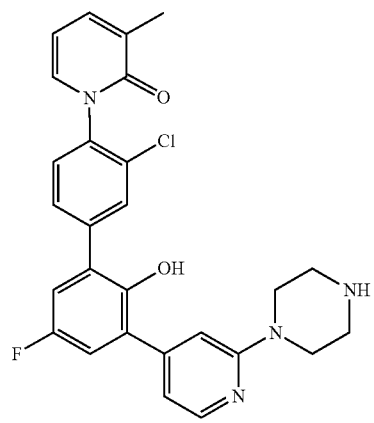 [SMILES: Cc1cccn(-c2ccc(-c3cc(F)cc(-c4ccnc(N5CCNCC5)c4)c3O)cc2Cl)c1=O]

The title compound was prepared following the procedure described for Example 443 using 1-(4-bromo-2-chlorophenyl)-3-methylpyridin-2(1H)-one, tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate and BBr$_3$ to afford the title compound (18% yield). $^1$H NMR (400 MHz, DMSO-d$_6$): δ 8.15 (d, J=4.8 Hz, 1H), 7.93-7.92 (m, 1H), 7.76-7.73 (m, 2H), 7.56 (dd, J=8.4, 2.0 Hz, 1H), 7.35 (d, J=8.0 Hz, 1H), 7.25-7.23 (m, 1H), 7.18-7.15 (m, 1H), 7.07 (dd, J=7.2, 4.8 Hz, 1H), 6.93 (s, 1H), 6.83 (dd, J=5.2, 0.8 Hz, 1H), 3.47-3.44 (m, 4H), 2.81-2.79 (m, 4H), 2.37 (s, 3H). N—H and O—H protons not observed. LCMS: 491.1 (M+H)$^+$.

Example 497

(R)-1-(3'-(2-(3-(aminomethyl)piperidin-1-yl)pyridin-4-yl)-3-chloro-5'-fluoro-2'-hydroxy-[1,1'-biphenyl]-4-yl)-3-methyl-1H-imidazol-2(3H)-one

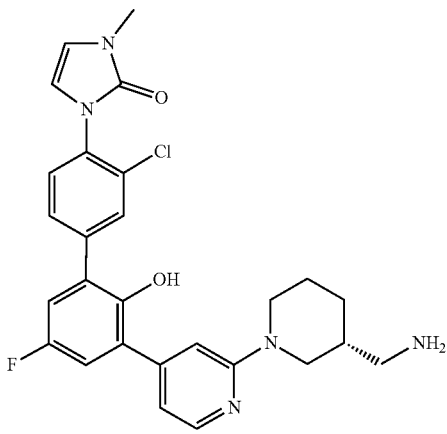 [SMILES: Cn1ccn(-c2ccc(-c3cc(F)cc(-c4ccnc(N5CCC[C@H](CN)C5)c4)c3O)cc2Cl)c1=O]

The title compound was prepared following the procedure described for Example 414 using 1-(3-chloro-5'-fluoro-3'-(2-fluoropyridin-4-yl)-2'-methoxy-[1,1'-biphenyl]-4-yl)-3-methyl-1H-imidazol-2(3H)-one, (S)-tert-butyl (piperidin-3-ylmethyl)carbamate and BBr$_3$ to afford the title compound (41% yield). $^1$H NMR (400 MHz, DMSO-d$_6$): δ 8.11 (d, J=5.2 Hz, 1H), 7.83 (d, J=2.0 Hz, 1H), 7.62 (dd, J=8.4, 2.0 Hz, 1H), 7.50 (d, J=8.4 Hz, 1H), 7.23-7.15 (m, 2H), 6.99 (s, 1H), 6.77 (dd, J=5.2, 0.8 Hz, 1H), 6.71 (d, J=2.8 Hz, 1H), 6.67 (d, J=2.8 Hz, 1H), 4.29-4.20 (m, 2H), 3.21 (s, 3H), 2.89-2.82 (m, 1H), 2.63-2.57 (m, 1H), 2.49-2.47 (m, 2H), 1.84-1.80 (m, 1H), 1.71-1.66 (m, 1H), 1.53-1.43 (m, 2H), 1.20-1.13 (m, 1H). Three N—H and O—H protons not observed. LCMS: 508.2 (M+H)$^+$.

Example 498

(S)-1-(3'-(2-(3-aminopyrrolidin-1-yl)pyridin-4-yl)-3-chloro-2'-hydroxy-5'-methyl-[1,1'-biphenyl]-4-yl)-3-methyl-1H-imidazol-2(3H)-one

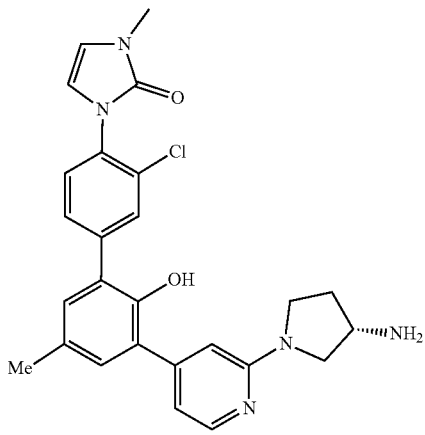 [SMILES: Cc1cc(-c2ccnc(N3CC[C@H](N)C3)c2)c(O)c(-c2ccc(-n3ccn(C)c3=O)c(Cl)c2)c1]

The title compound was prepared following the procedure described for Example 414 using 4-(3-bromo-2-methoxy-5-methylphenyl)-2-fluoropyridine, 1-(2-chloro-4-(4,4,5,5-tetramethyl-1,3,2-dioxaborolan-2-yl)phenyl)-3-methyl-1H-imidazol-2(3H)-one and (S)-tert-butyl pyrrolidin-3-ylcarbamate and BBr$_3$ to afford the title compound (35% yield). $^1$H NMR (400 MHz, DMSO-d$_6$): δ 8.07 (d, J=5.2 Hz, 1H), 7.75 (d, J=1.6 Hz, 1H), 7.57 (dd, J=8.0, 1.6 Hz, 1H), 7.49 (d, J=8.0 Hz, 1H), 7.13 (dd, J=14.8, 1.6 Hz, 2H), 6.71-6.66 (m, 3H), 6.51 (s, 1H), 3.57-3.51 (m, 3H), 3.43-3.41 (m, 1H), 3.21 (s, 3H), 3.11-3.06 (m, 1H), 2.31 (s, 3H), 2.07-2.03 (m, 1H), 1.73-1.68 (m, 1H). N—H and O—H protons not observed. LCMS: 476.1 (M+H)$^+$.

Example 499

1-(3-chloro-5'-fluoro-2'-hydroxy-3'-(2-(piperazin-1-yl)pyridin-4-yl)-[1,1'-biphenyl]-4-yl)-4-methyl-1H-1,2,4-triazol-5(4H)-one

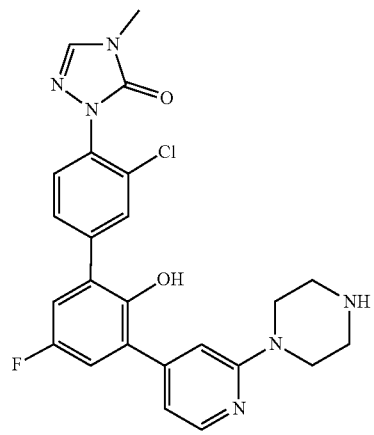

The title compound was prepared following the procedure described for Example 462 using 4-methyl-1H-1,2,4-triazol- 5(4H)-one, (4-bromo-2-chlorophenyl)boronic acid, tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate, and BBr₃ to afford the title compound. ¹H NMR (400 MHz, CD₃OD): δ 8.18 (d, J=5.2 Hz, 1H), 8.04 (s, 1H), 7.84 (d, J=2.0 Hz, 1H), 7.66 (dd, J=8.4, 2.0 Hz, 1H), 7.57 (d, J=8.0 Hz, 1H), 7.16-7.12 (m, 2H), 7.03 (s, 1H), 6.92 (dd, J=5.2, 1.2 Hz, 1H), 3.60-3.57 (m, 4H), 3.41 (s, 3H), 3.01-2.98 (m, 4H). N—H and O—H protons not observed. LCMS: 481.1 (M+H)⁺.

Example 500

(R)-1-(3-chloro-2'-hydroxy-5'-methyl-3'-(2-(3-methylpiperazin-1-yl)pyridin-4-yl)-[1,1'-biphenyl]-4-yl)-3-methyl-1H-imidazol-2(3H)-one

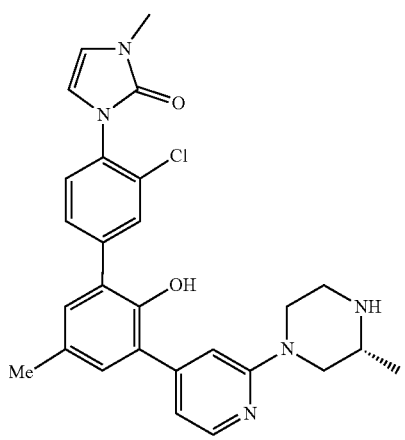 [SMILES: Cc1cc(-c2ccnc(N3CCN[C@H](C)C3)c2)c(O)c(-c2ccc(-n3ccn(C)c3=O)c(Cl)c2)c1]

The title compound was prepared following the procedure described for Example 414 using 1-(3-chloro-3'-(2-fluoropyridin-4-yl)-2'-methoxy-5'-methyl-[1,1'-biphenyl]-4-yl)-3-methyl-1H-imidazol-2(3H)-one, (R)-tert-butyl 2-methylpiperazine-1-carboxylate and BBr₃ to afford the title compound (26% yield). ¹H NMR (400 MHz, DMSO-d₆): δ 8.13 (d, J=5.2 Hz, 1H), 7.75 (d, J=2.0 Hz, 1H), 7.58 (dd, J=8.4, 2.0 Hz, 1H), 7.49 (d, J=8.0 Hz, 1H), 7.15 (d, J=2.0 Hz, 1H), 7.11 (d, J=1.6 Hz, 1H), 6.88 (s, 1H), 6.77 (dd, J=5.2, 1.2 Hz, 1H), 6.71 (d, J=2.8 Hz, 1H), 6.68 (d, J=2.8 Hz, 1H), 4.18-4.11 (m, 2H), 3.21 (s, 3H), 2.97-2.95 (m, 1H), 2.74-2.67 (m, 3H), 2.37-2.30 (m, 4H), 1.03 (d, J=6.4 Hz, 3H). N—H and O—H protons not observed. LCMS: 490.1 (M+H)⁺.

Example 501

(S)-1-(3-chloro-3'-(5-(3-(dimethylamino)piperidin-1-yl)pyridin-3-yl)-5'-fluoro-2'-hydroxy-[1,1'-biphenyl]-4-yl)-3-methyl-1H-imidazol-2(3H)-one

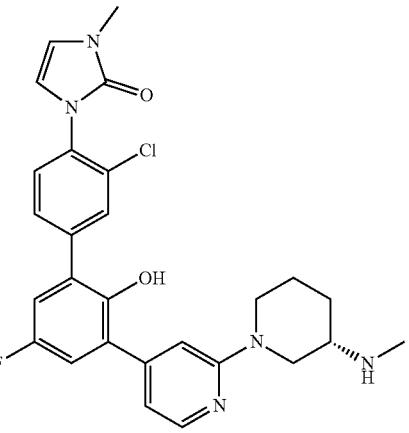

The title compound was prepared following the procedure described for Example 475 using (S)-1-(5-bromopyridin-3-yl)-N,N-dimethylpiperidin-3-amine, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one BBr₃ to afford the title compound (30% yield). ¹H NMR (400 MHz, DMSO-d₆): δ 8.69 (br s, 1H), 8.28 (d, J=2.8 Hz, 1H), 8.12 (d, J=1.6 Hz, 1H), 7.81 (d, J=2.0 Hz, 1H), 7.63 (dd, J=8.4, 2.0 Hz, 1H), 7.52 (d, J=8.4 Hz, 1H), 7.44 (t, J=2.4 Hz, 1H), 7.24-7.20 (m, 2H), 6.71 (d, J=2.8 Hz, 1H), 6.68 (d, J=2.8 Hz, 1H), 3.86-3.83 (m, 1H), 3.75-3.72 (m, 1H), 3.21 (s, 3H), 2.73-2.64 (m, 2H), 2.40-2.33 (m, 1H), 2.26 (s, 6H), 1.93-1.90 (m, 1H), 1.81-1.76 (m, 1H), 1.57-1.53 (m, 1H), 1.36-1.32 (m, 1H). LCMS: 522.2 (M+H)⁺.

Example 502

1-(3-chloro-5'-fluoro-2'-hydroxy-3'-(2-(piperazin-1-yl)pyridin-4-yl)-[1,1'-biphenyl]-4-yl)pyridin-2(1H)-one

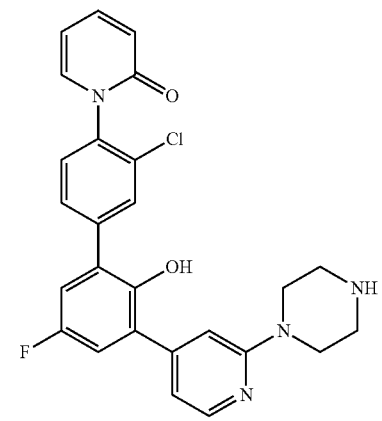 [SMILES: O=c1ccccn1-c1ccc(-c2cc(F)cc(-c3ccnc(N4CCNCC4)c3)c2O)cc1Cl]

829

The title compound was prepared following the procedure described for Example 496 using 4-bromo-2-chloro-1-iodobenzene, pyridin-2(1H)-one, tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate and BBr$_3$ to afford the title compound (27% yield). $^1$H NMR (400 MHz, DMSO-d$_6$): δ 8.16-8.13 (m, 2H), 7.92-7.89 (m, 1H), 7.76 (d, J=2.4 Hz, 1H), 7.58 (dd, J=8.4, 2.0 Hz, 1H), 7.36 (d, J=8.4 Hz, 1H), 7.24 (dd, J=9.2, 3.2 Hz, 1H), 7.19-7.14 (m, 3H), 6.93 (s, 1H), 6.83 (dd, J=4.8, 0.8 Hz, 1H), 3.47-3.44 (m, 4H), 2.81-2.78 (m, 4H). N—H and O—H protons not observed. LCMS: 477.2 (M+H)$^+$.

Example 503

(S)—N-(6-(3-aminopyrrolidin-1-yl)-4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)acetamide

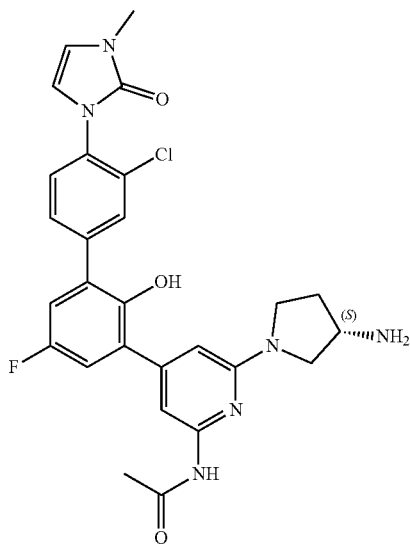

The title compound was prepared following the procedure described for Example 442 using (S)-tert-butyl (1-(4-(3-bromo-5-fluoro-2-methoxyphenyl)-6-chloropyridin-2-yl)pyrrolidin-3-yl)carbamate, 1-(2-chloro-4-(4,4,5,5-tetramethyl-1,3,2-dioxaborolan-2-yl)phenyl)-3-methyl-1H-imidazol-2(3H)-one, acetamide and BBr$_3$ to afford the title compound (6% yield). $^1$H NMR (400 MHz, DMSO-d$_6$): δ 9.98 (s, 1H), 7.80 (d, J=2.0 Hz, 1H), 7.62 (dd, J=8.4, 2.0 Hz, 1H), 7.51 (d, J=8.0 Hz, 1H), 7.42 (br s, 1H), 7.24 (dd, J=9.2, 3.2 Hz, 1H), 7.09 (dd, J=9.2, 3.2 Hz, 1H), 6.71 (d, J=2.8 Hz, 1H), 6.69 (d, J=3.2 Hz, 1H), 6.26 (s, 1H), 3.56-3.53 (m, 3H), 3.44-3.39 (m, 1H), 3.21 (s, 3H), 3.20-3.06 (m, 1H), 2.08 (s, 3H), 2.05-2.02 (m, 1H), 1.72-1.68 (m, 1H). N—H and O—H protons not observed. LCMS: 538.1 (M+H)$^+$.

Example 504

1-(3-chloro-5'-fluoro-2'-hydroxy-3'-(4-(piperazin-1-yl)-1H-benzo[d]imidazol-6-yl)-[1,1'-biphenyl]-4-yl)-3-methyl-1H-imidazol-2(3H)-one

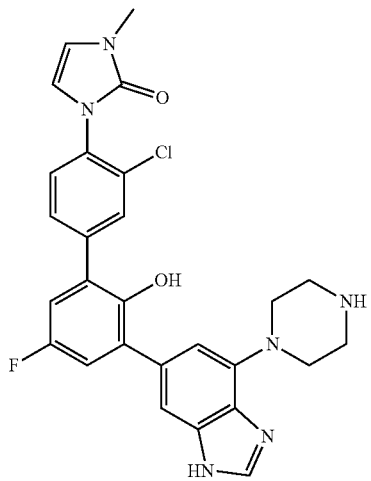

Step 1: tert-butyl 4-(1-(tetrahydro-2H-pyran-2-yl)-6-(4,4,5,5-tetramethyl-1,3,2-dioxaborolan-2-yl)-1H-benzo[d]imidazol-4-yl)piperazine-1-carboxylate To a solution of tert-butyl 4-(6-chloro-1-(tetrahydro-2H-pyran-2-yl)-1H-benzo[d]imidazol-4-yl)piperazine-1-carboxylate (30.0 mg, 71.3 mmol) and 4,4,4',4',5,5,5',5'-octamethyl-2,2'-bi(1,3,2-dioxaborolane) (27.2 mg, 107 mmol) in dioxane (5 mL) was added KOAc (17.4 mg, 178 mmol), Pd$_2$(dba)$_3$ (6.5 mg, 7.1 mmol) and x-phos (6.8 mg, 14 mmol). The reaction mixture was stirred at 100° C. for 8 hours. After the reaction was complete by LCMS, the reaction mixture was cooled and concentrated. The residue was purified by silica gel chromatography using petroleum ether and ethyl acetate (1:1) as the eluent to afford the title compound (20 mg, 54% yield) as a white solid. LCMS: 513.3 (M+H)$^+$.

Step 2: tert-butyl 4-(6-(3'-chloro-5-fluoro-2-methoxy-4'-(3-methyl-2-oxo-2,3-dihydro-1H-imidazol-1-yl)-[1,1'-biphenyl]-3-yl)-1-(tetrahydro-2H-pyran-2-yl)-1H-benzo[d]imidazol-4-yl)piperazine-1-carboxylate The title compound was prepared following the procedure described for Example 365 using tert-butyl 4-(1-(tetrahydro-2H-pyran-2-yl)-6-(4,4,5,5-tetramethyl-1,3,2-dioxaborolan-2-yl)-1H-benzo[d]imidazol-4-yl)piperazine-1-carboxylate and 1-(3'-bromo-3-chloro-5'-fluoro-2'-methoxy-[1,1'-biphenyl]-4-yl)-3-methyl-1H-imidazol-2(3H)-one to afford the title compound (54% yield). LCMS: 717.7 (M+H)$^+$.

Step 3: 1-(3-chloro-5'-fluoro-2'-hydroxy-3'-(4-(piperazin-1-yl)-1H-benzo[d]imidazol-6-yl)-[1,1'-biphenyl]-4-yl)-3-methyl-1H-imidazol-2(3H)-one The title compound was prepared following the procedure described for Example 365 using tert-butyl 4-(6-(3'-chloro-5-fluoro-2-methoxy-4'-(3-methyl-2-oxo-2,3-dihydro-1H- imidazol-1-yl)-[1,1'-biphenyl]-3-yl)-1-(tetrahydro-2H-pyran-2-yl)-1H-benzo[d]imidazol-4-yl)piperazine-1-carboxylate and BBr₃ to afford the title compound (29% yield). ¹H NMR (400 MHz, DMSO-d₆): δ 8.78 (br s, 2H), 8.52 (s, 1H), 7.83 (d, J=2.0 Hz, 1H), 7.63 (dd, J=8.0, 2.0 Hz, 1H), 7.53 (d, J=8.4 Hz, 1H), 7.42 (br s, 1H), 7.21 (d, J=8.8 Hz, 2H), 6.88-6.86 (m, 1H), 6.72 (d, J=2.8 Hz, 1H), 6.69 (d, J=2.8 Hz, 1H), 4.02-3.51 (m, 4H), 3.49-3.35 (m, 4H), 3.21 (s, 3H). N—H and O—H protons not observed. LCMS: 519.1 (M+H)⁺.

Example 505

3-(3-chloro-5'-fluoro-2'-hydroxy-3'-(2-(piperazin-1-yl)pyridin-4-yl)-[1,1'-biphenyl]-4-yl)oxazol-2(3H)-one

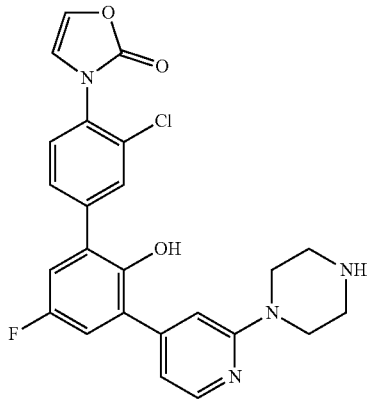

The title compound was prepared following the procedure described for Example 499 using 1,3,4-oxadiazol-2(3H)-one, (4-bromo-2-chlorophenyl)boronic acid and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound. ¹H NMR (400 MHz, CD₃OD): δ 8.11 (d, J=6.0 Hz, 1H), 7.74 (d, J=1.6 Hz, 1H), 7.56-7.50 (m, 2H), 7.19-7.17 (m, 1H), 7.11-7.10 (m, 1H), 7.09-7.07 (m, 2H), 7.05-7.04 (m, 2H), 3.82-3.79 (m, 4H), 3.30-3.28 (m, 4H). N—H and O—H protons not observed. LCMS: 467.1 (M+H)⁺.

Example 506

(S)-3-(3-chloro-5'-fluoro-2'-hydroxy-3'-(2-(piperazin-1-yl)pyridin-4-yl)-[1,1'-biphenyl]-4-yl)-4-methoxyoxazolidin-2-one

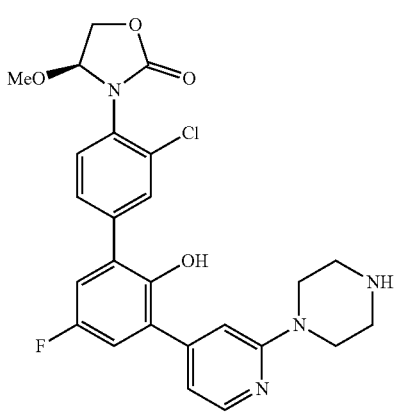 [SMILES: CO[C@H]1COC(=O)N1c1ccc(-c2cc(F)cc(-c3ccnc(N4CCNCC4)c3)c2O)cc1Cl]

The title compound was prepared following the procedure described for Example 505 using 1,3,4-oxadiazol-2(3H)-one, (4-bromo-2-chlorophenyl)boronic acid and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate and BBr₃ to afford the title compound (3% yield). ¹H NMR (400 MHz, CD₃OD): δ 8.11 (d, J=5.6 Hz, 1H), 7.71 (s, 1H), 7.50 (s, 2H), 7.14 (s, 1H), 7.07 (d, J=9.2 Hz, 2H), 7.01 (dd, J=5.6, 0.8 Hz, 1H), 5.45 (dd, J=6.0, 2.0 Hz, 1H), 4.60-4.56 (m, 1H), 4.37-4.34 (m, 1H), 3.80-3.77 (m, 4H), 3.29-3.26 (m, 3H), 3.23-3.20 (m, 4H). N—H and O—H protons not observed. LCMS: 499.2 (M+H)⁺.

Example 507

(R)-3-(3-chloro-5'-fluoro-2'-hydroxy-3'-(2-(piperazin-1-yl)pyridin-4-yl)-[1,1'-biphenyl]-4-yl)-4-methoxyoxazolidin-2-one

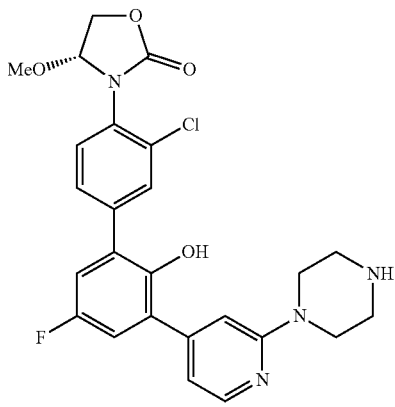 [SMILES: CO[C@@H]1COC(=O)N1c1ccc(-c2cc(F)cc(-c3ccnc(N4CCNCC4)c3)c2O)cc1Cl]

The title compound was prepared following the procedure described for Example 505 using 1,3,4-oxadiazol-2(3H)-one, (4-bromo-2-chlorophenyl)boronic acid and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate and BBr₃ to afford the title compound (3% yield). ¹H NMR (400 MHz, CD₃OD): δ 8.11 (d, J=5.2 Hz, 1H), 7.71 (d, J=0.8 Hz, 1H), 7.50 (d, J=1.6 Hz, 2H), 7.12 (s, 1H), 7.08 (s, 1H), 7.06 (s, 1H), 7.00-6.99 (m, 1H), 5.45 (dd, J=6.0, 2.0 Hz, 1H), 4.60-4.56 (m, 1H), 4.37-4.34 (m, 1H), 3.80-3.77 (m, 4H), 3.28-3.25 (m, 3H), 3.23-3.20 (m, 4H). N—H or O—H proton not observed. LCMS: 499.2 (M+H)⁺.

Example 508

(R)-1-(3-chloro-2'-hydroxy-5'-methyl-3'-(5-(3-methylpiperazin-1-yl)pyridin-3-yl)-[1,1'-biphenyl]-4-yl)-3-methyl-1H-imidazol-2(3H)-one

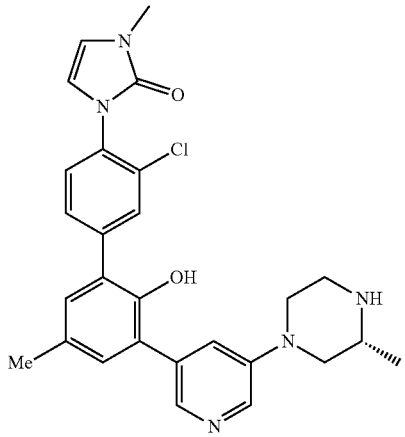 [SMILES: Cc1cc(-c2cncc(N3CCN[C@H](C)C3)c2)c(O)c(-c2ccc(-n3ccn(C)c3=O)c(Cl)c2)c1]

Step 1: 1-(3'-bromo-3-chloro-2'-methoxy-5'-methyl-[1,1'-biphenyl]-4-yl)-3-methyl-1H-imidazol-2(3H)-one The title compound was prepared following the procedures described for Example 414 using 1,3-dibromo-2-methoxy-5-methylbenzene and 1-(2-chloro-4-(4,4,5,5-tetramethyl-1,3,2-dioxaborolan-2-yl)phenyl)-3-methyl-1H-imidazol-2(3H)-one to afford the title compound (35% yield). LCMS: 407.2 (M+H)$^+$.

Step 2: (R)-tert-butyl 4-(5-(3'-chloro-2-methoxy-5-methyl-4'-(3-methyl-2-oxo-2,3-dihydro-1H-imidazol-1-yl)-[1,1'-biphenyl]-3-yl)pyridin-3-yl)-2-methylpiperazine-1-carboxylate The title compound was prepared following the procedure described for Example 414 using 1-(3'-bromo-3-chloro-2'-methoxy-5'-methyl-[1,1'-biphenyl]-4-yl)-3-methyl-1H-imidazol-2(3H)-one and (R)-(5-(4-(tert-butoxycarbonyl)-3-methylpiperazin-1-yl)pyridin-3-yl)boronic acid to afford the title compound (70% yield). LCMS: 604.3 (M+H)$^+$.

Step 3: (R)-1-(3-chloro-2'-hydroxy-5'-methyl-3'-(5-(3-methylpiperazin-1-yl)pyridin-3-yl)-[1,1'-biphenyl]-4-yl)-3-methyl-1H-imidazol-2(3H)-one The title compound was prepared following the procedure described for Example 414 using (R)-tert-butyl 4-(5-(3'-chloro-2-methoxy-5-methyl-4'-(3-methyl-2-oxo-2,3-dihydro-1H-imidazol-1-yl)-[1,1'-biphenyl]-3-yl)pyridin-3-yl)-2-methylpiperazine-1-carboxylate and BBr$_3$ to afford the title compound (14% yield). $^1$H NMR (400 MHz, DMSO-d$_6$): δ 8.24 (d, J=2.0 Hz, 1H), 8.10 (d, J=2.0 Hz, 1H), 7.75 (d, J=1.6 Hz, 1H), 7.58 (dd, J=8.4, 2.0 Hz, 1H), 7.50 (d, J=8.0 Hz, 1H), 7.37 (t, J=2.0 Hz, 1H), 7.13 (dd, J=10.8, 2.0 Hz, 2H), 6.69 (dd, J=9.6, 3.2 Hz, 2H), 3.62 (t, J=8.4 Hz, 2H), 3.21 (s, 3H), 2.96 (d, J=12.0 Hz, 1H), 2.83-2.77 (m, 2H), 2.65-2.59 (m, 1H), 2.51-2.49 (m, 3H), 2.31-2.23 (m, 1H), 1.03 (s, 3H). Two N—H or O—H protons not observed. LCMS: 490.2 (M+H)$^+$.

Example 509

(S)-1-(3'-(5-(3-aminopyrrolidin-1-yl)pyridin-3-yl)-3-chloro-2'-hydroxy-5'-methyl-[1,1'-biphenyl]-4-yl)-3-methyl-1H-imidazol-2(3H)-one

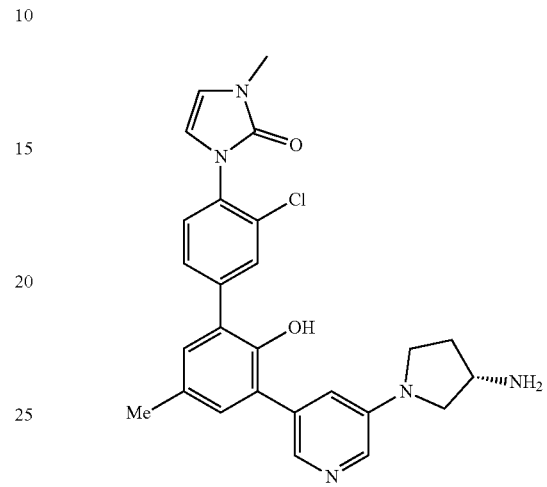

The title compound was prepared following the procedure described for Example 508 using 1-(3'-bromo-3-chloro-2'-methoxy-5'-methyl-[1,1'-biphenyl]-4-yl)-3-methyl-1H-imidazol-2(3H)-one and (S)-(5-(3-((tert-butoxycarbonyl)amino)pyrrolidin-1-yl)pyridin-3-yl)boronic acid to afford the title compound. $^1$H NMR (400 MHz, DMSO-d$_6$): δ 7.94 (d, J=2.0 Hz, 1H), 7.85 (d, J=2.8 Hz, 1H), 7.75 (d, J=2.0 Hz, 1H), 7.58 (dd, J=8.0, 2.0 Hz, 1H), 7.50 (t, J=4.0 Hz, 1H), 7.12 (dd, J=13.2, 1.6 Hz, 2H), 6.95 (t, J=2.4 Hz, 1H), 6.69 (dd, J=12.8, 2.8 Hz, 2H), 3.62-3.56 (m, 1H), 3.48-3.39 (m, 3H), 3.21 (s, 3H), 2.97-2.93 (m, 1H), 2.31 (s, 3H), 2.12-2.04 (m, 1H), 1.77-1.69 (m, 1H). N—H and O—H protons not observed. LCMS: 476.1 (M+H)$^+$.

Example 510

(S)-1-(3'-(5-(3-aminopyrrolidin-1-yl)pyridin-3-yl)-3,5'-dichloro-2'-hydroxy-[1,1'-biphenyl]-4-yl)-3-methyl-1H-imidazol-2(3H)-one

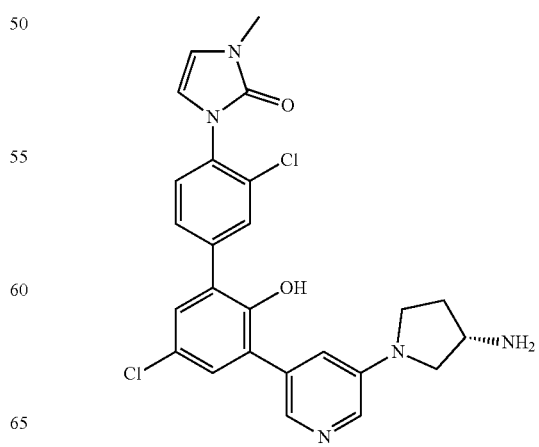

835

Step 1: 1-(3'-bromo-3,5'-dichloro-2'-methoxy-[1,1'-biphenyl]-4-yl)-3-methyl-1H-imidazol-2(3H)—one The title compound was prepared following the procedure described for Example 508 using 1-(2-chloro-4-(4,4,5,5-tetramethyl-1,3,2-dioxaborolan-2-yl)phenyl)-3-methyl-1H-imidazol-2(3H)-one and 1,3-dibromo-5-chloro-2-methoxybenzene to afford the title compound (26% yield). LCMS: 426.9 (M+H)+.

Step 2: 1-(3,5'-dichloro-2'-methoxy-3'-(4,4,5,5-tetramethyl-1,3,2-dioxaborolan-2-yl)-[1,1'-biphenyl]-4-yl)-3-methyl-1H-imidazol-2(3H)-one The title compound was prepared following the procedure described for Example 508 using 1-(3'-bromo-3,5'-dichloro-2'-methoxy-[1,1'-biphenyl]-4-yl)-3-methyl-1H-imidazol-2(3H)-one and 4,4,4',4',5,5,5',5'-octamethyl-2,2'-bi(1,3,2-dioxaborolane) to afford the title compound (58% yield). LCMS: 474.9 (M+H)+.

Step 3: (S)-tert-butyl (1-(5-(3',5-dichloro-2-methoxy-4'-(3-methyl-2-oxo-2,3-dihydro-1H-imidazol-1-yl)-[1,1'-biphenyl]-3-yl)pyridin-3-yl)pyrrolidin-3-yl)carbamate The title compound was prepared following the procedure described for Example 508 using 1-(3,5'-dichloro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and (S)-tert-butyl (1-(5-bromopyridin-3-yl)pyrrolidin-3-yl)carbamate to afford the title compound (9% yield). LCMS: 610.5 (M+H)+.

Step 4: (S)-1-(3'-(5-(3-aminopyrrolidin-1-yl)pyridin-3-yl)-3,5'-dichloro-2'-hydroxy-[1,1'-biphenyl]-4-yl)-3-methyl-1H-imidazol-2(3H)-one The title compound was prepared following the procedure described for Example 508 using (S)-tert-butyl (1-(5-(3',5-dichloro-2-methoxy-4'-(3-methyl-2-oxo-2,3-dihydro-1H-imidazol-1-yl)-[1,1'-biphenyl]-3-yl)pyridin-3-yl)pyrrolidin-3-yl)carbamate and BBr3 to afford the title compound (8% yield). 1H NMR (400 MHz, CD3OD): δ 7.86 (s, 1H), 7.77 (d, J=1.6 Hz, 1H), 7.70 (d, J=2.0 Hz, 1H), 7.50 (dd, J=8.0, 1.6 Hz, 1H), 7.40 (d, J=8.0 Hz, 1H), 7.20 (dd, J=7.2, 2.8 Hz, 2H), 7.04 (d, J=2.4 Hz, 1H), 6.55 (dd, J=15.2, 3.2 Hz, 2H), 3.64-3.61 (m, 1H), 3.51-3.45 (m, 2H), 3.43-3.38 (m, 1H), 3.32 (s, 3H), 3.06-3.03 (m, 1H), 2.20-2.17 (m, 1H), 1.85-1.80 (m, 1H). LCMS: 496.1 (M+H)+.

836

Example 511

1-(3'-(2-(3,8-diazabicyclo[3.2.1]octan-3-yl)pyridin-4-yl)-3-chloro-5'-fluoro-2'-hydroxy-[1,1'-biphenyl]-4-yl)-3-methyl-1H-imidazol-2(3H)-one

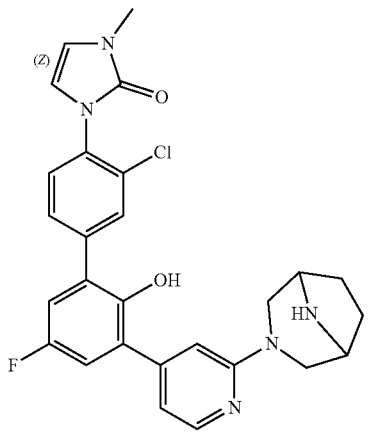 [SMILES: Cn1ccn(-c2ccc(-c3cc(F)cc(-c4ccnc(N5CC6CCC(C5)N6)c4)c3O)cc2Cl)c1=O]

The title compound was prepared following the procedures described for Example 414 using 1-(3-chloro-5'-fluoro-3'-(2-fluoropyridin-4-yl)-2'-methoxy-[1,1'-biphenyl]-4-yl)-3-methyl-1H-imidazol-2(3H)-one, tert-butyl 3,8-diazabicyclo[3.2.1]octane-8-carboxylate and BBr3 to afford the title compound. 1H NMR (400 MHz, DMSO-d6): δ 8.13 (d, J=5.6 Hz, 1H), 7.80 (d, J=2.0 Hz, 1H), 7.63-7.60 (m, 1H), 7.52 (d, J=8.0 Hz, 1H), 7.25-7.18 (m, 2H), 6.82 (d, J=5.2 Hz, 2H), 6.71 (d, J=3.2 Hz, 1H), 6.68 (d, J=2.8 Hz, 1H), 3.90 (d, J=15.6 Hz, 2H), 3.59 (s, 2H), 3.21 (s, 3H), 2.91 (d, J=9.6 Hz, 2H), 1.72-1.64 (m, 4H). N—H and O—H protons not observed. LCMS: 506.1 (M+H)+.

Example 512

1-(3'-(5-(3,8-diazabicyclo[3.2.1]octan-3-yl)pyridin-3-yl)-3-chloro-5'-fluoro-2'-hydroxy-[1,1'-biphenyl]-4-yl)-3-methyl-1H-imidazol-2(3H)-one

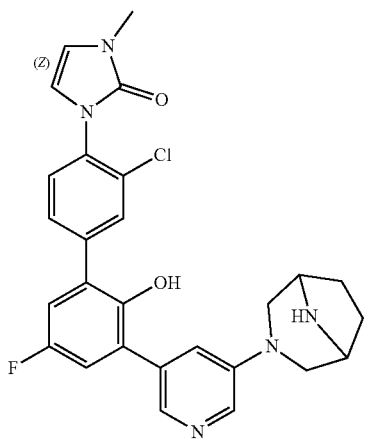

The title compound was prepared following the procedures described for Example 510 using (5-(8-(tert-butoxycarbonyl)-3,8-diazabicyclo[3.2.1]octan-3-yl)pyridin-3-yl)boronic acid and 1-(3'-bromo-3-chloro-5'-fluoro-2'-methoxy-[1,1'-biphenyl]-4-yl)-3-methyl-1H-imidazol-2(3H)-one and BBr₃ to afford the title compound. ¹H NMR (400 MHz, DMSO-d₆): δ 8.17 (d, J=2.8 Hz, 1H), 8.11 (d, J=1.6 Hz, 1H), 7.81 (d, J=1.6 Hz, 1H), 7.64-7.61 (m, 1H), 7.52 (d, J=8.4 Hz, 1H), 7.31 (s, 1H), 7.25-7.19 (m, 2H), 6.71 (dd, J=12.4, 2.8 Hz, 2H), 3.61 (s, 2H), 3.54 (d, J=10.8 Hz, 2H), 3.21 (s, 3H), 2.86 (d, J=10.4 Hz, 2H), 1.74 (s, 4H). N—H and O—H protons not observed. LCMS: 507.2 (M+H)⁺.

Example 513

1-(3-chloro-5'-fluoro-2'-hydroxy-3'-(2-(8-methyl-3,8-diazabicyclo[3.2.1]octan-3-yl)pyridin-4-yl)-[1,1'-biphenyl]-4-yl)-3-methyl-1H-imidazol-2(3H)-one

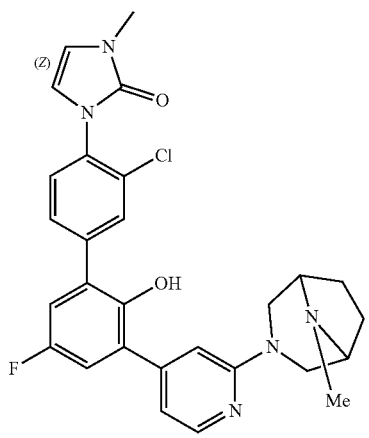 [SMILES: CN1C2CCC1CN(c1cc(-c3cc(F)cc(-c4ccc(-n5ccn(C)c5=O)c(Cl)c4)c3O)ccn1)C2]

The title compound was prepared following the procedures described for Example 469 using 1-(3'-(2-(3,8-diazabicyclo[3.2.1]octan-3-yl)pyridin-4-yl)-3-chloro-5'-fluoro-2'-hydroxy-[1,1'-biphenyl]-4-yl)-3-methyl-1H-imidazol-2(3H)-one and HCHO to afford the title compound. ¹H NMR (400 MHz, DMSO-d₆): δ 8.69 (s, 1H), 8.13 (d, J=5.6 Hz, 1H), 7.80 (d, J=2.0 Hz, 1H), 7.62-7.60 (m, 1H), 7.53-7.51 (m, 1H), 7.25-7.18 (m, 2H), 6.81 (d, J=4.4 Hz, 2H), 6.70 (dd, J=8.0, 3.2 Hz, 2H), 3.83 (d, J=9.6 Hz, 2H), 3.29 (s, 2H), 3.21 (s, 3H), 2.95 (d, J=10.4 Hz, 2H), 2.24 (s, 3H), 1.95-1.93 (m, 2H), 1.58-1.54 (m, 2H). LCMS: 520.2 (M+H)⁺.

Example 514

1-(3-chloro-5'-fluoro-2'-hydroxy-3'-(5-(8-methyl-3,8-diazabicyclo[3.2.1]octan-3-yl)pyridin-3-yl)-[1,1'-biphenyl]-4-yl)-3-methyl-1H-imidazol-2(3H)-one

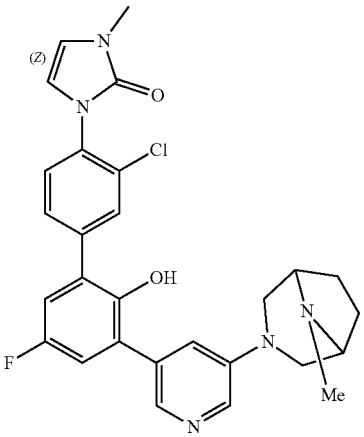

The title compound was prepared following the procedure described for Example 469 using 1-(3'-(5-(3,8-diazabicyclo[3.2.1]octan-3-yl)pyridin-3-yl)-3-chloro-5'-fluoro-2'-hydroxy-[1,1'-biphenyl]-4-yl)-3-methyl-1,3-dihydro-2H-imidazol-2-one and HCHO ¹H NMR (400 MHz, DMSO-d₆): δ 8.66 (s, 1H), 8.17 (d, J=2.8 Hz, 1H), 8.10 (d, J=1.6 Hz, 1H), 7.81 (d, J=2.0 Hz, 1H), 7.63-7.61 (m, 1H), 7.52 (d, J=8.0 Hz, 1H), 7.29 (s, 1H), 7.24-7.18 (m, 2H), 6.70 (dd, J=12.4, 2.8 Hz, 2H), 3.47 (d, J=9.2 Hz, 2H), 3.30 (d, J=9.2 Hz, 2H), 3.21 (s, 3H), 2.91 (d, J=9.6 Hz, 2H), 2.24 (s, 3H), 1.98-1.96 (m, 2H), 1.66-1.62 (m, 2H). LCMS: 520.1 (M+H)⁺.

Example 515

(S)—N-(4-(3'-chloro-5-fluoro-2-hydroxy-4'-(3-methyl-2-oxo-2,3-dihydro-1H-imidazol-1-yl)-[1,1'-biphenyl]-3-yl)-6-(3-(dimethylamino)pyrrolidin-1-yl)pyridin-2-yl)acetamide

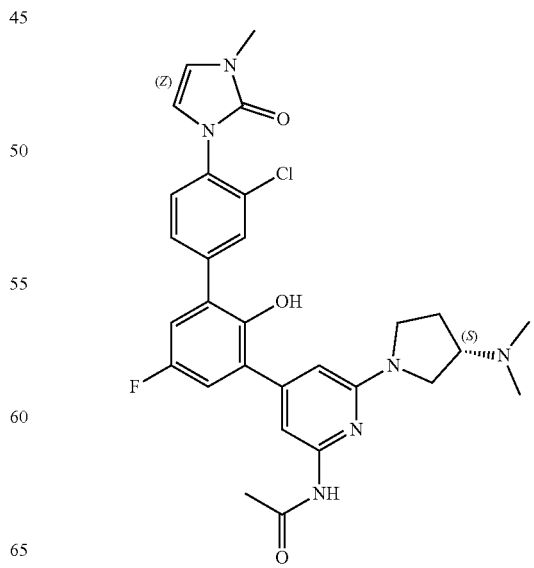

839

Step 1: 4-(3-bromo-5-fluoro-2-methoxyphenyl)-2,6-dichloropyridine

The title compound was prepared following the procedure described for Example 365 using 1,3-dibromo-5-fluoro-2-methoxybenzene and (2,6-dichloropyridin-4-yl)boronic acid to afford the title compound. LCMS: 351.9 (M+H)$^+$ Step 2: (S)-tert-butyl (1-(4-(3-bromo-5-fluoro-2-methoxyphenyl)-6-chloropyridin-2-yl)pyrrolidin-3-yl)carbamate The title compound was prepared following the procedure described for Example 414 using 4-(3-bromo-5-fluoro-2-methoxyphenyl)-2,6-dichloropyridine and (S)-tert-butyl pyrrolidin-3-ylcarbamate to afford the title compound. LCMS: 500.1 (M+H)$^+$.

Step 3: (S)-tert-butyl (1-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)carbamate The title compound was prepared following the procedure described for Example 414 using (S)-tert-butyl (1-(4-(3-bromo-5-fluoro-2-methoxyphenyl)-6-chloropyridin-2-yl)pyrrolidin-3-yl)carbamate and 1-(2-chloro-4-(4,4,5,5-tetramethyl-1,3,2-dioxaborolan-2-yl)phenyl)-3-methyl-1H-imidazol-2(3H)— one to afford the title compound. LCMS: 571.1 (M+H)$^+$ Step 4: (S)-tert-butyl (1-(6-acetamido-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)carbamate The title compound was prepared following the procedure described for Example 442 using (S)-tert-butyl (1-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)carbamate and acetamide to afford the title compound. LCMS: 651.3 (M+H)$^+$.

Step 5: (S)—N-(6-(3-aminopyrrolidin-1-yl)-4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)acetamide The title compound was prepared following the procedure described for Example 365 using (S)-tert-butyl (1-(6-acetamido-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)carbamate and BBr$_3$ to afford the title compound. LCMS: 537.5 (M+H)$^+$.

Step 6: (S)—N-(4-(3'-chloro-5-fluoro-2-hydroxy-4'-(3-methyl-2-oxo-2,3-dihydro-1H-imidazol-1-yl)-[1,1'-biphenyl]-3-yl)-6-(3-(dimethylamino)pyrrolidin-1-yl)pyridin-2-yl)acetamide The title compound was prepared following the procedure described for Example 469 using (S)—N-(6-(3-aminopyrrolidin-1-yl)-4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)acetamide and HCHO to afford the title compound. $^1$H NMR (400 MHz, DMSO-d$_6$): δ 7.82 (s, 1H), 7.81-7.61 (m, 1H), 7.55-7.51 (m, 1H), 7.43 (s, 1H), 7.15 (dd, J=5.2, 3.6 Hz, 2H), 6.69 (d, J=2.8 Hz, 1H), 6.65 (d, J=2.8 Hz, 1H), 6.59 (s, 1H), 4.11-4.02 (m, 2H), 3.89-3.83 (m, 1H), 3.80-3.76 (m, 1H), 3.63-3.57 (m, 1H), 3.37 (s, 3H), 3.03 (m, 6H), 2.67-2.59 (m, 1H), 2.40-2.33 (m, 1H), 2.21 (s, 3H). Two N—H and O—H protons not observed. LCMS: 566.2 (M+H)$^+$.

840

Example 516

1-(3-chloro-5'-fluoro-2'-hydroxy-3'-(5-(4-(methylamino)piperidin-1-yl)pyridin-3-yl)-[1,1'-biphenyl]-4-yl)-3-methyl-1H-imidazol-2(3H)-one

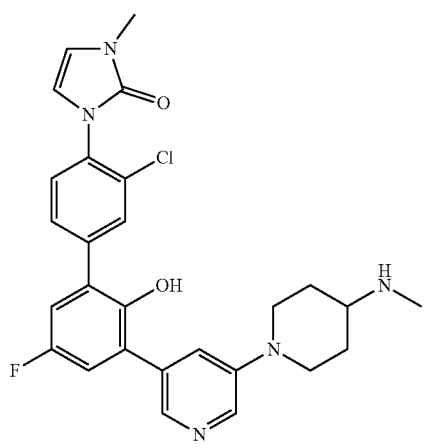 [SMILES: CNC1CCN(c2cncc(-c3cc(F)cc(-c4ccc(-n5ccn(C)c5=O)c(Cl)c4)c3O)c2)CC1]

The title compound was prepared following the procedures described for Example 510 using 3,5-dibromopyridine, tert-butyl methyl(piperidin-4-yl)carbamate, 4,4,4',4',5,5,5',5'-octamethyl-2,2'-bi(1,3,2-dioxaborolane), 1-(3'-bromo-3-chloro-5'-fluoro-2'-methoxy-[1,1'-biphenyl]-4-yl)-3-methyl-1H-imidazol-2(3H)-one and BBr$_3$ to afford the title compound. $^1$H NMR (400 MHz, CD$_3$OD): δ 8.42 (s, 2H), 8.22 (s, 1H), 7.82 (d, J=2.0 Hz, 1H), 7.64-7.61 (m, 1H), 7.56 (d, J=8.0 Hz, 1H), 7.34-7.31 (m, 1H), 7.24 (dd, J=8.8, 3.2 Hz, 1H), 6.70 (d, J=2.8 Hz, 1H), 6.65 (d, J=3.2 Hz, 1H), 4.17 (d, J=13.6 Hz, 2H), 3.33 (s, 4H), 3.17-3.11 (m, 2H), 2.78 (s, 3H), 2.28 (d, J=10.8 Hz, 2H), 1.79-1.75 (m, 2H). LCMS: 508.1 (M+H)$^+$.

Example 517

(S)-1-(3'-(2-(3-aminopyrrolidin-1-yl)-6-methylpyridin-4-yl)-3-chloro-5'-fluoro-2'-hydroxy-[1,1'-biphenyl]-4-yl)-3-methyl-1H-imidazol-2(3H)-one

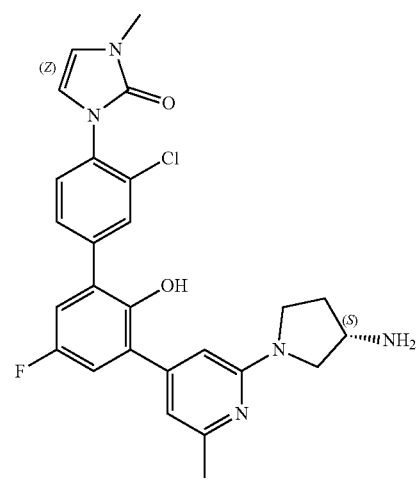

Step 1: (S)-tert-butyl (1-(4-(3'-chloro-5-fluoro-2-methoxy-4'-(3-methyl-2-oxo-2,3-dihydro-1H-imidazol-1-yl)-[1,1'-biphenyl]-3-yl)-6-methylpyridin-2-yl)pyrrolidin-3-yl)carbamate The title compound was prepared following the procedures described for Example 515 using (S)-tert-butyl (1-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)carbamate and methylboronic acid to afford the title compound (92% yield). LCMS: 608.3 (M+H)$^+$.

Step 2: (S)-1-(3'-(2-(3-aminopyrrolidin-1-yl)-6-methylpyridin-4-yl)-3-chloro-5'-fluoro-2'-hydroxy-[1,1'-biphenyl]-4-yl)-3-methyl-1H-imidazol-2(3H)-one The title compound was prepared following the procedure described for Example 515 using (S)-tert-butyl (1-(4-(3'-chloro-5-fluoro-2-methoxy-4'-(3-methyl-2-oxo-2,3-dihydro-1H-imidazol-1-yl)-[1,1'-biphenyl]-3-yl)-6-methylpyridin-2-yl)pyrrolidin-3-yl)carbamate and BBr$_3$ to afford the title compound. $^1$H NMR (400 MHz, DMSO-d$_6$): δ 7.81 (s, 1H), 7.61 (d, J=8.0 Hz, 1H), 7.51 (d, J=8.0 Hz, 1H), 7.22 (dd, J=8.8, 2.8 Hz, 1H), 7.15-7.13 (m, 1H), 6.71 (d, J=8.0 Hz, 2H), 6.58 (s, 1H), 6.35 (s, 1H), 4.19 (br s, 2H), 3.56-3.54 (m, 3H), 3.51-3.49 (m, 1H), 3.40 (s, 3H), 3.38-3.36 (m, 1H), 2.33 (s, 3H), 2.04-2.01 (m, 1H), 1.71-1.67 (m, 1H). N—H or O—H proton not observed. LCMS: 494.2 (M+H)$^+$.

Example 518

(S)-1-(3'-(2-(3-aminopyrrolidin-1-yl)-6-methylpyridin-4-yl)-3-chloro-2'-hydroxy-5'-methyl-[1,1'-biphenyl]-4-yl)-3-methyl-1H-imidazol-2(3H)-one

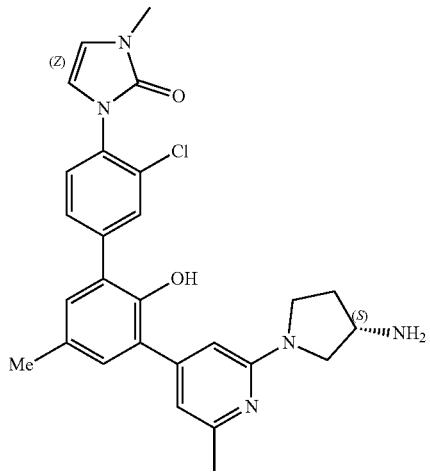

The title compound was prepared following the procedures described for Example 515 using (3'-bromo-3-chloro-2'-methoxy-5'-methyl-[1,1'-biphenyl]-4-yl)-3-methyl-1H-imidazol-2(3H)-one and 4,4,4',4',5,5,5',5'-octamethyl-2,2'-bi(1,3,2-dioxaborolane), (S)-tert-butyl (1-(4-iodo-6-methylpyridin-2-yl)pyrrolidin-3-yl)carbamate and BBr$_3$ to afford the title compound. $^1$H NMR (400 MHz, DMSO-d$_6$): δ 7.74 (d, J=2.0 Hz, 1H), 7.57 (dd, J=8.4, 2.0 Hz, 1H), 7.48 (d, J=8.4 Hz, 1H), 7.13 (d, J=2.0 Hz, 1H), 7.08 (d, J=1.6 Hz, 1H), 6.71 (d, J=3.2 Hz, 1H), 6.68 (d, J=2.8 Hz, 1H), 6.54 (s, 1H), 6.30 (s, 1H), 3.58-3.51 (m, 3H), 3.49-3.39 (m, 1H), 3.21 (s, 3H), 3.11-3.06 (m, 1H), 2.33 (s, 3H), 2.30 (s, 3H), 2.06-2.00 (m, 1H), 1.71-1.69 (m, 1H). N—H and O—H protons not observed. LCMS: 490.2 (M+H)$^+$.

Example 519

(S)—N-(4-(3'-chloro-5-fluoro-2-hydroxy-4'-(3-methyl-2-oxo-2,3-dihydro-1H-imidazol-1-yl)-[1,1'-biphenyl]-3-yl)-6-(3-(methylamino)pyrrolidin-1-yl)pyridin-2-yl)acetamide

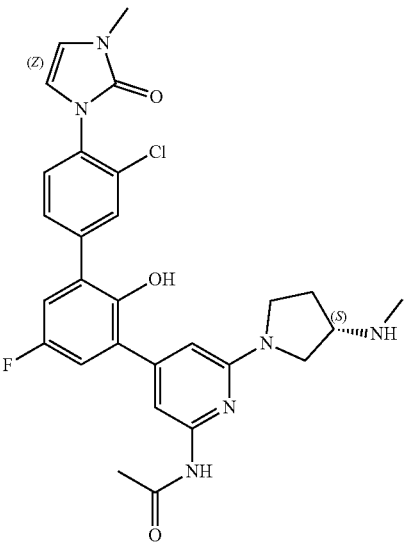

The title compound was prepared following the procedures described for Example 515 using (S)-tert-butyl (1-(6-acetamido-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)(methyl)carbamate and BBr$_3$ to afford the title compound. $^1$H NMR (400 MHz, DMSO-d$_6$): δ 9.92 (s, 1H), 7.79 (d, J=2.0 Hz, 1H), 7.62 (dd, J=8.0, 1.6 Hz, 1H), 7.51 (d, J=8.0 Hz, 1H), 7.43 (br s, 1H), 7.23 (dd, J=9.2, 3.2 Hz, 1H), 7.10 (dd, J=8.8, 3.2 Hz, 1H), 6.71 (d, J=2.8 Hz, 1H), 6.68 (d, J=3.2 Hz, 1H), 6.26 (d, J=0.8 Hz, 1H), 3.59-3.56 (m, 1H), 3.51-3.48 (m, 1H), 3.46-3.42 (m, 1H), 3.26-3.21 (m, 5H), 2.31 (s, 3H), 2.08-2.04 (m, 4H), 1.82-1.77 (m, 1H). N—H or O—H proton not observed. LCMS: 551.1 (M+H)$^+$.

Example 520

1-(3-chloro-5'-fluoro-2'-hydroxy-3'-(2-(piperazin-1-yl)pyridin-4-yl)-[1,1'-biphenyl]-4-yl)-4-methyl-1H-tetrazol-5(4H)-one

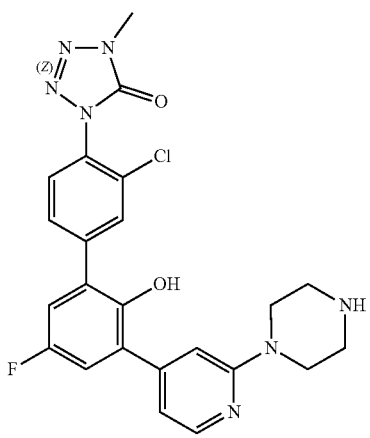

Step 1: 1-(2-chloro-4-nitrophenyl)-4-methyl-1H-tetrazol-5(4H)-one

To a solution of 2-chloro-1-fluoro-4-nitrobenzene (702 mg, 4.00 mmol) and 1-methyl-1H-tetrazol-5(4H)-one (400 mg, 4.00 mmol) in NMP (20 mL) was added $K_2CO_3$ (1.66 g, 12.0 mmol). The reaction mixture was stirred at 80° C. overnight. After the reaction was complete by TLC, the reaction mixture was diluted with $H_2O$ (80 mL) and extracted with EA (20 mL×3). The combined organic layers were washed with brine, dried over sodium sulfate, filtered, and concentrated. The residue was purified by silica gel chromatography using petroleum ether and ethyl acetate (2:1) as the eluent to afford the title compound (800 mg, 78% yield) as a yellow solid. $^1$H NMR (400 MHz, $CDCl_3$): δ 8.47 (d, J=2.4 Hz, 1H), 8.30 (dd, J=8.4, 2.4 Hz, 1H), 7.73 (d, J=8.4 Hz, 1H), 3.75 (s, 3H).

Step 2: 1-(4-amino-2-chlorophenyl)-4-methyl-1H-tetrazol-5(4H)-one

To a solution of 1-(2-chloro-4-nitrophenyl)-4-methyl-1H-tetrazol-5(4H)-one (800 mg, 3.15 mmol) in MeOH/$H_2O$ (1:1, 30 mL) was added $NH_4Cl$ (2.51 g, 47.0 mmol) and Fe (2.63 g, 47.0 mmol). The reaction mixture was stirred at 70° C. overnight. After the reaction was complete by LCMS, the reaction mixture was filtered. The filtrate was concentrated. The residue was diluted with $H_2O$ (60 mL) and extracted with EA (20 mL×3). The combined organic layers were washed with brine, dried over sodium sulfate, filtered, and concentrated. The residue was purified by silica gel chromatography using petroleum ether and ethyl acetate (1:1) as the eluent to afford the title compound (600 mg, 84% yield) as a pale yellow solid. LCMS: 226.0 $(M+H)^+$.

Step 3: 1-(4-bromo-2-chlorophenyl)-4-methyl-1H-tetrazol-5(4H)-one

A solution of 1-(4-amino-2-chlorophenyl)-4-methyl-1H-tetrazol-5(4H)-one (225 mg, 1.00 mmol) and $NaNO_2$ (138 mg, 2.00 mmol) in HCl (1 mL) was stirred at rt for 30 min. The reaction mixture was added to a solution of CuBr (215 mg, 1.50 mmol) in HCl (0.5 mL). Then the mixture was stirred at rt for 2 hrs. After the reaction was complete by LCMS, the reaction mixture was adjusted pH to 8-10 with NaOH and extracted with EA (10 mL×3). The combined organic layers were washed with brine, dried over sodium sulfate, filtered, and concentrated. The residue was purified by silica gel chromatography using petroleum ether and ethyl acetate (1:1) as the eluent to afford the title compound (150 mg, 52% yield) as a yellow solid. LCMS: 288.9 $(M+H)^+$.

Step 4: tert-butyl 4-(4-(3'-chloro-5-fluoro-2-methoxy-4'-(4-methyl-5-oxo-4,5-dihydro-1H-tetrazol-1-yl)-[1,1'-biphenyl]-3-yl)pyridin-2-yl)piperazine-1-carboxylate The title compound was prepared following the procedure described for Example 365 using 1-(4-bromo-2-chlorophenyl)-4-methyl-1H-tetrazol-5(4H)-one and tert-butyl 4-(4-(5-fluoro-2-methoxy-3-(4,4,5,5-tetramethyl-1,3,2-dioxaborolan-2-yl)phenyl)pyridin-2-yl)piperazine-1-carboxylate to afford the title compound (45% yield). LCMS: 596.0 $(M+H)^+$.

Step 5: 1-(3-chloro-5'-fluoro-2'-hydroxy-3'-(2-(piperazin-1-yl)pyridin-4-yl)-[1,1'-biphenyl]-4-yl)-4-methyl-1H-tetrazol-5(4H)-one The title compound was prepared following the procedure described for Example 365 using tert-butyl 4-(4-(3'-chloro-5-fluoro-2-methoxy-4'-(4-methyl-5-oxo-4,5-dihydro-1H-tetrazol-1-yl)-[1,1'-biphenyl]-3-yl)pyridin-2-yl)piperazine-1-carboxylate and $BBr_3$ to afford the title compound. $^1$H NMR (400 MHz, $CD_3OD$): δ 8.07 (d, J=5.2 Hz, 1H), 7.81 (d, J=2.0 Hz, 1H), 7.61 (dd, J=8.4, 1.6 Hz, 1H), 7.54 (d, J=8.0 Hz, 1H), 7.08-7.02 (m, 2H), 6.92 (s, 1H), 6.92-6.79 (m, 1H), 3.61 (s, 3H), 3.48-3.45 (m, 4H), 2.89-2.86 (m, 4H). N—H and O—H protons not observed. LCMS: 482.2 $(M+H)^+$.

Example 521

2-(4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)piperazin-1-yl)acetic acid

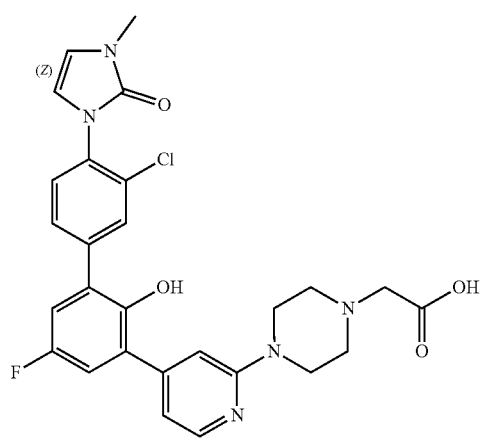

The title compound was prepared following the procedures described for Example 470 using 1-(3-chloro-5'-fluoro-2'-methoxy-3'-(2-(piperazin-1-yl)pyridin-4-yl)-[1,1'-biphenyl]-4-yl)-3-methyl-1H-imidazol-2(3H)-one, ethyl 2-bromoacetate and NaOH to afford the title compound $^1$H NMR (400 MHz, DMSO-d$_6$): δ 8.81 (br s, 1H), 8.16 (d, J=5.2 Hz, 1H), 7.81 (d, J=1.6 Hz, 1H), 7.63 (dd, J=8.0, 1.6 Hz, 1H), 7.52 (d, J=8.0 Hz, 1H), 7.26-7.19 (m, 2H), 6.97 (s, 1H), 6.86-6.84 (m, 1H), 6.71 (d, J=3.2 Hz, 1H), 6.69 (d, J=2.8 Hz, 1H), 3.59-3.56 (m, 4H), 3.21 (s, 3H), 3.19 (s, 2H), 2.68-2.66 (m, 4H). O—H proton not observed. LCMS: 538.2 (M+H)$^+$.

Example 522

(R)-1-(3-chloro-5'-fluoro-2'-hydroxy-3'-(4-(3-methylpiperazin-1-yl)-1H-benzo[d]imidazol-6-yl)-[1,1'-biphenyl]-4-yl)-3-methyl-1H-imidazol-2(3H)-one

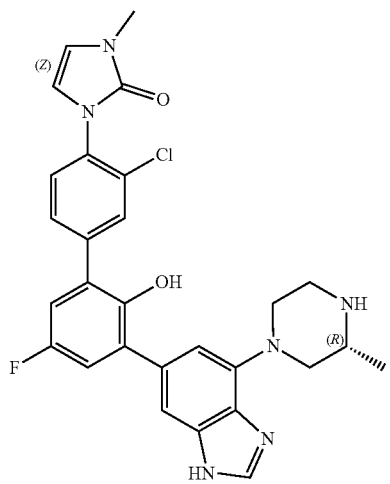

The title compound was prepared following the procedures described for Example 504 using 4-bromo-6-chloro-1-(tetrahydro-2H-pyran-2-yl)-1H-benzo[d]imidazole, (R)-tert-butyl 2-methylpiperazine-1-carboxylate, 4,4,4',4',5,5,5',5'-octamethyl-2,2'-bi(1,3,2-dioxaborolane), 1-(3'-bromo-3-chloro-5'-fluoro-2'-methoxy-[1,1'-biphenyl]-4-yl)-3-methyl-1H-imidazol-2(3H)-one and BBr$_3$ to afford the title compound. $^1$H NMR (400 MHz, DMSO-d$_6$): δ 12.29 (br s, 1H), 8.09 (s, 1H), 7.84 (d, J=2.0 Hz, 1H), 7.68-7.65 (m, 1H), 7.54 (d, J=10.8 Hz, 1H), 7.21-7.15 (m, 3H), 6.72-6.64 (m, 3H), 4.29-4.26 (m, 2H), 3.25 (s, 3H), 3.11-2.98 (m, 3H), 2.94-2.73 (m, 1H), 2.49-1.80 (m, 1H), 1.08 (d, J=7.6 Hz, 3H). N—H and O—H protons not observed. LCMS: 533.1 (M+H)$^+$.

Example 523

(S)—N-(6-(3-aminopyrrolidin-1-yl)-4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)propionamide

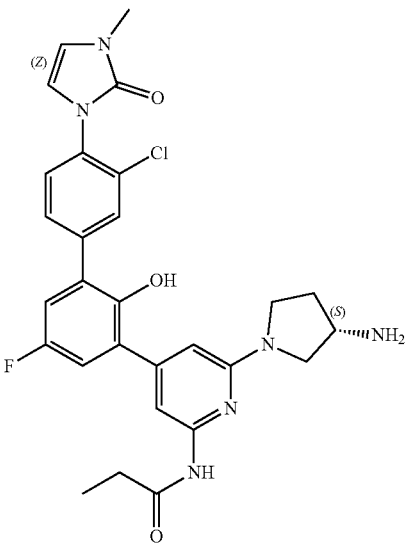

The title compound was prepared following the procedures described for Example 515 using (S)-tert-butyl (1-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)carbamate, propionamide and BBr$_3$ to afford the title compound. $^1$H NMR (400 MHz, DMSO-d$_6$): δ 9.84 (s, 1H), 7.81 (d, J=2.0 Hz, 1H), 7.61 (dd, J=8.0, 2.0 Hz, 1H), 7.51 (d, J=8.4 Hz, 1H), 7.46 (s, 1H), 7.22 (dd, J=8.8, 2.8 Hz, 1H), 7.10 (dd, J=9.2, 3.2 Hz, 1H), 6.71 (d, J=2.8 Hz, 1H), 6.68 (d, J=3.2 Hz, 1H), 6.26 (s, 1H), 4.27 (br s, 2H), 3.58-3.51 (m, 3H), 3.44-3.42 (m, 1H), 3.21 (s, 3H), 3.12-3.07 (m, 1H), 2.42-2.37 (m, 2H), 2.07-2.02 (m, 1H), 1.74-1.66 (m, 1H), 1.05 (t, J=7.2 Hz, 3H). N—H or O—H proton not observed. LCMS: 551.1 (M+H)$^+$.

847
Example 524

(S)—N-(6-(3-aminopyrrolidin-1-yl)-4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)isobutyramide

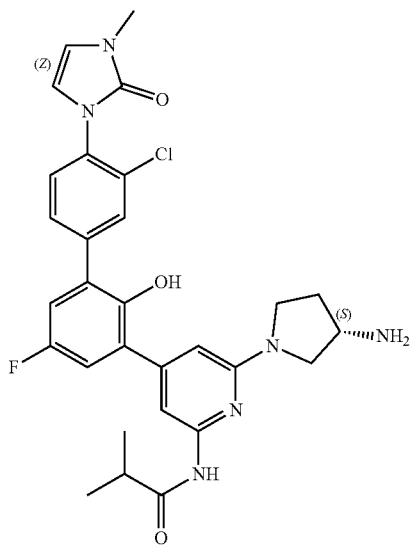

The title compound was prepared following the procedure described for Example 515 using (S)-tert-butyl (1-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)carbamate, isobutyramide and BBr$_3$ to afford the title compound. $^1$H NMR (400 MHz, DMSO-d$_6$): δ 9.83 (s, 1H), 7.81 (d, J=2.0 Hz, 1H), 7.62 (dd, J=8.0, 2.0 Hz, 1H), 7.52-7.49 (m, 2H), 7.22 (dd, J=8.8, 2.8 Hz, 1H), 7.10 (dd, J=9.2, 3.2 Hz, 1H), 6.71 (d, J=2.8 Hz, 1H), 6.68 (d, J=2.8 Hz, 1H), 6.26 (s, 1H), 4.14 (br s, 2H), 3.59-3.51 (m, 3H), 3.44-3.42 (m, 1H), 3.21 (s, 3H), 3.12-3.07 (m, 1H), 2.84-2.77 (m, 1H), 2.07-2.02 (m, 1H), 1.74-1.66 (m, 1H), 1.05 (t, J=6.4 Hz, 6H). N—H or O—H proton not observed. LCMS: 565.1 (M+H)$^+$.

848
Example 525

(S)—N-(6-(3-aminopyrrolidin-1-yl)-4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)cyclopropanecarboxamide

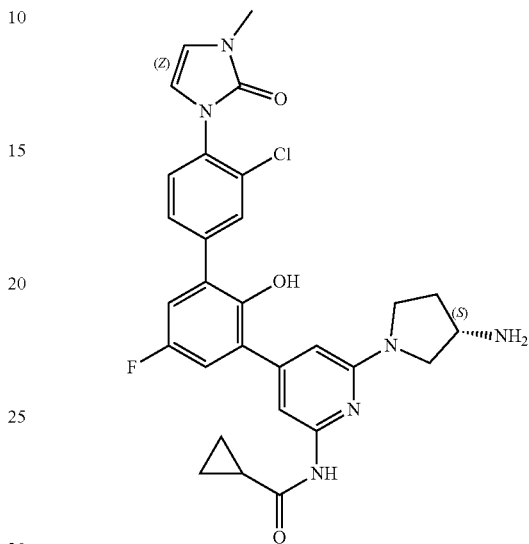

The title compound was prepared following the procedure described for Example 515 using (S)-tert-butyl (1-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)pyrrolidin-3-yl)carbamate, cyclopropanecarboxamide and BBr$_3$ to afford the title compound. $^1$H NMR (400 MHz, DMSO-d$_6$): δ 10.20 (s, 1H), 7.79 (d, J=1.6 Hz, 1H), 7.62 (dd, J=8.0, 1.6 Hz, 1H), 7.51 (d, J=8.0 Hz, 1H), 7.45 (d, J=10.0 Hz, 1H), 7.23 (dd, J=9.2, 3.2 Hz, 1H), 7.10 (dd, J=8.8, 2.8 Hz, 1H), 6.71 (d, J=2.8 Hz, 1H), 6.68 (d, J=2.8 Hz, 1H), 6.26 (s, 1H), 4.36 (br s, 2H), 3.62-3.52 (m, 3H), 3.45-3.42 (m, 1H), 3.21 (s, 3H), 3.14-3.09 (m, 1H), 2.08-2.03 (m, 2H), 1.75-1.69 (m, 1H), 0.77-0.75 (m, 4H). N—H or O—H proton not observed. LCMS: 563.1 (M+H)$^+$.

Example 526

1-(3-chloro-5'-fluoro-2'-hydroxy-3'-(4-(piperazin-1-yl)-1H-indazol-6-yl)-[1,1'-biphenyl]-4-yl)-3-methyl-1H-imidazol-2(3H)-one

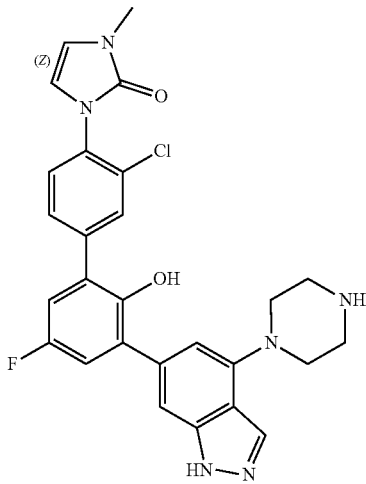

The title compound was prepared following the procedures described for Example 504 using tert-butyl 4-(1-(4-methoxybenzyl)-6-(4,4,5,5-tetramethyl-1,3,2-dioxaborolan-2-yl)-1H-indazol-4-yl)piperazine-1-carboxylate and 1-(3'-bromo-3-chloro-5'-fluoro-2'-methoxy-[1,1'-biphenyl]-4-yl)-3-methyl-1H-imidazol-2(3H)-one, TFA and BBr$_3$ to afford the title compound. $^1$H NMR (400 MHz, CD$_3$OD): δ 8.01 (s, 1H), 7.74 (d, J=1.6 Hz, 1H), 7.52 (d, J=1.6 Hz, 1H), 7.39 (d, J=8.4 Hz, 1H), 7.17 (s, 1H), 7.01-6.98 (m, 2H), 6.60-6.53 (m, 3H), 3.25-3.21 (m, 7H), 3.02-3.00 (m, 4H). N—H and O—H protons not observed. LCMS: 519.1 (M+H)$^+$.

Example 527

1-(3-chloro-5'-fluoro-3'-(2-(4-(3-fluoropropyl)piperazin-1-yl)pyridin-4-yl)-2'-hydroxy-[1,1'-biphenyl]-4-yl)-3-methyl-1H-imidazol-2(3H)-one

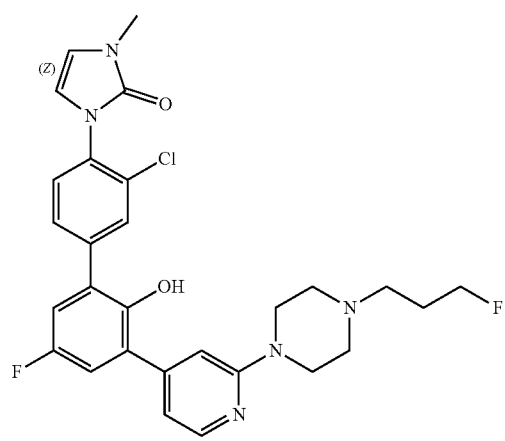 [SMILES: Cn1ccn(-c2ccc(-c3cc(F)cc(-c4ccnc(N5CCN(CCCF)CC5)c4)c3O)cc2Cl)c1=O]

Step 1: 1-(3-chloro-5'-fluoro-3'-(2-(4-(3-fluoropropyl)piperazin-1-yl)pyridin-4-yl)-2'-methoxy-[1,1'-biphenyl]-4-yl)-3-methyl-1H-imidazol-2(3H)-one The title compound was prepared following the procedures described for Example 470 using 1-(3-chloro-5'-fluoro-2'-methoxy-3'-(2-(piperazin-1-yl)pyridin-4-yl)-[1,1'-biphenyl]-4-yl)-3-methyl-1H-imidazol-2(3H)-one and 1-bromo-3-fluoropropane to afford the title compound (86% yield). LCMS: 554.5 (M+H)$^+$.

Step 2: 1-(3-chloro-5'-fluoro-3'-(2-(4-(3-fluoropropyl)piperazin-1-yl)pyridin-4-yl)-2'-hydroxy-[1,1'-biphenyl]-4-yl)-3-methyl-1H-imidazol-2(3H)-one To a solution of 1-(3-chloro-5'-fluoro-3'-(2-(4-(3-fluoropropyl)piperazin-1-yl)pyridin-4-yl)-2'-methoxy-[1,1'-biphenyl]-4-yl)-3-methyl-1H-imidazol-2(3H)-one (75.0 mg, 0.135 mmol) in DMF (1.5 mL) was added piperazine (1.740 g, 20.25 mmol). The reaction mixture was stirred at 150° C. for 5 hrs under microwave. After the reaction was complete by LCMS, the reaction mixture was cooled to rt, diluted with H$_2$O (40 mL) and extracted with DCM (10 mL×3). The combined organic layers were washed with brine, dried over sodium sulfate, filtered, and concentrated. The residue was purified by prep-HPLC to afford the title compound as a yellow solid. $^1$H NMR (400 MHz, DMSO-d$_6$): δ 8.70 (s, 1H), 8.16 (d, J=5.2 Hz, 1H), 7.80 (d, J=1.6 Hz, 1H), 7.61 (dd, J=8.0, 1.6 Hz, 1H), 7.52 (d, J=8.0 Hz, 1H), 7.25-7.19 (m, 2H), 6.96 (s, 1H), 6.83 (d, J=4.4 Hz, 1H), 6.72 (d, J=3.2 Hz, 1H), 6.68 (d, J=3.2 Hz, 1H), 4.57 (t, J=6.0 Hz, 1H), 4.45 (t, J=6.0 Hz, 1H), 3.54-3.52 (m, 4H), 3.21 (s, 3H), 2.48-2.40 (m, 5H), 1.90-1.80 (m, 2H). O—H proton not observed. LCMS: 540.2 (M+H)$^+$.

Example 528

1-(3-chloro-5'-fluoro-2'-hydroxy-3'-(2-(4-(oxetan-3-yl)piperazin-1-yl)pyridin-4-yl)-[1,1'-biphenyl]-4-yl)-3-methyl-1H-imidazol-2(3H)-one

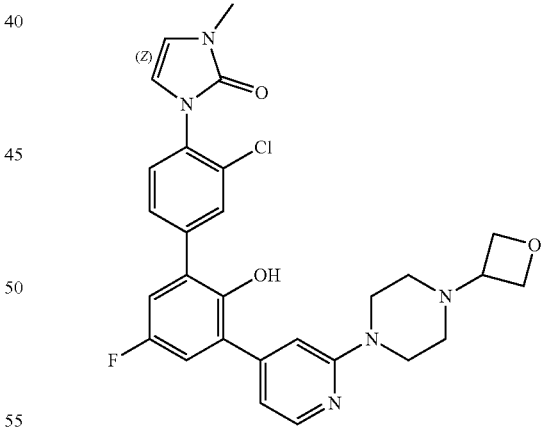

The title compound was prepared following the procedures described for Example 527 using 1-(3-chloro-5'-fluoro-2'-methoxy-3'-(2-(piperazin-1-yl)pyridin-4-yl)-[1,1'-biphenyl]-4-yl)-3-methyl-1H-imidazol-2(3H)-one, oxetan-3-one and piperazine to afford the title compound. $^1$H NMR (400 MHz, DMSO-d$_6$): δ 8.70 (s, 1H), 8.17 (d, J=5.2 Hz, 1H), 7.80 (d, J=2.0 Hz, 1H), 7.61 (dd, J=8.4, 2.0 Hz, 1H), 7.52 (d, J=8.4 Hz, 1H), 7.26-7.18 (m, 2H), 6.96 (s, 1H), 6.83 (dd, J=5.2, 1.2 Hz, 1H), 6.72 (d, J=3.2 Hz, 1H), 6.68 (d, J=2.8 Hz, 1H), 4.57 (t, J=6.4 Hz, 2H), 4.48 (t, J=6.0 Hz, 2H), 3.57-3.55 (m, 4H), 3.45-3.42 (m, 1H), 3.21 (s, 3H), 2.37-2.35 (m, 4H). LCMS: 536.2 (M+H)$^+$.

Example 529

(R)-1-(3,5'-dichloro-2'-hydroxy-3'-(5-(3-methylpiperazin-1-yl)pyridin-3-yl)-[1,1'-biphenyl]-4-yl)-3-methyl-1H-imidazol-2(3H)-one

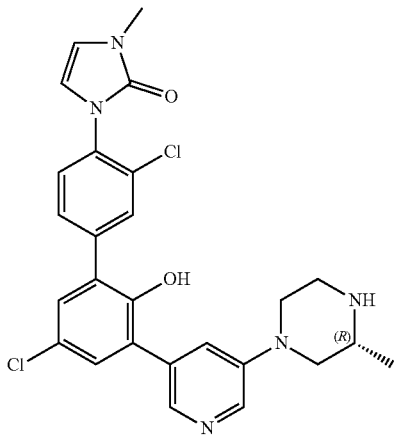

The title compound was prepared following the procedures described for Example 510 using 1-(3,5'-dichloro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and (R)-tert-butyl 4-(5-bromopyridin-3-yl)-2-methylpiperazine-1-carboxylate to afford the title compound. $^1$H NMR (400 MHz, DMSO-d$_6$+D$_2$O): δ 8.46-8.42 (m, 2H), 8.07 (s, 1H), 7.82 (d, J=2.0 Hz, 1H), 7.64-7.62 (m, 1H), 7.57-7.53 (m, 2H), 7.50 (d, J=2.8 Hz, 1H), 6.73 (d, J=2.8 Hz, 1H), 6.69 (d, J=2.8 Hz, 1H), 4.11-4.03 (m, 2H), 3.46-3.40 (m, 2H), 3.26-3.17 (m, 5H), 3.04-2.98 (m, 1H), 1.30 (d, J=6.4 Hz, 3H). N—H and O—H protons not observed. LCMS: 510.2 (M+H)$^+$.

Example 530

1-(3-chloro-5'-fluoro-2'-hydroxy-3'-(2-(4-isopropylpiperazin-1-yl)pyridin-4-yl)-[1,1'-biphenyl]-4-yl)-3-methyl-1H-imidazol-2(3H)-one

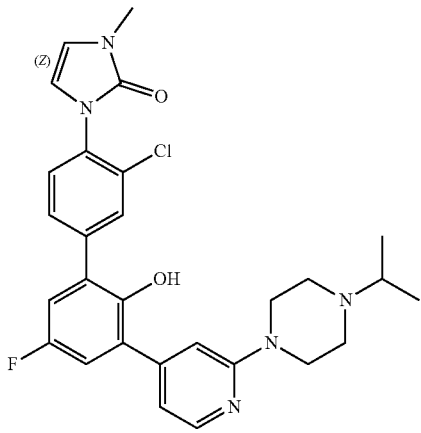 [SMILES: CC(C)N1CCN(c2cc(-c3cc(F)cc(-c4ccc(-n5ccn(C)c5=O)c(Cl)c4)c3O)ccn2)CC1]

The title compound was prepared following the procedure described for Example 527 using 1-(3-chloro-5'-fluoro-2'-methoxy-3'-(2-(piperazin-1-yl)pyridin-4-yl)-[1,1'-biphenyl]-4-yl)-3-methyl-1H-imidazol-2(3H)-one, 2-bromopropane and piperazine to afford the title compound $^1$H NMR (400 MHz, DMSO-d$_6$): δ 8.69 (s, 1H), 8.15 (d, J=4.8 Hz, 1H), 7.80 (d, J=1.6 Hz, 1H), 7.61 (dd, J=8.4, 2.0 Hz, 1H), 7.52 (d, J=8.4 Hz, 1H), 7.26-7.18 (m, 2H), 6.94 (s, 1H), 6.83 (dd, J=9.2, 0.8 Hz, 1H), 6.72 (d, J=3.2 Hz, 1H), 6.69 (d, J=2.8 Hz, 1H), 3.52-3.50 (m, 4H), 3.21 (s, 3H), 2.70-2.67 (m, 1H), 2.55-2.52 (m, 4H), 1.00 (d, J=6.4 Hz, 6H). LCMS: 522.3 (M+H)$^+$.

Example 531

1-(3-chloro-3'-(2-(4-cyclopropylpiperazin-1-yl)pyridin-4-yl)-5'-fluoro-2'-hydroxy-[1,1'-biphenyl]-4-yl)-3-methyl-1H-imidazol-2(3H)-one

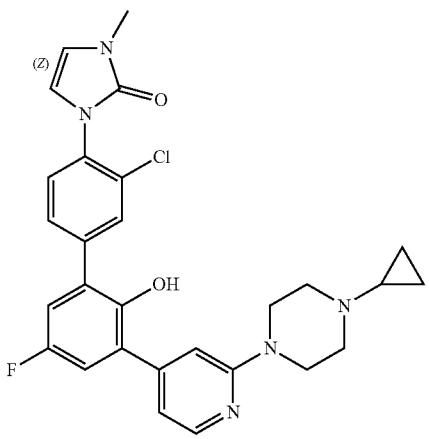 [SMILES: Cn1ccn(-c2ccc(-c3cc(F)cc(-c4ccnc(N5CCN(C6CC6)CC5)c4)c3O)cc2Cl)c1=O]

The title compound was prepared following the procedure described for Example 414 using 1-(3-chloro-5'-fluoro-3'-(2-fluoropyridin-4-yl)-2'-methoxy-[1,1'-biphenyl]-4-yl)-3-methyl-1H-imidazol-2(3H)-one, 1-cyclopropylpiperazine and piperazine. $^1$H NMR (400 MHz, DMSO-d$_6$): δ 8.69 (s, 1H), 8.15 (d, J=5.2 Hz, 1H), 7.80 (d, J=2.0 Hz, 1H), 7.61 (dd, J=8.0, 2.0 Hz, 1H), 7.52 (d, J=8.0 Hz, 1H), 7.26-7.18 (m, 2H), 6.95 (s, 1H), 6.83 (dd, J=9.2, 0.8 Hz, 1H), 6.72 (d, J=2.8 Hz, 1H), 6.68 (d, J=3.2 Hz, 1H), 3.50-3.48 (m, 4H), 3.21 (s, 3H), 2.64-2.61 (m, 4H), 1.66-1.63 (m, 1H), 0.45-0.43 (m, 2H), 0.37-0.34 (m, 2H). LCMS: 519.8 (M+H)$^+$.

Example 532

1-(3-chloro-3'-(2-(3,4-dihydroquinoxalin-1(2H)-yl)pyridin-4-yl)-5'-fluoro-2'-hydroxy-[1,1'-biphenyl]-4-yl)-3-methyl-1H-imidazol-2(3H)-one

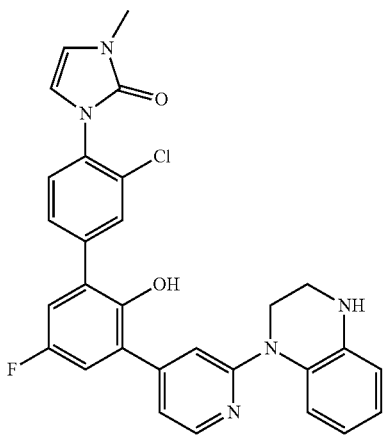 [SMILES: Cn1ccn(-c2ccc(-c3cc(F)cc(-c4ccnc(N5CCNc6ccccc65)c4)c3O)cc2Cl)c1=O]

The title compound was prepared following the procedures described for Example 414 using (2-(4-(tert-butoxycarbonyl)-3,4-dihydroquinoxalin-1(2H)-yl)pyridin-4-yl)boronic acid and 1-(3'-bromo-3-chloro-5'-fluoro-2'-methoxy-[1,1'-biphenyl]-4-yl)-3-methyl-1H-imidazol-2(3H)-one and BBr$_3$ to afford the title compound. $^1$H NMR (400 MHz, DMSO-d$_6$): δ 8.80 (s, 1H), 8.25 (d, J=5.2 Hz, 1H), 7.80 (s, 1H), 7.60 (dd, J=8.0, 2.0 Hz, 1H), 7.49 (d, J=8.0 Hz, 1H), 7.27 (s, 1H), 7.21 (d, J=8.4 Hz, 2H), 7.15 (dd, J=8.8, 2.8 Hz, 1H), 6.95 (d, J=5.2 Hz, 1H), 6.79 (t, J=7.2 Hz, 1H), 6.71 (d, J=3.2 Hz, 1H), 6.68 (d, J=3.6 Hz, 1H), 6.62 (d, J=8.0 Hz, 1H), 6.49-6.45 (m, 1H), 6.03 (s, 1H), 3.96-3.94 (m, 2H), 3.30-3.28 (m, 2H), 3.21 (s, 3H). LCMS: 528.0 (M+H)$^+$.

Example 533

(S)-1-(3'-(4-(3-aminopyrrolidin-1-yl)-1H-benzo[d]imidazol-6-yl)-3-chloro-5'-fluoro-2'-hydroxy-[1,1'-biphenyl]-4-yl)-3-methyl-1H-imidazol-2(3H)-one

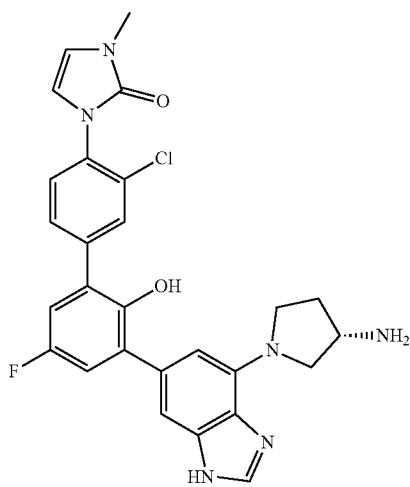 [SMILES: Cn1ccn(-c2ccc(-c3cc(F)cc(-c4cc(N5CC[C@H](N)C5)c5nc[nH]c5c4)c3O)cc2Cl)c1=O]

The title compound was prepared following the procedure described for Example 504 using 4-bromo-6-chloro-1-(tetrahydro-2H-pyran-2-yl)-1H-benzo[d]imidazole, (S)-tert-butyl pyrrolidin-3-ylcarbamate, 4,4,4',4',5,5,5',5'-octamethyl-2,2'-bi(1,3,2-dioxaborolane) and 1-(3'-bromo-3-chloro-5'-fluoro-2'-methoxy-[1,1'-biphenyl]-4-yl)-3-methyl-1H-imidazol-2(3H)-one to afford the title compound. $^1$H NMR (400 MHz, CD$_3$OD): δ 7.92 (s, 1H), 7.74 (d, J=2.0 Hz, 1H), 7.53 (dd, J=8.0, 1.6 Hz, 1H), 7.38 (d, J=8.4 Hz, 1H), 6.99-6.94 (m, 3H), 6.56 (d, J=3.2 Hz, 1H), 6.53 (d, J=3.2 Hz, 1H), 6.36 (s, 1H), 3.83-3.77 (m, 2H), 3.64-3.59 (m, 2H), 3.50-3.46 (m, 1H), 3.21 (s, 3H), 2.24-2.19 (m, 1H), 1.84-1.79 (m, 1H). N—H and O—H protons not observed. LCMS: 519.2 (M+H)$^+$.

Example 534

(R)-1-(3,5'-difluoro-2'-hydroxy-3'-(2-(3-methylpiperazin-1-yl)pyridin-4-yl)-[1,1'-biphenyl]-4-yl)-3-methyl-1H-imidazol-2(3H)-one

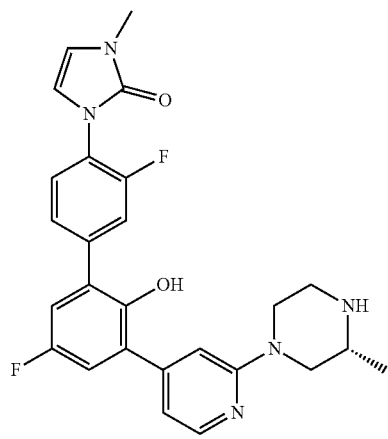 [SMILES: C[C@@H]1CN(c2cc(-c3cc(F)cc(-c4ccc(-n5ccn(C)c5=O)c(F)c4)c3O)ccn2)CCN1]

The title compound was prepared following the procedures described for Example 414 using 4-(3-bromo-5-fluoro-2-methoxyphenyl)-2-fluoropyridine, 1-(2-fluoro-4-(4,4,5,5-tetramethyl-1,3,2-dioxaborolan-2-yl)phenyl)-3-methyl-1H-imidazol-2(3H)-one, (R)-tert-butyl 2-methylpiperazine-1-carboxylate and BBr$_3$ to afford the title compound. $^1$H NMR (400 MHz, DMSO-d$_6$): δ 8.14 (d, J=5.2 Hz, 1H), 7.62-7.58 (m, 2H), 7.50-7.47 (m, 1H), 7.24-7.16 (m, 2H), 6.93 (s, 1H), 6.81-6.73 (m, 3H), 4.18-4.13 (m, 2H), 3.21 (s, 3H), 2.95-2.93 (m, 1H), 2.73-2.69 (m, 3H), 2.36-2.31 (m, 1H), 1.00. (d, J=6.4 Hz, 3H). N—H and O—H protons not observed. LCMS: 478.2 (M+H)$^+$.

Example 535

1-(3-chloro-5'-fluoro-2'-hydroxy-3'-(4-(piperazin-1-yl)-1H-benzo[d][1,2,3]triazol-6-yl)-[1,1'-biphenyl]-4-yl)-3-methyl-1H-imidazol-2(3H)-one

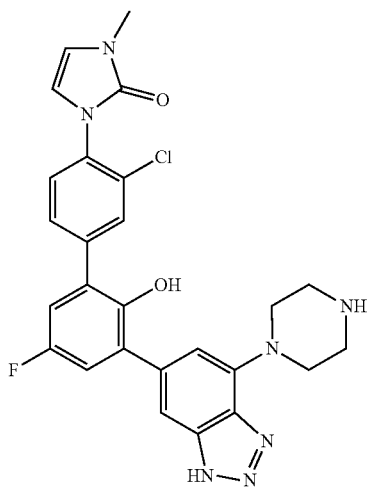 [SMILES: Cn1ccn(-c2ccc(-c3cc(F)cc(-c4cc(N5CCNCC5)c5nn[nH]c5c4)c3O)cc2Cl)c1=O]

The title compound was prepared following the procedures described for Example 504 using tert-butyl 4-(1-(tetrahydro-2H-pyran-2-yl)-6-(4,4,5,5-tetramethyl-1,3,2-dioxaborolan-2-yl)-1H-benzo[d][1,2,3]triazol-4-yl)piperazine-1-carboxylate, 1-(3'-bromo-3-chloro-5'-fluoro-2'-methoxy-[1,1'-biphenyl]-4-yl)-3-methyl-1H-imidazol-2(3H)-one and BBr$_3$ to afford the title compound. $^1$H NMR (400 MHz, DMSO-d$_6$): δ 7.82 (d, J=2.0 Hz, 1H), 7.64 (dd, J=8.0, 2.0 Hz, 1H), 7.52 (d, J=8.4 Hz, 1H), 7.30 (s, 1H), 7.23-7.20 (m, 2H), 6.72-6.67 (m, 3H), 3.59-3.57 (m, 4H), 3.21 (s, 3H), 2.97-2.94 (m, 4H). N—H and O—H protons not observed. LCMS: 520.2 (M+H)$^+$.

Example 536

(R)-1-(3-chloro-5'-fluoro-2'-hydroxy-3'-(4-(3-methylpiperazin-1-yl)-1H-benzo[d][1,2,3]triazol-6-yl)-[1,1'-biphenyl]-4-yl)-3-methyl-1H-imidazol-2(3H)-one

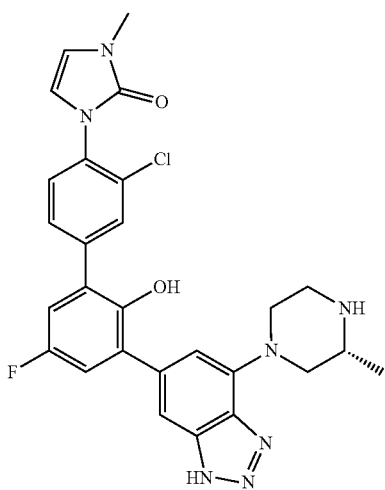 [SMILES: C[C@@H]1CN(c2cc(-c3cc(F)cc(-c4ccc(-n5ccn(C)c5=O)c(Cl)c4)c3O)cc3[nH]nnc23)CCN1]

The title compound was prepared following the procedures described for Example 536 using 6-bromo-4-fluoro-1-(tetrahydro-2H-pyran-2-yl)-1H-benzo[d][1,2,3]triazole, (R)-tert-butyl 2-methylpiperazine-1-carboxylate, 1-(3'-bromo-3-chloro-5'-fluoro-2'-methoxy-[1,1'-biphenyl]-4-yl)-3-methyl-1H-imidazol-2(3H)-one and 4,4,4',4',5,5,5',5'-octamethyl-2,2'-bi(1,3,2-dioxaborolane) to afford the title compound. $^1$H NMR (400 MHz, DMSO-d$_6$): δ 7.82 (d, J=2.0 Hz, 1H), 7.64 (dd, J=8.4, 2.0 Hz, 1H), 7.52 (d, J=8.4 Hz, 1H), 7.28 (s, 1H), 7.21 (d, J=9.2 Hz, 2H), 6.71 (d, J=3.2 Hz, 1H), 6.68 (d, J=2.8 Hz, 1H), 6.64 (s, 1H), 4.32-4.27 (m, 2H), 3.21 (s, 3H), 2.93-2.91 (m, 1H), 2.84-2.81 (m, 2H), 2.78-2.67 (m, 1H), 2.49-2.44 (m, 1H), 1.00 (d, J=6.4 Hz, 3H). N—H and O—H protons not observed. LCMS: 533.8 (M+H)$^+$.

Example 537

(S)-1-(3'-(4-(3-aminopyrrolidin-1-yl)-1H-benzo[d][1,2,3]triazol-6-yl)-3-chloro-5'-fluoro-2'-hydroxy-[1,1'-biphenyl]-4-yl)-3-methyl-1H-imidazol-2(3H)-one

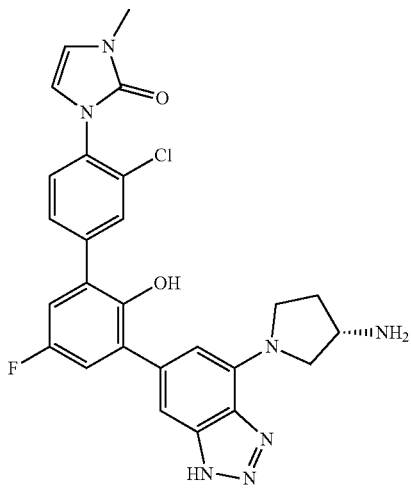 [SMILES: Cn1ccn(-c2ccc(-c3cc(F)cc(-c4cc(N5CC[C@H](N)C5)c5nn[nH]c5c4)c3O)cc2Cl)c1=O]

The title compound was prepared following the procedure described for Example 536 using 6-bromo-4-fluoro-1-(tetrahydro-2H-pyran-2-yl)-1H-benzo[d][1,2,3]triazole, (S)-tert-butyl pyrrolidin-3-ylcarbamate and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one to afford the title compound (19% yield). $^1$H NMR (400 MHz, CD$_3$OD): δ 7.87 (d, J=2.0 Hz, 1H), 7.66 (dd, J=8.0, 1.6 Hz, 1H), 7.52 (d, J=8.4 Hz, 1H), 7.15-7.10 (m, 2H), 7.06 (s, 1H), 6.70 (d, J=2.8 Hz, 1H), 6.66 (d, J=2.8 Hz, 1H), 6.39 (s, 1H), 4.13-4.01 (m, 2H), 3.89-3.80 (m, 3H), 3.35 (s, 3H), 2.42-2.35 (m, 1H), 2.05-1.99 (m, 1H). N—H and O—H protons not observed. LCMS: 519.8 (M+H)$^+$.

Example 538

(R)-1-(5'-chloro-3-fluoro-2'-hydroxy-3'-(2-(3-methylpiperazin-1-yl)pyridin-4-yl)-[1,1'-biphenyl]-4-yl)-3-methyl-1H-imidazol-2(3H)-one

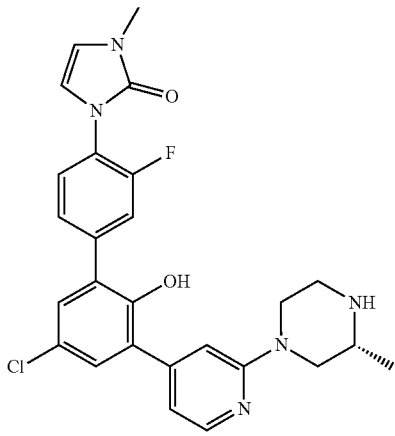 [SMILES: C[C@@H]1CN(c2cc(-c3cc(Cl)cc(-c4ccc(-n5ccn(C)c5=O)c(F)c4)c3O)ccn2)CCN1]

The title compound was prepared following the procedures described for Example 414 using 1-(5'-chloro-3-fluoro-3'-(2-fluoropyridin-4-yl)-2'-methoxy-[1,1'-biphenyl]-4-yl)-3-methyl-1H-imidazol-2(3H)-one, (R)-tert-butyl 2-methylpiperazine-1-carboxylate and BBr$_3$ to afford the title compound. $^1$H NMR (400 MHz, DMSO-d$_6$): δ 8.13 (d, J=5.2 Hz, 1H), 7.61-7.60 (m, 1H), 7.58-7.57 (m, 2H), 7.48 (dd, J=8.0, 1.6 Hz, 1H), 7.37 (d, J=2.4 Hz, 1H), 7.32 (d, J=2.4 Hz, 1H), 6.93 (s, 1H), 6.79-6.78 (m, 2H), 6.76-6.73 (m, 1H), 4.19-4.13 (m, 2H), 3.21 (s, 3H), 2.97-2.92 (m, 1H), 2.74-2.67 (m, 3H), 2.43-2.32 (m, 1H), 1.03 (d, J=6.4 Hz, 3H). N—H or O—H proton not observed. LCMS: 494.2 (M+H)$^+$.

Example 539

(S)-1-(3'-(2-(3-aminopyrrolidin-1-yl)pyridin-4-yl)-3,5'-dichloro-2'-hydroxy-[1,1'-biphenyl]-4-yl)-3-methyl-1H-imidazol-2(3H)-one

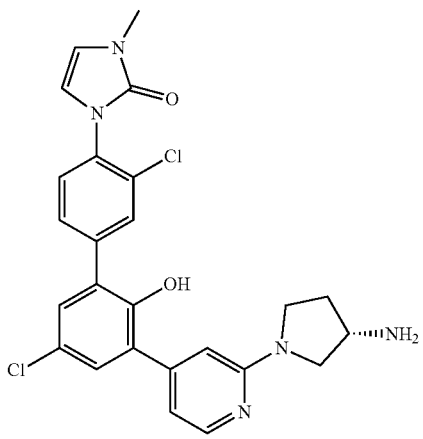 [SMILES: Cn1ccn(-c2ccc(-c3cc(Cl)cc(-c4ccnc(N5CC[C@H](N)C5)c4)c3O)cc2Cl)c1=O]

The title compound was prepared following the procedures described for Example 538 using 4-(3-bromo-5-chloro-2-methoxyphenyl)-2-fluoropyridine, 1-(2-chloro-4-(4,4,5,5-tetramethyl-1,3,2-dioxaborolan-2-yl)phenyl)-3-methyl-1H-imidazol-2(3H)-one and (S)-tert-butyl pyrrolidin-3-ylcarbamate to afford the title compound. $^1$H NMR (400 MHz, DMSO-d$_6$): δ 8.08 (d, J=5.2 Hz, 1H), 7.83 (d, J=2.0 Hz, 1H), 7.60 (dd, J=8.4, 2.0 Hz, 1H), 7.50 (d, J=8.4 Hz, 1H), 7.36 (d, J=2.8 Hz, 1H), 7.31 (d, J=2.8 Hz, 1H), 6.72-6.68 (m, 3H), 6.58 (s, 1H), 3.65-3.51 (m, 4H), 3.21 (s, 3H), 3.14-3.09 (m, 1H), 2.09-2.04 (m, 1H), 1.79-1.71 (m, 1H). N—H and O—H protons not observed. LCMS: 496.0 (M+H)$^+$.

Example 540

(R)-1-(3,5'-dichloro-2'-hydroxy-3'-(2-(3-methylpiperazin-1-yl)pyridin-4-yl)-[1,1'-biphenyl]-4-yl)-3-methyl-1H-imidazol-2(3H)-one

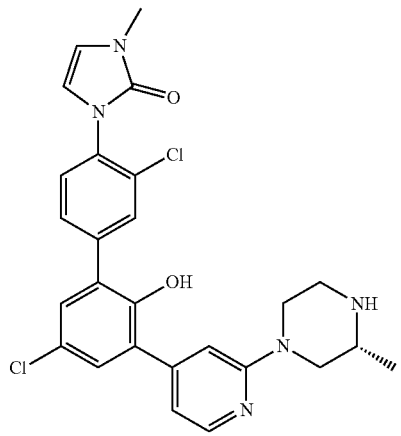 [SMILES: C[C@@H]1CN(c2cc(-c3cc(Cl)cc(-c4ccc(-n5ccn(C)c5=O)c(Cl)c4)c3O)ccn2)CCN1]

The title compound was prepared following the procedures described for Example 538 using 1-(3,5'-dichloro-3'-(2-fluoropyridin-4-yl)-2'-methoxy-[1,1'-biphenyl]-4-yl)-3-methyl-1H-imidazol-2(3H)— one and (R)-tert-butyl 2-methylpiperazine-1-carboxylate to afford the title compound (21% yield). $^1$H NMR (400 MHz, DMSO-d$_6$): δ 8.13 (d, J=5.2 Hz, 1H), 7.81 (d, J=1.6 Hz, 1H), 7.60 (dd, J=8.0, 1.6 Hz, 1H), 7.51 (d, J=8.0 Hz, 1H), 7.37 (d, J=2.8 Hz, 1H), 7.32 (d, J=2.8 Hz, 1H), 6.93 (s, 1H), 6.79 (d, J=5.2 Hz, 1H), 6.71 (d, J=2.8 Hz, 1H), 6.68 (d, J=2.8 Hz, 1H), 4.19-4.14 (m, 2H), 3.21 (s, 3H), 2.96-2.94 (m, 1H), 2.71-2.67 (m, 3H), 2.37-2.32 (m, 1H), 1.03 (d, J=6.4 Hz, 3H). N—H and O—H protons not observed. LCMS: 510.2 (M+H)$^+$.

Example 541

(S)-1-(2'-amino-3'-(2-(3-aminopyrrolidin-1-yl)pyridin-4-yl)-3-chloro-5'-fluoro-[1,1'-biphenyl]-4-yl)-3-methyl-1H-imidazol-2(3H)-one

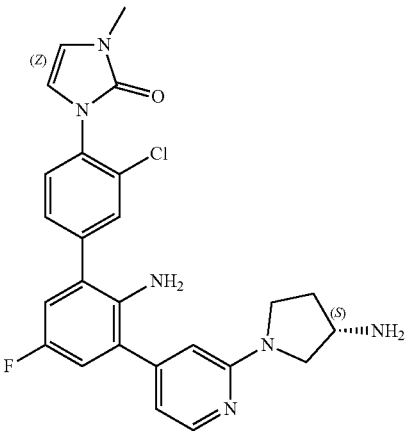

Step 1: 2-bromo-4-fluoro-6-(2-fluoropyridin-4-yl)aniline

The title compound was prepared following the procedure described for Example 414 using 2,6-dibromo-4-fluoroaniline and (2-fluoropyridin-4-yl)boronic acid to afford the title compound (83% yield). LCMS: 287.0 (M+H)$^+$.

Step 2: 1-(2'-amino-3-chloro-5'-fluoro-3'-(2-fluoropyridin-4-yl)-[1,1'-biphenyl]-4-yl)-3-methyl-1H-imidazol-2(3H)-one The title compound was prepared following the procedure described for Example 414 using 2-bromo-4-fluoro-6-(2-fluoropyridin-4-yl)aniline and 1-(2-chloro-4-(4,4,5,5-tetramethyl-1,3,2-dioxaborolan-2-yl)phenyl)-3-methyl-1H-imidazol-2(3H)-one to afford the title compound (88% yield). LCMS: 413.1 (M+H)$^+$.

Step 3: (S)-tert-butyl (1-(4-(2-amino-3'-chloro-5-fluoro-4'-(3-methyl-2-oxo-2,3-dihydro-1H-imidazol-1-yl)-[1,1'-biphenyl]-3-yl)pyridin-2-yl)pyrrolidin-3-yl)carbamate The title compound was prepared following the procedure described for Example 414 using 1-(2'-amino-3-chloro-5'-fluoro-3'-(2-fluoropyridin-4-yl)-[1,1'-biphenyl]-4-yl)-3-methyl-1H-imidazol-2(3H)-one and (S)-tert-butyl pyrrolidin-3-ylcarbamate to afford the title compound (88% yield). LCMS: 579.6 (M+H)$^+$.

Step 4: (S)-1-(2'-amino-3'-(2-(3-aminopyrrolidin-1-yl)pyridin-4-yl)-3-chloro-5'-fluoro-[1,1'-biphenyl]-4-yl)-3-methyl-1H-imidazol-2(3H)-one The title compound was prepared following the procedure described for Example 494 using (S)-tert-butyl (1-(4-(2-amino-3'-chloro-5-fluoro-4'-(3-methyl-2-oxo-2,3-dihydro-1H-imidazol-1-yl)-[1,1'-biphenyl]-3-yl)pyridin-2-yl)pyrrolidin-3-yl)carbamate and TFA to afford the title compound.
$^1$H NMR (400 MHz, DMSO-d$_6$): δ 8.13 (d, J=5.2 Hz, 1H), 7.72 (s, 1H), 7.58-7.53 (m, 2H), 7.04-6.97 (m, 2H), 6.73-6.64 (m, 3H), 6.47 (s, 1H), 4.58-4.31 (m, 4H), 3.71-3.66 (m, 3H), 3.63-3.56 (m, 1H), 3.54-3.23 (m, 1H), 3.21 (s, 3H), 2.18-2.12 (m, 1H), 1.86-1.79 (m, 1H). LCMS: 479.2 (M+H)$^+$.

Example 542

(R)-1-(2'-amino-3-chloro-5'-fluoro-3'-(2-(3-methylpiperazin-1-yl)pyridin-4-yl)-[1,1'-biphenyl]-4-yl)-3-methyl-1H-imidazol-2(3H)-one

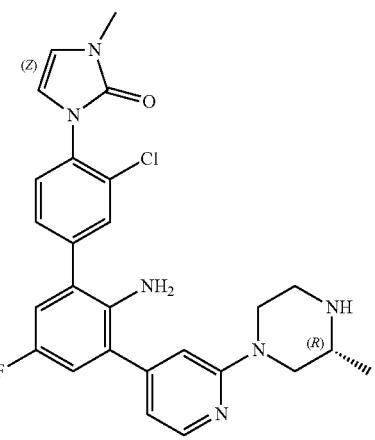

The title compound was prepared following the procedure described for Example 541 using 1-(2'-amino-3-chloro-5'-fluoro-3'-(2-fluoropyridin-4-yl)-[1,1'-biphenyl]-4-yl)-3-methyl-1H-imidazol-2(3H)-one, (R)-tert-butyl 2-methylpiperazine-1-carboxylate and TFA to afford the title compound.
$^1$H NMR (400 MHz, DMSO-d$_6$): δ 8.18 (d, J=5.2 Hz, 1H), 7.72 (d, J=0.8 Hz, 1H), 7.55 (d, J=1.6 Hz, 2H), 7.04-6.98 (m, 2H), 6.84 (s, 1H), 6.73-6.67 (m, 3H), 4.36 (s, 2H), 4.19 (t, J=10.4 Hz, 2H), 3.21 (s, 3H), 2.99-2.96 (m, 1H), 2.74-2.72 (m, 3H), 2.42-2.39 (m, 1H), 1.04 (d, J=6.0 Hz, 3H). N—H proton not observed. LCMS: 493.2 (M+H)$^+$.

Example 543

(R)-1-(3-chloro-5'-fluoro-2'-hydroxy-3'-(4-(3-methylpiperazin-1-yl)-1H-indazol-6-yl)-[1,1'-biphenyl]-4-yl)-3-methyl-1H-imidazol-2(3H)-one

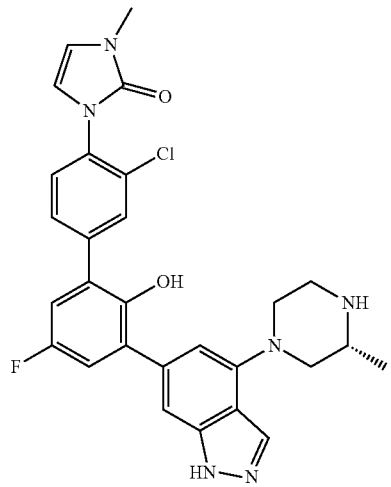 [SMILES: C[C@@H]1CN(c2cc(-c3cc(F)cc(-c4ccc(-n5ccn(C)c5=O)c(Cl)c4)c3O)cc3[nH]ncc23)CCN1]

The title compound was prepared following the procedure described for Example 504 using (R)-tert-butyl 4-(1-(4-methoxybenzyl)-6-(4,4,5,5-tetramethyl-1,3,2-dioxaborolan-2-yl)-1H-indazol-4-yl)-2-methylpiperazine-1-carboxylate, 1-(3'-bromo-3-chloro-5'-fluoro-2'-methoxy-[1,1'-biphenyl]-4-yl)-3-methyl-1H-imidazol-2(3H)-one, TFA and BBr$_3$ to afford the title compound. $^1$H NMR (400 MHz, CD$_3$OD): δ 8.02 (s, 1H), 7.74 (d, J=1.6 Hz, 1H), 7.55-7.53 (m, 1H), 7.40 (d, J=8.0 Hz, 1H), 7.18 (s, 1H), 7.02-6.98 (m, 2H), 6.60-6.53 (m, 3H), 3.65-3.62 (m, 2H), 3.22 (s, 3H), 3.10-3.09 (m, 3H), 2.86-2.82 (m, 1H), 2.56-2.53 (m, 1H), 1.12 (d, J=6.4 Hz, 3H). N—H and O—H protons not observed. LCMS: 533.5 (M+H)$^+$.

Example 544

(R)—N-(4-(3'-chloro-5-fluoro-2-hydroxy-4'-(3-methyl-2-oxo-2,3-dihydro-1H-imidazol-1-yl)-[1,1'-biphenyl]-3-yl)-6-(3-methylpiperazin-1-yl)pyridin-2-yl)acetamide

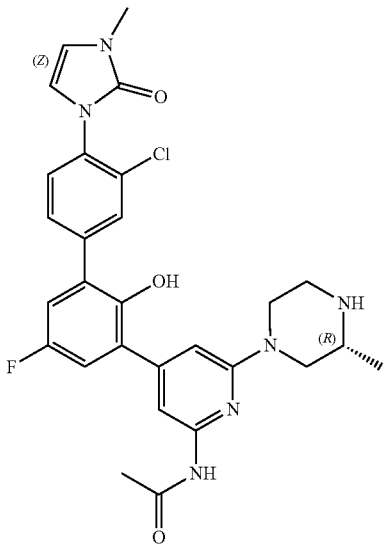

The title compound was prepared following the procedure described for Example 515 using 4-(3-bromo-5-fluoro-2-methoxyphenyl)-2,6-dichloropyridine, (R)-tert-butyl 2-methylpiperazine-1-carboxylate, 1-(2-chloro-4-(4,4,5,5-tetramethyl-1,3,2-dioxaborolan-2-yl)phenyl)-3-methyl-1H-imidazol-2(3H)-one and acetamide to afford the title compound. $^1$H NMR (400 MHz, DMSO-d$_6$): δ 10.10 (s, 1H), 9.05 (br s, 1H), 8.69 (br s, 2H), 7.80 (d, J=2.4 Hz, 1H), 7.62 (dd, J=8.0, 1.6 Hz, 2H), 7.52 (d, J=8.0 Hz, 1H), 7.26 (dd, J=8.8, 2.8 Hz, 1H), 7.14 (dd, J=8.8, 3.2 Hz, 1H), 6.75 (s, 1H), 6.72 (d, J=2.8 Hz, 1H), 6.68 (d, J=2.8 Hz, 1H), 4.40-4.35 (m, 2H), 3.41-3.89 (m, 1H), 3.32-3.31 (m, 1H), 3.21 (s, 3H), 3.15-3.05 (m, 2H), 2.93-2.87 (m, 1H), 2.09 (s, 3H), 1.27 (d, J=6.8 Hz, 3H). LCMS: 551.2 (M+H)$^+$.

Example 545

(R)-1-(3-fluoro-2'-hydroxy-5'-methyl-3'-(5-(3-methylpiperazin-1-yl)pyridin-3-yl)-[1,1'-biphenyl]-4-yl)-3-methyl-1H-imidazol-2(3H)-one

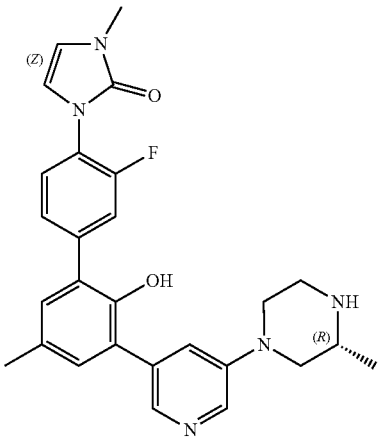

The title compound was prepared following the procedure described for Example 508 using 1-(2-fluoro-4-(4,4,5,5-tetramethyl-1,3,2-dioxaborolan-2-yl)phenyl)-3-methyl-1H-imidazol-2(3H)-one, 1,3-dibromo-2-methoxy-5-methylbenzene and (R)-(5-(4-(tert-butoxycarbonyl)-3-methylpiperazin-1-yl)pyridin-3-yl)boronic acid to afford the title compound. $^1$H NMR (400 MHz, DMSO-d$_6$): δ 8.23 (d, J=2.8 Hz, 1H), 8.10 (d, J=1.6 Hz, 1H), 7.59-7.52 (m, 2H), 7.45 (dd, J=8.0, 1.6 Hz, 1H), 7.38-7.37 (m, 1H), 7.14 (d, J=2.0 Hz, 1H), 7.11 (d, J=1.6 Hz, 1H), 6.76-6.72 (m, 2H), 3.64-3.59 (m, 2H), 3.21 (s, 3H), 2.98-2.95 (m, 1H), 2.83-2.77 (m, 2H), 2.65-2.59 (m, 1H), 2.31 (s, 3H), 2.29-2.23 (m, 1H), 1.03 (d, J=6.4 Hz, 3H). N—H and O—H protons not observed. LCMS: 474.3 (M+H)$^+$.

Example 546

(R)-1-(3-fluoro-2'-hydroxy-5'-methyl-3'-(2-(3-methylpiperazin-1-yl)pyridin-4-yl)-[1,1'-biphenyl]-4-yl)-3-methyl-1H-imidazol-2(3H)-one

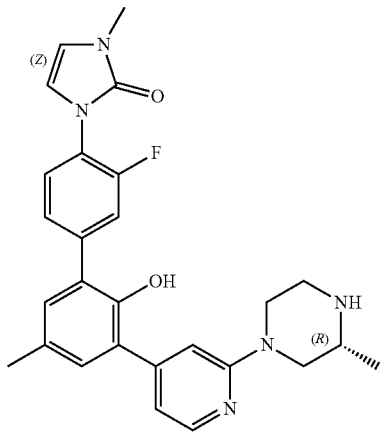

The title compound was prepared following the procedure described for Example 414 using 1-(3-fluoro-3'-(2-fluoropyridin-4-yl)-2'-methoxy-5'-methyl-[1,1'-biphenyl]-4-yl)-3-methyl-1H-imidazol-2(3H)-one, (R)-tert-butyl 2-methylpiperazine-1-carboxylate and BBr₃ to afford the title compound. ¹H NMR (400 MHz, DMSO-d₆): δ 8.12 (d, J=5.2 Hz, 1H), 7.59-7.51 (m, 2H), 7.45 (dd, J=8.4, 1.6 Hz, 1H), 7.14 (d, J=2.0 Hz, 1H), 7.11 (d, J=2.0 Hz, 1H), 6.88 (s, 1H), 6.77-6.72 (m, 3H), 4.17-4.11 (m, 2H), 3.21 (s, 3H), 2.96-2.94 (m, 1H), 2.72-2.65 (m, 3H), 2.36-2.30 (m, 4H), 1.02 (d, J=6.0 Hz, 3H). N—H and O—H protons not observed. LCMS: 474.3 (M+H)⁺.

Example 547

1-(3-chloro-5'-fluoro-2'-hydroxy-3'-(8-(piperazin-1-yl)quinoxalin-6-yl)-[1,1'-biphenyl]-4-yl)-3-methyl-1H-imidazol-2(3H)-one

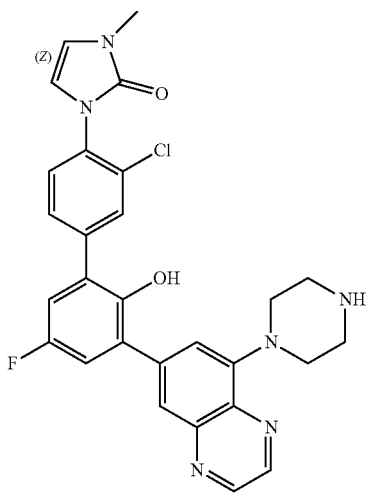 [SMILES: Cn1ccn(-c2ccc(-c3cc(F)cc(-c4cc(N5CCNCC5)c5nccnc5c4)c3O)cc2Cl)c1=O]

The title compound was prepared following the procedures described for Example 504 using 5-bromo-7-chloroquinoxaline, tert-butyl piperazine-1-carboxylate, 4,4,4',4',5,5,5',5'-octamethyl-2,2'-bi(1,3,2-dioxaborolane) and 1-(3'-bromo-3-chloro-5'-fluoro-2'-methoxy-[1,1'-biphenyl]-4-yl)-3-methyl-1H-imidazol-2(3H)-one to afford the title compound. ¹H NMR (400 MHz, DMSO-d₆): δ 8.92 (d, J=1.6 Hz, 1H), 8.88 (dd, J=1.6 Hz, 1H), 7.85 (d, J=2.0 Hz, 1H), 7.78 (d, J=1.6 Hz, 1H), 7.67 (dd, J=8.4, 2.0 Hz, 1H), 7.53 (d, J=8.0 Hz, 1H), 7.37-7.33 (m, 2H), 7.29-7.26 (m, 1H), 6.72 (d, J=2.8 Hz, 1H), 6.69 (d, J=2.8 Hz, 1H), 3.33-3.30 (m, 4H), 3.21 (s, 3H), 2.99-2.96 (m, 4H). N—H and O—H protons not observed. LCMS: 530.8 (M+H)⁺.

Example 548

(S)-1-(3'-(8-(3-aminopyrrolidin-1-yl)quinoxalin-6-yl)-3-chloro-5'-fluoro-2'-hydroxy-[1,1'-biphenyl]-4-yl)-3-methyl-1H-imidazol-2(3H)-one

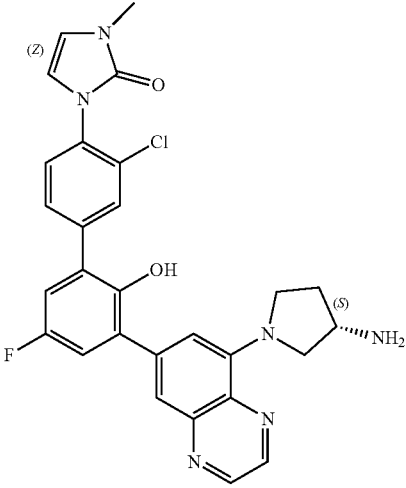

The title compound was prepared following the procedure described for Example 504 using 5-bromo-7-chloroquinoxaline, (S)-tert-butyl pyrrolidin-3-ylcarbamate, 4,4,4',4',5,5,5',5'-octamethyl-2,2'-bi(1,3,2-dioxaborolane) and 1-(3'-bromo-3-chloro-5'-fluoro-2'-methoxy-[1,1'-biphenyl]-4-yl)-3-methyl-1H-imidazol-2(3H)-one to afford the title compound. ¹H NMR (400 MHz, CDCl₃): δ 8.71 (d, J=1.2 Hz, 1H), 8.63 (s, 1H), 7.78 (d, J=1.6 Hz, 1H), 7.60-7.53 (m, 2H), 7.44 (s, 1H), 7.14-7.06 (m, 2H), 6.74 (s, 1H), 6.46 (d, J=3.2 Hz, 1H), 6.34 (d, J=3.2 Hz, 1H), 4.11-4.07 (m, 1H), 3.99-3.93 (m, 1H), 3.85-3.81 (m, 1H), 3.79-3.74 (m, 1H), 3.66-3.62 (m, 1H), 3.35 (s, 1H), 2.28-2.20 (m, 1H), 1.88-1.75 (m, 1H). N—H and O—H protons not observed. LCMS: 530.8 (M+H)⁺.

Example 549

(R)-1-(3-chloro-5'-fluoro-2'-hydroxy-3'-(8-(3-methylpiperazin-1-yl)quinoxalin-6-yl)-[1,1'-biphenyl]-4-yl)-3-methyl-1H-imidazol-2(3H)-one

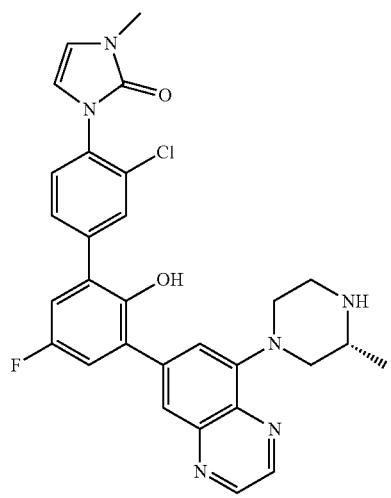 [SMILES: C[C@@H]1CN(c2cc(-c3cc(F)cc(-c4ccc(-n5ccn(C)c5=O)c(Cl)c4)c3O)cc3nccnc23)CCN1]

865

The title compound was prepared following the procedure described for Example 504 using 5-bromo-7-chloroquinoxaline, (R)-tert-butyl 2-methylpiperazine-1-carboxylate, 4,4,4',4',5,5,5',5'-octamethyl-2,2'-bi(1,3,2-dioxaborolane) and 1-(3'-bromo-3-chloro-5'-fluoro-2'-methoxy-[1,1'-biphenyl]-4-yl)-3-methyl-1H-imidazol-2(3H)-one to afford the title compound. ¹H NMR (400 MHz, DMSO-d₆): δ 8.92 (d, J=2.0 Hz, 1H), 8.88 (d, J=2.0 Hz, 1H), 7.85 (d, J=2.0 Hz, 1H), 7.77 (d, J=1.6 Hz, 1H), 7.67 (dd, J=8.4, 2.0 Hz, 1H), 7.53 (d, J=8.4 Hz, 1H), 7.36-7.26 (m, 3H), 6.72 (d, J=2.8 Hz, 1H), 6.69 (d, J=2.8 Hz, 1H), 3.87-3.85 (m, 1H), 3.80-3.77 (m, 1H), 3.32 (s, 3H), 3.05-2.97 (m, 3H), 2.80-2.74 (m, 1H), 2.50-2.43 (m, 1H), 1.03 (d, J=6.0 Hz, 3H). N—H and O—H protons not observed. LCMS: 544.8 (M+H)⁺.

Example 550

1-(3'-(5-(4,7-diazaspiro[2.5]octan-7-yl)pyridin-3-yl)-3-chloro-5'-fluoro-2'-hydroxy-[1,1'-biphenyl]-4-yl)-3-methyl-1H-imidazol-2(3H)-one

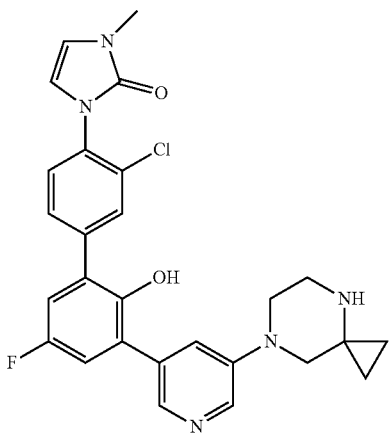 [SMILES: Cn1ccn(-c2ccc(-c3cc(F)cc(-c4cncc(N5CCNC6(CC6)C5)c4)c3O)cc2Cl)c1=O]

The title compound was prepared following the procedures described for Example 508 using 1-(3'-bromo-3-chloro-5'-fluoro-2'-methoxy-[1,1'-biphenyl]-4-yl)-3-methyl-1H-imidazol-2(3H)-one and (5-(4-(tert-butoxycarbonyl)-4,7-diazaspiro[2.5]octan-7-yl)pyridin-3-yl)boronic acid to afford the title compound. ¹H NMR (400 MHz, DMSO-d₆): δ 9.36-9.24 (m, 2H), 8.94 (br s, 1H), 8.41 (s, 1H), 8.37 (s, 1H), 7.83-7.77 (m, 2H), 7.63 (dd, J=2.0, 8.0 Hz, 1H), 7.55 (d, J=8.4 Hz, 1H), 7.31 (d, J=8.4 Hz, 2H), 6.73 (d, J=2.8 Hz, 1H), 6.68 (d, J=2.8 Hz, 1H), 3.63 (br s, 2H), 3.51 (br s, 2H), 3.41 (br s, 2H), 3.21 (s, 3H), 1.09-1.05 (m, 2H), 0.96 (t, J=6.4 Hz, 2H).

LCMS: 506.1 (M+H)⁺.

Example 551

(R)-1-(3-chloro-5'-fluoro-2'-hydroxy-3'-(4-(3-methylpiperazin-1-yl)-1H-indol-6-yl)-[1,1'-biphenyl]-4-yl)-3-methyl-1H-imidazol-2(3H)-one

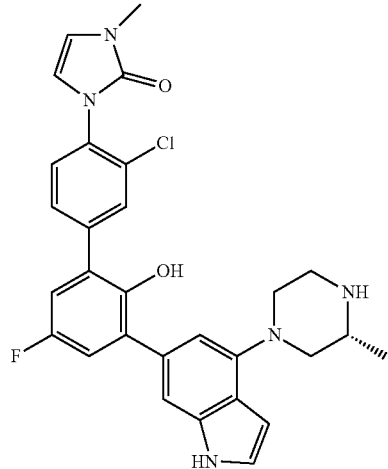 [SMILES: C[C@@H]1CN(c2cc(-c3cc(F)cc(-c4ccc(-n5ccn(C)c5=O)c(Cl)c4)c3O)cc3[nH]ccc23)CCN1]

Step 1: 4-bromo-6-chloro-1-((2-(trimethylsilyl)ethoxy)methyl)-1H-indole

To a solution of 4-bromo-6-chloro-1H-indole (1.00 g, 4.34 mmol) in DMF (20 mL) was added 60% NaH (367 mg, 8.68 mmol) and stirred for 30 min at 0° C. Then, SEM-Cl (1.08 g, 8.51 mmol) was added and stirred for 2 hours at 0° C. under N₂. After the reaction was complete by LCMS, the reaction mixture was quenched with water (50 mL) and extracted with EA (20 mL) three times. The combined organic layers were washed with brine, dried over sodium sulfate, filtered, and concentrated. The residue was purified by silica gel chromatography (PE/EA=10/1) to afford the title compound (750 mg, 48% yield) as brown oil. LCMS: 360.0 (M+H)⁺.

Step 2: (R)-tert-butyl 4-(6-chloro-1-((2-(trimethylsilyl)ethoxy)methyl)-1H-indol-4-yl)-2-methylpiperazine-1-carboxylate The title compound was prepared following the procedure described for Example 504 using (R)-tert-butyl 2-methylpiperazine-1-carboxylate and 4-bromo-6-chloro-1-((2-(trimethylsilyl)ethoxy)methyl)-1H-indole to afford the title compound (66% yield). LCMS: 480.2 (M+H)⁺

Step 3: (R)-tert-butyl 2-methyl-4-(6-(4,4,5,5-tetramethyl-1,3,2-dioxaborolan-2-yl)-1-((2-(trimethylsilyl)ethoxy)methyl)-1H-indol-4-yl)piperazine-1-carboxylate The title compound was prepared following the procedure described for Example 504 using (R)-tert-butyl 4-(6-chloro-1-((2-(trimethylsilyl)ethoxy)methyl)-1H-indol-4-yl)-2-methylpiperazine-1-carboxylate and 4,4,4',4',5,5,5',5'-octamethyl-2,2'-bi(1,3,2-dioxaborolane) to afford the title compound (59% yield). LCMS: 572.4 (M+H)⁺.

Step 4: (R)-tert-butyl 4-(6-(3'-chloro-5-fluoro-2-methoxy-4'-(3-methyl-2-oxo-2,3-dihydro-1H-imidazol-1-yl)-[1,1'-biphenyl]-3-yl)-1-((2-(trimethylsilyl)ethoxy)methyl)-1H-indol-4-yl)-2-methylpiperazine-1-carboxylate The title compound was prepared following the procedure described for Example 504 using 1-(3'-bromo-3-chloro-5'-fluoro-2'-methoxy-[1,1'-biphenyl]-4-yl)-3-methyl-1H-imidazol-2(3H)-one and (R)-tert-butyl 2-methyl-4-(6-(4,4,5,5-tetramethyl-1,3,2-dioxaborolan-2-yl)-1-((2-(trimethylsilyl)ethoxy)methyl)-1H-indol-4-yl)piperazine-1-carboxylate to afford the title compound (69% yield). LCMS: 776.3 (M+H)⁺.

Step 5: (R)-1-(3-chloro-5'-fluoro-2'-methoxy-3'-(4-(3-methylpiperazin-1-yl)-1H-indol-6-yl)-[1,1'-biphenyl]-4-yl)-3-methyl-1H-imidazol-2(3H)-one The title compound was prepared following the procedure described for Example 494 using (R)-tert-butyl 4-(6-(3'-chloro-5-fluoro-2-methoxy-4'-(3-methyl-2-oxo-2,3-dihydro-1H-imidazol-1-yl)-[1,1'-biphenyl]-3-yl)-1-((2-(trimethylsilyl)ethoxy)methyl)-1H-indol-4-yl)-2-methylpiperazine-1-carboxylate, TFA and KOH to afford the title compound (10% yield).

LCMS: 546.2 (M+H)⁺.

Step 6: (R)-1-(3-chloro-5'-fluoro-2'-hydroxy-3'-(4-(3-methylpiperazin-1-yl)-1H-indol-6-yl)-[1,1'-biphenyl]-4-yl)-3-methyl-1H-imidazol-2(3H)-one 2,2,2-trifluoroacetate The title compound was prepared following the procedure described for Example B-605 using (R)-1-(3-chloro-5'-fluoro-2'-methoxy-3'-(4-(3-methylpiperazin-1-yl)-1H-indol-6-yl)-[1,1'-biphenyl]-4-yl)-3-methyl-1H-imidazol-2(3H)-one and piperazine to afford the title compound. ¹H NMR (400 MHz, CD₃OD): δ 10.69 (s, 1H), 7.74 (d, J=2.0 Hz, 1H), 7.54 (dd, J=2.0, 8.4 Hz, 1H), 7.39 (d, J=8.4 Hz, 1H), 7.24 (s, 1H), 7.20 (d, J=2.8 Hz, 1H), 6.99-6.94 (m, 2H), 6.67 (s, 1H), 6.57 (d, J=2.8 Hz, 1H), 6.53 (d, J=2.8 Hz, 1H), 6.44 (d, J=2.0 Hz, 1H), 3.75-3.72 (m, 2H), 3.60-3.56 (m, 1H), 3.46-3.38 (m, 2H), 3.25 (s, 3H), 3.09-2.98 (m, 1H), 2.85-2.80 (m, 1H), 1.33 (d, J=6.4 Hz, 3H). N—H and O—H proton not observed. LCMS: 532.3 (M+H)⁺.

Example 552

1-(3-chloro-5'-fluoro-2'-hydroxy-3'-(2-(piperazin-1-yl)-6-(1H-pyrazol-4-yl)pyridin-4-yl)-[1,1'-biphenyl]-4-yl)-3-methyl-1H-imidazol-2(3H)-one

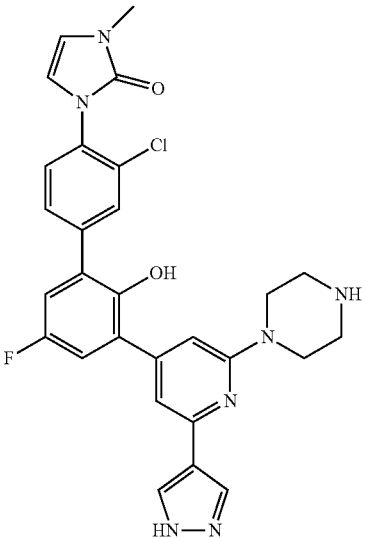 [SMILES: Cn1ccn(-c2ccc(-c3cc(F)cc(-c4cc(-c5cn[nH]c5)nc(N5CCNCC5)c4)c3O)cc2Cl)c1=O]

Step 1: tert-butyl 4-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperazine-1-carboxylate The title compound was prepared following the procedure described for Example 515 using tert-butyl 4-(4-(3-bromo-5-fluoro-2-methoxyphenyl)-6-chloropyridin-2-yl)piperazine-1-carboxylate and 1-(2-chloro-4-(4,4,5,5-tetramethyl-1,3,2-dioxaborolan-2-yl)phenyl)-3-methyl-1H-imidazol-2(3H)-one to afford the title compound (40% yield). LCMS: 628.2 (M+H)⁺.

Step 2: tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)-6-(1-(tetrahydro-2H-pyran-2-yl)-1H-pyrazol-4-yl)pyridin-2-yl)piperazine-1-carboxylate The title compound was prepared following the procedure described for Example 517 using tert-butyl 4-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperazine-1-carboxylate and 1-(tetrahydro-2H-pyran-2-yl)-4-(4,4,5,5-tetramethyl-1,3,2-dioxaborolan-2-yl)-1H-pyrazole to afford the title compound (38% yield). LCMS: 744.3 (M+H)⁺.

Step 5: 1-(3-chloro-5'-fluoro-2'-hydroxy-3'-(2-(piperazin-1-yl)-6-(1H-pyrazol-4-yl)pyridin-4-yl)-[1,1'-biphenyl]-4-yl)-3-methyl-1H-imidazol-2(3H)-one 2,2,2-trifluoroacetate The title compound was prepared following the procedure described for Example 515 using tert-butyl 4-(4-(3'-chloro-5-fluoro-2-methoxy-4'-(3-methyl-2-oxo-2,3-dihydro-1H-

869 imidazol-1-yl)-[1,1'-biphenyl]-3-yl)-6-(1-(tetrahydro-2H-pyran-2-yl)-1H-pyrazol-4-yl)pyridin-2-yl)piperazine-1-carboxylate and BBr₃ to afford the title compound. ¹H NMR (400 MHz, DMSO-d₆+D₂O): δ 8.19 (s, 2H), 7.83 (d, J=2.0 Hz, 1H), 7.64 (dd, J=1.6, 8.0 Hz, 1H), 7.54 (d, J=8.0 Hz, 1H), 7.29-7.23 (m, 3H), 6.86 (s, 1H), 6.72 (d, J=2.8 Hz, 2H), 6.69 (d, J=3.2 Hz, 1H), 3.83 (t, J=4.8 Hz, 4H), 3.27-3.22 (m, 7H). N—H and O—H protons not observed. LCMS: 546.2 (M+H)⁺.

Example 553

1-(3-chloro-5'-fluoro-2'-hydroxy-3'-(2-(piperazin-1-yl)-6-(1H-pyrazol-5-yl)pyridin-4-yl)-[1,1'-biphenyl]-4-yl)-3-methyl-1H-imidazol-2(3H)-one

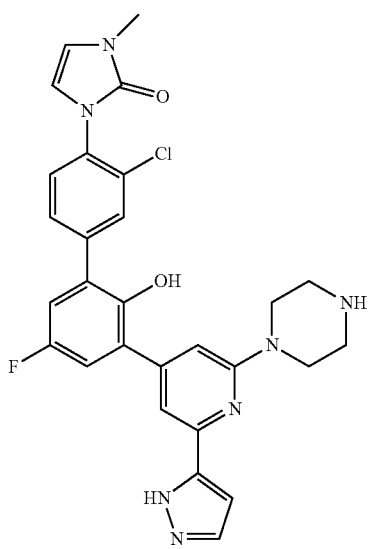 [SMILES: Cn1ccn(-c2ccc(-c3cc(F)cc(-c4cc(-c5ccn[nH]5)nc(N5CCNCC5)c4)c3O)cc2Cl)c1=O]

The title compound was prepared following the procedure described for Example 552 using tert-butyl 4-(6-chloro-4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperazine-1-carboxylate, 1-(tetrahydro-2H-pyran-2-yl)-5-(4,4,5,5-tetramethyl-1,3,2-dioxaborolan-2-yl)-1H-pyrazole and BBr₃ (27% yield). ¹H NMR (400 MHz, DMSO-d₆+D₂O): δ 7.83 (d, J=2.0 Hz, 1H), 7.08 (d, J=1.6 Hz, 1H), 7.64 (dd, J=1.6, 8.0 Hz, 1H), 7.54 (d, J=8.4 Hz, 1H), 7.46 (s, 1H), 7.30-7.25 (m, 2H), 6.98 (s, 1H), 6.86 (d, J=1.6 Hz, 1H), 6.72 (d, J=2.8 Hz, 1H), 6.68 (d, J=2.8 Hz, 1H), 3.84 (t, J=5.2 Hz, 4H), 3.24-3.22 (m, 7H). N—H and O—H protons not observed. LCMS: 546.2 (M+H)⁺.

870

Example 554

1-(3'-(2-(3,6-diazabicyclo[3.2.1]octan-3-yl)pyridin-4-yl)-3-chloro-5'-fluoro-2'-hydroxy-[1,1'-biphenyl]-4-yl)-3-methyl-1H-imidazol-2(3H)-one

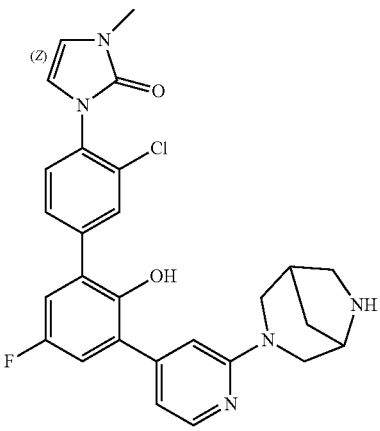 [SMILES: Cn1ccn(-c2ccc(-c3cc(F)cc(-c4ccnc(N5CC6CNC(C6)C5)c4)c3O)cc2Cl)c1=O]

The title compound was prepared following the procedure described for Example 414 using 1-(3-chloro-5'-fluoro-3'-(2-fluoropyridin-4-yl)-2'-methoxy-[1,1'-biphenyl]-4-yl)-3-methyl-1H-imidazol-2(3H)-one, tert-butyl 3,6-diazabicyclo[3.2.1]octane-6-carboxylate and BBr₃ to afford the title compound. ¹H NMR (400 MHz, DMSO-d₆): δ 8.13 (d, J=5.2 Hz, 1H), 7.82 (d, J=2.0 Hz, 1H), 7.62 (dd, J=2.0, 8.0 Hz, 1H), 7.51 (d, J=8.4 Hz, 1H), 7.24-7.15 (m, 2H), 6.82-6.80 (m, 2H), 6.70 (d, J=3.2 Hz, 1H), 6.68 (d, J=2.8 Hz, 1H), 4.13-4.01 (m, 1H), 3.89-3.85 (m, 1H), 3.58-3.52 (m, 1H), 3.21 (s, 3H), 3.16-2.81 (m, 5H), 1.71 (s, 2H). N—H and O—H protons not observed. LCMS: 506.1 (M+H)⁺.

Example 555

1-(3-chloro-3'-(2-((3R,5S)-3,5-dimethylpiperazin-1-yl)pyridin-4-yl)-5'-fluoro-2'-hydroxy-[1,1'-biphenyl]-4-yl)-3-methyl-1H-imidazol-2(3H)-one

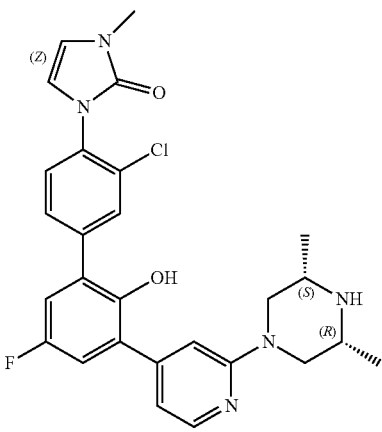

The title compound was prepared following the procedure described for Example 515 using (3R,5S)-1-(4-(3-bromo-5-fluoro-2-methoxyphenyl)pyridin-2-yl)-3,5-dimethylpipera-

Example 556

(S)-1-(3-chloro-5'-fluoro-2'-hydroxy-3'-(2-(3-(hydroxymethyl)piperazin-1-yl)pyridin-4-yl)-[1,1'-biphenyl]-4-yl)-3-methyl-1H-imidazol-2(3H)-one zine and 1-(2-chloro-4-(4,4,5,5-tetramethyl-1,3,2-dioxaborolan-2-yl)phenyl)-3-methyl-1H-imidazol-2(3H)-one and BBr₃ to afford the title compound. ¹H NMR (400 MHz, DMSO-d₆): δ 8.13 (d, J=5.2 Hz, 1H), 7.80 (d, J=2.0 Hz, 1H), 7.62 (dd, J=2.0, 8.4 Hz, 1H), 7.52 (d, J=8.0 Hz, 1H), 7.24 (dd, J=3.2, 9.2 Hz, 1H), 7.19 (dd, J=3.2, 9.2 Hz, 1H), 6.92 (s, 1H), 6.79 (dd, J=1.2, 5.2 Hz, 1H), 6.72 (d, J=3.2 Hz, 1H), 6.68 (d, J=2.8 Hz, 1H), 4.21-4.18 (m, 2H), 3.21 (s, 3H), 2.77-2.73 (m, 2H), 2.25 (t, J=11.2 Hz, 2H), 1.03 (d, J=6.0 Hz, 6H). N—H and O—H protons not observed. LCMS: 508.2 (M+H)⁺.

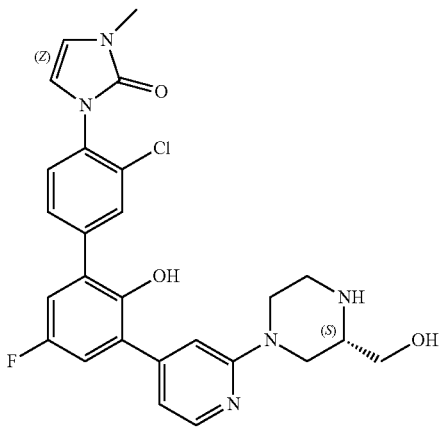

The title compound was prepared following the procedures described for Example 414 using (S)-tert-butyl 2-(hydroxymethyl)piperazine-1-carboxylate and 1-(3-chloro-5'-fluoro-3'-(2-fluoropyridin-4-yl)-2'-methoxy-[1,1'-biphenyl]-4-yl)-3-methyl-1H-imidazol-2(3H)-one and BBr₃ to afford the title compound. ¹H NMR (400 MHz, DMSO-d₆): δ 8.15 (d, J=5.2 Hz, 1H), 7.81 (d, J=2.0 Hz, 1H), 7.62 (dd, J=2.0, 8.4 Hz, 1H), 7.52 (d, J=8.0 Hz, 1H), 7.24 (dd, J=3.2, 9.2 Hz, 1H), 7.19 (dd, J=3.2, 9.2 Hz, 1H), 6.92 (s, 1H), 6.81 (dd, J=0.8, 5.2 Hz, 1H), 6.72 (d, J=3.2 Hz, 1H), 6.68 (d, J=2.8 Hz, 1H), 4.66 (s, 1H), 4.24 (d, J=10.8 Hz, 1H), 4.12 (d, J=11.2 Hz, 1H), 3.38-3.36 (m, 2H), 3.21 (s, 3H), 2.99-2.97 (m, 1H), 2.79-2.65 (m, 3H), 2.45-2.40 (m, 1H). N—H and O—H protons not observed. LCMS: 510.2 (M+H)⁺.

Example 557

1-(3-chloro-2'-hydroxy-5'-methyl-3'-(4-(piperazin-1-yl)-1H-indol-6-yl)-[1,1'-biphenyl]-4-yl)-3-methyl-1H-imidazol-2(3H)-one

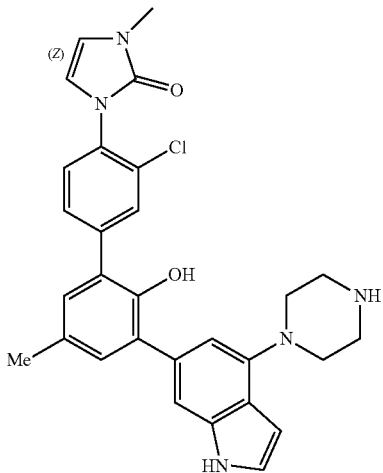 [SMILES: Cc1cc(-c2ccc(-n3ccn(C)c3=O)c(Cl)c2)c(O)c(-c2cc(N3CCNCC3)c3cc[nH]c3c2)c1]

The title compound was prepared following the procedure described for Example 504 using tert-butyl 4-(6-(4,4,5,5-tetramethyl-1,3,2-dioxaborolan-2-yl)-1H-indol-4-yl)piperazine-1-carboxylate and 1-(3'-bromo-3-chloro-2'-methoxy-5'-methyl-[1,1'-biphenyl]-4-yl)-3-methyl-1H-imidazol-2(3H)-one and BBr₃ to afford the title compound. ¹H NMR (400 MHz, DMSO-d₆): δ 11.19 (s, 1H), 8.81 (s, 2H), 8.16 (s, 1H), 7.77 (d, J=2.0 Hz, 1H), 7.60 (dd, J=2.0, 8.0 Hz, 1H), 7.50 (d, J=8.0 Hz, 1H), 7.34 (t, J=2.4 Hz, 1H), 7.25 (s, 1H), 7.10 (d, J=5.6 Hz, 2H), 6.72 (d, J=3.2 Hz, 1H), 6.69 (d, J=3.2 Hz, 1H), 6.64 (s, 1H), 6.51 (s, 1H), 3.36 (s, 8H), 3.21 (s, 3H), 2.32 (s, 3H). LCMS: 514.2 (M+H)⁺.

Example 558

(S)-1-(3'-(4-(3-aminopyrrolidin-1-yl)-1H-indazol-6-yl)-3-chloro-5'-fluoro-2'-hydroxy-[1,1'-biphenyl]-4-yl)-3-methyl-1H-imidazol-2(3H)-one

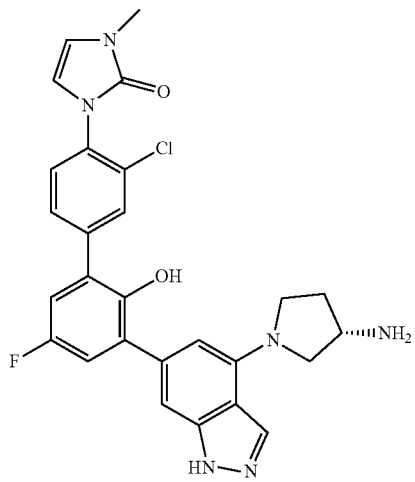 [SMILES: Cn1ccn(-c2ccc(-c3cc(F)cc(-c4cc(N5CC[C@H](N)C5)c5cn[nH]c5c4)c3O)cc2Cl)c1=O]

The title compound was prepared following the procedure described for Example 504 using (S)-tert-butyl (1-(1-(4-methoxybenzyl)-6-(4,4,5,5-tetramethyl-1,3,2-dioxaborolan-2-yl)-1H-indazol-4-yl)pyrrolidin-3-yl)carbamate and 1-(3'-bromo-3-chloro-5'-fluoro-2'-methoxy-[1,1'-biphenyl]-4-yl)-3-methyl-1H-imidazol-2(3H)-one, TFA and BBr$_3$ to afford the title compound. $^1$H NMR (400 MHz, DMSO-d$_6$): δ 12.95 (br s, 1H), 8.41 (s, 1H), 8.22-8.07 (m, 4H), 7.83 (d, J=1.6 Hz, 1H), 7.64 (dd, J=1.6, 8.0 Hz, 1H), 7.53 (d, J=8.4 Hz, 1H), 7.21-7.13 (m, 2H), 6.95 (s, 1H), 6.72 (d, J=2.8 Hz, 1H), 6.69 (d, J=2.8 Hz, 1H), 6.15 (s, 1H), 4.02-3.98 (m, 1H), 3.90-3.83 (m, 2H), 3.72-3.62 (m, 2H), 3.21 (s, 3H), 2.41-2.36 (m, 1H), 2.14-2.13 (m, 1H). LCMS: 519.3 (M+H)$^+$.

Example 559

1-(3'-(2-(4,7-diazaspiro[2.5]octan-7-yl)pyridin-4-yl)-3-chloro-5'-fluoro-2'-hydroxy-[1,1'-biphenyl]-4-yl)-3-methyl-1H-imidazol-2(3H)-one

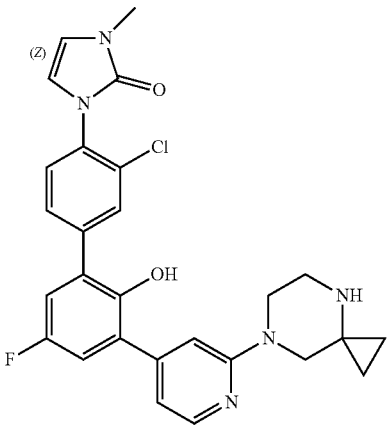 [SMILES: Cn1ccn(-c2ccc(-c3cc(F)cc(-c4ccnc(N5CCNC6(CC6)C5)c4)c3O)cc2Cl)c1=O]

The title compound was prepared following the procedure described for Example 414 using 1-(3-chloro-5'-fluoro-3'-(2-fluoropyridin-4-yl)-2'-methoxy-[1,1'-biphenyl]-4-yl)-3-methyl-1H-imidazol-2(3H)-one, tert-butyl 4,7-diazaspiro[2.5]octane-4-carboxylate and BBr$_3$ (17% yield). $^1$H NMR (400 MHz, DMSO-d$_6$): δ 8.67 (br s, 1H), 8.12 (d, J=5.2 Hz, 1H), 7.80 (d, J=2.0 Hz, 1H), 7.61 (dd, J=2.0, 8.4 Hz, 1H), 7.52 (d, J=8.4 Hz, 1H), 7.25-7.17 (m, 2H), 6.88 (s, 1H), 6.79 (dd, J=1.2, 5.2 Hz, 1H), 6.72 (d, J=2.8 Hz, 1H), 6.68 (d, J=3.2 Hz, 1H), 3.50-3.48 (m, 2H), 3.37 (s, 2H), 3.21 (s, 3H), 2.86-2.84 (m, 2H), 0.52-0.45 (m, 4H). N—H or OH proton not observed. LCMS: 506.2 (M+H)$^+$.

Example 560

(S)-7-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)tetrahydro-1H-oxazolo[3,4-a]pyrazin-3(5H)-one

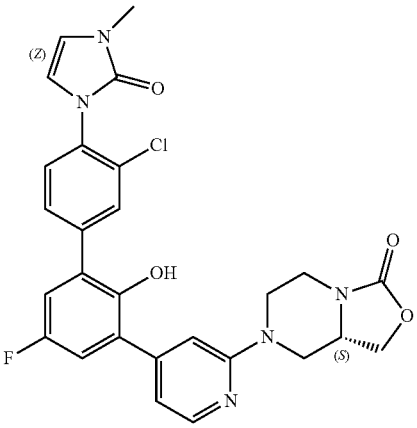

The title compound was prepared following the procedure described for Example 556 using 1-(3-chloro-5'-fluoro-3'-(2-fluoropyridin-4-yl)-2'-methoxy-[1,1'-biphenyl]-4-yl)-3-methyl-1H-imidazol-2(3H)-one, (S)-tert-butyl 2-(hydroxymethyl)piperazine-1-carboxylate and BBr$_3$. $^1$H NMR (400 MHz, DMSO-d$_6$): δ 8.69-8.56 (m, 1H), 8.18 (d, J=5.2 Hz, 1H), 7.81 (d, J=2.0 Hz, 1H), 7.62 (dd, J=2.0, 8.4 Hz, 1H), 7.53 (d, J=8.4 Hz, 1H), 7.27-7.21 (m, 2H), 7.04 (s, 1H), 6.89 (dd, J=1.2, 5.2 Hz, 1H), 6.72 (d, J=3.2 Hz, 1H), 6.68 (d, J=2.8 Hz, 1H), 4.57 (dd, J=2.4, 12.8 Hz, 1H), 4.44-4.30 (m, 2H), 4.01 (dd, J=5.6, 9.2 Hz, 1H), 3.91-3.84 (m, 1H), 3.64 (dd, J=2.4, 13.2 Hz, 1H), 3.21 (s, 3H), 3.10-3.03 (m, 1H), 2.89-2.75 (m, 2H). LCMS: 536.2 (M+H)$^+$.

Example 561

1-(3-chloro-3'-(5-(3,3-dimethylpiperazin-1-yl)pyridin-3-yl)-5'-fluoro-2'-hydroxy-[1,1'-biphenyl]-4-yl)-3-methyl-1H-imidazol-2(3H)-one

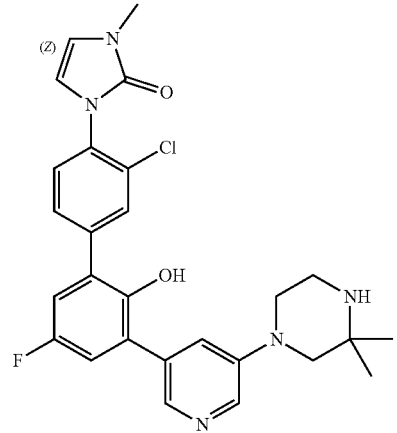 [SMILES: Cn1ccn(-c2ccc(-c3cc(F)cc(-c4cncc(N5CCNC(C)(C)C5)c4)c3O)cc2Cl)c1=O]

The title compound was prepared following the procedures described for Example 550 using 1-(3'-bromo-3-chloro-5'-fluoro-2'-methoxy-[1,1'-biphenyl]-4-yl)-3-methyl-1H-imidazol-2(3H)-one and (5-(4-(tert-butoxycarbonyl)-3,3-dimethylpiperazin-1-yl)pyridin-3-yl)boronic acid BBr$_3$ to afford the title compound. $^1$H NMR (400 MHz, DMSO-d): δ 8.27 (d, J=2.8 Hz, 1H), 8.14 (d, J=1.6 Hz, 1H), 7.81 (d, J=2.0 Hz, 1H), 7.83 (dd, J=2.0, 8.4 Hz, 1H), 7.53 (d, J=8.4 Hz, 1H), 7.41 (t, J=2.4 Hz, 1H), 7.25-7.19 (m, 2H), 6.72 (d, J=3.2 Hz, 1H), 6.68 (d, J=2.8 Hz, 1H), 3.21 (s, 3H), 3.16 (t, J=5.2 Hz, 2H), 3.01 (s, 2H), 2.96-2.94 (m, 2H), 1.16 (s, 6H). N—H and O—H protons not observed. LCMS: 508.3 (M+H)$^+$.

Example 562

1-(3-chloro-2'-hydroxy-5'-methyl-3'-(8-(piperazin-1-yl)quinoxalin-6-yl)-[1,1'-biphenyl]-4-yl)-3-methyl-1H-imidazol-2(3H)-one

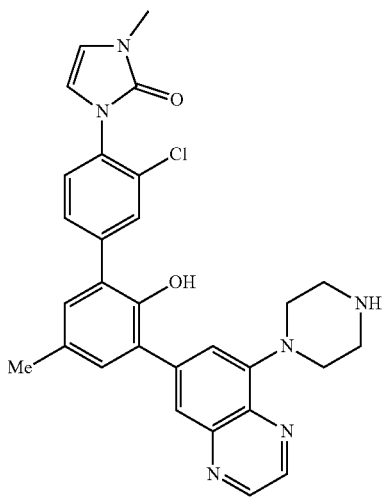 [SMILES: Cc1cc(-c2ccc(-n3ccn(C)c3=O)c(Cl)c2)c(O)c(-c2cc(N3CCNCC3)c3nccnc3c2)c1]

The title compound was prepared following the procedures described for Example 547 using tert-butyl 4-(7-(4,4,5,5-tetramethyl-1,3,2-dioxaborolan-2-yl)quinoxalin-5-yl)piperazine-1-carboxylate and 1-(3'-bromo-3-chloro-2'-methoxy-5'-methyl-[1,1'-biphenyl]-4-yl)-3-methyl-1H-imidazol-2(3H)-one and BBr$_3$ to afford the title compound. $^1$H NMR (400 MHz, DMSO-d$_6$+D$_2$O): δ 8.90 (d, J=2.0 Hz, 1H), 8.86 (d, J=2.0 Hz, 1H), 7.79 (d, J=2.0 Hz, 1H), 7.73 (d, J=1.6 Hz, 1H), 7.62 (dd, J=2.0, 8.0 Hz, 1H), 7.51 (d, J=8.0 Hz, 1H), 7.31 (d, J=1.6 Hz, 1H), 7.27 (d, J=2.0 Hz, 1H), 7.19 (d, J=2.0 Hz, 1H), 6.72 (d, J=3.2 Hz, 1H), 6.69 (d, J=3.2 Hz, 1H), 3.33-3.32 (m, 4H), 3.22 (s, 3H), 2.97-2.94 (m, 4H), 2.35 (s, 3H). N—H and O—H protons not observed. LCMS: 527.3 (M+H)$^+$.

Example 563

1-(3-chloro-3'-(2-(3,3-dimethylpiperazin-1-yl)pyridin-4-yl)-5'-fluoro-2'-hydroxy-[1,1'-biphenyl]-4-yl)-3-methyl-1H-imidazol-2(3H)-one

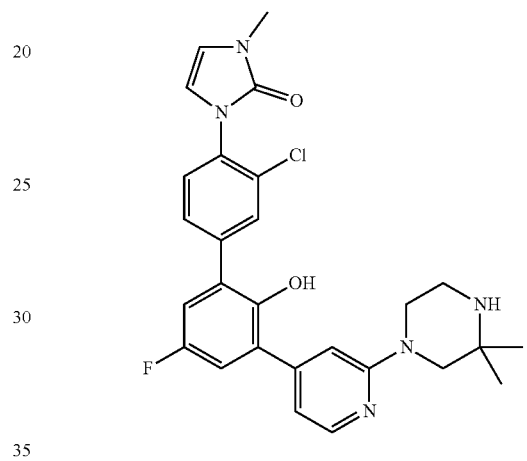

The title compound was prepared following the procedure described for Example 414 using 1-(3-chloro-5'-fluoro-3'-(2-fluoropyridin-4-yl)-2'-methoxy-[1,1'-biphenyl]-4-yl)-3-methyl-1H-imidazol-2(3H)-one, tert-butyl 2,2-dimethylpiperazine-1-carboxylate and BBr$_3$. $^1$H NMR (400 MHz, DMSO-d$_6$): δ 8.03 (d, J=5.2 Hz, 1H), 7.71 (d, J=2.0 Hz, 1H), 7.51 (dd, J=2.0, 8.0 Hz, 1H), 7.40 (d, J=8.0 Hz, 1H), 7.00 (d, J=8.4 Hz, 2H), 6.90 (s, 1H), 6.75 (dd, J=1.2, 5.2 Hz, 1H), 6.57 (d, J=3.2 Hz, 1H), 6.63 (d, J=2.8 Hz, 1H), 3.45-3.43 (m, 2H), 3.28 (s, 2H), 3.24 (s, 3H), 2.91-2.87 (m, 2H), 1.11 (s, 6H). N—H and O—H protons not observed. LCMS: 508.3 (M+H)$^+$.

TABLE 29

Following compounds were prepared using similar procedures as described for Examples 365-563.

| Ex. No. | Name/Structure | $^1$H NMR Data | LCMS (M + H)$^+$ |
| --- | --- | --- | --- |
| 564 | (S)-1-(3'-(4-(3-aminopyrrolidin-1-yl)-1H-benzo[d]imidazol-6-yl)-3-chloro-2'-hydroxy-5'-methyl-[1,1'-biphenyl]-4-yl)-3-methyl-1H-imidazol-2(3H)-one | $^1$H NMR (400 MHz, DMSO-d$_6$): δ 8.00 (s, 1H), 7.76 (d, J = 1.6 Hz, 1H), 7.59 (dd, J = 2.0, 8.4 Hz, | 515.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| 565 | 1-(3-chloro-2'-hydroxy-5'-methyl-3'-(4-(piperazin-1-yl)-1H-benzo[d][1,2,3]triazol-6-yl)-[1,1'-biphenyl]-4-yl)-3-methyl-1H-imidazol-2(3H)-one | 1H), 7.49 (d, J = 8.0 Hz, 1H), 7.09 (dd, J = 1.6 Hz, 2H), 6.90 (s, 1H), 6.71 (d, J = 2.8 Hz, 1H), 6.68 (d, J = 2.8 Hz, 1H), 6.26 (s, 1H), 3.98-3.94 (m, 1H), 3.81-3.77 (m, 1H), 3.71-3.63 (m, 3H), 3.21 (s, 3H), 2.31 (s,3H), 2.19-2.13 (m, 1H), 1.83-1.79 (m, 1H). N—H and O—H protons not observed. | |
| | | $^1$H NMR (400 MHz, DMSO-d$_6$): δ 8.27 (br s, 1H), 7.77 (d, J = 1.6 Hz, 1H), 7.60 (dd, J = 2.0, 8.4 Hz, 1H), 7.50 (d, J = 8.0 Hz, 1H), 7.26 (s, 1H), 7.15 (d, J = 5.6 Hz, 2H), 6.71-6.67 (m, 3H), 3.62 (br s, 4H), 3.21 (s, 3H), 3.03 (br s, 4H), 2.32 (s, 3H). N—H and O—H protons not observed | 516.1 |
| 566 | 1-(3-chloro-2'-hydroxy-5'-methyl-3'-(2-(piperazin-1-yl)-6-(1H-pyrazol-4-yl)pyridin-4-yl)-[1,1'-biphenyl]-4-yl)-3-methyl-1H-imidazol-2(3H)-one | $^1$H NMR (400 MHz, DMSO-d$_6$): δ 12.92 (br s, 1H), 8.26-7.99 (m, 2H), 7.76 (d, J = 1.6 Hz, 1H), | 543.2 |

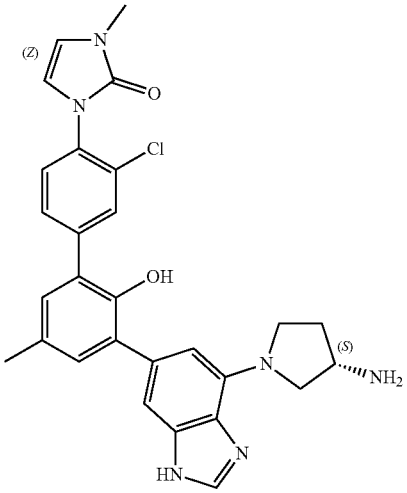

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | 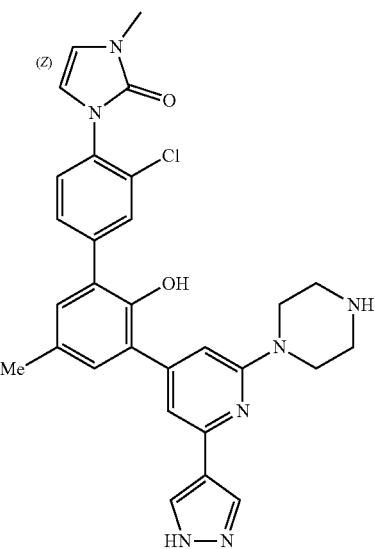 | 7.59 (dd, J = 1.6, 8.0 Hz, 1H), 7.50 (d, J = 8.0 Hz, 1H), 7.16 (dd, J = 1.6, 8.4 Hz, 2H), 7.07 (s, 1H), 6.71-6.66 (m, 3H), 3.49 (t, J = 4.8 Hz, 4H), 3.21 (s, 3H), 2.82 (t, J = 4.8 Hz, 4H), 2.32 (s, 3H). N—H and O—H protons not observed | |
| 567 | (R)-1-(3-chloro-2'-hydroxy-5'-methyl-3'-(4-(3-methylpiperazin-1-yl)-1H-indol-6-yl)-[1,1'-biphenyl]-4-yl)-3-methyl-1H-imidazol-2(3H)-one | ¹H NMR (400 MHz, CD₃OD): δ 7.71 (d, J = 1.2 Hz, 1H), 7.52 (d, J = 8.4 Hz, 1H), 7.36 (d, J = 8.4 Hz, 1H), 7.22-7.17 (m, 2H), 7.03 (s, 1H), 6.99 (s, 1H), 6.64 (s, 1H), 6.57 (d, J = 3.2 Hz, 1H), 6.52 (d, J = 2.8 Hz, 1H), 6.43 (d, J = 2.8 Hz, 1H), 3.75-3.71 (m, 2H), 3.60-3.54 (m, 1H), 3.46-3.34 (m, 2H), 3.21 (s, 3H), 3.07-2.96 (m, 1H), 2.85-2.79 (m, 1H), 2.25 (s, 3H), 1.33 (d, J = 6.4 Hz, 3H). N—H and O—H protons not observed | 528.3 |
| 568 | 1-(3-chloro-5'-fluoro-2'-hydroxy-3''-(piperazin-1-yl)-5''-(1H-pyrazol-5-yl)-[1,1':3',1''-terphenyl]-4-yl)-3-methyl-1H-imidazol-2(3H)-one | ¹H NMR (400 MHz, DMSO-d₆): δ 7.83 (d, J = 2.0 Hz, 1H), 7.77-7.67 (m, 1H), 7.64 (dd, J = 2.0, 8.0 | 543.2 |

| Ex. No. | Name/Structure | ¹H NMR Data | LCMS (M + H)⁺ |
|---|---|---|---|
| | 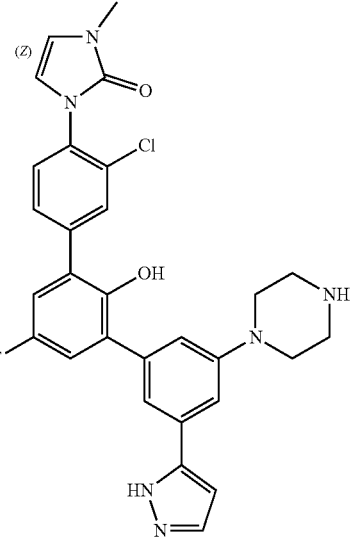 | Hz, 1H), 7.63 (d, J = 8.0 Hz, 1H), 7.38 (br s, 2H), 7.21-7.16 (m, 2H), 7.03 (s, 1H), 6.76 (d, J = 2.4 Hz, 1H), 6.72 (d, J = 3.2 Hz, 1H), 6.69 (d, J = 2.8 Hz, 1H), 3.23 (s, 3H), 3.19 (t, J = 4.8 Hz, 4H), 2.88 (t, J = 4.8 Hz, 4H). N—H and O—H protons not observed | |
| 569 | 1-(3-chloro-2'-hydroxy-5'-methyl-3''-(piperazin-1-yl)-5''-(1H-pyrazol-5-yl)-[1,1':3',1''-terphenyl]-4-yl)-3-methyl-1H-imidazol-2(3H)-one | ¹H NMR (400 MHz, DMSO-d₆): δ 7.77 (d, J = 2.0 Hz, 1H), 7.68 (br s, 1H), 7.61 (dd, J = 2.0, 8.0 Hz, 1H), 7.50 (d, J = 8.0 Hz, 1H), 7.34 (br s, 2H), 7.13 (s, 2H), 6.99 (s, 1H), 6.74 (d, J = 2.4 Hz, 1H), 6.71 (d, J = 2.8 Hz, 1H), 6.68 (d, J = 3.2 Hz, 1H), 3.23 (s, 3H), 3.17 (t, J = 4.4 Hz, 4H), 2.87 (t, J = 4.8 Hz, 4H), 2.32 (s, 3H). N—H and O—H protons not observed | 539.2 |
| 570 | 1-(3-chloro-2'-hydroxy-5'-methyl-3''-(piperazin-1-yl)-5''-(1H-pyrazol-4-yl)-[1,1':3',1''-terphenyl]-4-yl)-3-methyl-1H-imidazol-2(3H)-one | ¹H NMR (400 MHz, CD₃OD): δ 7.88 (s, 2H), 7.68 (d, J = 1.6 Hz, 1H), 7.50 (dd, J = 1.6, 8.0 Hz, | 541.7 |

| Ex. No. | Name/Structure | $^1$H NMR Data | LCMS (M + H)$^+$ |
|---|---|---|---|
| | 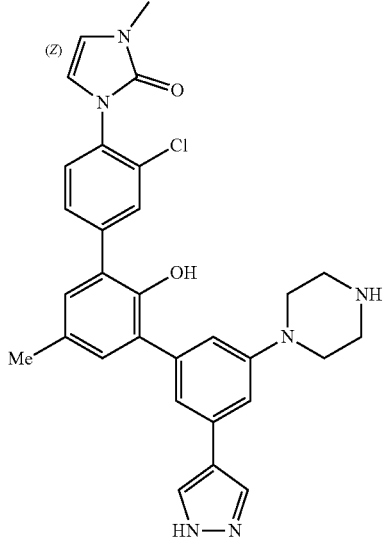 | 1H), 7.35 (d, J = 8.0 Hz, 1H), 7.14 (s, 1H), 7.10 (s, 1H), 7.00 (d, J = 8.0 Hz, 2H), 6.89 (s, 1H), 6.55 (d, J = 2.8 Hz, 1H), 6.51 (d, J = 2.8 Hz, 1H), 3.23 (s, 3H), 3.21 (br s, 4H), 3.00 (t, J = 4.8 Hz, 4H), 2.24 (s, 3H). N—H and O—H protons not observed | |
| 571 | 1-(3-chloro-5'-fluoro-2'-hydroxy-3''-(piperazin-1-yl)-5''-(1H-pyrazol-4-yl)-[1,1':3',1''-terphenyl]-4-yl)-3-methyl-1H-imidazol-2(3H)-one<br>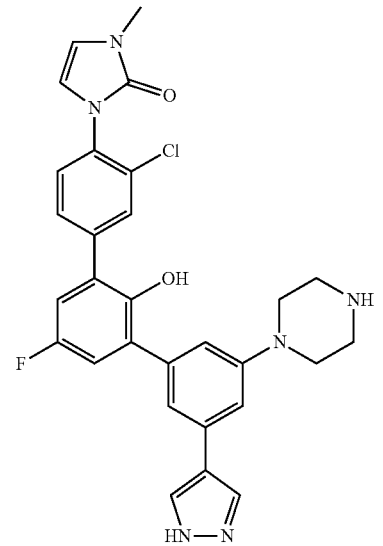 [SMILES: Cn1ccn(-c2ccc(-c3cc(F)cc(-c4cc(-c5cn[nH]c5)cc(N5CCNCC5)c4)c3O)cc2Cl)c1=O] | $^1$H NMR (400 MHz, DMSO-d$_6$): δ 8.78 (s, 2H), 8.50 (s, 1H), 8.11 (s, 2H), 7.83 (d, J = 1.6 Hz, 1H), 7.63 (dd, J = 2.0, 8.4 Hz, 1H), 7.53 (d, J = 8.4 Hz, 1H), 7.29 (s, 1H), 7.24-7.16 (m, 3H), 6.98 (s, 1H), 6.72 (d, J = 3.2 Hz, 1H), 6.69 (d, J = 2.8 Hz, 1H), 3.46 (t, J = 4.8 Hz, 4H), 3.27 (br s, 4H), 3.21 (s, 3H). | 545.2 |
| 572 | 1-(3'-(5-(3,6-diazabicyclo[3.2.1]octan-3-yl)pyridin-3-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 8.13 (d, J = 2.8 Hz, 1H), 8.09 (s, 1H), 7.83 (d, J = 2.0 Hz, 1H), | 506.2 |

TABLE 29-continued

Following compounds were prepared using similar procedures as described for Examples 365-563.

| Ex. No. | Name/Structure | $^1$H NMR Data | LCMS $(M + H)^+$ |
|---|---|---|---|
| | | 7.63 (dd, J = 2.4, 8.4 Hz, 1H), 7.52 (d, J = 8.4 Hz, 1H), 7.30 (s, 1H), 7.23-7.15 (m, 2H), 6.72 (d, J = 3.2 Hz, 1H), 6.68 (d, J = 2.8 Hz, 1H), 3.66-3.52 (m, 4H), 3.21 (s, 3H), 2.95-2.80 (m, 4H), 1.69 (s, 2H). N—H and O—H protons not observed | |
| 573 | 1-(3'-(4-(3,8-diazabicyclo[3.2.1]octan-3-yl)-1H-indazol-6-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$ + D$_2$O): δ 8.13 (s, 1H), 7.82 (d, J = 2.0 Hz, 1H), 7.64 (dd, J = 2.0, 8.4 Hz, 1H), 7.52 (d, J = 8.0 Hz, 1H), 7.20-7.13 (m, 3H), 6.72 (d, J = 2.8 Hz, 1H), 6.69 (d, J = 3.2 Hz, 1H), 6.43 (s, 1H), 3.59-3.54 (m, 4H), 3.22 (s, 3H), 3.03-3.00 (m, 2H), 1.88-1.86 (m, 2H), 1.76-1.75 (m, 2H). N—H and O—H protons not observed | 545.2 |
| 574 | (R)-1-(3-chloro-2'-hydroxy-5'-methyl-3'-(8-(3-methylpiperazin-1-yl)quinoxalin-6-yl)-[1,1'-biphenyl]-4-yl)-3-methyl-1H-imidazol-2(3H)-one | $^1$H NMR (400 MHz, DMSO-d$_6$): δ 8.90 (d, J = 1.6 Hz, 1H), 8.86 (d, J = 2.0 Hz, 1H), 7.79 (d, J = | 541.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | | 1.6 Hz, 1H), 7.72 (d, J = 1.2 Hz, 1H), 7.62 (dd, J = 1.6, 8.0 Hz, 1H), 7.51 (d, J = 8.0 Hz, 1H), 7.30 (d, J = 1.2 Hz, 1H), 7.26 (d, J = 2.0 Hz, 1H), 7.19 (d, J = 1.6 Hz, 1H), 6.71 (d, J = 2.8 Hz, 1H), 6.68 (d, J = 2.8 Hz, 1H), 3.84 (d, J = 11.2 Hz, 1H), 3.78 (d, J = 10.8 Hz, 1H), 3.21 (s, 3H), 3.05-2.97 (m, 3H), 2.80-2.73 (m, 1H), 2.44 (t, J = 10.4 Hz, 1H), 2.35 (s, 3H), 1.03 (d, J = 6.0 Hz, 3H). N—H and O—H protons not observed | |
| 575 | (S)-1-(3'-(8-(3-aminopyrrolidin-1-yl)quinoxalin-6-yl)-3-chloro-2'-hydroxy-5'-methyl-[1,1'-biphenyl]-4-yl)-3-methyl-1H-imidazol-2(3H)-one | ¹H NMR (400 MHz, DMSO-d₆): δ 8.79 (d, J = 1.6 Hz, 1H), 8.69 (d, J = 1.6 Hz, 1H), 7.79 (d, J = 1.6 Hz, 1H), 7.62 (dd, J = 2.0, 8.4 Hz, 1H), 7.50 (d, J = 8.4 Hz, 1H), 7.37 (d, J = 1.2 Hz, 1H), 7.23 (d, J = 1.6 Hz, 1H), 7.17 (d, J = 1.6 Hz, 1H), 6.86 (d, J = 2.8 Hz, 1H), 6.71 (d, J = 2.8 Hz, 1H), 6.69 (d, J = 3.2 Hz, 1H), 3.99-3.95 (m, 1H), 3.86-3.87 (m, 2H), 3.59-3.48 (m, 2H), 3.21 (s, 3H), 2.34 (s, 3H), 2.10-2.05 (m, 1H), 1.75-1.71 (m, 1H). N—H and O—H protons not observed | 527.2 |
| 576 | (R)-1-(3-chloro-5'-fluoro-2'-hydroxy-3'-(1-methyl-4-(3-methylpiperazin-1-yl)-1H-benzo[d]imidazol-6-yl)-[1,1'-biphenyl]-4-yl)-3-methyl-1H-imidazol-2(3H)-one | ¹H NMR (400 MHz, DMSO-d₆): δ 8.07 (s, 1H), 7.82 (d, J = 2.0 Hz, 1H), 7.64 (dd, J = 2.0, 8.0 Hz, | 547.3 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|

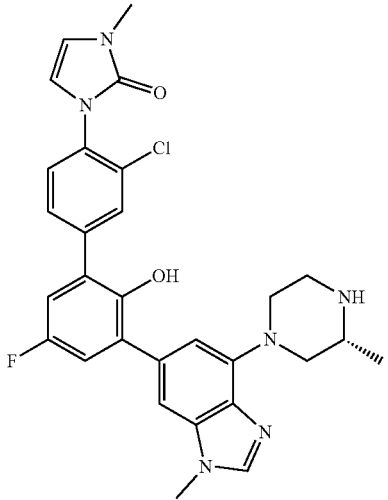 [SMILES: C[C@@H]1CN(c2cc(-c3cc(F)cc(-c4ccc(-n5ccn(C)c5=O)c(Cl)c4)c3O)cc3c2ncn3C)CCN1]

| | | 1H), 7.52 (d, J = 8.4 Hz, 1H), 7.21-7.17 (m, 3H), 6.72-6.66 (m, 3H), 4.23 (t, J = 13.2 Hz, 2H), 3.81 (s, 3H), 3.21 (s, 3H), 2.95-2.89 (m, 3H), 2.70-2.65 (m, 1H), 2.36-2.31 (m, 1H), 1.03 (d, J = 7.2 Hz, 3H). N—H and O—H protons not observed | |
| 577 | 1-(3-chloro-3'-(4-((3R,5S)-3,5-dimethylpiperazin-1-yl)-1H-indazol-6-yl)-5'-fluoro-2'-hydroxy-[1,1'-biphenyl]-4-yl)-3-methyl-1H-imidazol-2(3H)-one | $^1$H NMR (400 MHz, DMSO-d$_6$): δ 13.30 (br s, 1H), 9.17-9.15 (m, 1H), 8.56-8.46 (m, 2H), 8.30 (s, 1H), 7.84 (d, J = 2.0 Hz, 1H), 7.64 (dd, J = 2.0, 8.4 Hz, 1H), 7.53 (d, J = 8.4 Hz, 1H), 7.31 (s, 1H), 7.23 (d, J = 9.2 Hz, 2H), 6.73-6.65 (m, 3H), 3.91 (d, J = 12.4 Hz, 2H), 3.61 (br s, 2H), 3.22 (s, 3H), 3.80 (t, J = 12.8 Hz, 2H), 1.31 (d, J = 6.4 Hz, 6H) | 547.3 |
| 578 | (S)-1-(3'-(4-(3-aminopiperidin-1-yl)-1H-indazol-6-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 13.06-12.96 (m, 1H), 8.11 (s, 1H), 7.82 (d, J = 1.6 Hz, 1H), 7.84 | 533.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| | | (dd, J = 1.6, 8.4 Hz, 1H), 7.52 (d, J = 8.0 Hz, 1H), 7.20-7.18 (m, 3H), 6.71(d, J = 2.8 Hz, 1H), 6.69 (d, J = 2.8 Hz, 1H), 6.54 (s, 1H), 3.71-3.68 (m, 1H), 3.58-3.55 (m, 1H), 3.21 (s, 3H), 2.96-2.92 (m, 1H), 2.84-2.79 (m, 1H), 2.63-2.57 (m, 1H), 1.91-1.80 (m, 2H), 1.70-1.67 (m, 1H), 1.23-1.20 (m, 1H). N—H and O—H protons not observed | |
| 579 | (R)-1-(3-chloro-5'-fluoro-2'-hydroxy-3'-(1-methyl-4-(3-methylpiperazin-1-yl)-1H-indol-6-yl)-[1,1'-biphenyl]-4-yl)-3-methyl-1H-imidazol-2(3H)-one | $^1$H NMR (400 MHz, DMSO-d$_6$): δ 7.82 (d, J = 1.6 Hz, 1H), 7.64 (dd, J = 2.0, 8.4 Hz, 1H), 7.52 (d, J = 8.0 Hz, 1H), 7.28 (d, J = 2.8 Hz, 1H), 7.24 (s, 1H), 7.19-7.15 (m, 2H), 6.72 (d, J = 2.8 Hz, 1H), 6.70 (d, J = 2.8 Hz, 1H), 6.63 (s, 1H), 6.40 (d, J = 2.8 Hz, 1H), 3.78 (s, 3H), 3.50-3.47 (m, 2H), 3.21 (s, 3H), 2.97-2.96 (m, 3H), 2.67-2.65 (m, 1H), 2.33 (d, J = 10.4 Hz, 1H), 1.03 (d, J = 6.4 Hz, 3H). Two N—H and O—H proton not observed | 546.3 |
| 580 | (R)-1-(3-chloro-5'-fluoro-2'-hydroxy-3'-(1-methyl-4-(3-methylpiperazin-1-yl)-1H-indazol-6-yl)-[1,1'-biphenyl]-4-yl)-3-methyl-1H-imidazol-2(3H)-one | $^1$H NMR (400 MHz, DMSO-d$_6$): δ 8.47 (s, 1H), 7.82 (d, J = 2.0 Hz, 1H), 7.64 (dd, J = 2.0, 8.0 Hz, | 547.3 |

| Ex. No. | Name/Structure | ¹H NMR Data | LCMS (M + H)⁺ |
|---|---|---|---|
| | 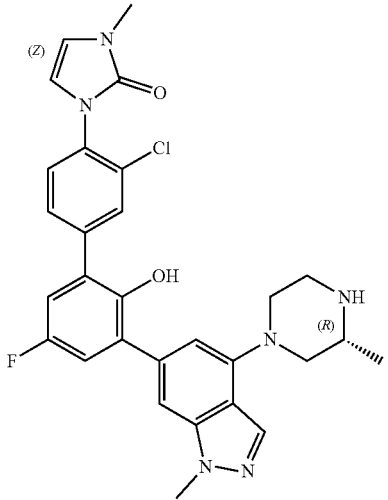 | 1H), 7.52 (d, J = 8.0 Hz, 1H), 7.30 (s, 1H), 7.18 (d, J = 9.2 Hz, 2H), 6.72 (d, J = 3.2 Hz, 1H), 6.69 (d, J = 2.8 Hz, 1H), 6.48 (s, 1H), 4.15 (s, 3H), 3.65 (d, J = 10.0 Hz, 2H), 3.21-3.19 (m, 5H), 3.13-3.07 (m, 1H), 2.84 (t, J = 10.4 Hz, 1H), 2.57 (t, J = 11.2 Hz, 1H), 1.17 (d, J = 6.4 Hz, 3H). N—H and O—H protons not observed | |
| 581 | 1-(3'-(4-(4-aminopiperidin-1-yl)-1H-indazol-6-yl)-3-chloro-5'-fluoro-2'-hydroxy-[1,1'-biphenyl]-4-yl)-3-methyl-1H-imidazol-2(3H)-one 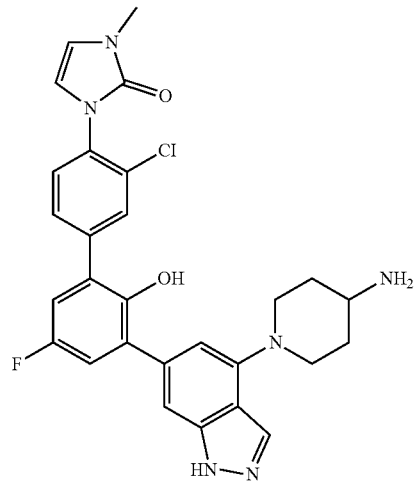 | ¹H NMR (400 MHz, DMSO-d₆): δ 13.04 (s, 1H), 8.54 (s, 1H), 8.14 (s, 1H), 7.92 (d, J = 4.0 Hz, 3H), 7.82 (d, J = 1.6 Hz, 1H), 7.65-7.62 (m, 1H), 7.54 (d, J = 8.0 Hz, 1H), 7.23-7.19 (m, 3H), 6.73-6.70 (m, 2H), 6.58 (s, 1H), 3.87-3.84 (m, 2H), 3.26-3.21 (m, 4H), 2.93-2.86 (m, 2H), 2.05-2.03 (m, 2H), 1.79-1.76 (m, 2H) | 533.2 |
| 582 | 1-(3-chloro-3'-(4-(4-ethylpiperazin-1-yl)-1H-indazol-6-yl)-5'-fluoro-2'-hydroxy-[1,1'-biphenyl]-4-yl)-3-methyl-1H-imidazol-2(3H)-one | ¹H NMR (400 MHz, DMSO-d₆): δ 13.04 (s, 1H), 8.50 (s, 1H), 8.10 (s, 1H), 7.852 (s, 1H), 7.63 | 547.3 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| | | (d, J = 8.0 Hz, 1H), 7.52 (d, J = 8.4 Hz, 1H), 7.21-7.18 (m, 3H), 6.71 (d, J = 2.8 Hz, 1H), 6.69 (d, J = 3.2 Hz, 1H), 6.55 (s, 1H), 3.31 (br s, 4H), 3.21 (s, 3H), 2.61 (br s, 4H), 2.45-2.40 (m, 2H), 1.06 (t, J = 7.2 Hz, 3H) | |
| 583 | (S)-1-(3-chloro-5'-fluoro-2'-hydroxy-3'-(4-(3-(methylamino)pyrrolidin-1-yl)-1H-indazol-6-yl)-[1,1'-biphenyl]-4-yl)-3-methyl-1H-imidazol-2(3H)-one | $^1$H NMR (400 MHz, DMSO-d$_6$ + D$_2$O): δ 8.21 (s, 1H), 7.82 (d, J = 2.0 Hz, 1H), 7.64 (dd, J = 1.6, 8.4 Hz, 1H), 7.53 (d, J = 8.4 Hz, 1H), 7.21-7.14 (m, 3H), 6.91 (s, 1H), 6.72 (d, J = 3.2 Hz, 1H), 6.70 (d, J = 3.2 Hz, 1H), 6.11 (s, 1H), 3.86-3.79 (m, 2H), 3.69-3.50 (m, 3H), 3.23 (s, 3H), 2.49 (s, 3H), 2.32-2.27 (m, 1H), 2.04-1.99 (m, 1H). N—H and O—H protons not observed | 533.3 |
| 584 | (R)-1-(3-chloro-5'-fluoro-2'-hydroxy-3'-(8-(3-methylpiperazin-1-yl)imidazo[1,2-a]pyridin-6-yl)-[1,1'-biphenyl]-4-yl)-3-methyl-1H-imidazol-2(3H)-one | $^1$H NMR (400 MHz, DMSO-d$_6$): δ 8.33 (s, 1H), 7.90 (s, 1H), 7.83 (d, J = 1.6 Hz, 1H), 7.64 (dd, J = | 533.3 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | | 2.0, 8.4 Hz, 1H), 7.54-7.50 (m, 2H), 7.28-7.22 (m, 2H), 6.72 (d, J = 2.8 Hz, 1H), 6.69 (d, J = 3.2 Hz, 1H), 6.55 (s, 1H), 4.32 (d, J = 10.8 Hz, 1H), 4.24 (d, J = 11.6 Hz, 1H), 3.21 (s, 3H), 3.09-2.95 (m, 3H), 2.77-2.74 (m, 1H), 2.48-2.42 (m, 1H), 1.09 (d, J = 6.4 Hz, 3H). N—H and O—H protons not observed | |
| 585 | (R)-1-(3-chloro-2'-hydroxy-5'-methyl-3'-(4-(3-methylpiperazin-1-yl)-1H-indazol-6-yl)-[1,1'-biphenyl]-4-yl)-3-methyl-1H-imidazol-2(3H)-one | ¹H NMR (400 MHz, DMSO-d₆): δ 13.07 (s, 1H), 8.30 (s, 1H), 8.19 (s, 1H), 7.77 (d, J = 2.4 Hz, 1H), 7.60 (dd, J = 2.0, 8.0 Hz, 1H), 7.50 (d, J = 8.0 Hz, 1H), 7.21-7.14 (m, 3H), 6.72 (d, J = 3.6 Hz, 1H), 6.69 (d, J = 2.8 Hz, 1H), 6.58 (s, 1H), 3.74 (d, J = 10.0 Hz, 2H), 3.26-3.24 (m, 1H), 3.21 (s, 3H), 3.01-2.94 (m, 1H), 2.75-2.67 (m, 1H), 2.32 (s, 3H), 1.24-1.23 (m, 5H). N—H or O—H proton not observed | 529.2 |
| 586 | (R)-1-(3'-(4-(3-aminopiperidin-1-yl)-1H-indazol-6-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 8.31 (br s, 3H), 8.23 (s, 1H), 7.83 (d, J = 2.0 Hz, 1H), 7.64 (dd, | 533.3 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | 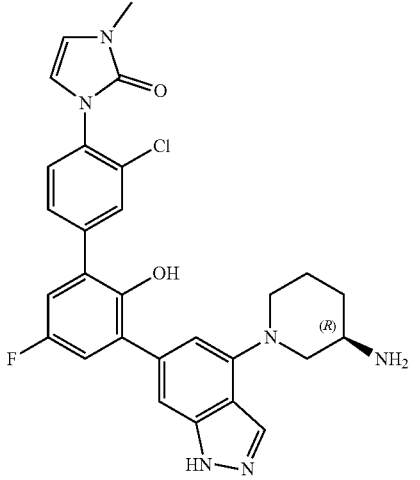 | J = 2.0, 8.4 Hz, 1H), 7.52 (d, J = 8.4 Hz, 1H), 7.27 (s, 1H), 7.23-7.18 (m, 2H), 6.72 (d, J = 2.8 Hz, 1H), 6.69 (d, J = 2.8 Hz, 1H), 6.63 (s, 1H), 3.83 (d, J = 11.6 Hz, 1H), 3.50-3.47 (m, 2H), 3.23 (s, 3H), 3.09-2.98 (m, 2H), 2.06-2.03 (m, 2H), 1.77-1.62 (m, 2H). N—H or O—H proton not observed | |
| 587 | 1-(3-chloro-5'-fluoro-2'-hydroxy-3'-(4-(4-isopropylpiperazin-1-yl)-1H-indazol-6-yl)-[1,1'-biphenyl]-4-yl)-3-methyl-1H-imidazol-2(3H)-one<br>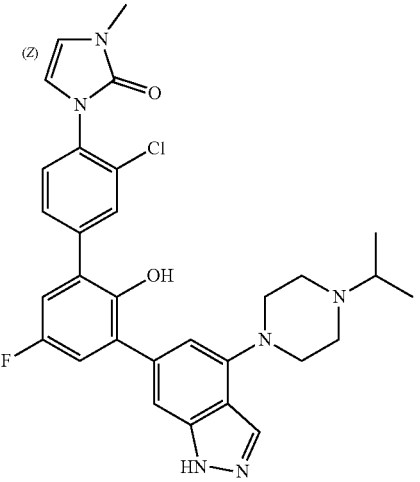 | ¹H NMR (400 MHz, DMSO-d₆): δ 13.05 (s, 1H), 8.53 (s, 1H), 8.10 (s, 1H), 7.82 (d, J = 1.6 Hz, 1H), 7.63 (d, J = 1.6 Hz, 1H), 7.52 (d, J = 8.4 Hz, 1H), 7.21-7.18 (m, 3H), 6.72 (d, J = 2.8 Hz, 1H), 6.70 (d, J = 2.8 Hz, 1H), 6.55 (s, 1H), 3.28 (br s, 4H), 3.21 (s, 3H), 2.69 (br s, 5H), 1.04 (t, J = 6.0 Hz, 6H) | 561.3 |
| 588 | 1-(3-chloro-5'-fluoro-2'-hydroxy-3'-(4-(4-methylpiperazin-1-yl)-1H-indazol-6-yl)-[1,1'-biphenyl]-4-yl)-3-methyl-1H-imidazol-2(3H)-one | ¹H NMR (400 MHz, DMSO-d₆): δ 13.05 (s, 1H), 8.52 (s, 1H), 8.11 (s, 1H), 7.82 (d, J = 1.6 Hz, | 533.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | 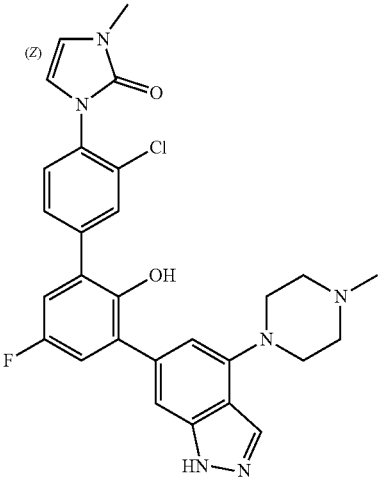 | 1H), 7.64 (dd, J = 2.0, 8.0 Hz, 1H), 7.52 (d, J = 8.4 Hz, 1H), 7.21-7.19 (m, 3H), 6.72 (d, J = 3.2 Hz, 1H), 6.69 (d, J = 3.2 Hz, 1H), 6.55 (s, 1H), 3.29 (br s, 4H), 3.21 (s, 3H), 2.56 (br s, 4H), 2.27 (s, 3H) | |
| 589 | 1-(3-chloro-3'-(4-(3,3-dimethylpiperazin-1-yl)-1H-indazol-6-yl)-5'-fluoro-2'-hydroxy-[1,1'-biphenyl]-4-yl)-3-methyl-1H-imidazol-2(3H)-one<br>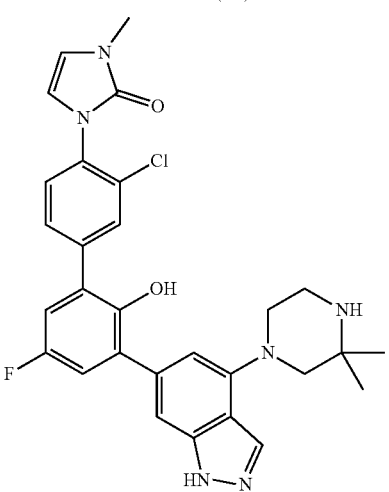 | ¹H NMR (400 MHz, DMSO-d₆): δ 9.40 (br s, 2H), 8.17 (s, 1H), 7.83 (d, J = 1.6 Hz, 1H), 7.64 (dd, J = 1.6, 8.0 Hz, 1H), 7.53 (d, J = 8.4 Hz, 1H), 7.30 (s, 1H), 7.22 (d, J = 9.2 Hz, 2H), 6.72 (d, J = 3.2 Hz, 1H), 6.69 (d, J = 3.2 Hz, 1H), 6.63 (s, 1H), 3.47 (br s, 2H), 3.36 (br s, 2H), 3.30 (s, 2H), 3.21 (s, 3H), 1.51 (s, 6H). N—H or O—H proton not observed | 547.3 |
| 590 | 1-(3-chloro-5'-fluoro-2'-hydroxy-3'-(4-morpholino-1H-indazol-6-yl)-[1,1'-biphenyl]-4-yl)-3-methyl-1H-imidazol-2(3H)-one | ¹H NMR (400 MHz, DMSO-d₆): δ 13.09 (s, 1H), 8.54 (s, 1H), 8.17 (s, 1H), 7.83 (d, J = 1.6 Hz, | 520.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | 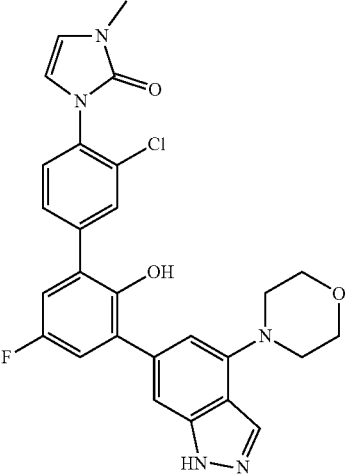 [SMILES: Cn1ccn(-c2ccc(-c3cc(F)cc(-c4cc(N5CCOCC5)c5cn[nH]c5c4)c3O)cc2Cl)c1=O] | 1H), 7.84 (dd, J = 1.6, 8.0 Hz, 1H), 7.53 (d, J = 8.0 Hz, 1H), 7.25-7.19 (m, 3H), 6.72 (d, J = 2.8 Hz, 1H), 6.70 (d, J = 2.8 Hz, 1H), 6.58 (s, 1H), 3.85-3.82 (m, 4H), 3.28-3.27 (m, 4H), 3.21 (s, 3H). O—H proton observed | |
| 591 | (R)-1-(3-chloro-5'-fluoro-2'-hydroxy-3'-(8-(3-methylpiperazin-1-yl)quinolin-6-yl)-[1,1'-biphenyl]-4-yl)-3-methyl-1H-imidazol-2(3H)-one 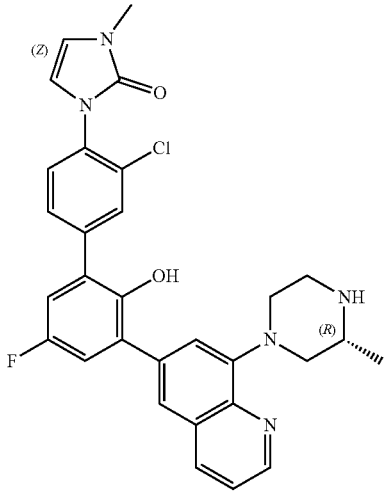 | ¹H NMR (400 MHz, DMSO-d₆): δ 8.67 (dd, J = 1.6, 4.0 Hz, 1H), 8.32 (dd, J = 1.6, 8.0 Hz, 1H), 7.84 (d, J = 2.0 Hz, 1H), 7.69-7.64 (m, 2H), 7.54-7.50 (m, 2H), 7.30-7.23 (m, 3H), 6.72 (d, J = 3.2 Hz, 1H), 6.69 (d, J = 3.2 Hz, 1H), 3.92 (d, J = 11.2 Hz, 1H), 3.82 (t, J = 10.4 Hz, 1H), 3.21 (s, 3H), 3.04-2.96 (m, 3H), 2.73-2.71 (m, 1H), 2.40 (d, J = 10.4 Hz, 1H), 1.03 (d, J = 6.0 Hz, 3H). N—H and O—H protons not observed | 544.2 |
| 592 | (R)-1-(3-chloro-5'-fluoro-2'-hydroxy-3'-(4-(3-propylpiperazin-1-yl)-1H-indazol-6-yl)-[1,1'-biphenyl]-4-yl)-3-methyl-1H-imidazol-2(3H)-one | ¹H NMR (400 MHz, DMSO-d₆): δ 13.05 (s, 1H), 8.06 (s, 1H), 7.82 (d, J = 2.0 Hz, 1H), 7.64 (dd, | 561.3 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | 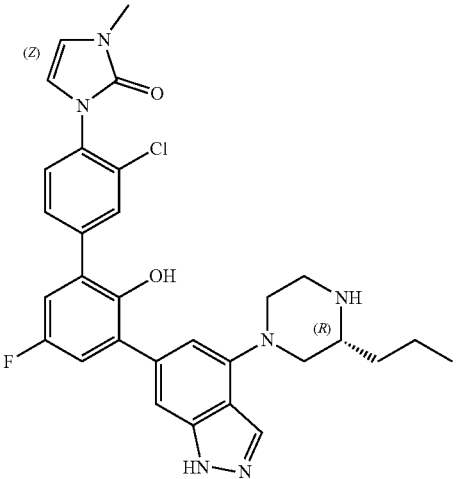 | J = 2.0, 8.4 Hz, 1H), 7.52 (d, J = 8.0 Hz, 1H), 7.21-7.19 (m, 3H), 6.72 (d, J = 2.4 Hz, 1H), 6.69 (d, J = 2.8 Hz, 1H), 6.54 (s, 1H), 3.63 (d, J = 10.4 Hz, 2H), 3.21 (s, 3H), 3.02-2.94 (m, 2H), 2.85-2.76 (m, 2H), 2.44 (t, J = 10.4 Hz, 1H), 1.44-1.35 (m, 4H), 0.93-0.89 (m, 3H). N—H and O—H protons not observed | |
| 593 | (R)-1-(3'-(4-(3-aminopyrrolidin-1-yl)-1H-indazol-6-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 12.89 (br s, 1H), 8.37 (br s, 3H), 8.17 (s, 1H), 7.82 (d, J = 2.0 Hz, 1H), 7.64 (dd, J = 1.6, 8.0 Hz, 1H), 7.52 (d, J = 8.4 Hz, 1H), 7.21-7.13 (m, 2H), 6.95 (s, 1H), 6.72 (d, J = 3.2 Hz, 1H), 6.69 (d, J = 2.8 Hz, 1H), 6.15 (s, 1H), 3.99-3.86 (m, 3H), 3.69-3.66 (m, 2H), 2.39-2.35 (m, 1H), 2.18-2.16 (m, 1H). N—H and O—H protons not observed | 519.2 |
| 594 | (R)-1-(3-chloro-3'-(4-(3-ethylpiperazin-1-yl)-1H-indazol-6-yl)-5'-fluoro-2'-hydroxy-[1,1'-biphenyl]-4-yl)-3-methyl-1H-imidazol-2(3H)-one | ¹H NMR (400 MHz, DMSO-d₆): δ 13.05 (s, 1H), 8.06 (s, 1H), 7.82 (d, J = 1.6 Hz, 1H), 7.64 (dd, | 547.3 |

TABLE 29-continued

Following compounds were prepared using similar procedures as described for Examples 365-563.

| Ex. No. | Name/Structure | $^1$H NMR Data | LCMS $(M + H)^+$ |
|---|---|---|---|
| | 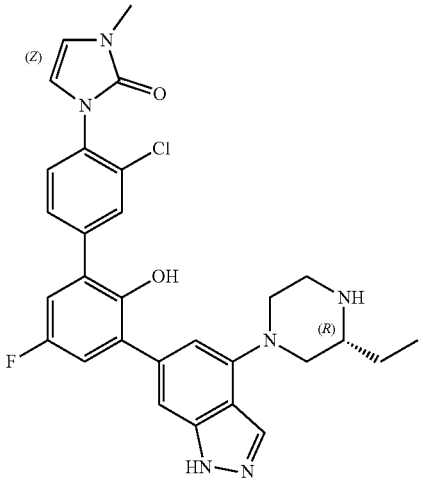 | J = 1.6, 8.0 Hz, 1H), 7.52 (d, J = 8.0 Hz, 1H), 7.21-7.19 (m, 3H), 6.72 (d, J = 2.8 Hz, 1H), 6.69 (d, J = 2.8 Hz, 1H), 6.54 (s, 1H), 3.63 (t, J = 10.0 Hz, 2H), 3.21 (s, 3H), 3.02-2.94 (m, 2H), 2.79-2.73 (m, 2H), 2.43 (t, J = 10.8 Hz, 1H), 1.43-1.38 (m, 2H), 0.95 (t, J = 7.6 Hz, 3H). N—H or O—H protons not observed | |
| 595 | (S)-1-(3-chloro-5'-fluoro-2'-hydroxy-3'-(4-(3-methylpiperazin-1-yl)-1H-indazol-6-yl)-[1,1'-biphenyl]-4-yl)-3-methyl-1H-imidazol-2(3H)-one<br>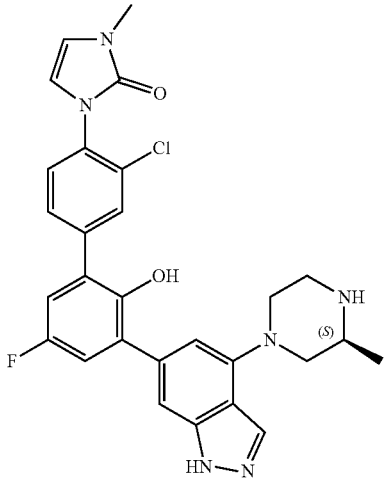 | $^1$H NMR (400 MHz, DMSO-d$_6$ + D$_2$O): δ 8.26 (s, 1H), 7.83 (d, J = 2.0 Hz, 1H), 7.55 (dd, J = 2.0, 8.4 Hz, 1H), 7.53 (d, J = 8.0 Hz, 1H), 7.32 (s, 1H), 7.22 (d, J = 8.8 Hz, 2H), 6.73 (d, J = 3.2 Hz, 1H), 6.69 (d, J = 3.2 Hz, 1H), 6.65 (s, 1H), 3.84-3.81 (m, 2H), 3.47-3.41 (m, 2H), 3.34-3.28 (m, 1H), 3.22 (s, 3H), 3.16-3.12 (m, 1H), 2.98-2.92 (m, 1H), 1.35 (d, J = 6.4 Hz, 3H). N—H or O—H protons not observed | 533.3 |
| 596 | (S)-1-(3-chloro-5'-fluoro-2'-hydroxy-3'-(4-(3-methylpiperidin-1-yl)-1H-indazol-6-yl)-[1,1'-biphenyl]-4-yl)-3-methyl-1H-imidazol-2(3H)-one | $^1$H NMR (400 MHz, DMSO-d$_6$ + D$_2$O): δ 8.06 (s, 1H), 7.82 (d, J = 1..6 Hz, 1H), 7.64 (dd, J = 2.0, | 532.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| | 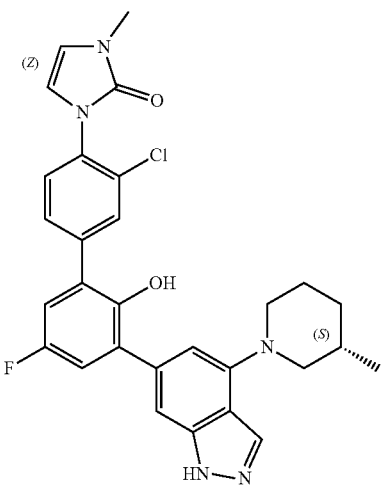 | 8.4 Hz, 1H), 7.53 (d, J = 8.0 Hz, 1H), 7.21-7.18 (m, 3H), 6.72 (d, J = 2.8 Hz, 1H), 6.69 (d, J = 2.8 Hz, 1H), 6.65 (s, 1H), 3.71-3.64 (m, 2H), 3.22 (s, 3H), 2.80-2.74 (m, 1H), 2.50-2.47 (m, 1H), 1.88-1.71 (m, 4H), 1.14-1.05 (m, 1H), 0.97 (d, J = 6.0 Hz, 3H). N—H and O—H protons not observed | |
| 597 | (R)-1-(3-chloro-5'-fluoro-2'-hydroxy-3'-(4-(3-isopropylpiperazin-1-yl)-1H-indazol-6-yl)-[1,1'-biphenyl]-4-yl)-3-methyl-1H-imidazol-2(3H)-one | $^1$H NMR (400 MHz, DMSO-d$_6$): δ 13.05 (s, 1H), 8.03 (s, 1H), 7.82 (d, J = 1..6Hz, 1H), 7.64 (dd, J = 2.0, 8.0 Hz, 1H), 7.52 (d, J = 8.0 Hz, 1H), 7.21-7.18 (m, 3H), 6.72 (d, J = 3.2 Hz, 1H), 6.69 (d, J = 3.2 Hz, 1H), 6.65 (s, 1H), 3.69 (d, J = 10.8 Hz, 1H), 3.60 (d, J = 10.8 Hz, 1H), 3.21 (s, 3H), 3.05-3.02 (m, 1H), 2.95-2.90 (m, 1H), 2.78-2.73 (m, 1H), 2.62-2.58 (m, 1H), 2.49-2.46 (m, 1H), 1.65-1.60 (m, 1H), 0.96 (d, J = 7.2 Hz, 6H). N—H and O—H protons not observed | 561.4 |
| 598 | (S)-1-(3'-(4-(7-amino-5-azaspiro[2.4]heptan-5-yl)-1H-indazol-6-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 8.42-8.41 (m, 3H), 8.17(s, 1H), 7.83 (d, J = 2.0 Hz, 1H), 7.64 (dd, J = 2.0, 8.0 Hz, 1H), | 545.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| | | 7.52 (d, J = 8.0 Hz, 1H), 7.25-7.12 (m, 2H), 6.95 (s, 1H), 6.72 (d, J = 2.8 Hz, 1H), 6.69 (d, J = 3.2 Hz, 1H), 6.13 (s, 1H), 4.16 (d, J = 9.2 Hz, 1H), 4.19-4.04 (m, 1H), 3.89 (d, J = 11.2 Hz, 1H), 3.50 (t, J = 4.4 Hz, 1H), 3.36 (d, J = 9.6 Hz, 1H), 3.21 (s, 3H), 1.22-1.17 (m, 1H), 0.92-0.83 (m, 2H), 0.78-0.74 (m, 1H). N—H or O—H proton not observed | |
| 599 | 1-(3'-(4-(2,5-diazabicyclo[2.2.1]heptan-2-yl)-1H-indazol-6-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 13.01 (br s, 0.5H), 9.50 (br s, 1H), 8.97 (br s, 1H), 8.49 (br s, 0.5H), 8.15 (s, 1H), 7.83 (d, J = 2.0 Hz, 1H), 7.64 (dd, J = 2.0, 8.4 Hz, 1H), 7.53 (d, J = 8.0 Hz, 1H), 7.22-7.17 (m, 2H), 7.03 (s, 1H), 6.72 (d, J = 2.8 Hz, 1H), 6.69 (d, J = 2.8 Hz, 1H), 6.30 (s, 1H), 4.82 (s, 1H), 4.48 (s, 1H), 4.17-4.06 (m, 1H), 3.79-3.73 (m, 1H), 3.38-3.28 (m, 2H), 3.21 (s, 3H), 2.23 (d, J = 10.8 Hz, 1H), 1.98 (d, J = 10.0 Hz, 1H) | 531.2 |
| 600 | 1-(3'-(4-(2,5-diazabicyclo[2.2.2]octan-2-yl)-1H-indazol-6-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 13.05 (br s, 0.5H), 9.31 (s, 2H), 8.49 (br s, 0.6H), 8.15 (s, 1H), | 545.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | | 7.83 (d, J = 2.0 Hz, 1H), 7.64 (dd, J = 2.0, 8.0 Hz, 1H), 7.52 (d, J = 8.4 Hz, 1H), 7.22-7.17 (m, 2H), 7.04 (s, 1H), 6.72 (d, J = 2.8 Hz, 1H), 6.69 (d, J = 2.8 Hz, 1H), 6.36 (s, 1H), 4.37 (s, 1H), 4.04 (d, J = 10.4 Hz, 1H), 3.83-3.80 (m, 2H), 3.49-3.34 (m, 2H), 3.21 (s, 3H), 2.15-2.12 (m, 2H), 1.90-1.87 (m, 2H) | |
| 601 | 1-(3-chloro-5'-fluoro-3'-(4-(hexahydro-1H-pyrido[1,2-a]pyrazin-2(6H)-yl)-1H-indazol-6-yl)-2'-hydroxy-[1,1'-biphenyl]-4-yl)-3-methyl-1H-imidazol-2(3H)-one | ¹H NMR (400 MHz, DMSO-d₆ + D₂O): δ 8.11 (s, 1H), 7.82 (s, 1H), 7.64 (d, J = 7.6 Hz, 1H), 7.52 (d, J = 8.0 Hz, 1H), 7.21-7.19 (m, 3H), 6.70 (d, J = 8.4 Hz, 2H), 6.53 (s, 1H), 3.73-3.71 (m, 1H), 3.61-3.58 (m, 1H), 3.22 (s, 3H), 2.95-2.81 (m, 3H), 2.59-2.38 (m, 2H), 2.15-2.01 (m, 2H), 1.73-1.49 (m, 4H), 1.31-1.18 (m, 2H). N—H or O—H protons not observed | 573.3 |
| 602 | (R)-1-(3-chloro-5'-fluoro-2'-hydroxy-3'-(8-(3-methylpiperazin-1-yl)-[1,2,4]triazolo[1,5-a]pyridin-6-yl)-[1,1'-biphenyl]-4-yl)-3-methyl-1H-imidazol-2(3H)-one | ¹H NMR (400 MHz, DMSO-d₆): δ 8.61 (s, 1H), 8.43 (s, 1H), 7.84 (d, J = 1.2 Hz, 1H), 7.65 (dd, J = 1.2, 8.4 Hz, 1H), 7.53 (d, | 534.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | 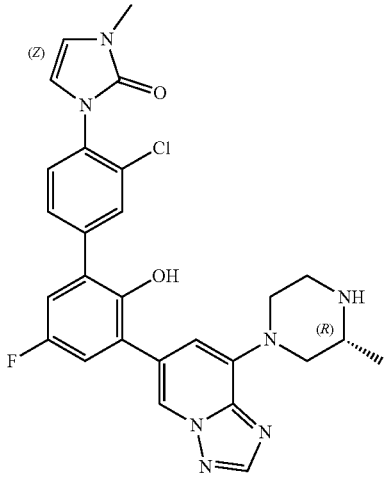 | J = 8.4 Hz, 1H), 7.35-7.25 (m, 2H), 6.90 (s, 1H), 6.72 (d, J = 2.8 Hz, 1H), 6.69 (d, J = 2.8 Hz, 1H), 4.21 (t, J = 12.4 Hz, 2H), 3.21 (s, 3H), 3.01-2.87 (m, 3H), 2.74-2.73 (m, 1H), 2.40 (t, J = 10.8 Hz, 1H), 1.04 (d, J = 6.0 Hz, 3H). N—H and O—H protons not observed | |
| 603 | (R)-6-(3'-chloro-5-fluoro-2-hydroxy-4'-(3-methyl-2-oxo-2,3-dihydro-1H-imidazol-1-yl)-[1,1'-biphenyl]-3-yl)-4-(3-methylpiperazin-1-yl)-1H-benzo[d]imidazol-2(3H)-one<br>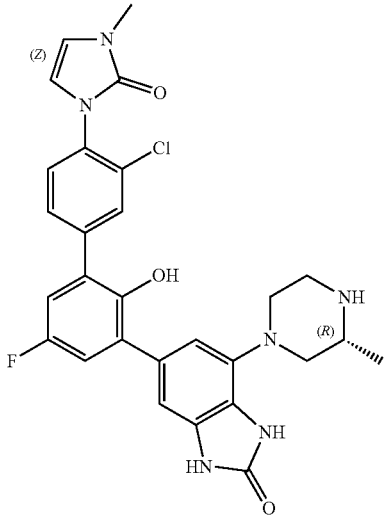 | ¹H NMR (400 MHz, DMSO-d₆): δ 10.62 (s, 2H), 7.80 (d, J = 1.6 Hz, 1H), 7.62 (dd, J = 1.6, 8.0 Hz, 1H), 7.51 (d, J = 8.4 Hz, 1H), 7.15-7.09 (m, 2H), 6.83 (d, J = 1.2 Hz, 1H), 6.72-6.68 (m, 3H), 3.23-3.17 (m, 5H), 2.95-2.91 (m, 3H), 2.60-2.53 (m, 1H), 2.21 (t, J = 10.0 Hz, 1H), 0.92 (d, J = 2.4 Hz, 3H). One N—H and one O—H proton not observed | 549.3 |
| 604 | 1-(3-chloro-5'-fluoro-2'-hydroxy-3'-(1-methyl-4-(4-methylpiperazin-1-yl)-1H-indazol-6-yl)-[1,1'-biphenyl]-4-yl)-3-methyl-1H-imidazol-2(3H)-one | ¹H NMR (400 MHz, DMSO-d₆): δ 8.52 (s, 1H), 8.08 (s, 1H), 7.83 (d, J = 2.0 Hz, 1H), 7.64 (dd, J = | 547.3 |

| Ex. No. | Name/Structure | $^1$H NMR Data | LCMS (M + H)$^+$ |
|---|---|---|---|
| | 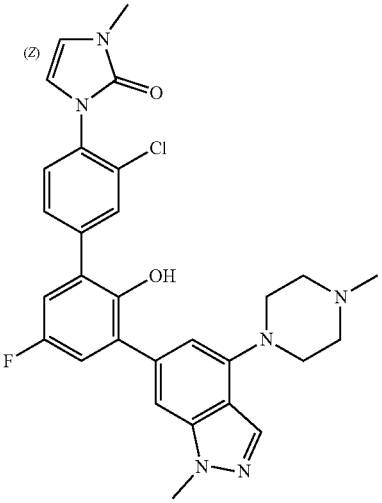 | 2.0, 8.4 Hz, 1H), 7.52 (d, J = 8.0 Hz, 1H), 7.30 (s, 1H), 7.23-7.21 (m, 2H), 6.72 (d, J = 2.8 Hz, 1H), 6.69 (d, J = 3.2 Hz, 1H), 6.60 (s, 1H), 4.02 (s, 3H), 3.29 (br s, 4H), 3.21 (s, 3H), 2.56 (br s, 4H), 2.27 (s, 3H) | |
| 605 | (R)-1-(3-chloro-5'-fluoro-2'-hydroxy-3'-(1-methyl-4-(3-methylpiperazin-1-yl)-1H-benzo[d][1,2,3]triazol-6-yl)-[1,1'-biphenyl]-4-yl)-3-methyl-1H-imidazol-2(3H)-one<br>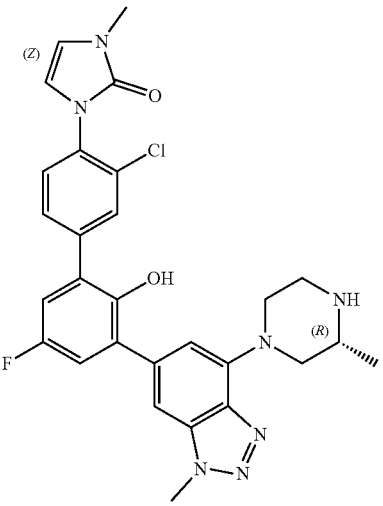 | $^1$H NMR (400 MHz, DMSO-d$_6$): δ 7.83 (s, 1H), 7.65-7.63 (m, 1H), 7.53(d, J = 8.0 Hz, 1H), 7.31 (s, 1H), 7.24-7.22 (m, 2H), 6.72-6.68 (m, 3H), 4.41 (d, J = 10.8 Hz, 1H), 4.34 (d, J = 10.4 Hz, 1H), 4.25 (s, 3H), 3.21 (s, 3H), 3.00-2.84 (m, 5H), 1.06 (d, J = 6.4 Hz, 3H). N—H and O—H protons not observed | 548.3 |
| 606 | 1-(3-chloro-5'-fluoro-3'-(4-(hexahydropyrrolo[1,2-a]pyrazin-2(1H)-yl)-1H-indazol-6-yl)-2'-hydroxy-[1,1'-biphenyl]-4-yl)-3-methyl-1H-imidazol-2(3H)-one | $^1$H NMR (400 MHz, DMSO-d$_6$): δ 13.03 (s, 1H), 8.50 (s, 1H), 8.11 (s, 1H), 7.82 (d, J = 1.6 Hz, 1H), 7.64 (dd, J = 1.6, 8.0 | 559.3 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | 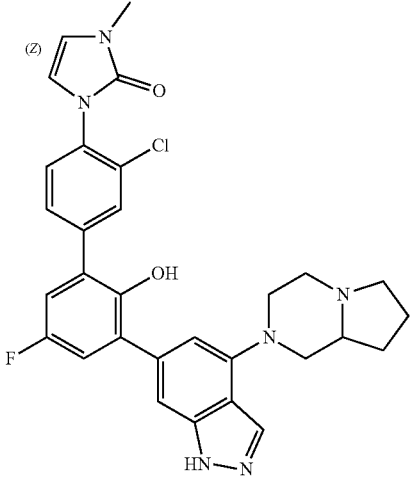 [SMILES: Cn1ccn(-c2ccc(-c3cc(F)cc(-c4cc(N5CCN6CCCC6C5)c5cn[nH]c5c4)c3O)cc2Cl)c1=O] | Hz, 1H), 7.52 (d, J = 8.4 Hz, 1H), 7.21-7.18 (m, 3H), 6.71 (d, J = 2.8 Hz, 1H), 6.69 (d, J = 2.8 Hz, 1H), 6.57 (s, 1H), 3.56 (d, J = 10.4 Hz, 1H), 3.78 (d, J = 11.2 Hz, 1H), 3.21 (s, 3H), 3.10-2.94 (m, 3H), 2.64-2.69 (m, 1H), 2.43-2.38 (m, 1H), 2.23-2.13 (m, 2H), 1.86-1.70 (m, 3H), 1.41-1.38 (m, 1H) | |
| 607 | 1-(3'-(4-(3,8-diazabicyclo[3.2.1]octan-3-yl)-1-methyl-1H-indazol-6-yl)-3-chloro-5'-fluoro-2'-hydroxy-[1,1'-biphenyl]-4-yl)-3-methyl-1H-imidazol-2(3H)-one 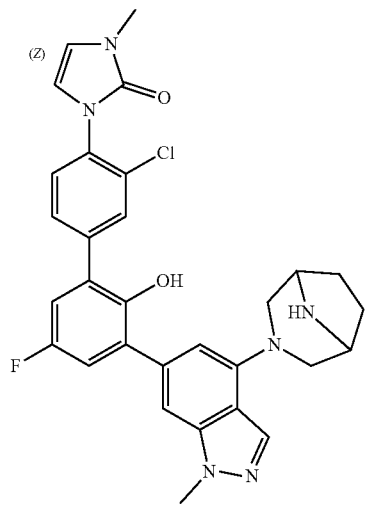 [SMILES: Cn1ccn(-c2ccc(-c3cc(F)cc(-c4cc(N5CC6CCC(C5)N6)c5cnn(C)c5c4)c3O)cc2Cl)c1=O] | ¹H NMR (400 MHz, DMSO-d₆): δ 8.10 (s, 1H), 7.83 (d, J = 1.6 Hz, 1H), 7.64 (dd, J = 1.6, 8.0 Hz, 1H), 7.52 (d, J = 8.0 Hz, 1H), 7.22-7.17 (m, 3H), 6.72 (d, J = 3.2 Hz, 1H), 6.69 (d, J = 2.8 Hz, 1H), 6.46 (s, 1H), 3.99 (s, 3H), 3.57 (d, J = 10.4 Hz, 2H), 3.51 (br s, 2H), 3.21 (s, 3H), 2.99 (d, J = 10.0 Hz, 2H), 1.87-1.85 (m, 2H), 1.73-1.71 (m, 2H). N—H and O—H protons not observed | 559.2 |
| 608 | (R)-1-(3-chloro-5'-fluoro-2'-hydroxy-3'-(4-(3-methylpiperazin-1-yl)-1-tosyl-1H-indol-6-yl)-[1,1'-biphenyl]-4-yl)-3-methyl-1H-imidazol-2(3H)-one | ¹H NMR (400 MHz, DMSO-d₆): δ 7.89 (d, J = 8.4 Hz, 2H), 7.84 (d, J = 2.0 Hz, 1H), 7.75-7.74 (m, | 686.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| | 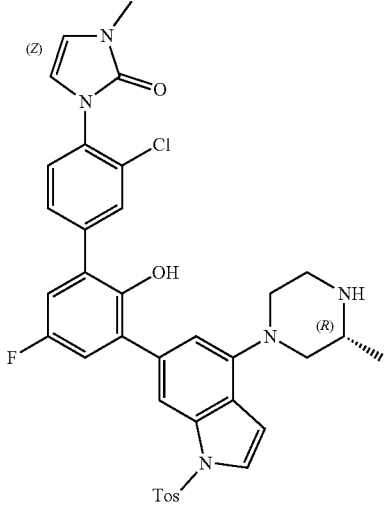 | 2H), 7.66 (dd, J = 2.0, 8.0 Hz, 1H), 7.54 (d, J = 8.4 Hz, 1H), 7.39 (d, J = 7.6 Hz, 2H), 7.23-7.14 (m, 2H), 6.84 (s, 1H), 6.80 (d, J = 3.6 Hz, 1H), 6.73 (d, J = 2.4 Hz, 1H), 6.70 (d, J = 3.2 Hz, 1H), 3.34-3.31 (m, 3H), 3.22 (s, 3H), 2.91-2.88 (m, 3H), 2.68-2.62 (m, 1H), 2.35-2.30 (m, 4H), 0.99 (d, J = 6.4 Hz, 3H). N—H and O—H protons not observed | |
| 609 | 1-(3-chloro-5'-fluoro-3'-(4-(hexahydro-1H-pyrido[1,2-a]pyrazin-2(6H)-yl)-1-methyl-1H-indazol-6-yl)-2'-hydroxy-[1,1'-biphenyl]-4-yl)-3-methyl-1H-imidazol-2(3H)-one<br>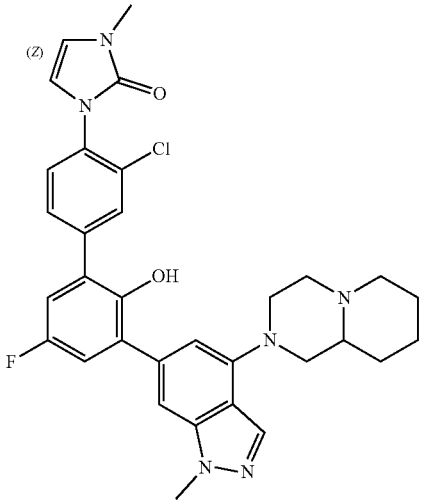 [SMILES: Cn1ccn(-c2ccc(-c3cc(F)cc(-c4cc(N5CCN6CCCCC6C5)c5cnn(C)c5c4)c3O)cc2Cl)c1=O] | $^1$H NMR (400 MHz, DMSO-d$_6$): δ 8.50 (s, 1H), 8.08 (s, 1H), 7.83 (d, J = 1.2 Hz, 1H), 7.64 (dd, J = 1.2, 8.0 Hz, 1H), 7.52 (d, J = 8.4 Hz, 1H), 7.28 (s, 1H), 7.21 (d, J = 8.4 Hz, 2H), 6.71 (d, J = 3.2 Hz, 1H), 6.69 (d, J = 2.8 Hz, 1H), 6.57 (s, 1H), 4.01(s, 3H), 3.72 (d, J = 11.2 Hz, 1H), 3.59 (d, J = 11.2 Hz, 1H), 3.21 (s, 3H), 2.94-2.89 (m, 1H), 2.82-2.79 (m, 2H), 2.58-2.37 (m, 2H), 2.15-1.99 (m, 2H), 1.74-1.48 (m, 4H), 1.30-1.16 (m, 2H) | 587.3 |
| 610 | (R)-1-(3-chloro-3'-(2-(4-(2,3-dihydroxypropyl)piperazin-1-yl)pyridin-4-yl)-5'-fluoro-2'-hydroxy-[1,1'-biphenyl]-4-yl)-3-methyl-1H-imidazol-2(3H)-one | $^1$H NMR (400 MHz, DMSO-d$_6$): δ 8.16 (d, J = 4.8 Hz, 1H), 7.81 (d, J = 1.6 Hz, 1H), 7.62 (dd, J = | 554.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | | 1.6, 8.0 Hz, 1H), 7.53 (d, J = 8.0 Hz, 1H), 7.26-7.19 (m, 2H), 6.95 (s, 1H), 6.85 (d, J = 4.8 Hz, 1H), 6.72 (d, J = 3.2 Hz, 1H), 6.69 (d, J = 3.2 Hz, 1H), 3.68-3.67 (m, 1H), 3.53 (br s, 4H), 3.35-3.34 (m, 2H), 3.22 (s, 3H), 2.57 (br s, 4H), 2.52-2.34 (m, 2H). NH and O—H protons not observed | |
| 611 | 1-(3-chloro-5'-fluoro-2'-hydroxy-3'-(2-(4-(oxetan-3-ylmethyl)piperazin-1-yl)pyridin-4-yl)-[1,1'-biphenyl]-4-yl)-3-methyl-1H-imidazol-2(3H)-one | ¹H NMR (400 MHz, DMSO-d₆): δ 8.71 (s, 1H), 8.15 (d, J = 5.2 Hz, 1H), 7.81 (d, J = 2.0 Hz, 1H), 7.62 (dd, J = 1.6, 8.4 Hz, 1H), 7.52 (d, J = 8.0 Hz, 1H), 7.26-7.18 (m, 2H), 6.95 (s, 1H), 6.84 (d, J = 4.8 Hz, 1H), 6.72 (d, J = 2.4 Hz, 1H), 6.69 (d, J = 2.8 Hz, 1H), 4.67-4.64 (m, 2H), 4.28 (t, J = 6.0 Hz, 2H), 3.51-3.49 (m, 4H), 3.24-3.21 (m, 4H), 2.66 (d, J = 7.2 Hz, 2H), 2.42 (t, J = 4.8 Hz, 4H) | 550.2 |
| 612 | 1-(3-chloro-5'-fluoro-2'-hydroxy-3'-(2-(piperidin-1-yl)pyridin-4-yl)-[1,1'-biphenyl]-4-yl)-3-methyl-1H-imidazol-2(3H)-one | ¹H NMR (400 MHz, DMSO-d₆): δ 8.69 (s, 1H), 8.14 (d, J = 4.8 Hz, 1H), 7.81 (d, J = 2.0 Hz, 1H), 7.62 (dd, J = 1.6, 8.0 Hz, 1H), 7.52 (d, J = 8.0 Hz, 1H), 7.25-7.18 (m, 2H), 6.93 (s, 1H), 6.77 (dd, J = 0.8, 5.2 Hz, 1H), 6.72 (d, J = 3.6 Hz, 1H), 6.69 (d, J = 2.4 Hz, 1H), 3.56 (t, J = 4.8 Hz, 4H), 3.21 (s, 3H), 1.62-1.55 (m, 6H) | 479.1 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| 613 | 1-(3-chloro-5'-fluoro-2'-hydroxy-3'-(2-(pyrrolidin-1-yl)pyridin-4-yl)-[1,1'-biphenyl]-4-yl)-3-methyl-1H-imidazol-2(3H)-one | ¹H NMR (400 MHz, DMSO-d₆): δ 8.68 (s, 1H), 8.10 (d, J = 5.2 Hz, 1H), 7.80 (d, J = 2.0 Hz, 1H), 7.82 (dd, J = 2.0, 8.0 Hz, 1H), 7.52 (d, J = 8.0 Hz, 1H), 7.25-7.17 (m, 2H), 6.72-6.69 (m, 3H), 6.58 (s, 1H), 3.42 (br s, 4H), 3.21 (s, 3H), 1.95 (brs, 4H). | 465.1 |
| 614 | 1-(3'-(2-(4-(tert-butyl)piperazin-1-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 8.70 (s, 1H), 8.15 (d, J = 5.2 Hz, 1H), 7.80 (d, J = 2.0 Hz, 1H), 7.61 (dd, J = 2.0, 8.0 Hz, 1H), 7.52 (d, J = 8.4 Hz, 1H), 7.26-7.18 (m, 2H), 6.93 (s, 1H), 6.82 (d, J = 4.8 Hz, 1H), 6.72 (d, J = 3.2 Hz, 1H), 6.69 (d, J = 3.2 Hz, 1H), 3.50 (br s, 4H), 3.21 (s, 3H), 2.59 (br s, 4H), 1.05 (s, 9H) | 536.3 |
| 615 | 1-(3-chloro-5'-fluoro-2'-hydroxy-3'-(2-morpholinopyridin-4-yl)-[1,1'-biphenyl]-4-yl)-3-methyl-1H-imidazol-2(3H)-one | ¹H NMR (400 MHz, DMSO-d₆): δ 8.73 (s, 1H), 8.09 (d, J = 5.2 Hz, 1H), 7.81 (d, J = 2.0 Hz, 1H), 7.62 (dd, J = 2.0, 8.4 Hz, 1H), 7.52 (d, J = 8.4 Hz, 1H), 7.26-7.20 (m, 2H), 6.97 (s, 1H), 6.89 (dd, J = 1.2, 5.6 Hz, 1H), 6.72 (d, J = 2.8 Hz, 1H), 6.69 (d, J = 2.8 Hz, 1H), 3.71 (t, J = 4.8 Hz, 4H), 3.49 (t, J = 4.8 Hz, 4H), 3.21 (s, 3H) | 481.1 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| 616 | 1-(3'-(2-(4-(2-aminoethyl)piperazin-1-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 8.13 (d, J = 5.2 Hz, 1H), 7.86 (d, J = 1.6 Hz, 1H), 7.63 (dd, J = 2.0, 8.4 Hz, 1H), 7.49 (d, J = 8.4 Hz, 1H), 7.23-7.16 (m, 2H), 7.03 (s, 1H), 6.86 (d, J = 5.6 Hz, 1H), 6.71 (d, J = 3.2 Hz, 1H), 6.68 (d, J = 2.8 Hz, 1H), 3.51 (t, J = 4.4 Hz, 4H), 3.21 (s, 3H), 2.66 (t, J = 6.4 Hz, 2H), 2.46 (t, J = 4.8 Hz, 4H), 2.35 (t, J = 6.4 Hz, 2H). N—H and O—H protons not observed | 523.2 |
| 617 | 1-(3-chloro-5'-fluoro-2'-hydroxy-3'-(2-(4-(3-hydroxypropyl)piperazin-1-yl)pyridin-4-yl)-[1,1'-biphenyl]-4-yl)-3-methyl-1H-imidazol-2(3H)-one | ¹H NMR (400 MHz, DMSO-d₆): δ 8.73 (br s, 1H), 8.16 (d, J = 5.2 Hz, 1H), 7.81 (d, J = 1.6 Hz, 1H), 7.62 (dd, J = 2.0, 8.4 Hz, 1H), 7.52 (d, J = 8.0 Hz, 1H), 7.26-7.18 (m, 2H), 6.95 (s, 1H), 6.84 (d, J = 5.2 Hz, 1H), 6.72 (d, J = 2.8 Hz, 1H), 6.69 (d, J = 3.2 Hz, 1H), 4.43 (br s, 1H), 3.52 (br s, 4H), 3.46 (t, J = 6.4 Hz, 2H), 3.21 (s, 3H), 2.50-2.46 (m, 4H), 2.38 (t, J = 7.2 Hz, 2H), 1.65-1.58 (m, 2H) | 538.2 |
| 618 | 1-(3-chloro-5'-fluoro-2'-hydroxy-3'-(2-(4-(tetrahydrofuran-3-yl)piperazin-1-yl)pyridin-4-yl)-[1,1'-biphenyl]-4-yl)-3-methyl-1H-imidazol-2(3H)-one | ¹H NMR (400 MHz, DMSO-d₆): δ 8.71 (s, 1H), 8.16 (d, J = 5.2 Hz, 1H), 7.81 (d, J = 2.0 Hz, 1H), 7.62 (dd, J = 1.6, 8.0 Hz, 1H), 7.52 (d, J = 8.4 Hz, 1H), 7.26-7.18 (m, 2H), 6.95 (s, 1H), 6.84 (d, J = 5.2 Hz, 1H), 6.72 (d, J = 3.2 Hz, 1H), 6.69 (d, J = 2.8 Hz, 1H), 3.83-3.77 (m, 2H), 3.69-3.63 (m, 1H), 3.55-3.51 (m, 5H), 3.21 (s, 3H), 2.93-2.90 (m, 1H), 2.57-2.53 (m, 2H), 2.46-2.41 (m, 2H), 2.02-1.98 (m, 1H), 1.80-1.75 (m, 1H) | 550.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| 619 | 1-(3-chloro-3'-(2-(4-cyclobutylpiperazin-1-yl)pyridin-4-yl)-5'-fluoro-2'-hydroxy-[1,1'-biphenyl]-4-yl)-3-methyl-1H-imidazol-2(3H)-one | ¹H NMR (400 MHz, DMSO-d₆): δ 8.70 (s, 1H), 8.15 (d, J = 5.2 Hz, 1H), 7.80 (d, J = 2.0 Hz, 1H), 7.61 (dd, J = 2.0, 8.0 Hz, 1H), 7.52 (d, J = 8.4 Hz, 1H), 7.26-7.18 (m, 2H), 6.94 (s, 1H), 6.83 (d, J = 4.8 Hz, 1H), 6.72 (d, J = 2.8 Hz, 1H), 6.68 (d, J = 2.8 Hz, 1H), 3.52 (br s, 4H), 3.21 (s, 3H), 2.74-2.70 (m, 1H), 2.33 (br s, 4H), 2.00-1.98 (m, 2H), 1.84-1.78 (m, 2H), 1.67-1.63 (m, 2H) | 534.2 |
| 620 | 1-(3'-(2-(4-(3-aminopropyl)piperazin-1-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 8.12 (d, J = 5.2 Hz, 1H), 7.88 (d, J = 2.0 Hz, 1H), 7.63 (dd, J = 2.0, 8.4 Hz, 1H), 7.48 (d, J = 8.0 Hz, 1H), 7.20-7.14 (m, 2H), 7.07 (s, 1H), 6.87 (d, J = 5.6 Hz, 1H), 6.71 (d, J = 2.8 Hz, 1H), 6.67 (d, J = 2.8 Hz, 1H), 3.50-3.49 (m, 4H), 3.21 (s, 3H), 2.57 (t, J = 6.4 Hz, 2H), 2.44 (t, J = 4.4 Hz, 4H), 2.34 (t, J = 7.6 Hz, 2H), 1.56-1.53 (m, 2H). N—H and O—H protons not observed | 537.2 |
| 621 | (S)-1-(3-chloro-3'-(2-(4-(2,3-dihydroxypropyl)piperazin-1-yl)pyridin-4-yl)-5'-fluoro-2'-hydroxy-[1,1'-biphenyl]-4-yl)-3-methyl-1H-imidazol-2(3H)-one | ¹H NMR (400 MHz, DMSO-d₆): δ 8.71 (s, 1H), 8.16 (d, J = 4.8 Hz, 1H), 7.80 (d, J = 2.0 Hz, | 554.3 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | | 1H), 7.62 (dd, J = 2.0, 8.4 Hz, 1H), 7.52 (d, J = 8.4 Hz, 1H), 7.26-7.18 (m, 2H), 6.96 (s, 1H), 6.84 (d, J = 4.8 Hz, 1H), 6.72 (d, J = 2.8 Hz, 1H), 6.69 (d, J = 3.2 Hz, 1H), 4.56-4.33 (m, 2H), 3.67 (s, 1H), 3.52 (br s, 4H), 3.35-3.34 (m, 2H), 3.21 (s, 3H), 2.56-2.51 (m, 4H), 2.35-2.32 (m, 2H) | |
| 622 | (R)-1-(3-chloro-5'-fluoro-2'-hydroxy-3'-(2-(3-hydroxypiperidin-1-yl)pyridin-4-yl)-[1,1'-biphenyl]-4-yl)-3-methyl-1H-imidazol-2(3H)-one | ¹H NMR (400 MHz, DMSO-d₆): δ 8.71 (s, 1H), 8.13 (d, J = 5.6 Hz, 1H), 7.81 (d, J = 1.6 Hz, 1H), 7.62 (dd, J = 2.0, 8.4 Hz, 1H), 7.52 (d, J = 8.0 Hz, 1H), 7.26-7.18 (m, 2H), 6.92 (s, 1H), 6.77 (d, J = 4.8 Hz, 1H), 6.72 (d, J = 2.8 Hz, 1H), 6.69 (d, J = 3.2 Hz, 1H), 4.83 (d, J = 4.8 Hz, 1H), 4.27-4.23 (m, 1H), 4.07-4.04 (m, 1H), 3.52-3.48 (m, 1H), 3.21 (s, 3H), 2.94-2.88 (m, 1H), 2.74-2.67 (m, 1H), 1.93-1.90 (m, 1H), 1.74-1.70 (m, 1H), 1.45-1.32 (m, 2H) | 495.2 |
| 623 | 1-(3'-(2-(1,4-diazepan-1-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 8.10 (d, J = 4.8 Hz, 1H), 7.80 (d, J = 2.0 Hz, 1H), 7.62 (dd, J = 2.0, 8.0 Hz, 1H), 7.52 (d, J = 8.0 Hz, 1H), 7.25-7.17 (m, 2H), 6.74-6.65 (m, 4H), 3.72-3.66 (m, 4H), 3.21 (s, 3H), 2.86 (t, J = 5.2 Hz, 2H), 2.69 (t, J = 6.0 Hz, 2H), 1.79-1.76 (m, 2H). N—H and O—H protons not observed | 494.2 |

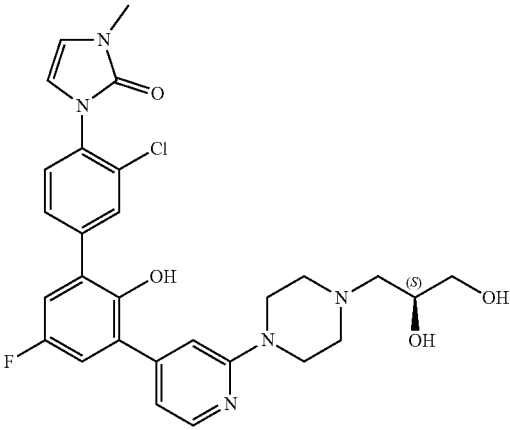

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| 624 | 1-(3-chloro-5'-fluoro-3'-(2-(hexahydro-1H-pyrido[1,2-a]pyrazin-2(6H)-yl)pyridin-4-yl)-2'-hydroxy-[1,1'-biphenyl]-4-yl)-3-methyl-1H-imidazol-2(3H)-one | $^1$H NMR (400 MHz, DMSO-d$_6$): δ 8.71 (s, 1H), 8.15 (d, J = 4.8 Hz, 1H), 7.80 (d, J = 2.0 Hz, 1H), 7.62 (dd, J = 2.0, 8.0 Hz, 1H), 7.52 (d, J = 8.0 Hz, 1H), 7.26-7.18 (m, 2H), 6.95 (s, 1H), 6.82 (d, J = 5.2 Hz, 1H), 6.72 (d, J = 3.2 Hz, 1H), 6.68 (d, J = 3.2 Hz, 1H), 4.24-4.15 (m, 2H), 3.21 (s, 3H), 2.89-2.75 (m, 3H), 2.50-2.44 (m, 1H), 2.16-2.10 (m, 1H), 1.97-1.84 (m, 2H), 1.73-7.70 (m, 1H), 1.63-1.47 (m, 3H), 1.27-1.15 (m, 2H) | 534.2 |
| 625 | 1-(3-chloro-5'-fluoro-3'-(2-(hexahydropyrrolo[1,2-a]pyrazin-2(1H)-yl)pyridin-4-yl)-2'-hydroxy-[1,1'-biphenyl]-4-yl)-3-methyl-1H-imrdazol-2(3H)-one | $^1$H NMR (400 MHz, DMSO-d$_6$): δ 8.71 (s, 1H), 8.15 (d, J = 5.2 Hz, 1H), 7.80 (d, J = 2.0 Hz, 1H), 7.62 (dd, J = 1.6, 8.4 Hz, 1H), 7.52 (d, J = 8.4 Hz, 1H), 7.26-7.19 (m, 2H), 6.97 (s, 1H), 6.82 (d, J = 5.2 Hz, 1H), 6.72 (d, J = 2.8 Hz, 1H), 6.69 (d, J = 3.2 Hz, 1H), 4.45 (d, J = 11.6 Hz, 1H), 4.28 (d, J = 12.8 Hz, 1H), 3.21 (s, 3H), 3.06-3.00 (m, 2H), 2.88-2.83 (m, 1H), 2.54-2.51 (m, 1H), 2.16-2.02 (m, 2H), 1.94-1.65 (m, 4H), 1.39-1.35 (m, 1H) | 520.2 |
| 626 | (S)-1-(3-chloro-5'-fluoro-2'-hydroxy-3'-(2-(3-hydroxypyrrolidin-1-yl)pyridin-4-yl)-[1,1'-biphenyl]-4-yl)-3-methyl-1H-imidazol-2(3H)-one | $^1$H NMR (400 MHz, DMSO-d$_6$): δ 8.69 (s, 1H), 8.10 (d, J = 5.2 Hz, 1H), 7.81 (s, 1H), 7.62 (d, J = | 481.1 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | 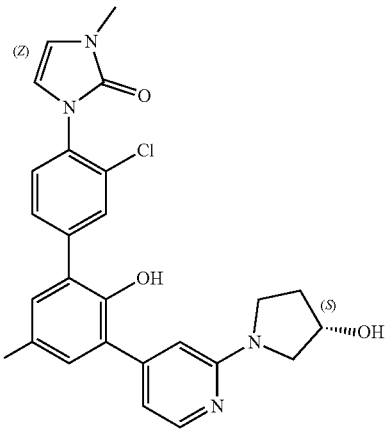 | 8.4 Hz, 1H), 7.52 (d, J = 8.4 Hz, 1H), 7.25-7.17 (m, 2H), 6.72-6.69 (m, 3H), 6.57 (s, 1H), 4.95 (s, 1H), 4.40 (s, 1H), 3.54-3.47 (m, 3H), 3.36-3.33 (m, 1H), 3.21 (s,3H), 2.03-1.92 (m, 2H) | |
| 627 | (R)-1-(3-chloro-5'-fluoro-2'-hydroxy-3'-(2-(3-hydroxypyrrolidin-1-yl)pyridin-4-yl)-[1,1'-biphenyl]-4-yl)-3-methyl-1H-imidazol-2(3H)-one 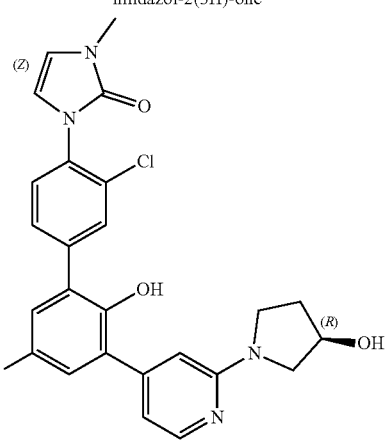 | ¹H NMR (400 MHz, DMSO-d₆): δ 8.67 (s, 1H), 8.10 (d, J = 5.2 Hz, 1H), 7.81 (d, J = 1.6 Hz, 1H), 7.62 (dd, J = 2.0, 8.4 Hz, 1H), 7.52 (d, J = 8.0 Hz, 1H), 7.25-7.18 (m, 2H), 6.72-6.68 (m, 3H), 6.57 (s, 1H), 4.93 (d, J = 3.6 Hz, 1H), 4.40 (br s, 1H), 3.54-3.47 (m, 3H), 3.36-3.31 (m, 1H), 3.18 (s, 3H), 2.06-1.99 (m, 1H), 1.91-1.87 (m, 1H) | 481.2 |
| 628 | (S)-1-(3-chloro-5'-fluoro-2'-hydroxy-3'-(2-(3-hydroxypiperidin-1-yl)pyridin-4-yl)-[1,1'-biphenyl]-4-yl)-3-methyl-1H-imidazol-2(3H)-one 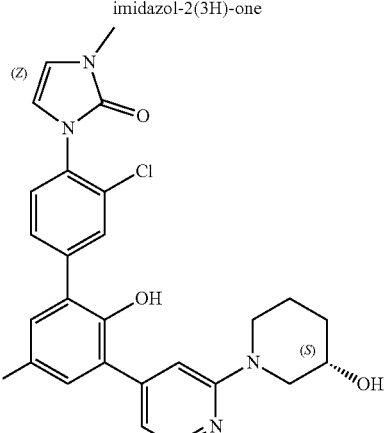 | ¹H NMR (400 MHz, DMSO-d₆): δ 8.70 (s, 1H), 8.12 (d, J = 5.6 Hz, 1H), 7.81 (d, J = 2.0 Hz, 1H), 7.62 (dd, J = 2.4, 8.8 Hz, 1H), 7.52 (d, J = 8.4 Hz, 1H), 7.26-7.18 (m, 2H), 6.92 (s, 1H), 6.77 (dd, J = 1.2, 5.2 Hz, 1H), 6.72 (d, J = 2.8 Hz, 1H), 6.69 (d, J = 3.2 Hz, 1H), 4.82 (d, J = 4.4 Hz, 1H), 4.24 (dd, J = 3.6, 12.4 Hz, 1H), 4.07-4.04 (m, 1H), 3.52-3.47 (m, 1H), 3.21 (s, 3H), 2.94-2.88 (m, 1H), 2.75-2.67 (m, 1H), 1.92-1.86 (m, 1H), 1.74-1.70 (m, 1H), 1.45-1.35 (m, 2H) | 495.1 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| 629 | 1-(3'-(2-(4-benzylpiperazin-1-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 8.70 (s, 1H), 8.15 (d, J = 5.2 Hz, 1H), 7.80 (d, J = 1.6 Hz, 1H), 7.61 (dd, J = 2.0, 8.4 Hz, 1H), 7.52 (d, J = 8.0 Hz, 1H), 7.34 (d, J = 4.4Hz, 4H), 7.28-7.17 (m, 3H), 6.94 (s, 1H), 6.83 (d, J = 4.8 Hz, 1H), 6.72 (d, J = 3.2 Hz, 1H), 6.68 (d, J = 2.8 Hz, 1H), 3.54-3.53 (m, 6H), 3.21 (s, 3H), 2.50-2.46 (m, 4H) | 570.2 |
| 630 | (R)-5-(3'-chloro-5-fluoro-2-hydroxy-4'-(3-methyl-2-oxo-2,3-dihydro-IH-imidazol-1-yl)-[1,1'-biphenyl]-3-yl)-1-(3-hydroxypropyl)-3-(3-methylpiperazin-1-yl)pyridin-2(1H)-one | ¹H NMR (400 MHz, DMSO-d₆): δ 7.80 (d, J = 2.0 Hz, 1H), 7.61 (dd, J = 2.0, 8.0 Hz, 1H), 7.52-7.50 (m, 2H), 7.19-7.13 (m, 2H), 6.86 (d, J = 2.4 Hz, 1H), 6.72 (d, J = 2.8 Hz, 1H), 6.68 (d, J = 2.8 Hz, 1H), 4.73-4.38 (m, 1H), 3.99 (t, J = 6.8 Hz, 2H), 3.58 (t, J = 10.8 Hz, 2H), 3.44 (t, J = 6.0 Hz, 2H), 3.21 (s, 3H), 2.90-2.78 (m, 3H), 2.41-2.36 (m, 1H), 2.05 (t, J = 10.8 Hz, 1H), 1.84-1.79 (m, 2H), 0.97 (d, J = 6.4 Hz, 3H). N—H or O—H protons not observed | 568.2 |
| 631 | 1-(3-chloro-5'-fluoro-2'-hydroxy-3'-(2-(3-phenylpiperazin-1-yl)pyridin-4-yl)-[1,1 biphenyl]-4-yl)-3-methyl-1H-imidazol-2(3H)-one | ¹H NMR (400 MHz, DMSO-d₆): δ 8.67 (br s, 1H), 8.16 (d, J = 5.2 Hz, 1H), 7.80 (d, J = 2.0 Hz, | 556.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | | 1H), 7.61 (dd, J = 2.0, 8.0 Hz, 1H), 7.53-7.47 (m, 3H), 7.37-7.19 (m, 5H), 6.98 (s, 1H), 6.83 (d, J = 4.8 Hz, 1H), 6.71 (d, J = 3.2 Hz, 1H), 6.68 (d, J = 2.8 Hz, 1H), 4.31-4.24 (m, 2H), 3.76 (d, J = 12.8 Hz, 2H), 3.21 (s, 3H), 3.10-3.08 (m, 1H), 2.87-2.85 (m, 2H), 2.67-2.61 (m, 1H) | |
| 632 | (S)-1-(3-chloro-5'-fluoro-2'-hydroxy-3'-(2-(3-methylpiperidin-1-yl)pyridin-4-yl)-[1,1'-biphenyl]-4-yl)-3-methyl-1H-imidazol-2(3H)-one | ¹H NMR (400 MHz, DMSO-$d_6$): δ 8.69 (s, 1H), 8.13 (d, J = 5.2 Hz, 1H), 7.80 (d, J = 2.0 Hz, 1H), 7.62 (dd, J = 2.4, 8.4 Hz, 1H), 7.52 (d, J = 8.4 Hz, 1H), 7.26-7.18 (m, 2H), 6.94 (s, 1H), 6.77 (d, J = 4.8 Hz, 1H), 6.72 (d, J = 2.8 Hz, 1H), 6.68 (d, J = 3.2 Hz, 1H), 4.28-4.24 (m, 2H), 3.21 (s, 3H), 2.81-2.75 (m, 1H), 2.45-2.38 (m, 1H), 1.81-1.44 (m, 4H), 1.16-1.10 (m, 1H), 0.91 (d, J = 6.8 Hz, 3H) | 493.1 |
| 633 | 1-(3-chloro-5'-fluoro-2'-hydroxy-3'-(2-(4-(3-methoxypropyl)piperazin-1-yl)pyridin-4-yl)-[1,1'-biphenyl]-4-yl)-3-methyl-1H-imidazol-2(3H)-one | ¹H NMR (400 MHz, DMSO-$d_6$): δ 8.70 (s, 1H), 8.16 (d, J = 5.2 Hz, 1H), 7.80 (d, J = 1.6 Hz, 1H), 7.62 (dd, J = 2.4, 8.0 Hz, 1H), 7.52 (d, J = 8.4 Hz, 1H), 7.26-7.18 (m, 2H), 6.95 (s, 1H), 6.83 (d, J = 5.2 Hz, 1H), 6.72 (d, J = 3.2 Hz, 1H), 6.68 (d, J = 3.2 Hz, 1H), 3.52 (br s, 4H), 3.36 (t, J = 6.4 Hz, 2H), 3.31 (s, 3H), 3.21 (s, 3H), 2.45 (br s, 4H), 2.36 (t, J = 7.2 Hz, 2H), 1.73-1.66 (m, 2H) | 552.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| 634 | 1-(3-chloro-5'-fluoro-2'-hydroxy-3'-(2-(4-(tetrahydro-2H-pyran-4-yl)piperazin-1-yl)pyridin-4-yl)-[1,1'-biphenyl]-4-yl)-3-methyl-1H-imidazol-2(3H)-one | $^1$H NMR (400 MHz, CD$_3$OD): δ 8.02 (d, J = 6.8 Hz, 1H), 7.70 (d, J = 2.0 Hz, 1H), 7.59 (s, 1H), 7.51 (dd, J = 2.0, 8.0 Hz, 1H), 7.45 (d, J = 8.0 Hz, 1H), 7.38 (d, J = 6.8 Hz, 1H), 7.27 (dd, J = 3.2, 8.8 Hz, 1H), 7.16 (dd, J = 3.2, 8.8 Hz, 1H), 6.59 (d, J = 3.2 Hz, 1H), 6.54 (d, J = 3.2 Hz, 1H), 4.41-4.32 (m, 2H), 4.01 (dd, J = 4.0, 11.6 Hz, 2H), 3.74 (br s, 4H), 3.61-3.48 (m, 1H), 3.46-3.34 (m, 4H), 3.26 (s, 3H), 2.08-2.05 (m, 2H), 1.92-1.73 (m, 2H). N—H or O—H protons not observed | 564.3 |
| 635 | (S)-1-(3-chloro-5'-fluoro-2'-hydroxy-3'-(2-(3-morpholinopyrrolidin-1-yl)pyridin-4-yl)-[1,1'-biphenyl]-4-yl)-3-methyl-1H-imidazol-2(3H)-one | $^1$H NMR (400 MHz, DMSO-d$_6$): δ 8.68 (s, 1H), 8.10 (d, J = 5.2 Hz, 1H), 7.81 (d, J = 2.0 Hz, 1H), 7.61 (dd, J = 2.0, 8.0 Hz, 1H), 7.52 (d, J = 8.0 Hz, 1H), 7.25-7.17 (m, 2H), 6.74 (dd, J = 1.2, 5.6 Hz, 1H), 6.72 (d, J = 3.2 Hz, 1H), 6.69 (d, J = 3.2 Hz, 1H), 6.60 (s, 1H), 3.76-3.72 (m, 1H), 3.65-3.60 (m, 5H), 3.40-3.29 (m, 2H), 3.21 (s, 3H), 3.19-3.15 (m, 1H), 2.90-2.88 (m, 1H), 2.46-2.40 (m, 3H), 2.22-2.17 (m, 1H), 1.83-1.78 (m, 1H). | 550.2 |
| 636 | 1-(3'-(2-(1,7-diazaspiro[4.4]nonan-7-yl)pyridin-4-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 8.09 (d, J = 4.8 Hz, 1H), 7.81 (s, 1H), 7.62 (d, J = 8.0 Hz, 1H), 7.52 (d, J = 8.4 Hz, 1H), 7.24-7.17 (m, 2H), 6.72-6.69 (m, 3H), 6.54 (s, 1H), 3.50-3.49 (m, 2H), 3.34 (br s, 2H), 3.21 (s, 3H), 2.87-2.86 (m, 2H), 1.91 (br s, 2H), 1.74-1.68 (m, 4H). N—H and O—H protons not observed | 520.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| 637 | 1-(3-chloro-5'-fluoro-2'-hydroxy-3'-(2-(1-methyl-1,7-diazaspiro[4.4]nonan-7-yl)pyridin-4-yl)-[1,1'-biphenyl]-4-yl)-3-methyl-1H-imidazol-2(3H)-one | ¹H NMR (400 MHz, DMSO-d₆): δ 8.68 (s, 1H), 8.10 (d, J = 5.2 Hz, 1H), 7.80 (d, J = 1.2 Hz, 1H), 7.63-7.60 (m, 1H), 7.52 (d, J = 8.4 Hz, 1H), 7.25-7.18 (m, 2H), 6.74-6.68 (m, 3H), 6.58 (s, 1H), 3.62 (t, J = 8.0 Hz, 1H), 3.43-3.32 (m, 2H), 3.21-3.17 (m, 4H), 2.74-2.67 (m, 2H), 2.26 (s,3H), 2.10-2.07 (m, 1H), 1.77-1.654 (m, 5H) | 534.2 |
| 638 | (R)-1-(3-chloro-5'-fluoro-2'-hydroxy-3'-(2-(3-hydroxypropoxy)-6-(3-methylpiperazin-1-yl)pyridin-4-yl)-[1,1'-biphenyl]-4-yl)-3-methyl-1H-imidazol-2(3H)-one | ¹H NMR (400 MHz, DMSO-d₆): δ 7.80 (d, J = 1.6 Hz, 1H), 7.61 (dd, J = 2.0, 8.0 Hz, 1H), 7.22 (dd, J = 3.2, 9.2 Hz, 1H), 7.15 (dd, J = 3.2, 8.8 Hz, 1H), 6.71 (d, J = 3.2 Hz, 1H), 6.89 (d, J = 3.2 Hz, 1H), 6.41 (s, 1H), 6.17 (s, 1H), 4.50 (brs, 1H), 4.27 (t, J = 6.4 Hz, 2H), 4.14-4.08 (m, 2H), 3.55 (t, J = 6.0 Hz, 2H), 3.21 (s, 3H), 2.96-2.94 (m, 1H), 2.74-2.66 (m, 3H), 2.38-2.33 (m, 1H), 1.90-1.82 (m, 2H), 1.03 (d, J = 6.4 Hz, 3H). N—H and O—H protons not observed | 568.2 |
| 639 | (S)-1-(3-chloro-5'-fluoro-2'-hydroxy-3'-(2-(3-(2-hydroxypropan-2-yl)piperazin-1-yl)pyridin-4-yl)-[1,1'-biphenyl]-4-yl)-3-methyl-1H-imidazol-2(3H)-one | ¹H NMR (400 MHz, DMSO-d₆): δ 8.15 (d, J = 4.8 Hz, 1H), 7.80 (d, J = 1.6 Hz, 1H), 7.62 (dd, J = | 538.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| | 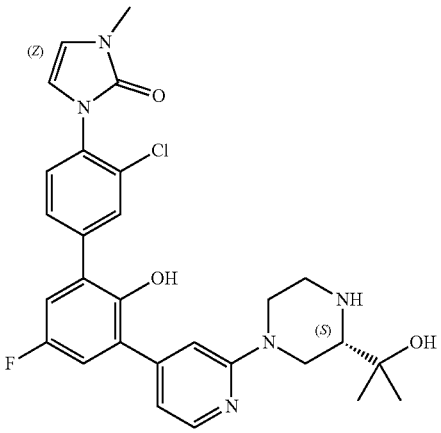 | 1.6, 8.0 Hz, 1H), 7.52 (d, J = 8.4 Hz, 1H), 7.24 (dd, J = 2.8, 8.8 Hz, 1H), 7.19 (dd, J = 2.8, 8.8 Hz, 1H), 6.91 (s, 1H), 6.80 (d, J = 3.2 Hz, 1H), 6.72 (d, J = 3.2 Hz, 1H), 6.68 (d, J = 2.8 Hz, 1H), 4.42 (br s, 1H), 4.34-4.32 (m, 1H), 4.16-4.14 (m, 1H), 3.21 (s, 3H), 3.05-3.03 (m, 1H), 2.73-2.66 (m, 2H), 2.46-2.42 (m, 2H), 1.14 (d, J = 8.4 Hz, 6H). Two N—H or O—H proton not observed | |
| 640 | 1-(3-chloro-5'-fluoro-2'-hydroxy-3'-(2-(3-(2-hydroxyethyl)piperazin-1-yl)pyridin-4-yl)-[1,1'-biphenyl]-4-yl)-3-methyl-1H-imidazol-2(3H)-one | $^1$H NMR (400 MHz, DMSO-d$_6$): δ 8.15 (d, J = 5.2 Hz, 1H), 7.81 (d, J = 2.4 Hz, 1H), 7.82 (dd, J = 2.4, 8.0 Hz, 1H), 7.52 (d, J = 8.4 Hz, 1H), 7.24 (dd, J = 3.6, 9.2 Hz, 1H), 7.19 (dd, J = 3.2, 8.8 Hz, 1H), 6.92 (s, 1H), 6.81 (dd, J = 0.8, 4.8 Hz, 1H), 6.72 (d, J = 3.2 Hz, 1H), 6.69 (d, J = 2.8 Hz, 1H), 4.20-4.10 (m, 2H), 3.55 (t, J = 6.0 Hz, 2H), 3.21 (s, 3H), 2.98-2.95 (m, 1H), 2.78-2.66 (m, 3H), 2.50-2.40 (m, 1H), 1.55-1.50 (m, 2H). N—H and O—H protons not observed | 524.2 |
| 641 | 1-(3'-(2-(1,6-diazaspiro[3.4]octan-6-yl)pyridin-4-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 8.10 (d, J = 5.6 Hz, 1H), 7.81 (s, 1H), 7.62 (d, J = 8.0 Hz, 1H), 7.52 (d, J = 8.4 Hz, 1H), 7.24 (dd, J = 3.2, 9.2 Hz, 1H), 7.18 (dd, J = 3.2, 8.8 Hz, 1H), 6.74-6.68 (m, 3H), 6.57 (s, 1H), 3.53-3.28 (m, 6H), 3.21 (s, 3H), 2.31-2.21 (m, 2H), 2.11 (t, J = 6.8 Hz, 2H). Two N—H and O—H proton not observed | 506.1 |

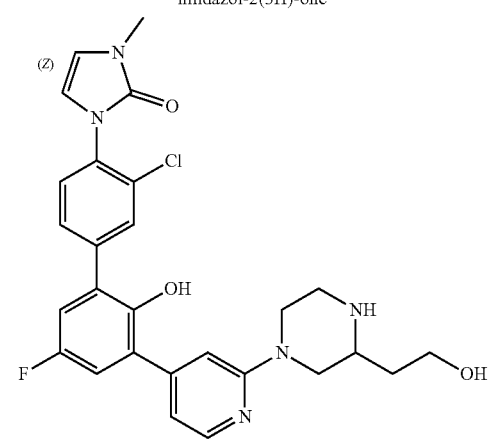

TABLE 29-continued

Following compounds were prepared using similar procedures as described for Examples 365-563.

| Ex. No. | Name/Structure | ¹H NMR Data | LCMS (M + H)⁺ |
|---|---|---|---|
| 642 | 1-(3-chloro-5'-fluoro-2'-hydroxy-3'-(2-(1-methyl-1,6-diazaspiro[3.4]octan-6-yl)pyridin-4-yl)-[1,1'-biphenyl]-4-yl)-3-methyl-1H-imidazol-2(3H)-one | ¹H NMR (400 MHz, DMSO-d₆): δ 8.69 (s, 1H), 8.11 (d, J = 5.2 Hz, 1H), 7.81 (d, J = 1.6 Hz, 1H), 7.62 (dd, J = 2.0, 8.4 Hz, 1H), 7.52 (d, J = 8.4 Hz, 1H), 7.26-7.18 (m, 2H), 6.75-6.68 (m, 3H), 6.58 (s, 1H), 3.58-3.52 (m, 2H), 3.41-3.35 (m, 2H), 3.21 (s, 3H), 3.16-3.02 (m, 2H), 2.18-1.97 (m, 7H) | 520.2 |
| 643 | 1-(3-chloro-3'-(2-(3-cyclopropylpiperazin-1-yl)pyridin-4-yl)-5'-fluoro-2'-hydroxy-[1,1'-biphenyl]-4-yl)-3-methyl-1H-imidazol-2(3H)-one | ¹H NMR (400 MHz, DMSO-d₆): δ 8.15 (d, J = 4.8 Hz, 1H), 7.81 (d, J = 1.6 Hz, 1H), 7.62 (dd, J = 1.6, 8.0 Hz, 1H), 7.52 (d, J = 8.0 Hz, 1H), 7.26-7.18 (m, 2H), 6.93 (s, 1H), 6.82-6.81 (m, 1H), 6.72 (d, J = 2.8 Hz, 1H), 6.68 (d, J = 3.6 Hz, 1H), 4.24 (d, J = 10.8 Hz, 1H), 4.09 (d, J = 11.6 Hz, 1H), 3.21 (s,3H), 2.97 (d, J = 11.6 Hz, 1H), 2.79-2.55 (m, 3H), 1.90-1.85 (m, 1H), 0.78-0.73 (m, 1H), 0.43-0.40 (m, 2H), 0.26-0.25 (m, 2H). N—H and O—H protons not observed | 520.2 |
| 644 | (R)-2-(4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)piperazin-2-yl)acetamide | ¹H NMR (400 MHz, DMSO-d₆): δ 8.15 (d, J = 5.2 Hz, 1H), 7.80 (d, J = 2.0 Hz, 1H), 7.62 (dd, J = 0.8, 8.0 Hz, 1H), 7.52 (d, J = 8.0 Hz, 1H), 7.42 (br s, 1H), 7.26-7.17 (m, 2H), 6.91 (s, 1H), 6.85 (br s, 1H), 6.82 (d, J = 5.2 Hz, 1H), 6.72 (d, J = 2.8 Hz, 1H), 6.69 (d, J = 2.4 Hz, 1H), 4.20 (d, J = 11.6 Hz, 1H), 4.08 (d, J = 10.8 Hz, 1H), 3.21 (s, 3H), 2.98-2.93 (m, 2H), 2.77-2.67 (m, 2H), 2.48-2.42 (m, 1H), 2.24-2.13 (m, 2H). N—H and O—H protons not observed | 537.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| 645 | 1-(3-chloro-5'-fluoro-2'-hydroxy-3'-(2-(4-(2-methoxyethyl)piperazin-1-yl)pyridin-4-yl)-[1,1'-biphenyl]-4-yl)-3-methyl-1H-imidazol-2(3H)-one | $^1$H NMR (400 MHz, DMSO-d$_6$): δ 8.70 (s, 1H), 8.16 (d, J = 4.8 Hz, 1H), 7.81 (d, J = 1.6 Hz, 1H), 7.62 (dd, J = 1.6, 8.0 Hz, 1H), 7.52 (d, J = 8.0 Hz, 1H), 7.26-7.18 (m, 2H), 6.95 (s, 1H), 6.84 (d, J = 5.2 Hz, 1H), 6.72 (d, J = 2.8 Hz, 1H), 6.69 (d, J = 3.2 Hz, 1H), 3.52-3.46 (m, 6H), 3.25 (s, 3H), 3.21 (s, 3H), 2.52-2.50 (m, 6H) | 538.2 |
| 646 | 1-(3-chloro-3'-(2-(4-(cyclobutylmethyl)piperazin-1-yl)pyridin-4-yl)-5'-fluoro-2'-hydroxy-[1,1'-biphenyl]-4-yl)-3-methyl-1H-imidazol-2(3H)-one | $^1$H NMR (400 MHz, DMSO-d$_6$): δ 8.70 (s, 1H), 8.15 (d, J = 4.8 Hz, 1H), 7.80 (d, J = 1.6 Hz, 1H), 7.61 (dd, J = 2.4, 8.0 Hz, 1H), 7.52 (d, J = 8.0 Hz, 1H), 7.26-7.18 (m, 2H), 6.94 (s, 1H), 6.83 (d, J = 5.2 Hz, 1H), 6.72 (d, J = 2.8 Hz, 1H), 6.69 (d, J = 2.8 Hz, 1H), 3.50 (brs, 4H), 3.21 (s, 3H), 2.55-2.50 (m, 1H), 2.42-2.36 (m, 6H), 2.07-2.02 (m, 2H), 1.87-1.78 (m, 2H), 1.70-1.63 (m, 2H) | 548.3 |
| 647 | 1-(3-chloro-5'-fluoro-3'-(2-(hexahydropyrazino[2,1-c][1,4]oxazin-8(1H)-yl)pyridin-4-yl)-2'-hydroxy-[1,1'-biphenyl]-4-yl)-3-methyl-1H-imidazol-2(3H)-one | $^1$H NMR (400 MHz, DMSO-d$_6$): δ 8.71 (s, 1H), 8.16 (d, J = 5.2 Hz, 1H), 7.80 (d, J = 1.6 Hz, 1H), 7.62 (dd, J = 2.0, 8.4 Hz, | 536.2 |

TABLE 29-continued

Following compounds were prepared using similar procedures as described for Examples 365-563.

| Ex. No. | Name/Structure | ¹H NMR Data | LCMS (M + H)⁺ |
|---|---|---|---|
| | | 1H), 7.52 (d, J = 8.4 Hz, 1H), 7.26-7.18 (m, 2H), 6.97 (s, 1H), 6.85 (d, J = 5.2 Hz, 1H), 6.72 (d, J = 2.8 Hz, 1H), 6.69 (d, J = 2.8 Hz, 1H), 4.28-4.24 (m, 1H), 4.17-4.14 (m, 1H), 3.77 (dd, J = 2.0, 10.4 Hz, 1H), 3.57-3.52 (m, 1H), 3.21-3.14 (m, 4H), 2.91-2.80 (m, 2H), 2.70-2.67 (m, 1H), 2.43-2.33 (m, 1H), 2.24-2.07 (m, 3H). O—H proton not observed | |
| 648 | 1-(3-chloro-5'-fluoro-3'-(2-(hexahydropyrrolo[3,4-b][1,4]oxazin-6(2H)-yl)pyridin-4-yl)-2'-hydroxy-[1,1'-biphenyl]-4-yl)-3-methyl-1H-imidazol-2(3H)-one 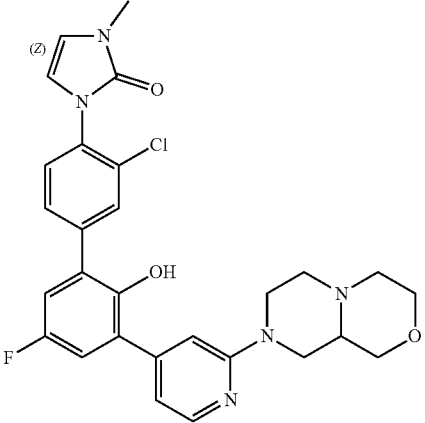 [SMILES: Cn1ccn(-c2ccc(-c3cc(F)cc(-c4ccnc(N5CCN6CCOCC6C5)c4)c3O)cc2Cl)c1=O] | ¹H NMR (400 MHz, DMSO-d₆): δ 8.68 (br s, 1H), 8.10 (d, J = 5.2 Hz, 1H), 7.80 (d, J = 2.0 Hz, 1H), 7.62 (dd, J = 2.0, 8.4 Hz, 1H), 7.52 (d, J = 8.0 Hz, 1H), 7.25-7.18 (m, 2H), 6.74-6.68 (m, 3H), 6.57 (s, 1H), 3.97 (s, 1H), 3.68 (d, J = 11.2 Hz, 1H), 3.54-3.41 (m, 6H), 3.21 (s, 3H), 2.97-2.90 (m, 1H), 2.56-2.50 (m, 1H). N—H or O—H proton not observed | 522.1 |
| 649 | 1-(3-chloro-5'-fluoro-2'-hydroxy-3'-(2-(4-methylHexahydropyrrolo[3,4-b][1,4]oxazin-6(2H)-yl)pyridin-4-yl)-[1,1'-biphenyl]-4-yl)-3-methyl-1H-imidazol-2(3H)-one 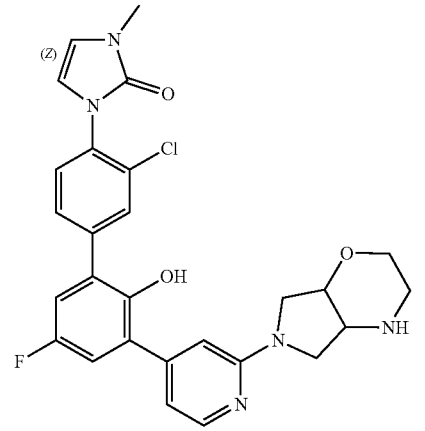 | ¹H NMR (400 MHz, DMSO-d₆): δ 8.69 (s, 1H), 8.10 (d, J = 5.2 Hz, 1H), 7.80 (d, J = 1.6 Hz, 1H), 7.62 (dd, J = 2.0, 8.0 Hz, 1H), 7.52 (d, J = 8.0 Hz, 1H), 7.26-7.18 (m, 2H), 6.75-6.68 (m, 3H), 6.59 (s, 1H), 4.10 (d, J = 2.4 Hz, 1H), 3.78-3.75 (m, 1H), 3.57-3.52 (m, 4H), 3.43-3.37 (m, 2H), 3.21 (s, 3H), 2.62-2.60 (m, 1H), 2.41-2.38 (m, 1H), 2.34 (s, 3H) | 536.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| 650 | (R)-1-(3-chloro-5'-fluoro-2'-hydroxy-3'-(6-(3-methylpiperazin-1-yl)pyridazin-4-yl)-[1,1'-biphenyl]-4-yl)-3-methyl-1H-imidazol-2(3H)-one | $^1$H NMR (400 MHz, DMSO-d$_6$): δ 8.75 (d, J = 1.6 Hz, 1H), 7.85 (s, 1H), 7.63 (dd, J = 2.0, 8.4 Hz, 1H), 7.52 (d, J = 8.4 Hz, 1H), 7.40 (s, 1H), 7.34-7.28 (m, 2H), 6.72 (d, J = 2.8 Hz, 1H), 6.68 (d, J = 3.2 Hz, 1H), 4.28-4.25 (m, 2H), 3.21 (s, 3H), 2.99-2.96 (m, 1H), 2.82-2.71 (m, 3H), 2.45-2.42 (m, 1H), 1.04 (d, J = 4.8 Hz, 3H). Two N—H and O—H proton not observed | 495.1 |
| 651 | 1-(3-chloro-5'-fluoro-2'-hydroxy-3'-(2-(4-neopentylpiperazin-1-yl)pyridin-4-yl)-[1,1'-biphenyl]-4-yl)-3-methyl-1H-imidazol-2(3H)-one | $^1$H NMR (400 MHz, DMSO-d$_6$): δ 8.71 (s, 1H), 8.15 (d, J = 5.2 Hz, 1H), 7.80 (d, J = 1.6 Hz, 1H), 7.63-7.60 (m, 1H), 7.52 (d, J = 8.4 Hz, 1H), 7.25-7.19 (m, 2H), 6.93 (s, 1H), 6.83 (d, J = 4.8 Hz, 1H), 6.72 (d, J = 2.8 Hz, 1H), 6.69 (d, J = 2.8 Hz, 1H), 3.52 (br s, 4H), 3.21 (s, 3H), 2.58-2.57 (m, 4H), 2.10(s, 2H), 0.89 (s, 9H) | 550.2 |
| 652 | 3-(4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)piperazin-1-yl)-2,2-dimethylpropanenitrile | $^1$H NMR (400 MHz, DMSO-d$_6$): δ 8.71 (s, 1H), 8.16 (d, J = 5.2 Hz, 1H), 7.81 (d, J = 1.6 Hz, 1H), 7.62 (dd, J = 2.0, 8.4 Hz, | 561.2 |

TABLE 29-continued

Following compounds were prepared using similar procedures as described for Examples 365-563.

| Ex. No. | Name/Structure | $^1$H NMR Data | LCMS (M + H)$^+$ |
|---|---|---|---|
| | 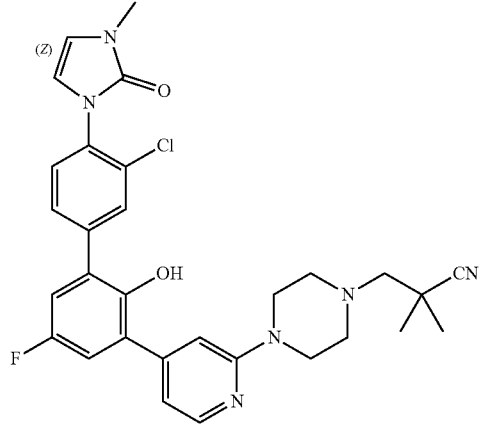 [SMILES: Cn1ccn(-c2ccc(-c3cc(F)cc(-c4ccnc(N5CCN(CC(C)(C)C#N)CC5)c4)c3O)cc2Cl)c1=O] | 1H), 7.52 (d, J = 8.0 Hz, 1H), 7.26-7.19 (m, 2H), 6.96 (s, 1H), 6.85 (d, J = 4.8 Hz, 1H), 6.72 (d, J = 3.2 Hz, 1H), 6.69 (d, J = 3.2 Hz, 1H), 3.56 (t, J = 4.4 Hz, 4H), 3.21 (s, 3H), 2.69 (t, J = 4.4 Hz, 4H), 2.50-2.49 (m, 2H), 1.10 (s, 6H) | |
| 653 | 1-(3-chloro-5'-fluoro-2'-hydroxy-3'-(2-(piperidin-3-yl)pyridin-4-yl)-[1,1'-biphenyl]-4-yl)-3-methyl-1H-imidazol-2(3H)-one 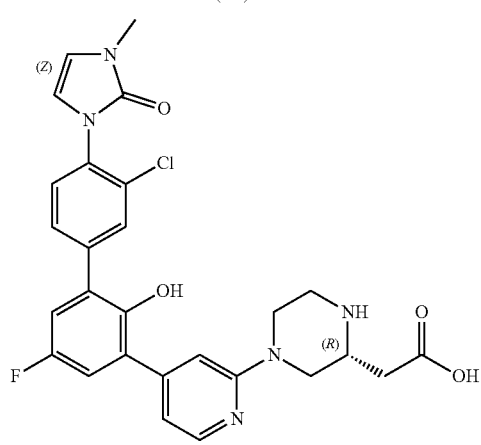 | $^1$H NMR (400 MHz, DMSO-d$_6$): δ 8.12 (d, J = 5.6 Hz, 1H), 7.70 (d, J = 1.6 Hz, 1H), 7.51 (dd, J = 2.0, 8.4 Hz, 1H), 7.42 (d, J = 8.0 Hz, 1H), 7.13-6.99 (m, 4H), 5.58 (d, J = 3.2 Hz, 1H), 5.54 (d, J = 3.2 Hz, 1H), 4.38-4.29 (m, 2H), 3.68-3.67 (m, 1H), 3.44-3.27 (m, 2H), 3.25 (s, 3H), 3.22-3.03 (m, 2H), 2.68-2.64 (m, 2H). N—H and O—H protons not observed | 538.2 |

Example 654

1-(3-chloro-5'-fluoro-2'-hydroxy-3'-(2-(piperidin-3-yl)pyridin-4-yl)-[1,1'-biphenyl]-4-yl)-3-methyl-1H-imidazol-2(3H)-one

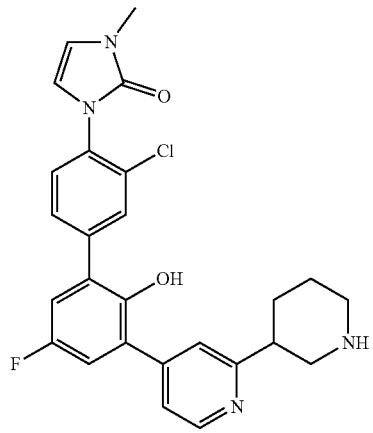 [SMILES: Cn1ccn(-c2ccc(-c3cc(F)cc(-c4ccnc(C5CCCNC5)c4)c3O)cc2Cl)c1=O]

Step 1: tert-butyl 4-chloro-5',6'-dihydro-[2,3'-bipyridine]-1'(2'H)-carboxylate The title compound was prepared following the procedures described for Example 504 using 2-bromo-4-chloropyridine and tert-butyl 3-(4,4,5,5-tetramethyl-1,3,2-dioxaborolan-2-yl)-5,6-dihydropyridine-1(2H)-carboxylate to afford the title compound. LCMS: 295.1 (M+H)$^+$

Step 2: (1'-(tert-butoxycarbonyl)-1',2',5',6'-tetrahydro-[2,3'-bipyridin]-4-yl)boronic acid The title compound was prepared following the procedure described for Example 504 using tert-butyl 4-chloro-5',6'-dihydro-[2,3'-bipyridine]-1'(2'H)-carboxylate and 4,4,4',4',5,5,5',5'-octamethyl-2,2'-bi(1,3,2-dioxaborolane) to afford the title compound. LCMS: 305.2 (M+H)$^+$.

Step 3: tert-butyl 4-(3'-chloro-5-fluoro-2-methoxy-4'-(3-methyl-2-oxo-2,3-dihydro-1H-imidazol-1-yl)-[1,1'-biphenyl]-3-yl)-5',6'-dihydro-[2,3'-bipyridine]-1'(2'H)-carboxylate The title compound was prepared following the procedure described for Example 504 using 1-(3'-bromo-3-chloro-5'-fluoro-2'-methoxy-[1,1'-biphenyl]-4-yl)-3-methyl-1H-imidazol-2(3H)-one and (1'-(tert-butoxycarbonyl)-1',2',5',6'-tetrahydro-[2,3'-bipyridin]-4-yl)boronic acid to afford the title compound. LCMS: 591.2 (M+H)$^+$.

Step 4: tert-butyl 3-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperidine-1-carboxylate To a solution of tert-butyl 4-(3'-chloro-5-fluoro-2-methoxy-4'-(3-methyl-2-oxo-2,3-dihydro-1H-imidazol-1-yl)-[1,1'-biphenyl]-3-yl)-5',6'-dihydro-[2,3'-bipyridine]-1'(2'H)-carboxylate (100 mg, 0.17 mmol) in MeOH (5 mL) was added 10% Pd/C (20 mg) and stirred at rt for 3 hours under H$_2$ (1 atm). After the reaction was complete by LCMS, the reaction mixture was filtered and concentrated. The residue was purified by silica gel chromatography (DCM/MeOH=40/1) to afford the title compound as a white solid. LCMS: 593.2 (M+H)$^+$.

Step 5: 1-(3-chloro-5'-fluoro-2'-hydroxy-3'-(2-(piperidin-3-yl)pyridin-4-yl)-[1,1'-biphenyl]-4-yl)-3-methyl-1H-imidazol-2(3H)-one The title compound was prepared following the procedures described for Example 504 using tert-butyl 3-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)piperidine-1-carboxylate and BBr$_3$ to afford the title compound. $^1$H NMR (400 MHz, DMSO-d$_6$): δ 8.51 (d, J=5.2 Hz, 1H), 7.88 (s, 1H), 7.64 (dd, J=2.0, 8.0 Hz, 1H), 7.52-7.45 (m, 3H), 7.26-7.21 (m, 2H), 6.72 (d, J=3.2 Hz, 1H), 6.88 (d, J=2.8 Hz, 1H), 3.21 (s, 3H), 3.04-3.01 (m, 1H), 2.99-2.91 (m, 1H), 2.84-2.78 (m, 1H), 2.71-2.66 (m, 1H), 2.53-2.51 (m, 1H), 1.97-1.94 (m, 1H), 1.72-1.65 (m, 2H), 1.52-1.48 (m, 1H). N—H and O—H protons not observed. LCMS: 479.2 (M+H)$^+$.

Example 655

1-(3-chloro-5'-fluoro-3'-(2-(hexahydropyrrolo[3,4-b]pyrrol-5(1H)-yl)pyridin-4-yl)-2'-hydroxy-[1,1'-biphenyl]-4-yl)-3-methyl-1H-imidazol-2(3H)-one

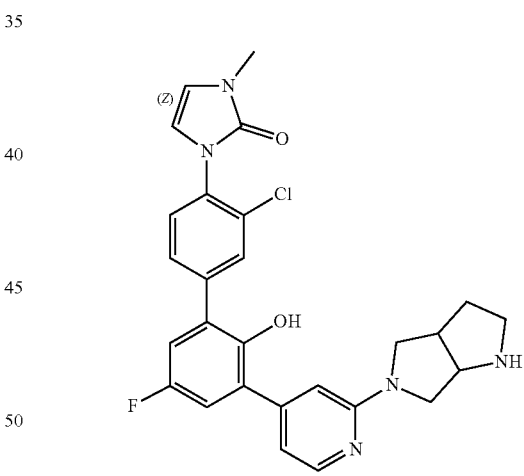

The title compound was prepared following the procedures described for Example 414 using 1-(3-chloro-5'-fluoro-3'-(2-fluoropyridin-4-yl)-2'-hydroxy-[1,1'-biphenyl]-4-yl)-3-methyl-1H-imidazol-2(3H)-one, tert-butyl hexahydropyrrolo[3,4-b]pyrrole-1(2H)-carboxylate and TFA to afford the title compound. $^1$H NMR (400 MHz, DMSO-d$_6$): δ 8.10 (d, J=4.8 Hz, 1H), 7.81 (d, J=1.6 Hz, 1H), 7.62 (dd, J=2.0, 8.4 Hz, 1H), 7.52 (d, J=8.0 Hz, 1H), 7.25-7.16 (m, 2H), 6.76-6.38 (m, 3H), 6.62 (s, 1H), 3.86-3.83 (m, 1H), 3.64-3.52 (m, 2H), 3.75-3.33 (m, 2H), 3.25-3.23 (m, 1H), 3.21 (s, 3H), 2.88-2.80 (m, 2H), 1.89-1.84 (m, 1H), 1.62-1.61 (m, 1H). N—H and O—H protons not observed. LCMS: 506.1 (M+H)$^+$.

Example 656

1-(3'-(2-(3,6-diazabicyclo[3.2.0]heptan-3-yl)pyridin-4-yl)-3-chloro-5'-fluoro-2'-hydroxy-[1,1'-biphenyl]-4-yl)-3-methyl-1H-imidazol-2(3H)-one

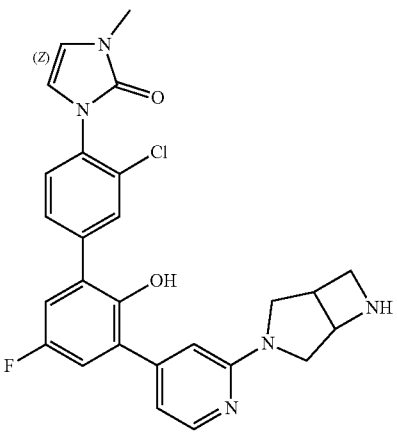 [SMILES: Cn1ccn(-c2ccc(-c3cc(F)cc(-c4ccnc(N5CC6CNC6C5)c4)c3O)cc2Cl)c1=O]

The title compound was prepared following the procedures described for Example 414 using 1-(3-chloro-5'-fluoro-3'-(2-fluoropyridin-4-yl)-2'-hydroxy-[1,1'-biphenyl]-4-yl)-3-methyl-1H-imidazol-2(3H)-one, tert-butyl 3,6-diazabicyclo[3.2.0]heptane-6-carboxylate and TFA to afford the title compound. $^1$H NMR (400 MHz, DMSO-$d_6$): δ 8.15 (d, J=5.2 Hz, 1H), 7.82 (d, J=1.6 Hz, 1H), 7.62 (dd, J=2.0, 8.4 Hz, 1H), 7.52 (d, J=8.0 Hz, 1H), 7.26-7.18 (m, 2H), 6.84-6.78 (m, 2H), 6.72 (d, J=2.8 Hz, 1H), 6.69 (d, J=2.8 Hz, 1H), 4.41-4.38 (m, 1H), 3.90-3.80 (m, 2H), 3.69-3.65 (m, 1H), 3.21 (s, 3H), 3.16-3.09 (m, 4H). N—H and O—H protons not observed. LCMS: 492.1 (M+H)$^+$.

Example 657

1-(3-chloro-5'-fluoro-2'-hydroxy-3'-(1',2',5',6'-tetrahydro-[2,3'-bipyridin]-4-yl)-[1,1'-biphenyl]-4-yl)-3-methyl-1H-imidazol-2(3H)-one

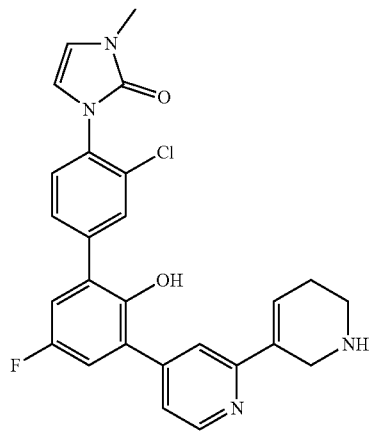

The title compound was prepared following the procedures described for Example 654 using tert-butyl 4-(3'-chloro-5-fluoro-2-hydroxy-4'-(3-methyl-2-oxo-2,3-dihydro-1H-imidazol-1-yl)-[1,1'-biphenyl]-3-yl)-5',6'-dihydro-[2,3'-bipyridine]-1'(2'H)-carboxylate and TFA to afford the title compound 2,2,2-trifluoroacetate. The salt was purified by C18 (0.1% HCl aqueous solution) to afford the title compound as hydrochloride salt. $^1$H NMR (400 MHz, DMSO-$d_6$): δ 9.53-9.43 (m, 2H), 9.06-8.94 (m, 1H), 8.63 (d, J=5.2 Hz, 1H), 7.97-7.95 (m, 1H), 7.84 (d, J=1.2 Hz, 1H), 7.66-7.61 (m, 2H), 7.55 (d, J=8.4 Hz, 1H), 7.37-7.32 (m, 2H), 7.01 (br s, 1H), 6.73 (d, J=2.8 Hz, 1H), 6.69 (d, J=3.2 Hz, 1H), 4.13 (s, 2H), 3.25-3.24 (m, 2H), 3.21 (s, 3H), 2.56-2.51 (m, 2H). LCMS: 477.2 (M+H)$^+$.

Example 658

1-(3-chloro-5'-fluoro-2'-hydroxy-3'-(2-(1-methylhexahydropyrrolo[3,4-b]pyrrol-5(1H)-yl)pyridin-4-yl)-[1,1'-biphenyl]-4-yl)-3-methyl-1H-imidazol-2(3H)-one

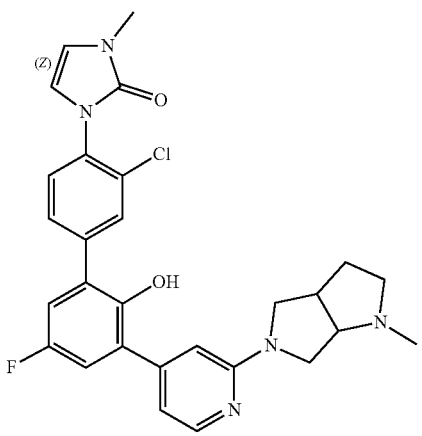 [SMILES: CN1CCC2CN(c3cc(-c4cc(F)cc(-c5ccc(-n6ccn(C)c6=O)c(Cl)c5)c4O)ccn3)CC21]

The title compound was prepared following the procedures described for Example 469 using 1-(3-chloro-5'-fluoro-3'-(2-(hexahydropyrrolo[3,4-b]pyrrol-5(1H)-yl)pyridin-4-yl)-2'-hydroxy-[1,1'-biphenyl]-4-yl)-3-methyl-1H-imidazol-2(3H)-one, HCHO and NaBH$_3$(CN) to afford the title compound. $^1$H NMR (400 MHz, DMSO-$d_6$): δ 8.70 (s, 1H), 8.10 (d, J=4.8 Hz, 1H), 7.80 (d, J=2.0 Hz, 1H), 7.62 (dd, J=1.6, 8.0 Hz, 1H), 6.52 (d, J=8.0 Hz, 1H), 7.26-7.18 (m, 2H), 6.75-6.69 (m, 3H), 6.60 (s, 1H), 3.65-3.60 (m, 2H), 3.30-3.22 (m, 1H), 3.21 (s, 3H), 3.01 (t, J=8.4 Hz, 1H), 2.89-2.86 (m, 2H), 2.21 (s, 3H), 2.25-2.22 (m, 1H), 2.07-1.99 (m, 1H), 1.63-1.59 (m, 1H). O—H proton not observed. LCMS: 520.2 (M+H)$^+$.

Example 659

1-(3-chloro-5'-fluoro-2'-hydroxy-3'-(2-(6-methyl-3,6-diazabicyclo[3.2.0]heptan-3-yl)pyridin-4-yl)-[1,1'-biphenyl]-4-yl)-3-methyl-1H-imidazol-2(3H)-one

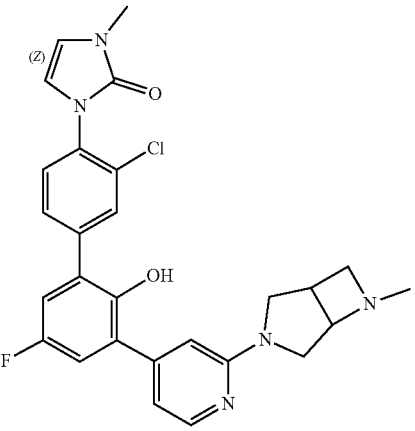 [SMILES: CN1CC2CN(c3cc(-c4cc(F)cc(-c5ccc(-n6ccn(C)c6=O)c(Cl)c5)c4O)ccn3)CC21]

The title compound was prepared following the procedures described for Example 469 using 1-(3'-(2-(3,6-diazabicyclo[3.2.0]heptan-3-yl)pyridin-4-yl)-3-chloro-5'-fluoro-2'-hydroxy-[1,1'-biphenyl]-4-yl)-3-methyl-1H-imidazol-2(3H)-one, HCHO and NaBH$_3$(CN) to afford the title compound. $^1$H NMR (400 MHz, DMSO-d$_6$): δ 8.74 (br s, 1H), 8.13 (d, J=4.8 Hz, 1H), 7.81 (d, J=1.6 Hz, 1H), 7.62 (dd, J=2.4, 8.8 Hz, 1H), 7.53 (d, J=8.0 Hz, 1H), 7.26-7.18 (m, 2H), 6.77 (d, J=5.6 Hz, 1H), 6.72 (d, J=2.8 Hz, 1H), 6.69-6.68 (m, 2H), 3.83-3.77 (m, 3H), 3.44-3.39 (m, 1H), 3.21 (s, 3H), 3.18-3.05 (m, 4H), 2.26 (s, 3H). LCMS: 506.2 (M+H)$^+$.

Example 660

(R)-5-(3'-chloro-5-fluoro-2-hydroxy-4'-(3-methyl-2-oxo-2,3-dihydro-1H-imidazol-1-yl)-[1,1'-biphenyl]-3-yl)-1-(3-methoxypropyl)-3-(3-methylpiperazin-1-yl)pyridin-2(1H)-one

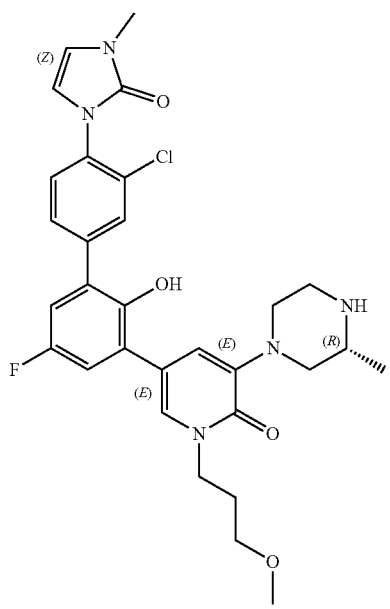

Step 1: (R)-tert-butyl 4-(5-bromo-1-(3-methoxypropyl)-2-oxo-1,2-dihydropyridin-3-yl)-2-methylpiperazine-1-carboxylate The title compound was prepared following the procedure described for Example 372 using 3,5-dibromo-1-(3-methoxypropyl)pyridin-2(1H)-one and (R)-tert-butyl 2-methylpiperazine-1-carboxylate to afford the title compound. LCMS: 444.1 (M+H)$^+$.

Step 2: (R)-tert-butyl 4-(5-(3'-chloro-5-fluoro-2-methoxy-4'-(3-methyl-2-oxo-2,3-dihydro-1H-imidazol-1-yl)-[1,1'-biphenyl]-3-yl)-1-(3-methoxypropyl)-2-oxo-1,2-dihydropyridin-3-yl)-2-methylpiperazine-1-carboxylate The title compound was prepared following the procedure described for Example 372 using (R)-tert-butyl 4-(5-bromo-1-(3-methoxypropyl)-2-oxo-1,2-dihydropyridin-3-yl)-2-methylpiperazine-1-carboxylate and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one to afford the title compound. LCMS: 696.3 (M+H)$^+$.

Step 3: (R)-tert-butyl 4-(5-(3'-chloro-5-fluoro-2-hydroxy-4'-(3-methyl-2-oxo-2,3-dihydro-1H-imidazol-1-yl)-[1,1'-biphenyl]-3-yl)-1-(3-methoxypropyl)-2-oxo-1,2-dihydropyridin-3-yl)-2-methylpiperazine-1-carboxylate The title compound was prepared following the procedure described for Example 551 using (R)-tert-butyl 4-(5-(3'-chloro-5-fluoro-2-methoxy-4'-(3-methyl-2-oxo-2,3-dihydro-1H-imidazol-1-yl)-[1,1'-biphenyl]-3-yl)-1-(3-methoxypropyl)-2-oxo-1,2-dihydropyridin-3-yl)-2-methylpiperazine-1-carboxylate and piperazine to afford the title compound. LCMS: 682.3 (M+H)$^+$.

Step 4: (R)-5-(3'-chloro-5-fluoro-2-hydroxy-4'-(3-methyl-2-oxo-2,3-dihydro-1H-imidazol-1-yl)-[1,1'-biphenyl]-3-yl)-1-(3-methoxypropyl)-3-(3-methylpiperazin-1-yl)pyridin-2(1H)-one The title compound was prepared following the procedure described for Example 551 using (R)-tert-butyl 4-(5-(3'-chloro-5-fluoro-2-hydroxy-4'-(3-methyl-2-oxo-2,3-dihydro-1H-imidazol-1-yl)-[1,1'-biphenyl]-3-yl)-1-(3-methoxypropyl)-2-oxo-1,2-dihydropyridin-3-yl)-2-methylpiperazine-1-carboxylate and TFA to afford the title compound. $^1$H NMR (400 MHz, DMSO-d$_6$): δ 7.80 (d, J=1.6 Hz, 1H), 7.61 (dd, J=2.0, 8.0 Hz, 1H), 7.52-7.50 (m, 2H), 7.20-7.14 (m, 2H), 6.86 (d, J=2.4 Hz, 1H), 6.72 (d, J=2.8 Hz, 1H), 6.68 (d, J=2.0 Hz, 1H), 3.97 (t, J=7.2 Hz, 2H), 3.58 (d, J=10.8 Hz, 2H), 3.38 (t, J=10.0 Hz, 2H), 3.25 (s, 3H), 3.21 (s, 3H), 2.90-2.78 (m, 3H), 2.41-2.36 (m, 1H), 2.04 (t, J=10.4 Hz, 1H), 1.94-1.88 (m, 2H), 0.97 (d, J=6.4 Hz, 3H). N—H or O—H protons not observed. LCMS: 582.3 (M+H)$^+$.

Example 661

5-(3'-chloro-5-fluoro-2-hydroxy-4'-(3-methyl-2-oxo-2,3-dihydro-1H-imidazol-1-yl)-[1,1'-biphenyl]-3-yl)-3-(4-isopropylpiperazin-1-yl)-1-methylpyridin-2(1H)-one

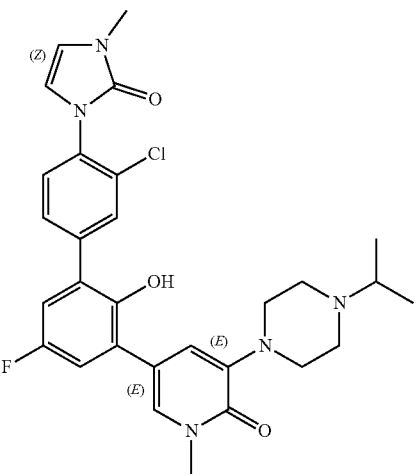 [SMILES: CC(C)N1CCN(c2cc(-c3cc(F)cc(-c4ccc(-n5ccn(C)c5=O)c(Cl)c4)c3O)cn(C)c2=O)CC1]

The title compound was prepared following the procedures described for Example 660 using 5-bromo-3-(4-isopropylpiperazin-1-yl)-1-methylpyridin-2(1H)-one and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr$_3$ to afford the title compound. $^1$H NMR (400 MHz, DMSO-d$_6$): δ 8.64 (s, 1H), 7.80 (d, J=2.0 Hz, 1H), 7.62-7.58 (m, 2H), 7.52 (d, J=8.4 Hz, 1H), 7.16 (d, J=9.2 Hz, 2H), 6.87 (d, J=2.0 Hz, 1H), 6.72 (d, J=2.8 Hz, 1H), 6.69 (d, J=2.8 Hz, 1H), 3.48 (s, 3H), 3.21 (s, 3H), 3.16-3.04 (m, 4H), 2.67-2.58 (m, 5H), 1.01 (d, J=6.4 Hz, 6H).
LCMS: 552.3 (M+H)$^+$.

Example 662

1-(3'-(2-(4-(bicyclo[1.1.1]pentan-1-yl)piperazin-1-yl)pyridin-4-yl)-3-chloro-5'-fluoro-2'-hydroxy-[1,1'-biphenyl]-4-yl)-3-methyl-1H-imidazol-2(3H)-one

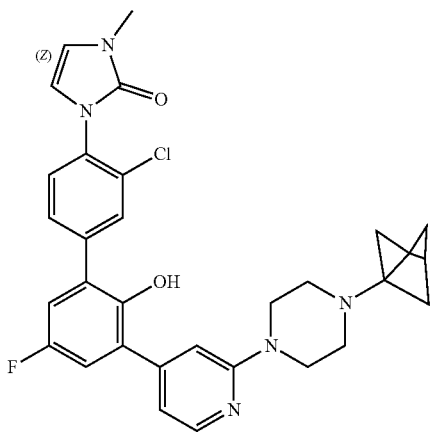 [SMILES: Cn1ccn(-c2ccc(-c3cc(F)cc(-c4ccnc(N5CCN(C67CC8CC86C7)CC5)c4)c3O)cc2Cl)c1=O]

The title compound was prepared following the procedure described for Example 414 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 1-(bicyclo[1.1.1]pentan-1-yl)piperazine to afford the title compound. $^1$H NMR (400 MHz, DMSO-d$_6$): δ 8.72 (s, 1H), 8.16 (d, J=5.6 Hz, 1H), 7.80 (d, J=2.0 Hz, 1H), 7.61 (dd, J=2.4, 8.4 Hz, 1H), 7.52 (d, J=8.4 Hz, 1H), 7.26-7.19 (m, 2H), 6.96 (s, 1H), 6.84 (d, J=4.8 Hz, 1H), 6.72 (d, J=3.2 Hz, 1H), 6.69 (d, J=3.2 Hz, 1H), 3.53 (br s, 4H), 3.21 (s, 3H), 2.47-2.32 (m, 4H), 1.73 (s, 6H), 1.23 (s, 1H). LCMS: 546.2 (M+H)$^+$.

Example 663

1-(3-chloro-5'-fluoro-2'-hydroxy-3'-(5-(4-isopropylpiperazin-1-yl)pyridin-3-yl)-[1,1'-biphenyl]-4-yl)-3-methyl-1H-imidazol-2(3H)-one

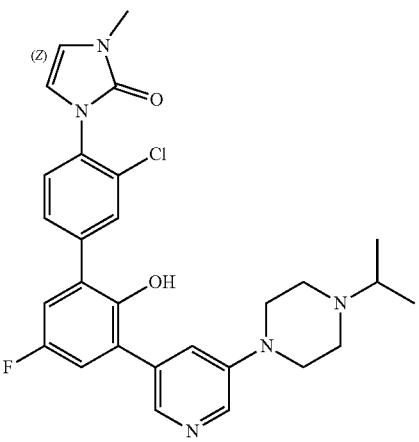 [SMILES: CC(C)N1CCN(c2cncc(-c3cc(F)cc(-c4ccc(-n5ccn(C)c5=O)c(Cl)c4)c3O)c2)CC1]

The title compound was prepared following the procedures described for Example 508 using 1-(5-bromopyridin-3-yl)-4-isopropylpiperazine and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one BBr$_3$ to afford the title compound. $^1$H NMR (400 MHz, CD$_3$OD): δ 8.26 (d, J=2.8 Hz, 1H), 8.20 (d, J=1.2 Hz, 1H), 7.84 (d, J=2.0 Hz, 1H), 7.65 (dd, J=2.0, 8.4 Hz, 1H), 7.61 (t, J=2.0 Hz, 1H), 7.54 (d, J=8.4 Hz, 1H), 7.15 (d, J=8.8 Hz, 2H), 6.70 (d, J=2.8 Hz, 1H), 6.66 (d, J=2.8 Hz, 1H), 3.39-3.37 (m, 7H), 2.82-2.78 (m, 5H), 1.17 (d, J=6.8 Hz, 6H). N—H or O—H proton not observed. LCMS: 522.3 (M+H)$^+$.

Example 664

1-(3'-(5-(4-(tert-butyl)piperazin-1-yl)pyridin-3-yl)-3-chloro-5'-fluoro-2'-hydroxy-[1,1'-biphenyl]-4-yl)-3-methyl-1H-imidazol-2(3H)-one

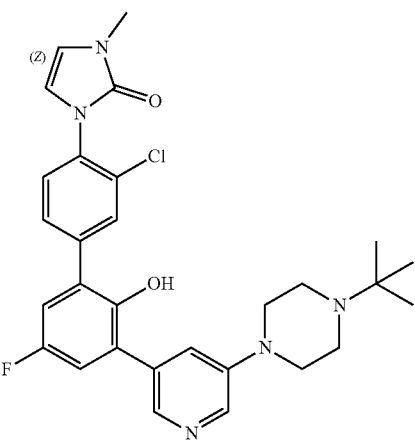

The title compound was prepared following the procedure described for Example 508 using 1-(tert-butyl)piperazine, 3,5-dibromopyridine, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr$_3$ to afford the title compound. $^1$H NMR (400 MHz, CD$_3$OD): δ 8.13 (d, J=2.8 Hz, 1H), 8.07 (d, J=1.6 Hz, 1H), 7.71 (d, J=2.0 Hz, 1H), 7.52 (dd, J=1.6, 8.0 Hz, 1H), 7.47 (t, J=2.0 Hz, 1H), 7.41 (d, J=8.4 Hz, 1H), 7.02 (d, J=8.8 Hz, 2H), 6.57 (d, J=2.8 Hz, 1H), 6.53 (d, J=3.2 Hz, 1H), 3.26-3.25 (m, 7H), 2.76 (t, J=4.8 Hz, 4H), 1.07 (s, 9H). N—H or O—H proton not observed. LCMS: 536.3 (M+H)$^+$.

Example 665

4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-1,4-diazepan-5-one

Step 1: 3-((2-((4-bromopyridin-2-yl)amino)ethyl)(tert-butoxycarbonyl)amino)propanoic acid A mixture of tert-butyl 5-oxo-1,4-diazepane-1-carboxylate (500 mg, 2.33 mmol), t-BuOK (786 mg, 7.00 mmol) and 4-bromo-2-fluoropyridine (1.23 g, 7.00 mmol) in toluene (23 mL) was stirred at 110° C. overnight. After the reaction was complete by LCMS, the reaction mixture was concentrated. The residue was purified by C18 (acetonitrile:water=5% to 50%) to afford the title compound (266 mg, 22% yield) as a yellow solid. LCMS: 388.1 (M+H)$^+$

Step 2: tert-butyl 4-(4-bromopyridin-2-yl)-5-oxo-1,4-diazepane-1-carboxylate The title compound was prepared using 3-((2-((4-bromopyridin-2-yl)amino)ethyl)(tert-butoxycarbonyl)amino)propanoic acid, DIEA and HATU to afford the title compound (56% yield). LCMS: 370.1 (M+H)$^+$

Step 3: (2-(4-(tert-butoxycarbonyl)-7-oxo-1,4-diazepan-1-yl)pyridin-4-yl)boronic acid The title compound was prepared following the procedure described for Example 508 using tert-butyl 4-(4-bromopyridin-2-yl)-5-oxo-1,4-diazepane-1-carboxylate and 4,4,4',4',5,5,5',5'-octamethyl-2,2'-bi(1,3,2-dioxaborolane) to afford the title compound (100% yield). LCMS: 336.2 (M+H)$^+$

Step 4: 4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-1,4-diazepan-5-one The title compound was prepared following the procedure described for Example 508 using 1-(3'-bromo-3-chloro-5'-fluoro-2'-methoxy-[1,1'-biphenyl]-4-yl)-3-methyl-1H-imidazol-2(3H)-one and (2-(4-(tert-butoxycarbonyl)-7-oxo-1,4-diazepan-1-yl)pyridin-4-yl)boronic acid and BBr$_3$ to afford the title compound. $^1$H NMR (400 MHz, DMSO-d$_6$): δ 8.46 (d, J=4.8 Hz, 1H), 7.84 (s, 1H), 7.82 (d, J=2.0 Hz, 1H), 7.62 (dd, J=2.0, 8.0 Hz, 1H), 7.53 (d, J=8.0 Hz, 1H), 7.40 (dd, J=1.6, 5.2 Hz, 1H), 7.29 (dd, J=3.2, 8.8 Hz, 1H), 7.21 (dd, J=3.2, 9.2 Hz, 1H), 6.72 (d, J=3.2 Hz, 1H), 6.68 (d, J=3.2 Hz, 1H), 4.11-4.09 (m, 2H), 3.21 (s, 3H), 2.97-2.90 (m, 4H), 2.79-2.77 (m, 2H). N—H and O—H protons not observed. LCMS: 508.2 (M+H)$^+$.

Example 666

(S)-1-(3-chloro-5'-fluoro-2'-hydroxy-3'-(2-(3-(methoxymethyl)piperazin-1-yl)pyridin-4-yl)-[1,1'-biphenyl]-4-yl)-3-methyl-1H-imidazol-2(3H)-one

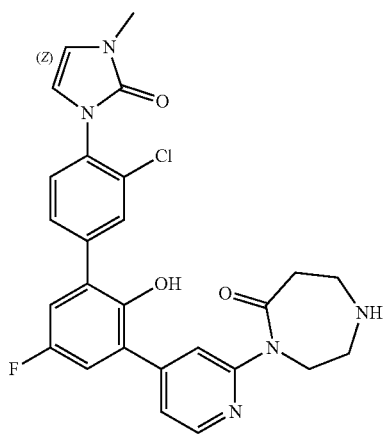 [SMILES: Cn1ccn(-c2ccc(-c3cc(F)cc(-c4ccnc(N5CCNCCC5=O)c4)c3O)cc2Cl)c1=O]

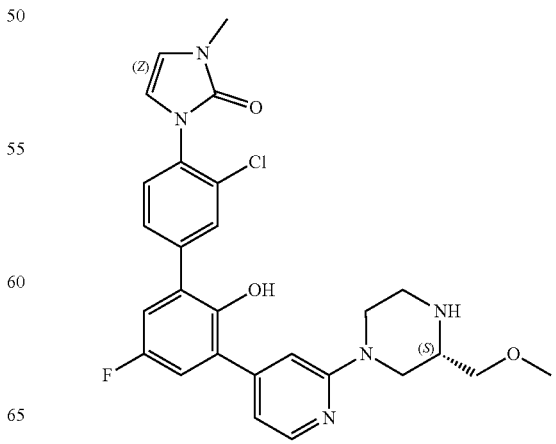

Step 1: (S)-tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-2-(hydroxymethyl)piperazine-1-carboxylate The title compound was prepared following the procedure described for Example 414 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and (S)-tert-butyl 2-(hydroxymethyl)piperazine-1-carboxylate to afford the title compound. LCMS: 624.2 (M+H)$^+$ Step 2: (S)-tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-2-(methoxymethyl)piperazine-1-carboxylate To a solution of (S)-tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-2-(hydroxymethyl)piperazine-1-carboxylate (50 mg, 0.080 mmol) in CH$_3$I (5 mL) was added Ag$_2$O (186 mg, 0.80 mmol) and stirred at 50° C. for 72 hours. After the reaction was completed by LCMS, the reaction mixture was quenched with water (20 mL) and extracted with EA (10 mL) three times. The combined organic layers were washed with brine, dried over sodium sulfate, filtered, and concentrated. The residue was purified by silica gel chromatography (PE/EA=1/1) to afford the title compound (25 mg, 49% yield) as a yellow solid. LCMS: 638.3 (M+H)$^+$.

Step 3: (S)-tert-butyl 4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-2-(methoxymethyl)piperazine-1-carboxylate The title compound was prepared following the procedure described for Example 551 using (S)-tert-butyl 4-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-2-(methoxymethyl)piperazine-1-carboxylate and piperazine to afford the title compound (33% yield). LCMS: 624.3 (M+H)$^+$ Step 4: (S)-1-(3-chloro-5'-fluoro-2'-hydroxy-3'-(2-(3-(methoxymethyl)piperazin-1-yl)pyridin-4-yl)-[1,1'-biphenyl]-4-yl)-3-methyl-1H-imidazol-2(3H)-one 2,2,2-trifluoroacetate The title compound was prepared following the procedure described for Example 551 using (S)-tert-butyl 4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-2-(methoxymethyl)piperazine-1-carboxylate and HCl/EtOH to afford the title compound (35% yield). $^1$H NMR (400 MHz, CD$_3$OD): δ 8.10 (d, J=6.0 Hz, 1H), 7.69 (d, J=1.6 Hz, 1H), 7.50 (dd, J=2.0, 8.0 Hz, 1H), 7.42 (d, J=8.4 Hz, 1H), 7.19 (s, 1H), 7.11-7.04 (m, 3H), 6.58 (d, J=2.8 Hz, 1H), 6.53 (d, J=3.2 Hz, 1H), 4.32 (t, J=12.0 Hz, 2H), 3.64-3.61 (m, 1H), 3.56-3.52 (m, 2H), 3.41-3.38 (m, 1H), 3.36 (s, 3H), 3.30-3.29 (m, 1H), 3.25 (s, 3H), 3.21-3.20 (m, 2H). N—H and O—H protons not observed. LCMS: 524.3 (M+H)$^+$.

Example 667

(R)-1-(3-chloro-5'-fluoro-2'-hydroxy-3'-(2-(3-isopropylpiperazin-1-yl)pyridin-4-yl)-[1,1'-biphenyl]-4-yl)-3-methyl-1H-imidazol-2(3H)-one

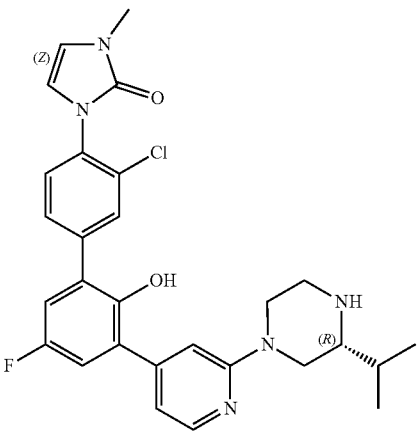

The title compound was prepared following the procedure described for Example 470 using 1-(3-chloro-5'-fluoro-3'-(2-fluoropyridin-4-yl)-2'-hydroxy-[1,1'-biphenyl]-4-yl)-3-methyl-1H-imidazol-2(3H)-one, (R)-tert-butyl 2-isopropylpiperazine-1-carboxylate, TFA and Na$_2$CO$_3$ to afford the title compound (18% yield). $^1$H NMR (400 MHz, DMSO-d$_6$): δ 8.15 (d, J=5.2 Hz, 1H), 7.80 (d, J=2.0 Hz, 1H), 7.62 (dd, J=2.0, 8.4 Hz, 1H), 7.52 (d, J=8.0 Hz, 1H), 7.26-7.18 (m, 2H), 6.92 (s, 1H), 6.80 (d, J=5.2 Hz, 1H), 6.72 (d, J=2.8 Hz, 1H), 6.68 (d, J=3.2 Hz, 1H), 4.25 (d, J=11.6 Hz, 1H), 4.10 (d, J=9.2 Hz, 1H), 3.21 (s, 3H), 3.01-2.99 (m, 1H), 2.76-2.65 (m, 2H), 2.50-2.33 (m, 2H), 1.65-1.60 (m, 1H), 0.95 (d, J=6.8 Hz, 6H). N—H and O—H protons not observed. LCMS: 522.3 (M+H)$^+$.

Example 668

3-(4-(tert-butyl)piperazin-1-yl)-5-(3'-chloro-5-fluoro-2-hydroxy-4'-(3-methyl-2-oxo-2,3-dihydro-1H-imidazol-1-yl)-[1,1'-biphenyl]-3-yl)-1-methylpyridin-2(1H)-one

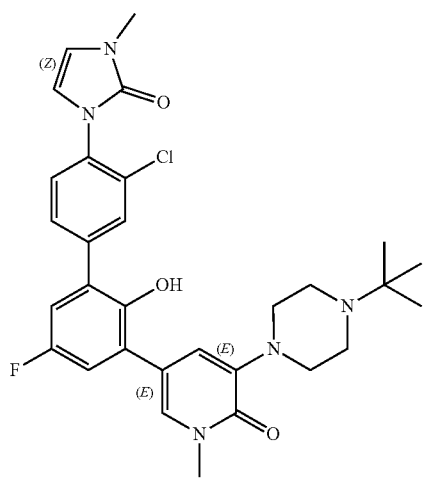 [SMILES: Cn1cc(-c2cc(F)cc(-c3ccc(-n4ccn(C)c4=O)c(Cl)c3)c2O)cc(N2CCN(C(C)(C)C)CC2)c1=O]

The title compound was prepared following the procedure described for Example 372 using 5-bromo-3-(4-(tert-butyl)piperazin-1-yl)-1-methylpyridin-2(1H)-one and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2 (3H)-one and BBr$_3$ to afford the title compound.

$^1$H NMR (400 MHz, DMSO-d$_6$): δ 8.63 (s, 1H), 7.80 (d, J=1.6 Hz, 1H), 7.62-7.58 (m, 2H), 7.52 (d, J=8.0 Hz, 1H), 7.16 (d, J=8.8 Hz, 2H), 6.81 (s, 1H), 6.71 (d, J=2.8 Hz, 1H), 6.68 (d, J=2.8 Hz, 1H), 3.48 (s, 3H), 3.21 (s, 3H), 3.10 (br s, 4H), 2.64 (br s, 4H), 1.05 (s, 9H). LCMS: 566.3 (M+H)$^+$.

TABLE 30

Following compounds were prepared using similar procedures as described for Examples 365-668.

| Ex. No. | Name/Structure | $^1$H NMR Data | LCMS (M + H)$^+$ |
|---|---|---|---|
| 669 | 1-(3-chloro-5'-fluoro-2'-hydroxy-3'-(2-(4-(prop-2-yn-1-yl)piperazin-1-yl)pyridin-4-yl)-[1,1'-biphenyl]-4-yl)-3-methyl-1H-imidazol-2(3H)-one | $^1$H NMR (400 MHz, DMSO-d$_6$): δ 8.72 (s, 1H), 8.16 (d, J = 5.2 Hz, 1H), 7.81 (d, J = 1.6 Hz, 1H), 7.62 (dd, J = 2.0, 8.4 Hz, 1H), 7.52 (d, J = 8.0 Hz, 1H), 7.26-7.19 (m, 2H), 6.97 (s, 1H), 6.85 (d, J = 4.8 Hz, 1H), 6.72 (d, J = 3.2 Hz, 1H), 6.69 (d, J = 3.2 Hz, 1H), 3.56-3.55 (m, 4H), 3.34-3.32 (m, 2H), 3.21 (s, 3H), 3.18 (t, J = 2.4 Hz, 1H), 2.55 (t, J = 4.4 Hz, 4H) | 518.2 |
| 670 | 1-(3-chloro-5'-fluoro-2'-hydroxy-3'-(8-(4-isopropylpiperazin-1-yl)imidazo[1,2-a]pyridin-6-yl)-[1,1'-biphenyl]-4-yl)-3-methyl-1H-imidazol-2(3H)-one | $^1$H NMR (400 MHz, DMSO-d$_6$): δ 8.72 (s, 1H), 8.33 (s, 1H), 7.80 (s, 1H), 7.83 (d, J = 1.6 Hz, 1H), 7.65-7.62 (m, 1H), 7.54-7.50 (m, 2H), 7.27-7.23 (m, 2H), 6.72 (d, J = 3.2 Hz, 1H), 6.70 (d, J = 2.8 Hz, 1H), 6.54 (s, 1H), 3.55 (br s, 1H), 3.21 (s, 3H), 2.67-2.65 (m, 4H), 2.01-1.99 (m, 4H), 1.03 (d, J = 5.2 Hz, 6H) | 561.3 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| 671 | (R)-1-(3-chloro-5'-fluoro-2'-hydroxy-3''-(3-methylpiperazin-1-yl)-[1,1':3',1''-terphenyl]-4-yl)-3-methyl-1H-imidazol-2(3H)-one | ¹H NMR (400 MHz, DMSO-d₆): δ 7.80 (d, J = 1.6 Hz, 1H), 7.62 (dd, J = 1.6, 8.0 Hz, 1H), 7.51 (d, J = 8.0 Hz, 1H), 7.28 (t, J = 8.0 Hz, 1H), 7.18-7.07 (m, 3H), 6.95-6.92 (m, 2H), 6.71 (d, J = 2.8 Hz, 1H), 6.68 y (d, J = 3.2 Hz, 1H), 3.58-3.53 (m, 2H), 3.21 (s, 3H), 2.98-2.95 (m, 1H), 2.83-2.77 <m, 2H), 2.61-2.54 (m, 1H), 2.22 (t, J = 10.4 Hz, 1H), 1.03 (d, J = 6.4 Hz, 3H), N-H and O-H protons not observed | 493.3 |
| 672 | 1-(3-chloro-5'-fluoro-2'-hydroxy-3'-(4-(4-isopropylpiperazin-1-yl)-1-methyl-1H-indazol-6-yl)-[1,1'-biphenyl]-4-yl)-3-methyl-1H-imidazol-2(3H)-one | ¹H NMR (400 MHz, DMSO-d₆): δ 8.51 (s, 1H), 8.07 (s, 1H), 7.83 (d, J = 1.6 Hz, 1H), 7.64 (dd, J = 1.6, 8.4 Hz, 1H), 7.52 (d, J = 8.0 Hz, 1H), 7.29 (s, 1H), 7.23-7.20 (m, 2H), 6.72 (d, J = 3.2 Hz, 1H), 6.69 (d, J = 3.2 Hz, 1H), 6.59 (s, 1H), 4.01 (s, 3H), 3.31-3.30 (m, 4H), 3.21 (s, 3H), 2.74-2.65 (m, 5H), 1.03 (d, J = 5.2 Hz, 6H) | 575.2 |
| 673 | (R)-1-(3-chloro-5'-fluoro-2'-hydroxy-3'-(2-(2-methylmorpholino)pyridin-4-yl)-[1,1'-biphenyl]-4-yl)-3-methyl-1H-imidazol-2(3H)-one | ¹H NMR (400 MHz, CD₃OD): δ 8.20 (d, J = 5.2 Hz, 1H), 7.83 (d, J = 2.0 Hz, 1H), 7.64 (dd, J = 2.0, | 495.3 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | | 8.0 Hz, 1H), 7.53 (d, J = 8.4 Hz, 1H), 7.14 (d, J = 8.4 Hz, 2H), 7.03 (s, 1H), 6.95-6.93 (m, 1H), 6.70 (d, J = 2.8 Hz, 1H), 6.66 (d, J = 2.4 Hz, 1H), 4.17-4.14 (m, 1H), 4.07-4.00 (m, 2H), 3.77-3.70 (m, 2H), 3.38 (s, 3H), 3.00-2.93 (m, 1H), 2.65-2.60 (m, 1H), 1.27 (d, J = 6.0 Hz, 3H), N-H and O-H protons not observed | |
| 674 | 1-(3'-(2-(1-oxa-6-azaspiro[3.4]octan-6-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 8.70 (s, 1H), 8.11 (d, J = 5.2 Hz, 1H), 7.80 (d, J = 2.0 Hz, 1H), 7.62 (dd, J = 1.6, 8.0 Hz, 1H), 7.52 (d, J = 8.4 Hz, 1H), 7.26-7.18 (m, 2H), 6.76-6.68 (m, 3H), 6.59 (s, 1H), 4.45-4.40 (m, 2H), 3.81-3.79 (m, 1H), 3.57-3.52 (m, 2H), 3.43-3.36 (m, 1H), 3.21 (s, 3H), 2.76-2.65 (m, 2H), 2.37-2.33 (m, 1H), 2.17-2.11 (m, 1H) | 507.1 |
| 675 | 2-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)hexahydropyrazino[1,2-c][1,3]oxazin-6(2H)-one | 1H NMR (400 MHz, DMSO-d₆): δ 8.730 (s, 1H), 8.18 (d, J = 5.2 Hz, 1H), 7.81 (d, J = 1.6 Hz, 1H), 7.62 (dd, J = 2.0, 8.0 Hz, 1H), 7.53 (d, J = 8.4 Hz, 1H), 7.27-7.19 (m, 2H), 7.02 (s, 1H), 6.89 (d, J = 5.2 Hz, 1H), 6.72 (d, J = 3.2 Hz, 1H), 6.68 (d, J = 3.2 Hz, 1H), 4.43-4.34 (m, 2H), 4.24-4.14 (m, 3H), 3.56-3.55 (m, 1H), 3.21 (s, 3H), 2.97-2.83 (m, 2H), 2.65 (t, J = 11.6 Hz, 1H), 2.18-2.16 (m, 1H), 1.83-1.75 (m, 1H) | 550.1 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| 676 | 1-(3-chloro-5'-fluoro-2'-hydroxy-3'-(2-(3-(2-methoxyethyl)piperazin-1-yl)pyridin-4-yl)-[1,1'-biphenyl]-4-yl)-3-methyl-1H-imidazol-2(3H)-one | ¹H NMR (400 MHz, DMSO-d₆): δ 8.15 (d, J = 5.2 Hz, 1H), 7.81 (d, J = 1.6 Hz, 1H), 7.62 (dd, J = 2.0, 8.4 Hz, 1H), 7.52 (d, J = 8.0 Hz, 1H), 7.24 (dd, J = 3.2, 9.2 Hz, 1H), 7.19 (dd, J = 3.6, 9.2 Hz, 1H), 6.93 (s, 1H), 6.81 (d, J = 5.2 Hz, 1H), 6.72 (d, J = 3.2 Hz, 1H), 6.69 (d, J = 3.2 Hz, 1H), 4.19-4.10 (m, 2H), 3.45 (t, J = 6.8 Hz, 2H), 3.24 (s, 3H), 3.21 (s, 3H), 2.97-2.94 (m, 1H), 2.77-2.65 (m, 3H), 2.46-2.40 (m, 1H), 1.66-1.54 (m, 2H), Two N—H or O—H proton not observed | 538.2 |
| 677 | (R)-1-(3-chloro-4'',5'-difluoro-2'-hydroxy-3''-(3-methylpiperazin-1-yl)-[1,1':3',1''-terphenyl]-4-yl)-3-methyl-1H-imidazol-2(3H)-one | ¹H NMR (400 MHz, DMSO-d₆-HCl salt): δ 9.36-9.34 (m, 1H), 9.05-9.01 (m, 1H), 8.62-8.59 (m, 1H), 7.82 (d, J = 1.6 Hz, 1H), 7.63 (dd, J = 1.6, 8.4 Hz, 1H), 7.53 (d, J = 8.4 Hz, 1H), 7.29-7.16 (m, 5H), 6.72 (d, J = 3.2 Hz, 1H), 6.69 (d, J = 2.8 Hz, 1H), 3.58-3.36 (m, 4H), 3.21 (s, 3H), 3.17-3.05 (m, 2H), 3.92-2.86 (m, 1H), 1.30 (d, J = 6.4 Hz, 3H) | 511.2 |
| 678 | 1-(3-chloro-5'-fluoro-2'-hydroxy-3'-(2-(4-isopropyl-1,4-diazepan-1-yl)pyridin-4-yl)-[1,1'-biphenyl]-4-yl)-3-methyl-1H-imidazol-2(3H)-one | ¹H NMR (400 MHz, DMSO-d₆): δ 8.71-8.69 (m, 1H), 8.10 (d, J = 5.2 Hz, 1H), 7.80 (d, J = 2.0 | 536.2 |

TABLE 30-continued

Following compounds were prepared using similar procedures as described for Examples 365-668.

| Ex. No. | Name/Structure | $^1$H NMR Data | LCMS (M + H)$^+$ |
|---|---|---|---|
| | 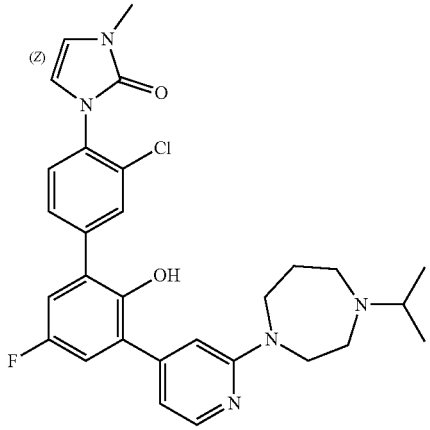 [SMILES: CC(C)N1CCCN(c2cc(-c3cc(F)cc(-c4ccc(-n5ccn(C)c5=O)c(Cl)c4)c3O)ccn2)CC1] | Hz, 1H), 7.61 (dd, J = 2.0, Hz, 1H), 7.61 (dd, J = 2.0, 8.4 Hz, 1H), 7.52 (d, J = 8.0 Hz, 1H), 7.25-7.18 (m, 2H), 6.72-6.68 (m, 4H), 3.69-3.64 (m, 4H), 3.33-3.24 (m, 2H), 3.21 (s, 3H), 2.90-2.83 (m, 1H), 2.69-2.67 (m, 2H), 1.83-1.77 (m, 2H), 0.93 (d, J = 6.8 Hz, 6H) | |
| 679 | methyl 2-(4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)piperazin-2-yl)acetate | $^1$H NMR (400 MHz, CD$_3$CD): δ 8.06 (d, J = 5.2 Hz, 1H), 7.70 (d, J = 2.0 Hz, 1H), 7.51 (dd, J = 2.0, 8.4 Hz, 1H), 7.40 (d, J = 8.4 Hz, 1H), 7.40 (d, J = 8.4 Hz, 1H), 7.01 (d, J = 8.85 Hz, 2H), 6.91 (s, 1H), 6.79 (dd, J = 1.6, 5.2 Hz, 1H), 6.57 (d, J = 2.8 Hz, 1H), 6.53 (d, J = 3.2 Hz, 1H), 4.10 (d, J = 12.0 Hz, 1H), 4.01 (d, J = 12.0 Hz, 1H), 3.61 (s, 3H), 3.24 (s, 3H), 3.10-2.79 (m, 4H), 2.62-2.35 (m, 3H), N—H and O—H protons not observed | 552.2 |
| 680 | (R)-1-(3'-(2-(3-(aminomethyl)piperazin-1-yl)pyridin-4-yl)-3-chloro-5'-fluoro-2'-hydroxy-[1,1'-biphenyl]-4-yl)-3-methyl-1H-imidazol-2(3H)-one | $^1$H NMR (400 MHz, CD$_3$OD): δ 8.14 (d, J = 5.6 Hz, 1H), 7.70 (d, J = 1.6 Hz, 1H), 7.50 (dd, J = 2.0, 8.4 Hz, 1H), 7.42 (d, J = 8.0 Hz, 1H), 7.19-7.16 (m, 1H), 7.10-7.04 (m, 3H), 6.59 (d, J = 2.8 Hz, 1H), 6.54 (d, J = 2.8 Hz, 1H), 4.45-4.42 (m, 1H), 4.19-1.15 (m, 1H), 3.65-3.62 (m, 1H), 3.50-3.38 (m, 2H), 3.34-3.31 (m, 1H), 3.28-3.25 (m, 6H), N—H and O—H protons not observed | 509.2 |

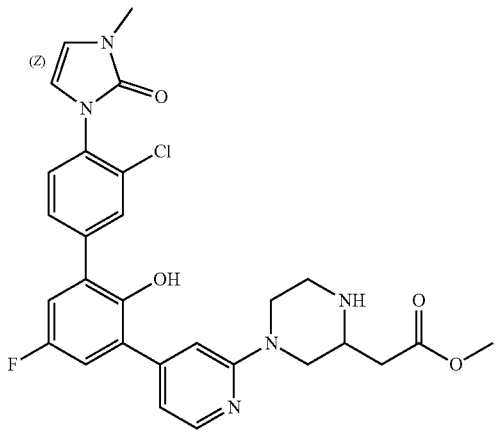 [SMILES: COC(=O)CC1CN(c2cc(-c3cc(F)cc(-c4ccc(-n5ccn(C)c5=O)c(Cl)c4)c3O)ccn2)CCN1]

TABLE 30-continued

Following compounds were prepared using similar procedures as described for Examples 365-668.

| Ex. No. | Name/Structure | ¹H NMR Data | LCMS (M + H)⁺ |
|---|---|---|---|
| 681 | 1-(3-chloro-3'-(2-(4-(2-cyclopropylethyl)piperazin-1-yl)pyridin-4-yl)-5'-fluoro-2'-hydroxy-[1,1'-biphenyl]-4-yl)-3-methyl-1H-imidazol-2(3H)-one | ¹H NMR (400 MHz, DMSO-d₆): δ 8.67-8.63 (m, 1H), 8.11 (d, J = 4.8 Hz, 1H), 7.77 (d, J = 2.0 Hz, 1H), 7.57 (dd, J = 2.0, 8.4 Hz, 1H), 7.48 (d, J = 8.0 Hz, 1H), 7.21-7.14 (m, 2H), 6.91 (s, 1H), 6.79 (d, J = 4.8 Hz, 1H), 6.68 (d, J = 3.2 Hz, 1H), 6.64 (d, J = 2.8 Hz, 1H), 3.47 (t, J = 4.4 Hz, 4H), 3.17 (s, 3H), 2.42 (t, J = 4.4 Hz, 4H), 2.35 (t, J = 7.6 Hz, 2H), 1.37-1.30 (m, 2H), 0.64-0.62 (m, 1H), 0.37-0.33 (m, 2H), 0.04-0.01 (m, 2H) | 548.2 |
| 682 | 1-(3-chloro-5'-fluoro-2'-hydroxy-3'-(2-(4-isobutylpiperazin-1-yl)pyridin-4-yl)-[1,1'-biphenyl]-4-yl)-3-methyl-1H-imidazol-2(3H)-one | ¹H NMR (400 MHz, DMSO-d₆): δ 8.72 (s, 1H), 8.16 (d, J = 5.2 Hz, 1H), 7.81 (d, J = 1.6 Hz, 1H), 7.62 (dd, J = 2.0, 8.4 Hz, 1H), 7.52 (d, J = 8.0 Hz, 1H), 7.26-7.19 (m, 2H), 6.95 (s, 1H), 6.84 (d, J = 4.8 Hz, 1H), 6.72 (d, J = 3.2 Hz, 1H), 6.69 (d, J = 2.8 Hz, 1H), 3.52 (br s, 4H), 3.21 (S.3H), 2.43 (t, J = 4.4 Hz, 4H), 2.08 (d, J = 7.6 Hz, 2H), 1.85-1.78 (m, 1H), 0.88 (d, J = 6.4 Hz, 6H) | 536.2 |
| 683 | 1-(3'-(2-(1-oxa-7-azaspiro[4.4]nonan-7-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆): δ 8.70 (s, 1H), 8.10 (d, J = 5.2 Hz, 1H), 7.80 (d, J = 2.0 Hz, 1H), | 521.2 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | 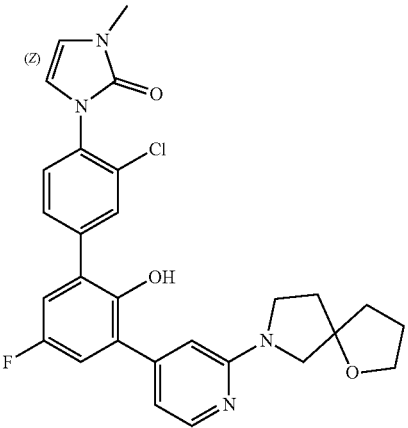 [SMILES: Cn1ccn(-c2ccc(-c3cc(F)cc(-c4ccnc(N5CCC6(CCCO6)C5)c4)c3O)cc2Cl)c1=O] | 7.62 (dd, J = 1.6, 8.0 Hz, 1H), 7.52 (d, J = 8.0 Hz, 1H), 7.25-7.18 (m, 2H), 6.74-6.69 (m, 3H), 6.56 (s, 1H), 3.80-3.74 (m, 2H), 3.56-3.37 (m, 4H), 3.21 (s, 3H), 2.04-1.90 (m, 6H) | |
| 684 | 1-(3-chloro-3'-(2-((2R,6R)-2,6-dimethylmorpholino)pyridin-4-yl)-5'-fluoro-2'-hydroxy-[1,1'-biphenyl]-4-yl)-3-methyl-1H-imidazol-2(3H)-one | ¹H NMR (400 MHz, DMSO-d₆): δ 8.72 (s, 1H), 8.15 (d, J = 5.2 Hz, 1H), 7.81 (d, J = 1.6 Hz, 1H), 7.62 (dd, J = 2.0, 8.4 Hz, 1H), 7.52 (d, J = 8.0 Hz, 1H), 7.27-7.18 (m, 2H), 6.94 (s, 1H), 6.85-6.83 (m, 1H), 6.72 (d, J = 3.6 Hz, 1H), 6.69 (d, J = 3.2 Hz, 1H), 4.05-4.01 (m, 2H), 3.62 (dd, J = 3.2, 12.8 Hz, 2H), 3.30-3.23 (m, 2H), 3.21 (s, 3H), 1.17 (d, J = 6.8 Hz, 6H) | 509.1 |
| 685 | 1-(3-chloro-5'-fluoro-2'-hydroxy-3'-(2-(3-hydroxy-3-methylpyrrolidin-1-yl)pyridin-4-yl)-[1,1'-biphenyl]-4-yl)-3-methyl-1H-imidazol-2(3H)-one | ¹H NMR (400 MHz, DMSO-d₆): δ 8.69 (s, 1H), 8.09 (d, J = 5.2 Hz, 1H), 7.80 (d, J = 2.0 Hz, 1H), 7.62 (dd, J = 2.0, 8.4 Hz, 1H), 7.52 (d, J = 8.4 Hz, 1H), 7.25-7.17 (m, 2H), 6.72-6.69 (m, 3H), 6.54 (s, 1H), 4.78 (s, 1H), 3.53-3.50 (m, 2H), 3.43-3.41 (m, 1H), 3.30-3.28 (m, 1H), 3.21 (s, 3H), 1.94-1.86 (m, 2H), 1.35 (s, 3H) | 495.2 |

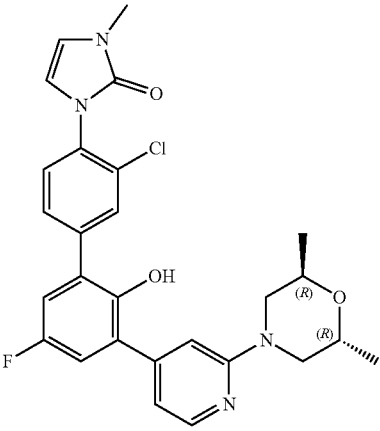

TABLE 30-continued

Following compounds were prepared using similar procedures as described for Examples 365-668.

| Ex. No. | Name/Structure | $^1$H NMR Data | LCMS (M + H)$^+$ |
|---|---|---|---|
| 686 | 1-(3'-(2-(3-amino-3-methylpyrrolidin-1-yl)pyridin-4-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 8.09 (d, J = 5.6 Hz, 1H), 7.81 (d, J = 2.0 Hz, 1H), 7.62 (dd, J = 2.0, 8.4 Hz, 1H), 7.52 (d, J = 8.0 Hz, 1H), 7.24 (dd, J = 3.2, 9.2 Hz, 1H), 7.18 (dd, J = 3.6, 9.2 Hz, 1H), 6.72-6.69 (m, 3H), 6.54 (s, 1H), 3.57-3.44 (m, 2H), 3.28 (s, 2H), 3.21 (s, 3H), 1.84 (t, J = 6.8 Hz, 2H), 1.26 (s, 3H), N—H and O—H protons not observed | 494.1 |
| 687 | 5-(3'-chloro-5-fluoro-2-hydroxy-4'-(3-methyl-2-oxo-2,3-dihydro-1H-imidazol-1-yl)-[1,1'-biphenyl]-3-yl)-1-methyl-3-(1,7-diazaspiro[4.4]nonan-7-yl)pyridin-2(1H)-one | 1H NMR (400 MHz, DMSO-d$_6$): δ 7.79 (d, J = 1.6 Hz, 1H), 7.59 (d, J = 1.6 Hz, 1H), 7.50 (d, J = 8.0 Hz, 1H), 7.27 (d, J = 2.4 Hz, 1H), 7.14-7.10 (m, 2H), 6.70 (dd, J = 2.8, 11.2 Hz, 2H), 6.38 (d, J = 2.4 Hz, 1H), 3.46-3.29 (m, 7H), 3.20 (s, 3H), 2.84-2.81 (m, 2H), 1.78-1.66 (m, 6H), N—H and O—H protons not observed | 550.2 |
| 688 | 1-(3'-(2-(1,6-diazaspiro[3.5]nonan-6-yl)pyridin-4-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$-HCl salt): δ 9.40-9.12 (m, 3H), 8.16 (d, J = 6.0 Hz, 1H), 7.84 (s, | 520.3 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | 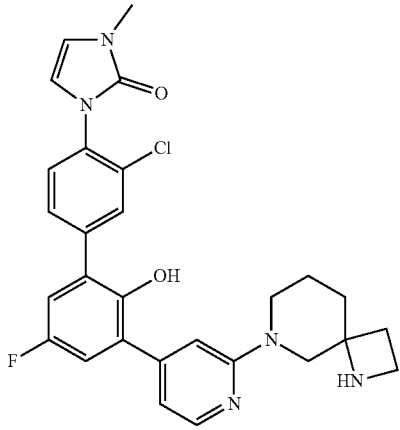 [SMILES: Cn1ccn(-c2ccc(-c3cc(F)cc(-c4ccnc(N5CCCC6(CCN6)C5)c4)c3O)cc2Cl)c1=O] | 1H), 7.64 (dd, J = 1.6, 8.4 Hz, 1H), 7.56-7.35 (m, 4H), 7.21-7.18 (m, 1H), 6.73 (d, J = 3.2 Hz, 1H), 6.69 (d, J = 2.8 Hz, 1H), 4.55-4.48 (m, 1H), 4.01-3.85 (m, 5H), 3.33-3.21 (m, 4H), 2.36-2.26 (m, 3H), 1.95-1.88 (m, 1H), 1.76 (br s, 2H) | |
| 689 | (R)-4-(3'-chloro-5-fluoro-2-hydroxy-4'-(3-methyl-2-oxo-2,3-dihydro-1H-imidazol-1-yl)-[1,1'-biphenyl]-3-yl)-1-methyl-6-(3-methylpiperazin-1-yl)pyridin-2(1H)-one<br>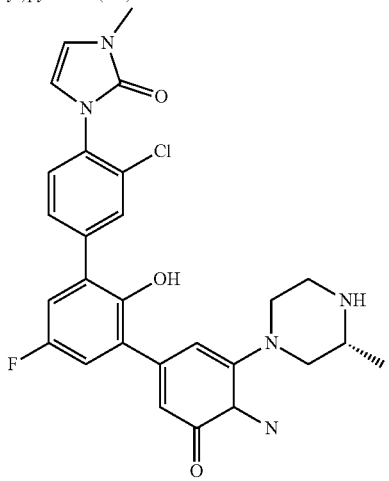 | ¹H NMR (400 MHz, DMSO-d₆): δ 7.80 (d, J = 1.6 Hz, 1H), 7.61 (dd, J = 2.0, 8.4 Hz, 1H), 7.52 (d, J = 8.0 Hz, 1H), 7.25 (dd, J = 3.2, 8.8 Hz, 1H), 7.19 (dd, J = 3.2, 9.2 Hz, 1H), 6.72 (d, J = 2.8 Hz, 1H), 6.68 (d, J = 2.8 Hz, 1H), 6.28 (d, J = 1.2 Hz, 1H), 6.96 (d, J = 1.6 Hz, 1H), 3.43 (s, 3H), 3.21 (s, 3H), 3.07-3.041 (m, 2H), 2.94-2.82 (m, 3H), 2.59-2.50 (m, 1H), 2.31-2.29 (m, 1H), 1.00 (d, J = 7.2 Hz, 3H), N—H and O—H protons not observed | 524.2 |
| 690 | 1-(3-chloro-5'-fluoro-2'-hydroxy-3'-(2-(1-oxidothiomorpholino)pyridin-4-yl)-[1,1'-biphenyl]-4-yl)-3-methyl-1H-imidazol-2(3H)-one<br>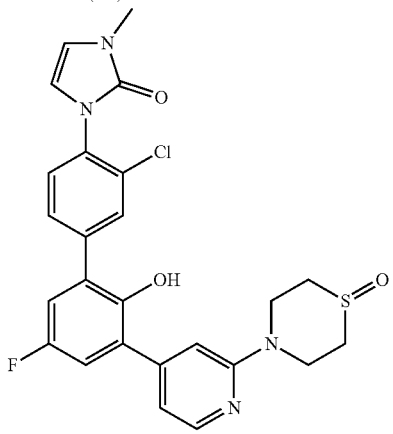 | ¹H NMR (400 MHz, DMSO-d₆-TFA salt): δ 8.88-8.87 (m, 1H), 8.19 (d, J = 5.6 Hz, 1H), 7.82 (d, J = 2.0 Hz, 1H), 7.63 (dd, J = 2.0, 8.0 Hz, 1H), 7.54 (d, J = 8.0 Hz, 1H), 7.32-7.25 (m, 3H), 7.00 (d, J = 5.2 Hz, 1H), 6.73 (d, J = 3.2 Hz, 1H), 6.68 (d, J = 2.8 Hz, 1H), 4.25-4.16 (m, 2H), 4.05-3.99 (m, 2H), 3.21 (s, 3H), 2.97-2.92 (m, 2H), 2.75-2.67 (m, 2H) | 513.2 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| 691 | (S)-1-(3-chloro-5'-fluoro-2'-hydroxy-3'-(2-(3-methoxypyrrolidin-1-yl)pyridin-4-yl)-[1,1'-biphenyl]-4-yl)-3-methyl-1H-imidazol-2(3H)-one | ¹H NMR (400 MHz, DMSO-d₆): δ 8.69 (s, 1H), 8.11 (d, J = 5.2 Hz, 1H), 7.80 (d, J = 2.0 Hz, 1H), 7.60 (d, J = 2.0 Hz, 1H), 7.52 (d, J = 8.0 Hz, 1H), 7.24-7.18 (m, 2H), 6.74-6.68 (m, 3H), 6.59 (s, 1H), 4.12 (s, 1H), 3.52-3.51 (m, 3H), 3.45-3.40 (m, 1H), 3.26 (s, 3H), 3.20 (s, 3H), 2.07-2.05 (m, 2H) | 495.1 |
| 692 | 1-(3'-(5-(1,7-diazaspiro[4.4]nonan-7-yl)pyridin-3-yl)-3-chloro-5'-fluoro-2'-hydroxy-[1,1'-biphenyl]-4-yl)-3-methyl-1H-imidazol-2(3H)-one | ¹H NMR (400 MHz, CD₃OD-TFA salt): δ 8.26-8.25 (m, 1H), 7.97 (s, 1H), 7.73-7.70 (m, 2H), 7.51 (dd, J = 2.0, 8.4 Hz, 1H), 7.44 (d, J = 8.0 Hz, 1H), 7.22-7.11 (m, 2H), 6.58 (d, J = 2.8 Hz, 1H), 6.54 (d, J = 3.2 Hz, 1H), 3.82-3.80 (m, 1H), 3.61 (t, J = 8.0 Hz, 2H), 3.52 (d, J = 11.6 Hz, 1H), 3.41-3.38 (m, 2H), 3.25 (s, 3H), 2.41 (t, J = 8.0 Hz, 2H), 2.19-2.10 (m, 4H) | 520.2 |
| 693 | 1-(3-chloro-5'-fluoro-2'-hydroxy-3'-(2-(1-methyl-1,6-diazaspiro[3.5]nonan-6-yl)pyridin-4-yl)-[1,1'-biphenyl]-4-yl)-3-methyl-1H-imidazol-2(3H)-one | ¹H NMR (400 MHz, CD₃OD): δ 8.11 (t, J = 7.2 Hz, 1H), 7.79-7.71 (m, 2H), 7.61 (d, J = 8.0 Hz, 1H), 7.53 (d, J = 8.0 Hz, 1H), 7.42-7.36 (m, 2H), 7.25 (d, J = 7.2 Hz, 1H), 6.68 (d, J = 2.8 Hz, 1H), 6.63 (d, J = 2.8 Hz, 1H), 4.51-3.59 (m, 6H), 3.34 (s, 3H), 2.92 (d, J = 16.0 Hz, 3H), 2.52-1.94 (m, 6H) | 534.2 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| 694 | 1-(3'-(2-(1,7-diazaspiro[4.5]decan-7-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, CD₃OD-HCl salt): δ 8.00 (d, J = 6.8 Hz, 1H), 7.70 (d, J = 1.6 Hz, 1H), 7.61 (s, 1H), 7.51 (dd, J = 1.6, 8.0 Hz, 1H), 7.44 (d, J = 8.0 Hz, 1H), 7.34 (dd, J = 1.2, 6.8 Hz, 1H), 7.28 (dd, J = 3.2, 8.8 Hz, 1H), 7.16 (dd, J = 2.0, 8.4 Hz, 1H), 6.59 (d, J = 2.8 Hz, 1H), 6.54 (d, J = 3.2 Hz, 1H), 4.09-4.06 (m, 1H), 3.93-3.90 (m, 1H), 3.48-3.34 (m, 3H), 3.25 (s, 3H), 2.18-1.19 (m, 9H) | 534.2 |
| 695 | 1-(3-chloro-5'-fluoro-2'-hydroxy-3'-(2-(1-methyl-1,7-diazaspiro[4.5]decan-7-yl)pyridin-4-yl)-[1,1'-biphenyl]-4-yl)-3-methyl-1H-imidazol-2(3H)-one | ¹H NMR (400 MHz, DMSO-d₆): δ 8.70 (s, 1H), 8.11 (d, J = 5.6 Hz, 1H), 7.80 (d, J = 2.0 Hz, 1H), 7.62 (dd, J = 1.6, 8.0 Hz, 1H), 7.52 (d, J = 8.0 Hz, 1H), 7.25-7.18 (m, 2H), 6.92 (s, 1H), 6.76-6.69 (m, 3H), 4.30-4.27 (m, 1H), 4.03-4.00 (m, 1H), 3.21 (s, 3H), 2.81-2.64 (m, 4H), 2.32 (s, 3H), 1.77-1.40 (m, 8H) | 548.2 |
| 696 | 5-(3'-chloro-5-fluoro-2-hydroxy-4'-(3-methyl-2-oxo-2,3-dihydro-1H-imidazol-1-yl)-[1,1'-biphenyl]-3-yl)-1-methyl-3-(1-methyl-1,7-diazaspiro[4.4]nonan-7-yl)pyridin-2(1H)-one | ¹H NMR (400 MHz, DMSO-d₆ + D₂O): δ 7.80 (d, J = 1.6 Hz, 1H), 7.61 (dd, J = 1.6, 8.0 Hz, 1H), 7.53-7.48 (m, 2H), 7.19-7.15 (m, | 564.3 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | 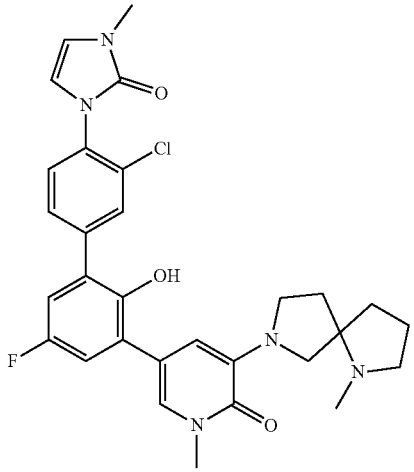 [SMILES: CN1CCCC12CCN(c1cc(-c3cc(F)cc(-c4ccc(-n5ccn(C)c5=O)c(Cl)c4)c3O)cn(C)c1=O)C2] | 2H), 6.75-6.68 (m, 3H), 4.42-4.21 (m, 1H), 3.66-3.50 (m, 5H), 3.30-3.16 (m, 6H), 2.91-2.82 (m, 3H), 2.22-1.96 (m, 6H) | |
| 697 | 1-(3'-(2-(3-(2-aminoethyl)piperazin-1-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆-TFA salt): δ 9.20-9.17 (m, 1H), 9.01-8.99 (m, 1H), 8.79 (s, 1H), 8.22 (d, J = 4.8 Hz, 1H), 7.85-7.81 (m, 3H), 7.62 (dd, J = 2.0, 8.0 Hz, 1H), 7.55 (d, J = 8.0 Hz, 1H), 7.28 (dd, J = 3.2, 9.2 Hz, 1H), 7.22 (dd, J = 3.2, 8.8 Hz, 1H), 7.13 (s, 1H), 6.99 (d, J = 5.6 Hz, 1H), 6.73 (d, J = 3.2 Hz, 1H), 6.68 (d, J = 3.2 Hz, 1H), 4.41-4.35 (m, 2H), 3.46-3.38 (m, 2H), 3.21 (s, 3H), 3.16-2.98(m, 5H), 1.94-1.89 (m, 2H) | 523.3 |
| 698 | (R)-2-(4-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)piperazin-2-yl)acetonitrile | ¹H NMR (400 MHz, CD₃CD): δ 8.08 (d, J = 5.2 Hz, 1H), 7.70 (d, J = 1.6 Hz, 1H), 7.51 (dd, J = 2.0, 8.4 Hz, 1H), 7.40 (d, J = 8.0 Hz, 1H), 7.01 (d, J = 8.8 Hz, 2H), 6.92 (s, 1H), 6.81 (d, J = 5.2 Hz, 1H), 6.57 (d, J = 2.8 Hz, 1H), 6.53 (d, J = 3.2 Hz, 1H), 4.19-4.16 (m, 1H), 3.94 (d, J = 12.4 Hz, 1H), 3.25 (s, 3H), 3.04-2.81 (m, 4H), 2.72-2.57 (m, 3H),N—H and O—H protons not observed | 519.2 |

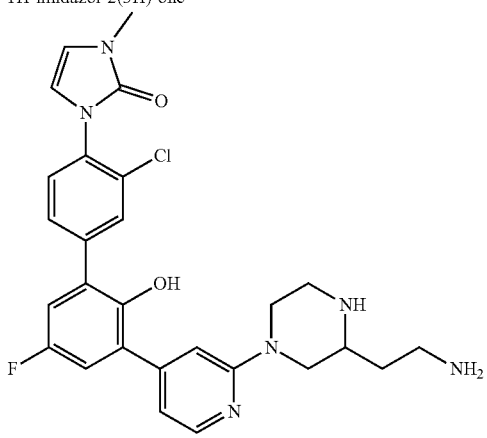

TABLE 30-continued

Following compounds were prepared using similar procedures as described for Examples 365-668.

| Ex. No. | Name/Structure | $^1$H NMR Data | LCMS (M + H)$^+$ |
|---|---|---|---|
| 699 | 1-(3-chloro-5'-fluoro-2'-hydroxy-3''-(4-isopropylpiperazin-1-yl)-[1,1':3',1''-terphenyl]-4-yl)-3-methyl-1H-imidazol-2(3H)-one | $^1$H NMR (400 MHz, DMSO-d$_6$): δ 8.47 (s, 1H), 7.81 (s, 1H), 7.62 (d, J = 8.0 Hz, 1H), 7.52 (d, J = 8.0 Hz, 1H), 7.28 (t, J = 8.0 Hz, 1H), 7.18-7.08 (m, 3H), 6.97-6.94 (m, 2H), 6.72-6.69 (m, 2H), 3.21 (s, 3H), 3.07 (hr s, 4H), 2.69-2.66 (m, 1H), 2.58 (br s, 4H), 1.01 (d, J = 6.4 Hz, 6H) | 521.3 |
| 700 | 1-(3-chloro-5'-fluoro-2'-hydroxy-3'-(5-(1-methyl-1,7-diazaspiro[4.4]nonan-7-yl)pyridin-3-yl)-[1,1'-biphenyl]-4-yl)-3-methyl-1H-imidazol-2(3H)-one | $^1$H NMR (400 MHz, DMSO-d$_6$): δ 8.65 (s, 1H), 8.00-7.90 (m, 3H), 7.81-7.61 (m, 2H), 7.23-7.18 (m, 2H), 7.02 (s, 1H), 6.71-6.68 (m, 2H), 3.46-3.39 (m, 2H), 3.23 (s, 3H), 3.02 (d, J = 9.2 Hz, 2H), 2.72-2.65 (m, 2H), 2.25-2.23 (m, 4H), 2.15-2.12 (m, 2H), 1.77-1.72 (m, 3H) | 534.2 |
| 701 | 1-(3-chloro-5'-fluoro-3'-(2-(3-(4-fluoropiperidin-1-yl)pyrrolidin-1-yl)pyridin-4-yl)-2'-hydroxy-[1,1'-biphenyl]-4-yl)-3-methyl-1H-imidazol-2(3H)-one | $^1$H NMR (400 MHz, DMSO-d$_6$): δ 8.68 (s, 1H), 8.10 (d, J = 5.2 Hz, 1H), 7.80 (d, J = 2.0 Hz, 1H), 7.62 (dd, J = 1.6, 8.0 Hz, | 566.2 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | 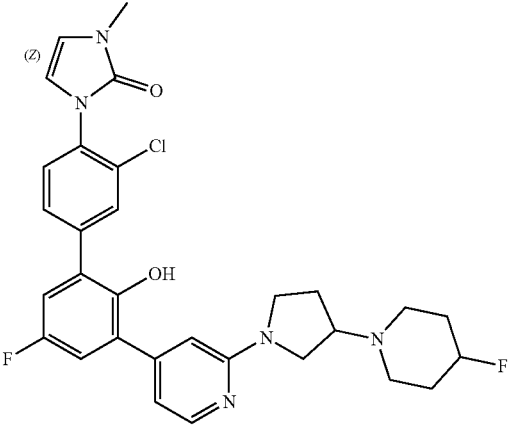 [SMILES: Cn1ccn(-c2ccc(-c3cc(F)cc(-c4ccnc(N5CCC(N6CCC(F)CC6)C5)c4)c3O)cc2Cl)c1=O] | 1H), 7.52 (d, J = 8.4 Hz, 1H), 7.26-7.18 (m, 2H), 6.75-.6.68 (m, 3H), 6.60 (s, 1H), 4.73-4.61 (m, 1H), 3.77-3.60 (m, 2H), 3.21 (s, 3H), 3.17-3.12 (m, 2H), 2.96-2.89 (m, 1H), 2.67-2.59 (m, 2H), 2.39-2.30 (m, 1H), 2.24-2.19 (m, 1H), 1.93-1.72 (m, 6H) | |
| 702 | 1-(3-chloro-5'-fluoro-2'-hydroxy-3'-(2-(4-isopropylpiperazin-1-yl)-6-methoxypyridin-4-yl)-[1,1'-biphenyl]-4-yl)-3-methyl-1H-imidazol-2(3H)-one 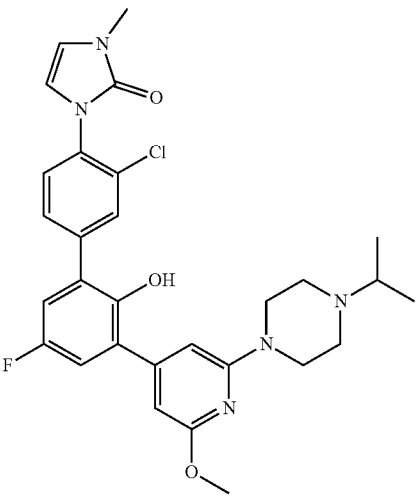 [SMILES: COc1cc(-c2cc(F)cc(-c3ccc(-n4ccn(C)c4=O)c(Cl)c3)c2O)cc(N2CCN(C(C)C)CC2)n1] | ¹H NMR (400 MHz, DMSO-d₆): δ 8.62 (s, 1H), 7.80 (d, J = 1.6 Hz, 1H), 7.61 (dd, J = 2.0, 8.4 Hz, 1H), 7.52 (d, J = 8.0 Hz, 1H), 7.24-7.14 (m, 2H), 6.72 (d, J = 2.8 Hz, 1H), 6.69 (d, J = 2.8 Hz, 1H), 6.44 (s, 1H), 6.21 (s, 1H), 3.81 (s, 3H), 3.50 (t, J = 4.4 Hz, 4H), 3.21 (s, 3H), 2.70-2.67 (m, 1H), 2.54-2.51 (m, 4H), 1.00 (d, J = 6.4 Hz, 6H) | 552.3 |
| 703 | 1-(3-chloro-5'-fluoro-2'-hydroxy-3'-(2-(4-isopropylpiperazin-1-yl)-6-methylpyridin-4-yl)-[1,1'-biphenyl]-4-yl)-3-methyl-1H-imidazol-2(3H)-one | ¹H NMR (400 MHz, DMSO-d₆-TFA salt): δ 9.48 (br s, 1H), 8.70 (br s, 1H), 7.80 (d, J = 2.0 Hz, | 536.3 |

TABLE 30-continued

Following compounds were prepared using similar procedures as described for Examples 365-668.

| Ex. No. | Name/Structure | $^1$H NMR Data | LCMS $(M + H)^+$ |
|---|---|---|---|
| | 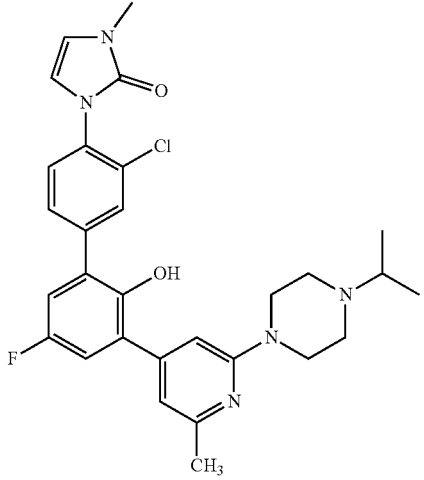 [SMILES: Cc1cc(-c2cc(F)cc(-c3ccc(-n4ccn(C)c4=O)c(Cl)c3)c2O)cc(N2CCN(C(C)C)CC2)n1] | 1H), 7.61 (dd, J = 1.6, 8.0 Hz, 1H), 7.53 (d, J = 8.4 Hz, 1H), 7.26 (dd, J = 2.8, 8.8 Hz, 1H), 7.19 (dd, J = 3.2, 8.8 Hz, 1H), 6.90 (s, 1H), 6.86 (s, 1H), 6.72 (d, J = 2.8 Hz, 1H), 6.68 (d, J = 3.2 Hz, 1H), 4.54-4.50 (m, 2H), 3.53-3.50 (m, 3H), 3.20 (s, 3H), 3.12-3.05 (m, 4H), 2.40 (s, 3H), 1.29 (d, J = 6.4 Hz, 6H) | |
| 704 | 1-(3-chloro-3'-(2-ethyl-6-(4-isopropylpiperazin-1-yl)pyridin-4-yl)-5'-fluoro-2'-hydroxy-[1,1'-biphenyl]-4-yl)-3-methyl-1H-imidazol-2(3H)-one<br>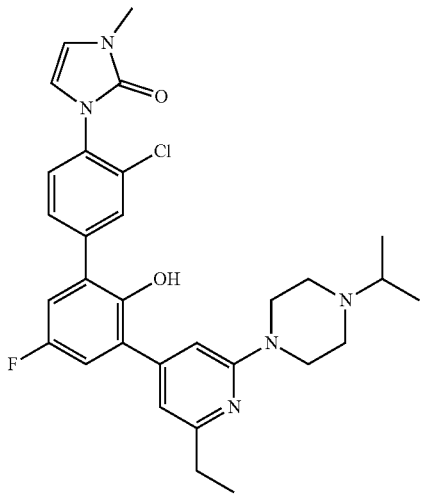 | $^1$H NMR (400 MHz, DMSO-d$_6$): δ 8.63 (s, 1H), 7.80 (d, J = 1.6 Hz, 1H), 7.61 (dd, J = 1.6, 8.4 Hz, 1H), 7.51 (d, J = 8.0 Hz, 1H), 7.22 (dd, J = 3.2, 9.2 Hz, 1H), 7.15 (dd, J = 3.2, 8.8 Hz, 1H), 6.73-6.68 (m, 4H), 3.50 (s, 4H), 3.20 (s, 3H), 2.67-2.60 (m, 3H), 2.53-2.49 (m, 4H), 1.22 (t, J = 7.6 Hz, 3H), 1.00 (d, J = 6.8 Hz, 6H) | 550.3 |
| 705 | 2-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-2,7-diazaspiro[4.4]nonan-3-one | $^1$H NMR (400 MHz, DMSO-d$_6$): δ 8.48 (s, 1H), 8.40 (d, J = 5.2 Hz, 1H), 7.84 (d, J = 2.0 Hz, 1H), | 534.2 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | [Structure] | 7.63 (dd, J = 2.0, 8.4 Hz, 1H), 7.51 (d, J = 8.4 Hz, 1H), 7.35 (dd, J = 1.2, 4.8 Hz, 1H), 7.27 (d, J = 8.8 Hz, 1H), 7.17 (d, J = 8.4 Hz, 1H), 6.71 (d, J = 3.2 Hz, 1H), 6.67 (d, J = 3.2 Hz, 1H), 4.00-3.90 (m, 2H), 3.20 (s, 3H), 2.92-2.88 (m, 2H), 2.80-2.70 (m, 2H), 2.64 (s, 2H), 1.82-1.76 (m, 2H), N—H and O—H protons not observed | |
| 706 | 1-(3-chloro-3'',5'-difluoro-2'-hydroxy-5''-(piperazin-1-yl)-[1,1':3,1''-terphenyl]-4-yl)-3-methyl-1H-imidazol-2(3H)-one [Structure] | ¹H NMR (400 MHz, DMSO-d₆): δ 7.81 (d, J = 1.6 Hz, 1H), 7.62 (dd, J = 1.6, 8.0 Hz, 1H), 7.52 (d, J = 8.0 Hz, 1H), 7.21-7.15 (m, 2H), 6.88 (s, 1H), 6.75-6.68 (m, 4H), 3.21 (s, 3H), 3.13 (t, J = 4.8 Hz, 4H), 2.83 (t, J = 4.8 Hz, 4H), N—H and O—H protons not observed | 497.2 |
| 707 | 1-(3-chloro-3'-(2-(1,1-dioxidothiomorpholino)pyridin-4-yl)-5'-fluoro-2'-hydroxy-[1,1'-biphenyl]-4-yl)-3-methyl-1H-imidazol-2(3H)-one [Structure] | ¹H NMR (400 MHz, DMSO-d₆): δ 8.73 (s, 1H), 8.23 (d, J = 5.2 Hz, 1H), 7.81 (d, J = 1.6 Hz, 1H), 7.62 (dd, J = 2.0, 8.4 Hz, 1H), 7.53 (d, J = 8.0 Hz, 1H), 7.28-7.24 (m, 2H), 7.15 (s, 1H), 6.95 (d, J = 4.8 Hz, 1H), 6.72 (d, J = 3.2 Hz, 1H), 6.68 (d, J = 3.2 Hz, 1H), 4.11 (br s, 4H), 3.21 (s, 3H), 3.12 (br s, 4H) | 529.1 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| 708 | 1-(3-chloro-5'-fluoro-2'-hydroxy-3'-(5-(3-hydroxy-3-methylpyrrolidin-1-yl)pyridin-3-yl)-[1,1'-biphenyl]-4-yl)-3-methyl-1H-imidazol-2(3H)-one | ¹H NMR (400 MHz, DMSO-D₆): δ 8.66 (s, 1H), 7.98 (d, J = 1.6 Hz, 1H), 7.87 (d, J = 2.8 Hz, 1H), 7.81 (d, J = 2.0 Hz, 1H), 1H), 7.52 (d, J = 8.4 Hz, 1H), 7.24-7.17 (m, 2H), 6.98 (s, 1H), 6.72 (d, J = 3.2 Hz, 1H), 6.69 (d, J = 3.2 Hz, 1H), 4.83 (s, 1H), 3.45-3.35 (m, 2H), 3.27-3.24 (m, 1H), 3.21 (s, 3H), 1.96-1.88 (m, 2H), 1.37 (s, 3H), N—H or O—H was not observed | 495.2 |
| 709 | (S)-1-(3-chloro-5'-fluoro-2'-hydroxy-3'-(2-(3-hydroxy-3-methylpyrrolidin-1-yl)pyridin-4-yl)-[1,1'-biphenyl]-4-yl)-3-methyl-1,3-dihydro-2H-imidazol-2-one | ¹H NMR (400 MHz, DMSO-d₆): δ 8.69 (s, 1H), 8.09 (d, J = 5.2 Hz, 1H), 7.80 (d, J = 2.0 Hz, 1H), 7.62 (dd, J = 2.0, 8.4 Hz, 1H), 7.52 (d, J = 8.4 Hz, 1H), 7.25-7.17 (m, 2H), 6.72-6.69 (m, 3H), 6.54 (s, 1H), 4.78 (s, 1H), 3.53-3.50 (m, 2H), 3.43-3.41 (m, 1H), 3.30-3.28 (m, 1H), 3.21 (s, 3H), 1.94-1.86 (m, 2H), 1.35 (s, 3H) | 495.2 |
| 710 | (R)-1-(3-chloro-5'-fluoro-2'-hydroxy-3'-(2-(3-hydroxy-3-methylpyrrolidin-1-yl)pyridin-4-yl)-[1,1'-biphenyl]-4-yl)-3-methyl-1,3-dihydro-2H-imidazol-2-one | ¹H NMR (400 MHz, DMSO-d₆): δ 8.69 (s, 1H), 8.09 (d, J = 5.2 Hz, 1H), 7.80 (d, J = 2.0 Hz, 1H), 7.62 (dd, J = 2.0, 8.4 Hz, 1H), 7.52 (d, J = 8.4 Hz, 1H), 7.25-7.17 (m, 2H), 6.72-6.69 (m, 3H), 6.54 (s, 1H), 4.78 (s, 1H), 3.53-3.50 (m, 2H), 3.43-3.41 (m, 1H), 3.30-3.28 (m, 1H), 3.21 (s, 3H), 1.94-1.86 (m, 2H), 1.35 (s, 3H) | 495.2 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| 711 | (S)-1-(3'-(2-(3-amino-3-methylpyrrolidin-1-yl)pyridin-4-yl)-3-chloro-5'-fluoro-2'-hydroxy-[1,1'-biphenyl]-4-yl)-3-methyl-1,3-dihydro-2H-imidazol-2-one | ¹H NMR (400 MHz, DMSO-d₆): δ 8.09 (d, J = 5.6 Hz, 1H), 7.81 (d, J = 2.0 Hz, 1H), 7.62 (dd, J = 2.0, 8.4 Hz, 1H), 7.52 (d, J = 8.0 Hz, 1H), 7.24 (dd, J = 3.2, 9.2 Hz, 1H), 7.18 (dd, J = 3.6, 9.2 Hz, 1H), 6.72-6.69 (m, 3H), 6.54 (s, 1H), 3.57-3.44 (m, 2H), 3.28 (s, 2H), 3.21 (s, 3H), 1.84 (t, J = 6.8 Hz, 2H), 1.26 (s, 3H), N—H and O—H protons not observed | 494.1 |
| 712 | 2-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-7-methyl-2,7-diazaspiro[4.4]nonan-3-one | ¹H NMR (400 MHz, DMSO-d₆): δ 8.80 (br s, 1H), 8.45 (s, 1H), 8.41 (d, J = 5.6 Hz, 1H), 7.80 (d, J = 2.0 Hz, 1H), 7.62 (dd, J = 2.4, 8.4 Hz, 1H), 7.53 (d, J = 8.0 Hz, 1H), 7.33-7.27 (m, 2H), 7.19 (dd, J = 3.2, 9.2 Hz, 1H), 6.71 (d, J = 2.8 Hz, 1H), 6.68 (d, J = 3.2 Hz, 1H), 4.03 (d, J = 10.4 Hz, 1H), 3.93 (d, J = 11.2 Hz, 1H), 3.20 (s, 3H), 2.68 (s, 2H), 2.61-2.55 (m, 3H), 2.46-2.44 (m, 1H), 2.26 (s, 3H), 1.91-1.86 (m, 2H) | 548.2 |
| 713 | 1-(3-chloro-3'',5'-difluoro-2'-hydroxy-5''-(4-isopropylpiperazin-1-yl)-[1,1':3',1''-terphenyl]-4-yl)-3-methyl-1H-imidazol-2(3H)-one | ¹H NMR (400 MHz, DMSO-d₆): δ 8.59 (s, 1H), 7.81 (d, J = 1.6 Hz, 1H), 7.62 (dd, J = 2.0, 8.4 Hz, | 539.3 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | 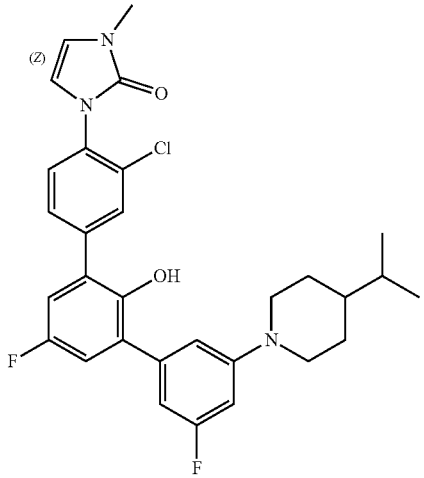 [SMILES: CC(C)C1CCN(c2cc(F)cc(-c3cc(F)cc(-c4ccc(-n5ccn(C)c5=O)c(Cl)c4)c3O)c2)CC1] | 1H), 7.52 (d, J = 8.4 Hz, 1H), 7.22-7.15(m, 2H), 6.84 (s, 1H), 6.77-6.69 (m, 4H), 3.30 (hr s, 1H), 3.21 (br s, 7H), 2.67 (br s, 1H), 2.57 (br s, 3H), 1.02 (d, J = 6.8 Hz, 6H) | |
| 714 | 1-(3-chloro-5'-fluoro-2'-hydroxy-3'-(2-(3-hydroxy-3-methylpiperidin-1-yl)pyridin-4-yl)-[1,1'-biphenyl]-4-yl)-3-methyl-1H-imidazol-2(3H)-one<br>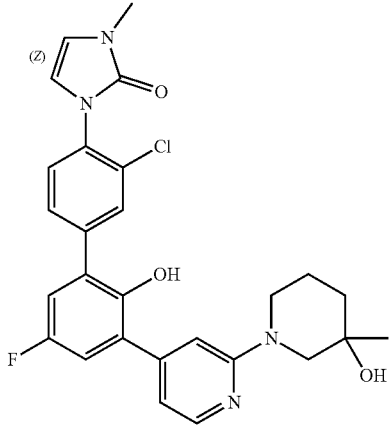 [SMILES: Cn1ccn(-c2ccc(-c3cc(F)cc(-c4ccnc(N5CCCC(C)(O)C5)c4)c3O)cc2Cl)c1=O] | ¹H NMR (400 MHz, DMSO-d₆): δ 8.70 (s, 1H), 8.10 (d, J = 5.2 Hz, 1H), 7.80 (d, J = 2.0 Hz, 1H), 7.62 (dd, J = 2.0, 8.4 Hz, 1H), 7.26-7.17 (m, 2H), 6.92 (s, 1H), 6.75-6.69 (m, 3H), 4.39 (s, 1H), 3.64-3.60 (m, 1H), 3.44-3.39 (m, 3H), 3.21 (s, 3H), 1.77-1.73 (m, 1H), 1.58-1.49 (m, 3H), 1.13 (s, 3H) | 509.2 |
| 715 | (R)-1-(3-chloro-5'-fluoro-2'-hydroxy-3'-(2-(3-methoxypropoxy)-6-(3-methylpiperazin-1-yl)pyridin-4-yl)-[1,1'-biphenyl]-4-yl)-3-methyl-1H-imidazol-2(3H)-one | ¹H NMR (400 MHz, DMSO-d₆): δ 7.80 (d, J = 2.0 Hz, 1H), 7.61 (dd, J = 1.6, 8.0 Hz, 1H), 7.52 (d, J = 8.0 Hz, 1H),7.22 (dd, J = | 582.3 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | 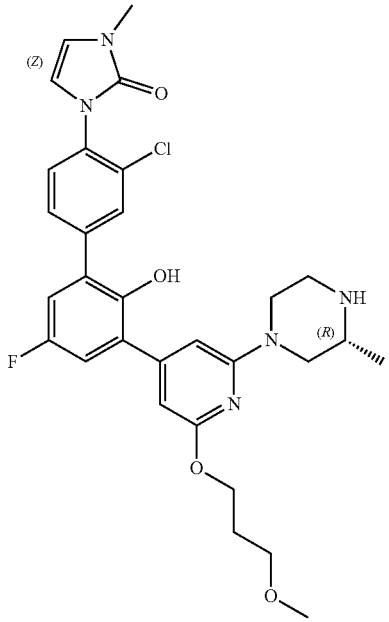 | 3.2, 8.4 Hz, 1H), 7.15 (dd, J = 3.2, 9.2 Hz, 1H), 6.72 (d, J = 3.2Hz, 1H),6.69(d, J = 2.8 Hz, 1H), 6.42 (s, 1H), 6.17 (s, 1H), 4.26 (t, J = 5.6 Hz, 2H), 4.14-4.08 (m, 2H), 3.46 (I, J = 6.4 Hz, 2H), 3.24 (s, 3H), 3.21 (s, 3H), 2.96-2.94 (m, 1H), 2.71-2.67 (m, 3H), 2.35 (t, J = 10.8 Hz, 1H), 1.97-1.91 (m, 2H), 1.03 (d, J = 6.0 Hz, 3H), N—H and O—H protons not observed. | |
| 716 | (R)-1-(3'-(2-(3-amino-3-methylpyrrolidin-1-yl)pyridin-4-yl)-3-chloro-5'-fluoro-2'-hydroxy-[1,1'-biphenyl]-4-yl)-3-methyl-1,3-dihydro-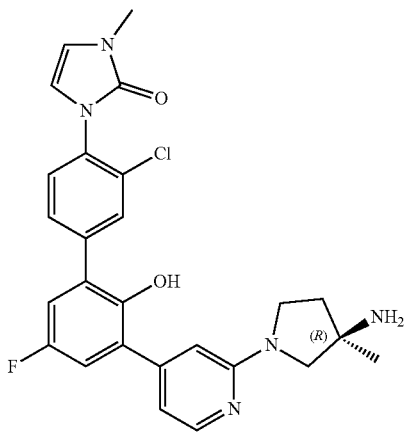 | ¹H NMR (400 MHz, DMSO-d₆): δ 8.09 (d, J = 5.6 Hz, 1H), 7.81 (d, J = 2.0 Hz, 1H), 7.62 (dd, J = 2.0, 8.4 Hz, 1H), 7.52 (d, J = 8.0 Hz, 1H),7.24 (dd, J = 3.2, 9.2 Hz, 1H), 7.18 (dd, J = 3.6, 9.2 Hz, 1H), 6.72-6.69 (m, 3H), 6.54 (s, 1H), 3.57-3.44 (m, 2H), 3.28 (s, 2H), 3.21 (s, 3H), 1.84(t, J = 6.8 Hz, 2H), 1.26 (s, 3H), N—H and O—H protons not observed | 494.1 |
| 717 | 4-(3'-chloro-5-fluoro-2-hydroxy-4'-(3-methyl-2-oxo-2,3-dihydro-1H-imidazol-1-yl)-[1,1'-biphenyl]-3-yl)-6-(4-isopropylpiperazin-1-yl)-1-methylpyridin-2(1H)-one | ¹H NMR (400 MHz, DMSO-d₆): δ 8.80 (s, 1H), 7.80 (d, J = 2.0 Hz, 1H), 7.61 (dd, J = 2.0, 9.2 Hz, 1H), 7.52 (d, J = 8.0 Hz, | 552.2 |

TABLE 30-continued

Following compounds were prepared using similar procedures as described for Examples 365-668.

| Ex. No. | Name/Structure | ¹H NMR Data | LCMS (M + H)⁺ |
|---|---|---|---|
| | 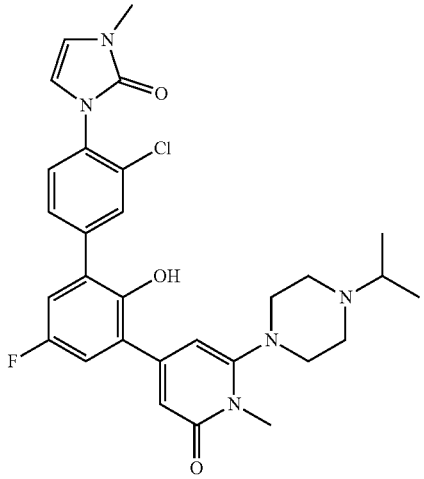 [SMILES: CC(C)N1CCN(c2cc(-c3cc(F)cc(-c4ccc(-n5ccn(C)c5=O)c(Cl)c4)c3O)cc(=O)n2C)CC1] | 1H), 7.27-7.18 (m, 2H), 6.71 (d, J = 3.2 Hz, 1H), 6.69 (d, J = 2.8 Hz, 1H), 6.29 (d, J = 1.6 Hz, 1H), 5.99 (d, J = 1.6 Hz, 1H), 3.43 (s, 3H), 3.21 (s, 3H), 2.94 (br s, 4H), 2.73-2.70 (m, 1H), 2.61 (br s, 4H), 1.01 (d, J = 6.8 Hz, 6H) | |
| 718 | 1-(3-chloro-3'-(2-(3-cyclopropyl-3-hydroxypyrrolidin-1-yl)pyridin-4-yl)-5'-fluoro-2'-hydroxy-[1,1'-biphenyl]-4-yl)-3-methyl-1H-imidazol-2(3H)-one<br>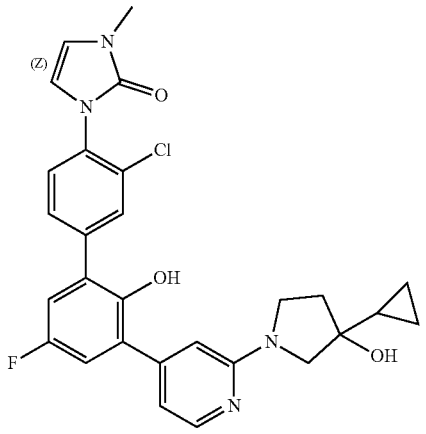 | ¹H NMR (400 MHz, DMSO-d₆): δ 8.67 (s, 1H), 8.09 (d, J = 5.2 Hz, 1H), 7.80 (d, J = 2.0 Hz, 1H), 7.62 (dd, J = 2.0, 8.4 Hz, 1H), 7.52 (d, J = 8.4 Hz, 1H), 7.25-7.17 (m, 2H), 6.72-6.68 (m, 3H), 6.55 (s, 1H), 4.45 (s, 1H), 3.60-3.46 (m, 2H), 3.40-3.33 (m, 2H), 3.21 (s, 3H), 1.91-1.87 (m, 2H), 1.06-1.01 (m, 1H), 0.43-0.31 (m, 4H) | 521.1 |
| 719 | 1-(3''-(4-(tert-butyl)piperazin-1-yl)-3-chloro-4'',5'-difluoro-2'-hydroxy-[1,1':3',1''-terphenyl]-4-yl)-3-methyl-1H-imidazol-2(3H)-one<br>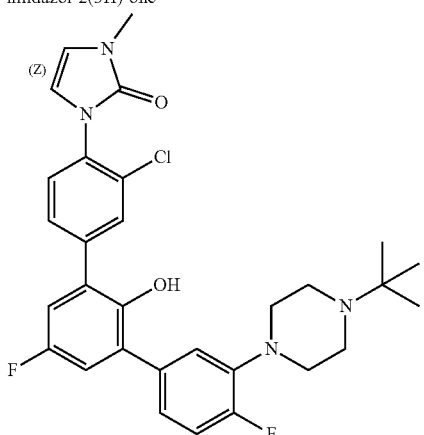 | ¹H NMR (400 MHz, DMSO-d₆): δ 8.56 (s, 1H), 7.81 (d, J = 1.6 Hz, 1H), 7.62 (dd, J = 1.6, 8.0 Hz, 1H), 7.52 (d, J = 8.4 Hz, 1H), 7.22-7.14 (m, 5H), 6.72 (d, J=3.2 Hz, 1H), 6.69 (d, J = 2.8 Hz, 1H), 3.21 (s, 3H), 3.05 (br s, 4H), 2.67 (br s, 4H), 1.05 (s, 9H) | 553.3 |

TABLE 30-continued

Following compounds were prepared using similar procedures as described for Examples 365-668.

| Ex. No. | Name/Structure | $^1$H NMR Data | LCMS (M + H)$^+$ |
|---|---|---|---|
| 720 | 1-(3-chloro-4'',5'-difluoro-2'-hydroxy-3''-(4-isopropylpiperazin-1-yl)-[1,1':3',1''-terphenyl]-4-yl)-3-methyl-1H-imidazol-2(3H)-one | $^1$H NMR (400 MHz, DMSO-d$_6$): δ 8.56 (s, 1H), 7.81 (d, J = 2.0 Hz, 1H), 7.62 (dd, J = 2.0, 8.4 Hz, 1H), 7.52 (d, J = 8.0 Hz, 1H), 7.22-7.13 (m, 5H), 6.72 (d, J = 3.2 Hz, 1H), 6.69 (d, J = 3.2 Hz, 1H), 3.21 (s, 3H), 3.06 (brs, 4H), 2.71-2.65 (brs, 1H), 2.60 (br s, 4H), 1.01 (d, J = 6.8 Hz, 6H) | 539.2 |
| 721 | 1-(3'-(2-(1-amino-3-azabicyclo[3.1.0]hexan-3-yl)pyridin-4-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$): δ 8.08 (d, J = 5.2 Hz, 1H), 7.80 (d, J = 2.0 Hz, 1H), 7.61 (dd, J = 1.6, 8.0 Hz, 1H), 7.52 (d, J = 8.4 Hz, 1H), 7.25-7.16 (m, 2H), 6.75-6.68 (m, 3H), 6.55 (s, 1H), 3.79 (d, J = 6.0 Hz, 1H), 3.55 (d, J = 10.4 Hz, 1H), 3.47-3.43 (m, 1H), 3.28-3.25 (m, 1H), 3.20 (s, 3H), 1.43-1.42 (m, 1H), 0.90-0.88 (m, 1H), 0.42-0.41 (m, 1H), Three N—H and O—H proton not observed | 492.1 |

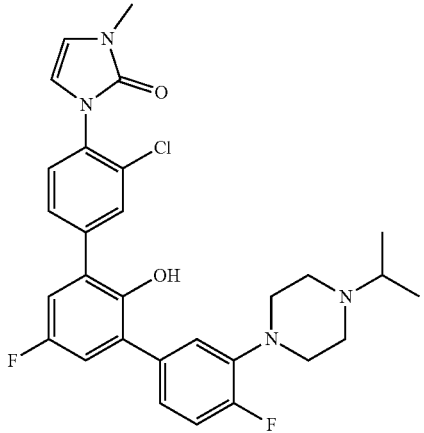 [SMILES: CC(C)N1CCN(c2cc(-c3cc(F)cc(-c4ccc(-n5ccn(C)c5=O)c(Cl)c4)c3O)ccc2F)CC1]

Example 722

1-(3-chloro-5'-fluoro-2'-hydroxy-3'-(5-(4-isopropylpiperazin-1-yl)-6-methylpyridin-3-yl)-[1,1'-biphenyl]-4-yl)-3-methyl-1H-imidazol-2(3H)-one

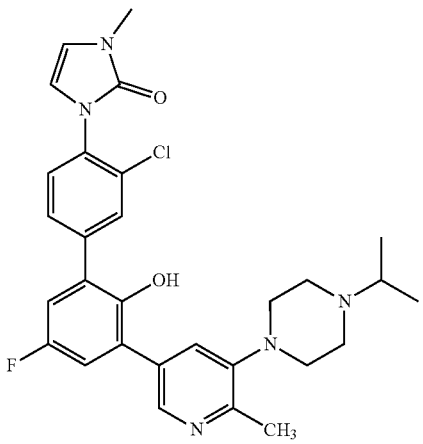

Step 1: 1-(5-chloro-2-methylpyridin-3-yl)-4-isopropylpiperazine

To a solution of 3-bromo-5-chloro-2-methylpyridine (0.2 g, 0.97 mmol, 1.0 eq) in toluene (4 mL) were added 1-isopropylpiperazine (124 mg, 0.97 mmol, 1.0 eq), $Pd_2(dba)_3$ (18 mg, 0.02 mmol, 0.02 eq), BINAP (25 mg, 0.04 mmol, 0.04 eq), sodium tert-butoxide (135 mg, 1.4 mmol, 1.5 eq). The reaction mixture was stirred at 70° C. for 4 hours under nitrogen atmosphere. After the reaction was complete by LCMS, the reaction mixture was concentrated and purified by flash column chromatography (PE:EA=4:1) to afford the title compound as a brown solid. LCMS: 254.1 $(M+H)^+$.

Step 2: (5-(4-isopropylpiperazin-1-yl)-6-methylpyridin-3-yl) boronic acid

A solution of 1-(5-chloro-2-methylpyridin-3-yl)-4-isopropylpiperazine (0.5 g, 1.97 mmol, 1.0 eq), 4,4,4',4',5,5,5',5'-octamethyl-2,2'-bi(1,3,2-dioxaborolane) (0.75 g, 2.96 mmol, 1.5 eq), $Pd_2(dba)_3$ (144 mg, 0.16 mmol, 0.08 eq), X-phos (150 mg, 0.32 mmol, 0.16 eq), KOAc (579 mg, 5.9 mmol, 3.0 eq) in dioxane (12 mL) was stirred at 100° C. for 10 hours under nitrogen atmosphere. After the reaction was complete by LCMS, the reaction mixture was filtered and concentrated to afford the crude title compound which was used in the next step without further purification. LCMS: 264.2 $(M+H)^+$.

Step 3: 2-bromo-4-fluoro-6-(5-(4-isopropylpiperazin-1-yl)-6-methylpyridin-3-yl)phenol A solution of (5-(4-isopropylpiperazin-1-yl)-6-methylpyridin-3-yl)boronic acid (0.5 g, 1.89 mmol, 1.0 eq), 2,6-dibromo-4-fluorophenol (2.3 g, 8.5 mmol, 4.5 eq), $Pd(dppf)Cl_2$ (139 mg, 0.19 mmol, 0.1 eq), $K_3PO_4$ (1.2 g, 5.7 mmol, 3.0 eq) in dioxane/$H_2O$ (10 mL, 5:1) was stirred at 100° C. for 0.5 hour under nitrogen atmosphere. The reaction mixture was concentrated and purified by flash column chromatography (DCM:MeOH=15:1) to afford the title compound (0.26 g, 32% yield) as a yellow solid. LCMS: 408.1 $(M+H)^+$.

Step 4: 1-(3-chloro-5'-fluoro-2'-hydroxy-3'-(5-(4-isopropylpiperazin-1-yl)-6-methylpyridin-3-yl)-[1,1'-biphenyl]-4-yl)-3-methyl-1H-imidazol-2(3H)-one A solution of 2-bromo-4-fluoro-6-(5-(4-isopropylpiperazin-1-yl)-6-methylpyridin-3-yl)phenol (0.26 g, 0.64 mmol, 1.0 eq), 1-(2-chloro-4-(4,4,5,5-tetramethyl-1,3,2-dioxaborolan-2-yl)phenyl)-3-methyl-1H-imidazol-2(3H)-one (0.53 g, 1.6 mmol, 2.5 eq), $Pd(dppf)Cl_2$ (46 mg, 0.06 mmol, 0.1 eq), $K_3PO_4$ (0.4 g, 1.9 mmol, 3.0 eq) in dioxane/$H_2O$ (6 mL, 5:1) was stirred at 100° C. for 0.5 hour under nitrogen atmosphere. After the reaction was complete by LCMS, the reaction mixture was concentrated and purified by flash column chromatography (DCM:MeOH=15:1) and reversed phase flash ($H_2O$:ACN=3:2) to afford the title compound (129 mg, 37% yield) as a yellow solid. $^1$H NMR (400 MHz, DMSO-$d_6$): δ 8.70 (s, 1H), 8.31 (d, J=1.6 Hz, 1H), 7.80 (d, J=1.6 Hz, 1H), 7.62 (dd, J=2.0, 8.0 Hz, 1H), 7.53-7.51 (m, 2H), 7.22 (d, J=8.8 Hz, 2H), 6.70 (dd, J=2.8, 12.4 Hz, 2H), 3.21 (s, 3H), 2.93-2.91 (m, 4H), 2.70-2.67 (m, 1H), 2.62 (s, 4H), 2.47 (s, 3H), 1.01 (d, J=6.4 Hz, 6H). LCMS: 536.2 $(M+H)^+$.

Example 723

3-(3-amino-3-methylpyrrolidin-1-yl)-5-(3'-chloro-5-fluoro-2-hydroxy-4'-(3-methyl-2-oxo-2,3-dihydro-1H-imidazol-1-yl)-[1,1'-biphenyl]-3-yl)-1-methylpyridin-2(1H)-one

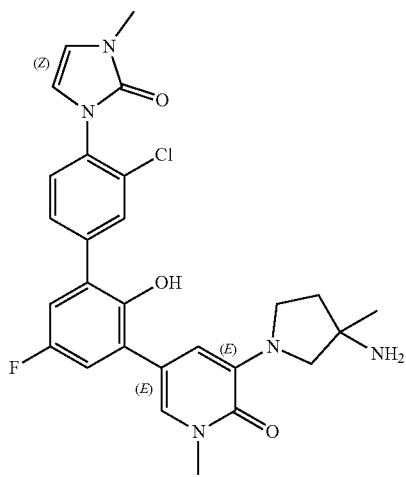 [SMILES: Cn1cc(-c2cc(F)cc(-c3ccc(-n4ccn(C)c4=O)c(Cl)c3)c2O)cc(N2CCC(C)(N)C2)c1=O]

The title compound was prepared following the procedure described for Example 372 using 3,5-dibromo-1-methylpyridin-2(1H)-one, tert-butyl (3-methylpyrrolidin-3-yl)carbamate, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and $BBr_3$ to afford the title compound (0.3% yield). $^1$H NMR (400 MHz, DMSO-$d_6$+$D_2O$): δ 7.80 (d, J=2.0 Hz, 1H), 7.61 (dd, J=1.6, 8.0 Hz, 1H), 7.51 (d, J=8.4 Hz, 1H), 7.28 (d, J=2.0 Hz, 1H), 7.15-7.10 (m, 2H), 6.70 (dd, J=3.2, 12.4 Hz, 2H), 6.41 (d, J=1.6 Hz, 1H), 3.56-3.54 (m, 1H), 3.43-3.41 (m, 4H), 3.34-3.30 (m, 2H), 3.27 (s, 3H), 1.75 (t, J=7.2 Hz, 2H), 1.22 (s, 3H). LCMS: 524.2 (M+H)+.

Example 724

1-(3-chloro-5'-fluoro-2'-hydroxy-3'-(2-(4-(1-methoxy-2-methylpropan-2-yl)piperazin-1-yl)pyridin-4-yl)-[1,1'-biphenyl]-4-yl)-3-methyl-1H-imidazol-2(3H)-one

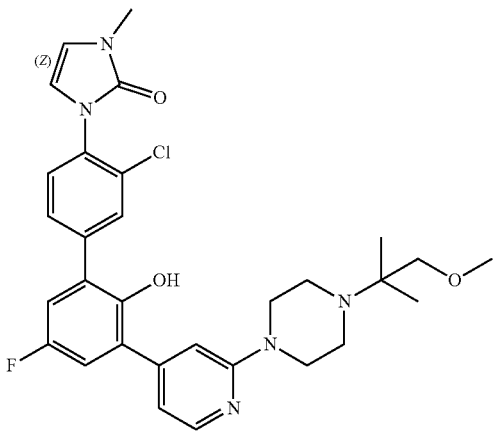

Step 1: 1-(3-chloro-5'-fluoro-3'-(2-(4-(1-hydroxy-2-methylpropan-2-yl)piperazin-1-yl)pyridin-4-yl)-2'-methoxy-[1,1'-biphenyl]-4-yl)-3-methyl-1H-imidazol-2(3H)-one The title compound was prepared following the procedure described for Example 414 using 1-(3-chloro-5'-fluoro-3'-(2-fluoropyridin-4-yl)-2'-methoxy-[1,1'-biphenyl]-4-yl)-3-methyl-1H-imidazol-2 (3H)-one and 2-methyl-2-(piperazin-1-yl)propan-1-ol hydrochloride to afford the title compound (28% yield). LCMS: 566.2 (M+H)+.

Step 2: 1-(3-chloro-5'-fluoro-2'-methoxy-3'-(2-(4-(1-methoxy-2-methylpropan-2-yl)piperazin-1-yl)pyridin-4-yl)-[1,1'-biphenyl]-4-yl)-3-methyl-1H-imidazol-2(3H)-one The title compound was prepared following the procedure described for Example 527 using 1-(3-chloro-5'-fluoro-3'-(2-(4-(1-hydroxy-2-methylpropan-2-yl)piperazin-1-yl)pyridin-4-yl)-2'-methoxy-[1,1'-biphenyl]-4-yl)-3-methyl-1H-imidazol-2(3H)-one, NaH and CH₃I to afford the title compound (45.5% yield). LCMS: 580.2 (M+H)+.

Step 3: 1-(3-chloro-5'-fluoro-2'-hydroxy-3'-(2-(4-(1-methoxy-2-methylpropan-2-yl)piperazin-1-yl)pyridin-4-yl)-[1,1'-biphenyl]-4-yl)-3-methyl-1H-imidazol-2(3H)-one The title compound was prepared following the procedure described for Example 527 using 1-(3-chloro-5'-fluoro-2'-methoxy-3'-(2-(4-(1-methoxy-2-methylpropan-2-yl)piperazin-1-yl)pyridin-4-yl)-[1,1'-biphenyl]-4-yl)-3-methyl-1H-imidazol-2(3H)-one and piperazine to afford the title compound (35% yield). 1H NMR (400 MHz, DMSO-d₆): δ 8.70 (s, 1H), 8.14 (d, J=5.2 Hz, 1H), 7.80 (d, J=1.6 Hz, 1H), 7.61 (dd, J=2.0, 8.0 Hz, 1H), 7.52 (d, J=8.4 Hz, 1H), 7.25-7.17 (m, 2H), 6.92 (s, 1H), 6.81 (d, J=4.8 Hz, 1H), 6.70 (dd, J=2.8, 12.0 Hz, 2H), 3.46-(m, 4H), 3.25 (s, 5H), 3.20 (s, 3H), 2.66-2.64 (m, 4H), 1.01 (s, 6H). LCMS: 566.3 (M+H)+.

Example 725

5-(3'-chloro-5-fluoro-2-hydroxy-4'-(3-methyl-2-oxo-2,3-dihydro-1H-imidazol-1-yl)-[1,1'-biphenyl]-3-yl)-3-(3-hydroxy-3-methylpyrrolidin-1-yl)-1-methylpyridin-2(1H)-one

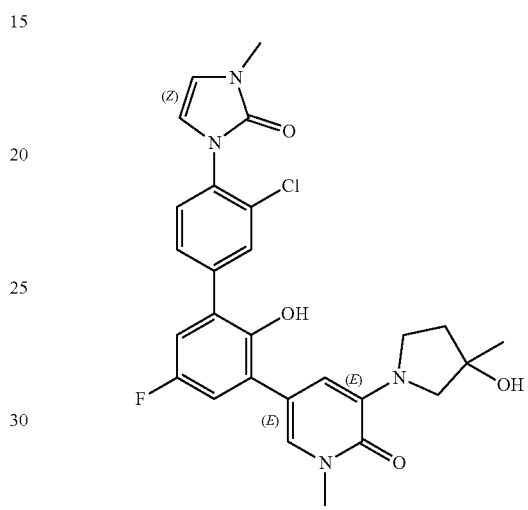

Step 1: 5-bromo-3-(3-hydroxy-3-methylpyrrolidin-1-yl)-1-methylpyridin-2(1H)-one

The title compound was prepared following the procedure described for Example 372 using 3,5-dibromo-1-methylpyridin-2(1H)-one and 3-methylpyrrolidin-3-ol to afford the title compound (14% yield). LCMS: 287.3 (M+H)+.

Step 2: 5-(3'-chloro-5-fluoro-2-methoxy-4'-(3-methyl-2-oxo-2,3-dihydro-1H-imidazol-1-yl)-[1,1'-biphenyl]-3-yl)-3-(3-hydroxy-3-methylpyrrolidin-1-yl)-1-methylpyridin-2(1H)-one The title compound was prepared following the procedure described for Example 372 using 5-bromo-3-(3-hydroxy-3-methylpyrrolidin-1-yl)-1-methylpyridin-2(1H)-one and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one to afford the title compound (33% yield). LCMS: 539.2 (M+H)+.

Step 3: 5-(3'-chloro-5-fluoro-2-hydroxy-4'-(3-methyl-2-oxo-2,3-dihydro-1H-imidazol-1-yl)-[1,1'-biphenyl]-3-yl)-3-(3-hydroxy-3-methylpyrrolidin-1-yl)-1-methylpyridin-2(1H)-one The title compound was prepared following the procedure described for Example 527 using 5-(3'-chloro-5-fluoro-2-methoxy-4'-(3-methyl-2-oxo-2,3-dihydro-1H-imidazol-1-yl)-[1,1'-biphenyl]-3-yl)-3-(3-hydroxy-3-methylpyrrolidin-1-yl)-1-methylpyridin-2(1H)-one and piperazine to afford the title compound (8.7% yield). 1H NMR (400 MHz, DMSO-d$_6$): δ 8.57 (br s, 1H), 7.79 (d, J=1.6 Hz, 1H), 7.60 (dd, J=2.0, 8.0 Hz, 1H), 7.51 (d, J=8.4 Hz, 1H), 7.29 (d, J=2.0 Hz, 1H), 7.16-7.10 (m, 2H), 6.70 (dd, J=2.8, 11.6 Hz, 2H), 6.43 (s, 1H), 3.53-3.37 (m, 7H), 3.20 (s, 3H), 1.84-1.75 (m, 2H), 1.31 (s, 3H). O—H proton not observed. LCMS: 525.2 (M+H)$^+$.

Example 726

1-(3-chloro-3'-(2-((3R,4R)-3,4-dihydroxypyrrolidin-1-yl)pyridin-4-yl)-5'-fluoro-2'-hydroxy-[1,1'-biphenyl]-4-yl)-3-methyl-1H-imidazol-2(3H)-one

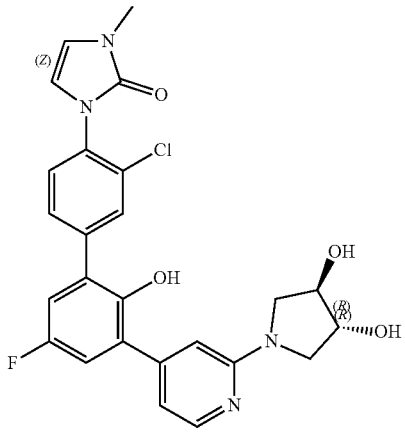

The title compound was prepared following the procedure described for Example 414 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and (3R,4R)-pyrrolidine-3,4-diol to afford the title compound (9.4% yield). $^1$H NMR (400 MHz, DMSO-d$_6$): δ 8.69 (s, 1H), 8.09 (d, J=5.6 Hz, 1H), 7.80 (d, J=2.0 Hz, 1H), 7.62 (dd, J=1.6, 8.0 Hz, 1H), 7.52 (d, J=8.4 Hz, 1H), 7.25-7.16 (m, 2H), 6.72-6.68 (m, 3H), 6.55 (s, 1H), 5.10 (d, J=3.2 Hz, 2H), 4.04 (s, 2H), 3.58-3.04 (m, 2H), 3.37-3.34 (m, 2H), 3.20 (s, 3H). LCMS: 497.1 (M+H)$^+$.

Example 727

1-(3-chloro-5'-fluoro-2'-hydroxy-3'-(2-(1-isopropyl-hexahydropyrrolo[3,4-b]pyrrol-5(1H)— yl)pyridin-4-yl)-[1,1'-biphenyl]-4-yl)-3-methyl-1H-imidazol-2(3H)-one

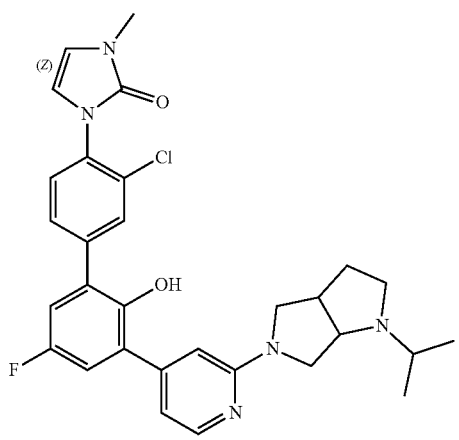 [SMILES: CC(C)N1CCC2CN(c3cc(-c4cc(F)cc(-c5ccc(-n6ccn(C)c6=O)c(Cl)c5)c4O)ccn3)CC21]

Step 1: tert-butyl 5-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)hexahydropyrrolo[3,4-b]pyrrole-1(2H)-carboxylate The title compound was prepared following the procedure described for Example 414 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and tert-butyl hexahydropyrrolo[3,4-b]pyrrole-1(2H)-carboxylate to afford the title compound (28% yield). LCMS: 606.2 (M+H)$^+$.

Step 2: 1-(3-chloro-5'-fluoro-3'-(2-(hexahydropyrrolo[3,4-b]pyrrol-5(1H)-yl)pyridin-4-yl)-2'-hydroxy-[1,1'-biphenyl]-4-yl)-3-methyl-1H-imidazol-2(3H)-one 2,2,2-trifluoroacetate The title compound was prepared following the procedure described for Example 470 using tert-butyl 3-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-3,8-diazabicyclo[3.2.1]octane-8-carboxylate and TFA to afford the title compound (99% yield). LCMS: 506.2 (M+H)$^+$ Step 3: 1-(3-chloro-5'-fluoro-2'-hydroxy-3'-(2-(1-isopropylhexahydropyrrolo[3,4-b]pyrrol-5(1H)— yl)pyridin-4-yl)-[1,1'-biphenyl]-4-yl)-3-methyl-1H-imidazol-2(3H)-one The title compound was prepared following the procedure described for Example 515 using 1-(3-chloro-5'-fluoro-3'-(2-(hexahydropyrrolo[3,4-b]pyrrol-5(1H)-yl)pyridin-4-yl)-2'-hydroxy-[1,1'-biphenyl]-4-yl)-3-methyl-1H-imidazol-2 (3H)-one 2,2,2-trifluoroacetate and acetone to afford the title compound (40% yield). $^1$H NMR (400 MHz, DMSO-d$_6$): δ 8.69 (s, 1H), 8.10 (d, J=5.2 Hz, 1H), 7.80 (d, J=2.0 Hz, 1H), 7.62 (dd, J=2.0, 8.4 Hz, 1H), 7.52 (d, J=8.0 Hz, 1H), 7.24-7.18 (m, 2H), 6.76-6.75 (m, 1H), 6.71 (d, J=2.8 Hz, 1H), 6.69 (d, J=2.8 Hz, 1H), 6.63 (s, 1H), 3.50-3.39 (m, 5H), 3.20 (s, 3H), 2.93-2.67 (m, 3H), 2.49-2.47 (m, 1H), 2.03-2.01 (m, 1H), 1.56-1.54 (m, 1H), 1.03 (dd, J=6.4, 17.2 Hz, 6H). LCMS: 548.2 (M+H)$^+$.

Example 728

(R)-1-(3-chloro-5'-fluoro-2'-hydroxy-3'-(5-(3-hydroxy-3-methylpyrrolidin-1-yl)pyridin-3-yl)-[1,1'-biphenyl]-4-yl)-3-methyl-1H-imidazol-2(3H)-one

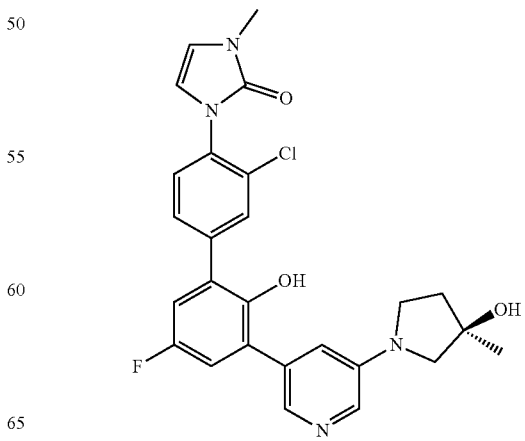

Step 1: (R)-1-(5-bromopyridin-3-yl)-3-methylpyrrolidin-3-ol

The title compound was prepared following the procedure described for Example 550 using (R)-3-methylpyrrolidin-3-ol and 3,5-dibromopyridine to afford the title compound. LCMS: 257.2 (M+H)+

Step 2: (R)-(5-(3-hydroxy-3-methylpyrrolidin-1-yl)pyridin-3-yl)boronic acid

The title compound was prepared following the procedure described for Example 550 using (R)-1-(5-bromopyridin-3-yl)-3-methylpyrrolidin-3-ol and 4,4,4',4',5,5,5',5'-octamethyl-2,2'-bi(1,3,2-dioxaborolane) to afford the title compound. LCMS: 223.1 (M+H)+

Step 3: (R)-1-(3-chloro-5'-fluoro-2'-hydroxy-3'-(5-(3-hydroxy-3-methylpyrrolidin-1-yl)pyridin-3-yl)-[1,1'-biphenyl]-4-yl)-3-methyl-1H-imidazol-2(3H)-one The title compound was prepared following the procedure described for Example 722 using (R)-(5-(3-hydroxy-3-methylpyrrolidin-1-yl)pyridin-3-yl)boronic acid and 1-(3'-bromo-3-chloro-5'-fluoro-2'-hydroxy-[1,1'-biphenyl]-4-yl)-3-methyl-1H-imidazol-2(3H)-one to afford the title compound. $^1$H NMR (400 MHz, CD$_3$OD): δ 7.87 (d, J=1.2 Hz, 1H), 7.74 (d, J=2.8 Hz, 1H), 7.71 (d, J=2.0 Hz, 1H), 7.52 (dd, J=2.0, 8.4 Hz, 1H), 7.41 (d, J=8.4 Hz, 1H), 7.04-6.99 (m, 3H), 6.57 (d, J=2.8 Hz, 1H), 6.53 (d, J=2.8 Hz, 1H), 3.48-3.35 (m, 2H), 3.25 (br s, 5H), 2.00-1.93 (m, 2H), 1.38 (s, 3H). LCMS: 495.2 (M+H)+.

Example 729

(S)-1-(3-chloro-5'-fluoro-2'-hydroxy-3'-(5-(3-hydroxy-3-methylpyrrolidin-1-yl)pyridin-3-yl)-[1,1'-biphenyl]-4-yl)-3-methyl-1H-imidazol-2(3H)-one

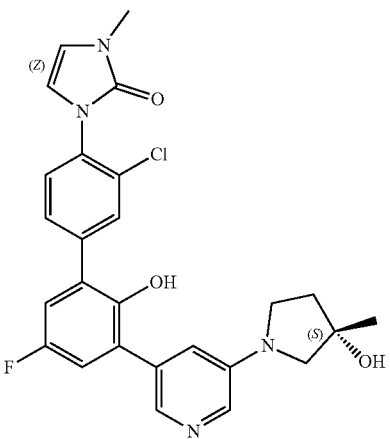

The title compound was prepared following the procedures described for Example 728 using (S)-(5-(3-hydroxy-3-methylpyrrolidin-1-yl)pyridin-3-yl)boronic acid and 1-(3'-bromo-3-chloro-5'-fluoro-2'-hydroxy-[1,1'-biphenyl]-4-yl)-3-methyl-1H-imidazol-2(3H)-one to afford the title compound. $^1$H NMR (400 MHz, DMSO-d$_6$): δ 8.65 (s, 1H), 7.97 (d, J=1.6 Hz, 1H), 7.87 (d, J=2.0 Hz, 1H), 7.81 (d, J=1.6 Hz, 1H), 7.63 (dd, J=2.0, 8.4 Hz, 1H), 7.52 (d, J=8.4 Hz, 1H), 7.24-7.17 (m, 2H), 6.99-6.98 (m, 1H), 6.72 (d, J=2.8 Hz, 1H), 6.69 (d, J=3.2 Hz, 1H), 4.82 (s, 1H), 3.43-3.38 (m, 2H), 3.32-3.30 (m, 2H), 3.21 (s, 3H), 1.94-1.92 (m, 2H), 1.37 (s, 3H). LCMS: 495.2 (M+H)+.

Example 730

1-(3-chloro-5'-fluoro-2'-hydroxy-3'-(2-(8-isopropyl-3,8-diazabicyclo[3.2.1]octan-3-yl)pyridin-4-yl)-[1,1'-biphenyl]-4-yl)-3-methyl-1H-imidazol-2(3H)-one

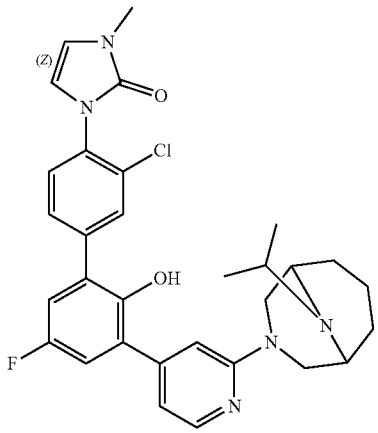 [SMILES: CC(C)CN1C2CCCC1CN(c1cc(-c3cc(F)cc(-c4ccc(-n5ccn(C)c5=O)c(Cl)c4)c3O)ccn1)C2]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and tert-butyl 3,8-diazabicyclo[3.2.1]octane-8-carboxylate, TFA, NaCNBH$_3$ and acetone to afford the title compound. $^1$H NMR (400 MHz, DMSO-d$_6$): δ 8.69 (s, 1H), 8.13 (d, J=5.2 Hz, 1H), 7.80 (d, J=1.6 Hz, 1H), 7.61 (dd, J=2.0, 8.4 Hz, 1H), 7.52 (d, J=8.0 Hz, 1H), 7.25-7.18 (m, 2H), 6.80 (d, J=5.6 Hz, 2H), 6.70 (dd, J=3.2, 12.4 Hz, 2H), 3.77 (d, J=11.6 Hz, 2H), 3.55 (s, 2H), 3.20 (s, 3H), 2.98 (d, J=10.0 Hz, 2H), 2.52-2.50 (m, 1H), 1.82-1.80 (m, 2H), 1.56-1.55 (m, 2H), 1.03 (d, J=6.0 Hz, 6H). LCMS: 548.3 (M+H)+.

Example 731

1-(3-chloro-5'-fluoro-2'-hydroxy-3'-(2-(3-hydroxy-3-(hydroxymethyl)pyrrolidin-1-yl)pyridin-4-yl)-[1,1'-biphenyl]-4-yl)-3-methyl-1H-imidazol-2(3H)-one

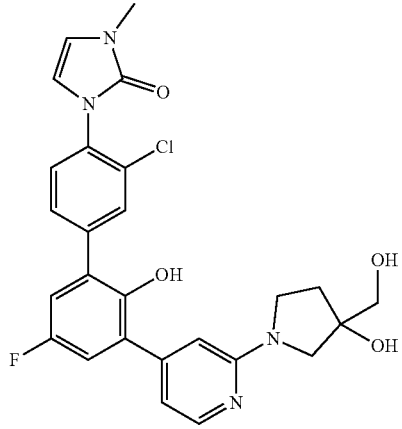 [SMILES: Cn1ccn(-c2ccc(-c3cc(F)cc(-c4ccnc(N5CCC(O)(CO)C5)c4)c3O)cc2Cl)c1=O]

The title compound was prepared following the procedure described for Example 724 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 3-(hydroxymethyl)pyrrolidin-3-ol to afford the title compound (12% yield). $^1$H NMR (400 MHz, DMSO-$d_6$): δ 8.70 (s, 1H), 8.10 (d, J=5.2 Hz, 1H), 7.80 (d, J=2.0 Hz, 1H), 7.62 (dd, J=2.0, 8.0 Hz, 1H), 7.52 (d, J=8.4 Hz, 1H), 7.25-7.17 (m, 2H), 6.72-6.69 (m, 3H), 6.55 (s, 1H), 4.85 (t, J=5.6 Hz, 1H), 4.74 (s, 1H), 3.58-3.38 (m, 5H), 3.32-3.28 (m, 1H), 3.21 (s, 3H), 2.10-2.02 (m, 1H), 1.80-1.76 (m, 1H). LCMS: 511.2 (M+H)$^+$.

Example 732

1-(3'-(2-(4-(tert-butyl)piperazin-1-yl)-6-methoxypyridin-4-yl)-3-chloro-5'-fluoro-2'-hydroxy-[1,1'-biphenyl]-4-yl)-3-methyl-1H-imidazol-2(3H)-one

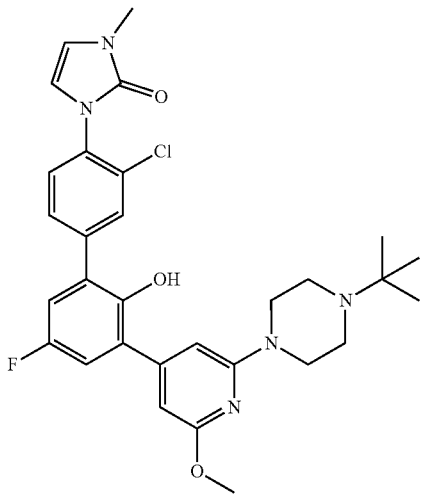 [SMILES: COc1cc(-c2cc(F)cc(-c3ccc(-n4ccn(C)c4=O)c(Cl)c3)c2O)cc(N2CCN(C(C)(C)C)CC2)n1]

Step 1: 1-(tert-butyl)-4-(4-iodo-6-methoxypyridin-2-yl)piperazine

The title compound was prepared following the procedure described for Example 414 using 2-fluoro-4-iodo-6-methoxypyridine and 1-(tert-butyl)piperazine to afford the title compound (90% yield). LCMS: 376.1 (M+H)$^+$.

Step 2: 1-(tert-butyl)-4-(6-methoxy-4-(4,4,5,5-tetramethyl-1,3,2-dioxaborolan-2-yl)pyridin-2-yl)piperazine The title compound was prepared following the procedure described for Example 550 using 1-(tert-butyl)-4-(4-iodo-6-methoxypyridin-2-yl)piperazine and 4,4,4',4',5,5,5',5'-octamethyl-2,2'-bi(1,3,2-dioxaborolane) to afford the title compound (27% yield). LCMS: 376.3 (M+H)$^+$.

Step 3: 1-(3'-(2-(4-(tert-butyl)piperazin-1-yl)-6-methoxypyridin-4-yl)-3-chloro-5'-fluoro-2'-hydroxy-[1,1'-biphenyl]-4-yl)-3-methyl-1H-imidazol-2(3H)-one The title compound was prepared following the procedure described for Example 728 using 1-(tert-butyl)-4-(6-methoxy-4-(4,4,5,5-tetramethyl-1,3,2-dioxaborolan-2-yl)pyridin-2-yl)piperazine and 1-(3'-bromo-3-chloro-5'-fluoro-2'-hydroxy-[1,1'-biphenyl]-4-yl)-3-methyl-1H-imidazol-2(3H)-one to afford the title compound (0.9% yield). $^1$H NMR (400 MHz, CD$_3$OD): δ 7.70 (d, J=2.0 Hz, 1H), 7.51 (dd, J=2.0, 8.4 Hz, 1H), 7.39 (d, J=8.0 Hz, 1H), 7.01-6.94 (m, 1H), 6.57 (d, J=5.6 Hz, 1H), 6.71 (d, J=3.2 Hz, 1H), 6.53 (d, J=3.2 Hz, 1H), 6.33 (s, 1H), 6.14 (s, 1H), 3.79 (s, 3H), 3.54-3.51 (m, 4H), 3.25 (s, 3H), 2.73-2.69 (m, 4H), 1.07 (s, 9H). LCMS: 566.3 (M+H)$^+$.

Example 733

1-(3-chloro-3'-(2-(4-(1,3-dimethoxypropan-2-yl)piperazin-1-yl)pyridin-4-yl)-5'-fluoro-2'-hydroxy-[1,1'-biphenyl]-4-yl)-3-methyl-1H-imidazol-2(3H)-one

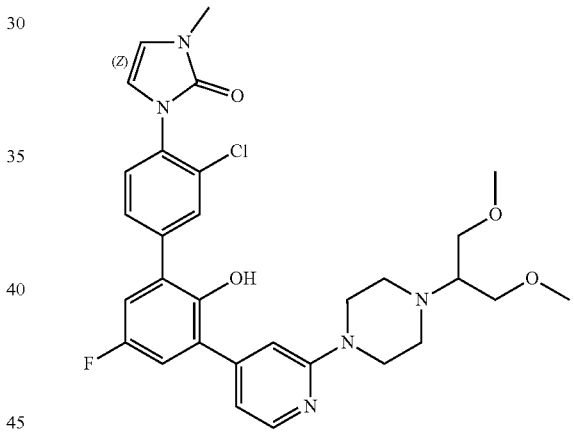

The title compound was prepared following the procedures described for Example 727 using tert-butyl 4-(4-(3-bromo-5-fluoro-2-methoxyphenyl)pyridin-2-yl)piperazine-1-carboxylate and 1-(2-chloro-4-(4,4,5,5-tetramethyl-1,3,2-dioxaborolan-2-yl)phenyl)-3-methyl-1H-imidazol-2(3H)-one, BBr$_3$, 1,3-dimethoxypropan-2-one and NaCNBH$_3$ to afford the title compound. $^1$H NMR (400 MHz, CD$_3$OD): δ 8.18 (d, J=5.6 Hz, 1H), 7.83 (d, J=1.6 Hz, 1H), 7.64 (dd, J=1.6, 8.0 Hz, 1H), 7.53 (d, J=8.4 Hz, 1H), 7.15-7.13 (m, 2H), 7.02 (s, 1H), 6.91 (d, J=5.2 Hz, 1H), 6.70 (d, J=2.8 Hz, 1H), 6.66 (d, J=2.8 Hz, 1H), 3.64-3.51 (m, 8H), 3.38 (s, 3H), 3.37 (s, 6H), 2.87-2.83 (m, 5H). LCMS: 582.3 (M+H)$^+$.

Example 734

1-(3''-(4-(tert-butyl)piperazin-1-yl)-3-chloro-5'-fluoro-2'-hydroxy-[1,1':3',1''-terphenyl]-4-yl)-3-methyl-1H-imidazol-2(3H)-one

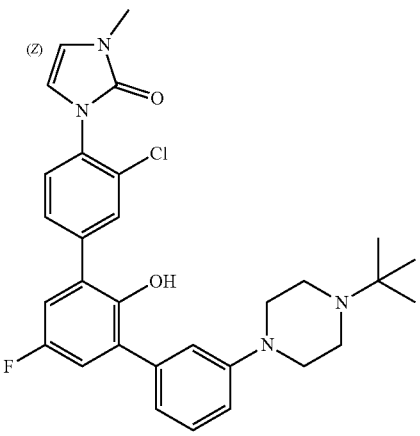 [SMILES: Cn1ccn(-c2ccc(-c3cc(F)cc(-c4cccc(N5CCN(C(C)(C)C)CC5)c4)c3O)cc2Cl)c1=O]

Step 1: 1-(3-bromophenyl)-4-(tert-butyl)piperazine

To a solution of 1-bromo-3-iodobenzene (63.8 g, 225 mmol, 4.0 eq.) and 1-(tert-butyl)piperazine (8.0 g, 56.3 mmol, 1.0 eq.) in dioxane (300 mL) were added $Cs_2CO_3$ (55.0 g, 169 mmol, 3.0 eq.), xant-phos (6.5 g, 11.3 mmol, 0.2 eq.) and $Pd_2(dba)_3$ (5.2 g, 5.63 mmol, 0.1 eq.). Then, the reaction mixture was stirred at 85° C. for 16 hours under nitrogen atmosphere. After the reaction was complete by LCMS, solvent was removed under reduced pressure, the residue was purified by flash column chromatography (DCM:EA=1:1) to give the title compound (6.0 g, 36% yield) as a brown oil. LCMS: 297.1 $(M+H)^+$.

Step 2: 1-(tert-butyl)-4-(3-(4,4,5,5-tetramethyl-1,3,2-dioxaborolan-2-yl)phenyl)piperazine To a solution of 1-(3-bromophenyl)-4-(tert-butyl)piperazine (500 mg, 1.68 mmol, 1.0 eq) and 4,4,4',4',5,5,5',5'-octamethyl-2,2'-bi(1,3,2-dioxaborolane) (470 mg, 1.85 mmol, 1.1 eq.) in dioxane (20 mL) were added KOAc (494 mg, 5.04 mmol, 3.0 eq.) and $Pd(dppf)Cl_2$ (123 mg, 0.168 mmol, 0.1 eq.). Then, the reaction mixture was stirred at 90° C. for 16 hours under nitrogen atmosphere. After the reaction was completed by LCMS, solvent removed under reduced pressure and the residue was purified by flash column chromatography (DCM:EA=1:2) to give the title compound (400 mg, 69% yield) as a brown oil. LCMS: 345.3 $(M+H)^+$.

Step 3: 1-(3''-(4-(tert-butyl)piperazin-1-yl)-3-chloro-5'-fluoro-2'-hydroxy-[1,1':3',1''-terphenyl]-4-yl)-3-methyl-1H-imidazol-2(3H)-one A solution of 1-(tert-butyl)-4-(3-(4,4,5,5-tetramethyl-1,3,2-dioxaborolan-2-yl)phenyl)piperazine (200 mg, 0.58 mmol, 1.0 eq.) and 1-(3'-bromo-3-chloro-5'-fluoro-2'-hydroxy-[1,1'-biphenyl]-4-yl)-3-methyl-1H-imidazol-2(3H)-one (231 mg, 0.58 mmol, 1.0 eq.) in dioxane/$H_2O$ (8 mL, v/v=8:1) were added $K_2CO_3$ (240 mg, 1.74 mmol, 3.0 eq.) and Pd (dppf)$Cl_2$ (85 mg, 0.116 mmol, 0.2 eq.). Then, the reaction mixture was stirred at 110° C. for 4 hours under nitrogen atmosphere. After the reaction was complete by LCMS, solvent was removed under reduced pressure and the residue was purified by flash column chromatography (EA:MeOH=10:1) to give a crude product which was further purified by reversed phase flash to afford the title compound (150 mg, 48% yield) as a white solid. $^1$H NMR (400 MHz, DMSO-$d_6$) δ 8.45 (s, 1H), 7.81 (d, J=1.8 Hz, 1H), 7.62 (dd, J=8.2, 1.8 Hz, 1H), 7.51 (d, J=8.2 Hz, 1H), 7.28 (t, J=7.9 Hz, 1H), 7.20-7.05 (m, 3H), 6.94 (dd, J=14.3, 5.2 Hz, 2H), 6.70 (dd, J=10.9, 3.0 Hz, 2H), 3.21 (s, 3H), 3.17-3.14 (m, 4H), 2.66-2.64 (m, 4H), 1.05 (s, 9H). LCMS: 535.3 $(M+H)^+$.

Example 735

6-(4-(tert-butyl)piperazin-1-yl)-4-(3'-chloro-5-fluoro-2-hydroxy-4'-(3-methyl-2-oxo-2,3-dihydro-1H-imidazol-1-yl)-[1,1'-biphenyl]-3-yl)-1-methylpyridin-2(1H)-one

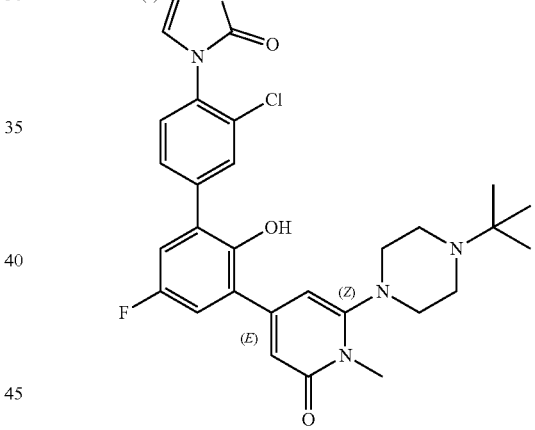

The title compound was prepared following the procedure described for Example 372 using 6-fluoro-4-iodo-1-methylpyridin-2(1H)-one, 1-(tert-butyl)piperazine, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and $BBr_3$ to afford the title compound. $^1$H NMR (400 MHz, DMSO-$d_6$): δ 8.81 (s, 1H), 7.80 (d, J=2.0 Hz, 1H), 7.61 (dd, J=2.0, 8.4 Hz, 1H), 7.52 (d, J=8.4 Hz, 1H), 7.27-7.18 (m, 2H), 6.72 (d, J=2.8 Hz, 1H), 6.69 (d, J=2.8 Hz, 1H), 6.30 (d, J=1.2 Hz, 1H), 5.99 (d, J=1.2 Hz, 1H), 3.42 (s, 3H), 3.21 (s, 3H), 2.94 (br s, 4H), 2.67 (br s, 4H), 1.05 (s, 9H). LCMS: 566.3 $(M+H)^+$.

Example 736

7-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-1,7-diazaspiro[4.4]nonan-2-one

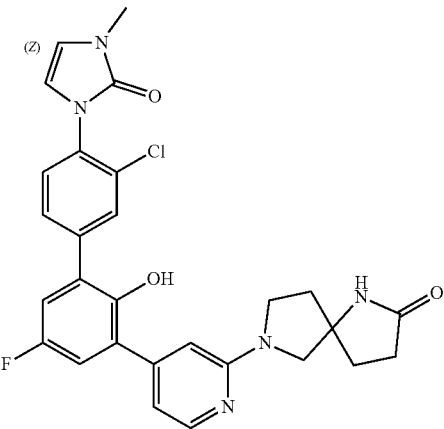 [SMILES: Cn1ccn(-c2ccc(-c3cc(F)cc(-c4ccnc(N5CCC6(CCC(=O)N6)C5)c4)c3O)cc2Cl)c1=O]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 1,7-diazaspiro[4.4]nonan-2-one 2,2,2-trifluoroacetate to afford the title compound. $^1$H NMR (400 MHz, DMSO-d$_6$): δ 8.70 (s, 1H), 8.11 (d, J=5.2 Hz, 1H), 8.09 (s, 1H), 7.80 (s, 1H), 7.62 (d, J=7.2 Hz, 1H), 7.53 (d, J=8.0 Hz, 1H), 7.26-7.18 (m, 2H), 6.76 (d, J=5.2 Hz, 1H), 6.72 (d, J=2.8 Hz, 1H), 6.68 (d, J=2.8 Hz, 1H), 6.59 (s, 1H), 3.62-3.47 (m, 3H), 3.40-3.35 (m, 1H), 3.21 (s, 3H), 2.33-2.26 (m, 2H), 2.04 (t, J=7.6 Hz, 4H). LCMS: 534.2 (M+H)$^+$.

Example 737

1-(3-chloro-3'-(2-(3-ethyl-3-hydroxypyrrolidin-1-yl)pyridin-4-yl)-5'-fluoro-2'-hydroxy-[1,1'-biphenyl]-4-yl)-3-methyl-1H-imidazol-2(3H)-one

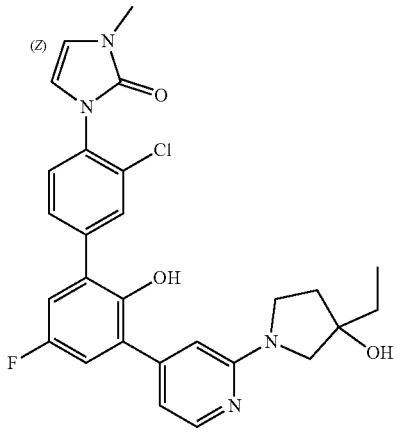 [SMILES: CCC1(O)CCN(c2cc(-c3cc(F)cc(-c4ccc(-n5ccn(C)c5=O)c(Cl)c4)c3O)ccn2)C1]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 3-ethylpyrrolidin-3-ol to afford the title compound. $^1$H NMR (400 MHz, DMSO-d$_6$): δ 8.68 (s, 1H), 8.09 (d, J=5.2 Hz, 1H), 7.80 (d, J=2.0 Hz, 1H), 7.61 (dd, J=1.6, 8.0 Hz, 1H), 7.52 (d, J=8.4 Hz, 1H), 7.25-7.17 (m, 2H), 6.72-6.68 (m, 3H), 6.54 (s, 1H), 4.55 (s, 1H), 3.55-3.39 (m, 3H), 3.32-3.26 (m, 1H), 3.20 (s, 3H), 1.89-1.83 (m, 2H), 1.64-1.60 (m, 2H), 0.96 (t, J=6.8 Hz, 3H). LCMS: 509.2 (M+H)$^+$.

Example 738

1-(3-chloro-5'-fluoro-2'-hydroxy-3'-(5-(4-isopropylpiperazin-1-yl)-6-methoxypyridin-3-yl)-[1,1'-biphenyl]-4-yl)-3-methyl-1H-imidazol-2(3H)-one

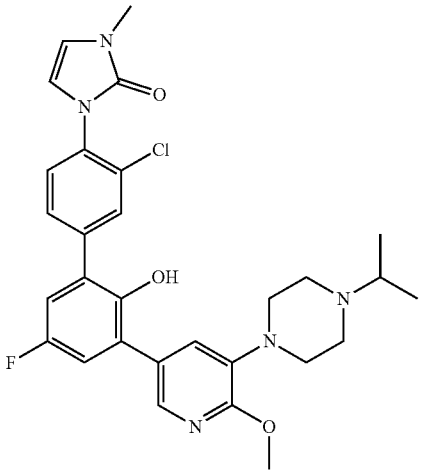

Step 1: 1-(5-chloro-2-methoxypyridin-3-yl)-4-isopropylpiperazine

A mixture of 3-bromo-5-chloro-2-methoxypyridine (4.0 g, 18.0 mmol, 1.0 eq), 1-isopropylpiperazine (3.5 g, 27.0 mmol, 1.5 eq), Pd$_2$(dba)$_3$ (1.65 g, 1.8 mmol, 0.1 eq), xantphos (2.1 g, 3.6 mmol, 0.2 eq), Cs$_2$CO$_3$ (17.6 g, 54.1 mmol, 3.0 eq) in dioxane (150 mL) was stirred at 100° C. for 10 hours under nitrogen atmosphere. After the reaction was complete by LCMS and TLC, the reaction mixture was cooled, diluted with EA and filtered. The filtrate was added water and extracted with EA. The combined organic layers were washed with brine, dried over sodium sulfate, filtered, and concentrated under reduced pressure. The residue was purified by silica gel chromatography using petroleum ether and ethyl acetate (20:1) as the eluent to afford the title compound (3.1 g, 64% yield) as a brown oil. LCMS: 270.1 (M+H)$^+$.

Step 2: 1-isopropyl-4-(2-methoxy-5-(4,4,5,5-tetramethyl-1,3,2-dioxaborolan-2-yl)pyridin-3-yl)piperazine A mixture of 1-(5-chloro-2-methoxypyridin-3-yl)-4-isopropylpiperazine (3.1 g, 11.5 mmol, 1.0 eq), 4,4,4',4',5,5,5',5'-octamethyl-2,2'-bi(1,3,2-dioxaborolane) (3.5 g, 13.8 mmol, 1.2 eq.), Pd$_2$(dba)$_3$ (527 mg, 0.58 mmol, 0.05 eq), X-phos (548 g, 1.15 mmol, 0.10 eq), KOAc (3.4 g, 34.6 mmol, 3.0 eq) in dioxane (100 mL) was stirred at 100° C. for 10 hours under nitrogen atmosphere. After the complete by LCMS and TLC, the reaction mixture was cooled and filtered. The filtrate was concentrated under reduced pressure to afford the crude title compound which was used to the next step without further purification. LCMS: 362.3 (M+H)+.

Step 3: 2-bromo-4-fluoro-6-(5-(4-isopropylpiperazin-1-yl)-6-methoxypyridin-3-yl)phenol A mixture of 1-isopropyl-4-(2-methoxy-5-(4,4,5,5-tetramethyl-1,3,2-dioxaborolan-2-yl)pyridin-3-yl)piperazine (3.2 g, 11.5 mmol, 1.0 eq), 2,6-dibromo-4-fluorophenol (12.4 g, 46.0 mmol, 4.0 eq), $K_3PO_4$ (7.3 g, 34.5 mmol, 3.0 eq) and $Pd(dppf)Cl_2$ (841 mg, 1.15 mmol, 0.1 eq) in dioxane:water (50:1, 220 mL) was stirred at 100° C. for 1 h under nitrogen atmosphere. After the reaction was complete by LCMS and TLC, the resulting mixture was diluted with DCM and filtrated. The filtrate was concentrated. The residue was purified by silica gel chromatography using DCM:$CH_3OH$=20:1 to afford the title compound (2.1 g, 43% yield) as black solid. LCMS: 426.1 (M+H)+.

Step 4: 1-(3-chloro-5'-fluoro-2'-hydroxy-3'-(5-(4-isopropylpiperazin-1-yl)-6-methoxypyridin-3-yl)-[1,1'-biphenyl]-4-yl)-3-methyl-1H-imidazol-2(3H)-one A mixture of 2-bromo-4-fluoro-6-(5-(4-isopropylpiperazin-1-yl)-6-methoxypyridin-3-yl)phenol (1.0 g, 2.35 mmol, 1.0 eq), 1-(2-chloro-4-(4,4,5,5-tetramethyl-1,3,2-dioxaborolan-2-yl)phenyl)-3-methyl-1H-imidazol-2(3H)-one (1.6 g, 4.70 mmol, 2.0 eq), $K_3PO_4$ (996 mg, 4.7 mmol, 2.0 eq) and $Pd(dppf)Cl_2$ (176 mg, 0.24 mmol, 0.1 eq) in dioxane:water (50:1, 30 mL) was stirred at 100° C. for 1 h under nitrogen atmosphere. After the reaction was complete by LCMS and TLC, the resulting mixture was diluted with DCM and filtrated. The filtrate was concentrated. The residue was purified by silica gel chromatography using DCM:$CH_3OH$=10:1 to afford the title compound as yellow solid (260 mg, 20% yield). $^1H$ NMR (400 MHz, DMSO-$d_6$) δ 8.62 (s, 1H), 7.92 (s, 1H), 7.81 (d, J=1.5 Hz, 1H), 7.62 (dd, J=8.2, 1.7 Hz, 1H), 7.52 (d, J=8.2 Hz, 1H), 7.34 (s, 1H), 7.20 (d, J=9.0 Hz, 2H), 6.70 (dd, J=12.4, 2.9 Hz, 2H), 3.93 (s, 3H), 3.32 (s, 3H), 3.05-3.00 (m, 4H), 2.69-2.67 (m, 1H), 2.63-2.50 (m, 4H) 1.01 (d, J=6.4 Hz, 6H). LCMS: 552.3 (M+H)+.

Example 739

1-(3-chloro-3'-(2-((3S,4R)-3,4-dihydroxypyrrolidin-1-yl)pyridin-4-yl)-5'-fluoro-2'-hydroxy-[1,1'-biphenyl]-4-yl)-3-methyl-1H-imidazol-2(3H)-one

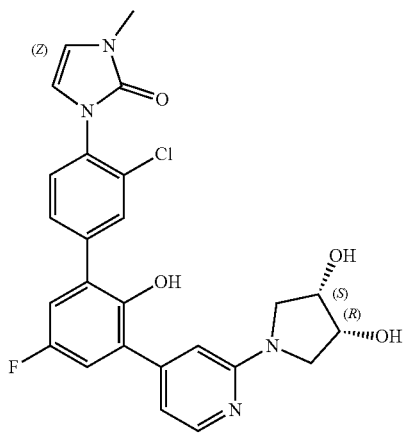

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and (3S,4R)-pyrrolidine-3,4-diol to afford the title compound (25% yield). $^1H$ NMR (400 MHz, DMSO-$d_6$): δ 8.69 (s, 1H), 8.10 (d, J=5.2 Hz, 1H), 7.81 (s, 1H), 7.62 (d, J=8.0 Hz, 1H), 7.52 (d, J=8.0 Hz, 1H), 7.25-7.17 (m, 2H), 6.72-6.69 (m, 3H), 6.54 (s, 1H), 4.91 (d, J=4.4 Hz, 2H), 4.15 (d, J=3.2 Hz, 2H), 3.59-3.55 (m, 2H), 3.21 (s, 3H). O—H protons not observed. LCMS: 497.1 (M+H)+.

Example 740

1-(3-chloro-5'-fluoro-2'-hydroxy-3'-(5-(8-isopropyl-3,8-diazabicyclo[3.2.1]octan-3-yl)pyridin-3-yl)-[1,1'-biphenyl]-4-yl)-3-methyl-1H-imidazol-2(3H)-one

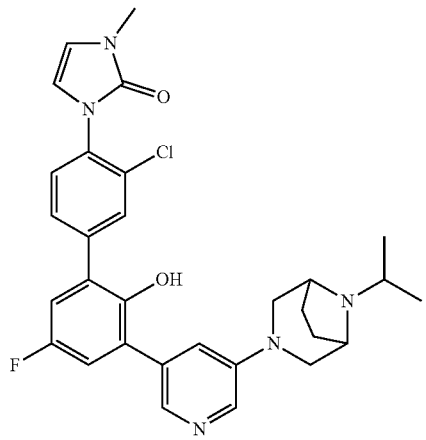 [SMILES: CC(C)N1C2CCC1CN(c1cncc(-c3cc(F)cc(-c4ccc(-n5ccn(C)c5=O)c(Cl)c4)c3O)c1)C2]

Step 1: tert-butyl 3-(5-(3'-chloro-5-fluoro-2-hydroxy-4'-(3-methyl-2-oxo-2,3-dihydro-1H-imidazol-1-yl)-[1,1'-biphenyl]-3-yl)pyridin-3-yl)-3,8-diazabicyclo[3.2.1]octane-8-carboxylate The title compound was prepared following the procedure described for Example 722 using 1-(3'-bromo-3-chloro-5'-fluoro-2'-hydroxy-[1,1'-biphenyl]-4-yl)-3-methyl-1H-imidazol-2(3H)-one and (5-(8-(tert-butoxycarbonyl)-3,8-diazabicyclo[3.2.1]octan-3-yl)pyridin-3-yl)boronic acid to afford the title compound (59% yield). LCMS: 606.2 (M+H)+.

Step 2: 1-(3'-(5-(3,8-diazabicyclo[3.2.1]octan-3-yl)pyridin-3-yl)-3-chloro-5'-fluoro-2'-hydroxy-[1,1'-biphenyl]-4-yl)-3-methyl-1H-imidazol-2(3H)-one The title compound was prepared following the procedure described for Example 727 using tert-butyl 3-(5-(3'-chloro-5-fluoro-2-hydroxy-4'-(3-methyl-2-oxo-2,3-dihydro-1H-imidazol-1-yl)-[1,1'-biphenyl]-3-yl)pyridin-3-yl)-3,8-diazabicyclo[3.2.1]octane-8-carboxylate and TFA to afford the title compound (100% yield). LCMS: 506.2 (M+H)+.

Step 3: 1-(3-chloro-5'-fluoro-2'-hydroxy-3'-(5-(8-isopropyl-3,8-diazabicyclo[3.2.1]octan-3-yl)pyridin-3-yl)-[1,1'-biphenyl]-4-yl)-3-methyl-1H-imidazol-2(3H)-one The title compound was prepared following the procedure described for Example 727 using 1-(3'-(5-(3,8-diazabicyclo

[3.2.1]octan-3-yl)pyridin-3-yl)-3-chloro-5'-fluoro-2'-hydroxy-[1,1'-biphenyl]-4-yl)-3-methyl-1H-imidazol-2(3H)-one, acetone and NaCNBH₃ to afford the title compound (32% yield). ¹H NMR (400 MHz, DMSO-d₆): δ 8.67 (s, 1H), 8.17 (s, 1H), 8.11 (s, 1H), 7.81 (s, 1H), 7.62 (d, J=8.0 Hz, 1H), 7.53 (d, J=8.0 Hz, 1H), 7.31-7.19 (m, 3H), 6.72 (d, J=2.8 Hz, 1H), 6.69 (d, J=2.8 Hz, 1H), 3.61 (br s, 2H), 3.46-3.44 (m, 2H), 3.21 (s, 3H), 2.97-2.94 (m, 2H), 2.68-2.56 (m, 1H), 1.85-1.69 (m, 4H), 1.06 (d, J=4.4 Hz, 6H). LCMS: 548.3 (M+H)⁺.

Example 741

1-(3-chloro-3'-(2-(3-(dimethylamino)-3-methylpyrrolidin-1-yl)pyridin-4-yl)-5'-fluoro-2'-hydroxy-[1,1'-biphenyl]-4-yl)-3-methyl-1H-imidazol-2(3H)-one

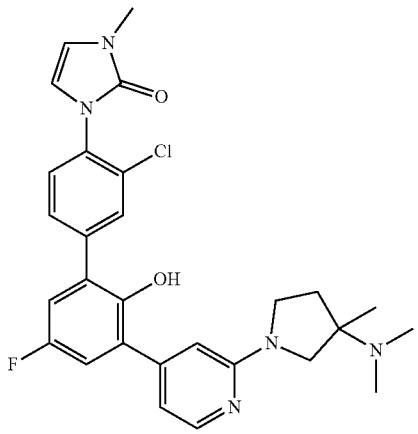 [SMILES: CN(C)C1(C)CCN(c2cc(-c3cc(F)cc(-c4ccc(-n5ccn(C)c5=O)c(Cl)c4)c3O)ccn2)C1]

Step 1: tert-butyl (1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-3-methylpyrrolidin-3-yl)carbamate The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and tert-butyl (3-methylpyrrolidin-3-yl)carbamate to afford the title compound. LCMS: 594.2 (M+H)⁺.

Step 2: 1-(3'-(2-(3-amino-3-methylpyrrolidin-1-yl)pyridin-4-yl)-3-chloro-5'-fluoro-2'-hydroxy-[1,1'-biphenyl]-4-yl)-3-methyl-1H-imidazol-2(3H)-one The title compound was prepared following the procedure described for Example 727 using tert-butyl (1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-3-methylpyrrolidin-3-yl)carbamate and TFA to afford the title compound. LCMS: 494.2 (M+H)⁺

Step 3: 1-(3-chloro-3'-(2-(3-(dimethylamino)-3-methylpyrrolidin-1-yl)pyridin-4-yl)-5'-fluoro-2'-hydroxy-[1,1'-biphenyl]-4-yl)-3-methyl-1H-imidazol-2(3H)-one The title compound was prepared following the procedure described for Example 727 using 1-(3'-(2-(3-amino-3-methylpyrrolidin-1-yl)pyridin-4-yl)-3-chloro-5'-fluoro-2'-hydroxy-[1,1'-biphenyl]-4-yl)-3-methyl-1H-imidazol-2(3H)-one, HCHO and NaCNBH₃ to afford the title compound. ¹H NMR (400 MHz, DMSO-d₆): δ 8.69 (s, 1H), 8.10 (d, J=5.2 Hz, 1H), 7.80 (d, J=1.6 Hz, 1H), 7.62 (d, J=8.0 Hz, 1H), 7.52 (d, J=8.4 Hz, 1H), 7.26-7.18 (m, 2H), 6.73-6.68 (m, 3H), 6.57 (s, 1H), 3.60-3.59 (m, 1H), 3.56-3.37 (m, 2H), 3.33-3.24 (m, 1H), 3.21 (s, 3H), 2.20 (s, 6H), 1.92-1.90 (m, 2H), 1.01 (s, 3H). LCMS: 522.2 (M+H)⁺.

Example 742

(R)-1-(3'-(5-(3-amino-3-methylpyrrolidin-1-yl)pyridin-3-yl)-3-chloro-5'-fluoro-2'-hydroxy-[1,1'-biphenyl]-4-yl)-3-methyl-1H-imidazol-2(3H)-one

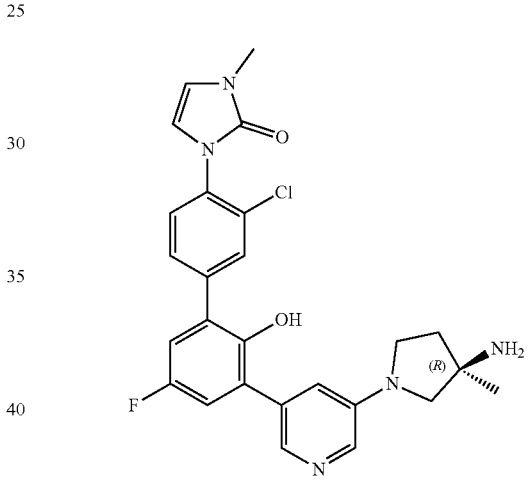

The title compound was prepared following the procedures described for Example 740 using tert-butyl (R)-(5-(3-((tert-butoxycarbonyl)amino)-3-methylpyrrolidin-1-yl)pyridin-3-yl)boronic acid, 1-(3'-bromo-3-chloro-5'-fluoro-2'-methoxy-[1,1'-biphenyl]-4-yl)-3-methyl-1H-imidazol-2(3H)-one and BBr₃ to afford the title compound. ¹H NMR (400 MHz, CD₃OD): δ 7.88 (s, 1H), 7.75 (d, J=2.4 Hz, 1H), 7.71 (d, J=2.0 Hz, 1H), 7.52 (dd, J=1.6, 8.0 Hz, 1H), 7.40 (d, J=8.4 Hz, 1H), 7.04-6.99 (m, 3H), 3.49 (d, J=9.2 Hz, 1H), 3.37 (s, 1H), 3.25 (s, 3H), 3.21-3.19 (m, 2H), 1.94 (t, J=7.2 Hz, 2H), 1.29 (s, 3H). N—H and O—H protons not observed. LCMS: 494.2 (M+H)⁺.

Example 743

1-(3-chloro-5'-fluoro-2'-hydroxy-3'-(2-(7-hydroxy-5-azaspiro[2.4]heptan-5-yl)pyridin-4-yl)-[1,1'-biphenyl]-4-yl)-3-methyl-1H-imidazol-2(3H)-one

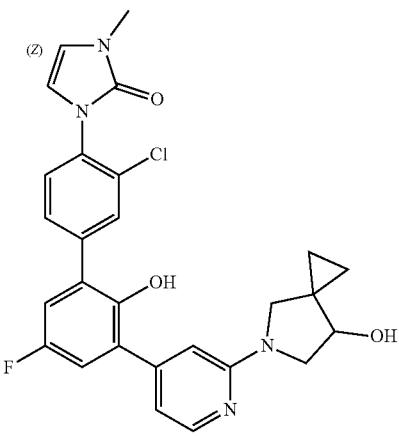 [SMILES: Cn1ccn(-c2ccc(-c3cc(F)cc(-c4ccnc(N5CC(O)C6(CC6)C5)c4)c3O)cc2Cl)c1=O]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 5-azaspiro[2.4]heptan-7-ol to afford the title compound. $^1$H NMR (400 MHz, DMSO-$d_6$) δ 8.68 (s, 1H), 8.10 (d, J=5.2 Hz, 1H), 7.80 (d, J=1.6 Hz, 1H), 7.69-7.55 (m, 1H), 7.52 (d, J=8.2 Hz, 1H), 7.21 (m, 2H), 6.82-6.62 (m, 2H), 6.54 (s, 1H), 4.92 (d, J=3.4 Hz, 1H), 3.78 (s, 1H), 3.71 (dd, J=10.8, 5.0 Hz, 1H), 3.63 (d, J=9.9 Hz, 1H), 3.47 (d, J=11.4 Hz, 1H), 3.24 (s, 1H), 3.21 (s, 3H), 0.92-0.80 (m, 1H), 0.67-0.50 (m, 3H). N—H and O—H proton not observed. LCMS: 507.2 (M+H)$^+$.

Example 744

1-(3'-(2-(3-amino-3-methylpiperidin-1-yl)pyridin-4-yl)-3-chloro-5'-fluoro-2'-hydroxy-[1,1'-biphenyl]-4-yl)-3-methyl-1H-imidazol-2(3H)-one

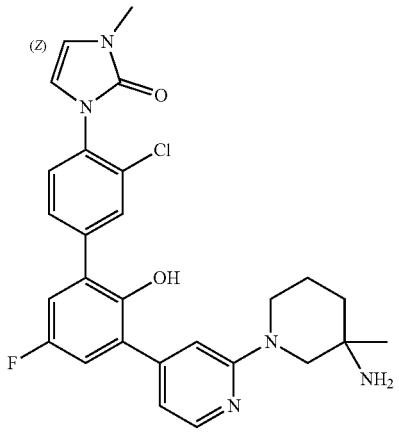 [SMILES: Cn1ccn(-c2ccc(-c3cc(F)cc(-c4ccnc(N5CCCC(C)(N)C5)c4)c3O)cc2Cl)c1=O]

Step 1: tert-butyl(1-(4-(3'-chloro-5-fluoro-2-methoxy-4'-(3-methyl-2-oxo-2,3-dihydro-1H-imidazol-1-yl)-[1,1'-biphenyl]-3-yl)pyridin-2-yl)-3-methylpiperidin-3-yl)carbamate The title compound was prepared following the procedure described for Example 414 using tert-butyl 7-(5-bromo-1-methyl-2-oxo-1,2-dihydropyridin-3-yl)-1,7-diazaspiro[4.4]nonane-1-carboxylate and 1-(3-chloro-5'-fluoro-2'-methoxy-3'(4,4,5,5-tetramethyl-1,3,2-dioxaborolan-2-yl)-[1,1'-biphenyl]-4-yl)-3-methyl-1H-imidazol-2(3H)-one to afford the title compound (79.5% yield). LCMS: 622.3 (M+H)$^+$.

Step 2: 1-(3'-(2-(3-amino-3-methylpiperidin-1-yl)pyridin-4-yl)-3-chloro-5'-fluoro-2'-hydroxy-[1,1'-biphenyl]-4-yl)-3-methyl-1H-imidazol-2(3H)-one The title compound was prepared following the procedure described for Example 365 using tert-butyl 7-(5-(3'-chloro-5-fluoro-2-methoxy-4'-(3-methyl-2-oxo-2,3-dihydro-1H-imidazol-1-yl)-[1,1'-biphenyl]-3-yl)-1-methyl-2-oxo-1,2-dihydropyridin-3-yl)-1,7-diazaspiro[4.4]nonane-1-carboxylate and BBr$_3$ to afford the title compound. $^1$H NMR (400 MHz, DMSO-$d_6$) δ 8.10 (d, J=5.2 Hz, 1H), 7.83 (s, 1H), 7.62 (d, J=9.2 Hz, 1H), 7.51 (d, J=8.2 Hz, 1H), 7.26-7.19 (m, 1H), 7.20-7.13 (m, 1H), 6.97 (s, 1H), 6.76 (d, J=5.2 Hz, 1H), 6.70 (dd, J=13.2, 2.8 Hz, 2H), 3.54 (s, 1H), 3.32 (s, 3H), 3.21 (s, 3H), 1.67 (s, 1H), 1.49 (dd, J=14.4, 6.9 Hz, 3H), 1.06 (d, J=19.2 Hz, 3H). N—H and O—H protons not observed. LCMS: 508.2 (M+H)$^+$.

Example 745

1-(3'-(5-(3-amino-3-methylpyrrolidin-1-yl)pyridin-3-yl)-3-chloro-5'-fluoro-2'-hydroxy-[1,1'-biphenyl]-4-yl)-3-methyl-1H-imidazol-2(3H)-one

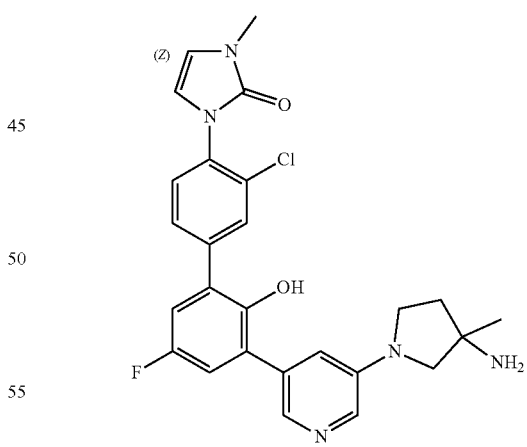

Step 1: 3-(5-(3-((tert-butoxycarbonyl)amino)-3-methylpyrrolidin-1-yl)pyridin-3-yl)-3'-chloro-5-fluoro-4'-(3-methyl-2-oxo-2,3-dihydro-1H-imidazol-1-yl)-[1,1'-biphenyl]-2-yl acetate The title compound was prepared following the procedure described for Example 740 using tert-butyl (3-methyl-1-(5-(4,4,5,5-tetramethyl-1,3,2-dioxaborolan-2-yl)pyridin-3-yl)

pyrrolidin-3-yl)carbamate and 3-bromo-3'-chloro-5-fluoro-4'-(3-methyl-2-oxo-2,3-dihydro-1H-imidazol-1-yl)-[1,1'-biphenyl]-2-yl acetate to afford the title compound (54% yield). LCMS: 636.2 (M+H)⁺.

Step 2: tert-butyl (1-(5-(3'-chloro-5-fluoro-2-hydroxy-4'-(3-methyl-2-oxo-2,3-dihydro-1H-imidazol-1-yl)-[1,1'-biphenyl]-3-yl)pyridin-3-yl)-3-methylpyrrolidin-3-yl)carbamate The title compound was prepared using 3-(5-(3-((tert-butoxycarbonyl)amino)-3-methylpyrrolidin-1-yl)pyridin-3-yl)-3'-chloro-5-fluoro-4'-(3-methyl-2-oxo-2,3-dihydro-1H-imidazol-1-yl)-[1,1'-biphenyl]-2-yl acetate and LiOH to afford the title compound LCMS: 594.2 (M+H)⁺.

Step 3: 1-(3'-(5-(3-amino-3-methylpyrrolidin-1-yl)pyridin-3-yl)-3-chloro-5'-fluoro-2'-hydroxy-[1,1'-biphenyl]-4-yl)-3-methyl-1H-imidazol-2(3H)-one The title compound was prepared following the procedure described for Example 740 using tert-butyl (1-(5-(3'-chloro-5-fluoro-2-hydroxy-4'-(3-methyl-2-oxo-2,3-dihydro-1H-imidazol-1-yl)-[1,1'-biphenyl]-3-yl)pyridin-3-yl)-3-methylpyrrolidin-3-yl)carbamate and TFA to afford the title compound. ¹H NMR (400 MHz, DMSO-d₆) δ 7.98 (s, 1H), 7.86 (d, J=8.0 Hz, 1H), 7.82 (s, 1H), 7.63 (d, J=8.0 Hz, 1H), 7.52 (d, J=8.2 Hz, 1H), 7.23-7.18 (m, 2H), 6.98 (s, 1H), 6.72-6.68 (m, 2H), 3.50-3.44 (m, 1H), 3.21 (s, 3H), 3.19-3.14 (m, 3H), 1.86 (t, J=6.6 Hz, 2H), 1.27 (s, 3H). N—H and O—H protons not observed. LCMS: 494.2 (M+H)⁺.

Example 746

(S)-1-(3'-(5-(3-amino-3-methylpyrrolidin-1-yl)pyridin-3-yl)-3-chloro-5'-fluoro-2'-hydroxy-[1,1'-biphenyl]-4-yl)-3-methyl-1H-imidazol-2(3H)-one

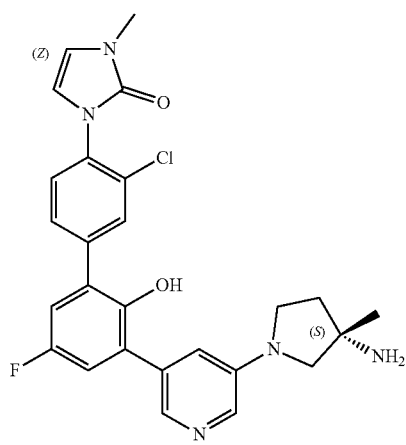

Step 1: (S)-(5-(3-((tert-butoxycarbonyl)amino)-3-methylpyrrolidin-1-yl)pyridin-3-yl)boronic acid The title compound was prepared following the procedure described for Example 745 using (S)-tert-butyl (3-methylpyrrolidin-3-yl)carbamate and 4,4,4',4',5,5,5',5'-octamethyl-2,2'-bi(1,3,2-dioxaborolane) to afford the title compound (crude). LCMS: 404.3 (M+H)⁺.

Step 2: (S)-3-(5-(3-((tert-butoxycarbonyl)amino)-3-methylpyrrolidin-1-yl)pyridin-3-yl)-3'-chloro-5-fluoro-4'-(3-methyl-2-oxo-2,3-dihydro-1H-imidazol-1-yl)-[1,1'-biphenyl]-2-yl acetate The title compound was prepared following the procedure described for Example 745 using 3-bromo-3'-chloro-5-fluoro-4'-(3-methyl-2-oxo-2,3-dihydro-1H-imidazol-1-yl)-[1,1'-biphenyl]-2-yl acetate and (S)-(5-(3-((tert-butoxycarbonyl)amino)-3-methylpyrrolidin-1-yl)pyridin-3-yl)boronic acid to afford the title compound (51% yield). LCMS: 636.2 (M+H)⁺.

Step 3: (S)-tert-butyl (1-(5-(3'-chloro-5-fluoro-2-hydroxy-4'-(3-methyl-2-oxo-2,3-dihydro-1H-imidazol-1-yl)-[1,1'-biphenyl]-3-yl)pyridin-3-yl)-3-methylpyrrolidin-3-yl)carbamate A solution of (S)-tert-butyl (1-(5-(3'-chloro-5-fluoro-2-hydroxy-4'-(3-methyl-2-oxo-2,3-dihydro-1H-imidazol-1-yl)-[1,1'-biphenyl]-3-yl)pyridin-3-yl)-3-methylpyrrolidin-3-yl)carbamate (89 mg, 0.14 mmol) and LiOH (59 mg, 1.4 mmol) in MeOH/H₂O (2 mL, MeOH:H₂O=1:1) was stirred at rt for 2 hours under N₂. After the reaction was complete by LCMS, the reaction mixture was concentrated. The residue was diluted with water (10 mL) and extracted with EA three times. The combined organic layers were washed with brine, dried over sodium sulfate and filtered. The filtrate was used to the next step without further purification. LCMS: 594.2 (M+H)⁺.

Step 4: (S)-1-(3'-(5-(3-amino-3-methylpyrrolidin-1-yl)pyridin-3-yl)-3-chloro-5'-fluoro-2'-hydroxy-[1,1'-biphenyl]-4-yl)-3-methyl-1H-imidazol-2(3H)-one The title compound was prepared following the procedure described for Example 740 using (S)-tert-butyl (1-(5-(3'-chloro-5-fluoro-2-hydroxy-4'-(3-methyl-2-oxo-2,3-dihydro-1H-imidazol-1-yl)-[1,1'-biphenyl]-3-yl)pyridin-3-yl)-3-methylpyrrolidin-3-yl)carbamate and TFA to afford the title compound (37% yield). ¹H NMR (400 MHz, DMSO-d₆): δ 7.87 (d, J=1.2 Hz, 1H), 7.75 (d, J=2.8 Hz, 1H), 7.71 (d, J=2.0 Hz, 1H), 7.52 (dd, J=8.0, 2.0 Hz, 1H), 7.40 (d, J=1.2 Hz, 1H), 7.04-6.98 (m, 3H), 6.57 (d, J=2.8 Hz, 1H), 6.53 (d, J=3.2 Hz, 1H) 3.50-3.46 (m, 1H), 3.38-3.34 (m, 1H), 3.24 (s, 3H), 3.18 (s, 2H), 1.95-1.91 (m, 2H), 1.29 (s, 3H). N—H and O—H protons not observed. LCMS: 494.2 (M+H)⁺.

Example 747

1-(3-chloro-5'-fluoro-2'-hydroxy-3'-(2-(6-isopropyl-3,6-diazabicyclo[3.2.0]heptan-3-yl)pyridin-4-yl)-[1,1'-biphenyl]-4-yl)-3-methyl-1H-imidazol-2(3H)-one

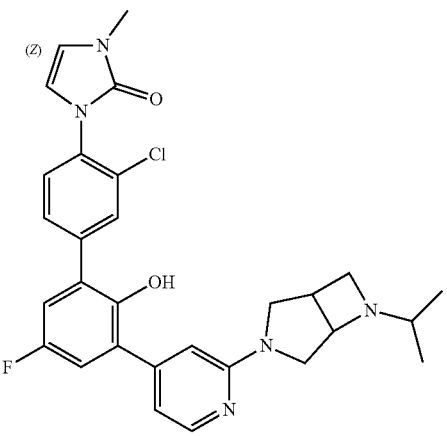 [SMILES: CC(C)N1CC2CN(c3cc(-c4cc(F)cc(-c5ccc(-n6ccn(C)c6=O)c(Cl)c5)c4O)ccn3)CC21]

The title compound was prepared following the procedures described for Example 727 using 1-(3'-(2-(3,6-diazabicyclo[3.2.0]heptan-3-yl)pyridin-4-yl)-3-chloro-5'-fluoro-2'-hydroxy-[1,1'-biphenyl]-4-yl)-3-methyl-1H-imidazol-2(3H)-one to afford the title compound (29% yield). $^1$H NMR (400 MHz, DMSO-d$_6$): δ 8.71 (s, 1H), 8.12 (d, J=5.2 Hz, 1H), 7.80 (s, 1H), 7.62 (d, J=8.4 Hz, 1H), 7.52 (d, J=8.0 Hz, 1H), 7.25-7.19 (m, 2H), 7.76-6.64 (m, 4H), 3.86-3.76 (m, 2H), 3.64 (d, J=11.6 Hz, 1H), 3.50 (t, J=9.2 Hz, 1H), 3.37 (s, 1H), 3.20-3.18 (m, 4H), 3.10-3.07 (m, 2H), 2.99-2.97 (m, 1H), 0.85 (dd, J=33.2, 6.0 Hz, 6H). LCMS: 534.3 (M+H)$^+$.

Example 748

1-(3-chloro-5'-fluoro-2'-hydroxy-3'-(2-(1-isopropyl-1,6-diazaspiro[3.4]octan-6-yl)pyridin-4-yl)-[1,1'-biphenyl]-4-yl)-3-methyl-1H-imidazol-2(3H)-one

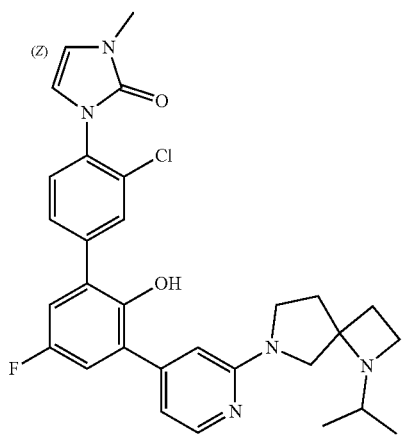 [SMILES: CC(C)N1CCC12CCN(c1cc(-c3cc(F)cc(-c4ccc(-n5ccn(C)c5=O)c(Cl)c4)c3O)ccn1)C2]

The title compound was prepared following the procedures described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and tert-butyl 1,6-diazaspiro[3.4]octane-1-carboxylate, TFA and acetone to afford the title compound. $^1$H NMR (400 MHz, DMSO-d$_6$): 8.67 (s, 1H), 8.11 (d, J=4.0 Hz, 1H), 7.81 (s, 1H), 7.60-7.54 (m, 2H), 7.25-7.18 (m, 2H), 6.74-6.58 (m, 4H), 3.64-3.42 (m, 4H), 3.21 (s, 3H), 3.12-3.02 (m, 2H), 2.67-2.65 (m, 1H), 2.15-1.91 (m, 4H) 0.88 (d, J=5.6 Hz, 6H). LCMS: 548.2 (M+H)$^+$.

Example 749

(S)-1-(3''-(3-amino-3-methylpyrrolidin-1-yl)-3-chloro-5'-fluoro-2'-hydroxy-[1,1':3',1''-terphenyl]-4-yl)-3-methyl-1H-imidazol-2(3H)-one

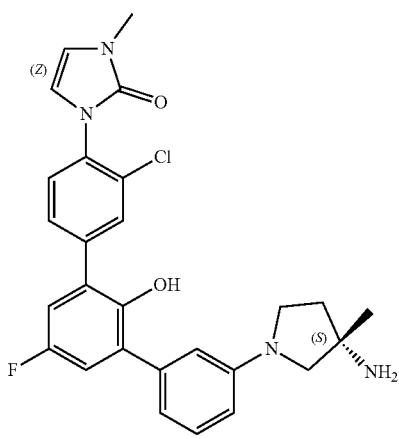

The title compound was prepared following the procedures described for Example 734 using 1-bromo-3-iodobenzene, tert-butyl (S)-(3-methylpyrrolidin-3-yl)carbamate hydrochloride, 4,4,4',4',5,5,5',5'-octamethyl-2,2'-bi(1,3,2-dioxaborolane), 1-(3'-bromo-3-chloro-5'-fluoro-2'-methoxy-[1,1'-biphenyl]-4-yl)-3-methyl-1,3-dihydro-2H-imidazol-2-one and BBr$_3$ to afford the title compound. $^1$H NMR (400 MHz, DMSO-d$_6$) δ 7.80 (s, 1H), 7.62 (d, J=8.3 Hz, 1H), 7.51 (d, J=8.2 Hz, 1H), 7.22 (t, J=7.9 Hz, 1H), 7.16 (dd, J=8.8, 3.2 Hz, 1H), 7.09 (d, J=9.2 Hz, 1H), 6.77-6.67 (m, 3H), 6.63 (s, 1H), 6.48 (d, J=8.2 Hz, 1H), 3.42 (d, J=8.2 Hz, 2H), 3.21 (s, 3H), 3.11 (dd, J=22.4, 9.2 Hz, 2H), 1.84 (t, J=6.8 Hz, 2H), 1.25 (s, 3H). Three N—H and O—H proton not observed. LCMS: 493.2 (M+H)$^+$.

Example 750

1-(3'-(2-(3-amino-3-(hydroxymethyl)pyrrolidin-1-yl)pyridin-4-yl)-3-chloro-5'-fluoro-2'-hydroxy-[1,1'-biphenyl]-4-yl)-3-methyl-1H-imidazol-2(3H)-one

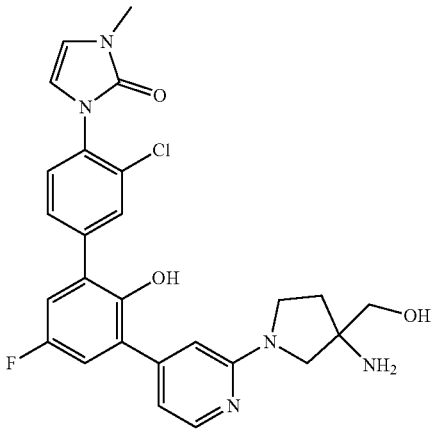 [SMILES: Cn1ccn(-c2ccc(-c3cc(F)cc(-c4ccnc(N5CCC(N)(CO)C5)c4)c3O)cc2Cl)c1=O]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1,3-dihydro-2H-imidazol-2-one, tert-butyl (3-(hydroxymethyl)pyrrolidin-3-yl)carbamate and TFA to afford the title compound. $^1$H NMR (400 MHz, DMSO-d): δ 8.09 (d, J=5.2 Hz, 1H), 7.81 (s, 1H), 7.62 (d, J=8.4 Hz, 1H), 7.52 (d, J=8.0 Hz, 1H), 7.25-7.15 (m, 2H), 6.72-6.68 (m, 3H), 6.53 (s, 1H), 4.86 (s, 1H), 5.58-3.49 (m, 2H), 3.43-3.35 (m, 3H), 3.21 (s, 3H), 3.15 (d, J=10.4 Hz, 1H), 2.00-1.92 (m, 1H), 1.71-1.64 (m, 1H). N—H and O—H protons not observed. LCMS: 510.3 (M+H)$^+$.

Example 751

1-(3-chloro-5'-fluoro-2'-hydroxy-3'-(2-(1-isopropyl-1,7-diazaspiro[4.4]nonan-7-yl)pyridin-4-yl)-[1,1'-biphenyl]-4-yl)-3-methyl-1H-imidazol-2(3H)-one

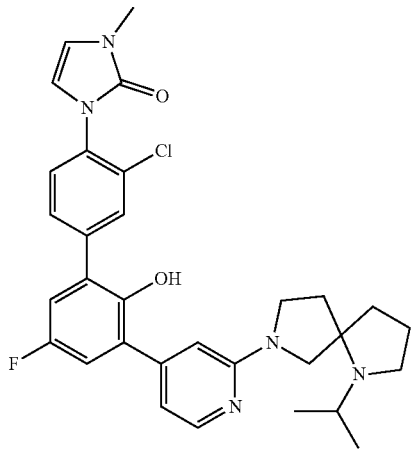 [SMILES: CC(C)N1CCCC12CCN(c1cc(-c3cc(F)cc(-c4ccc(-n5ccn(C)c5=O)c(Cl)c4)c3O)ccn1)C2]

The title compound was prepared following the procedures described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and tert-butyl 1,7-diazaspiro[4.4]nonane-1-carboxylate, TFA, acetone and NaCNBH$_3$ to afford the title compound. $^1$H NMR (400 MHz, DMSO-d$_6$): δ 8.66 (s, 1H), 8.09 (d, J=5.2 Hz, 1H), 7.80 (s, 1H), 7.61 (d, J=8.4 Hz, 1H), 7.52 (d, J=8.0 Hz, 1H), 7.25-7.17 (m, 2H), 6.73-6.68 (m, 3H), 3.62 (t, J=8.4 Hz, 1H), 3.31-3.25 (m, 1H), 3.21-3.12 (m, 6H), 2.87-2.76 (m, 2H), 2.09-2.00 (m, 1H), 1.72-1.65 (m, 5H), 1.05-1.02 (m, 6H). O—H proton not observed. LCMS: 562.3 (M+H)$^+$.

Example 752

1-(3-chloro-3'-(2-((3R,4R)-3-(dimethylamino)-4-hydroxypyrrolidin-1-yl)pyridin-4-yl)-5'-fluoro-2'-hydroxy-[1,1'-biphenyl]-4-yl)-3-methyl-1H-imidazol-2(3H)-one

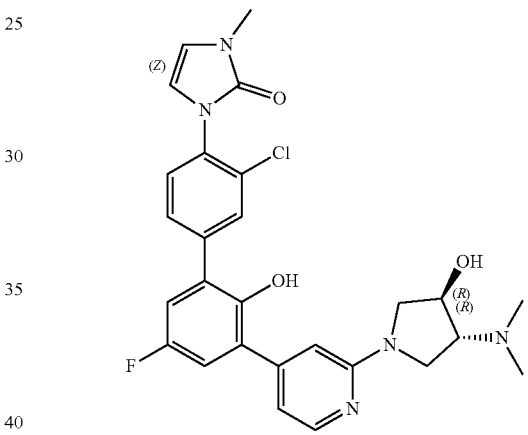

The title compound was prepared following the procedures described for Example 727 using 1-(3-chloro-5'-fluoro-3'-(2-fluoropyridin-4-yl)-2'-hydroxy-[1,1'-biphenyl]-4-yl)-3-methyl-1,3-dihydro-2H-imidazol-2-one, tert-butyl ((3R,4R)-4-hydroxypyrrolidin-3-yl)carbamate, TFA, HCHO and NaCNBH$_3$ to afford the title compound. $^1$H NMR (400 MHz, DMSO-d$_6$): δ 8.68 (s, 1H), 8.10 (d, J=5.2 Hz, 1H), 7.80 (s, 1H), 7.61 (d, J=8.0 Hz, 1H), 7.52 (d, J=8.0 Hz, 1H), 7.25-7.18 (m, 2H), 7.75-6.68 (m, 3H), 6.59 (s, 1H), 5.17 (d, J=4.4 Hz, 1H), 4.25 (t, J=5.6 Hz, 1H), 3.74-3.63 (m, 2H), 3.29 (s, 1H), 3.24-3.20 (m, 4H), 2.72-2.71 (m, 1H), 2.25 (s, 6H). LCMS: 524.2 (M+H)$^+$.

Example 753

(R)-3-(3-amino-3-methylpyrrolidin-1-yl)-5-(3'-chloro-5-fluoro-2-hydroxy-4'-(3-methyl-2-oxo-2,3-dihydro-1H-imidazol-1-yl)-[1,1'-biphenyl]-3-yl)-1-methylpyridin-2(1H)-one

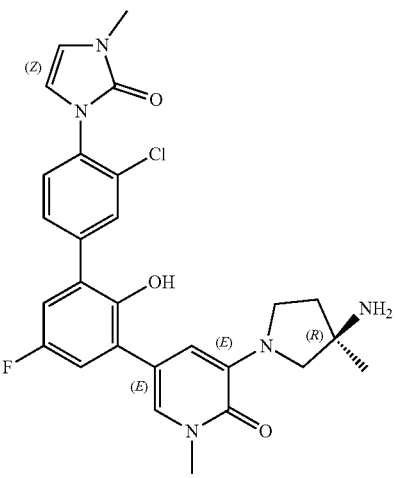

The title compound was prepared following the procedure described for Example 668 using tert-butyl (R)-(1-(5-bromo-1-methyl-2-oxo-1,2-dihydropyridin-3-yl)-3-methylpyrrolidin-3-yl)carbamate, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1,3-dihydro-2H-imidazol-2-one and BBr₃ to afford the title compound. ¹H NMR (400 MHz, DMSO-d₆): δ 7.79 (s, 1H), 7.60 (d, J=8.0 Hz, 1H), 7.50 (d, J=8.0 Hz, 1H), 7.27 (s, 1H), 7.15-7.10 (m, 2H), 6.71 (d, J=2.8 Hz, 1H), 6.68 (d, J=2.8 Hz, 1H), 6.37 (s, 1H), 3.56-3.53 (m, 1H), 3.53 (s, 3H), 3.51-3.46 (m, 1H) 3.44-3.42 (m, 2H), 3.20 (s, 3H), 1.723 (t, J=6.8 Hz, 2H), 1.21 (s, 3H). LCMS: 524.2 (M+H)⁺.

Example 754

1-(3''-(4-(tert-butyl)piperazin-1-yl)-3-chloro-5',5''-difluoro-2'-hydroxy-[1,1':3',1''-terphenyl]-4-yl)-3-methyl-1H-imidazol-2(3H)-one

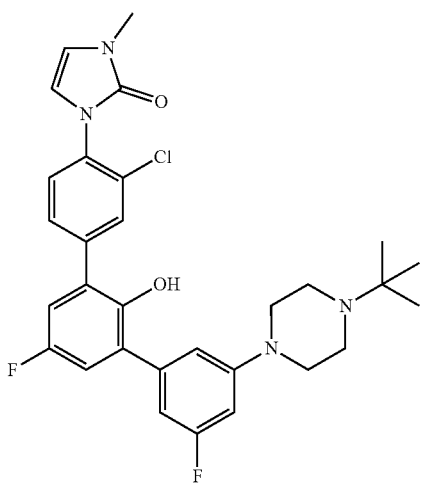 [SMILES: Cn1ccn(-c2ccc(-c3cc(F)cc(-c4cc(F)cc(N5CCN(C(C)(C)C)CC5)c4)c3O)cc2Cl)c1=O]

The title compound was prepared following the procedure described for Example 734 using 1-(tert-butyl)piperazine, 1,3-dibromo-5-fluorobenzene, 4,4,4',4',5,5,5',5'-octamethyl-2,2'-bi(1,3,2-dioxaborolane), 1-(3'-bromo-3-chloro-5'-fluoro-2'-methoxy-[1,1'-biphenyl]-4-yl)-3-methyl-1H-imidazol-2(3H)-one and BBr₃ to afford the title compound. ¹H NMR (400 MHz, DMSO-d₆): δ 7.81 (s, 1H), 7.62 (d, J=8.0 Hz, 1H), 7.53 (d, J=8.4 Hz, 1H), 7.21-7.14 (m, 2H), 6.88 (s, 1H), 6.77-6.68 (m, 4H), 3.25 (s, 7H), 3.37 (br s, 4H), 1.07 (d, J=18.4 Hz, 9H). O—H proton not observed. LCMS: 553.2 (M+H)⁺.

Example 755

1-(3'-(2-(7-amino-5-azaspiro[2.4]heptan-5-yl)pyridin-4-yl)-3-chloro-5'-fluoro-2'-hydroxy-[1,1'-biphenyl]-4-yl)-3-methyl-1H-imidazol-2(3H)-one

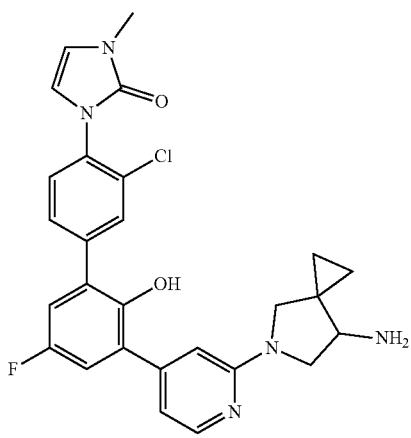 [SMILES: Cn1ccn(-c2ccc(-c3cc(F)cc(-c4ccnc(N5CC(N)C6(CC6)C5)c4)c3O)cc2Cl)c1=O]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and tert-butyl 5-azaspiro[2.4]heptan-7-ylcarbamate and TFA to afford the title compound. ¹H NMR (400 MHz, DMSO-d): δ 8.09 (d, J=5.2 Hz, 1H), 7.81 (s, 1H), 7.62 (d, J=8.4 Hz, 1H), 7.52 (d, J=8.0 Hz, 1H), 7.25-7.17 (m, 2H), 6.72-6.68 (m, 3H), 6.54 (s, 1H), 3.73 (d, J=3.6 Hz, 1H), 3.53 (d, J=10.0 Hz, 1H), 3.25-3.16 (m, 8H), 0.59 (s, 1H), 0.59 (s, 1H), 0.57 (s, 1H). N—H and O—H protons not observed. LCMS: 506.2 (M+H)⁺.

Example 756

1-(3-chloro-3'-(6-ethyl-5-(4-isopropylpiperazin-1-yl)pyridin-3-yl)-5'-fluoro-2'-hydroxy-[1,1'-biphenyl]-4-yl)-3-methyl-1H-imidazol-2(3H)-one

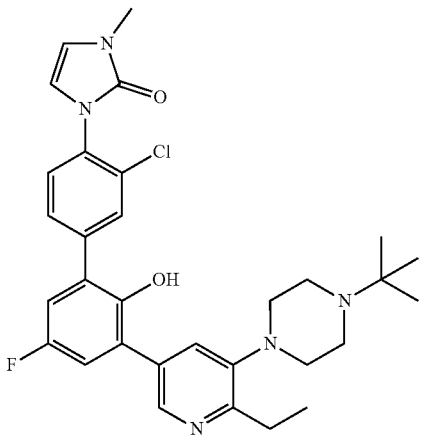 [SMILES: CCc1ncc(-c2cc(F)cc(-c3ccc(-n4ccn(C)c4=O)c(Cl)c3)c2O)cc1N1CCN(C(C)(C)C)CC1]

The title compound was prepared following the procedures described for Example 459 using 5-bromo-2-chloro-3-iodopyridine, 1-isopropylpiperazine, 4,4,4',4',5,5,5',5'-octamethyl-2,2'-bi(1,3,2-dioxaborolane), 1-(3'-bromo-3-chloro-5'-fluoro-2'-methoxy-[1,1'-biphenyl]-4-yl)-3-methyl-1H-imidazol-2(3H)-one, ethylboronic acid and piperazine to afford the title compound. $^1$H NMR (400 MHz, DMSO-$d_6$): 8.70 (s, 1H), 8.40 (s, 1H), 7.82 (s, 1H), 7.64-7.54 (m, 3H), 7.25-7.21 (m, 2H), 6.71-6.68 (m, 2H), 3.21 (s, 3H), 2.90-2.82 (m, 4H), 2.70-2.67 (m, 2H), 2.62-2.50 (m, 5H), 1.27 (t, J=7.2 Hz, 3H) 1.01 (d, J=5.6 Hz, 6H). LCMS: 550.2 (M+H)$^+$.

Example 757

1-(3'-(2-(8-amino-8-methyl-3-azabicyclo[3.2.1]octan-3-yl)pyridin-4-yl)-3-chloro-5'-fluoro-2'-hydroxy-[1,1'-biphenyl]-4-yl)-3-methyl-1H-imidazol-2(3H)-one

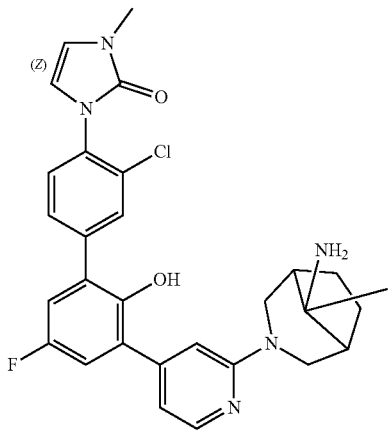 [SMILES: CCC1(N)C2CCC1CN(c1cc(-c3cc(F)cc(-c4ccc(-n5ccn(C)c5=O)c(Cl)c4)c3O)ccn1)C2]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one, tert-butyl (8-methyl-3-azabicyclo[3.2.1]octan-8-yl)carbamate and TFA to afford the title compound (72% yield). $^1$H NMR (400 MHz, DMSO-$d_6$): 8.15 (d, J=3.6 Hz, 1H), 7.81 (s, 1H), 7.61-7.53 (m, 2H), 7.25-7.19 (m, 2H), 6.83-6.80 (m, 2H), 6.71-6.68 (m, 2H), 3.85 (d, J=11.6 Hz, 2H), 3.21 (s, 3H), 3.17-3.14 (m, 2H), 2.01-1.92 (m, 4H), 1.46 (d, J=7.2 Hz, 2H), 1.28 (s, 3H). N—H and O—H protons not observed. LCMS: 534.2 (M+H)$^+$.

Example 758

(R)-1-(3''-(3-amino-3-methylpyrrolidin-1-yl)-3-chloro-5'-fluoro-2'-hydroxy-[1,1':3',1''-terphenyl]-4-yl)-3-methyl-1H-imidazol-2(3H)-one

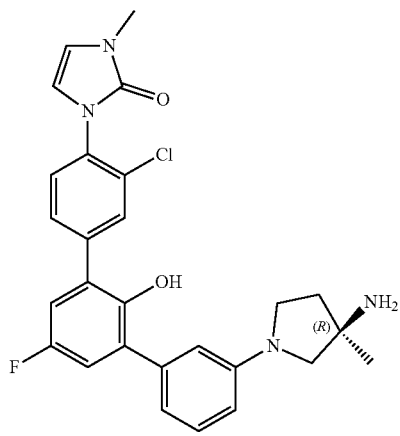

The title compound was prepared following the procedures described for Example 734 using 1-(3'-bromo-3-chloro-5'-fluoro-2'-methoxy-[1,1'-biphenyl]-4-yl)-3-methyl-1,3-dihydro-2H-imidazol-2-one, tert-butyl (R)-(3-methyl-1-(3-(4,4,5,5-tetramethyl-1,3,2-dioxaborolan-2-yl)phenyl)pyrrolidin-3-yl)carbamate and BBr$_3$ to afford the title compound. $^1$H NMR (400 MHz, DMSO-$d_6$): δ 7.80 (d, J=1.2 Hz, 1H), 7.61 (d, J=8.0 Hz, 1H), 7.51 (d, J=8.0 Hz, 1H), 7.22 (t, J=8.0 Hz, 1H), 7.16 (d, J=3.2 Hz, 1H), 7.08 (dd, J=9.2 Hz, 3.2 Hz, 1H), 6.74-6.68 (m, 3H), 6.62 (s, 1H), 6.48 (d, J=8.0 Hz, 1H), 3.42-3.38 (m, 2H), 3.20 (s, 3H), 3.14-3.06 (m, 2H), 1.83 (t, J=6.8 Hz, 2H), 1.24 (s, 3H). N—H and O—H protons not observed. LCMS: 493.2 (M+H)$^+$.

Example 759

(S)-3-(3-amino-3-methylpyrrolidin-1-yl)-5-(3'-chloro-5-fluoro-2-hydroxy-4'-(3-methyl-2-oxo-2,3-dihydro-1H-imidazol-1-yl)-[1,1'-biphenyl]-3-yl)-1-methylpyridin-2(1H)-one

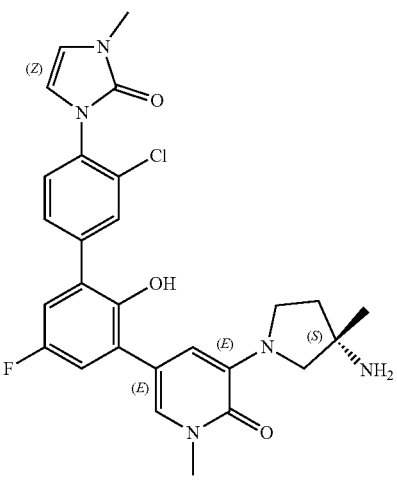

The title compound was prepared following the procedure described for Example 753 using 3,5-dibromo-1-methylpyridin-2(1H)-one, (S)-tert-butyl (3-methylpyrrolidin-3-yl)carbamate, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and BBr$_3$ to afford the title compound (2% yield). $^1$H NMR (400 MHz, DMSO-d$_6$+D$_2$O): δ 7.80 (s, 1H), 7.61 (d, J=8.4 Hz, 1H), 7.51 (d, J=8.4 Hz, 1H), 7.30 (s, 1H), 7.15-7.12 (m, 2H), 6.72-6.68 (m, 2H), 6.48 (s, 1H), 3.61-3.54 (m, 1H), 3.47 (s, 3H), 3.43-3.29 (m, 3H), 3.23 (s, 3H), 3.18 (s, 2H), 1.81 (t, J=7.2 Hz, 2H), 1.25 (s, 3H). N—H and O—H protons not observed. LCMS: 524.2 (M+H)$^+$.

Example 760

(S)-1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)pyrrolidine-3-carboxamide

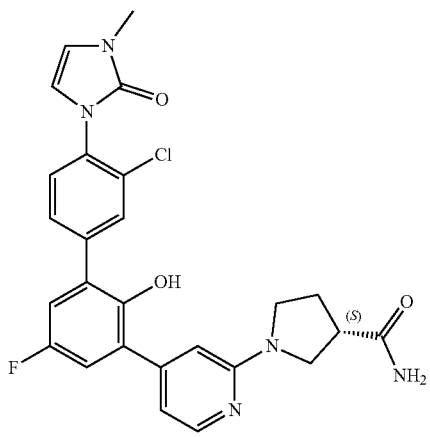

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and (S)-pyrrolidine-3-carboxamide to afford the title compound. $^1$H NMR (400 MHz, DMSO-d$_6$): δ 8.70 (s, 1H), 8.11 (d, J=5.2 Hz, 1H), 7.80 (s, 1H), 7.62 (d, J=8.0 Hz, 1H), 7.52 (d, J=8.0 Hz, 1H), 7.47 (s, 1H), 7.26-7.17 (m, 2H), 6.94 (s, 1H), 6.75-6.68 (m, 3H), 6.59 (s, 1H), 3.68-3.63 (m, 1H), 3.59-3.52 (m, 1H), 3.51-3.46 (m, 1H), 3.44-3.36 (m, 1H), 3.21 (s, 3H), 3.08-3.00 (m, 1H), 2.18-2.05 (m, 2H). LCMS: 508.2 (M+H)$^+$.

Example 761

(R)-1-(4-(3'-chloro-5-fluoro-2-hydroxy-4'-(3-methyl-2-oxo-2,3-dihydro-H-imidazol-1-yl)-[1,1'-biphenyl]-3-yl)pyridin-2-yl)pyrrolidine-3-carboxamide

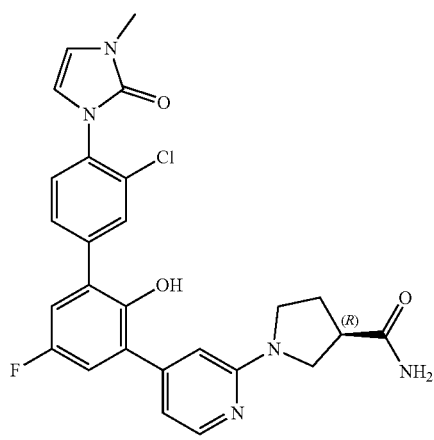

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and (R)-pyrrolidine-3-carboxamide to afford the title compound. $^1$H NMR (400 MHz, DMSO-d$_6$): δ 8.69 (s, 1H), 8.10 (d, J=5.2 Hz, 1H), 7.80 (d, J=1.6 Hz, 1H), 7.61 (dd, J=8.0 Hz, 1.6 Hz, 1H), 7.53-7.46 (m, 1H), 7.25-7.17 (m, 2H), 6.94 (s, 1H), 6.74-6.68 (m, 3H), 6.58 (s, 1H), 3.55-3.45 (m, 2H), 3.42-3.36 (m, 1H), 3.20 (s, 3H), 3.03 (t, J=7.6 Hz, 1H), 2.16-2.07 (m, 2H). N—H and O—H protons not observed. LCMS: 508.2 (M+H)$^+$.

Example 762

1-(3-chloro-5'-fluoro-2'-hydroxy-3'-(2-(4-hydroxy-4-methylpiperidin-1-yl)pyridin-4-yl)-[1,1'-biphenyl]-4-yl)-3-methyl-1,3-dihydro-2H-imidazol-2-one

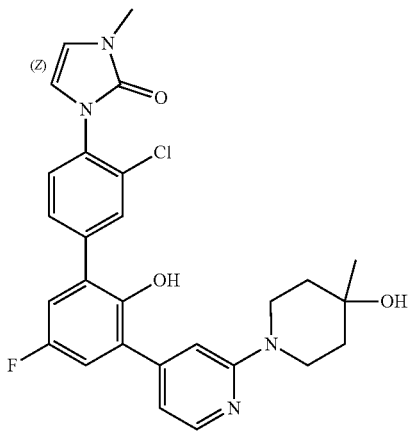 [SMILES: Cn1ccn(-c2ccc(-c3cc(F)cc(-c4ccnc(N5CCC(C)(O)CC5)c4)c3O)cc2Cl)c1=O]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 4-methylpiperidin-4-ol to afford the title compound. H NMR (400 MHz, DMSO-d$_6$) δ 8.68 (s, 1H), 8.13 (d, J=5.1 Hz, 1H), 7.80 (s, 1H), 7.62 (d, J=8.3 Hz, 1H), 7.52 (d, J=8.2 Hz, 1H), 7.25-7.17 (m, 2H), 6.94 (s, 1H), 6.76 (d, J=5.1 Hz, 1H), 6.70 (dd, J=12.5, 3.0 Hz, 2H), 4.33 (s, 1H), 3.88-3.85 (m, 2H), 3.40-3.36 (m, 2H), 3.21 (s, 3H), 1.54-1.47 (m, 4H), 1.15 (s, 3H). LCMS: 509.2 (M+H)$^+$.

Example 763

5-(3'-chloro-5-fluoro-2-hydroxy-4'-(3-methyl-2-oxo-2,3-dihydro-1H-imidazol-1-yl)-[1,1'-biphenyl]-3-yl)-3-(4-(1-methoxy-2-methylpropan-2-yl)piperazin-1-yl)-1-methylpyridin-2(1H)-one

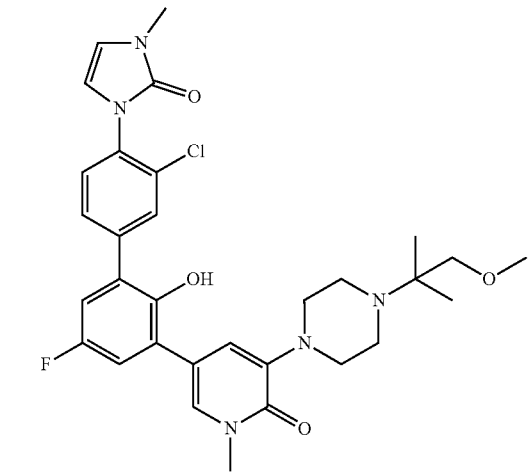 [SMILES: COCC(C)(C)N1CCN(c2cc(-c3cc(F)cc(-c4ccc(-n5ccn(C)c5=O)c(Cl)c4)c3O)cn(C)c2=O)CC1]

The title compound was prepared following the procedures described for Example 753 using 3,5-dibromo-1-methylpyridin-2(1H)-one, 1-(1-methoxy-2-methylpropan-2-yl)piperazine, 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one and piperazine to afford the title compound. $^1$H NMR (400 MHz, CD$_3$OD): δ 7.70 (s, 1H), 7.50 (d, J=8.4 Hz, 1H), 7.44-7.39 (m, 2H), 7.00-6.93 (m, 3H), 6.57 (d, J=5.6 Hz, 1H), 6.53 (d, J=5.6 Hz, 1H), 3.54 (s, 3H), 3.25 (s, 8H), 3.07 (s, 4H), 2.77 (s, 4H), 1.03 (s, 6H). LCMS: 596.3 (M+H)$^+$.

TABLE 31

Following compounds were prepared using similar procedures as described for Examples 365-763.

| Ex. No. | Name/Structure | $^1$H NMR Data | LCMS (M + H)$^+$ |
|---|---|---|---|
| 764 | N-(1-(3''-chloro-5'-fluoro-2'-hydroxy-4''-(3-methyl-2-oxo-2,3-dihydro-1H-imidazol-1-yl)-[1,1':3',1''-terphenyl]-3-yl)cyclopropyl)acetamide | $^1$H NMR (400 MHz, DMSO-d$_6$): δ 8.58-8.54 (m, 2H), 7.80 (d, J = 2.0 Hz, 1H), 7.62 (dd, J = 1.6 Hz, 8.4 Hz, 1H), 7.52 (d, J = 8.0 Hz, 1H), 7.40-7.31 (m, 2H), 7.26 (s, 1H), 7.20-7.16 (m, 2H), 7.09 (dd, J = 3.2 Hz, 8.8 Hz, 1H), 6.71 (d, J = 2.8 Hz, 1H), 6.68(d, J = 2.8 Hz, 1H), 3.21 (s, 3H), 1.84 (s, 3H), 1.24-1.11 (m, 4H) | 490.0 (M − H)$^-$ |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 765 | (S)-6-(3-amino-3-methylpyrrolidin-1-yl)-4-(3'-chloro-5-fluoro-2-hydroxy-4'-(3-methyl-2-oxo-2,3-dihydro-1H-imidazol-1-yl)-[1,1'-biphenyl]-3-yl)-1-methylpyridin-2(1H)-one | $^1$H NMR (400 MHz, DMSO-d$_6$) δ 7.80 (d, J = 1.7 Hz, 1H), 7.60 (dd, J = 8.2, 1.8 Hz, 1H), 7.51 (d, J = 8.2 Hz, 1H), 7.23 (dd, J = 9.0, 3.2 Hz, 1H), 7.15 (dd, J = 9.0, 3.0 Hz, 1H), 6.70 (dd, J = 11.6, 3.0 Hz, 2H), 6.06 (s, 1H), 5.86 (s, 1H), 3.51 (dd, J = 16.9, 7.6 Hz, 1H), 3.40 (s, 3H), 3.30-3.23 (m, 1H), 3.21 (s, 3H), 3.13 (d, J = 9.4 Hz, 1H), 3.02 (d, J = 9.4 Hz, 1H), 1.79 (t, J = 7.0 Hz, 2H), 1.25 (s, 3H). N—H and O—H protons not observed. | 524.2 |
| 766 | 3''-chloro-5'-fluoro-2'-hydroxy-4-methyl-4''-(3-methyl-2-oxo-2,3-dihydro-1H-imidazol-1-yl)-[1,1':3',1''-terphenyl]-3-carboxamide | $^1$H NMR (400 MHz, DMSO-d$_6$) δ 8.46 (s, 1H), 7.82 (d, J = 1.6 Hz, 1H), 7.73 (s, 1H), 7.66-7.49 (m, 4H), 7.36 (s, 1H), 7.31 (d, J = 8.0 Hz, 1H), 7.20 (m, 2H), 6.70 (dd, J = 12.6, 3.0 Hz, 2H), 3.21 (s, 3H), 2.42 (s, 3H) | 452.1 |

| Ex. No. | Name/Structure | $^1$H NMR Data | LCMS (M + H)$^+$ |
|---|---|---|---|
| 767 | N-(5-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-5-azaspiro[2.4]heptan-7-yl)acetamide | $^1$H NMR (400 MHz, DMSO-d$_6$): δ 8.68 (s, 1H), 8.17-8.11 (m, 2H), 7.80 (d, J = 2.0 Hz, 1H), 7.63-7.60 (m, 1H), 7.52 (d, J = 8.4 Hz, 1H), 7.25-7.18 (m, 2H), 6.76-6.68 (m, 3H), 6.57 (s, 1H), 3.66 (s, 1H), 3.63 (s, 1H), 3.33 (s, 1H), 3.30 (s, 1H), 3.21 (s, 3H), 1.82 (s, 3H), 0.61-0.60 (m, 4H). N—H and O—H protons not observed | 548.2 |
| 768 | N-(1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-3-methylazetidin-3-yl)acetamide | $^1$H NMR (400 MHz, CD$_3$OD) δ 7.97 (d, J = 5.4 Hz, 1H), 7.69 (d, J = 1.8 Hz, 1H), 7.51 (dd, J = 8.2, 1.8 Hz, 1H), 7.40 (d, J = 8.2 Hz, 1H), 7.07-6.92 (m, 2H), 6.77 (dd, J = 5.4, 1.2 Hz, 1H), 6.63-6.46 (m, 3H), 4.05 (d, J = 8.2 Hz, 2H), 3.85 (d, J = 8.2 Hz, 2H), 3.25 (s, 3H), 1.84 (s, 3H), 1.54 (s, 3H). N—H and O—H protons not observed | 522.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 769 | 1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-3-methylpyrrolidine-3-carboxylic acid | $^1$H NMR (400 MHz, DMSO-d$_6$): δ 8.11 (d, J = 5.2 Hz, 1H), 7.80 (d, J = 2.0 Hz, 1H), 7.63-7.61 (m, 1H), 7.52 (d, J = 0.4 Hz, 1H), 7.25-7.18 (m, 2H), 6.75-6.68 (m, 3H), 6.59 (s, 1H), 3.86 (d, J = 10.4 Hz, 1H), 3.53-3.44 (m, 3H), 3.29 (s, 3H), 3.39-3.36 (m, 1H), 1.89-1.86 (m, 1H), 1.33 (s, 3H). O—H protons not observed | 523.2 |
| 770 | 1-(3-chloro-5'-fluoro-2'-hydroxy-3'-(2-(1-hydroxy-3-azabicyclo[3.1.0]hexan-3-yl)pyridin-4-yl)-[1,1'-biphenyl]-4-yl)-3-methyl-1H-imidazol-2(3H)-one | $^1$H NMR (400 MHz, DMSO-d$_6$) δ 8.67 (s, 1H), 8.09 (d, J = 5.0 Hz, 1H), 7.80 (s, 1H), 7.62 (d, J = 8.1 Hz, 1H), 7.52 (d, J = 8.2 Hz, 1H), 7.25-7.17 (m, 2H), 6.76 (d, J = 4.8 Hz, 1H), 6.70 (d, J = 9.4 Hz, 2H), 6.58 (s, 1H), 5.96 (s, 1H), 3.91 (d, J = 9.8 Hz, 1H), 3.49 (s, 2H), 3.39 (d, J = 9.7 Hz, 1H), 3.21 (s, 3H), 1.62 (s, 1H), 1.08-1.04 (m, 1H), 0.50-0.48 (m, 1H) | 493.1 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 771 | 1-(3″-(3-amino-3-methylbut-1-yn-1-yl)-3-chloro-5′-fluoro-2′-hydroxy-[1,1′:3′,1″-terphenyl]-4-yl)-3-methyl-1H-imidazol-2(3H)-one | ¹H NMR (400 MHz, DMSO-d₆) δ 7.82 (d, J = 1.6 Hz, 1H), 7.63 (d, J = 10.2 Hz, 1H), 7.58 (s, 1H), 7.53 (d, J = 8.1 Hz, 2H), 7.46-7.42 (m, 1H), 7.36 (d, J = 7.8 Hz, 1H), 7.21-7.15 (m, 2H), 6.72 (d, J = 3.0 Hz, 1H), 6.69 (d, J = 3.0 Hz, 1H), 3.21 (s, 3H), 1.42 (s, 6H). N—H and O—H protons not observed | 476.2 |
| 772 | 1-(3-chloro-5′-fluoro-2′-hydroxy-3′-(3-hydroxy-3-methylbut-1-yn-1-yl)-[1,1′:3′,1″-terphenyl]-4-yl)-3-methyl-1H-imidazol-2(3H)-one | ¹H NMR (400 MHz, DMSO-d₆): δ 8.64 (s, 1H), 7.82 (d, J = 1.6 Hz, 1H), 7.64-7.60 (m, 2H), 7.55-7.52 (m, 2H), 7.47-7.43 (m, 1H), 7.38 (d, J = 7.6 Hz, 1H), 7.22-7.15 (m, 2H), 6.70 (dd, J = 3.2, 12.8 Hz, 2H), 5.47 (s, 1H), 3.21 (s, 3H), 1.48 (s, 6H) | 477.1 |

TABLE 31-continued

Following compounds were prepared using similar procedures as described for Examples 365-763.

| Ex. No. | Name/Structure | $^1$H NMR Data | LCMS $(M + H)^+$ |
|---|---|---|---|
| 773 | 1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-3-methylpyrrolidine-3-carboxamide | $^1$H NMR (400 MHz, DMSO-$d_6$): δ 9.20 (s, 1H), 8.02 (d, J = 6.8 Hz, 1H), 7.82 (d, J = 2.0 Hz, 1H), 7.82-7.62 (m, 1H), 7.54 (d, J = 8.4 Hz, 1H), 7.47 (s, 1H), 7.42-7.36 (m, 2H), 7.17-7.11 (m, 3H), 6.70 (dd, J = 3.2, 19.2 Hz, 2H), 4.02 (d, J = 10.4 Hz, 1H), 3.70 (s, 1H), 3.62-3.56 (m, 2H), 3.21 (s, 3H), 2.43-2.40 (m, 1H), 2.03-2.00 (m, 1H), 1.36 (s, 3H) | 522.2 |
| 774 | (S)-N-(1-(4-(3'-chloro-5-fluoro-2-hydroxy-4'-(3-methyl-2-oxo-2,3-dihydro-1H-imidazol-1-yl)-[1,1'-biphenyl]-3-yl)-1-methyl-6-oxo-1,6-dihydropyridin-2-yl)-3-methylpyrrolidin-3-yl)acetamide | $^1$H NMR (400 MHz, DMSO-$d_6$) δ 8.72 (s, 1H), 7.89 (s, 1H), 7.79 (s, 1H), 7.61 (d, J = 8.1 Hz, 1H), 7.52 (d, J = 8.2 Hz, 1H), 7.24 (dd, J = 9.0, 3.2 Hz, 1H), 7.15 (dd, J = 8.8, 3.2 Hz, 1H), 6.70 (dd, J = 11.6, 3.0 Hz, 2H), 6.09 (s, 1H), 5.86 (s, 1H), 3.53 (d, J = 9.7 Hz, 1H), 3.42 (s, 1H), 3.38 (s, 3H), 3.29-3.25 (m, 1H), 3.24 (s, 1H), 3.21 (s, 3H), 2.31 (d, J = 12.9 Hz, 1H), 1.87 (d, J = 12.2 Hz, 1H), 1.79 (s, 3H), 1.42 (s, 3H) | 566.3 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 775 | (R)-1-(3-chloro-4″,5′-difluoro-2′-hydroxy-3″-(3-hydroxy-3-methylpyrrolidin-1-yl)-[1,1′:3′,1″-terphenyl]-4-yl)-3-methyl-1H-imidazol-2(3H)-one | ¹H NMR (400 MHz, DMSO-d$_6$) δ 8.45 (s, 1H), 7.80 (d, J = 1.8 Hz, 1H), 7.61 (dd, J = 8.2, 1.8 Hz, 1H), 7.51 (d, J = 8.2 Hz, 1H), 7.21-7.05 (m, 3H), 6.80 (t, J = 6.8 Hz, 2H), 6.70 (dd, J = 11.8, 3.0 Hz, 2H), 4.74 (s, 1H), 3.60-3.50 (m, 1H), 3.42-3.36 (m, 2H), 3.28 (s, 1H), 3.21 (s, 3H), 1.94-1.78 (m, 2H), 1.34 (s, 3H) | 512.2 |
| 776 | tert-butyl(1-(4-(3′-chloro-5-fluoro-2-hydroxy-4′-(3-methyl-2-oxo-2,3-dihydro-1H-imidazol-1-yl)-[1,1′-biphenyl]-3-yl)pyridin-2-yl)-3-methylpyrrolidin-3-yl)carbamate | ¹H NMR (400 MHz, DMSO-d$_6$): δ 8.67 (s, 1H), 8.09 (d, J = 5.6 Hz, 1H), 7.80 (d, J = 2.0 Hz, 1H), 7.61 (dd, J = 8.0 Hz, 1.6 Hz, 1H), 7.25-7.16 (m, 2H), 7.16 (m, 1H), 6.72-6.68 (m, 3H), 6.54 (s, 1H), 3.73 (d, J = 10.4 Hz, 1H), 3.48-3.36 (m, 3H), 3.28 (s, 3H), 2.32-2.30 (m, 1H), 1.91-1.85 (m, 1H), 1.38 (s, 12H). N—H and O—H protons not observed | 594.3 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 777 | (R)-4-(3'-chloro-5-fluoro-2-hydroxy-4'-(3-methyl-2-oxo-2,3-dihydro-1H-imidazol-1-yl)-[1,1'-biphenyl]-3-yl)-6-(3-hydroxy-3-methylpyrrolidin-1-yl)-1-methylpyridin-2(1H)-one | ¹H NMR (400 MHz, DMSO-d₆): δ 8.72 (s, 1H), 7.79 (d, J = 1.6 Hz, 1H), 7.60 (dd, J = 9.2 Hz, 2.0 Hz, 1H), 7.51 (d, J = 8.4 Hz, 1H), 7.24-7.21 (m, 1H), 7.15 (dd, J = 8.8 Hz, 3.2 Hz, 1H), 6.69 (dd, J = 11.6 Hz, 2.8 Hz, 1H), 6.05 (s, 1H), 5.86 (s, 1H), 3.40 (s, 3H), 3.30-3.23 (m, 3H), 3.20 (s, 3H), 3.07-3.04 (m, 1H), 1.89-1.83 (m, 2H), 1.34 (s, 3H) | 525.2 |
| 778 | 1-(3'-(2-(4-amino-4-methylpiperidin-1-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆) δ 8.76 (s, 1H), 8.17 (d, J = 5.2 Hz, 1H), 7.91 (s, 2H), 7.81 (s, 1H), 7.62 (d, J = 8.0 Hz, 1H), 7.54 (d, J = 8.0 Hz, 1H), 7.27 (d, J = 6.8 Hz, 1H), 7.22 (s, 2H), 7.09 (s, 1H), 6.96 (s, 1H), 6.89 (s, 1H), 6.70 (dd, J = 17.9, 2.9 Hz, 2H), 4.06 (d, J = 14.0 Hz, 2H), 3.21 (s, 3H), 1.71 (s, 4H), 1.37 (s, 3H) | 508.2 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 779 | 1-(3-chloro-5'-fluoro-2'-hydroxy-3'-(2-(7-hydroxy-7-methyl-5-azaspiro[2.4]heptan-5-yl)pyridin-4-yl)-[1,1'-biphenyl]-4-yl)-3-methyl-1H-imidazol-2(3H)-one | ¹H NMR (400 MHz, DMSO-d₆): δ 8.69 (s, 1H), 8.09 (d, J = 4.8 Hz, 1H), 7.80 (d, J = 2.0 Hz, 1H), 7.61 (dd, J = 2.0 Hz, 8.0 Hz, 1H), 7.52 (d, J = 8.4 Hz, 1H), 7.26-7.17 (m, 2H), 6.72-6.68 (m, 3H), 6.52 (s, 1H), 4.65 (s, 1H), 3.58(d, J = 10.4 Hz, 1H), 3.52 (s, 2H), 3.36 (d, J = 8.0 Hz, 1H), 3.21(s, 3H), 1.09 (s, 3H), 0.84-0.80 (m, 1H), 0.61-0.58 (m, 1H), 0.53-0.45 (m, 2H) | 521.2 |
| 780 | N-(3-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-8-methyl-3-azabicyclo[3.2.1]octan-8-yl)acetamide | ¹H NMR (400 MHz, DMSO-d₆): δ 9.08 (s, 1H), 8.09 (d, J = 6.0 Hz, 1H), 7.82 (s, 1H), 7.62 (d, J = 5.6 Hz, 1H), 7.57-7.53 (m, 2H), 7.36-7.12 (m, 4H), 6.72 (d, J = 3.2 Hz, 1H), 6.69 (d, J = 2.8 Hz, 1H), 3.82 (d, J = 11.6 Hz, 2H), 3.40-3.38 (m, 2H), 3.21 (s, 3H), 2.6-2.49 (m, 2H), 1.94-1.91 (m, 2H), 1.80 (s, 3H), 1.52 (d, J = 7.6 Hz, 2H), 1.46 (s, 3H) | 576.2 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 781 | 1-(3-chloro-5'-fluoro-3'-(2-((3R,4R)-3-fluoro-4-hydroxypyrrolidin-1-yl)pyridin-4-yl)-2'-hydroxy-[1,1'-biphenyl]-4-yl)-3-methyl-1H-imidazol-2(3H)-one | ¹H NMR (400 MHz, DMSO-$d_6$): δ 8.71 (s, 1H), 8.13 (d, J = 5.2 Hz, 1H), 7.81 (s, 1H), 7.62 (d, J = 8.0 Hz, 1H), 7.52 (d, J = 8.4 Hz, 1H), 7.27-7.20 (m, 2H), 6.78 (d, J = 5.2 Hz, 1H), 6.70 (d, J = 8.0 Hz, 2H), 6.63 (s, 1H), 5.54 (d, J = 3.6 Hz, 1H), 5.08 (d, J = 51.2 Hz, 1H), 4.37-4.34 (m, 1H), 3.76-3.48 (m, 4H), 3.21(s, 3H) | 499.1 |
| 782 | N-(3-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-8-methyl-3-azabicyclo[3.2.1]octan-8-yl)acetamide | ¹H NMR (400 MHz, DMSO-$d_6$): δ 13.56 (s, 1H), 9.25 (s, 1H), 8.09 (d, J = 5.6 Hz , 1H), 8.00 (d, J = 6.4 Hz, 1H), 7.83 (s, 1H), 7.64 (dd, J = 8.0 Hz, 2.8Hz, 1H), 7.55(d, J = 8.0 Hz, 1H), 7.42-7.37 (m, 2H), 7.23 (s, 1H), 7.16-7.10 (m, 1H), 6.73-6.67 (m, 2H), 4.07 (d, J = 11.2, 1H), 3.73-3.71 (m, 2H), 3.56-3.47 (m, 2H), 3.21 (s, 3H), 2.01-1.98 (m, 1H), 1.81 (s, 3H), 1.47 (s, 3H) | 536.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 783 | 1-(3-chloro-5'-fluoro-2'-hydroxy-3'-(2-(3-hydroxy-3,4,4-trimethylpyrrolidin-1-yl)pyridin-4-yl)-[1,1'-biphenyl]-4-yl)-3-methyl-1H-imidazol-2(3H)-one | $^1$H NMR (400 MHz, DMSO-d$_6$): δ 8.67 (s, 1H), 8.09(d, J = 5.6 Hz, 1H), 7.80 (d, J = 6.0 Hz, 1H), 7.61 (dd, J = 8.0 Hz, 1.6 Hz, 1H), 7.52(d, J = 8.4Hz, 1H ), 7.25-7.16 (m, 2H), 6.72-6.68 (m, 3H), 6.50 (s, 1H), 4.62 (s, 1H), 3.47 (s, 2H), 3.36-3.34 (m, 2H), 3.20 (s, 3H), 1.18 (s, 3H), 1.02 (s, 3H), 0.94 (s, 3H) | 523.2 |
| 784 | 1-(3-chloro-5'-fluoro-2'-hydroxy-3'-(2-(3-hydroxy-3-(trifluoromethyl)pyrrolidin-1-yl)pyridin-4-yl)-[1,1'-biphenyl]-4-yl)-3-methyl-1H-imidazol-2(3H)-one | $^1$H NMR (400 MHz, DMSO-d$_6$): δ 8.72 (s, 1H), 8.14 (d, J = 5.2 Hz, 1H), 7.81 (s, 1H), 7.62 (d, J = 8.0 Hz, 1H), 7.53 (d, J = 8.0 Hz, 1H), 7.26-7.21 (m, 2H), 6.82 (d, J = 5.2 Hz, 1H), 6.72-6.67 (m, 3H), 6.46 (s, 1H), 3.73-3.33 (m, 4H), 3.21(s, 3H), 2.27 (s, 1H), 2.07 (s, 1H) | 549.2 |
| 785 | 1-(3-chloro-5'-fluoro-2'-hydroxy-3'-(2-(8-hydroxy-8-methyl-3-azabicyclo[3.2.1]octan-3-yl)pyridin-4-yl)-[1,1'-biphenyl]-4-yl)-3-methyl-1H-imidazol-2(3H)-one | $^1$H NMR (400 MHz, DMSO-d$_6$): δ 8.67 (s, 1H), 8.12 (d, J = 4.8 Hz, 1H), 7.80 (d, J = 1.6 Hz, 1H), 7.61 (dd, J = 8.0 Hz, 1.6 Hz, 1H), 7.52 (d, J = 8.4 Hz, 1H), 7.25-7.16 (m, 2H), 6.81-6.68 (m, 4H), 4.72 (s, 1H), 3.74-3.71 (m, 2H), 3.34 (s, 2H), 3.20 (s, 3H), 1.80-1.71 (m, 4H), 1.47 (d, J = 8.0 Hz, 1H), 1.23 (s, 3H) | 535.2 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 786 | 1-(3-chloro-5'-fluoro-3'-(2-((3S,4S)-3-fluoro-4-hydroxypyrrolidin-1-yl)pyridin-4-yl)-2'-hydroxy-[1,1'-biphenyl]-4-yl)-3-methyl-1H-imidazol-2(3H)-one | ¹H NMR (400 MHz, DMSO-d$_6$): δ 8.69 (s, 1H), 8.12 (d, J = 5.2 Hz, 1H), 7.80 (d, J = 2.0 Hz, 1H), 7.61 (dd, J = 4.4 Hz, 1.6 Hz, 1H), 7.52 (d, J = 8.0 Hz, 1H), 7.25-7.19 (m, 2H), 6.77 (d, J = 8.0 Hz, 1H), 6.72-6.68 (m, 2H), 6.63 (s, 1H), 5.53 (d, J = 3.2 Hz, 1H), 5.14-5.01 (m, 1H), 4.37-4.34 (m, 1H), 3.75-3.59 (m, 3H), 3.51-3.48 (m, 1H), 3.20 (s, 3H) | 499.1 |
| 787 | 1-(3-chloro-3'-(6-chloro-5-(4-isopropylpiperazin-1-yl)pyridin-3-yl)-5'-fluoro-2'-hydroxy-[1,1'-biphenyl]-4-yl)-3-methyl-1H-imidazol-2(3H)-one | ¹H NMR (400 MHz, DMSO-d$_6$): δ 8.86 (s, 1H), 8.23 (s, 1H), 7.82 (s, 1H), 7.70 (s, 1H), 7.63 (d, J = 8.0 Hz, 1H), 7.53 (d, J = 8.0 Hz, 1H), 7.32-7.26 (m, 2H), 6.70 (dd, J = 2.8, 13.6 Hz, 2H), 3.21 (s, 3H), 3.10 (m, 4H), 2.67 (m, 5H), 1.05 (d, J = 4.0 Hz, 6H) | 556.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 788 | 1-(3-chloro-3″-(1-(dimethylamino)cyclopropyl)-5′-fluoro-2′-hydroxy-[1,1′:3′,1″-terphenyl]-4-yl)-3-methyl-1H-imidazol-2(3H)-one | $^1$H NMR (400 MHz, DMSO-d$_6$): δ 8.56 (s, 1H), 7.80 (d, J = 1.2 Hz, 1H), 7.62 (dd, J = 1.6 Hz 8.0 Hz, 1H), 7.54-7.40 (m, 4H), 7.27 (d, J = 7.2 Hz, 1H), 7.21-7.13 (m, 2H), 6.72 (d, J = 2.8 Hz, 1H), 6.68 (d, J = 2.8 Hz, 1H), 3.21 (s, 3H), 2.17 (s, 6H), 0.87-0.78 (m, 4H) | 478.2 |
| 789 | 1-(3′-(5-(4-(tert-butyl)piperazin-1-yl)-6-chloropyridin-3-yl)-3-chloro-5′-fluoro-2′-hydroxy-[1,1′-biphenyl]-4-yl)-3-methyl-1H-imidazol-2(3H)-one | $^1$H NMR (400 MHz, DMSO-d$_6$): δ 8.85 (s, 1H), 8.23 (s, 1H), 7.82 (d, J = 2.0 Hz, 1H), 7.69 (s, 1H), 7.64 (d, J = 2.0 Hz, 1H), 7.53 (d, J = 8.4 Hz, 1H), 7.32-7.25 (m, 2H), 6.70 (dd, J = 13.6 Hz, 4.0 Hz, 2H), 3.21 (s, 3H), 3.09-3.02 (m, 4H), 2.75-2.63 (m, 4H), 1.08 (s, 9H) | 570.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 790 | N-(1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-4-methylpiperidin-4-yl)acetamide<br>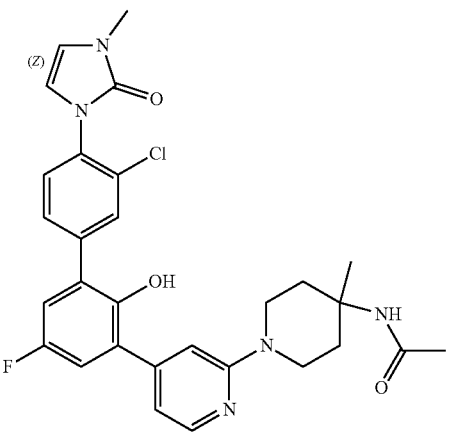 | $^1$H NMR (400 MHz, DMSO-d$_6$) δ 8.69-8.63 (m, 1H), 8.14 (d, J = 5.1 Hz, 1H), 7.82 (s, 1H), 7.62 (d, J = 8.2 Hz, 1H), 7.52 (d, J = 8.4 Hz, 1H), 7.43 (s, 1H), 7.25-7.17 (m, 2H), 6.98 (s, 1H), 6.79 (d, J = 4.8 Hz, 1H), 6.72 (d, J = 3.2 Hz, 1H), 6.68 (d, J = 2.8 Hz, 1H), 3.86 (d, J = 13.6 Hz, 2H), 3.27-3.21 (m, 4H), 2.11 (d, J = 14.0 Hz, 2H), 1.82 (s, 3H), 1.48 (d, J = 9.9 Hz, 2H), 1.26 (d, J = 24.4 Hz, 4H) | 550.2 |
| 791 | 1-(3'-(5-(4-(tert-butyl)piperazin-1-yl)-6-methylpyridin-3-yl)-3-chloro-5'-fluoro-2'-hydroxy-[1,1'-biphenyl]-4-yl)-3-methyl-1,3-dihydro-2H-imidazol-2-one<br>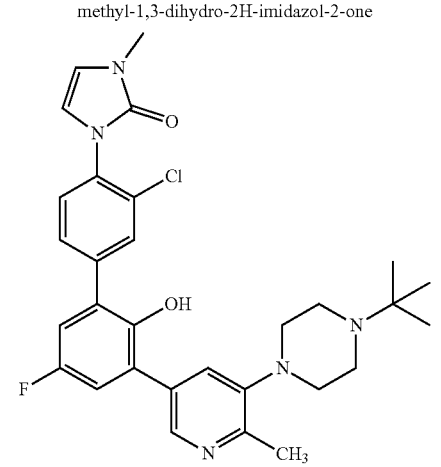 | $^1$H NMR (400 MHz, DMSO-d$_6$): δ 8.69 (s, 1H), 8.31 (d, J = 1.2 Hz, 1H), 7.81 (s, 1H), 7.63 (d, J = 1.2 Hz, 1H), 7.53-7.51(m, 2H), 7.23-7.20 (m, 2H), 6.72-6.68 (m, 2H), 3.21 (s, 3H) , 2.92 (s, 4H), 2.68 (s, 4H), 2.47 (s, 3H), 1.06 (s, 9H) | 550.3 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 792 | N-(1-(4-(3'-chloro-5-fluoro-2-hydroxy-4'-(3-methyl-2-oxo-2,3-dihydro-1H-imidazol-1-yl)-[1,1'-biphenyl]-3-yl)pyridin-2-yl)-3-methylpyrrolidin-3-yl)methanesulfonamide 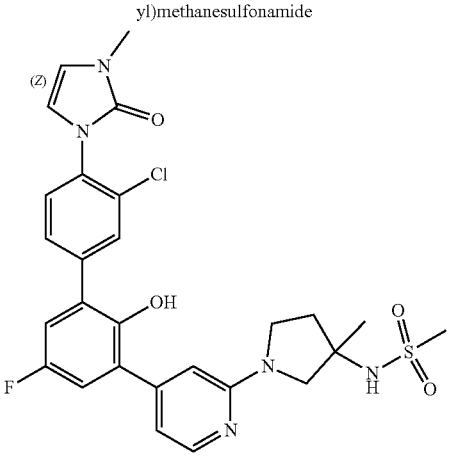 | ¹H NMR (400 MHz, CD₃OD) δ 8.01 (d, J = 5.4 Hz, 1H), 7.74 (d, J = 1.6 Hz, 1H), 7.56 (d, J = 8.3 Hz, 1H), 7.47 (d, J = 8.2 Hz, 1H), 7.27 (d, J = 8.4 Hz, 2H), 6.72 (d, J = 5.1 Hz, 1H), 6.59 (d, J = 10.5 Hz, 3H), 3.55 (qd, J = 17.4, 8.9 Hz, 2H), 3.36 (d, J = 19.7 Hz, 2H), 3.25 (s, 3H), 2.44 (s, 3H), 2.03-1.78 (m, 2H), 1.24 (d, J = 38.3 Hz, 3H) | 572.1 |
| 793 | (R)-N-(1-(5-(3'-chloro-5-fluoro-2-hydroxy-4'-(3-methyl-2-oxo-2,3-dihydro-1H-imidazol-1-yl)-[1,1'-biphenyl]-3-yl)pyridin-3-yl)-3-methylpyrrolidin-3-yl)acetamide 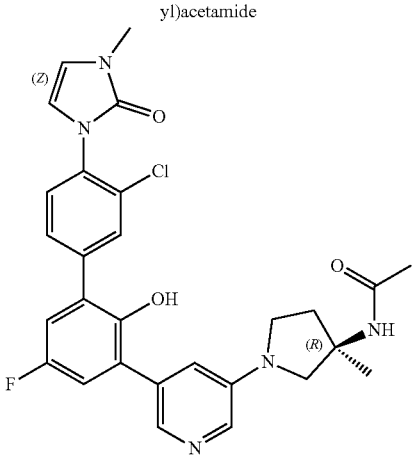 | ¹H NMR (400 MHz, CD₃OD) δ 7.88 (d, J = 1.6 Hz, 1H), 7.73 (dd, J = 15.6, 2.3 Hz, 2H), 7.52 (dd, J = 8.2, 1.9 Hz, 1H), 7.41 (d, J = 8.2 Hz, 1H), 7.10-6.92 (m, 3H), 6.56 (dd, J = 15.4, 3.0 Hz, 2H), 3.65 (d, J = 9.9 Hz, 1H), 3.38 (dd, J = 14.3, 7.4 Hz, 2H), 3.32 (t, J = 10.2 Hz, 1H), 3.25 (s, 3H), 2.52-2.26 (m, 1H), 1.97 (dt, J = 12.8, 7.6 Hz, 1H), 1.82 (s, 3H), 1.44 (s, 3H) | 536.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 794 | N-(1-(3″-chloro-5′-fluoro-2′-hydroxy-4′-(3-methyl-2-oxo-2,3-dihydro-1H-imidazol-1-yl)-[1,1′:3′,1″-terphenyl]-3-yl)cyclopropyl)-N-methylacetamide 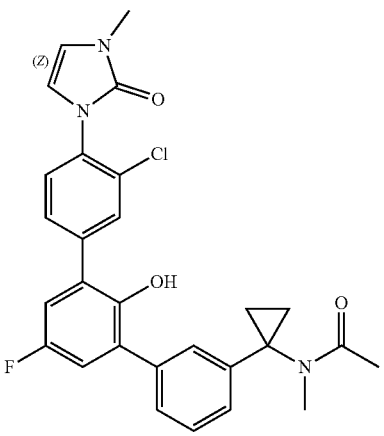 | $^1$H NMR (400 MHz, DMSO-d$_6$): δ 8.42 (br s, 1H), 7.80 (s, 1H), 7.61-7.41 (m, 5H), 7.19-6.95 (m, 4H), 6.70 (d, J = 9.2 Hz, 1H), 3.21 (s, 3H), 2.93 (s, 3H), 1.98 (s, 3H), 1.57-1.23 (m, 4H) | 506.2 |
| 795 | N-(4-(3″-chloro-5′-fluoro-2′-hydroxy-4″-(3-methyl-2-oxo-2,3-dihydro-1H-imidazol-1-yl)-[1,1′:3′,1″-terphenyl]-3-yl)-2-methylbut-3-yn-2-yl)acetamide 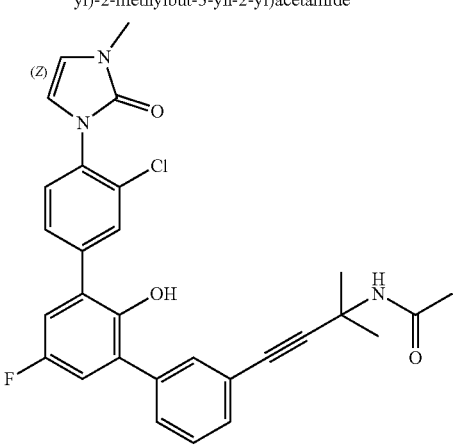 | $^1$H NMR (400 MHz, CD$_3$OD) δ 7.71 (s, 1H), 7.51 (d, J = 7.8 Hz, 2H), 7.40 (d, J = 8.1 Hz, 2H), 7.30 (d, J = 4.9 Hz, 2H), 7.03-6.87 (m, 2H), 6.55 (d, J = 11.6 Hz, 2H), 3.25 (s, 3H), 1.84 (s, 3H), 1.56 (s, 6H), 1.19 (s, 1H) | 518.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 796 | 1-(3-chloro-5'-fluoro-2'-hydroxy-3'-(3-(2-hydroxypropan-2-yl)quinolin-6-yl)-[1,1'-biphenyl]-4-yl)-3-methyl-1H-imidazol-2(3H)-one | $^1$H NMR (400 MHz, DMSO-d$_6$) δ 9.07 (d, J = 2.2 Hz, 1H), 8.72 (s, 1H), 8.37 (d, J = 2.1 Hz, 1H), 8.15 (d, J = 1.8 Hz, 1H), 8.04 (d, J = 8.7 Hz, 1H), 7.92 (dd, J = 8.7, 1.9 Hz, 1H), 7.86 (d, J = 1.9 Hz, 1H), 7.66 (dd, J = 8.2, 1.9 Hz, 1H), 7.54 (d, J = 8.2 Hz, 1H), 7.35-7.17 (m, 2H), 6.71 (dd, J = 9.9, 3.0 Hz, 2H), 5.39 (s, 1H), 3.21 (s, 3H), 1.58 (s, 6H) | 504.1 |
| 797 | 1-(3-chloro-5'-fluoro-2'-hydroxy-3'-(6-(4-isopropylpiperazin-1-yl)pyridazin-4-yl)-[1,1'-biphenyl]-4-yl)-3-methyl-1H-imidazol-2(3H)-one | $^1$H NMR (400 MHz, DMSO-d$_6$) δ 9.02 (s, 1H), 8.75 (d, J = 1.5 Hz, 1H), 7.82 (d, J = 1.9 Hz, 1H), 7.63 (dd, J = 8.2, 1.9 Hz, 1H), 7.54 (d, J = 8.2 Hz, 1H), 7.42-7.23 (m, 3H), 6.72 (d, J = 3.0 Hz, 1H), 6.69 (d, J = 3.0 Hz, 1H), 3.71-3.52 (m, 4H), 3.21 (s, 3H), 2.77-2.63 (m, 1H), 2.62-2.53 (m, 4H), 1.01 (d, J = 6.5 Hz, 6H) | 523.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 798 | 1-(3'-(6-(4-(tert-butyl)piperazin-1-yl)pyridazin-4-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$) δ 9.01 (s, 1H), 8.75 (s, 1H), 7.82 (d, J = 1.8 Hz, 1H), 7.68-7.59 (m, 1H), 7.54 (d, J = 8.2 Hz, 1H), 7.43-7.21 (m, 3H), 6.72 (d, J = 3.0 Hz, 1H), 6.69 (d, J = 3.0 Hz, 1H), 3.61 (s, 4H), 3.21 (s, 3H), 2.63 (s, 4H), 1.06 (s, 9H) | 537.2 |
| 799 | 1-(3-chloro-5'-fluoro-2'-hydroxy-3''-(1-(methylamino)cyclopropyl)-[1,1':3',1''-terphenyl]-4-yl)-3-methyl-1H-imidazol-2(3H)-one | $^1$H NMR (400 MHz, DMSO-d$_6$) δ 8.52 (s, 1H), 7.81 (d, J = 1.9 Hz, 1H), 7.62 (dd, J = 8.2, 1.9 Hz, 1H), 7.52 (d, J = 8.2 Hz, 1H), 7.48 (s, 1H), 7.38(d, J = 6.3 Hz, 2H), 7.29 (s, 1H), 7.22-7.10 (m, 2H), 6.72 (d, J = 3.0 Hz, 1H), 6.68 (d, J = 3.0 Hz, 1H), 3.21 (s, 3H), 2.20 (s, 3H), 0.92 (d, J = 4.6 Hz, 4H). N—H or O—H proton not observed | 464.2 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 800 | 1-(3″-(4-(tert-butyl)piperazin-1-yl)-3-chloro-5′-fluoro-2′-hydroxy-4″-methyl-[1,1′:3′,1″-terphenyl]-4-yl)-3-methyl-1H-imidazol-2(3H)-one | ¹H NMR (400 MHz, DMSO) δ 8.47 (s, 1H), 7.80 (d, J = 1.8 Hz, 1H), 7.62 (dd, J = 8.2, 1.8 Hz, 1H)., 7.51 (d, J = 8.2 Hz, 1H), 7.26-7.08 (m, 5H), 6.70 (dd, J = 11.6, 3.0 Hz, 2H), 3.21 (s, 3H), 2.90 (s, 4H), 2.69 (s, 4H), 2.28 (s, 3H), 1.07 (s, 9H). | 549.2 |
| 801 | 1-(3-chloro-5′-fluoro-2′-hydroxy-3′-(7-(2-hydroxypropan-2-yl)naphthalen-2-yl)-[1,1′-biphenyl]-4-yl)-3-methyl-1H-imidazol-2(3H)-one | ¹H NMR (400 MHz, DMSO-d₆) δ 8.63 (s, 1H), 8.07 (s, 1H), 8.01 (s, 1H), 7.97-7.83 (m, 3H), 7.71-7.62 (m, 3H), 7.54 (d, J = 8.2 Hz, 1H), 7.24 (td, J = 9.0, 3.1 Hz, 2H), 6.71 (dd, J = 9.3, 3.0 Hz, 2H), 5.17 (s, 1H), 3.21 (s, 3H), 1.53 (s, 6H) | 503.2 |

TABLE 31-continued

Following compounds were prepared using similar procedures as described for Examples 365-763.

| Ex. No. | Name/Structure | ¹H NMR Data | LCMS (M + H)+ |
|---|---|---|---|
| 802 | 1-(3'-(5-(4-(tert-butyl)piperazin-1-yl)-6-methoxypyridin-3-yl)-3-chloro-5'-fluoro-2'-hydroxy-[1,1'-biphenyl]-4-yl)-3-methyl-1,3-dihydro-2H-imidazol-2-one 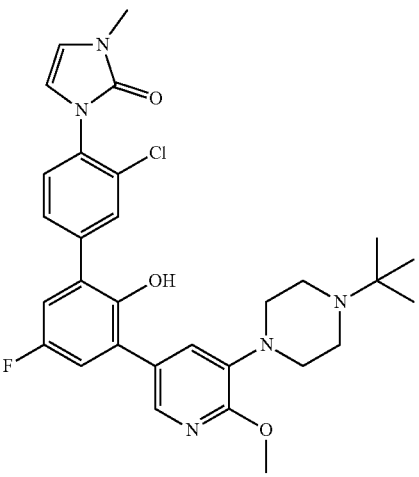 | ¹H NMR (400 MHz, DMSO-d₆) δ 8.61 (s, 1H), 7.92 (s, 1H), 7.81 (d, J = 1.8 Hz, 1H), 7.62 (dd, J = 8.2, 1.9 Hz, 1H), 7.52 (d, J = 8.2 Hz, 1H), 7.33 (s, 1H), 7.19 (d, J = 9.1 Hz, 2H), 6.70 (dd, J = 12.2, 3.0 Hz, 2H), 3.93 (s, 3H), 3.21 (s, 3H), 3.05 (s, 4H), 2.65 (s, 4H), 1.05 (s, 9H) | 566.2 |
| 803 | 1-(3''-(1-aminocyclopropyl)-3-chloro-5 fluoro-2'-hydroxy-[1,1':3',1''-terphenyl]-4-yl)-3-methyl-1H-imidazol-2(3H)-one 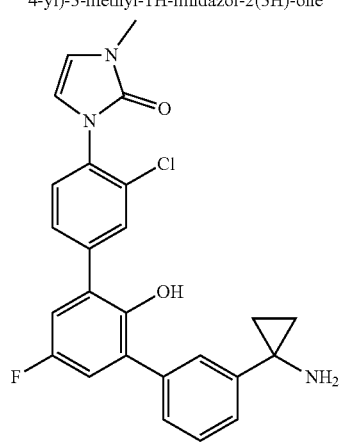 | ¹H NMR (400 MHz, DMSO-d₆) δ 7.81 (d, J = 1.9 Hz, 1H), 7.64-7.58 (m, 1H), 7.52 (d, J = 8.1 Hz, 2H), 7.35 (d, J = 6.1 Hz, 2H), 7.28 (s, 1H), 7.21-7.11 (m, 2H), 6.70 (dd, J = 12.1, 3.0 Hz, 2H), 3.21 (s, 3H), 0.98 (d, J = 4.7 Hz, 4H). Three N—H or O—H proton not observed | 450.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 804 | 1-(3-chloro-5'-fluoro-2'-hydroxy-3'-(5-(4-isopropylpiperazin-1-yl)-6-(trifluoromethyl)pyridin-3-yl)-[1,1'-biphenyl]-4-yl)-3-methyl-1H-imidazol-2(3H)-one | $^1$H NMR (400 MHz, DMSO-d$_6$) δ 8.97 (s, 1H), 8.62 (d, J = 1.5 Hz, 1H), 8.09 (s, 1H), 7.83 (d, J = 1.8 Hz, 1H), 7.64 (dd, J = 8.2, 1.9 Hz, 1H), 7.54 (d, J = 8.2 Hz, 1H), 7.35 (ddd, J = 26.3, 9.0, 3.1 Hz, 2H), 6.71 (dd, J = 13.5, 3.0 Hz, 2H), 3.21 (s, 3H), 2.99 (t, J = 4.6 Hz, 4H), 2.69 (dd, J = 13.1, 6.7 Hz, 1H), 2.60 (s, 4H), 1.01 (d, J = 6.5 Hz, 6H) | 590.2 |
| 805 | 1-(3'-(5-(4-(tert-butyl)piperazin-1-yl)-6-(trifluoromethyl)pyridin-3-yl)-3-chloro-5'-fluoro-2'-hydroxy-[1,1'-biphenyl]-4-yl)-3-methyl-1H-imidazol-2(3H)-one | $^1$H NMR (400 MHz, DMSO-d$_6$) δ 8.96 (s, 1H), 8.62 (s, 1H), 8.10 (s, 1H), 7.83 (d, J = 1.8 Hz, 1H), 7.64 (dd, J = 8.2, 1.9 Hz, 1H), 7.54 (d, J = 8.2 Hz, 1H), 7.38 (dd, J = 8.9, 3.2 Hz, 1H), 7.31 (dd, J = 9.0, 3.1 Hz, 1H), 6.70 (dd, J = 13.8, 3.0 Hz, 2H), 3.21 (s, 3H), 3.00 (s, 4H), 2.67 (s, 4H), 1.06 (s, 9H) | 604.2 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 806 | 1-(3'-(2-(1-amino-3-azabicyclo[3.2.0]heptan-3-yl)pyridin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d$_6$) δ 8.13 (d, J = 5.1 Hz, 1H), 7.81 (d, J = 1.9 Hz, 1H), 7.62 (dd, J = 8.2, 1.9 Hz, 1H), 7.52 (d, J = 8.2 Hz, 1H), 7.22 (ddd, J = 18.3, 9.0, 3.2 Hz, 2H), 6.81-6.75 (m, 1H), 6.74-6.64 (m, 3H), 3.77 (d, J = 11.0 Hz, 1H), 3.64 (d, J = 10.8 Hz, 1H), 3.42-3.36 (m, 1H), 3.21 (s, 3H), 3.13-3.01 (m, 1H), 2.58-2.50 (m, 1H), 2.15-1.92 (m, 3H), 1.36 (d, 7 = 5.0 Hz, 1H). N—H or O—H protons not observed. | 506.2 |
| 807 | (R)-1-(3-chloro-5'-fluoro-2'-hydroxy-3''-(3-hydroxy-3-methylpyrrolidin-1-yl)-[1,1':3',1''-terphenyl]-4-yl)-3-methyl-1H-imidazol-2(3H)-one | ¹H NMR (400 MHz, DMSO-d$_6$) δ 8.39 (s, 1H), 7.81 (d, J = 1.8 Hz, 1H), 7.62 (dd, J = 8.2, 1.9 Hz, 1H), 7.51 (d, J = 8.2 Hz, 1H), 7.22 (t, J = 7.9 Hz, 1H), 7.16 (dd, J = 9.0, 3.2 Hz, 1H), 7.09 (dd, J = 9.1, 3.2 Hz, 1H), 6.78-6.66 (m, 3H), 6.63 (s, 1H), 6.49 (d, J = 6.5 Hz, 1H), 4.77 (s, 1H), 3.40 (d, J = 7.5 Hz, 1H), 3.34-3.29 (s, 1H), 3.19 (d, J = 12.4 Hz, 5H), 1.99-1.76 (m, 2H), 1.35 (s, 3H) | 494.2 |

TABLE 31-continued

Following compounds were prepared using similar procedures as described for Examples 365-763.

| Ex. No. | Name/Structure | ¹H NMR Data | LCMS (M + H)⁺ |
|---|---|---|---|
| 808 | (R)-1-(3-chloro-5'-fluoro-2'-hydroxy-3''-(3-hydroxy-3-methylpyrrolidin-1-yl)-4''-methyl-[1,1':3',1''-terphenyl]-4-yl)-3-methyl-1H-imidazol-2(3H)-one | ¹H NMR (400 MHz, DMSO-d$_6$) δ 8.41 (s, 1H), 7.80 (d, J = 1.8 Hz, 1H), 7.61 (dd, J = 8.2, 1.8 Hz, 1H), 7.51 (d, J = 8.2 Hz, 1H), 7.20-7.02 (m, 3H), 6.98-6.88 (m, 2H), 6.70 (dd, J = 11.5, 3.0 Hz, 2H), 4.69 (s, 1H), 3.46 (d, J = 8.1 Hz, 1H), 3.28-3.16 (m, 5H), 3.09 (d, J = 9.3 Hz, 1H), 2.29 (s, 3H), 1.93-1.75 (m, 2H), 1.34 (s, 3H) | 508.2 |
| 809 | 1-(3''-(4-(tert-butyl)piperazin-1-yl)-3,4''-dichloro-5'-fluoro-2'-hydroxy-[1,1':3',1''-terphenyl]-4-yl)-3-methyl-1H-imidazol-2(3H)-one | ¹H NMR (400 MHz, DMSO-d$_6$) δ 8.64 (s, 1H), 7.81 (d, J = 1.9 Hz, 1H), 7.62 (dd, J = 8.2, 1.9 Hz, 1H), 7.49 (dd, J = 23.0, 8.2 Hz, 2H), 7.36-7.09 (m, 4H), 6.70 (dd, J = 12.1, 3.0 Hz, 2H), 3.21 (s, 3H), 3.03 (s, 4H), 2.68 (s, 4H), 1.06 (s, 9H). | 569.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 810 | 1-(3″-(4-(tert-butyl)piperazin-1-yl)-3-chloro-5′-fluoro-2′-hydroxy-4″-(trifluoromethyl)-[1,1′:3′,1″-terphenyl]-4-yl)-3-methyl-1H-imidazol-2(3H)-one 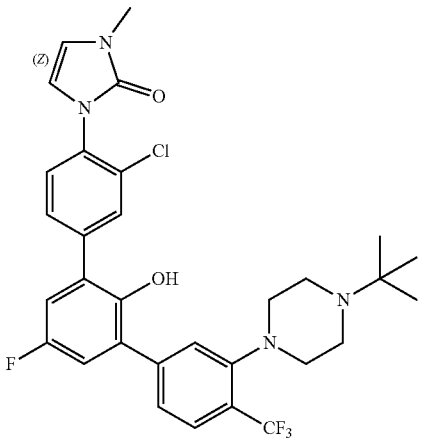 | $^1$H NMR (400 MHz, CD3OD) δ 7.83 (d, J = 1.7 Hz, 1H), 7.74 (d, J = 6.5 Hz, 2H), 7.64 (dd, J = 8.2, 1.7 Hz, 1H), 7.52 (t, J = 8.9 Hz, 2H), 7.13 (d, J = 8.8 Hz, 2H), 6.67 (dd, J = 15.4, 2.9 Hz, 2H), 3.37 (s, 3H), 3.08 (s, 4H), 2.87 (s, 4H), 1.20 (s, 9H) | 603.2 |
| 811 | 1-(3-chloro-5′-fluoro-2′-hydroxy-3″-(4-isopropylpiperazin-1-yl)-4″-(trifluoromethyl)-[1,1′:3′,1″-terphenyl]-4-yl)-3-methyl-1H-imidazol-2(3H)-one 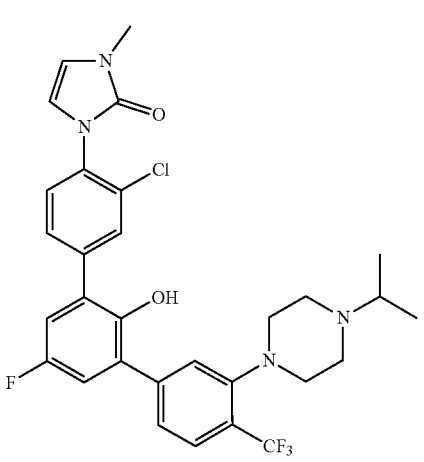 | $^1$H NMR (400 MHz, CD$_3$OD) δ 7.83 (d, J = 1.7 Hz, 1H), 7.75-7.73 (m, 2H), 7.66-7.60 (m, 1H), 7.57-7.49 (m, 2H), 7.13 (d, J = 8.8 Hz, 2H), 6.67 (dd, J = 15.3, 3.0 Hz, 2H), 3.37 (s, 3H), 3.07 (t, J = 4.4 Hz, 4H), 2.81 (s, 4H), 2.05 (d, J = 5.8 Hz, 1H), 1.18 (d, J = 6.5 Hz, 6H). | 589.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 812 | (R)-1-(3-chloro-5'-fluoro-2'-hydroxy-3'-(5-(3-hydroxy-3-methylpyrrolidin-1-yl)-6-methoxypyridin-3-yl)-[1,1'-biphenyl]-4-yl)-3-methyl-1H-imidazol-2(3H)-one | $^1$H NMR (400 MHz, DMSO-d$_6$) δ 8.53 (s, 1H), 7.80 (d, J = 1.5 Hz, 1H), 7.67-7.58 (m, 2H), 7.52 (d, J = 8.2 Hz, 1H), 7.16 (dd, J = 9.1, 6.9 Hz, 2H), 6.95 (s, 1H), 6.70 (dd, J = 12.1, 3.0 Hz, 2H), 4.68 (s, 1H), 3.88(s, 3H), 3.55-3.49 (m, 1H), 5 3.40 (d, J = 10.4 Hz, 2H), 3.27 (d, J = 10.6 Hz, 1H). 3.21 (s, 3H), 1.82 (s, 2H), 1.33 (s, 3H). | 525.2 |
| 813 | 1-(3''-(4-(tert-butyl)piperazin-1-yl)-3-chloro-4''-(difluoromethyl)-5'-fluoro-2'-hydroxy-[1,1':3',1''-terphenyl]-4-yl)-3-methyl-1H-imidazol-2(3H)-one | $^1$H NMR (400 MHz, DMSO-d$_6$) δ 8.68 (s, 1H), 7.82 (d, J = 1.8 Hz, 1H), 7.63 (d, J = 8.2 Hz, 2H), 7.52 (d, J = 8.2 Hz, 1H), 7.50-7.43 (m, 2H), 7.34-7.00 (m, 3H), 6.70 (dd, J = 12.6, 3.0 Hz, 2H), 3.21 (s, 3H), 2.94 (d, J = 4.4 Hz, 4H), 2.69 (s, 4H), 1.06 (s, 9H) | 585.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 814 | 1-(3-chloro-4″-(difluoromethyl)-5′-fluoro-2′-hydroxy-3″-(4-isopropylpiperazin-1-yl)-[1,1′:3′,1″-terphenyl]-4-yl)-3-methyl-1H-imidazol-2(3H)-one | $^1$H NMR (400 MHz, DMSO-d$_6$) δ 8.70 (s, 1H), 7.82 (d, J = 1.9 Hz, 1H), 7.68-7.57 (m, 2H), 7.46 (d, J = 8.2 Hz, 2H), 7.34-6.98 (m, 3H), 6.70 (dd, J = 12.3, 3.0 Hz, 2H), 3.21 (s, 3H), 2.96 - 2.94 (m, 4H), 2.64 (s, 5H), 1.02 (d, J = 6.5 Hz, 6H). | 571.2 |
| 815 | (S)-1-(3-chloro-5′-fluoro-2′-hydroxy-3?-(2-(7-hydroxy-7-methyl-5-azaspiro[2.4]heptan-5-yl)pyridin-4-yl)-[1,1′-biphenyl]-4-yl)-3-methyl-1,3-dihydro-2H-imidazol-2-one | $^1$H NMR (400 MHz, DMSO-d$_6$): δ 8.69 (s, 1H), 8.09 (d, J = 4.8 Hz, 1H), 7.80 (d, J = 2.0 Hz, 1H), 7.61 (dd, J = 2.0 Hz, 8.0 Hz, 1H), 7.52 (d, J = 8.4 Hz, 1H), 7.26-7.17 (m, 2H), 6.72-6.68 (m, 3H), 6.52 (s, 1H), 4.65 (s, 1H), 3.58(d, J = 10.4 Hz, 1H), 3.52 (s, 2H), 3.36 (d, J = 8.0 Hz, 1H), 3.21(s, 3H), 1.09 (s, 3H), 0.84-0.80 (m, 1H), 0.61-0.58 (m, 1H), 0.53-0.45 (m, 2H) | 521.2 |

TABLE 31-continued

Following compounds were prepared using similar procedures as described for Examples 365-763.

| Ex. No. | Name/Structure | $^1$H NMR Data | LCMS (M + H)$^+$ |
|---|---|---|---|
| 816 | (R)-1-(3-chloro-5'-fluoro-2'-hydroxy-3'-(2-(7-hydroxy-7-methyl-5-azaspiro[2.4]heptan-5-yl)pyridin-4-yl)-[1,1'-biphenyl]-4-yl)-3-methyl-1,3-dihydro-2H-imidazol-2-one | $^1$H NMR (400 MHz, DMSO-d$_6$): δ 8.69 (s, 1H), 8.09 (d, J = 4.8 Hz, 1H), 7.80 (d, J = 2.0 Hz, 1H), 7.61 (dd, J = 2.0 Hz, 8.0 Hz, 1H), 7.52 (d, J = 8.4 Hz, 1H), 7.26-7.17 (m, 2H), 6.72-6.68 (m, 3H), 6.52 (s, 1H), 4.65 (s, 1H), 3.58 (d, J = 10.4 Hz, 1H), 3.52 (s, 2H), 3.36 (d, J = 8.0 Hz, 1H), 3.21(s, 3H), 1.09 (s, 3H), 0.84-0.80 (m, 1H), 0.61-0.58 (m, 1H), 0.53-0.45 (m, 2H) | 521.2 |

Example 817

1-(3-chloro-5'-fluoro-2'-hydroxy-3'-(5-(4-isopropylpiperazin-1-yl)-6-(methylthio)pyridin-3-yl)-[1,1'-biphenyl]-4-yl)-3-methyl-1H-imidazol-2(3H)-one

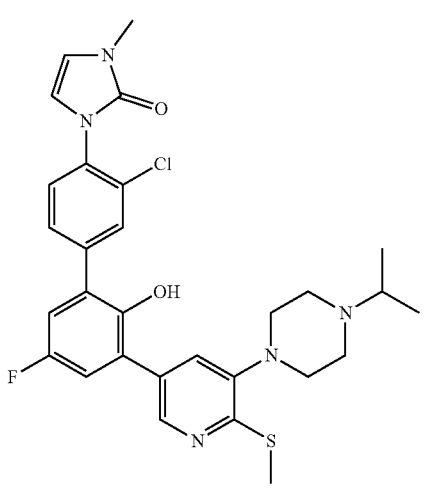 [SMILES: CSc1ncc(-c2cc(F)cc(-c3ccc(-n4ccn(C)c4=O)c(Cl)c3)c2O)cc1N1CCN(C(C)C)CC1]

Step 1: 1-(3-chloro-3'-(6-chloro-5-(4-isopropylpiperazin-1-yl)pyridin-3-yl)-5'-fluoro-2'-hydroxy-[1,1'-biphenyl]-4-yl)-3-methyl-1H-imidazol-2(3H)-one The title compound was prepared following the procedure described for Example 459 using 1-(3'-bromo-3-chloro-5'-fluoro-2'-hydroxy-[1,1'-biphenyl]-4-yl)-3-methyl-1H-imidazol-2(3H)-one and (6-chloro-5-(4-isopropylpiperazin-1-yl)pyridin-3-yl)boronic acid to afford the title compound. LCMS: 556.2 (M+H)$^+$.

Step 2: 1-(3-chloro-5'-fluoro-2'-hydroxy-3'-(5-(4-isopropylpiperazin-1-yl)-6-(methylthio)pyridin-3-yl)-[1,1'-biphenyl]-4-yl)-3-methyl-1H-imidazol-2(3H)-one A solution of 1-(3-chloro-3'-(6-chloro-5-(4-isopropylpiperazin-1-yl)pyridin-3-yl)-5'-fluoro-2'-hydroxy-[1,1'-biphenyl]-4-yl)-3-methyl-1H-imidazol-2(3H)-one (100 mg, 0.18 mmol) and sodium methanethiolate (100 mg, 8.0 mmol) in NMP (2 mL) was stirred in a MW at 120° C. for 2 hours. After the reaction was complete by LCMS, the reaction mixture was cooled to rt and concentrated. The residue was purified by chiral HPLC to afford the title compound. $^1$H NMR (400 MHz, DMSO-d$_6$) δ 8.73 (s, 1H), 8.37 (d, J=1.8 Hz, 1H), 7.82 (d, J=1.8 Hz, 1H), 7.63 (dd, J=8.2, 1.8 Hz, 1H), 7.53 (t, J=5.3 Hz, 2H), 7.24 (dt, J=9.6, 3.1 Hz, 2H), 6.71 (dd, J=12.0, 3.0 Hz, 2H), 3.21 (s, 3H), 2.99 (s, 4H), 2.70 (d, J=6.8 Hz, 1H), 2.61 (s, 4H), 2.47 (s, 3H), 1.02 (d, J=6.5 Hz, 6H). LCMS: 568.2 (M+H)$^+$.

Example 818

1-(5'-fluoro-2'-hydroxy-3'-(5-(4-isopropylpiperazin-1-yl)-6-(methylthio)pyridin-3-yl)-3-(methylthio)-[1,1'-biphenyl]-4-yl)-3-methyl-1H-imidazol-2(3H)-one

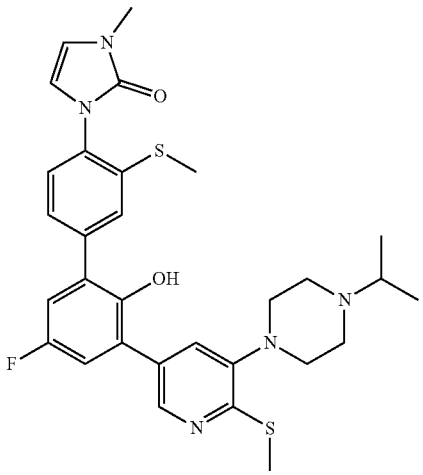 [SMILES: CSc1cc(-c2cc(F)cc(-c3cnc(SC)c(N4CCN(C(C)C)CC4)c3)c2O)ccc1-n1ccn(C)c1=O]

The title compound was prepared following the procedure described for Example 817 using 1-(3-chloro-3'-(6-chloro-5-(4-isopropylpiperazin-1-yl)pyridin-3-yl)-5'-fluoro-2'-hydroxy-[1,1'-biphenyl]-4-yl)-3-methyl-1H-imidazol-2(3H)-one and methanethiolate to afford the title compound. $^1$H NMR (400 MHz, DMSO-$d_6$) δ 8.64 (s, 1H), 8.38 (s, 1H), 7.52 (d, J=12.3 Hz, 2H), 7.43 (d, J=8.1 Hz, 1H), 7.31 (d, J=8.1 Hz, 1H), 7.23 (d, J=8.9 Hz, 2H), 6.68 (d, J=2.9 Hz, 1H), 6.56 (d, J=2.9 Hz, 1H), 3.20 (s, 3H), 2.99 (s, 4H), 2.67 (s, 1H), 2.61 (s, 4H), 2.47 (s, 3H), 2.44 (s, 3H), 1.01 (s, 6H). LCMS: 580.2 (M+H)$^+$.

Example 819

(S)-1-(3-chloro-3'-(2-(3-ethyl-3-hydroxypyrrolidin-1-yl)pyridin-4-yl)-5'-fluoro-2'-hydroxy-[1,1'-biphenyl]-4-yl)-3-methyl-1H-imidazol-2(3H)-one

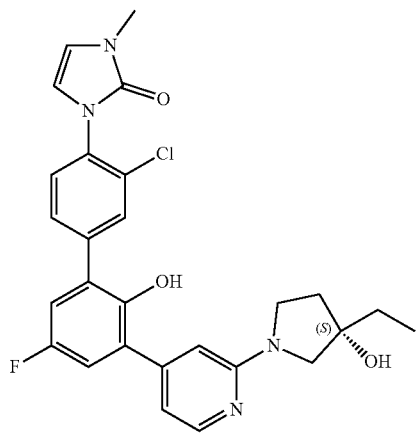

The title compound was prepared following the procedure described for Example 737 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 3-ethylpyrrolidin-3-ol to give the racemic material that was separated by chiral SFC purification to afford the title compound. $^1$H NMR (400 MHz, DMSO-$d_6$) δ 8.70 (s, 1H), 8.09 (d, J=5.2 Hz, 1H), 7.81 (d, J=1.9 Hz, 1H), 7.62 (dd, J=8.2, 1.9 Hz, 1H), 7.52 (d, J=8.2 Hz, 1H), 7.21 (ddd, J=23.5, 9.0, 3.2 Hz, 2H), 6.81-6.65 (m, 3H), 6.55 (s, 1H), 4.56 (s, 1H), 3.69-3.37 (m, 3H), 3.29 (s, 1H), 3.21 (s, 3H), 1.96-1.77 (m, 2H), 1.63 (dd, J=7.5, 2.7 Hz, 2H), 0.96 (t, J=7.4 Hz, 3H). LCMS: 509.2 (M+H)$^+$.

Example 820

(R)-1-(3-chloro-3'-(2-(3-ethyl-3-hydroxypyrrolidin-1-yl)pyridin-4-yl)-5'-fluoro-2'-hydroxy-[1,1'-biphenyl]-4-yl)-3-methyl-1H-imidazol-2(3H)-one

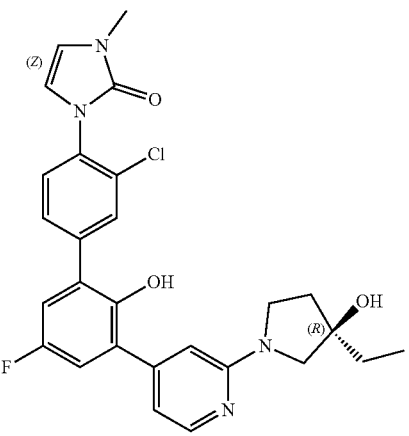

The title compound was prepared following the procedure described for Example B-705 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 3-ethylpyrrolidin-3-ol to give the racemic material that was separated by chiral SFC purification to afford the title compound. $^1$H NMR (400 MHz, DMSO-$d_6$) δ 8.70 (s, 1H), 8.09 (d, J=5.2 Hz, 1H), 7.81 (d, J=1.9 Hz, 1H), 7.62 (dd, J=8.2, 1.9 Hz, 1H), 7.52 (d, J=8.2 Hz, 1H), 7.21 (ddd, J=23.5, 9.0, 3.2 Hz, 2H), 6.81-6.65 (m, 3H), 6.55 (s, 1H), 4.56 (s, 1H), 3.69-3.37 (m, 3H), 3.29 (s, 1H), 3.21 (s, 3H), 1.96-1.77 (m, 2H), 1.63 (dd, J=7.5, 2.7 Hz, 2H), 0.96 (t, J=7.4 Hz, 3H). LCMS: 509.2 (M+H)$^+$.

Example 821

1-(3'-(5-(4-(tert-butyl)piperazin-1-yl)-6-(methylthio)pyridin-3-yl)-3-chloro-5'-fluoro-2'-hydroxy-[1,1'-biphenyl]-4-yl)-3-methyl-1H-imidazol-2(3H)-one

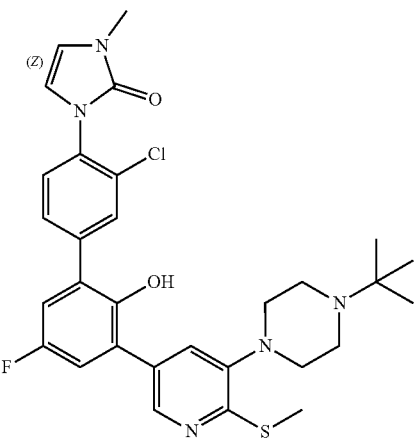 [SMILES: CSc1ncc(-c2cc(F)cc(-c3ccc(-n4ccn(C)c4=O)c(Cl)c3)c2O)cc1N1CCN(C(C)(C)C)CC1]

The title compound was prepared following the procedure described for Example 817 using 1-(3'-bromo-3-chloro-5'-fluoro-2'-hydroxy-[1,1'-biphenyl]-4-yl)-3-methyl-1H-imidazol-2(3H)-one and (5-(4-(tert-butyl)piperazin-1-yl)-6-chloropyridin-3-yl)boronic acid and sodium methanethiolate in NMP to afford the title compound. $^1$H NMR (400 MHz, DMSO-$d_6$) δ 8.71 (s, 1H), 8.37 (d, J=1.6 Hz, 1H), 7.82 (d, J=1.8 Hz, 1H), 7.63 (dd, J=8.2, 1.8 Hz, 1H), 7.54 (dd, J=7.8, 4.9 Hz, 2H), 7.23 (ddd, J=12.0, 9.1, 3.1 Hz, 2H), 6.70 (dd, J=12.4, 3.0 Hz, 2H), 3.21 (s, 3H), 2.98 (s, 4H), 2.67 (s, 4H), 2.47 (s, 3H), 1.06 (s, 9H). LCMS: 582.2 (M+H)$^+$.

Example 822

1-(3-chloro-5'-fluoro-2'-hydroxy-3'-(2-(3'-methyl-[1,3'-bipyrrolidin]-1'-yl)pyridin-4-yl)-[1,1'-biphenyl]-4-yl)-3-methyl-1H-imidazol-2(3H)-one

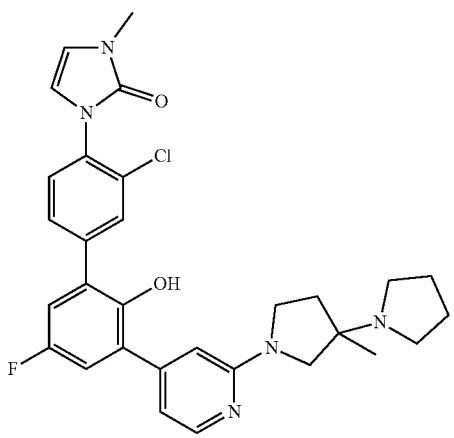 [SMILES: Cn1ccn(-c2ccc(-c3cc(F)cc(-c4ccnc(N5CCC(C)(N6CCCC6)C5)c4)c3O)cc2Cl)c1=O]

To a solution of 1-(3'-(2-(3-amino-3-methylpyrrolidin-1-yl)pyridin-4-yl)-3-chloro-5'-fluoro-2'-hydroxy-[1,1'-biphenyl]-4-yl)-3-methyl-1H-imidazol-2(3H)-one (100 mg, 0.2 mmol) in toluene (2 mL) was added KI (17 mg, 0.1 mmol), DIEA (0.2 mL) and 1,4-dibromobutane (87 mg, 0.4 mmol). The reaction mixture was stirred at 80° C. for 48 hours. After the reaction was complete by LCMS, the reaction mixture was cooled to rt and removed the solvent under reduced pressure to give the residue which was purified by Prep-HPLC to afford the title compound. $^1$H NMR (400 MHz, DMSO-$d_6$) δ 8.64 (s, 1H), 8.09 (d, J=5.2 Hz, 1H), 7.80 (d, J=1.9 Hz, 1H), 7.62 (dd, J=8.2, 1.9 Hz, 1H), 7.52 (d, J=8.2 Hz, 1H), 7.22 (ddd, J=18.6, 9.0, 3.2 Hz, 2H), 6.71 (dd, J=11.9, 3.1 Hz, 3H), 6.56 (s, 1H), 3.55 (d, J=7.0 Hz, 1H), 3.49-3.35 (m, 3H), 3.21 (s, 3H), 2.77-2.53 (m, 4H), 2.06 (dd, J=13.9, 6.9 Hz, 1H), 1.93-1.79 (m, 1H), 1.68 (s, 4H), 1.10 (s, 3H). LCMS: 548.2 (M+H)$^+$.

Example 823

1-(3'-(5-(4-(tert-butyl)piperazin-1-yl)-6-(difluoromethoxy)pyridin-3-yl)-3-chloro-5'-fluoro-2'-hydroxy-[1,1'-biphenyl]-4-yl)-3-methyl-1H-imidazol-2(3H)-one

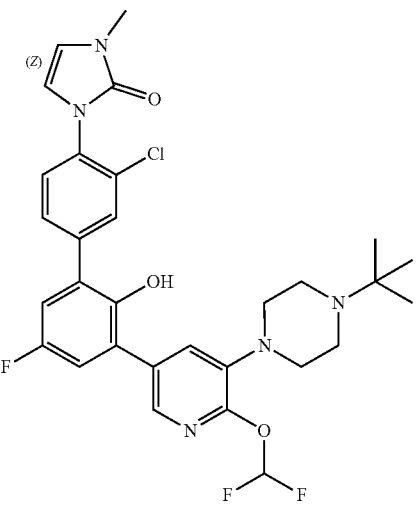 [SMILES: Cn1ccn(-c2ccc(-c3cc(F)cc(-c4cnc(OC(F)F)c(N5CCN(C(C)(C)C)CC5)c4)c3O)cc2Cl)c1=O]

Step 1: 3-bromo-5-chloro-2-(difluoromethoxy)pyridine

To a solution of 3-bromo-5-chloropyridin-2-ol (2.1 g, 100 mmol) in MeCN (50 mL), was added $Na_2CO_3$ (2.1 g, 20.0 mmol) and 2,2-difluoro-2-(fluorosulfonyl)acetic acid (2.7 g, 15.0 mmol) dropwise at 0° C. Then, the reaction mixture was stirred at rt for 16 hours under nitrogen atmosphere. After the reaction complete by LCMS, the solvent was removed under reduced pressure. The residue was dissolved in $H_2O$ (150 mL) and extracted with EA (50 mL×3). The combined organic layers were washed with brine, dried over $Na_2SO_4$, filtered and concentrated to afford the title compound (2.0 g, 77% yield) as yellow oil, which was used to the next step without further purification. LCMS: 257.9 (M+H)$^+$.

Step 2: 1-(tert-butyl)-4-(5-chloro-2-(difluoromethoxy)pyridin-3-yl)piperazine The title compound was prepared following the procedure described for Example 738 using 3-bromo-5-chloro-2-(difluoromethoxy)pyridine and 1-(tert-butyl)piperazine to afford the title compound. LCMS: 320.1 (M+H)$^+$.

Step 3: (5-(4-(tert-butyl)piperazin-1-yl)-6-(difluoromethoxy)pyridin-3-yl)boronic acid The title compound was prepared following the procedure described for Example 738 using 1-(tert-butyl)-4-(5-chloro-2-(difluoromethoxy)pyridin-3-yl)piperazine and 4,4,4',4',5,5,5',5'-octamethyl-2,2'-bi(1,3,2-dioxaborolane) to afford the title compounds as crude material which was used in the next step without further purification. LCMS: 330.2 (M+H)$^+$.

Step 4: 2-bromo-6-(5-(4-(tert-butyl)piperazin-1-yl)-6-(difluoromethoxy)pyridin-3-yl)-4-fluorophenol The title compound was prepared following the procedure described for Example 738 using (5-(4-(tert-butyl)piperazin-1-yl)-6-(difluoromethoxy)pyridin-3-yl)boronic acid and 2,6-dibromo-4-fluorophenol to afford the title compound. LCMS: 474.1 (M+H)$^+$.

Step 5: 1-(3'-(5-(4-(tert-butyl)piperazin-1-yl)-6-(difluoromethoxy)pyridin-3-yl)-3-chloro-5'-fluoro-2'-hydroxy-[1,1'-biphenyl]-4-yl)-3-methyl-1H-imidazol-2(3H)-one The title compound was prepared following the procedure described for Example 738 using 2-bromo-6-(5-(4-(tert-butyl)piperazin-1-yl)-6-(difluoromethoxy)pyridin-3-yl)-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-d$_6$) δ 8.78 (s, 1H), 8.01-7.59 (m, 4H), 7.54 (t, J=7.9 Hz, 2H), 7.30-7.21 (m, 2H), 6.71 (dd, J=12.6, 3.0 Hz, 2H), 3.21 (s, 3H), 3.08 (s, 4H), 2.67 (s, 4H), 1.06 (s, 9H). LCMS: 602.3 (M+H)$^+$.

Example 824

1-(3-chloro-3'-(6-(difluoromethoxy)-5-(4-isopropylpiperazin-1-yl)pyridin-3-yl)-5'-fluoro-2'-hydroxy-[1,1'-biphenyl]-4-yl)-3-methyl-1H-imidazol-2(3H)-one

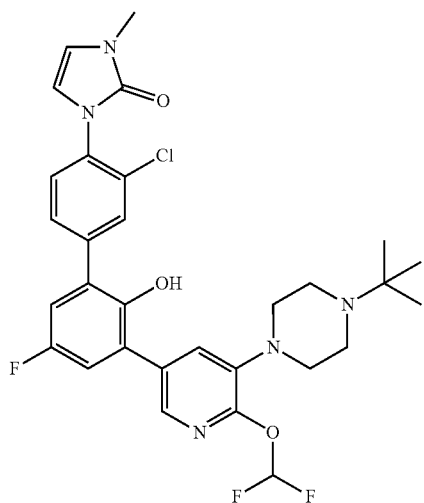 [SMILES: Cn1ccn(-c2ccc(-c3cc(F)cc(-c4cnc(OC(F)F)c(N5CCN(C(C)(C)C)CC5)c4)c3O)cc2Cl)c1=O]

The title compound was prepared following the procedures described for Example 823 using 2-bromo-6-(6-(difluoromethoxy)-5-(4-isopropylpiperazin-1-yl)pyridin-3-yl)-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-d$_6$) δ 8.76 (s, 1H), 8.01-7.92 (m, 1H), 7.84-7.76 (m, 2H), 7.68-7.45 (m, 3H), 7.31-7.14 (m, 2H), 6.70 (dd, J=13.1, 3.0 Hz, 2H), 3.21 (s, 3H), 3.08 (s, 4H), 2.66 (d, J=32.8 Hz, 5H), 1.01 (d, J=6.5 Hz, 6H). LCMS: 588.3 (M+H)$^+$.

Example 825

(R)-1-(3-chloro-5'-fluoro-2'-hydroxy-3'-(5-(3-hydroxy-3-methylpyrrolidin-1-yl)-6-methylpyridin-3-yl)-[1,1'-biphenyl]-4-yl)-3-methyl-1H-imidazol-2(3H)-one

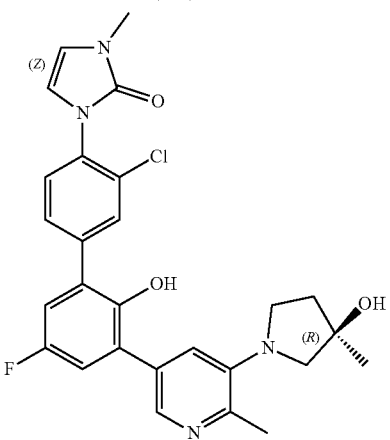

The title compound was prepared following the procedures described for Example 722 using 3-bromo-5-chloro-2-methylpyridine, (R)-3-methylpyrrolidin-3-ol, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. 1H NMR (400 MHz, CD$_3$OD) δ 8.09 (d, J=1.6 Hz, 1H), 7.82 (d, J=1.8 Hz, 1H), 7.64 (dd, J=8.2, 1.9 Hz, 1H), 7.52 (d, J=8.2 Hz, 1H), 7.42 (d, J=1.6 Hz, 1H), 7.11 (d, J=8.8 Hz, 2H), 6.67 (dd, J=15.2, 3.0 Hz, 2H), 3.67 (d, J=8.3 Hz, 1H), 3.42 (d, J=9.7 Hz, 1H), 3.37 (s, 3H), 3.29 (s, 1H), 3.23 (d, J=9.6 Hz, 1H), 2.60 (s, 3H), 2.05 (d, J=7.5 Hz, 2H), 1.48 (s, 3H). LCMS: 509.2 (M+H)$^+$.

Example 826

1-(3'-(5-(4-(tert-butyl)piperazin-1-yl)-6-(difluoromethyl)pyridin-3-yl)-3-chloro-5'-fluoro-2'-hydroxy-[1,1'-biphenyl]-4-yl)-3-methyl-1H-imidazol-2(3H)-one

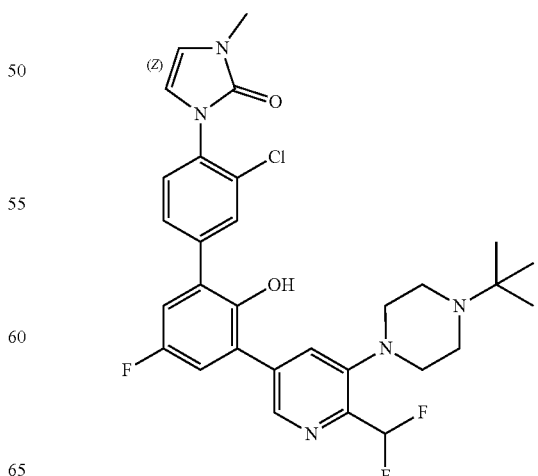

Step 1: 5-bromo-3-(4-(tert-butyl)piperazin-1-yl) picolinaldehyde

A solution of 5-bromo-3-fluoropicolinaldehyde (1.0 g, 4.9 mmol), 1-1-(tert-butyl)piperazine (1.4 g, 9.8 mmol) and $K_2CO_3$ (1.4 g, 9.8 mmol) in dioxane/$H_2O$ (10:1, 30 mL) was stirred at 100° C. for 6 hours under nitrogen atmosphere. After the reaction was complete by LCMS, the reaction mixture was cooled to rt and extracted with EtOAc (50 mL×3). The combined organic layers were washed with brine, dried over $Na_2SO_4$, filtered and concentrated. The residue was purified by flash column chromatography (DCM:$CH_3OH$=15:1) to give 5-bromo-3-(4-isopropylpiperazin-1-yl)picolinaldehyde (1.1 g, 69% yield) as a yellow solid. LCMS: 326.1 (M+H)$^+$.

Step 2: 1-(5-bromo-2-(difluoromethyl)pyridin-3-yl)-4-(tert-butyl)piperazine

To a solution of 5-bromo-3-(4-(tert-butyl)piperazin-1-yl) picolinaldehyde (500 mg, 1.50 mmol) in DCM (20 mL) was added DAST (741 mg, 4.6 mmol) dropwise at −30° C. under nitrogen atmosphere. The reaction mixture was stirred at rt for 16 h. After the reaction was complete by LCMS, the reaction mixture was added aqueous $NaHCO_3$ and extracted with DCM (50 mL×3). The combined organic layers were washed with brine, dried over $Na_2SO_4$, filtered and concentrated. The residue was purified by flash column chromatography (PE:EA=1:1) to give 1-(5-bromo-2-(difluoromethyl)pyridin-3-yl)-4-(tert-butyl)piperazine (300 mg, 56% yield) as yellow oil. LCMS: 348.1 (M+H)$^+$.

Step 3: (5-(4-(tert-butyl)piperazin-1-yl)-6-(difluoromethyl)pyridin-3-yl)boronic acid The title compound was prepared following the procedure described for Example 722 using 1-(5-bromo-2-(difluoromethyl)pyridin-3-yl)-4-(tert-butyl)piperazine and 4,4,4',4',5,5,5',5'-octamethyl-2,2'-bi(1,3,2-dioxaborolane) to afford the title compound as crude (100% yield) that was used without further purification. LCMS: 314.2 (M+H)$^+$

Step 4: 2-bromo-6-(5-(4-(tert-butyl)piperazin-1-yl)-6-(difluoromethyl)pyridin-3-yl)-4-fluorophenol The title compound was prepared following the procedure described for Example 722 using (5-(4-(tert-butyl)piperazin-1-yl)-6-(difluoromethyl)pyridin-3-yl)boronic acid and 2,6-dibromo-4-fluorophenol to afford the title compound (60% yield). LCMS: 458.1 (M+H)$^+$

Step 5: 1-(3'-(5-(4-(tert-butyl)piperazin-1-yl)-6-(difluoromethyl)pyridin-3-yl)-3-chloro-5'-fluoro-2'-hydroxy-[1,1'-biphenyl]-4-yl)-3-methyl-1H-imidazol-2(3H)-one The title compound was prepared following the procedure described for Example 722 using 2-bromo-6-(5-(4-(tert-butyl)piperazin-1-yl)-6-(difluoromethyl)pyridin-3-yl)-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound (30% yield). $^1$H NMR (400 MHz, $CD_3OD$): δ 8.61 (d, J=1.6 Hz, 1H), 8.09 (s, 1H), 7.83 (d, J=1.6 Hz, 1H), 7.65-7.63 (m, 1H), 7.54 (d, J=8.0 Hz, 1H), 7.32-7.05 (m, 3H), 6.70-6.65 (m, 2H), 3.37 (s, 3H), 3.15-3.12 (m, 4H), 2.95-2.89 (m, 4H), 1.22 (s, 9H). LCMS: 586.3 (M+H)$^+$

Example 827

1-(3''-(4-(tert-butyl)piperazin-1-yl)-3,5''-dichloro-5'-fluoro-2'-hydroxy-[1,1':3',1''-terphenyl]-4-yl)-3-methyl-1H-imidazol-2(3H)-one

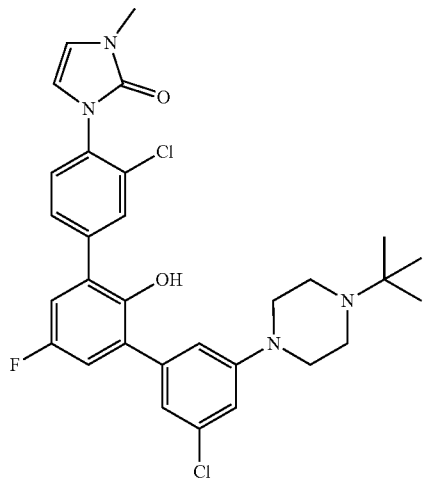 [SMILES: Cn1ccn(-c2ccc(-c3cc(F)cc(-c4cc(Cl)cc(N5CCN(C(C)(C)C)CC5)c4)c3O)cc2Cl)c1=O]

The title compound was prepared following the procedures described for Example 722 using 1-(tert-butyl)piperazine, 1,3-dibromo-5-chlorobenzene, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO) δ 8.63 (s, 1H), 7.81 (d, J=1.8 Hz, 1H), 7.62 (dd, J=8.2, 1.9 Hz, 1H), 7.52 (d, J=8.2 Hz, 1H), 7.19 (ddd, J=15.6, 9.0, 3.2 Hz, 2H), 7.04-6.89 (m, 3H), 6.71 (dd, J=11.0, 3.0 Hz, 2H), 3.21 (s, 7H), 2.63 (s, 4H), 1.04 (s, 9H). LCMS: 569.2 (M+H)$^+$.

Example 828

1-(3''-(4-(tert-butyl)piperazin-1-yl)-3-chloro-5'-fluoro-2'-hydroxy-5''-methyl-[1,1':3',1''-terphenyl]-4-yl)-3-methyl-1H-imidazol-2(3H)-one

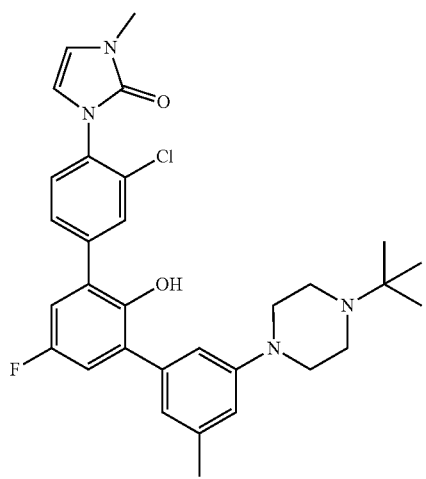 [SMILES: Cc1cc(-c2cc(F)cc(-c3ccc(-n4ccn(C)c4=O)c(Cl)c3)c2O)cc(N2CCN(C(C)(C)C)CC2)c1]

1107

The title compound was prepared following the procedures described for Example 722 using 1-(tert-butyl)piperazine, 1,3-dibromo-5-methylbenzene, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO) δ 8.43 (s, 1H), 7.81 (d, J=1.8 Hz, 1H), 7.62 (dd, J=8.2, 1.9 Hz, 1H), 7.51 (d, J=8.2 Hz, 1H), 7.16 (dd, J=9.0, 3.2 Hz, 1H), 7.09 (dd, J=9.1, 3.2 Hz, 1H), 6.87 (s, 1H), 6.78 (d, J=11.8 Hz, 2H), 6.71 (dd, J=9.9, 3.0 Hz, 2H), 3.21 (s, 3H), 3.14 (s, 4H), 2.64 (s, 4H), 2.30 (s, 3H), 1.05 (s, 9H). LCMS: 549.2 (M+H)$^+$.

Example 829

1-(3-chloro-5'-fluoro-2'-hydroxy-3'-(5-(7-hydroxy-7-methyl-5-azaspiro[2.4]heptan-5-yl)-6-methylpyridin-3-yl)-[1,1'-biphenyl]-4-yl)-3-methyl-1H-imidazol-2(3H)-one

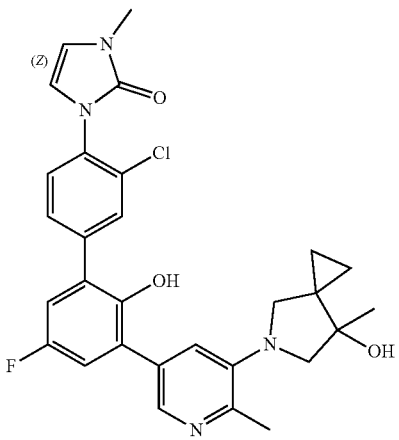 [SMILES: Cc1ncc(-c2cc(F)cc(-c3ccc(-n4ccn(C)c4=O)c(Cl)c3)c2O)cc1N1CC(C)(O)C2(CC2)C1]

The title compound was prepared following the procedures described for Example 722 using 3-bromo-5-chloro-2-methylpyridine, 7-methyl-5-azaspiro[2.4]heptan-7-ol, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-$d_6$) δ 8.64 (s, 1H), 8.07 (d, J=1.6 Hz, 1H), 7.80 (d, J=1.8 Hz, 1H), 7.62 (dd, J=8.2, 1.9 Hz, 1H), 7.52 (d, J=8.2 Hz, 1H), 7.30-7.17 (m, 3H), 6.70 (dd, J=13.4, 3.0 Hz, 2H), 4.60 (s, 1H), 3.47 (d, J=9.0 Hz, 1H), 3.38 (t, J=6.0 Hz, 2H), 3.26 (d, J=9.0 Hz, 1H), 3.21 (s, 3H), 2.51 (s, 3H), 1.11 (s, 3H), 0.80 (dd, J=9.2, 3.9 Hz, 1H), 0.60 (dd, J=9.6, 5.4 Hz, 1H), 0.52-0.43 (m, 2H). LCMS: 535.2 (M+H)$^+$.

1108

Example 830

1-(3-chloro-5'-fluoro-2'-hydroxy-3''-(4-(1-methoxy-2-methylpropan-2-yl)piperazin-1-yl)-[1,1':3',1''-terphenyl]-4-yl)-3-methyl-1H-imidazol-2(3H)-one

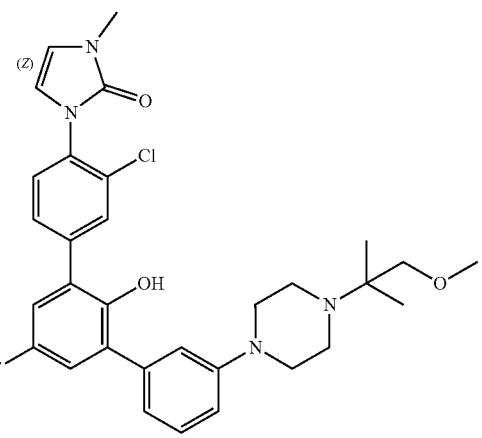

The title compound was prepared following the procedures described for Example 734 using 1-bromo-3-iodobenzene, 1-(1-methoxy-2-methylpropan-2-yl)piperazine, 4,4,4',4',5,5,5',5'-octamethyl-2,2'-bi(1,3,2-dioxaborolane) and 1-(3'-bromo-3-chloro-5'-fluoro-2'-hydroxy-[1,1'-biphenyl]-4-yl)-3-methyl-1H-imidazol-2(3H)-one to afford the title compound. $^1$H NMR (400 MHz, DMSO-$d_6$) δ 8.45 (s, 1H), 7.81 (d, J=1.8 Hz, 1H), 7.62 (dd, J=8.2, 1.8 Hz, 1H), 7.51 (d, J=8.2 Hz, 1H), 7.28 (t, J=7.9 Hz, 1H), 7.17 (dd, J=9.0, 3.2 Hz, 1H), 7.11 (dd, J=9.1, 3.2 Hz, 1H), 7.07 (s, 1H), 6.95 (dd, J=12.3, 8.1 Hz, 2H), 6.70 (dd, J=11.0, 3.0 Hz, 2H), 3.26-3.25 (m, 5H), 3.21 (s, 3H), 3.13 (s, 4H), 2.71 (s, 4H), 1.02 (s, 6H). LCMS: 565.2 (M+H)$^+$.

Example 831

1-(3-chloro-3'-(6-(difluoromethyl)-5-(4-isopropylpiperazin-1-yl)pyridin-3-yl)-5'-fluoro-2'-hydroxy-[1,1'-biphenyl]-4-yl)-3-methyl-1H-imidazol-2(3H)-one

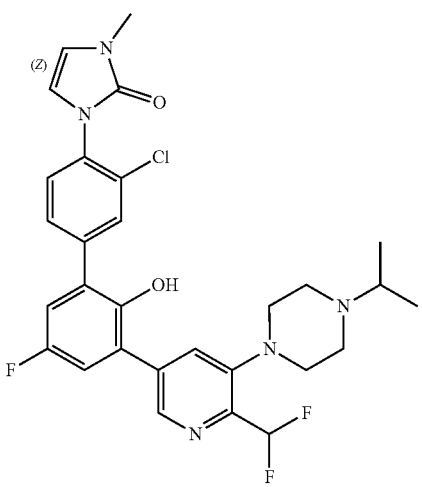 [SMILES: CC(C)N1CCN(c2cc(-c3cc(F)cc(-c4ccc(-n5ccn(C)c5=O)c(Cl)c4)c3O)cnc2C(F)F)CC1]

1109

The title compound was prepared following the procedure described for Example 826 using 5-bromo-3-fluoropicolinaldehyde, 1-isopropylpiperazine, DAST, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, CD$_3$OD): δ 8.62 (d, J=1.6 Hz, 1H), 8.09 (s, 1H), 7.83 (d, J=1.6 Hz, 1H), 7.65-7.63 (m, 1H), 7.54 (d, J=8.0 Hz, 1H), 7.23-7.16 (m, 3H), 6.70-6.65 (m, 2H), 3.37 (s, 3H), 3.15-3.12 (m, 4H), 2.90-2.83 (m, 5H), 1.18 (d, J=6.4 Hz, 6H). LCMS: 572.3 (M+H)$^+$.

Example 832

(R)-1-(3-chloro-5'-fluoro-2'-hydroxy-3'-(6-(3-hydroxy-3-methylpyrrolidin-1-yl)pyridazin-4-yl)-[1,1'-biphenyl]-4-yl)-3-methyl-1H-imidazol-2(3H)-one

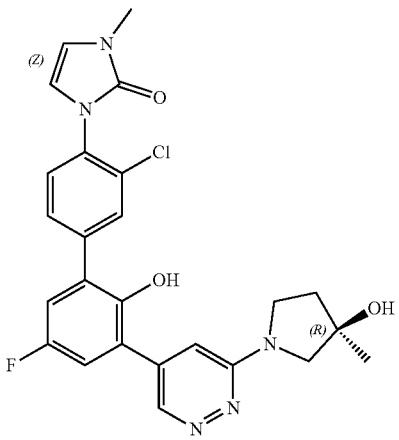

The title compound was prepared following the procedures described for Example 724 using 1-(3'-bromo-3-chloro-5'-fluoro-2'-methoxy-[1,1'-biphenyl]-4-yl)-3-methyl-1H-imidazol-2(3H)—one, 4,4,4',4',5,5,5',5'-octamethyl-2,2'-bi(1,3,2-dioxaborolane), 5-bromo-3-chloropyridazine, (R)-3-methylpyrrolidin-3-ol and piperazine to afford the title compound. $^1$H NMR (400 MHz, DMSO-d$_6$) δ 8.96 (s, 1H), 8.66 (d, J=1.7 Hz, 1H), 7.82 (d, J=1.9 Hz, 1H), 7.63 (dd, J=8.2, 1.9 Hz, 1H), 7.53 (d, J=8.2 Hz, 1H), 7.32 (ddd, J=12.5, 9.0, 3.2 Hz, 2H), 6.95 (d, J=1.5 Hz, 1H), 6.70 (dd, J=14.3, 3.0 Hz, 2H), 4.84 (s, 1H), 3.57 (dd, J=27.0, 18.4 Hz, 3H), 3.36 (d, J=10.8 Hz, 1H), 3.21 (s, 3H), 1.96 (dd, J=11.5, 7.7 Hz, 2H), 1.38 (s, 3H). LCMS: 496.1 (M+H)$^+$.

1110

Example 833

1-(3-chloro-5'-fluoro-2'-hydroxy-3'-(5-(7-hydroxy-7-methyl-5-azaspiro[2.4]heptan-5-yl)-6-methoxypyridin-3-yl)-[1,1'-biphenyl]-4-yl)-3-methyl-1H-imidazol-2(3H)-one

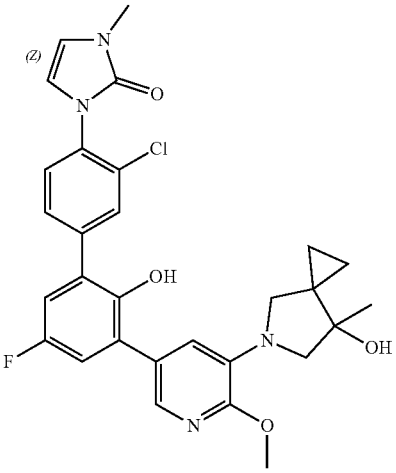 [SMILES: COc1ncc(-c2cc(F)cc(-c3ccc(-n4ccn(C)c4=O)c(Cl)c3)c2O)cc1N1CC(C)(O)C2(CC2)C1]

The title compound was prepared following the procedure described for Example 738 using 3-bromo-5-chloro-2-methoxypyridine, 7-methyl-5-azaspiro[2.4]heptan-7-ol, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1,3-dihydro-2H-imidazol-2-one to afford the title compound. $^1$H NMR (400 MHz, CD$_3$OD) δ 7.84 (d, J=1.9 Hz, 1H), 7.71-7.57 (m, 2H), 7.52 (d, J=8.2 Hz, 1H), 7.06 (dd, J=15.9, 5.4 Hz, 3H), 6.68 (dd, J=15.0, 3.0 Hz, 2H), 3.99 (s, 3H), 3.79 (d, J=9.5 Hz, 1H), 3.63 (s, 2H), 3.37 (s, 3H), 3.27 (d, J=9.6 Hz, 1H), 1.18 (s, 3H), 0.99-0.83 (m, 1H), 0.76 (d, J=4.0 Hz, 1H), 0.67-0.48 (m, 2H). LCMS: 551.2 (M+H)$^+$.

Example 834

1-(3-chloro-5'-fluoro-2'-hydroxy-3'-(5-(3-hydroxy-3-methylazetidin-1-yl)-6-methoxypyridin-3-yl)-[1,1'-biphenyl]-4-yl)-3-methyl-1H-imidazol-2(3H)-one

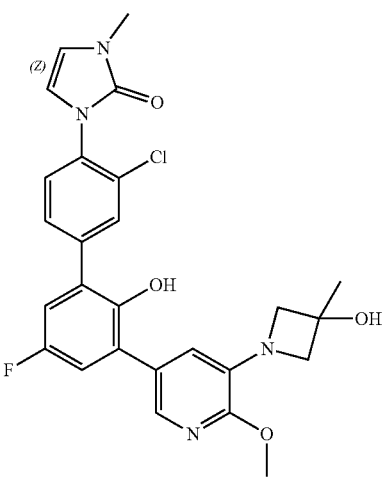 [SMILES: COc1ncc(-c2cc(F)cc(-c3ccc(-n4ccn(C)c4=O)c(Cl)c3)c2O)cc1N1CC(C)(O)C1]

The title compound was prepared following the procedure described for Example 738 using 3-bromo-5-chloro-2-methoxypyridine, 3-methylazetidin-3-ol, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1,3-dihydro-2H-imidazol-2-one to afford the title compound. $^1$H NMR (400 MHz, DMSO-$d_6$) δ 8.52 (s, 1H), 7.80 (d, J=1.8 Hz, 1H), 7.67 (d, J=1.9 Hz, 1H), 7.61 (dd, J=8.2, 1.8 Hz, 1H), 7.52 (d, J=8.2 Hz, 1H), 7.16 (ddd, J=17.8, 9.0, 3.1 Hz, 2H), 6.84 (d, J=1.9 Hz, 1H), 6.70 (dd, J=12.3, 3.0 Hz, 2H), 5.41 (s, 1H), 3.87 (s, 3H), 3.81 (d, J=8.1 Hz, 2H), 3.67 (d, J=7.9 Hz, 2H), 3.21 (s, 3H), 1.45 (s, 3H). LCMS: 511.1 (M+H)$^+$.

Example 835

1-(3-chloro-5'-fluoro-2'-hydroxy-3'-(5-(8-isopropyl-3,8-diazabicyclo[3.2.1]octan-3-yl)-6-methylpyridin-3-yl)-[1,1'-biphenyl]-4-yl)-3-methyl-1H-imidazol-2(3H)-one

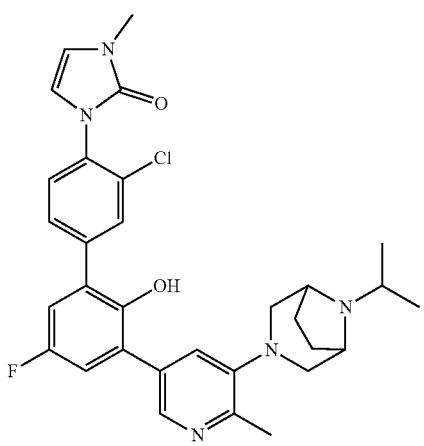 [SMILES: Cc1ncc(-c2cc(F)cc(-c3ccc(-n4ccn(C)c4=O)c(Cl)c3)c2O)cc1N1CC2CCC(C1)N2C(C)C]

Step 1: tert-butyl 3-(5-chloro-2-methylpyridin-3-yl)-3,8-diazabicyclo[3.2.1]octane-8-carboxylate The title compound was prepared following the procedure described for Example 722 using 3-bromo-5-chloro-2-methylpyridine and tert-butyl 3,8-diazabicyclo[3.2.1]octane-8-carboxylate to afford the title compound. LCMS: 338.2 (M+H)$^+$.

Step 2: (5-(8-(tert-butoxycarbonyl)-3,8-diazabicyclo[3.2.1]octan-3-yl)-6-methylpyridin-3-yl)boronic acid The title compound was prepared following the procedure described for Example 722 using tert-butyl 3-(5-chloro-2-methylpyridin-3-yl)-3,8-diazabicyclo[3.2.1]octane-8-carboxylate and 4,4,4',4',5,5,5',5'-octamethyl-2,2'-bi(1,3,2-dioxaborolane) to afford the title compound. LCMS: 348.2 (M+H)$^+$.

Step 3: tert-butyl 3-(5-(3-bromo-5-fluoro-2-hydroxyphenyl)-2-methylpyridin-3-yl)-3,8-diazabicyclo[3.2.1]octane-8-carboxylate The title compound was prepared following the procedure described for Example 722 using tert-butyl 3-(5-(3-bromo-5-fluoro-2-hydroxyphenyl)-2-methylpyridin-3-yl)-3,8-diazabicyclo[3.2.1]octane-8-carboxylate and 2,6-dibromo-4-fluorophenol to afford the title compound. LCMS: 492.1 (M+H)$^+$.

Step 4: tert-butyl 3-(5-(3'-chloro-5-fluoro-2-hydroxy-4'-(3-methyl-2-oxo-2,3-dihydro-1H-imidazol-1-yl)-[1,1'-biphenyl]-3-yl)-2-methylpyridin-3-yl)-3,8-diazabicyclo[3.2.1]octane-8-carboxylate The title compound was prepared following the procedure described for Example 722 using tert-butyl 3-(5-(3-bromo-5-fluoro-2-hydroxyphenyl)-2-methylpyridin-3-yl)-3,8-diazabicyclo[3.2.1]octane-8-carboxylate and 1-(2-chloro-4-(4,4,5,5-tetramethyl-1,3,2-dioxaborolan-2-yl)phenyl)-3-methyl-1H-imidazol-2(3H)-one to afford the title compound. LCMS: 620.2 (M+H)$^+$.

Step 5: 1-(3'-(5-(3,8-diazabicyclo[3.2.1]octan-3-yl)-6-methylpyridin-3-yl)-3-chloro-5'-fluoro-2'-hydroxy-[1,1'-biphenyl]-4-yl)-3-methyl-1H-imidazol-2(3H)-one A mixture of tert-butyl 3-(5-(3'-chloro-5-fluoro-2-hydroxy-4'-(3-methyl-2-oxo-2,3-dihydro-1H-imidazol-1-yl)-[1,1'-biphenyl]-3-yl)-2-methylpyridin-3-yl)-3,8-diazabicyclo[3.2.1]octane-8-carboxylate (100 mg) and TFA (1 mL) in DCM (2 mL) was stirred at room temperature for 1 h. The reaction was monitor by the LCMS. Upon completion, the mixture was added aqueous NaHCO$_3$ to adjust the pH to 7, and it was then extracted with DCM, dried over Na$_2$SO$_4$, filtered, and concentrated to afford the title compound. LCMS: 520.2 (M+H)$^+$.

Step 6: 1-(3-chloro-5'-fluoro-2'-hydroxy-3'-(5-(8-isopropyl-3,8-diazabicyclo[3.2.1]octan-3-yl)-6-methylpyridin-3-yl)-[1,1'-biphenyl]-4-yl)-3-methyl-1H-imidazol-2(3H)-one The title compound was prepared following the procedure described for Example 727 using 1-(3'-(5-(3,8-diazabicyclo[3.2.1]octan-3-yl)-6-methylpyridin-3-yl)-3-chloro-5'-fluoro-2'-hydroxy-[1,1'-biphenyl]-4-yl)-3-methyl-1H-imidazol-2(3H)-one, acetone, NaBH$_3$CN, AcOH in methanol to afford the title compound. $^1$H NMR (400 MHz, DMSO-$d_6$) δ 8.67 (s, 1H), 8.31 (d, J=1.7 Hz, 1H), 7.81 (d, J=1.8 Hz, 1H), 7.68-7.56 (m, 2H), 7.52 (d, J=8.2 Hz, 1H), 7.21 (d, J=9.1 Hz, 2H), 6.70 (dd, J=13.9, 3.0 Hz, 2H), 3.53 (s, 2H), 3.21 (s, 3H), 2.96 (d, J=10.2 Hz, 2H), 2.83 (d, J=9.1 Hz, 2H), 2.60 (d, J=52.5 Hz, 3H), 1.86 (d, J=7.8 Hz, 4H), 1.02 (d, J=6.0 Hz, 6H). LCMS: 562.2 (M+H)$^+$.

Example 836

1-(3-chloro-5'-fluoro-2'-hydroxy-3'-(5-(8-isopropyl-3,8-diazabicyclo[3.2.1]octan-3-yl)-6-methoxypyridin-3-yl)-[1,1'-biphenyl]-4-yl)-3-methyl-1H-imidazol-2(3H)-one

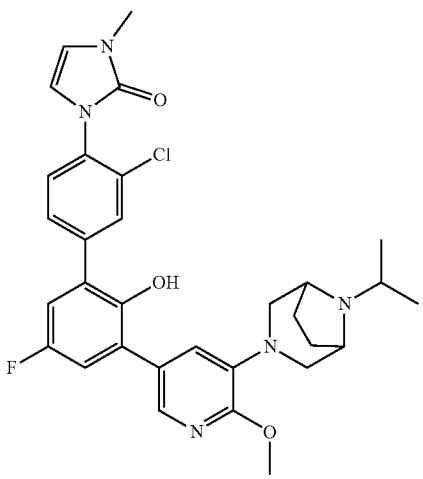 [SMILES: COc1ncc(-c2cc(F)cc(-c3ccc(-n4ccn(C)c4=O)c(Cl)c3)c2O)cc1N1CC2CCC(C1)N2C(C)C]

The title compound was prepared following the procedure described for Example 835 using 3-bromo-5-chloro-2-methoxypyridine, tert-butyl 3,8-diazabicyclo[3.2.1]octane-8-carboxylate, 4,4,4',4',5,5,5',5'-octamethyl-2,2'-bi(1,3,2-dioxaborolane), 2,6-dibromo-4-fluorophenol, 1-(2-chloro-4-(4,4,5,5-tetramethyl-1,3,2-dioxaborolan-2-yl)phenyl)-3-methyl-1H-imidazol-2(3H)-one, TFA, NaBH₃CN, AcOH and acetone to afford the title compound. ¹H NMR (400 MHz, DMSO-d₆) δ 8.56 (s, 1H), 7.83 (dd, J=24.6, 1.6 Hz, 2H), 7.62 (dd, J=8.2, 1.7 Hz, 1H), 7.52 (d, J=8.2 Hz, 1H), 7.29-7.11 (m, 3H), 6.70 (dd, J=12.5, 3.0 Hz, 2H), 3.93 (s, 3H), 3.49 (s, 2H), 3.25 (d, J=8.7 Hz, 2H), 3.21 (s, 3H), 2.83 (d, J=10.5 Hz, 2H), 2.54 (s, 1H), 1.79 (s, 4H), 1.00 (d, J=6.0 Hz, 6H). LCMS: 578.3 (M+H)⁺.

Example 837

(S)-1-(3-chloro-5'-fluoro-2'-hydroxy-3'-(6-(3-hydroxy-3-methylpyrrolidin-1-yl)pyridazin-4-yl)-[1,1'-biphenyl]-4-yl)-3-methyl-1H-imidazol-2(3H)-one

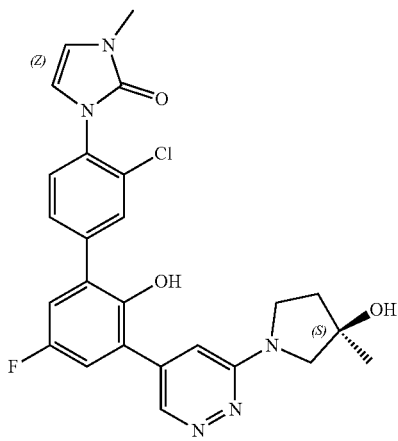

The title compound was prepared following the procedure described for Example 832 using 1-(3-chloro-3'-(6-chloropyridazin-4-yl)-5'-fluoro-2'-methoxy-[1,1'-biphenyl]-4-yl)-3-methyl-1H-imidazol-2(3H)-one, (S)-3-methylpyrrolidin-3-ol and piperazine to afford the title compound. 1H NMR (400 MHz, DMSO-d₆) δ 8.98 (s, 1H), 8.66 (d, J=1.6 Hz, 1H), 7.82 (d, J=1.8 Hz, 1H), 7.63 (dd, J=8.2, 1.9 Hz, 1H), 7.55 (s, 1H), 7.32 (s, 2H), 6.94 (s, 1H), 6.70 (dd, J=14.2, 3.0 Hz, 2H), 4.84 (s, 1H), 3.67-3.43 (m, 3H), 3.36 (d, J=10.7 Hz, 1H), 3.21 (s, 3H), 2.02-1.81 (m, 2H), 1.38 (s, 3H). LCMS: 496.1 (M+H)⁺.

Example 838

1-(3-chloro-5'-fluoro-2'-hydroxy-3'-(5-(3-hydroxy-3-(hydroxymethyl)azetidin-1-yl)-6-methoxypyridin-3-yl)-[1,1'-biphenyl]-4-yl)-3-methyl-1H-imidazol-2(3H)-one

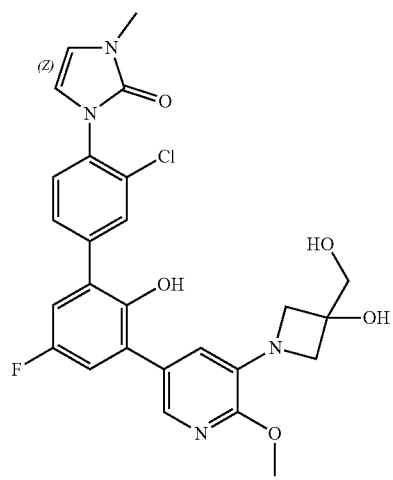 [SMILES: COc1ncc(-c2cc(F)cc(-c3ccc(-n4ccn(C)c4=O)c(Cl)c3)c2O)cc1N1CC(O)(CO)C1]

The title compound was prepared following the procedure described for Example 834 using 3-bromo-5-chloro-2-methoxypyridine and 3-(hydroxymethyl)azetidin-3-ol, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. ¹H NMR (400 MHz, CD₃OD) δ 7.70 (d, J=1.8 Hz, 1H), 7.59 (d, J=1.9 Hz, 1H), 7.51 (dd, J=8.2, 1.8 Hz, 1H), 7.40 (d, J=8.2 Hz, 1H), 7.00-6.89 (m, 2H), 6.83 (d, J=1.9 Hz, 1H), 6.55 (dd, J=15.3, 2.9 Hz, 2H), 3.94 (d, J=8.7 Hz, 2H), 3.86 (s, 3H), 3.69-3.54 (m, 4H), 3.25 (s, 3H). LCMS: 527.0 (M+H)⁺.

Example 839

1-(3-chloro-5'-fluoro-2'-hydroxy-3'-(5-(3-hydroxy-3-(hydroxymethyl)azetidin-1-yl)-6-methylpyridin-3-yl)-[1,1'-biphenyl]-4-yl)-3-methyl-1H-imidazol-2(3H)-one

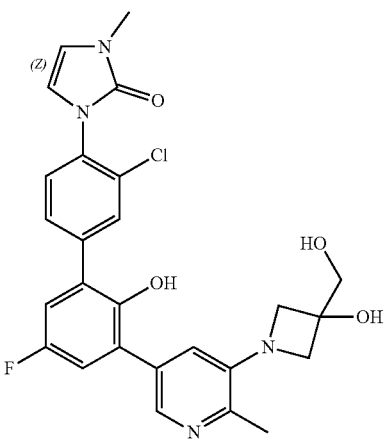 [SMILES: Cc1ncc(-c2cc(F)cc(-c3ccc(-n4ccn(C)c4=O)c(Cl)c3)c2O)cc1N1CC(O)(CO)C1]

The title compound was prepared following the procedure described for Example 834 using 3-bromo-5-chloro-2-methylpyridine, 3-(hydroxymethyl)azetidin-3-ol, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-$d_6$) δ 8.63 (s, 1H), 8.02 (d, J=1.6 Hz, 1H), 7.80 (d, J=1.8 Hz, 1H), 7.62 (dd, J=8.2, 1.9 Hz, 1H), 7.52 (d, J=8.2 Hz, 1H), 7.18 (ddd, J=17.4, 9.0, 3.2 Hz, 2H), 6.94 (d, J=1.6 Hz, 1H), 6.70 (dd, J=12.9, 3.0 Hz, 2H), 5.49 (s, 1H), 4.88 (t, J=5.9 Hz, 1H), 3.97 (d, J=7.7 Hz, 2H), 3.64 (d, J=7.7 Hz, 2H), 3.53 (d, J=5.9 Hz, 2H), 3.21 (s, 3H), 2.38 (s, 3H). LCMS: 511.2 (M+H)$^+$.

Example 840

1-(3'-(2-(4-(tert-butyl)-1,4-diazepan-1-yl)pyridin-4-yl)-3-chloro-5'-fluoro-2'-hydroxy-[1,1'-biphenyl]-4-yl)-3-methyl-1H-imidazol-2(3H)-one

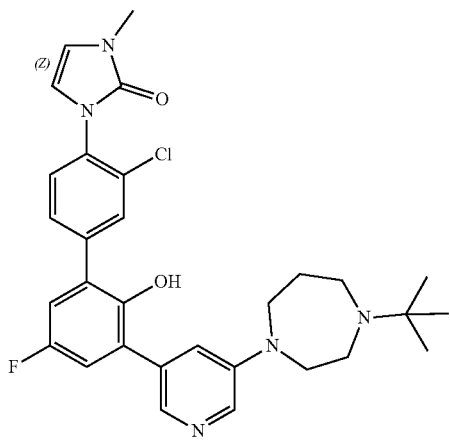 [SMILES: Cn1ccn(-c2ccc(-c3cc(F)cc(-c4cncc(N5CCCN(C(C)(C)C)CC5)c4)c3O)cc2Cl)c1=O]

The title compound was prepared following the procedure described for Example 727 using 1-(3-chloro-5'-fluoro-3'-(2-fluoropyridin-4-yl)-2'-hydroxy-[1,1'-biphenyl]-4-yl)-3-methyl-1H-imidazol-2(3H)-one and 1-(tert-butyl)-1,4-diazepane to afford the title compound. $^1$H NMR (400 MHz, DMSO-$d_6$) δ 8.62 (s, 1H), 8.09 (d, J=5.1 Hz, 1H), 7.80 (d, J=1.8 Hz, 1H), 7.61 (dd, J=8.2, 1.9 Hz, 1H), 7.52 (d, J=8.2 Hz, 1H), 7.21 (ddd, J=19.1, 9.0, 3.2 Hz, 2H), 6.87-6.55 (m, 4H), 3.68 (dd, J=14.4, 8.3 Hz, 4H), 3.31 (s, 3H), 2.75 (s, 2H), 2.53 (d, J=6.2 Hz, 2H), 1.82-1.65 (m, 2H), 1.02 (s, 9H). LCMS: 550.2 (M+H)$^+$.

Example 841

1-(3-chloro-5'-fluoro-2'-hydroxy-3"-(3-hydroxy-3-(hydroxymethyl)azetidin-1-yl)-4"-methyl-[1,1':3',1"-terphenyl]-4-yl)-3-methyl-1H-imidazol-2(3H)-one

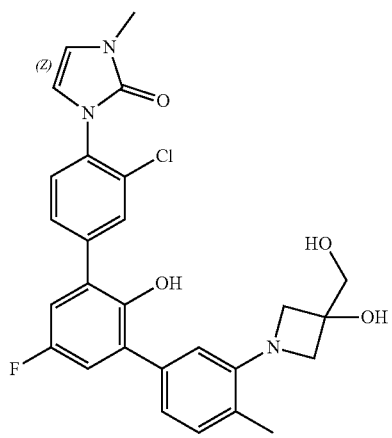 [SMILES: Cc1ccc(-c2cc(F)cc(-c3ccc(-n4ccn(C)c4=O)c(Cl)c3)c2O)cc1N1CC(O)(CO)C1]

The title compound was prepared following the procedures described for Example 834 using 2-bromo-4-chloro-1-methylbenzene, 3-(hydroxymethyl)azetidin-3-ol hemioxalate, 4,4,4',4',5,5,5',5'-octamethyl-2,2'-bi(1,3,2-dioxaborolane) and 1-(3'-bromo-3-chloro-5'-fluoro-2'-hydroxy-[1,1'-biphenyl]-4-yl)-3-methyl-1H-imidazol-2(3H)-one to afford the title compound. $^1$H NMR (400 MHz, DMSO-$d_6$) δ 8.40 (s, 1H), 7.83 (s, 1H), 7.65-7.58 (m, 1H), 7.50 (d, J=8.2 Hz, 1H), 7.13 (dd, J=9.1, 3.1 Hz, 1H), 7.05 (d, J=8.0 Hz, 2H), 6.87 (d, J=7.2 Hz, 1H), 6.69 (dd, J=11.8, 3.0 Hz, 2H), 6.63 (s, 1H), 5.41 (s, 1H), 4.84 (s, 1H), 3.92 (d, J=7.6 Hz, 2H), 3.60 (d, J=7.5 Hz, 2H), 3.53 (d, J=5.5 Hz, 2H), 3.21 (s, 3H), 2.18 (s, 3H). LCMS: 510.1 (M+H)$^+$.

Example 842

(R)-1-(3,4"-dichloro-5'-fluoro-2'-hydroxy-3"-(3-hydroxy-3-methylpyrrolidin-1-yl)-[1,1':3',1"-terphenyl]-4-yl)-3-methyl-1H-imidazol-2(3H)-one

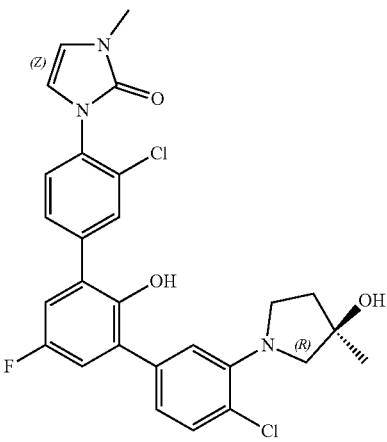

The title compound was prepared following the procedures described for Example 728 using 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one, 2-bromo-1-chloro-4-iodobenzene, (R)-3-methylpyrrolidin-3-ol and $BBr_3$ to afford the title compound. $^1$H NMR (400 MHz, DMSO-$d_6$) δ 8.56 (s, 1H), 7.80 (d, J=1.8 Hz, 1H), 7.62 (dd, J=8.2, 1.9 Hz, 1H), 7.52 (d, J=8.2 Hz, 1H), 7.33 (d, J=8.2 Hz, 1H), 7.16 (ddd, J=18.7, 9.0, 3.2 Hz, 2H), 7.03 (d, J=1.7 Hz, 1H), 6.94 (dd, J=8.2, 1.8 Hz, 1H), 6.70 (dd, J=12.4, 3.0 Hz, 2H), 4.72 (s, 1H), 3.63 (d, J=7.3 Hz, 1H), 3.51 (d, J=9.8 Hz, 1H), 3.34 (d, J=3.8 Hz, 1H), 3.23 (d, J=13.6 Hz, 4H), 1.94-1.73 (m, 2H), 1.34 (s, 3H). LCMS: 528.2 (M+H)$^+$.

Example 843

1-(3-chloro-5'-fluoro-2'-hydroxy-3'-(5-(3-hydroxy-3-methylazetidin-1-yl)-6-methylpyridin-3-yl)-[1,1'-biphenyl]-4-yl)-3-methyl-1H-imidazol-2(3H)-one

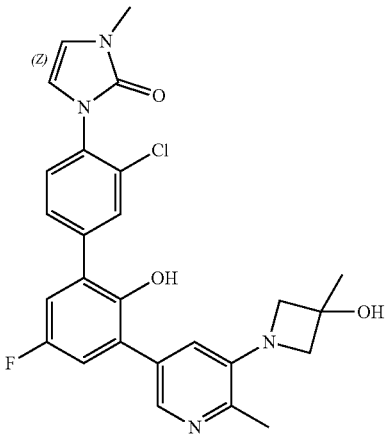 [SMILES: Cc1ncc(-c2cc(F)cc(-c3ccc(-n4ccn(C)c4=O)c(Cl)c3)c2O)cc1N1CC(C)(O)C1]

The title compound was prepared following the procedure described for Example 834 using 3-bromo-5-chloro-2-methylpyridine, 3-methylazetidin-3-ol, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO) δ 8.60 (s, 1H), 8.03 (d, J=1.7 Hz, 1H), 7.80 (d, J=1.8 Hz, 1H), 7.62 (dd, J=8.2, 1.9 Hz, 1H), 7.52 (d, J=8.2 Hz, 1H), 7.19 (ddd, J=17.7, 9.0, 3.2 Hz, 2H), 6.94 (d, J=1.6 Hz, 1H), 6.70 (dd, J=13.1, 3.0 Hz, 2H), 5.46 (s, 1H), 3.84 (d, J=7.6 Hz, 2H), 3.72 (d, J=7.4 Hz, 2H), 3.21 (s, 3H), 2.38 (s, 3H), 1.49 (s, 3H). LCMS: 495.2 (M+H)$^+$.

Example 844

1-(3'-(5-(4-(tert-butyl)-1,4-diazepan-1-yl)-6-methylpyridin-3-yl)-3-chloro-5'-fluoro-2'-hydroxy-[1,1'-biphenyl]-4-yl)-3-methyl-1H-imidazol-2(3H)-one

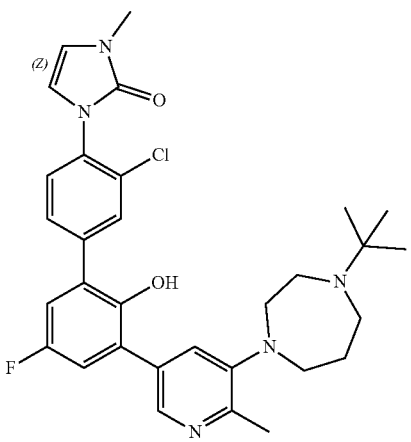 [SMILES: Cc1ncc(-c2cc(F)cc(-c3ccc(-n4ccn(C)c4=O)c(Cl)c3)c2O)cc1N1CCCN(C(C)(C)C)CC1]

The title compound was prepared following the procedure described for Example 722 using 3-bromo-5-chloro-2-methylpyridine, 1-(tert-butyl)-1,4-diazepane, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO) δ 8.24 (s, 1H), 7.81 (s, 1H), 7.65-7.57 (m, 2H), 7.52 (d, J=8.2 Hz, 1H), 7.21 (d, J=9.0 Hz, 2H), 6.70 (dd, J=13.5, 3.0 Hz, 2H), 4.09 (d, J=5.1 Hz, 1H), 3.21 (s, 3H), 3.17 (d, J=4.9 Hz, 6H), 3.11 (s, 2H), 2.81 (s, 3H), 1.81 (s, 2H), 1.06 (s, 9H). LCMS: 564.2 (M+H)$^+$.

Example 845

1-(3-chloro-5'-fluoro-2'-hydroxy-3''-(3-hydroxy-3-methylazetidin-1-yl)-4''-methyl-[1,1':3',1''-terphenyl]-4-yl)-3-methyl-1H-imidazol-2(3H)-one

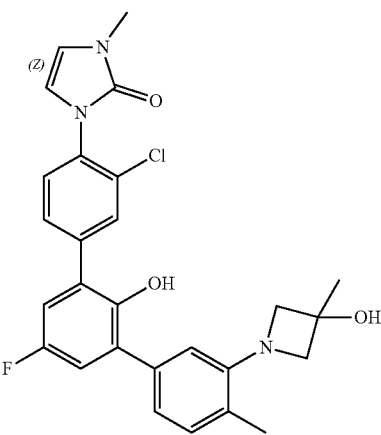 [SMILES: Cc1ccc(-c2cc(F)cc(-c3ccc(-n4ccn(C)c4=O)c(Cl)c3)c2O)cc1N1CC(C)(O)C1]

The title compound was prepared following the procedures described for Example 841 using 2-bromo-4-chloro-1-methylbenzene, 3-methylazetidin-3-ol, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^{1}$H NMR (400 MHz, DMSO-d$_{6}$) δ 8.39 (s, 1H), 7.80 (s, 1H), 7.61-7.50 (m, 2H), 7.15-7.05 (m, 3H), 6.87 (d, J=6.8 Hz, 1H), 6.39 (d, J=2.4 Hz, 2H), 6.60 (s, 1H), 5.40 (s, 1H), 3.81-3.61 (m, 4H), 3.20 (s, 3H), 2.17 (s, 3H), 1.48 (s, 3H). LCMS: 494.2 (M+H)$^{+}$.

Example 846

1-(3-chloro-5'-fluoro-2'-hydroxy-3''-(8-isopropyl-3,8-diazabicyclo[3.2.1]octan-3-yl)-[1,1':3',1''-terphenyl]-4-yl)-3-methyl-1H-imidazol-2(3H)-one

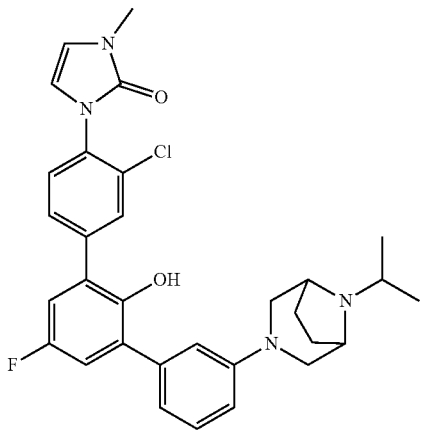 [SMILES: CC(C)N1C2CCC1CN(c1cccc(-c3cc(F)cc(-c4ccc(-n5ccn(C)c5=O)c(Cl)c4)c3O)c1)C2]

The title compound was prepared following the procedure described for Example 835 using 1-bromo-3-chlorobenzene, tert-butyl 3,8-diazabicyclo[3.2.1]octane-8-carboxylate, 4,4,4',4',5,5,5',5'-octamethyl-2,2'-bi(1,3,2-dioxaborolane), 2,6-dibromo-4-fluorophenol, 1-(2-chloro-4-(4,4,5,5-tetramethyl-1,3,2-dioxaborolan-2-yl)phenyl)-3-methyl-1,3-dihydro-2H-imidazol-2-one, TFA, NaCNBH$_{3}$, and acetone to afford the title compound. $^{1}$H NMR (400 MHz, DMSO-d$_{6}$) δ 8.41 (s, 1H), 7.80 (d, J=1.8 Hz, 1H), 7.61 (dd, J=8.2, 1.9 Hz, 1H), 7.51 (d, J=8.2 Hz, 1H), 7.25 (t, J=7.9 Hz, 1H), 7.13 (ddd, J=24.2, 9.1, 3.2 Hz, 2H), 6.98-6.76 (m, 3H), 6.70 (dd, J=11.3, 3.0 Hz, 2H), 3.56 (s, 2H), 3.36 (d, J=10.1 Hz, 2H), 3.21 (s, 3H), 2.89 (d, J=10.0 Hz, 2H), 2.65-2.55 (m, 1H), 1.91-1.76 (m, 2H), 1.64 (d, J=7.0 Hz, 2H), 1.03 (d, J=6.0 Hz, 6H). LCMS: 547.2 (M+H)$^{+}$.

Example 847

1-(3-chloro-3'-(5-(4-(2-cyclopropylpropan-2-yl)piperazin-1-yl)-6-methoxypyridin-3-yl)-5'-fluoro-2'-hydroxy-[1,1'-biphenyl]-4-yl)-3-methyl-1H-imidazol-2(3H)-one

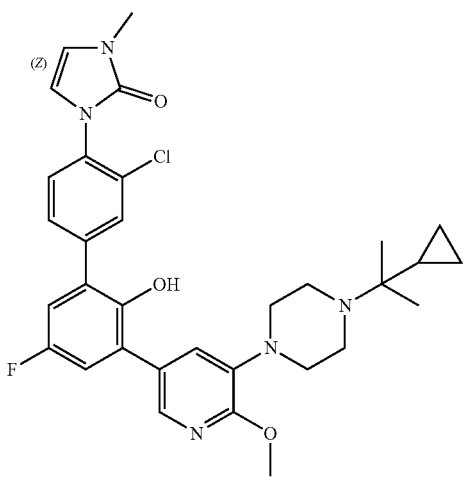 [SMILES: COc1ncc(-c2cc(F)cc(-c3ccc(-n4ccn(C)c4=O)c(Cl)c3)c2O)cc1N1CCN(C(C)(C)C2CC2)CC1]

Step 1: 1-benzyl-4-(2-cyclopropylpropan-2-yl)piperazine

To a solution of N-benzyl-2-chloro-N-(2-chloroethyl)ethanamine hydrochloride (2.7 g, 10.0 mmol) and 2-cyclopropylpropan-2-amine hydrochloride (1.4 g, 10.0 mmol) in i-PrOH (60 mL) was added Na$_{2}$CO$_{3}$ (5.3 g, 50 mL). The reaction mixture was stirred at 80° C. overnight under nitrogen atmosphere. After the reaction complete by LCMS, the reaction mixture was cooled to room temperature, filtered and concentrated. The residue was purified by silica gel column (EA:MeOH=20:1) to give the title compound (2.0 g, 77% yield) as yellow oil. LCMS: 259.2 (M+H)$^{+}$.

Step 2: 1-(2-cyclopropylpropan-2-yl)piperazine

To a solution of 1-benzyl-4-(2-cyclopropylpropan-2-yl)piperazine (2.0 g, 7.7 mmol) in MeOH (35 mL) was added 10% Pd/C (400 mg). The reaction mixture was stirred at room temperature overnight under hydrogen atmosphere. After the reaction complete by LCMS, the reaction mixture was filtered and concentrated to give the title compound (1.0 g, 77% yield) as yellow oil which was used to the next step without further purification. LCMS: 169.2 (M+H)$^{+}$.

Step 3: 1-(3-chloro-3'-(5-(4-(2-cyclopropylpropan-2-yl)piperazin-1-yl)-6-methoxypyridin-3-yl)-5'-fluoro-2'-hydroxy-[1,1'-biphenyl]-4-yl)-3-methyl-1H-imidazol-2(3H)-one The title compound was prepared following the procedures described for Example 738 using 3-bromo-5-chloro-2-methoxypyridine, 1-(2-cyclopropylpropan-2-yl)piperazine, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-$d_6$) δ 8.61 (s, 1H), 7.92 (s, 1H), 7.81 (d, J=1.8 Hz, 1H), 7.62 (dd, J=8.2, 1.9 Hz, 1H), 7.52 (d, J=8.2 Hz, 1H), 7.35 (s, 1H), 7.23-7.12 (m, 2H), 6.70 (dd, J=12.4, 3.0 Hz, 2H), 3.93 (s, 3H), 3.21 (s, 3H), 3.06 (s, 4H), 2.79 (s, 4H), 0.87 (s, 7H), 0.39-0.24 (m, 4H). LCMS: 592.2 (M+H)$^+$.

Example 848

1-(3'-(5-(4-(tert-butyl)piperazin-1-yl)-6-ethylpyridin-3-yl)-3-chloro-5'-fluoro-2'-hydroxy-[1,1'-biphenyl]-4-yl)-3-methyl-1H-imidazol-2(3H)-one

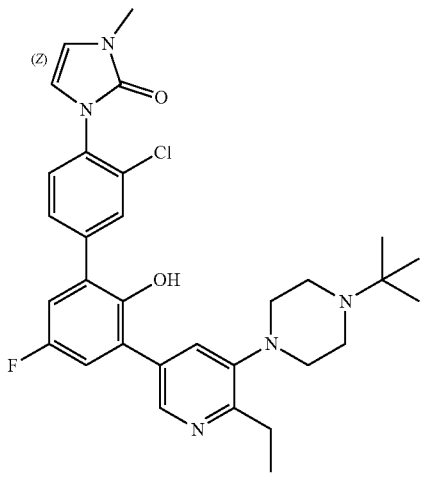 [SMILES: CCc1ncc(-c2cc(F)cc(-c3ccc(-n4ccn(C)c4=O)c(Cl)c3)c2O)cc1N1CCN(C(C)(C)C)CC1]

The title compound was prepared following the procedure described for Example 722 using 3-bromo-5-chloro-2-ethylpyridine, 1-(tert-butyl)piperazine, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-$d_6$) δ 8.70 (s, 1H), 8.40 (d, J=1.8 Hz, 1H), 7.81 (d, J=1.8 Hz, 1H), 7.59 (ddd, J=29.4, 17.9, 5.0 Hz, 3H), 7.23 (td, J=9.5, 3.2 Hz, 2H), 6.70 (dd, J=12.8, 3.0 Hz, 2H), 3.21 (s, 3H), 2.90 (d, J=4.4 Hz, 4H), 2.83 (q, J=7.5 Hz, 2H), 2.69 (s, 4H), 1.27 (t, J=7.5 Hz, 3H), 1.06 (s, 9H). LCMS: 564.2 (M+H)$^+$.

Example 849

1-(3-Chloro-3'-(6-cyclopropyl-5-(7-hydroxy-7-methyl-5-azaspiro[2.4]heptan-5-yl)pyridin-3-yl)-5'-fluoro-2'-hydroxy-[1,1'-biphenyl]-4-yl)-3-methyl-1H-imidazol-2(3H)-one

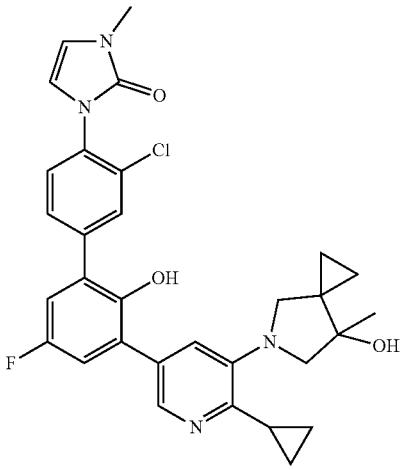 [SMILES: Cn1ccn(-c2ccc(-c3cc(F)cc(-c4cnc(C5CC5)c(N5CC(C)(O)C6(CC6)C5)c4)c3O)cc2Cl)c1=O]

Step 1: 3-Bromo-5-chloro-2-cyclopropylpyridine

To a mixture of 3-bromo-5-chloro-2-iodopyridine (2 g, 8.6 mmol), cyclopropylboronic acid (2.71 g, 31.5 mmol) in toluene/$H_2O$ (40 mL/8 mL) was added Pd(OAc)$_2$ (284 mg, 1.26 mmol), PCy$_3$ (530 mg, 1.89 mmol) and K$_3$PO$_4$ (4.0 g, 18.8 mmol). The reaction mixture was stirred at 80° C. overnight under N$_2$. After the reaction was indicated by LCMS, the reaction mixture was concentrated and purified by HPLC to afford 3-bromo-5-chloro-2-cyclopropylpyridine (546 mg, 27.3% yield). LCMS: 231.9 (M+H)$^+$.

Step 2: 5-(5-Chloro-2-cyclopropylpyridin-3-yl)-7-methyl-5-azaspiro[2.4]heptan-7-ol The title compound was prepared following the procedure described for Example 756 using 3-bromo-5-chloro-2-cyclopropylpyridine and 7-methyl-5-azaspiro[2.4]heptan-7-ol to afford the title compound (44% yield). LCMS: 279.1 (M+H)$^+$.

Step 3: (6-cyclopropyl-5-(7-hydroxy-7-methyl-5-azaspiro[2.4]heptan-5-yl)pyridin-3-yl)boronic acid The title compound was prepared following the procedure described for Example 756 using 5-(5-chloro-2-cyclopropylpyridin-3-yl)-7-methyl-5-azaspiro[2.4]heptan-7-ol and 4,4,4',4',5,5,5',5'-octamethyl-2,2'-bi(1,3,2-dioxaborolane) to afford the title compound (crude). LCMS: 289.2 (M+H)$^+$.

Step 4: 5-(5-(3-bromo-5-fluoro-2-hydroxyphenyl)-2-cyclopropylpyridin-3-yl)-7-methyl-5-azaspiro[2.4]heptan-7-ol The title compound was prepared following the procedure described for Example 756 using (6-cyclopropyl-5-(7-hydroxy-7-methyl-5-azaspiro[2.4]heptan-5-yl)pyridin-3-yl)

boronic acid and 2,6-dibromo-4-fluorophenol to afford the title compound (71.4% yield). LCMS: 433.1 (M+H)⁺.

Step 5: 1-(3-chloro-3'-(6-cyclopropyl-5-(7-hydroxy-7-methyl-5-azaspiro[2.4]heptan-5-yl)pyridin-3-yl)-5'-fluoro-2'-hydroxy-[1,1'-biphenyl]-4-yl)-3-methyl-1H-imidazol-2(3H)-one The title compound was prepared following the procedure described for Example B-888 using 5-(5-(3-bromo-5-fluoro-2-hydroxyphenyl)-2-cyclopropylpyridin-3-yl)-7-methyl-5-azaspiro[2.4]heptan-7-ol and 1-(2-chloro-4-(4,4,5,5-tetramethyl-1,3,2-dioxaborolan-2-yl)phenyl)-3-methyl-1H-imidazol-2(3H)-one to afford the title compound (7.7% yield). $^1$H NMR (400 MHz, DMSO-d$_6$) δ 8.64 (s, 1H), 8.09 (s, 1H), 7.80 (d, J=1.6 Hz, 1H), 7.61 (s, 1H), 7.52 (d, J=8.2 Hz, 1H), 7.27 (s, 1H), 7.19 (d, J=9.2 Hz, 2H), 6.70 (dd, J=13.0, 2.9 Hz, 2H), 4.61 (s, 1H), 3.55-3.40 (m, 3H), 3.30 (s, 1H), 3.21 (s, 3H), 2.30 (s, 1H), 1.11 (s, 3H), 1.04 (s, 2H), 0.96 (d, J=6.9 Hz, 2H), 0.81 (d, J=9.1 Hz, 1H), 0.61 (d, J=4.5 Hz, 1H), 0.49-0.48 (m, 2H). LCMS: 561.2 (M+H)⁺.

Example 850

1-(3-Chloro-5'-fluoro-2'-hydroxy-3'-(6-methoxy-5-(4-(1-methoxy-2-methylpropan-2-yl)piperazin-1-yl)pyridin-3-yl)-[1,1'-biphenyl]-4-yl)-3-methyl-1H-imidazol-2(3H)-one

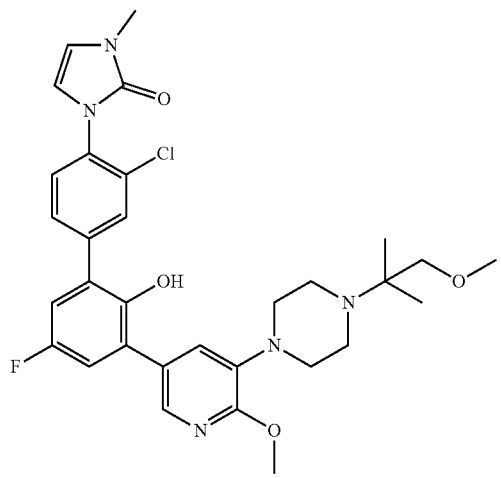 [SMILES: COCC(C)(C)N1CCN(c2cc(-c3cc(F)cc(-c4ccc(-n5ccn(C)c5=O)c(Cl)c4)c3O)cnc2OC)CC1]

The title compound was prepared following the procedures described for Example 738 using 3-bromo-5-chloro-2-methoxypyridine, 1-(1-methoxy-2-methylpropan-2-yl)piperazine, 4,4',4',5,5,5',5'-octamethyl-2,2'-bi(1,3,2-dioxaborolane), 2,6-dibromo-4-fluorophenol, and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-d$_6$) δ 8.61 (s, 1H), 7.93 (s, 1H), 7.81 (d, J=1.6 Hz, 1H), 7.66-7.58 (m, 1H), 7.52 (d, J=8.2 Hz, 1H), 7.34 (s, 1H), 7.19 (d, J=9.0 Hz, 2H), 6.70 (dd, J=12.7, 2.9 Hz, 2H), 3.93 (s, 3H), 3.26-3.28 (m, 5H), 3.21 (s, 3H), 3.09-3.02 (m, 4H), 2.71-2.69 (m, 4H), 1.04 (s, 6H). LCMS: 596.2 (M+H)⁺.

Example 851

1-(3''-(4-(tert-Butyl)-1,4-diazepan-1-yl)-3-chloro-5'-fluoro-2'-hydroxy-[1,1':3',1''-terphenyl]-4-yl)-3-methyl-1H-imidazol-2(3H)-one

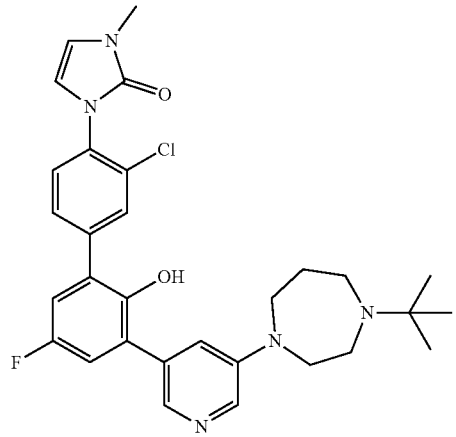 [SMILES: Cn1ccn(-c2ccc(-c3cc(F)cc(-c4cncc(N5CCCN(C(C)(C)C)CC5)c4)c3O)cc2Cl)c1=O]

The title compound was prepared following the procedures described for Example 734 using 1-(3-bromophenyl)-4-(tert-butyl)-1,4-diazepane and 1-(3-chloro-5'-fluoro-2'-methoxy-3'-(4,4,5,5-tetramethyl-1,3,2-dioxaborolan-2-yl)-[1,1'-biphenyl]-4-yl)-3-methyl-1H-imidazol-2(3H)-one followed by BBr$_3$ to afford the title compound. $^1$H NMR (400 MHz, DMSO-d$_6$) δ 8.40 (s, 1H), 7.80 (s, 1H), 7.61 (dd, J=8.2, 1.9 Hz, 1H), 7.52 (s, 1H), 7.27-7.12 (m, 2H), 7.09 (dd, J=9.1, 3.1 Hz, 1H), 6.84 (s, 1H), 6.80-6.64 (m, 4H), 3.68-3.41 (m, 4H), 3.30-3.28 (m, 2H), 3.21 (s, 3H), 2.77-2.71 (m, 2H), 1.77-1.75 (m, 2H), 1.03 (s, 9H). LCMS: 549.4 (M+H)⁺.

Example 852

(R)-1-(3-Chloro-3'-(6-ethyl-5-(3-hydroxy-3-methylpyrrolidin-1-yl)pyridin-3-yl)-5'-fluoro-2'-hydroxy-[1,1'-biphenyl]-4-yl)-3-methyl-1H-imidazol-2(3H)-one

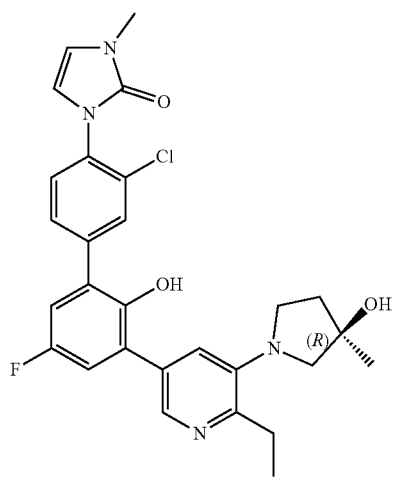

1125

Step 1: 3-Bromo-5-chloro-2-ethylpyridine

To a solution of 3-bromo-5-chloro-2-ethylpyridine (2.0 g, 7.40 mmol) in THF (40 mL) was added diethylzinc (11 mL, 11 mmol, 1 mol/L in hexane) dropwise at −78° C. The reaction mixture was stirred at room temperature for 16 hours under nitrogen atmosphere. After the reaction was indicated by LCMS, the reaction mixture was diluted with sat. NaHCO$_3$ and extracted with EA (40 mL*3). The combined organic layers were washed with brine, dried over Na$_2$SO$_4$, filtered and concentrated. the residue was purified by flash column chromatography (PE:EA=10:1) to give 3-bromo-5-chloro-2-ethylpyridine (800 mg, 50% yield) as a yellow liquid. LCMS: 219.9 (M+H)$^+$.

Step 2: (R)-1-(5-Chloro-2-ethylpyridin-3-yl)-3-methylpyrrolidin-3-ol

The title compound was prepared following the procedure described for Example 849 using 3-bromo-5-chloro-2-ethylpyridine and (R)-3-methylpyrrolidin-3-ol to afford the title compound (69% yield). LCMS: 241.1 (M+H)$^+$.

Step 3: (R)-(6-Ethyl-5-(3-hydroxy-3-methylpyrrolidin-1-yl)pyridin-3-yl)boronic acid The title compound was prepared following the procedure described for Example 849 using (R)-1-(5-chloro-2-ethylpyridin-3-yl)-3-methylpyrrolidin-3-ol and 4,4,4',4',5,5,5',5'-octamethyl-2,2'-bi(1,3,2-dioxaborolane) to afford the title compound (100% yield) which was used to the next step without further purification. LCMS: 251.1 (M+H)$^+$.

Step 4: (R)-1-(5-(3-Bromo-5-fluoro-2-hydroxyphenyl)-2-ethylpyridin-3-yl)-3-methylpyrrolidin-3-ol The title compound was prepared following the procedure described for Example 849 using (R)-(6-ethyl-5-(3-hydroxy-3-methylpyrrolidin-1-yl)pyridin-3-yl)boronic acid and 2,6-dibromo-4-fluorophenol to afford the title compound (48% yield). LCMS: 395.1 (M+H)$^+$.

Step 5: (R)-1-(5-(3-Bromo-5-fluoro-2-hydroxyphenyl)-2-ethylpyridin-3-yl)-3-methylpyrrolidin-3-ol The title compound was prepared following the procedure described for Example 849 using (R)-1-(5-(3-bromo-5-fluoro-2-hydroxyphenyl)-2-ethylpyridin-3-yl)-3-methylpyrrolidin-3-ol and 1-(2-chloro-4-(4,4,5,5-tetramethyl-1,3,2-dioxaborolan-2-yl)phenyl)-3-methyl-1H-imidazol-2(3H)-one to afford the title compound (21% yield). $^1$H NMR (400 MHz, DMSO-d$_6$) δ 8.65 (s, 1H), 8.16 (d, J=1.4 Hz, 1H), 7.81 (d, J=1.7 Hz, 1H), 7.62 (dd, J=8.2, 1.8 Hz, 1H), 7.52 (d, J=8.2 Hz, 1H), 7.30 (s, 1H), 7.22-7.19 (m, 2H), 6.72-6.68 (m, 2H), 4.75 (s, 1H), 3.50-3.46 (m, 1H), 3.28 (d, J=8.0 Hz, 1H), 3.23-3.20 (m, 4H), 3.10 (d, J=8.0 Hz, 1H), 2.86-2.78 (m, 2H), 1.92-1.83 (m, 2H), 1.35 (s, 3H), 1.26 (t, J=7.4 Hz, 3H). LCMS: 523.3 (M+H)$^+$.

1126

Example 853

1-(3'-(5-(4-(tert-Butyl)-1,4-diazepan-1-yl)-6-methoxypyridin-3-yl)-3-chloro-5'-fluoro-2'-hydroxy-[1,1'-biphenyl]-4-yl)-3-methyl-1H-imidazol-2(3H)-one

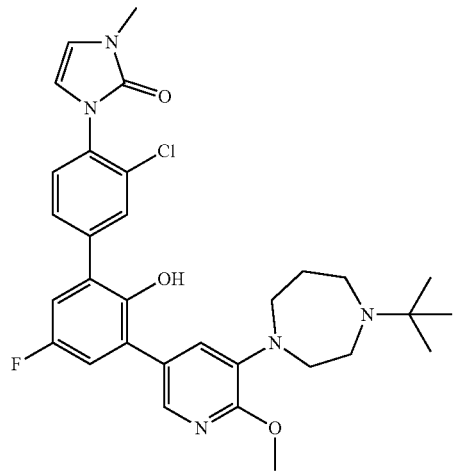 [SMILES: COc1ncc(-c2cc(F)cc(-c3ccc(-n4ccn(C)c4=O)c(Cl)c3)c2O)cc1N1CCCN(C(C)(C)C)CC1]

The title compound was prepared following the procedure described for Example 738 using 1-(tert-butyl)-4-(5-chloro-2-methoxypyridin-3-yl)-1,4-diazepane, 4,4,4',4',5,5,5',5'-octamethyl-2,2'-bi(1,3,2-dioxaborolane), 2,6-dibromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-d$_6$) δ 7.78 (dd, J=13.6, 1.7 Hz, 2H), 7.60 (d, J=1.8 Hz, 1H), 7.52 (d, J=8.2 Hz, 1H), 7.28 (d, J=1.7 Hz, 1H), 7.17 (dd, J=9.0, 3.9 Hz, 2H), 6.70 (dd, J=12.6, 3.0 Hz, 2H), 3.91 (s, 3H), 3.40-3.34 (m, 3H), 3.23-3.20 (m, 4H), 2.74 (d, J=39.1 Hz, 4H), 1.80-1.76 (m, 2H), 1.04 (s, 9H). One N—H or O—H proton not observed. LCMS: 580.2 (M+H)$^+$.

Example 854

1-(3-Chloro-5'-fluoro-2'-hydroxy-3''-(7-hydroxy-7-methyl-5-azaspiro[2.4]heptan-5-yl)-4''-methyl-[1,1':3',1''-terphenyl]-4-yl)-3-methyl-1H-imidazol-2(3H)-one

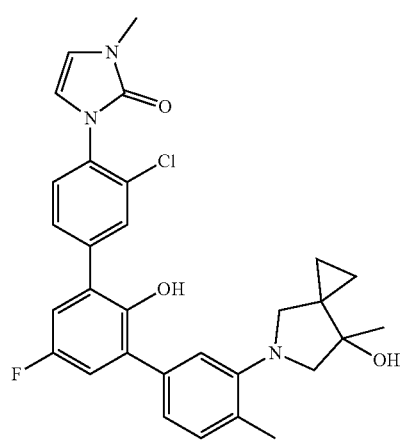 [SMILES: Cc1ccc(-c2cc(F)cc(-c3ccc(-n4ccn(C)c4=O)c(Cl)c3)c2O)cc1N1CC(C)(O)C2(CC2)C1]

The title compound was prepared following the procedure described for Example 849 using 5-(5-chloro-2-methylphenyl)-7-methyl-5-azaspiro[2.4]heptan-7-ol, 4,4,4',4',5,5,5',5'-octamethyl-2,2'-bi(1,3,2-dioxaborolane), 1-(3'-bromo-3-chloro-5'-fluoro-2'-hydroxy-[1,1'-biphenyl]-4-yl)-3-methyl-1H-imidazol-2(3H)-one to afford the title compound. $^1$H NMR (400 MHz, DMSO-d$_6$) δ 8.42 (s, 1H), 7.80 (d, J=1.8, 1H), 7.61 (dd, J=8.2, 1.9, 1H), 7.51 (d, J=8.2, 1H), 7.23-7.05 (m, 3H), 7.02-6.85 (m, 2H), 6.70 (dd, J=11.7, 3.0, 2H), 4.54 (s, 1H), 3.45-3.34 (m, 3H), 3.26 (d, J=8.9, 1H), 3.2 (s, 3H) 2.30 (s, 3H), 1.12 (s, 3H), 0.85-0.74 (m, 1H), 0.61-0.53 (m, 1H), 0.51-0.39 (m, 2H). LCMS: 534.2 (M+H)$^+$.

TABLE 32

Following compounds were prepared using similar procedures as described for Examples 1 through 854.

| Ex. No. | Name/Structure | $^1$H NMR Data | LCMS (M + H)$^+$ |
|---|---|---|---|
| 855 | 1-(4'''-amino-3-chloro-5'-fluoro-2'-hydroxy-[1,1:3',1'':3'',1'''-quaterphenyl]-4-yl)-3-methyl-1,3-dihydro-2H-imidazol-2-one | $^1$H NMR (400 MHz, DMSO-d$_6$) δ 8.34 ( s, 1H), 7.83 (d, J = 1.8, 1H), 7.71 (s, 1H), 7.64 (dd, J = 8.2, 1.8 Hz, 1H), 7.53 (dd, J = 7.8, 4.4 Hz, 2H), 7.44 (dd, J = 17.8, 8.0 Hz, 4H), 7.20 (dt, J = 7.3, 3.2 Hz, 2H), 6.93-6.56 (m, 4H), 5.22 (s, 2H), 3.21 (s, 3H). | 486.1 |
| 856 | 1-(3-chloro-5'-fluoro-2'-hydroxy-3'-(5-(4-(1-methoxy-2-methylpropan-2-yl)piperazin-1-yl)-6-methylpyridin-3-yl)-[1,1'-biphenyl]-4-yl)-3-methyl-1H-imidazol-2(3H)-one | $^1$H NMR (400 MHz, DMSO-d$_6$) δ 8.69 (s, 1H), 8.31 (s, 1H), 7.81 (s, 1H), 7.63 (d, J = 8.0 Hz, 1H), 7.52 (d, J = 8.3 Hz, 2H), 7.30-7.18 (m, 2H), 6.70 (dd, J = 13.0, 2.9 Hz, 2H), 3.28-3.26 (s, 5H), 3.21 (s, 3H), 2.91-2.90 (m, 4H), 2.75-2.73 (m, 4H), 2.47 (s, 3H), 1.03 (s, 6H) | 580.2 |

TABLE 32-continued

Following compounds were prepared using similar procedures as described for Examples 1 through 854.

| Ex. No. | Name/Structure | $^1$H NMR Data | LCMS $(M + H)^+$ |
|---|---|---|---|
| 857 | 1-(3-chloro-5'-fluoro-2',4'''-dihydroxy-[1,1':3',1'':3'',1'''-quaterphenyl]-4-yl)-3-methyl-1H-imidazol-2(3H)-one | $^1$H NMR (400 MHz, DMSO-d$_6$) δ 9.54 (s, 1H), 8.61 (s, 1H), 7.83 (d, J = 1.7 Hz, 1H), 7.75 (s, 1H), 7.64 (dd, J = 8.2, 1.7 Hz, 1H), 7.60-7.48 (m, 6H), 7.25-7.19 (m, 2H), 6.86 (d, J = 8.5 Hz, 2H), 6.72-6.69 (m, 2H), 3.21 (s, 3H) | 487.0 |
| 858 | 1-(3-chloro-5'-fluoro-2'-hydroxy-4'''-(hydroxymethyl)-[1,1':3',1'':3'',1'''-quaterphenyl]-4-yl)-3-methyl-1H-imidazol-2(3H)-one | $^1$H NMR (400 MHz, DMSO-d$_6$) δ 8.65 (s, 1H), 7.83 (s, 2H), 7.73-7.60 (m, 4H), 7.59-7.48 (m, 3H), 7.42 (d, J = 7.9 Hz, 2H), 7.27-7.20 (m, 2H), 6.72-6.69 (m, 2H), 5.21 (t, J = 5.6 Hz, 1H), 4.55 (d, J = 5.6 Hz, 2H), 3.21 (s, 3H) | 501.0 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 859 | 1-(3''-(4-(tert-butyl)piperazin-1-yl)-3-chloro-5'-fluoro-2'-methoxy-[1,1':3',1''-terphenyl]-4-yl)-3-methyl-1H-imidazol-2(3H)-one | $^1$H NMR (400 MHz, DMSO-d$_6$) δ 7.83 (d, J = 1.9 Hz, 1H), 7.66 (dd, J = 8.2, 1.9 Hz, 1H), 7.55 (d, J = 8.2 Hz, 1H), 7.33-7.25 (m, 3H), 7.12 (s, 1H), 7.02-6.95 (m, 2H), 6.74-6.72 (m, 2H), 3.21 (s, 3H), 3.17-3.14 (m, 4H), 3.14 (s, 3H), 2.67-2.64 (m, 4H), 1.05 (s, 9H) | 549.2 |
| 860 | 3'-chloro-5-fluoro-3-(5-(4-isopropylpiperazin-1-yl)-6-methoxypyridin-3-yl)-4'-(3-methyl-2-oxo-2,3-dihydro-1H-imidazol-1-yl)-[1,1'-biphenyl]-2-ylacetate | $^1$H NMR (400 MHz, DMSO-d$_6$) δ 7.84 (d, J = 1.9 Hz, 1H), 7.73 (s, 1H), 7.56 (d, J = 2.1 Hz, 2H), 7.47 (d, J = 8.9 Hz, 2H), 7.26 (d, J = 1.9 Hz, 1H), 6.73 (dd, J = 6.6, 3.0 Hz, 2H), 3.93 (s, 3H), 3.20 (s, 3H), 3.03 (s, 4H), 2.59 (s, 5H), 1.91 (s, 3H), 1.00 (d, J = 6.5 Hz, 6H) | 594.1 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 861 | 1-(3-chloro-3'-(2-(3,3-difluoro-4-hydroxy-4-methylpyrrolidin-1-yl)pyridin-4-yl)-5'-fluoro-2'-hydroxy-[1,1'-biphenyl]-4-yl)-3-methyl-1H-imidazol-2(3H)-one | $^1$H NMR (400 MHz, CD$_3$OD) δ 8.14 (d, J = 5.4 Hz, 1H), 7.82 (d, J = 1.7 Hz, 1H), 7.67-7.42 (m, 2H), 7.19-7.09 (m, 2H), 6.90 (d, J = 5.3 Hz, 1H), 6.76-6.49 (m, 3H), 4.10-3.78 (m, 2H), 3.76-3.49 (m, 2H), 3.37 (s, 3H), 1.43 (t, J = 21.8 Hz, 3H). N—H or O—H protons not observed | 531.1 |
| 862 | 1-(3'''-amino-3-chloro-5'-fluoro-2'-hydroxy-[1,1':3',1'':3'',1'''-quaterphenyl]-4-yl)-3-methyl-1H-imidazol-2(3H)-one | $^1$H NMR (400 MHz, DMSO-d$_6$) δ 8.64 (s, 1H), 7.83 (d, J = 1.8 Hz, 1H), 7.75 (s, 1H), 7.64 (dd, J = 8.2, 1.8 Hz, 1H), 7.59-7.47 (m, 4H), 7.21 (d, J = 9.1 Hz, 2H), 7.11 (t, J = 7.8 Hz, 1H), 6.91 (s, 1H), 6.84 (d, J = 7.7 Hz, 1H), 6.70 (dd, J = 10.4, 3.0 Hz, 2H), 6.58 (d, J = 7.9 Hz, 1H), 5.15 (s, 2H), 3.21 (s, 3H). | 486.1 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 863 | 1-(4''''-(aminomethyl)-3-chloro-5'-fluoro-2'-hydroxy-[1,1':3',1'':3'',1'''-quaterphenyl]-4-yl)-3-methyl-1H-imidazol-2(3H)-one | $^1$H NMR (400 MHz, DMSO-d$_6$) δ 7.91-7.77 (m, 2H), 7.72-7.61 (m, 4H), 7.53 (t, J = 7.7 Hz, 3H), 7.43 (d, J = 8.1 Hz, 2H), 7.23 (ddd, J = 17.4, 9.1, 3.2 Hz, 2H), 6.70 (dd, J = 11.1, 3.0 Hz, 2H), 3.76 (s, 2H), 3.21 (s, 3H). N—H or O—H protons not observed. | 500.2 |
| 864 | 1-(3-chloro-5'-fluoro-2',3''''-dihydroxy-[1,1':3',1'':3'',1''''-quaterphenyl]-4-yl)-3-methyl-1H-imidazol-2(3H)-one | $^1$H NMR (400 MHz, DMSO-d$_6$) δ 9.52 (s, 1H), 8.57 (s, 1H), 7.86-7.75 (m, 2H), 7.68-7.46 (m, 5H), 7.31-7.17 (m, 3H), 7.16-7.06 (m, 2H), 6.78 (dd, J = 8.0, 1.7 Hz, 1H), 6.70 (dd, J = 10.5, 3.0 Hz, 2H), 3.21 (s, 3H) | 487.1 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 865 | 1-(3-chloro-5'-fluoro-2'-hydroxy-3'''-(hydroxymethyl)-[1,1':3',1'':3'',1'''-quaterphenyl]-4-yl)-3-methyl-1H-imrdazol-2(3H)-one | $^1$H NMR (400 MHz, DMSO-d$_6$) δ 8.65 (s, 1H), 7.83 (s, 2H), 7.65 (dd, J = 10.6, 4.2 Hz, 3H), 7.56 (td, J = 13.9, 7.9 Hz, 4H), 7.44 (t, J = 7.6 Hz, 1H), 7.34 (d, J = 7.5 Hz, 1H), 7.24 (ddd, J = 15.1, 9.0, 3.1 Hz, 2H), 6.70 (dd, J = 11.0, 3.0 Hz, 2H), 5.23 (t, J = 5.8 Hz, 1H), 4.58 (d, J = 5.8 Hz, 2H), 3.21 (s, 3H) | 501.1 |
| 866 | 1-(3'''-(aminomethyl)-3-chloro-5'-fluoro-2'-hydroxy-[1,1':3',1'':3'',1'''-quaterphenyl]-4-yl)-3-methyl-1H-imidazol-2(3H)-one | $^1$H NMR (400 MHz, DMSO-d$_6$) δ 7.84 (s, 2H), 7.70 (s, 1H), 7.64 (d, J = 10.0 Hz, 2H), 7.54 (dd, J = 11.8, 7.7 Hz, 4H), 7.41 (s, 1H), 7.33 (d, J = 7.3 Hz, 1H), 7.23 (s, 2H), 6.70 (dd, J = 11.3, 2.9 Hz, 2H), 3.80 (s, 2H), 3.21 (s, 3H). NH or O—H protons not observed. | 500.0 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 867 | 1-(3-chloro-5'-fluoro-2'-hydroxy-3''-(4-(tetrahydrofuran-3-yl)piperazin-1-yl)-[1,1':3',1''-terphenyl]-4-yl)-3-methyl-1H-imidazol-2(3H)-one | $^1$H NMR (400 MHz, DMSO-d$_6$) δ 8.46 (s, 1H), 7.81 (d, J = 1.9 Hz, 1H), 7.62 (dd, J = 8.2, 1.9 Hz, 1H), 7.51 (d, J = 8.2 Hz, 1H), 7.29 (t, J = 7.9 Hz, 1H), 7.22-7.05 (m, 3H), 6.98-6.94 (m, 2H), 6.72-6.68 (m, 2H), 3.96-3.73 (m, 2H), 3.69-3.62 (m, 1H), 3.55-3.50 (m, 1H), 3.26-3.08 (m, 7H), 2.95-2.90 (s, 1H), 2.64-2.55 (m, 2H), 2.51-2.49 (m, 2H), 2.07-1.94 (m, 1H), 1.81-1.73 (m, 1H) | 549.3 |
| 868 | 1-(3-chloro-3''-(4-cyclobutylpiperazin-1-yl)-5'-fluoro-2'-hydroxy-[1,1':3',1''-terphenyl]-4-yl)-3-methyl-1H-imidazol-2(3H)-one | $^1$H NMR (400 MHz, DMSO-d$_6$) δ 8.46 (s, 1H), 7.80 (d, J = 1.7 Hz, 1H), 7.67-7.57 (m, 1H), 7.51 (d, J = 8.2 Hz, 1H), 7.27 (d, J = 7.9 Hz, 1H), 7.23-7.03 (m, 3H), 6.98-6.94 (m, 2H), 6.72-6.68 (m, 2H), 3.21-3.17 (m, 7H), 2.74-2.72 (m, 1H), 2.39-2.32 (m, 4H), 1.99-1.98 (m, 2H), 1.84-1.79 (s, 2H), 1.72-1.56 (m, 2H) | 533.3 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 869 | 1-(3-chloro-5'-fluoro-2'-hydroxy-3'-(6-methoxy-5-(4-(tetrahydrofuran-3-yl)piperazin-1-yl)pyridin-3-yl)-[1,1'-biphenyl]-4-yl)-3-methyl-1H-imidazol-2(3H)-one | ¹H NMR (400 MHz, CD₃OD) δ 7.95 (d, J = 2.0 Hz, 1H), 7.82 (d, J = 1.9 Hz, 1H), 7.62 (d, J = 1.9 Hz, 1H), 7.52 (d, J = 8.2 Hz, 1H), 7.45 (d, J = 2.1 Hz, 1H), 7.09 (dd, J = 8.8, 1.5 Hz, 2H), 6.67 (dd, J= 15.2, 3.0 Hz, 2H), 4.03 (s, 3H), 4.01-3.88 (m, 2H), 3.80 (dd, J = 15.7, 8.4 Hz, 1H), 3.71 (dd, J = 8.7, 6.6 Hz, 1H), 3.37 (s, 3H), 3.18-3.17 (m, 5H), 2.69 (dd, J = 24.0, 18.7 Hz, 4H), 2.22-2.09 (m, 1H), 1.97-1.84 (m, 1H). O—H protons not observed | 580.2 |
| 870 | 1-(3-chloro-5'-fluoro-2'-hydroxy-2''-(piperazin-1-yl)-[1,1':3',1''-terphenyl]-4-yl)-3-methyl-1H-imidazol-2(3H)-one | 1H NMR (400 MHz, DMSO-d₆) δ 11.22 (s, 1H), 7.87 (d, J = 1.9 Hz, 1H), 7.68 (d, J = 2.0 Hz, 1H), 7.50 (dd, J = 14.5, 7.8 Hz, 3H), 7.36-7.27 (m, 4H), 6.72 (dd, J = 11.7, 3.0 Hz, 2H), 3.21 (s, 3H), 2.89-2.88 (m, 4H), 2.73 (s, 4H). N—H or O—H proton not observed | 479.2 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 871 | (S)-1-(3-chloro-5'-fluoro-2'-hydroxy-3'-(5-(3-hydroxy-3-(hydroxymethyl)azetidin-1-yl)-6-methoxypyridin-3-yl)-[1,1'-biphenyl]-4-yl)-3-methyl-1H-imidazol-2(3H)-one | 1H NMR (400 MHz, DMSO-d₆) δ 8.51 (s, 1H), 7.80 (d, J = 1.9 Hz, 1H), 7.59 (dd, J = 8.0, 1.9 Hz, 2H), 7.51 (d, J = 8.2 Hz, 1H), 7.15 (t, J = 8.8 Hz, 2H), 6.86 (d, J = 1.9 Hz, 1H), 6.70 (dd, J = 12.7, 3.0 Hz, 2H), 4.49 (s, 1H), 3.87 (s, 3H), 3.66 (s, 1H), 3.41 (t, J = 11.1 Hz, 1H), 3.34 (d, J = 10.9 Hz, 1H), 3.21 (s, 3H), 3.08 (s, 1H), 1.15 (s, 3H), 1.00 (s, 3H), 0.95 (s, 3H) | 553.2 |
| 872 | (R)-1-(3-chloro-5'-fluoro-2'-hydroxy-3'-(5-(3-hydroxy-3-(hydroxymethyl)azetidin-1-yl)-6-methoxypyridin-3-yl)-[1,1'-biphenyl]-4-yl)-3-methyl-1H-imidazol-2(3H)-one | 1H NMR (400 MHz, DMSO-d₆) δ 8.51 (s, 1H), 7.80 (d, J = 1.9 Hz, 1H), 7.64-7.56 (m, 2H), 7.51 (d, J = 8.2 Hz, 1H), 7.16 (dd, J = 10.2, 7.3 Hz, 2H), 6.86 (d, J = 1.9 Hz, 1H), 6.70 (dd, J = 12.7, 3.0 Hz, 2H), 4.50 (s, 1H), 3.87 (s, 3H), 3.67 (d, J = 10.9 Hz, 1H), 3.43 (d, J = 9.1 Hz, 1H), 3.34 (d, J = 10.9 Hz, 1H), 3.21 (s, 3H), 3.07 (d, J = 9.1 Hz, 1H), 1.15 (s, 3H), 1.00 (s, 3H), 0.95 (s, 3H) | 553.2 |

TABLE 32-continued

Following compounds were prepared using similar procedures as described for Examples 1 through 854.

| Ex. No. | Name/Structure | $^1$H NMR Data | LCMS $(M + H)^+$ |
|---|---|---|---|
| 873 | (S)-1-(3-chloro-5'-fluoro-2'-hydroxy-3'-(5-(7-hydroxy-7-methyl-5-azaspiro[2.4]heptan-5-yl)-6-methylpyridin-3-yl)-[1,1'-biphenyl]-4-yl)-3-methyl-1,3-dihydro-2H-imidazol-2-one | — | 535.2 |
| 874 | (R)-1-(3-chloro-5'-fluoro-2'-hydroxy-3'-(5-(7-hydroxy-7-methyl-5-azaspiro[2.4]heptan-5-yl)-6-methylpyridin-3-yl)-[1,1'-biphenyl]-4-yl)-3-methyl-1,3-dihydro-2H-imidazol-2-one | — | 535.2 |

TABLE 32-continued

Following compounds were prepared using similar procedures as described for Examples 1 through 854.

| Ex. No. | Name/Structure | $^1$H NMR Data | LCMS $(M + H)^+$ |
|---|---|---|---|
| 875 | (S)-1-(3-chloro-5'-fluoro-2'-hydroxy-3'-(5-(7-hydroxy-7-methyl-5-azaspiro[2.4]heptan-5-yl)-6-methoxypyridin-3-yl)-[1,1'-biphenyl]-4-yl)-3-methyl-1,3-dihydro-2H-imidazol-2-one<br />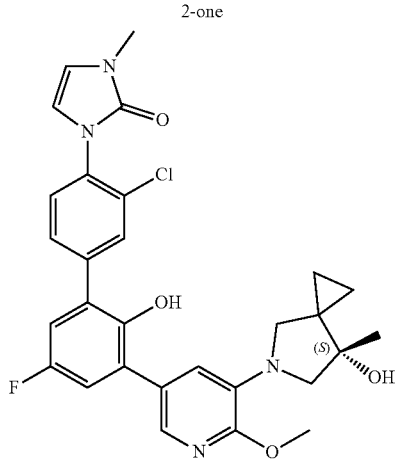 | — | 551.2 |
| 876 | (R)-1-(3-chloro-5'-fluoro-2'-hydroxy-3'-(5-(7-hydroxy-7-methyl-5-azaspiro[2.4]heptan-5-yl)-6-methoxypyridin-3-yl)-[1,1'-biphenyl]-4-yl)-3-methyl-1,3-dihydro-2H-imidazol-2-one<br />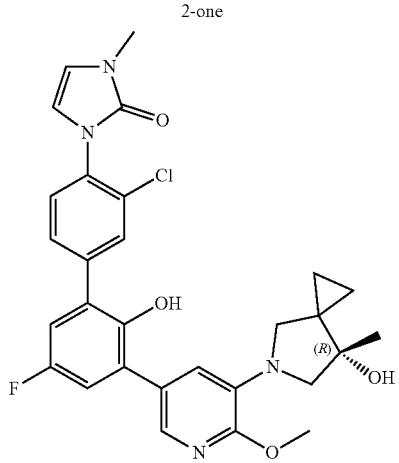 | — | 551.2 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 877 | 3'-chloro-5-fluoro-3-(5-(4-isopropylpiperazin-1-yl)-6-methylpyridin-3-yl)-4'-(3-methyl-2-oxo-2,3-dihydro-1H-imidazol-1-yl)-[1,1'-biphenyl]-2-ylmethyl carbonate | ¹H NMR (400 MHz, CD₃OD) δ 8.12 (d, J = 1.9 Hz, 1H), 7.62 (s, 1H), 7.51 (d, J = 1.9 Hz, 1H), 7.45 (d, J = 1.4 Hz, 2H), 7.33-7.15 (m, 2H), 6.57 (q, J = 3.0 Hz, 2H), 3.44 (s, 3H), 3.24 (d, J = 3.2 Hz, 3H), 2.99-2.89 (m, 4H), 2.69 (d, J = 12.9 Hz, 5H), 2.47 (s, 3H), 1.06 (d, J = 6.5 Hz, 6H) | 594.2 |
| 878 | ((3'-chloro-5-fluoro-3-(5-(4-isopropylpiperazin-1-yl)-6-methylpyridin-3-yl)-4'-(3-methyl-2-oxo-2,3-dihydro-1H-imidazol-1-yl)-[1,1'-biphenyl]-2-yl)oxy)methyl methyl carbonate | ¹H NMR (400 MHz, CD₃OD) δ 8.18 (d, J = 1.8 Hz, 1H), 7.76 (d, J = 1.9 Hz, 1H), 7.67-7.55 (m, 2H), 7.46 (d, J = 8.2 Hz, 1H), 7.19 (d, J = 8.7 Hz, 2H), 6.57 (dd, J = 8.7, 3.0 Hz, 2H), 4.86 (s, 2H), 3.30 (s, 3H), 3.25 (s, 3H), 2.99 (d, J = 4.3 Hz, 4H), 2.74-2.73 (m, 5H), 2.48 (s, 3H), 1.08 (d, J = 6.5 Hz, 6H). | 624.2 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 879 | 1-(3-chloro-5'-fluoro-2'-hydroxy-3'-(5-(1-isopropyl-1,6-diazaspiro[3.4]octan-6-yl)-6-methoxypyridin-3-yl)-[1,1'-biphenyl]-4-yl)-3-methyl-1H-imidazol-2(3H)-one | ¹H NMR (400 MHz, DMSO-d₆) δ 8.53 (s, 1H), 7.80 (d, J = 1.8 Hz, 1H), 7.69 (d, J = 1.8 Hz, 1H), 7.61 (dd, J = 8.2, 1.9 Hz, 1H), 7.52 (d, J = 8.2 Hz, 1H), 7.17 (ddd, J = 10.4, 7.1, 3.1 Hz, 2H), 7.02 (d, J = 1.7 Hz, 1H), 6.70 (dd, J = 12.4, 3.0 Hz, 2H), 3.90 (s, 3H), 3.63 (d, J = 10.3 Hz, 1H), 3.41 (t, J = 8.1 Hz, 1H), 3.25 (d, J = 9.8 Hz, 1H), 3.20 (d, J = 10.2 Hz, 4H), 3.09 (s, 1H), 2.98 (d, J = 6.9 Hz, 1H), 2.67 (s, 1H), 2.12 (t, J = 9.2 Hz, 1H), 1.98 (dd, J = 13.9, 6.4 Hz, 2H), 1.89 (s, 1H), 0.90 (dd, J = 9.1, 6.1 Hz, 6H) | 578.2 |
| 880 | 1-(3-chloro-3'-(5-(4-cyclobutylpiperazin-1-yl)-6-methoxypyridin-3-yl)-5'-fluoro-2'-hydroxy-[1,1'-biphenyl]-4-yl)-3-methyl-1H-imidazol-2(3H)-one | ¹H NMR (400 MHz, DMSO-d₆) δ 8.61 (s, 1H), 7.92 (d, J = 1.9 Hz, 1H), 7.80 (d, J = 1.9 Hz, 1H), 7.62 (dd, J = 8.2, 1.9 Hz, 1H), 7.52 (d, J = 8.2 Hz, 1H), 7.34 (d, J = 1.9 Hz, 1H), 7.19 (d, J = 9.1 Hz, 2H), 6.70 (dd, J = 12.4, 3.0 Hz, 2H), 3.92 (s, 3H), 3.21 (s, 3H), 3.10-3.05 (m, 4H), 2.78 (s, 1H), 2.42-2.41 (m, 4H), 1.98-1.96 (m, 2H), 1.86-1.80 (m, 2H), 1.70-1.55 (m, 2H) | 564.2 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 881 | (S)-1-(3-chloro-3'-(2-(3,3-difluoro-4-hydroxy-4-methylpyrrolidin-1-yl)pyridin-4-yl)-5'-fluoro-2'-hydroxy-[1,1'-biphenyl]-4-yl)-3-methyl-1,3-dihydro-2H-imidazol-2-one | ¹H NMR (400 MHz, CD$_3$OD) δ 8.14 (d, J = 5.4 Hz, 1H), 7.82 (d, J = 1.7 Hz, 1H), 7.67-7.42 (m, 2H), 7.19-7.09 (m, 2H), 6.90 (d, J = 5.3 Hz, 1H), 6.76-6.49 (m, 3H), 4.10-3.78 (m, 2H), 3.76-3.49 (m, 2H), 3.37 (s, 3H), 1.43 (t, J = 21.8 Hz, 3H). O—H protons not observed | 531.1 |
| 882 | (R)-1-(3-chloro-3'-(2-(3,3-difluoro-4-hydroxy-4-methylpyrrolidin-1-yl)pyridin-4-yl)-5'-fluoro-2'-hydroxy-[1,1'-biphenyl]-4-yl)-3-methyl-1,3-dihydro-2H-imidazol-2-one | ¹H NMR (400 MHz, CD$_3$OD) δ 8.14 (d, J = 5.4 Hz, 1H), 7.82 (d, J = 1.7 Hz, 1H), 7.67-7.42 (m, 2H), 7.19-7.09 (m, 2H), 6.90 (d, J = 5.3 Hz, 1H), 6.76-6.49 (m, 3H), 4.10-3.78 (m, 2H), 3.76-3.49 (m, 2H), 3.37 (s, 3H), 1.43 (t, J = 21.8 Hz, 3H). O—H protons not observed | 531.1 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 883 | 1-(3-chloro-3'-(5-(4-cyclobutylpiperazin-1-yl)-6-methylpyridin-3-yl)-5'-fluoro-2?-hydroxy-[1,1'-biphenyl]-4-yl)-3-methyl-1H-imidazol-2(3H)-one | $^1$H NMR (400 MHz, DMSO-d$_6$) δ 8.69 (s, 1H), 8.31 (d, J = 1.7 Hz, 1H), 7.81 (d, J = 1.8 Hz, 1H), 7.62 (dd, J = 8.2, 1.8 Hz, 1H), 7.52 (d, J = 8.3 Hz, 2H), 7.22 (d, J = 9.0 Hz, 2H), 6.70 (dd, J = 13.0, 3.0 Hz, 2H), 3.21 (s, 3H), 2.93 (s, 4H), 2.83-2.74 (m, 1H), 2.46 (s, 7H), 1.99 (d, J = 3.1 Hz, 2H), 1.81 (d, J = 8.9 Hz, 2H), 1.72-1.58 (m, 2H) | 548.2 |
| 884 | (S)-1-(3-chloro-5'-fluoro-2'-hydroxy-3'-(5-(3-hydroxy-3,4,4-trimethylpyrrolidin-1-yl)-6-methylpyridin-3-yl)-[1,1'-biphenyl]-4-yl)-3-methyl-1H-imidazol-2(3H)-one | 1H NMR (400 MHz, DMSO-d$_6$) δ 7.98 (s, 1H), 7.80 (s, 1H), 7.62 (d, J = 8.4 Hz, 1H), 7.53 (d, J = 8.1 Hz, 1H), 7.18 (dd, J = 15.8, 7.6 Hz, 3H), 6.71 (d, J = 11.4 Hz, 2H), 3.70 (d, J = 10.1 Hz, 1H), 3.49 (d, J = 8.6 Hz, 1H), 3.25 (s, 3H), 3.22-3.12 (m, 1H), 2.98 (d, J = 8.7 Hz, 1H), 2.52 (s, 3H), 1.19 (s, 3H), 1.01 (d, J = 11.5 Hz, 6H). O—H protons not observed | 537.2 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 885 | (R)-1-(3-chloro-5'-fluoro-2'-hydroxy-3'-(5-(3-hydroxy-3,4,4-trimethylpyrrolidin-1-yl)-6-methylpyridin-3-yl)-[1,1'-biphenyl]-4-yl)-3-methyl-1,3-dihydro-2H-imidazol-2-one | 1H NMR (400 MHz, DMSO-d₆) δ 7.98 (s, 1H), 7.80 (s, 1H), 7.62 (d, J = 8.1 Hz, 1H), 7.52 (d, J = 8.2 Hz, 1H), 7.14 (s, 3H), 6.70 (d, J = 12.0 Hz, 2H), 3.69 (d, J = 9.9 Hz, 1H), 3.48 (d, J = 8.6 Hz, 1H), 3.24 (s, 3H), 3.19 (s, 1H), 2.98 (d, J = 8.8 Hz, 1H), 2.51 (s, 3H), 1.19 (s, 3H), 1.01 (d, J = 11.4 Hz, 6H). O—H protons not observed | 537.2 |
| 886 | 1-(3''-(4-(tert-butyl)piperazin-1-yl)-3-deutero-5'-fluoro-2'-hydroxy-[1,1':3',1''-terphenyl]-4-yl)-3-(trichloromethyl)-1H-imidazol-2(3H)-one | ¹H NMR (400 MHz, CD₃OD) δ 7.83 (d, J = 1.9 Hz, 1H), 7.63 (d, J = 1.9 Hz, 1H), 7.51 (d, J = 8.2 Hz, 1H), 7.37 (s, 1H), 7.16(s, 1H), 7.09-7.01 (m, 4H), 6.66 (dd, J = 14.9, 3.0 Hz, 2H), 3.32-3.23 (m, 4H), 2.90-2.87 (m, 4H), 1.19 (s, 9H). O—H proton not observed | 538.2 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 887 | N-(5-(3'-(4-(tert-butyl)piperazin-1-yl)-5-fluoro-2-hydroxy-[1,1'-biphenyl]-3-yl)pyrazin-2-yl)acetamide | ¹H NMR (400 MHz, DMSO-d₆) δ 12.86 (s, 1H), 11.06 (s, 1H), 9.45-9.07 (m, 2H), 7.98 (dd, J = 10.0, 3.0 Hz, 1H), 7.30-7.19 (m, 2H), 7.12 (s, 1H), 6.94 (s, 2H), 3.15-3.10 (m, 4H), 2.77-2.52 (m, 4H), 2.17 (s, 3H), 1.06 (s, 9H). | 464.2 |
| 888 | N-(2-chloro-5'-fluoro-2'-hydroxy-3''-(piperazin-1-yl)-[1,1':3',1''-terphenyl]-3-yl)acetamide | ¹H NMR (400 MHz, DMSO-d₆) δ 9.50 (s, 1H), 7.77 (d, J = 8.0 Hz, 1H), 7.35 (t, J = 7.8 Hz, 1H), 7.28 (t, J = 7.9 Hz, 1H), 7.17 (d, J = 7.4 Hz, 1H), 7.10 (dd, J = 10.6, 7.5 Hz, 2H), 6.99-6.91 (m, 3H), 3.13 (d, J = 5.0 Hz, 4H), 2.89-2.91 (m, 4H), 2.12 (s, 3H). N—H or O—H protons not observed | 440.2 |
| 889 | 1-(3-chloro-5'-fluoro-2'-hydroxy-2''-(piperazin-1-ylmethyl)-[1,1':3',1''-terphenyl]-4-yl)-3-methyl-1H-imidazol-2(3H)-one | ¹H NMR (400 MHz, DMSO-d₆) δ 7.81 (d, J = 1.9 Hz, 1H), 7.58 (dd, J = 8.2, 1.9 Hz, 1H), 7.48 (dd, J = 7.7, 5.2 Hz, 1H), 7.42 (ddd, J = 19.9, 10.0, 4.8 Hz, 3H), 7.32-7.25 (m, 1H), 7.22 (dd, J = 9.1, 3.2 Hz, 1H), 6.91 (dd, J = 9.0, 3.2 Hz, 1H), 6.71 (dd, J = 6.8, 3.0 Hz, 2H), 3.64 (d, J = 12.2 Hz, 1H), 3.36 (s, 2H), 3.20 (s, 3H), 2.72 (s, 2H), 2.68-2.51 (m, 6H). N—H or O—H protons not observed | 493.2 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 890 | 1-(3-chloro-5'-fluoro-2'-hydroxy-3'-(6-methyl-5-(4-(tetrahydrofuran-3-yl)piperazin-1-yl)pyridin-3-yl)-[1,1'-biphenyl]-4-yl)-3-methyl-1H-imidazol-2(3H)-one | $^1$H NMR (400 MHz, DMSO-d$_6$) δ 8.69 (s, 1H), 8.32 (d, J = 1.9 Hz, 1H), 7.81 (d, J = 1.9 Hz, 1H), 7.62 (dd, J = 8.2, 1.9 Hz, 1H), 7.52 (d, J = 8.2 Hz, 2H), 7.22 (d, J = 9.1 Hz, 2H), 6.70 (dd, J = 13.2, 3.0 Hz, 2H), 3.80 (dd, J = 10.0, 6.2 Hz, 2H), 3.67 (d, J = 7.7 Hz, 1H), 3.52 (dd, J = 8.4, 6.7 Hz, 1H), 3.21 (s, 3H), 2.96 (dd, J = 15.3, 5.7 Hz, 5H), 2.62 (s, 4H), 2.47 (s, 3H), 2.07-1.93 (m, 1H), 1.86-1.68 (m, 1H) | 564.2 |
| 891 | 1-(3-chloro-5'-fluoro-2'-hydroxy-3'-(5-(1-isopropyl-1,6-diazaspiro[3.4]octan-6-yl)-6-methylpyridin-3-yl)-[1,1'-biphenyl]-4-yl)-3-methyl-1H-imidazol-2(3H)-one | 1H NMR (400 MHz, DMSO-d$_6$) δ 10.28 (s, 1H), 9.98 (s, 1H), 9.79 (d, J = 8.4 Hz, 1H), 9.69 (d, J = 8.2 Hz, 1H), 9.48 (s, 1H), 9.37 (d, J = 8.9 Hz, 2H), 8.87 (dd, J = 14.3, 2.9 Hz, 2H), 5.78 (d, J = 10.3 Hz, 1H), 5.42 (d, J = 12.4 Hz, 5H), 5.28 (s, 1H), 5.21 (d, J = 10.2 Hz, 2H), 4.90 (d, J = 6.1Hz, 1H), 4.67 (s, 3H), 4.40 (d, J = 11.9 Hz, 1H), 4.30-4.05 (m, 3H), 3.12 (dd, J = 11.0, 6.1 Hz, 6H). O—H proton not observed | 562.2 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 892 | 1-(3-chloro-5'-fluoro-2'-hydroxy-3''-(1-isopropyl-1,6-diazaspiro[3.4]octan-6-yl)-[1,1':3',1''-terphenyl]-4-yl)-3-methyl-1H-imidazol-2(3H)-one | $^1$H NMR (400 MHz, CD$_3$OD) δ 7.73 (s, 1H), 7.53 (d, J = 6.4 Hz, 1H), 7.39 (d, J = 8.2 Hz, 1H), 7.19(t, J = 7.9 Hz, 1H), 6.93 (t, J = 8.5 Hz, 2H), 6.70 (d, J = 7.6 Hz, 1H), 6.62 (s, 1H), 6.54 (dt, J = 7.8, 4.0 Hz, 3H), 3.43 (dd, J = 22.3, 10.6 Hz, 2H), 3.25 (s, 4H), 3.07 (d, J = 28.0 Hz, 2H), 2.74 (s, 1H), 2.37-1.81 (m, 4H), 1.19 (s, 2H), 0.90 (d, J = 4.8 Hz, 6H) | 547.2 |
| 893 | N-(2-chloro-5'-fluoro-2'-hydroxy-3''-(3-hydroxy-3-methylpyrrolidin-1-yl)-[1,1':3',1''-terphenyl]-3-yl)acetamide | $^1$H NMR (400 MHz, DMSO-d$_6$) δ 9.50 (s, 1H), 8.19 (s, 1H), 7.77 (d, J = 7.7 Hz, 1H), 7.35 (t, J = 7.8 Hz, 1H), 7.24-7.14 (m, 2H), 7.09 (dd, J = 9.3, 3.2 Hz, 1H), 6.90 (dd, J = 8.6, 3.2 Hz, 1H), 6.74 (d, J = 7.5 Hz, 1H), 6.63 (s, 1H), 6.47 (d, J = 8.0 Hz, 1H), 4.76 (s, 1H), 3.49-3.34 (m, 2H), 3.21 (d, J = 9.9 Hz, 2H), 2.12 (s, 3H), 1.97-1.79 (m, 2H), 1.35 (s, 3H) | 455.4 |
| 894 | N-(2-(3'-(4-(tert-butyl)piperazin-1-yl)-5-fluoro-2-hydroxy-[1,1'-biphenyl]-3-yl)pyrimidin-5-yl)acetamide | $^1$H NMR (400 MHz, DMSO-d$_6$) δ 13.35 (s, 1H), 10.63 (s, 1H), 9.17 (s, 2H), 8.04 (dd, J = 9.8, 3.2 Hz, 1H), 7.35-7.23 (m, 2H), 7.15 (s, 1H), 7.02 (d, J = 7.7 Hz, 1H), 6.93 (d, J = 7.9 Hz, 1H), 3.16 (s, 4H), 2.66 (s, 4H), 2.15 (s, 3H), 1.05 (s, 9H) | 464.2 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 895 | 1-(3-chloro-5'-fluoro-2'-hydroxy-3'-(2-(3-methyl-3-((2,2,2-trifluoroethyl)amino)pyrrolidin-1-yl)pyridin-4-yl)-[1,1'-biphenyl]-4-yl)-3-methyl-1H-imidazol-2(3H)-one | 1H NMR (400 MHz, DMSO-d$_6$) δ 8.68 (s, 1H), 8.09 (d, J = 5.2 Hz, 1H), 7.80 (d, J = 1.9 Hz, 1H), 7.61 (dd, J = 8.2, 1.9 Hz, 1H), 7.52 (d, J = 8.2 Hz, 1H), 7.21 (ddd, J = 23.5, 9.0, 3.2 Hz, 2H), 6.70 (dd, J = 12.3, 3.0 Hz, 3H), 6.54 (s, 1H), 3.59 - 3.41 (m, 2H), 3.37 (d, J = 10.6 Hz, 1H), 3.26 (d, J = 9.8 Hz, 2H), 3.21 (s, 3H), 2.61 (t, J = 8.4 Hz, 1H), 2.04-1.93 (m, 1H), 1.85- 1.72 (m, 1H), 1.22 (s, 3H) | 576.2 |
| 896 | N-(6-(3'-(4-(tert-butyl)piperazin-1-yl)-5-fluoro-2-hydroxy-[1,1'-biphenyl]-3-yl)pyridazin-3-yl)acetamide | 1H NMR (400 MHz, CD$_3$OD) δ 8.54 (d, J = 9.7 Hz, 1H), 8.31 (d, J = 9.7 Hz, 1H), 7.61-7.55 (m, 1H), 7.23 (t, J = 7.9 Hz, 1H), 7.16 (s, 1H), 7.08 (dd, J = 8.8, 3.0 Hz, 1H), 7.00 (d, J = 7.5 Hz, 1H), 6.91 (d, J = 8.3 Hz, 1H), 3.18 (s, 4H), 2.76 (s, 4H), 2.16 (s, 3H), 1.07 (s, 9H). N—H or O—H proton not observed | 464.2 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 897 | (S)-1-(3-chloro-3'-(5-(3,3-difluoro-4-hydroxy-4-methylpyrrolidin-1-yl)-6-methylpyridin-3-yl)-5'-fluoro-2'-hydroxy-[1,1'-biphenyl]-4-yl)-3-methyl-1H-imidazol-2(3H)-one | ¹H NMR (400 MHz, DMSO-d₆) δ 8.63 (s, 1H), 8.18(s, 1H), 7.81 (d, J = 1.7 Hz, 1H), 7.66-7.59 (m, 1H), 7.52 (d, J = 8.2 Hz, 1H), 7.29 (s, 1H), 7.22 (d, J = 9.0 Hz, 2H), 6.70 (dd, J = 13.6, 2.9 Hz, 2H), 5.78 (s, 1H), 3.99-3.82 (m, 1H), 3.68 (dd, J = 19.7, 13.6 Hz, 1H), 3.49 (d, J = 7.7 Hz, 1H), 3.31 (s, 1H), 3.21 (s, 3H), 2.49-2.41 (m, 3H), 1.36 (s, 3H) | 545.1 |
| 898 | (R)-1-(3-chloro-3'-(5-(3,3-difluoro-4-hydroxy-4-methylpyrrolidin-1-yl)-6-methylpyridin-3-yl)-5'-fluoro-2'-hydroxy-[1,1'-biphenyl]-4-yl)-3-methyl-1H-imidazol-2(3H)-one | ¹H NMR (400 MHz, DMSO-d₆) δ 8.67 (s, 1H), 8.18 (d, J = 1.6 Hz, 1H), 7.81 (d, J = 1.9 Hz, 1H), 7.62 (dd, J = 8.2, 1.9 Hz, 1H), 7.52 (d, J = 8.2 Hz, 1H), 7.29 (d, J = 1.6 Hz, 1H), 7.22 (d, J = 9.1 Hz, 2H), 6.70 (dd, J = 13.6, 3.0 Hz, 2H), 5.78 (s, 1H), 3.91 (dt, J = 22.2, 11.0 Hz, 1H), 3.68 (ddd, J = 18.1, 11.2, 7.0 Hz, 1H), 3.53-3.46 (m, 1H), 3.33 (s, 1H), 3.21 (s, 3H), 2.46 (s, 3H), 1.36 (d, J = 1.9 Hz, 3H) | 545.1 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 899 | (S)-1-(3-chloro-3'-(5-(3,3-difluoro-4-hydroxy-4-methylpyrrolidin-1-yl)-6-methoxypyridin-3-yl)-5'-fluoro-2'-hydroxy-[1,1'-biphenyl]-4-yl)-3-methyl-1H-imidazol-2(3H)-one | $^1$H NMR (400 MHz, DMSO-d$_6$) δ 8.56 (s, 1H), 7.80 (d, J = 1.9 Hz, 1H), 7.74 (d, J = 1.8 Hz, 1H), 7.62 (dd, J = 8.2, 1.9 Hz, 1H), 7.53 (s, 1H), 7.19 (d, J = 9.1 Hz, 2H), 7.03 (d, J = 1.8 Hz, 1H), 6.70 (d, J = 9.6 Hz, 2H), 5.77 (s, 1H), 3.98 (dd, J = 23.0, 12.0 Hz, 1H), 3.91 (s, 3H), 3.83-3.70 (m, 1H), 3.58-3.48 (m, 1H), 3.40 (d, J = 10.3 Hz, 1H), 3.21 (s, 3H), 1.33 (d, J = 1.6 Hz, 3H) | 561.1 |
| 900 | (R)-1-(3-chloro-3'-(5-(3,3-difluoro-4-hydroxy-4-methylpyrrolidin-1-yl)-6-methoxypyridin-3-yl)-5'-fluoro-2'-hydroxy-[1,1'-biphenyl]-4-yl)-3-methyl-1H-imidazol-2(3H)-one | $^1$H NMR (400 MHz, DMSO-d$_6$) δ 8.57 (s, 1H), 7.84 (s, 1H), 7.75 (d, J = 1.7 Hz, 1H), 7.63 (dd, J = 8.3, 1.7 Hz, 1H), 7.50 (d, J = 8.2 Hz, 1H), 7.16 (d, J = 8.8 Hz, 2H), 7.07 (s, 1H), 6.69 (dd, J = 13.5, 3.0 Hz, 2H), 5.77 (s, 1H), 3.97 (dd, J = 22.7, 11.3 Hz, 1H), 3.90 (s, 3H), 3.83-3.69 (m, 1H), 3.50 (d, J = 8.6 Hz, 1H), 3.40 (d, J = 8.1 Hz, 1H), 3.21 (s, 3H), 1.33 (d, J = 1.7 Hz, 3H) | 561.1 |

TABLE 32-continued

Following compounds were prepared using similar procedures as described for Examples 1 through 854.

| Ex. No. | Name/Structure | $^1$H NMR Data | LCMS (M + H)$^+$ |
|---|---|---|---|
| 901 | 4-(tert-butyl)-1-(3″-chloro-5′-fluoro-2′-hydroxy-4″-(3-methyl-2-oxo-2,3-dihydro-1H-imidazol-1-yl)-[1,1′:3′,1″-terphenyl]-3-yl)piperazin-2-one | $^1$H NMR (400 MHz, DMSO-d$_6$) δ 8.66 (s, 1H), 7.82 (d, J = 1.8 Hz, 1H), 7.62 (d, J = 1.8 Hz, 1H), 7.59-7.42 (m, 4H), 7.36 (s, 1H), 7.25-7.13 (m, 2H), 6.72-6.68 (m, 2H), 3.67-3.65 (m, 2H), 3.31 (s, 2H), 3.21 (s, 3H), 2.86-2.84 (m, 2H), 1.08 (s, 9H) | 549.2 |
| 902 | (S)-1-(3-chloro-5′-fluoro-2′-hydroxy-3′-(5-(1-isopropyl-1,6-diazaspiro[3.4]octan-6-yl)-6-methoxypyridin-3-yl)-[1,1′-biphenyl]-4-yl)-3-methyl-1,3-dihydro-2H-imidazol-2-one | $^1$H NMR (400 MHz, DMSO-d$_6$) δ 8.53 (s, 1H), 7.80 (d, J = 1.8 Hz, 1H), 7.69 (d, J = 1.8 Hz, 1H), 7.61 (dd, J = 8.2, 1.9 Hz, 1H), 7.52 (d, J = 8.2 Hz, 1H), 7.17 (ddd, J = 10.4, 7.1, 3.1 Hz, 2H), 7.02 (d, J = 1.7 Hz, 1H), 6.70 (dd, J = 12.4, 3.0 Hz, 2H), 3.90 (s, 3H), 3.63 (d, J = 10.3 Hz, 1H), 3.41 (t, J = 8.1 Hz, 1H), 3.25 (d, J = 9.8 Hz, 1H), 3.20 (d, J = 10.2 Hz, 4H), 3.09 (s, 1H), 2.98 (d, J = 6.9 Hz, 1H), 2.67 (s, 1H), 2.12 (t, J = 9.2 Hz, 1H), 1.98 (dd, J = 13.9, 6.4 Hz, 2H), 1.89 (s, 1H), 0.90 (dd, J = 9.1, 6.1 Hz, 6H) | 578.2 |

TABLE 32-continued

Following compounds were prepared using similar procedures as described for Examples 1 through 854.

| Ex. No. | Name/Structure | ¹H NMR Data | LCMS (M + H)⁺ |
|---|---|---|---|
| 903 | (R)-1-(3-chloro-5'-fluoro-2'-hydroxy-3'-(5-(1-isopropyl-1,6-diazaspiro[3.4]octan-6-yl)-6-methoxypyridin-3-yl)-[1,1'-biphenyl]-4-yl)-3-methyl-1,3-dihydro-2H-imidazol-2-one | ¹H NMR (400 MHz, DMSO-d$_6$) δ 8.53 (s, 1H), 7.80 (d, J = 1.8 Hz, 1H), 7.69 (d, J = 1.8 Hz, 1H), 7.61 (dd, J = 8.2, 1.9 Hz, 1H), 7.52 (d, J = 8.2 Hz, 1H), 7.17 (ddd, J = 10.4, 7.1, 3.1 Hz, 2H), 7.02 (d, J = 1.7 Hz, 1H), 6.70 (dd, J = 12.4, 3.0 Hz, 2H), 3.90 (s, 3H), 3.63 (d, J = 10.3 Hz, 1H), 3.41 (t, J = 8.1 Hz, 1H), 3.25 (d, J = 9.8 Hz, 1H), 3.20 (d, J = 10.2 Hz, 4H), 3.09 (s, 1H), 2.98 (d, J = 6.9 Hz, 1H), 2.67 (s, 1H), 2.12 (t, J = 9.2 Hz, 1H), 1.98 (dd, J = 13.9, 6.4 Hz, 2H), 1.89 (s, 1H), 0.90 (dd, J = 9.1, 6.1 Hz, 6H) | 578.2 |
| 904 | 1-(3''-(4-(tert-butyl)piperazin-1-yl)-3,5''-dichloro-4'',5'-difluoro-2'-hydroxy-[1,1':3',1''-terphenyl]-4-yl)-3-methyl-1H-imidazol-2(3H)-one | ¹H NMR (400 MHz, DMSO-d$_6$) δ 8.68 (s, 1H), 7.81 (d, J = 1.9 Hz, 1H), 7.62 (dd, J = 8.2, 1.9 Hz, 1H), 7.52 (d, J = 8.2 Hz, 1H), 7.31 (dd, J = 6.2, 1.9 Hz, 1H), 7.22 (d, J = 9.1 Hz, 2H), 7.15-7.08 (m, 1H), 6.72 (d, J = 3.0 Hz, 1H), 6.69 (d, J = 3.0 Hz, 1H), 3.21 (s, 3H), 3.09-3.07 (m, 4H), 2.68-2.66 (s, 4H), 1.05 (s, 9H) | 587.3 |

Example 905

1-(3'-(3-(4-(tert-butyl)piperazin-1-yl)isoxazol-5-yl)-3-chloro-5'-fluoro-2'-hydroxy-[1,1'-biphenyl]-4-yl)-3-methyl-1H-imidazol-2(3H)-one

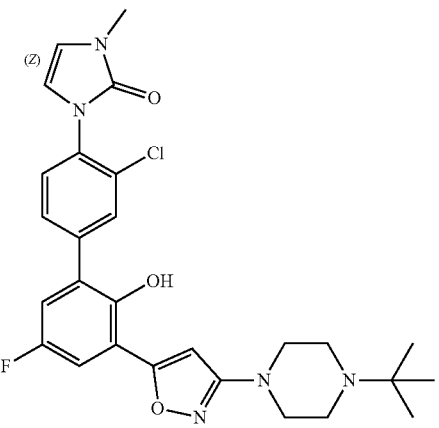 [SMILES: Cn1ccn(-c2ccc(-c3cc(F)cc(-c4cc(N5CCN(C(C)(C)C)CC5)no4)c3O)cc2Cl)c1=O]

Step 1: 1-(3-Bromo-5-fluoro-2-methoxyphenyl)ethanone

To a solution of 1-(3-bromo-5-fluoro-2-hydroxyphenyl)ethanone (4.0 g, 17.2 mmol) and CH₃I (3.7 g, 25.8 mmol) in acetone (120 mL) was added K₂CO₃ (7.1 g, 51.5 mmol). The reaction mixture was stirred at 60° C. for 4 hours under nitrogen atmosphere. After the reaction was complete by LCMS, the reaction mixture was cooled and removed the solvent under reduced pressure. The residue was diluted with H₂O (50 mL) and extracted with DCM (50 mL×3). The combined organic layers were washed with brine, dried over Na₂SO₄, filtered and removed the solvent under reduced pressure to give 1-(3-bromo-5-fluoro-2-methoxyphenyl)ethanone (2.94 g, 69% yield) as yellow liquid which was used to the next step without further purification. LCMS: 247.1 (M+H)⁺.

Step 2: methyl 3-(3-bromo-5-fluoro-2-methoxyphenyl)-3-oxopropanedithioate

To a solution of 1-(3-bromo-5-fluoro-2-methoxyphenyl)ethanone (400 mg, 1.6 mmol) in DMF/hexane (11 mL) was added NaH (58 mg, 2.4 mmol). The reaction mixture was stirred at 0° C. for 10 minutes. Then the reaction mixture was added dimethyl carbonotrithioate (246 mg, 1.8 mmol). The reaction mixture was stirred at room temperature for 4 hours under nitrogen atmosphere. After the reaction was complete by LCMS, the reaction mixture was removed the solvent under reduced pressure. The residue was diluted with H₂O (10 mL) and extracted with EA (10 mL×3). The combined organic layers were washed with brine, dried over Na₂SO₄, filtered and concentrated. The residue was purified by flash column chromatography to give methyl 3-(3-bromo-5-fluoro-2-methoxyphenyl)-3-oxopropanedithioate (437 mg, 80% yield) as a yellow solid. LCMS: 337.2 (M+H)⁺.

Step 3: 1-(3-bromo-5-fluoro-2-methoxyphenyl)-3-(4-(tert-butyl)piperazin-1-yl)-3-thioxopropan-1-one A solution of methyl 3-(3-bromo-5-fluoro-2-methoxyphenyl)-3-oxopropanedithioate (337 mg, 1.0 mmol) and 1-(tert-butyl)piperazine (156 mg, 1.1 mmol) in toluene (10 mL) was stirred at 115° C. overnight under nitrogen atmosphere. After the reaction was indicated by LCMS, the reaction mixture was cooled and removed the solvent under reduced pressure to give 1-(3-bromo-5-fluoro-2-methoxyphenyl)-3-(4-(tert-butyl)piperazin-1-yl)-3-thioxopropan-1-one (431 mg, 100% yield) as a yellow solid which was used to the next step without further purification. LCMS: 431.1 (M+H)⁺.

Step 4: 5-(3-bromo-5-fluoro-2-methoxyphenyl)-3-(4-(tert-butyl)piperazin-1-yl)isoxazole To a solution of 1-(3-bromo-5-fluoro-2-methoxyphenyl)-3-(4-(tert-butyl)piperazin-1-yl)-3-thioxopropan-1-one (431 mg, 1 mmol) in EtOH (10 mL) was added NH₂OH·HCl (278 mg, 4.0 mmol) and a solution of KOH (224 mg, 4.0 mmol) in H₂O (1 mL). The reaction mixture was stirred at 85° C. overnight under nitrogen atmosphere. After the reaction was indicated by LCMS, the reaction mixture was cooled and removed the solvent under reduced pressure. The residue was diluted with H₂O (30 mL) and extracted with EA (10 mL×3). The combined organic layers were washed with brine, dried over Na₂SO₄, filtered and concentrated. The residue was purified by flash column chromatography to give 5-(3-bromo-5-fluoro-2-methoxyphenyl)-3-(4-(tert-butyl)piperazin-1-yl)isoxazole (50 mg, 12% yield) as a yellow solid. LCMS: 412.1 (M+H)⁺.

Step 5: 1-(3'-(3-(4-(tert-butyl)piperazin-1-yl)isoxazol-5-yl)-3-chloro-5'-fluoro-2'-methoxy-[1,1'-biphenyl]-4-yl)-3-methyl-1H-imidazol-2(3H)-one To a solution of 5-(3-bromo-5-fluoro-2-methoxyphenyl)-3-(4-(tert-butyl)piperazin-1-yl)isoxazole (50 mg, 0.12 mmol) and 1-(2-chloro-4-(4,4,5,5-tetramethyl-1,3,2-dioxaborolan-2-yl)phenyl)-3-methyl-1H-imidazol-2(3H)-one (40.5 mg, 0.12 mmol) in dioxane/H₂O (v/v=8:1, 3 mL) was added Pd(dppf)Cl₂ (18 mg, 0.024 mmol) and Na₂CO₃ (38 mg, 0.36 mmol). The reaction mixture was stirred at 110° C. for 4 hours under nitrogen atmosphere. After the reaction was indicated by LCMS, the reaction mixture was cooled and removed the solvent under reduced pressure. The residue was purified by flash column chromatography (EA:MeOH=10:1) to give 1-(3'-(3-(4-(tert-butyl)piperazin-1-yl)isoxazol-5-yl)-3-chloro-5'-fluoro-2'-methoxy-[1,1'-biphenyl]-4-yl)-3-methyl-1H-imidazol-2(3H)-one (50 mg, 77% yield) as a brown solid. LCMS: 540.2 (M+H)⁺.

Step 6: 1-(3'-(3-(4-(tert-butyl)piperazin-1-yl)isoxazol-5-yl)-3-chloro-5'-fluoro-2'-hydroxy-[1,1'-biphenyl]-4-yl)-3-methyl-1H-imidazol-2(3H)-one To a solution of 1-(3'-(3-(4-(tert-butyl)piperazin-1-yl)isoxazol-5-yl)-3-chloro-5'-fluoro-2'-methoxy-[1,1'-biphenyl]-4-yl)-3-methyl-1H-imidazol-2(3H)-one (40 mg, 0.074 mmol) in DCM (1 mL) was added BBr₃ (4 mL, 1 mol/L in DCM). The reaction mixture was stirred at room temperature overnight under nitrogen atmosphere. After the reaction was indicated by LCMS, MeOH (5 mL) was added to quench the reaction. The reaction mixture was removed the solvent under reduced pressure. The residue was purified by prep-HPLC to give 1-(3'-(3-(4-(tert-butyl)piperazin-1-yl)isoxazol-5-yl)-3-chloro-5'-fluoro-2'-hydroxy-[1,1'-biphenyl]-4-yl)-3-methyl-1H-imidazol-2(3H)-one (8.3 mg, 21% yield) as a yellow solid. ¹H NMR (400 MHz, DMSO-d₆) δ 9.47 (s, 1H), 7.80 (d, J=1.9 Hz, 1H), 7.61 (dd, J=8.2, 1.9 Hz, 1H), 7.55 (d, J=8.2 Hz, 1H), 7.49 (dd, J=9.1, 3.2 Hz, 1H), 7.33 (dd, J=8.8, 3.2 Hz, 1H), 6.76 (s, 1H), 6.73 (d, J=3.0 Hz, 1H), 6.68 (d, J=3.0 Hz, 1H), 3.23-3.21 (m, 7H), 2.67-2.61 (m, 4H), 1.05 (s, 9H). LCMS: 526.3 (M+H)+.

Example 906

1-(3-chloro-5'-fluoro-2'-hydroxy-3''-((3R,5S)-4-isopropyl-3,5-dimethylpiperazin-1-yl)-[1,1':3',1''-terphenyl]-4-yl)-3-methyl-1H-imidazol-2(3H)-one

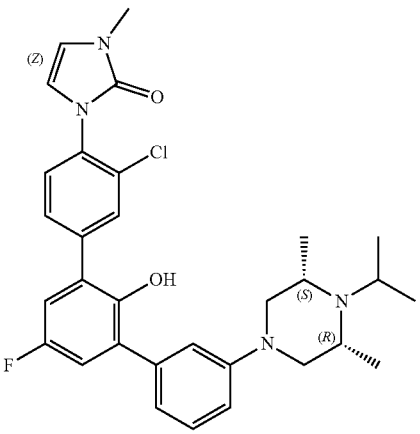

The title compound was prepared following the procedure described for Example 734 using (2R,6S)-tert-butyl 2,6-dimethylpiperazine-1-carboxylate and 1-bromo-3-iodobenzene to afford the title compound (37.3% yield). 1H NMR (400 MHz, DMSO-d6) δ 8.42 (s, 1H), 7.80 (d, J=1.9 Hz, 1H), 7.62 (dd, J=8.2, 1.9 Hz, 1H), 7.51 (d, J=8.2 Hz, 1H), 7.25 (t, J=7.9 Hz, 1H), 7.14 (ddd, J=20.1, 9.1, 3.2 Hz, 2H), 6.93-6.81 (m, 2H), 6.77 (d, J=9.0 Hz, 1H), 6.70 (dd, J=11.3, 3.0 Hz, 2H), 3.35 (d, J=12.0 Hz, 2H), 3.21 (s, 4H), 3.11-2.96 (m, 4H), 1.05 (t, J=6.8 Hz, 12H). LCMS: 549 (M+H)+.

Example 907

N-(5-(3'-(4-(tert-butyl)piperazin-1-yl)-5-fluoro-2-hydroxy-[1,1'-biphenyl]-3-yl)pyrimidin-2-yl)acetamide

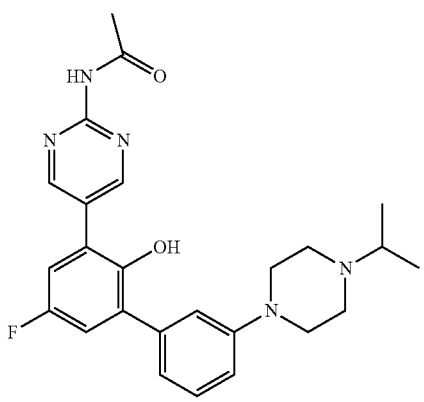 [SMILES: CC(=O)Nc1ncc(-c2cc(F)cc(-c3cccc(N4CCN(C(C)C)CC4)c3)c2O)cn1]

The title compound was prepared following the procedure described for Example 734 using N-(5-(4,4,5,5-tetramethyl-1,3,2-dioxaborolan-2-yl)pyrimidin-2-yl)acetamide and 3-bromo-3'-(4-(tert-butyl)piperazin-1-yl)-5-fluoro-[1,1'-biphenyl]-2-ol to afford the title compound (13.7% yield). 1H NMR (400 MHz, DMSO-d6) δ 10.63 (s, 1H), 8.82 (s, 2H), 8.56 (s, 1H), 7.34-7.19 (m, 2H), 7.13 (dd, J=9.2, 3.2 Hz, 1H), 7.07 (s, 1H), 6.95 (t, J=7.8 Hz, 2H), 3.16 (s, 4H), 2.65 (s, 4H), 2.22 (s, 3H), 1.05 (s, 9H). LCMS: 464 (M+H)+.

Example 908

N-(5-(3'-(4-(tert-butyl)piperazin-1-yl)-5-fluoro-2-hydroxy-[1,1'-biphenyl]-3-yl)pyridin-2-yl)acetamide

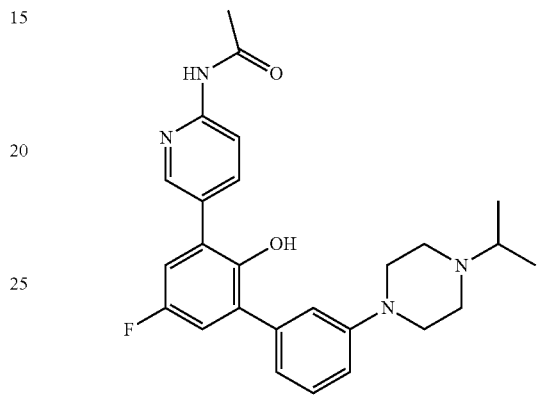

The title compound was prepared following the procedure described for Example 907 using N-(5-(4,4,5,5-tetramethyl-1,3,2-dioxaborolan-2-yl)pyridin-2-yl)acetamide and 3-bromo-3'-(4-(tert-butyl)piperazin-1-yl)-5-fluoro-[1,1'-biphenyl]-2-ol to afford the title compound (17.6% yield). 1H NMR (400 MHz, DMSO-d6) δ 10.56 (s, 1H), 8.49 (d, J=1.8 Hz, 1H), 8.33 (s, 1H), 8.12 (d, J=8.6 Hz, 1H), 7.96 (dd, J=8.6, 2.4 Hz, 1H), 7.27 (t, J=7.9 Hz, 1H), 7.15 (dd, J=9.1, 3.2 Hz, 1H), 7.07 (dd, J=9.1, 3.1 Hz, 2H), 6.94 (dd, J=13.8, 5.1 Hz, 2H), 3.15 (s, 4H), 2.65 (s, 4H), 2.09 (d, J=17.4 Hz, 3H), 1.05 (s, 9H). LCMS: 463 (M+H)+.

Example 909

1-(3-chloro-5'-fluoro-2'-hydroxy-3''-(1-isopropyl-1,7-diazaspiro[4.4]nonan-7-yl)-[1,1':3',1''-terphenyl]-4-yl)-3-methyl-1H-imidazol-2(3H)-one

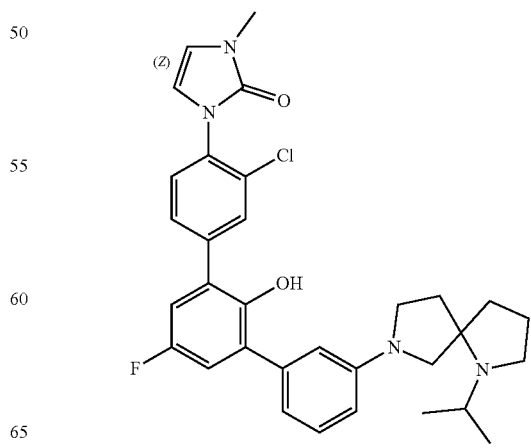

The title compound was prepared following the procedure described for Example 727 using 1-(3-chloro-5'-fluoro-2'-hydroxy-3"-(1,7-diazaspiro[4.4]nonan-7-yl)-[1,1':3',1"-terphenyl]-4-yl)-3-methyl-1H-imidazol-2(3H)-one and acetone in the presence of NaBH3CN in methanol/AcOH. $^1$H NMR (400 MHz, DMSO-$d_6$) δ 8.37 (s, 1H), 7.80 (d, J=1.9 Hz, 1H), 7.61 (dd, J=8.2, 1.9 Hz, 1H), 7.51 (d, J=8.2 Hz, 1H), 7.22 (t, J=7.9 Hz, 1H), 7.16 (dd, J=9.0, 3.2 Hz, 1H), 7.10 (dd, J=9.1, 3.2 Hz, 1H), 6.76 (d, J=7.7 Hz, 1H), 6.70 (dd, J=11.1, 3.0 Hz, 2H), 6.66-6.64 (m, 1H), 6.52 (dd, J=8.2, 1.8 Hz, 1H), 3.40 (t, J=8.6 Hz, 1H), 3.26-3.12 (m, 6H), 2.98 (d, J=9.3 Hz, 1H), 2.87-2.72 (m, 2H), 2.04 (dt, J=14.8, 9.6 Hz, 1H), 1.76-1.66 (m, 5H), 1.06-1.02 (m, 6H). LCMS: 561.3 (M+H)$^+$.

Example 910

1-(3"-(4-(tert-butyl)piperazin-1-yl)-3-chloro-5'-fluoro-2'-hydroxy-5-methoxy-[1,1':3',1"-terphenyl]-4-yl)-3-methyl-1H-imidazol-2(3H)-one

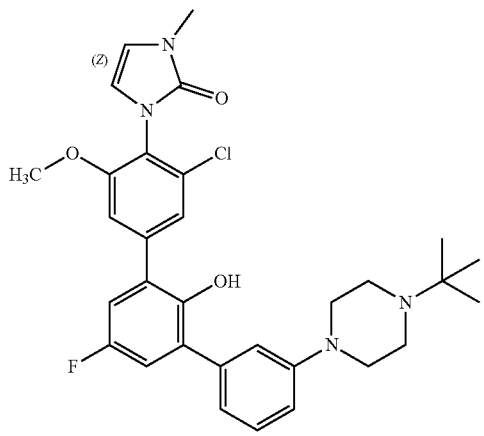 [SMILES: COc1cc(-c2cc(F)cc(-c3cccc(N4CCN(C(C)(C)C)CC4)c3)c2O)cc(Cl)c1-n1ccn(C)c1=O]

Step 1: 2-chloro-6-methoxy-4-(4,4,5,5-tetramethyl-1,3,2-dioxaborolan-2-yl)aniline To a solution of 2-chloro-6-methoxyaniline (500 mg, 3.17 mmol) and 4,4,4',4',5,5,5',5'-octamethyl-2,2'-bi(1,3,2-dioxaborolane) (1.61 g, 6.35 mmol) in Dioxane (30 mL) was added [Ir(COD)Me]$_2$ (211 mg, 0.317 mmol) and DiBPy (85 mg, 0.317 mmol). The reaction mixture was stirred at 70° C. for 2 hours under nitrogen atmosphere. After the reaction was indicated by LCMS, the reaction mixture was cooled and removed the solvent under reduced pressure. The residue was purified by flash column chromatography (PE:EA=10:1) to give 2-chloro-6-methoxy-4-(4,4,5,5-tetramethyl-1,3,2-dioxaborolan-2-yl)aniline (880 mg, 98% yield) as a yellow solid. LCMS: 284.1 (M+H)$^+$.

Step 2: 2-chloro-6-methoxy-4-(4,4,5,5-tetramethyl-1,3,2-dioxaborolan-2-yl)aniline To a solution of 2-chloro-6-methoxy-4-(4,4,5,5-tetramethyl-1,3,2-dioxaborolan-2-yl)aniline (880 mg, 3.1 mmol) and 1,3-dibromo-5-fluoro-2-(methoxymethoxy)benzene (3.9 g, 12.4 mmol) in Dioxane/H$_2$O (v/v=8:1, 30 mL) was added Pd(dppf)Cl$_2$ (454 mg, 0.62 mmol) and Na$_2$CO$_3$ (986 mg, 9.3 mmol). The reaction mixture was stirred at 110° C. for 4 hours under nitrogen atmosphere. After the reaction was indicated by LCMS, the reaction mixture was cooled and removed the solvent under reduced pressure. The residue was purified by flash column chromatography (PE:EA=4:1) to give 3'-bromo-3-chloro-5'-fluoro-5-methoxy-2'-(methoxymethoxy)-[1,1'-biphenyl]-4-amine (540 mg, 45% yield) as yellow oil. LCMS: 390.0 (M+H)$^+$.

Step 3: 3-(3'-bromo-3-chloro-5'-fluoro-5-methoxy-2'-(methoxymethoxy)-[1,1'-biphenyl]-4-yl)-1-(2,2-dimethoxyethyl)-1-methylurea To a solution of 3'-bromo-3-chloro-5'-fluoro-5-methoxy-2'-(methoxymethoxy)-[1,1'-biphenyl]-4-amine (540 mg, 1.38 mmol) in THF (30 mL) was added TEA (836 mg, 8.28 mmol) and triphosgene (143 mg, 0.483 mmol) at 0° C. After the reaction mixture was stirred for 30 minute, 2,2-dimethoxy-N-methylethanamine (165 mg, 1.38 mmol) was added to the mixture. The reaction mixture was stirred at room temperature overnight under nitrogen atmosphere. After the reaction was indicated by LCMS, the reaction mixture was diluted with H$_2$O (40 mL) and extracted with EA (30 mL*3). The combined organic layers were washed with brine, dried over Na$_2$SO$_4$, filtered and concentrated. The residue was purified by flash column chromatography (PE:EA=1:2) to give 3-(3'-bromo-3-chloro-5'-fluoro-5-methoxy-2'-(methoxymethoxy)-[1,1'-biphenyl]-4-yl)-1-(2,2-dimethoxyethyl)-1-methylurea (360 mg, 49% yield) as yellow oil. LCMS: 535.1 (M+H)$^+$.

Step 4: 1-(3'-bromo-3-chloro-5'-fluoro-2'-hydroxy-5-methoxy-[1,1'-biphenyl]-4-yl)-3-methyl-1H-imidazol-2(3H)-one To a solution of 3-(3'-bromo-3-chloro-5'-fluoro-5-methoxy-2'-(methoxymethoxy)-[1,1'-biphenyl]-4-yl)-1-(2,2-dimethoxyethyl)-1-methylurea (360 mg, 0.67 mmol) in MeOH (6 mL) was added conc. HCl (6 mL) and H$_2$O (3 mL). The reaction mixture was stirred at room temperature overnight. After the reaction was indicated by LCMS, the reaction mixture was removed the solvent under reduced pressure, diluted with H$_2$O (50 mL) and extracted with EA (20 mL×3). The combined organic layers were washed with brine, dried over Na$_2$SO$_4$, filtered and concentrated. The residue was purified by flash column chromatography (PE:EA=1:2) to give 1-(3'-bromo-3-chloro-5'-fluoro-2'-hydroxy-5-methoxy-[1,1'-biphenyl]-4-yl)-3-methyl-1H-imidazol-2(3H)-one (260 mg, 91% yield) as colorless oil. LCMS: 427.0 (M+H)$^+$.

Step 5: 1-(3"-(4-(tert-butyl)piperazin-1-yl)-3-chloro-5'-fluoro-2'-hydroxy-5-methoxy-[1,1':3',1"-terphenyl]-4-yl)-3-methyl-1H-imidazol-2(3H)-one To a solution of 1-(3'-bromo-3-chloro-5'-fluoro-2'-hydroxy-5-methoxy-[1,1'-biphenyl]-4-yl)-3-methyl-1H-imidazol-2(3H)-one (260 mg, 0.61 mmol) and 1-(tert-butyl)-4-(3-(4,4,5,5-tetramethyl-1,3,2-dioxaborolan-2-yl)phenyl)piperazine (209 mg, 0.61 mmol) in dioxane/H$_2$O (v/v=8:1, 10 mL) was added Pd(dppf)Cl$_2$ (88 mg, 0.12 mmol) and Na$_2$CO$_3$ (193 mg, 1.8 mmol). The reaction mixture was stirred at 110° C. for 4 hours under nitrogen atmosphere. After the reaction was indicated by LCMS, the reaction mixture was cooled and removed the solvent under reduced pressure. The residue was purified by flash column chromatography (100% EA) to give the crude which was further purified by prep-HPLC to give 1-(3"-(4-(tert-butyl)piperazin-1-yl)-3-chloro-5'-fluoro-2'-hydroxy-5-methoxy-[1,1': 3',1''-terphenyl]-4-yl)-3-methyl-1H-imidazol-2(3H)-one (31.2 mg, 9% yield) as a white solid. $^1$H NMR (400 MHz, DMSO-d$_6$) δ 8.46 (s, 1H), 7.37 (d, J=1.7 Hz, 1H), 7.32-7.25 (m, 2H), 7.22 (dd, J=9.0, 3.2 Hz, 1H), 7.12 (dd, J=9.2, 3.2 Hz, 1H), 7.07 (s, 1H), 6.98-6.62 (m, 2H), 6.65 (d, J=3.0 Hz, 1H), 6.47 (d, J=3.0 Hz, 1H), 3.83 (s, 3H), 3.19-3.15 (m, 7H), 2.66-2.64 (m, 4H), 1.05 (s, 9H). LCMS: 565.4 (M+H)$^+$.

Example 911

1-(3-chloro-5'-fluoro-2'-hydroxy-3'-(5-(1-isopropyl-1,7-diazaspiro[4.4]nonan-7-yl)-6-methylpyridin-3-yl)-[1,1'-biphenyl]-4-yl)-3-methyl-1H-imidazol-2(3H)-one

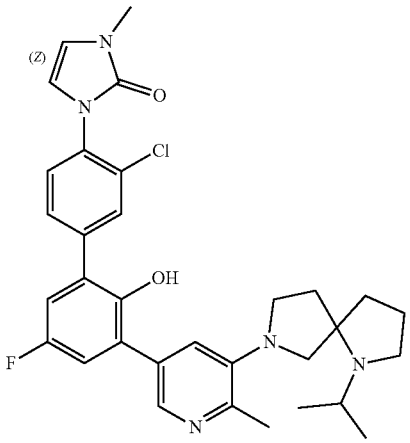 [SMILES: Cc1ncc(-c2cc(F)cc(-c3ccc(-n4ccn(C)c4=O)c(Cl)c3)c2O)cc1N1CCC2(CCCN2C(C)C)C1]

The title compound was prepared following the procedure described for Example 909 using 1-(3-chloro-5'-fluoro-2'-hydroxy-3'-(6-methyl-5-(1,7-diazaspiro[4.4]nonan-7-yl)pyridin-3-yl)-[1,1'-biphenyl]-4-yl)-3-methyl-1H-imidazol-2(3H)-one and propan-2-one to afford the title compound (27% yield). $^1$H NMR (400 MHz, CD$_3$OD) δ 8.13 (s, 1H), 7.83 (s, 1H), 7.65 (d, J=9.8 Hz, 1H), 7.53 (d, J=8.2 Hz, 1H), 7.46 (s, 1H), 7.13 (d, J=8.7 Hz, 2H), 6.68 (dd, J=15.7, 2.9 Hz, 2H), 3.52 (d, J=9.2 Hz, 1H), 3.48-3.42 (m, 1H), 3.42-3.36 (m, 5H), 3.00 (s, 1H), 2.93 (d, J=8.9 Hz, 2H), 2.60 (s, 3H), 2.33-2.19 (m, 1H), 1.98 (s, 1H), 1.88 (dd, J=31.9, 7.0 Hz, 4H), 1.26-1.16 (m, 6H). O—H proton not observed. LCMS: 576.2 (M+H)$^+$.

Example 912

N-(6-(3'-(4-(tert-butyl)piperazin-1-yl)-5-fluoro-2-hydroxy-[1,1'-biphenyl]-3-yl)pyridin-3-yl)acetamide

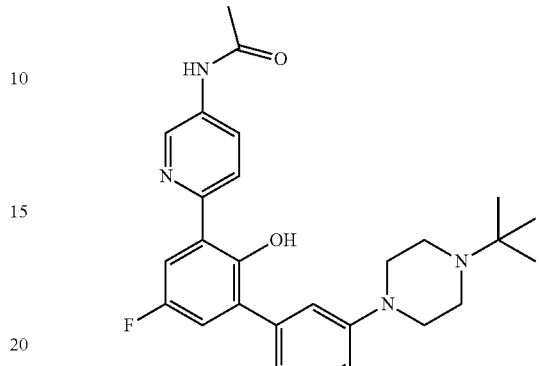

The title compound was prepared following the procedure described for Example 908 using 1-(tert-butyl)-4-(5'-fluoro-2'-methoxy-3'-(4,4,5,5-tetramethyl-1,3,2-dioxaborolan-2-yl)-[1,1'-biphenyl]-3-yl)piperazine, and N-(6-bromopyridin-3-yl)acetamide followed by BBr$_3$. $^1$H NMR (400 MHz, DMSO-d$_6$) δ 14.47 (s, 1H), 10.43 (s, 1H), 8.83 (d, J=2.2 Hz, 1H), 8.26 (s, 2H), 7.82 (dd, J=10.2, 3.1 Hz, 1H), 7.20 (ddd, J=20.9, 15.4, 9.9 Hz, 3H), 7.07-6.82 (m, 2H), 3.15 (s, 4H), 2.65 (s, 4H), 2.12 (s, 3H), 1.05 (s, 9H). LCMS: 463.3 (M+H)$^+$.

Example 913

1-(3-chloro-5'-fluoro-2'-hydroxy-3'-(5-(1-isopropyl-1,7-diazaspiro[4.4]nonan-7-yl)-6-methoxypyridin-3-yl)-[1,1'-biphenyl]-4-yl)-3-methyl-1H-imidazol-2(3H)-one

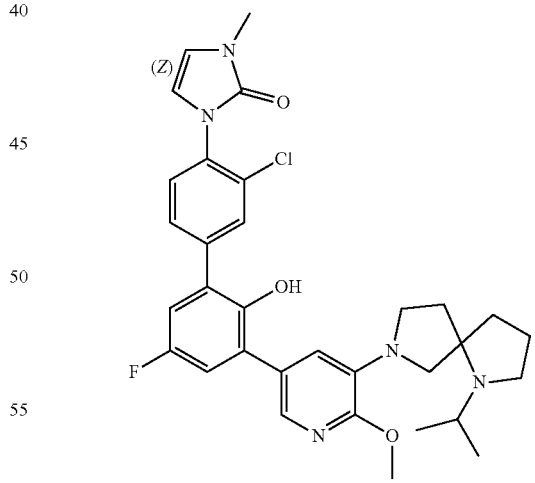

The title compound was prepared following the procedure described for Example 911 using 1-(3-chloro-5'-fluoro-2'-hydroxy-3'-(6-methoxy-5-(1,7-diazaspiro-[4.4]nonan-7-yl)pyridin-3-yl)-[1,1'-biphenyl]-4-yl)-3-methyl-1H-imidazol-2(3H)-one and acetone to afford the title compound. $^1$H NMR (400 MHz, DMSO-d$_6$) δ 8.52 (s, 1H), 7.79 (d, J=1.9 Hz, 1H), 7.66 (d, J=1.8 Hz, 1H), 7.61 (dd, J=8.2, 1.9 Hz, 1H), 7.52 (d, J=8.2 Hz, 1H), 7.16 (dt, J=7.9, 3.2 Hz, 2H), 6.97 (d, J=1.8 Hz, 1H), 6.70 (dd, J=12.6, 3.0 Hz, 2H), 3.88 (s, 3H), 3.38 (dd, J=13.3, 8.9 Hz, 3H), 3.21 (s, 3H), 3.17 (d, J=6.8 Hz, 1H), 2.94 (d, J=9.8 Hz, 1H), 2.79 (d, J=27.8 Hz, 2H), 1.99 (d, J=11.4 Hz, 1H), 1.79-1.56 (m, 5H), 1.04 (dd, J=11.9, 6.5 Hz, 6H). LCMS: 592.2 (M+H)+.

Example 914

1-(3'-(6-amino-5-(4-(tert-butyl)piperazin-1-yl)pyridin-3-yl)-3-chloro-5'-fluoro-2'-hydroxy-[1,1'-biphenyl]-4-yl)-3-methyl-1H-imidazol-2(3H)-one

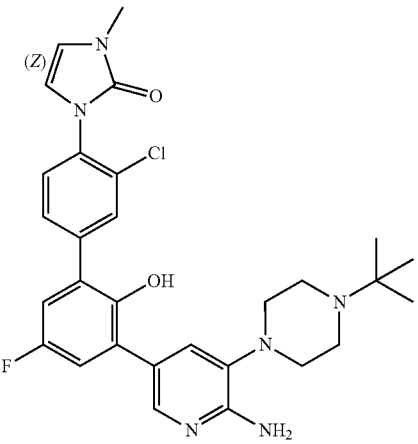 [SMILES: Cn1ccn(-c2ccc(-c3cc(F)cc(-c4cnc(N)c(N5CCN(C(C)(C)C)CC5)c4)c3O)cc2Cl)c1=O]

The title compound was prepared following the procedure described for Example 722 using 2-(6-amino-5-(4-(tert-butyl)piperazin-1-yl)pyridin-3-yl)-6-bromo-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-$d_6$) δ 8.49 (s, 1H), 7.91 (d, J=2.0 Hz, 1H), 7.80 (d, J=1.9 Hz, 1H), 7.61 (dd, J=8.2, 1.9 Hz, 1H), 7.51 (d, J=8.2 Hz, 1H), 7.36 (d, J=1.9 Hz, 1H), 7.12 (ddd, J=9.7, 6.8, 3.2 Hz, 2H), 6.70 (dd, J=11.9, 3.0 Hz, 2H), 5.66 (s, 2H), 3.21 (s, 3H), 2.87 (s, 4H), 2.70 (s, 4H), 1.06 (s, 9H). LCMS: 551.2 (M+H)+.

Example 915

1-(3-chloro-5'-fluoro-2'-hydroxy-3'-(2-(1-imino-1-oxidothiomorpholino)pyridin-4-yl)-[1,1'-biphenyl]-4-yl)-3-methyl-1H-imidazol-2(3H)-one

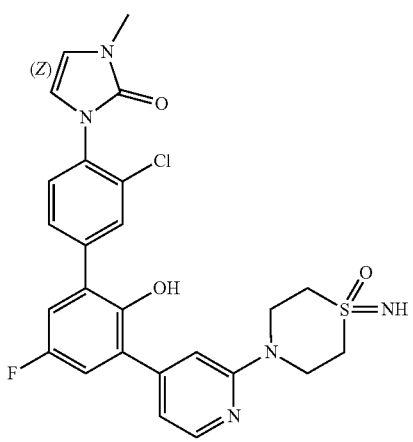 [SMILES: Cn1ccn(-c2ccc(-c3cc(F)cc(-c4ccnc(N5CCS(=N)(=O)CC5)c4)c3O)cc2Cl)c1=O]

Step 1: 1-(3-chloro-5'-fluoro-2'-(methoxymethoxy)-3'-(2-thiomorpholinopyridin-4-yl)-[1,1'-biphenyl]-4-yl)-3-methyl-1H-imidazol-2(3H)-one The title compound was prepared following the procedure described for Example 726 using 1-(3-chloro-5'-fluoro-3'-(2-fluoropyridin-4-yl)-2'-(methoxymethoxy)-[1,1'-biphenyl]-4-yl)-3-methyl-1H-imidazol-2(3H)-one and thiomorpholine to afford the title compound. LCMS: 541.2 (M+H)+.

Step 2: 1-(3-chloro-5'-fluoro-3'-(2-(1-imino-1-oxidothiomorpholino)pyridin-4-yl)-2'-(methoxymethoxy)-[1,1'-biphenyl]-4-yl)-3-methyl-1H-imidazol-2(3H)-one To a solution of 1-(3-chloro-5'-fluoro-2'-(methoxymethoxy)-3'-(2-thiomorpholinopyridin-4-yl)-[1,1'-biphenyl]-4-yl)-3-methyl-1H-imidazol-2(3H)-one (250 mg, 0.46 mmol) in MeOH (6 mL) was added PhI(OAc)$_2$ (521 mg, 1.6 mmol) and NH$_2$COONH$_4$ (124 mg, 1.6 mmol). The reaction mixture was stirred at room temperature for 12 hours under nitrogen atmosphere. After the reaction was complete by LCMS, the reaction mixture was removed the solvent under reduced pressure. The residue was further purified by prep-TLC to afford the title compound (17% yield). LCMS: 572.1 (M+H)+.

Step 3: 1-(3-chloro-5'-fluoro-2'-hydroxy-3'-(2-(1-imino-1-oxidothiomorpholino)pyridin-4-yl)-[1,1'-biphenyl]-4-yl)-3-methyl-1H-imidazol-2(3H)-one To a solution of 1-(3-chloro-5'-fluoro-3'-(2-(1-imino-1-oxidothiomorpholino)pyridin-4-yl)-2'-(methoxymethoxy)-[1,1'-biphenyl]-4-yl)-3-methyl-1H-imidazol-2(3H)-one (45 mg, 0.08 mmol) in MeOH (3 mL) was added HCl (6N, 1 mL). The reaction mixture was stirred at room temperature for 12 hours under nitrogen atmosphere. After the reaction was indicated by LCMS, the reaction mixture was removed the solvent under reduced pressure. The residue was purified by prep-HPLC to afford the title compound (5.9 mg, 14% yield). $^1$H NMR (400 MHz, CD$_3$OD) δ 8.14 (d, J=5.2 Hz, 1H), 7.71 (d, J=1.9 Hz, 1H), 7.51 (dd, J=8.2, 1.9 Hz, 1H), 7.41 (d, J=8.2 Hz, 1H), 7.08-6.95 (m, 3H), 6.85 (dd, J=5.2, 1.2 Hz, 1H), 6.55 (dd, J=16.1, 3.0 Hz, 2H), 4.24 (dd, J=10.6, 4.6 Hz, 2H), 3.98-3.88 (m, 2H), 3.25 (s, 3H), 3.06 (t, J=4.1 Hz, 4H). N—H or O—H protons not observed. LCMS: 528.2 (M+H)+.

Example 916

1-(4-(2-(3-(4-(tert-Butyl)piperazin-1-yl)phenyl)-3-hydroxy-6-methylpyridin-4-yl)-2-chlorophenyl)-3-methyl-1H-imidazol-2(3H)-one

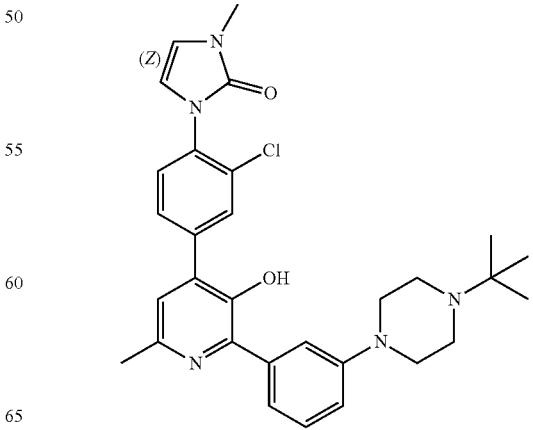

Step 1: 2-Bromo-4-iodo-6-methylpyridin-3-ol

A mixture of 2-bromo-6-methylpyridin-3-ol (5.0 g, 26.6 mmol), I₂ (10.0 g, 40.0 mmol) and Na₂CO₃ (8.5 g, 80.0 mmol) in water (150 mL) was stirred at 50° C. for 8 hours. After the reaction mixture was cooled to room temperature, the reaction mixture was adjusted pH=3-4 with 3 N HCl and extracted with EA. The combined organic layer was concentrated in vacuo. The residue was purification by FCC (EA/PE=1/3) to afford 2-bromo-4-iodo-6-methylpyridin-3-ol (5.5 g, 68% yield). LCMS: 313 (M+H)⁺.

Step 2: 1-(4-(2-bromo-3-hydroxy-6-methylpyridin-4-yl)-2-chlorophenyl)-3-methyl-1H-imidazol-2(3H)-one To a solution of 2-bromo-4-iodo-6-methylpyridin-3-ol (1.0 g, 2.5 mmol) in 1,4-dioxane/H₂O (30 mL/5 mL) was added 1-(2-chloro-4-(4,4,5,5-tetramethyl-1,3,2-dioxaborolan-2-yl)phenyl)-3-methyl-1H-imidazol-2(3H)-one (1.3 g, 3.1 mmol, 80% purity), Pd(dppf)Cl₂ (150 mg, 0.2 mmol) and K₃PO₄ (1.6 g, 7.5 mmol). The reaction mixture was stirred at 60° C. for 2 hours under N₂. The reaction mixture was cooled, added water, and extracted with ethyl acetate (100 mL×3). The combined organic layers were concentrated. The residue was purified by FCC (DCM/MeOH=20/1) to obtain 1-(4-(2-bromo-3-hydroxy-6-methylpyridin-4-yl)-2-chlorophenyl)-3-methyl-1H-imidazol-2(3H)-one (0.4 g, 29.5% yield). LCMS: 394 (M+H)⁺.

Step 3: 1-(4-(2-(3-(4-(tert-butyl)piperazin-1-yl)phenyl)-3-hydroxy-6-methylpyridin-4-yl)-2-chlorophenyl)-3-methyl-1H-imidazol-2(3H)-one To a solution of 1-(4-(2-bromo-3-hydroxy-6-methylpyridin-4-yl)-2-chlorophenyl)-3-methyl-1H-imidazol-2(3H)-one (300.0 mg, 0.76 mmol) in dioxane/H₂O (15 mL/3 mL) was added 1-(tert-butyl)-4-(3-(4,4,5,5-tetramethyl-1,3,2-dioxaborolan-2-yl)phenyl)piperazine (340.0 mg, 1.0 mmol), Pd(dppf)Cl₂ (55.6 mg, 0.08 mmol) and K₃PO₄ (485.0 mg, 2.3 mmol). The reaction mixture was stirred at 100° C. for 4 hours under N₂. LCMS showed the reaction was completed. The reaction mixture was cooled, added water, and extracted with ethyl acetate (50 mL×3). Combined organic layers were concentrated. The residue was purified by silica chromatographic column (DCM/MeOH=10/1) to afford 1-(4-(2-(3-(4-(tert-butyl)piperazin-1-yl)phenyl)-3-hydroxy-6-methylpyridin-4-yl)-2-chlorophenyl)-3-methyl-1H-imidazol-2(3H)-one (61.6 mg, 15% yield) as a yellow solid. ¹H NMR (400 MHz, DMSO-d₆) δ 8.79 (s, 1H), 7.85 (d, J=2.0 Hz, 1H), 7.67 (d, J=8.4 Hz, 2.0 Hz, 1H), 7.65 (d, J=1.6 Hz, 1H), 7.38 (s, 1H), 7.28 (dd, J=15.2 Hz, 7.2 Hz, 2H), 7.18 (s, 1H), 6.97 (d, J=7.2 Hz, 1H), 6.72 (dd, J=10.0 Hz, 2.8 Hz, 2H), 3.21 (s, 3H), 3.16 (s, 4H), 2.68 (s, 4H), 2.46 (s, 3H), 1.07 (s, 9H). LCMS: 532.2 (M+H)⁺.

Example 917

1-(4-(4-(3-(4-(tert-Butyl)piperazin-1-yl)phenyl)-3-hydroxy-6-methylpyridin-2-yl)-2-chlorophenyl)-3-methyl-1H-imidazol-2(3H)-one

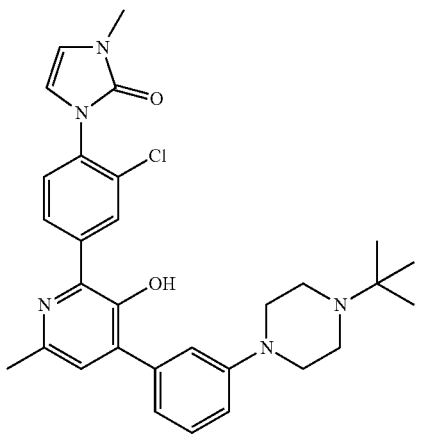 [SMILES: Cc1cc(-c2cccc(N3CCN(C(C)(C)C)CC3)c2)c(O)c(-c2ccc(-n3ccn(C)c3=O)c(Cl)c2)n1]

The title compound was prepared following the procedures described for Example 916 using 2,4-dibromo-6-methylpyridin-3-ol, 1-(tert-butyl)-4-(3-(4,4,5,5-tetramethyl-1,3,2-dioxaborolan-2-yl)phenyl)piperazine, and 1-(2-chloro-4-(4,4,5,5-tetramethyl-1,3,2-dioxaborolan-2-yl)phenyl)-3-methyl-1H-imidazol-2(3H)-one to afford the title compound. ¹H NMR (400 MHz, DMSO-d₆) δ 8.90 (s, 1H), 8.11 (d, J=1.4 Hz, 1H), 8.02-7.94 (m, 1H), 7.52 (d, J=8.3 Hz, 1H), 7.31 (t, J=7.9 Hz, 1H), 7.14 (d, J=17.7 Hz, 2H), 6.99 (t, J=7.5 Hz, 2H), 6.71 (dd, J=9.0, 2.9 Hz, 2H), 3.19 (s, 7H), 2.65 (s, 4H), 2.47 (s, 3H), 1.05 (s, 9H). LCMS: 532.2 (M+H)⁺.

Example 918

1-(3″-(4-(tert-butyl)piperazin-1-yl)-3-chloro-5′-fluoro-2′-hydroxy-[1,1′:3′,1″-terphenyl]-4-yl)-3-methylimidazolidin-2-one

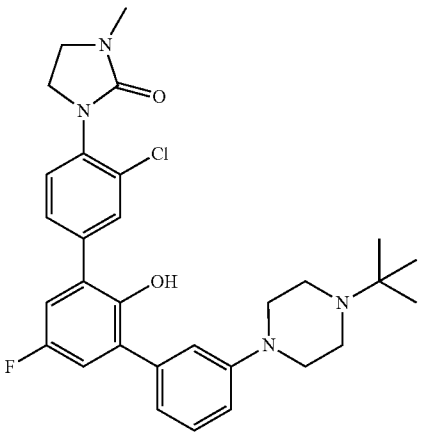 [SMILES: CN1CCN(c2ccc(-c3cc(F)cc(-c4cccc(N5CCN(C(C)(C)C)CC5)c4)c3O)cc2Cl)C1=O]

The title compound was prepared following the procedures described for Example 734 using 1-(2-chloro-4-(4,4, 5,5-tetramethyl-1,3,2-dioxaborolan-2-yl)phenyl)-3-methyl-imidazolidin-2-one and 3-bromo-3'-(4-(tert-butyl)piperazin-1-yl)-5-fluoro-[1,1'-biphenyl]-2-ol to afford the title compound. $^1$H NMR (400 MHz, DMSO-d$_6$) δ 8.39 (s, 1H), 7.71 (d, J=2.0 Hz, 1H), 7.54 (dd, J=8.3, 2.0 Hz, 1H), 7.45 (d, J=8.3 Hz, 1H), 7.28 (t, J=7.9 Hz, 1H), 7.15-6.96 (m, 3H), 6.95 (t, J=8.2 Hz, 2H), 3.75-3.70 (m, 2H), 3.51-3.46 (m, 2H), 3.21-3.08 (m, 4H), 2.76 (d, J=7.5 Hz, 3H), 2.66-2.61 (m, 4H), 1.05 (s, 9H). LCMS: 537.3 (M+H)$^+$.

Example 919

N-(3''-(4-(tert-butyl)piperazin-1-yl)-3-chloro-5'-fluoro-2'-hydroxy-[1,1':3',1''-terphenyl]-4-yl)acetamide

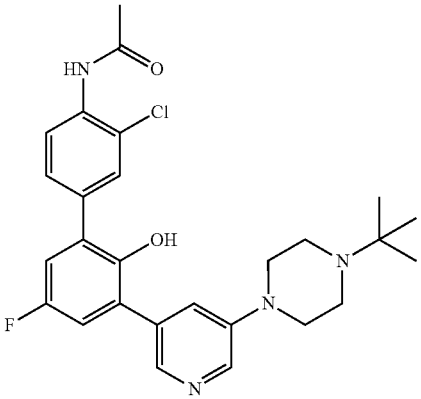 [SMILES: CC(=O)Nc1ccc(-c2cc(F)cc(-c3cncc(N4CCN(C(C)(C)C)CC4)c3)c2O)cc1Cl]

The title compound was prepared following the procedures described for Example 918 using N-(2-chloro-4-(4,4,5,5-tetramethyl-1,3,2-dioxaborolan-2-yl)phenyl)acetamide, 2,6-dibromo-4-fluorophenol, 1-(tert-butyl)-4-(3-(4,4,5,5-tetramethyl-1,3,2-dioxaborolan-2-yl)phenyl)piperazine to afford the title compound. $^1$H NMR (400 MHz, DMSO-d$_6$) δ 9.56 (s, 1H), 8.33 (s, 0.6H), 8.17 (s, 0.6H), 7.78 (d, J=8.4 Hz, 1H), 7.69 (d, J=1.9 Hz, 1H), 7.49 (dd, J=8.4, 1.9 Hz, 1H), 7.27 (t, J=7.9 Hz, 1H), 7.09 (ddd, J=17.4, 9.1, 3.2 Hz, 3H), 6.94 (dd, J=13.7, 5.0 Hz, 2H), 3.16 (s, 4H), 2.66 (s, 4H), 2.12 (s, 3H), 1.06 (s, 9H). LCMS: 496 (M+H)$^+$.

Example 920

1-(4-{6-[3-(4-tert-Butyl-piperazin-1-yl)-phenyl]-5-hydroxy-2-methyl-pyrimidin-4-yl}-2-chloro-phenyl)-3-methyl-1,3-dihydro-imidazol-2-one

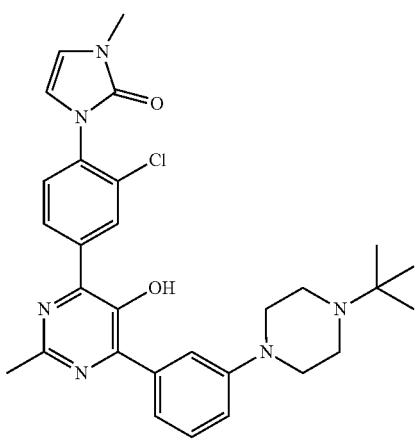 [SMILES: Cc1nc(-c2cccc(N3CCN(C(C)(C)C)CC3)c2)c(O)c(-c2ccc(-n3ccn(C)c3=O)c(Cl)c2)n1]

The title compound was prepared following the procedures described for Example 916 using 4,6-dichloro-5-methoxy-2-methyl-pyrimidine, 1-tert-butyl-4-[3-(4,4,5,5-tetramethyl-[1,3,2]dioxaborolan-2-yl)-phenyl]-piperazine and 1-[2-chloro-4-(4,4,5,5-tetramethyl-[1,3,2]dioxaborolan-2-yl)-phenyl]-3-methyl-1,3-dihydro-imidazol-2-one followed by BBr$_3$ to afford the title compound. $^1$H NMR (400 MHz, CD$_3$OD) δ 8.26 (d, J=1.8 Hz, 1H), 8.09 (dd, J=8.3, 1.9 Hz, 1H), 7.47 (dd, J=11.4, 5.0 Hz, 2H), 7.34 (dt, J=15.7, 7.7 Hz, 2H), 7.04 (dd, J=8.1, 1.5 Hz, 1H), 6.57 (dd, J=8.0, 3.0 Hz, 2H), 3.46-3.29 (m, 4H), 3.25 (s, 3H), 3.18-3.14 (m, 4H), 2.57 (s, 3H), 1.26 (d, J=10.6 Hz, 9H). O—H proton not observed. LCMS: 533.2 (M+H)$^+$.

Example 921

1-(3''-(4-(tert-Butyl)piperazin-1-yl)-3-chloro-5'-fluoro-2'-hydroxy-[1,1':3',1''-terphenyl]-4-yl)-3-methylurea

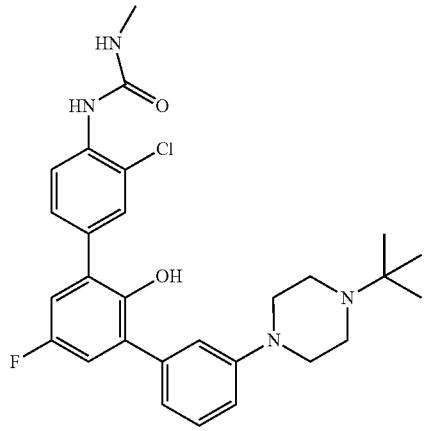 [SMILES: CNC(=O)Nc1ccc(-c2cc(F)cc(-c3cccc(N4CCN(C(C)(C)C)CC4)c3)c2O)cc1Cl]

Step 1: 1-(4-bromo-2-chlorophenyl)-3-methylurea

To a solution of 4-bromo-2-chloroaniline (1.5 g, 7.2 mmol) in DMF (25 mL) was added TEA (0.88 g, 8.6 mmol) and CDI (1.76 g, 10.8 mmol) at 0° C. After the reaction mixture was stirred for 5 hours, methanamine (1.2 mL, 10.8 mmol) was added to the mixture. The reaction mixture was stirred at room temperature for 2 hours under nitrogen atmosphere. After the reaction was complete by LCMS, the reaction mixture was diluted with H$_2$O (20 mL) and extracted with EA (20 mL×3). The combined organic layers were washed with brine, dried over Na$_2$SO$_4$, filtered and concentrated. The residue was purified by flash column chromatography to afford 1-(4-bromo-2-chlorophenyl)-3-methylurea (700 mg, 37% yield). LCMS: 263.0 (M+H)$^+$.

Step 2: 1-(3''-(4-(tert-butyl)piperazin-1-yl)-3-chloro-5'-fluoro-2'-hydroxy-[1,1':3',1''-terphenyl]-4-yl)-3-methylurea The title compound was prepared following the procedures described for Example 1 using 3-bromo-3'-(4-(tert-butyl)piperazin-1-yl)-5-fluoro-[1,1'-biphenyl]-2-ol and 1-(2-chloro-4-(4,4,5,5-tetramethyl-1,3,2-dioxaborolan-2-yl)phenyl)-3-methylurea to give the crude which was further purified by prep-HPLC to afford the title compound (7.8% yield). ¹H NMR (400 MHz, DMSO-d₆) δ 8.29-8.17 (m, 2H), 8.09 (s, 1H), 7.63 (d, J=2.0 Hz, 1H), 7.43 (dd, J=8.6, 2.0 Hz, 1H), 7.26 (d, J=7.9 Hz, 1H), 7.06 (td, J=9.2, 6.0 Hz, 3H), 6.93 (dd, J=14.8, 6.2 Hz, 3H), 3.20-3.04 (m, 4H), 2.68 (d, J=4.6 Hz, 3H), 2.66-2.60 (m, 4H), 1.05 (s, 9H). LCMS: 511.2 (M+H)⁺.

Example 922

1-(3'-(5-(4-(tert-Butyl)piperazin-1-yl)-6-(dimethylamino)pyridin-3-yl)-3-chloro-5'-fluoro-2'-hydroxy-[1,1'-biphenyl]-4-yl)-3-methyl-1H-imidazol-2(3H)-one

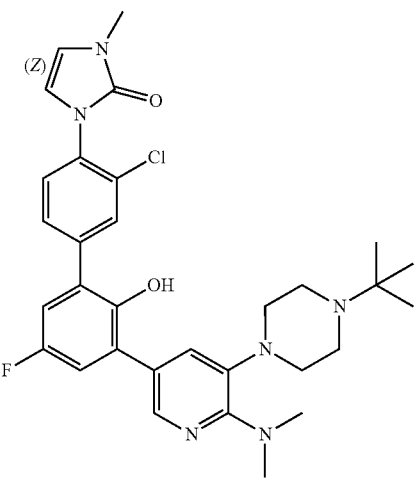 [SMILES: CN(C)c1ncc(-c2cc(F)cc(-c3ccc(-n4ccn(C)c4=O)c(Cl)c3)c2O)cc1N1CCN(C(C)(C)C)CC1]

Step 1: tert-Butyl 1-(5-bromo-2-nitropyridin-3-yl)-4-(tert-butyl)piperazine

To a solution of 5-bromo-3-fluoro-2-nitropyridine (2.5 g, 11.4 mmol) in DMF (35 mL) was added 1-(tert-butyl)piperazine (2.5 g, 17.0 mmol) and TEA (2.5 mL). The reaction mixture was stirred at 90° C. for 12 hours. After the reaction was indicated by LCMS, the reaction mixture was cooled and removed the solvent under reduced pressure. The residue was dissolved in H₂O (25 mL) and extracted with EA (15 mL×3). The combined organic layers were washed with brine, dried over Na₂SO₄, filtered, and concentrated to afford the title compound. (85% yield). LCMS: 343.2 (M+H)⁺.

Step 2: 5-Bromo-3-(4-(tert-butyl)piperazin-1-yl)pyridin-2-amine

A solution of tert-butyl 1-(5-bromo-2-nitropyridin-3-yl)-4-(tert-butyl)piperazine (1.6 g, 4.6 mmol), Fe (3.8 g, 35 mmol) and NH₄Cl (3.6 g, 35 mmol) in MeOH/H₂O (40 mL, 1:1) was stirred at 70° C. for 2 hours. After the reaction was indicated by LCMS, the reaction mixture was cooled and filtered. The filtrate was dissolved in H₂O (25 mL) and extracted with EA (15 mL×3). The combined organic layers were washed with brine, dried over Na₂SO₄, filtered, and concentrated to afford the title compound. (83% yield). LCMS: 313.2 (M+H)⁺.

Step 3: tert-butyl 5-bromo-3-(4-(tert-butyl)piperazin-1-yl)-N,N-dimethylpyridin-2-amine A solution of 5-bromo-3-(4-(tert-butyl)piperazin-1-yl)pyridin-2-amine (1.0 g, 3.2 mmol) and NaH (200 mg, 4.8 mmol) in DMF (20 mL) was stirred at 0° C. for 0.5 hours. Then to the reaction mixture was added CH₃I (0.3 mL, 4.2 mmol). The reaction mixture was stirred at room temperature for 2 hours. After the reaction was indicated by LCMS, the reaction mixture was diluted with sat. NaHCO₃ and extracted with EA (10 mL×3). The combined organic layers were washed with brine, dried over Na₂SO₄, filtered and concentrated. The residue was purified by flash column chromatography to afford the title compound. (83% yield). LCMS: 341.1 (M+H)⁺.

Step 4: tert-butyl 7-(5-(3'-chloro-5-fluoro-2-hydroxy-4'-(3-methyl-2-oxo-2,3-dihydro-1H-imidazol-1-yl)-[1,1'-biphenyl]-3-yl)-2-methoxypyridin-3-yl)-1,7-diazaspiro[4.4]nonane-1-carboxylate The title compound was prepared following the procedures described for Example 914 using 2-bromo-6-(5-(4-(tert-butyl)piperazin-1-yl)-6-(dimethylamino)pyridin-3-yl)-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. ¹H NMR (400 MHz, DMSO-d₆) δ 8.58 (s, 1H), 8.04 (d, J=2.0 Hz, 1H), 7.80 (d, J=1.8 Hz, 1H), 7.62 (dd, J=8.2, 1.9 Hz, 1H), 7.52 (d, J=8.2 Hz, 1H), 7.34 (d, J=1.9 Hz, 1H), 7.17 (ddd, J=12.2, 9.1, 3.2 Hz, 2H), 6.71 (dd, J=11.5, 3.0 Hz, 2H), 3.21 (s, 3H), 3.00 (s, 4H), 2.97 (s, 6H), 2.69 (s, 4H), 1.05 (s, 9H). LCMS: 579.3 (M+H)⁺.

Example 923

1-(3'-(5-(4-(tert-Butyl)piperazin-1-yl)-6-(methylamino)pyridin-3-yl)-3-chloro-5'-fluoro-2'-hydroxy-[1,1'-biphenyl]-4-yl)-3-methyl-1H-imidazol-2(3H)-one

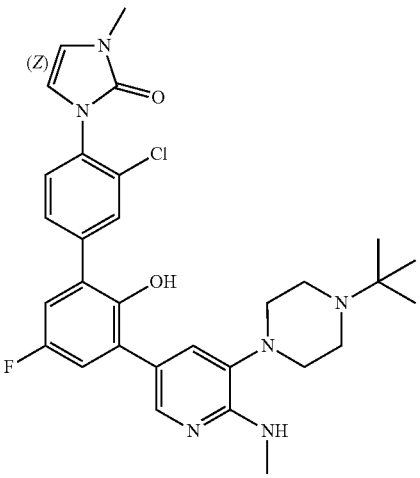 [SMILES: CNc1ncc(-c2cc(F)cc(-c3ccc(-n4ccn(C)c4=O)c(Cl)c3)c2O)cc1N1CCN(C(C)(C)C)CC1]

The title compound was prepared following the procedures described for Example 922 using 2-bromo-6-(5-(4-(tert-butyl)piperazin-1-yl)-6-(methylamino)pyridine-3-yl)-4-fluorophenol and 1-(2-chloro-4-(4,4,5,5-tetramethyl-1,3,2-dioxaborolan-2-yl)phenyl)-3-methyl-1H-imidazol-2(3H)-one to afford the title compound. ¹H NMR (400 MHz, DMSO-d₆) δ 8.48 (s, 1H), 7.98 (d, J=1.9 Hz, 1H), 7.80 (d, J=1.9 Hz, 1H), 7.61 (dd, J=8.2, 1.9 Hz, 1H), 7.51 (d, J=8.2 Hz, 1H), 7.35 (d, J=2.0 Hz, 1H), 7.12 (dq, J=9.2, 3.2 Hz, 2H), 6.70 (dd, J=11.3, 3.0 Hz, 2H), 5.89 (d, J=4.5 Hz, 1H), 3.21 (s, 3H), 2.89 (d, J=4.8 Hz, 3H), 2.84 (s, 4H), 2.71 (s, 4H), 1.06 (s, 9H). LCMS: 565.2 (M+H)+.

Example 924

1-(3''-(4-(tert-Butyl)piperazin-1-yl)-3-chloro-5'-fluoro-2'-hydroxy-5-isobutoxy-[1,1':3',1''-terphenyl]-4-yl)-3-methyl-1H-imidazol-2(3H)-one

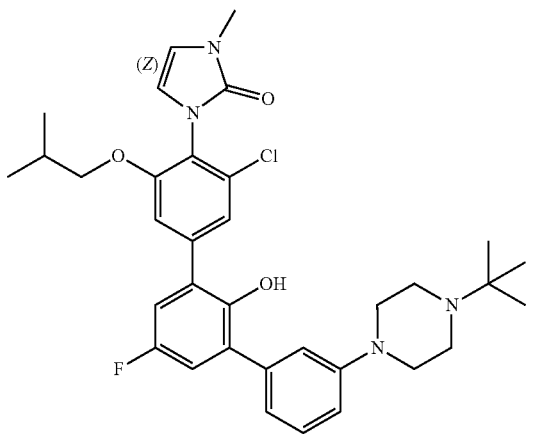 [SMILES: CC(C)COc1cc(-c2cc(F)cc(-c3cccc(N4CCN(C(C)(C)C)CC4)c3)c2O)cc(Cl)c1-n1ccn(C)c1=O]

The title compound was prepared following the procedures described for Example 910 using 2-chloro-6-isobutoxy-4-(4,4,5,5-tetramethyl-1,3,2-dioxaborolan-2-yl)aniline, 1,3-dibromo-5-fluoro-2-(methoxymethoxy)benzene and 1-(tert-butyl)-4-(3-(4,4,5,5-tetramethyl-1,3,2-dioxaborolan-2-yl)phenyl)piperazine to afford the title compound. $^1$H NMR (400 MHz, DMSO-d$_6$) δ 8.47 (s, 1H), 7.35 (d, J=1.7 Hz, 1H), 7.32-7.17 (m, 3H), 7.14-7.10 (m, 1H), 7.06 (s, 1H), 7.00-6.89 (m, 2H), 6.68 (d, J=3.0 Hz, 1H), 6.47 (d, J=3.0 Hz, 1H), 3.84 (t, J=8.0 Hz, 2H), 3.24-3.08 (m, 7H), 2.64 (s, 4H), 1.94-1.90 (m, 1H), 1.05 (s, 9H), 0.88 (dd, J=6.7, 2.5 Hz, 6H). LCMS: 607.0 (M+H)+.

Example 925

1-(3''-(4-(tert-Butyl)piperazin-1-yl)-3-chloro-5-ethoxy-5'-fluoro-2'-hydroxy-[1,1':3',1''-terphenyl]-4-yl)-3-methyl-1H-imidazol-2(3H)-one

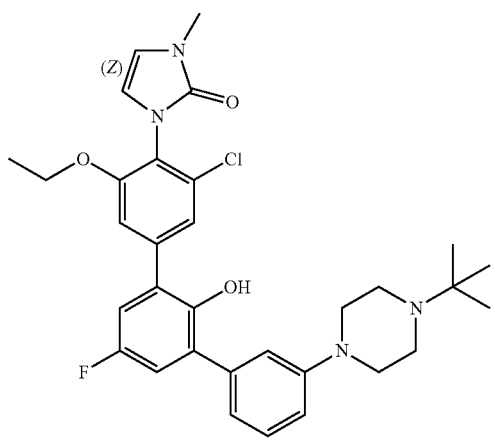 [SMILES: CCOc1cc(-c2cc(F)cc(-c3cccc(N4CCN(C(C)(C)C)CC4)c3)c2O)cc(Cl)c1-n1ccn(C)c1=O]

The title compound was prepared following the procedures described for Example 910 using 2-chloro-6-ethoxy-4-(4,4,5,5-tetramethyl-1,3,2-dioxaborolan-2-yl)aniline, 1,3-dibromo-5-fluoro-2-(methoxymethoxy)benzene and 1-(tert-butyl)-4-(3-(4,4,5,5-tetramethyl-1,3,2-dioxaborolan-2-yl)phenyl)piperazine to afford the title compound. $^1$H NMR (400 MHz, DMSO-d$_6$) δ 8.47 (s, 1H), 7.36 (d, J=1.7 Hz, 1H), 7.36-7.26 (m, 2H), 7.20 (dd, J=9.0, 3.2 Hz, 1H), 7.12 (dd, J=9.1, 3.2 Hz, 1H), 7.06 (s, 1H), 7.00-6.91 (m, 2H), 6.66 (d, J=3.0 Hz, 1H), 6.48 (d, J=3.0 Hz, 1H), 4.13 (q, J=6.9 Hz, 2H), 3.20-3.15 (m, 7H), 2.66-2.64 (m, 4H), 1.24 (t, J=6.9 Hz, 3H), 1.05 (s, 9H). LCMS: 579.3 (M+H)+.

Example 926

1-(3'-(5-(4-(tert-Butyl)piperazin-1-yl)-6-(methoxy-d$_3$)pyridin-3-yl)-3-chloro-5'-fluoro-2'-hydroxy-[1,1'-biphenyl]-4-yl)-3-methyl-1,3-dihydro-2H-imidazol-2-one

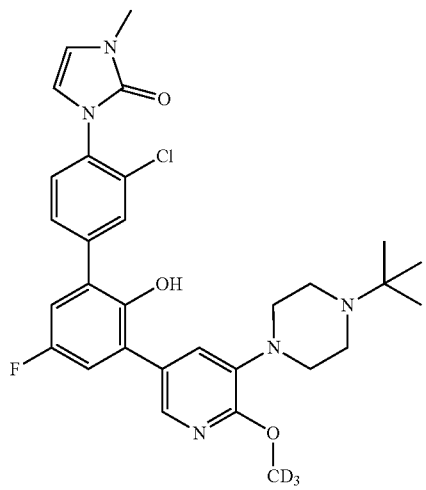 [SMILES: [2H]C([2H])([2H])Oc1ncc(-c2cc(F)cc(-c3ccc(-n4ccn(C)c4=O)c(Cl)c3)c2O)cc1N1CCN(C(C)(C)C)CC1]

Step 1: 3-Bromo-5-chloro-2-(methoxy-d$_3$)pyridine

A solution of CD$_3$OD (5 mL) in THF (20 mL) and 3-bromo-5-chloro-2-fluoropyridine (500 mg, 2.38 mmol) was stirred at 70° C. for 3 hrs. After the reaction was complete by LCMS, the reaction mixture was cooled, diluted with H$_2$O and extracted with EA (30 mL×3). The combined organic layers were washed with brine and concentrated. The residue was purified by silica chromatographic column to afford the title compound (83% yield). LCMS: 227 (M+H)+.

Step 2: 1-(3'-(5-(4-(tert-Butyl)piperazin-1-yl)-6-(methoxy-d$_3$)pyridin-3-yl)-3-chloro-5'-fluoro-2'-hydroxy-[1,1'-biphenyl]-4-yl)-3-methyl-1,3-dihydro-2H-imidazol-2-one The title compound was prepared following the procedures described for Example 738 using 3-bromo-5-chloro-2-(methoxy-d$_3$)pyridine, 2,6-dibromo-4-fluorophenol, and 1-(2-chloro-4-(4,4,5,5-tetramethyl-1,3,2-dioxaborolan-2-yl)phenyl)-3-methyl-1H-imidazol-2(3H)-one to afford the title compound. $^1$H NMR (400 MHz, DMSO-d$_6$) δ 8.63 (s, 1H), 7.92 (s, 1H), 7.81 (d, J=1.9 Hz, 1H), 7.62 (dd, J=8.2, 1.9 Hz, 1H), 7.52 (d, J=8.2 Hz, 1H), 7.33 (s, 1H), 7.26-7.14 (m, 2H), 6.71 (dd, J=11.7, 3.0 Hz, 2H), 3.21 (s, 3H), 3.04 (s, 4H), 2.65 (s, 4H), 1.05 (s, 9H). LCMS: 569 (M+H)+.

TABLE 33

Following compounds were prepared using similar procedures as described for Examples 1 through 926.

| Ex. No. | Name/Structure | $^1$H NMR Data | LCMS (M + H)$^+$ |
|---|---|---|---|
| 927 | 1-(3''-(4-(tert-butyl)piperazin-1-yl)-3-chloro-5'-fluoro-2'-hydroxy-5-methyl-[1,1':3',1''-terphenyl]-4-yl)-3-methyl-1H-imidazol-2(3H)-one | $^1$H NMR (400 MHz, DMSO-d$_6$) δ 8.45 (s, 1H), 7.64 (d, J = 1.6 Hz, 1H), 7.52 (d, J = 1.2 Hz, 1H), 7.28 (t, J = 7.9 Hz, 1H), 7.18-7.02 (m, 3H), 6.95 (t, J = 8.8 Hz, 2H), 6.74 (d, J = 3.0 Hz, 1H), 6.58 (d, J = 3.0 Hz, 1H), 3.22 (s, 3H), 3.15 (d, J = 4.8 Hz, 4H), 2.65 (dd, J = 10.1, 5.6 Hz, 4H), 2.17 (s, 3H), 1.05 (s, 9H) | 549.1 |
| 928 | 1-(3''-(4-(tert-butyl)piperazin-1-yl)-3-chloro-5'-fluoro-2'-hydroxy-[1,1':3',1''-terphenyl]-4-yl)-1H-imidazol-2(3H)-one | $^1$H NMR (400 MHz, DMSO-d$_6$) δ 10.24 (s, 1H), 8.46 (s, 1H), 7.80 (d, J = 1.7 Hz, 1H), 7.61 (dd, J = 8.2, 1.7 Hz, 1H), 7.52 (d, J = 8.2 Hz, 1H), 7.28 (t, J = 7.9 Hz, 1H), 7.21-7.03 (m, 3H), 6.96 (t, J = 8.8 Hz, 2H), 6.59 (dd, J = 11.5, 9.0 Hz, 2H), 3.16 (s, 4H), 2.65 (s, 4H), 1.05 (s, 9H) | 521.2 |
| 929 | 1-(3''-(4-(tert-butyl)piperazin-1-yl)-3-chloro-5-ethyl-5'-fluoro-2'-hydroxy-[1,1':3',1''-terphenyl]-4-yl)-3-methyl-1H-imidazol-2(3H)-one | $^1$H NMR (400 MHz, DMSO-d$_6$) δ 8.47 (s, 1H), 7.66 (d, J = 1.9 Hz, 1H), 7.52 (d, J = | 563.2 |

TABLE 33-continued

Following compounds were prepared using similar procedures as described for Examples 1 through 926.

| Ex. No. | Name/Structure | $^1$H NMR Data | LCMS (M + H)$^+$ |
|---|---|---|---|
| | 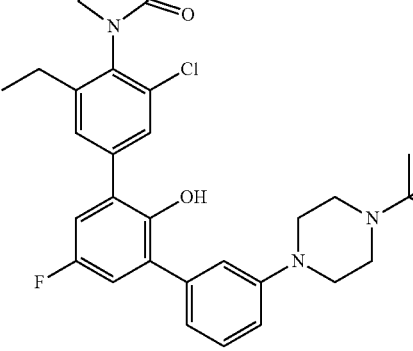 | 1.9 Hz, 1H), 7.28 (t, J = 7.9 Hz, 1H), 7.18 (dd, J = 9.0, 3.2 Hz, 1H), 7.11 (dd, J = 9.1, 3.2 Hz, 1H), 7.07 (s, 1H), 6.99-6.90 (m, 2H), 6.74 (d, J = 3.0 Hz, 1H), 6.59 (d, J = 3.0 Hz, 1H), 3.22 (s, 3H), 3.19-3.09 (m, 4H), 2.67-2.63 (m, 4H), 2.51-2.48 (m, 2H), 1.11 (t, J = 7.6 Hz, 3H), 1.05 (s, 9H) | |
| 930 | 1-(3''-(4-(tert-butyl)piperazin-1-yl)-3-chloro-5-cyclopropoxy-5'-fluoro-2'-hydroxy-[1,1':3',1''-terphenyl]-4-yl)-3-methyl-1H-imidazol-2(3H)-one | $^1$H NMR (400 MHz, DMSO-d$_6$) δ 9.73 (s, 1H), 7.53 (s, 1H), 7.34 (s, 1H), 7.30-7.21 (m, 2H), 7.07 (dd, J = 18.1, 11.2 Hz, 3H), 6.92 (d, J = 8.6 Hz, 1H), 6.65 (d, J = 2.9 Hz, 1H), 6.51 (d, J = 2.9 Hz, 1H), 4.00 (s, 1H), 3.17 (d, J = 12.3 Hz, 7H), 2.66 (s, 4H), 1.06 (s, 9H), 0.79 (s, 2H), 0.65 (d, J = 5.4 Hz, 2H) | 591.1 |
| 931 | 1-(3''-(4-(tert-butyl)piperazin-1-yl)-2-chloro-4-cyclopropoxy-5'-fluoro-2'-hydroxy-[1,1':3',1''-terphenyl]-3-yl)-3-methyl-1,3-dihydro-2H-imidazol-2-one | — | 591.1 |

TABLE 33-continued

Following compounds were prepared using similar procedures as described for Examples 1 through 926.

| Ex. No. | Name/Structure | $^1$H NMR Data | LCMS (M + H)$^+$ |
|---|---|---|---|
| 932 | 1-(3''-(4-(tert-butyl)piperazin-1-yl)-3-chloro-5'-fluoro-2'-hydroxy-5-isopropyl-[1,1':3',1''-terphenyl]-4-yl)-3-methyl-1H-imidazol-2(3H)-one | $^1$H NMR (400 MHz, DMSO-d$_6$) δ 8.44 (s, 1H), 7.65 (d, J = 1.8 Hz, 1H), 7.55 (d, J = 1.8 Hz, 1H), 7.28 (t, J = 7.9 Hz, 1H), 7.17 (dd, J = 9.0, 3.2 Hz, 1H), 7.11 (dd, J = 9.1, 3.2 Hz, 1H), 7.06 (s, 1H), 6.95 (dd, J = 14.7, 5.4 Hz, 2H), 6.74 (d, J = 2.9 Hz, 1H), 6.58 (d, J = 2.9 Hz, 1H), 3.22 (s, 3H), 3.16-3.14 (m, 4H), 2.83-2.79 (m, 1H), 2.65-2.63 (s, 4H), 1.17 (dd, J = 6.8, 3.4 Hz, 6H), 1.05 (s, 9H) | 577.3 |
| 933 | 1-(3''-(4-(tert-butyl)piperazin-1-yl)-3-chloro-5-cyclopropyl-5'-fluoro-2'-hydroxy-[1,1':3',1''-terphenyl]-4-yl)-3-methyl-1H-imidazol-2(3H)-one | $^1$H NMR (400 MHz, DMSO-d$_6$) δ 8.42 (s, 1H), 7.60 (d, J = 1.5 Hz, 1H), 7.28 (t, J = 8.0 Hz, 1H), 7.17 (dd, J = 9.1, 3.1 Hz, 1H), 7.13-7.07 (m, 2H), 7.06 (s, 1H), 6.95 (t, J = 8.1 Hz, 2H), 6.74 (d, J = 2.9 Hz, 1H), 6.59 (d, J = 2.9 Hz, 1H), 3.22 (s, 3H), 3.18-3.15 (m, 4H), 2.68-2.65 (m, 4H), 1.74-1.69 (m, 1H), 1.06 (s, 9H), 0.91-0.61 (m, 4H) | 575.3 |
| 934 | (R)-1-(3''-(4-(tert-butyl)piperazin-1-yl)-3-chloro-5'-fluoro-2'-hydroxy-5-isopropyl-[1,1':3',1''-terphenyl]-4-yl)-3-methyl-1,3-dihydro-2H-imidazol-2-one | $^1$H NMR (400 MHz, DMSO-d$_6$) δ 8.44 (s, 1H), 7.65 (d, J = 1.8 Hz, 1H), 7.55 (d, J = | 577.3 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| | 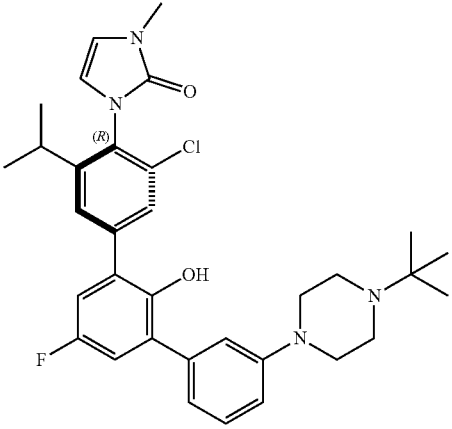 | 1.8 Hz, 1H), 7.28 (t, J = 7.9 Hz, 1H), 7.17 (dd, J = 9.0, 3.2 Hz, 1H), 7.11 (dd, J = 9.1, 3.2 Hz, 1H), 7.06 (s, 1H), 6.95 (dd, J = 14.7, 5.4 Hz, 2H), 6.74 (d, J = 2.9 Hz, 1H), 6.58 (d, J = 2.9 Hz, 1H), 3.22 (s, 3H), 3.16-3.14 (m, 4H), 2.83-2.79 (m, 1H), 2.65-2.63 (s, 4H), 1.17 (dd, J = 6.8, 3.4 Hz, 6H), 1.05 (s, 9H) | |
| 935 | (S)-1-(3''-(4-(tert-butyl)piperazin-1-yl)-3-chloro-5'-fluoro-2'-hydroxy-5-isopropyl-[1,1':3',1''-terphenyl]-4-yl)-3-methyl-1,3-dihydro-2H-imidazol-2-one 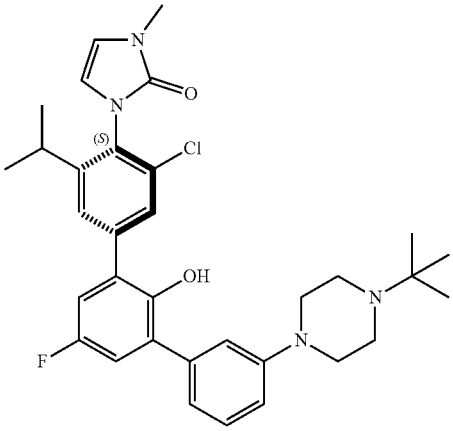 | ¹H NMR (400 MHz, DMSO-d₆) δ 8.44 (s, 1H), 7.65 (d, J = 1.8 Hz, 1H), 7.55 (d, J = 1.8 Hz, 1H), 7.28 (t, J = 7.9 Hz, 1H), 7.17 (dd, J = 9.0, 3.2 Hz, 1H), 7.11 (dd, J = 9.1, 3.2 Hz, 1H), 7.06 (s, 1H), 6.95 (dd, J = 14.7, 5.4 Hz, 2H), 6.74 (d, J = 2.9 Hz, 1H), 6.58 (d, J = 2.9 Hz, 1H), 3.22 (s, 3H), 3.16-3.14 (m, 4H), 2.83-2.79 (m, 1H), 2.65-2.63 (s, 4H), 1.17 (dd, J = 6.8, 3.4 Hz, 6H), 1.05 (s, 9H) | 577.3 |
| 936 | 1-(6-(3'-(4-(tert-butyl)piperazin-1-yl)-5-fluoro-2-hydroxy-[1,1'-biphenyl]-3-yl)-2-methylpyridin-3-yl)-3-methyl-1H-imidazol-2(3H)-one | ¹H NMR (400 MHz, DMSO-d₆) δ 14.60 (s, 1H), 8.26 (d, J = 8.7 Hz, 1H), 8.01-7.79 (m, 2H), 7.31-7.16 (m, 2H), 7.11 (s, 1H), 7.02 (d, J = 7.7 Hz, 1H), 6.92 (dd, J = 8.2, 1.9 Hz, 1H), 6.82 (d, J = 3.2 Hz, 1H), 6.78 (d, J = 3.2 Hz, 1H), 3.22 (s, 3H), 3.16 (dd, J = 9.2, 5.0 Hz, 4H), 2.68-2.61 (m, 4H), 2.48 (s, 3H), 1.05 (s, 9H). | 515.6 |

TABLE 33-continued

Following compounds were prepared using similar procedures as described for Examples 1 through 926.

| Ex. No. | Name/Structure | $^1$H NMR Data | LCMS (M + H)$^+$ |
|---|---|---|---|
| 937 | 1-(3''-(4-(tert-butyl)piperazin-1-yl)-3-chloro-5'-fluoro-2'-hydroxy-5-isopropoxy-[1,1':3',1''-terphenyl]-4-yl)-3-methyl-1,3-dihydro-2H-imidazol-2-one | $^1$H NMR (400 MHz, DMSO-d$_6$) δ 8.45 (s, 1H), 7.34 (d, J = 1.7 Hz, 1H), 7.30-7.23 (m, 2H), 7.19 (dd, J = 9.0, 3.2 Hz, 1H), 7.11 (dd, J = 9.2, 3.2 Hz, 1H), 7.06 (s, 1H), 7.00-6.89 (m, 2H), 6.65 (d, J = 3.0 Hz, 1H), 6.45 (d, J = 3.0 Hz, 1H), 4.69-4.62 (m, 1H), 3.19 (s, 3H), 3.18-3.15 (m, 4H), 2.67-2.64 (m, 4H), 1.21 (t, J = 5.7 Hz, 6H), 1.05 (s, 9H) | 593.3 |
| 938 | 1-(3'-(5-(4-(tert-butyl)piperazin-1-yl)-6-methoxypyridin-3-yl)-3-chloro-5'-fluoro-2'-hydroxy-[1,1'-biphenyl]-4-yl)-3-(methyl-d3)-1,3-dihydro-2H-imidazol-2-one | $^1$H NMR (400 MHz, DMSO-d$_6$) δ 8.61 (s, 1H), 7.92 (d, J = 2.0 Hz, 1H), 7.81 (d, J = 1.9 Hz, 1H), 7.62 (dd, J = 8.2, 1.9 Hz, 1H), 7.53 (s, 1H), 7.33 (d, J = 2.0 Hz, 1H), 7.19 (dd, J = 9.1, 1.0 Hz, 2H), 6.70 (dd, J = 11.6, 3.0 Hz, 2H), 3.93 (s, 3H), 3.05 (s, 4H), 2.65 (s, 4H), 1.05 (s, 9H) | 569.1 |
| 939 | 1-(3'-(5-(4-(tert-butyl)piperazin-1-yl)-6-methoxypyridin-3-yl)-3,5'-difluoro-2'-hydroxy-[1,1'-biphenyl]-4-yl)-3-methyl-1H-imidazol-2(3H)-one | $^1$H NMR (400 MHz, DMSO-d$_6$) δ 8.57 (s, 1H), 7.92 (d, J = 2.0 Hz, 1H), 7.60 (dd, J = | 550.3 |

TABLE 33-continued

Following compounds were prepared using similar procedures as described for Examples 1 through 926.

| Ex. No. | Name/Structure | 1H NMR Data | LCMS (M + H)+ |
|---|---|---|---|
| | 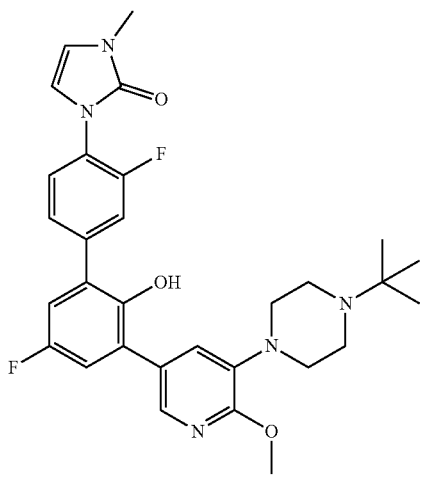 [SMILES: COc1ncc(-c2cc(F)cc(-c3ccc(-n4ccn(C)c4=O)c(F)c3)c2O)cc1N1CCN(C(C)(C)C)CC1] | 7.7, 5.0 Hz, 2H), 7.50 (d, J = 1.7 Hz, 1H), 7.33 (d, J = 2.0 Hz, 1H), 7.18 (dd, J = 9.1, 1.3 Hz, 2H), 6.75 (dd, J = 11.0, 2.4 Hz, 2H), 3.93 (s, 3H), 3.21 (s, 3H), 3.05 (s, 4H), 2.65 (s, 4H), 1.05 (s, 9H) | |
| 940 | 1-(6-(3'-(4-(tert-butyl)piperazin-1-yl)-5-fluoro-2-hydroxy-[1,1'-biphenyl]-3-yl)-4-methylpyridin-3-yl)-3-methyl-1H-imidazol-2(3H)-one | 1H NMR (400 MHz, DMSO-d) δ 14.43 (s, 1H), 8.51 (s, 1H), 8.37 (s, 1H), 7.96 (dd, J = 10.3, 3.1 Hz, 1H), 7.31-7.19 (m, 2H), 7.14 (s, 1H), 7.02 (d, J = 7.8 Hz, 1H), 6.92 (dd, J = 8.2, 2.0 Hz, 1H), 6.80 (dd, J = 17.9, 3.0 Hz, 2H), 3.23 (s, 3H), 3.16-3.07 (m, 4H), 2.68-2.59 (m, 4H), 2.36 (s, 3H), 1.05 (s, 9H) | 516.3 |
| 941 | 3-(3'-(5-(4-(tert-butyl)piperazin-1-yl)-6-methoxypyridin-3-yl)-3-chloro-5'-fluoro-2'-hydroxy-[1,1'-biphenyl]-4-yl)-1,4-dimethyl-1H-imidazol-2(3H)-one | 1H NMR (400 MHz, DMSO-d6) δ 8.65 (s, 1H), 7.92 (d, J = 1.9 Hz, 1H), 7.84 (d, J = | 580.2 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| | 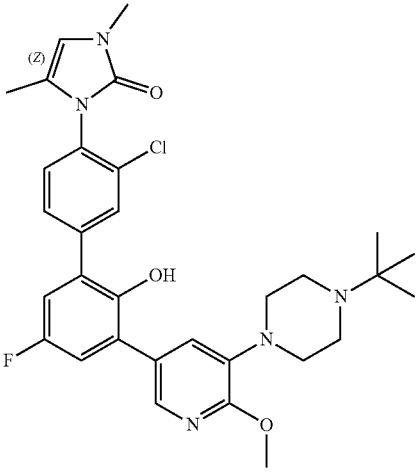 [SMILES: COc1ncc(-c2cc(F)cc(-c3ccc(-n4c(C)cn(C)c4=O)c(Cl)c3)c2O)cc1N1CCN(C(C)(C)C)CC1] | 1.8 Hz, 1H), 7.64 (dd, J = 8.1, 1.8 Hz, 1H), 7.49 (d, J = 8.1 Hz, 1H), 7.34 (d, J = 1.8 Hz, 1H), 7.21 (dt, J = 8.3, 4.2 Hz, 2H), 6.42 (s, 1H), 3.93 (s, 3H), 3.16 (s, 3H), 3.04 (s, 4H), 2.65 (s, 4H), 1.80 (s, 3H), 1.05 (s, 9H). | |
| 942 | 1-(3'-(6-(4-(tert-butyl)piperazin-1-yl)pyrimidin-4-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆) δ 15.28 (s, 1H), 8.59 (s, 1H), 8.17 (dd, J = 10.3, 3.1 Hz, 1H), 7.87 (d, J = 1.9 Hz, 1H), 7.68 (dd, J = 8.2, 1.9 Hz, 1H), 7.57-7.30 (m, 3H), 6.78-6.67 (m, 2H), 3.78 (s, 4H), 3.21 (s, 3H), 2.59 (s, 4H), 1.05 (s, 9H). | 537.3 |
| 943 | 1-(3-chloro-5'-fluoro-3''-(hexahydropyrrolo[3,4-c]pyrrol-2(1H)-yl)-2'-hydroxy-[1,1':3',1''-terphenyl]-4-yl)-3-methyl-1,3-dihydro-2H-imidazol-2-one | ¹H NMR (400 MHz, CD₃OD) δ 7.81 (d, J = 1.4 Hz, 1H), 7.62 (d, J = 8.2 Hz, 1H), 7.47 (d, J = 8.2 Hz, 1H), 7.28 (t, J = 7.8 Hz, 1H), 7.05-6.98 (m, 2H), 6.87-6.84 (m, 2H), 6.73 (d, J = 9.0 Hz, 1H), 6.67-6.61 (m, 2H), 3.42-3.32 (m, 5H), 3.30-3.27 (m, 2H), 3.20-3.15 (m, 2H), 2.98 (s, 2H), 2.82 (d, J = 11.2 Hz, 2H) | 505.2 |

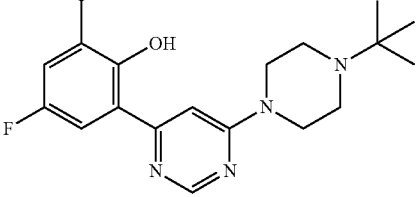

TABLE 33-continued

Following compounds were prepared using similar procedures as described for Examples 1 through 926.

| Ex. No. | Name/Structure | $^1$H NMR Data | LCMS (M + H)$^+$ |
|---|---|---|---|
| 944 | 1-(6-(3'-(4-(tert-butyl)piperazin-1-yl)-5-fluoro-2-hydroxy-[1,1'-biphenyl]-3-yl)pyridin-3-yl)-3-methyl-1H-imidazol-2(3H)-one | $^1$H NMR (400 MHz, DMSO-d$_6$) δ 14.39 (s, 1H), 9.10 (d, J = 2.2 Hz, 1H), 8.45 (dt, J = 21.6, 5.7 Hz, 2H), 7.94 (dd, J = 10.1, 2.9 Hz, 1H), 7.31-7.19 (m, 3H), 7.14 (s, 1H), 7.02 (d, J = 7.5 Hz, 1H), 6.92 (d, J = 8.1 Hz, 1H), 6.86 (d, J = 3.0 Hz, 1H), 3.23 (s, 3H), 3.15 (s, 4H), 2.65 (s, 4H), 1.05 (s, 9H)) | 502.2 |
| 945 | 1-(3''-(4-(tert-butyl)piperazin-1-yl)-3,5'-difluoro-2'-hydroxy-[1,1':3',1''-terphenyl]-4-yl)-3-methyl-1H-imidazol-2(3H)-one | $^1$H NMR (400 MHz, DMSO-d$_6$) δ 8.44 (s, 1H), 7.64-7.55 (m, 2H), 7.49 (d, J = 8.4 Hz, 1H), 7.28 (t, J = 7.9 Hz, 1H), 7.20-7.04 (m, 3H), 6.95 (t, J = 8.8 Hz, 2H), 6.75 (d, J = 11.6 Hz, 2H), 3.19 (d, J = 20.1 Hz, 7H), 2.65 (s, 4H), 1.05 (s, 9H) | 519.2 |
| 946 | 1-(3-chloro-5'-fluoro-2'-hydroxy-3''-(5-isopropylhexahydropyrrolo[3,4-c]pyrrol-2(1H)-yl)-[1,1':3',1''-terphenyl]-4-yl)-3-methyl-1,3-dihydro-2H-imidazol-2-one | $^1$H NMR (400 MHz, DMSO-d$_6$) δ 8.41 (s, 1H), 7.80 (d, J = 1.9 Hz, 1H), 7.62 (dd, J = 8.2, 1.9 Hz, 1H), | 547.2 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
|  | 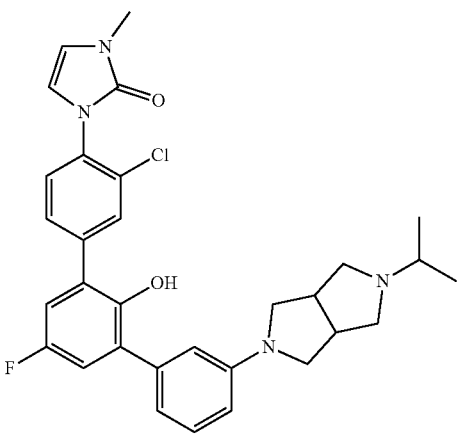 [SMILES: CC(C)N1CC2CN(c3cccc(-c4cc(F)cc(-c5ccc(-n6ccn(C)c6=O)c(Cl)c5)c4O)c3)CC2C1] | 7.51 (d, J = 8.2 Hz, 1H), 7.24 (t, J = 7.9 Hz, 1H), 7.16 (dd, J = 9.0, 3.2 Hz, 1H), 7.10 (dd, J = 9.1, 3.2 Hz, 1H), 6.83 (d, J = 7.7 Hz, 1H), 6.78 (s, 1H), 6.71 (d, J = 3.0 Hz, 1H), 6.69 (d, J = 3.0 Hz, 1H), 6.64 (dd, J = 8.2, 1.9 Hz, 1H), 3.41 (t, J = 8.5 Hz, 2H), 3.21 (s, 3H), 3.15-3.06 (m, 2H), 2.87-2.84 (m, 2H), 2.70-2.66 (m, 2H), 2.50-2.44 (m, 2H), 2.37-2.23 (m, 1H), 1.00 (d, J = 6.3 Hz, 6H) |  |
| 948 | 1-(3'-(5-(4-(tert-butyl)piperazin-1-yl)-6-methoxypyridin-3-yl)-5'-fluoro-2'-hydroxy-3-methyl-[1,1'-biphenyl]-4-yl)-3-methyl-1,3-dihydro-2H-imidazol-2-one<br>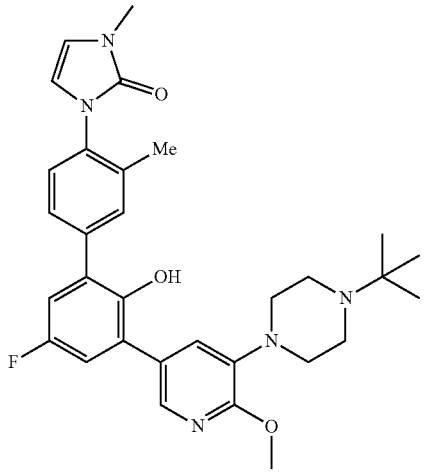 [SMILES: COc1ncc(-c2cc(F)cc(-c3ccc(-n4ccn(C)c4=O)c(C)c3)c2O)cc1N1CCN(C(C)(C)C)CC1] | ¹H NMR (400 MHz, DMSO-d₆) δ 8.44 (s, 1H), 7.91 (d, J = 1.9 Hz, 1H), 7.52 (s, 1H), 7.48-7.45 (m, 1H), 7.33 (d, J = 1.9 Hz, 1H), 7.26 (d, J = 8.1 Hz, 1H), 7.15 (dd, J = 9.1, 3.2 Hz, 1H), 7.10 (dd, J = 9.1, 3.2 Hz, 1H), 6.71 (d, J = 2.9 Hz, 1H), 6.65 (d, J = 2.9 Hz, 1H), 3.92 (s, 3H), 3.21 (s, 3H), 3.10-3.00 (m, 4H), 2.70-2.60 (m, 4H), 2.21 (s, 3H), 1.05 (s, 9H) | 546.3 |
| 949 | 1-(3''-(4-(tert-butyl)piperazin-1-yl)-5'-fluoro-2'-hydroxy-3-methyl-[1,1':3',1''-terphenyl]-4-yl)-3-methyl-1,3-dihydro-2H-imidazol-2-one | ¹H NMR (400 MHz, DMSO-d₆) δ 8.29 (s, 1H), 7.52 (s, 1H), 7.50-7.42 (m, 1H), 7.33-7.22 (m, 2H), 7.12-7.03 (m, 3H), 6.98-6.91 (m, 2H), 6.71 (d, J = 2.9 Hz, 1H), 6.65 (d, J = 2.9 Hz, 1H), 3.21 (s, 3H), 3.18-3.14 (m, 4H), 2.67-2.63 (m, 4H), 2.21 (s, 3H), 1.05 (s, 9H) | 515.3 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| 950 | 1-(3'-(6-(4-(tert-butyl)piperazin-1-yl)pyridin-2-yl)-3-chloro-5'-fluoro-2'-hydroxy-[1,1'-biphenyl]-4-yl)-3-methyl-1H-imidazol-2(3H)-one 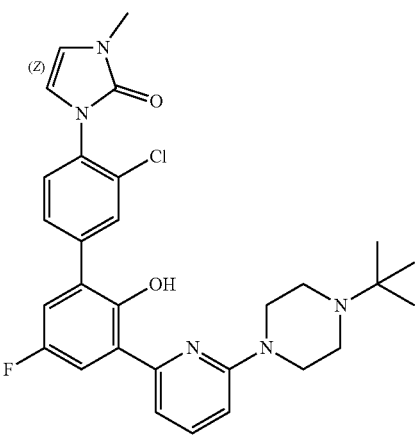 [SMILES: Cn1ccn(-c2ccc(-c3cc(F)cc(-c4cccc(N5CCN(C(C)(C)C)CC5)n4)c3O)cc2Cl)c1=O] | ¹H NMR (400 MHz, DMSO-d₆) δ 15.16 (s, 1H), 7.88 (dd, J = 10.3, 3.1 Hz, 1H), 7.80 (dd, J = 14.2, 5.2 Hz, 2H), 7.66 (dd, J = 8.2, 1.9 Hz, 1H), 7.52 (dd, J = 8.0, 3.7 Hz, 2H), 7.30 (dd, J = 8.9, 3.0 Hz, 1H), 6.97 (d, J = 8.7 Hz, 1H), 6.75-6.67 (m, 2H), 3.43 (s, 4H), 3.22 (s, 3H), 2.64 (s, 4H), 1.03 (s, 9H) | 536.2 |
| 951 | 1-(3''-(1-(tert-butyl)-1,2,3,6-tetrahydropyridin-4-yl)-3-chloro-5'-fluoro-2'-hydroxy-[1,1':3',1''-terphenyl]-4-yl)-3-methyl-1H-imidazol-2(3H)-one 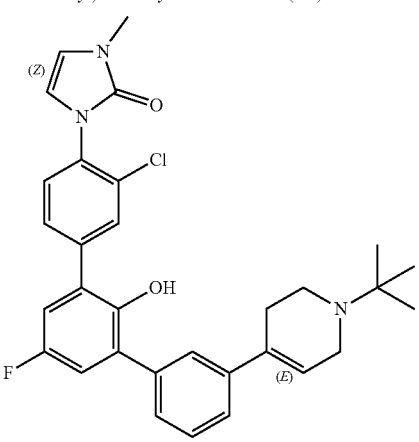 | ¹H NMR (400 MHz, DMSO-d₆) δ 8.57 (s, 1H), 7.82 (d, J = 1.8 Hz, 1H), 7.69-7.57 (m, 2H), 7.52 (d, J = 8.2 Hz, 1H), 7.42 (t, J = 5.4 Hz, 3H), 7.18 (dt, J = 12.0, 3.2 Hz, 2H), 6.71 (dd, J = 11.4, 3.0 Hz, 2H), 6.22 (s, 1H), 3.24 (d, J = 2.9 Hz, 2H), 3.21 (s, 3H), 2.70 (t, J = 5.4 Hz, 2H), 2.49-2.44 (m, 2H), 1.07 (s, 9H) | 532.2 |
| 952 | 1-(3''-(4-(tert-butyl)piperazin-1-yl)-3-chloro-5'-fluoro-2',5-dihydroxy-[1,1':3',1''-terphenyl]-4-yl)-3-methyl-1H-imidazol-2(3H)-one | ¹H NMR (400 MHz, DMSO-d₆) δ 10.33 (s, 1H), 8.44 (s, 1H), 7.28 (s, 1H), 7.17 (d, | 551.3 |

| Ex. No. | Name/Structure | ¹H NMR Data | LCMS (M + H)⁺ |
|---|---|---|---|
| | 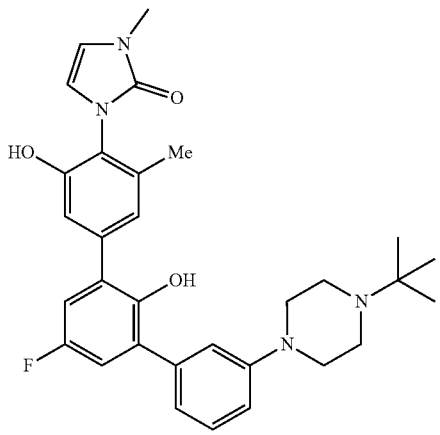 [SMILES: Cc1cc(-c2cc(F)cc(-c3cccc(N4CCN(C(C)(C)C)CC4)c3)c2O)cc(O)c1-n1ccn(C)c1=O] | J = 1.7 Hz, 1H), 7.09 (ddd, J = 12.5, 7.1, 2.6 Hz, 4H), 6.95 (d, J = 7.3 Hz, 2H), 6.64 (d, J = 3.0 Hz, 1H), 6.45 (d, J = 3.0 Hz, 1H), 3.19-3.15 (m,, 7H), 2.65 (s, 4H), 1.05 (s, 9H) | |
| 953 | 1-(3'-(4-(4-(tert-butyl)piperazin-1-yl)pyridin-2-yl)-3-chloro-5'-fluoro-2'-hydroxy-[1,1'-biphenyl]-4-yl)-3-methyl-1H-imidazol-2(3H)-one<br>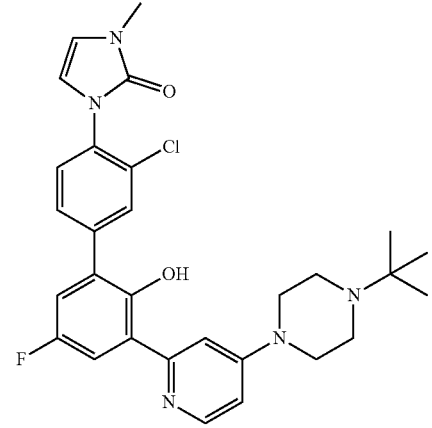 | ¹H NMR (400 MHz, DMSO-d₆) δ 8.18 (d, J = 6.3 Hz, 1H), 8.10 (dd, J = 10.5, 3.1 Hz, 1H), 7.90 (d, J = 1.9 Hz, 1H), 7.69 (dd, J = 8.2, 2.0 Hz, 1H), 7.51 (dd, J = 11.5, 5.1 Hz, 2H), 7.31 (dd, J = 9.0, 3.0 Hz, 1H), 6.92 (d, J = 4.2 Hz, 1H), 6.71 (s, 2H), 3.57-3.43 (m, 4H), 3.21 (s, 3H), 2.67-2.57 (m, 4H), 1.06 (s, 9H) | 536.1 |
| 954 | 1-(3'-(6-amino-5-(1-isopropyl-1,6-diazaspiro[3.4]octan-6-yl)pyridin-3-yl)-3-chloro-5'-fluoro-2'-hydroxy-[1,1'-biphenyl]-4-yl)-3-methyl-1H-imidazol-2(3H)-one | ¹H NMR (400 MHz, DMSO-d₆) δ 8.47 (s, 1H), 7.81 (dd, J = 16.0, 2.0 Hz, 2H), 7.61 (dd, J = 8.0, 2.0 Hz, 1H), 7.51 (d, J = 8.0 Hz, 1H), 7.21 (dd, J = 36.0, 6.0 Hz, 1H), 7.12 (d, J = 9.2 Hz, 2H), 6.70 (dd, J = 12.4, 3.2 Hz, 2H), 5.50 (s, 2H), 3.45-3.36 (m, 1H), 3.16 (s, 3H), 3.13-2.81 (m, 5H), 2.61 (d, J = 52.0 Hz, 1H), 2.20 (s, 1H), 2.02-1.97 (m, 3H), 0.94 (m, J = 4.8 Hz, 6H) | 563.1 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| 955 | (S)-1-(3-chloro-5'-fluoro-2'-hydroxy-3'-(5-(1-isopropyl-1,7-diazaspiro[4.4]nonan-7-yl)-6-methylpyridin-3-yl)-[1,1'-biphenyl]-4-yl)-3-methyl-1,3-dihydro-2H-imidazol-2-one | ¹H NMR (400 MHz, CD₃OD) δ 8.13 (s, 1H), 7.83 (s, 1H), 7.65 (d, J = 9.8 Hz, 1H), 7.53 (d, J = 8.2 Hz, 1H), 7.46 (s, 1H), 7.13 (d, J = 8.7 Hz, 2H), 6.68 (dd, J = 15.7, 2.9 Hz, 2H), 3.52 (d, J = 9.2 Hz, 1H), 3.48-3.42 (m, 1H), 3.42-3.36 (m, 5H), 3.00 (s, 1H), 2.93 (d, J = 8.9 Hz, 2H), 2.60 (s, 3H), 2.33-2.19 (m, 1H), 1.98 (s, 1H), 1.88 (dd, J = 31.9, 7.0 Hz, 4H), 1.26-1.16 (m, 6H). | 576.2 |
| 956 | (R)-1-(3-chloro-5'-fluoro-2'-hydroxy-3'-(5-(1-isopropyl-1,7-diazaspiro[4.4]nonan-7-yl)-6-methylpyridin-3-yl)-[1,1'-biphenyl]-4-yl)-3-methyl-1,3-dihydro-2H-imidazol-2-one | ¹H NMR (400 MHz, CD₃OD) δ 8.13 (s, 1H), 7.83 (s, 1H), 7.65 (d, J = 9.8 Hz, 1H), 7.53 (d, J = 8.2 Hz, 1H), 7.46 (s, 1H), 7.13 (d, J = 8.7 Hz, 2H), 6.68 (dd, J = 15.7, 2.9 Hz, 2H), 3.52 (d, J = 9.2 Hz, 1H), 3.48-3.42 (m, 1H), 3.42-3.36 (m, 5H), 3.00 (s, 1H), 2.93 (d, J = 8.9 Hz, 2H), 2.60 (s, 3H), 2.33-2.19 (m, 1H), 1.98 (s, 1H), 1.88 (dd, J = 31.9, 7.0 Hz, 4H), 1.26-1.16 (m, 6H). | 576.2 |
| 957 | (S)-1-(3-chloro-5'-fluoro-2'-hydroxy-3'-(5-(1-isopropyl-1,7-diazaspiro[4.4]nonan-7-yl)-6-methoxypyridin-3-yl)-[1,1'-biphenyl]-4-yl)-3-methyl-1,3-dihydro-2H-imidazol-2-one | ¹H NMR (400 MHz, DMSO-d₆) δ 8.52 (s, 1H), 7.79 (d, J = 1.9 Hz, 1H), 7.66 (d, J = 1.8 Hz, 1H), 7.61 (dd, J = 8.2, 1.9 Hz, | 592.2 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| | | 1H), 7.52 (d, J = 8.2 Hz, 1H), 7.16 (dt, J = 7.9, 3.2 Hz, 2H), 6.97 (d, J = 1.8 Hz, 1H), 6.70 (dd, J = 12.6, 3.0 Hz, 2H), 3.88 (s, 3H), 3.38 (dd, J = 13.3, 8.9 Hz, 3H), 3.21 (s, 3H), 3.17 (d, J = 6.8 Hz, 1H), 2.94 (d, J = 9.8 Hz, 1H), 2.79 (d, J = 27.8 Hz, 2H), 1.99 (d, J = 11.4 Hz, 1H), 1.79-1.56 (m, 5H), 1.04 (dd, J = 11.9, 6.5 Hz, 6H) | |
| 958 | (R)-1-(3-chloro-5'-fluoro-2'-hydroxy-3'-(5-(1-isopropyl-1,7-diazaspiro[4.4]nonan-7-yl)-6-methoxypyridin-3-yl)-[1,1'-biphenyl]-4-yl)-3-methyl-1,3-dihydro-2H-imidazol-2-one | ¹H NMR (400 MHz, DMSO-d₆) δ 8.52 (s, 1H), 7.79 (d, J = 1.9 Hz, 1H), 7.66 (d, J = 1.8 Hz, 1H), 7.61 (dd, J = 8.2, 1.9 Hz, 1H), 7.52 (d, J = 8.2 Hz, 1H), 7.16 (dt, J = 7.9, 3.2 Hz, 2H), 6.97 (d, J = 1.8 Hz, 1H), 6.70 (dd, J = 12.6, 3.0 Hz, 2H), 3.88 (s, 3H), 3.38 (dd, J = 13.3, 8.9 Hz, 3H), 3.21 (s, 3H), 3.17 (d, J = 6.8 Hz, 1H), 2.94 (d, J = 9.8 Hz, 1H), 2.79 (d, J = 27.8 Hz, 2H), 1.99 (d, J = 11.4 Hz, 1H), 1.79-1.56 (m, 5H), 1.04 (dd, J = 11.9, 6.5 Hz, 6H) | 592.2 |
| 959 | 1-(4-(5'-(4-(tert-butyl)piperazin-1-yl)-3-hydroxy-6'-methoxy-6-methyl-[2,3'-bipyridin]-4-yl)-2-chlorophenyl)-3-methyl-1,3-dihydro-2H-imidazol-2-one | ¹H NMR (400 MHz, DMSO-d₆) δ 8.98 (s, 1H), 8.28 (d, J = 1.8 Hz, 1H), 7.84 (d, J = | 563.2 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| | 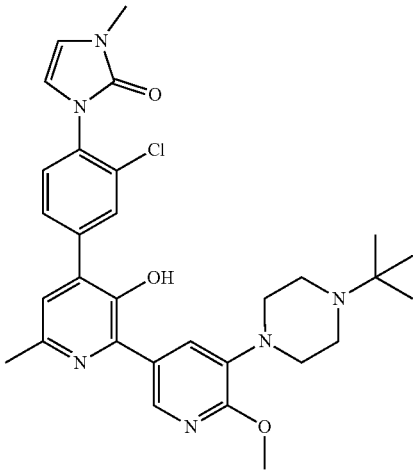 [SMILES: COc1ncc(-c2nc(C)cc(-c3ccc(-n4ccn(C)c4=O)c(Cl)c3)c2O)cc1N1CCN(C(C)(C)C)CC1] | 1.8 Hz, 1H), 7.68-7.65 (m, 2H), 7.56 (d, J = 8.2 Hz, 1H), 7.18 (s, 1H), 6.73 (d, J = 3.0 Hz, 1H), 6.70 (d, J = 3.0 Hz, 1H), 3.94 (s, 3H), 3.21 (s, 3H), 3.10-3.00 (m, 4H), 2.75-2.65 (m, 4H), 2.47 (s, 3H), 1.07 (s, 9H) | |
| 960 | 1-(3-chloro-5'-fluoro-2'-hydroxy-3'-(5-(4-(1-hydroxy-2-methylpropan-2-yl)piperazin-1-yl)-6-methoxypyridin-3-yl)-[1,1'-biphenyl]-4-yl)-3-methyl-1H-imidazol-2(3H)-one 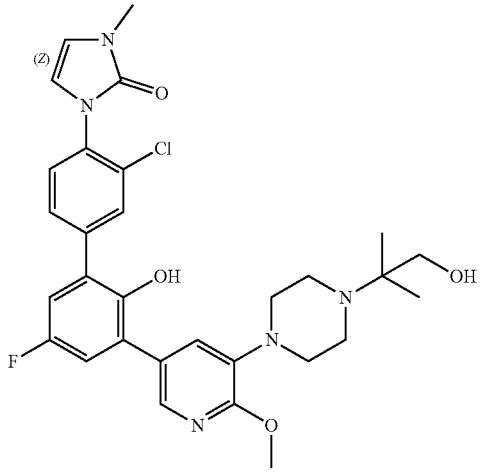 [SMILES: COc1ncc(-c2cc(F)cc(-c3ccc(-n4ccn(C)c4=O)c(Cl)c3)c2O)cc1N1CCN(C(C)(C)CO)CC1] | ¹H NMR (400 MHz, DMSO-d₆) δ 8.61 (s, 1H), 7.92 (s, 1H), 7.81 (d, J = 1.9 Hz, 1H), 7.62 (dd, J = 8.2, 1.9 Hz, 1H), 7.52 (d, J = 8.2 Hz, 1H), 7.34 (s, 1H), 7.19 (d, J = 9.1 Hz, 2H), 6.70 (dd, J = 12.6, 3.0 Hz, 2H), 4.26 (s, 1H), 3.93 (s, 3H), 3.29-3.24 (m, 2H), 3.21 (s, 3H), 3.04 (s, 4H), 2.84-2.58 (m, 4H), 0.99 (s, 6H) | 582.2 |
| 961 | 1-(4-(5'-(4-(tert-butyl)piperazin-1-yl)-3-hydroxy-6,6'-dimethyl-[2,3'-bipyridin]-4-yl)-2-chlorophenyl)-3-methyl-1H-imidazol-2(3H)-one | ¹H NMR (400 MHz, DMSO-d₆) δ 9.07 (s, 1H), 8.63 (d, J = 1.8 Hz, 1H), 7.85 (dd, J = | 547.2 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| | 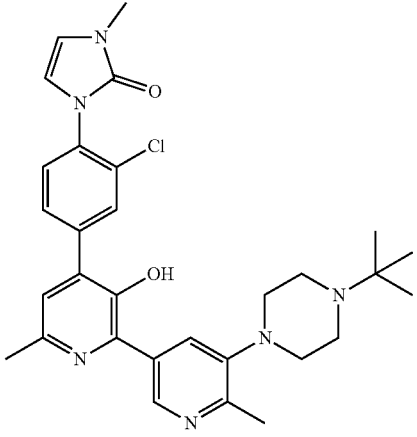 [SMILES: Cc1cc(-c2ccc(-n3ccn(C)c3=O)c(Cl)c2)c(O)c(-c2cnc(C)c(N3CCN(C(C)(C)C)CC3)c2)n1] | 8.4, 1.8 Hz, 2H), 7.67 (dd, J = 8.2, 1.9 Hz, 1H), 7.56 (d, J = 8.2 Hz, 1H), 7.22 (s, 1H), 6.71 (dd, J = 12.3, 3.0 Hz, 2H), 3.21 (s, 3H), 2.92 (s, 4H), 2.71 (s, 4H), 2.49-2.44 (m, 6H), 1.07 (s, 9H) | |
| 962 | 1-(4-(6'-amino-5'-(4-(tert-butyl)piperazin-1-yl)-3-hydroxy-6-methyl-[2,3'-bipyridin]-4-yl)-2-chlorophenyl)-3-methyl-1H-imidazol-2(3H)-one | ¹H NMR (400 MHz, DMSO-d₆) δ 8.83 (s, 1H), 8.32 (s, 1H), 7.84 (d, J = 1.8 Hz, 1H), 7.72 (s, 1H), 7.66 (dd, J = 8.2, 1.9 Hz, 1H), 7.55 (d, J = 8.2 Hz, 1H), 7.10 (s, 1H), 6.71 (dd, J = 12.4, 3.0 Hz, 2H), 5.77 (s, 2H), 3.21 (s, 3H), 2.89 (s, 8H), 2.45 (s, 3H), 1.10 (s, 9H) | 548.2 |
| 963 | 1-(4-(5'-(4-(tert-butyl)piperazin-1-yl)-3-hydroxy-6-methyl-6'-(methylamino)-[2,3'-bipyridin]-4-yl)-2-chlorophenyl)-3-methyl-1H-imidazol-2(3H)-one | ¹H NMR (400 MHz, DMSO-d₆) δ 8.80 (s, 1H), 8.41 (d, J = 1.8 Hz, 1H), 7.83 (d, J = 1.9 Hz, 1H), 7.72-7.67 (m, 1H), 7.65 (dd, J = 8.2, 1.9 Hz, 1H), 7.55 (d, J = 8.2 Hz, 1H), 7.09 (s, 1H), 6.71 (dd, J = 12.1, 3.0 Hz, 2H), 3.21 (s, 3H), 2.91 (d, J = 4.8 Hz, 3H), 2.80 (d, J = 40.4 Hz, 8H), 2.45 (s, 3H), 1.09 (s, 9H) | 562.3 |

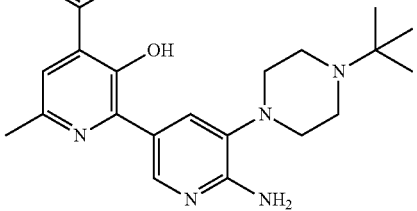

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| 964 | 1-(4-(5'-(4-(tert-butyl)piperazin-1-yl)-6'-(dimethylamino)-3-hydroxy-6-methyl-[2,3'-bipyridin]-4-yl)-2-chlorophenyl)-3-methyl-1H-imidazol-2(3H)-one | ¹H NMR (400 MHz, DMSO-d₆) δ 8.91 (s, 1H), 8.40 (s, 1H), 7.84 (d, J = 1.8 Hz, 1H), 7.73-7.62 (m, 2H), 7.56 (d, J = 8.2 Hz, 1H), 7.15 (s, 1H), 6.71 (dd, J = 12.0, 3.0 Hz, 2H), 3.21 (s, 3H), 2.99 (s, 10H), 2.69 (d, J = 18.9 Hz, 4H), 2.46 (s, 3H), 1.07 (s, 9H) | 576.3 |
| 965 | 1-{3-Chloro-5'-fluoro-2'-hydroxy-3'-[5-(1-isopropyl-1,6-diaza-spiro[3.4]oct-6-yl)-6-methylamino-pyridin-3-yl]-biphenyl-4-yl}-3-methyl-1,3-dihydro-imidazol-2-one | ¹H NMR (400 MHz, DMSO-d₆) δ 8.45 (s, 1H), 7.91 (d, J = 1.6 Hz, 1H), 7.79 (d, J = 1.6 Hz, 1H), 7.61 (dd, J = 8.2, 1.6 Hz, 1H), 7.51 (d, J = 8.0 Hz, 1H), 7.25 (s, 1H), 7.12 (d, J = 9.2 Hz, 2H), 6.70 (dd, J = 12.4, 3.2 Hz, 2H), 5.63 (d, J = 4.4 Hz, 1H), 3.34 (s, 1H), 3.21 (s, 3H), 3.10-2.92 (m, 5H), 2.90 (d, J = 4.8 Hz, 3H), 2.67 (s, 1H), 2.22 (s, 1H), 2.08-1.93 (m, 3H), 0.90 (d, J = 4.0 Hz, 6H) | 577.1 |
| 966 | (S)-1-(3-chloro-5'-fluoro-2'-hydroxy-3"-(1-isopropyl-1,7-diazaspiro[4.4]nonan-7-yl)-[1,1':3',1"-terphenyl]-4-yl)-3-methyl-1,3-dihydro-2H-imidazol-2-one | ¹H NMR (400 MHz, DMSO-d₆) δ 8.37 (s, 1H), 7.80 (d, J = 1.9 Hz, 1H), 7.61 (dd, J = | 561.3 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| | 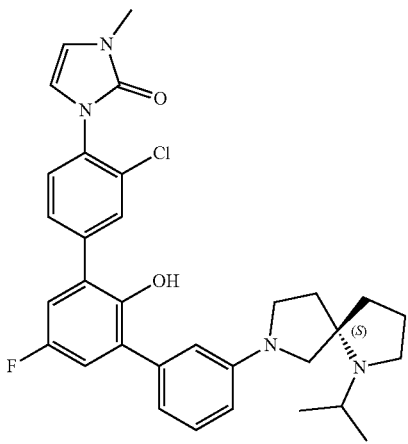 | 8.2, 1.9 Hz, 1H), 7.51 (d, J = 8.2 Hz, 1H), 7.22 (t, J = 7.9 Hz, 1H), 7.16 (dd, J = 9.0, 3.2 Hz, 1H), 7.10 (dd, J = 9.1, 3.2 Hz, 1H), 6.76 (d, J = 7.7 Hz, 1H), 6.70 (dd, J = 11.1, 3.0 Hz, 2H), 6.66-6.64 (m, 1H), 6.52 (dd, J = 8.2, 1.8 Hz, 1H), 3.40 (t, J = 8.6 Hz, 1H), 3.26-3.12 (m, 6H), 2.98 (d, J = 9.3 Hz, 1H), 2.87-2.72 (m, 2H), 2.04 (dt, J = 14.8, 9.6 Hz, 1H), 1.76-1.66 (m, 5H), 1.06-1.02 (m, 6H) | |
| 967 | (R)-1-(3-chloro-5'-fluoro-2'-hydroxy-3''-(1-isopropyl-1,7-diazaspiro[4.4]nonan-7-yl)-[1,1':3',1''-terphenyl]-4-yl)-3-methyl-1,3-dihydro-2H-imidazol-2-one<br>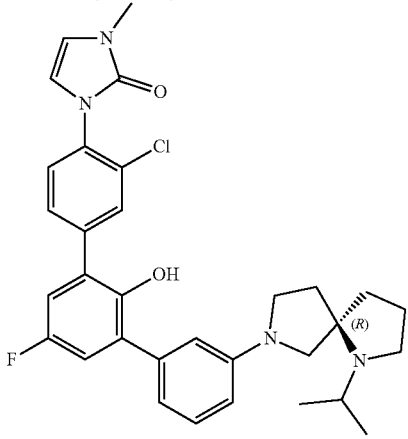 | ¹H NMR (400 MHz, DMSO-d₆) δ 8.37 (s, 1H), 7.80 (d, J = 1.9 Hz, 1H), 7.61 (dd, J = 8.2, 1.9 Hz, 1H), 7.51 (d, J = 8.2 Hz, 1H), 7.22 (t, J = 7.9 Hz, 1H), 7.16 (dd, J = 9.0, 3.2 Hz, 1H), 7.10 (dd, J = 9.1, 3.2 Hz, 1H), 6.76 (d, J = 7.7 Hz, 1H), 6.70 (dd, J = 11.1, 3.0 Hz, 2H), 6.66-6.64 (m, 1H), 6.52 (dd, J = 8.2, 1.8 Hz, 1H), 3.40 (t, J = 8.6 Hz, 1H), 3.26-3.12 (m, 6H), 2.98 (d, J = 9.3 Hz, 1H), 2.87-2.72 (m, 2H), 2.04 (dt, J = 14.8, 9.6 Hz, 1H), 1.76-1.66 (m, 5H), 1.06-1.02 (m, 6H) | 561.3 |
| 968 | 1-(3'-(6-amino-5-(1-isopropyl-1,7-diazaspiro[4.4]nonan-7-yl)pyridin-3-yl)-3-chloro-5'-fluoro-2'-hydroxy-[1,1'biphenyl]-4-yl)-3-methyl-1H-imidazol-2(3H)-one | ¹H NMR (400 MHz, DMSO-d₆) δ 8.47 (s, 1H), 7.79 (s, 2H), 7.61 (dd, J = 8.2, 1.9 Hz, 1H), 7.52 (d, J = 8.2 Hz, 1H), 7.26 (s, 1H), 7.12 (d, J = 9.1 Hz, 2H), 6.70 (dd, J = 14.8, 3.0 Hz, 2H), 5.75 (s, 2H), 3.21 (s, 8H), 2.32-1.55 (m, 6H), 1.18 (d, J = 44.3 Hz, 8H) | 577.2 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| 969 | 1-(3-chloro-3'-(6-(dimethylamino)-5-(1-isopropyl-1,7-diazaspiro[4.4]nonan-7-yl)pyridin-3-yl)-5'-fluoro-2'-hydroxy-[1,1'-biphenyl]-4-yl)-3-methyl-1H-imidazol-2(3H)-one | ¹H NMR (400 MHz, CD₃OD) δ 7.88 (d, J = 1.9 Hz, 1H), 7.80 (d, J = 1.8 Hz, 1H), 7.61 (dd, J = 8.2, 1.9 Hz, 1H), 7.49 (d, J = 8.2 Hz, 1H), 7.28 (d, J = 1.9 Hz, 1H), 7.09-6.98 (m, 2H), 6.64 (dd, J = 15.9, 3.0 Hz, 2H), 3.38 (d, J = 9.7 Hz, 1H), 3.34 (s, 3H), 3.25 (dd, J = 12.9, 6.3 Hz, 2H), 2.94 (d, J = 7.2 Hz, 1H), 2.88 (s, 1H), 2.85 (s, 6H), 2.24-2.15 (m, 1H), 1.99-1.73 (m, 5H), 1.31 (d, J = 18.6 Hz, 2H), 1.16 (t, J = 6.8 Hz, 6H). O—H proton not observed | 605.3 |
| 970 | 1-(3-chloro-5'-fluoro-2'-hydroxy-3'-(5-(1-isopropyl-1,7-diazaspiro[4.4]nonan-7-yl)-6-(methylamino)pyridin-3-yl)-[1,1'-biphenyl]-4-yl)-3-methyl-1H-imidazol-2(3H)-one | ¹H NMR (400 MHz, CD₃OD) δ 7.94-7.81 (m, 2H), 7.78 (s, 1H), 7.59 (dd, J = 8.2, 1.7 Hz, 1H), 7.52 (d, J = 8.2 Hz, 1H), 7.22 (s, 1H), 7.14 (dd, J = 8.7, 3.1 Hz, 1H), 6.66 (dd, J = 20.1, 3.0 Hz, 2H), 4.01 (s, 1H), 3.67 (t, J = 24.1 Hz, 3H), 3.44 (t, J = 11.8 Hz, 2H), 3.35 (s, 3H), 3.19 (s, 3H), 2.99 (dd, J = 5.5, 7.7 Hz, 1H), 2.66 (s, 1H), 2.38-2.12 (m, 5H), 1.54-1.31 (m, 6H). N—H or O—H protons not observed | 591.3 |
| 971 | 1-(4-(2-(8-(4-(tert-butyl)piperazin-1-yl)imidazo[1,2-a]pyridin-6-yl)-3-hydroxy-6-methylpyridin-4-yl)-2-chlorophenyl)-3-methyl-1H-imidazol-2(3H)-one | ¹H NMR (400 MHz, DMSO-d₆) δ 8.76 (s, 1H), 8.36 (s, 1H), 7.93 (s, 1H), 7.86 (s, 1H), 7.67 (d, J = 7.6 | 575.1 |

TABLE 33-continued

Following compounds were prepared using similar procedures as described for Examples 1 through 926.

| Ex. No. | Name/Structure | ¹H NMR Data | LCMS (M + H)⁺ |
|---|---|---|---|
| | | Hz, 1H), 7.61-7.43 (m, 2H), 7.28 (dd, J = 8.8, 6.0 Hz, 2H), 6.72 (d, J = 5.2 Hz, 2H), 6.56 (s, 1H), 3.58 (s, 4H), 3.25 (s, 3H), 2.75 (s, 4H), 1.10 (s, 9H) | |
| 972 | 1-(2-chloro-4-(3-hydroxy-5'-(1-isopropyl-1,7-diazaspiro[4.4]nonan-7-yl)-6'-methoxy-6-methyl-[2,3'-bipyridin]-4-yl)phenyl)-3-methyl-1H-imidazol-2(3H)-one | ¹H NMR (400 MHz, DMSO-d₆) δ 8.88 (s, 1H), 8.04 (s, 1H), 7.83 (d, J = 1.8 Hz, 1H), 7.66 (dd, J = 8.2, 1.9 Hz, 1H), 7.56 (d, J = 8.2 Hz, 1H), 7.31 (s, 1H), 7.17 (s, 1H), 6.71 (dd, J = 12.6, 3.0 Hz, 2H), 3.90 (s, 3H), 3.47-3.36 (m, 4H), 3.21 (s, 3H), 2.89 (dd, J = 45.1, 20.2 Hz, 3H), 2.46 (s, 3H), 2.04 (d, J = 8.0 Hz, 1H), 1.71 (s, 5H), 1.07 (dd, J = 12.3, 6.2 Hz, 6H) | 589.2 |
| 973 | 1-(2-chloro-4-(3-hydroxy-5'-(1-isopropyl-1,7-diazaspiro[4.4]nonan-7-yl)-6,6'-dimethyl-[2,3'-bipyridin]-4-yl)phenyl)-3-methyl-1H-imidazol-2(3H)-one | ¹H NMR (400 MHz, DMSO-d₆) δ 8.99 (s, 1H), 8.43 (s, 1H), 7.84 (d, J = 1.8 Hz, 1H), 7.66 (dd, J = | 573.2 |

| Ex. No. | Name/Structure | ¹H NMR Data | LCMS (M + H)⁺ |
|---|---|---|---|
| | 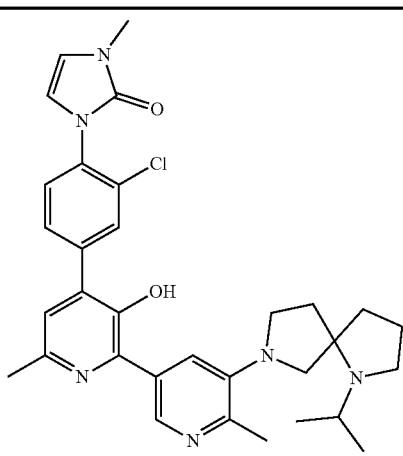 | 8.2, 1.9 Hz, 1H), 7.56 (d, J = 8.2 Hz, 2H), 7.21 (s, 1H), 6.71 (dd, J = 13.1, 3.0 Hz, 2H), 3.21 (s, 5H), 2.77 (d, J = 34.8 Hz, 3H), 2.51 (s, 3H), 2.47 (s, 3H), 2.09-1.72 (m, 8H), 1.08 (s, 6H). | |
| 974 | 1-(2-chloro-4-(3-hydroxy-5'-(1-isopropyl-1,6-diazaspiro[3.4]octan-6-yl)-6,6'-dimethyl-[2,3'-bipyridin]-4-yl)phenyl)-3-methyl-1H-imidazol-2(3H)-one<br>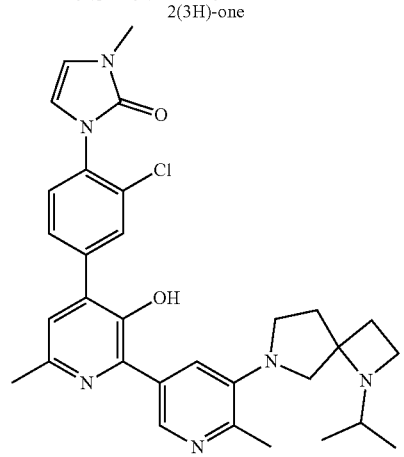 | ¹H NMR (400 MHz, DMSOd₆) δ 9.01 (s, 1H), 8.46 (d, J = 1.6 Hz, 1H), 7.85 (d, J = 1.8 Hz, 1H), 7.67 (dd, J = 8.2, 1.9 Hz, 1H), 7.59 (dd, J = 18.1, 4.8 Hz, 2H), 7.21 (s, 1H), 6.71 (dd, J = 12.8, 3.0 Hz, 2H), 3.60 (d, J = 9.8 Hz, 1H), 3.26-3.15 (m, 6H), 3.12 (s, 1H), 2.99 (d, J = 10.0 Hz, 2H), 2.72 (s, 1H), 2.47 (s, 3H), 2.22 (dd, J = 19.4, 9.7 Hz, 1H), 2.00 (dd, J = 22.3, 10.7 Hz, 3H), 1.19 (dd, J = 20.4, 13.2 Hz, 1H), 0.95 (dd, J = 14.2, 6.0 Hz, 6H), 0.85 (dt, J = 9.1, 5.7 Hz, 1H) | 559.2 |
| 975 | 1-(4-(6'-amino-3-hydroxy-5'-(1-isopropyl-1,6-diazaspiro[3.4]octan-6-yl)-6-methyl-[2,3'-bipyridin]-4-yl)-2-chlorophenyl)-3-methyl-1H-imidazol-2(3H)-one | ¹H NMR (400 MHz, DMSO-d₆) δ 8.16 (d, J = 1.9 Hz, 1H), 7.87 (s, 1H), 7.72 (d, J = 1.9 Hz, 1H), 7.67 (dd, J = 8.2, 1.9 Hz, 1H), 7.53 (d, J = 8.2 Hz, 1H), 7.15 (s, 1H), 6.65 (dd, J = 13.8, 3.0 Hz, 2H), 3.63 (d, J = 10.5 Hz, 1H), 3.34 (s, 3H), 3.25-3.05 (m, 5H), 2.93 (s, 1H), 2.51 (s, 3H), 2.46-2.39 (m, 1H), 2.26-2.18 (m, 3H), 1.09 (t, J = 5.7 Hz, 6H). N—H or O—H protons not observed | 560.1 |

Example 976

1-(4-(3-Amino-2-(3-(4-(tert-butyl)piperazin-1-yl)phenyl)pyridin-4-yl)-2-chlorophenyl)-3-methyl-1H-imidazol-2(3H)-one

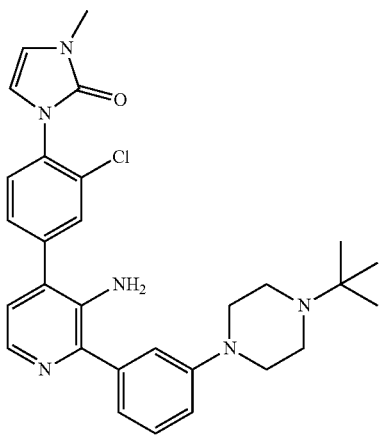 [SMILES: Cn1ccn(-c2ccc(-c3ccnc(-c4cccc(N5CCN(C(C)(C)C)CC5)c4)c3N)cc2Cl)c1=O]

Step 1: 2-(3-(4-(tert-Butyl)piperazin-1-yl)phenyl)-4-chloropyridin-3-amine

A solution of 2,4-dichloropyridin-3-amine (500 mg, 3.1 mmol), 1-(tert-butyl)-4-(3-(4,4,5,5-tetramethyl-1,3,2-dioxaborolan-2-yl)phenyl)piperazine (1.27 g, 3.68 mmol), Pd(PPh₃)₄ (355 mg, 0.31 mmol) and Na₂CO₃ (975 mg, 9.2 mmol) in dioxane/H₂O (15 mL/3 mL) was stirred at 100° C. for 16 hours under N₂. After the reaction was complete by LCMS, the reaction mixture was cooled, filtered and extracted with EA. The combined organic layer was washed with brine, dried over Na₂SO₄, filtered and concentrated. The residue was purified by FCC to afford 2-(3-(4-(tert-butyl)piperazin-1-yl)phenyl)-4-chloropyridin-3-amine (795 mg, 75% yield) as yellow oil.

LCMS: 345.2 (M+H)⁺.

Step 2: 1-(4-(3-amino-2-(3-(4-(tert-butyl)piperazin-1-yl)phenyl)pyridin-4-yl)-2-chlorophenyl)-3-methyl-1H-imidazol-2(3H)-one A solution of 2-(3-(4-(tert-butyl)piperazin-1-yl)phenyl)-4-chloropyridin-3-amine (150 mg, 0.43 mmol), 1-(2-chloro-4-(4,4,5,5-tetramethyl-1,3,2-dioxaborolan-2-yl)phenyl)-3-methyl-1H-imidazol-2(3H)-one (146 mg, 0.43 mmol), Pd(PPh₃)₄ (50 mg, 0.043 mmol) and K₂CO₃ (137 mg, 1.29 mmol) in dioxane/H₂O (15 mL/3 mL) was stirred at 100° C. for 16 hours under N₂. After the reaction was complete by LCMS, the reaction mixture was cooled, filtered, and extracted with DCM. The combined organic layers were washed with brine, dried over Na₂SO₄, filtered and concentrated. The residue was purified by FCC to afford 1-(4-(3-amino-2-(3-(4-(tert-butyl)piperazin-1-yl)phenyl)pyridin-4-yl)-2-chlorophenyl)-3-methyl-1H-imidazol-2(3H)-one (37.1 mg, 16.7% yield) as white solid. ¹H NMR (400 MHz, DMSO-d₆) δ 8.01 (d, J=4.8 Hz, 1H), 7.77 (s, 1H), 7.59 (s, 2H), 7.33 (t, J=7.9 Hz, 1H), 7.13 (s, 1H), 7.02 (ddd, J=10.3, 8.9, 3.4 Hz, 3H), 6.70 (dd, J=17.6, 3.0 Hz, 2H), 4.60 (s, 2H), 3.21 (s, 3H), 3.19-3.09 (m, 4H), 2.76-2.58 (m, 4H), 1.05 (s, 9H). LCMS: 517.2 (M+H)⁺.

TABLE 34

Following compounds were prepared using similar procedures as described for Examples 1 through 976.

| Ex. No. | Name/Structure | ¹H NMR Data | LCMS (M + H)⁺ |
|---|---|---|---|
| 977 | 1-(2-chloro-4-(3-hydroxy-5'-(1-isopropyl-1,6-diazaspiro[3.4]octan-6-yl)-6'-methoxy-6-methyl-[2,3'-bipyridin]-4-yl)phenyl)-3-methyl-1H-imidazol-2(3H)-one | ¹H NMR (400 MHz, DMSO-d₆) δ 8.89 (s, 1H), 8.07 (d, J = 1.7 Hz, 1H), 7.84 (d, J = 1.8 Hz, 1H), 7.66 (dd, J =8.2, 1.8 Hz, 1H), 7.56 (d, J = 8.2 Hz, 1H), 7.34 (d, J = 1.5 Hz, 1H), 7.17 (s, 1H), 6.71 (dd, J = 12.3, 3.0 Hz, 2H), 3.91 (s, 3H), 3.65 (d, J = 10.0 Hz, 1H), 3.44-3.38 (m, 1H), 3.27 (d, J =7.0 Hz, 1H), 3.21 (s, 3H), 3.14 (d, J = 21.6 Hz, 2H), 3.01 (d, J = 17.9 Hz, 1H), 2.67 (s, 1H), 2.46 (s, 3H), 2.20-2.10 (m, 1H), 2.06-1.89 (m, 3H), 0.91 (dd, J = 9.6, 6.1 Hz, 6H) | 575.3 |

TABLE 34-continued

Following compounds were prepared using similar procedures as described for Examples 1 through 976.

| Ex. No. | Name/Structure | ¹H NMR Data | LCMS (M + H)⁺ |
|---|---|---|---|
| 978 | 1-(4-(6'-amino-3-hydroxy-5'-(1-isopropyl-1,7-diazaspiro[4.4]nonan-7-yl)-6-methyl-[2,3'-bipyridin]-4-yl)-2-chlorophenyl)-3-methyl-1H-imidazol-2(3H)-one | ¹H NMR (400 MHz, DMSO-d₆) δ 8.79 (s, 1H), 8.21 (s, 1H), 7.83 (s, 1H), 7.65 (d, J = 8.2 Hz, 1H), 7.61-7.47 (m, 2H), 7.09 (s, 1H), 6.71 (dd, J = 12.3, 2.9 Hz, 2H), 5.58 (s, 2H), 3.29-3.25 (m, 1H), 3.21 (s, 3H), 3.17 (d, J = 8.9 Hz, 2H), 3.08 (s, 1H), 2.84-2.71 (m, 2H), 2.67 (d, J = 9.1 Hz, 1H), 2.45 (s, 3H), 2.05 (dd, J = 21.1, 9.0 Hz, 1H), 1.69 (d, J = 7.5 Hz, 5H), 1.05 (d, J = 6.5 Hz, 6H) | 574.3 |
| 979 | 1-(4-(2-(3-(4-(tert-butyl)piperazin-1-yl)phenyl)-3-hydroxypyridin-4-yl)-2-chlorophenyl)-3-methyl-1H-imidazol-2(3H)-one | H NMR (400 MHz, CD₃OD) δ 8.33 (d, J = 5.6 Hz, 1H), 7.99 (d, J = 2.0 Hz, 1H), 7.82-7.70 (m, 2H), 7.63 (d, J = 8.0 Hz, 1H), 7.54 (t, J = 8.0 Hz, 1H), 7.47 (d, J = 2.0 Hz, 1H), 7.41-7.33 (m, 1H), 7.27 (dd, J = 8.0, 2.0 Hz, 1H), 6.68 (dd, J = 12.0, 2.8 Hz, 2H), 4.03 (d, J = 13.2 Hz, 2H), 3.74 (d, J = 11.2 Hz, 2H), 3.35 (s, 3H), 3.30 (d, J = 12.0 Hz, 2H), 3.16 (t, J = 12.0 Hz, 2H), 1.49 (s, 9H). O—H proton not observed | 518.1 |
| 980 | 1-(2-chloro-4-(3-hydroxy-5'-(1-isopropyl-1,6-diazaspiro[3.4]octan-6-yl)-6-methyl-6'-(methylamino)-[2,3'-bipyridin]-4-yl)phenyl)-3-methyl-1H- | ¹H NMR (400 MHz, CD₃OD) δ 8.27 (d, J = 2.0 Hz, 1H), 7.88 (d, J = 1.6 Hz, 1H), 7.68 (dd, J = | 574.0 |

TABLE 34-continued

Following compounds were prepared using similar procedures as described for Examples 1 through 976.

| Ex. No. | Name/Structure | ¹H NMR Data | LCMS (M + H)⁺ |
|---|---|---|---|
| | imidazol-2(3H)-one | 8.0, 2.0 Hz, 2H), 7.53 (d, J = 8.0 Hz, 1H), 7.15 (s, 1H), 6.67 (d, J = 3.2 Hz, 1H), 6.64 (d, J = 3.2 Hz, 1H), 3.55 (t, J = 11.6 Hz, 1H), 3.34 (s, 3H), 3.15-3.12 (m, 4H), 3.08 (d, J = 10.0 Hz, 1H), 3.00 (s, 3H), 2.92 (d, J = 10.0 Hz, 1H), 2.52 (s, 3H), 2.46-2.31 (m, 1H), 2.25-2.16 (m, 3H), 1.09 (t, J = 5.9 Hz, 6H). N—H or O—H protons not observed. | |
| 981 | 1-(2-chloro-4-(3-hydroxy-2-(3-(1-isopropyl-1,7-diazaspiro[4.4]nonan-7-yl)phenyl)-6-methylpyridin-4-yl)phenyl)-3-methyl-1H-imidazol-2(3H)-one | ¹H NMR (400 MHz, DMSO-d₆) δ 8.69 (s, 1H), 7.84 (d, J = 2.0 Hz, 1H), 7.66 (dd, J = 8.0, 2.0 Hz, 1H), 7.55 (d, J = 8.0 Hz, 1H), 7.22 (t, J = 8.0 Hz, 1H), 7.17 (s, 1H), 7.04 (d, J = 7.6 Hz, 1H), 6.95 (s, 1H), 6.72 (d, J = 3.2 Hz, 1H), 6.70 (d, J = 3.2 Hz, 1H), 6.54 (d, J = 6.4 Hz, 1H), 3.40 (t, J = 8.4 Hz, 1H), 3.24-3.12 (m, 6H), 2.97 (d, J = 9.2 Hz, 1H), 2.81 (d, J = 22.4 Hz, 2H), 2.46 (s, 3H), 2.08 (d, J = 11.2 Hz, 1H), 1.72 (s, 5H), 1.04 (dd, J = 6.0, 4.4 Hz, 6H) | 578.2 |
| 982 | 1-(3'-(5-(4-(tert-butyl)piperazin-1-yl)-6-methoxypyridin-3-yl)-3-chloro-5'-fluoro-2'-hydroxy-[1,1'-biphenyl]-4-yl)- | ¹H NMR (400 MHz, DMSO-d₆) δ 8.60 (s, 1H), 7.92 (d, J = 2.0 Hz, | 580.1 |

TABLE 34-continued

Following compounds were prepared using similar procedures as described for Examples 1 through 976.

| Ex. No. | Name/Structure | ¹H NMR Data | LCMS (M + H)⁺ |
|---|---|---|---|
| | 3,4-dimethyl-1H-imidazol-2(3H)-one 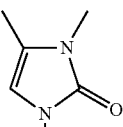 | 1H), 7.79 (d, J = 2.0 Hz, 1H), 7.60 (dd, J = 8.0, 2.0 Hz, 1H), 7.49 (d, J = 8.0 Hz, 1H), 7.33 (s, 1H), 7.19 (d, J = 9.2 Hz, 2H), 6.43 (d, J = 1.2 Hz, 1H), 3.93 (s, 3H), 3.12 (s, 3H), 3.05 (s, 4H), 2.65 (s, 4H), 2.00 (m, 3H), 1.05 (s, 9H) | |
| 983 | 1-(2-chloro-4-(3-hydroxy-2-(3-(1-isopropyl-1,6-diazaspiro[3.4]octan-6-yl)phenyl)-6-methylpyridin-4-yl)phenyl)-3-methyl-1H-imidazol-2(3H)-one 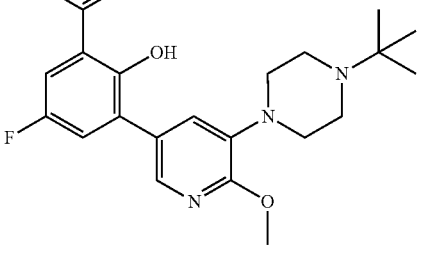 | ¹H NMR (400 MHz, DMSO-d₆) δ 8.67 (s, 1H), 7.84 (d, J = 1.8 Hz, 1H), 7.67 (dd, J = 8.2, 1.9 Hz, 1H), 7.55 (d, J = 8.2 Hz, 1H), 7.23 (t, J = 7.9 Hz, 1H), 7.17 (s, 1H), 7.07 (d, J = 7.6 Hz, 1H), 6.98 (s, 1H), 6.71 (dd, J = 10.2, 3.0 Hz, 2H), 6.56 (d, J = 8.1 Hz, 1H), 3.41 (dd, J = 19.0, 9.4 Hz, 2H), 3.27 (s, 1H), 3.21 (s, 3H), 3.16 (dd, J = 17.2, 7.0 Hz, 2H), 3.01 (dd, J = 14.4, 7.1 Hz, 1H), 2.68 (dd, J = 12.1, 6.0 Hz, 1H), 2.46 (s, 3H), 2.20 (dt, J = 23.6, 11.9 Hz, 1H), 2.13-1.94 (m, 2H), 1.90 (d, J = 8.3 Hz, 1H), 0.94-0.82 (m, 6H) | 544.2 |
| 984 | 1-(4-(6'-amino-5'-(4-(tert-butyl)piperazin-1-yl)-3-hydroxy-[2,3'-bipyridin]-4-yl)-2-chlorophenyl)-3- | ¹H NMR (400 MHz, DMSO-d₆) δ 9.16 (s, 1H), 8.34 (s, 1H), 8.24 | 534.1 |

TABLE 34-continued

Following compounds were prepared using similar procedures as described for Examples 1 through 976.

| Ex. No. | Name/Structure | ¹H NMR Data | LCMS (M + H)⁺ |
|---|---|---|---|
| | methyl-1H-imidazol-2(3H)-one<br>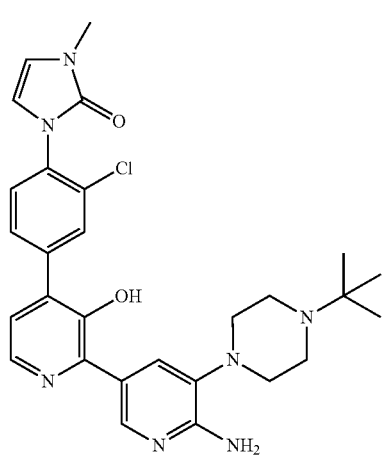 [SMILES: Cn1ccn(-c2ccc(-c3ccnc(-c4cnc(N)c(N5CCN(C(C)(C)C)CC5)c4)c3O)cc2Cl)c1=O] | (d, J = 4.6 Hz, 1H), 7.86 (s, 1H), 7.76-7.61 (m, 2H), 7.57 (d, J = 8.2 Hz, 1H), 7.23 (d, J = 4.8 Hz, 1H), 6.71 (dd, J = 11.9, 3.0 Hz, 2H), 5.81 (s, 2H), 3.21 (s, 3H), 2.78 (d, J = 87.6 Hz, 8H), 1.10 (s, 9H) | |
| 985 | 1-(2-chloro-4-(3-hydroxy-5'-(1-isopropyl-1,7-diazaspiro[4.4]nonan-7-yl)-6-methyl-6'-(methylamino)-[2,3'-bipyridin]-4-yl)phenyl)-3-methyl-1H-imidazol-2(3H)-one<br>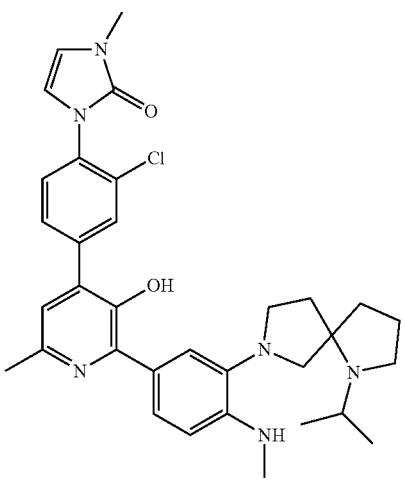 [SMILES: CNc1ccc(-c2nc(C)cc(-c3ccc(-n4ccn(C)c4=O)c(Cl)c3)c2O)cc1N1CCC2(CCCN2C(C)C)C1] | ¹H NMR (400 MHz, DMSO-d₆) δ 9.63 (s, 1H), 8.34 (dd, J = 8.6, 1.5 Hz, 1H), 8.02 (d, J = 16.2 Hz, 1H), 7.86 (d, J = 1.8 Hz, 1H), 7.71-7.53 (m, 2H), 7.34 (s, 1H), 6.72 (dd, J = 20.2, 3.0 Hz, 2H), 3.94-3.80 (m, 3H), 3.60 (t, J = 11.2 Hz, 2H), 3.34 (dd, J = 11.1, 6.3 Hz, 1H), 3.22 (s, 3H), 3.10 (d, J = 4.3 Hz, 3H), 2.98 (d, J = 7.4 Hz, 1H), 2.80 (d, J = 7.4 Hz, 1H), 2.52 (s, 3H), 2.31-1.91 (m, 5H), 1.30 (ddd, J = 54.1, 37.3, 6.4 Hz, 6H). N—H or O—H proton not observed | 588.3 |
| 986 | 1-(4-(5'-(4-(tert-butyl)piperazin-1-yl)-3-hydroxy-6'-(methylamino)-[2,3'-bipyridin]-4-yl)-2-chlorophenyl)-3- | ¹H NMR (400 MHz, DMSO-d₆) δ 9.25-9.01 (m, 1H), 8.43 (s, 1H), | 548.2 |

TABLE 34-continued

Following compounds were prepared using similar procedures as described for Examples 1 through 976.

| Ex. No. | Name/Structure | ¹H NMR Data | LCMS (M + H)⁺ |
|---|---|---|---|
| | methyl-1H-imidazol-2(3H)-one | 8.23 (d, J = 4.7 Hz, 1H), 7.85 (s, 1H), 7.74-7.62 (m, 2H), 7.57 (d, J = 8.2 Hz, 1H), 7.22 (d, J = 4.8 Hz, 1H), 6.71 (dd, J = 11.6,3.0 Hz, 2H), 5.98 (s, 1H), 3.21 (s, 3H), 2.92 (d, J = 4.8 Hz, 3H), 2.85 (s, 4H), 2.71 (d, J = 32.3 Hz, 4H), 1.08 (s, 9H) | |
| 987 | 1-(3-chloro-3'-(6-(dimethylamino)-5-(1-isopropyl-1,6-diazaspiro[3.4]octan-6-yl)pyridin-3-yl)-5'-fluoro-2'-hydroxy-[1,1'-biphenyl]-4-yl)-3-methyl-1H-imidazol-2(3H)-one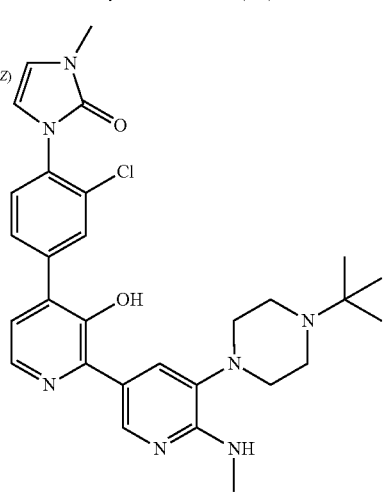 | ¹H NMR (400 MHz, DMSO-d₆) δ 8.56 (s, 1H), 7.94 (d, J = 1.6 Hz, 1H), 7.80 (d, J = 1.6 Hz, 1H), 7.60 (d, J = 12.0 Hz, 1H), 7.52 (d, J = 8.2 Hz, 1H), 7.25-7.08 (m, 3H), 6.72 (d, J = 3.2 Hz, 1H), 6.69 (d, J = 3.2 Hz, 1H), 3.48 (d, J = 9.6 Hz, 1H), 3.25-3.21 (m, 4H), 3.14-3.08 (m, 2H), 2.94 (d, J = 10.4 Hz, 2H), 2.78 (s, 6H), 2.64-2.61 (m, 1H), 2.19-2.17 (m, 1H), 2.02-1.91 (m, 3H), 0.91 (dd, J = 21.6, 10.8 Hz, 6H) | 591.1 |
| 988 | 1-(4-(5'-(4-(tert-butyl)piperazin-1-yl)-6'-(dimethylamino)-3-hydroxy-[2,3'-bipyridin]-4-yl)-2-chlorophenyl)-3- | ¹H NMR (400 MHz, DMSO) δ 9.25 (s, 1H), 8.45 (s, 1H), 8.27 (d, J = | 562.2 |

TABLE 34-continued

Following compounds were prepared using similar procedures as described for Examples 1 through 976.

| Ex. No. | Name/Structure | $^1$H NMR Data | LCMS (M + H)$^+$ |
|---|---|---|---|
| | methyl-1H-imidazol-2(3H)-one 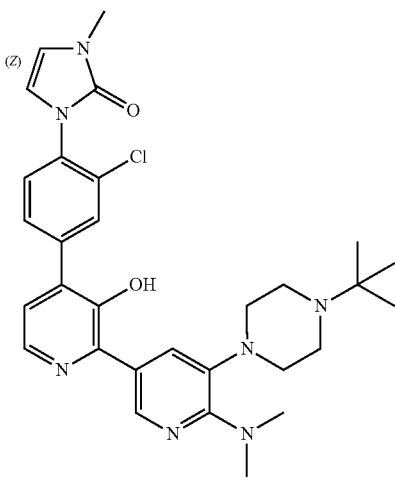 [SMILES: CN(C)c1ncc(-c2nccc(-c3ccc(-n4ccn(C)c4=O)c(Cl)c3)c2O)cc1N1CCN(C(C)(C)C)CC1] | 4.8 Hz, 1H), 7.86 (d, J = 1.7 Hz, 1H), 7.68 (dd, J = 15.4, 7.2 Hz, 2H), 7.58 (d, J = 8.2 Hz, 1H), 7.28 (d, J = 4.8 Hz, 1H), 6.71 (dd, J = 12.2, 3.0 Hz, 2H), 3.29 (s, 6H), 3.21 (s, 3H), 3.00 (s, 8H), 1.12 (t, J = 43.5 Hz, 9H). | |
| 989 | 1-(4-(2-(8-(4-(tert-butyl)piperazin-1-yl)imidazo[1,2-a]pyridin-6-yl)-3-hydroxy-6-methylpyridin-4-yl)-2-chlorophenyl)-3-methyl-1H-imidazol-2(3H)-one 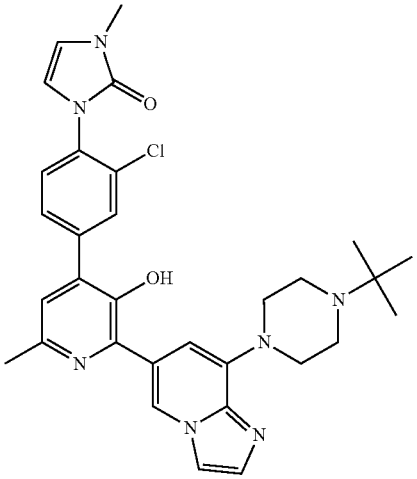 [SMILES: Cc1cc(-c2ccc(-n3ccn(C)c3=O)c(Cl)c2)c(O)c(-c2cc(N3CCN(C(C)(C)C)CC3)c3nccn3c2)n1] | $^1$H NMR (400 MHz, CD$_3$OD) δ 8.65 (d, J = 1.2 Hz, 1H), 7.90 (d, J = 2.0 Hz, 1H), 7.85 (d, J = 1.2 Hz, 1H), 7.69 (dd, J = 8.0, 2.0 Hz, 1H), 7.53 (t, J = 4.4 Hz, 2H), 7.18 (d, J = 12.0 Hz, 1H), 7.15 (d, J = 1.2 Hz, 1H), 6.67 (d, J = 3.2 Hz, 1H), 6.63 (d, J = 3.2 Hz, 1H), 3.61-3.40 (m, 4H), 3.34 (s, 3H), 3.04 (t, J = 4.4 Hz, 4H), 2.53 (s, 3H), 1.23 (s, 9H). O—H proton not observed | 572.1 |
| 990 | 1-(2-chloro-4-(6'-(dimethylamino)-3-hydroxy-5'-(1-isopropyl-1,6-diazaspiro[3.4]octan-6-yl)-6-methyl-[2,3'-bipyridin]-4-yl)phenyl)-3-methyl- | $^1$H NMR (400 MHz, CD$_3$OD) δ 8.23 (d, J = 2.0 Hz, 1H), 7.88 (d, J = 2.0 Hz, 1H), 7.68 (dd, J = | 588.1 |

TABLE 34-continued

Following compounds were prepared using similar procedures as described for Examples 1 through 976.

| Ex. No. | Name/Structure | ¹H NMR Data | LCMS (M + H)⁺ |
|---|---|---|---|
| | 1H-imidazol-2(3H)-one 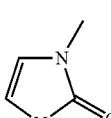 | 8.0, 2.0 Hz, 1H), 7.58 (d, J = 2.0 Hz, 1H), 7.53 (d, J = 8.0 Hz, 1H), 7.18 (s, 1H), 6.67 (d, J = 3.2 Hz, 1H), 6.64 (d, J = 3.2 Hz, 1H), 3.68 (d, J = 10.4 Hz, 1H), 3.34 (s, 3H), 3.31-3.16 (m, 4H), 3.06 (d, J = 9.6 Hz, 1H), 2.92-2.79 (m, 7H), 2.52 (s, 3H), 2.42-2.27 (m, 1H), 2.23-1.99 (m, 3H), 1.05 (dd, J = 15.2, 6.0 Hz, 6H). O—H proton not observed | |

Example 991

1-(4-(2-(3-(4-(tert-Butyl)piperazin-1-yl)phenyl)-3-hydroxy-6-methylpyridin-4-yl)-2-chlorophenyl)-3-(methyl-d₃)-1,3-dihydro-2H-imidazol-2-one

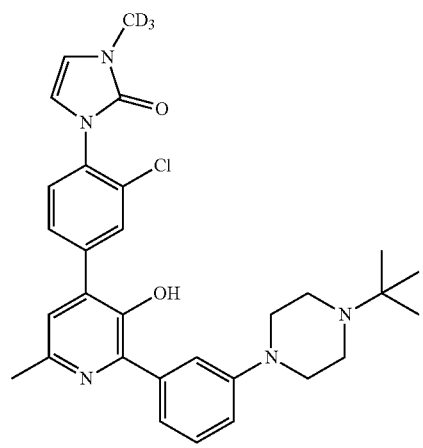 [SMILES: [2H]C([2H])([2H])n1ccn(-c2ccc(-c3cc(C)nc(-c4cccc(N5CCN(C(C)(C)C)CC5)c4)c3O)cc2Cl)c1=O]

Step 1: 1-(4-(2-Bromo-3-(methoxymethoxy)-6-methylpyridin-4-yl)-2-chlorophenyl)-3-(trideuteromethyl)-1H-imidazol-2(3H)-one The title compound was prepared following the procedure described for Example 910 using 1-(2-chloro-4-(4,4,5,5-tetramethyl-1,3,2-dioxaborolan-2-yl)phenyl)-3-(trideuteromethyl)-1H-imidazol-2(3H)-one and 1-(4-(2-bromo-3-hydroxy-6-methylpyridin-4-yl)-2-chlorophenyl)-3-methyl-1H-imidazol-2(3H)-one to afford 1-(4-(2-bromo-3-(methoxymethoxy)-6-methylpyridin-4-yl)-2-chlorophenyl)-3-(trideuteromethyl)-1H-imidazol-2(3H)-one (50 mg, 41% yield) as a yellow solid. LCMS: 441.0 (M+H)⁺

Step 2: 1-(4-(2-(3-(4-(tert-Butyl)piperazin-1-yl)phenyl)-3-(methoxymethoxy)-6-methylpyridin-4-yl)-2-chlorophenyl)-3-(trideuteromethyl)-1H-imidazol-2(3H)-one The title compound was prepared following the procedure described for Example 910 using 1-(4-(2-bromo-3-(methoxymethoxy)-6-methylpyridin-4-yl)-2-chlorophenyl)-3-(trideuteromethyl)-1H-imidazol-2(3H)-one and to 1-(tert-butyl)-4-(3-(4,4,5,5-tetramethyl-1,3,2-dioxaborolan-2-yl)phenyl)piperazine afford 1-(4-(2-(3-(4-(tert-butyl)piperazin-1-yl)phenyl)-3-(methoxymethoxy)-6-methylpyridin-4-yl)-2-chlorophenyl)-3-(trideuteromethyl)-1H-imidazol-2(3H)-one (50 mg, 76% yield) as a yellow solid. LCMS: 579.1 (M+H)⁺.

Step 3: 1-(4-(2-(3-(4-(tert-Butyl)piperazin-1-yl)phenyl)-3-hydroxy-6-methylpyridin-4-yl)-2-chlorophenyl)-3-(trideuteromethyl)-1H-imidazol-2(3H)-one The title compound was prepared following the procedure described for Example 910 using 1-(4-(2-(3-(4-(tert-butyl)piperazin-1-yl)phenyl)-3-(methoxymethoxy)-6-methylpyridin-4-yl)-2-chlorophenyl)-3-(trideuteromethyl)-1H-imidazol-2(3H)-one to afford 1-(4-(2-(3-(4-(tert-butyl)piperazin-1-yl)phenyl)-3-hydroxy-6-methylpyridin-4-yl)-2-chlorophenyl)-3-(trideuteromethyl)-1H-imidazol-2(3H)-one (20.5 mg, 72% yield) as a yellow solid. ¹H NMR (400 MHz, CD₃OD) δ 7.90 (d, J=2.0 Hz, 1H), 7.70 (dd, J=8.0, 2.0 Hz, 1H), 7.53 (d, J=8.0 Hz, 1H), 7.38 (t, J=8.0 Hz, 1H), 7.34 (s, 1H), 7.22 (d, J=6.6 Hz, 2H), 7.07 (dd, J=8.0, 2.0 Hz, 1H), 6.67 (d, J=3.2 Hz, 1H), 6.64 (d, J=3.2 Hz, 1H), 3.31 (s, 4H), 2.90 (s, 4H), 2.51 (s, 3H), 1.19 (s, 9H). O—H proton not observed.

LCMS: 535.2 (M+H)⁺.

Example 992

1-(4-(3-Amino-2-(3-(4-(tert-butyl)piperazin-1-yl)phenyl)-6-methylpyridin-4-yl)-2-chlorophenyl)-3-methyl-1H-imidazol-2(3H)-one

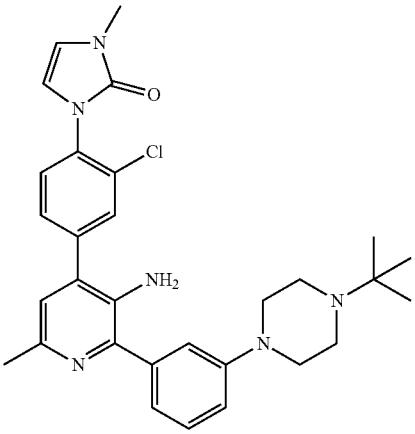 [SMILES: Cc1cc(-c2ccc(-n3ccn(C)c3=O)c(Cl)c2)c(N)c(-c2cccc(N3CCN(C(C)(C)C)CC3)c2)n1]

Step 1: 2,4-Dichloro-6-methylpyridin-3-amine

To a solution of 2,4-dichloro-6-methyl-3-nitropyridine (2.0 g, 9.8 mmol) in MeOH/dioxane (40 mL/40 mL) was added Raney Nickel (0.5 g). The reaction mixture was stirred at rt for 48 hours under $H_2$. The reaction mixture was filtered. The filtrate was concentrated in vacuo to afford 2,4-dichloro-6-methylpyridin-3-amine (1.6 g, 94% yield). LCMS: 177.0 $(M+H)^+$.

Step 2: 2-(3-(4-(tert-butyl)piperazin-1-yl)phenyl)-4-chloro-6-methylpyridin-3-amine To a solution of 2,4-dichloro-6-methylpyridin-3-amine (120 mg, 0.68 mmol), 1-(tert-butyl)-4-(3-(4,4,5,5-tetramethyl-1,3,2-dioxaborolan-2-yl)phenyl)piperazine (280 mg, 0.81 mmol) in dioxane/$H_2O$ (v/v=8:1, 10 mL) was added Pd(PPh$_3$)$_4$ (81 mg, 0.07 mmol) and Na$_2$CO$_3$ (230 mg, 2.10 mmol). The reaction mixture was stirred at 100° C. overnight under nitrogen atmosphere. After the reaction was indicated by LCMS, the reaction mixture was cooled and removed the solvent under reduced pressure. The residue was purified by FCC (DCM/MeOH=20/1) to afford 2-(3-(4-(tert-butyl)piperazin-1-yl)phenyl)-4-chloro-6-methylpyridin-3-amine (180 mg, 75% yield) as a yellow solid. LCMS: 359.2 $(M+H)^+$.

Step 3: 1-(4-(3-amino-2-(3-(4-(tert-butyl)piperazin-1-yl)phenyl)-6-methylpyridin-4-yl)-2-chlorophenyl)-3-methyl-1H-imidazol-2(3H)-one The title compound was prepared following the procedure described for Example 976 using 2-(3-(4-(tert-butyl)piperazin-1-yl)phenyl)-4-chloro-6-methylpyridin-3-amine and 1-(2-chloro-4-(4,4,5,5-tetramethyl-1,3,2-dioxaborolan-2-yl)phenyl)-3-methyl-1H-imidazol-2(3H)-one to afford 1-(4-(3-amino-2-(3-(4-(tert-butyl)piperazin-1-yl)phenyl)-6-methylpyridin-4-yl)-2-chlorophenyl)-3-methyl-1H-imidazol-2(3H)-one (29.3 mg, 16% yield) as a yellow solid. $^1$H NMR (400 MHz, CD$_3$OD) δ 7.75 (d, J=1.3 Hz, 1H), 7.62-7.51 (m, 2H), 7.40 (t, J=8.0 Hz, 1H), 7.15 (s, 1H), 7.07 (t, J=6.4 Hz, 2H), 7.00 (s, 1H), 6.67 (d, J=3.2 Hz, 1H), 6.65 (d, J=3.2 Hz, 1H), 3.34 (s, 3H), 3.23 (m, 4H), 2.85 (s, 4H), 2.45 (s, 3H), 1.17 (s, 9H). N—H or O—H protons not observed. LCMS: 531.2 $(M+H)^+$.

Example 993

1-(4-(5'-(4-(tert-Butyl)piperazin-1-yl)-3-hydroxy-6'-methyl-[2,3'-bipyridin]-4-yl)-2-chlorophenyl)-3-methyl-1H-imidazol-2(3H)-one

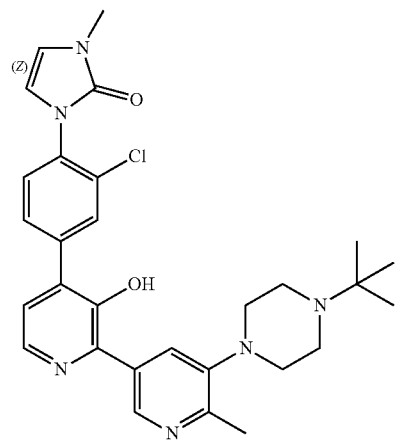 [SMILES: Cc1ncc(-c2nccc(-c3ccc(-n4ccn(C)c4=O)c(Cl)c3)c2O)cc1N1CCN(C(C)(C)C)CC1]

The title compound was prepared following the procedure described for Example 722 using (5-(4-(tert-butyl)piperazin-1-yl)-6-methylpyridin-3-yl)boronic acid, 1-(2-chloro-4-(2-chloro-3-methoxypyridin-4-yl)phenyl)-3-methyl-1H-imidazol-2(3H)-one and BBr3 to afford the title compound. $^1$H NMR (400 MHz, DMSO) δ 9.41 (s, 1H), 8.66 (d, J=1.5 Hz, 1H), 8.31 (d, J=4.8 Hz, 1H), 7.87 (d, J=7.3 Hz, 2H), 7.68 (dd, J=8.2, 1.8 Hz, 1H), 7.58 (d, J=8.2 Hz, 1H), 7.35 (d, J=4.8 Hz, 1H), 6.72 (dd, J=12.2, 3.0 Hz, 2H), 3.20 (d, J=12.0 Hz, 3H), 2.94 (s, 4H), 2.71 (d, J=33.2 Hz, 4H), 2.49-2.39 (s, 3H), 1.09 (s, 9H). LCMS: 533.2 $(M+H)^+$.

Example 994

1-(2-Chloro-4-(6'-(dimethylamino)-3-hydroxy-5'-(1-isopropyl-1,7-diazaspiro[4.4]nonan-7-yl)-6-methyl-[2,3'-bipyridin]-4-yl)phenyl)-3-methyl-1H-imidazol-2(3H)-one

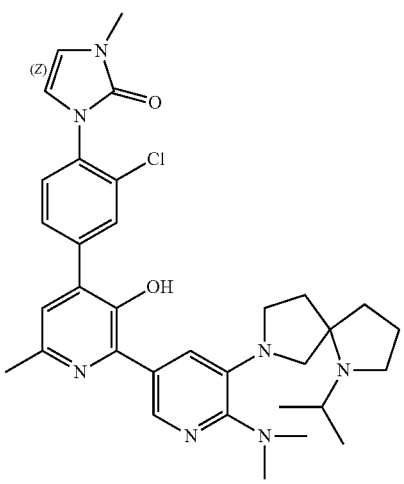 [SMILES: Cc1cc(-c2ccc(-n3ccn(C)c3=O)c(Cl)c2)c(O)c(-c2cnc(N(C)C)c(N3CCC4(CCCN4C(C)C)C3)c2)n1]

The title compound was prepared following the procedure described for Example 727 using 1-(2-chloro-4-(6'-(dimethylamino)-3-hydroxy-6-methyl-5'-(1,7-diazaspiro[4.4]nonan-7-yl)-[2,3'-bipyridin]-4-yl)phenyl)-3-methyl-1H-imidazol-2(3H)-one and acetone to afford the title compound. ¹H NMR (400 MHz, DMSO-d₆) δ 8.88 (s, 1H), 8.26 (d, J=1.7 Hz, 1H), 7.83 (d, J=1.6 Hz, 1H), 7.66 (dd, J=8.2, 1.7 Hz, 1H), 7.56 (d, J=8.2 Hz, 1H), 7.50 (d, J=1.5 Hz, 1H), 7.15 (s, 1H), 6.71 (dd, J=11.8, 3.0 Hz, 2H), 3.29-3.22 (m, 2H), 3.21 (s, 3H), 3.13 (dd, J=18.5, 9.5 Hz, 2H), 2.82 (s, 1H), 2.81 (d, J=4.7 Hz, 6H), 2.75 (dd, J=12.5, 8.8 Hz, 2H), 2.46 (s, 3H), 2.03 (dd, J=20.9, 9.0 Hz, 1H), 1.86-1.64 (m, 5H), 1.05 (t, J=6.6 Hz, 6H). LCMS: 602.3 (M+H)⁺.

Example 995

(S)-1-(2-chloro-4-(3-hydroxy-2'-(3-hydroxy-3-methylpyrrolidin-1-yl)-6-methyl-[2,4'-bipyridin]-4-yl)phenyl)-3-methyl-1H-imidazol-2(3H)-one

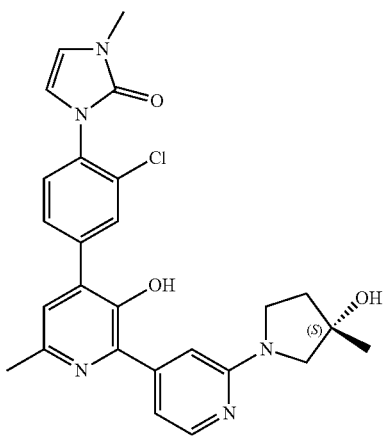

Step 1: (S)-1-(4-bromopyridin-2-yl)-3-methylpyrrolidin-3-ol

To a solution of 4-bromo-2-fluoropyridine (100 mg, 0.57 mmol) in DMSO (5 mL) was added (S)-3-methylpyrrolidin-3-ol HCl salt (80 mg, 0.57 mmol). The reaction mixture was stirred at 90° C. overnight. The reaction mixture was cooled, added water, and extracted with EA. The combined organic layers were concentrated in vacuo. The residue was purification by FCC (EA/PE=1/3) to afford (S)-1-(4-bromopyridin-2-yl)-3-methylpyrrolidin-3-ol (110 mg, 75% yield). LCMS: 257.1 (M+H)⁺.

Step 2: (S)-3-methyl-1-(4-(4,4,5,5-tetramethyl-1,3,2-dioxaborolan-2-yl)pyridin-2-yl)pyrrolidin-3-ol The title compound was prepared following the procedure described for Example 728 using (S)-1-(4-bromopyridin-2-yl)-3-methylpyrrolidin-3-ol and 4,4,4',4',5,5,5',5'-octamethyl-2,2'-bi(1,3,2-dioxaborolane) to afford (S)-3-methyl-1-(4-(4,4,5,5-tetramethyl-1,3,2-dioxaborolan-2-yl)pyridin-2-yl)pyrrolidin-3-ol (130 mg, 100% yield) as a yellow solid. LCMS: 305.2 (M+H)⁺.

Step 3: (S)-1-(2-chloro-4-(2'-(3-hydroxy-3-methylpyrrolidin-1-yl)-3-(methoxymethoxy)-6-methyl-[2,4'-bipyridin]-4-yl)phenyl)-3-methyl-1H-imidazol-2(3H)-one The title compound was prepared following the procedure described for Example 910 using (S)-3-methyl-1-(4-(4,4,5,5-tetramethyl-1,3,2-dioxaborolan-2-yl)pyridin-2-yl)pyrrolidin-3-ol and 1-(4-(2-bromo-3-(methoxymethoxy)-6-methylpyridin-4-yl)-2-chlorophenyl)-3-methyl-1H-imidazol-2(3H)— one to afford (S)-1-(2-chloro-4-(2'-(3-hydroxy-3-methylpyrrolidin-1-yl)-3-(methoxymethoxy)-6-methyl-[2,4'-bipyridin]-4-yl)phenyl)-3-methyl-1H-imidazol-2(3H)-one (40 mg, 27% yield) as a yellow solid. LCMS: 536.1 (M+H)⁺.

Step 4: (S)-1-(2-chloro-4-(3-hydroxy-2'-(3-hydroxy-3-methylpyrrolidin-1-yl)-6-methyl-[2,4'-bipyridin]-4-yl)phenyl)-3-methyl-1H-imidazol-2(3H)-one The title compound was prepared following the procedure described for Example 910 using (S)-1-(2-chloro-4-(2'-(3-hydroxy-3-methylpyrrolidin-1-yl)-3-(methoxymethoxy)-6-methyl-[2,4'-bipyridin]-4-yl)phenyl)-3-methyl-1H-imidazol-2(3H)-one to afford the title compound (10.5 mg, 37% yield) as a yellow solid. ¹H NMR (400 MHz, CD₃OD) δ 8.08 (d, J=5.6 Hz, 1H), 7.87 (d, J=1.6 Hz, 1H), 7.68 (dd, J=8.0, 2.0 Hz, 1H), 7.54 (d, J=8.0 Hz, 1H), 7.26 (s, 1H), 7.01 (dd, J=5.6, 1.0 Hz, 1H), 6.94 (s, 1H), 6.67 (d, J=3.2 Hz, 1H), 6.64 (d, J=3.2 Hz, 1H), 3.71-3.59 (m, 2H), 3.54 (d, J=10.8 Hz, 1H), 3.44 (d, J=10.8 Hz, 1H), 3.34 (s, 3H), 2.53 (s, 3H), 2.08-2.03 (m, 2H), 1.47 (s, 3H). O—H protons not observed. LCMS: 492.2 (M+H)⁺.

Example 996

(R)-1-(2-chloro-4-(3-hydroxy-2'-(3-hydroxy-3-methylpyrrolidin-1-yl)-6-methyl-[2,4'-bipyridin]-4-yl)phenyl)-3-methyl-1H-imidazol-2(3H)-one

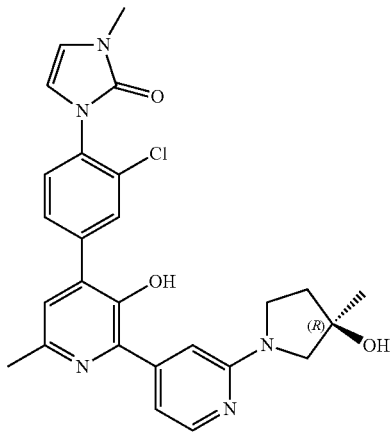

The title compound was prepared following the procedures described for Example 995 using 4-bromo-2-fluoropyridine and (S)-3-methylpyrrolidin-3-ol to afford the title compound (57 mg, 41.6% yield) as a yellow solid. ¹H NMR (400 MHz, CD₃OD) δ 8.09 (d, J=5.6 Hz, 1H), 7.87 (d, J=1.6 Hz, 1H), 7.68 (dd, J=8.0, 2.0 Hz, 1H), 7.54 (d, J=8.0 Hz, 1H), 7.25 (s, 1H), 6.99 (dd, J=5.6, 1.0 Hz, 1H), 6.92 (s, 1H), 6.67 (d, J=3.2 Hz, 1H), 6.64 (d, J=3.2 Hz, 1H), 3.68-3.61 (m, 2H), 3.55 (d, J=10.8 Hz, 1H), 3.42 (d, J=10.8 Hz, 1H), 3.34 (s, 3H), 2.52 (s, 3H), 2.08-2.03 (m, 2H), 1.47 (s, 3H). O—H protons not observed. LCMS: 492.2 (M+H)⁺.

Example 997

1-(4-(5'-(4-(tert-butyl)piperazin-1-yl)-3-hydroxy-6'-methoxy-6-methyl-[2,3'-bipyridin]-4-yl)-2-fluorophenyl)-3-methyl-1H-imidazol-2(3H)-one

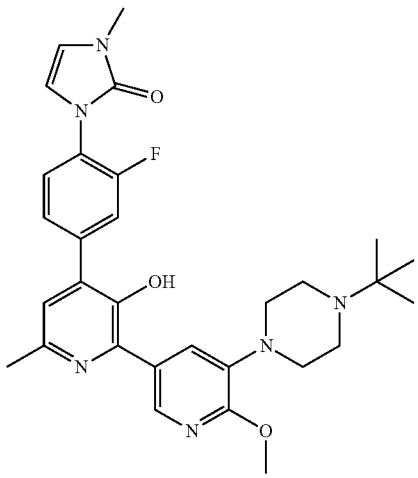 [SMILES: COc1ncc(-c2nc(C)cc(-c3ccc(-n4ccn(C)c4=O)c(F)c3)c2O)cc1N1CCN(C(C)(C)C)CC1]

Step 1: 2-Bromo-4-iodo-6-methylpyridin-3-ol

A mixture of 2-bromo-6-methylpyridin-3-ol (5.0 g, 26.6 mmol), I₂ (10.0 g, 40.0 mmol) and Na₂CO₃ (8.5 g, 80.0 mmol) in water (300 mL) was stirred at 50° C. for 8 hours. After the reaction mixture was cooled to room temperature, adjusted pH=3-4 with 3 N HCl and extracted with EA. The combined organic layers were concentrated in vacuo. The residue was purification by FCC (EA/PE=1/3) to afford 2-bromo-4-iodo-6-methylpyridin-3-ol (5.5 g, 68% yield). LCMS: 313.8 (M+H)⁺.

Step 2: 1-(4-(2-bromo-3-hydroxy-6-methylpyridin-4-yl)-2-fluorophenyl)-3-methyl-1H-imidazol-2(3H)-one To a solution of 2-bromo-4-iodo-6-methylpyridin-3-ol (1.5 g, 4.8 mmol) in 1,4-dioxane/H₂O was added 1-(2-fluoro-4-(4,4,5,5-tetramethyl-1,3,2-dioxaborolan-2-yl)phenyl)-3-methyl-1H-imidazol-2(3H)-one (1.5 g, 4.8 mmol, from B-612), Pd(dppf)Cl₂ (0.35 g, 0.05 mmol) and K₃PO₄ (3.0 g, 15.0 mmol). The reaction mixture was stirred at 60° C. for 3 hours under N₂. The reaction mixture was cooled to rt, added water, and extracted with EA. The combined organic layers were concentrated. The residue was purified by FCC (DCM/MeOH=20/1) to afford 1-(4-(2-bromo-3-hydroxy-6-methylpyridin-4-yl)-2-fluorophenyl)-3-methyl-1H-imidazol-2(3H)-one (0.7 g, 35% yield). LCMS: 378 (M+H)⁺.

Step 3: 1-(4-(2-bromo-3-(methoxymethoxy)-6-methylpyridin-4-yl)-2-fluorophenyl)-3-methyl-1H-imidazol-2(3H)-one To a solution of 1-(4-(2-bromo-3-hydroxy-6-methylpyridin-4-yl)-2-fluorophenyl)-3-methyl-1H-imidazol-2(3H)-one (700 mg, 1.86 mmol) in DMF (10 mL) was added NaH (110 mg, 2.78 mmol) at 0° C. The reaction mixture was stirred at rt for 30 min. Then, bromo(methoxy)methane (460 mg, 3.70 mmol) was added. The reaction mixture was stirred at rt for 2 hours. To the reaction mixture was added water to quench the reaction and extracted with EA. The combined organic layer was concentrated. The residue was purified by FCC (DCM/MeOH=20/1) to afford 1-(4-(2-bromo-3-(methoxymethoxy)-6-methylpyridin-4-yl)-2-fluorophenyl)-3-methyl-1H-imidazol-2(3H)-one (700 mg, 90% yield) as a yellow solid. LCMS: 422 (M+H)⁺.

Step 4: 1-(4-(5'-(4-(tert-butyl)piperazin-1-yl)-6'-methoxy-3-(methoxymethoxy)-6-methyl-[2,3'-bipyridin]-4-yl)-2-fluorophenyl)-3-methyl-1H-imidazol-2(3H)-one To a solution of 1-(4-(2-bromo-3-(methoxymethoxy)-6-methylpyridin-4-yl)-2-fluorophenyl)-3-methyl-1H-imidazol-2(3H)-one (100 mg, 0.24 mmol) in 1,4-dioxane/H₂O (5:1, 10 mL) was added 1-(tert-butyl)-4-(2-methoxy-5-(4,4,5,5-tetramethyl-1,3,2-dioxaborolan-2-yl)pyridin-3-yl)piperazine (100 mg, 0.26 mmol), Pd(dppf)Cl₂ (18 mg, 0.05 mmol) and Na₂CO₃ (80 mg, 0.72 mmol). The reaction mixture was stirred at 100° C. for 8 hours under N₂. The reaction mixture was cooled, added water, and extracted with EA. The combined organic layers were concentrated. The residue was purified by FCC (DCM/MeOH=20/1) to afford the title compound (80 mg, 57% yield). LCMS: 591 (M+H)⁺.

Step 5: 1-(4-(5'-(4-(tert-butyl)piperazin-1-yl)-3-hydroxy-6'-methoxy-6-methyl-[2,3'-bipyridin]-4-yl)-2-fluorophenyl)-3-methyl-1H-imidazol-2(3H)-one The title compound was prepared following the procedure described for Example 910 using 1-(4-(5'-(4-(tert-butyl)piperazin-1-yl)-6'-methoxy-3-(methoxymethoxy)-6-methyl-[2,3'-bipyridin]-4-yl)-2-fluorophenyl)-3-methyl-1H-imidazol-2(3H)-one to afford the title compound (24.5 mg, 34% yield) as a yellow solid. ¹H NMR (400 MHz, DMSO-d₆) δ 8.93 (s, 1H), 8.28 (s, 1H), 7.70-7.56 (m, 3H), 7.53 (dd, J=8.2, 1.6 Hz, 1H), 7.18 (s, 1H), 6.83-6.68 (m, 2H), 3.94 (s, 3H), 3.22 (s, 3H), 3.04 (s, 4H), 2.67 (s, 4H), 2.47 (s, 3H), 1.06 (s, 9H). LCMS: 547.3 (M+H)⁺.

TABLE 35

Following compounds were prepared using similar procedures as described for Examples 1 through 997.

| Ex. No. | Name/Structure | ¹H NMR Data | LCMS (M + H)⁺ |
|---|---|---|---|
| 998 | 1-(4-(2'-(4-(tert-butyl)piperazin-1-yl)-3-hydroxy-6-methyl-[2,4'-bipyridin]-4-yl)-2-chlorophenyl)-3-methyl-1H-imidazol-2(3H)-one | ¹H NMR (300 MHz, DMSO-d₆) δ 9.11 (s, 1H), 8.22 (d, J = 4.8 Hz, 1H), 7.89 (s, 1H), | 533.2 |

TABLE 35-continued

Following compounds were prepared using similar procedures as described for Examples 1 through 997.

| Ex. No. | Name/Structure | $^1$H NMR Data | LCMS $(M + H)^+$ |
|---|---|---|---|
|  |  | 7.70 (d, J = 8.3 Hz, 1H), 7.60 (d, J = 8.0 Hz, 1H), 7.28 (d, J = 12.8 Hz, 2H), 7.13 (s, 1H), 6.75 (dd, J = 8.9, 2.9 Hz, 2H), 3.44 (d, J = 37.1 Hz, 4H), 3.24 (s, 3H), 2.78-2.55 (m, 4H), 2.51 (s, 3H), 1.19 (s, 9H) |  |
| 999 | 1-(4-(2-(3-(4-(tert-butyl)piperazin-1-yl)-5-chlorophenyl)-3-hydroxy-6-methylpyridin-4-yl)-2-chlorophenyl)-3-methyl-1H-imidazol-2(3H)-one | $^1$H NMR (300 MHz, CD$_3$OD) δ 7.93 (s, 1H), 7.73 (d, J = 8.2 Hz, 1H), 7.59 (d, J = 8.2 Hz, 1H), 7.35 (d, J = 10.4 Hz, 2H), 7.28 (s, 1H), 7.12 (s, 1H), 6.71 (dd, J = 11.3, 2.8 Hz, 2H), 3.51 (s, 4H), 3.39 (s, 3H), 3.25 (s, 4H), 2.57 (s, 3H), 1.38 (s, 9H). O—H proton not observed | 566.2 |
| 1000 | 1-(4-(2-(3-(4-(tert-butyl)piperazin-1-yl)-4-fluorophenyl)-3-hydroxy-6-methylpyridin-4-yl)-2-chlorophenyl)-3-methyl-1H-imidazol-2(3H)-one | $^1$H NMR (400 MHz, DMSO-d$_6$) δ 8.90 (s, 1H), 7.85 (d, J = 2.0 Hz, 1H), 7.66 (dd, J = 8.0, 2.0 Hz, 1H), 7.59-7.50 (m, 2H), 7.47 (dd, J = 8.0, 2.0 Hz, 1H), 7.24-7.13 (m, 2H), 6.71 (dd, J = 11.2, 3.2 Hz, 2H), 3.21 (s, 3H), 3.05 (s, 4H), 2.68 (s, 4H), 2.46 (s, 3H), 1.05 (s, 9H) | 550.3 |

TABLE 35-continued

Following compounds were prepared using similar procedures as described for Examples 1 through 997.

| Ex. No. | Name/Structure | $^1$H NMR Data | LCMS (M + H)$^+$ |
|---|---|---|---|
| 1001 | 1-(4-(5'-(4-(tert-butyl)piperazin-1-yl)-3-hydroxy-6,6'-dimethyl-[2,3'-bipyridin]-4-yl)-2-fluorophenyl)-3-methyl-1H-imidazol-2(3H)-one | $^1$H NMR (400 MHz, CD$_3$OD) δ 8.62 (d, J = 1.8 Hz, 1H), 7.98 (d, J = 1.8 Hz, 1H), 7.62 (dt, J = 7.0, 4.9 Hz, 2H), 7.54 (dd, J = 8.3, 1.7 Hz, 1H), 7.23 (s, 1H), 6.77-6.60 (m, 2H), 3.34 (d, J = 4.8 Hz, 3H), 3.13 (d, J = 4.3 Hz, 4H), 3.03 (s, 4H), 2.58 (s, 3H), 2.54 (s, 3H), 1.25 (s, 9H). O—H proton not observed | 531.3 |
| 1002 | 1-(4-(2-(5-(4-(tert-butyl)piperazin-1-yl)imidazo[1,2-a]pyridin-7-yl)-3-hydroxy-6-methylpyridin-4-yl)-2-chlorophenyl)-3-methyl-1H-imidazol-2(3H)-one | $^1$H NMR (400 MHz, DMSO-d$_6$) δ 8.75 (s, 1H), 7.84 (d, J = 1.9 Hz, 1H), 7.73 (s, 1H), 7.69-7.60 (m, 2H), 7.57-7.46 (m, 2H), 7.27 (ddd, J = 26.6, 9.0, 3.2 Hz, 2H), 6.71 (dd, J = 9.9, 3.0 Hz, 2H), 6.61 (d, J = 1.3 Hz, 1H), 3.21 (s, 3H), 3.13 (s, 4H), 2.78 (s, 4H), 1.09 (s, 9H) | 572.2 |
| 1003 | 1-(4-(2-(3-(4-(tert-butyl)piperazin-1-yl)phenyl)-3-hydroxy-6-methylpyridin-4-yl)-2-fluorophenyl)-3-methyl-1H-imidazol-2(3H)-one | 1H NMR (400 MHz, CD3OD) δ 7.68-7.52 (m, 3H), 7.39-7.32 (m, 2H), 7.22 (s, 1H), 7.21 | 516.2 |

TABLE 35-continued

Following compounds were prepared using similar procedures as described for Examples 1 through 997.

| Ex. No. | Name/Structure | $^1$H NMR Data | LCMS (M + H)$^+$ |
|---|---|---|---|
| | 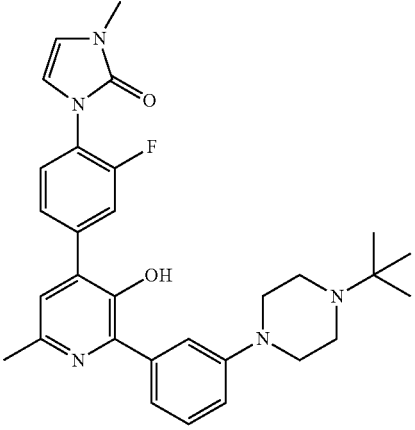 [SMILES: Cc1cc(-c2ccc(-n3ccn(C)c3=O)c(F)c2)c(O)c(-c2cccc(N3CCN(C(C)(C)C)CC3)c2)n1] | (d, J = 7.2 Hz, 1H), 7.07 (dd, J = 8.0, 2.0 Hz, 1H), 6.71 (d, J = 6.0 Hz, 1H), 6.65 d, J = 6.0 Hz, 1H), 3.34 (s, 3H), 3.32 (s, 4H), 2.84 (s, 4H), 2.51 (s, 3H), 1.18 (s, 9H). OH proton not observed. | |
| 1004 | 1-(4-(5'-(4-(tert-butyl)piperazin-1-yl)-3-hydroxy-6-methyl-[2,3'-bipyridin]-4-yl)-2-chlorophenyl)-3-methyl-1H-imidazol-2(3H)-one 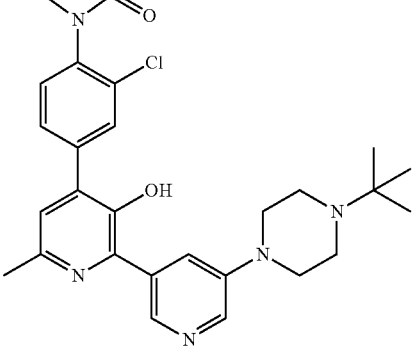 | 1H NMR (400 MHz, CD$_3$OD) δ 8.44 (d, J = 1.6 Hz, 1H), 8.25 (d, J = 2.8 Hz, 1H), 7.89 (d, J = 1.6 Hz, 1H), 7.86-7.78 (m, 1H), 7.69 (dd, J = 8.0, 2.0 Hz, 1H), 7.54 (d, J = 8.0 Hz, 1H), 7.24 (s, 1H), 6.68 (d, J = 3.2 Hz, 1H), 6.64 (d, J = 3.2 Hz, 1H), 3.39-3.32 (m, 7H), 2.90-2.76 (m, 4H), 2.53 (s, 3H), 1.17(s, 9H). O—H proton not observed | 533.2 |
| 1005 | 1-(4-(5'-(4-(tert-butyl)piperazin-1-yl)-3-hydroxy-6'-methoxy-[2,3'-bipyridin]-4-yl)-2-chlorophenyl)-3-methyl-1H-imidazol-2(3H)-one 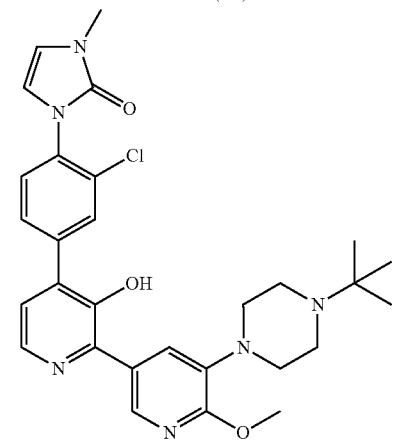 | $^1$H NMR (400 MHz, DMSO-d$_6$) δ 9.23 (s, 1H), 8.33 (d, J = 2.0 Hz, 1H), 8.25 (d, J = 4.8 Hz, 1H), 7.87 (t, J = 8.0 Hz, 1H), 7.68 (d, J = 9.6 Hz, 2H), 7.52 (d, J = 32.0, Hz, 1H), 7.27 (d, J = 21.2 Hz, 1H), 6.73 (d, J = 3.2 Hz, 1H), 6.70 (d, J = 3.2 Hz, 1H), 3.94 (s, 3H), 3.19 (s, 3H), 3.04 (s, 4H), 2.67 (s, 4H), 1.05 (s, 9H) | 549.2 |

TABLE 35-continued

Following compounds were prepared using similar procedures as described for Examples 1 through 997.

| Ex. No. | Name/Structure | $^1$H NMR Data | LCMS (M + H)$^+$ |
|---|---|---|---|
| 1006 | 1-(4-(2-(5-(4-(tert-butyl)piperazin-1-yl)imidazo[1,2-a]pyridin-7-yl)-3-hydroxy-6-methylpyridin-4-yl)-2-chlorophenyl)-3-methyl-1H-imidazol-2(3H)-one | $^1$H NMR (400 MHz, CD$_3$OD) δ 8.50 (s, 1H), 8.31 (d, J = 1.9 Hz, 1H), 8.16 (d, J = 2.2 Hz, 1H), 7.94-7.78 (m, 2H), 7.67 (dd, J = 8.2, 1.8 Hz, 1H), 7.59 (d, J = 8.2 Hz, 1H), 7.35 (s, 1H), 6.68 (dd, J = 17.8, 3.0 Hz, 2H), 3.84 (s, 4H), 3.61 (t, J = 11.5 Hz, 2H), 3.42 (t, J = 12.2 Hz, 2H), 3.36 (s, 3H), 2.60 (s, 3H), 1.55 (s, 9H). O—H proton not observed | 572.2 |
| 1007 | N-(4-(2-(3-(4-(tert-butyl)piperazin-1-yl)phenyl)-3-hydroxy-6-methylpyridin-4-yl)-2-chlorophenyl)acetamide | $^1$H NMR (400 MHz, DMSO-d$_6$) δ 9.59 (s, 1H), 8.66 (s, 1H), 7.83 (d, J = 8.4 Hz, 1H), 7.74 (d, J = 2.0 Hz, 1H), 7.55 (dd, J = 8.4, 2.0 Hz, 1H), 7.37 (s, 1H), 7.32-7.20 (m, 2H), 7.14 (s, 1H), 6.95 (dd, J = 7.4, 2.4 Hz, 1H), 3.22-3.04 (m, 4H), 2.66 (d, J = 4.0 Hz, 4H), 2.44 (s, 3H), 2.13 (s, 3H), 1.05 (s, 9H) | 493.2 |
| 1008 | N-(4-(2-(3-(4-(tert-butyl)piperazin-1-yl)phenyl)-3-hydroxy-6-methylpyridin-4-yl)-2-chlorophenyl)-2,2,2-trideuteroacetamide | $^1$H NMR (400 MHz, DMSO-d$_6$) δ 9.59 (s, 1H), 8.66 (s, 1H), 7.83 (d, J = 8.4 Hz, 1H), | 496.2 |

TABLE 35-continued

Following compounds were prepared using similar procedures as described for Examples 1 through 997.

| Ex. No. | Name/Structure | $^1$H NMR Data | LCMS $(M + H)^+$ |
|---|---|---|---|
| | 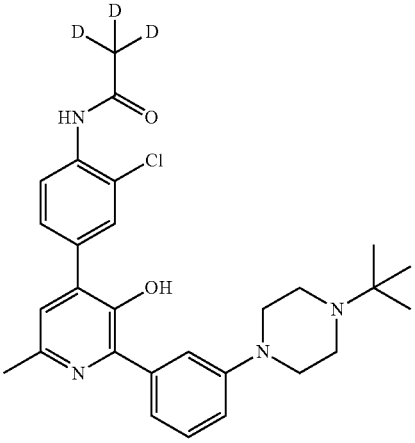 [SMILES: [2H]C([2H])([2H])C(=O)Nc1ccc(-c2cc(C)nc(-c3cccc(N4CCN(C(C)(C)C)CC4)c3)c2O)cc1Cl] | 7.74 (d, J = 1.9 Hz, 1H), 7.55 (dd, J = 8.4, 1.9 Hz, 1H), 7.37 (s, 1H), 7.32-7.21 (m, 2H), 7.14 (s, 1H), 6.98-6.91 (m, 1H), 3.14 (s, 4H), 2.66 (s, 4H), 2.44 (s, 3H), 1.05 (d, J = 4.1 Hz, 9H) | |
| 1009 | 6'-(4-(tert-butyl)piperazin-1-yl)-4-(3-chloro-4-(3-methyl-2-oxo-2,3-dihydro-1H-imidazol-1-yl)phenyl)-3-hydroxy-1',6-dimethyl-[2,4'-bipyridin]-2'(1'H)-one | $^1$H NMR (400 MHz, CD$_3$OD) δ 7.85 (d, J = 2.0 Hz, 1H), 7.66 (dd, J = 8.0, 2.0 Hz, 1H), 7.54 (d, J = 8.0 Hz, 1H), 7.25 (s, 1H), 6.83 (d, J = 1.6 Hz, 1H), 6.67 (d, J = 3.2 Hz, 1H), 6.64 (d, J = 3.2 Hz, 1H), 6.53 (d, J = 1.6 Hz, 1H), 3.62 (s, 3H), 3.33 (s, 3H), 3.12 (s, 4H), 2.90 (s, 4H), 2.53 (s, 3H), 1.18 (s, 9H). O—H proton not observed | 563.2 |
| 1010 | 1-(4-(2-(3-(4-(tert-butyl)piperazin-1-yl)-5-chloro-4-fluorophenyl)-3-hydroxy-6-methylpyridin-4-yl)-2-chlorophenyl)-3-methyl-1H-imidazol-2(3H)-one | $^1$H NMR (400 MHz, DMSO-d$_6$) δ 9.10 (s, 1H), 7.86 (d, J = 2.0 Hz, 1H), 7.67 (dd, J = | 584.2 |

| Ex. No. | Name/Structure | ¹H NMR Data | LCMS (M + H)⁺ |
|---|---|---|---|
| | 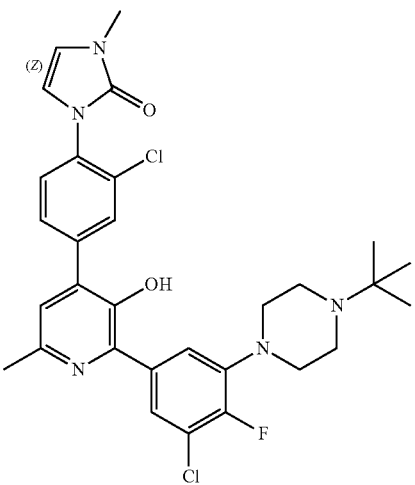 [SMILES: Cc1cc(-c2ccc(-n3ccn(C)c3=O)c(Cl)c2)c(O)c(-c2cc(Cl)c(F)c(N3CCN(C(C)(C)C)CC3)c2)n1] | 8.2, 2.0 Hz, 1H), 7.63-7.50 (m, 3H), 7.23 (s, 1H), 6.77-6.67 (m, 2H), 3.21 (s, 3H), 3.08 (d, J = 5.6 Hz, 4H), 2.72 (s, 4H), 2.47 (s, 3H), 1.07 (s, 9H) | |
| 1011 | 5'-(4-(tert-butyl)piperazin-1-yl)-4-(3-chloro-4-(3-methyl-2-oxo-2,3-dihydro-1H-imidazol-1-yl)phenyl)-3-hydroxy-1',6-dimethyl-[2,3'-bipyridin]-6'(1'H)-one 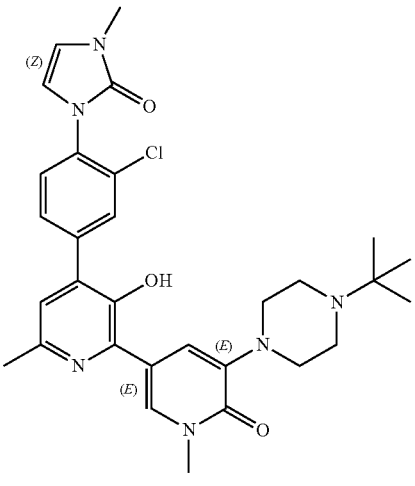 [SMILES: Cc1cc(-c2ccc(-n3ccn(C)c3=O)c(Cl)c2)c(O)c(-c2cc(N3CCN(C(C)(C)C)CC3)c(=O)n(C)c2)n1] | ¹H NMR (400 MHz, DMSO-d₆) δ 9.08 (s, 1H), 8.05 (s, 1H), 7.88 (s, 1H), 7.70-7.63 (m, 1H), 7.54 (d, J = 8.2 Hz, 1H), 7.35 (s, 1H), 7.12 (s, 1H), 6.75-6.67 (m, 2H), 3.51 (s, 3H), 3.21 (s, 3H), 3.08 (s, 4H), 2.64 (s, 4H), 2.44 (s, 3H), 1.04 (s, 9H) | 563.2 |
| 1012 | 1-(4-(2-(3-(4-(tert-butyl)piperazin-1-yl)phenyl)-3-hydroxy-6-methylpyridin-4-yl)-2-methylphenyl)-3-methyl-1H-imidazol-2(3H)-one | ¹H NMR (300 MHz, DMSO-d₆) δ 8.67 (s, 1H), 7.60 (s, 1H), 7.55 (d, J = 7.9 Hz, 1H), | 512.2 |

TABLE 35-continued

Following compounds were prepared using similar procedures as described for Examples 1 through 997.

| Ex. No. | Name/Structure | ¹H NMR Data | LCMS (M + H)⁺ |
|---|---|---|---|
| | 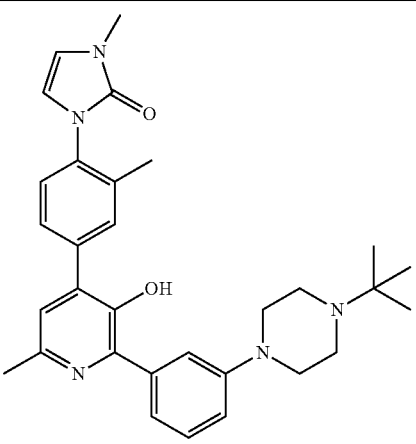 | 7.41 (s, 1H), 7.35-7.27 (m, 3H), 7.15 (s, 1H), 6.99 (d, J = 6.3 Hz, 1H), 6.75 (d, J = 2.9 Hz, 1H), 6.70 (d, J = 3.0 Hz, 1H), 3.25 (s, 3H), 3.18 (s, 4H), 2.69 (s, 4H), 2.49 (s, 3H), 2.26 (s, 3H), 1.09 (s, 9H) | |
| 1013 | 1-(4-(2-(3-(4-(tert-butyl)piperazin-1-yl)-4-chlorophenyl)-3-hydroxy-6-methylpyridin-4-yl)-2-chlorophenyl)-3-methyl-1H-imidazol-2(3H)-one 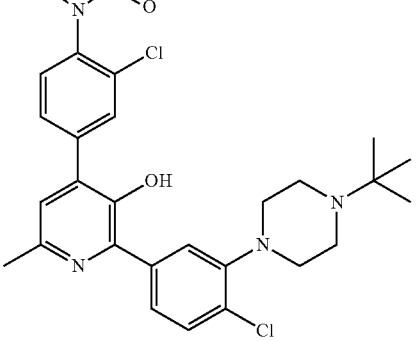 | ¹H NMR (400 MHz, DMSO-d₆) δ 8.99 (s, 1H), 7.85 (d, J = 1.9 Hz, 1H), 7.70-7.63 (m, 2H), 7.59-7.52 (m, 2H), 7.47 (d, J = 8.3 Hz, 1H), 7.21 (s, 1H), 6.75-6.67 (m, 2H), 3.21 (s, 3H), 3.02 (s, 4H), 2.70 (s, 4H), 2.47 (s, 3H), 1.07 (s, 9H) | 566.2 |
| 1014 | 1-(4-(2-(3-(4-(tert-butyl)piperazin-1-yl)-5-fluorophenyl)-3-hydroxy-6-methylpyridin-4-yl)-2-chlorophenyl)-3-methyl-1H-imidazol-2(3H)-one 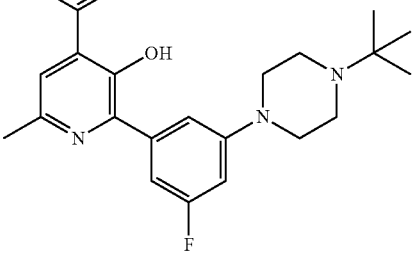 | ¹H NMR (400 MHz, DMSO-d₆) δ 8.96 (s, 1H), 7.86 (s, 1H), 7.67 (d, J = 8.3 Hz, 1H), 7.56 (d, J = 8.1 Hz, 1H), 7.23 (d, J = 10.4 Hz, 2H), 7.01 (d, J = 8.8 Hz, 1H), 6.78-6.70 (m, 3H), 3.21 (s, 3H), 3.18 (s, 4H), 2.64 (s, 4H), 2.46 (s, 3H), 1.05 (s, 9H). | 550.2 |

TABLE 35-continued

Following compounds were prepared using similar procedures as described for Examples 1 through 997.

| Ex. No. | Name/Structure | $^1$H NMR Data | LCMS $(M + H)^+$ |
|---|---|---|---|
| 1015 | 1-(4-(5'-(4-(tert-butyl)piperazin-1-yl)-3-hydroxy-6'-methoxy-6-methyl-[2,3'-bipyridin]-4-yl)-2-methylphenyl)-3-methyl-1H-imidazol-2(3H)-one | $^1$H NMR (400 MHz, DMSO-d$_6$) δ 8.79 (s, 1H), 8.28 (d, J = 1.9 Hz, 1H), 7.65 (d, J = 1.9 Hz, 1H), 7.56 (s, 1H), 7.52-7.47 (m, 1H), 7.30 (d, J = 8.1 Hz, 1H), 7.12 (s, 1H), 6.71 (d, J = 2.9 Hz, 1H), 6.65 (d, J = 2.9 Hz, 1H), 3.94 (s, 3H), 3.21 (s, 3H), 3.04 (s, 4H), 2.67 (s, 4H), 2.46 (s, 3H), 2.23 (s, 3H), 1.05 (s, 9H) | 543.3 |
| 1016 | 1-(3''-(4-(tert-butyl)piperazin-1-yl)-3-chloro-2'-hydroxy-5'-methyl-[1,1':3',1''-terphenyl]-4-yl)-3-methyl-1H-imidazol-2(3H)-one | $^1$H NMR (400 MHz, DMSO-d$_6$) δ 7.76 (d, J = 1.9 Hz, 1H), 7.59 (dd, J = 8.2, 1.9 Hz, 1H), 7.51 (d, J = 8.2 Hz, 1H), 7.36 (t, J = 7.9 Hz, 1H), 7.16-7.11 (m, 2H), 7.07 (dd, J = 9.8, 4.7 Hz, 2H), 7.01 (dd, J = 8.2, 1.9 Hz, 1H), 6.72 (d, J = 3.0 Hz, 1H), 6.68 (d, J = 3.0 Hz, 1H), 3.91 (d, J = 12.4 Hz, 2H), 3.60 (d, J = 11.7 Hz, 2H), 3.22 (s, 3H), 3.18-3.01 (m, 4H), 2.31 (s, 3H), 1.38 (s, 9H). O—H proton not observed | 531.2 |
| 1017 | 1-(4-(2-(6-(4-(tert-butyl)piperazin-1-yl)pyridazin-4-yl)-3-hydroxy-6-methylpyridin-4-yl)-2-chlorophenyl)-3-methyl-1H-imidazol-2(3H)-one | $^1$H NMR (400 MHz, CD$_3$OD) δ 9.35 (s, 1H), 8.16 (s, 1H), 7.85 (d, J = 1.9 Hz, 1H), 7.66 (dd, | 534.2 |

| Ex. No. | Name/Structure | ¹H NMR Data | LCMS (M + H)⁺ |
|---|---|---|---|
|  |  | J = 8.2, 1.9 Hz, 1H), 7.58 (d, J = 8.2 Hz, 1H), 7.35 (s, 1H), 6.67 (dd, J = 18.3, 3.0 Hz, 2H), 4.71 (s, 4H), 3.94-3.40 (m, 4H), 3.35 (d, J = 3.6 Hz, 3H), 2.58 (s, 3H), 1.49 (s, 9H). O—H proton not observed |  |

Example 1018

3-(3-(4-(tert-butyl)piperazin-1-yl)phenyl)-5-(3-chloro-4-(3-methyl-2-oxo-2,3-dihydro-1H-imidazol-1-yl)phenyl)-4-hydroxy-1-methylpyridin-2(1H)-one

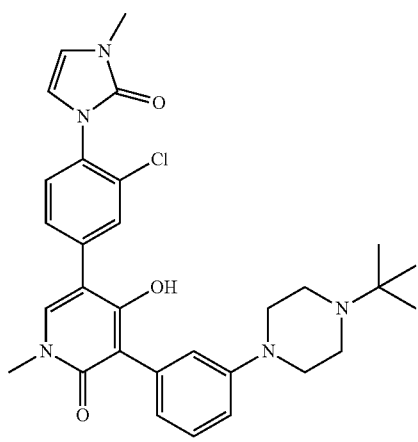 [SMILES: Cn1cc(-c2ccc(-n3ccn(C)c3=O)c(Cl)c2)c(O)c(-c2cccc(N3CCN(C(C)(C)C)CC3)c2)c1=O]

Step 1: 4-Methoxy-1-methylpyridin-2(1H)-one

To a solution of 4-methoxypyridin-2(1H)-one (200 mg, 1.6 mmol) in DMF (5 mL) was added NaH (96 mg, 2.4 mmol). The reaction mixture was stirred at rt for 30 min. CH₃I (340 mg, 2.4 mmol) was added dropwise. The reaction mixture was stirred at rt for 1 hour. The reaction mixture was quenched with water and extracted with EA. The combined organic layers were concentrated. The residue was purified by FCC (PE/EA=2/1) to afford the title compound (150 mg, 68% yield). LCMS: 140.1 (M+H)⁺.

Step 2: 3,5-Bibromo-4-methoxy-1-methylpyridin-2(1H)-one

To a solution of 4-methoxy-1-methylpyridin-2(1H)-one (145 mg, 1.04 mmol) in ACN (5 mL) was added NBS (410 mg, 2.30 mmol) and TFA (36 mg, 0.30 mmol). The reaction mixture was stirred at rt overnight. Then, to the reaction mixture was added DCM. The mixture was washed with sat. Na₂S₂O₄ and 1N HCl. The organic layer was concentrated. The residue was purified by FCC (PE/EA=1/1) to afford the title compound (200 mg, 65% yield). LCMS: 295.8 (M+H)⁺.

Step 3: 3-Bromo-5-(3-chloro-4-(3-methyl-2-oxo-2,3-dihydro-1H-imidazol-1-yl)phenyl)-4-methoxy-1-methylpyridin-2(1H)-one To a solution of 3,5-dibromo-4-methoxy-1-methylpyridin-2(1H)-one (500 mg, 1.68 mmol) in 1,4-dioxane/water (5/1, 20 mL) was added 1-(2-chloro-4-(4,4,5,5-tetramethyl-1,3,2-dioxaborolan-2-yl)phenyl)-3-methyl-1H-imidazol-2(3H)-one (245 mg, 0.73 mmol), Pd(dppf)Cl₂ (125 mg, 0.17 mmol) and Na₂CO₃ (540 mg, 5.05 mmol). The reaction mixture was stirred at 100° C. for 6 hours under N₂. The reaction mixture was cooled, added water, and extracted with EA. The combined organic layer was concentrated. The residue was purified by C18 column to afford 3-bromo-5-(3-chloro-4-(3-methyl-2-oxo-2,3-dihydro-1H-imidazol-1-yl)phenyl)-4-methoxy-1-methylpyridin-2(1H)-one (150 mg, 21% yield). LCMS: 424 (M+H)⁺.

Step 4: 3-(3-(4-(tert-Butyl)piperazin-1-yl)phenyl)-5-(3-chloro-4-(3-methyl-2-oxo-2,3-dihydro-1H-imidazol-1-yl)phenyl)-4-methoxy-1-methylpyridin-2(1H)-one To a solution of 3-bromo-5-(3-chloro-4-(3-methyl-2-oxo-2,3-dihydro-1H-imidazol-1-yl)phenyl)-4-methoxy-1-methylpyridin-2(1H)-one (100 mg, 0.24 mmol) in 1,4-dioxane/water (5/1, 10 mL) was added 1-(tert-butyl)-4-(3-(4,4,5,5-tetramethyl-1,3,2-dioxaborolan-2-yl)phenyl)piperazine (105 mg, 0.31 mmol), Pd(dppf)Cl₂ (18 mg, 0.03 mmol) and Na₂CO₃ (75 mg, 6.71 mmol). The reaction mixture was stirred at 100° C. for 6 hours under N₂. The reaction mixture was cooled, added water, and extracted with EA. The combined organic layers were concentrated. The residue was purified by FCC (DCM/MeOH=20/1) to afford the title compound (65 mg, 50% yield). LCMS: 562.2 (M+H)+.

Step 5: 3-(3-(4-(tert-Butyl)piperazin-1-yl)phenyl)-5-(3-chloro-4-(3-methyl-2-oxo-2,3-dihydro-1H-imidazol-1-yl)phenyl)-4-hydroxy-1-methylpyridin-2(1H)-one To a solution of 3-(3-(4-(tert-butyl)piperazin-1-yl)phenyl)-5-(3-chloro-4-(3-methyl-2-oxo-2,3-dihydro-1H-imidazol-1-yl)phenyl)-4-methoxy-1-methylpyridin-2(1H)-one (100 mg, 0.15 mmol) in DCM (2 mL) was added BBr$_3$ (5 mL, 1 N). The reaction mixture was stirred at rt overnight. The reaction mixture was cooled to 0° C., quenched the reaction with MeOH and concentrated. The residue was adjusted pH=8 with aq. NaHCO$_3$ and extracted with DCM/MeOH (10/1). The combined organic layers were concentrated. The residue was purified by HPLC to afford the title compound (13.5 mg, 12% yield). $^1$H NMR (400 MHz, DMSO-d$_6$) δ 9.33 (s, 1H) 7.80 (s, 1H), 7.71 (d, J=2.0 Hz, 1H), 7.54 (d, J=4.0 Hz, 1H), 7.45 (d, J=4.0 Hz, 1H), 7.21 (t, J=4.0 Hz, 1H), 6.88-6.84 (m, 2H), 6.72 (d, J=19.2 Hz, 1H), 6.69 (d, J=3.2 Hz, 1H), 6.64 (d, J=3.2 Hz, 1H), 3.42 (s, 3H), 3.19 (s, 3H), 3.12 (s, 4H), 2.66 (s, 4H), 1.05 (s, 9H). LCMS: 548.2 (M+H)+.

Example 1019

1-(4-(5'-(4-(tert-Butyl)piperazin-1-yl)-3-hydroxy-6,6'-dimethyl-[2,3'-bipyridin]-4-yl)-2-methylphenyl)-3-methyl-1,3-dihydro-2H-imidazol-2-one

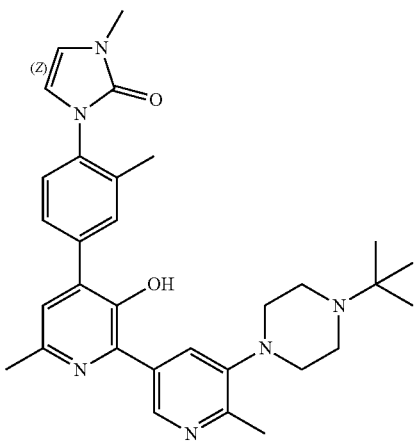 [SMILES: Cc1cc(-c2ccc(-n3ccn(C)c3=O)c(C)c2)c(O)c(-c2cnc(C)c(N3CCN(C(C)(C)C)CC3)c2)n1]

The title compound was prepared following the procedures described for Example 993 using 1-(3'-bromo-3-chloro-2'-(methoxymethoxy)-5'-methyl-[1,1'-biphenyl]-4-yl)-3-methyl-1H-imidazol-2(3H)— one and 1-(tert-butyl)-4-(2-methyl-5-(4,4,5,5-tetramethyl-1,3,2-dioxaborolan-2-yl)pyridin-3-yl)piperazine followed by deprotection with hydrochloric acid in methanol to afford the title compound. $^1$H NMR (400 MHz, DMSO-d$_6$) δ 8.88 (s, 1H), 8.63 (d, J=1.8 Hz, 1H), 7.84 (d, J=1.8 Hz, 1H), 7.53 (dd, J=18.4, 10.5 Hz, 2H), 7.31 (d, J=8.1 Hz, 1H), 7.16 (s, 1H), 6.68 (dd, J=24.2, 2.9 Hz, 2H), 3.21 (s, 3H), 2.91 (s, 4H), 2.70 (s, 4H), 2.48 (s, 3H), 2.47 (s, 3H), 2.23 (s, 3H), 1.06 (d, J=5.2 Hz, 9H). LCMS: 527.2 (M+H)+.

Example 1020

1-(4-(6-(3-(4-(tert-Butyl)piperazin-1-yl)phenyl)-5-hydroxypyridazin-4-yl)-2-chlorophenyl)-3-methyl-1H-imidazol-2(3H)-one

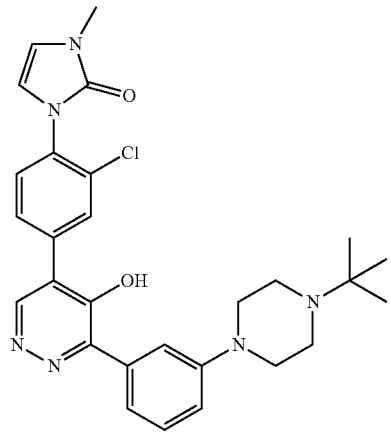 [SMILES: Cn1ccn(-c2ccc(-c3cnnc(-c4cccc(N5CCN(C(C)(C)C)CC5)c4)c3O)cc2Cl)c1=O]

Step 1: 3,5-Dichloro-4-methoxypyridazine

To a solution of 3,4,5-trichloropyridazine (2.0 g, 10.9 mmol) in MeOH (50 mL) was added MeONa (600 mg, 10.9 mmol) at 0° C. The reaction mixture was allowed to warm up to room temperature slowly and stirred at rt for 2 h. After the reaction was complete by LCMS, the reaction mixture was concentrated under reduced pressure. The residue was chromatographed on silica gel (PE:EA=4:1) to afford the title compound (610 mg, yield 80%) as a white solid. $^1$H NMR (400 MHz, CDCl$_3$) δ 9.01 (d, J=1.0 Hz, 1H), 4.15 (s, 3H). LCMS: 179.0 (M+H)+.

Step 2: 3-(3-(4-(tert-Butyl)piperazin-1-yl)phenyl)-5-chloro-4-methoxypyridazine

To a solution of 3,5-dichloro-4-methoxypyridazine (300 mg, 1.7 mmol) and 1-(tert-butyl)-4-(3-(4,4,5,5-tetramethyl-1,3,2-dioxaborolan-2-yl)phenyl)piperazine (558 mg, 1.7 mmol) in dioxane (20 mL) and H$_2$O (3 mL) was added Pd(dppf)Cl$_2$ (132 mg, 0.2 mmol) and Cs$_2$CO$_3$ (1.1 g, 3.4 mmol) under N$_2$ atmosphere. The reaction mixture was stirred at 100° C. for 16 hours under N$_2$. After the reaction was complete by LCMS, the reaction mixture was cooled and concentrated. The residue was purified by chromatograph on silica gel (PE:EA=1:1) to afford the title compound (400 mg, yield 66%) as a yellow solid. LCMS: 361.2 (M+H)+.

Step 3: 1-(4-(6-(3-(4-(tert-Butyl)piperazin-1-yl)phenyl)-5-methoxypyridazin-4-yl)-2-chlorophenyl)-3-methyl-1H-imidazol-2(3H)-one To a solution of 3-(3-(4-(tert-butyl)piperazin-1-yl)phenyl)-5-chloro-4-methoxypyridazine (530 mg, 1.47 mmol) and 1-(2-chloro-4-(4,4,5,5-tetramethyl-1,3,2-dioxaborolan-2-yl)phenyl)-3-methyl-1H-imidazol-2(3H)-one (588 mg, 1.76 mmol) in dioxane (50 mL) and H$_2$O (7 mL) under N$_2$ atmosphere was added Pd(dppf)Cl$_2$ (130 mg, 0.18 mmol) and Cs$_2$CO$_3$ (1.1 g, 3.5 mmol). The reaction was stirred at 100° C. for 16 hours under $N_2$. The reaction mixture was cooled and concentrated and purified by chromatograph on silica gel (DCM:MeOH=10:1) to afford the title compound (509 mg, 65% yield) as a brown solid. LCMS: 533.2 (M+H)$^+$.

Step 4: 1-(4-(6-(3-(4-(tert-Butyl)piperazin-1-yl)phenyl)-5-hydroxypyridazin-4-yl)-2-chlorophenyl)-3-methyl-1H-imidazol-2(3H)-one To a solution of 1-(4-(6-(3-(4-(tert-butyl)piperazin-1-yl)phenyl)-5-methoxypyridazin-4-yl)-2-chlorophenyl)-3-methyl-1H-imidazol-2(3H)-one (200 mg, 0.38 mmol) in DCM (10 mL) was added BBr$_3$ (376 mg, 1.5 mmol) dropwise at 0° C. After the addition, the reaction mixture was allowed to warm up to room temperature. The reaction mixture was stirred at 20° C. for 16 hours. After the reaction was complete by LCMS, the mixture was filtered. The filtered cake was stirred with DMF (1 mL) and EA (4 mL) to afford the title compound as HBr salt (21.4 mg, 11% yield) as an off-white solid. $^1$H NMR (400 MHz, DMSO-d) δ 13.71 (d, J=4.1 Hz, 1H), 9.16 (s, 1H), 8.70 (d, J=3.7 Hz, 1H), 8.22 (d, J=2.0 Hz, 1H), 7.92 (dd, J=8.4, 2.0 Hz, 1H), 7.77 (s, 1H), 7.55-7.48 (m, 2H), 7.37 (t, J=7.9 Hz, 1H), 7.12 (d, J=8.2 Hz, 1H), 6.74-6.66 (m, 2H), 3.89 (d, J=12.8 Hz, 2H), 3.64 (d, J=11.7 Hz, 2H), 3.20 (s, 5H), 3.06 (t, J=12.5 Hz, 2H), 1.38 (s, 9H). LCMS: 519.2 (M+H)$^+$.

TABLE 36

Following compounds were prepared using similar procedures as described for Examples 1 through 1020.

| Ex. No. | Name/Structure | $^1$H NMR Data | LCMS (M + H)$^+$ |
|---|---|---|---|
| 1021 | 1-(3''-(4-(tert-butyl)piperazin-1-yl)-3-chloro-2'-hydroxy-[1,1':3',1''-terphenyl]-4-yl)-3-methyl-1H-imidazol-2(3H)-one | $^1$H NMR (400 MHz, DMSO-d$_6$) δ 8.36 (s, 1H), 7.76 (d, J = 2.0 Hz, 1H), 7.58 (dd, J = 8.2, 2.0 Hz, 1H), 7.50 (d, J = 8.2 Hz, 1H), 7.31-7.21 (m, 3H), 7.07-7.00 (m, 2H), 6.96-6.89 (m, 2H), 6.75-6.66 (m, 2H), 3.21 (s, 3H), 3.15 (t, J = 5.0 Hz, 4H), 2.64 (t, J = 5.0 Hz, 4H), 1.05 (s, 9H) | 517.2 |
| 1022 | (R)-1-(2-chloro-4-(3-hydroxy-5'-(1-isopropyl-1,6-diazaspiro[3.4]octan-6-yl)-6'-methoxy-6-methyl-[2,3'-bipyridin]-4-yl)phenyl)-3-methyl-1,3-dihydro-2H-imidazol-2-one | $^1$H NMR (400 MHz, DMSO-d$_6$) δ 8.89 (s, 1H), 8.07 (d, J = 1.7 Hz, 1H), 7.84 (d, J = 1.8 Hz, 1H), 7.66 (dd, J = 8.2, 1.8 Hz, 1H), 7.56 (d, J = 8.2 Hz, 1H), 7.34 (d, J = 1.5 Hz, 1H), 7.17 (s, 1H), 6.71 (dd, J = 12.3, 3.0 Hz, 2H), 3.91 (s, 3H), 3.65 (d, J = 10.0 Hz, 1H), 3.44-3.38 (m, 1H), 3.27 (d, J = 7.0 Hz, 1H), 3.21 (s, 3H), 3.14 (d, J = 21.6 Hz, 2H), 3.01 (d, J = 17.9 Hz, 1H), 2.67 (s, 1H), 2.46 (s, 3H), 2.20-2.10 (m, 1H), 2.06-1.89 (m, 3H), 0.91 (dd, J = 9.6, 6.1 Hz, 6H) | 575.3 |
| 1023 | (S)-1-(2-chloro-4-(3-hydroxy-5'-(1-isopropyl-1,6-diazaspiro[3.4]octan-6-yl)-6'-methoxy-6-methyl-[2,3'-bipyridin]-4-yl)phenyl)-3-methyl-1,3-dihydro-2H-imidazol-2-one | $^1$H NMR (400 MHz, DMSO-d$_6$) δ 8.89 (s, 1H), 8.07 (d, J = 1.7 Hz, 1H), 7.84 (d, J = 1.8 Hz, 1H), 7.66 (dd, J = 8.2, 1.8 Hz, | 575.3 |

TABLE 36-continued

Following compounds were prepared using similar procedures as described for Examples 1 through 1020.

| Ex. No. | Name/Structure | $^1$H NMR Data | LCMS (M + H)$^+$ |
|---|---|---|---|
| | | 1H), 7.56 (d, J = 8.2 Hz, 1H), 7.34 (d, J = 1.5 Hz, 1H), 7.17 (s, 1H), 6.71 (dd, J = 12.3, 3.0 Hz, 2H), 3.91 (s, 3H), 3.65 (d, J = 10.0 Hz, 1H), 3.44-3.38 (m, 1H), 3.27 (d, J = 7.0 Hz, 1H), 3.21 (s, 3H), 3.14 (d, J = 21.6 Hz, 2H), 3.01 (d, J = 17.9 Hz, 1H), 2.67 (s, 1H), 2.46 (s, 3H), 2.20-2.10 (m, 1H), 2.06-1.89 (m, 3H), 0.91 (dd, J = 9.6, 6.1 Hz, 6H) | |
| 1024 | 1-(3''-(4-(tert-butyl)piperazin-1-yl)-3,5'-dichloro-2'-hydroxy-[1,1':3',1''-terphenyl]-4-yl)-3-methyl-1H-imidazol-2(3H)-one 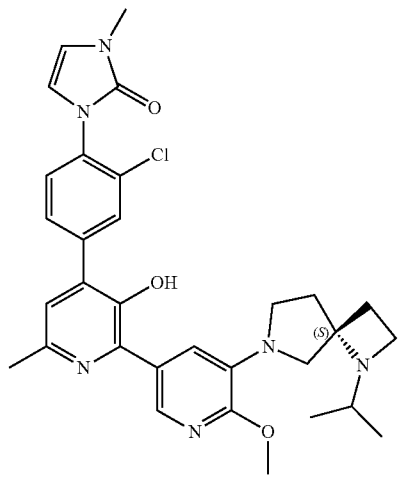 | 1H NMR (400 MHz, DMSO-d$_6$) δ 8.76 (s, 1H), 7.79 (d, J = 1.8 Hz, 1H), 7.60 (dd, J = 8.2, 1.9 Hz, 1H), 7.51 (d, J = 8.2 Hz, 1H), 7.33 (d, J = 2.7 Hz, 1H), 7.28 (dd, J = 9.4, 5.4 Hz, 2H), 7.05 (s, 1H), 6.96-6.92 (m, 2H), 6.70 (dd, J = 11.5,3.0 Hz, 2H), 3.21 (s, 3H), 3.17 (s, 4H), 2.66 (s, 4H), 1.05 (s, 9H). | 551.2 |
| 1025 | 1-(3''-(4-(tert-butyl)piperazin-1-yl)-3-chloro-2'-hydroxy-5'-(trifluoromethyl)-[1,1':3',1''-terphenyl]-4-yl)-3-methyl-1H-imidazol-2(3H)-one 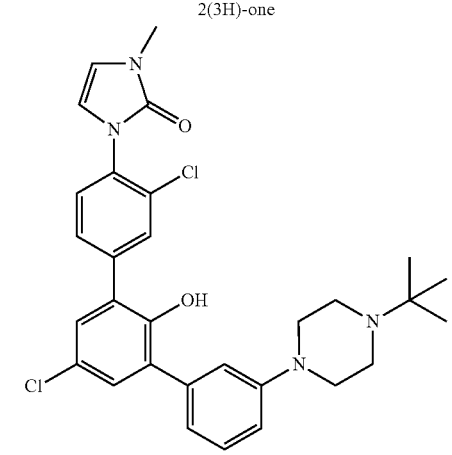 | $^1$H NMR (400 MHz, DMSO-d$_6$) δ 9.40 (s, 1H), 7.84 (d, J = 1.9 Hz, 1H), 7.63 (dd, J = 8.2, 2.0 Hz, 1H), 7.58 (d, J = 2.4 Hz, 1H), 7.53 (d, J = 8.2 Hz, 1H), 7.51 (d, J = 2.3 Hz, 1H), 7.30 (t, J = 7.9 Hz, 1H), 7.08 (s, 1H), 6.99-6.93 (m, 2H), 6.74-6.67 (m, 2H), 3.21 (s, 3H), 3.16 (d, J = 5.5 Hz, 4H), 2.65 (s, 4H), 1.05 (s, 9H) | 585.2 |

TABLE 36-continued

Following compounds were prepared using similar procedures as described for Examples 1 through 1020.

| Ex. No. | Name/Structure | $^1$H NMR Data | LCMS (M + H)$^+$ |
|---|---|---|---|
| 1026 | 1-(4-(2-(3-(4-(tert-butyl)piperazin-1-yl)-4,5-difluorophenyl)-3-hydroxy-6-methylpyridin-4-yl)-2-chlorophenyl)-3-methyl-1H-imidazol-2(3H)-one | $^1$H NMR (400 MHz, DMSO-d$_6$) δ 9.09 (s, 1H), 7.85 (s, 1H), 7.62 (d, J = 32.5 Hz, 2H), 7.41 (d, J = 26.1 Hz, 2H), 7.23 (s, 1H), 6.88-6.65 (m, 2H), 3.21 (d, J = 5.7 Hz, 3H), 3.08 (s, 4H), 2.68 (s, 4H), 2.46 (s, 3H), 1.05 (d, J = 5.2 Hz, 9H) | 568.2 |
| 1027 | 1-(4-(2-(5-(4-(tert-butyl)piperazin-1-yl)-2,3-difluorophenyl)-3-hydroxy-6-methylpyridin-4-yl)-2-chlorophenyl)-3-methyl-1H-imidazol-2(3H)-one | $^1$H NMR (400 MHz, DMSO-d$_6$) δ 9.02 (s, 1H), 7.85 (d, J = 1.9 Hz, 1H), 7.67 (dd, J = 8.2, 1.9 Hz, 1H), 7.56 (d, J = 8.2 Hz, 1H), 7.29 (s, 1H), 7.02 (ddd, J = 13.7, 6.4, 2.8 Hz, 1H), 6.79-6.66 (m, 3H), 3.21 (s, 3H), 3.12 (d, J = 4.9 Hz, 4H), 2.71-2.58 (m, 4H), 2.45 (s, 3H), 1.04 (s, 9H) | 568.2 |

Example 1028

1-(4-(2-(3-(4-(tert-Butyl)piperazin-1-yl)phenyl)-3-hydroxy-6-methoxypyridin-4-yl)-2-chlorophenyl)-3-methyl-1H-imidazol-2(3H)-one

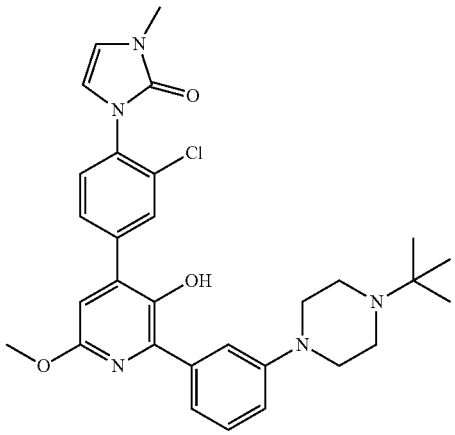 [SMILES: COc1cc(-c2ccc(-n3ccn(C)c3=O)c(Cl)c2)c(O)c(-c2cccc(N3CCN(C(C)(C)C)CC3)c2)n1]

Step 1: 2-Bromo-6-fluoro-4-iodopyridin-3-ol

To a solution of 2-bromo-6-fluoropyridin-3-ol (1.2 g, 6.3 mmol) in DMF (50 mL) was added NIS (2.1 g, 9.4 mmol). The reaction mixture was stirred at rt overnight. The solvent was removed in vacuo. The residue was purified by FCC (PE/EA=10/1) to afford the title compound (0.8 g, 40% yield). LCMS: 317 (M+H)$^+$.

Step 2: 2-Bromo-6-fluoro-4-iodo-3-methoxypyridine

To a solution of 2-bromo-6-fluoro-4-iodopyridin-3-ol (200 mg, 0.63 mmol) in DMF (10 mL) was added $K_2CO_3$ (175 mg, 1.26 mmol) and $CH_3I$ (135 mg, 0.95 mmol). The reaction mixture was stirred at rt overnight. The reaction mixture was added $H_2O$ and extracted with EA. The combined organic layers were concentrated. The residue was purified by FCC (PE/EA=20/1) to afford the title compound (180 mg, 85% yield). LCMS: 331 (M+H)$^+$.

Step 3: 2-bromo-4-iodo-3,6-dimethoxypyridine

To a solution of 2-bromo-6-fluoro-4-iodo-3-methoxypyridine (180 mg, 0.55 mmol) in MeOH (10 mL) was added NaOMe (43 mg, 0.82 mmol). The reaction mixture was stirred at 70° C. for 2 hours. The solvent was cooled and removed in vacuo. The residue was dissolved in EA, washed with water, and concentrated. The residue was purified by FCC (PE/EA=20/1) to afford the title compound (180 mg, 95% yield). LCMS: 344 (M+H)$^+$.

Step 4: 1-(4-(2-Bromo-3,6-dimethoxypyridin-4-yl)-2-chlorophenyl)-3-methyl-1H-imidazol-2(3H)— one To a solution of 2-bromo-4-iodo-3,6-dimethoxypyridine (100 mg, 0.29 mmol) in 1,4-dioxane/water (5/1, 10 mL) was added 1-(2-chloro-4-(4,4,5,5-tetramethyl-1,3,2-dioxaborolan-2-yl)phenyl)-3-methyl-1H-imidazol-2(3H)-one (95 mg, 0.29 mmol), Pd(dppf)Cl$_2$ (21 mg, 0.03 mmol) and Na$_2$CO$_3$ (100 mg, 0.9 mmol). The reaction mixture was stirred at 60° C. for 3 hours under N$_2$. The reaction mixture was cooled, added water, and extracted with EA. The combined organic layers were concentrated. The residue was purified by FCC (EA/PE=1/1) to afford the title compound (60 mg, 48% yield). LCMS: 424 (M+H)$^+$.

Step 5: 1-(4-(2-(3-(4-(tert-Butyl)piperazin-1-yl)phenyl)-3,6-dimethoxypyridin-4-yl)-2-chlorophenyl)-3-methyl-1H-imidazol-2(3H)-one To a solution of 1-(4-(2-bromo-3,6-dimethoxypyridin-4-yl)-2-chlorophenyl)-3-methyl-1H-imidazol-2(3H)-one (100 mg, 0.24 mmol) in 1,4-dioxane/water (5/1, 10 mL) was added 1-(tert-butyl)-4-(3-(4,4,5,5-tetramethyl-1,3,2-dioxaborolan-2-yl)phenyl)piperazine (81 mg, 0.24 mmol), Pd(dppf)Cl$_2$ (18 mg, 0.03 mmol) and Na$_2$CO$_3$ (75 mg, 0.7 mmol). The reaction mixture was stirred at 100° C. for 3 hours under N$_2$. The reaction mixture was cooled, added water and extracted with EA. The combined organic layers were concentrated. The residue was purified by FCC (DCM/MeOH=20/1) to afford the title compound (90 mg, 68% yield). LCMS: 562 (M+H)$^+$.

Step 6: 1-(4-(2-(3-(4-(tert-butyl)piperazin-1-yl)phenyl)-3-hydroxy-6-methoxypyridin-4-yl)-2-chlorophenyl)-3-methyl-1H-imidazol-2(3H)-one To a solution of 1-(4-(2-(3-(4-(tert-butyl)piperazin-1-yl)phenyl)-3,6-dimethoxypyridin-4-yl)-2-chlorophenyl)-3-methyl-1H-imidazol-2(3H)-one (90 mg, 0.16 mmol) in DCM (2 mL) was added BBr$_3$ (2 mL, 1 N). The reaction mixture was stirred at rt overnight. The reaction mixture was cooled to 0° C. and quenched with MeOH. The solution was removed. The residue was adjusted pH=8 with aq. NaHCO$_3$ and extracted with DCM/MeOH (10/1). The combined organic layers were concentrated. The residue was purified by HPLC to afford the title compound (43 mg, 40% yield). $^1$H NMR (400 MHz, DMSO-d$_6$) δ 8.56 (s, 1H), 7.86 (d, J=2.0 Hz, 1H), 7.66 (dd, J=8.0, 2.0 Hz, 1H), 7.58-7.50 (m, 2H), 7.40 (d, J=7.6 Hz, 1H), 7.30 (t, J=8.0 Hz, 1H), 6.97 (d, J=8.0 Hz, 1H), 6.77 (s, 1H), 6.72 (d, J=3.2 Hz, 1H), 6.71 (d, J=3.2 Hz, 1H), 3.87 (s, 3H), 3.20 (s, 3H), 3.16 (s, 4H), 2.68 (s, 4H), 1.06 (s, 9H). LCMS: 548 (M+H)$^+$.

Example 1029

1-(4-(2-(3-(4-(tert-Butyl)piperazin-1-yl)phenyl)-3-hydroxy-6-methoxypyridin-4-yl)-2-chlorophenyl)-3-methyl-1H-imidazol-2(3H)-one

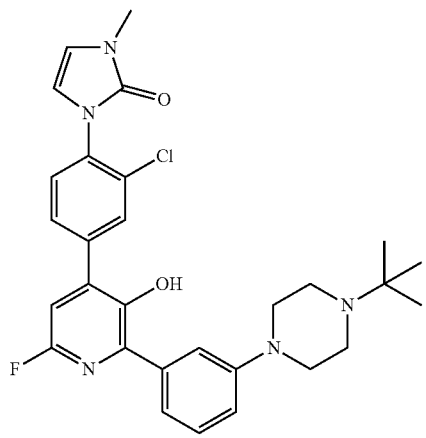

Step 1: 1-(4-(2-Bromo-6-fluoro-3-hydroxypyridin-4-yl)-2-chlorophenyl)-3-methyl-1H-imidazol-2(3H)-one To a solution of 2-bromo-6-fluoro-4-iodopyridin-3-ol (250 mg, 0.79 mmol, from B-1096) in 1,4-dioxane/water (5/1, 10 mL) was added 1-(2-chloro-4-(4,4,5,5-tetramethyl-1,3,2-dioxaborolan-2-yl)phenyl)-3-methyl-1H-imidazol-2(3H)-one (265 mg, 0.79 mmol), Pd(dppf)Cl$_2$ (60 mg, 0.08 mmol) and K$_3$PO$_4$ (500 mg, 2.4 mmol). The reaction mixture was stirred at 60° C. for 3 hours under N$_2$. The reaction mixture was cooled, added water, and extracted with EA. The combined organic layers were concentrated. The residue was purified by FCC (DCM/MeOH=20/1) to afford the title compound (180 mg, 57% yield). LCMS: 398 (M+H)$^+$.

Step 2: 1-(4-(2-Bromo-6-fluoro-3-(methoxymethoxy)pyridin-4-yl)-2-chlorophenyl)-3-methyl-1H-imidazol-2(3H)-one To a solution of 1-(4-(2-bromo-6-fluoro-3-hydroxypyridin-4-yl)-2-chlorophenyl)-3-methyl-1H-imidazol-2(3H)-one (180 mg, 0.45 mmol) in DMF (5 mL) was added NaH (36 mg, 0.90 mmol). The reaction mixture was stirred at 10° C. for 0.5 hours. Then bromo(methoxy)methane (85 mg, 0.69 mmol) was added. The reaction mixture was stirred at rt for 2 hours. The reaction mixture was added water to quench the reaction and extracted with EA. The combined organic layers were concentrated. The residue was purified by FCC (DCM/MeOH=20/1) to afford the title compound (170 mg, 85% yield). LCMS: 442 (M+H)$^+$.

Step 3: 1-(4-(2-(3-(4-(tert-Butyl)piperazin-1-yl)phenyl)-6-fluoro-3-(methoxymethoxy)pyridin-4-yl)-2-chlorophenyl)-3-methyl-1H-imidazol-2(3H)-one To a solution of 1-(4-(2-bromo-6-fluoro-3-(methoxymethoxy)pyridin-4-yl)-2-chlorophenyl)-3-methyl-1H-imidazol-2(3H)-one (110 mg, 0.25 mmol) in 1,4-dioxane/water (5/1, 10 mL) was added 1-(tert-butyl)-4-(3-(4,4,5,5-tetramethyl-1,3,2-dioxaborolan-2-yl)phenyl)piperazine (85 mg, 0.25 mmol), Pd(dppf)Cl$_2$ (19 mg, 0.03 mmol) and Na$_2$CO$_3$ (80 mg, 0.75 mmol). The reaction mixture was stirred at 100° C. for 3 hours under N$_2$. The reaction mixture was cooled, added water, and extracted with EA. The combined organic layers were concentrated. The residue was purified by FCC (EA/PE=1/1) to afford the title compound (90 mg, 66% yield). LCMS: 580 (M+H)$^+$.

Step 4: 1-(4-(2-(3-(4-(tert-Butyl)piperazin-1-yl)phenyl)-6-fluoro-3-hydroxypyridin-4-yl)-2-chlorophenyl)-3-methyl-1H-imidazol-2(3H)-one To a solution of 1-(4-(2-(3-(4-(tert-butyl)piperazin-1-yl)phenyl)-6-fluoro-3-(methoxymethoxy)pyridin-4-yl)-2-chlorophenyl)-3-methyl-1H-imidazol-2(3H)-one (90 mg, 0.16 mmol) in MeOH (3 mL)) was added HCl (2 mL, 4 N). The reaction mixture was stirred at rt for 3 hours. The reaction mixture was adjusted pH=8 with aq. NaHCO$_3$ and extracted with DCM. The combined organic layers were concentrated. The residue was purified by HPLC to afford the title compound (46 mg, 56% yield). $^1$H NMR (400 MHz, DMSO-d) δ 9.18 (s, 1H), 7.92 (d, J=2.0 Hz, 1H), 7.71 (dd, J=8.0, 2.0 Hz, 1H), 7.59 (d, J=8.0 Hz, 1H), 7.44 (s, 1H), 7.34-7.27 (m, 2H), 7.16 (d, J=3.2 Hz, 1H), 7.04-6.96 (m, 1H), 6.73 (d, J=3.2 Hz, 1H), 6.71 (d, J=3.2 Hz, 1H), 3.21 (s, 3H), 3.16 (s, 4H), 2.67 (s, 4H), 1.06 (s, 9H). LCMS: 536.2 (M+H)$^+$.

Example 1030

5-(3-(4-(tert-Butyl)piperazin-1-yl)phenyl)-3-(3-chloro-4-(3-methyl-2-oxo-2,3-dihydro-1H-imidazol-1-yl)phenyl)-4-hydroxy-1-methylpyridin-2(1H)-one

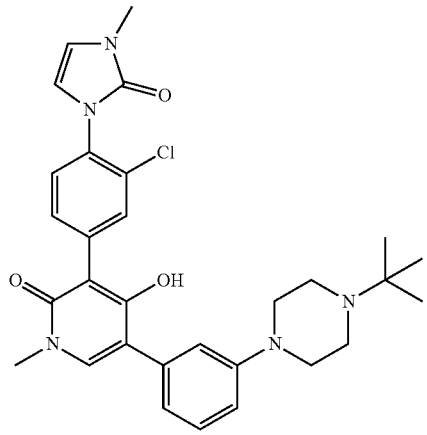 [SMILES: Cn1cc(-c2cccc(N3CCN(C(C)(C)C)CC3)c2)c(O)c(-c2ccc(-n3ccn(C)c3=O)c(Cl)c2)c1=O]

Step 1: 3-Bromo-5-(3-(4-(tert-butyl)piperazin-1-yl)phenyl)-4-methoxy-1-methylpyridin-2(1H)-one A solution of 3,5-dibromo-4-methoxy-1-methylpyridin-2(1H)-one (250 mg, 0.84 mmol), 1-(tert-butyl)-4-(3-(4,4,5,5-tetramethyl-1,3,2-dioxaborolan-2-yl)phenyl)piperazine (387 mg, 0.84 mmol), Pd(dppf)Cl$_2$ (62 mg, 0.084 mmol) and Na$_2$CO$_3$ (268 mg, 2.53 mmol), in dioxane/H$_2$O (8 mL/1 mL) was stirred at 100° C. for 4 h under N$_2$. LCMS showed the reaction was completed. The reaction mixture was cooled, suspended in H$_2$O, and extracted with EA. The combined organic layers were dried over Na$_2$SO$_4$, filtered and concentrated. The residue was purified by silica gel column chromatography (DCM/MeOH=10/1) to afford the title compound (248 mg, 56% yield). LCMS: 434.1 (M+H)$^+$.

Step 2: 5-(3-(4-(tert-Butyl)piperazin-1-yl)phenyl)-3-(3-chloro-4-(3-methyl-2-oxo-2,3-dihydro-1H-imidazol-1-yl)phenyl)-4-methoxy-1-methylpyridin-2(1H)-one A solution of 3-bromo-5-(3-(4-(tert-butyl)piperazin-1-yl)phenyl)-4-methoxy-1-methylpyridin-2(1H)-one (151 mg, 0.35 mmol), 1-(2-chloro-4-(4,4,5,5-tetramethyl-1,3,2-dioxaborolan-2-yl)phenyl)-3-methyl-1H-imidazol-2(3H)-one (116 mg, 0.35 mmol), Pd(dppf)Cl$_2$ (26 mg, 0.035 mmol) and Na$_2$CO$_3$ (111 mg, 1.05 mmol) in dioxane/H$_2$O (80 mL/1 mL) was stirred at 100° C. for 3 h under N$_2$. LCMS showed the reaction was completed. The reaction mixture was cooled, suspended in H$_2$O, and extracted with EA. The combined organic layers were dried over Na$_2$SO$_4$, filtered and concentrated. The residue was purified by silica gel column chromatography (DCM/MeOH=10/1) to afford the title compound (164.6 mg, 84% yield). LCMS: 562.2 (M+H)$^+$.

Step 3: 5-(3-(4-(tert-Butyl)piperazin-1-yl)phenyl)-3-(3-chloro-4-(3-methyl-2-oxo-2,3-dihydro-1H-imidazol-1-yl)phenyl)-4-hydroxy-1-methylpyridin-2(1H)-one To a solution of 5-(3-(4-(tert-butyl)piperazin-1-yl)phenyl)-3-(3-chloro-4-(3-methyl-2-oxo-2,3-dihydro-1H-imidazol-1-yl)phenyl)-4-methoxy-1-methylpyridin-2(1H)-one (164.6 mg, 0.29 mmol) in DMF (2 mL) was added piperazine (100 mg, 1.16 mmol). The reaction mixture was stirred at 145° C. for 2.5 h. LCMS showed the reaction was completed. The reaction mixture was suspended in H$_2$O and extracted with EA. The combined organic layers were dried over Na$_2$SO$_4$, filtered and concentrated. The residue was purified by HPLC to afford the title compound (8.2 mg, 12% yield). $^1$H NMR (300 MHz, DMSO) δ 7.70 (s, 1H), 7.64 (s, 1H), 7.57-7.40 (m, 2H), 7.27 (t, J=7.8 Hz, 1H), 7.02 (s, 1H), 6.91 (d, J=7.6 Hz, 2H), 6.73 (d, J=2.9 Hz, 1H), 6.68 (d, J=3.0 Hz, 1H), 3.46 (s, 3H), 3.22 (d, J=8.5 Hz, 3H), 3.19 (s, 4H), 2.72 (s, 4H), 1.10 (s, 9H). LCMS: 548.2 (M+H)$^+$.

Example 1031

1-(4-(2-(3-(4-(tert-Butyl)piperazin-1-yl)phenyl)-3-hydroxy-6-(methylamino)pyridin-4-yl)-2-chlorophenyl)-3-methyl-1H-imidazol-2(3H)-one

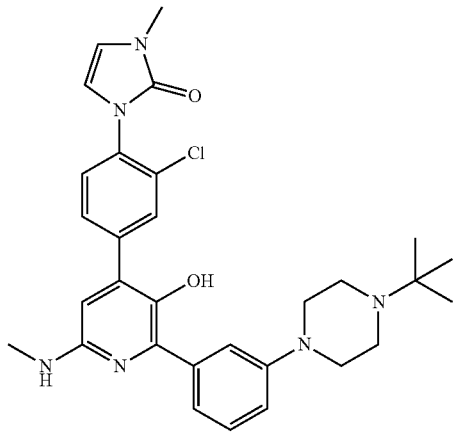 [SMILES: CNc1cc(-c2ccc(-n3ccn(C)c3=O)c(Cl)c2)c(O)c(-c2cccc(N3CCN(C(C)(C)C)CC3)c2)n1]

Step 1: 1-(4-(2-bromo-3-(methoxymethoxy)-6-(methylamino)pyridin-4-yl)-2-chlorophenyl)-3-methyl-1H-imidazol-2(3H)-one To a solution of 1-(4-(2-bromo-6-fluoro-3-(methoxymethoxy)pyridin-4-yl)-2-chlorophenyl)-3-methyl-1H-imidazol-2(3H)-one (200 mg, 0.45 mmol) in EtOH (5 mL) was added methanamine (2 mL, 1 N in MeOH). The reaction mixture was stirred at 70° C. for 3 hours. The reaction mixture was cooled, and solvent removed in vacuo. The residue was purified by FCC (DCM/MeOH=30/1) to afford the title compound (150 mg, 73% yield). LCMS: 453 (M+H)$^+$.

Step 2: 1-(4-(2-(3-(4-(tert-butyl)piperazin-1-yl)phenyl)-3-(methoxymethoxy)-6-(methylamino)pyridin-4-yl)-2-chlorophenyl)-3-methyl-1H-imidazol-2(3H)-one To a solution of 1-(4-(2-bromo-3-(methoxymethoxy)-6-(methylamino)pyridin-4-yl)-2-chlorophenyl)-3-methyl-1H-imidazol-2(3H)-one (150 mg, 0.33 mmol) in 1,4-dioxane/water (5/1, 10 mL) was added 1-(tert-butyl)-4-(3-(4,4,5,5-tetramethyl-1,3,2-dioxaborolan-2-yl)phenyl)piperazine (125 mg, 0.36 mmol), Pd(dppf)Cl$_2$ (24 mg, 0.03 mmol) and Na$_2$CO$_3$ (105 mg, 0.99 mmol). The reaction mixture was stirred at 100° C. for 3 hours under N$_2$. The reaction mixture was cooled, added water, and extracted with EA. The combined organic layers were concentrated. The residue was purified by FCC (DCM/MeOH=20/1) to afford the title compound (100 mg, 51% yield). LCMS: 591.2 (M+H)$^+$.

Step 3: 1-(4-(2-(3-(4-(tert-Butyl)piperazin-1-yl)phenyl)-3-hydroxy-6-(methylamino)pyridin-4-yl)-2-chlorophenyl)-3-methyl-1H-imidazol-2(3H)-one To a solution of 1-(4-(2-(3-(4-(tert-butyl)piperazin-1-yl)phenyl)-3-(methoxymethoxy)-6-(methylamino)pyridin-4-yl)-2-chlorophenyl)-3-methyl-1H-imidazol-2(3H)-one (100 mg, 0.17 mmol) in MeOH (3 my)) was added HCl (2 mL, 4 N). The reaction mixture was stirred at rt for 3 hours. The reaction mixture was adjusted pH=8 with aq. NaHCO$_3$ and extracted with DCM. The combined organic layers were concentrated. The residue was purified by HPLC to afford the title compound (14.5 mg, 26% yield). 1H NMR (400 MHz, DMSO-d$_6$) δ 7.86 (s, 1H), 7.79 (d, J=2.0 Hz, 1H), 7.61 (dd, J=8.0, 2.0 Hz, 1H), 7.53 (d, J=8.0 Hz, 1H), 7.49 (s, 1H), 7.36 (d, J=7.6 Hz, 1H), 7.25 (t, J=8.0 Hz, 1H), 6.91 (dd, J=8.0, 2.0 Hz, 1H), 6.72 (d, J=3.2 Hz, 1H), 6.69 (d, J=3.2 Hz, 1H), 6.39 (s, 1H), 6.07 (d, J=4.8 Hz, 1H), 3.19 (s, 3H), 3.16-3.06 (m, 4H), 2.80 (d, J=4.8 Hz, 3H), 2.70-2.59 (m, 4H), 1.05 (s, 9H). LCMS: 547.2 (M+H)$^+$.

TABLE 37

Following compounds were prepared using similar procedures as described for Examples 1 through 1031.

| Ex. No. | Name/Structure | $^1$H NMR Data | LCMS (M + H)$^+$ |
|---|---|---|---|
| 1032 | 7-(4-(3-chloro-4-(3-methyl-2-oxo-2,3-dihydro-1H-imidazol-1-yl)phenyl)-3-hydroxy-6-methyl-[2,4'-bipyridin]-2'-yl)-1,7-diazaspiro[4.4]nonan-2-one | $^1$H NMR (400 MHz, DMSO-d$_6$) 9.05 (s, 1H), 8.13 (d, J = 5.3 Hz, 1H), 8.08 (s, 1H), | 531.2 |

TABLE 37-continued

Following compounds were prepared using similar procedures as described for Examples 1 through 1031.

| Ex. No. | Name/Structure | ¹H NMR Data | LCMS (M + H)⁺ |
|---|---|---|---|
| | (Z) isomer structure | 7.85 (d, J = 1.9 Hz, 1H), 7.66 (dd, J = 8.2, 1.9 Hz, 1H), 7.56 (d, J = 8.2 Hz, 1H), 7.26 (s, 1H), 7.02 (d, J = 5.3 Hz, 1H), 6.89 (s, 1H), 6.71 (dd, J = 12.4, 3.0 Hz, 2H), 3.61 (dd, J = 16.4, 7.0 Hz, 1H), 3.55-3.44 (m, 2H), 3.39 (d, J = 10.4 Hz, 1H), 3.21 (s, 3H), 2.47 (s, 3H), 2.29 (dd, J = 15.6, 7.5 Hz, 2H), 2.07-2.00 (m, 4H) | |
| 1033 | (S)-1-(2-chloro-4-(3-hydroxy-2'-(7-hydroxy-7-methyl-5-azaspiro[2.4]heptan-5-yl)-6-methyl-[2,4'-bipyridin]-4-yl)phenyl)-1H-imidazol-2(3H)-one | ¹H NMR (400 MHz, DMSO-d₆) δ 9.04 (s, 1H), 8.11 (d, J = 5.3 Hz, 1H), 7.84 (d, J = 1.9 Hz, 1H), 7.66 (dd, J = 8.2, 1.9 Hz, 1H), 7.56 (d, J = 8.2 Hz, 1H), 7.25 (s, 1H), 6.99 (dd, J = 5.2, 1.0 Hz, 1H), 6.83 (s, 1H), 6.71 (dt, J = 6.2, 3.1 Hz, 2H), 4.65 (s, 1H), 3.61-3.51 (m, 3H), 3.34 (d, J = 4.7 Hz, 1H), 3.21 (s, 3H), 2.47 (s, 3H), 1.08 (d, J = 8.4 Hz, 3H), 0.83 (dd, J = 13.2, 7.2 Hz, 1H), 0.63-0.58 (m, 1H), 0.52 (d, J = 4.5 Hz, 2H) | 518.2 |
| 1034 | (R)-1-(2-chloro-4-(3-hydroxy-2'-(7-hydroxy-7-methyl-5-azaspiro[2.4]heptan-5-yl)-6-methyl-[2,4'-bipyridin]-4-yl)phenyl)-1H-imidazol-2(3H)-one | ¹H NMR (400 MHz, DMSO-d₆) δ 9.04 (s, 1H), 8.11 (d, J = 5.2 Hz, 1H), 7.84 (d, J = 1.9 Hz, 1H), 7.66 (dd, J = 8.2, 1.9 Hz, 1H), 7.56 (d, J = 8.2 Hz, 1H), 7.25 (s, 1H), 6.99 (d, J = 5.2 Hz, 1H), 6.83 (s, 1H), 6.71 (dt, J = 6.2, 3.1 Hz, 2H), 4.65 (s, 1H), 3.60-3.50 (m, 3H), 3.36 (d, J = 10.0 Hz, 1H), 3.21 (s, 3H), 2.47 (s, 3H), 1.10 (s, 3H), 0.83 (dd, J = 13.1, 7.2 Hz, 1H), 0.62-0.57 (m, 1H), 0.52 (d, J = 4.5 Hz, 2H) | 518.2 |

TABLE 37-continued

Following compounds were prepared using similar procedures as described for Examples 1 through 1031.

| Ex. No. | Name/Structure | ¹H NMR Data | LCMS (M + H)⁺ |
|---|---|---|---|
| 1035 | 1-(4-(2-(3-(4-(tert-butyl)piperazin-1-yl)phenyl)-3-hydroxy-6-methylpyridin-4-yl)-2-chlorophenyl)-1,3-dihydro-2H-imidazol-2-one | ¹H NMR (400 MHz, DMSO-d₆) δ 10.23 (s, 1H), 7.86 (d, J = 2.0 Hz, 1H), 7.66 (dd, J = 8.2, 1.9 Hz, 1H), 7.55 (d, J = 8.2 Hz, 1H), 7.40 (s, 1H), 7.29-7.25 (m, 2H), 7.17 (s, 1H), 6.99-6.92 (m, 1H), 6.60 (dd, J = 18.8, 3.0 Hz, 2H), 3.14 (t, J = 5.0 Hz, 4H), 2.66 (t, J = 4.9 Hz, 4H), 2.46 (s, 3H), 1.05 (s, 9H). N—H or O—H proton not observed | 518.2 |
| 1036 | (S)-1-(2-chloro-4-(2'-(3,3-difluoro-4-hydroxy-4-methylpyrrolidin-1-yl)-3-hydroxy-6-methyl-[2,4'-bipyridin]-4-yl)phenyl)-3-methyl-1,3-dihydro-2H-imidazol-2-one | ¹H NMR (400 MHz, DMSO-d₆) δ 9.08 (s, 1H), 8.16 (d, J = 5.3 Hz, 1H), 7.86 (d, J = 1.6 Hz, 1H), 7.67 (dd, J = 8.2, 1.8 Hz, 1H), 7.57 (d, J = 8.2 Hz, 1H), 7.27 (s, 1H), 7.10 (d, J = 5.1 Hz, 1H), 6.93 (s, 1H), 6.71 (dd, J = 11.5, 3.0 Hz, 2H), 5.87 (s, 1H), 4.00-3.81 (m, 2H), 3.61 (d, J = 8.5 Hz, 1H), 3.48 (d, J = 10.1 Hz, 1H), 3.21 (s, 3H), 2.48 (s, 3H), 1.36 (s, 3H) | 528.2 |
| 1037 | (R)-1-(2-chloro-4-(2'-(3,3-difluoro-4-hydroxy-4-methylpyrrolidin-1-yl)-3-hydroxy-6-methyl-[2,4'-bipyridin]-4-yl)phenyl)-3-methyl-1,3-dihydro-2H-imidazol-2-one | ¹H NMR (400 MHz, DMSO-d₆) δ 9.08 (s, 1H), 8.16 (d, J = 5.2 Hz, 1H), 7.86 (d, J = 1.5 Hz, 1H), 7.67 (dd, | 528.2 |

TABLE 37-continued

Following compounds were prepared using similar procedures as described for Examples 1 through 1031.

| Ex. No. | Name/Structure | ¹H NMR Data | LCMS (M + H)⁺ |
|---|---|---|---|
| | 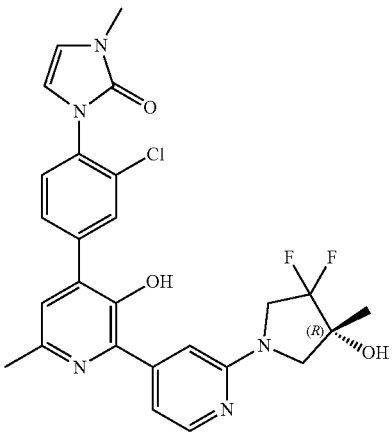 | J = 8.2, 1.8 Hz, 1H), 7.56 (d, J = 8.2 Hz, 1H), 7.27 (s, 1H), 7.10 (d, J = 5.1 Hz, 1H), 6.94 (s, 1H), 6.71 (dd, J = 11.5, 3.0 Hz, 2H), 5.87 (s, 1H), 3.90 (dd, J = 22.3, 7.4 Hz, 2H), 3.60 (d, J = 10.9 Hz, 1H), 3.48 (d, J = 10.1 Hz, 1H), 3.21 (s, 3H), 2.48 (s, 3H), 1.36 (s, 3H) | |
| 1038 | 1-(4-(2-(3-(4-(tert-butyl)piperazin-1-yl)phenyl)-3-hydroxypyridin-4-yl)-2-chlorophenyl)-1H-imidazol-2(3H)-one 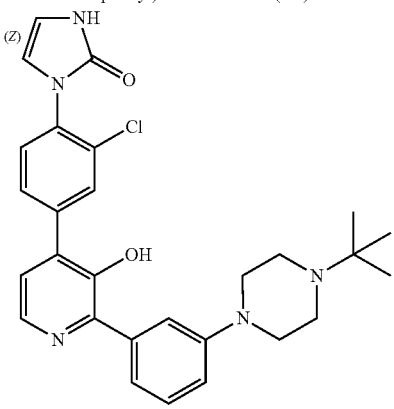 | ¹H NMR (400 MHz, DMSO-d₆) δ 10.24 (s, 1H), 9.10 (s, 1H), 8.27 (d, J = 4.8 Hz, 1H), 7.86 (d, J = 1.6 Hz, 1H), 7.67 (dd, J = 8.2, 1.8 Hz, 1H), 7.57 (d, J = 8.2 Hz, 1H), 7.40 (s, 1H), 7.32-7.26 (m, 3H), 6.98 (t, J = 5.9 Hz, 1H), 6.61 (dt, J = 19.5, 2.9 Hz, 2H), 3.16 (s, 4H), 2.67 (s, 4H), 1.06 (s, 9H) | 504.2 |
| 1039 | 1-(2-chloro-4-(3-hydroxy-5'-(8-isopropyl-3,8-diazabicyclo[3.2.1]octan-3-yl)-6'-methoxy-6-methyl-[2,3'-bipyridin]-4-yl)phenyl)-3-methyl-1H-imidazol-2(3H)-one 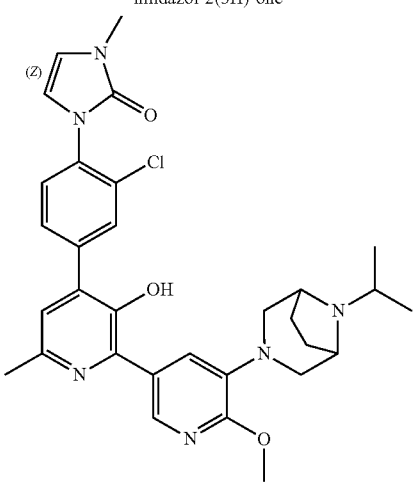 | ¹H NMR (400 MHz, DMSO-d₆) δ 8.37 (s, 2H), 8.24 (d, J = 1.8 Hz, 1H), 7.85 (d, J = 1.7 Hz, 1H), 7.70-7.64 (m, 1H), 7.61-7.54 (m, 2H), 7.19 (s, 1H), 6.71 (dd, J = 13.0, 3.0 Hz, 2H), 3.95 (s, 3H), 3.73 (s, 2H), 3.32 (d, J = 10.3 Hz, 2H), 3.23 (s, 3H), 2.96 (d, J = 11.1 Hz, 2H), 2.76 (s, 1H), 2.48 (s, 3H), 1.89 (s, 4H), 1.11 (d, J = 6.1 Hz, 6H) | 575.2 |

Example 1040

6-(3-(4-(tert-Butyl)piperazin-1-yl)phenyl)-4-(3-chloro-4-(3-methyl-2-oxo-2,3-dihydro-1H-imidazol-1-yl)phenyl)-5-hydroxypyridin-2(1H)-one

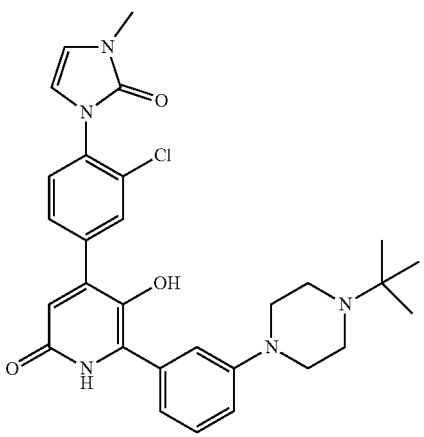 [SMILES: Cn1ccn(-c2ccc(-c3cc(=O)[nH]c(-c4cccc(N5CCN(C(C)(C)C)CC5)c4)c3O)cc2Cl)c1=O]

Step 1: 1-(4-(2-Bromo-6-((4-methoxybenzyl)oxy)-3-(methoxymethoxy)pyridin-4-yl)-2-chlorophenyl)-3-methyl-1H-imidazol-2(3H)-one To a solution of (4-methoxyphenyl)methanol (115 mg, 0.82 mmol) in DMF (15 mL) was added NaH (41 mg, 1.02 mmol). The reaction mixture was stirred at rt for 30 min. 1-(4-(2-bromo-6-fluoro-3-(methoxymethoxy)pyridin-4-yl)-2-chlorophenyl)-3-methyl-1H-imidazol-2(3H)-one (300 mg, 0.68 mmol) was added. The reaction mixture was stirred at 40° C. for 1 hour. The mixture was quenched with H$_2$O and extracted with EA. The combined organic layers were concentrated in vacuo. The residue was purified by FCC (EA/PE=1/1) to afford the title compound (260 mg, 68% yield). LCMS: 560 (M+H)$^+$.

Step 2: 1-(4-(2-(3-(4-(tert-Butyl)piperazin-1-yl)phenyl)-6-((4-methoxybenzyl)oxy)-3-(methoxymethoxy)pyridin-4-yl)-2-chlorophenyl)-3-methyl-1H-imidazol-2(3H)-one To a solution of 1-(4-(2-bromo-6-((4-methoxybenzyl)oxy)-3-(methoxymethoxy)pyridin-4-yl)-2-chlorophenyl)-3-methyl-1H-imidazol-2(3H)-one (220 mg, 0.39 mmol) in 1,4-dioxane/water (5/1, 10 mL) was added 1-(tert-butyl)-4-(3-(4,4,5,5-tetramethyl-1,3,2-dioxaborolan-2-yl)phenyl)piperazine (160 mg, 0.47 mmol), Pd(dppf)Cl$_2$ (30 mg, 0.04 mmol) and Na$_2$CO$_3$ (127 mg, 1.20 mmol). The reaction mixture was stirred at 100° C. for 3 hours under N$_2$. The reaction mixture was cooled, added water, and extracted with EA. The combined organic layers were concentrated. The residue was purified by FCC (DCM/MeOH=30/1) to afford the title compound (250 mg, 90% yield). LCMS: 698 (M+H)$^+$.

Step 3: 6-(3-(4-(tert-Butyl)piperazin-1-yl)phenyl)-4-(3-chloro-4-(3-methyl-2-oxo-2,3-dihydro-1H-imidazol-1-yl)phenyl)-5-hydroxypyridin-2(1H)-one To a solution of 1-(4-(2-(3-(4-(tert-butyl)piperazin-1-yl)phenyl)-6-((4-methoxybenzyl)oxy)-3-(methoxymethoxy)pyridin-4-yl)-2-chlorophenyl)-3-methyl-1H-imidazol-2(3H)-one (120 mg, 0.17 mmol) in MeOH (3 mL)) was added HCl (2 mL, 4 N). The reaction mixture was stirred at rt for 3 hours. The reaction mixture was adjusted pH=8 with aq. NaHCO$_3$ and extracted with DCM. The combined organic layers were concentrated. The residue was purified by HPLC to afford the title compound (26 mg, 28% yield). $^1$H NMR (300 MHz, DMSO-d$_6$) δ 8.13 (s, 1H), 7.86 (s, 1H), 7.64 (t, J=10.6 Hz, 1H), 7.60-7.46 (m, 1H), 7.39-7.16 (m, 3H), 6.99 (d, J=8.0 Hz, 1H), 6.78-6.68 (m, 2H), 6.47 (s, 1H), 3.24 (s, 3H), 3.19 (s, 4H), 2.68 (s, 4H), 1.08 (s, 9H). LCMS: 534 (M+H)$^+$.

Example 1041

1-(4-(2-(3-(4-(tert-butyl)piperazin-1-yl)phenyl)-3-hydroxy-6-methylpyridin-4-yl)-2-chlorophenyl)pyrrolidin-2-one

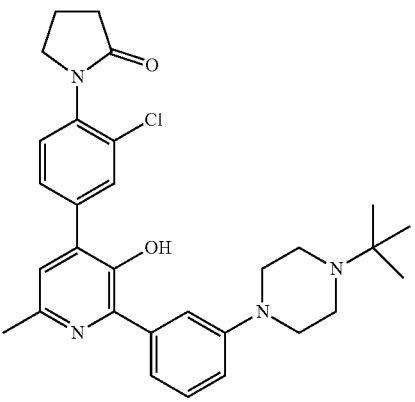 [SMILES: Cc1cc(-c2ccc(N3CCCC3=O)c(Cl)c2)c(O)c(-c2cccc(N3CCN(C(C)(C)C)CC3)c2)n1]

Step 1: 1-(4-(2-Bromo-3-(methoxymethoxy)-6-methylpyridin-4-yl)-2-chlorophenyl)pyrrolidin-2-one To a solution of 2-bromo-4-iodo-3-(methoxymethoxy)-6-methylpyridine (200 mg, 0.56 mmol) in dioxane/water (5/1, 15 mL) was added 1-(2-chloro-4-(4,4,5,5-tetramethyl-1,3,2-dioxaborolan-2-yl)phenyl)pyrrolidin-2-one (180 mg, 0.56 mmol), Pd(dppf)Cl$_2$ (40 mg, 0.06 mmol) and Na$_2$CO$_3$ (180 mg, 1.67 mmol). The reaction mixture was stirred at 50° C. for 2 hours under N$_2$. The reaction mixture was quenched with H$_2$O and extracted with EA. The combined organic layers were concentrated in vacuo. The residue was purified by FCC (EA/PE=1/1) to afford the title compound (60 mg, 15% yield). LCMS: 425 (M+H)$^+$.

Step 2: 1-(4-(2-(3-(4-(tert-Butyl)piperazin-1-yl)phenyl)-3-(methoxymethoxy)-6-methylpyridin-4-yl)-2-chlorophenyl)pyrrolidin-2-one To a solution of 1-(4-(2-bromo-3-(methoxymethoxy)-6-methylpyridin-4-yl)-2-chlorophenyl)pyrrolidin-2-one (60 mg, 0.14 mmol) in 1,4-dioxane/water (5/1, 15 mL) was added 1-(tert-butyl)-4-(3-(4,4,5,5-tetramethyl-1,3,2-dioxaborolan-2-yl)phenyl)piperazine (50 mg, 0.14 mmol), Pd(dppf)Cl$_2$ (10 mg, 0.01 mmol) and Na$_2$CO$_3$ (45 mg, 0.42 mmol). The reaction mixture was stirred at 100° C. for 3 hours under N$_2$. The reaction mixture was cooled, added water, and extracted with EA. The combined organic layer Step 3: 1-(4-(2-(3-(4-(tert-Butyl)piperazin-1-yl)phenyl)-3-hydroxy-6-methylpyridin-4-yl)-2-chlorophenyl)pyrrolidin-2-one To a solution of 1-(4-(2-(3-(4-(tert-butyl)piperazin-1-yl)phenyl)-3-(methoxymethoxy)-6-methylpyridin-4-yl)-2-chlorophenyl)pyrrolidin-2-one (70 mg, 0.12 mmol) in MeOH (35 mL) was added con. HCl (2 mL). The reaction mixture was stirred at 40° C. at rt for 2 hours. The reaction mixture was adjusted pH=8 with aq. NaHCO$_3$ and extracted with DCM. The combined organic layers were concentrated. The residue was purified by HPLC to the title compound (45 mg, 69% yield). $^1$H NMR (400 MHz, DMSO-d$_6$) δ 8.73 (s, 1H), 7.79 (d, J=1.7 Hz, 1H), 7.62 (dd, J=8.2, 1.8 Hz, 1H), 7.51 (d, J=8.2 Hz, 1H), 7.37 (s, 1H), 7.32-7.19 (m, 2H), 7.16 (s, 1H), 7.00-6.87 (m, 1H), 3.74 (t, J=6.9 Hz, 2H), 3.18-3.07 (m, 4H), 2.65 (dd, J=14.8, 10.2 Hz, 4H), 2.48-2.41 (m, 5H), 2.23-2.08 (m, 2H), 1.05 (s, 9H). LCMS: 519.2 (M+H)$^+$.

Example 1042

3''-(4-(tert-Butyl)piperazin-1-yl)-3-chloro-2'-hydroxy-4-(3-methyl-2-oxo-2,3-dihydro-1H-imidazol-1-yl)-[1,1':3',1''-terphenyl]-5'-carbaldehyde

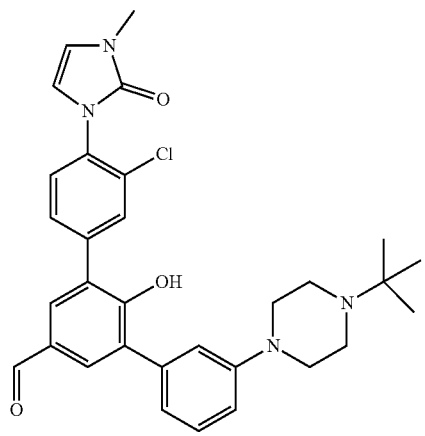 [SMILES: Cn1ccn(-c2ccc(-c3cc(C=O)cc(-c4cccc(N5CCN(C(C)(C)C)CC5)c4)c3O)cc2Cl)c1=O]

The title compound was prepared following the procedures described for Example 1020 using 3,5-dibromo-4-methoxybenzaldehyde, 1-(2-chloro-4-(4,4,5,5-tetramethyl-1,3,2-dioxaborolan-2-yl)phenyl)-3-methyl-1H-imidazol-2(3H)-one, 1-(tert-butyl)-4-(3-(4,4,5,5-tetramethyl-1,3,2-dioxaborolan-2-yl)phenyl)piperazine and BBr$_3$ to afford the title compound. $^1$H NMR (400 MHz, DMSO-d$_6$) δ 9.84 (s, 1H), 9.67 (s, 1H), 7.88 (s, 1H), 7.79 (d, J=1.9 Hz, 1H), 7.73 (d, J=1.9 Hz, 1H), 7.65 (dd, J=8.2, 1.9 Hz, 1H), 7.52 (d, J=8.2 Hz, 1H), 7.30 (t, J=7.9 Hz, 1H), 7.14 (s, 1H), 6.97 (dd, J=20.3, 8.9 Hz, 2H), 6.70 (dd, J=8.5, 3.0 Hz, 2H), 3.21 (s, 4H), 2.71 (d, J=34.1 Hz, 4H), 1.09 (d, J=6.4 Hz, 9H). LCMS: 545.2 (M+H)$^+$.

Example 1043

1-(4-(5'-(4-(tert-Butyl)piperazin-1-yl)-6-fluoro-3-hydroxy-6'-methyl-[2,3'-bipyridin]-4-yl)-2-chlorophenyl)-3-methyl-1H-imidazol-2(3H)-one

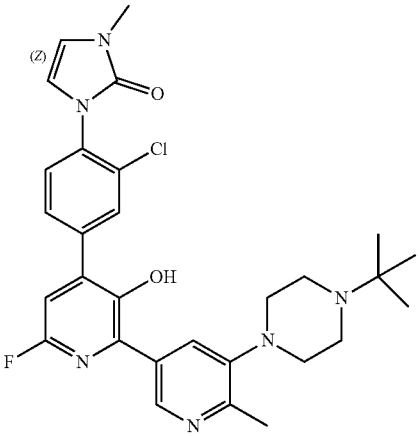 [SMILES: Cc1ncc(-c2nc(F)cc(-c3ccc(-n4ccn(C)c4=O)c(Cl)c3)c2O)cc1N1CCN(C(C)(C)C)CC1]

The title compound was prepared following the procedures described for Example 1029 using 1-(4-(2-bromo-6-fluoro-3-(methoxymethoxy)pyridin-4-yl)-2-chlorophenyl)-3-methyl-1H-imidazol-2(3H)— one, 1-(tert-butyl)-4-(2-methyl-5-(4,4,5,5-tetramethyl-1,3,2-dioxaborolan-2-yl)pyridin-3-yl)piperazine and hydrochloric acid to afford the title compound. $^1$H NMR (400 MHz, DMSO-d$_6$) δ 9.50 (s, 1H), 8.69 (d, J=1.6 Hz, 1H), 7.98-7.84 (m, 2H), 7.72 (dd, J=8.2, 1.9 Hz, 1H), 7.59 (d, J=8.2 Hz, 1H), 7.20 (d, J=2.9 Hz, 1H), 6.72 (dd, J=13.1, 3.0 Hz, 2H), 3.21 (s, 3H), 2.92 (s, 4H), 2.72 (s, 4H), 2.49 (s, 3H) 1.08 (s, 9H). LCMS: 551.2 (M+H)$^+$.

Example 1044

1-(4-(5'-(4-(tert-Butyl)piperazin-1-yl)-6-fluoro-3-hydroxy-6'-methoxy-[2,3'-bipyridin]-4-yl)-2-chlorophenyl)-3-methyl-1H-imidazol-2(3H)-one

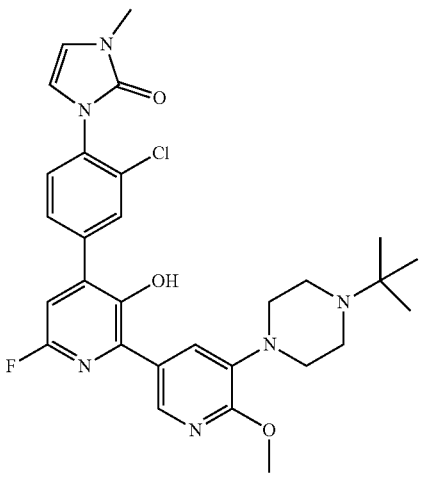 [SMILES: COc1ncc(-c2nc(F)cc(-c3ccc(-n4ccn(C)c4=O)c(Cl)c3)c2O)cc1N1CCN(C(C)(C)C)CC1]

The title compound was prepared following the procedures described for Example 1029 using 1-(4-(2-bromo-6-fluoro-3-(methoxymethoxy)pyridin-4-yl)-2-chlorophenyl)-3-methyl-1H-imidazol-2(3H)-one, 1-(tert-butyl)-4-(2-methoxy-5-(4,4,5,5-tetramethyl-1,3,2-dioxaborolan-2-yl)pyridin-3-yl)piperazine and hydrochloric acid to afford the title compound. $^1$H NMR (1H NMR (400 MHz, DMSO-$d_6$) δ 9.36 (s, 1H), 8.37 (d, J=1.6 Hz, 1H), 7.91 (d, J=1.7 Hz, 1H), 7.75-7.64 (m, 2H), 7.59 (d, J=8.2 Hz, 1H), 7.15 (d, J=2.9 Hz, 1H), 6.72 (dd, J=12.9, 3.0 Hz, 2H), 3.95 (s, 3H), 3.21 (s, 3H), 3.05 (s, 4H), 2.69 (s, 4H), 1.06 (s, 9H). LCMS: 567.1 (M+H)$^+$.

Example 1045

1-(3''-(4-(tert-Butyl)piperazin-1-yl)-3-chloro-5'-fluoro-2'-hydroxy-[1,1':3',1''-terphenyl]-4-yl)pyrrolidin-2-one

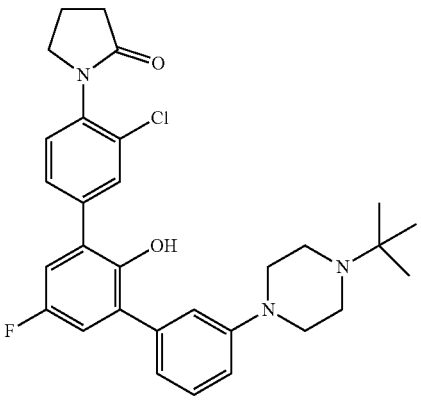 [SMILES: CC(C)(C)N1CCN(c2cccc(-c3cc(F)cc(-c4ccc(N5CCCC5=O)c(Cl)c4)c3O)c2)CC1]

The title compound was prepared following the procedures described for Example 1041 using 3-bromo-3'-(4-(tert-butyl)piperazin-1-yl)-5-fluoro-[1,1'-biphenyl]-2-ol and 1-(2-chloro-4-(4,4,5,5-tetramethyl-1,3,2-dioxaborolan-2-yl)phenyl)pyrrolidin-2-one to afford the title compound. $^1$H NMR (400 MHz, DMSO-$d_6$) δ 8.41 (s, 1H), 7.75 (d, J=1.8 Hz, 1H), 7.58 (dd, J=8.2, 1.9 Hz, 1H), 7.47 (d, J=8.2 Hz, 1H), 7.28 (t, J=7.9 Hz, 1H), 7.20-7.02 (m, 3H), 6.94 (dd, J=13.3, 4.9 Hz, 2H), 3.73 (t, J=6.9 Hz, 2H), 3.15 (d, J=4.7 Hz, 4H), 2.64 (d, J=4.5 Hz, 4H), 2.45 (t, J=8.0 Hz, 2H), 2.25-2.06 (m, 2H), 1.05 (s, 9H). LCMS: 522.2 (M+H)$^+$.

Example 1046

1-(4-(2-(3-(4-(tert-Butyl)piperazin-1-yl)phenyl)-3-hydroxy-6-methylpyridin-4-yl)-2-chlorophenyl)-3-methylimidazolidin-2-one

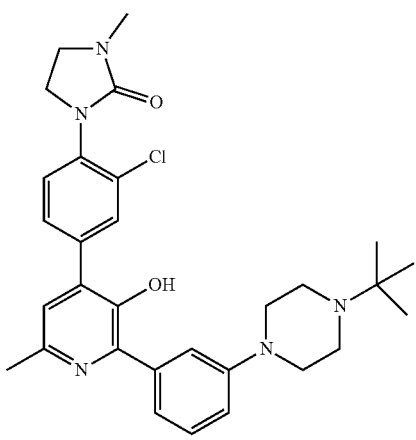 [SMILES: Cc1cc(-c2ccc(N3CCN(C)C3=O)c(Cl)c2)c(O)c(-c2cccc(N3CCN(C(C)(C)C)CC3)c2)n1]

The title compound was prepared following the procedures described for Example 1041 using 1-(4-(2-bromo-3-(methoxymethoxy)-6-methylpyridin-4-yl)-2-chlorophenyl)-3-methylimidazolidin-2-one, 1-(tert-butyl)-4-(3-(4,4,5,5-tetramethyl-1,3,2-dioxaborolan-2-yl)phenyl)piperazine and hydrochloric acid to afford the title compound. $^1$H NMR (400 MHz, DMSO-$d_6$) δ 8.65 (s, 1H), 7.76 (d, J=1.7 Hz, 1H), 7.60 (dd, J=8.2, 1.8 Hz, 1H), 7.50 (d, J=8.2 Hz, 1H), 7.38 (s, 1H), 7.32-7.21 (m, 2H), 7.16 (s, 1H), 6.96 (d, J=7.5 Hz, 1H), 3.79-3.70 (m, 2H), 3.52-3.48 (m, 2H), 3.15 (s, 4H), 2.78 (s, 3H), 2.67 (d, J=4.5 Hz, 4H), 2.46 (s, 3H), 1.06 (s, 9H). LCMS: 534.3 (M+H)$^+$.

Example 1047

1-(4-(2-(3-(4-(tert-butyl)piperazin-1-yl)phenyl)-6-fluoro-3-hydroxypyridin-4-yl)-2-chlorophenyl)-3-(methyl-d3)-1,3-dihydro-2H-imidazol-2-one

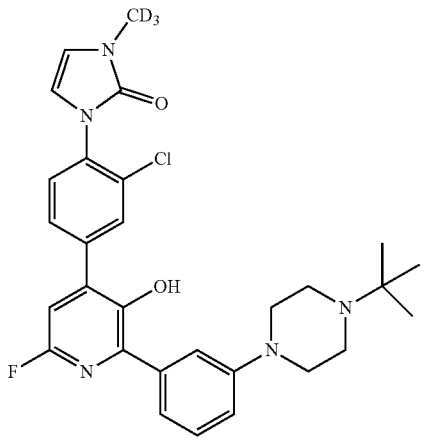 [SMILES: [2H]C([2H])([2H])n1ccn(-c2ccc(-c3cc(F)nc(-c4cccc(N5CCN(C(C)(C)C)CC5)c4)c3O)cc2Cl)c1=O]

The title compound was prepared following the procedures described for Example 1041 using 1-(4-(2-bromo-6-fluoro-3-hydroxypyridin-4-yl)-2-chlorophenyl)-3-deuterated-methyl-1H-imidazol-2(3H)-one and 1-(tert-butyl)-4-(3-(4,4,5,5-tetramethyl-1,3,2-dioxaborolan-2-yl)phenyl)piperazine to afford the title compound. $^1$H NMR (400 MHz, CD$_3$OD) δ 7.93 (d, J=1.8 Hz, 1H), 7.71 (dd, J=8.2, 1.8 Hz, 1H), 7.63-7.47 (m, 2H), 7.38 (dt, J=15.6, 7.6 Hz, 2H), 7.06 (d, J=8.8 Hz, 1H), 7.00 (d, J=2.7 Hz, 1H), 6.66 (dd, J=12.0, 2.9 Hz, 2H), 3.31 (s, 4H), 2.91 (s, 4H), 1.20 (s, 9H). O—H proton not observed. LCMS: 539.2 (M+H)$^+$.

Example 1048

4-(3-Chloro-4-(3-methyl-2-oxo-2,3-dihydro-1H-imidazol-1-yl)phenyl)-3-hydroxy-1'-(1-isopropylpiperidin-4-yl)-6-methyl-[2,3'-bipyridin]-6'(1'H)-one

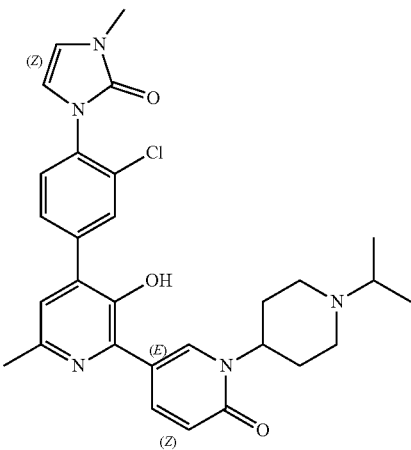 [SMILES: Cc1cc(-c2ccc(-n3ccn(C)c3=O)c(Cl)c2)c(O)c(-c2ccc(=O)n(C3CCN(C(C)C)CC3)c2)n1]

Step 1: tert-Butyl 4-(5-bromo-2-oxopyridin-1(2H)-yl)piperidine-1-carboxylate A solution of 5-bromopyridin-2-ol (1 g, 5.75 mmol), tert-butyl 4-(tosyloxy)piperidine-1-carboxylate (2.04 g, 5.75 mmol) and $K_2CO_3$ (2.38 g, 17.25 mmol) in DMF (20 mL) was stirred at 80° C. for 16 h under $N_2$. LCMS showed the reaction was completed. The reaction mixture was cooled, suspended in $H_2O$ and extracted with EA. The combined organic layers were dried over $Na_2SO_4$, filtered and concentrated. The residue was purified by silica chromatography column to afford the title compound (170 mg, 8.3% yield). LCMS: 357.1 $(M+H)^+$.

Step 2: tert-Butyl 4-(2-oxo-5-(4,4,5,5-tetramethyl-1,3,2-dioxaborolan-2-yl)pyridin-1(2H)— yl)piperidine-1-carboxylate A solution of tert-butyl 4-(5-bromo-2-oxopyridin-1(2H)-yl)piperidine-1-carboxylate (170 mg, 0.48 mmol), 4,4,4',4',5,5,5',5'-octamethyl-2,2'-bi(1,3,2-dioxaborolane) (180 mg, 0.71 mmol), Pd(dppf)Cl$_2$ (35 mg, 0.048 mmol) and KOAc (140 mg, 1.44 mmol) in dioxane (10 mL) was stirred at 90° C. overnight under $N_2$. LCMS showed the reaction was completed. The reaction mixture was filtered and concentrated to afford the title compound as black oil. LCMS: 405.2 $(M+H)^+$.

Step 3: tert-Butyl 4-(4-(3-chloro-4-(3-methyl-2-oxo-2,3-dihydro-1H-imidazol-1-yl)phenyl)-3-(methoxymethoxy)-6-methyl-6'-oxo-[2,3'-bipyridin]-1'(6'H)-yl)piperidine-1-carboxylate A solution of tert-butyl 4-(2-oxo-5-(4,4,5,5-tetramethyl-1,3,2-dioxaborolan-2-yl)pyridin-1(2H)— yl)piperidine-1-carboxylate (190 mg, 0.48 mmol), 1-(4-(2-bromo-3-(methoxymethoxy)-6-methylpyridin-4-yl)-2-chlorophenyl)-3-methyl-1H-imidazol-2(3H)-one (210 mg, 0.48 mmol), Pd(dppf)Cl$_2$ (35 mg, 0.048 mmol) and $Na_2CO_3$ (150 mg, 1.44 mmol) in dioxane/$H_2O$ (5 mL/1 mL) was stirred at 100° C. for 2 h under $N_2$. LCMS showed the reaction was completed. The reaction mixture was cooled, suspended in $H_2O$ and extracted with EA. The combined organic layers were dried over $Na_2SO_4$, filtered and concentrated. The residue was purified by silica chromatography column (DCM/MeOH=10/1) to afford the title compound (270 mg, 90% yield).

LCMS: 636.3 $(M+H)^+$.

Step 4: 4-(3-chloro-4-(3-methyl-2-oxo-2,3-dihydro-1H-imidazol-1-yl)phenyl)-3-hydroxy-6-methyl-1'-(piperidin-4-yl)-[2,3'-bipyridin]-6'(1'H)-one A solution of tert-butyl 4-(4-(3-chloro-4-(3-methyl-2-oxo-2,3-dihydro-1H-imidazol-1-yl)phenyl)-3-(methoxymethoxy)-6-methyl-6'-oxo-[2,3'-bipyridin]-1' (6'H)-yl)piperidine-1-carboxylate (270 mg, 0.42 mmol) in MeOH (5 mL) and HCl (2 mL) was stirred at 30° C. for 2 hour. After the reaction was complete by LCMS, the reaction mixture was concentrated, and NaHCO$_3$ was added to adjusted pH to 7 and extracted with EA. The combined organic layers were washed with brine and concentrated to afford the title compound (220 mg, crude). LCMS: 492.2 $(M+H)^+$.

Step 5: 4-(3-Chloro-4-(3-methyl-2-oxo-2,3-dihydro-1H-imidazol-1-yl)phenyl)-3-hydroxy-1'-(1-isopropylpiperidin-4-yl)-6-methyl-[2,3'-bipyridin]-6'(1'H)-one A solution of 4-(3-chloro-4-(3-methyl-2-oxo-2,3-dihydro-1H-imidazol-1-yl)phenyl)-3-hydroxy-6-methyl-1'-(piperidin-4-yl)-[2,3'-bipyridin]-6'(1'H)-one (220 mg, crude), propan-2-one (1 mL) in MeOH (5 mL) was stirred at rt for 15 min. Acetic acid (1 drop) and NaBH$_3$CN (30 mg, 4.47 mmol) were added. The reaction mixture was stirred at rt for 24 hours. After the reaction was complete by LCMS, the reaction mixture was concentrated, dissolved in $H_2O$ and extracted with EA. The combined organic layers were washed with brine and concentrated. The residue was purified by prep-HPLC to afford the title compound (46 mg, 20.3% yield). $^1$H NMR (400 MHz, DMSO-d$_6$) δ 8.71 (s, 1H), 8.12 (dd, J=9.5, 2.3 Hz, 1H), 7.91 (s, 1H), 7.68 (dd, J=8.2, 1.6 Hz, 1H), 7.49 (d, J=8.2 Hz, 1H), 7.07 (s, 1H), 6.70 (dd, J=18.3, 3.0 Hz, 2H), 6.46 (d, J=9.5 Hz, 1H), 4.71 (ddd, J=16.5, 10.8, 5.5 Hz, 1H), 3.21 (s, 3H), 2.93 (d, J=11.3 Hz, 2H), 2.80-2.68 (m, 1H), 2.43 (s, 3H), 2.31-2.21 (m, 2H), 1.87-1.71 (m, 4H), 0.99 (d, J=6.6 Hz, 6H). O—H proton not observed. LCMS: 534.2 $(M+H)^+$.

Example 1049

1-(4-(5'-(4-(tert-butyl)piperazin-1-yl)-6-fluoro-3,6'-dihydroxy-[2,3'-bipyridin]-4-yl)-2-chlorophenyl)-3-methyl-1,3-dihydro-2H-imidazol-2-one

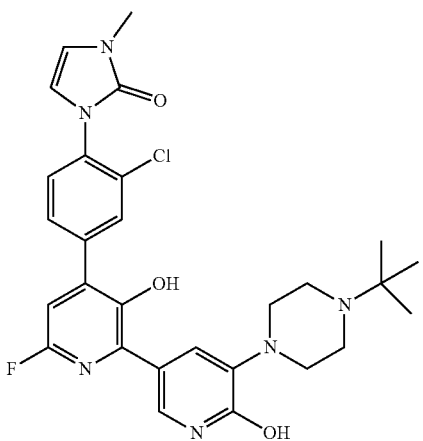 [SMILES: Cn1ccn(-c2ccc(-c3cc(F)nc(-c4cnc(O)c(N5CCN(C(C)(C)C)CC5)c4)c3O)cc2Cl)c1=O]

To a solution of 1-(4-(5'-(4-(tert-butyl)piperazin-1-yl)-6-fluoro-3-hydroxy-6'-methoxy-[2,3'-bipyridin]-4-yl)-2-chlorophenyl)-3-methyl-1H-imidazol-2(3H)-one (90 mg, 0.26 mmol) in DCM (3 mL) was added BBr$_3$ (3 mL) at 0° C. The reaction mixture was stirred at room temperature overnight under N$_2$. LCMS showed the reaction was completed. The reaction mixture was quenched with MeOH (1 mL). The pH was adjusted to neutral with NaHCO$_3$. The reaction mixture was suspended in H$_2$O and extracted with EA. The combined organic layers were dried over Na$_2$SO$_4$, filtered and concentrated. The residue was purified by Prep-HPLC to afford the title compound (24.1 mg, 18% yield). $^1$H NMR (400 MHz, DMSO-d$_6$) δ 11.65 (s, 1H), 9.41 (s, 1H), 7.89 (s, 2H), 7.68 (dd, J=8.2, 1.9 Hz, 1H), 7.57 (d, J=8.2 Hz, 1H), 7.36 (s, 1H), 7.03 (d, J=3.0 Hz, 1H), 6.71 (dd, J=16.4, 3.0 Hz, 2H), 3.21 (s, 3H), 3.11 (s, 4H), 2.66 (s, 4H), 1.06 (s, 9H). LCMS: 553.2 (M+H)$^+$.

Example 1050

1-(4-(2-(3-(4-(tert-butyl)piperazin-1-yl)phenyl)-6-fluoro-3-hydroxypyridin-4-yl)-2-methylphenyl)-3-methyl-1,3-dihydro-2H-imidazol-2-one

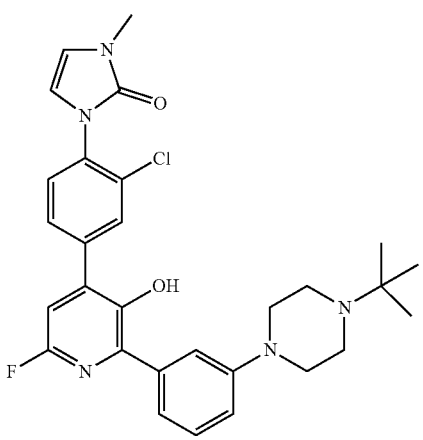 [SMILES: Cn1ccn(-c2ccc(-c3cc(F)nc(-c4cccc(N5CCN(C(C)(C)C)CC5)c4)c3O)cc2Cl)c1=O]

The title compound was prepared following the procedures described for Example 1029 using 1-(4-(2-bromo-6-fluoro-3-(methoxymethoxy)pyridin-4-yl)-2-methylphenyl)-3-methyl-1,3-dihydro-2H-imidazol-2-one, 1-(tert-butyl)-4-(3-(4,4,5,5-tetramethyl-1,3,2-dioxaborolan-2-yl)phenyl) piperazine and hydrochloric acid in methanol to afford the title compound. $^1$H NMR (400 MHz, DMSO-d$_6$) δ 9.01 (s, 1H), 7.63 (s, 1H), 7.56 (dd, J=8.6, 2.0 Hz, 3H), 7.43 (s, 1H), 7.34-7.28 (m, 3H), 7.07 (d, J=2.8 Hz, 1H), 7.00-6.97 (m, 1H), 6.72 (d, J=2.8 Hz, 1H), 6.67 (d, J=3.2 Hz, 1H), 3.21 (s, 3H), 3.16 (br, 4H), 2.66 (br, 4H), 2.24 (s, 3H), 1.05 (s, 9H). LCMS: 516.20 (M+H)$^+$.

Example 1051

1-(3''-(4-(tert-Butyl)piperazin-1-yl)-3-chloro-5'-fluoro-2'-hydroxy-[1,1':3',1''-terphenyl]-4-yl)-3-methyl-1,5-dihydro-2H-pyrrol-2-one

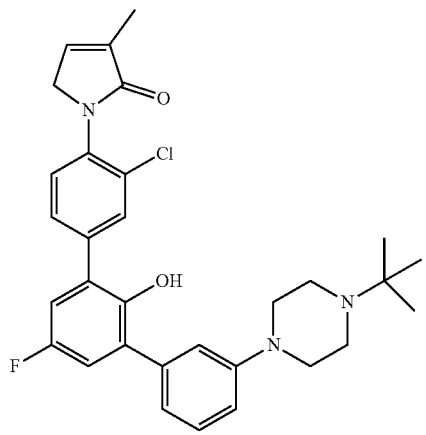 [SMILES: CC1=CCN(c2ccc(-c3cc(F)cc(-c4cccc(N5CCN(C(C)(C)C)CC5)c4)c3O)cc2Cl)C1=O]

Step 1: N-Allyl-4-bromo-2-chloroaniline

To a solution of 4-bromo-2-chloroaniline (2 g, 9.69 mmol) in DMF (50 mL) was added Na$_2$CO$_3$ (3.1 g, 29.1 mmol), 3-bromoprop-1-ene (1.7 mL). The reaction mixture was stirred at 80° C. overnight under N$_2$. The reaction mixture was concentrated. The residue was purified by silica chromatography column (PE/EA=5:1) to afford the title compound (1.2 g, 56% yield).

Step 2: N-Allyl-N-(4-bromo-2-chlorophenyl)methacrylamide

A solution of N-allyl-4-bromo-2-chloroaniline (980 mg, 3.98 mmol) in DCM (30 mL) was added TEA (1.8 g, 11.94 mmol) and methacryloyl chloride (624 mg, 5.97 mmol) at 0° C. The reaction mixture was stirred at room temperature for overnight under N$_2$. The reaction mixture was concentrated. The residue was purified by silica chromatography column (PE/EA=5:1) to afford the title compound (804 mg, 81% yield). LCMS: 314.1 (M+H)$^+$.

Step 3: 1-(4-Bromo-2-chlorophenyl)-3-methyl-1,5-dihydro-2H-pyrrol-2-one

To a solution of N-allyl-N-(4-bromo-2-chlorophenyl) methacrylamide (804 mg, 2.56 mmol) in toluene (20 mL)

was added 2$^{nd}$ generation Grubbs catalyst (109.4 mg, 0.13 mmol). The reaction mixture was stirred at 40° C. for 5 h under N$_2$. LCMS showed the reaction was completed, the reaction mixture was cooled and concentrated. The residue was purified by silica chromatography column (PE/EA=3:1) to afford the title compound (600 mg, 82% yield). LCMS: 286.1 (M+H)$^+$.

Step 4: 1-(2-Chloro-4-(4,4,5,5-tetramethyl-1,3,2-dioxaborolan-2-yl)phenyl)-3-methyl-1,5-dihydro-2H-pyrrol-2-one To a solution of 1-(4-bromo-2-chlorophenyl)-3-methyl-1,5-dihydro-2H-pyrrol-2-one (600 mg, 2.10 mmol) in 1,4-dioxane (20 mL) was added Pd(dppf)Cl$_2$ (153 mg, 0.21 mmol), 4,4,4',4',5,5,5',5'-octamethyl-2,2'-bi(1,3,2-dioxaborolane) (640 mg, 2.52 mmol), and KOAc (617 mg, 6.30 mmol), the mixture was stirred at 90° C. overnight under N$_2$. Solvent was removed under reduced pressure and concentrated, the residue was purified by silica chromatographic column (PE/EA=1/1) to afford the title compound (600 mg, 87% yield). LCMS: 334.1 (M+H)$^+$.

Step 5: 1-(3''-(4-(tert-Butyl)piperazin-1-yl)-3-chloro-5'-fluoro-2'-hydroxy-[1,1':3',1''-terphenyl]-4-yl)-3-methyl-1,5-dihydro-2H-pyrrol-2-one To a solution of 1-(2-chloro-4-(4,4,5,5-tetramethyl-1,3,2-dioxaborolan-2-yl)phenyl)-3-methyl-1,5-dihydro-2H-pyrrol-2-one (130 mg, 0.39 mmol) in 1,4-dioxane/H$_2$O (5 mL/0.5 mL) was added 3-bromo-3'-(4-(tert-butyl)piperazin-1-yl)-5-fluoro-[1,1'-biphenyl]-2-ol (158.7 mg, 0.39 mmol), Pd(dppf)Cl$_2$ (28.5 mg, 0.039 mmol) and K$_3$PO$_4$ (248.1 mg, 1.17 mmol) was stirred at 100° C. for 2 h under N$_2$. The reaction mixture was cooled, diluted with H$_2$O and extracted with EA. The combined organic layers were dried over Na$_2$SO$_4$, filtered and concentrated. The residue was purified by Prep-HPLC to afford the product (22.5 mg, 12% yield). $^1$H NMR (400 MHz, DMSO-d$_6$) δ 8.43 (s, 1H), 7.77 (d, J=1.6 Hz, 1H), 7.59 (dd, J=8.4, 2.0 Hz, 1H), 7.52 (d, J=8.0 Hz, 1H), 7.28 (t, J=8.0 Hz, 1H), 7.18-7.03 (m, 4H), 6.97-6.92 (m, 2H), 4.32 (t, J=2.0 Hz, 2H), 3.16 (br, 4H), 2.65 (br, 4H), 1.87 (d, J=1.6 Hz, 3H), 1.05 (s, 9H). LCMS: 534.1 (M+H)$^+$.

Example 1052

3-(3''-(4-(tert-butyl)piperazin-1-yl)-3-chloro-5'-fluoro-2'-hydroxy-[1,1':3',1''-terphenyl]-4-yl)thiazol-2(3H)-one

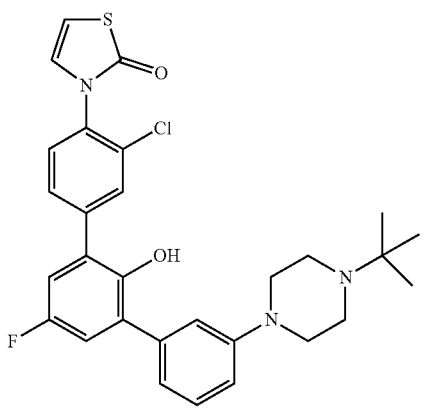 [SMILES: CC(C)(C)N1CCN(c2cccc(-c3cc(F)cc(-c4ccc(-n5ccsc5=O)c(Cl)c4)c3O)c2)CC1]

Step 1: 4-Bromo-2-chlorobenzoyl azide

A solution of 4-bromo-2-chlorobenzoic acid (2.0 g, 8.5 mmol), oxalyl dichloride (1.6 g, 12.7 mmol) in THF (50 mL), and DMF (1 drop) was added. The reaction mixture was stirred at 0° C. for 2 h under N$_2$. The solution was concentrated to afford the brown oil, then it was diluted with acetone, and NaN$_3$ (550 mg, 8.5 mmol) was added. The solution was stirred at r.t. for 1 h. The solution was concentrated to afford the title compound (2.5 g, crude). LCMS: 259.9 (M+H)$^+$.

Step 2: 3-(4-Bromo-2-chlorophenyl)thiazol-2(3H)-one

A solution of 4-bromo-2-chlorobenzoyl azide (2.5 g, Crude), 1,4-dithiane-2,5-diol (1.94 g, 12.8 mmol) in ACN (50 mL) was stirred at 80° C. for 21 h under N$_2$. H$_2$SO$_4$ (5 mL, 40%) solution was added, then it was stirred at r.t. for 16 h. The solution was diluted with H$_2$O and extracted with EA (30 mL×3), washed with brine. The combined organic layers were concentrated and purified by silica chromatography column to afford the title compound (900 mg, 36.5% yield). LCMS: 289.9 (M+H)$^+$.

Step 3: 3-(2-Chloro-4-(4,4,5,5-tetramethyl-1,3,2-dioxaborolan-2-yl)phenyl)thiazol-2(3H)-one To a solution of 3-(4-bromo-2-chlorophenyl)thiazol-2(3H)-one (750 mg, 2.59 mmol) in dioxane 15 mL). 4,4,4',4',5,5,5',5'-octamethyl-2,2'-bi(1,3,2-dioxaborolane) (980 mg, 3.88 mmol), Pd(dppf)Cl$_2$ (198 mg, 0.26 mmol) and KOAc (635 mg, 6.48 mmol) were added. The reaction mixture was stirred at 90° C. overnight under N$_2$. The solvent was removed under reduced pressure. The residue was concentrated to afford the title compound (900 mg, crude). LCMS: 338.1 (M+H)$^+$.

Step 4: 3-(3''-(4-(tert-Butyl)piperazin-1-yl)-3-chloro-5'-fluoro-2'-hydroxy-[1,1':3',1''-terphenyl]-4-yl)thiazol-2(3H)-one A reaction mixture of 3-(2-chloro-4-(4,4,5,5-tetramethyl-1,3,2-dioxaborolan-2-yl) phenyl) thiazol-2(3H)-one (200 mg, 0.59 mmol), 3-bromo-3'-(4-(tert-butyl) piperazin-1-yl)-5-fluoro-[1,1'-biphenyl]-2-ol (240 mg, 0.59 mmol), Pd(dppf)Cl$_2$ (45 mg, 0.059 mmol) and K$_3$PO$_4$ (375 mg, 1.77 mmol) in dioxane/H$_2$O (5 mL/1 mL) was stirred at 100° C. for 2 h under N$_2$. LCMS showed the reaction was completed. The reaction mixture was cooled, suspended in H$_2$O, and extracted with EA. The combined organic layers were dried over Na$_2$SO$_4$, filtered and concentrated. The residue was purified by silica chromatography column (DCM/MeOH=10/1) to afford the title compound (50.3 mg, 15.8% yield). LCMS: 537.2 (M+H)$^+$.

Example 1053

3-(4-(2-(3-(4-(tert-butyl)piperazin-1-yl)phenyl)-3-hydroxy-6-methylpyridin-4-yl)-2-chlorophenyl)thiazol-2(3H)-one

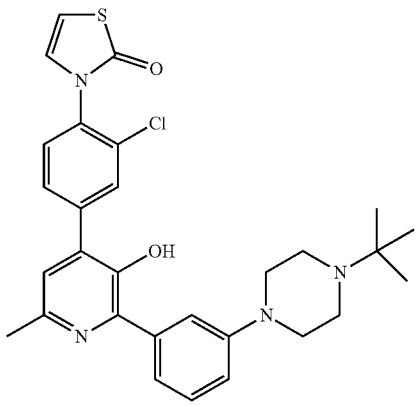 [SMILES: Cc1cc(-c2ccc(-n3ccsc3=O)c(Cl)c2)c(O)c(-c2cccc(N3CCN(C(C)(C)C)CC3)c2)n1]

The title compound was prepared following the procedures described for Example 1052 using 3-(4-(2-bromo-3-(methoxymethoxy)-6-methylpyridin-4-yl)-2-chlorophenyl)thiazol-2(3H)-one, 1-(tert-butyl)-4-(3-(4,4,5,5-tetramethyl-1,3,2-dioxaborolan-2-yl)phenyl)piperazine and hydrochloric acid in methanol to afford the title compound. $^1$H NMR (400 MHz, DMSO-$d_6$) δ 8.82 (s, 1H), 7.91 (d, J=1.8 Hz, 1H), 7.77-7.62 (m, 2H), 7.38 (d, J=2.0 Hz, 1H), 7.33-7.23 (m, 2H), 7.19 (s, 1H), 7.15 (d, J=5.4 Hz, 1H), 6.96 (dt, J=7.8, 1.9 Hz, 1H), 6.68 (d, J=5.4 Hz, 1H), 3.14 (br, 4H), 2.66 (br, 4H), 2.46 (s, 3H), 1.05 (s, 9H). LCMS: 535.2 (M+H)$^+$.

Example 1054

1-(4-{2-[3-(4-tert-Butyl-piperazin-1-yl)-phenyl]-6-fluoro-3-hydroxy-pyridin-4-yl}-2-fluoro-phenyl)-3-methyl-1,3-dihydro-imidazol-2-one

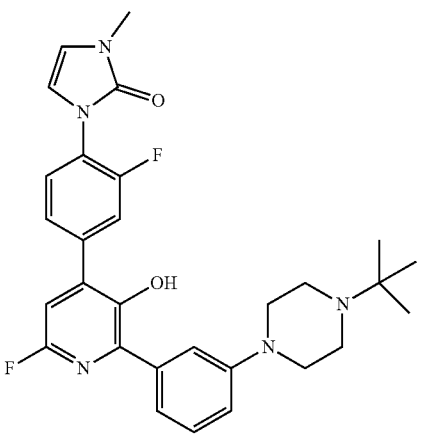 [SMILES: Cn1ccn(-c2ccc(-c3cc(F)nc(-c4cccc(N5CCN(C(C)(C)C)CC5)c4)c3O)cc2F)c1=O]

The title compound was prepared following the procedures described for Example 1029 using 1-(4-(2-bromo-6-fluoro-3-(methoxymethoxy)pyridin-4-yl)-2-fluorophenyl)-3-methyl-1,3-dihydro-2H-imidazol-2-one, 1-tert-butyl-4-[3-(4,4,5,5-tetramethyl-[1,3,2] dioxaborolan-2-yl)-phenyl]-piperazine and hydrochloric acid in methanol to afford the title compound. $^1$H NMR (400 MHz, DMSO-$d_6$) δ 9.14 (s, 1H), 7.73-7.65 (m, 2H), 7.59 (dd, J=8.4, 2.0 Hz, 1H), 7.44 (s, 1H), 7.33-7.28 (m, 2H), 7.14 (d, J=3.2 Hz, 1H), 7.00-6.97 (m, 1H), 6.78-6.74 (m, 2H), 3.31 (s, 3H), 3.21-3.14 (m, 4H), 2.67-2.64 (m, 4H), 1.06 (s, 9H). LCMS: 520.2 (M+H)$^+$.

Example 1055

1-(4-(2-(3-(4-(tert-butyl)piperazin-1-yl)phenyl)-3-hydroxy-6-methylpyridin-4-yl)-2-chlorophenyl)-3-methyl-1,5-dihydro-2H-pyrrol-2-one

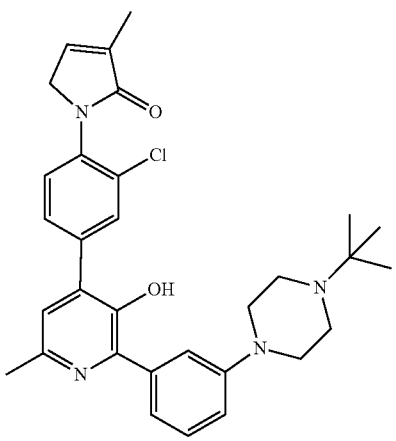 [SMILES: CC1=CCN(c2ccc(-c3cc(C)nc(-c4cccc(N5CCN(C(C)(C)C)CC5)c4)c3O)cc2Cl)C1=O]

The title compound was prepared following the procedures described for Example 1051 using 1-(4-(2-bromo-3-(methoxymethoxy)-6-methylpyridin-4-yl)-2-chlorophenyl)-3-methyl-1,5-dihydro-2H-pyrrol-2-one, 1-(tert-butyl)-4-(3-(4,4,5,5-tetramethyl-1,3,2-dioxaborolan-2-yl)phenyl)piperazine and hydrochloric acid in methanol to afford the title compound. $^1$H NMR (400 MHz, DMSO) δ 8.76 (s, 1H), 7.81 (d, J=2.0 Hz, 1H), 7.64 ((dd, J=8.4, 2.0 Hz, 1H)), 7.55 (d, J=8.4 Hz, 1H), 7.38 (s, 1H), 7.28-7.26 (m, 2H), 7.17-7.13 (m, 2H), 6.97-6.94 (m, 1H), 4.33 (br, 2H), 3.14 (t, J=4.4 Hz, 4H), 2.66 (t, J=4.8 Hz, 4H), 2.46 (s, 3H), 1.87 (d, J=1.6 Hz, 3H), 1.05 (s, 9H). LCMS: 531.2 (M+H)$^+$.

Example 1056

1-(4-(3-amino-2-(3-(4-(tert-butyl)piperazin-1-yl)phenyl)-6-fluoropyridin-4-yl)-2-chlorophenyl)-3-methyl-1,3-dihydro-2H-imidazol-2-one

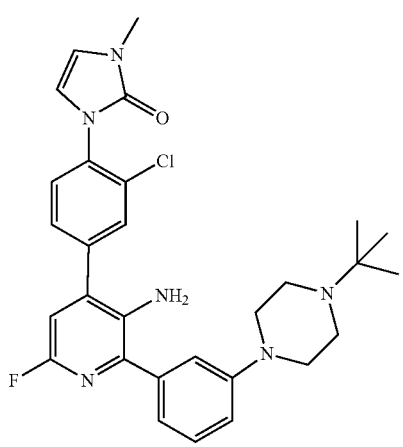 [SMILES: Cn1ccn(-c2ccc(-c3cc(F)nc(-c4cccc(N5CCN(C(C)(C)C)CC5)c4)c3N)cc2Cl)c1=O]

The title compound was prepared following the procedures described for Example 992 using 1-[4-(3-amino-2-bromo-6-fluoro-pyridin-4-yl)-2-chloro-phenyl]-3-methyl-1,3-dihydro-imidazol-2-one and 1-tert-butyl-4-[3-(4,4,5,5-tetramethyl-[1,3,2]dioxaborolan-2-yl)-phenyl]-piperazine to afford the title compound. $^1$H NMR (400 MHz, DMSO-$d_6$) δ 7.82 (d, J=1.2 Hz, 1H), 7.63-7.61 (m, 2H), 7.34 (t, J=8.0 Hz, 1H), 7.14 (s, 1H), 7.06-7.00 (m, 2H), 6.96 (d, J=3.2 Hz, 1H), 6.73 (d, J=3.2 Hz, 1H), 6.68 (d, J=3.2 Hz, 1H), 4.54 (s, 2H), 3.31 (s, 3H), 3.21-3.14 (m, 4H), 2.65-2.63 (m, 4H), 1.04 (s, 9H). LCMS: 535.2 (M+H)$^+$.

Example 1057

1-(4-(3-amino-4-(3-(4-(tert-butyl)piperazin-1-yl)phenyl)-6-fluoropyridin-2-yl)-2-chlorophenyl)-3-methyl-1,3-dihydro-2H-imidazol-2-one

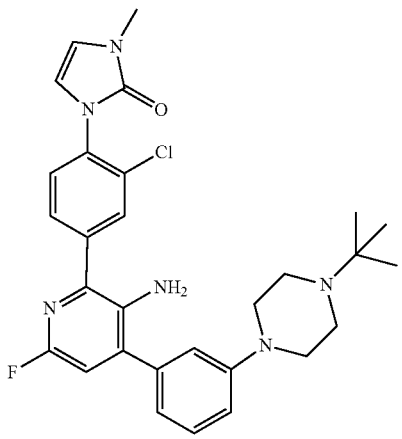 [SMILES: Cn1ccn(-c2ccc(-c3nc(F)cc(-c4cccc(N5CCN(C(C)(C)C)CC5)c4)c3N)cc2Cl)c1=O]

The title compound was prepared following the procedures described for Example 992 using 1-[4-(3-amino-4-bromo-6-fluoro-pyridin-2-yl)-2-chloro-phenyl]-3-methyl-1,3-dihydro-imidazol-2-one, 1-tert-butyl-4-[3-(4,4,5,5-tetramethyl-[1,3,2]dioxaborolan-2-yl)-phenyl]-piperazine to afford the title compound. $^1$H NMR (400 MHz, DMSO-$d_6$) δ 7.93 (d, J=1.2 Hz, 1H), 7.81-7.78 (m, 1H), 7.57 (d, J=8.4 Hz, 1H), 7.37 (t, J=8.4 Hz, 1H), 7.04-7.01 (m, 2H), 6.93-6.89 (m, 2H), 6.72 (d, J=2.8 Hz, 1H), 6.68 (d, J=2.8 Hz, 1H), 4.62 (s, 2H), 3.31 (s, 3H), 3.21-3.17 (m, 4H), 2.65-2.62 (m, 4H), 1.04 (s, 9H). LCMS: 535.2 (M+H)$^+$.

Example 1058

1-[2'-Amino-3-(4-tert-butyl-piperazin-1-yl)-3''-chloro-5'-fluoro-[1,1';3',1'']terphenyl-4''-yl]-3-methyl-1,3-dihydro-imidazol-2-one

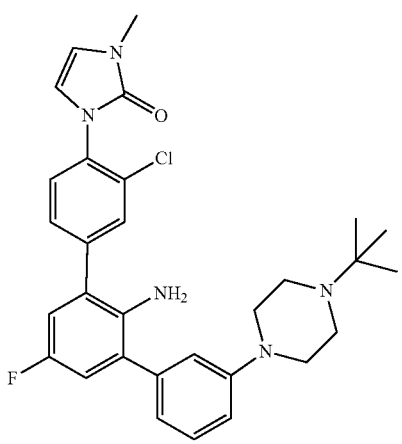 [SMILES: Cn1ccn(-c2ccc(-c3cc(F)cc(-c4cccc(N5CCN(C(C)(C)C)CC5)c4)c3N)cc2Cl)c1=O]

The title compound was prepared following the procedures described for Example 992 using 1-(2'-amino-3'-bromo-3-chloro-5'-fluoro-[1,1'-biphenyl]-4-yl)-3-methyl-1,3-dihydro-2H-imidazol-2-one and 1-tert-Butyl-4-[3-(4,4,5,5-tetramethyl-[1,3,2]dioxaborolan-2-yl)-phenyl]-piperazine to afford the title compound. $^1$H NMR (400 MHz, DMSO-$d_6$) δ 7.73 (s, 1H), 7.55 (s, 2H), 7.32 (t, J=8.0 Hz, 1H), 6.98-6.93 (m, 4H), 6.85 (d, J=8.0 Hz, 1H), 6.71 (d, J=3.2 Hz, 1H), 6.67 (d, J=3.2 Hz, 1H), 4.23 (s, 2H), 3.31 (s, 3H), 3.20-3.15 (m, 4H), 2.64-2.62 (m, 4H), 1.04 (s, 9H). LCMS: 534.2 (M+H)$^+$.

Example 1059

1-(4-(5'-(4-(tert-butyl)piperazin-1-yl)-6'-ethyl-6-fluoro-3-hydroxy-[2,3'-bipyridin]-4-yl)-2-chlorophenyl)-3-methyl-1,3-dihydro-2H-imidazol-2-one

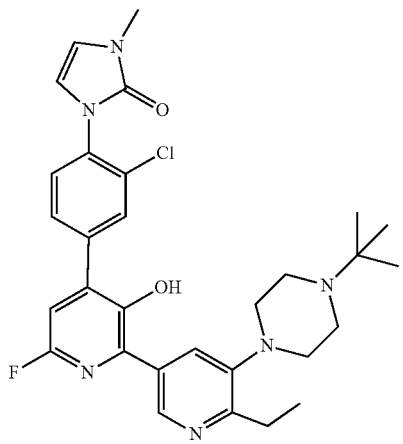 [SMILES: CCc1ncc(-c2nc(F)cc(-c3ccc(-n4ccn(C)c4=O)c(Cl)c3)c2O)cc1N1CCN(C(C)(C)C)CC1]

The title compound was prepared following the procedures described for Example 1029 using (5-(4-(tert-butyl)piperazin-1-yl)-6-ethylpyridin-3-yl)boronic acid (150 mg, 0.52 mmol), 1-(4-(2-bromo-6-fluoro-3-(methoxymethoxy)pyridin-4-yl)-2-chlorophenyl)-3-methyl-1,3-dihydro-2H-imidazol-2-one and hydrochloric acid to afford the title compound. $^1$H NMR (400 MHz, DMSO-$d_6$) δ 9.43 (s, 1H), 8.76 (d, J=1.7 Hz, 1H), 7.98-7.87 (m, 2H), 7.77-7.70 (m, 1H), 7.60 (d, J=8.3 Hz, 1H), 7.22 (d, J=3.0 Hz, 1H), 6.76-6.68 (m, 2H), 3.21 (s, 3H), 2.91 (br, 4H), 2.85 (q, J=7.5 Hz, 2H), 2.71 (br, 4H), 1.27 (t, J=7.5 Hz, 3H), 1.07 (s, 9H). LCMS: 565.2 (M+H)$^+$.

Example 1061

1-(3''-(4-(tert-Butyl)piperazin-1-yl)-3,5'-difluoro-2'-hydroxy-[1,1':3',1''-terphenyl]-4-yl)pyrrolidin-2-one

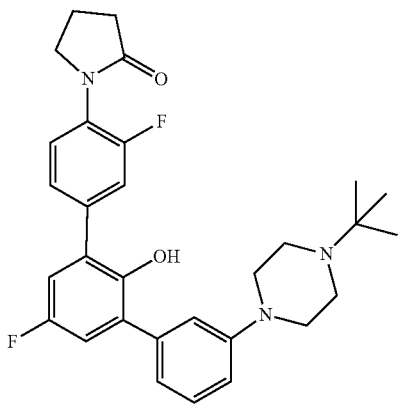 [SMILES: CC(C)(C)N1CCN(c2cccc(-c3cc(F)cc(-c4ccc(N5CCCC5=O)c(F)c4)c3O)c2)CC1]

The title compound was prepared following the procedures described for Example 1045 using 1-(2-fluoro-4-(4,4,5,5-tetramethyl-1,3,2-dioxaborolan-2-yl) phenyl)pyrrolidin-2-one, 3-bromo-3'-(4-(tert-butyl) piperazin-1-yl)-5-fluoro-[1,1'-biphenyl]-2-ol to afford the title compound. $^1$H NMR (400 MHz, DMSO-$d_6$) δ 8.37 (s, 1H), 7.56-7.48 (m, 3H), 7.44-7.42 (m, 1H), 7.15-6.96 (m, 3H), 6.94-6.92 (m, 2H), 3.79 (t, J=7.2 Hz, 2H), 3.15 (br, 4H), 2.65 (br, 4H), 2.47-2.43 (m, 2H), 2.16-2.13 (m, 2H), 1.05 (s, 9H). LCMS: 506.3 (M+H)$^+$.

Example 1062

1-(4-(2-(3-(4-(tert-Butyl)piperazin-1-yl)-5-chlorophenyl)-3-hydroxy-6-methylpyridin-4-yl)-2-fluorophenyl)-3-methyl-1,3-dihydro-2H-imidazol-2-one

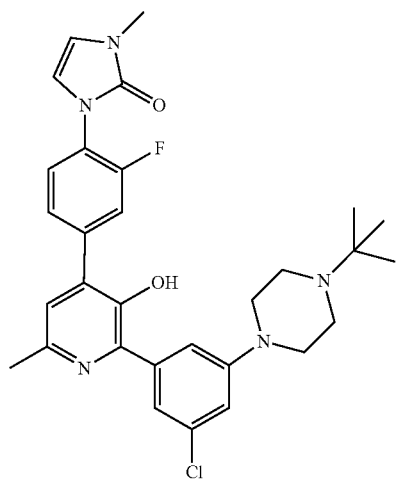 [SMILES: Cc1cc(-c2ccc(-n3ccn(C)c3=O)c(F)c2)c(O)c(-c2cc(Cl)cc(N3CCN(C(C)(C)C)CC3)c2)n1]

The title compound was prepared following the procedures described for Example 997 using 1-(tert-butyl)-4-(3-chloro-5-(4,4,5,5-tetramethyl-1,3,2-dioxaborolane-2-yl) phenyl)piperazine, 1-(4-(2-bromo-3-(methoxymethoxy)-6-methylpyridin-4-yl)-2-fluorophenyl)-3-methyl-1,3-dihydro-2H-imidazol-2-one and hydrochloric acid in methanol to afford the title compound. $^1$H NMR (400 MHz, DMSO) δ 8.94 (s, 1H), 7.66-7.63 (m, 2H), 7.53 (d, J=8.4 Hz, 1H), 7.36 (s, 1H), 7.25 (s, 1H), 7.21 (s, 1H), 6.95 (s, 1H), 6.78-6.74 (m, 2H), 3.21 (s, 3H), 3.18 (br, 4H), 2.65 (br, 4H), 2.46 (s, 3H), 1.05 (s, 9H). LCMS: 550.2 (M+H)$^+$.

Example 1063

Bromodomain Binding Assay

The bromodomain binding assay utilizes AlphaScreen technology. Compounds compete with a biotinylated peptide ligand (from histone H4: aa 1-21, K5/K8/K12/K16Ac-biotin) for binding to a hexahistidine (His$_6$)-tagged bromodomain. Peptide binding is detected by fluorescence signal after singlet oxygen energy transfer from peptide-bound AlphaScreen streptavidin-coated donor beads to His$_6$-tagged bromodomain-bound nickel-chelate acceptor beads (PerkinElmer). Briefly, 8 μL 2.5× bromodomain (E. coli expressed, N-terminal His$_6$-tagged human BRD4 bromodomain II [based on Genbank NM_058243, residues 349-460] or N-terminal His$_6$-tagged human BRD4 bromodomain I [residues 44-170]) in reaction buffer (50 mM HEPES [pH 7.5], 100 mM NaCl, 0.05% CHAPS, 0.1% BSA, 1% DMSO) is added to wells of an assay plate (384-well low flange white, flat bottom, polystyrene microplate, Corning #3572; buffer only is added to some wells as a negative control). A compound concentration series (10 concentrations, 3-fold serial dilutions previously prepared in 100% DMSO, or 100% DMSO only negative control) is delivered to the assay plate with an Echo 550 acoustic liquid handler (Labcyte), followed by plate centrifugation and incubation for 30 minutes at room temperature. Then 4 μL 5× biotinylated peptide ligand is added, followed by plate centrifugation and gentle shaking for 30 minutes at room temperature to mix. After this incubation, 4 μL 5× donor beads are added, and the plate is centrifuged, followed by brief gentle shaking to mix. Finally, 4 μL 5× acceptor beads are added, and the plate is centrifuged, followed by gentle shaking for 60 minutes at room temperature in the dark. AlphaScreen signal (excitation/emission: 680 nm/520-620 nm) is detected with an EnSpire multimode plate reader (PerkinElmer). Percentage peptide binding is plotted as a function of concentration, and curve fitting is used to determine competitive compound binding IC$_{50}$s.

Example 1064

Cell-Based Assay

The cell-based assay indirectly measures cell density (and therefore proliferation and/or survival) by detecting total ATP concentration in a homogeneous format. Briefly, human SKM-1 acute myeloid leukemia cells (Leibniz Institute DSMZ #ACC 547) proliferating in log phase are collected by centrifugation, re-suspended in culture media (RPMI 1640/15% FBS/100 U/mL penicillin/100 μg/mL streptomycin) and diluted to 34722 cells/mL in media after counting. Then 180 μL cells are plated per well into a 96-well tissue-culture treated, clear bottom plate (Corning #3603). A 96-well compound plate (Corning #3357) is then generated by serial dilution of compounds into DMSO over nine concentrations and adding separate negative (DMSO) and positive control (reference compound) wells. Each compound concentration is tested in triplicate. First, 1 μL from each well of the compound plate is added to 99 μL culture media in an intermediate plate and mixed by pipetting. Then 20 µL of the diluted compounds in media are added to the assay plate containing the cells. The assay plate is maintained for 4 days in a standard cell culture incubator. At the end of the incubation period, 100 µL ATPlite 1 step (PerkinElmer) is added to the assay plate wells, and the resulting luminescence is detected using an Infinite M1000 or a Spark multimode plate reader (Tecan). Data analysis is performed in Prism (GraphPad Software). For curve fitting, a non-linear regression, variable slope equation is used to calculate cellular $IC_{50}$s.

Biological Assay Data

TABLE C1

BRD4 BDI versus BRD4 BDII selectivity (Fold). Measured $IC_{50}$ values for BRD4 BDI or BRD4 BDII AlphaScreen assay: A = a single $IC_{50} \geq 0.01$ nM and $\leq 1.0$ nM; B = a single $IC_{50} \geq 1$ nM and $\leq 10$ nM; C = a single $IC_{50} \geq 10$ nM and $\leq 100$ nM; and D = a single $IC_{50} \geq 100$ nM.

| Ex. No. | BRD4 BDI $IC_{50}$ | BRD4 BDII $IC_{50}$ |
|---|---|---|
| 3 | D | C |
| 6 | D | C |
| 95 | D | c |
| 109 | D | B |
| 163 | D | B |
| 171 | D | B |
| 245 | D | B |
| 297 | D | B |
| 365 | D | B |
| 413 | D | A |

Each of the example compounds in Table C1, above, demonstrates >300-fold selectivity for BDII (i.e., BDI $IC_{50}$/BDII $IC_{50}$>300 for each compound).

TABLE C2

Measured values for a) $IC_{50}$s from BRD4 BDII AlphaScreen assay: A = a single $IC_{50} \geq 0.01$ nM and $\leq 1.0$ nM; B = a single $IC_{50} \geq 1$ nM and $\leq 10$ nM; C = a single $IC_{50} \geq 10$ nM and $\leq 100$ nM; D = a single $IC_{50} \geq 100$ nM; b) $GI_{50}$s from SKM-1 antiproliferation assay: AA = a single $IC_{50} \geq 0.3$ nM and $\leq 30$ nM; BB = a single $IC_{50} \geq 30$ nM and $\leq 300$ nM; CC = a single $IC_{50} \geq 300$ nM and $\leq 3$ µM; DD = a single $IC_{50} \geq 3$ µM.

| Ex. No. | BRD4 BDII $IC_{50}$ | SKM-1 $GI_{50}$ |
|---|---|---|
| 1 | | |
| 2 | | |
| 3 | C | |
| 5 | | |
| 6 | C | |
| 7 | D | |
| 8 | D | |
| 9 | D | |
| 11 | D | |
| 12 | D | |
| 13 | D | |
| 14 | D | |
| 15 | D | |
| 16 | D | |
| 17 | D | |
| 18 | D | |
| 19 | D | |
| 20 | C | |
| 21 | D | |
| 22 | D | |
| 23 | D | |
| 24 | C | |
| 25 | D | |
| 26 | D | |
| 27 | D | |
| 28 | C | |
| 29 | D | |
| 30 | D | |
| 31 | D | |
| 32 | C | |
| 33 | D | |
| 34 | C | |
| 35 | D | |
| 36 | D | |
| 37 | D | |
| 38 | D | |
| 39 | D | |
| 40 | D | |
| 41 | C | |
| 42 | C | |
| 43 | C | |
| 44 | C | |
| 45 | D | |
| 46 | D | |
| 47 | D | |
| 48 | D | |
| 49 | C | |
| 50 | C | |
| 52 | C | |
| 53 | D | |
| 54 | D | |
| 55 | D | |
| 56 | D | |
| 57 | D | |
| 58 | D | |
| 59 | D | |
| 60 | D | |
| 61 | D | |
| 62 | D | |
| 63 | C | |
| 64 | C | |
| 65 | C | |
| 66 | D | |
| 67 | D | |
| 68 | C | |
| 69 | D | |
| 70 | D | |
| 71 | D | |
| 72 | D | |
| 73 | D | |
| 74 | D | |
| 75 | D | |
| 76 | D | |
| 77 | D | |
| 78 | D | |
| 79 | D | |
| 81 | D | |
| 82 | D | |
| 83 | D | |
| 84 | D | |
| 85 | D | |
| 86 | C | |
| 87 | D | |
| 88 | D | |
| 89 | C | |
| 90 | D | |
| 91 | D | |
| 92 | D | |
| 93 | D | |
| 94 | D | |
| 95 | C | |
| 96 | D | |
| 97 | D | |
| 98 | C | |
| 99 | C | |

TABLE C2-continued

Measured values for a) IC$_{50}$s from BRD4 BDII AlphaScreen assay: A = a single IC$_{50}$ ≥ 0.01 nM and ≤ 1.0 nM; B = a single IC$_{50}$ ≥ 1 nM and ≤ 10 nM; C = a single IC$_{50}$ ≥ 10 nM and ≤ 100 nM; D = a single IC$_{50}$ ≥ 100 nM; b) GI$_{50}$s from SKM-1 antiproliferation assay: AA = a single IC$_{50}$ ≥ 0.3 nM and ≤ 30 nM; BB = a single IC$_{50}$ ≥ 30 nM and ≤ 300 nM; CC = a single IC$_{50}$ ≥ 300 nM and ≤ 3 μM; DD = a single IC$_{50}$ ≥ 3 μM.

| Ex. No. | BRD4 BDII IC$_{50}$ | SKM-1 GI$_{50}$ |
|---|---|---|
| 100 | B | |
| 101 | D | |
| 102 | C | |
| 103 | C | |
| 104 | D | |
| 105 | D | |
| 106 | D | |
| 107 | D | |
| 108 | D | |
| 109 | B | CC |
| 110 | C | |
| 111 | C | |
| 112 | C | |
| 113 | C | |
| 114 | D | |
| 115 | D | |
| 116 | D | |
| 117 | D | |
| 118 | D | |
| 119 | D | |
| 120 | C | |
| 121 | D | |
| 122 | D | |
| 123 | D | |
| 124 | D | |
| 125 | D | |
| 126 | C | |
| 127 | C | |
| 128 | C | |
| 129 | C | |
| 130 | D | |
| 131 | C | |
| 132 | C | |
| 133 | C | |
| 134 | D | |
| 135 | B | CC |
| 136 | D | |
| 137 | D | |
| 138 | D | |
| 139 | D | |
| 140 | C | |
| 141 | D | |
| 142 | C | |
| 143 | D | |
| 144 | D | |
| 145 | C | |
| 146 | D | |
| 147 | D | |
| 148 | D | |
| 149 | D | |
| 150 | C | |
| 151 | C | |
| 152 | C | |
| 153 | C | |
| 154 | C | |
| 155 | C | |
| 156 | D | |
| 157 | D | |
| 158 | D | |
| 159 | C | |
| 160 | D | |
| 162 | D | |
| 163 | B | BB |
| 164 | B | CC |
| 165 | D | |
| 166 | D | |
| 167 | B | |
| 168 | C | |
| 169 | B | |
| 170 | C | |
| 171 | B | |
| 172 | D | |
| 173 | B | CC |
| 174 | C | |
| 175 | C | |
| 176 | C | |
| 177 | C | |
| 178 | C | |
| 179 | C | |
| 180 | B | CC |
| 181 | D | |
| 182 | B | CC |
| 183 | C | |
| 184 | C | |
| 185 | D | |
| 186 | D | |
| 187 | C | |
| 188 | D | |
| 189 | B | BB |
| 190 | C | |
| 191 | D | |
| 192 | C | |
| 193 | B | CC |
| 194 | B | |
| 195 | C | |
| 196 | C | |
| 197 | B | |
| 198 | B | |
| 199 | B | CC |
| 200 | B | |
| 201 | C | |
| 202 | D | |
| 203 | B | |
| 204 | B | |
| 205 | B | |
| 206 | B | BB |
| 207 | D | |
| 208 | D | |
| 209 | B | BB |
| 210 | B | |
| 211 | D | |
| 212 | D | |
| 213 | C | |
| 214 | B | CC |
| 215 | B | |
| 216 | B | |
| 217 | B | CC |
| 218 | B | |
| 219 | C | |
| 220 | C | |
| 221 | B | |
| 222 | B | CC |
| 223 | C | |
| 224 | B | BB |
| 225 | D | |
| 226 | B | CC |
| 227 | D | |
| 228 | B | |
| 229 | C | |
| 230 | B | CC |
| 231 | B | CC |
| 232 | C | |
| 233 | D | |
| 234 | B | BB |
| 235 | B | BB |
| 236 | B | BB |
| 237 | A | BB |
| 238 | B | BB |

TABLE C2-continued

Measured values for a) IC$_{50}$s from BRD4 BDII AlphaScreen assay:
A = a single IC$_{50}$ ≥ 0.01 nM and ≤ 1.0 nM; B = a single
IC$_{50}$ ≥ 1 nM and ≤ 10 nM; C = a single IC$_{50}$ ≥ 10 nM
and ≤ 100 nM; D = a single IC$_{50}$ ≥ 100 nM; b) GI$_{50}$s from
SKM-1 antiproliferation assay: AA = a single IC$_{50}$ ≥ 0.3 nM
and ≤ 30 nM; BB = a single IC$_{50}$ ≥ 30 nM
and ≤ 300 nM; CC = a single IC$_{50}$ ≥ 300 nM
and ≤ 3 μM; DD = a single IC$_{50}$ ≥ 3 μM.

| Ex. No. | BRD4 BDII IC$_{50}$ | SKM-1 GI$_{50}$ |
| --- | --- | --- |
| 239 | B | CC |
| 240 | B | BB |
| 241 | B | |
| 242 | B | |
| 243 | D | |
| 244 | B | BB |
| 245 | B | BB |
| 246 | D | |
| 247 | B | |
| 248 | B | BB |
| 249 | B | BB |
| 250 | D | |
| 251 | C | BB |
| 252 | B | CC |
| 253 | B | CC |
| 254 | C | DD |
| 255 | B | BB |
| 256 | B | CC |
| 257 | D | DD |
| 258 | B | BB |
| 259 | B | BB |
| 260 | D | DD |
| 261 | B | BB |
| 262 | B | BB |
| 263 | C | CC |
| 264 | B | BB |
| 265 | B | BB |
| 266 | B | CC |
| 267 | B | BB |
| 268 | B | BB |
| 269 | B | CC |
| 270 | B | CC |
| 271 | C | CC |
| 272 | C | CC |
| 273 | C | CC |
| 274 | B | BB |
| 275 | B | BB |
| 276 | C | CC |
| 277 | D | CC |
| 278 | C | CC |
| 279 | B | CC |
| 280 | C | CC |
| 281 | C | CC |
| 282 | C | CC |
| 283 | C | CC |
| 284 | C | CC |
| 285 | C | CC |
| 286 | C | CC |
| 287 | D | CC |
| 288 | D | DD |
| 289 | B | BB |
| 290 | D | DD |
| 291 | C | CC |
| 292 | B | BB |
| 293 | B | BB |
| 294 | B | BB |
| 295 | B | BB |
| 296 | C | CC |
| 297 | B | BB |
| 298 | C | BB |
| 299 | C | DD |
| 300 | B | BB |
| 301 | B | BB |
| 302 | C | CC |
| 303 | D | DD |
| 304 | C | CC |
| 305 | B | BB |
| 306 | B | BB |
| 307 | D | DD |
| 308 | B | BB |
| 309 | C | DD |
| 310 | D | CC |
| 311 | B | CC |
| 312 | B | BB |
| 313 | D | DD |
| 314 | D | DD |
| 315 | C | CC |
| 316 | B | CC |
| 317 | B | BB |
| 318 | D | CC |
| 319 | B | CC |
| 320 | B | BB |
| 321 | C | BB |
| 322 | C | BB |
| 323 | B | BB |
| 324 | C | CC |
| 325 | B | BB |
| 326 | C | CC |
| 327 | B | BB |
| 328 | B | CC |
| 329 | D | CC |
| 330 | B | BB |
| 331 | B | BB |
| 332 | C | DD |
| 333 | B | BB |
| 334 | C | CC |
| 335 | B | CC |
| 336 | C | CC |
| 337 | B | BB |
| 338 | B | BB |
| 339 | C | CC |
| 340 | D | CC |
| 341 | C | CC |
| 342 | B | BB |
| 343 | B | BB |
| 344 | C | BB |
| 345 | D | CC |
| 346 | D | CC |
| 347 | C | CC |
| 348 | B | BB |
| 349 | C | CC |
| 350 | C | BB |
| 351 | C | CC |
| 352 | C | CC |
| 353 | B | BB |
| 354 | D | DD |
| 355 | B | BB |
| 356 | B | BB |
| 357 | B | BB |
| 358 | B | BB |
| 359 | B | BB |
| 360 | B | BB |
| 361 | C | BB |
| 362 | B | BB |
| 363 | C | CC |
| 364 | D | DD |
| 365 | B | AA |
| 366 | B | BB |
| 367 | D | CC |
| 368 | B | BB |
| 369 | C | DD |
| 370 | B | BB |
| 371 | C | CC |
| 372 | B | BB |
| 373 | C | CC |
| 374 | B | CC |
| 375 | C | CC |
| 376 | D | DD |

TABLE C2-continued

Measured values for a) IC$_{50}$s from BRD4 BDII AlphaScreen assay: A = a single IC$_{50}$ ≥ 0.01 nM and ≤ 1.0 nM; B = a single IC$_{50}$ ≥ 1 nM and ≤ 10 nM; C = a single IC$_{50}$ ≥ 10 nM and ≤ 100 nM; D = a single IC$_{50}$ ≥ 100 nM; b) GI$_{50}$s from SKM-1 antiproliferation assay: AA = a single IC$_{50}$ ≥ 0.3 nM and ≤ 30 nM; BB = a single IC$_{50}$ ≥ 30 nM and ≤ 300 nM; CC = a single IC$_{50}$ ≥ 300 nM and ≤ 3 µM; DD = a single IC$_{50}$ ≥ 3 µM.

| Ex. No. | BRD4 BDII IC$_{50}$ | SKM-1 GI$_{50}$ |
|---|---|---|
| 377 | B | BB |
| 378 | B | BB |
| 379 | B | BB |
| 380 | B | BB |
| 381 | D | CC |
| 382 | B | BB |
| 383 | B | AA |
| 384 | C | CC |
| 385 | D | CC |
| 386 | D | CC |
| 387 | B | BB |
| 388 | B | BB |
| 389 | B | BB |
| 390 | B | CC |
| 391 | B | BB |
| 392 | B | BB |
| 393 | B | BB |
| 394 | B | BB |
| 395 | B | BB |
| 396 | B | BB |
| 397 | B | BB |
| 398 | C | DD |
| 399 | B | BB |
| 400 | C | CC |
| 401 | D | CC |
| 402 | D | CC |
| 403 | B | AA |
| 404 | D | CC |
| 405 | B | BB |
| 406 | C | BB |
| 407 | B | AA |
| 408 | C | CC |
| 409 | B | AA |
| 411 | A | AA |
| 412 | A | BB |
| 413 | A | AA |
| 414 | A | BB |
| 415 | B | BB |
| 416 | C | DD |
| 417 | B | CC |
| 418 | C | CC |
| 420 | A | AA |
| 421 | A | BB |
| 422 | A | AA |
| 423 | A | AA |
| 424 | A | BB |
| 425 | A | BB |
| 426 | D | DD |
| 427 | B | CC |
| 428 | B | BB |
| 429 | A | AA |
| 430 | A | AA |
| 431 | D | DD |
| 432 | A | AA |
| 433 | B | AA |
| 434 | C | CC |
| 436 | B | BB |
| 437 | B | AA |
| 438 | B | BB |
| 439 | A | BB |
| 440 | A | BB |
| 441 | B | BB |
| 442 | A | AA |
| 444 | C | CC |
| 445 | B | CC |
| 446 | C | CC |
| 448 | C | CC |
| 449 | B | CC |
| 450 | B | BB |
| 451 | A | AA |
| 452 | A | AA |
| 453 | A | AA |
| 454 | B | CC |
| 455 | B | BB |
| 456 | A | AA |
| 457 | B | AA |
| 458 | B | AA |
| 459 | B | AA |
| 460 | B | AA |
| 461 | A | AA |
| 462 | B | BB |
| 463 | A | BB |
| 464 | A | BB |
| 465 | A | AA |
| 466 | A | AA |
| 467 | A | AA |
| 468 | B | CC |
| 469 | A | AA |
| 470 | B | AA |
| 471 | A | AA |
| 472 | B | AA |
| 473 | B | AA |
| 474 | A | AA |
| 475 | A | AA |
| 476 | A | AA |
| 477 | B | BB |
| 478 | A | AA |
| 479 | B | AA |
| 480 | B | CC |
| 481 | B | CC |
| 482 | A | AA |
| 483 | D | DD |
| 484 | B | AA |
| 485 | B | AA |
| 486 | B | BB |
| 487 | B | BB |
| 488 | B | AA |
| 489 | B | AA |
| 490 | A | AA |
| 491 | A | BB |
| 492 | B | BB |
| 493 | A | AA |
| 494 | B | BB |
| 495 | B | BB |
| 496 | D | DD |
| 497 | B | CC |
| 498 | A | AA |
| 499 | B | BB |
| 500 | B | AA |
| 501 | A | AA |
| 502 | D | DD |
| 503 | B | AA |
| 504 | B | AA |
| 505 | B | BB |
| 506 | C | CC |
| 507 | C | CC |
| 508 | B | AA |
| 509 | B | AA |
| 510 | C | BB |
| 511 | B | AA |
| 512 | B | AA |
| 513 | B | AA |
| 514 | B | AA |
| 515 | B | AA |
| 516 | B | AA |
| 517 | A | AA |
| 518 | A | AA |
| 519 | B | AA |

TABLE C2-continued

Measured values for a) IC$_{50}$s from BRD4 BDII AlphaScreen assay:
A = a single IC$_{50}$ ≥ 0.01 nM and ≤ 1.0 nM; B = a single
IC$_{50}$ ≥ 1 nM and ≤ 10 nM; C = a single IC$_{50}$ ≥ 10 nM
and ≤ 100 nM; D = a single IC$_{50}$ ≥ 100 nM; b) GI$_{50}$s from
SKM-1 antiproliferation assay: AA = a single IC$_{50}$ ≥ 0.3 nM
and ≤ 30 nM; BB = a single IC$_{50}$ ≥ 30 nM
and ≤ 300 nM; CC = a single IC$_{50}$ ≥ 300 nM
and ≤ 3 μM; DD = a single IC$_{50}$ ≥ 3 μM.

| Ex. No. | BRD4 BDII IC$_{50}$ | SKM-1 GI$_{50}$ |
|---|---|---|
| 520 | C | CC |
| 521 | B | BB |
| 522 | B | AA |
| 523 | B | AA |
| 524 | B | AA |
| 525 | B | AA |
| 526 | B | AA |
| 527 | A | AA |
| 528 | B | AA |
| 529 | B | AA |
| 530 | A | AA |
| 531 | B | BB |
| 532 | D | DD |
| 533 | B | AA |
| 534 | B | AA |
| 535 | B | AA |
| 536 | B | AA |
| 537 | B | BB |
| 538 | B | BB |
| 539 | B | AA |
| 540 | B | AA |
| 541 | B | BB |
| 542 | B | BB |
| 543 | A | AA |
| 544 | A | AA |
| 545 | A | AA |
| 546 | A | AA |
| 547 | A | AA |
| 548 | B | AA |
| 549 | B | AA |
| 550 | A | AA |
| 551 | A | AA |
| 552 | A | AA |
| 553 | B | AA |
| 554 | B | AA |
| 555 | B | AA |
| 556 | B | AA |
| 557 | B | AA |
| 558 | B | AA |
| 559 | A | BB |
| 560 | B | BB |
| 561 | A | AA |
| 562 | A | AA |
| 563 | A | AA |
| 564 | A | AA |
| 565 | A | AA |
| 566 | A | AA |
| 567 | B | AA |
| 568 | A | AA |
| 569 | B | BB |
| 570 | B | AA |
| 571 | B | AA |
| 572 | A | AA |
| 573 | A | AA |
| 574 | A | AA |
| 575 | A | AA |
| 576 | A | AA |
| 577 | A | AA |
| 578 | A | AA |
| 579 | A | AA |
| 580 | A | AA |
| 581 | A | BB |
| 582 | A | AA |
| 583 | B | AA |
| 584 | A | AA |
| 585 | B | AA |
| 586 | B | AA |
| 587 | B | AA |
| 588 | A | AA |
| 589 | B | AA |
| 590 | B | BB |
| 591 | A | AA |
| 592 | B | AA |
| 593 | A | AA |
| 594 | A | AA |
| 595 | B | AA |
| 596 | C | CC |
| 597 | B | AA |
| 598 | B | AA |
| 599 | B | BB |
| 600 | B | AA |
| 601 | A | AA |
| 602 | A | AA |
| 603 | A | BB |
| 604 | A | AA |
| 605 | A | AA |
| 606 | A | AA |
| 607 | A | AA |
| 608 | C | BB |
| 609 | A | AA |
| 610 | A | AA |
| 611 | A | AA |
| 612 | B | CC |
| 613 | B | BB |
| 614 | A | AA |
| 615 | B | BB |
| 616 | A | AA |
| 617 | A | AA |
| 618 | A | BB |
| 619 | A | AA |
| 620 | A | BB |
| 621 | A | AA |
| 622 | B | BB |
| 623 | A | AA |
| 624 | A | BB |
| 625 | A | AA |
| 626 | A | BB |
| 627 | A | BB |
| 628 | A | BB |
| 629 | A | BB |
| 630 | A | BB |
| 631 | A | BB |
| 632 | C | CC |
| 633 | A | AA |
| 634 | A | AA |
| 635 | B | AA |
| 636 | A | AA |
| 637 | A | AA |
| 638 | A | AA |
| 639 | A | AA |
| 640 | A | AA |
| 641 | A | AA |
| 642 | A | AA |
| 643 | A | BB |
| 644 | A | AA |
| 645 | A | AA |
| 646 | A | AA |
| 647 | A | AA |
| 648 | A | AA |
| 649 | B | BB |
| 650 | A | AA |
| 651 | A | BB |
| 652 | A | BB |
| 653 | A | CC |
| 654 | A | AA |
| 655 | A | AA |
| 656 | A | AA |
| 657 | A | AA |

TABLE C2-continued

Measured values for a) IC$_{50}$s from BRD4 BDII AlphaScreen assay:
A = a single IC$_{50}$ ≥ 0.01 nM and ≤ 1.0 nM; B = a single
IC$_{50}$ ≥ 1 nM and ≤ 10 nM; C = a single IC$_{50}$ ≥ 10 nM
and ≤ 100 nM; D = a single IC$_{50}$ ≥ 100 nM; b) GI$_{50}$s from
SKM-1 antiproliferation assay: AA = a single IC$_{50}$ ≥ 0.3 nM
and ≤ 30 nM; BB = a single IC$_{50}$ ≥ 30 nM
and ≤ 300 nM; CC = a single IC$_{50}$ ≥ 300 nM
and ≤ 3 μM; DD = a single IC$_{50}$ ≥ 3 μM.

| Ex. No. | BRD4 BDII IC$_{50}$ | SKM-1 GI$_{50}$ |
|---|---|---|
| 658 | A | AA |
| 659 | A | AA |
| 660 | A | AA |
| 661 | A | AA |
| 662 | B | BB |
| 663 | A | AA |
| 664 | A | AA |
| 665 | A | BB |
| 666 | A | AA |
| 667 | A | AA |
| 668 | A | AA |
| 669 | A | BB |
| 670 | A | AA |
| 671 | A | AA |
| 672 | A | AA |
| 673 | A | BB |
| 674 | A | BB |
| 675 | A | BB |
| 676 | A | AA |
| 677 | A | AA |
| 678 | A | AA |
| 679 | B | BB |
| 680 | A | BB |
| 681 | A | AA |
| 682 | A | AA |
| 683 | A | BB |
| 684 | B | BB |
| 685 | A | AA |
| 686 | A | AA |
| 687 | A | AA |
| 688 | A | AA |
| 689 | A | AA |
| 690 | A | BB |
| 691 | A | BB |
| 692 | A | AA |
| 693 | A | AA |
| 694 | B | AA |
| 695 | A | AA |
| 696 | A | AA |
| 697 | B | BB |
| 698 | A | AA |
| 699 | A | AA |
| 700 | A | AA |
| 701 | A | BB |
| 702 | A | AA |
| 703 | B | AA |
| 704 | A | AA |
| 705 | A | BB |
| 706 | A | AA |
| 707 | B | BB |
| 708 | A | AA |
| 709 | A | AA |
| 710 | A | AA |
| 711 | A | AA |
| 712 | A | BB |
| 713 | A | AA |
| 714 | A | BB |
| 715 | A | AA |
| 716 | A | AA |
| 717 | A | AA |
| 718 | A | AA |
| 719 | A | AA |
| 720 | A | AA |
| 721 | A | BB |
| 722 | A | AA |
| 723 | B | AA |
| 724 | A | AA |
| 725 | B | BB |
| 726 | A | AA |
| 727 | A | AA |
| 728 | B | AA |
| 729 | A | AA |
| 730 | A | AA |
| 731 | A | AA |
| 732 | B | AA |
| 733 | B | BB |
| 734 | A | AA |
| 735 | A | AA |
| 736 | A | AA |
| 737 | A | AA |
| 738 | A | AA |
| 739 | A | AA |
| 740 | A | AA |
| 741 | A | AA |
| 742 | A | AA |
| 743 | A | AA |
| 744 | A | AA |
| 745 | A | AA |
| 746 | A | AA |
| 747 | A | AA |
| 748 | A | AA |
| 749 | B | AA |
| 750 | A | AA |
| 751 | B | AA |
| 752 | A | AA |
| 753 | A | AA |
| 754 | A | AA |
| 755 | A | AA |
| 756 | A | AA |
| 757 | A | BB |
| 758 | A | AA |
| 759 | A | AA |
| 760 | A | BB |
| 761 | B | BB |
| 762 | B | BB |
| 763 | B | AA |
| 764 | B | CC |
| 765 | B | AA |
| 766 | B | BB |
| 767 | A | AA |
| 768 | B | BB |
| 769 | B | CC |
| 770 | B | BB |
| 771 | B | BB |
| 772 | C | CC |
| 773 | B | BB |
| 774 | B | BB |
| 775 | B | BB |
| 776 | C | BB |
| 777 | A | AA |
| 778 | B | AA |
| 779 | B | AA |
| 780 | B | BB |
| 781 | B | BB |
| 782 | A | BB |
| 783 | A | AA |
| 784 | B | BB |
| 785 | B | BB |
| 786 | B | BB |
| 787 | A | AA |
| 788 | C | CC |
| 789 | B | AA |
| 790 | A | AA |
| 791 | A | AA |
| 792 | D | CC |
| 793 | A | AA |
| 794 | C | CC |
| 795 | D | CC |

TABLE C2-continued

Measured values for a) IC$_{50}$s from BRD4 BDII AlphaScreen assay: A = a single IC$_{50}$ ≥ 0.01 nM and ≤ 1.0 nM; B = a single IC$_{50}$ ≥ 1 nM and ≤ 10 nM; C = a single IC$_{50}$ ≥ 10 nM and ≤ 100 nM; D = a single IC$_{50}$ ≥ 100 nM; b) GI$_{50}$s from SKM-1 antiproliferation assay: AA = a single IC$_{50}$ ≥ 0.3 nM and ≤ 30 nM; BB = a single IC$_{50}$ ≥ 30 nM and ≤ 300 nM; CC = a single IC$_{50}$ ≥ 300 nM and ≤ 3 μM; DD = a single IC$_{50}$ ≥ 3 μM.

| Ex. No. | BRD4 BDII IC$_{50}$ | SKM-1 GI$_{50}$ |
|---|---|---|
| 796 | B | BB |
| 797 | A | AA |
| 798 | A | AA |
| 799 | A | BB |
| 800 | A | AA |
| 801 | B | BB |
| 802 | A | AA |
| 803 | B | BB |
| 804 | B | AA |
| 805 | B | BB |
| 806 | B | AA |
| 807 | B | BB |
| 808 | B | BB |
| 809 | B | AA |
| 810 | B | BB |
| 811 | B | BB |
| 812 | A | AA |
| 813 | A | BB |
| 814 | A | AA |
| 815 | A | AA |
| 816 | A | AA |
| 817 | B | AA |
| 818 | D | BB |
| 819 | B | BB |
| 820 | B | AA |
| 821 | B | AA |
| 822 | B | AA |
| 823 | B | AA |
| 824 | B | AA |
| 825 | A | AA |
| 826 | A | AA |
| 827 | A | AA |
| 828 | A | AA |
| 829 | A | AA |
| 830 | B | AA |
| 831 | B | AA |
| 832 | A | AA |
| 833 | B | BB |
| 834 | B | AA |
| 835 | B | AA |
| 836 | B | AA |
| 837 | A | BB |
| 838 | A | BB |
| 839 | A | AA |
| 840 | A | AA |
| 841 | B | BB |
| 842 | B | BB |
| 843 | A | AA |
| 844 | B | AA |
| 845 | B | BB |
| 846 | A | AA |
| 847 | B | AA |
| 848 | C | AA |

TABLE C3

Measured values for a) IC$_{50}$s from BRD4 BDII AlphaScreen assay: A = a single IC$_{50}$ ≥ 0.01 nM and ≤ 1.0 nM; B = a single IC$_{50}$ ≥ 1 nM and ≤ 10 nM; C = a single IC$_{50}$ ≥ 10 nM and ≤ 100 nM; D = a single IC$_{50}$ ≥ 100 nM; b) GI$_{50}$s from SKM-1 antiproliferation assays: AA = a single IC$_{50}$ ≥ 0.3 nM and ≤ 30 nM; BB = a single IC$_{50}$ ≥ 30 nM and ≤ 300 nM; CC = a single IC$_{50}$ ≥ 300 nM and ≤ 3 μM; DD = a single IC$_{50}$ ≥ 3 μM.

| Ex. No. | BRD4 BD2 IC50 (μM) | SKM-1 GI50 (μM) |
|---|---|---|
| 849 | A | BB |
| 850 | B | AA |
| 851 | B | BB |
| 852 | A | AA |
| 853 | A | AA |
| 854 | B | BB |
| 855 | C | BB |
| 856 | B | AA |
| 857 | C | CC |
| 858 | C | CC |
| 859 | C | BB |
| 860 | D | AA |
| 861 | B | AA |
| 862 | C | CC |
| 863 | C | CC |
| 864 | C | CC |
| 865 | C | CC |
| 866 | C | CC |
| 867 | B | BB |
| 868 | B | AA |
| 869 | B | AA |
| 870 | B | CC |
| 871 | B | BB |
| 872 | A | BB |
| 873 | A | AA |
| 874 | A | AA |
| 875 | A | AA |
| 876 | A | AA |
| 877 | D | AA |
| 878 | D | AA |
| 879 | B | AA |
| 880 | A | AA |
| 881 | A | BB |
| 882 | B | AA |
| 883 | B | AA |
| 884 | B | BB |
| 885 | B | BB |
| 886 | B | AA |
| 887 | D | CC |
| 888 | D | CC |
| 889 | D | CC |
| 890 | B | AA |
| 891 | B | AA |
| 892 | B | AA |
| 893 | D | CC |
| 894 | D | CC |
| 895 | B | BB |
| 896 | D | CC |
| 897 | B | BB |
| 898 | B | BB |
| 899 | B | CC |
| 900 | A | BB |
| 901 | A | BB |
| 902 | A | AA |
| 903 | A | AA |
| 904 | A | BB |
| 905 | B | BB |
| 906 | A | AA |
| 907 | D | DD |
| 908 | D | DD |
| 909 | B | BB |
| 910 | C | BB |
| 911 | A | AA |
| 912 | D | CC |
| 913 | A | AA |
| 914 | B | AA |
| 915 | A | BB |
| 916 | A | AA |
| 917 | B | BB |

TABLE C3-continued

Measured values for a) IC$_{50}$s from BRD4 BDII AlphaScreen assay: A = a single IC$_{50}$ ≥ 0.01 nM and ≤ 1.0 nM; B = a single IC$_{50}$ ≥ 1 nM and ≤ 10 mM; C = a single IC$_{50}$ ≥ 10 nM and ≤ 100 mM; D = a single IC$_{50}$ ≥ 100 nM; b) GI$_{50}$s from SKM-1 antiproliferation assays: AA = a single IC$_{50}$ ≥ 0.3 nM and ≤ 30 nM; BB = a single IC$_{50}$ ≥ 30 nM and ≤ 300 mM; CC = a single IC$_{50}$ ≥ 300 nM and ≤ 3 μM; DD = a single IC$_{50}$ ≥ 3 μM.

| Ex. No. | BRD4 BD2 IC50 (μM) | SKM-1 GI50 (μM) |
|---|---|---|
| 918 | B | AA |
| 919 | B | CC |
| 920 | D | BB |
| 921 | C | CC |
| 922 | A | AA |
| 923 | A | AA |
| 924 | C | BB |
| 925 | C | BB |
| 926 | A | AA |
| 927 | C | BB |
| 928 | B | BB |
| 929 | D | CC |
| 930 | D | CC |
| 931 | D | CC |
| 932 | D | CC |
| 933 | C | BB |
| 934 | D | CC |
| 935 | D | CC |
| 936 | D | CC |
| 937 | C | BB |
| 938 | B | AA |
| 939 | B | AA |
| 940 | D | CC |
| 941 | B | AA |
| 942 | D | CC |
| 943 | B | AA |
| 944 | D | CC |
| 945 | B | AA |
| 946 | B | BB |
| 948 | B | AA |
| 949 | B | AA |
| 950 | D | CC |
| 951 | B | AA |
| 952 | D | CC |
| 953 | D | CC |
| 954 | B | AA |
| 955 | B | AA |
| 956 | B | AA |
| 957 | A | AA |
| 958 | A | AA |
| 959 | B | AA |
| 960 | B | AA |
| 961 | B | AA |
| 962 | B | AA |
| 963 | B | AA |
| 964 | A | AA |
| 965 | B | AA |
| 966 | B | BB |
| 967 | B | BB |
| 968 | B | AA |
| 969 | B | BB |
| 970 | B | AA |
| 971 | A | AA |
| 972 | A | AA |
| 973 | A | AA |
| 974 | A | AA |
| 975 | B | AA |
| 976 | B | AA |
| 977 | A | AA |
| 978 | A | AA |
| 979 | B | AA |
| 980 | B | AA |
| 981 | B | AA |
| 982 | B | BB |
| 983 | A | AA |
| 984 | C | AA |
| 985 | B | AA |
| 986 | B | AA |
| 987 | B | AA |
| 988 | B | AA |
| 989 | B | AA |
| 990 | B | AA |
| 991 | B | AA |
| 992 | B | AA |
| 993 | C | AA |
| 994 | B | AA |
| 995 | B | AA |
| 996 | B | AA |
| 997 | B | AA |
| 998 | B | AA |
| 999 | B | AA |
| 1000 | B | AA |
| 1001 | B | AA |
| 1002 | B | AA |
| 1003 | B | AA |
| 1004 | B | AA |
| 1005 | B | AA |
| 1006 | B | AA |
| 1007 | B | AA |
| 1008 | B | AA |
| 1009 | B | AA |
| 1010 | A | AA |
| 1011 | C | AA |
| 1012 | B | AA |
| 1013 | B | AA |
| 1014 | A | AA |
| 1015 | B | AA |
| 1016 | A | AA |
| 1017 | B | BB |
| 1018 | C | BB |
| 1019 | B | AA |
| 1020 | D | CC |
| 1021 | A | AA |
| 1022 | A | AA |
| 1023 | A | AA |
| 1024 | B | AA |
| 1025 | B | CC |
| 1026 | A | AA |
| 1027 | A | AA |
| 1028 | B | AA |
| 1029 | A | AA |
| 1030 | C | CC |
| 1031 | B | BB |
| 1032 | A | AA |
| 1033 | A | AA |
| 1034 | A | AA |
| 1035 | C | BB |
| 1036 | B | BB |
| 1037 | B | AA |
| 1038 | C | BB |
| 1039 | B | AA |
| 1040 | C | CC |
| 1041 | — | BB |
| 1042 | — | CC |
| 1043 | — | BB |
| 1044 | — | AA |
| 1045 | — | BB |
| 1046 | — | AA |
| 1047 | — | AA |
| 1048 | — | BB |
| 1049 | — | BB |
| 1050 | — | AA |
| 1051 | — | AA |
| 1052 | — | AA |
| 1053 | — | AA |
| 1054 | — | AA |
| 1055 | — | AA |
| 1056 | — | AA |

TABLE C3-continued

Measured values for a) $IC_{50}$s from BRD4 BDII AlphaScreen assay: A = a single $IC_{50} \geq 0.01$ nM and $\leq 1.0$ nM; B = a single $IC_{50} \geq 1$ nM and $\leq 10$ mM; C = a single $IC_{50} \geq 10$ nM and $\leq 100$ mM; D = a single $IC_{50} \geq 100$ nM; b) $GI_{50}$s from SKM-1 antiproliferation assays: AA = a single $IC_{50} \geq 0.3$ nM and $\leq 30$ nM; BB = a single $IC_{50} \geq 30$ nM and $\leq 300$ mM; CC = a single $IC_{50} \geq 300$ nM and $\leq 3$ μM; DD = a single $IC_{50} \geq 3$ μM.

| Ex. No. | BRD4 BD2 IC50 (μM) | SKM-1 GI50 (μM) |
|---|---|---|
| 1057 | — | AA |
| 1058 | — | AA |
| 1059 | — | AA |
| 1061 | — | — |
| 1062 | — | — |

INCORPORATION BY REFERENCE

All U.S. patents and U.S. and PCT published patent applications mentioned herein are hereby incorporated by reference in their entirety as if each individual patent or published application was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:
1. A compound having the structure of formula (XI),

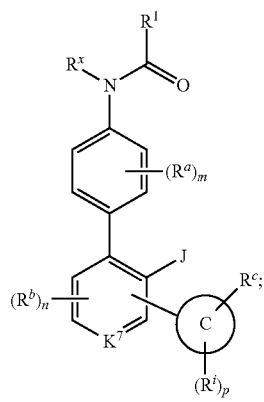

(XI)

or a pharmaceutically acceptable salt thereof;
wherein:
$K^7$ is N or CH;
Ring C represents substituted or unsubstituted arylene or heteroarylene;
$R^1$ and $R^x$, taken together with the intervening atoms, form an optionally substituted heterocycloalkyl ring, heterocycloalkenyl ring, or heteroaryl ring;

each occurrence of $R^a$ is independently selected from the group consisting of halo, —NH$_2$, —NH(alkyl), —NH(cycloalkyl), —N(alkyl)$_2$, hydroxyl, alkyl, alkoxy, cycloalkyl, cycloalkoxy, haloalkoxy, heterocycloalkoxy, cyano, aryloxy, heteroaryloxy, and haloalkyl;

J represents —OH, —O(alkyl), —OC(O)(alkyl), —OC(O)O(alkyl), —OC(O)NH(alkyl), —OC(O)N(alkyl)$_2$, —OCH$_2$OC(O)O(alkyl), —NH$_2$, —NHR$^j$, or —CHF$_2$;

$R^j$ is alkyl, alkenyl, alkynyl, aryl, heteroaryl, arylalkyl, heteroarylalkyl, cycloalkyl, heterocycloalkyl, (cycloalkyl)alkyl, or (heterocycloalkyl)alkyl;

each occurrence of $R^b$ is independently selected from the group consisting of halo, oxo, alkyl, alkoxyl, haloalkyl, cyano, cycloalkyl, aryl, aryloxy, —OH, —NH(alkyl), —C(O)H, —CO$_2$(alkyl) and —CO$_2$H;

$R^c$ represents optionally substituted heterocycloalkyl, cycloalkyl, alkyl, aryl, heteroaryl, (heterocycloalkyl)alkyl, heterocycloalkenyl, alkoxyl, alkynyl, aryloxy, haloalkyl, haloalkoxy, cycloalkoxyl, or heterocycloalkoxyl, or represents halo, —S(alkyl), —NH$_2$, —CO$_2$H, —CO$_2$(alkyl), or —NHCO(alkyl);

each occurrence of $R^i$ is independently halo, oxo, —S(alkyl), —NH$_2$, —NH(alkyl), —N(alkyl)$_2$, —OH, or cyano, or is selected from the group consisting of optionally substituted alkyl, haloalkyl, haloalkoxyl, alkoxyl, heterocycloalkyl, and cycloalkoxyl;

or $R^c$ and an occurrence of $R^i$, taken together with the intervening atoms, form an optionally substituted aryl, heteroaryl, cycloalkyl, or heterocycloalkyl ring;

or two adjacent occurrences of $R^i$, taken together with the intervening atoms, form an optionally substituted aryl, heteroaryl, cycloalkyl, or heterocycloalkyl ring; and m, n, and p are each independently 0, 1, or 2.

2. The compound of claim 1, wherein the compound has the structure of formula (XIai) or formula (XIaii):

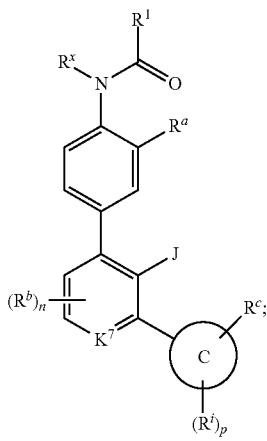

(XIai)

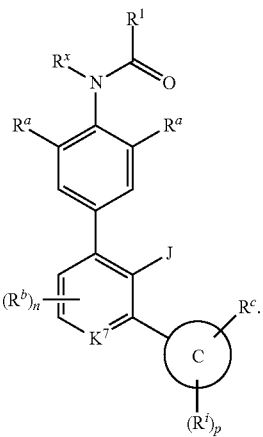
(XIaii)
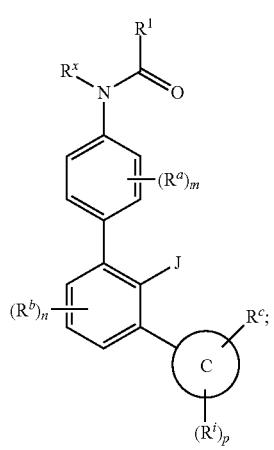
(XIbi)
3. The compound of claim 1, wherein the compound has the structure of formula (XIb) or formula (XIbh):
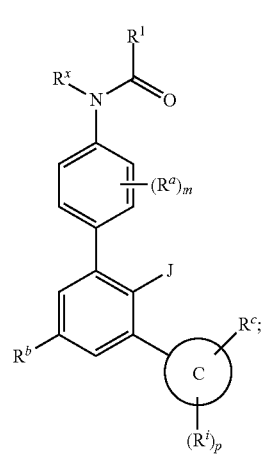
(XIbii)
(XIb)
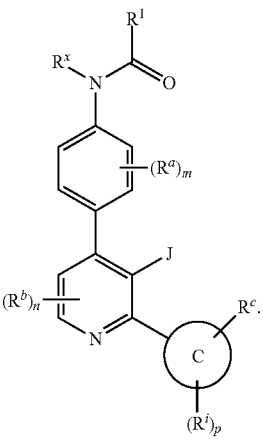
(XIbh)
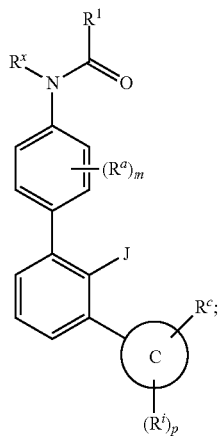
(XIbiii)
4. The compound of claim 1, wherein the compound has the structure of formula (XIbi), formula (XIbii), formula (XIbiii), formula (XIbhi), formula (XIbhii), formula (XIbhiii), or formula (XIbhiv):

(XIbhi)
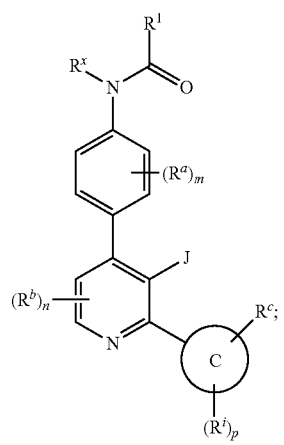
(XIbhii)
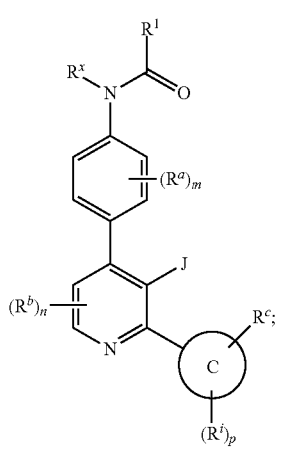
(XIbhiii)
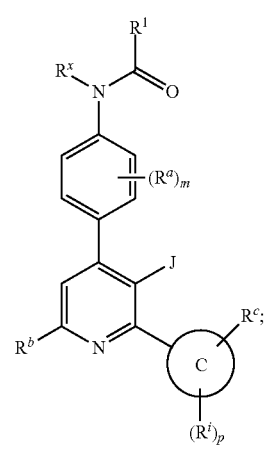
(XIbhiv)
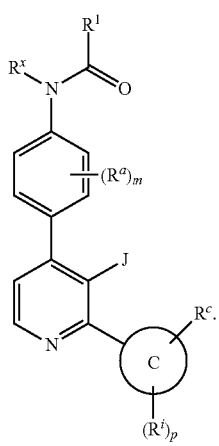
5. The compound of claim 1, wherein the compound has the structure of formula (XIcm), formula (XIcp), or formula (XIco):
(XIcm)
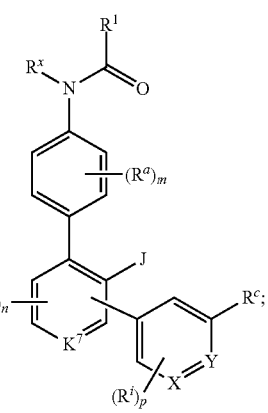
(XIcp)
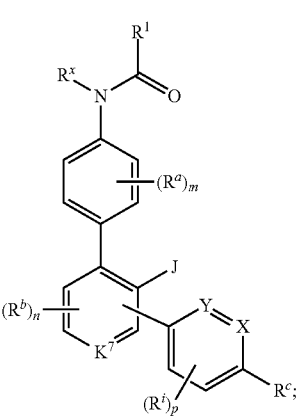

(XIco)
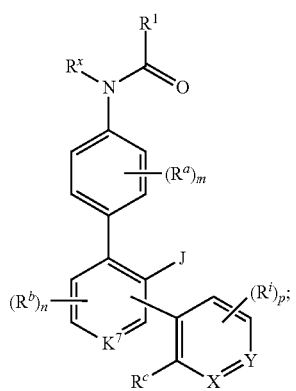
wherein X and Y are each independently selected from CH and N; and
at least one of X and Y is CH.
6. The compound of claim 5, wherein the compound has the structure of formula (XIcmi), formula (XIcmii), formula (XIcmiii), formula (XIcpi), formula (XIcpii), formula (XIcpiii), formula (XIcoi), formula (XIcoii), or formula (XIcoiii):
(XIcmi)
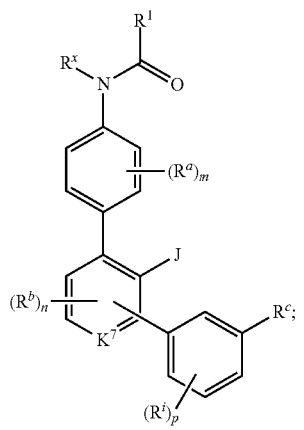
(XIcmii)
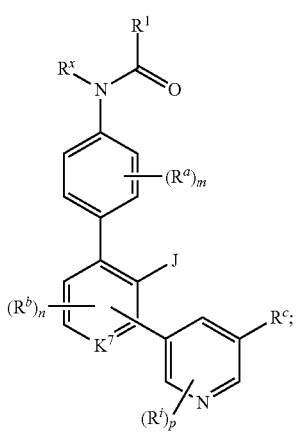
(XIcmiii)
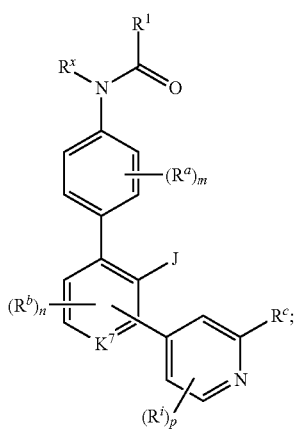
(XIcpi)
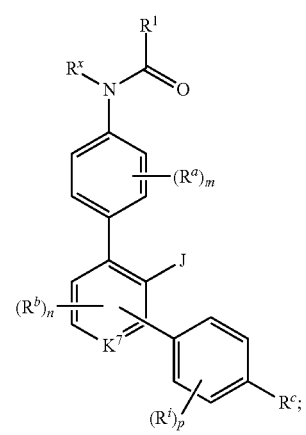
(XIcpii)
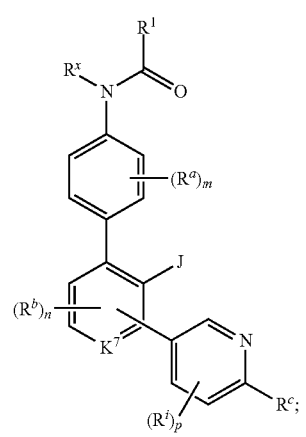

(XIcpiii)
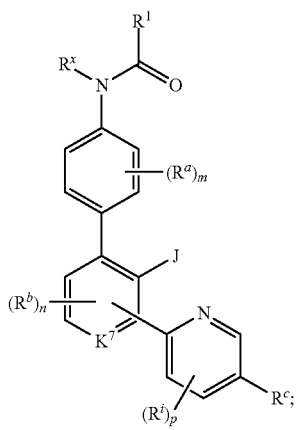
(XIcoi)
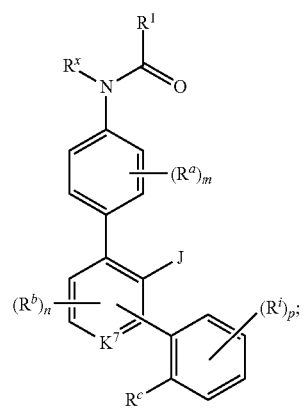
(XIcoii)
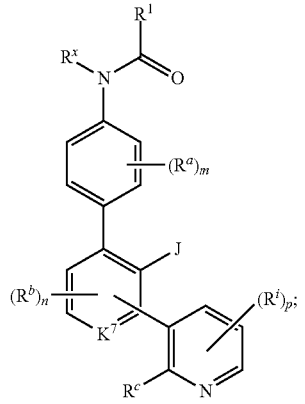
(XIcoiii)
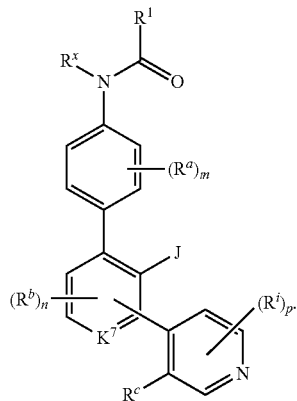
7. The compound of claim 1, wherein the compound has the structure of formula (Ie) or formula (Ieu):
(Ie)
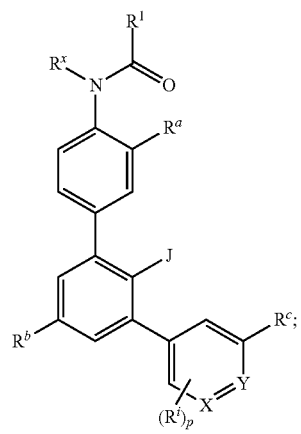
(Ieu)
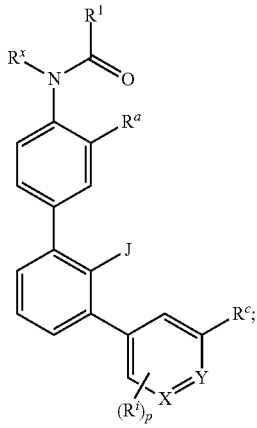
wherein X and Y are each independently selected from CH and N; and
at least one of X and Y is CH.
8. The compound of claim 7, wherein the compound has the structure of formula (Iei), formula (Ieii), or formula (Ieiii):

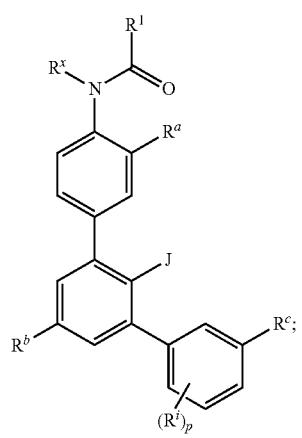
(Iei)
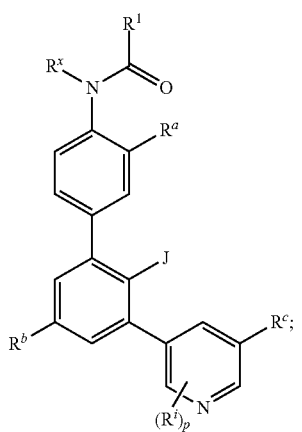
(Ieii)
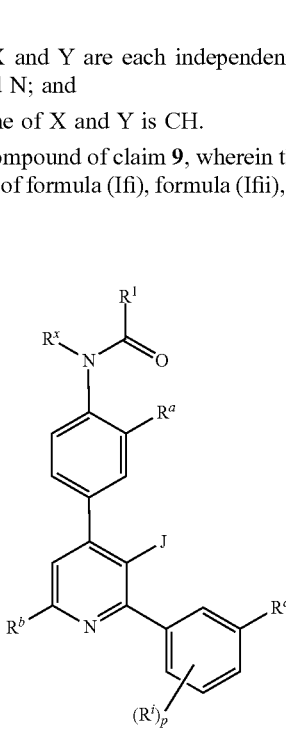
(Ieiii)
9. The compound of claim 1, wherein the compound has the structure of formula (If) or formula (Ifu):
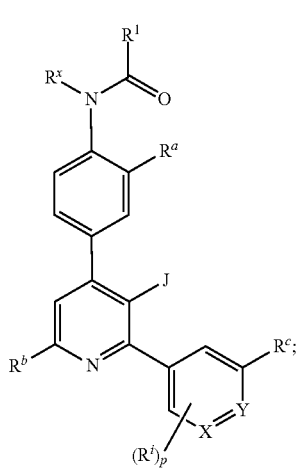
(If)
(Ifu)
wherein X and Y are each independently selected from CH and N; and
at least one of X and Y is CH.
10. The compound of claim 9, wherein the compound has the structure of formula (Ifi), formula (Ifii), or formula (Ifiii):
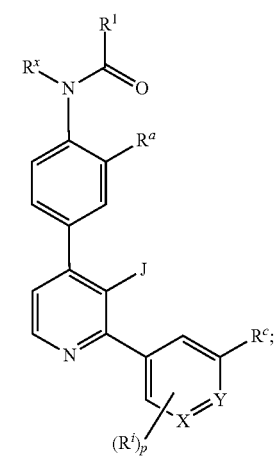
(Ifi)

(Ifii)
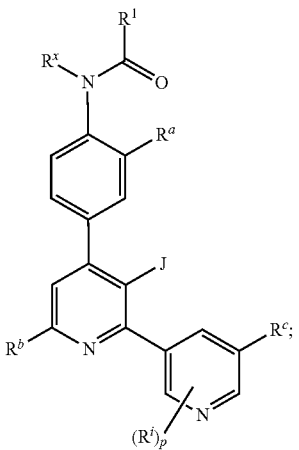
(Ifiii)
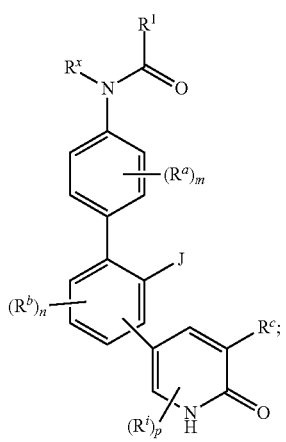
11. The compound of claim 1, wherein the compound has the structure of formula (XIgi), formula (XIgii), or formula (XIgiii):
(XIgi)
(XIgii)
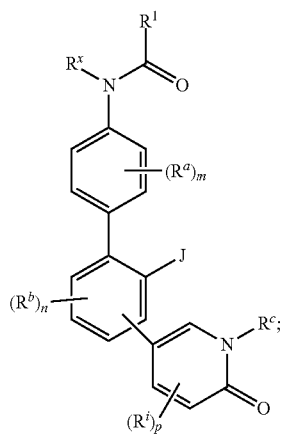
(XIgiii)
12. The compound of claim 1, wherein
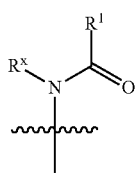
is selected from the group consisting of
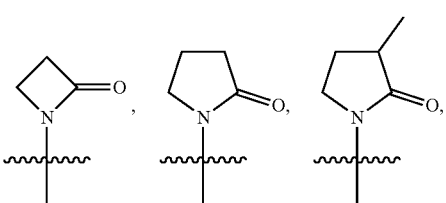

1341
-continued

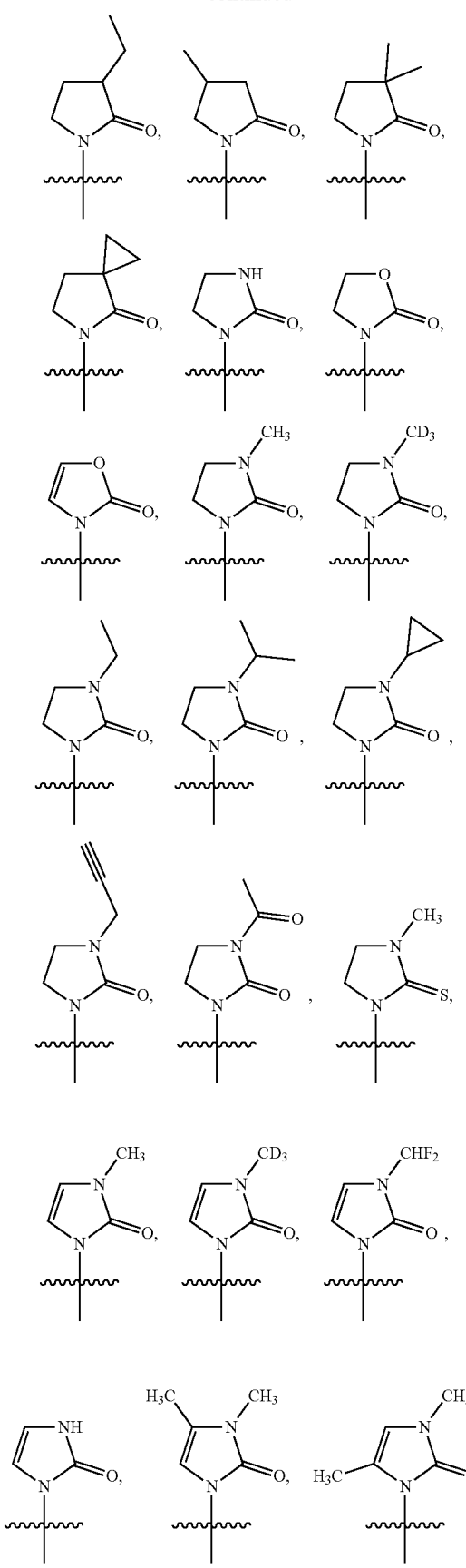

1342
-continued

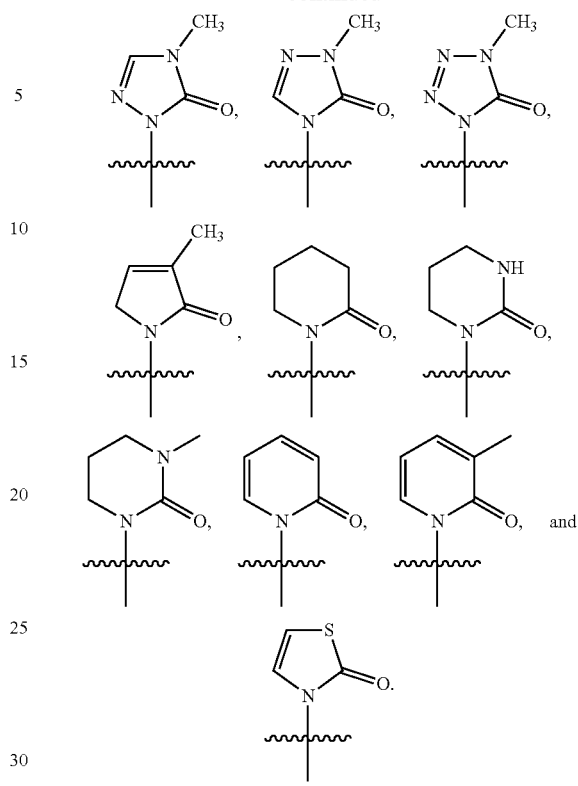

13. The compound of claim 1, wherein m is 1 or 2, optionally wherein each occurrence of $R^a$ is independently halo, alkyl, alkoxy, or cycloalkoxy.

14. The compound of claim 1, wherein J represents —OH or —NH$_2$.

15. The compound of claim 1, wherein n is 0 or 1, optionally wherein $R^b$ is halo or methyl.

16. The compound of claim 1, wherein p is 0 or 1, optionally wherein $R^i$ is alkyl or alkoxyl.

17. The compound of claim 1, wherein $R^c$ represents optionally substituted heterocycloalkyl.

18. The compound of claim 1, wherein $R^c$ is selected from the group consisting of

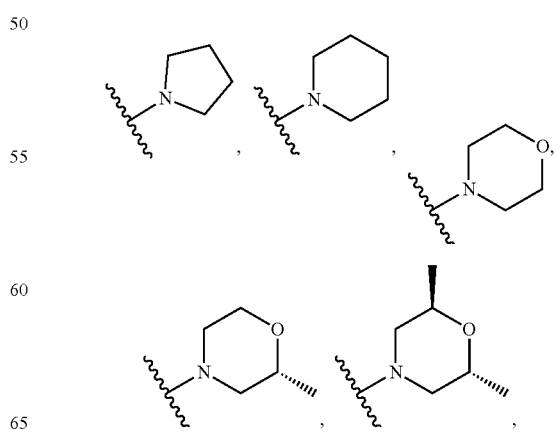

1343
-continued
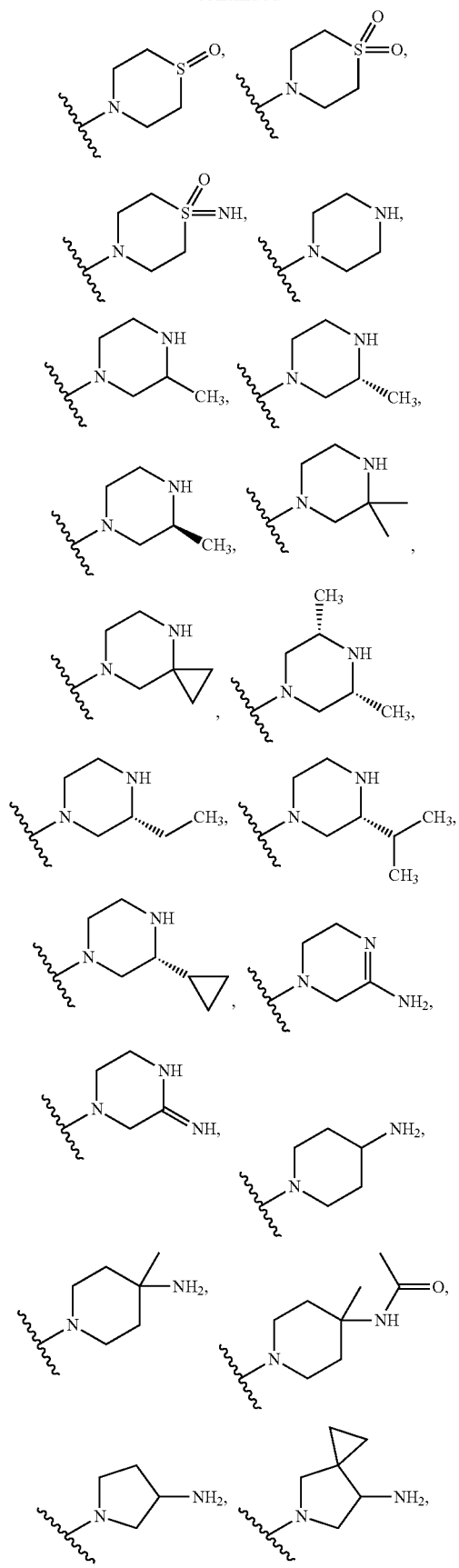
1344
-continued
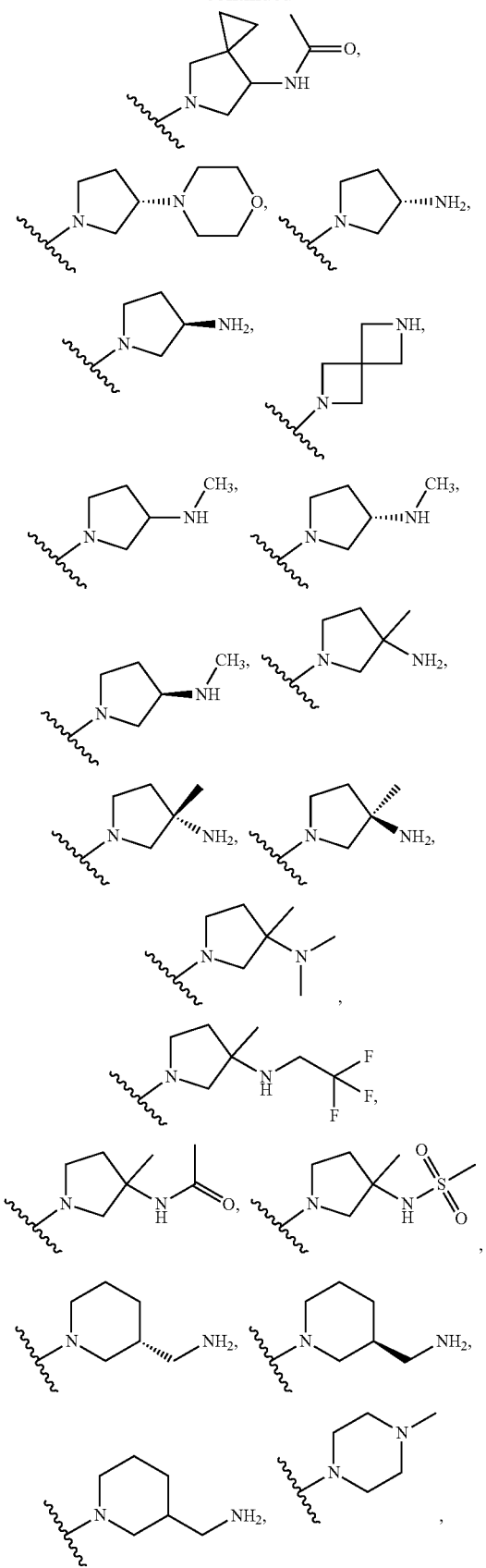

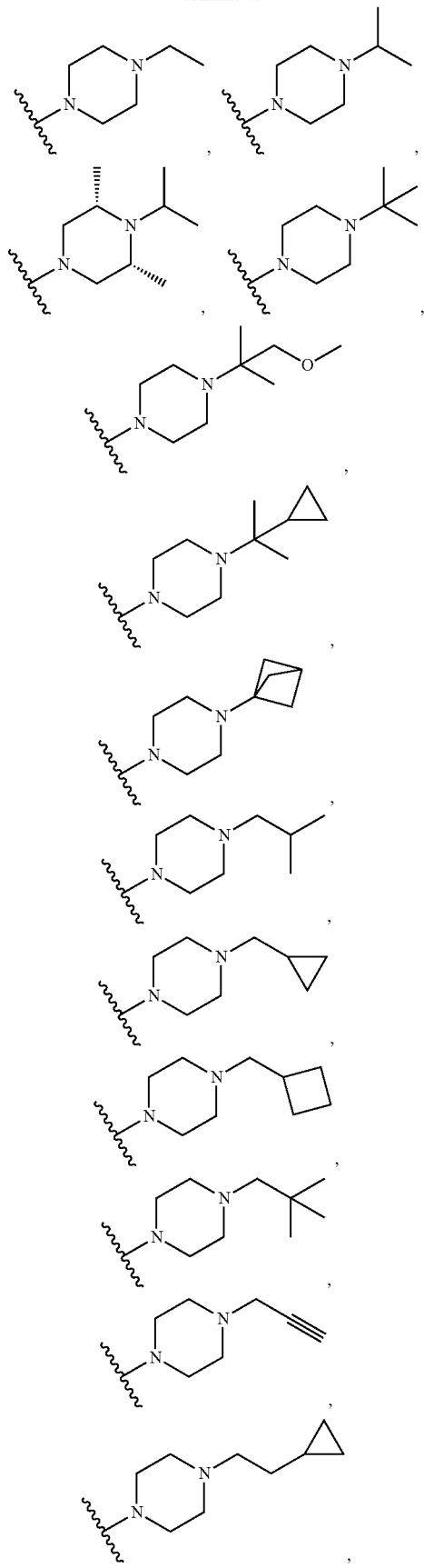
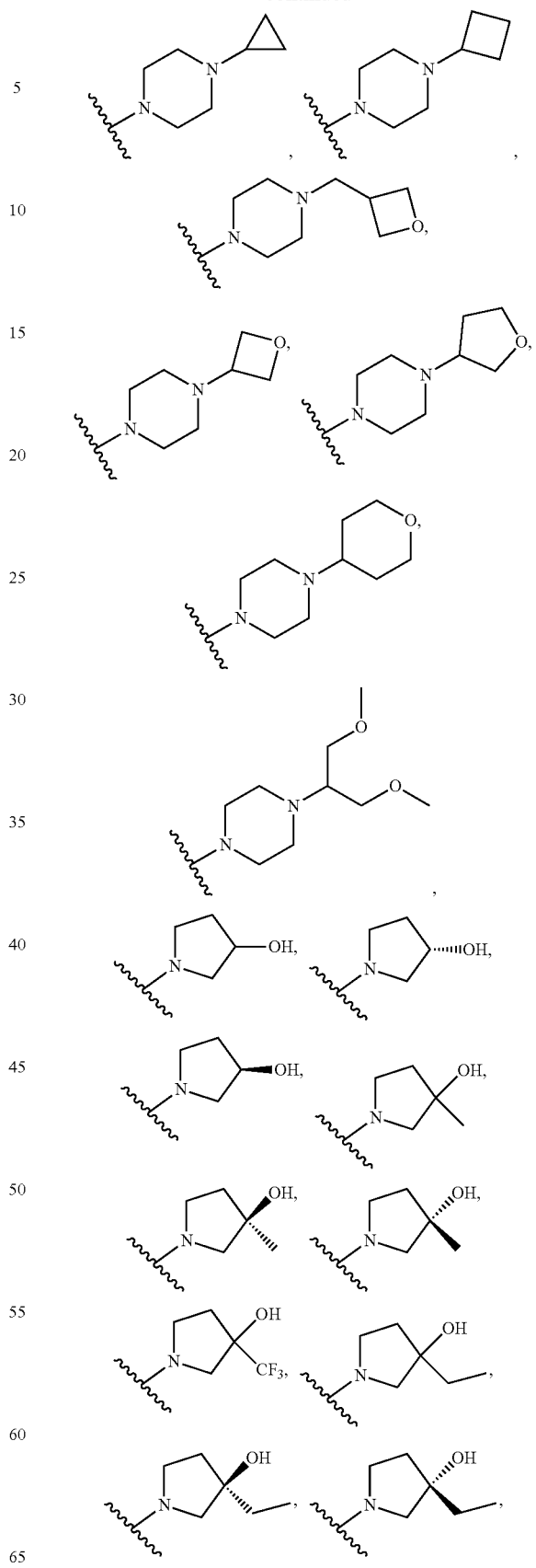

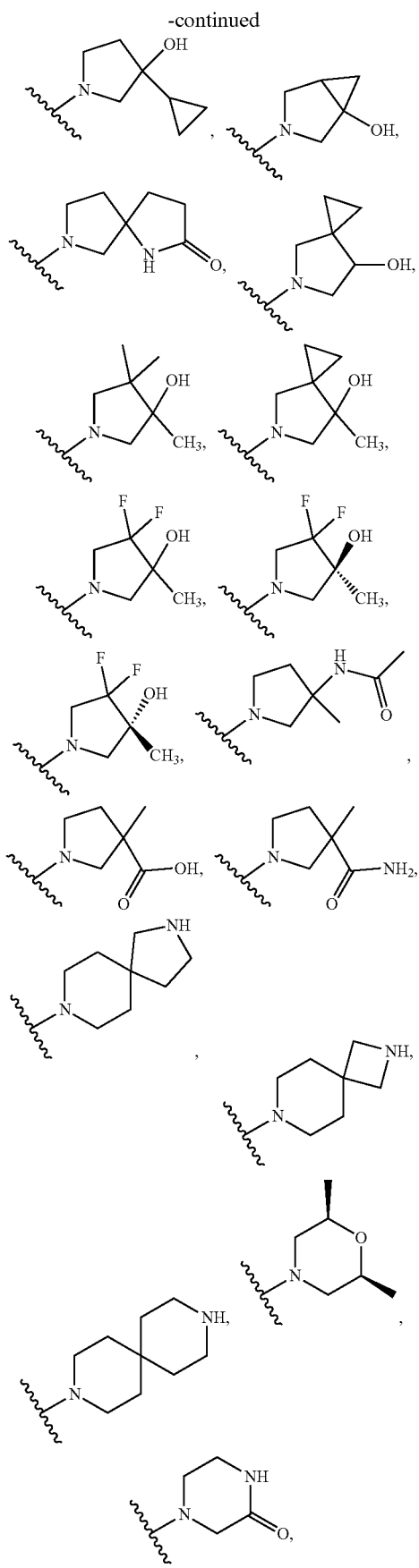
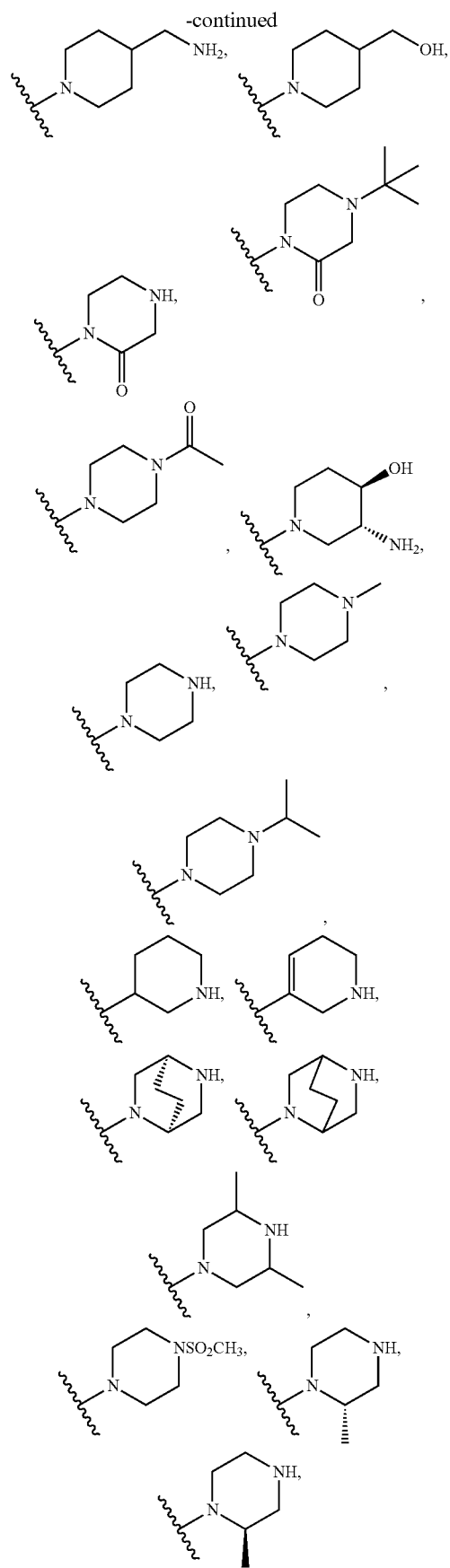

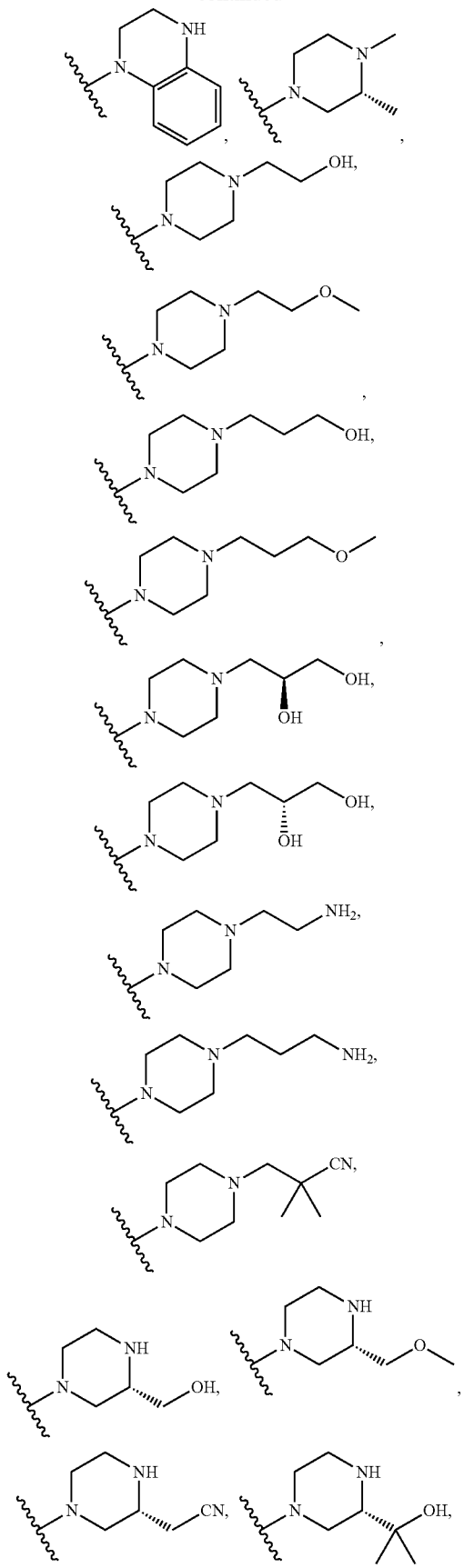
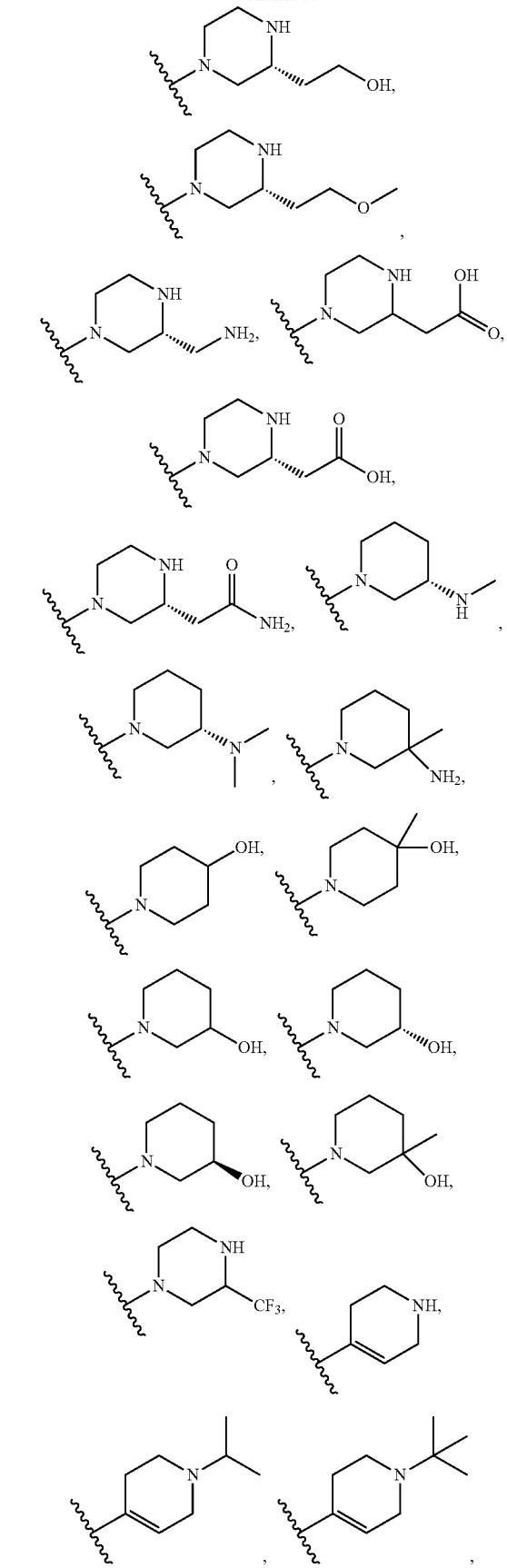

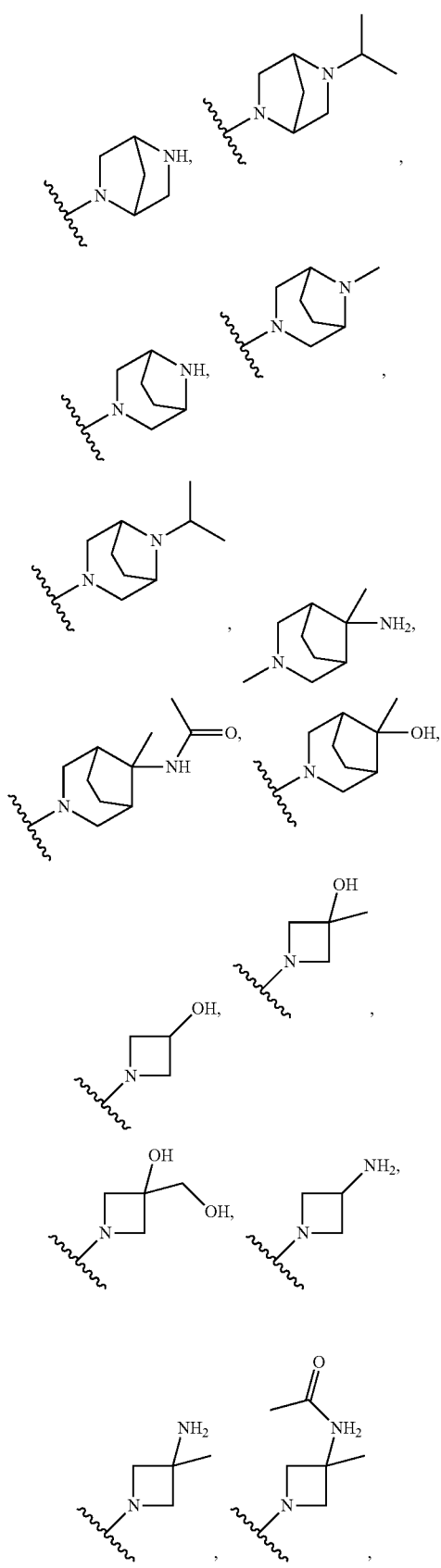
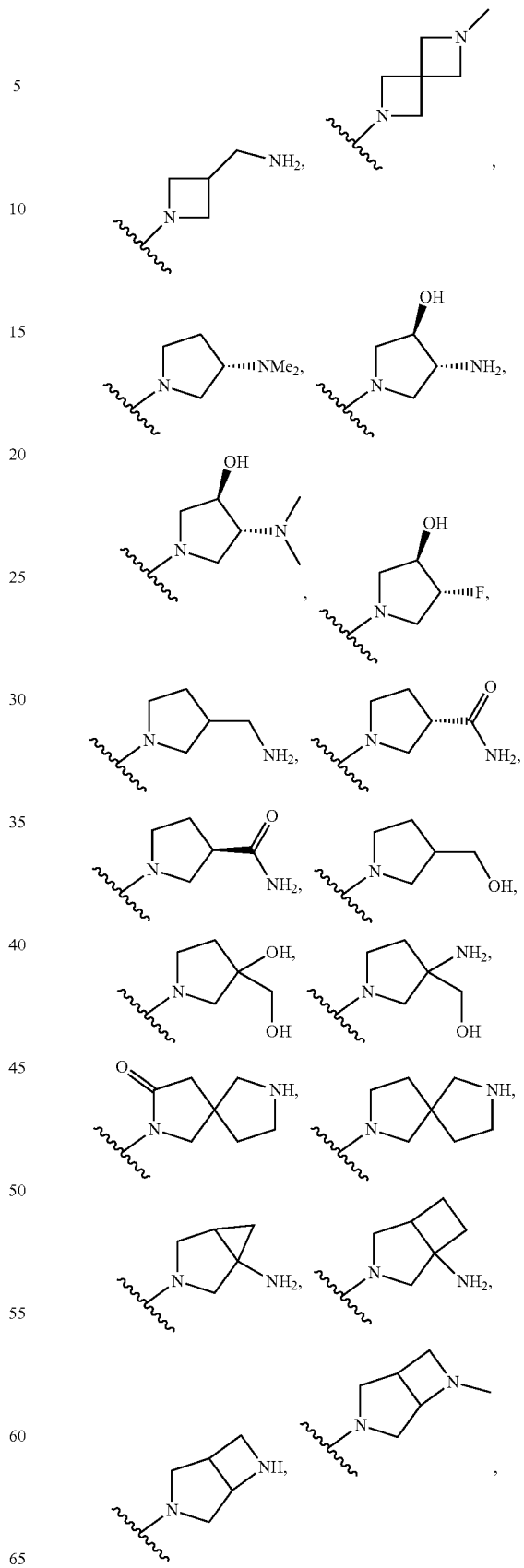

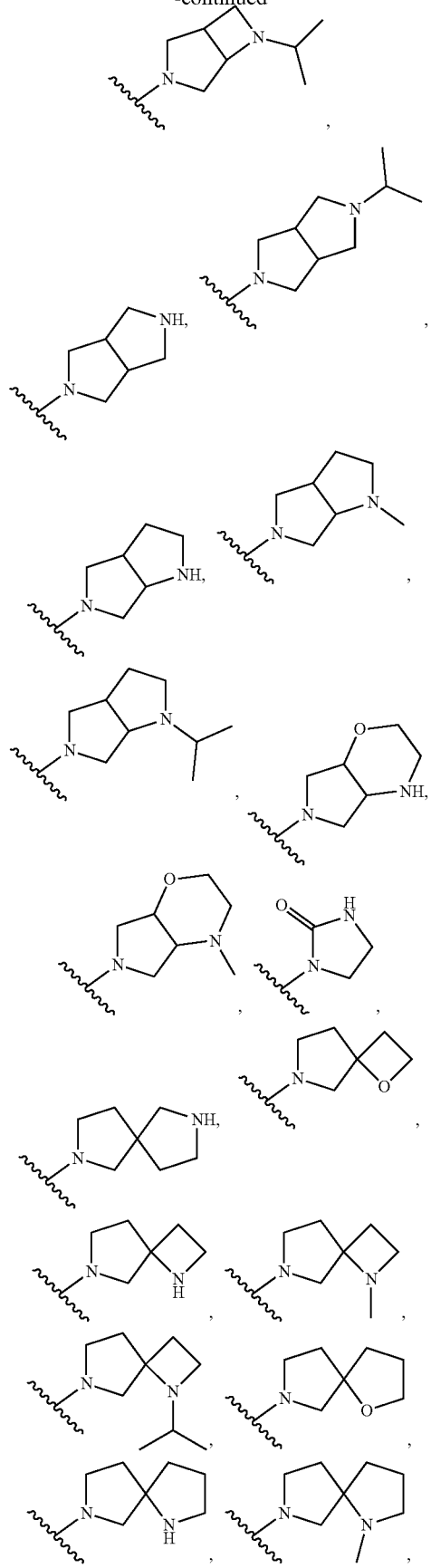
,
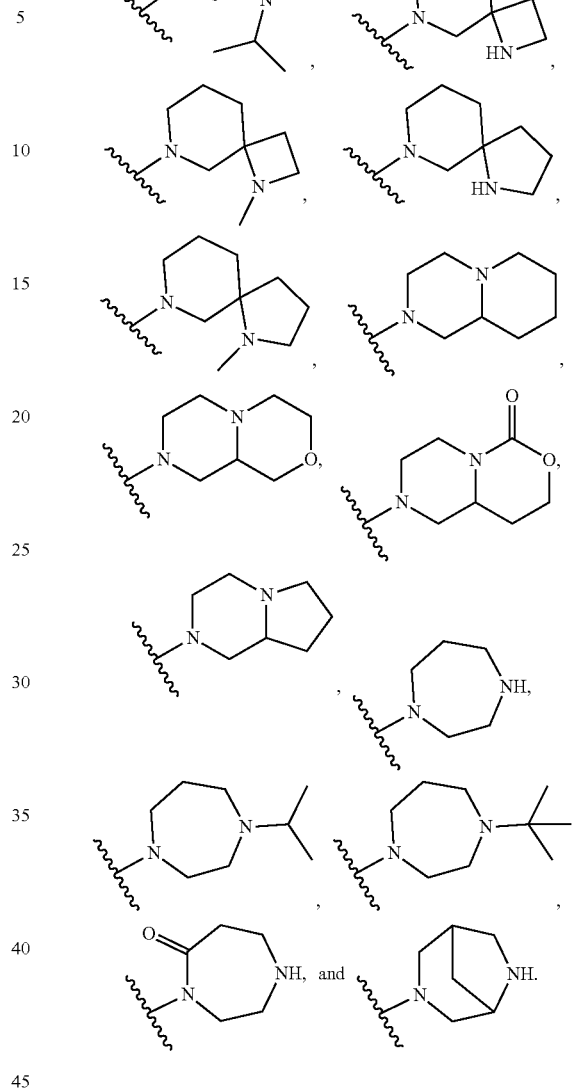
19. The compound of claim 1, selected from the following table:
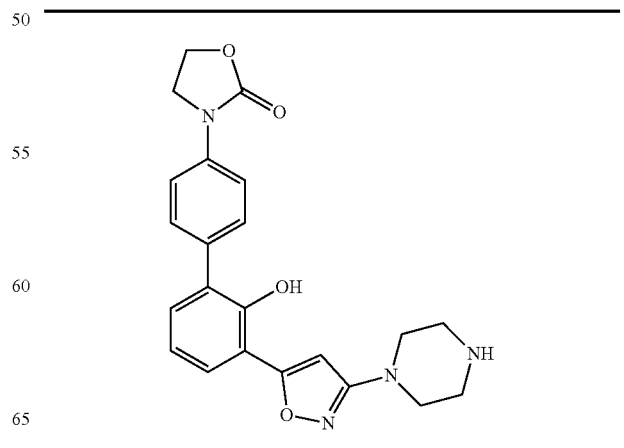

| 1355 | 1356 |
|---|---|
| 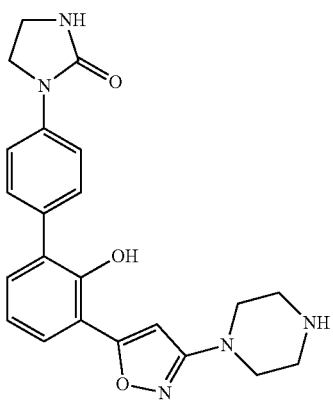 [SMILES: O=C1NCCN1c1ccc(-c2cccc(-c3cc(N4CCNCC4)no3)c2O)cc1] | 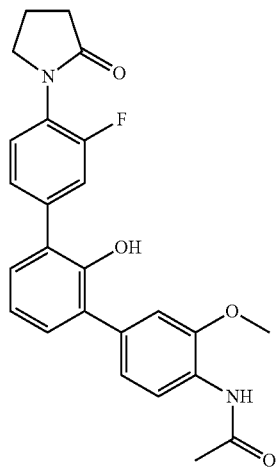 |
| 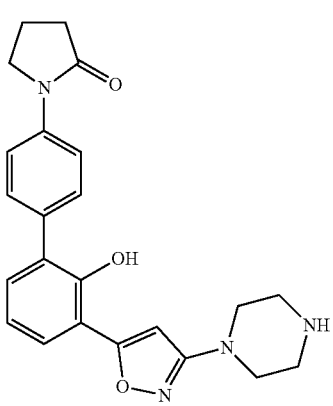 [SMILES: O=C1CCCN1c1ccc(-c2cccc(-c3cc(N4CCNCC4)no3)c2O)cc1] | 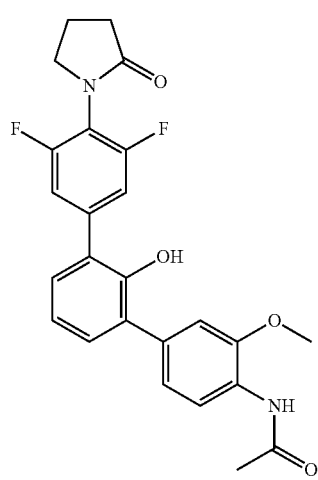 |
| 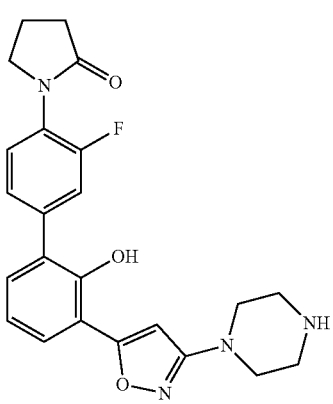 [SMILES: O=C1CCCN1c1ccc(-c2cccc(-c3cc(N4CCNCC4)no3)c2O)cc1F] | 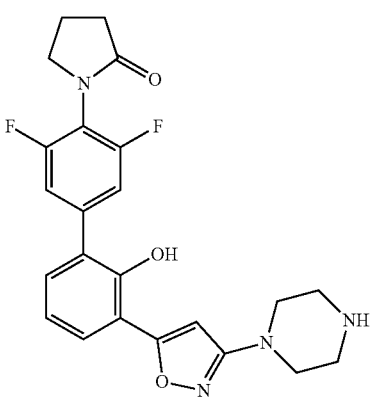 [SMILES: O=C1CCCN1c1c(F)cc(-c2cccc(-c3cc(N4CCNCC4)no3)c2O)cc1F] |

| 1357 -continued | 1358 -continued |
|---|---|
| 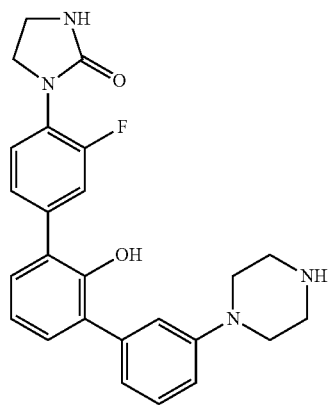 [SMILES: O=C1NCCN1c1ccc(-c2cccc(-c3cccc(N4CCNCC4)c3)c2O)cc1F] | 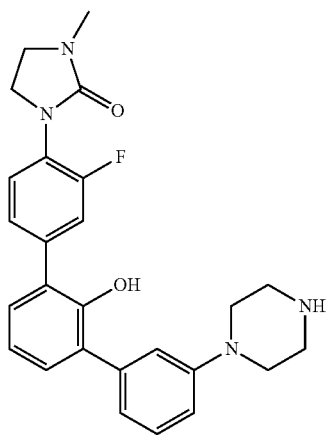 |
| 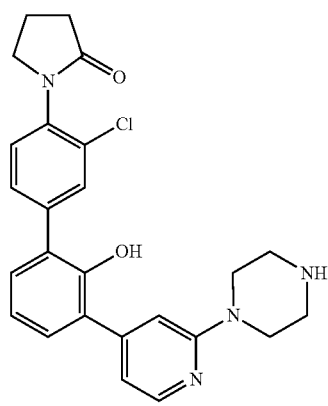 [SMILES: O=C1CCCN1c1ccc(-c2cccc(-c3ccnc(N4CCNCC4)c3)c2O)cc1Cl] | 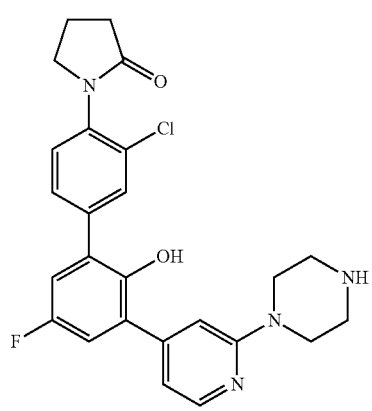 |
| 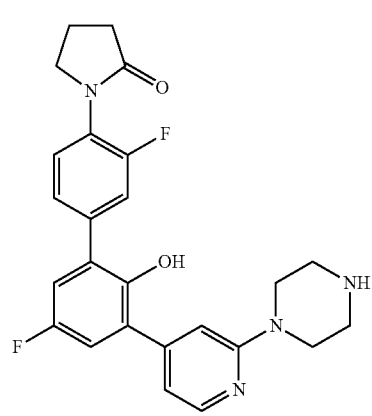 [SMILES: O=C1CCCN1c1ccc(-c2cc(F)cc(-c3ccnc(N4CCNCC4)c3)c2O)cc1F] | 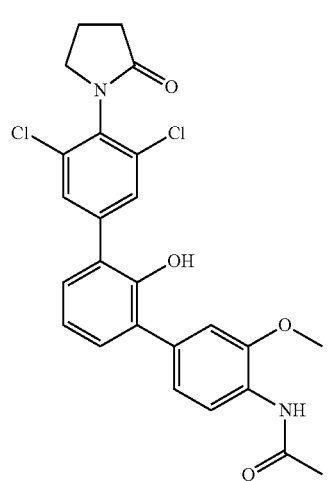 [SMILES: COc1cc(-c2cccc(-c3cc(Cl)c(N4CCCC4=O)c(Cl)c3)c2O)ccc1NC(C)=O] |

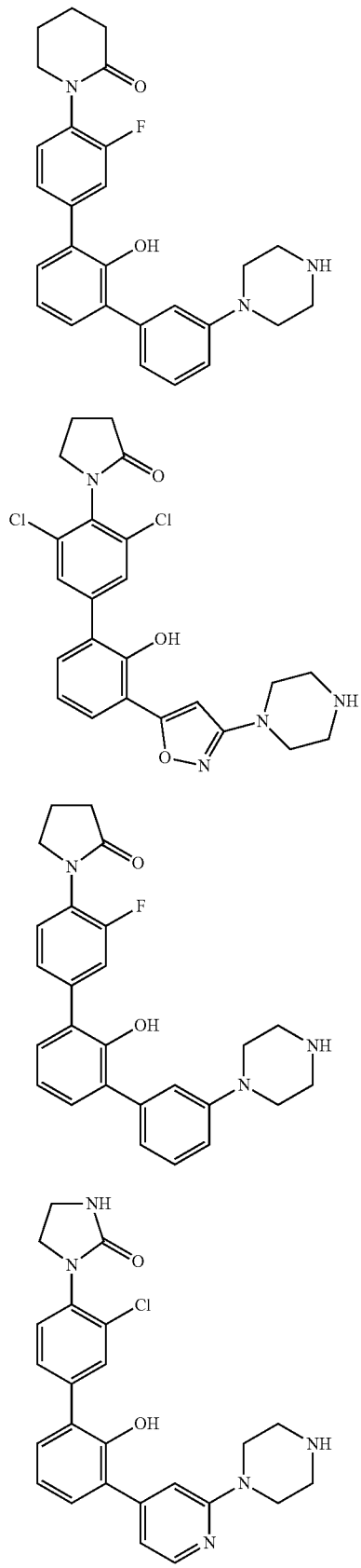
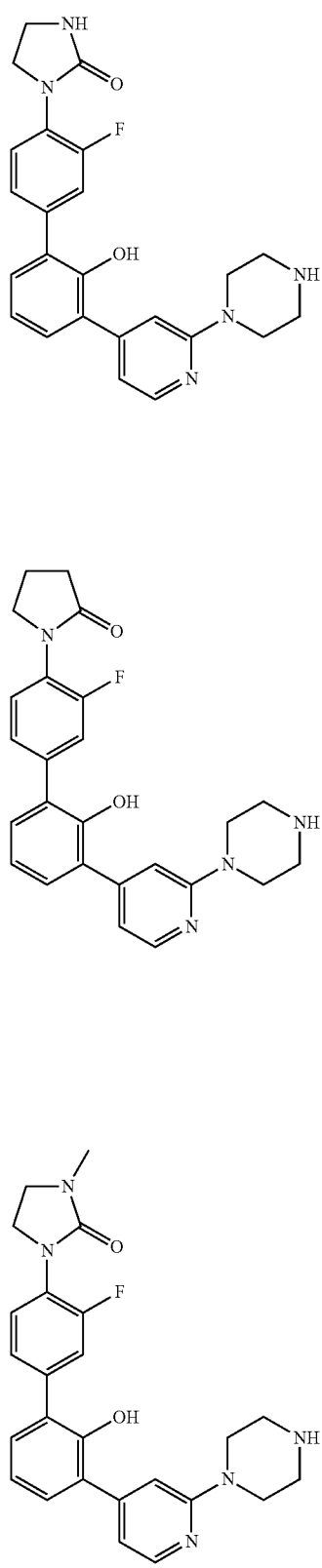

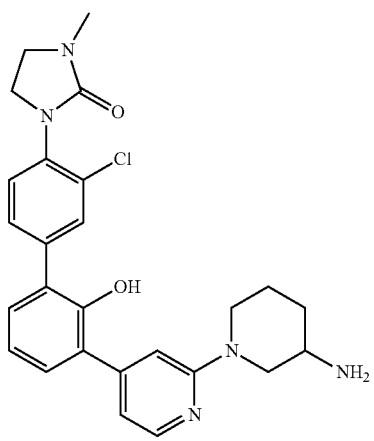 [SMILES: CN1CCN(c2ccc(-c3cccc(-c4ccnc(N5CCCC(N)C5)c4)c3O)cc2Cl)C1=O]
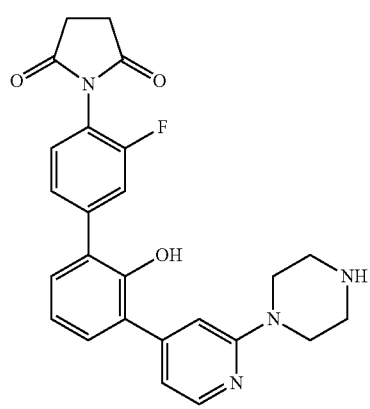 [SMILES: O=C1CCC(=O)N1c1ccc(-c2cccc(-c3ccnc(N4CCNCC4)c3)c2O)cc1F]
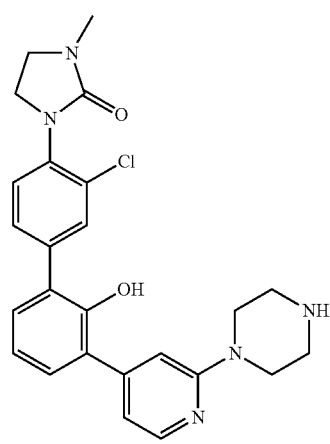 [SMILES: CN1CCN(c2ccc(-c3cccc(-c4ccnc(N5CCNCC5)c4)c3O)cc2Cl)C1=O]
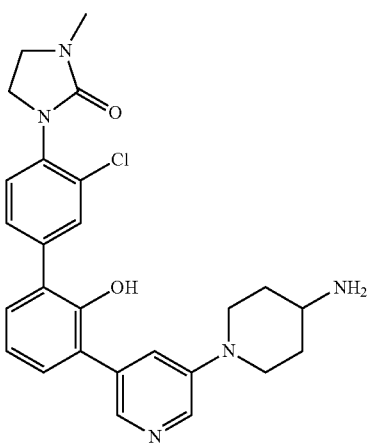 [SMILES: CN1CCN(c2ccc(-c3cccc(-c4cncc(N5CCC(N)CC5)c4)c3O)cc2Cl)C1=O]
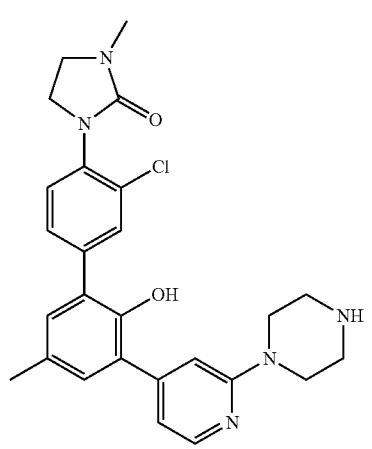 [SMILES: Cc1cc(-c2ccnc(N3CCNCC3)c2)c(O)c(-c2ccc(N3CCN(C)C3=O)c(Cl)c2)c1]
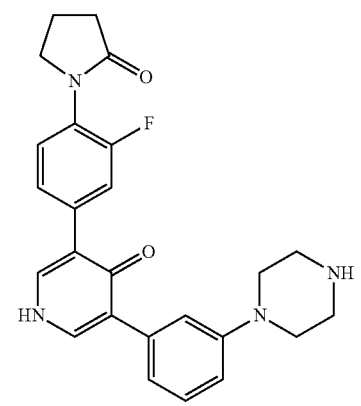 [SMILES: O=C1CCCN1c1ccc(-c2c[nH]cc(-c3cccc(N4CCNCC4)c3)c2=O)cc1F]

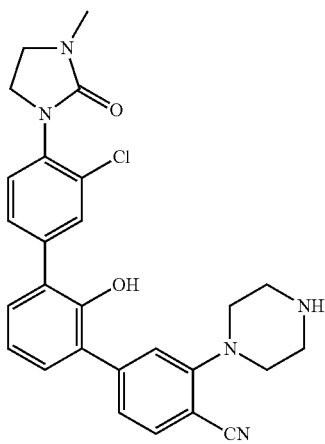 [SMILES: CN1CCN(c2ccc(-c3cccc(-c4ccc(C#N)c(N5CCNCC5)c4)c3O)cc2Cl)C1=O]
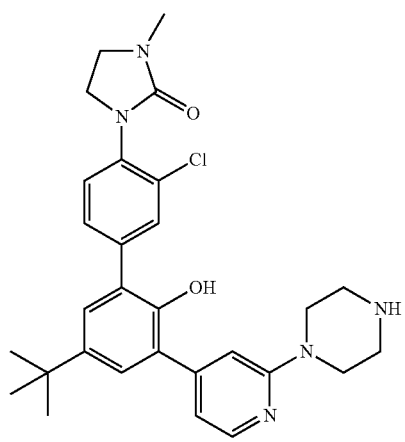
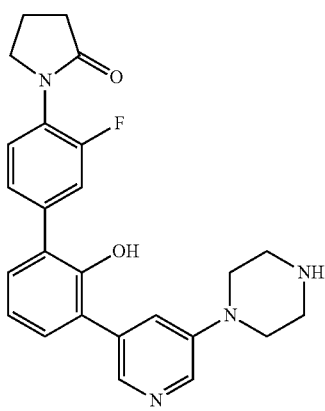 [SMILES: O=C1CCCN1c1ccc(-c2cccc(-c3cncc(N4CCNCC4)c3)c2O)cc1F]
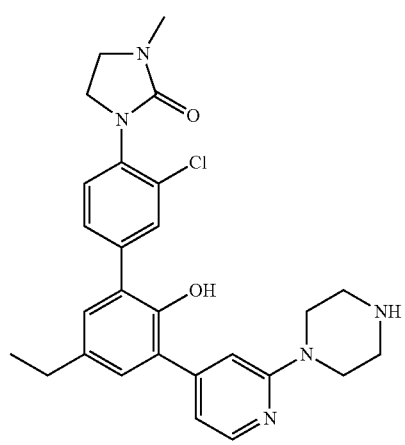
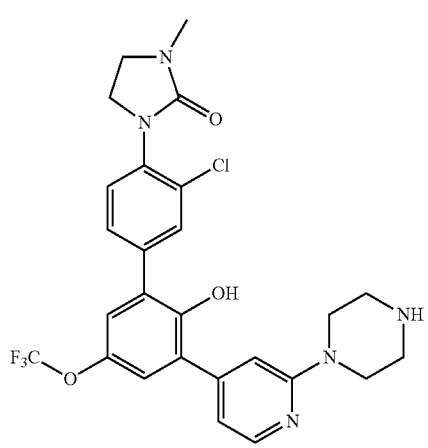 [SMILES: CN1CCN(c2ccc(-c3cc(OC(F)(F)F)cc(-c4ccnc(N5CCNCC5)c4)c3O)cc2Cl)C1=O]
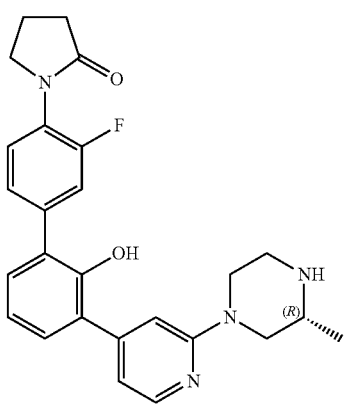

1365
-continued
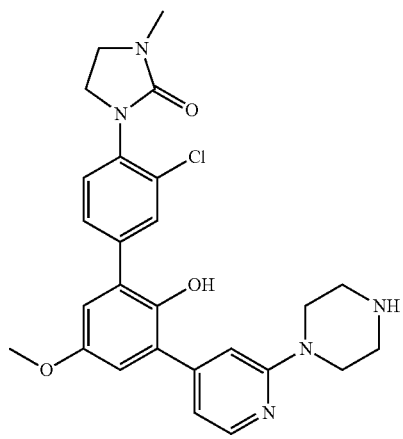 [SMILES: COc1cc(-c2ccnc(N3CCNCC3)c2)c(O)c(-c2ccc(N3CCN(C)C3=O)c(Cl)c2)c1]
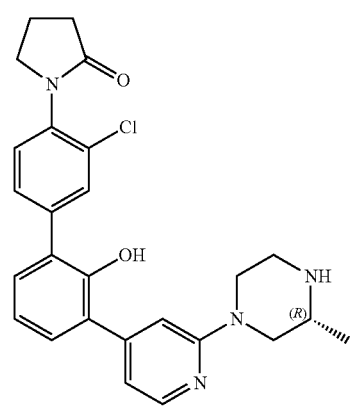
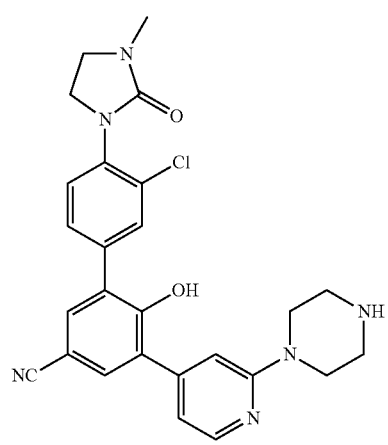 [SMILES: CN1CCN(c2ccc(-c3cc(C#N)cc(-c4ccnc(N5CCNCC5)c4)c3O)cc2Cl)C1=O]
1366
-continued
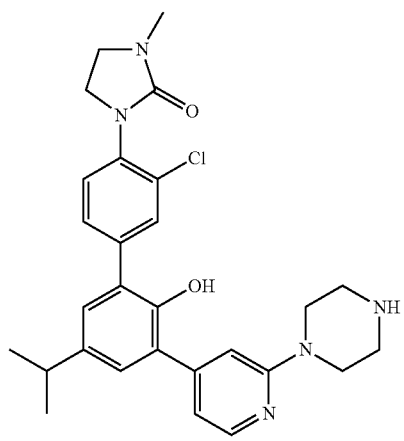 [SMILES: CC(C)c1cc(-c2ccnc(N3CCNCC3)c2)c(O)c(-c2ccc(N3CCN(C)C3=O)c(Cl)c2)c1]
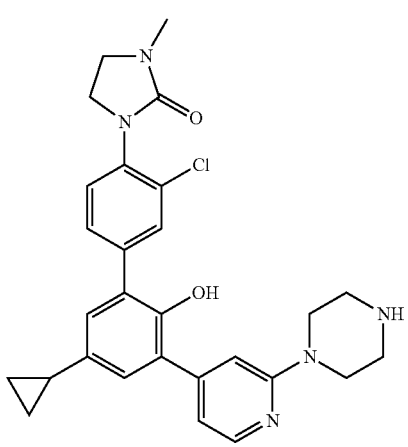 [SMILES: CN1CCN(c2ccc(-c3cc(C4CC4)cc(-c4ccnc(N5CCNCC5)c4)c3O)cc2Cl)C1=O]
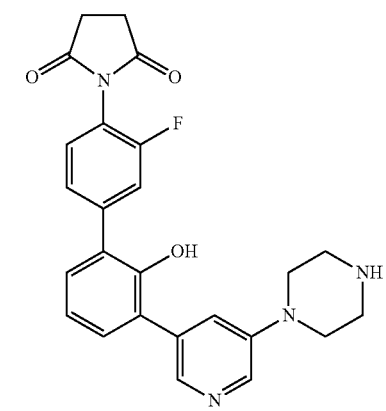 [SMILES: O=C1CCC(=O)N1c1ccc(-c2cccc(-c3cncc(N4CCNCC4)c3)c2O)cc1F]

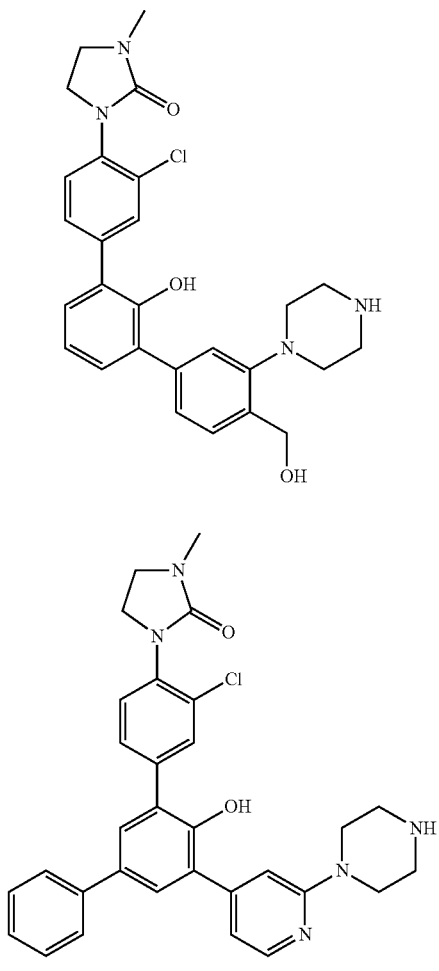
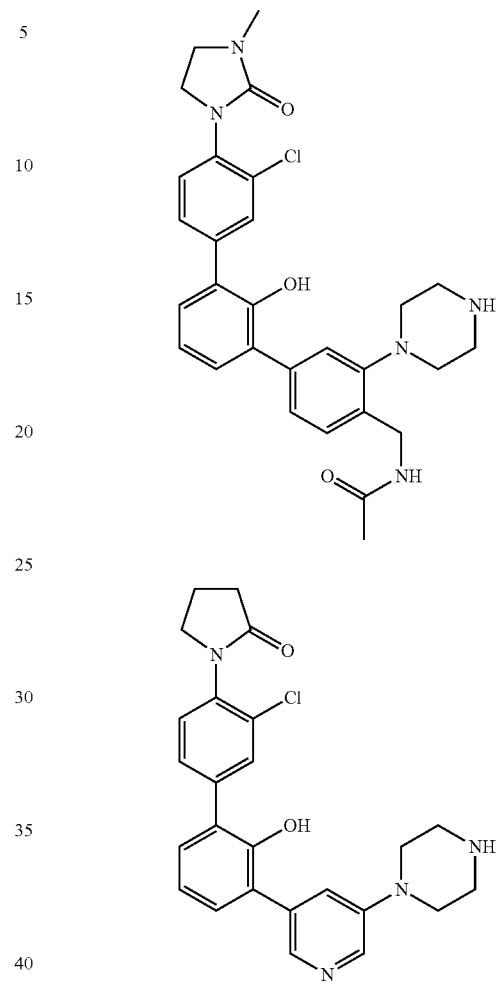
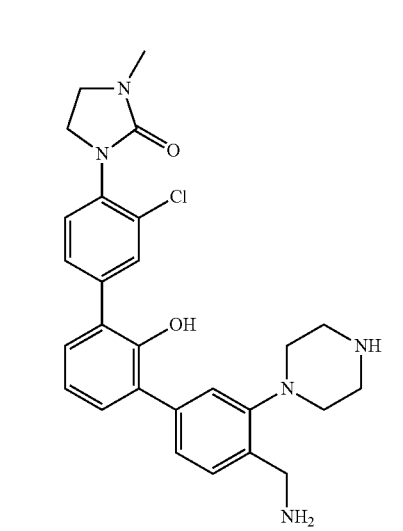 [SMILES: CN1CCN(c2ccc(-c3cccc(-c4ccc(CN)c(N5CCNCC5)c4)c3O)cc2Cl)C1=O]
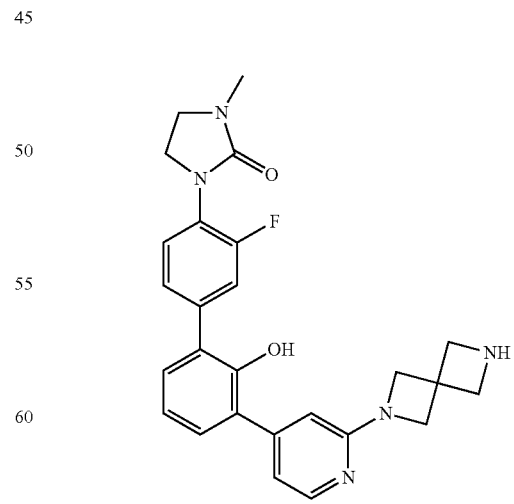

1369
-continued
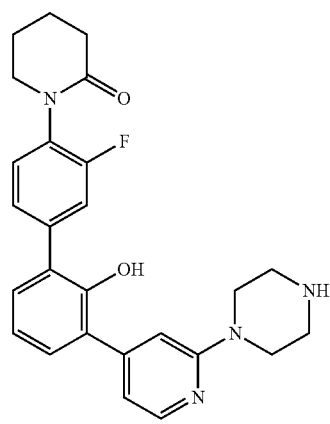 [SMILES: O=C1CCCCN1c1ccc(-c2cccc(-c3ccnc(N4CCNCC4)c3)c2O)cc1F]
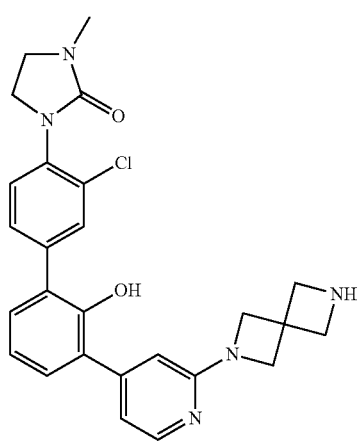 [SMILES: CN1CCN(c2ccc(-c3cccc(-c4ccnc(N5CC6(CNC6)C5)c4)c3O)cc2Cl)C1=O]
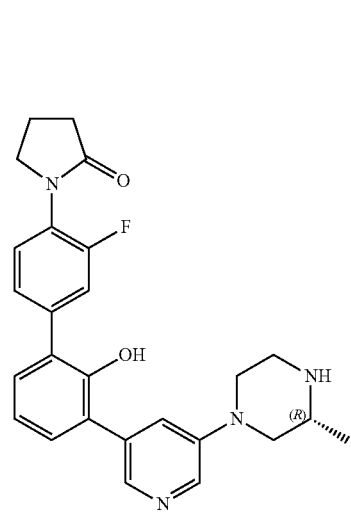
1370
-continued
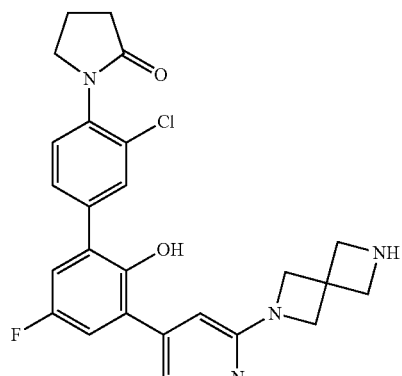
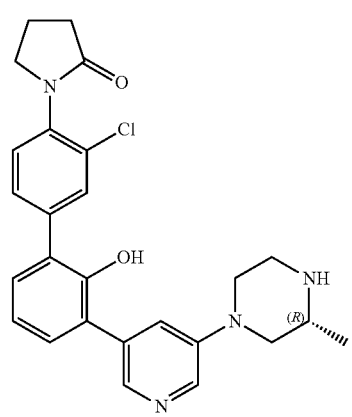
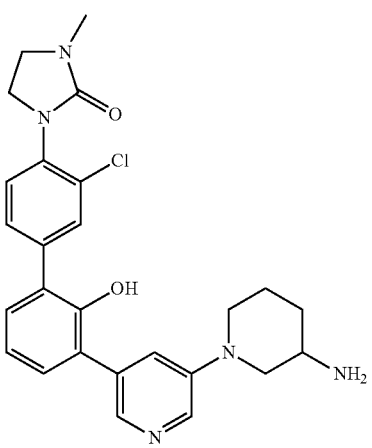 [SMILES: CN1CCN(c2ccc(-c3cccc(-c4cncc(N5CCCC(N)C5)c4)c3O)cc2Cl)C1=O]

1371
-continued
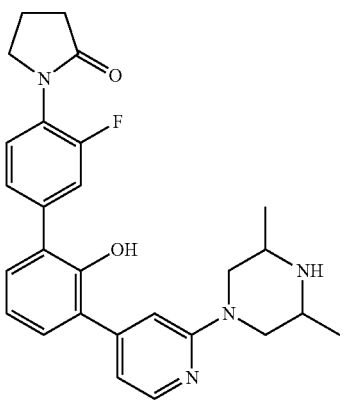 [SMILES: CC1CN(c2cc(-c3cccc(-c4ccc(N5CCCC5=O)c(F)c4)c3O)ccn2)CC(C)N1]
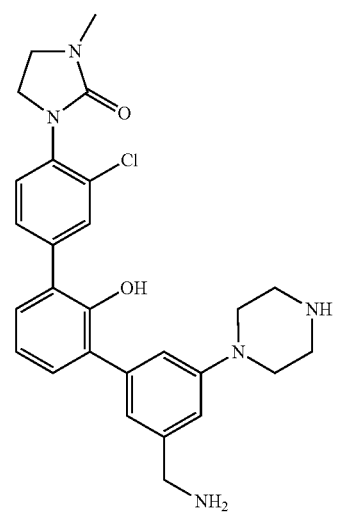 [SMILES: CN1CCN(c2ccc(-c3cccc(-c4cc(CN)cc(N5CCNCC5)c4)c3O)cc2Cl)C1=O]
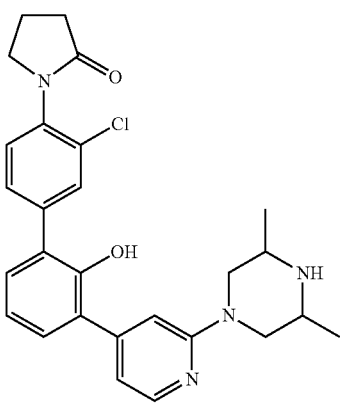
1372
-continued
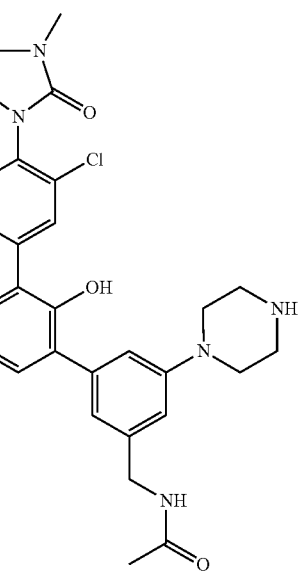
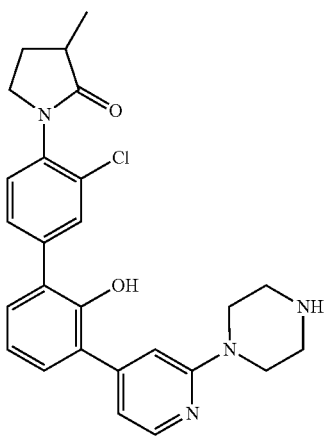 [SMILES: CC1CCN(c2ccc(-c3cccc(-c4ccnc(N5CCNCC5)c4)c3O)cc2Cl)C1=O]
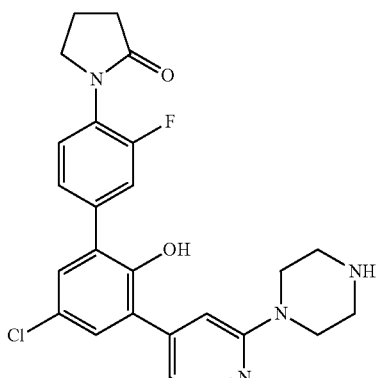

1373
-continued
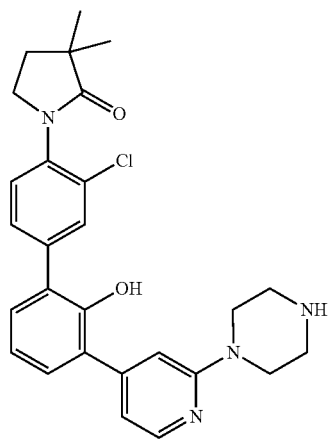 [SMILES: CC1(C)CCN(c2ccc(-c3cccc(-c4ccnc(N5CCNCC5)c4)c3O)cc2Cl)C1=O]
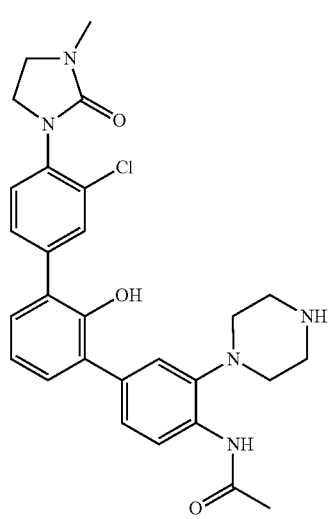 [SMILES: CC(=O)Nc1ccc(-c2cccc(-c3ccc(N4CCN(C)C4=O)c(Cl)c3)c2O)cc1N1CCNCC1]
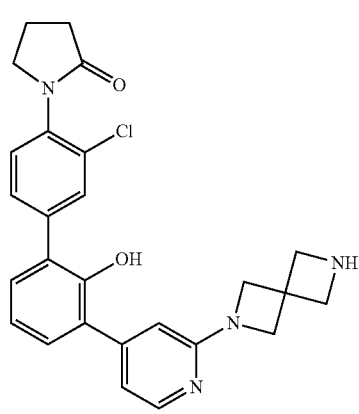 [SMILES: O=C1CCCN1c1ccc(-c2cccc(-c3ccnc(N4CC5(CNC5)C4)c3)c2O)cc1Cl]
1374
-continued
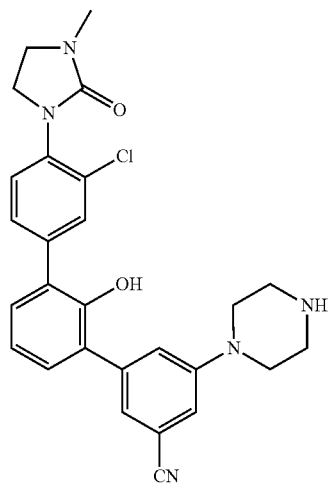 [SMILES: CN1CCN(c2ccc(-c3cccc(-c4cc(C#N)cc(N5CCNCC5)c4)c3O)cc2Cl)C1=O]
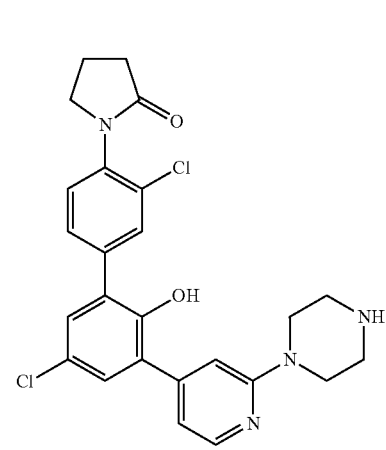 [SMILES: O=C1CCCN1c1ccc(-c2cc(Cl)cc(-c3ccnc(N4CCNCC4)c3)c2O)cc1Cl]

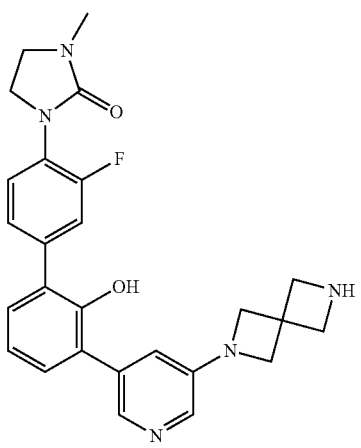 [SMILES: CN1CCN(c2ccc(-c3cccc(-c4cncc(N5CC6(CNC6)C5)c4)c3O)cc2F)C1=O]
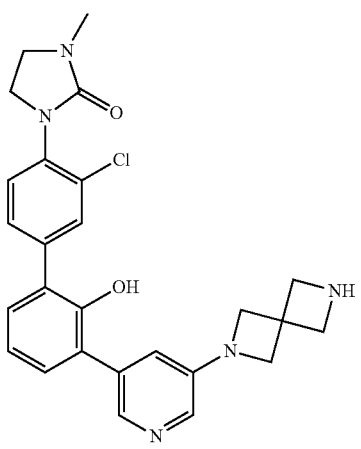 [SMILES: CN1CCN(c2ccc(-c3cccc(-c4cncc(N5CC6(CNC6)C5)c4)c3O)cc2Cl)C1=O]
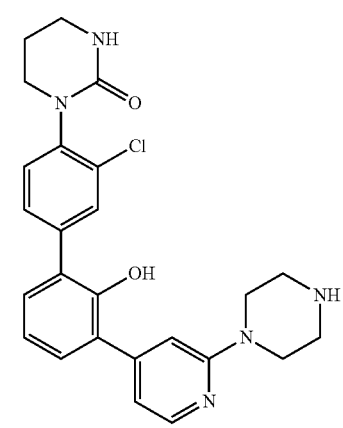 [SMILES: O=C1NCCCN1c1ccc(-c2cccc(-c3ccnc(N4CCNCC4)c3)c2O)cc1Cl]
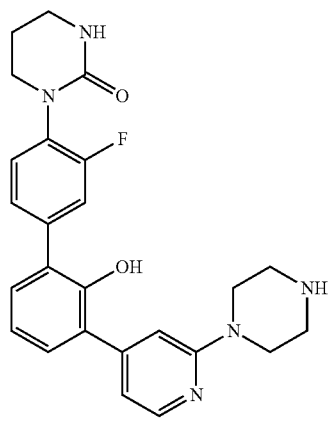 [SMILES: O=C1NCCCN1c1ccc(-c2cccc(-c3ccnc(N4CCNCC4)c3)c2O)cc1F]
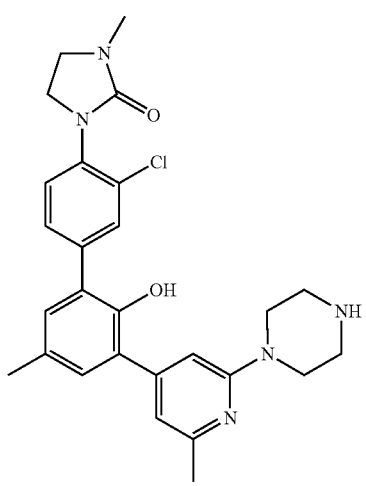 [SMILES: Cc1cc(-c2cc(C)nc(N3CCNCC3)c2)c(O)c(-c2ccc(N3CCN(C)C3=O)c(Cl)c2)c1]
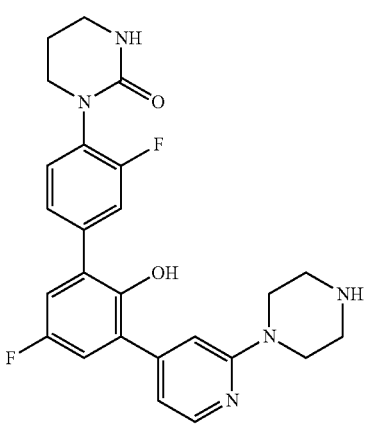 [SMILES: O=C1NCCCN1c1ccc(-c2cc(F)cc(-c3ccnc(N4CCNCC4)c3)c2O)cc1F]

| 1377 -continued | 1378 -continued |
|---|---|
| 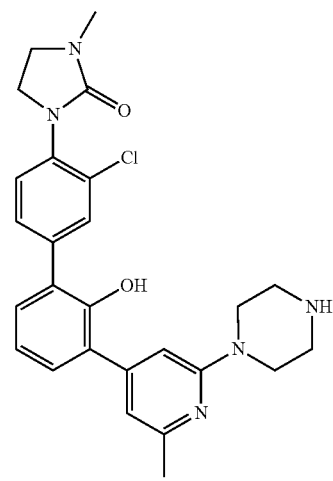 [SMILES: Cc1cc(-c2cccc(-c3ccc(N4CCN(C)C4=O)c(Cl)c3)c2O)cc(N2CCNCC2)n1] | 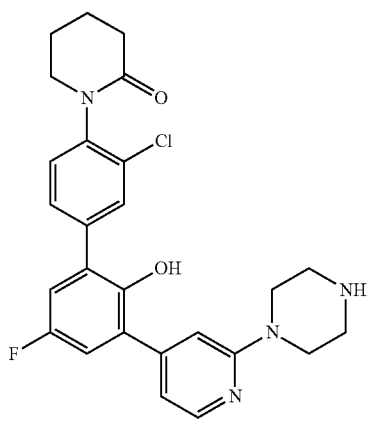 |
| 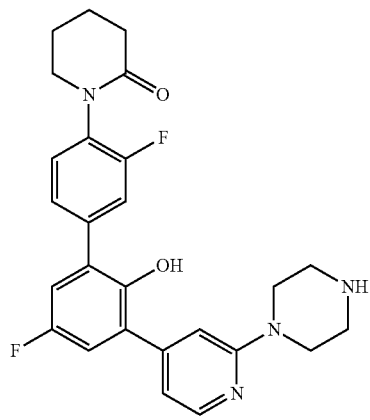 [SMILES: O=C1CCCCN1c1ccc(-c2cc(F)cc(-c3ccnc(N4CCNCC4)c3)c2O)cc1F] | 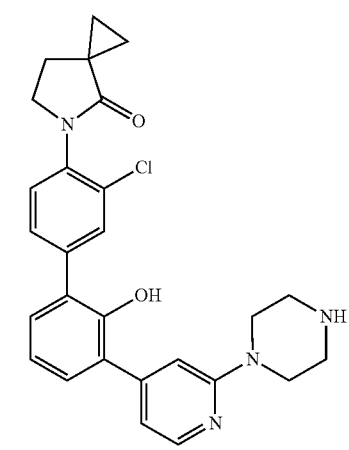 |
| 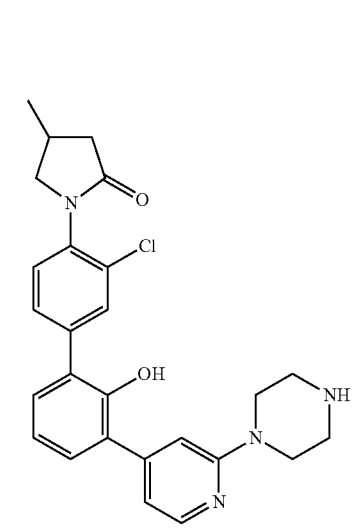 [SMILES: CC1CC(=O)N(c2ccc(-c3cccc(-c4ccnc(N5CCNCC5)c4)c3O)cc2Cl)C1] | 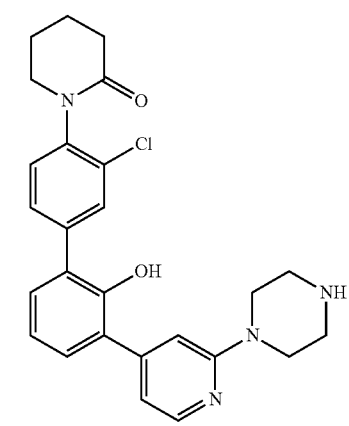 [SMILES: O=C1CCCCN1c1ccc(-c2cccc(-c3ccnc(N4CCNCC4)c3)c2O)cc1Cl] |

| 1379 -continued | 1380 -continued |
|---|---|
| 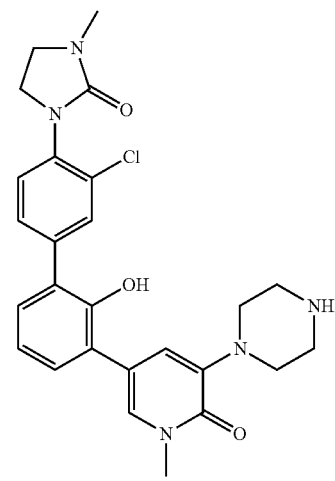 [SMILES: CN1CCN(c2ccc(-c3cccc(-c4cc(N5CCNCC5)c(=O)n(C)c4)c3O)cc2Cl)C1=O] | 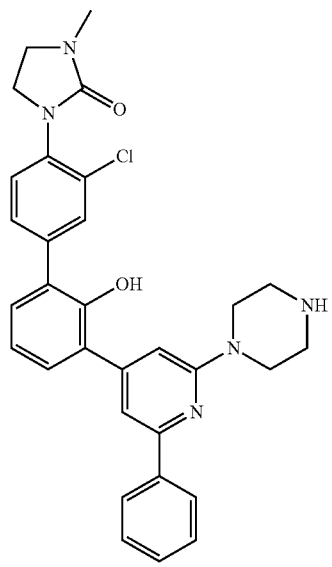 |
| 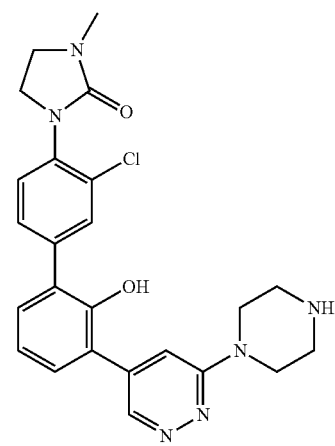 [SMILES: CN1CCN(c2ccc(-c3cccc(-c4cnnc(N5CCNCC5)c4)c3O)cc2Cl)C1=O] | 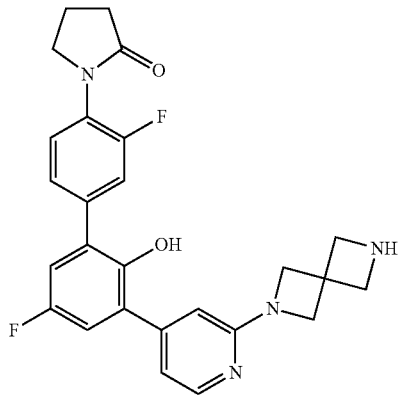 |
| 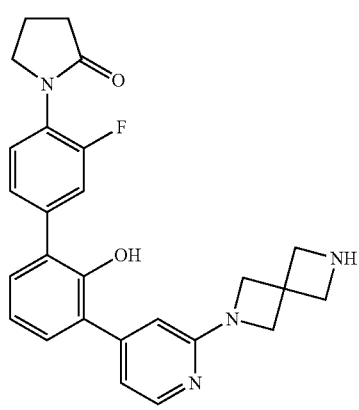 [SMILES: O=C1CCCN1c1ccc(-c2cccc(-c3ccnc(N4CC5(CNC5)C4)c3)c2O)cc1F] | 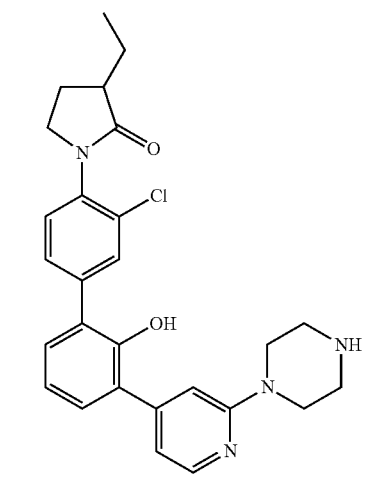 [SMILES: CCC1CCN(c2ccc(-c3cccc(-c4ccnc(N5CCNCC5)c4)c3O)cc2Cl)C1=O] |

1381
-continued
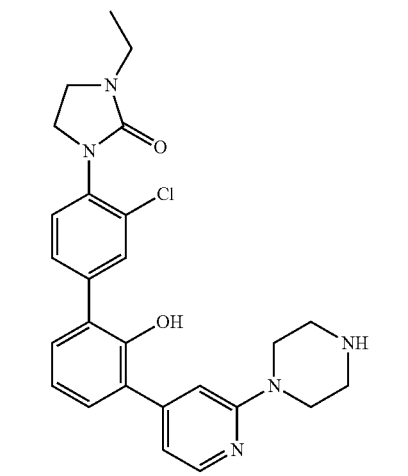 [SMILES: CCN1CCN(c2ccc(-c3cccc(-c4ccnc(N5CCNCC5)c4)c3O)cc2Cl)C1=O]
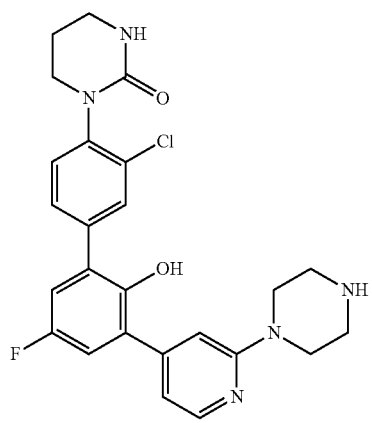 [SMILES: O=C1NCCCN1c1ccc(-c2cc(F)cc(-c3ccnc(N4CCNCC4)c3)c2O)cc1Cl]
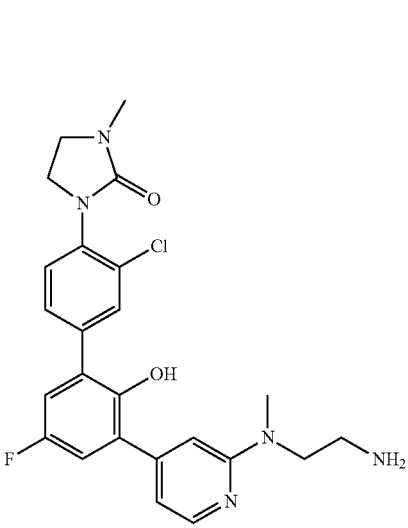 [SMILES: CN1CCN(c2ccc(-c3cc(F)cc(-c4ccnc(N(C)CCN)c4)c3O)cc2Cl)C1=O]
1382
-continued
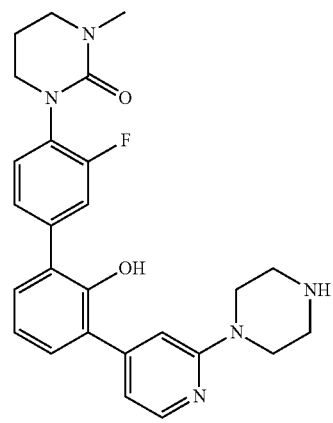 [SMILES: CN1CCCN(c2ccc(-c3cccc(-c4ccnc(N5CCNCC5)c4)c3O)cc2F)C1=O]
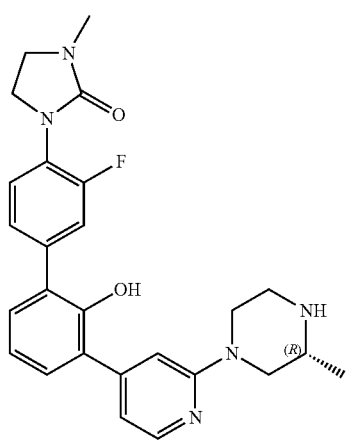
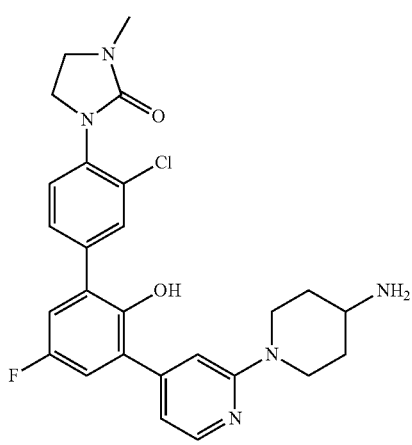 [SMILES: CN1CCN(c2ccc(-c3cc(F)cc(-c4ccnc(N5CCC(N)CC5)c4)c3O)cc2Cl)C1=O]

1383 -continued
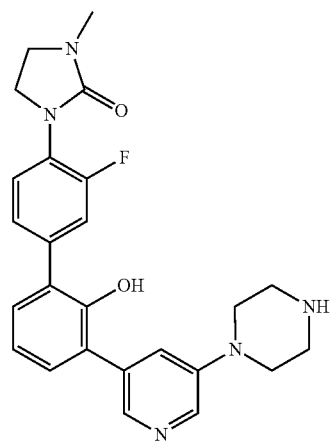 [SMILES: CN1CCN(c2ccc(-c3cccc(-c4cncc(N5CCNCC5)c4)c3O)cc2F)C1=O]
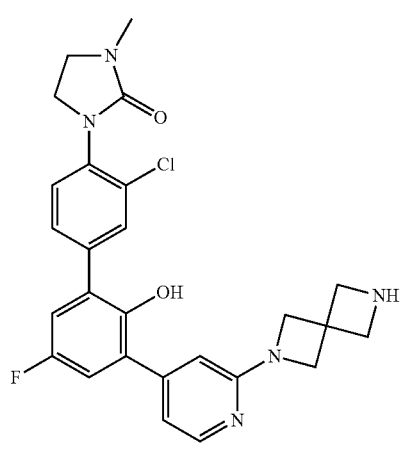 [SMILES: CN1CCN(c2ccc(-c3cc(F)cc(-c4ccnc(N5CC6(CNC6)C5)c4)c3O)cc2Cl)C1=O]
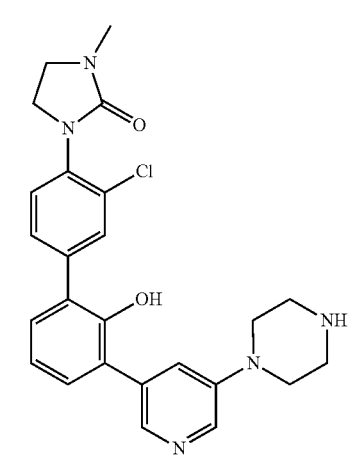 [SMILES: CN1CCN(c2ccc(-c3cccc(-c4cncc(N5CCNCC5)c4)c3O)cc2Cl)C1=O]
1384 -continued
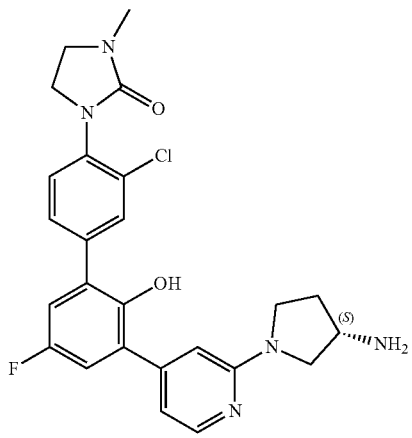
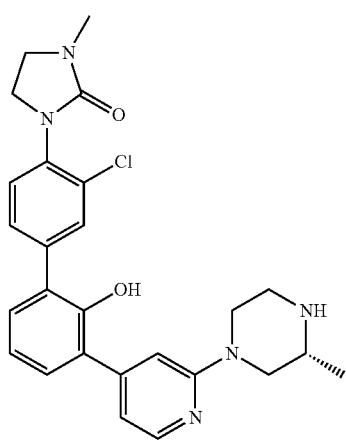 [SMILES: C[C@@H]1CN(c2cc(-c3cccc(-c4ccc(N5CCN(C)C5=O)c(Cl)c4)c3O)ccn2)CCN1]
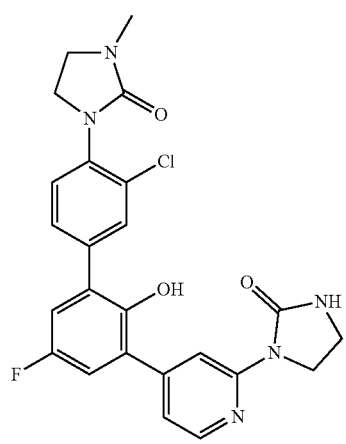 [SMILES: CN1CCN(c2ccc(-c3cc(F)cc(-c4ccnc(N5CCNC5=O)c4)c3O)cc2Cl)C1=O]

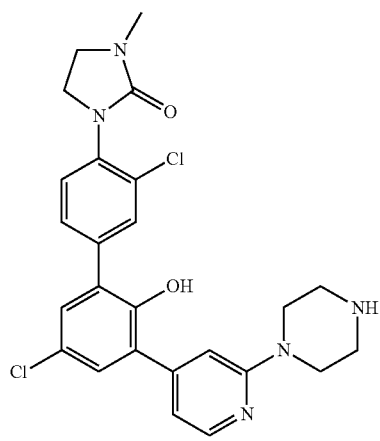 [SMILES: CN1CCN(c2ccc(-c3cc(Cl)cc(-c4ccnc(N5CCNCC5)c4)c3O)cc2Cl)C1=O]
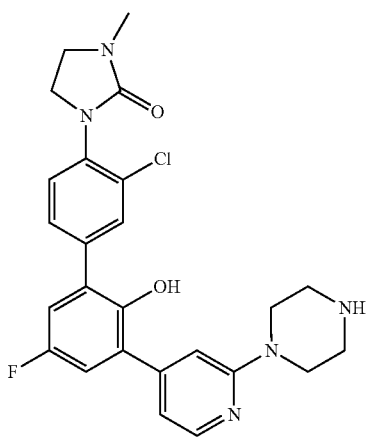
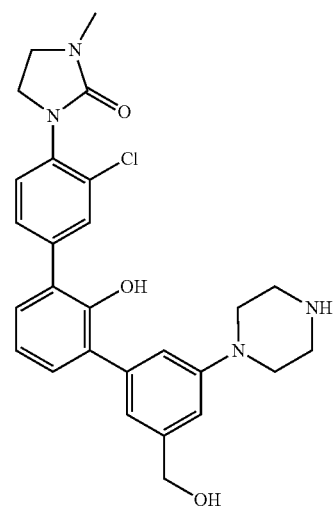 [SMILES: CN1CCN(c2ccc(-c3cccc(-c4cc(CO)cc(N5CCNCC5)c4)c3O)cc2Cl)C1=O]
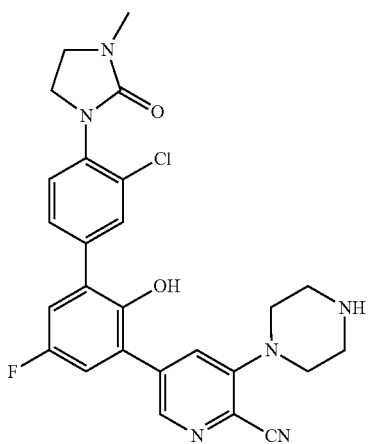
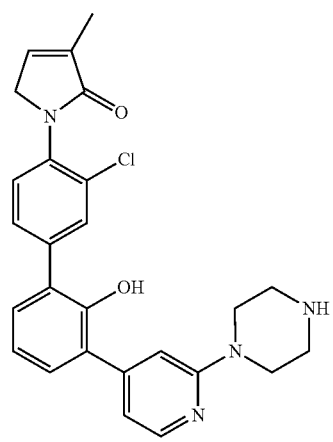 [SMILES: CC1=CCN(c2ccc(-c3cccc(-c4ccnc(N5CCNCC5)c4)c3O)cc2Cl)C1=O]
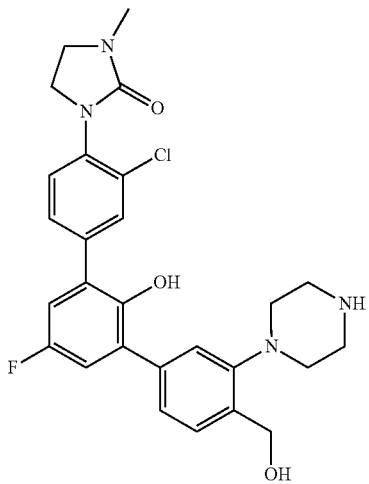 [SMILES: CN1CCN(c2ccc(-c3cc(F)cc(-c4ccc(CO)c(N5CCNCC5)c4)c3O)cc2Cl)C1=O]

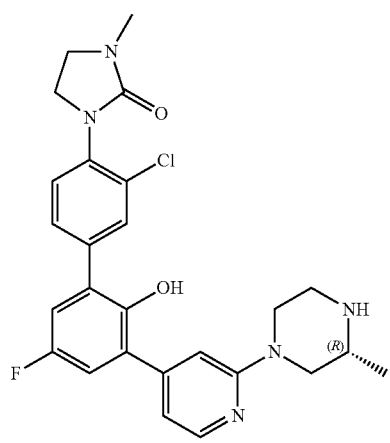
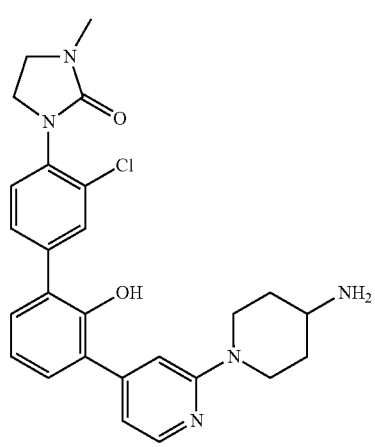 [SMILES: CN1CCN(c2ccc(-c3cccc(-c4ccnc(N5CCC(N)CC5)c4)c3O)cc2Cl)C1=O]
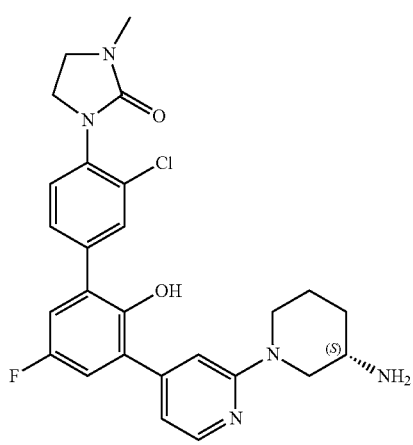
20. The compound of claim 1, selected from the following table:
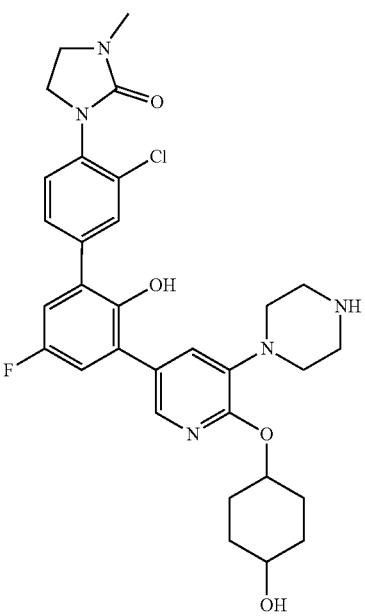 [SMILES: CN1CCN(c2ccc(-c3cc(F)cc(-c4cnc(OC5CCC(O)CC5)c(N5CCNCC5)c4)c3O)cc2Cl)C1=O]
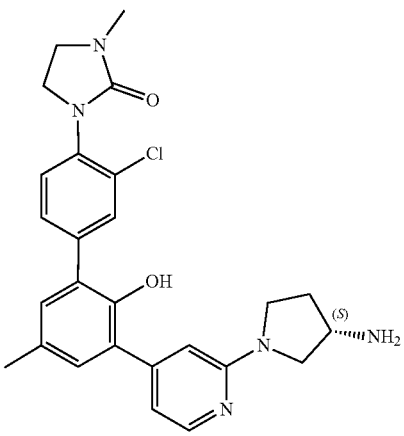
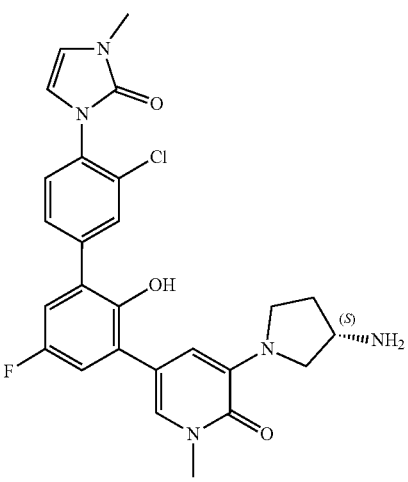

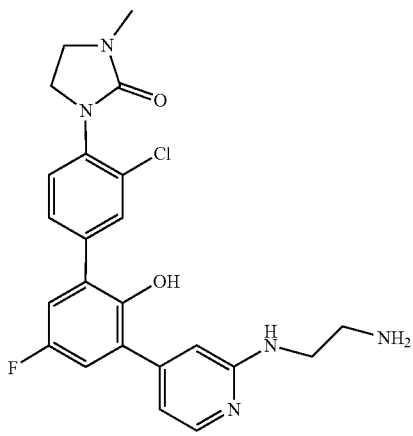 [SMILES: CN1CCN(c2ccc(-c3cc(F)cc(-c4ccnc(NCCN)c4)c3O)cc2Cl)C1=O]
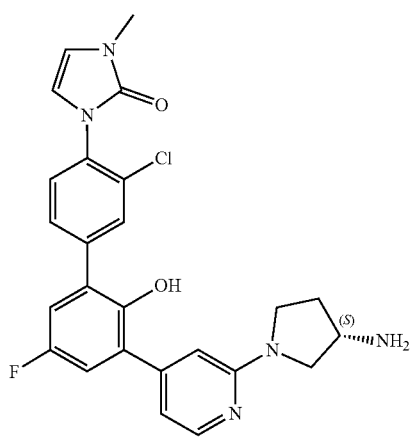
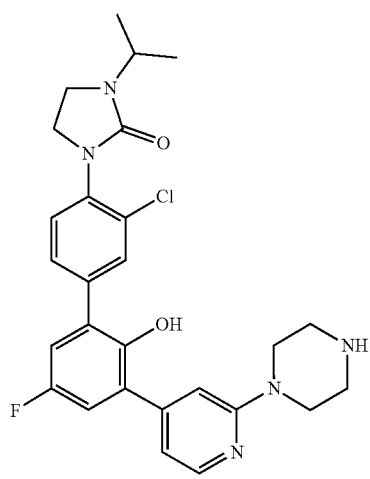 [SMILES: CC(C)N1CCN(c2ccc(-c3cc(F)cc(-c4ccnc(N5CCNCC5)c4)c3O)cc2Cl)C1=O]
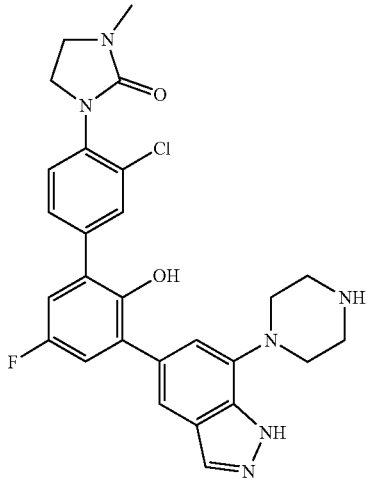 [SMILES: CN1CCN(c2ccc(-c3cc(F)cc(-c4cc(N5CCNCC5)c5[nH]ncc5c4)c3O)cc2Cl)C1=O]
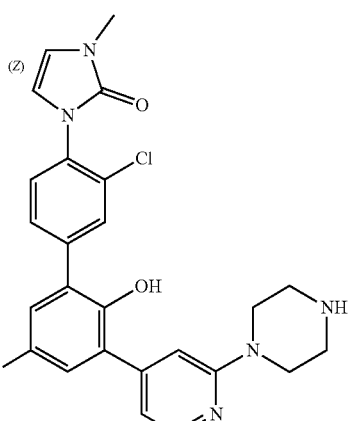
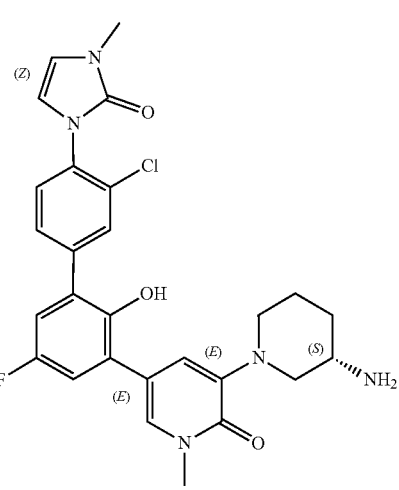

1391
-continued
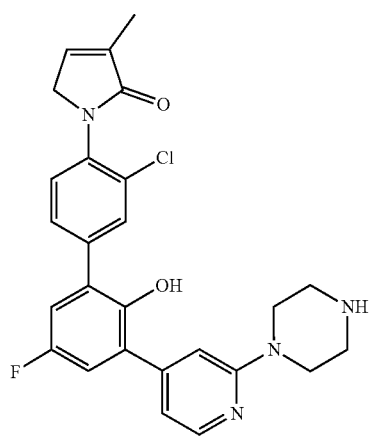
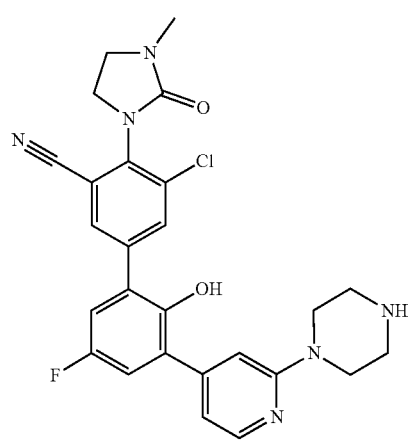 [SMILES: CN1CCN(c2c(Cl)cc(-c3cc(F)cc(-c4ccnc(N5CCNCC5)c4)c3O)cc2C#N)C1=O]
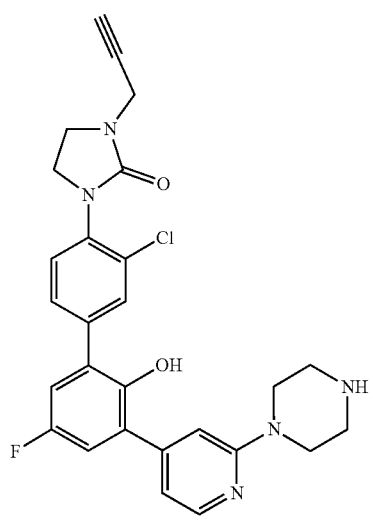 [SMILES: C#CCN1CCN(c2ccc(-c3cc(F)cc(-c4ccnc(N5CCNCC5)c4)c3O)cc2Cl)C1=O]
1392
-continued
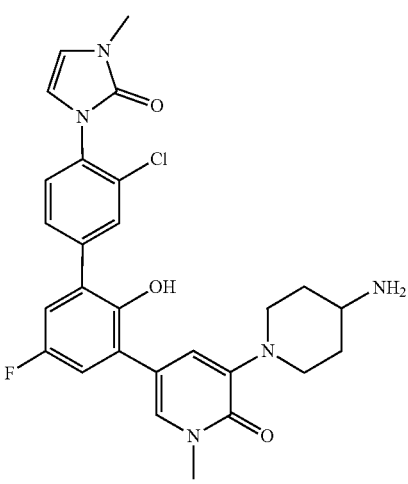 [SMILES: Cn1cc(-c2cc(F)cc(-c3ccc(-n4ccn(C)c4=O)c(Cl)c3)c2O)cc(N2CCC(N)CC2)c1=O]
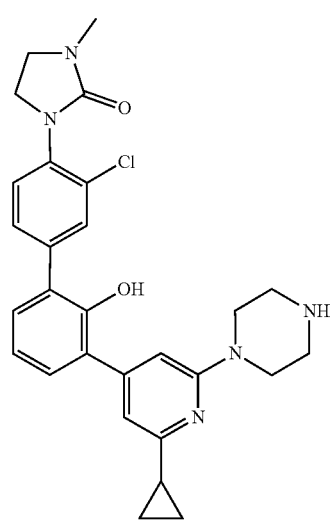 [SMILES: CN1CCN(c2ccc(-c3cccc(-c4cc(C5CC5)nc(N5CCNCC5)c4)c3O)cc2Cl)C1=O]
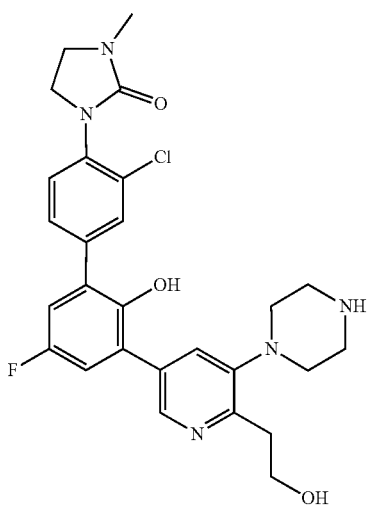 [SMILES: CN1CCN(c2ccc(-c3cc(F)cc(-c4cnc(CCO)c(N5CCNCC5)c4)c3O)cc2Cl)C1=O]

1393
-continued
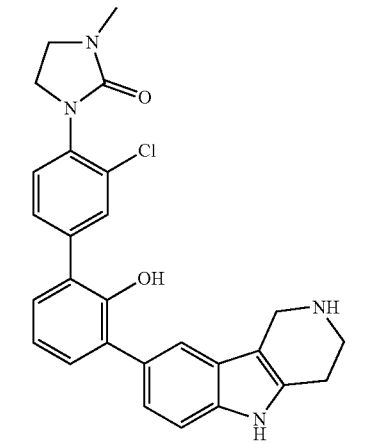 [SMILES: CN1CCN(c2ccc(-c3cccc(-c4ccc5[nH]c6c(c5c4)CNCC6)c3O)cc2Cl)C1=O]
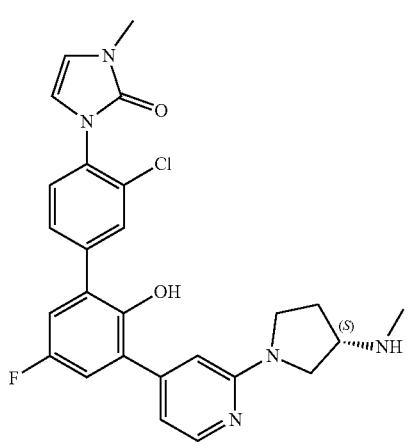
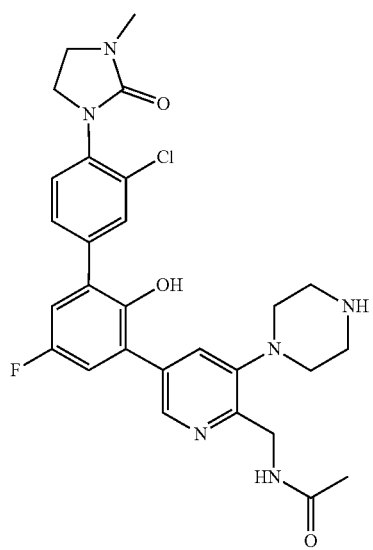
1394
-continued
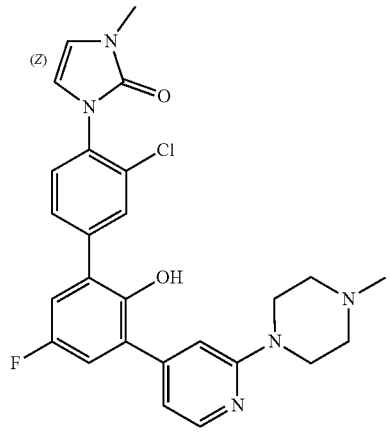 [SMILES: CN1CCN(c2cc(-c3cc(F)cc(-c4ccc(-n5ccn(C)c5=O)c(Cl)c4)c3O)ccn2)CC1]
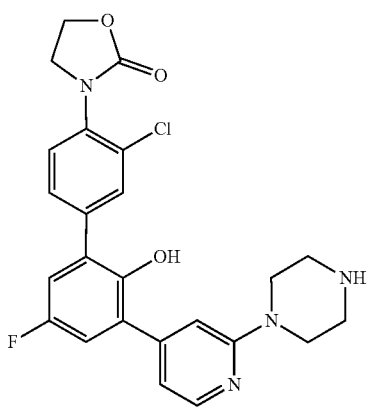 [SMILES: O=C1OCCN1c1ccc(-c2cc(F)cc(-c3ccnc(N4CCNCC4)c3)c2O)cc1Cl]
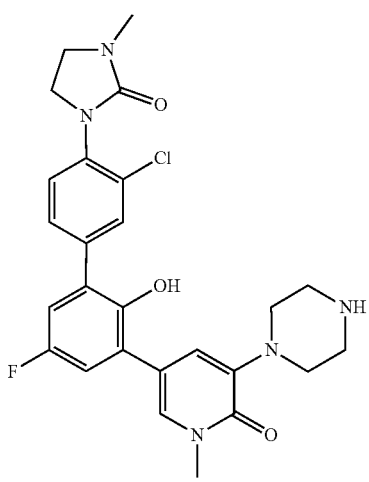 [SMILES: CN1CCN(c2ccc(-c3cc(F)cc(-c4cc(N5CCNCC5)c(=O)n(C)c4)c3O)cc2Cl)C1=O]

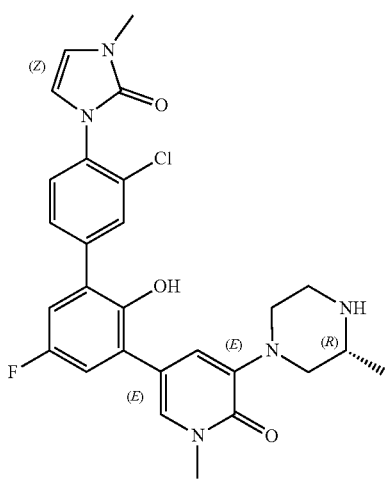
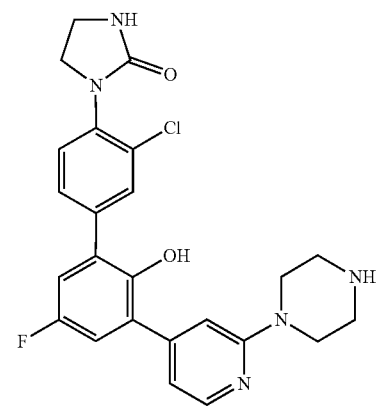 [SMILES: O=C1NCCN1c1ccc(-c2cc(F)cc(-c3ccnc(N4CCNCC4)c3)c2O)cc1Cl]
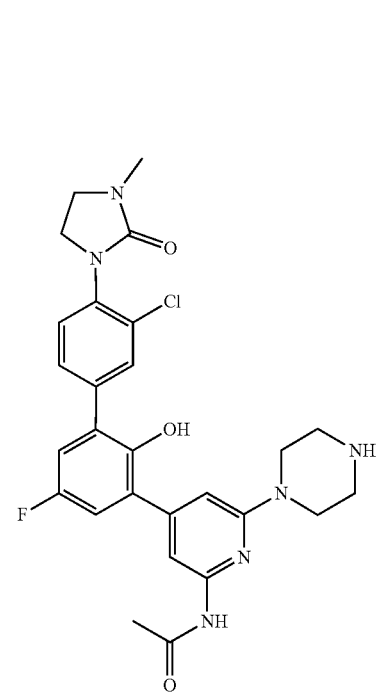 [SMILES: CC(=O)Nc1cc(-c2cc(F)cc(-c3ccc(N4CCN(C)C4=O)c(Cl)c3)c2O)cc(N2CCNCC2)n1]
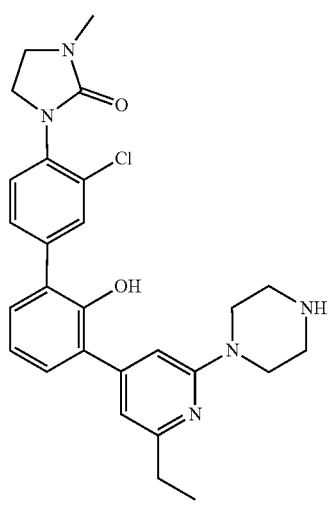 [SMILES: CCc1cc(-c2cccc(-c3ccc(N4CCN(C)C4=O)c(Cl)c3)c2O)cc(N2CCNCC2)n1]
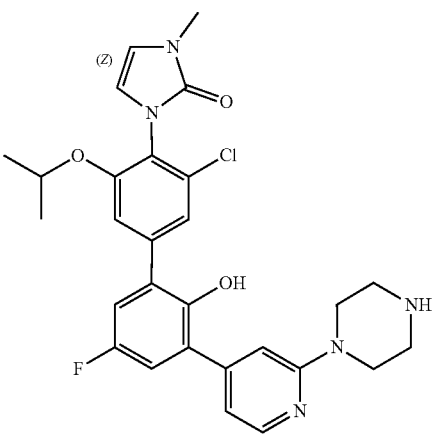 [SMILES: CC(C)Oc1cc(-c2cc(F)cc(-c3ccnc(N4CCNCC4)c3)c2O)cc(Cl)c1-n1ccn(C)c1=O]
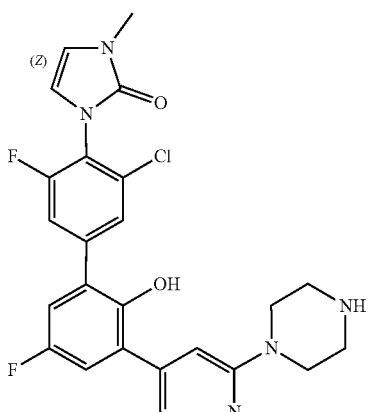

1397
-continued
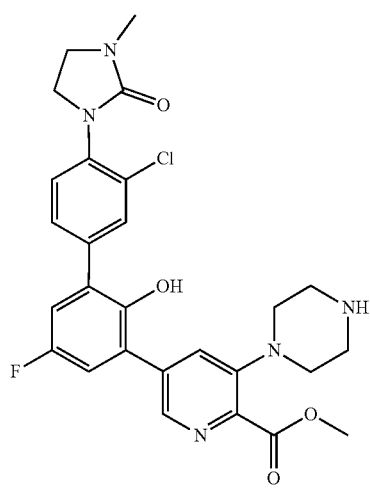 [SMILES: COC(=O)c1ncc(-c2cc(F)cc(-c3ccc(N4CCN(C)C4=O)c(Cl)c3)c2O)cc1N1CCNCC1]
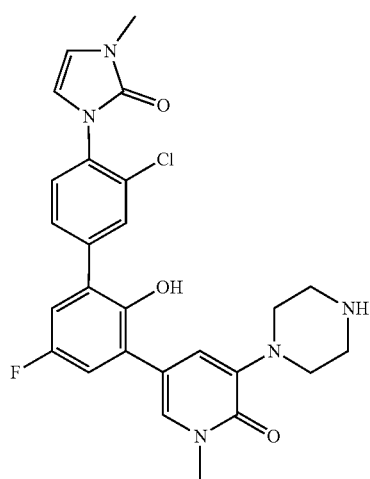 [SMILES: Cn1cc(-c2cc(F)cc(-c3ccc(-n4ccn(C)c4=O)c(Cl)c3)c2O)cc(N2CCNCC2)c1=O]
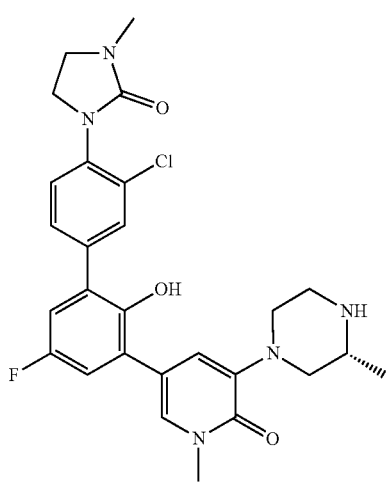 [SMILES: C[C@@H]1CN(c2cc(-c3cc(F)cc(-c4ccc(N5CCN(C)C5=O)c(Cl)c4)c3O)cn(C)c2=O)CCN1]
1398
-continued
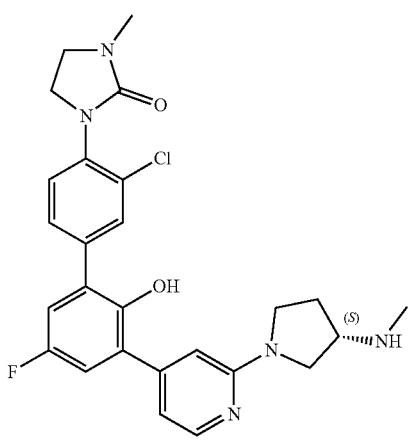
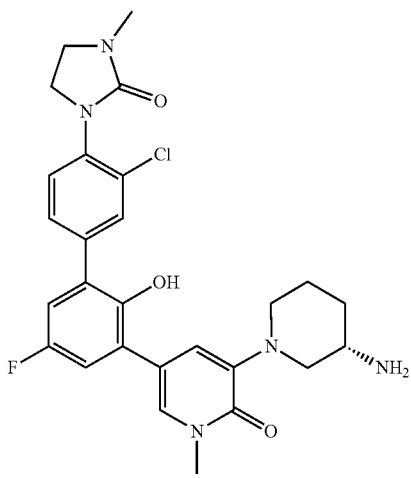 [SMILES: CN1CCN(c2ccc(-c3cc(F)cc(-c4cc(N5CCC[C@H](N)C5)c(=O)n(C)c4)c3O)cc2Cl)C1=O]
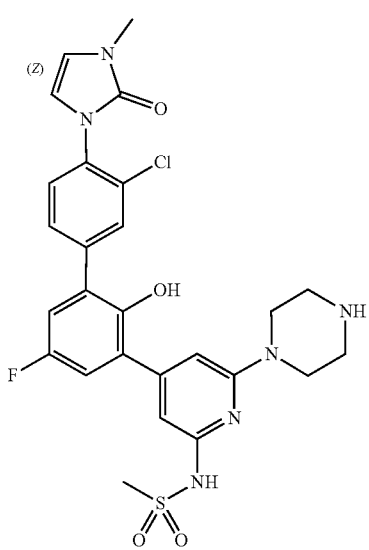 [SMILES: Cn1ccn(-c2ccc(-c3cc(F)cc(-c4cc(NS(C)(=O)=O)nc(N5CCNCC5)c4)c3O)cc2Cl)c1=O]

1399
-continued
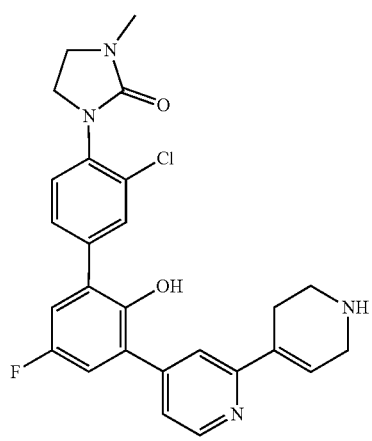 [SMILES: CN1CCN(c2ccc(-c3cc(F)cc(-c4ccnc(C5=CCNCC5)c4)c3O)cc2Cl)C1=O]
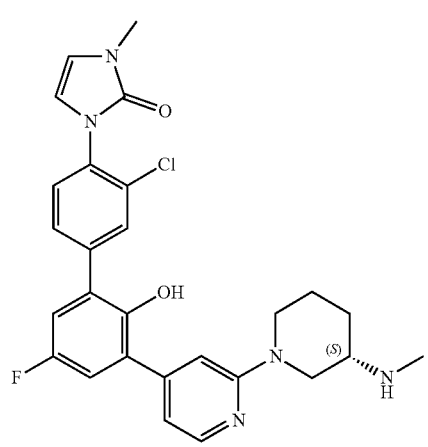
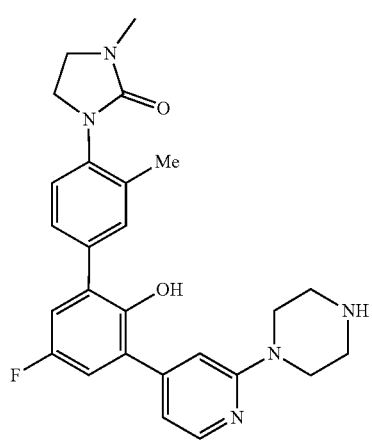 [SMILES: Cc1cc(-c2cc(F)cc(-c3ccnc(N4CCNCC4)c3)c2O)ccc1N1CCN(C)C1=O]
1400
-continued
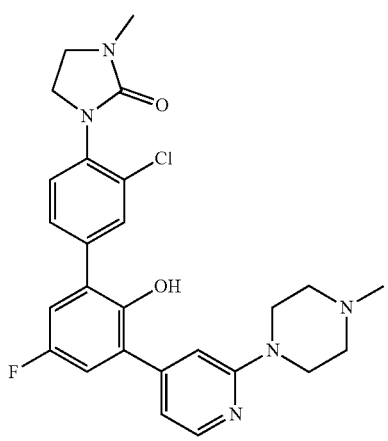 [SMILES: CN1CCN(c2cc(-c3cc(F)cc(-c4ccc(N5CCN(C)C5=O)c(Cl)c4)c3O)ccn2)CC1]
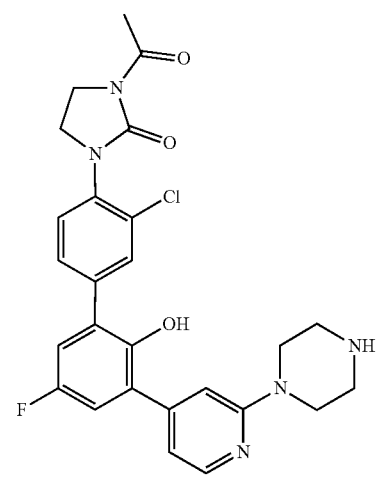 [SMILES: CC(=O)N1CCN(c2ccc(-c3cc(F)cc(-c4ccnc(N5CCNCC5)c4)c3O)cc2Cl)C1=O]
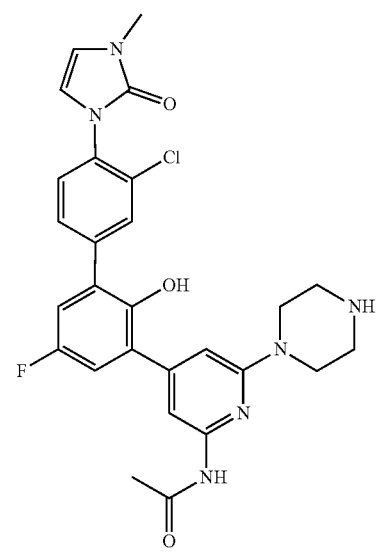 [SMILES: CC(=O)Nc1cc(-c2cc(F)cc(-c3ccc(-n4ccn(C)c4=O)c(Cl)c3)c2O)cc(N2CCNCC2)n1]

1401
-continued
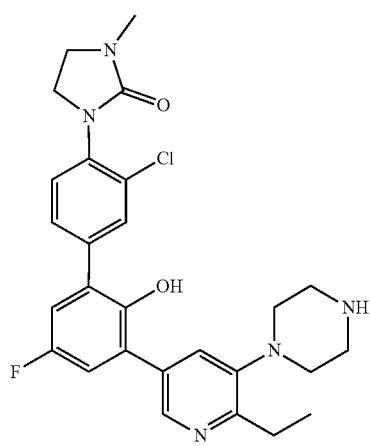 [SMILES: CCc1ncc(-c2cc(F)cc(-c3ccc(N4CCN(C)C4=O)c(Cl)c3)c2O)cc1N1CCNCC1]
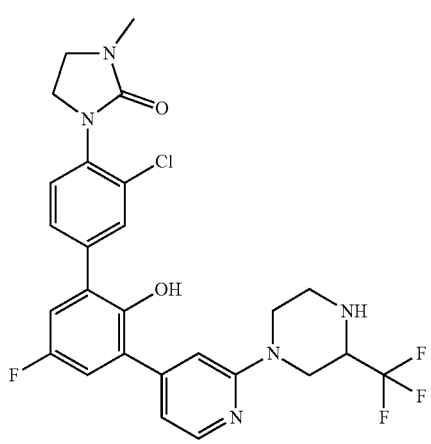 [SMILES: CN1CCN(c2ccc(-c3cc(F)cc(-c4ccnc(N5CCNC(C(F)(F)F)C5)c4)c3O)cc2Cl)C1=O]
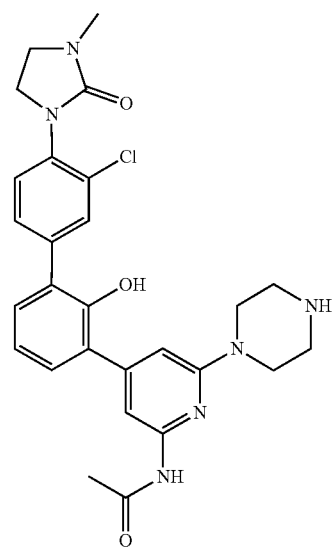 [SMILES: CC(=O)Nc1cc(-c2cccc(-c3ccc(N4CCN(C)C4=O)c(Cl)c3)c2O)cc(N2CCNCC2)n1]
1402
-continued
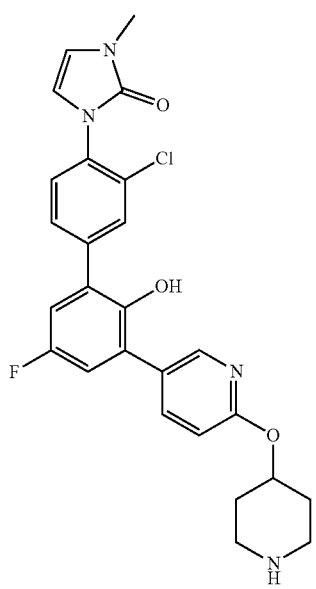 [SMILES: Cn1ccn(-c2ccc(-c3cc(F)cc(-c4ccc(OC5CCNCC5)nc4)c3O)cc2Cl)c1=O]
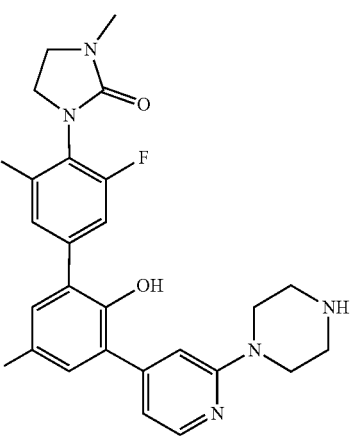
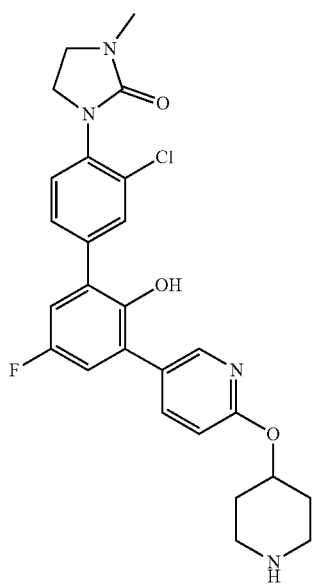 [SMILES: CN1CCN(c2ccc(-c3cc(F)cc(-c4ccc(OC5CCNCC5)nc4)c3O)cc2Cl)C1=O]

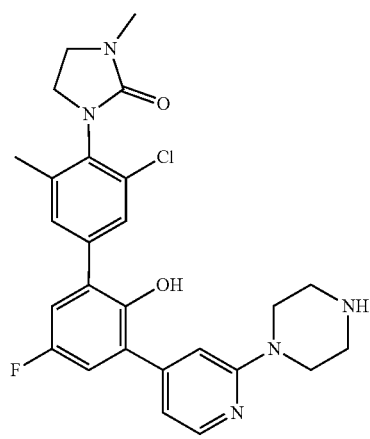 [SMILES: Cc1cc(-c2cc(F)cc(-c3ccnc(N4CCNCC4)c3)c2O)cc(Cl)c1N1CCN(C)C1=O]
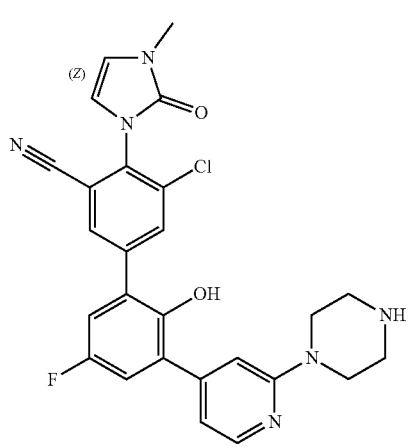 [SMILES: Cn1ccn(-c2c(Cl)cc(-c3cc(F)cc(-c4ccnc(N5CCNCC5)c4)c3O)cc2C#N)c1=O]
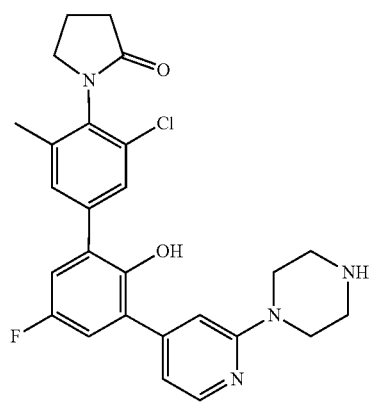 [SMILES: Cc1cc(-c2cc(F)cc(-c3ccnc(N4CCNCC4)c3)c2O)cc(Cl)c1N1CCCC1=O]
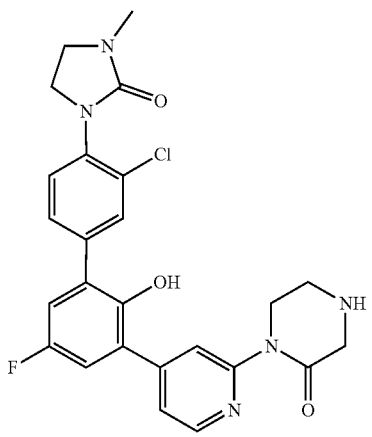 [SMILES: CN1CCN(c2ccc(-c3cc(F)cc(-c4ccnc(N5CCNCC5=O)c4)c3O)cc2Cl)C1=O]
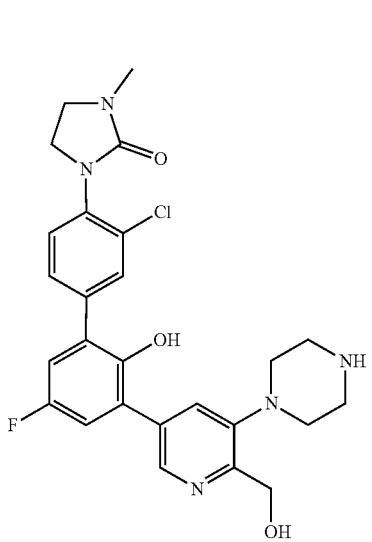 [SMILES: CN1CCN(c2ccc(-c3cc(F)cc(-c4cnc(CO)c(N5CCNCC5)c4)c3O)cc2Cl)C1=O]
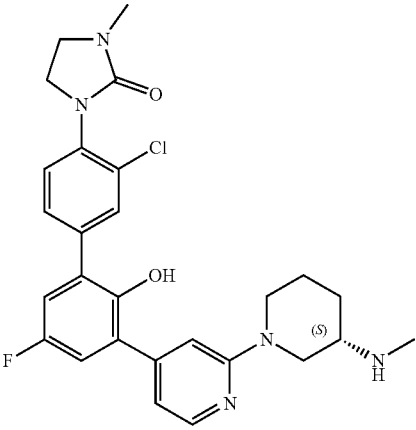

1405
-continued
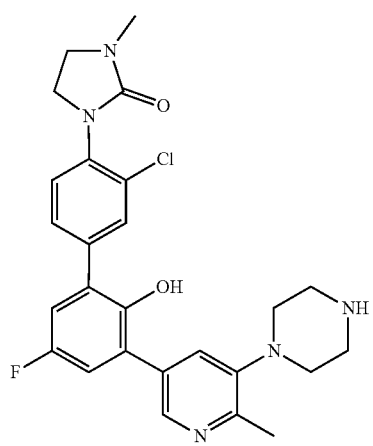 [SMILES: Cc1ncc(-c2cc(F)cc(-c3ccc(N4CCN(C)C4=O)c(Cl)c3)c2O)cc1N1CCNCC1]
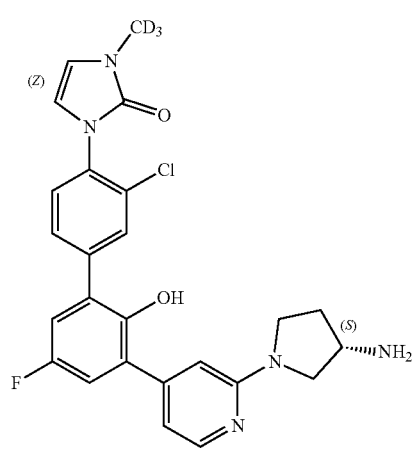
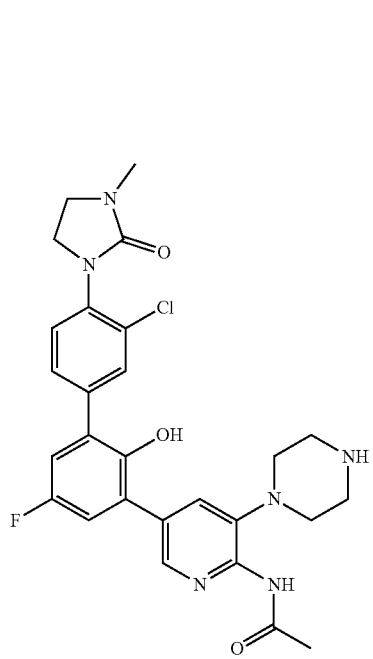
1406
-continued
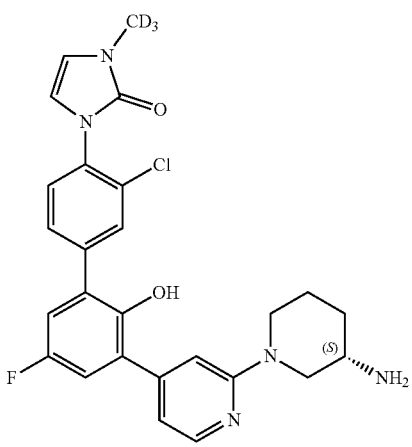
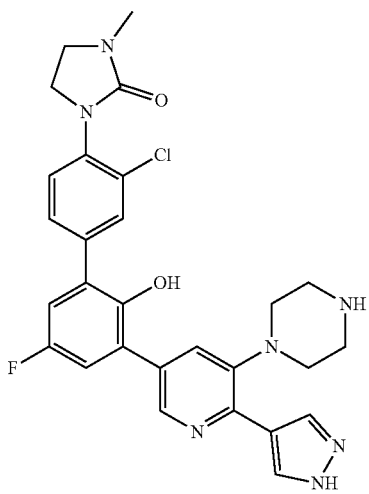 [SMILES: CN1CCN(c2ccc(-c3cc(F)cc(-c4cnc(-c5cn[nH]c5)c(N5CCNCC5)c4)c3O)cc2Cl)C1=O]
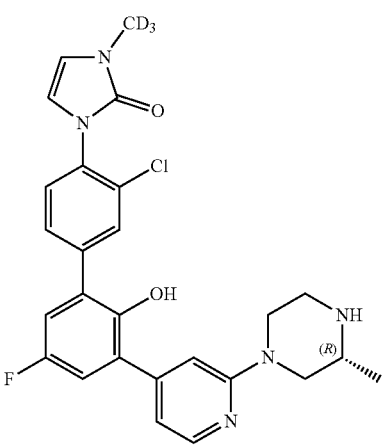

1407
-continued
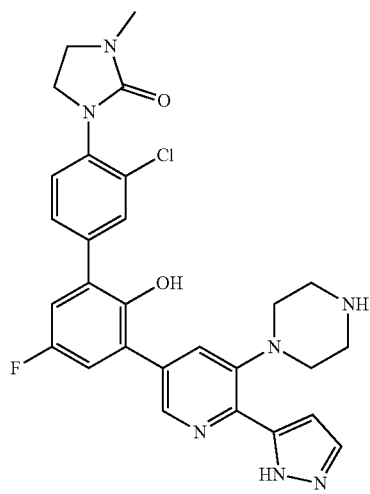 [SMILES: CN1CCN(c2ccc(-c3cc(F)cc(-c4cnc(-c5ccn[nH]5)c(N5CCNCC5)c4)c3O)cc2Cl)C1=O]
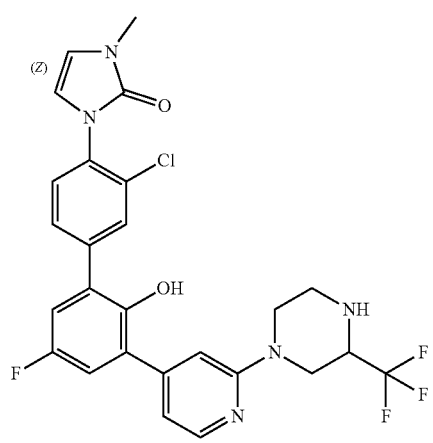 [SMILES: Cn1ccn(-c2ccc(-c3cc(F)cc(-c4ccnc(N5CCNC(C(F)(F)F)C5)c4)c3O)cc2Cl)c1=O]
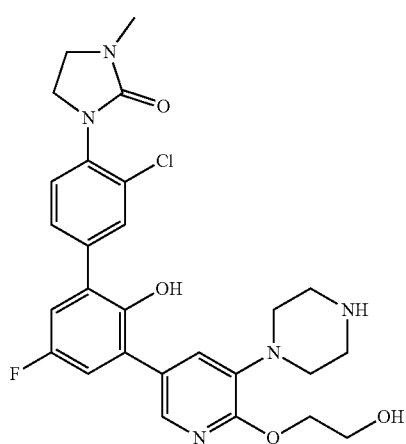 [SMILES: CN1CCN(c2ccc(-c3cc(F)cc(-c4cnc(OCCO)c(N5CCNCC5)c4)c3O)cc2Cl)C1=O]
1408
-continued
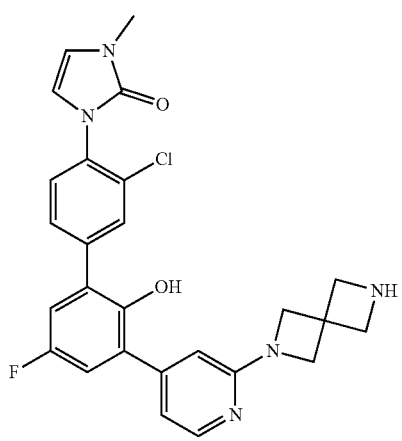 [SMILES: Cn1ccn(-c2ccc(-c3cc(F)cc(-c4ccnc(N5CC6(CNC6)C5)c4)c3O)cc2Cl)c1=O]
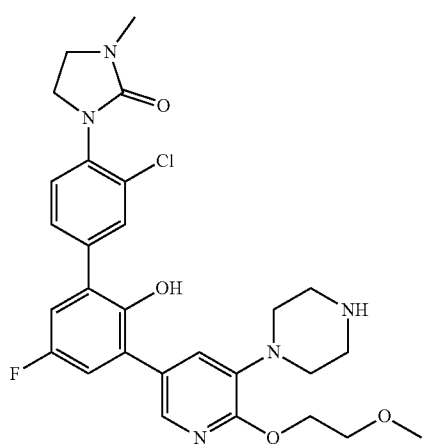 [SMILES: COCCOc1ncc(-c2cc(F)cc(-c3ccc(N4CCN(C)C4=O)c(Cl)c3)c2O)cc1N1CCNCC1]
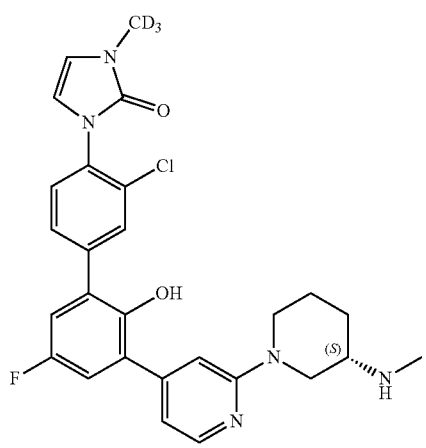

| 1409 -continued | 1410 -continued |
|---|---|
| 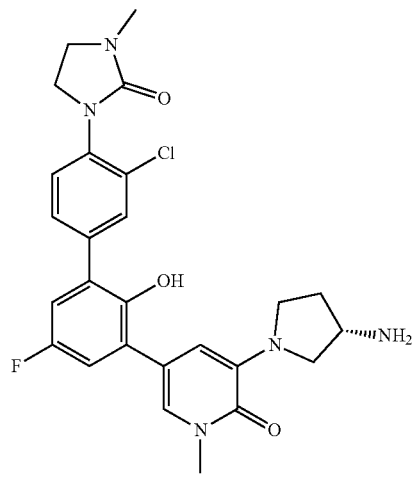 | 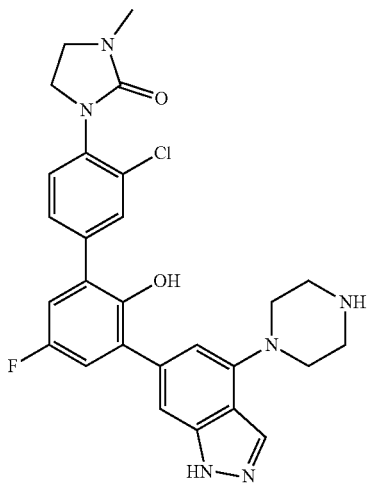 |
| 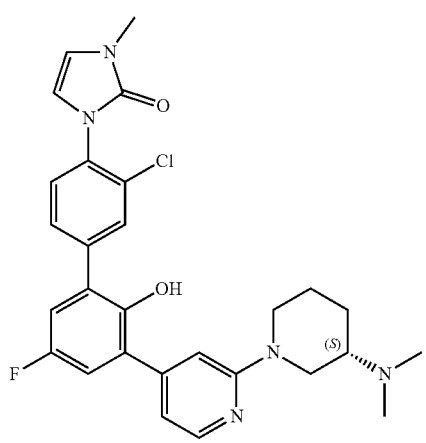 | 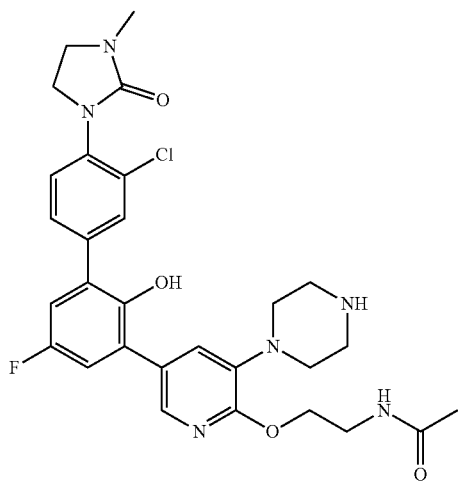 |
| 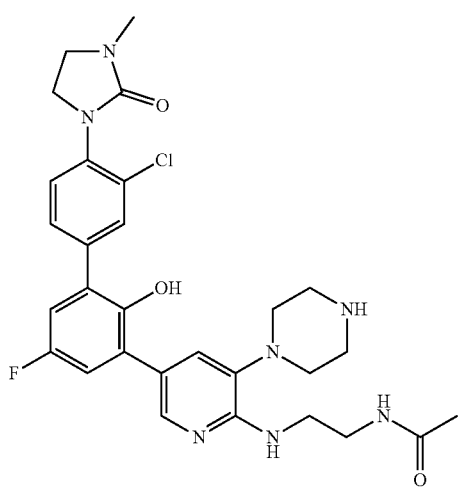 [SMILES: CC(=O)NCCNc1ncc(-c2cc(F)cc(-c3ccc(N4CCN(C)C4=O)c(Cl)c3)c2O)cc1N1CCNCC1] | 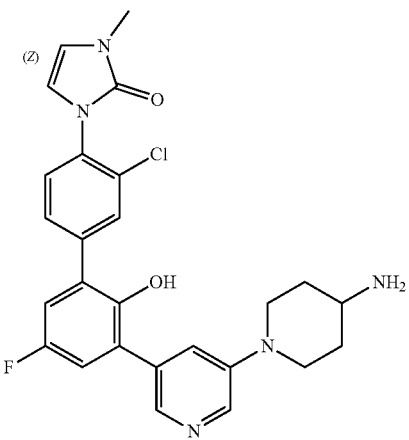 [SMILES: Cn1ccn(-c2ccc(-c3cc(F)cc(-c4cncc(N5CCC(N)CC5)c4)c3O)cc2Cl)c1=O] |

1411
-continued
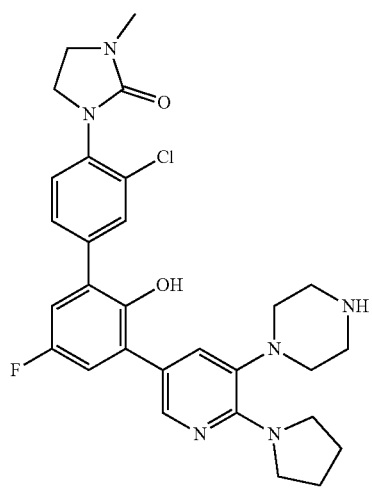 [SMILES: CN1CCN(c2ccc(-c3cc(F)cc(-c4cnc(N5CCCC5)c(N5CCNCC5)c4)c3O)cc2Cl)C1=O]
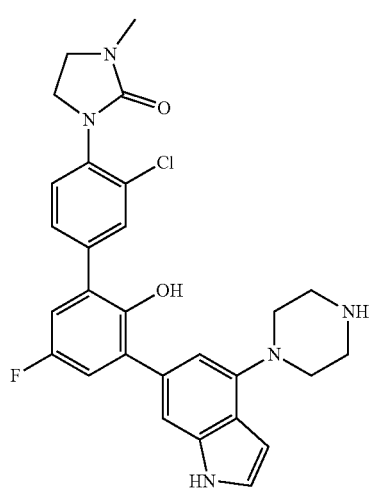
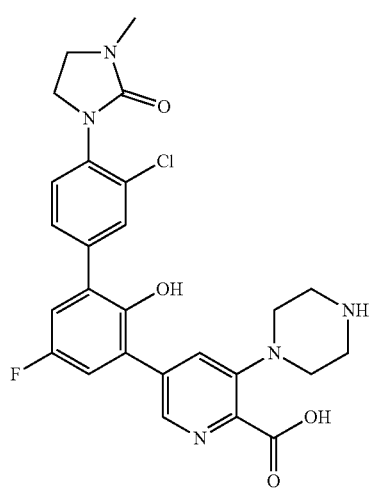
1412
-continued
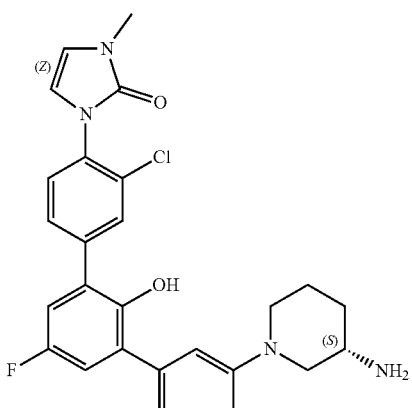
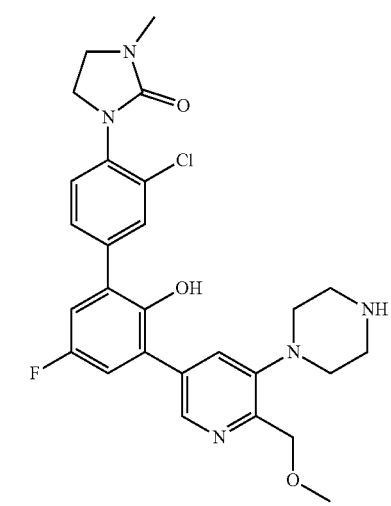 [SMILES: COCc1ncc(-c2cc(F)cc(-c3ccc(N4CCN(C)C4=O)c(Cl)c3)c2O)cc1N1CCNCC1]
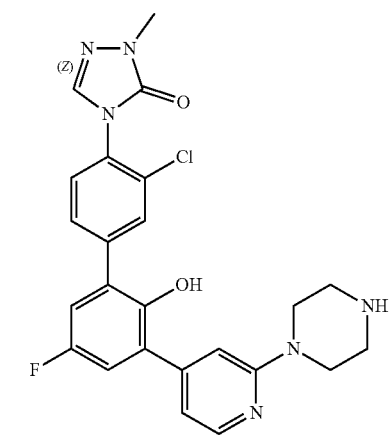

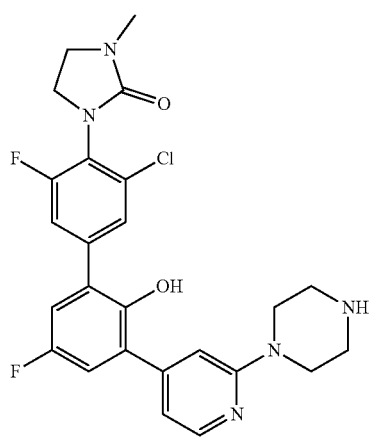 [SMILES: CN1CCN(c2c(F)cc(-c3cc(F)cc(-c4ccnc(N5CCNCC5)c4)c3O)cc2Cl)C1=O]
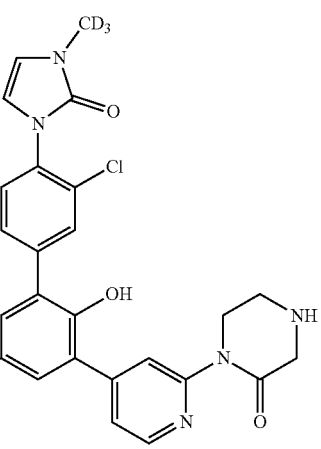
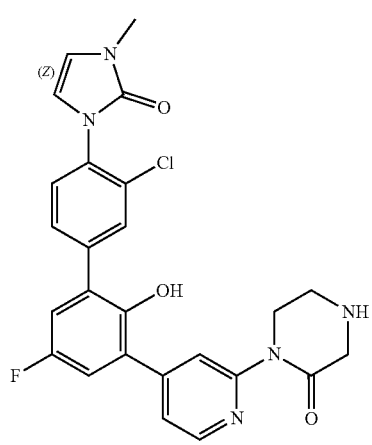
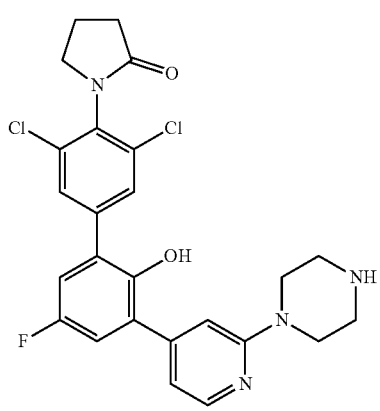
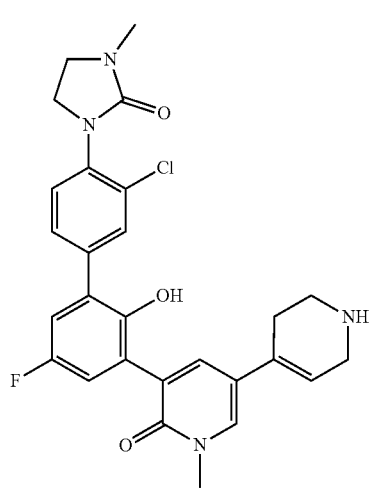 [SMILES: CN1CCN(c2ccc(-c3cc(F)cc(-c4cc(C5=CCNCC5)cn(C)c4=O)c3O)cc2Cl)C1=O]
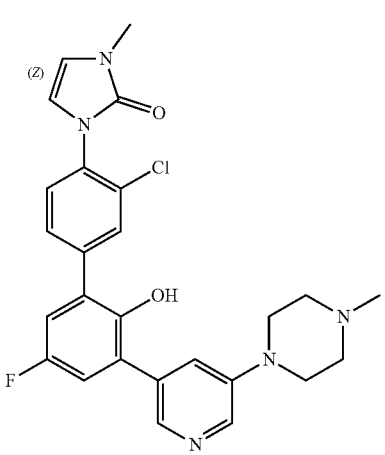 [SMILES: CN1CCN(c2cncc(-c3cc(F)cc(-c4ccc(-n5ccn(C)c5=O)c(Cl)c4)c3O)c2)CC1]

-continued
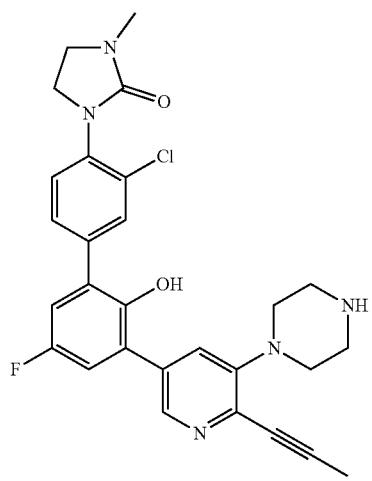 [SMILES: CC#Cc1ncc(-c2cc(F)cc(-c3ccc(N4CCN(C)C4=O)c(Cl)c3)c2O)cc1N1CCNCC1]
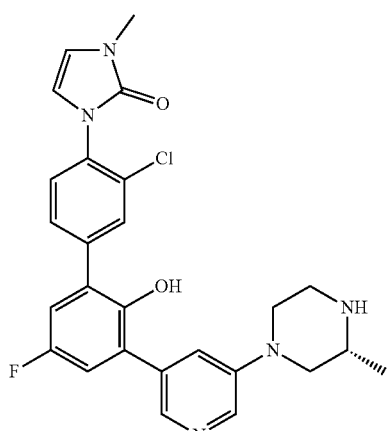
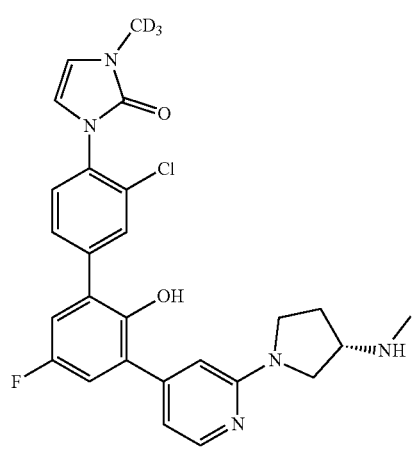 [SMILES: [2H]C([2H])([2H])n1ccn(-c2ccc(-c3cc(F)cc(-c4ccnc(N5CC[C@H](NC)C5)c4)c3O)cc2Cl)c1=O]
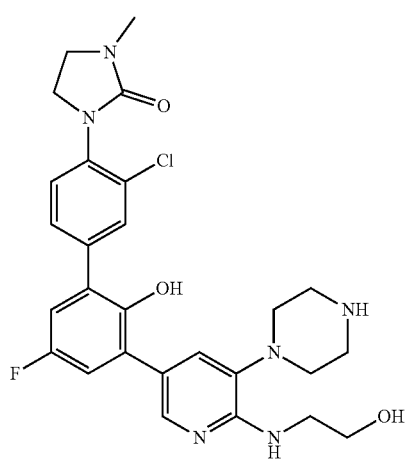
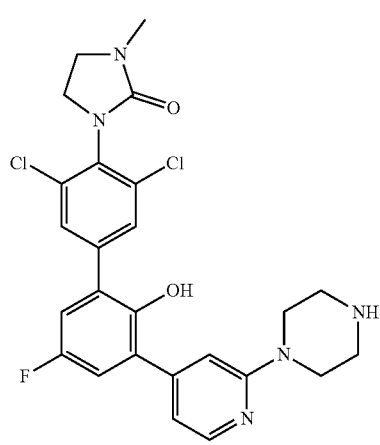 [SMILES: CN1CCN(c2c(Cl)cc(-c3cc(F)cc(-c4ccnc(N5CCNCC5)c4)c3O)cc2Cl)C1=O]
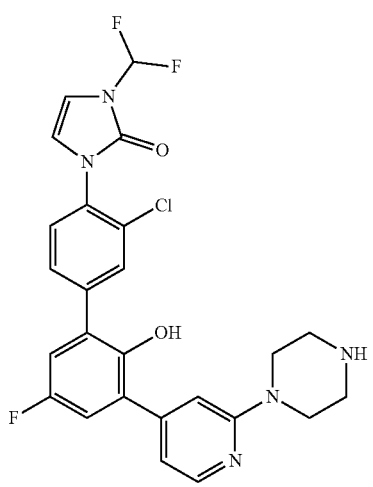 [SMILES: O=c1n(-c2ccc(-c3cc(F)cc(-c4ccnc(N5CCNCC5)c4)c3O)cc2Cl)ccn1C(F)F]

1417
-continued
1418
-continued
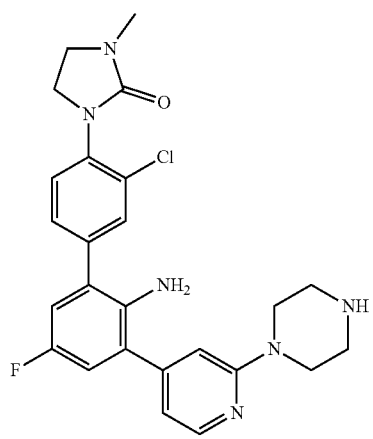
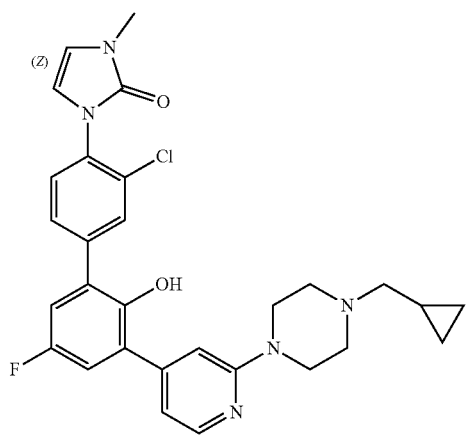
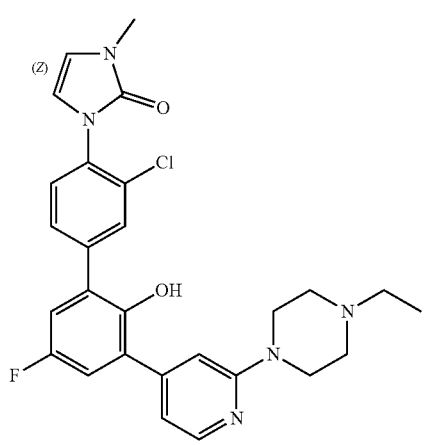 [SMILES: CCN1CCN(c2cc(-c3cc(F)cc(-c4ccc(-n5ccn(C)c5=O)c(Cl)c4)c3O)ccn2)CC1]
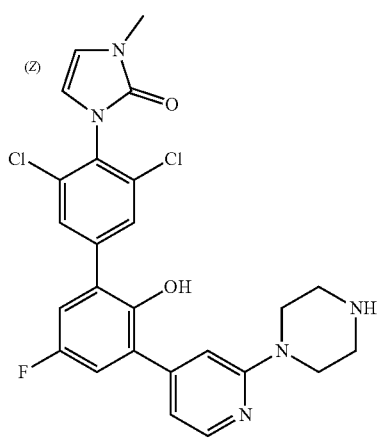
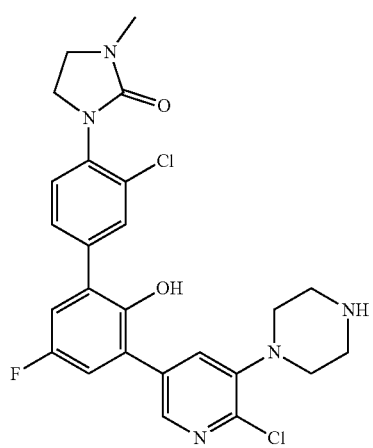 [SMILES: CN1CCN(c2ccc(-c3cc(F)cc(-c4cnc(Cl)c(N5CCNCC5)c4)c3O)cc2Cl)C1=O]
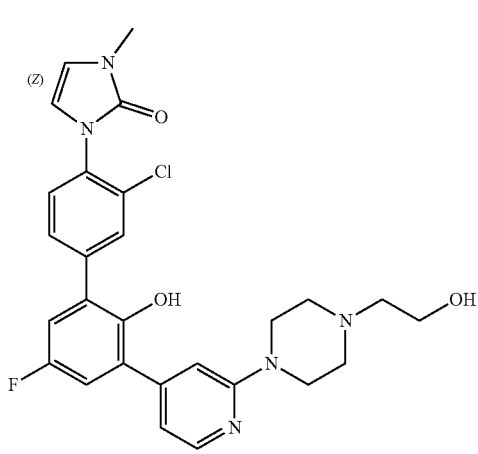 [SMILES: Cn1ccn(-c2ccc(-c3cc(F)cc(-c4ccnc(N5CCN(CCO)CC5)c4)c3O)cc2Cl)c1=O]

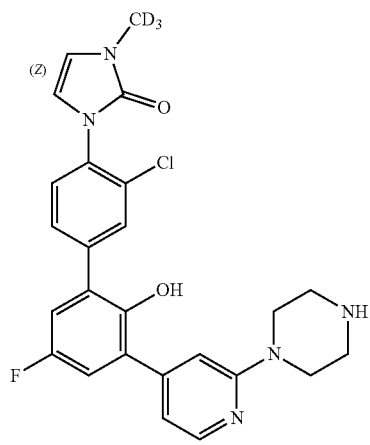 [SMILES: [2H]C([2H])([2H])n1ccn(-c2ccc(-c3cc(F)cc(-c4ccnc(N5CCNCC5)c4)c3O)cc2Cl)c1=O]
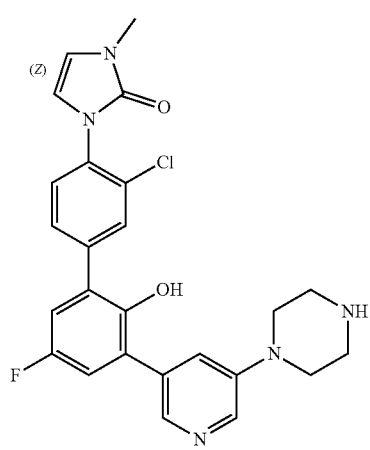 [SMILES: Cn1ccn(-c2ccc(-c3cc(F)cc(-c4cncc(N5CCNCC5)c4)c3O)cc2Cl)c1=O]
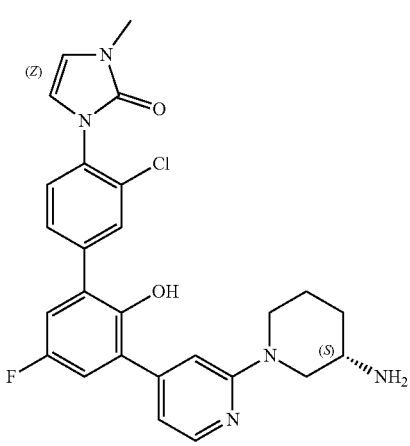
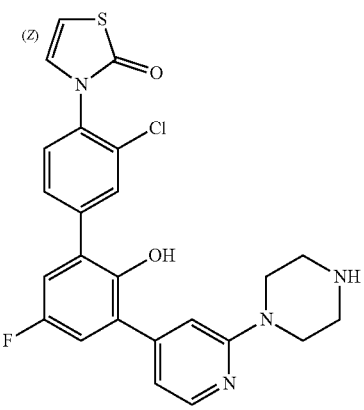
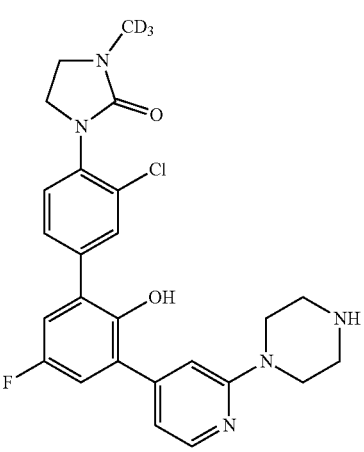 [SMILES: [2H]C([2H])([2H])N1CCN(c2ccc(-c3cc(F)cc(-c4ccnc(N5CCNCC5)c4)c3O)cc2Cl)C1=O]
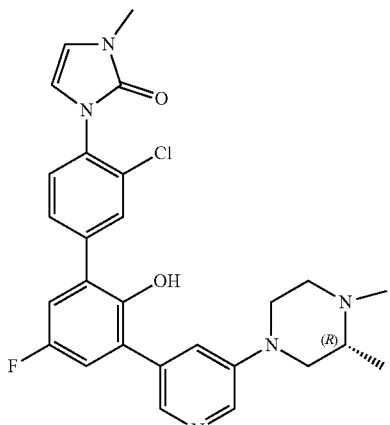

| 1421 -continued | 1422 -continued |
|---|---|
| 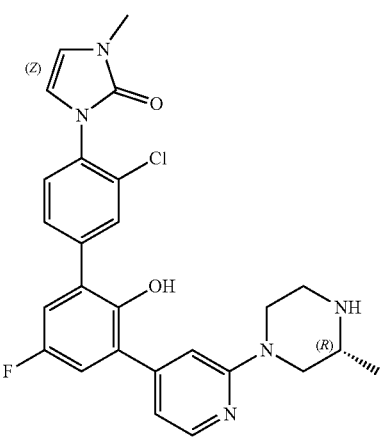 | 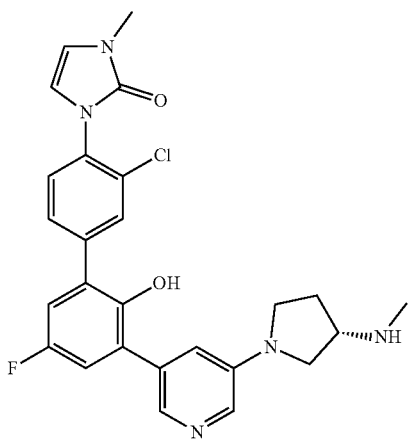 |
| 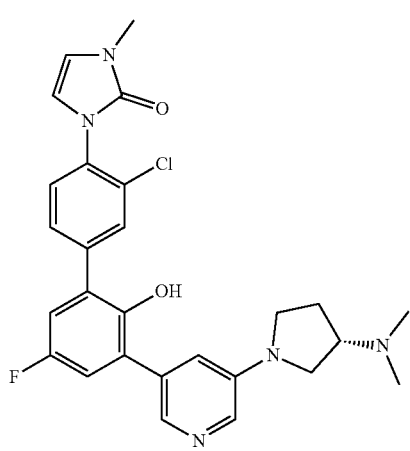 [SMILES: CN(C)[C@H]1CCN(c2cncc(-c3cc(F)cc(-c4ccc(-n5ccn(C)c5=O)c(Cl)c4)c3O)c2)C1] | 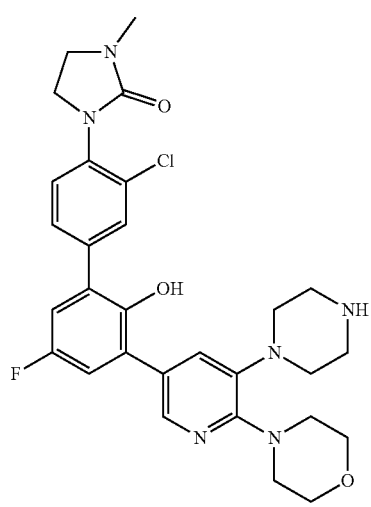 [SMILES: CN1CCN(c2ccc(-c3cc(F)cc(-c4cnc(N5CCOCC5)c(N5CCNCC5)c4)c3O)cc2Cl)C1=O] |
| 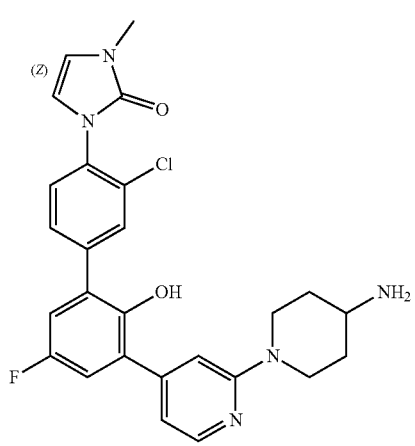 | 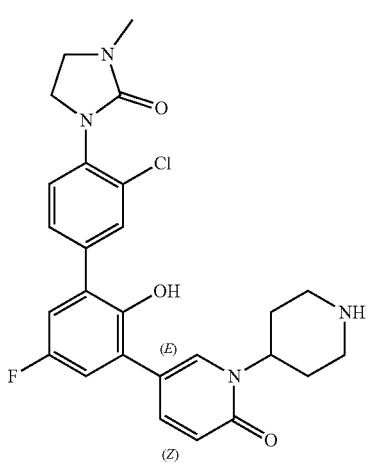 [SMILES: CN1CCN(c2ccc(-c3cc(F)cc(-c4ccc(=O)n(C5CCNCC5)c4)c3O)cc2Cl)C1=O] |

| 1423 -continued | 1424 -continued |
|---|---|
| 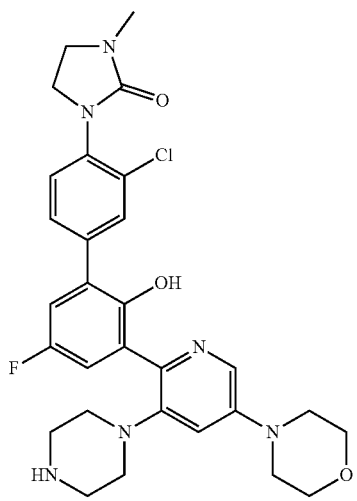 [SMILES: CN1CCN(c2ccc(-c3cc(F)cc(-c4ncc(N5CCOCC5)cc4N4CCNCC4)c3O)cc2Cl)C1=O] | 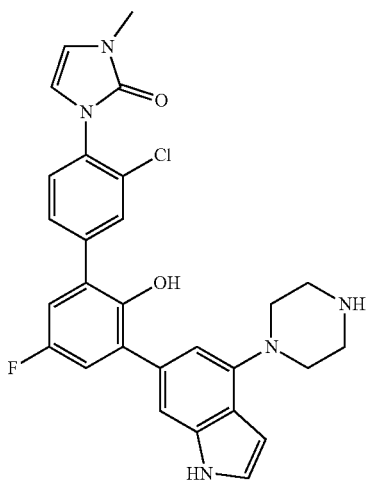 |
| 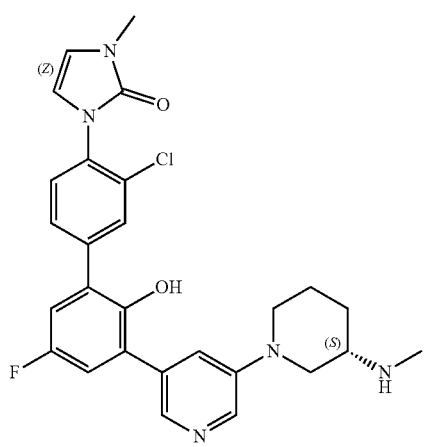 | 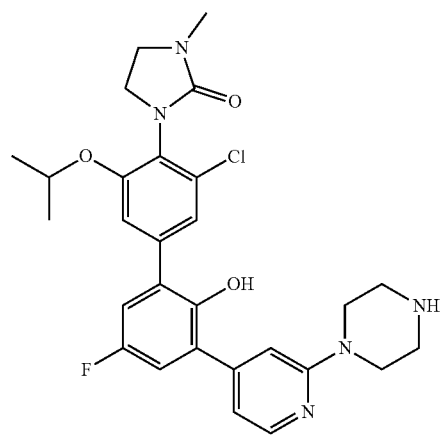 |
| 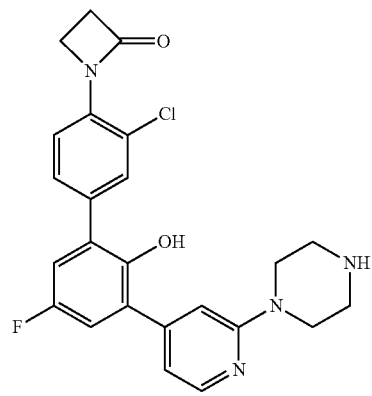 [SMILES: O=C1CCN1c1ccc(-c2cc(F)cc(-c3ccnc(N4CCNCC4)c3)c2O)cc1Cl] | 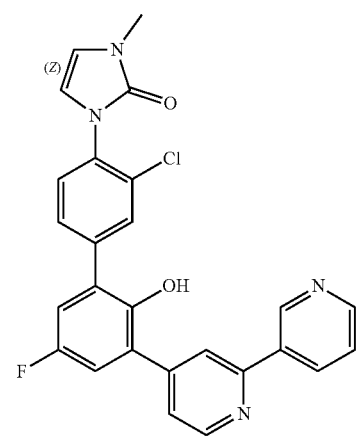 |

1425
-continued
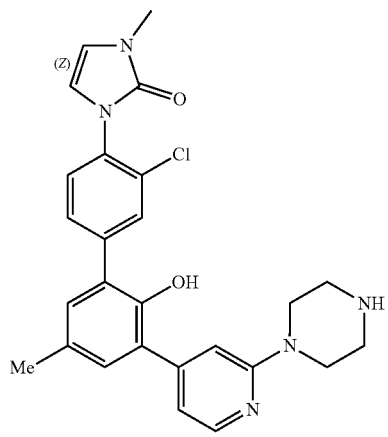
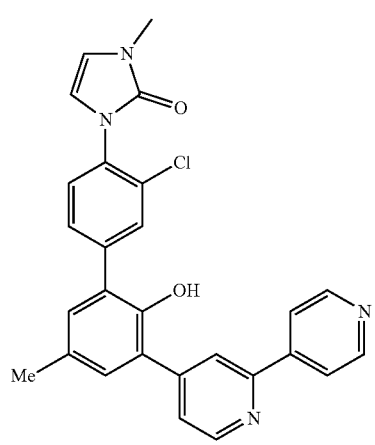 [SMILES: Cc1cc(-c2ccnc(-c3ccncc3)c2)c(O)c(-c2ccc(-n3ccn(C)c3=O)c(Cl)c2)c1]
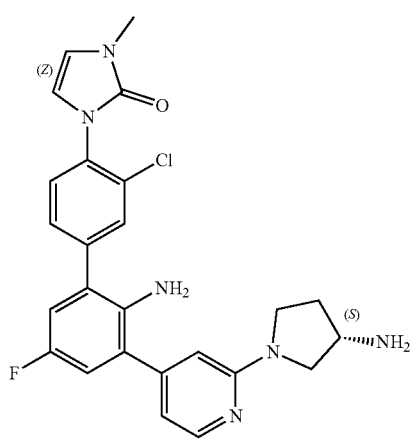
1426
-continued
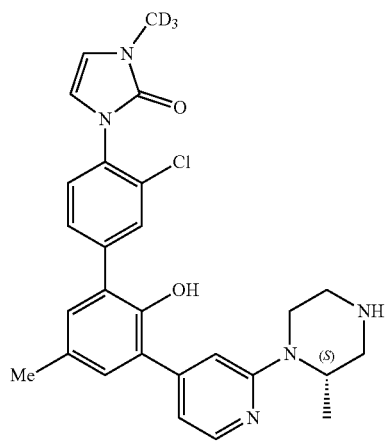
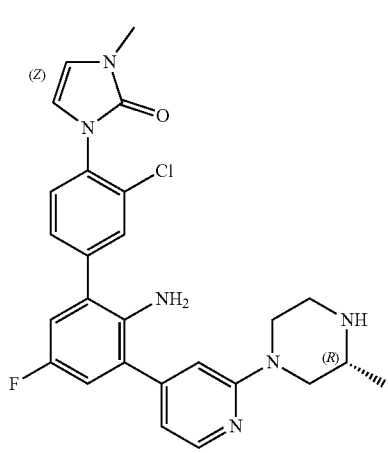
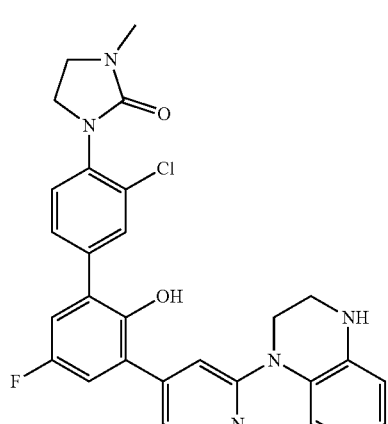

1427
-continued
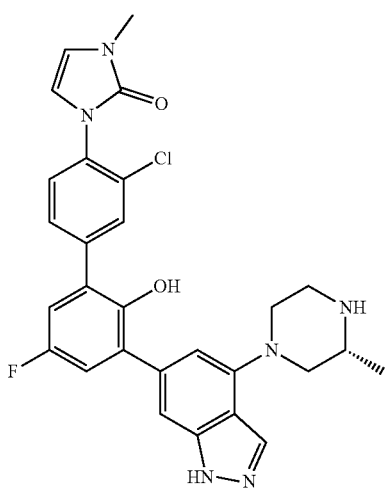
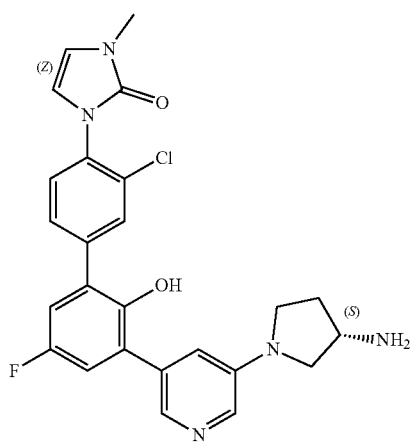
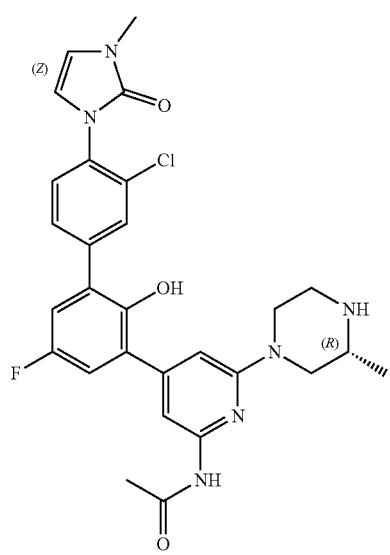
1428
-continued
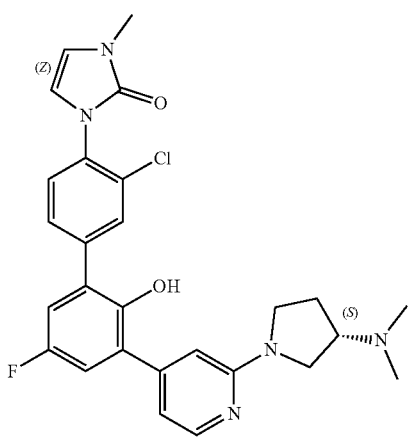
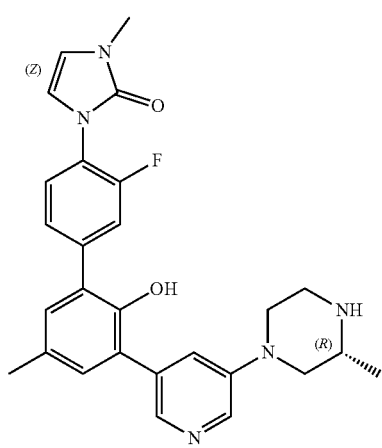
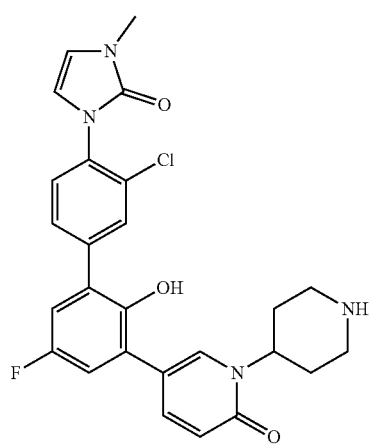 [SMILES: Cn1ccn(-c2ccc(-c3cc(F)cc(-c4ccc(=O)n(C5CCNCC5)c4)c3O)cc2Cl)c1=O]

1429
-continued
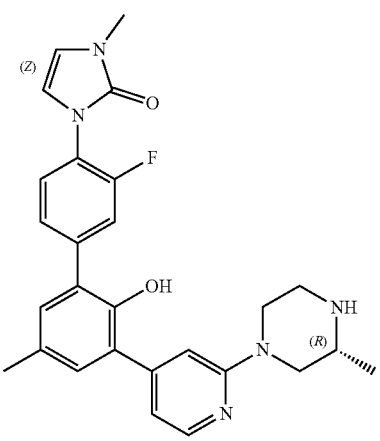
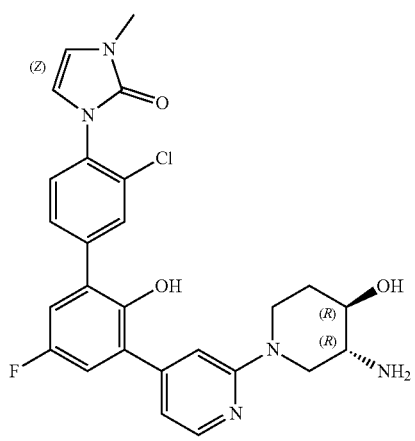
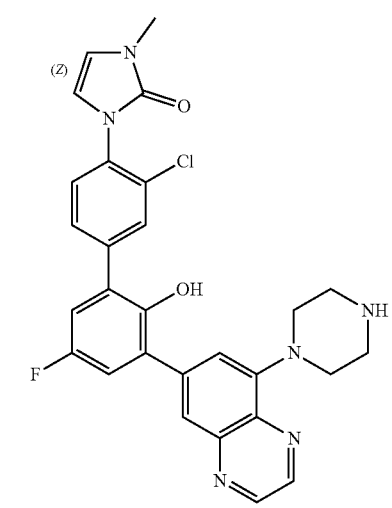
1430
-continued
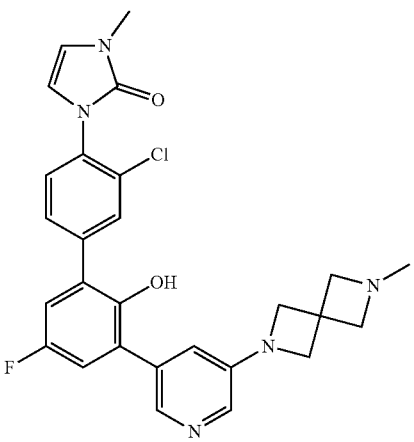 [SMILES: CN1CC2(C1)CN(c1cncc(-c3cc(F)cc(-c4ccc(-n5ccn(C)c5=O)c(Cl)c4)c3O)c1)C2]
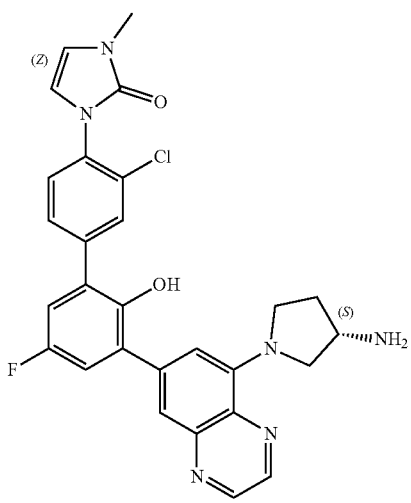
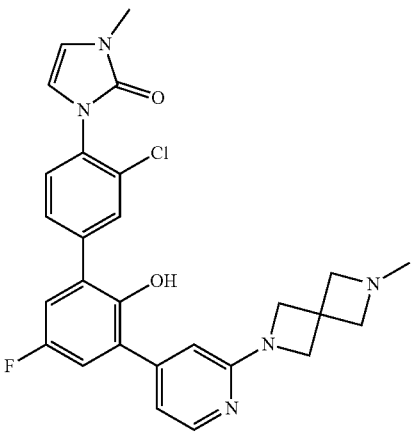 [SMILES: CN1CC2(C1)CN(c1cc(-c3cc(F)cc(-c4ccc(-n5ccn(C)c5=O)c(Cl)c4)c3O)ccn1)C2]

1431
-continued
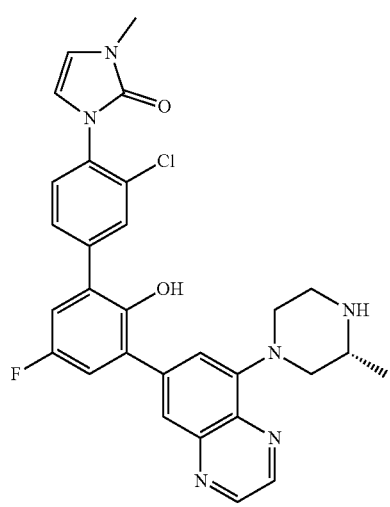 [SMILES: C[C@@H]1CN(c2cc(-c3cc(F)cc(-c4ccc(-n5ccn(C)c5=O)c(Cl)c4)c3O)cc3nccnc23)CCN1]
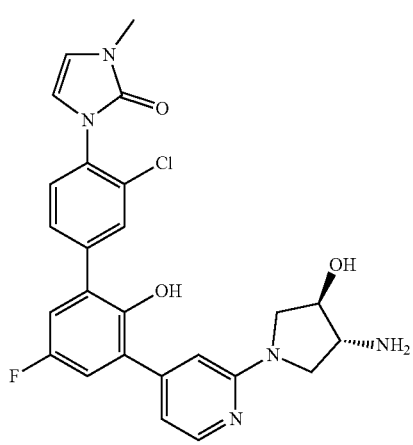 [SMILES: Cn1ccn(-c2ccc(-c3cc(F)cc(-c4ccnc(N5C[C@@H](N)[C@H](O)C5)c4)c3O)cc2Cl)c1=O]
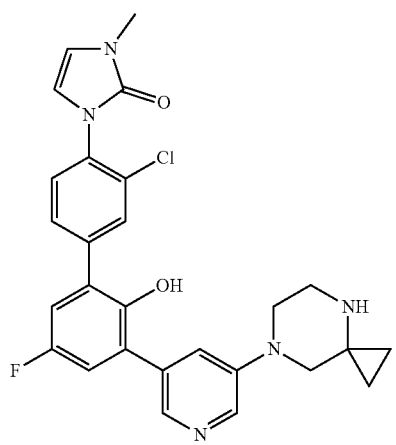 [SMILES: Cn1ccn(-c2ccc(-c3cc(F)cc(-c4cncc(N5CCNC6(CC6)C5)c4)c3O)cc2Cl)c1=O]
1432
-continued
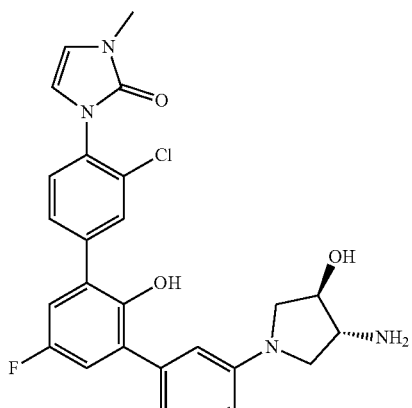
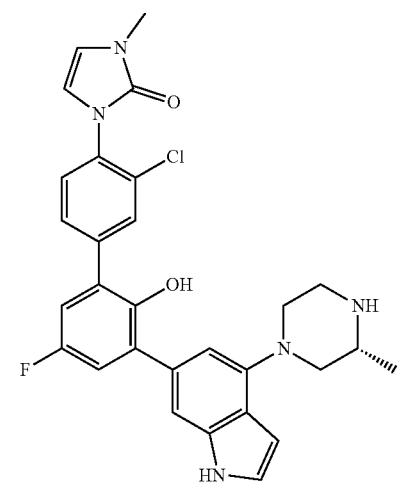 [SMILES: C[C@@H]1CN(c2cc(-c3cc(F)cc(-c4ccc(-n5ccn(C)c5=O)c(Cl)c4)c3O)cc3[nH]ccc23)CCN1]
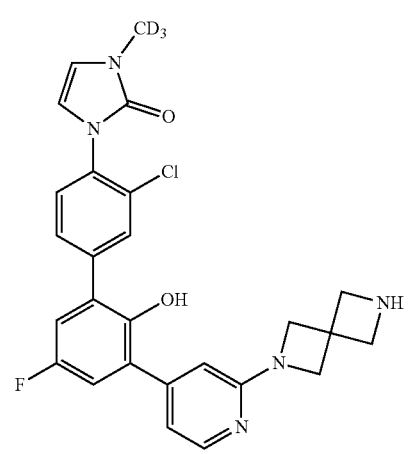 [SMILES: [2H]C([2H])([2H])n1ccn(-c2ccc(-c3cc(F)cc(-c4ccnc(N5CC6(CNC6)C5)c4)c3O)cc2Cl)c1=O]

1433
-continued
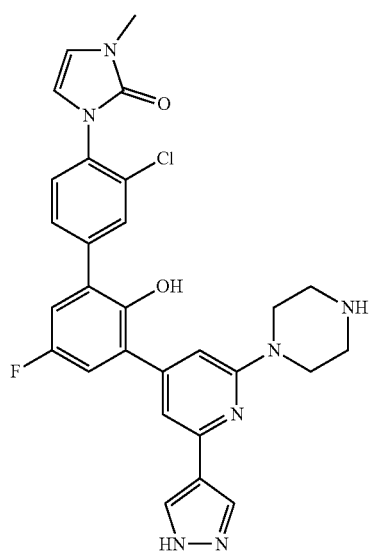
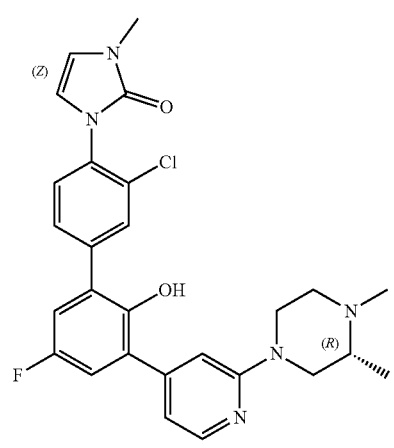
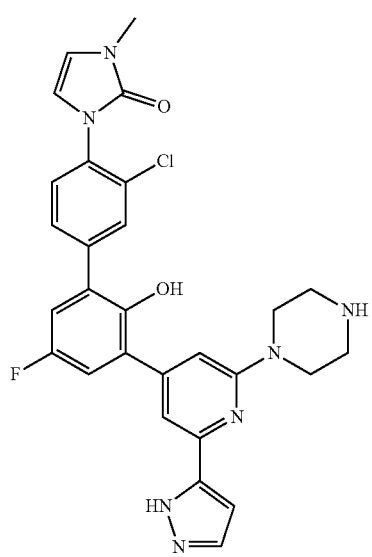
1434
-continued
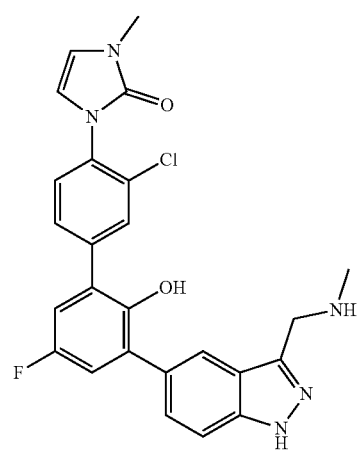 [SMILES: CNCc1n[nH]c2ccc(-c3cc(F)cc(-c4ccc(-n5ccn(C)c5=O)c(Cl)c4)c3O)cc12]
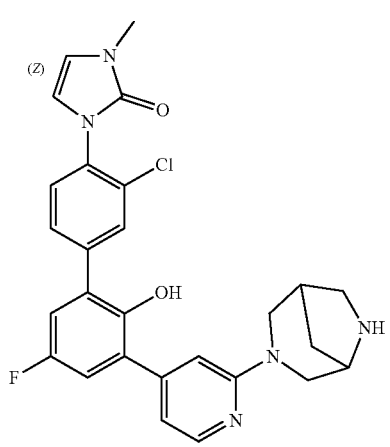 [SMILES: Cn1ccn(-c2ccc(-c3cc(F)cc(-c4ccnc(N5CC6CNC(C6)C5)c4)c3O)cc2Cl)c1=O]
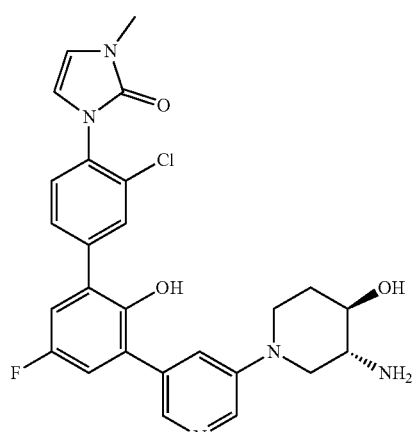

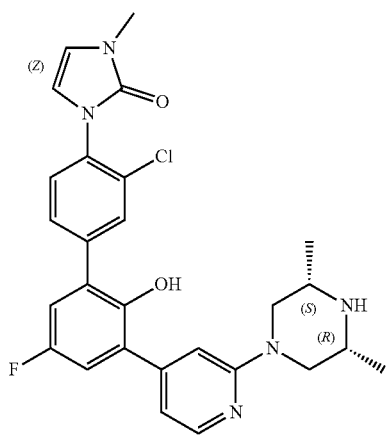
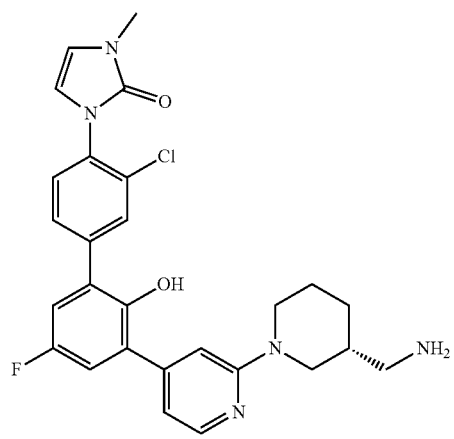
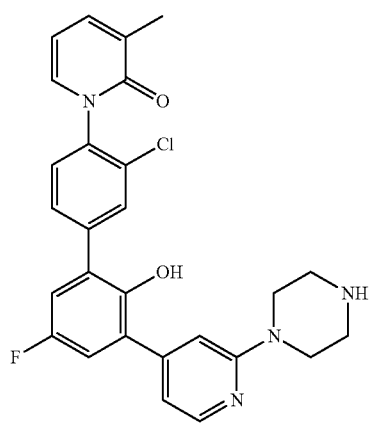 [SMILES: Cc1cccn(-c2ccc(-c3cc(F)cc(-c4ccnc(N5CCNCC5)c4)c3O)cc2Cl)c1=O]
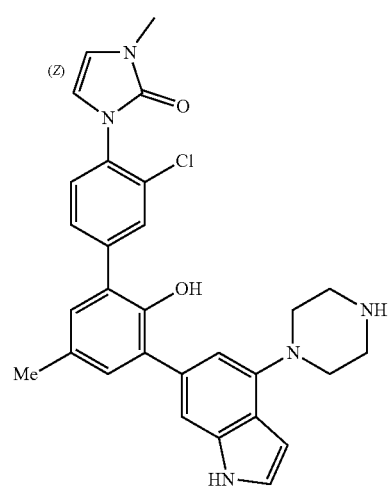
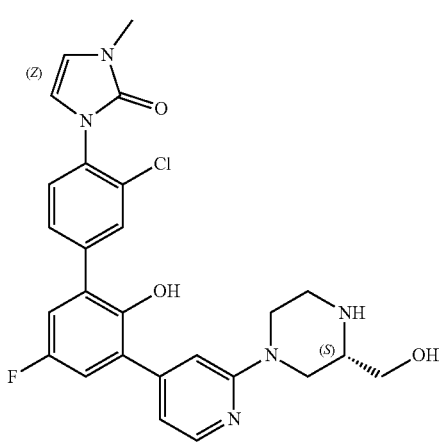
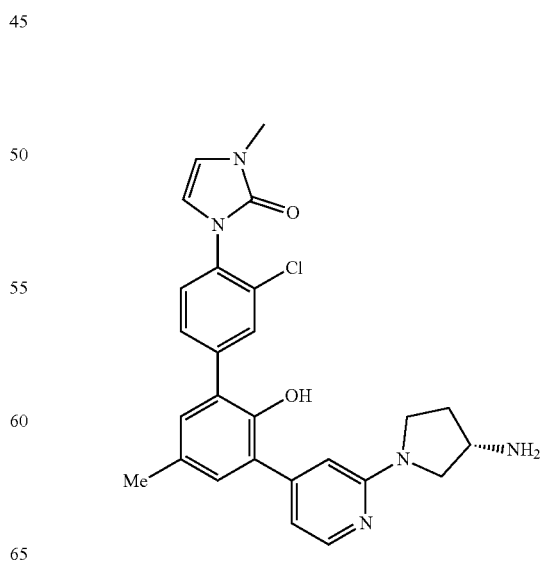

1437
-continued
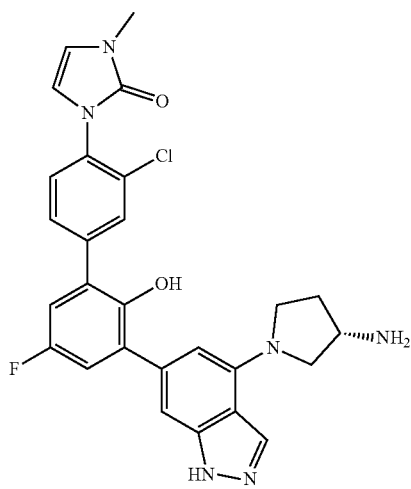 [SMILES: Cn1ccn(-c2ccc(-c3cc(F)cc(-c4cc(N5CC[C@H](N)C5)c5cn[nH]c5c4)c3O)cc2Cl)c1=O]
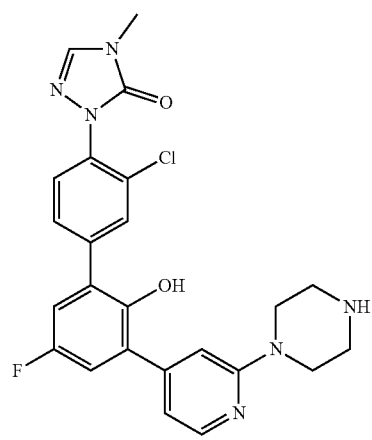 [SMILES: Cn1cnn(-c2ccc(-c3cc(F)cc(-c4ccnc(N5CCNCC5)c4)c3O)cc2Cl)c1=O]
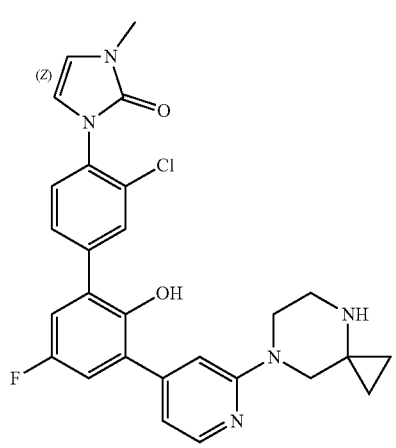 [SMILES: Cn1ccn(-c2ccc(-c3cc(F)cc(-c4ccnc(N5CCNC6(CC6)C5)c4)c3O)cc2Cl)c1=O]
1438
-continued
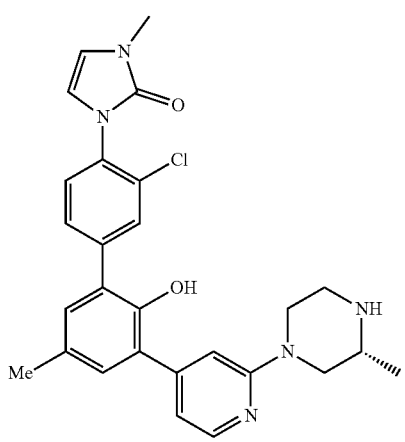 [SMILES: Cc1cc(-c2ccnc(N3CCN[C@H](C)C3)c2)c(O)c(-c2ccc(-n3ccn(C)c3=O)c(Cl)c2)c1]
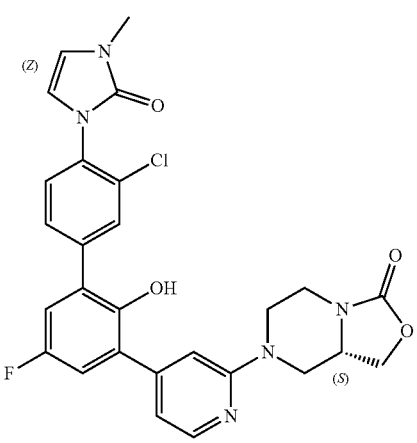
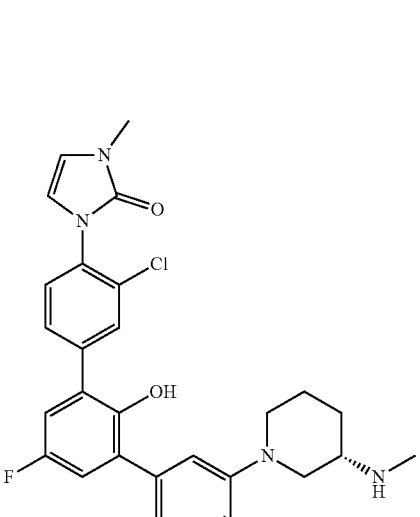

| 1439 -continued | 1440 -continued |
|---|---|
| 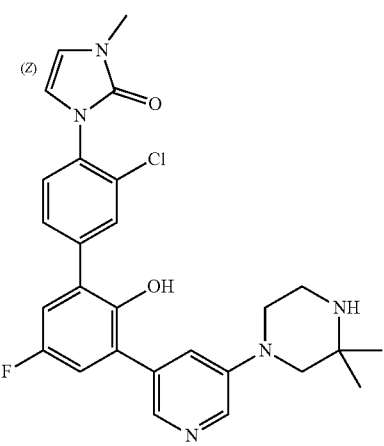 | 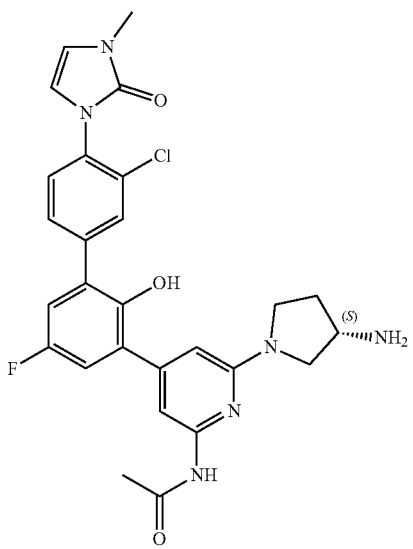 |
| 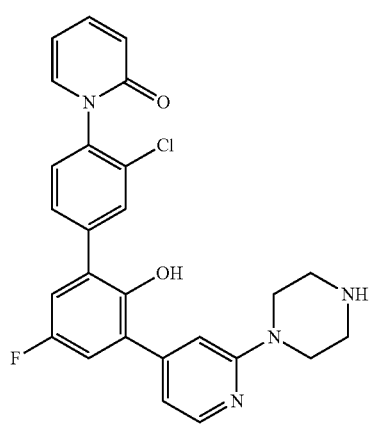 [SMILES: O=c1ccccn1-c1ccc(-c2cc(F)cc(-c3ccnc(N4CCNCC4)c3)c2O)cc1Cl] | 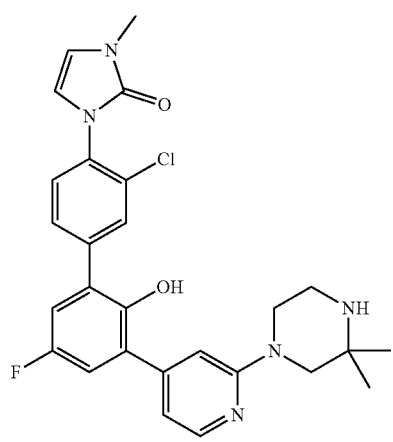 |
| 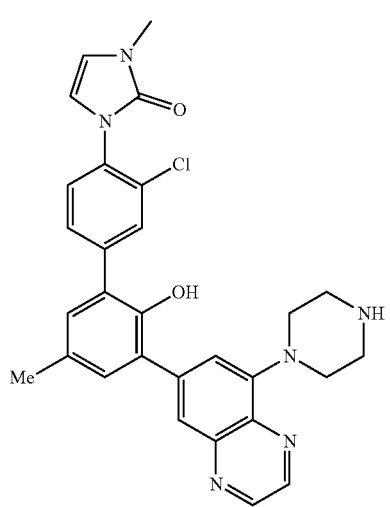 [SMILES: Cc1cc(-c2ccc(-n3ccn(C)c3=O)c(Cl)c2)c(O)c(-c2cc(N3CCNCC3)c3nccnc3c2)c1] | 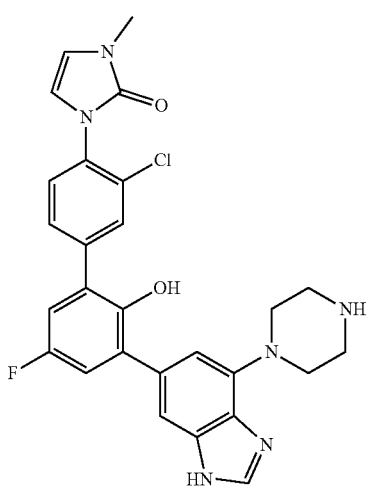 [SMILES: Cn1ccn(-c2ccc(-c3cc(F)cc(-c4cc(N5CCNCC5)c5nc[nH]c5c4)c3O)cc2Cl)c1=O] |

1441
-continued
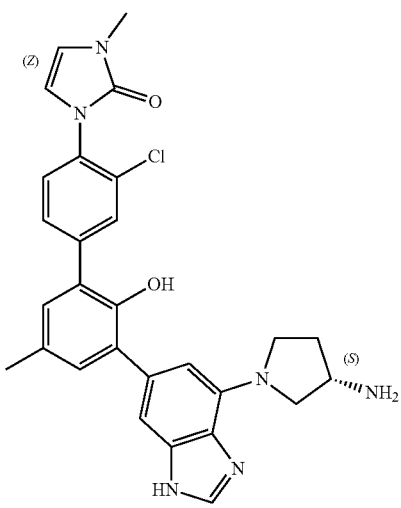
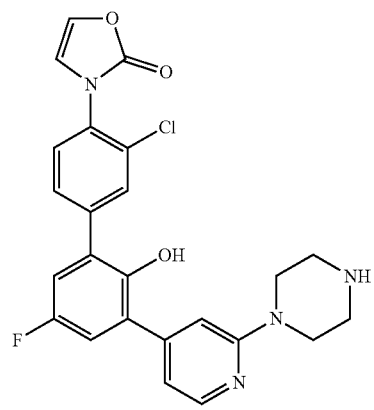 [SMILES: O=c1occn1-c1ccc(-c2cc(F)cc(-c3ccnc(N4CCNCC4)c3)c2O)cc1Cl]
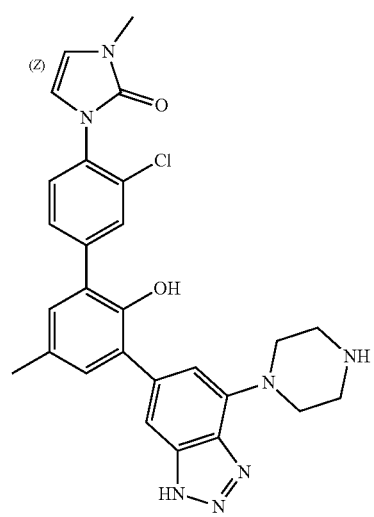 [SMILES: Cc1cc(-c2ccc(-n3ccn(C)c3=O)c(Cl)c2)c(O)c(-c2cc(N3CCNCC3)c3nn[nH]c3c2)c1]
1442
-continued
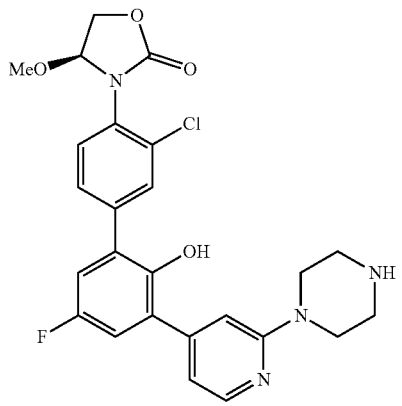 [SMILES: CO[C@H]1COC(=O)N1c1ccc(-c2cc(F)cc(-c3ccnc(N4CCNCC4)c3)c2O)cc1Cl]
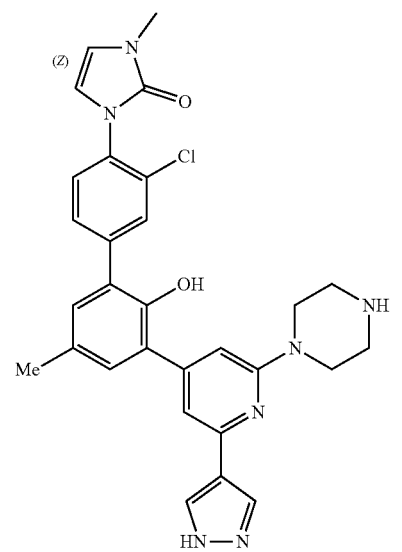 [SMILES: Cc1cc(-c2cc(-c3cn[nH]c3)nc(N3CCNCC3)c2)c(O)c(-c2ccc(-n3ccn(C)c3=O)c(Cl)c2)c1]
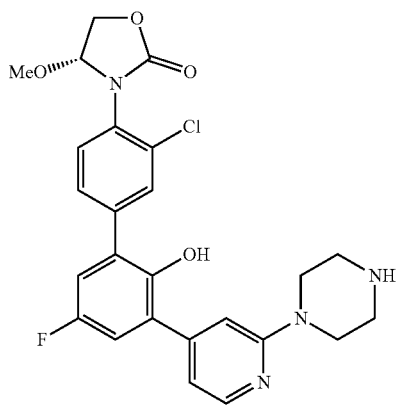 [SMILES: CO[C@@H]1COC(=O)N1c1ccc(-c2cc(F)cc(-c3ccnc(N4CCNCC4)c3)c2O)cc1Cl]

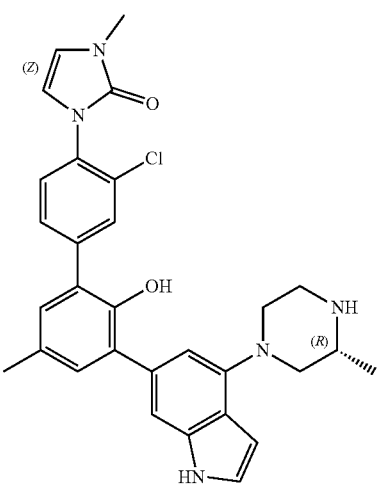
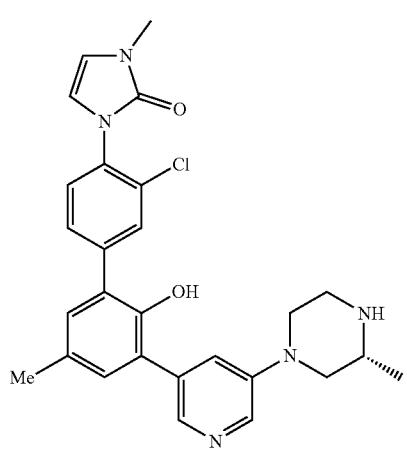
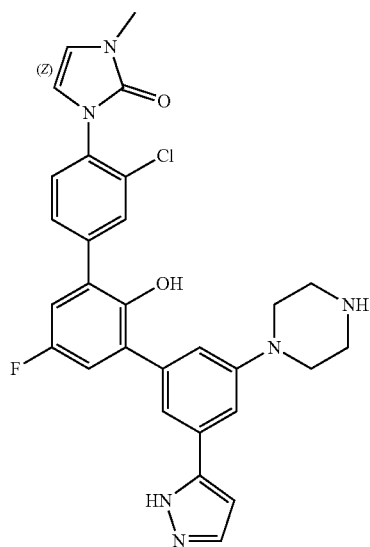 [SMILES: Cn1ccn(-c2ccc(-c3cc(F)cc(-c4cc(-c5ccn[nH]5)cc(N5CCNCC5)c4)c3O)cc2Cl)c1=O]
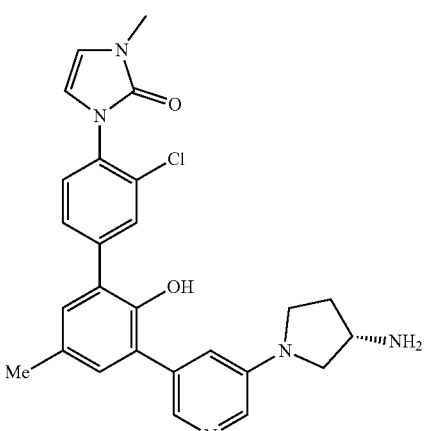
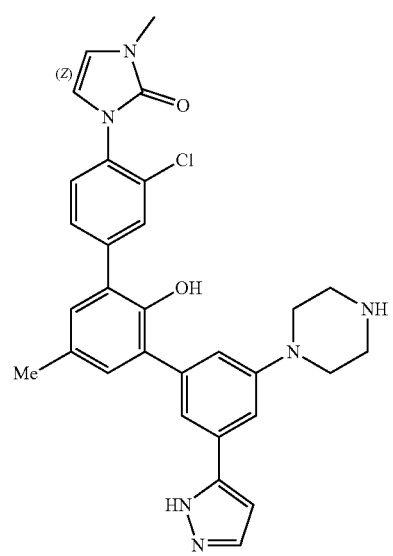 [SMILES: Cc1cc(-c2cc(-c3ccn[nH]3)cc(N3CCNCC3)c2)c(O)c(-c2ccc(-n3ccn(C)c3=O)c(Cl)c2)c1]
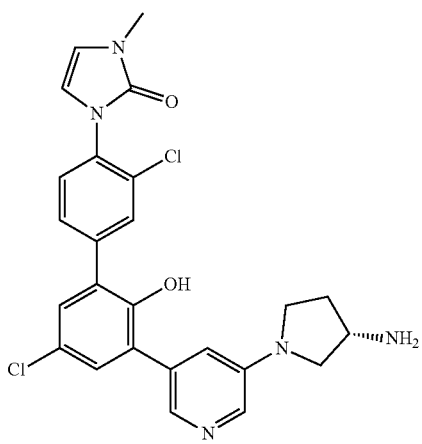 [SMILES: Cn1ccn(-c2ccc(-c3cc(Cl)cc(-c4cncc(N5CC[C@H](N)C5)c4)c3O)cc2Cl)c1=O]

1445
-continued
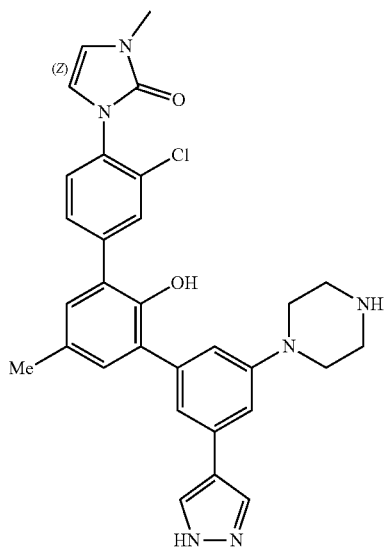 [SMILES: Cc1cc(-c2cc(-c3cn[nH]c3)cc(N3CCNCC3)c2)c(O)c(-c2ccc(-n3ccn(C)c3=O)c(Cl)c2)c1]
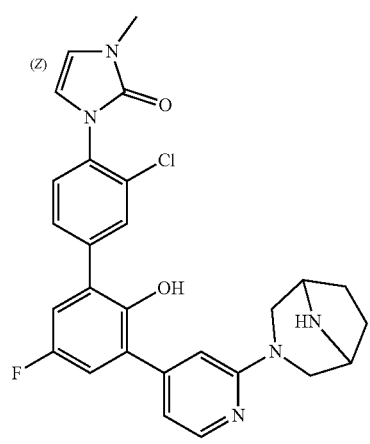
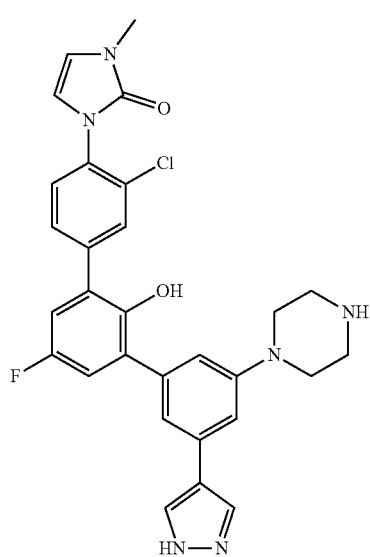
1446
-continued
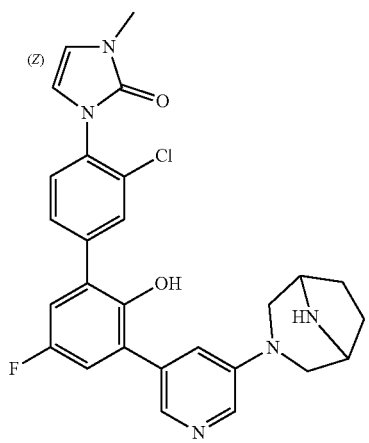 [SMILES: Cn1ccn(-c2ccc(-c3cc(F)cc(-c4cncc(N5CC6CCC(C5)N6)c4)c3O)cc2Cl)c1=O]
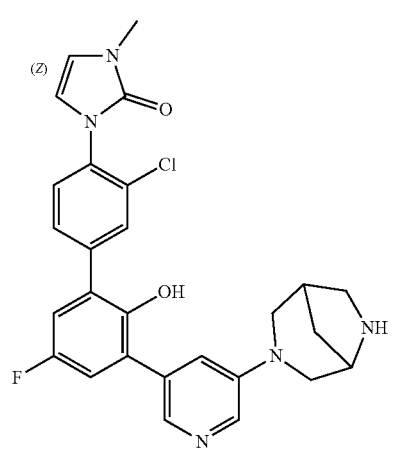 [SMILES: Cn1ccn(-c2ccc(-c3cc(F)cc(-c4cncc(N5CC6CNC(C6)C5)c4)c3O)cc2Cl)c1=O]
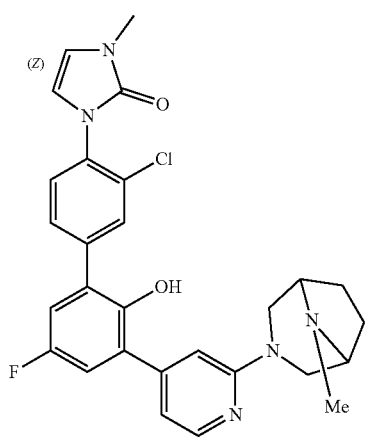 [SMILES: CN1C2CCC1CN(c1cc(-c3cc(F)cc(-c4ccc(-n5ccn(C)c5=O)c(Cl)c4)c3O)ccn1)C2]

1447
-continued
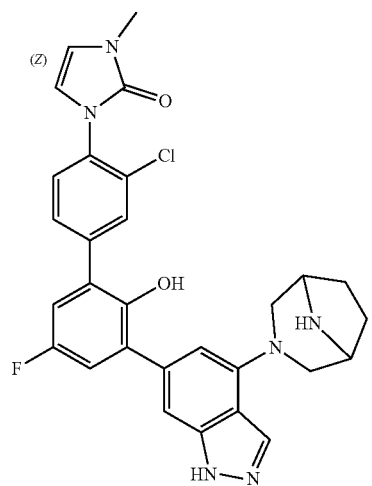 [SMILES: Cn1ccn(-c2ccc(-c3cc(F)cc(-c4cc(N5CC6CCC(C5)N6)c5cn[nH]c5c4)c3O)cc2Cl)c1=O]
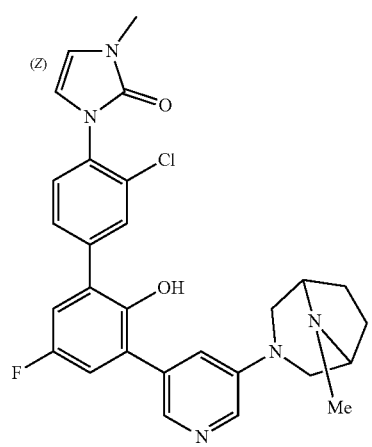 [SMILES: CN1C2CCC1CN(c1cncc(-c3cc(F)cc(-c4ccc(-n5ccn(C)c5=O)c(Cl)c4)c3O)c1)C2]
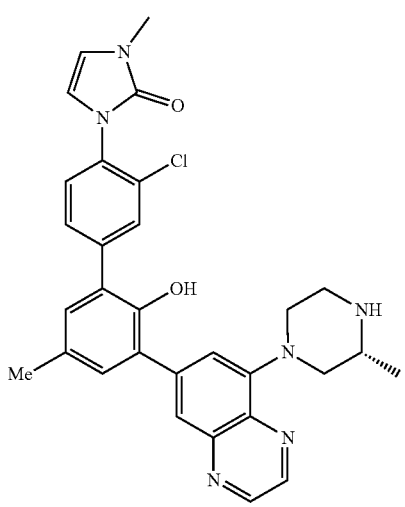 [SMILES: Cc1cc(-c2ccc(-n3ccn(C)c3=O)c(Cl)c2)c(O)c(-c2cc(N3CCN[C@H](C)C3)c3nccnc3c2)c1]
1448
-continued
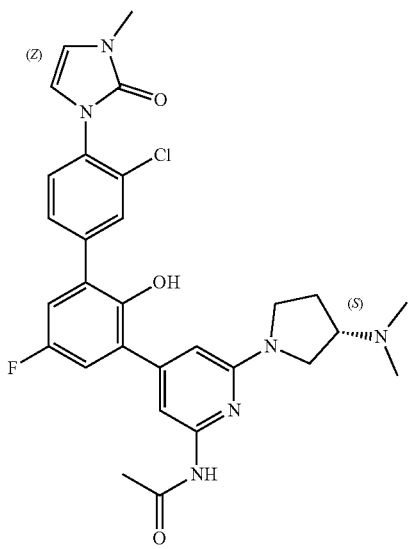
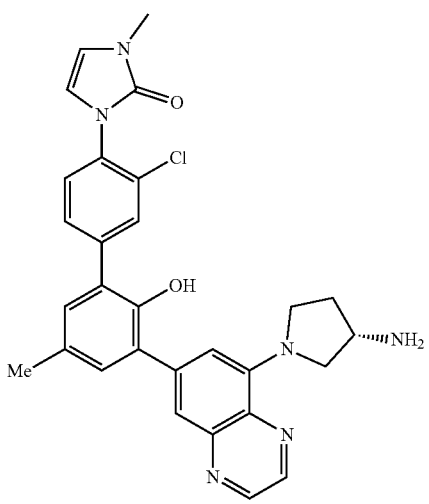 [SMILES: Cc1cc(-c2ccc(-n3ccn(C)c3=O)c(Cl)c2)c(O)c(-c2cc(N3CC[C@H](N)C3)c3nccnc3c2)c1]
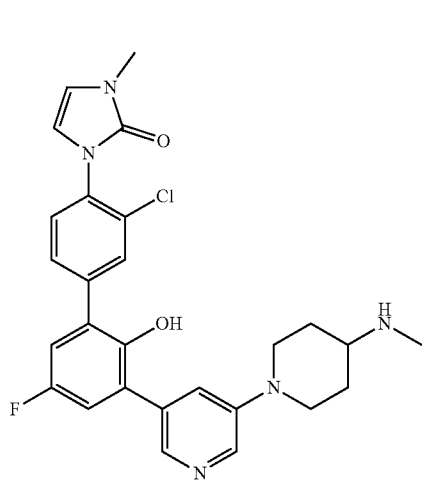 [SMILES: CNC1CCN(c2cncc(-c3cc(F)cc(-c4ccc(-n5ccn(C)c5=O)c(Cl)c4)c3O)c2)CC1]

| 1449 -continued | 1450 -continued |
|---|---|
| 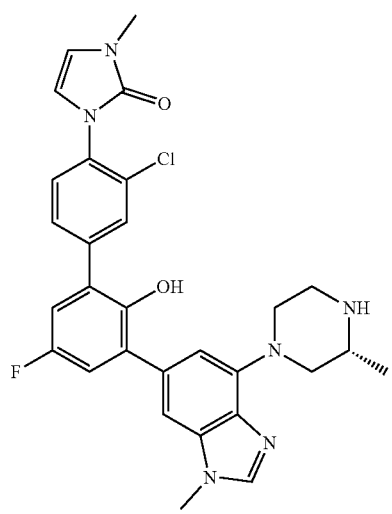 [SMILES: C[C@@H]1CN(c2cc(-c3cc(F)cc(-c4ccc(-n5ccn(C)c5=O)c(Cl)c4)c3O)cc3c2ncn3C)CCN1] | 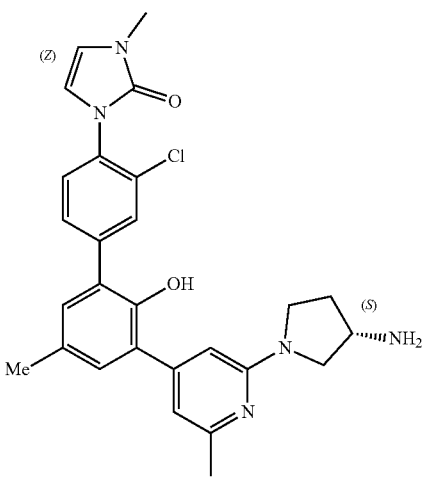 |
| 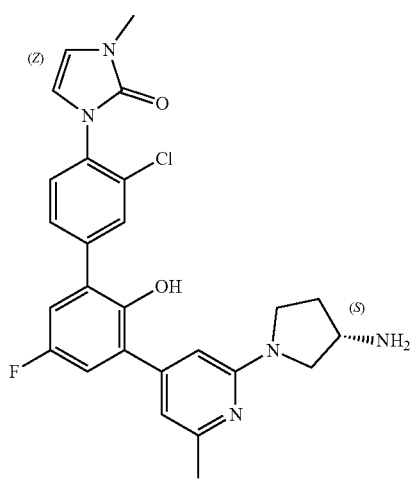 | 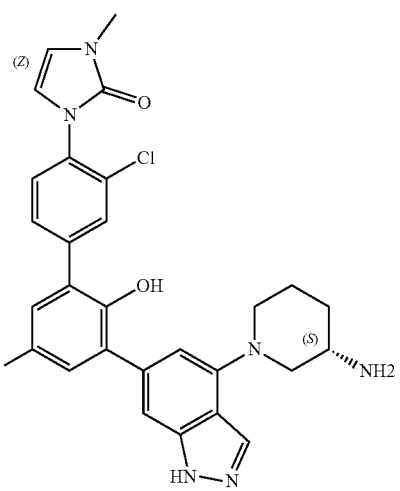 |
| 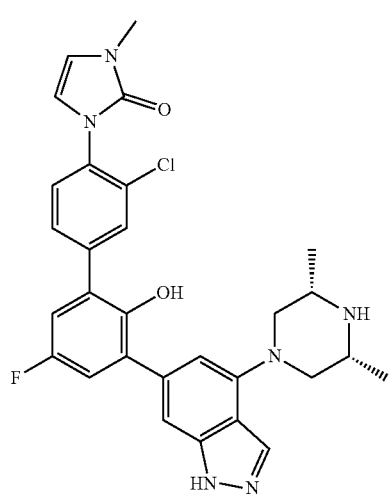 [SMILES: C[C@@H]1CN(c2cc(-c3cc(F)cc(-c4ccc(-n5ccn(C)c5=O)c(Cl)c4)c3O)cc3[nH]ncc23)C[C@H](C)N1] | 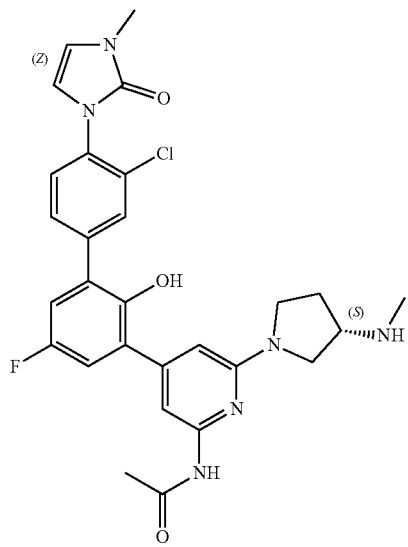 |

1451
-continued
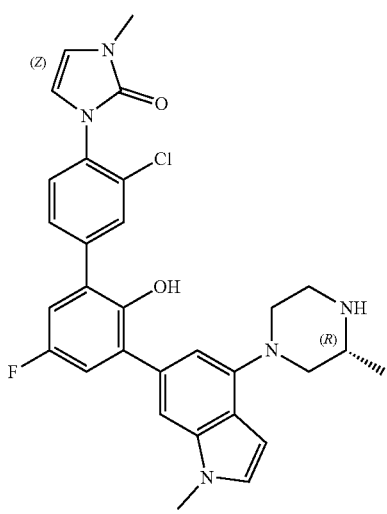
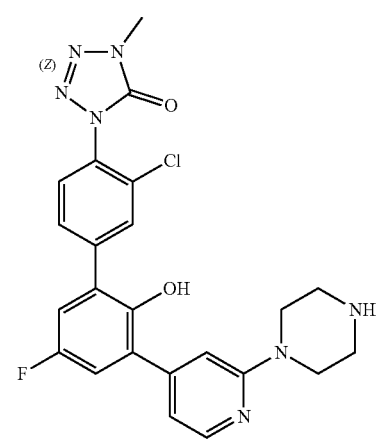
1452
-continued
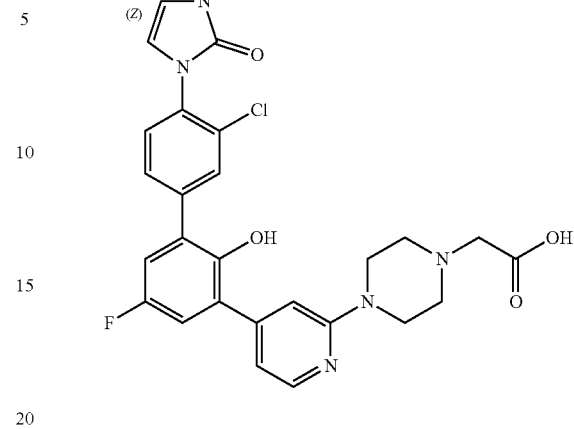
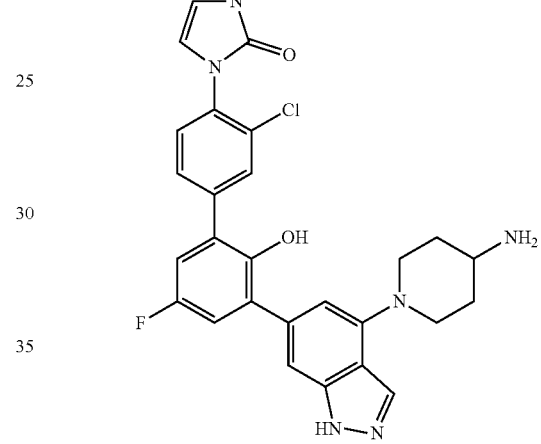
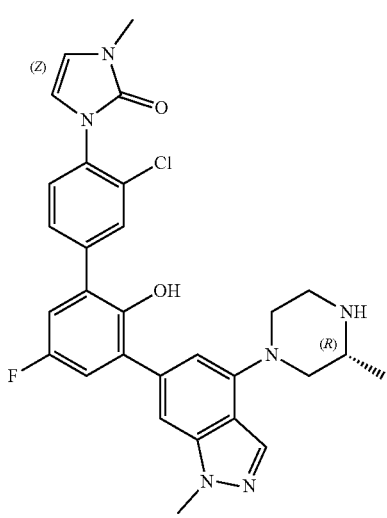
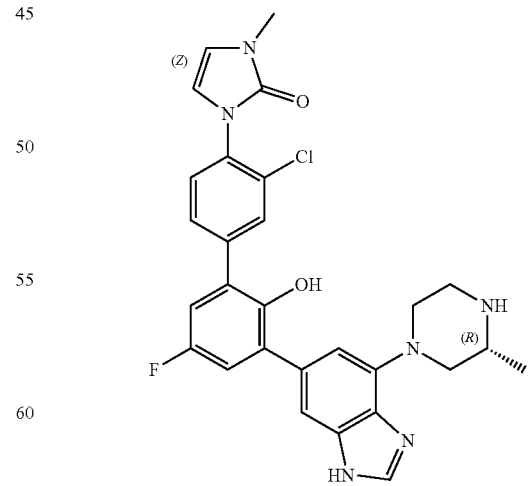

1453
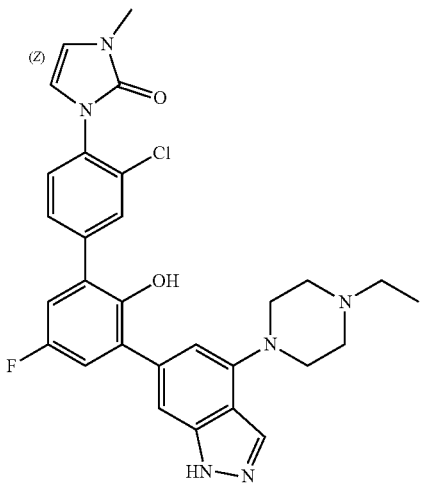
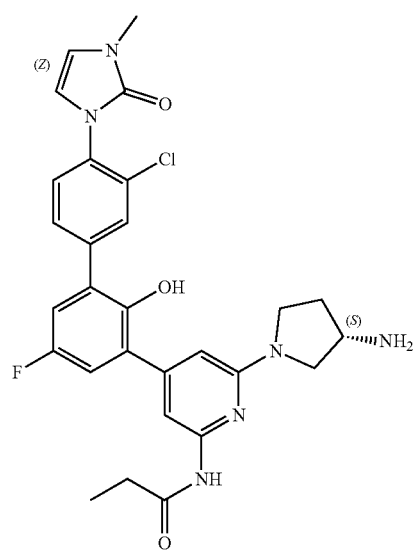
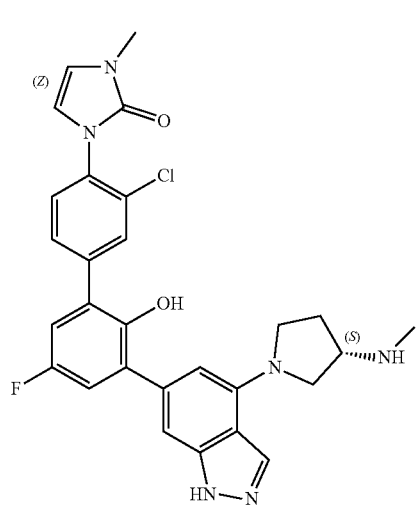
1454
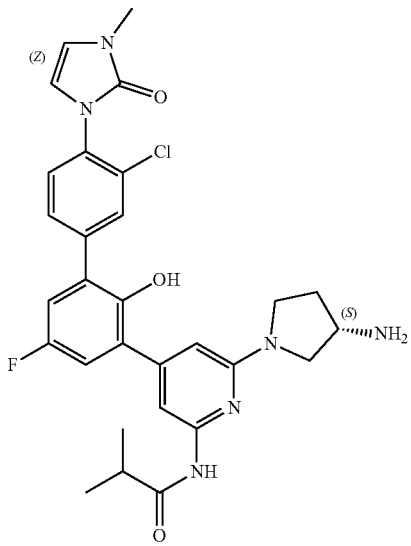
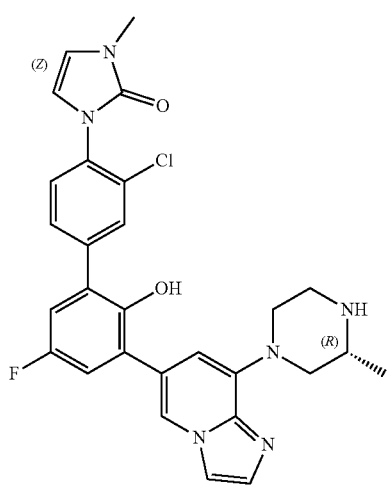
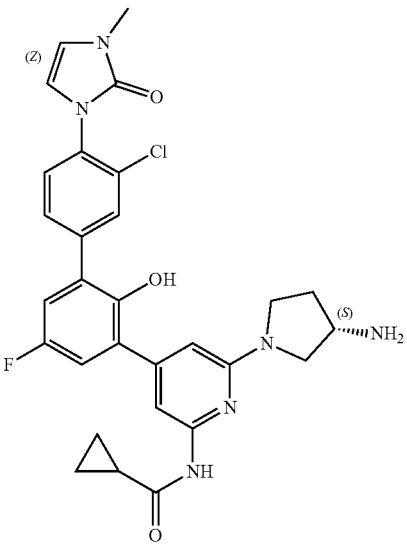

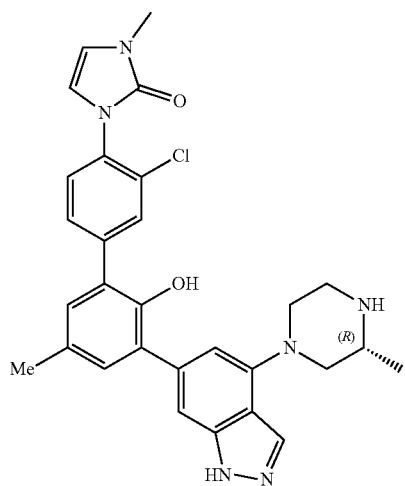
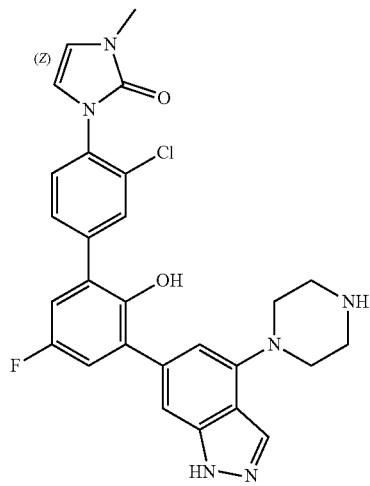
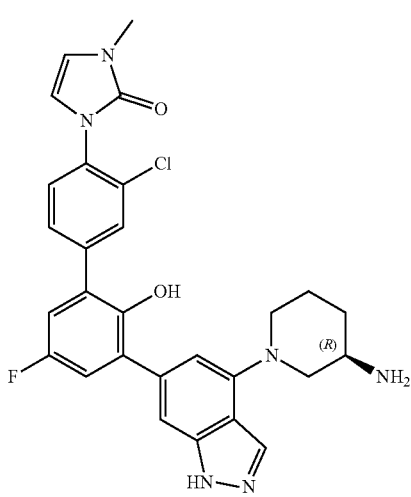
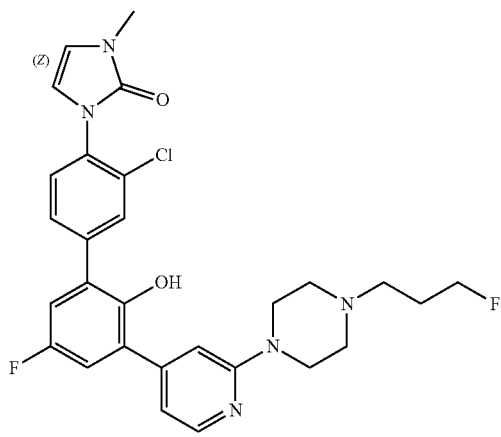
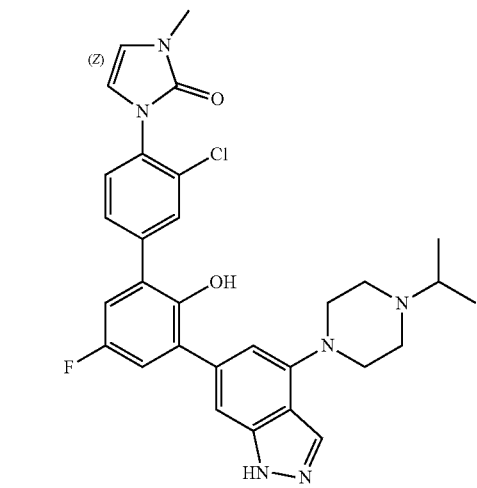
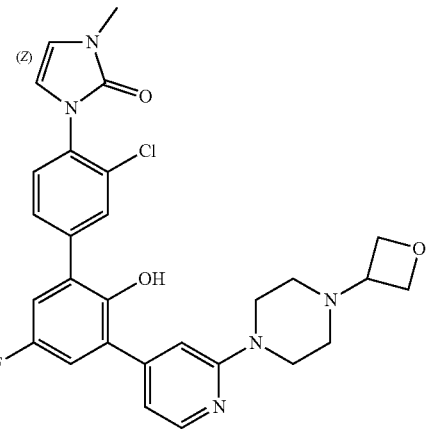

1457
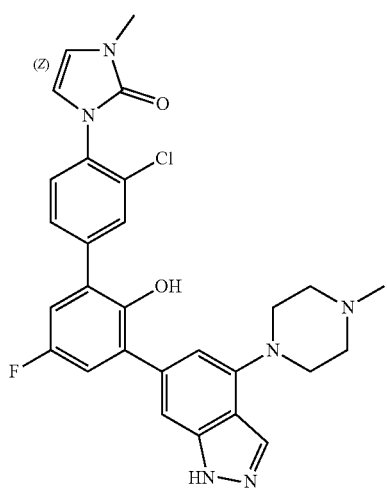
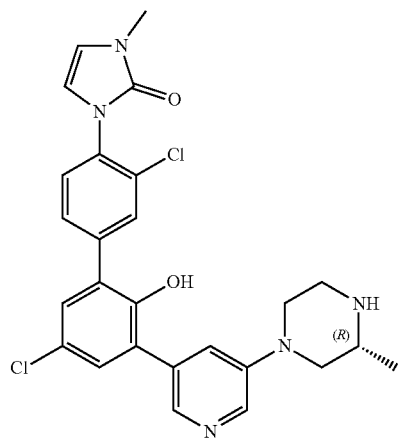
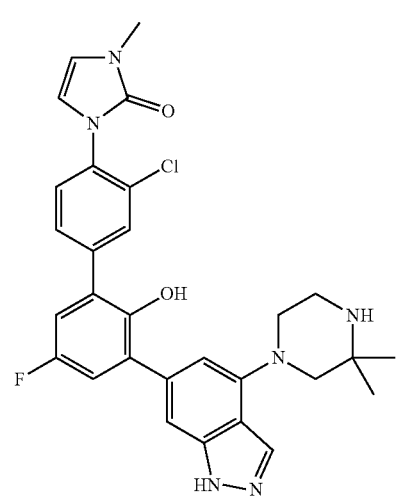 [SMILES: Cn1ccn(-c2ccc(-c3cc(F)cc(-c4cc(N5CCNC(C)(C)C5)c5cn[nH]c5c4)c3O)cc2Cl)c1=O]
1458
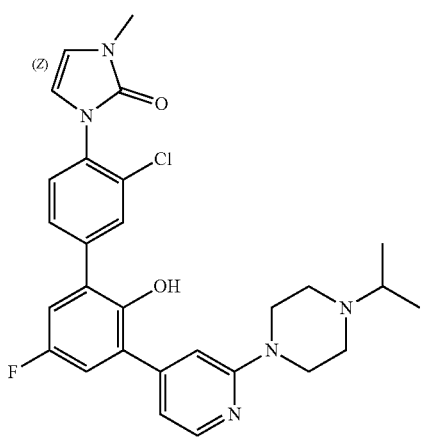
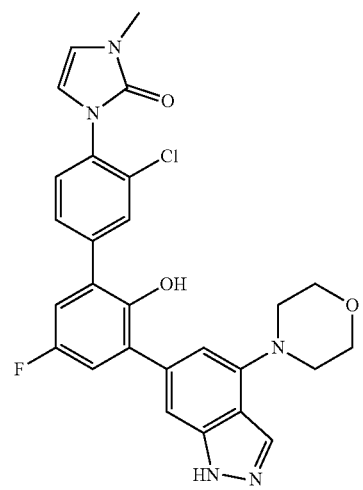
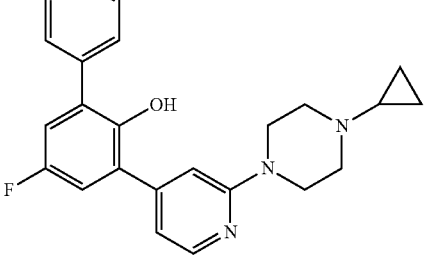

1459
-continued
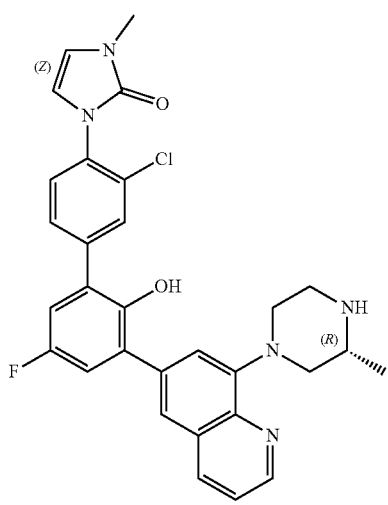
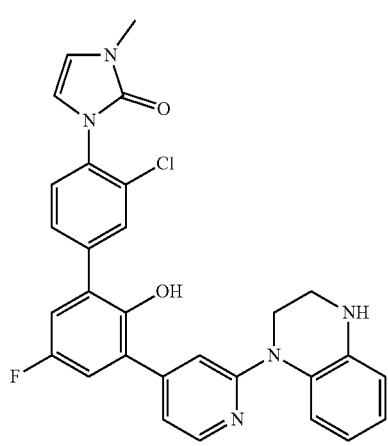 [SMILES: Cn1ccn(-c2ccc(-c3cc(F)cc(-c4ccnc(N5CCNc6ccccc65)c4)c3O)cc2Cl)c1=O]
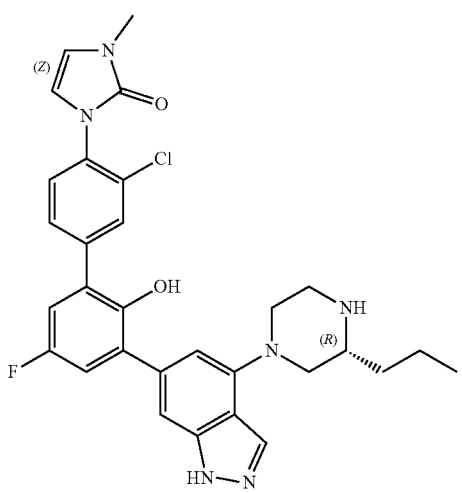
1460
-continued
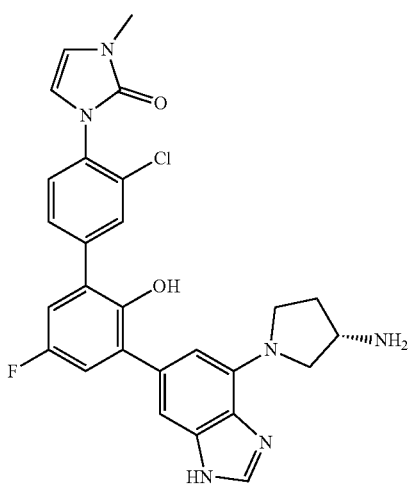 [SMILES: Cn1ccn(-c2ccc(-c3cc(F)cc(-c4cc(N5CC[C@H](N)C5)c5nc[nH]c5c4)c3O)cc2Cl)c1=O]
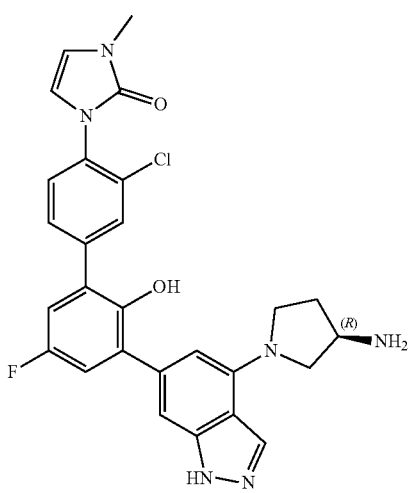
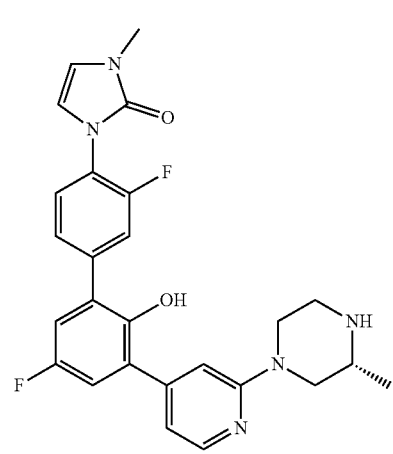 [SMILES: C[C@@H]1CN(c2cc(-c3cc(F)cc(-c4ccc(-n5ccn(C)c5=O)c(F)c4)c3O)ccn2)CCN1]

| 1461 -continued | 1462 -continued |
|---|---|
| 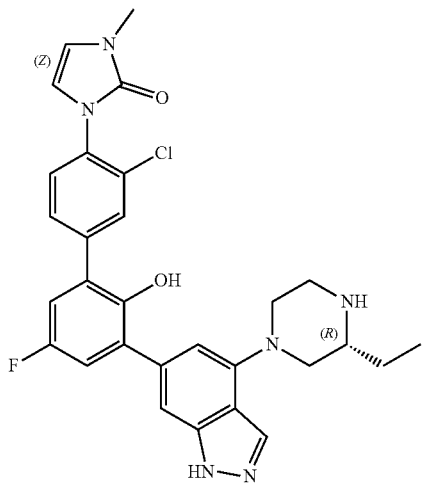 | 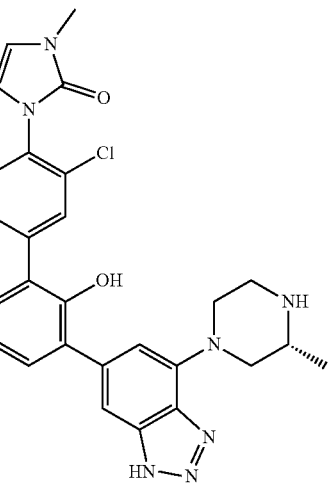 |
| 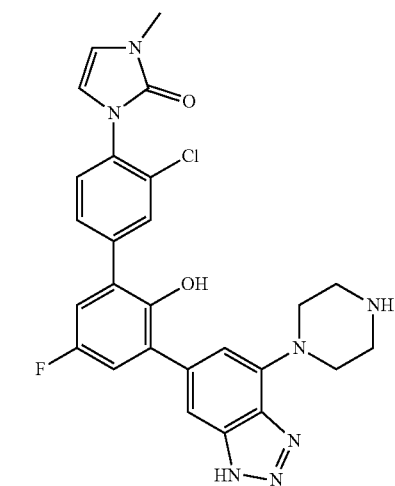 [SMILES: Cn1ccn(-c2ccc(-c3cc(F)cc(-c4cc(N5CCNCC5)c5nn[nH]c5c4)c3O)cc2Cl)c1=O] | 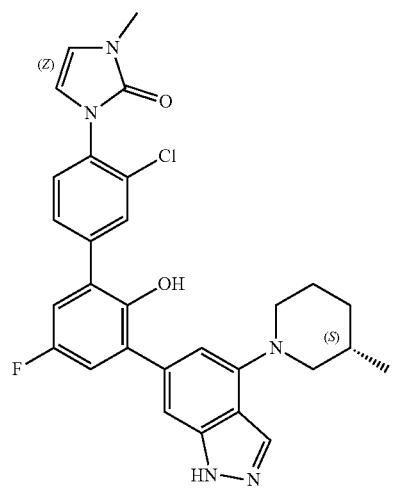 |
| 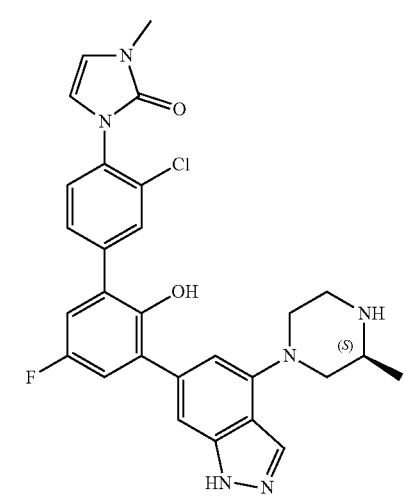 | 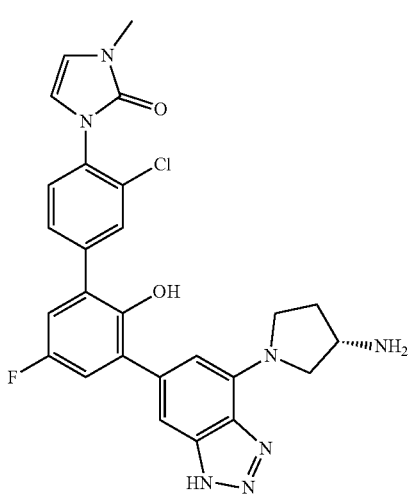 [SMILES: Cn1ccn(-c2ccc(-c3cc(F)cc(-c4cc(N5CC[C@H](N)C5)c5nn[nH]c5c4)c3O)cc2Cl)c1=O] |

1463
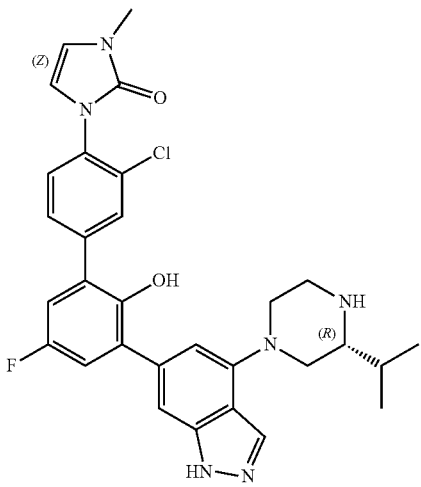
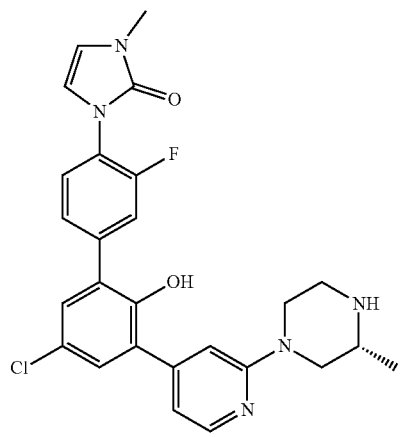 [SMILES: C[C@@H]1CN(c2cc(-c3cc(Cl)cc(-c4ccc(-n5ccn(C)c5=O)c(F)c4)c3O)ccn2)CCN1]
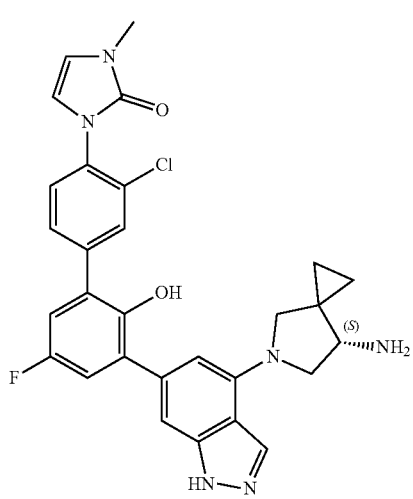
1464
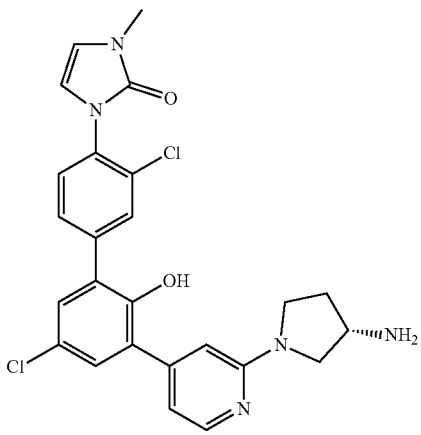 [SMILES: Cn1ccn(-c2ccc(-c3cc(Cl)cc(-c4ccnc(N5CC[C@H](N)C5)c4)c3O)cc2Cl)c1=O]
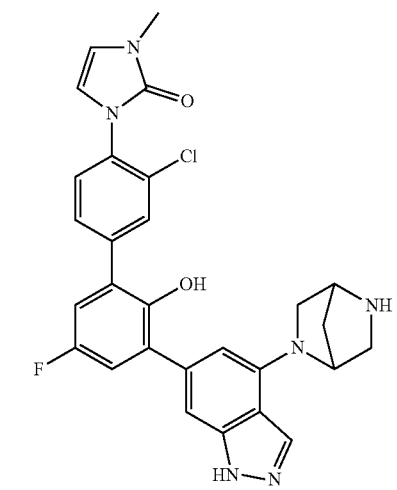 [SMILES: Cn1ccn(-c2ccc(-c3cc(F)cc(-c4cc(N5CC6CC5CN6)c5cn[nH]c5c4)c3O)cc2Cl)c1=O]
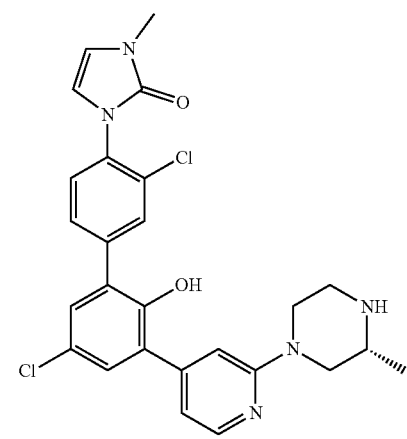 [SMILES: C[C@@H]1CN(c2cc(-c3cc(Cl)cc(-c4ccc(-n5ccn(C)c5=O)c(Cl)c4)c3O)ccn2)CCN1]

1465
-continued
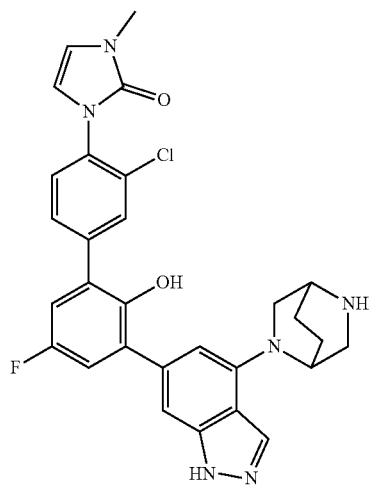 [SMILES: Cn1ccn(-c2ccc(-c3cc(F)cc(-c4cc(N5CC6CCC5CN6)c5cn[nH]c5c4)c3O)cc2Cl)c1=O]
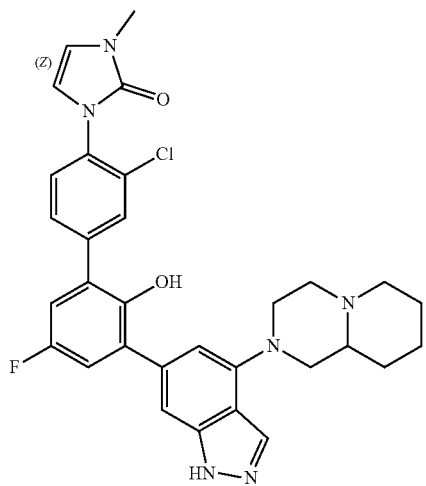
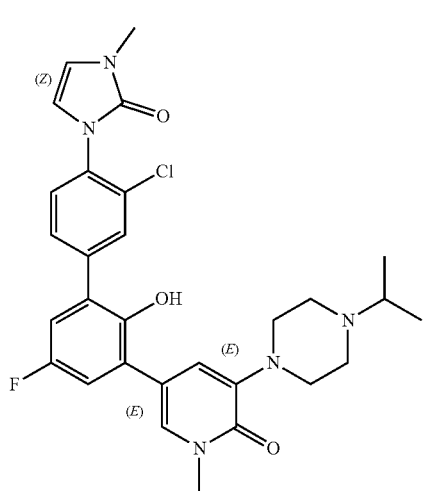
1466
-continued
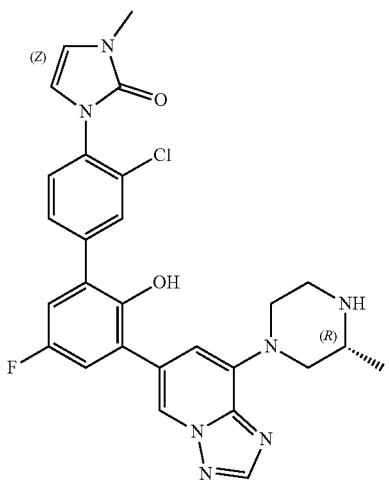
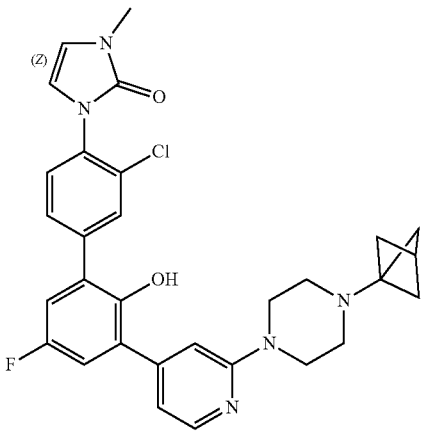
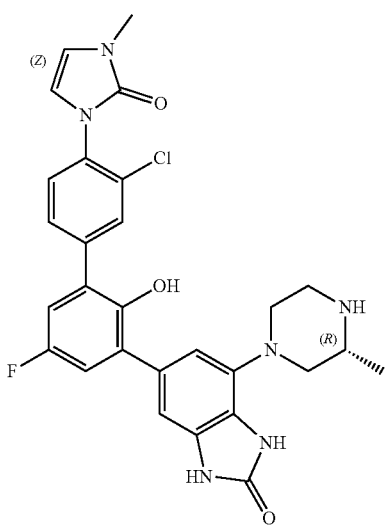

1467
-continued
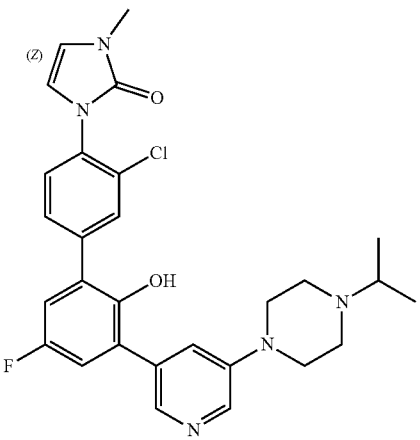 [SMILES: CC(C)N1CCN(c2cncc(-c3cc(F)cc(-c4ccc(-n5ccn(C)c5=O)c(Cl)c4)c3O)c2)CC1]
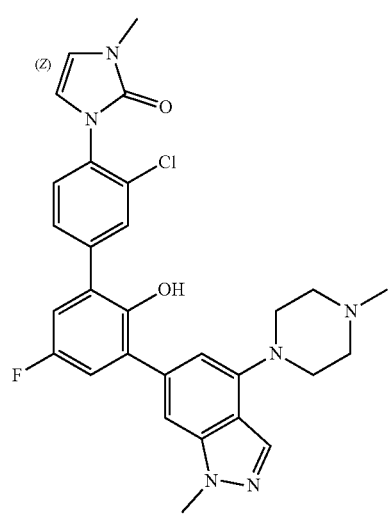 [SMILES: CN1CCN(c2cc(-c3cc(F)cc(-c4ccc(-n5ccn(C)c5=O)c(Cl)c4)c3O)cc3c2cnn3C)CC1]
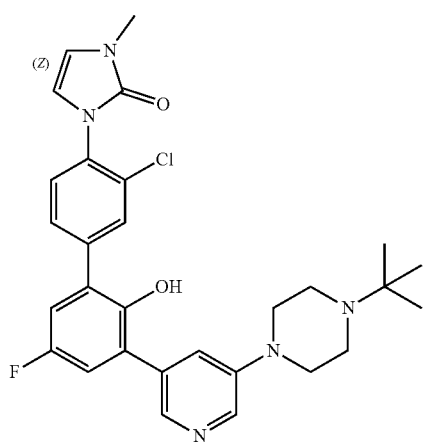 [SMILES: Cn1ccn(-c2ccc(-c3cc(F)cc(-c4cncc(N5CCN(C(C)(C)C)CC5)c4)c3O)cc2Cl)c1=O]
1468
-continued
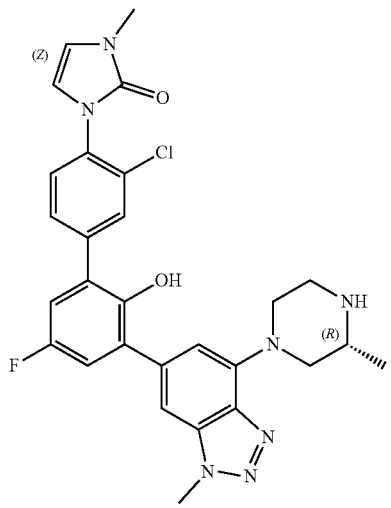
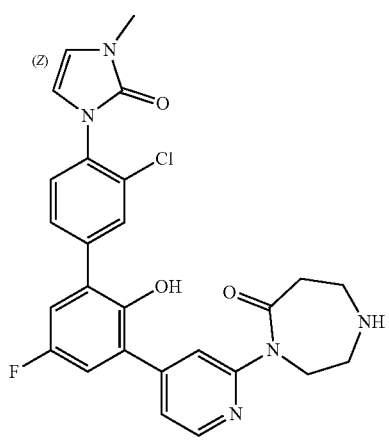 [SMILES: Cn1ccn(-c2ccc(-c3cc(F)cc(-c4ccnc(N5CCNCCC5=O)c4)c3O)cc2Cl)c1=O]
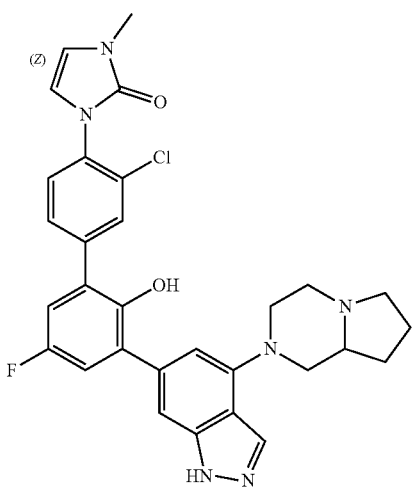 [SMILES: Cn1ccn(-c2ccc(-c3cc(F)cc(-c4cc(N5CCN6CCCC6C5)c5cn[nH]c5c4)c3O)cc2Cl)c1=O]

1469
-continued
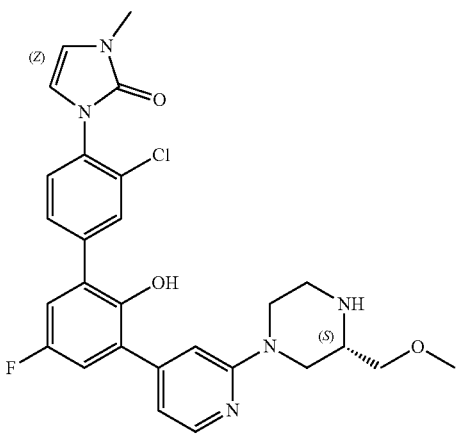
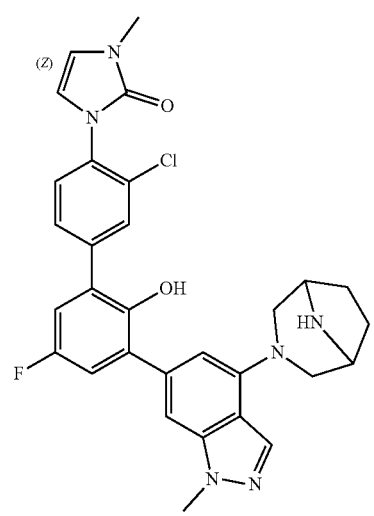 [SMILES: Cn1ccn(-c2ccc(-c3cc(F)cc(-c4cc(N5CC6CCC(C5)N6)c5cnn(C)c5c4)c3O)cc2Cl)c1=O]
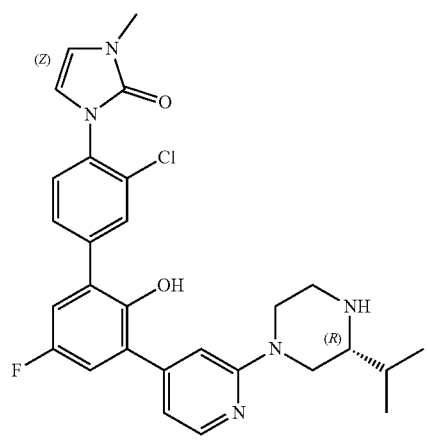
1470
-continued
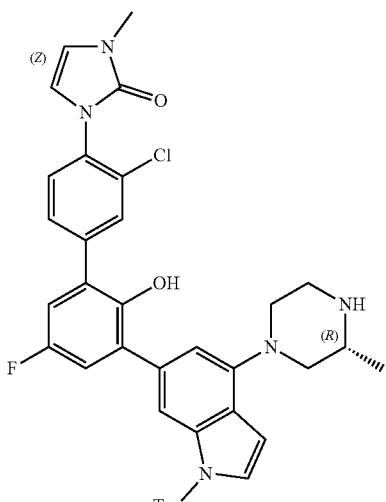
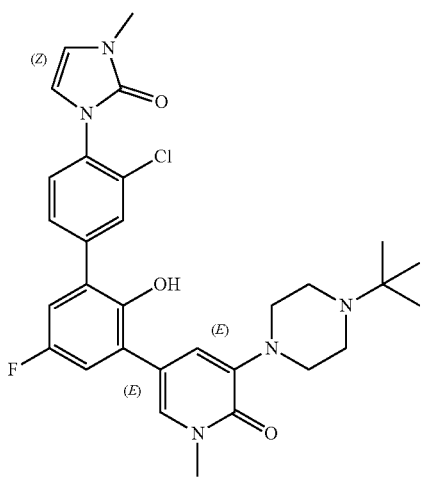
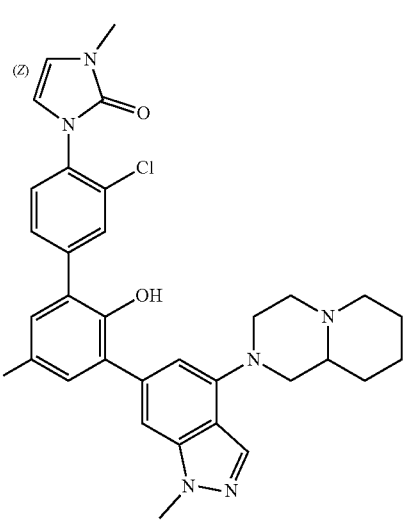

| 1471 -continued | 1472 -continued |
|---|---|
| 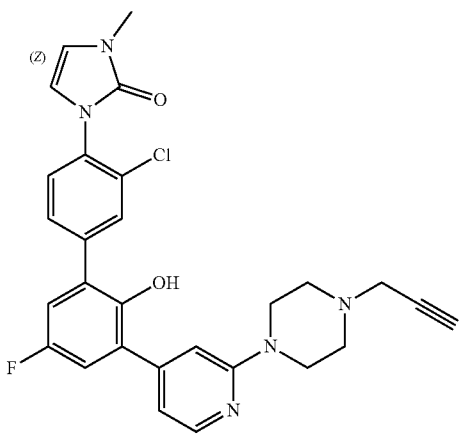 [SMILES: C#CCN1CCN(c2cc(-c3cc(F)cc(-c4ccc(-n5ccn(C)c5=O)c(Cl)c4)c3O)ccn2)CC1] | 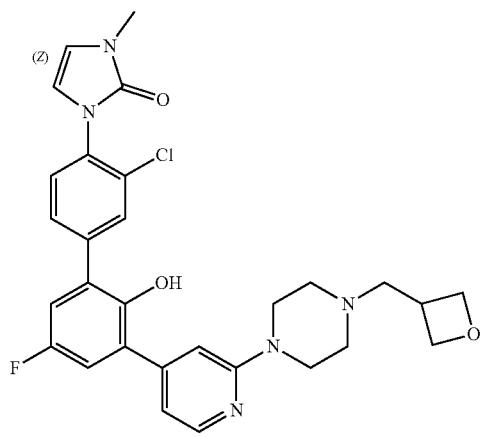 |
| 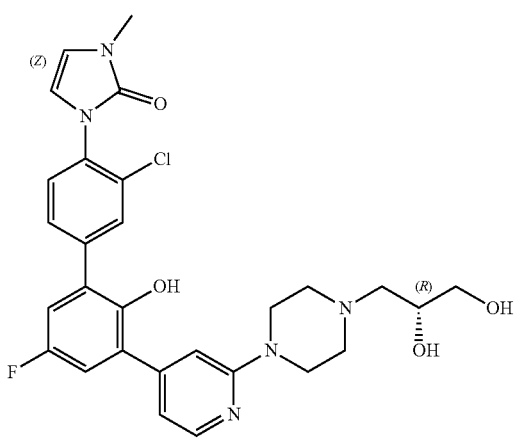 | 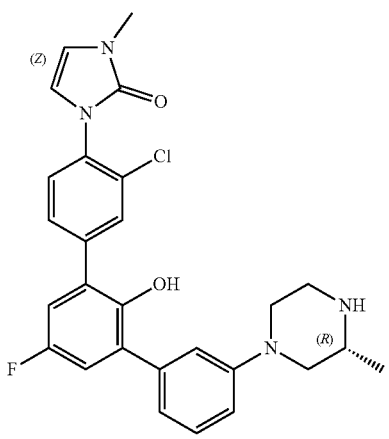 |
| 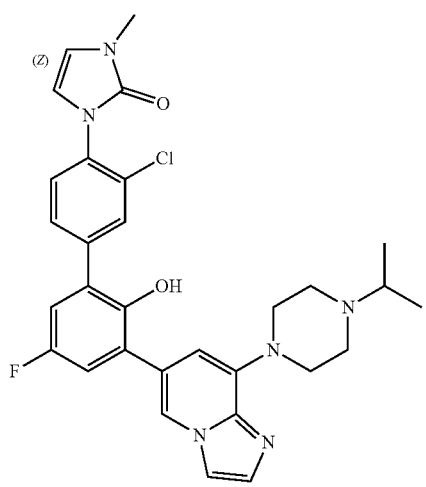 [SMILES: CC(C)N1CCN(c2cc(-c3cc(F)cc(-c4ccc(-n5ccn(C)c5=O)c(Cl)c4)c3O)cn3ccnc23)CC1] | 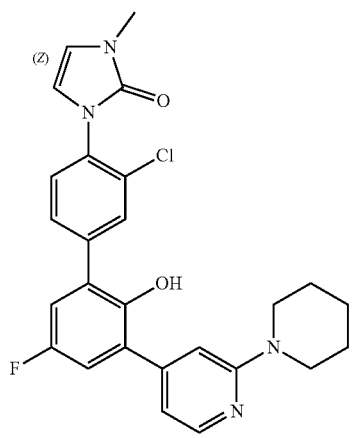 [SMILES: Cn1ccn(-c2ccc(-c3cc(F)cc(-c4ccnc(N5CCCCC5)c4)c3O)cc2Cl)c1=O] |

1473
-continued
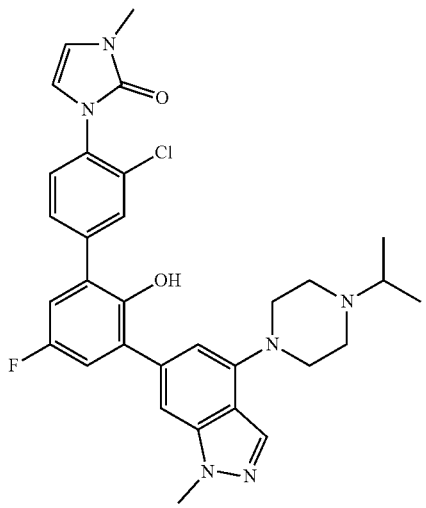 [SMILES: CC(C)N1CCN(c2cc(-c3cc(F)cc(-c4ccc(-n5ccn(C)c5=O)c(Cl)c4)c3O)cc3c2cnn3C)CC1]
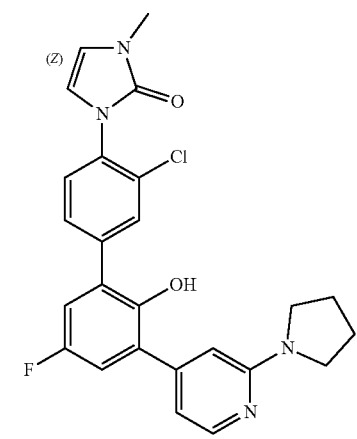 [SMILES: Cn1ccn(-c2ccc(-c3cc(F)cc(-c4ccnc(N5CCCC5)c4)c3O)cc2Cl)c1=O]
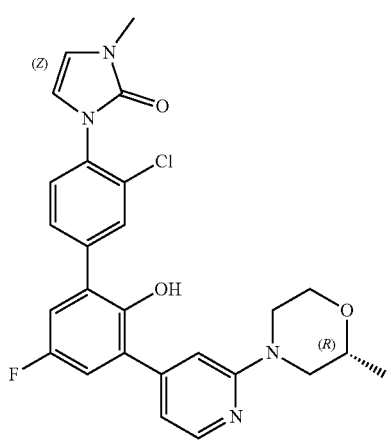
1474
-continued
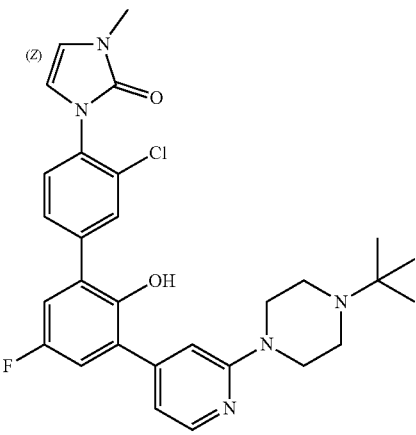 [SMILES: Cn1ccn(-c2ccc(-c3cc(F)cc(-c4ccnc(N5CCN(C(C)(C)C)CC5)c4)c3O)cc2Cl)c1=O]
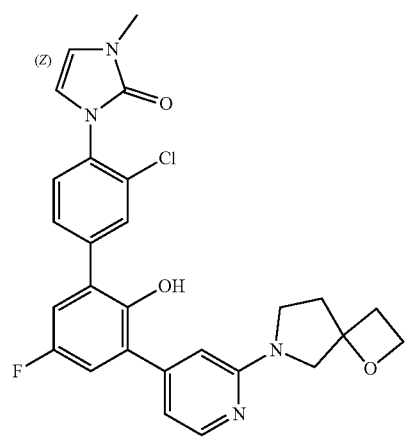 [SMILES: Cn1ccn(-c2ccc(-c3cc(F)cc(-c4ccnc(N5CCC6(CCO6)C5)c4)c3O)cc2Cl)c1=O]
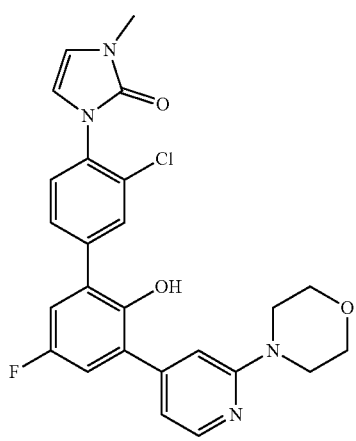

1475
-continued
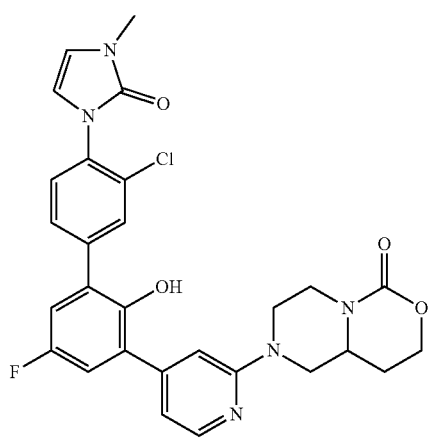 [SMILES: Cn1ccn(-c2ccc(-c3cc(F)cc(-c4ccnc(N5CCN6C(=O)OCCC6C5)c4)c3O)cc2Cl)c1=O]
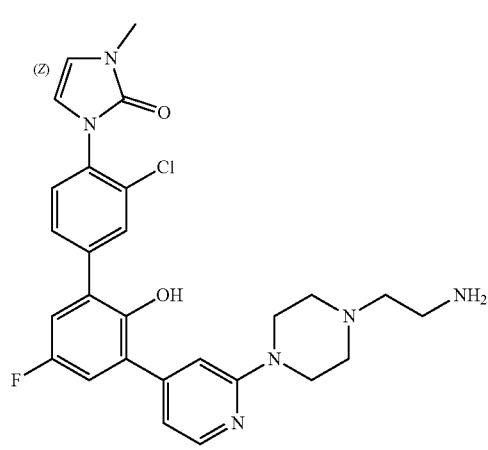 [SMILES: Cn1ccn(-c2ccc(-c3cc(F)cc(-c4ccnc(N5CCN(CCN)CC5)c4)c3O)cc2Cl)c1=O]
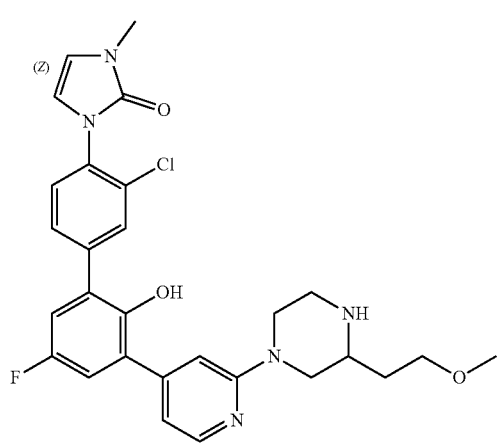 [SMILES: COCCC1CN(c2cc(-c3cc(F)cc(-c4ccc(-n5ccn(C)c5=O)c(Cl)c4)c3O)ccn2)CCN1]
1476
-continued
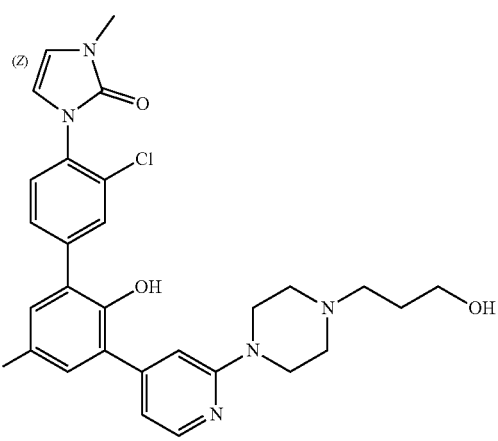
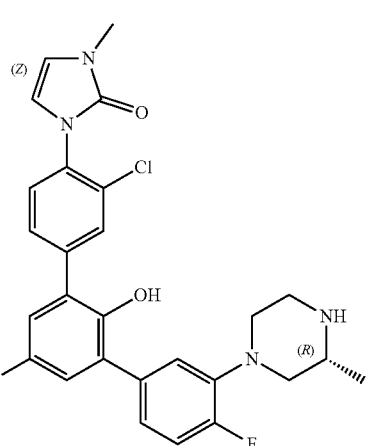
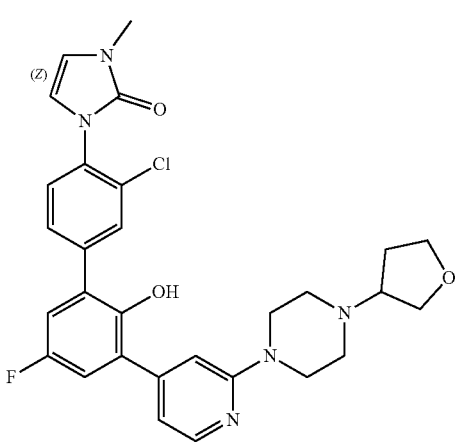 [SMILES: Cn1ccn(-c2ccc(-c3cc(F)cc(-c4ccnc(N5CCN(C6CCOC6)CC5)c4)c3O)cc2Cl)c1=O]

| 1477 -continued | 1478 -continued |
|---|---|
| 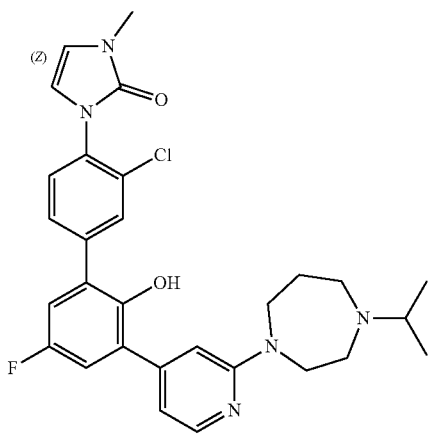 [SMILES: CC(C)N1CCCN(c2cc(-c3cc(F)cc(-c4ccc(-n5ccn(C)c5=O)c(Cl)c4)c3O)ccn2)CC1] | 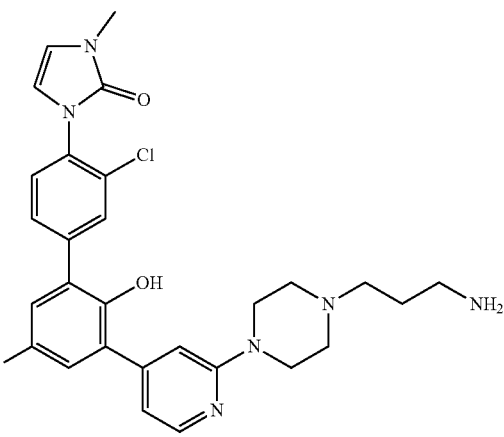 |
| 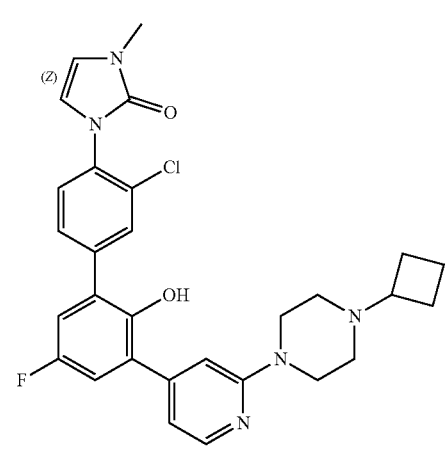 [SMILES: Cn1ccn(-c2ccc(-c3cc(F)cc(-c4ccnc(N5CCN(C6CCC6)CC5)c4)c3O)cc2Cl)c1=O] | 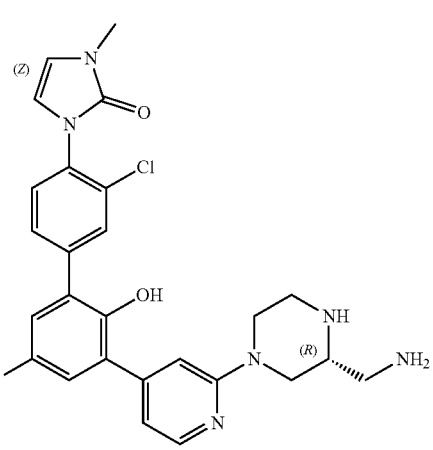 |
| 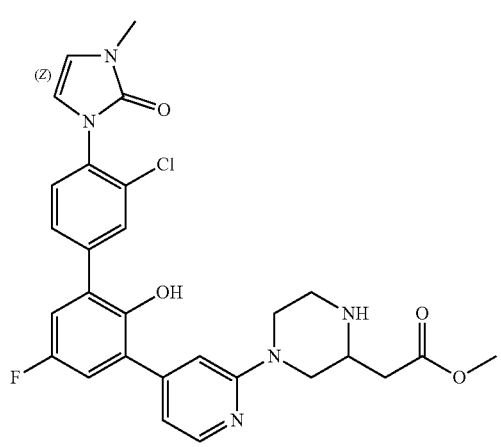 [SMILES: COC(=O)CC1CN(c2cc(-c3cc(F)cc(-c4ccc(-n5ccn(C)c5=O)c(Cl)c4)c3O)ccn2)CCN1] | 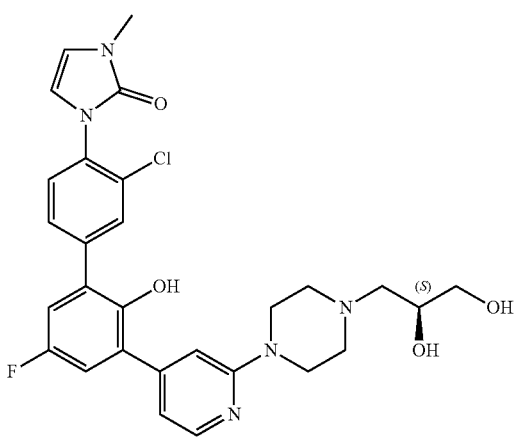 |

1479
-continued
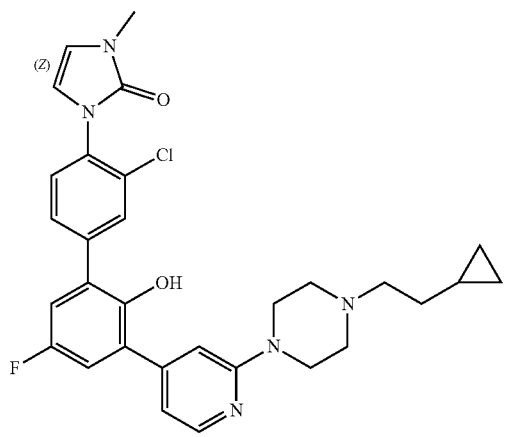 [SMILES: Cn1ccn(-c2ccc(-c3cc(F)cc(-c4ccnc(N5CCN(CCC6CC6)CC5)c4)c3O)cc2Cl)c1=O]
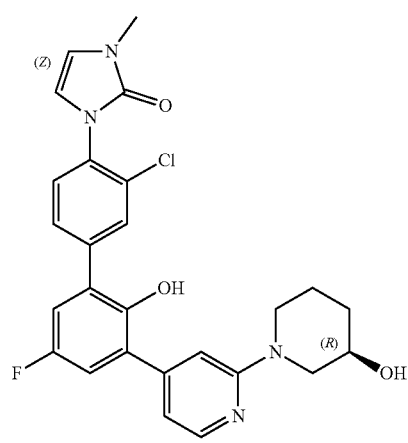
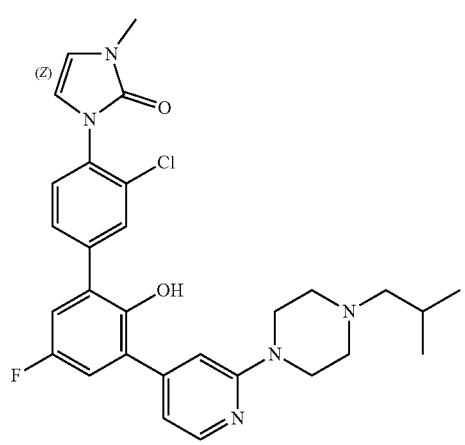 [SMILES: CC(C)CN1CCN(c2cc(-c3cc(F)cc(-c4ccc(-n5ccn(C)c5=O)c(Cl)c4)c3O)ccn2)CC1]
1480
-continued
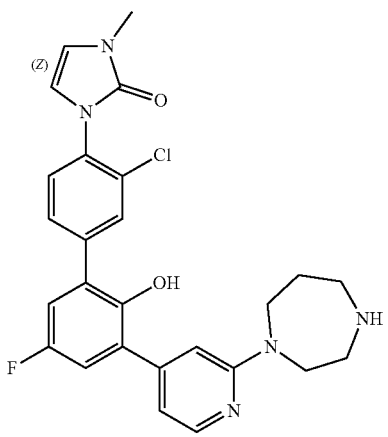 [SMILES: Cn1ccn(-c2ccc(-c3cc(F)cc(-c4ccnc(N5CCCNCC5)c4)c3O)cc2Cl)c1=O]
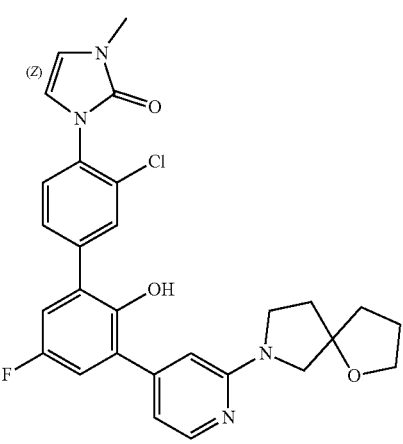 [SMILES: Cn1ccn(-c2ccc(-c3cc(F)cc(-c4ccnc(N5CCC6(CCCO6)C5)c4)c3O)cc2Cl)c1=O]
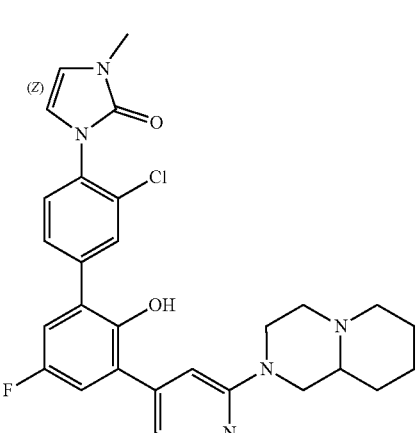

1481
-continued
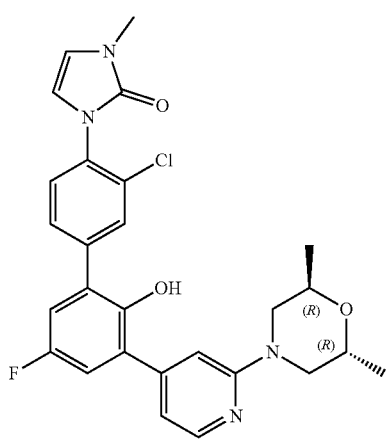
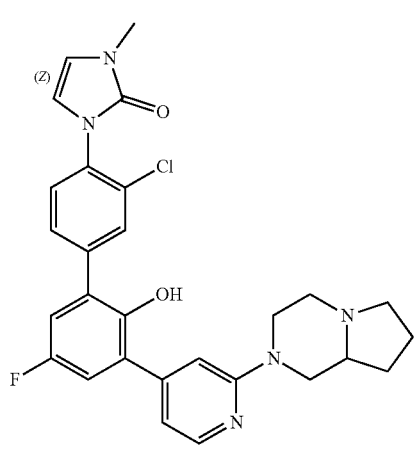 [SMILES: Cn1ccn(-c2ccc(-c3cc(F)cc(-c4ccnc(N5CCN6CCCC6C5)c4)c3O)cc2Cl)c1=O]
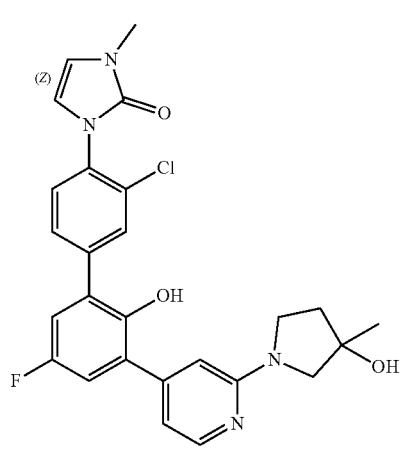 [SMILES: Cn1ccn(-c2ccc(-c3cc(F)cc(-c4ccnc(N5CCC(C)(O)C5)c4)c3O)cc2Cl)c1=O]
1482
-continued
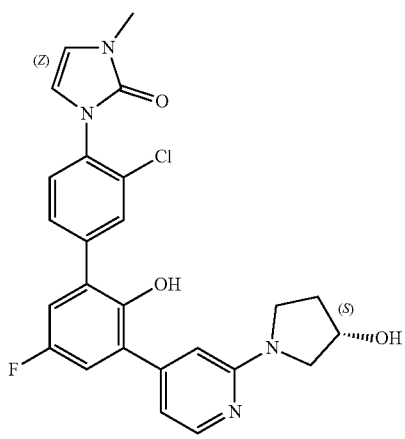
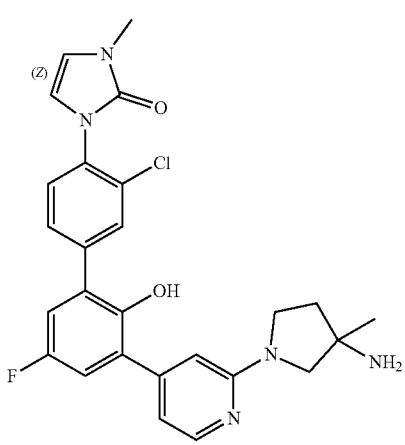 [SMILES: Cn1ccn(-c2ccc(-c3cc(F)cc(-c4ccnc(N5CCC(C)(N)C5)c4)c3O)cc2Cl)c1=O]
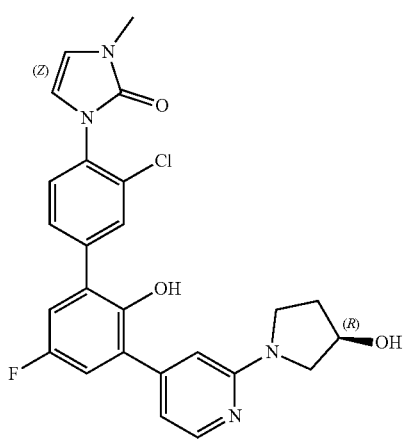

1483
-continued
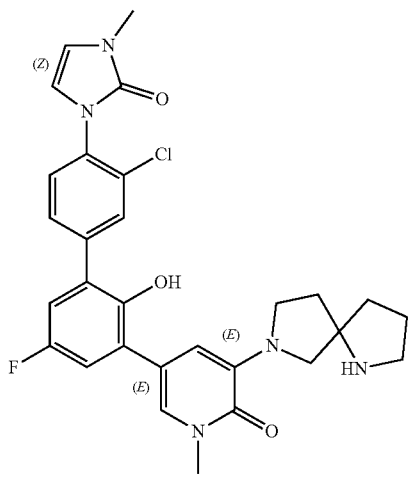 [SMILES: Cn1cc(-c2cc(F)cc(-c3ccc(-n4ccn(C)c4=O)c(Cl)c3)c2O)cc(N2CCC3(CCCN3)C2)c1=O]
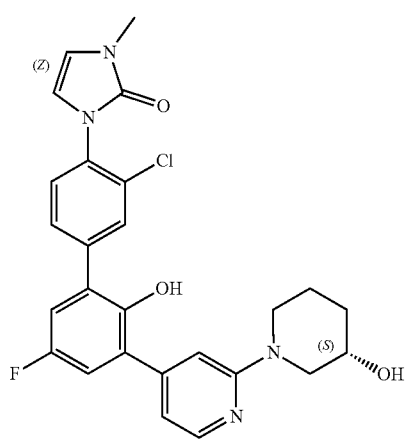
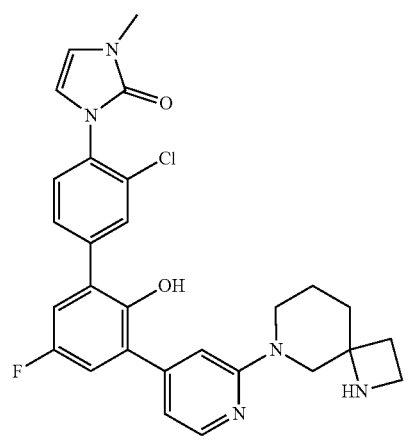 [SMILES: Cn1ccn(-c2ccc(-c3cc(F)cc(-c4ccnc(N5CCCC6(CCN6)C5)c4)c3O)cc2Cl)c1=O]
1484
-continued
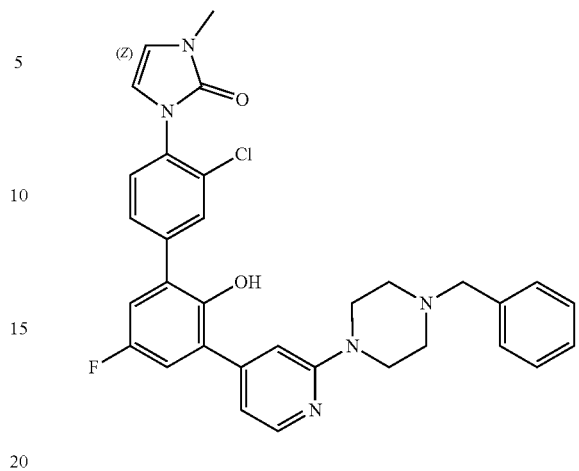
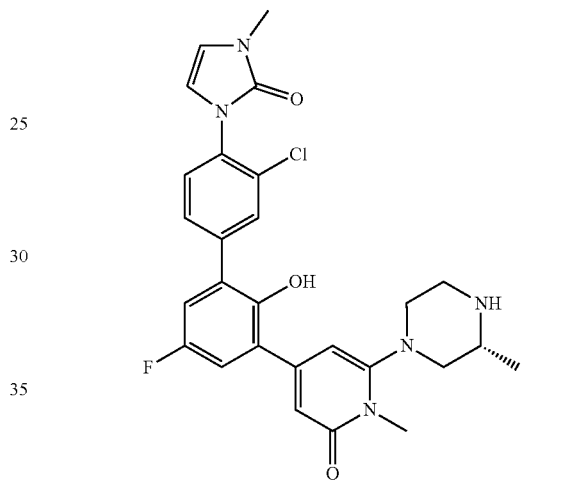
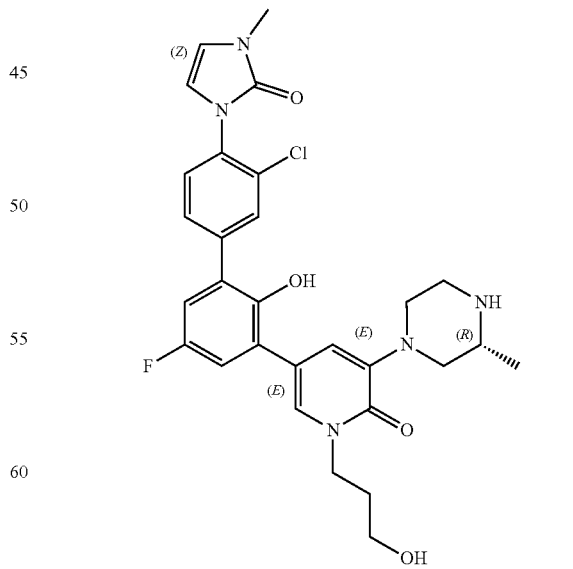

1485
-continued
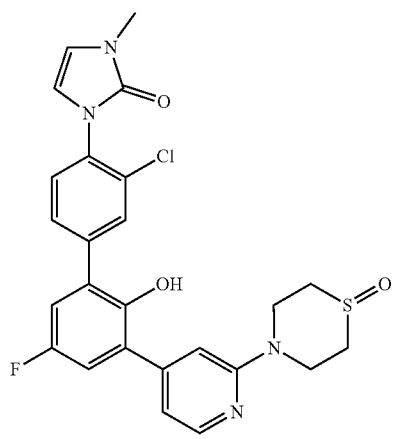 [SMILES: Cn1ccn(-c2ccc(-c3cc(F)cc(-c4ccnc(N5CCS(=O)CC5)c4)c3O)cc2Cl)c1=O]
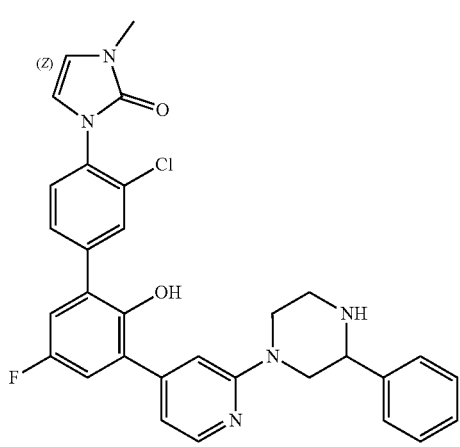 [SMILES: Cn1ccn(-c2ccc(-c3cc(F)cc(-c4ccnc(N5CCNC(c6ccccc6)C5)c4)c3O)cc2Cl)c1=O]
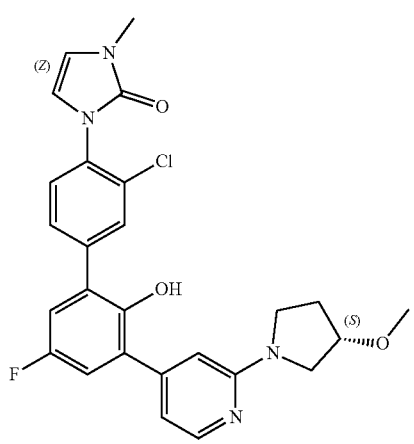
1486
-continued
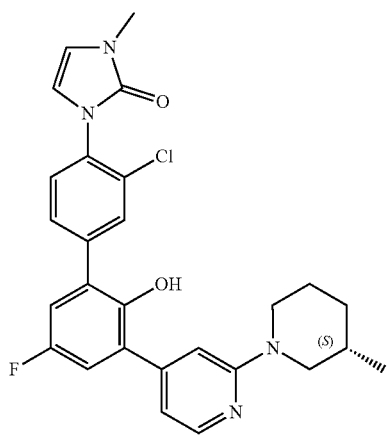
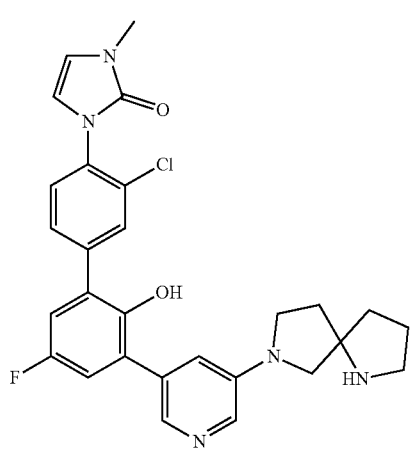 [SMILES: Cn1ccn(-c2ccc(-c3cc(F)cc(-c4cncc(N5CCC6(CCCN6)C5)c4)c3O)cc2Cl)c1=O]
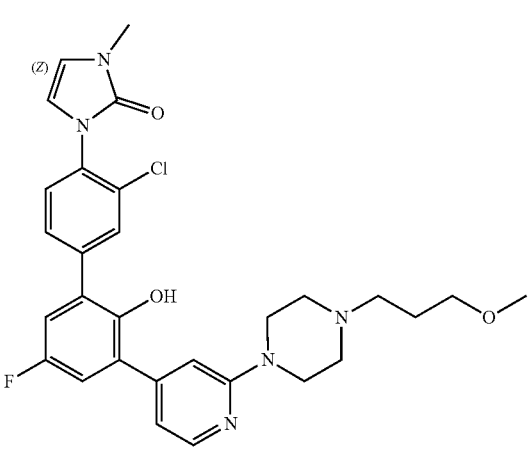 [SMILES: COCCCN1CCN(c2cc(-c3cc(F)cc(-c4ccc(-n5ccn(C)c5=O)c(Cl)c4)c3O)ccn2)CC1]

| 1487 | 1488 |
|---|---|
| 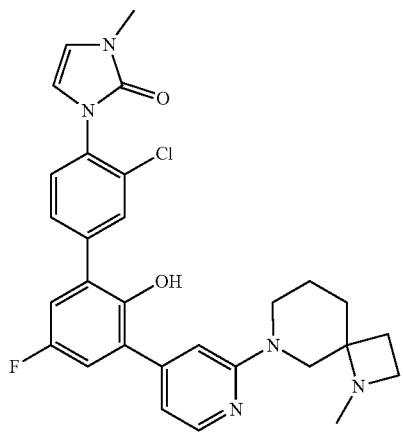 [SMILES: CN1CCC12CCCN(c1cc(-c3cc(F)cc(-c4ccc(-n5ccn(C)c5=O)c(Cl)c4)c3O)ccn1)C2] | 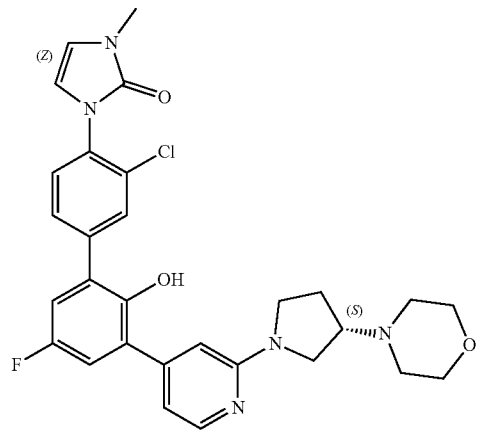 |
| 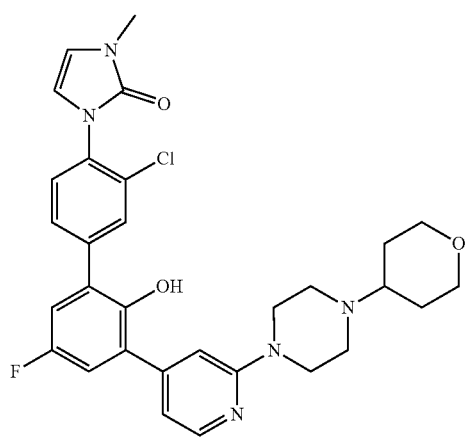 [SMILES: Cn1ccn(-c2ccc(-c3cc(F)cc(-c4ccnc(N5CCN(C6CCOCC6)CC5)c4)c3O)cc2Cl)c1=O] | 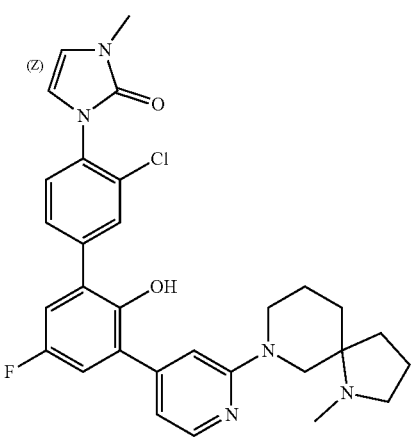 |
| 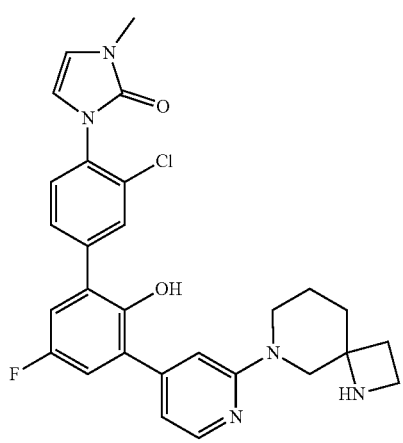 [SMILES: Cn1ccn(-c2ccc(-c3cc(F)cc(-c4ccnc(N5CCCC6(CCN6)C5)c4)c3O)cc2Cl)c1=O] | 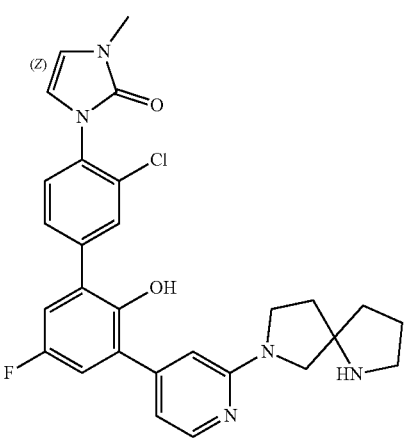 [SMILES: Cn1ccn(-c2ccc(-c3cc(F)cc(-c4ccnc(N5CCC6(CCCN6)C5)c4)c3O)cc2Cl)c1=O] |

1489
-continued
1490
-continued
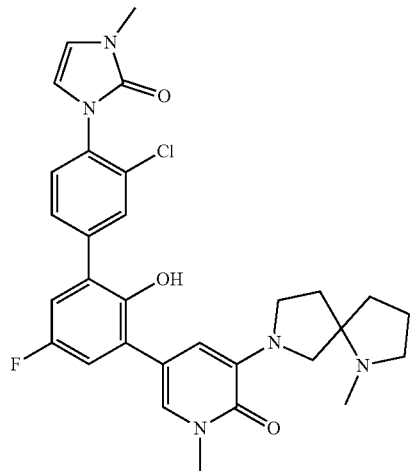 [SMILES: CN1CCCC12CCN(c1cc(-c3cc(F)cc(-c4ccc(-n5ccn(C)c5=O)c(Cl)c4)c3O)cn(C)c1=O)C2]
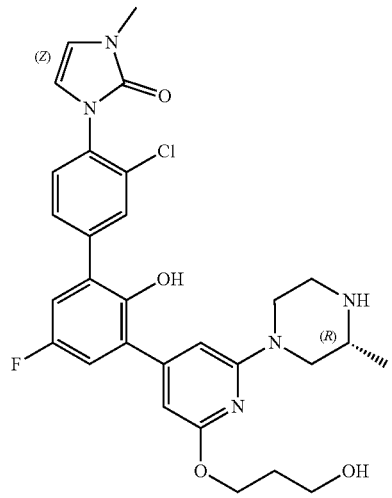
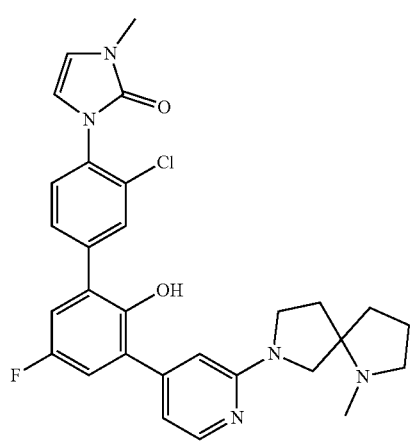
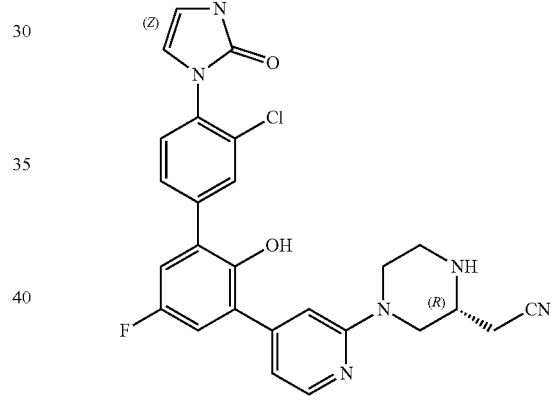
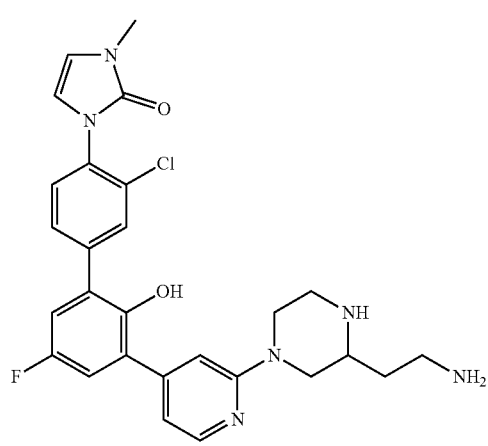 [SMILES: Cn1ccn(-c2ccc(-c3cc(F)cc(-c4ccnc(N5CCNC(CCN)C5)c4)c3O)cc2Cl)c1=O]
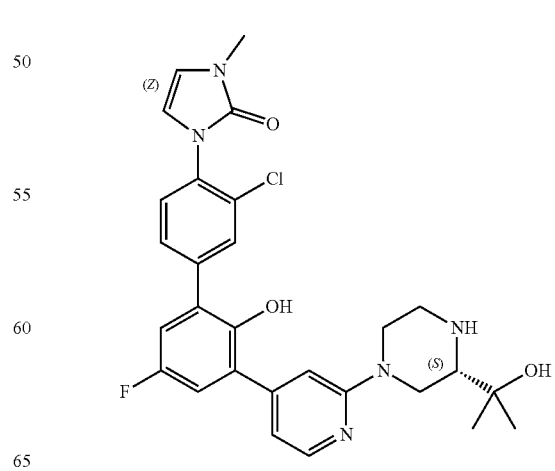

1491 -continued
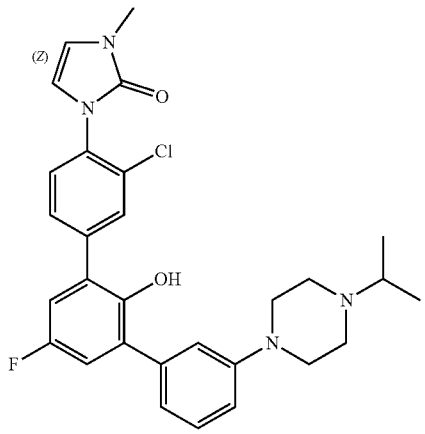
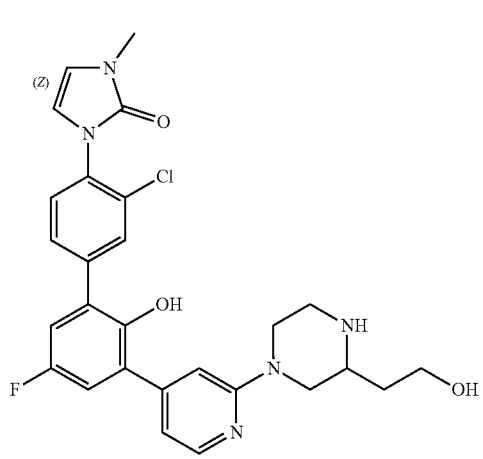
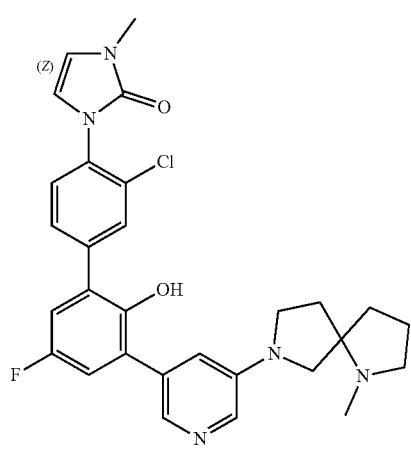 [SMILES: CN1CCCC12CCN(c1cncc(-c3cc(F)cc(-c4ccc(-n5ccn(C)c5=O)c(Cl)c4)c3O)c1)C2]
1492 -continued
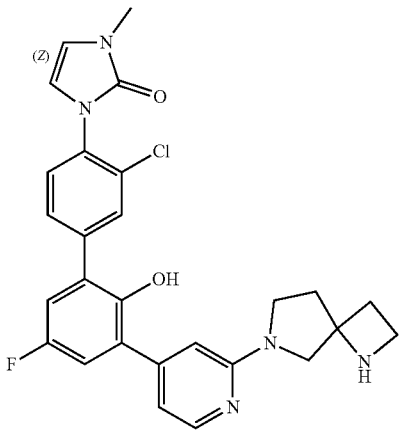 [SMILES: Cn1ccn(-c2ccc(-c3cc(F)cc(-c4ccnc(N5CCC6(CCN6)C5)c4)c3O)cc2Cl)c1=O]
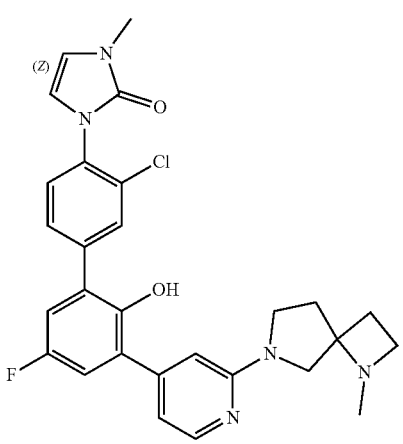 [SMILES: CN1CCC12CCN(c1cc(-c3cc(F)cc(-c4ccc(-n5ccn(C)c5=O)c(Cl)c4)c3O)ccn1)C2]

1493
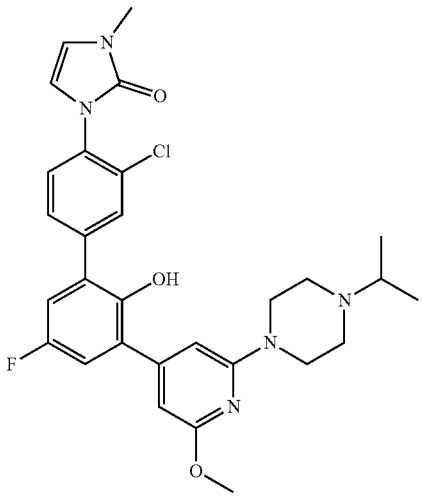 [SMILES: COc1cc(-c2cc(F)cc(-c3ccc(-n4ccn(C)c4=O)c(Cl)c3)c2O)cc(N2CCN(C(C)C)CC2)n1]
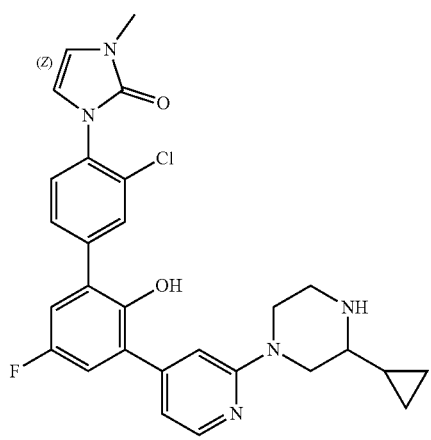 [SMILES: Cn1ccn(-c2ccc(-c3cc(F)cc(-c4ccnc(N5CCNC(C6CC6)C5)c4)c3O)cc2Cl)c1=O]
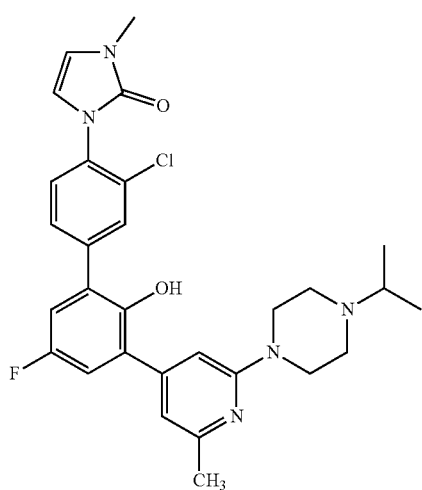 [SMILES: Cc1cc(-c2cc(F)cc(-c3ccc(-n4ccn(C)c4=O)c(Cl)c3)c2O)cc(N2CCN(C(C)C)CC2)n1]
1494
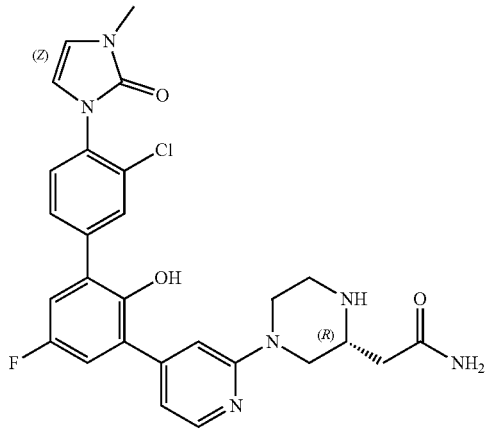
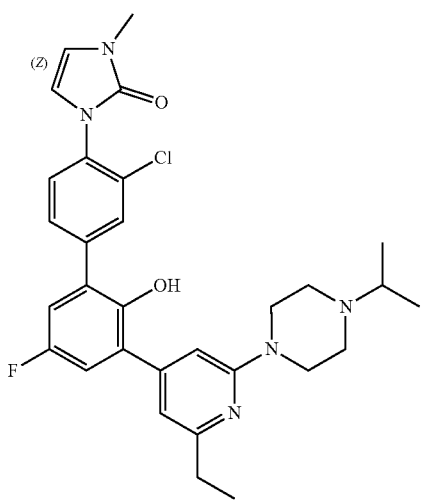
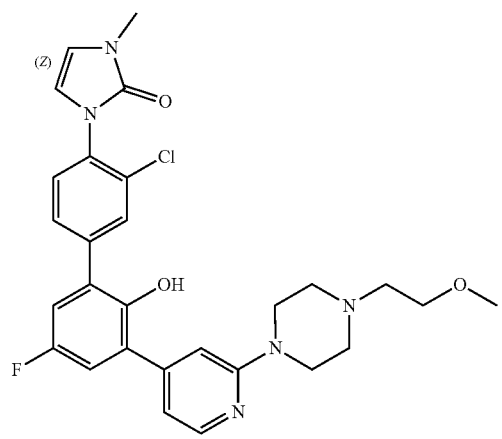

1495
-continued
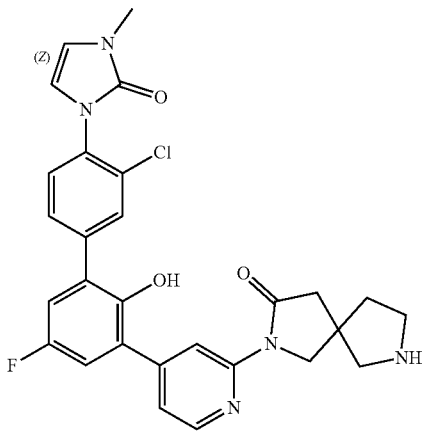 [SMILES: Cn1ccn(-c2ccc(-c3cc(F)cc(-c4ccnc(N5CC6(CCNC6)CC5=O)c4)c3O)cc2Cl)c1=O]
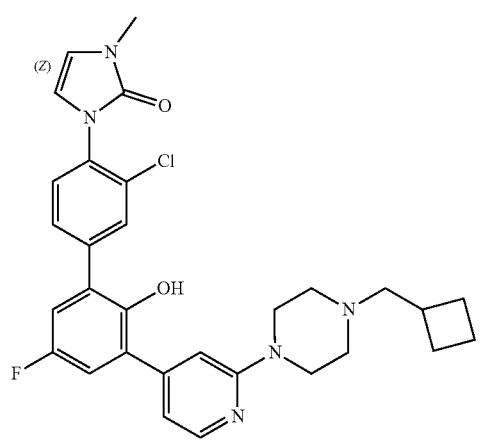
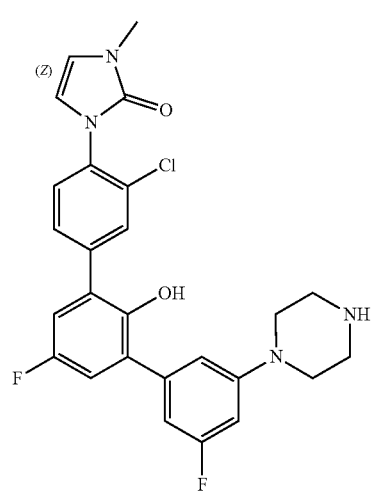
1496
-continued
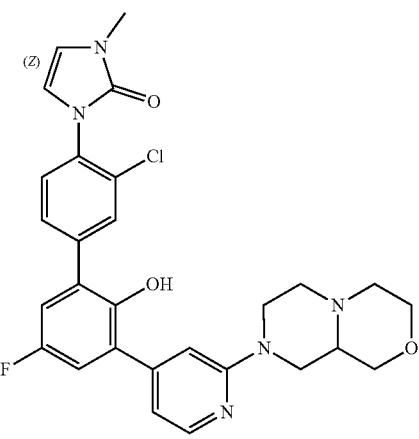
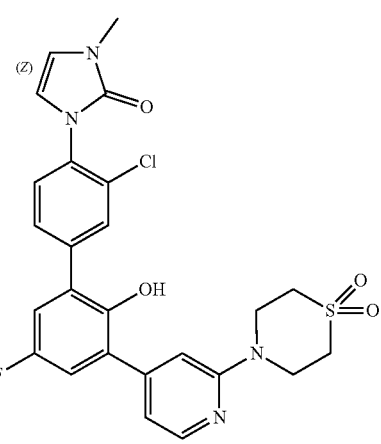
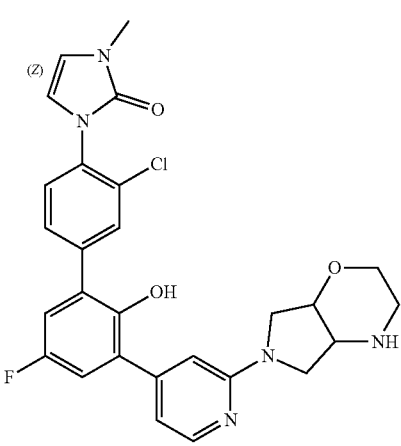

1497
-continued
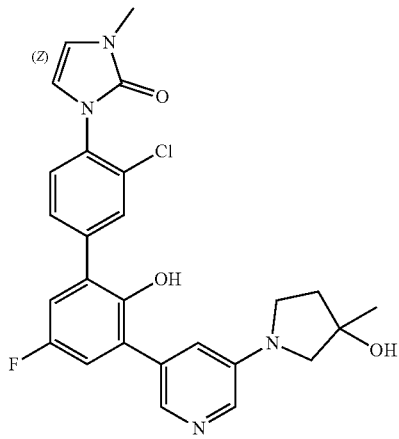
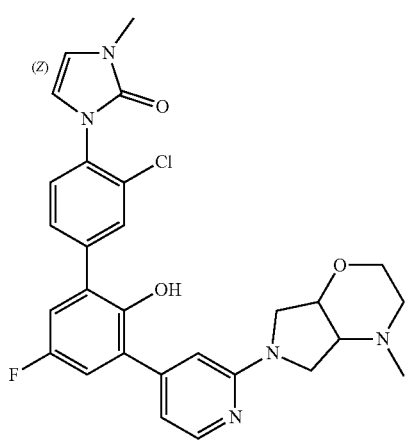
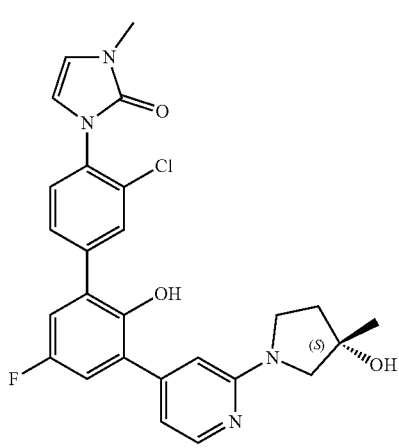
1498
-continued
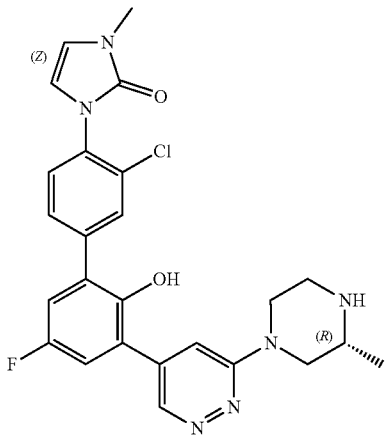
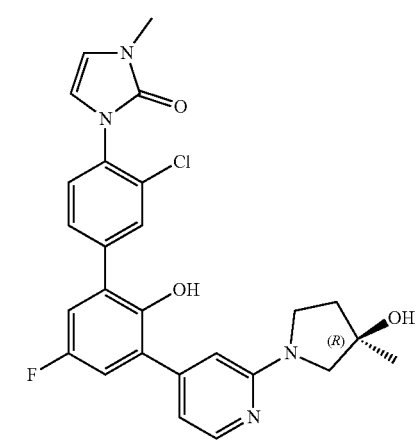
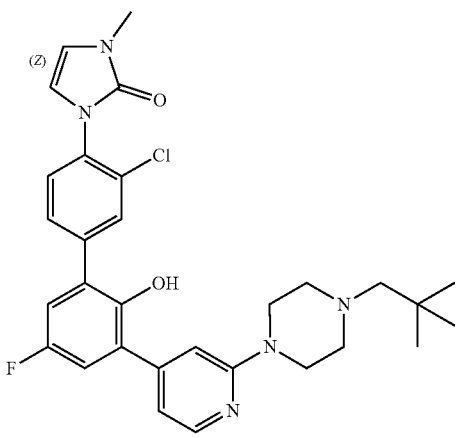

| 1499 -continued | 1500 -continued |
|---|---|
| 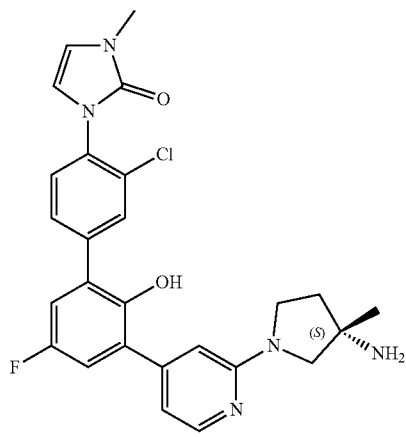 | 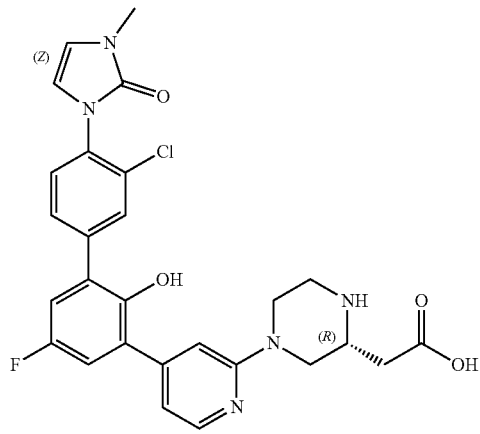 |
| 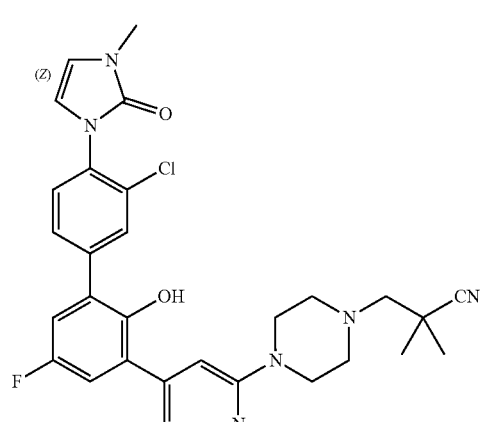 | 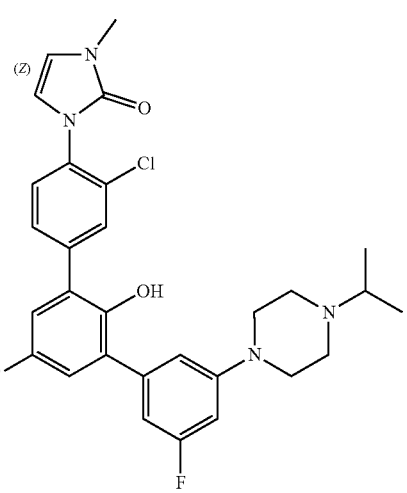 |
| 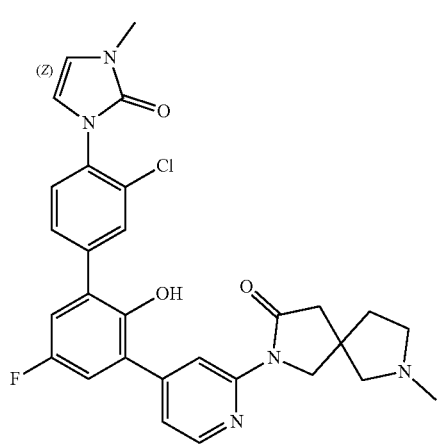 [SMILES: CN1CCC2(CC(=O)N(c3cc(-c4cc(F)cc(-c5ccc(-n6ccn(C)c6=O)c(Cl)c5)c4O)ccn3)C2)C1] | 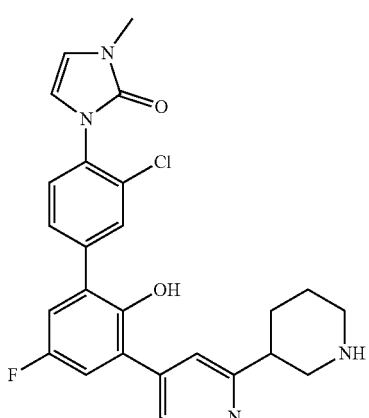 |

1501
-continued
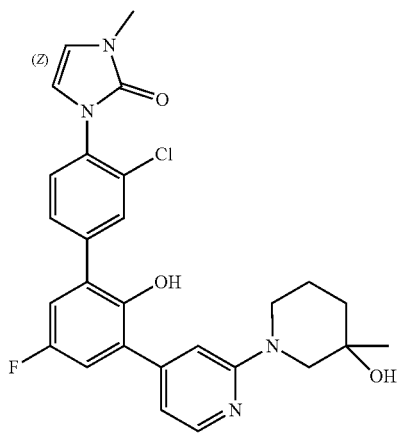
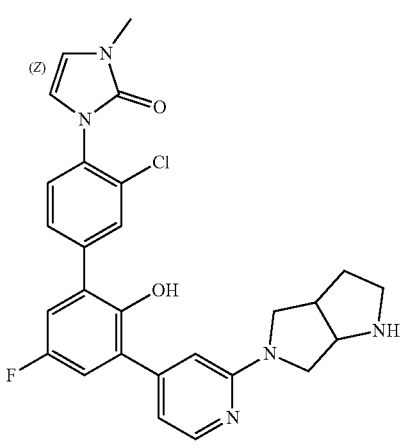
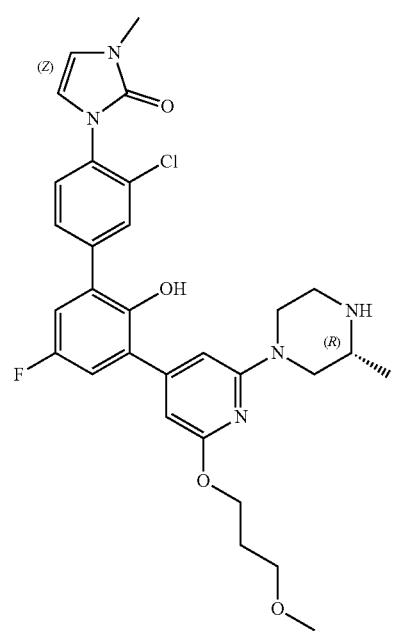
1502
-continued
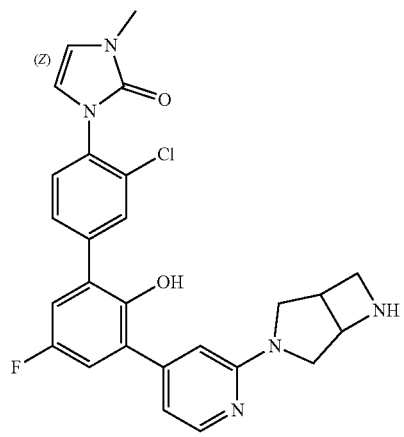
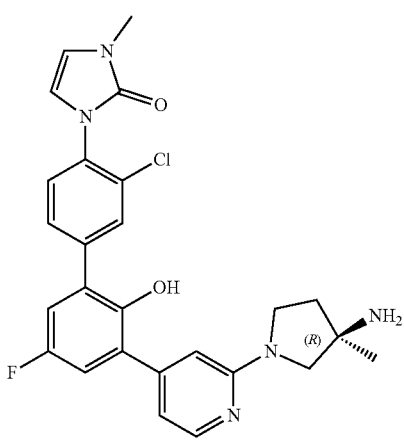
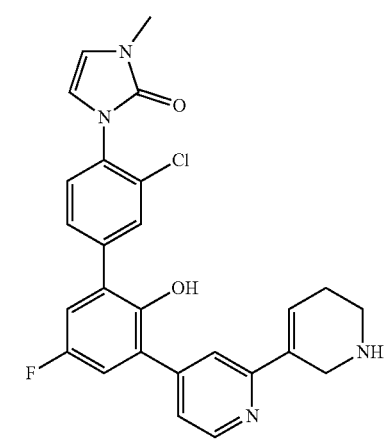 [SMILES: Cn1ccn(-c2ccc(-c3cc(F)cc(-c4ccnc(C5=CCCNC5)c4)c3O)cc2Cl)c1=O]

1503
-continued
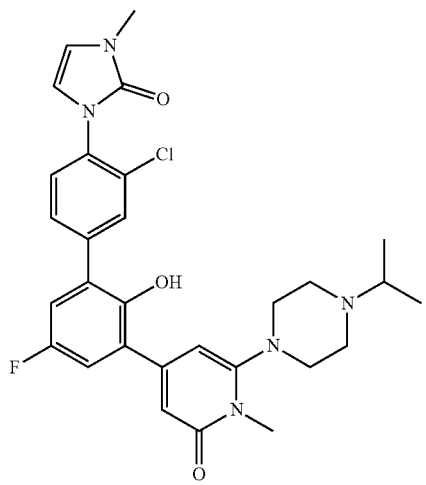 [SMILES: CC(C)N1CCN(c2cc(-c3cc(F)cc(-c4ccc(-n5ccn(C)c5=O)c(Cl)c4)c3O)cc(=O)n2C)CC1]
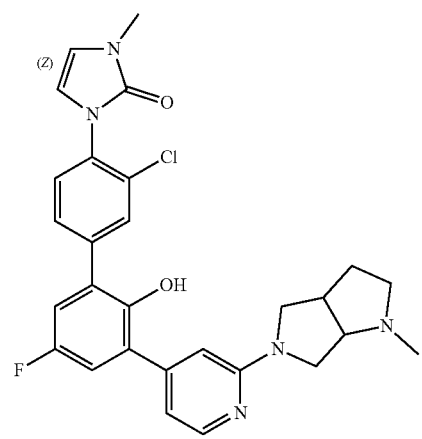
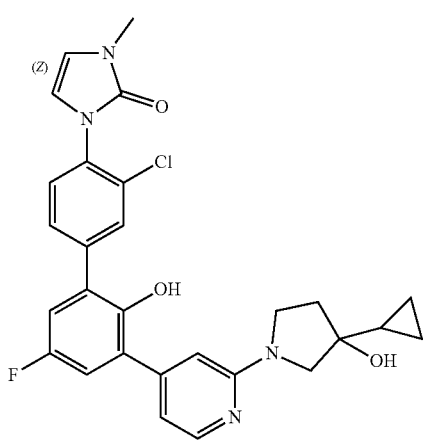
1504
-continued
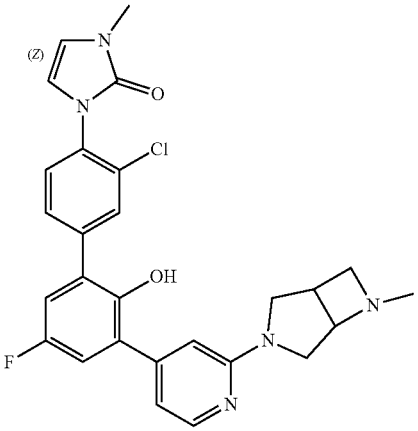
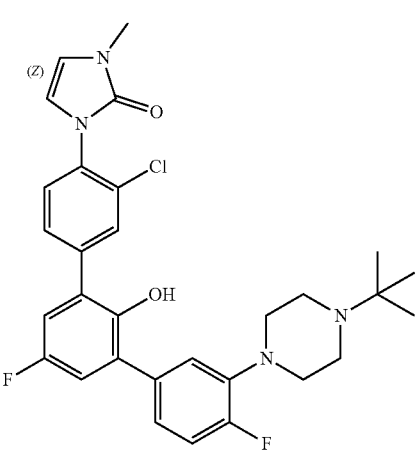 [SMILES: Cn1ccn(-c2ccc(-c3cc(F)cc(-c4ccc(F)c(N5CCN(C(C)(C)C)CC5)c4)c3O)cc2Cl)c1=O]
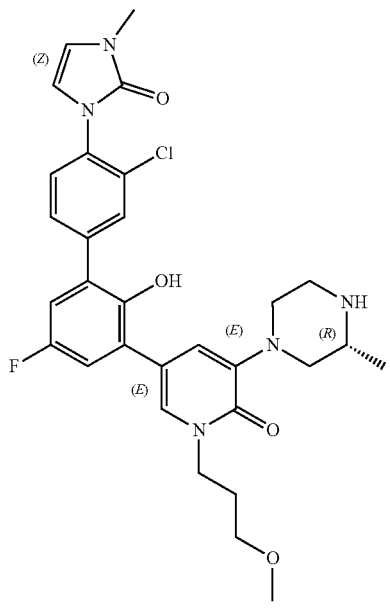

1505
-continued
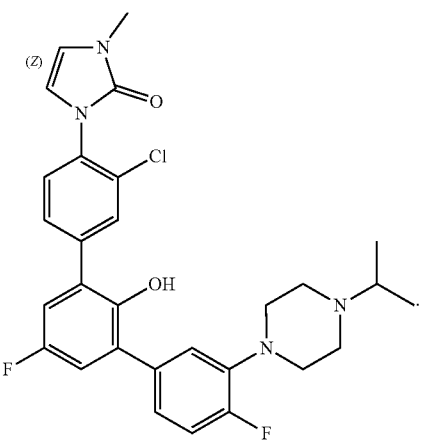
1506
-continued
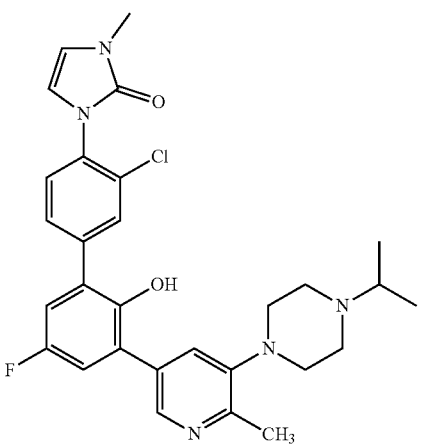
21. The compound of claim 1, selected from the following table:
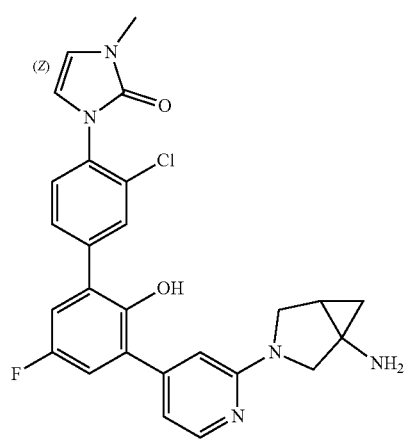
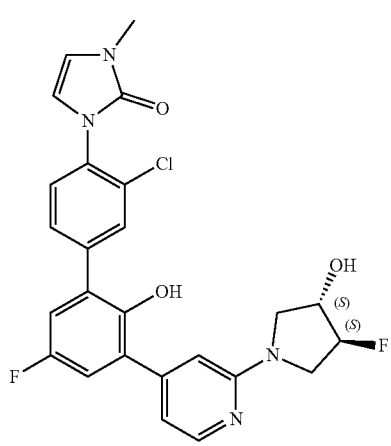
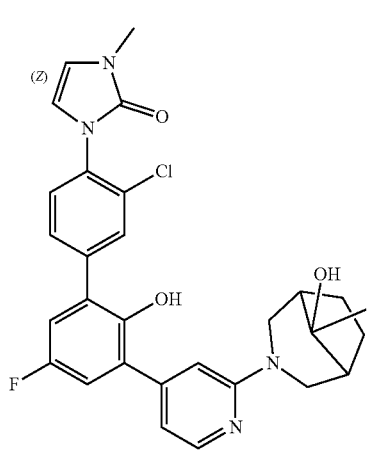
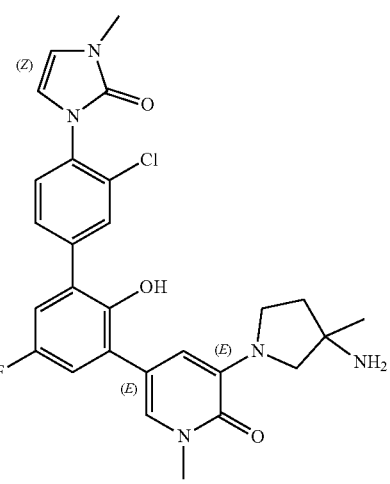

1507
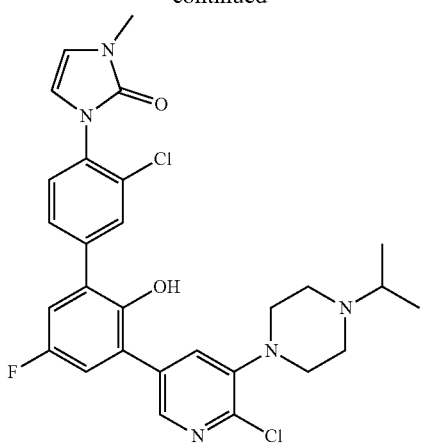
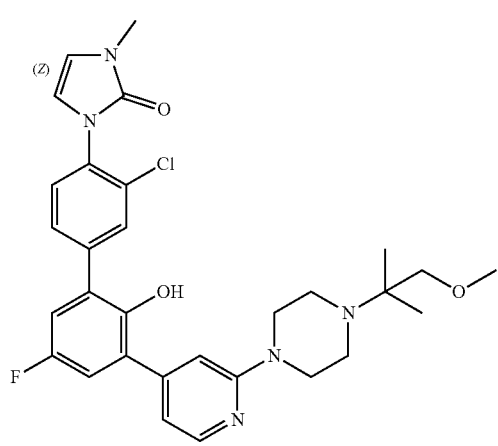
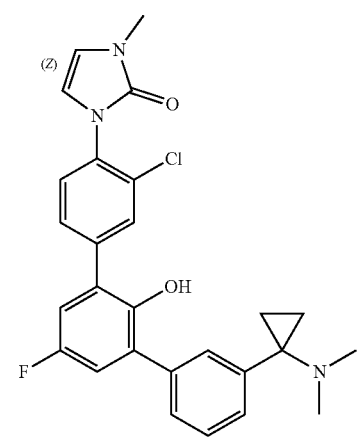
1508
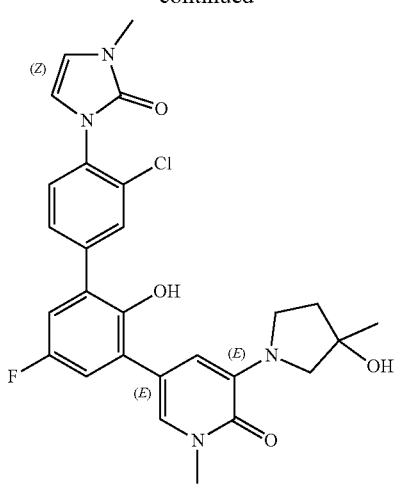
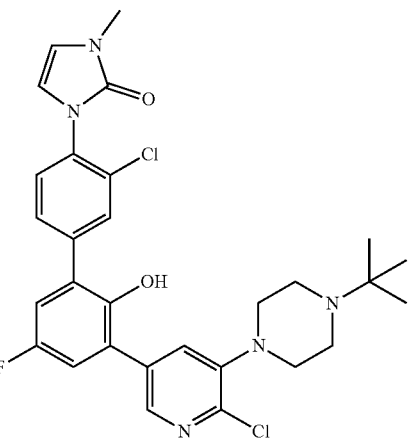
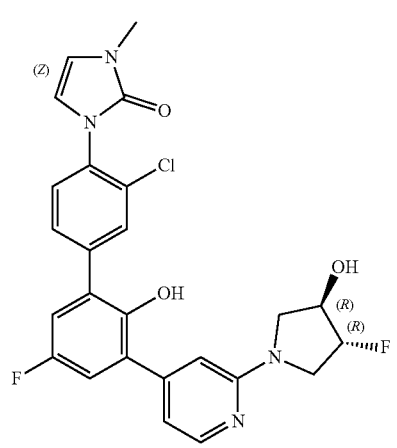

1509
-continued
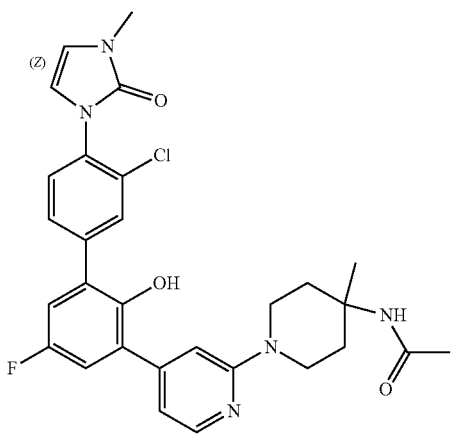
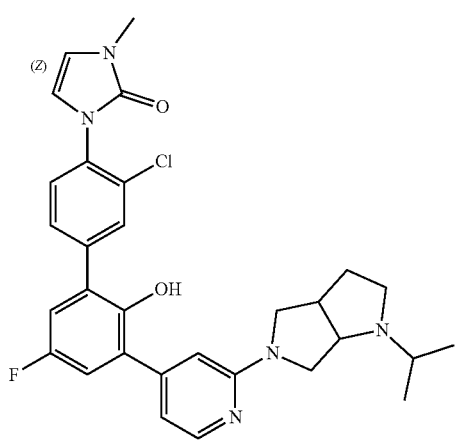
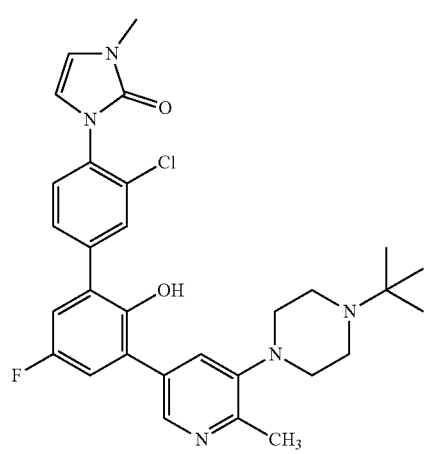
1510
-continued
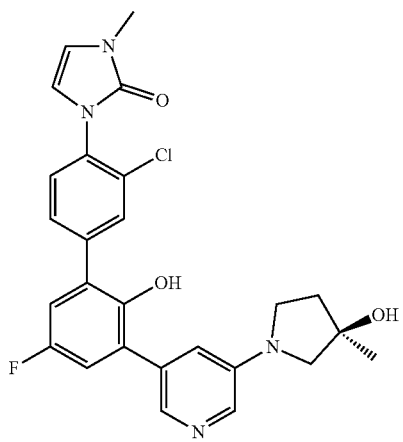
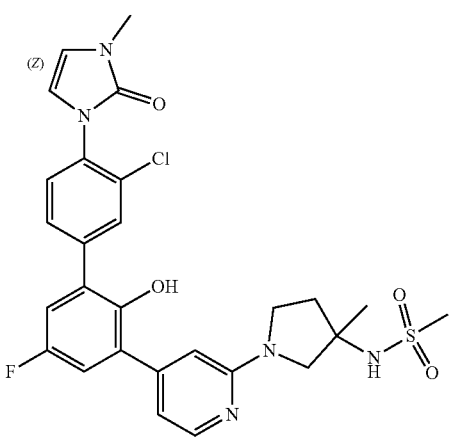
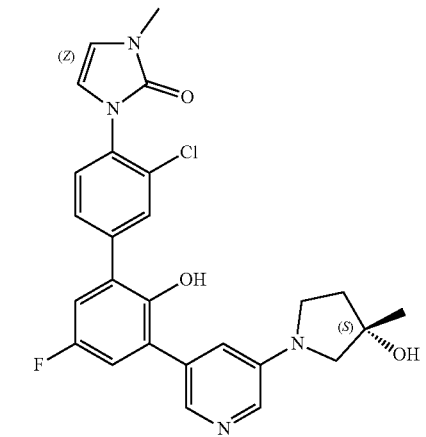

1511
-continued
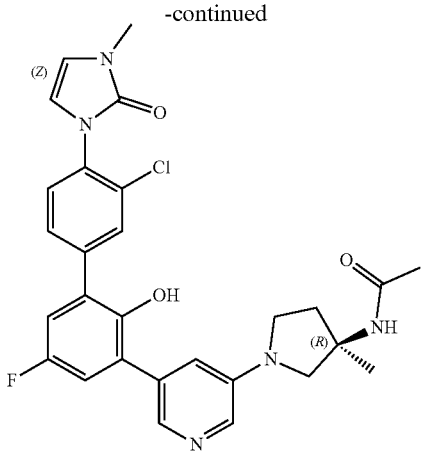
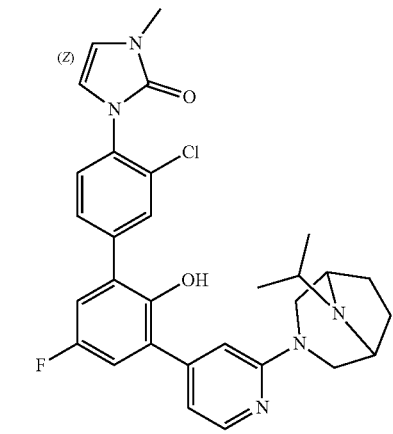
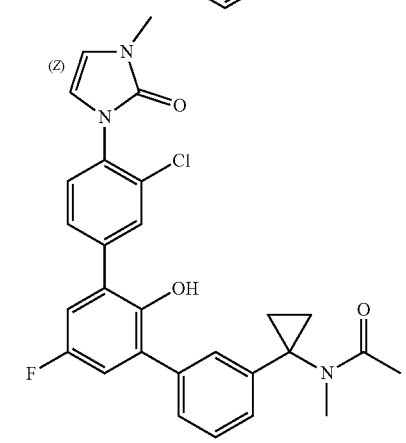
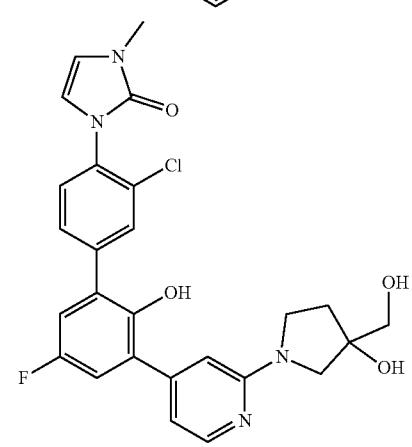
1512
-continued
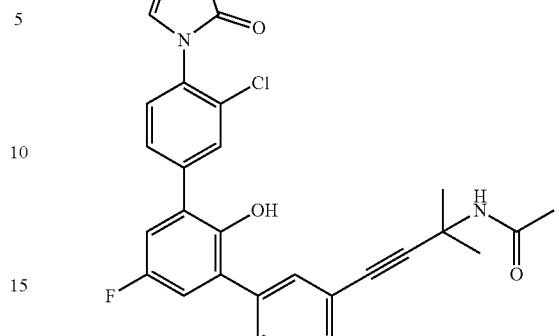
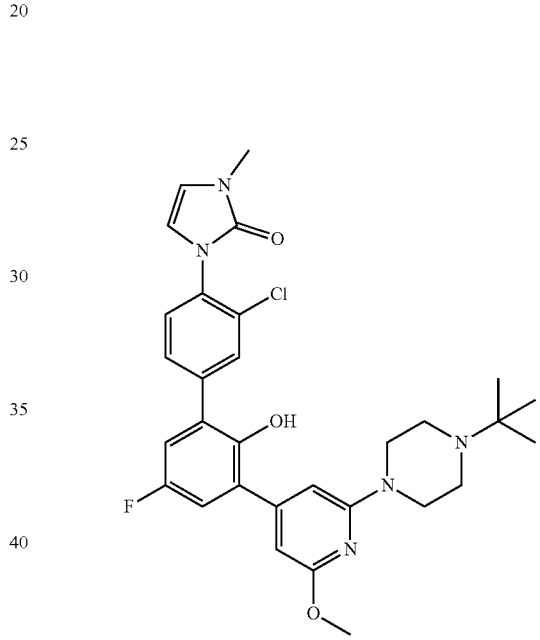
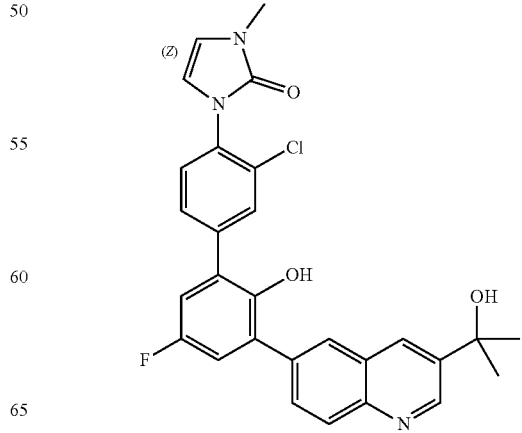

1513
-continued
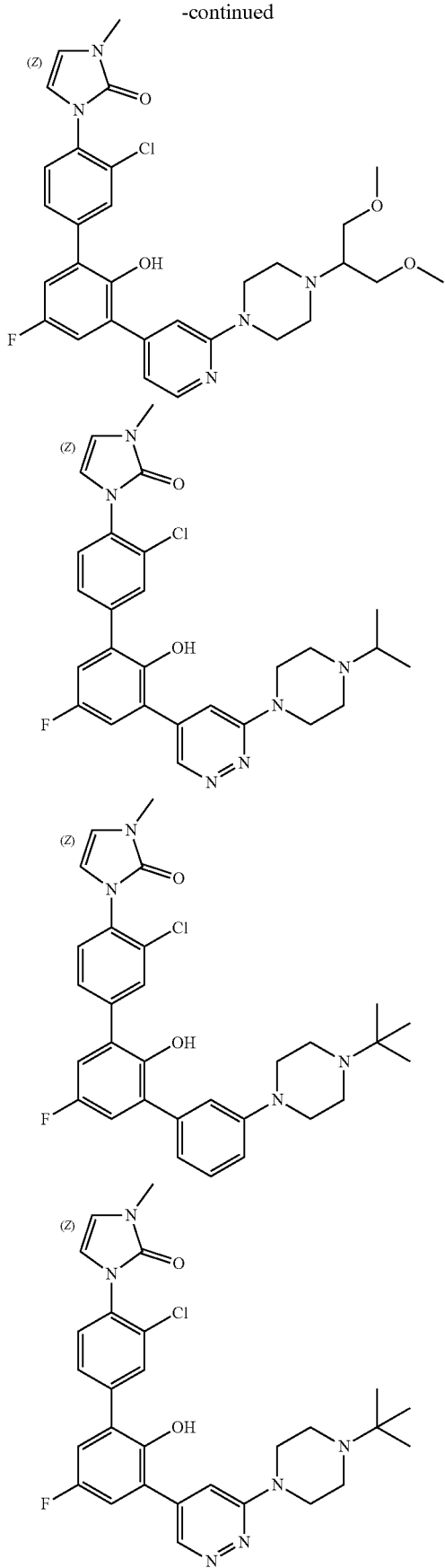
1514
-continued
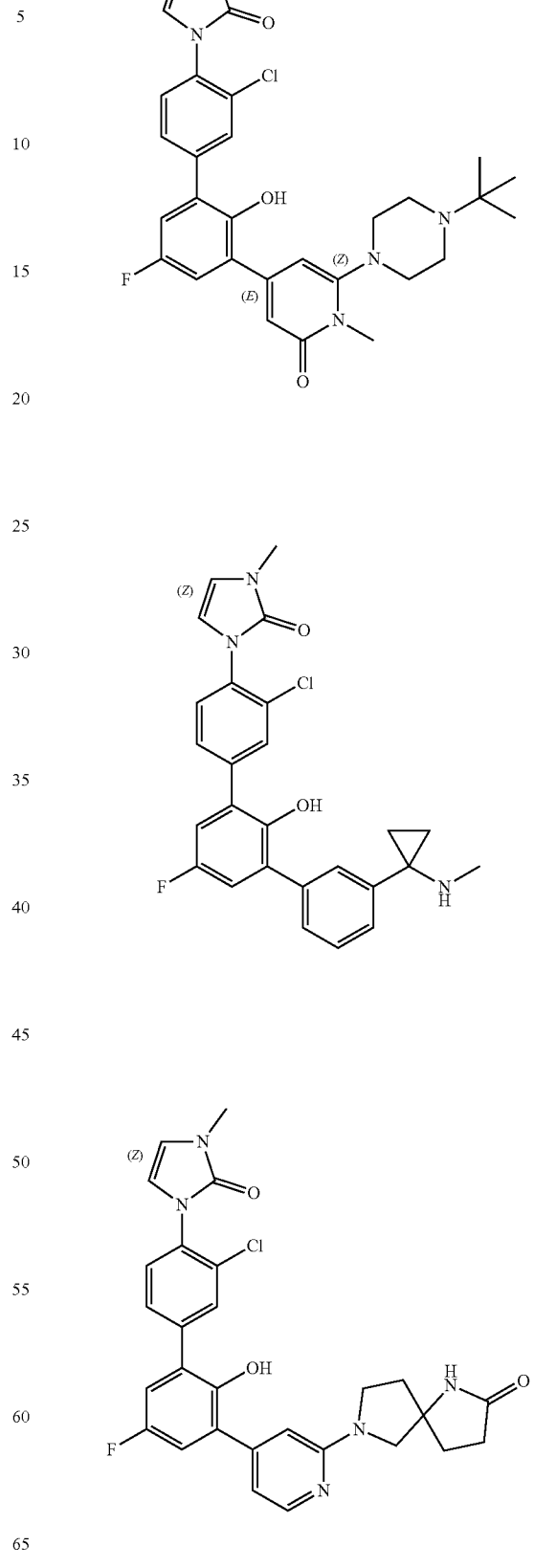

1515
-continued
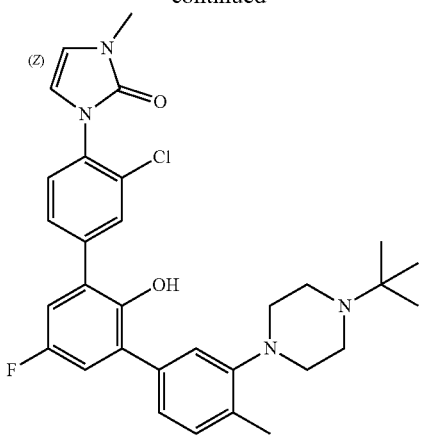
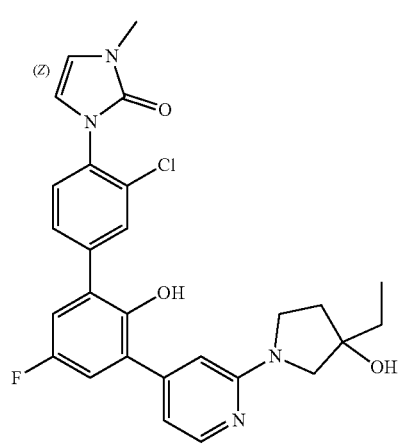
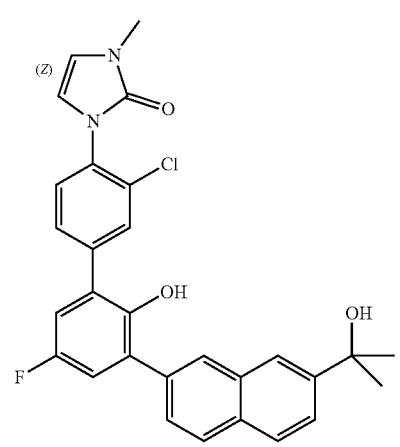
1516
-continued
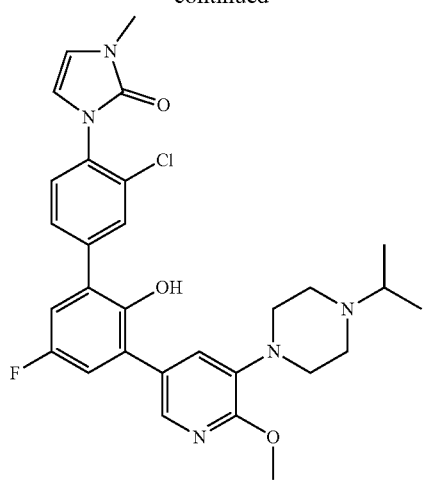
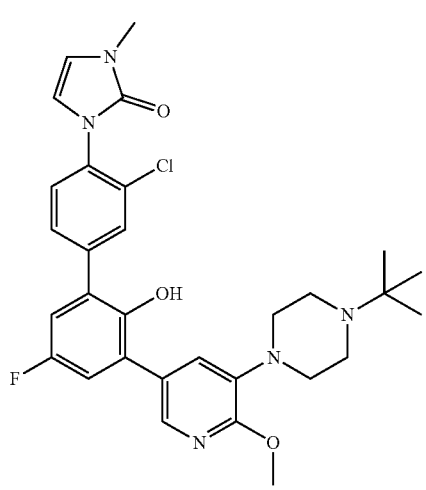
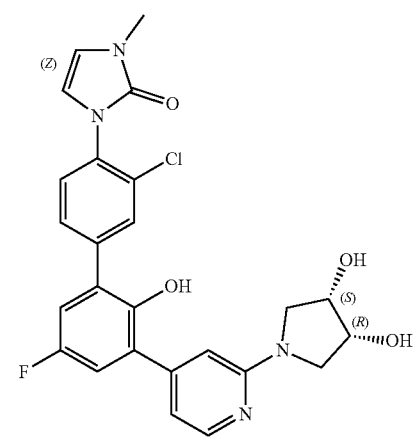

1517
-continued
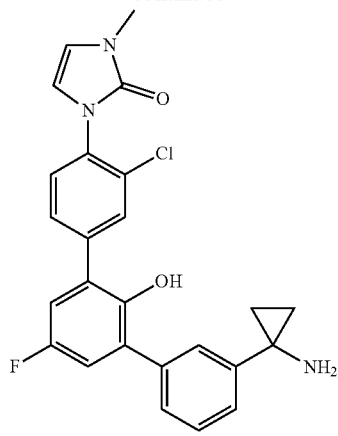
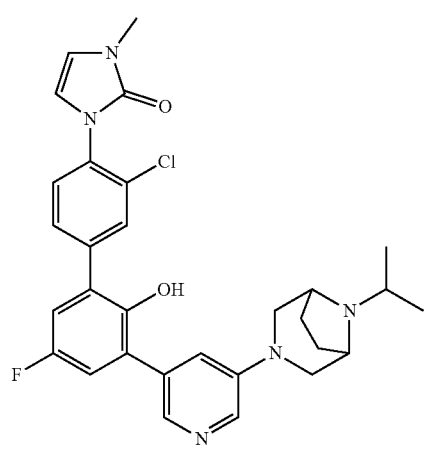
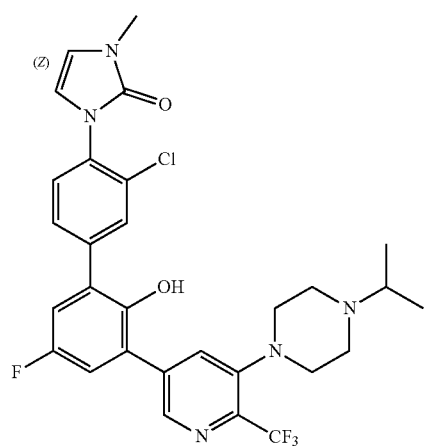
1518
-continued
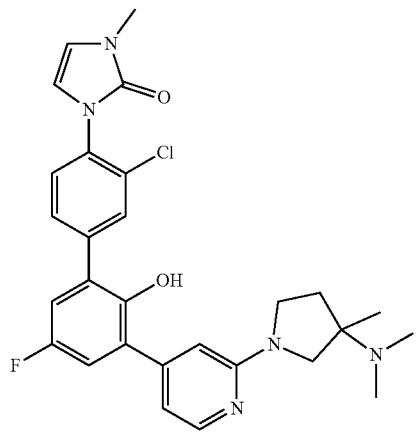
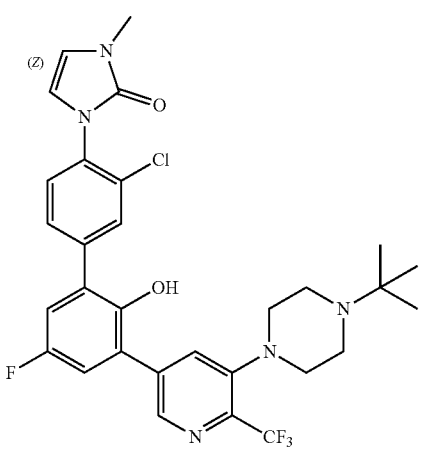
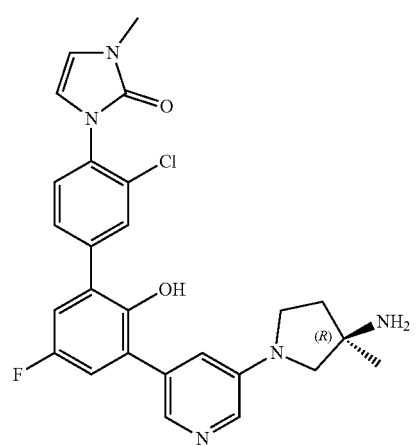

1519
-continued
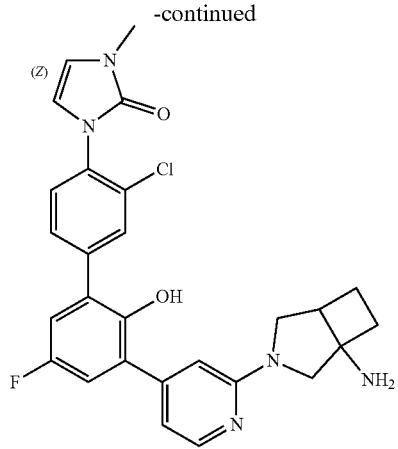
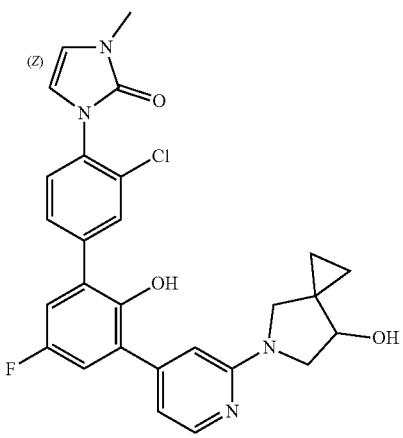
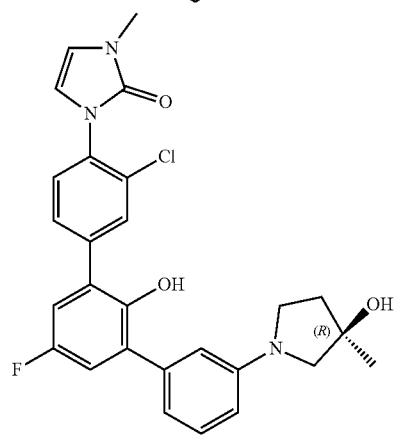
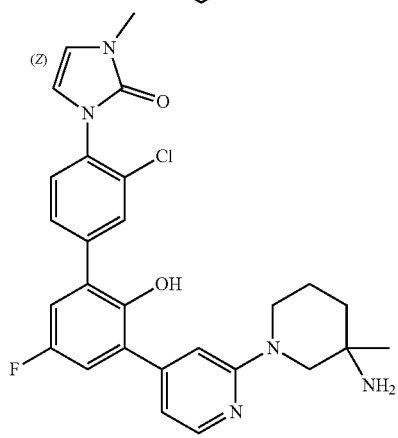
1520
-continued
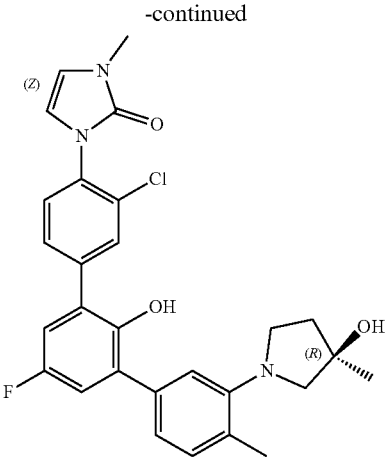
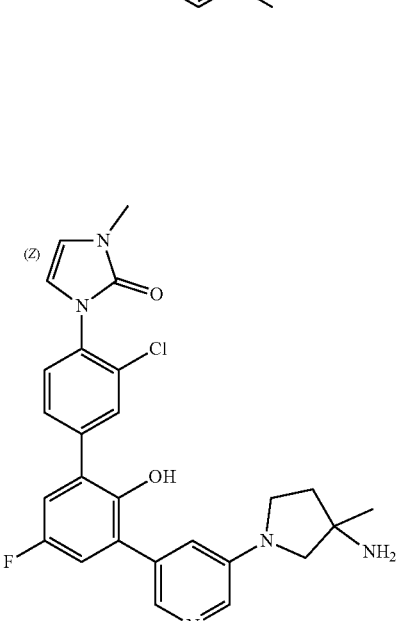
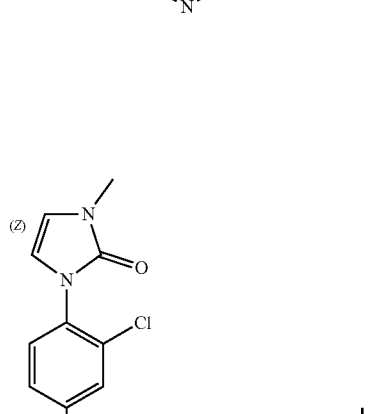

1521
-continued
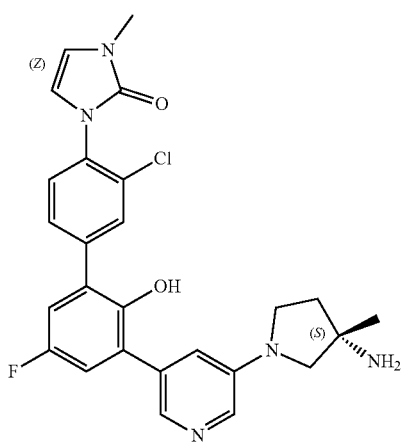
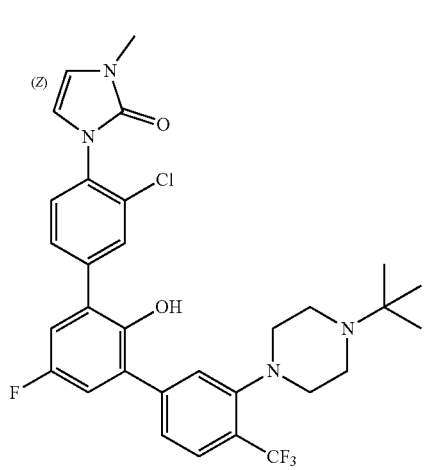
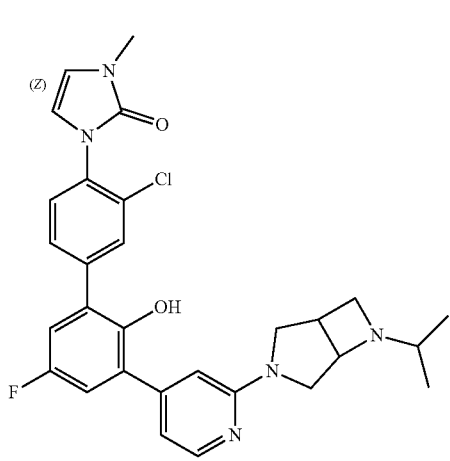
1522
-continued
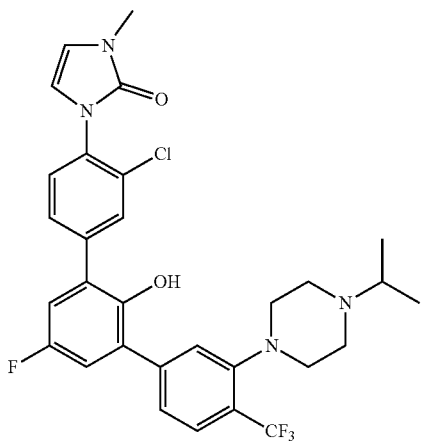
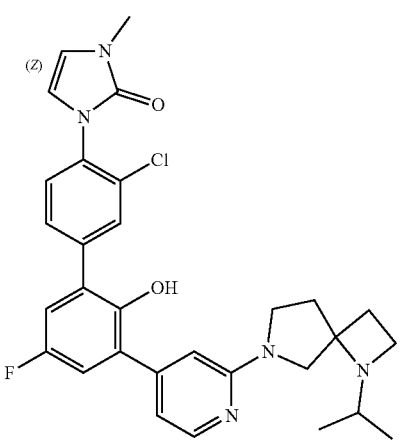
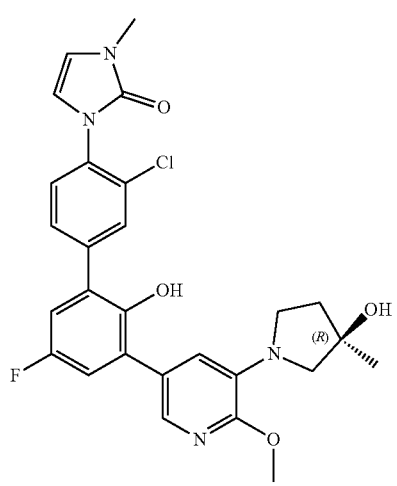

1523
-continued
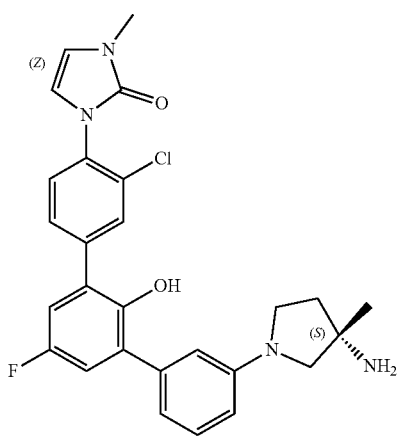
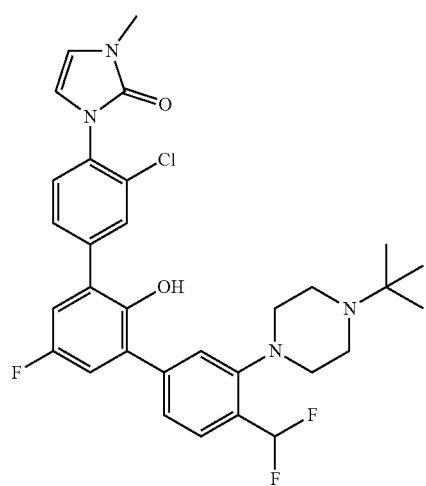
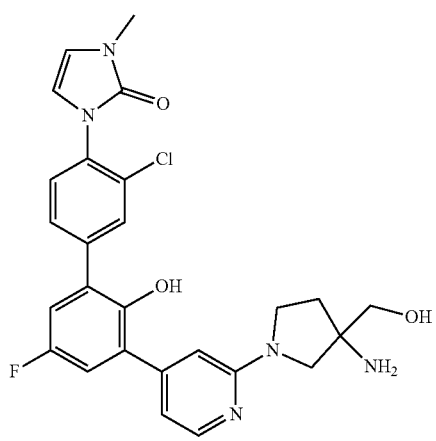
1524
-continued
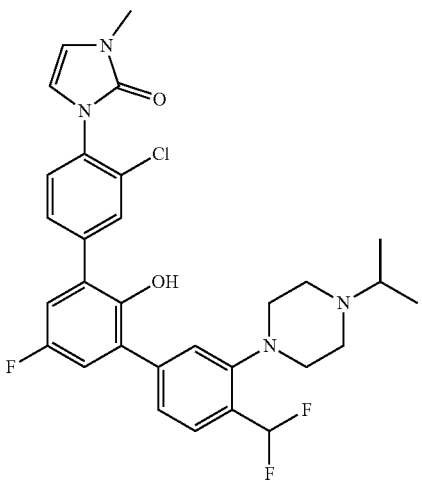
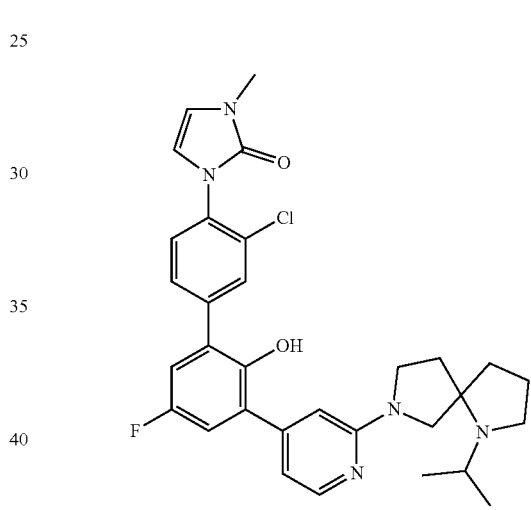
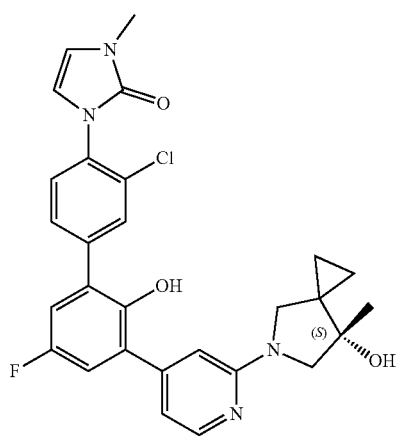

1525
-continued
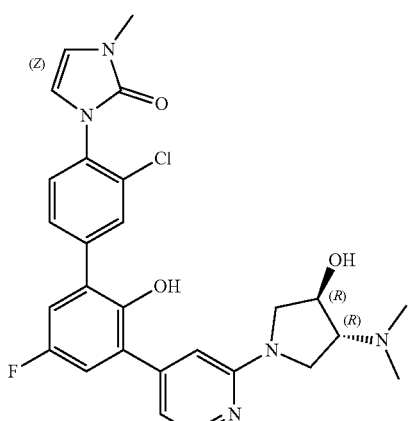
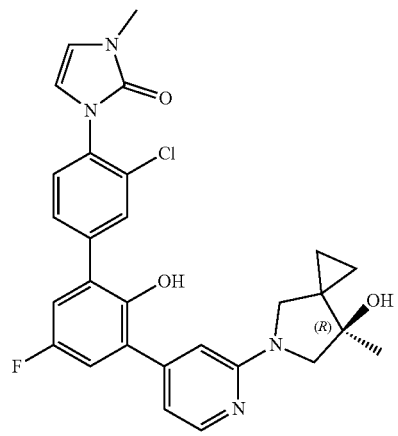
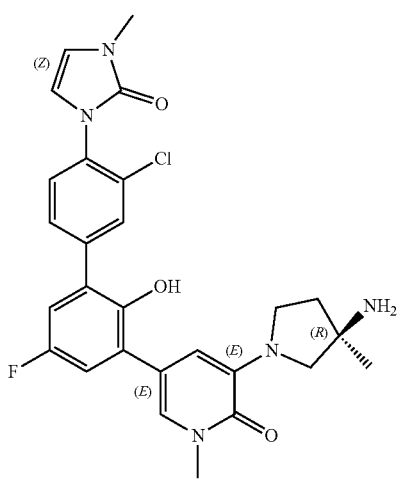
1526
-continued
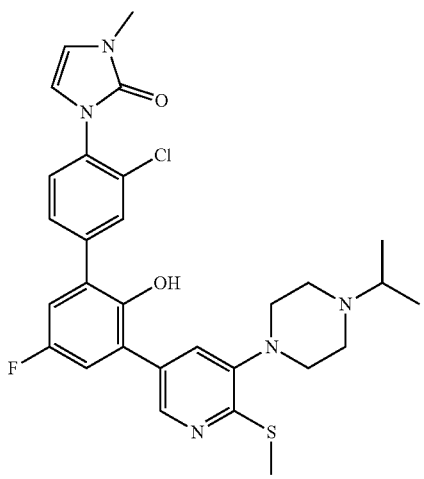
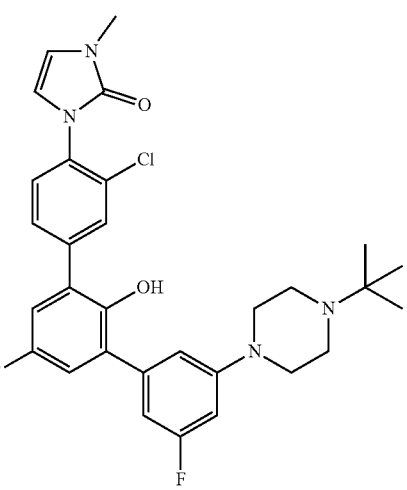
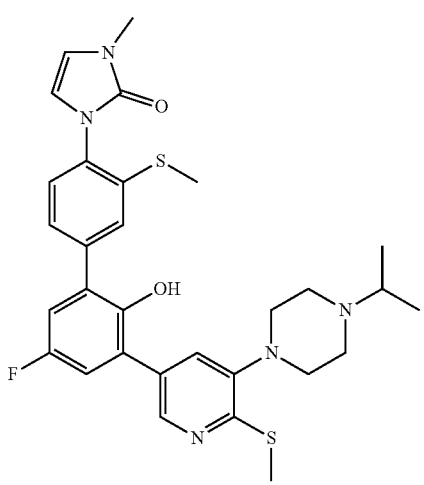

1527
-continued
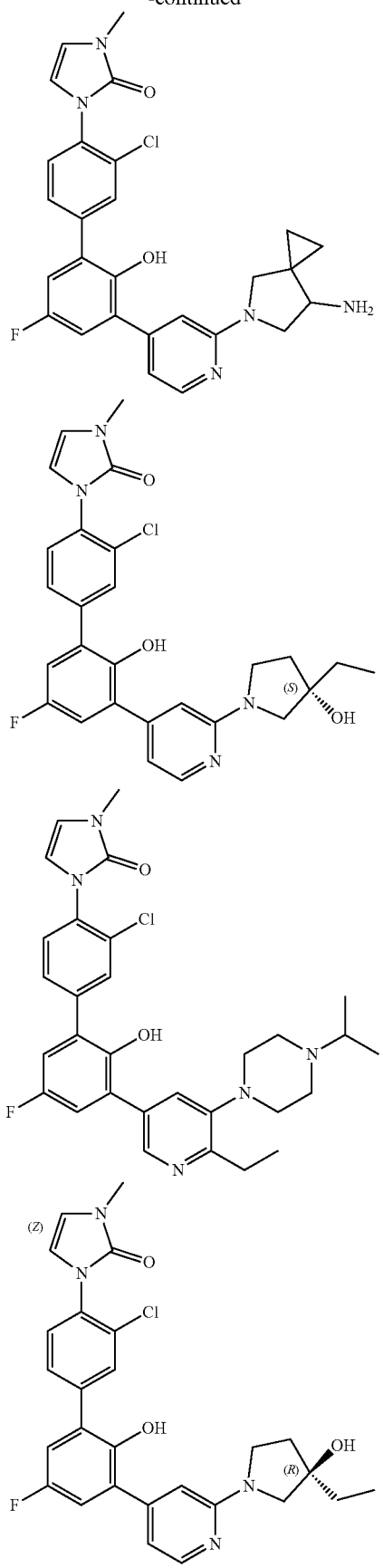
1528
-continued
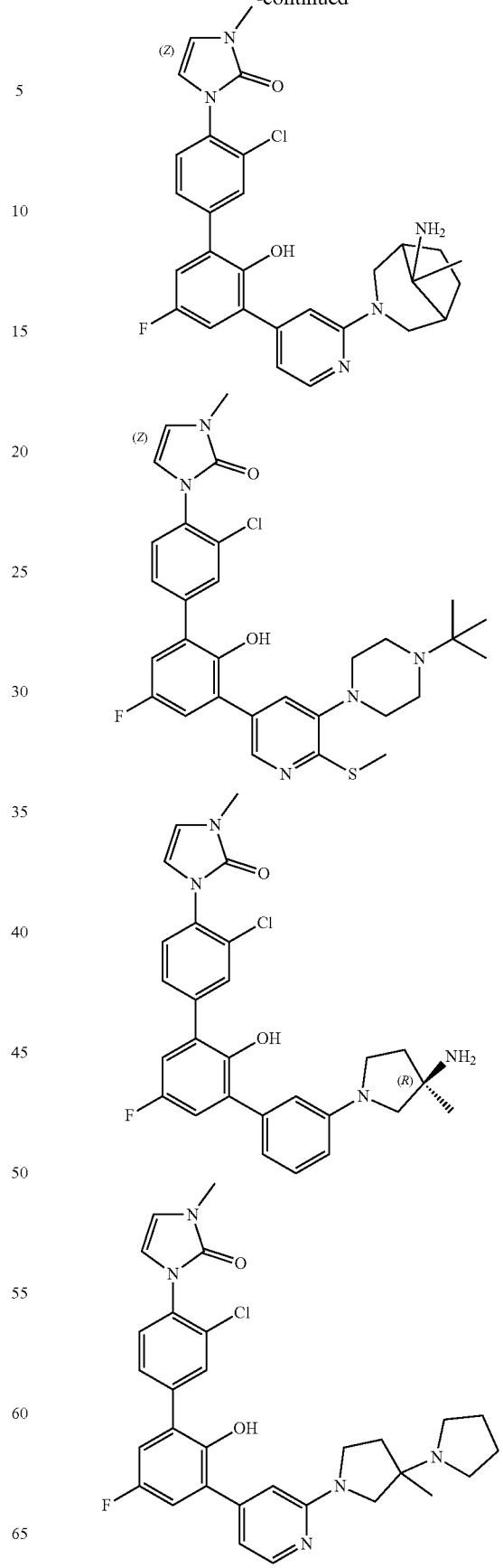

1529
-continued
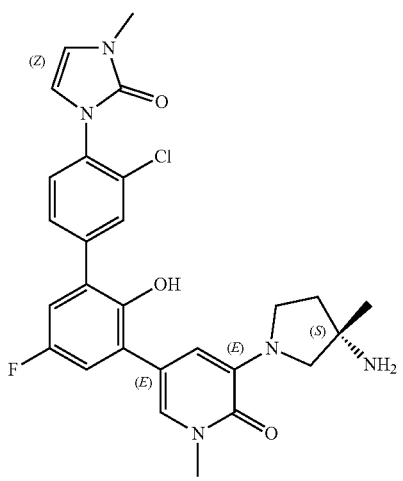
1530
-continued
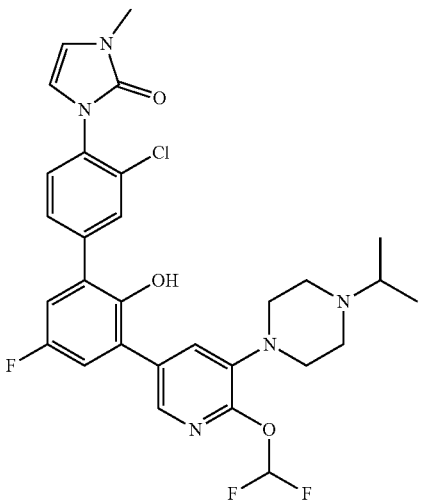
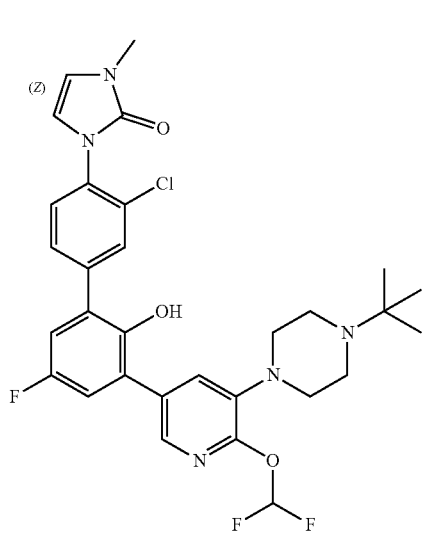
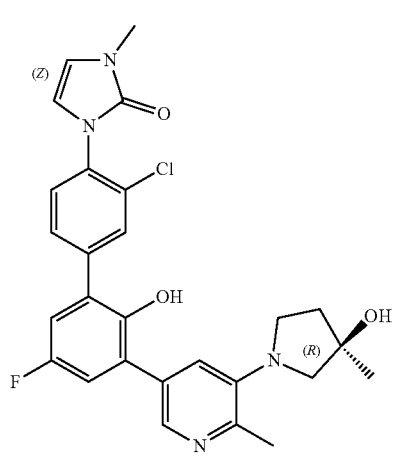

1531
-continued
1532
-continued
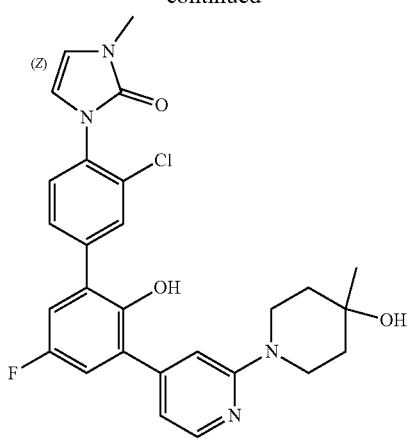
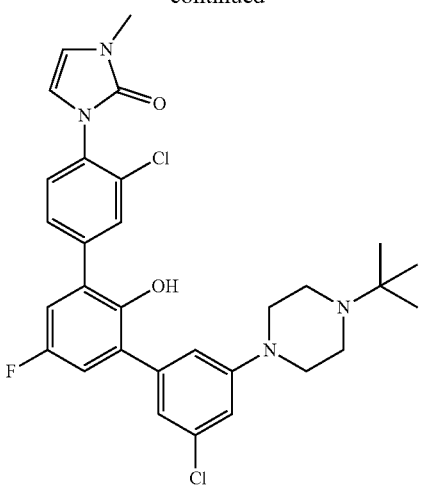
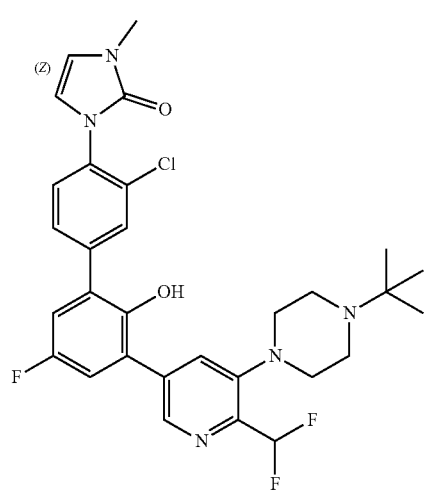
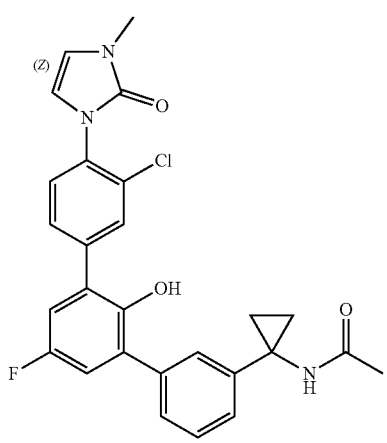
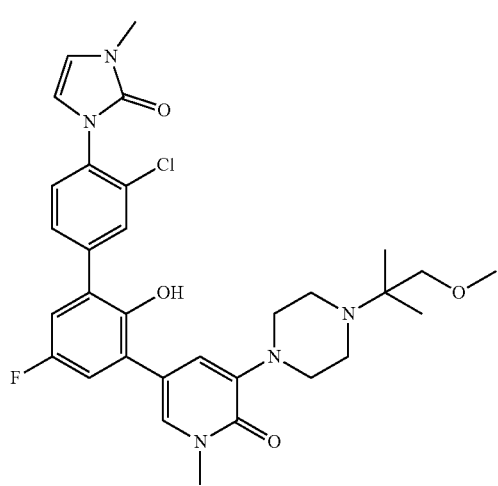
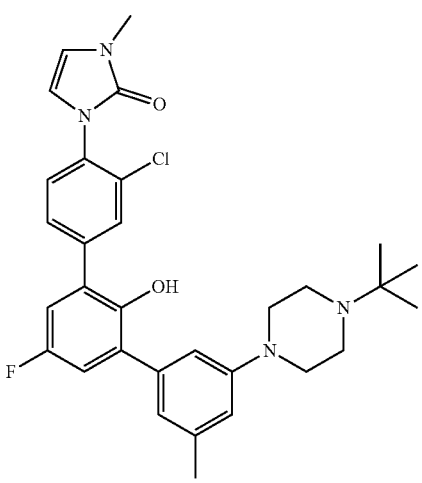

1533
-continued
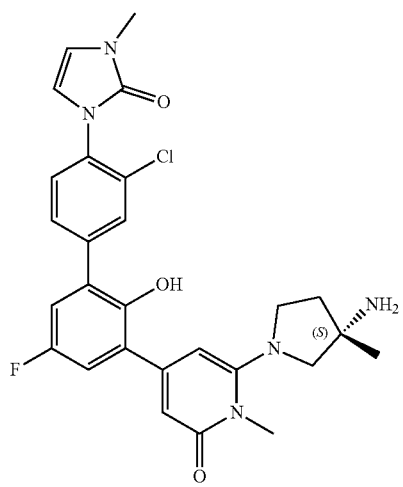
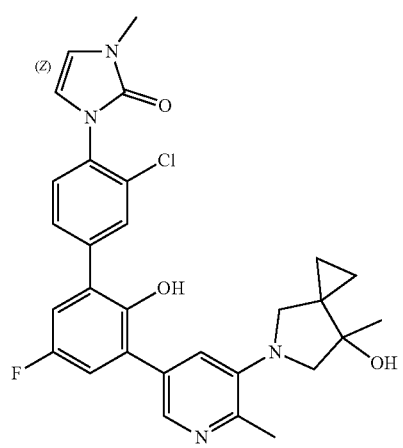
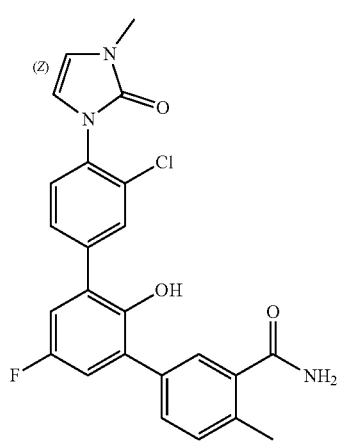
1534
-continued
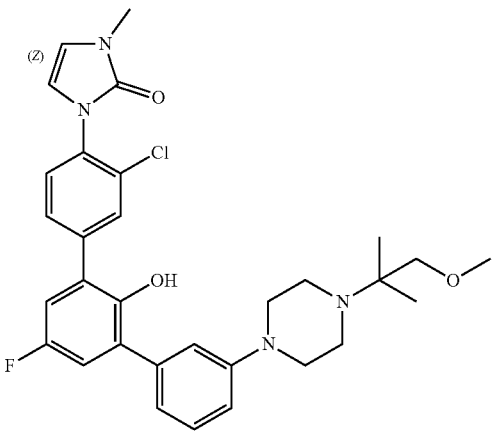
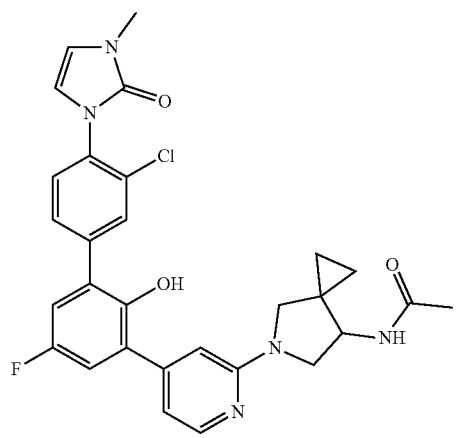
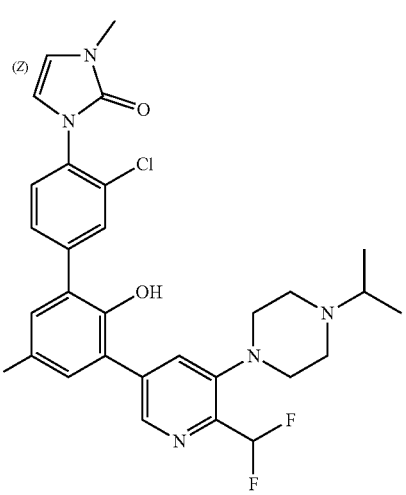

1535
-continued
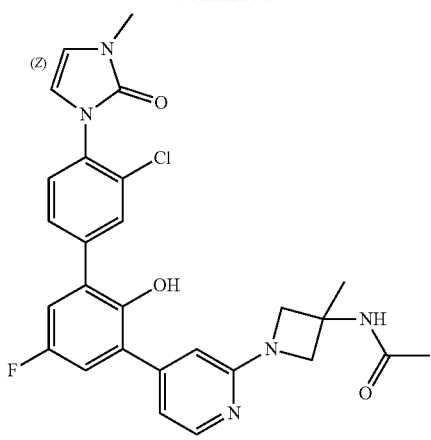
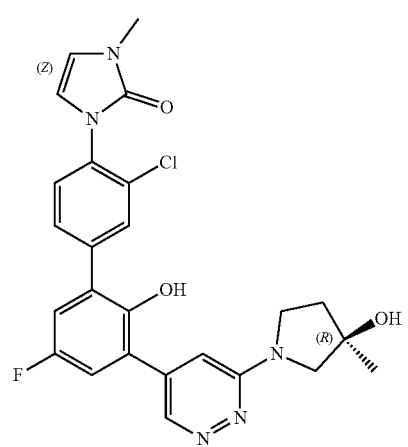
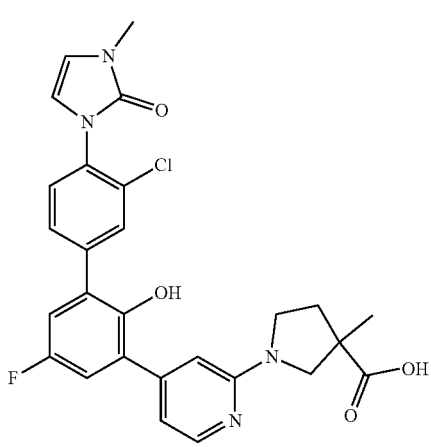
1536
-continued
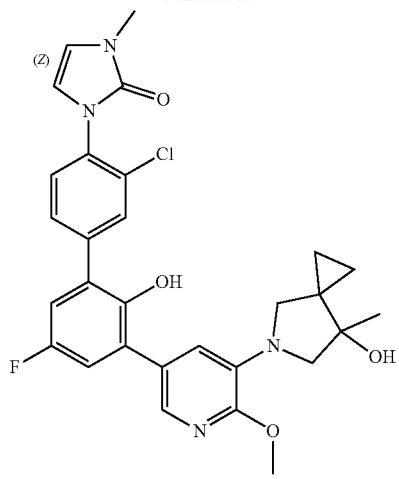
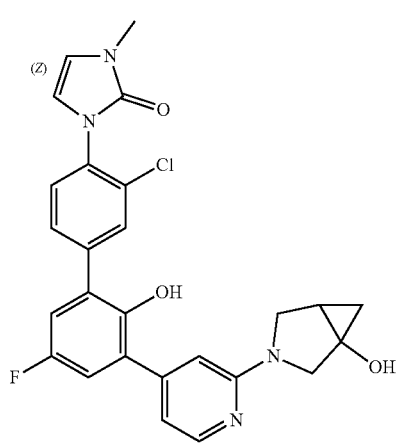
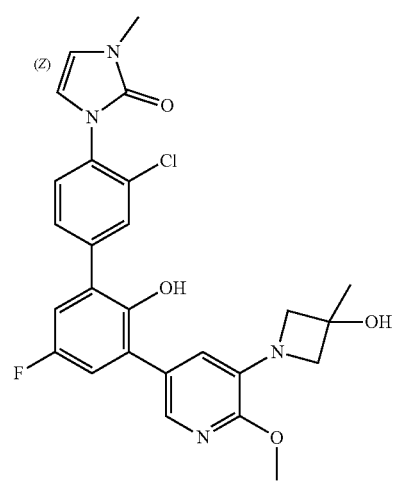

1537
-continued
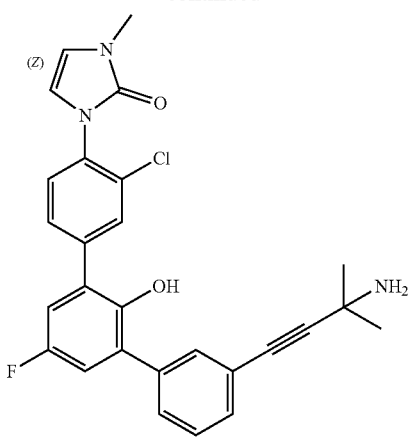
1538
-continued
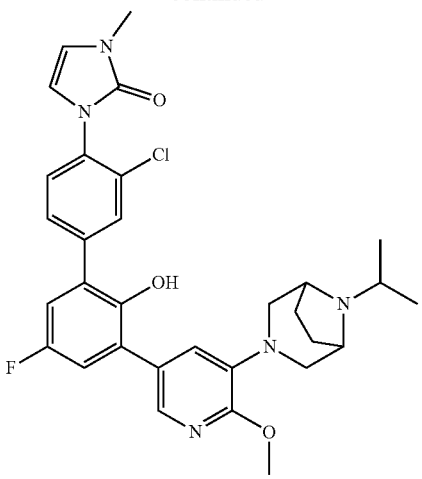
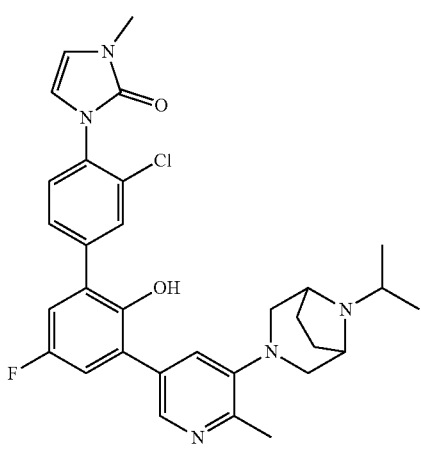
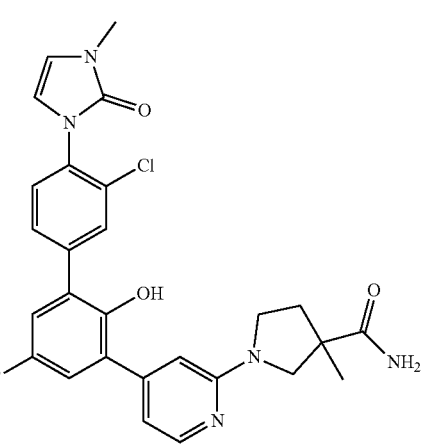
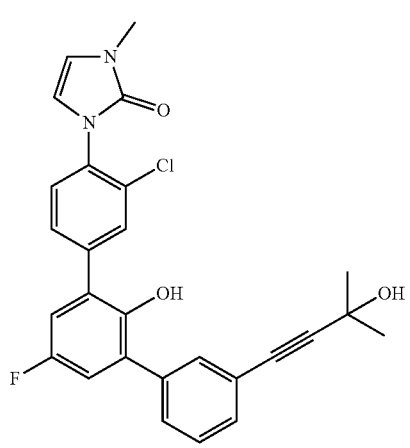
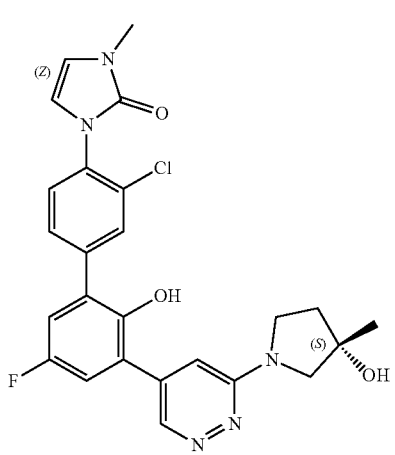

1539
-continued
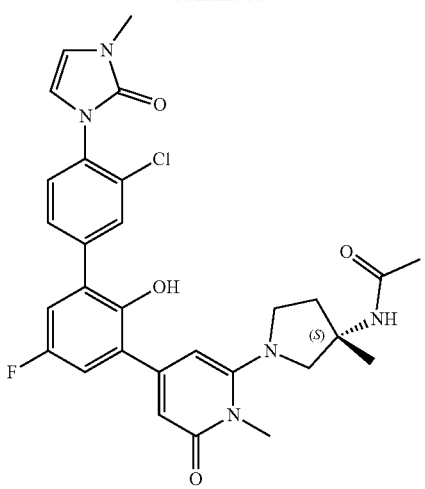
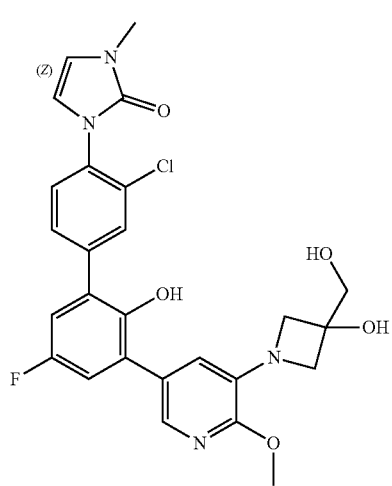
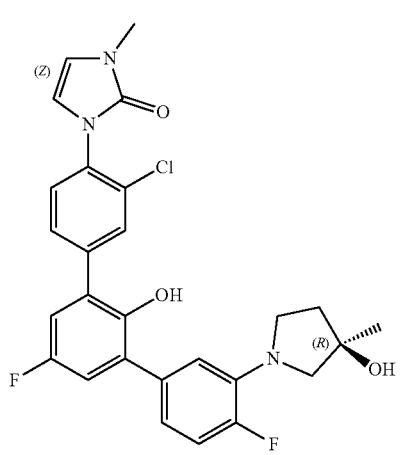
1540
-continued
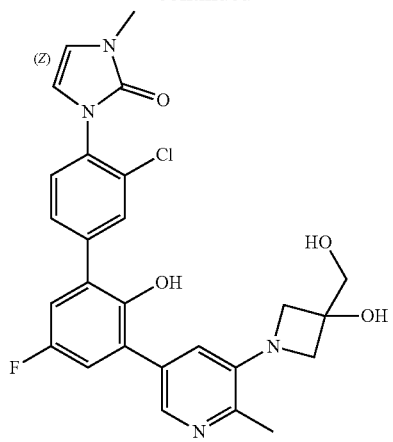
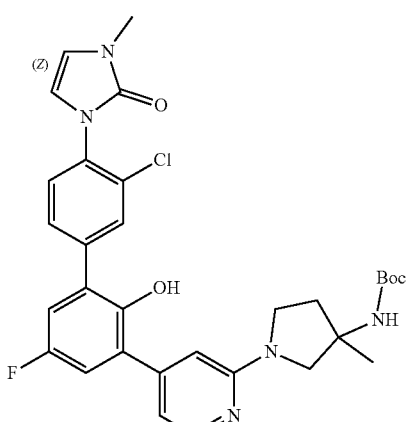

-continued
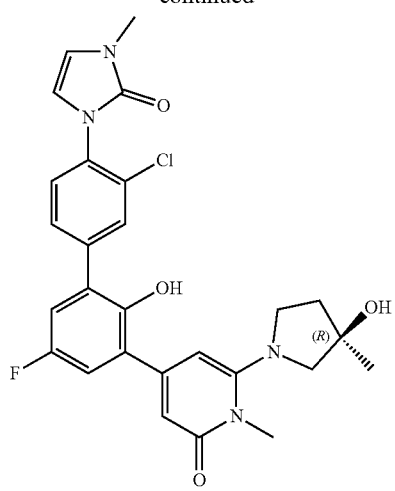
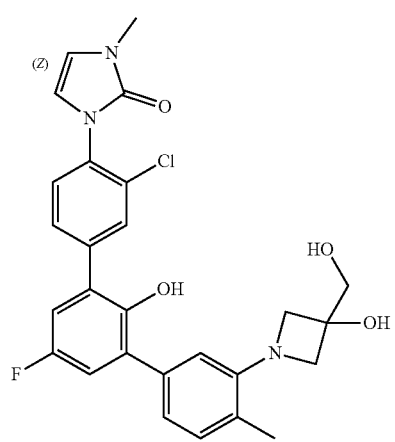
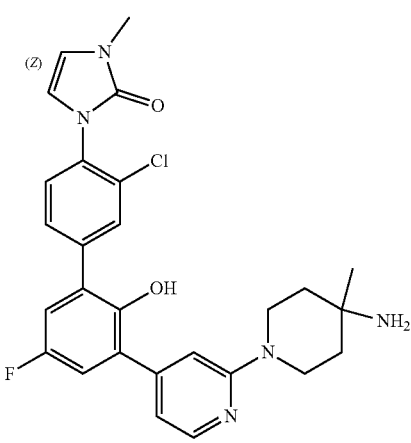
-continued
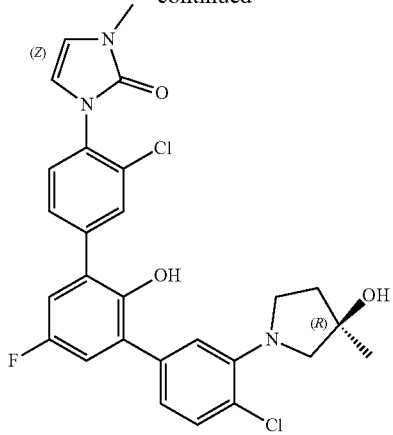
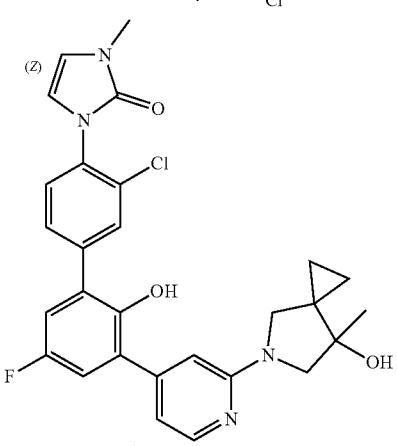
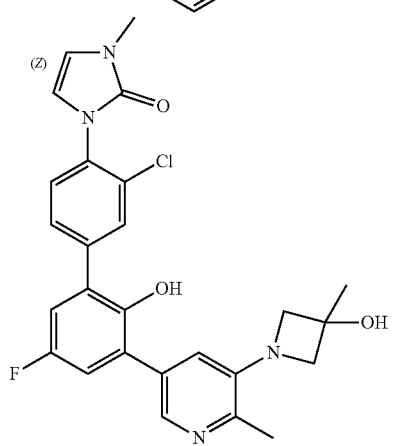
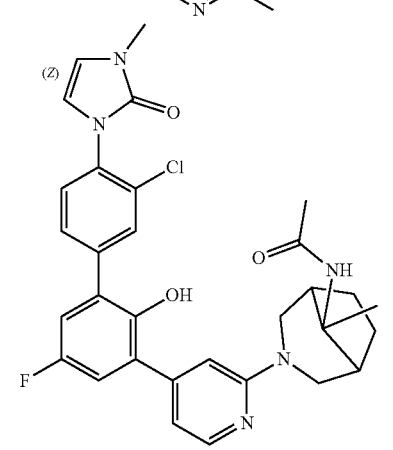

1543
-continued
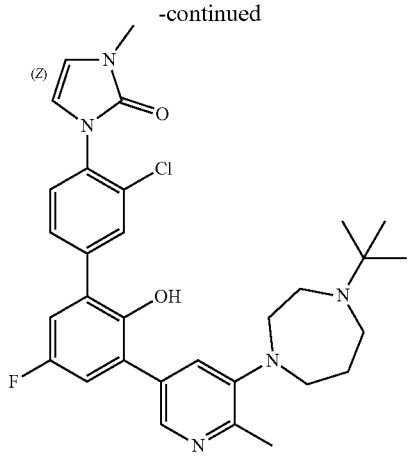
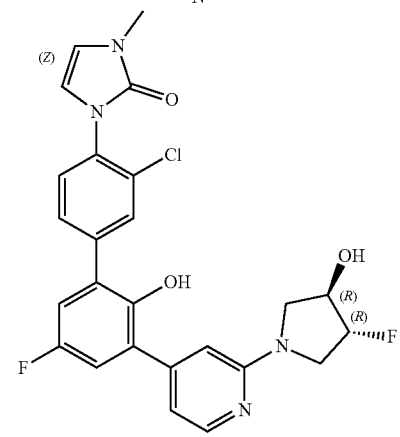
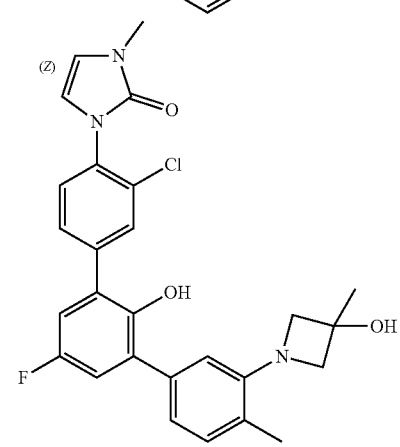
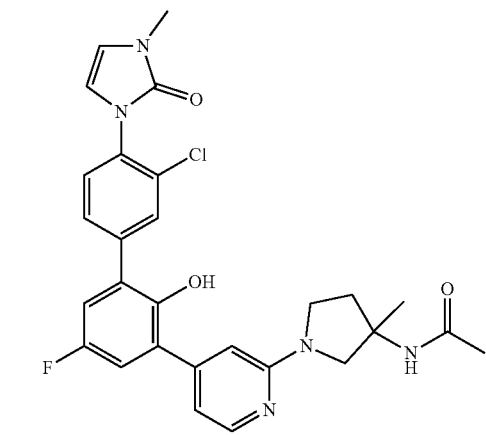
1544
-continued
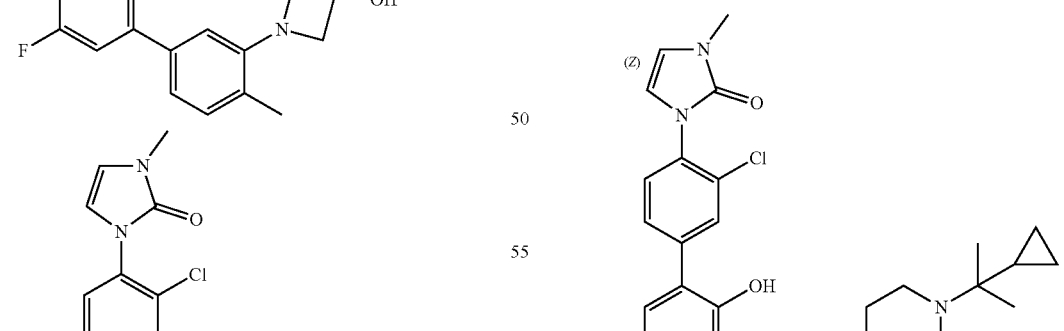
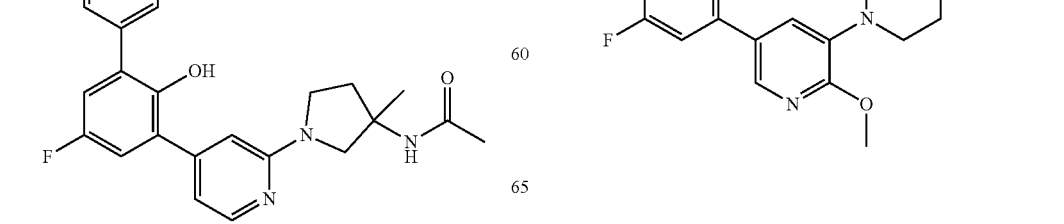

1545
-continued
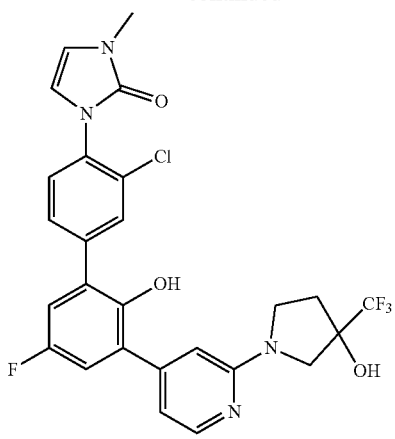
1546
-continued
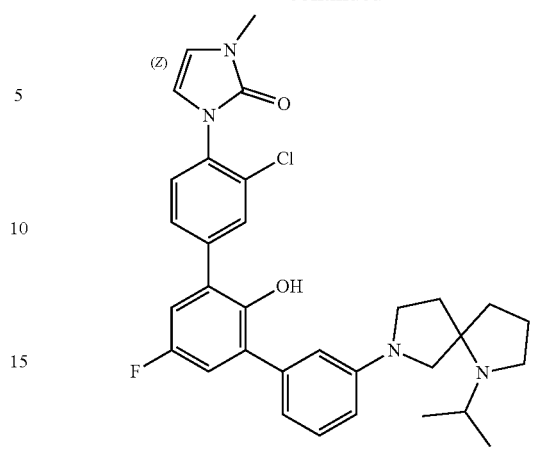
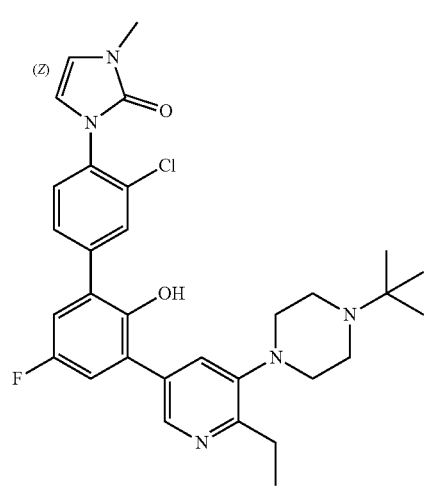
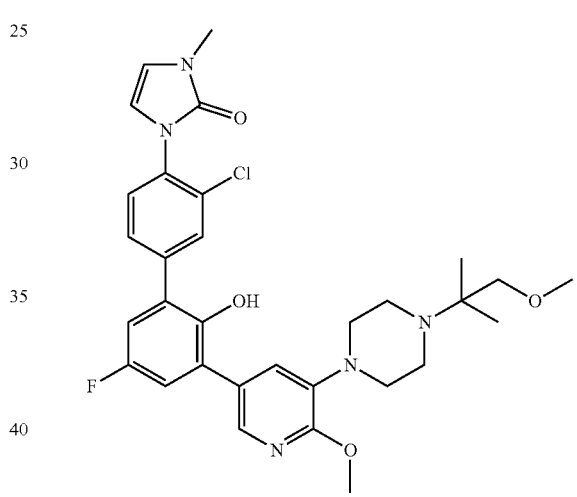
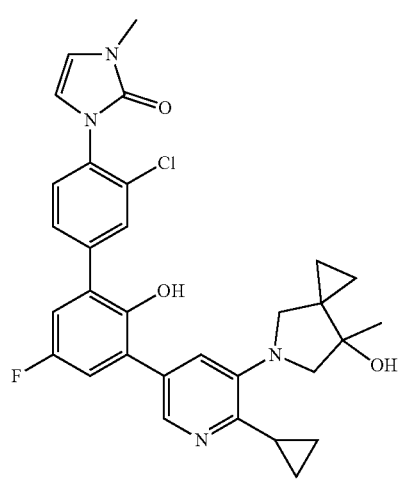
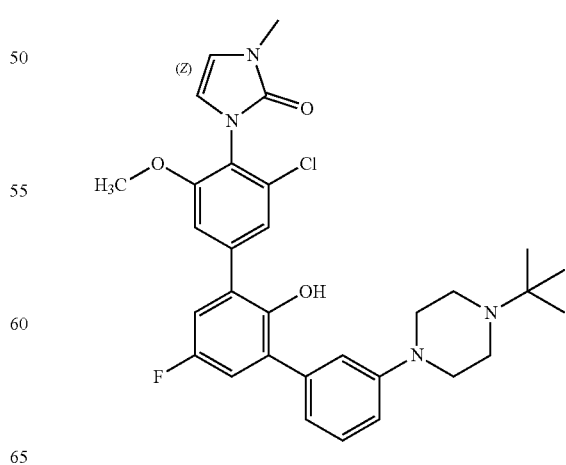

1547
-continued
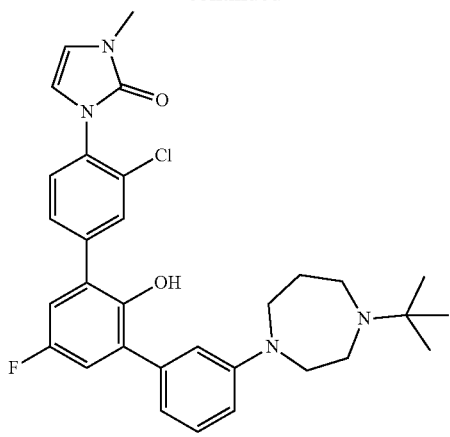
(Z)
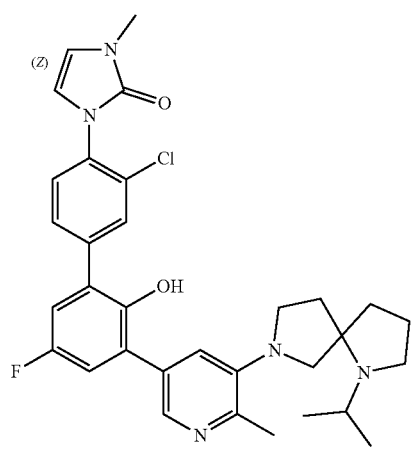
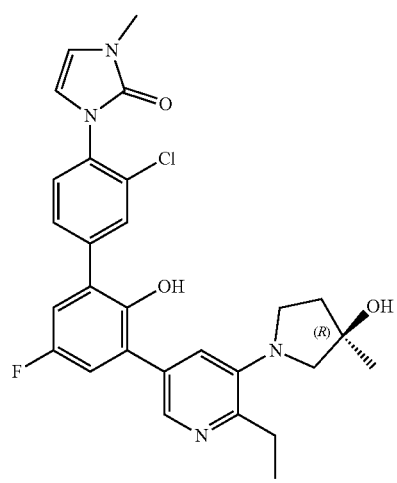
1548
-continued
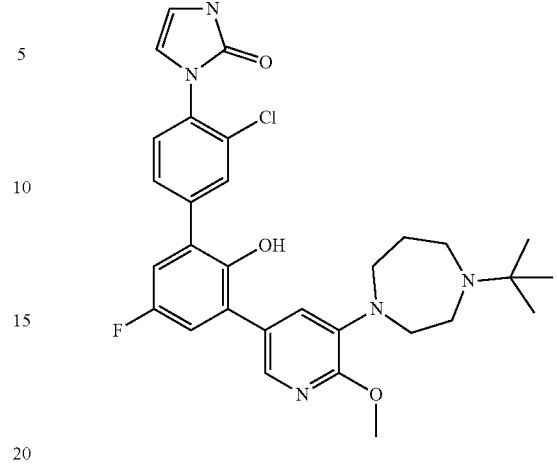
(Z)
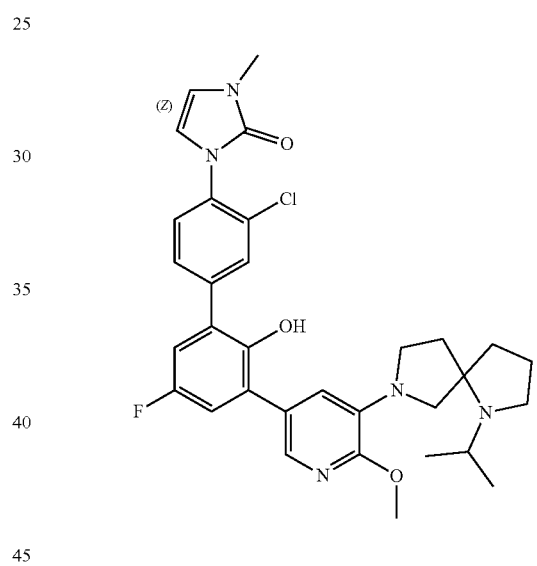
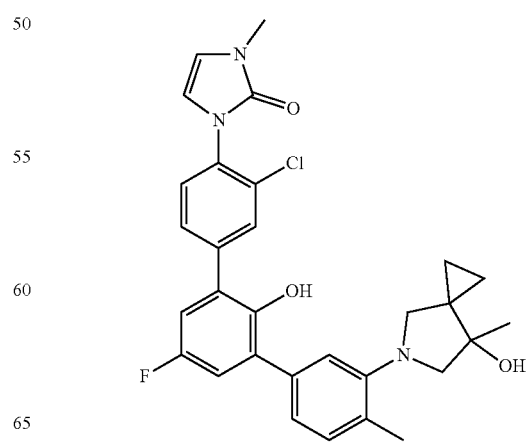

1549
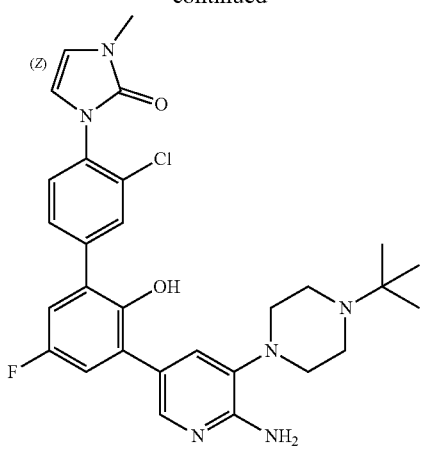
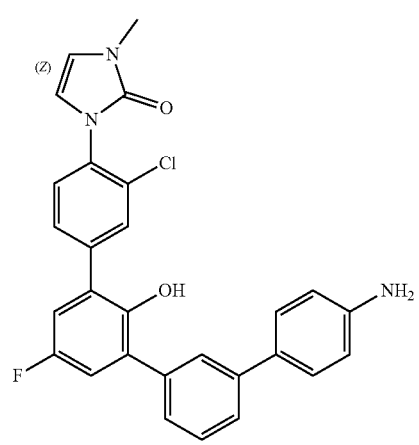
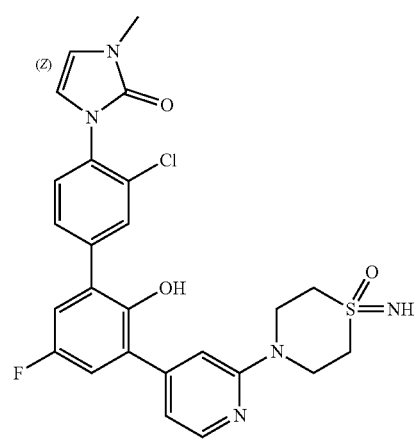
1550
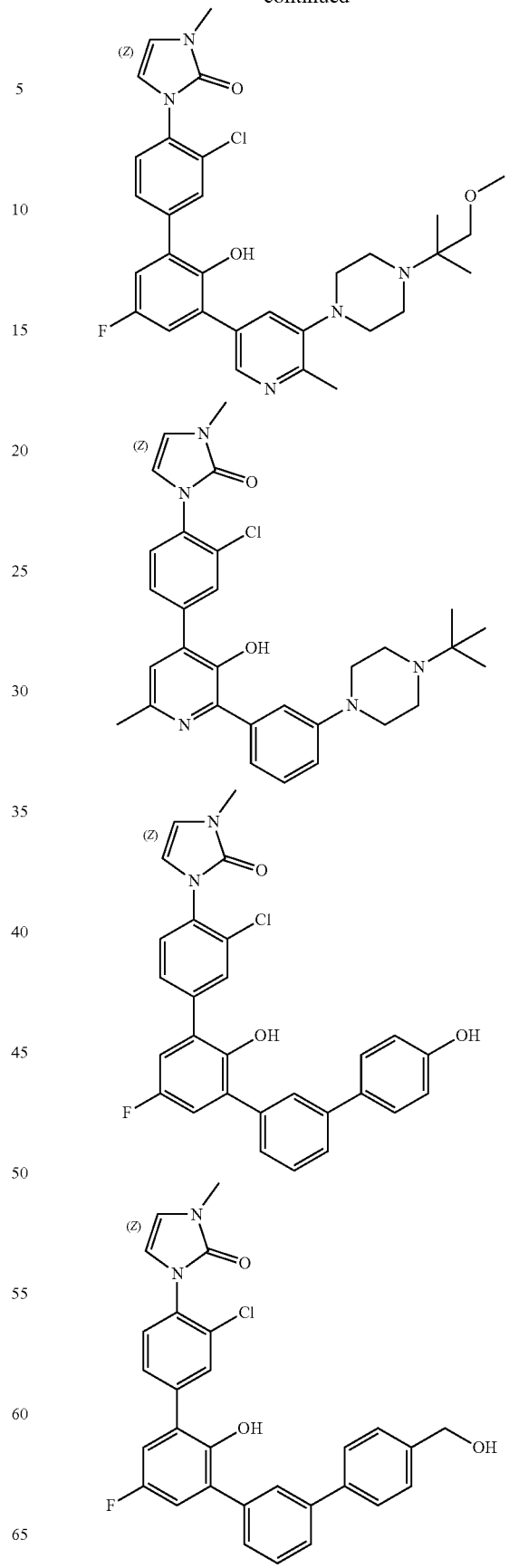

1551 -continued
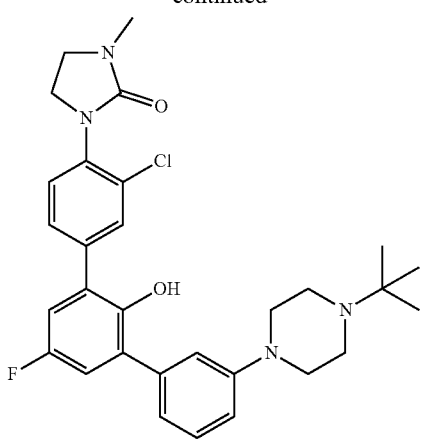
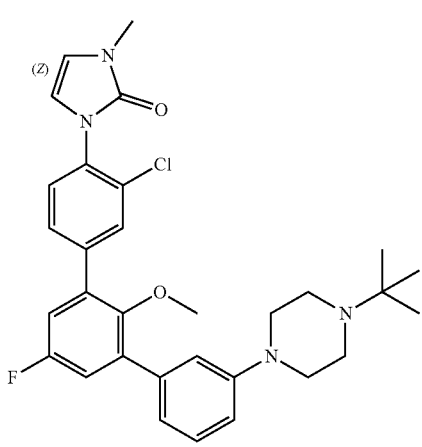
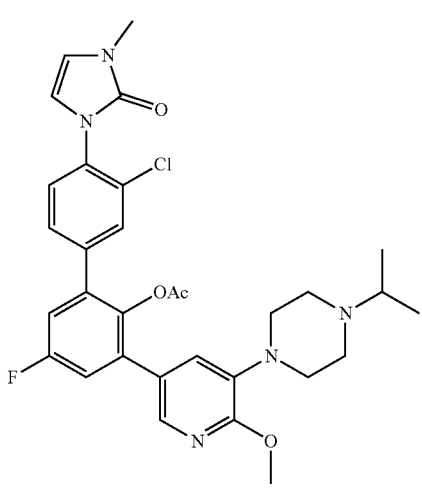
1552 -continued
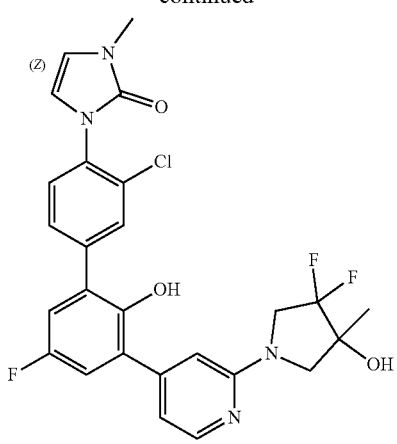
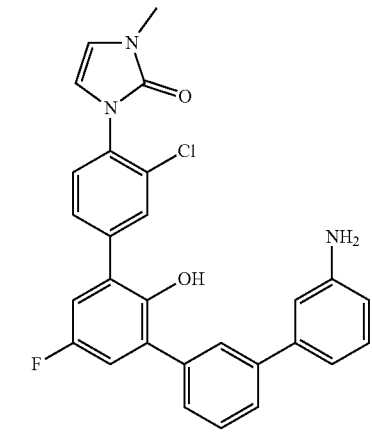
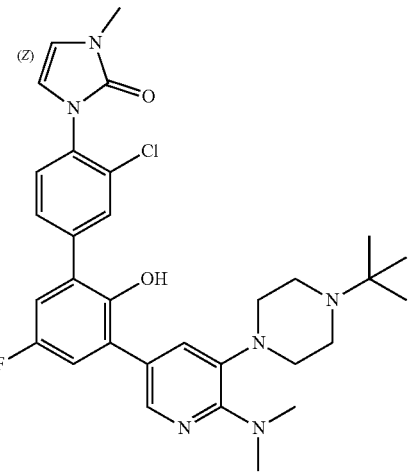

1553
-continued
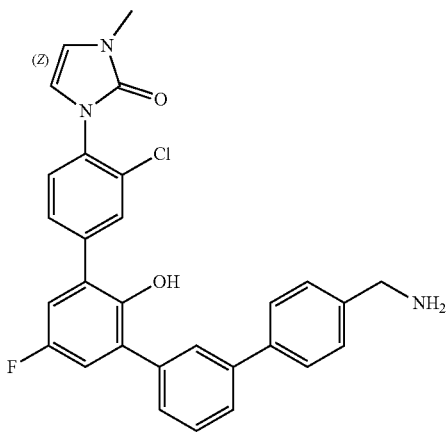
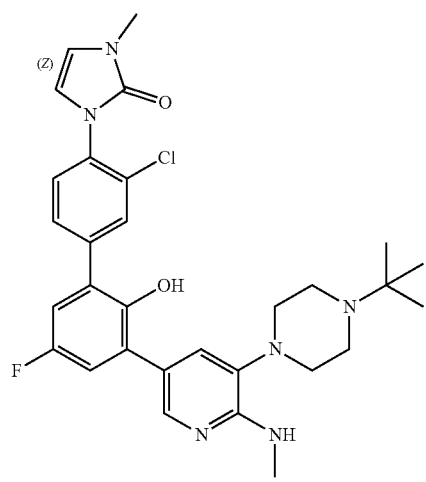
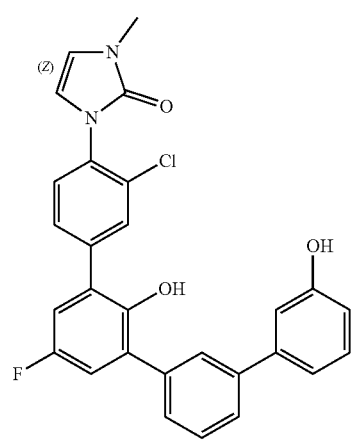
1554
-continued
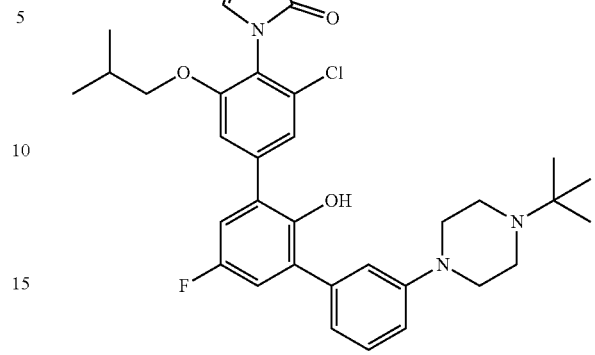
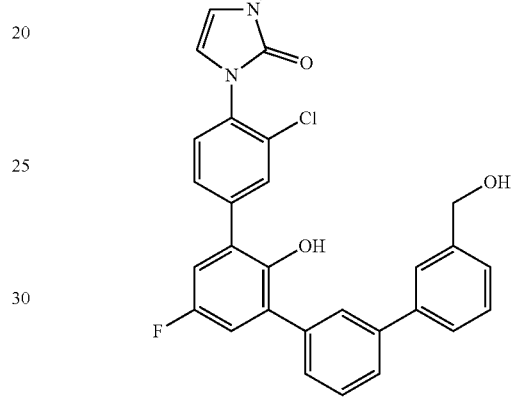
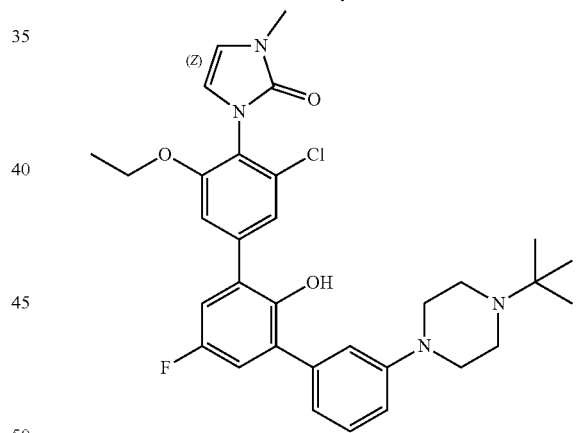
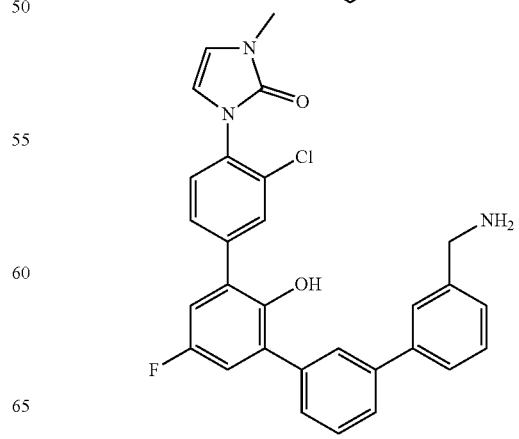

1555 -continued
1556 -continued
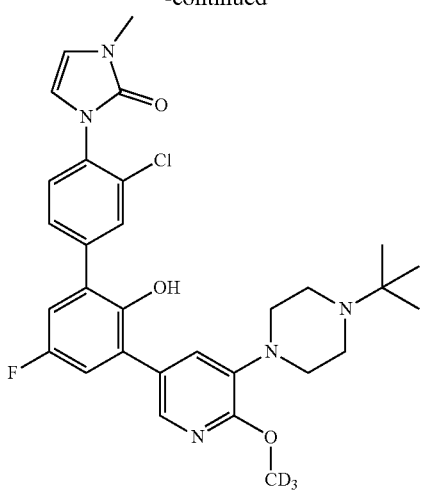
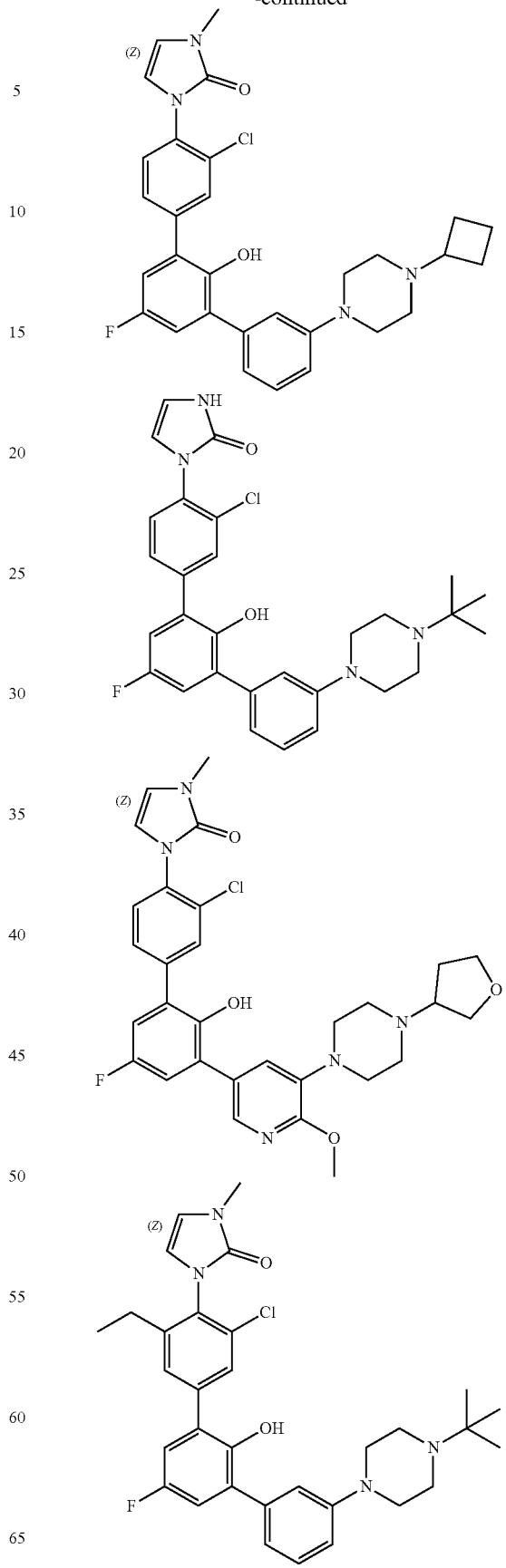

1557
-continued
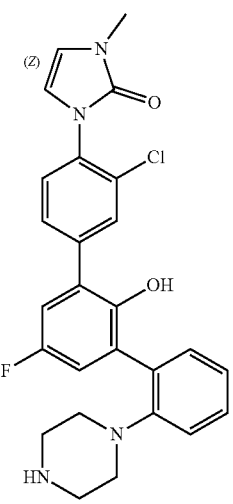
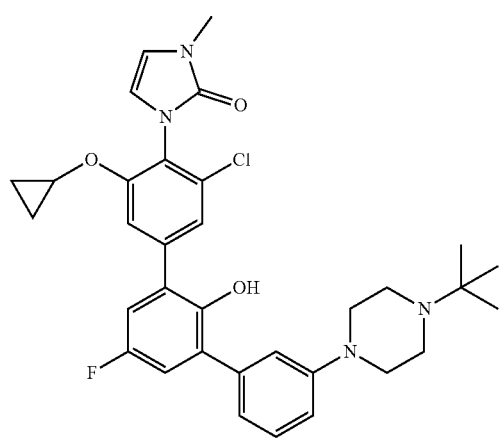
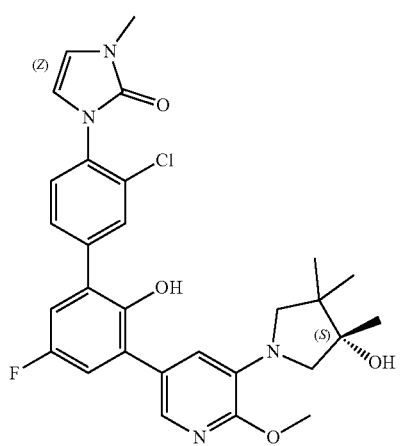
1558
-continued
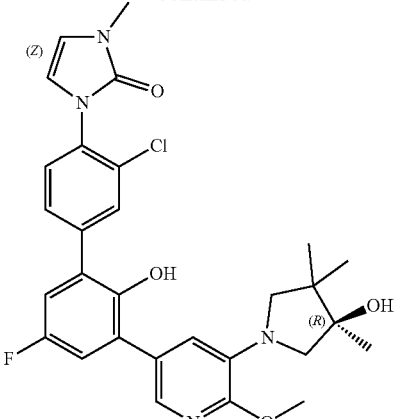
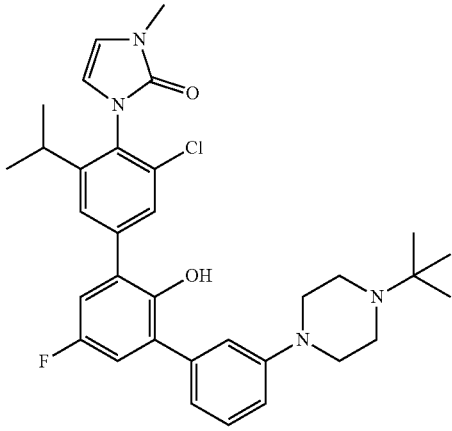
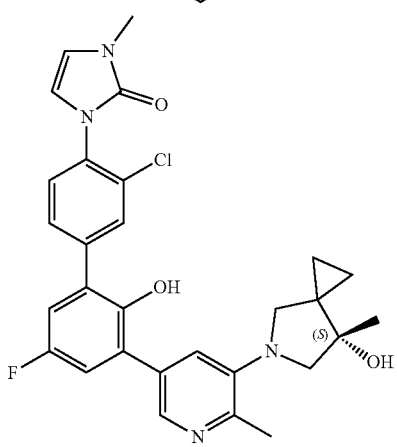
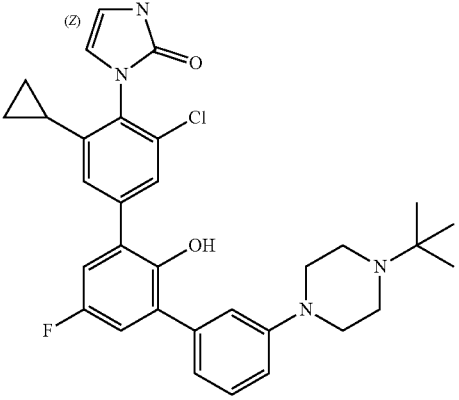

1559
-continued
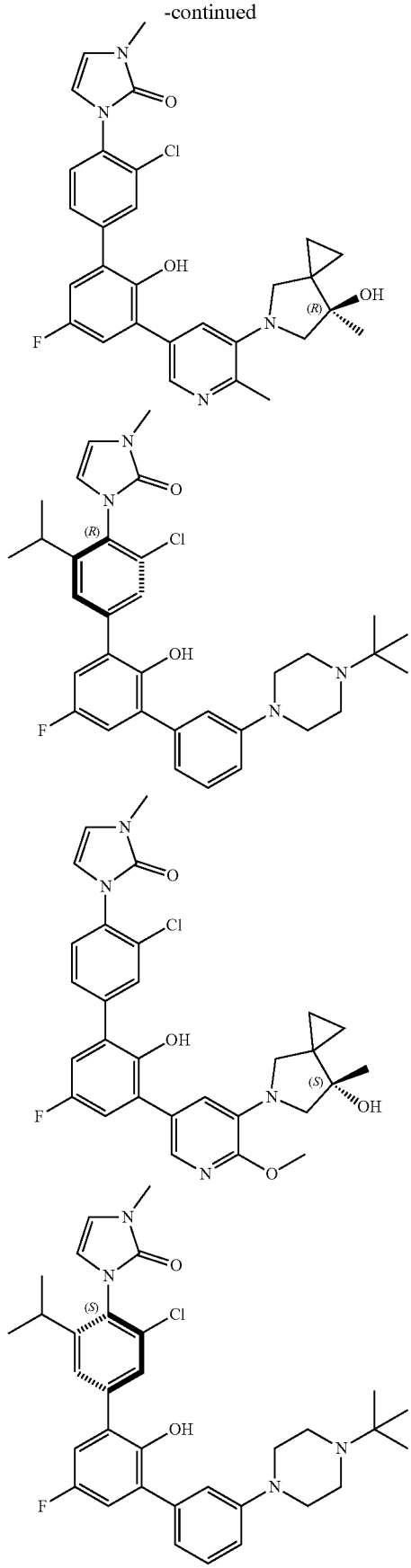
1560
-continued
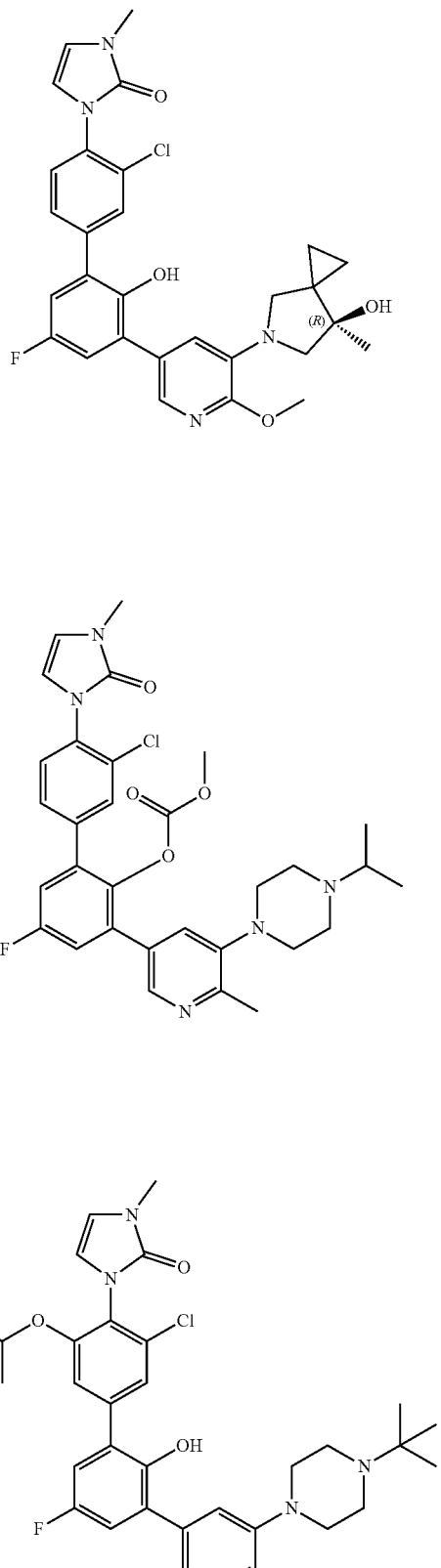

1561
-continued
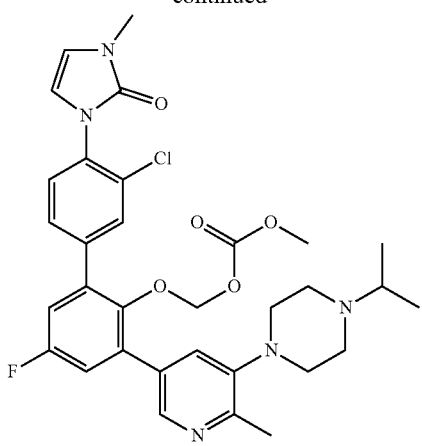
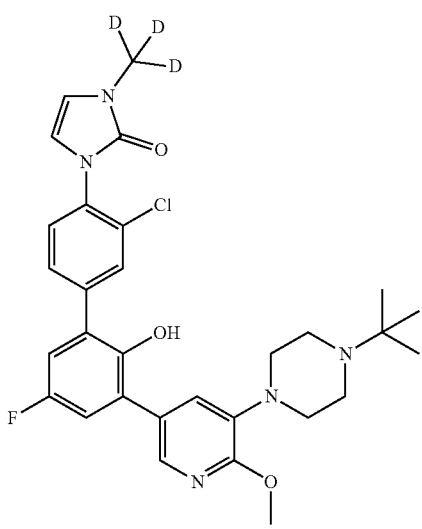
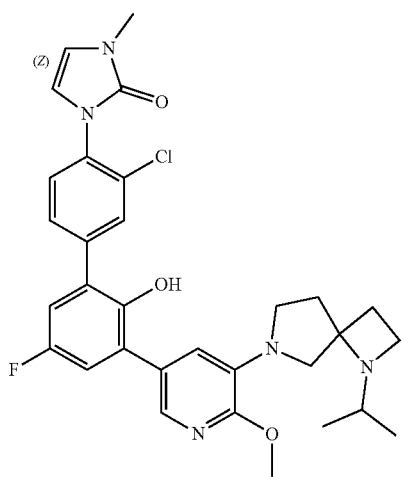
1562
-continued
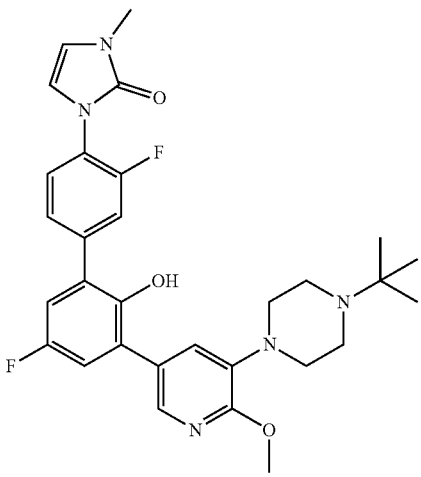
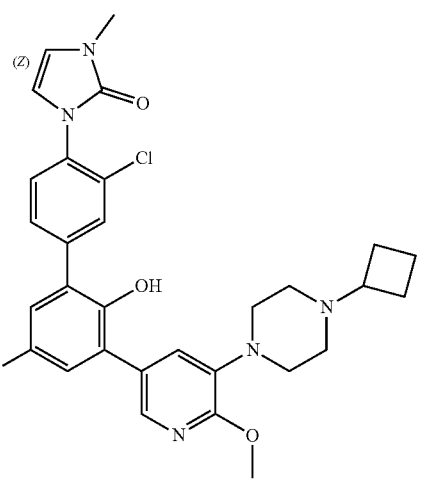
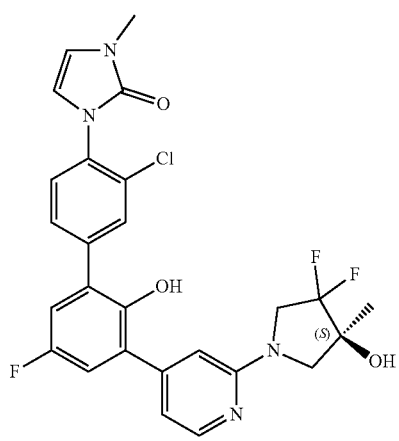

1563
-continued
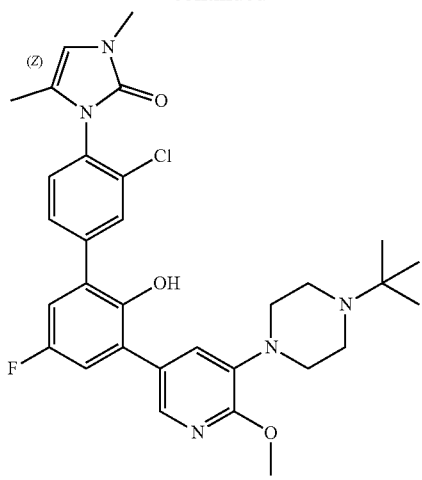
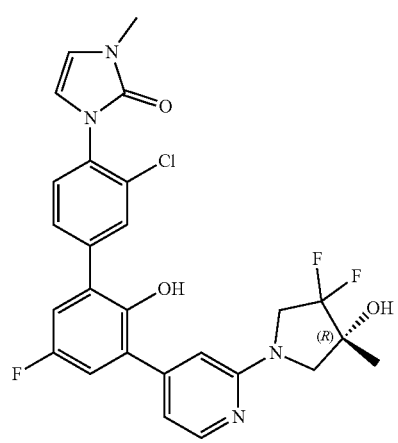
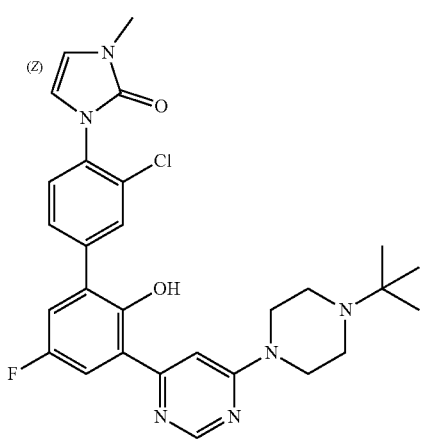
1564
-continued
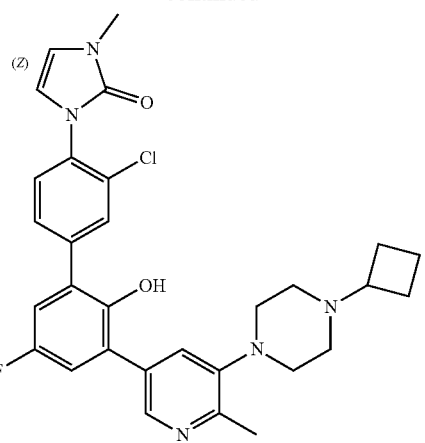
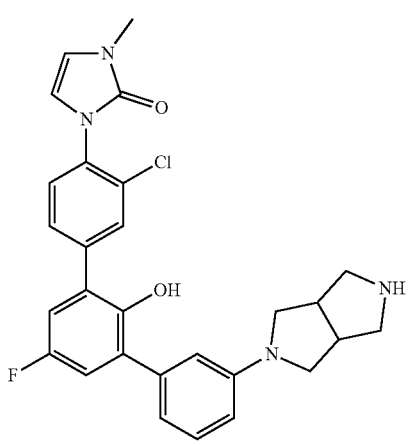
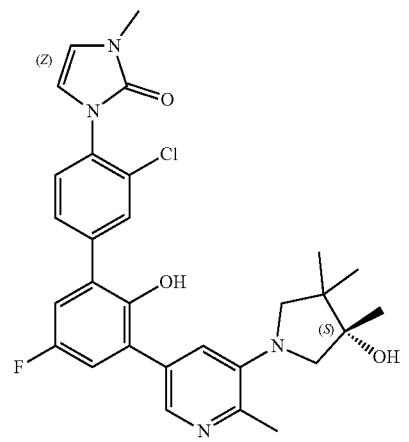

1565
-continued
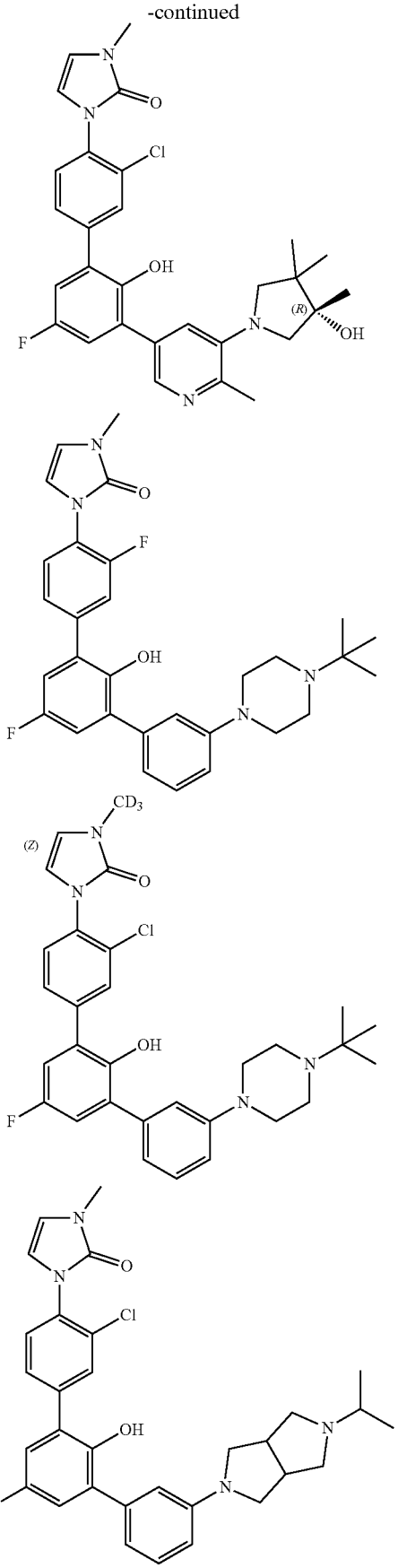
1566
-continued
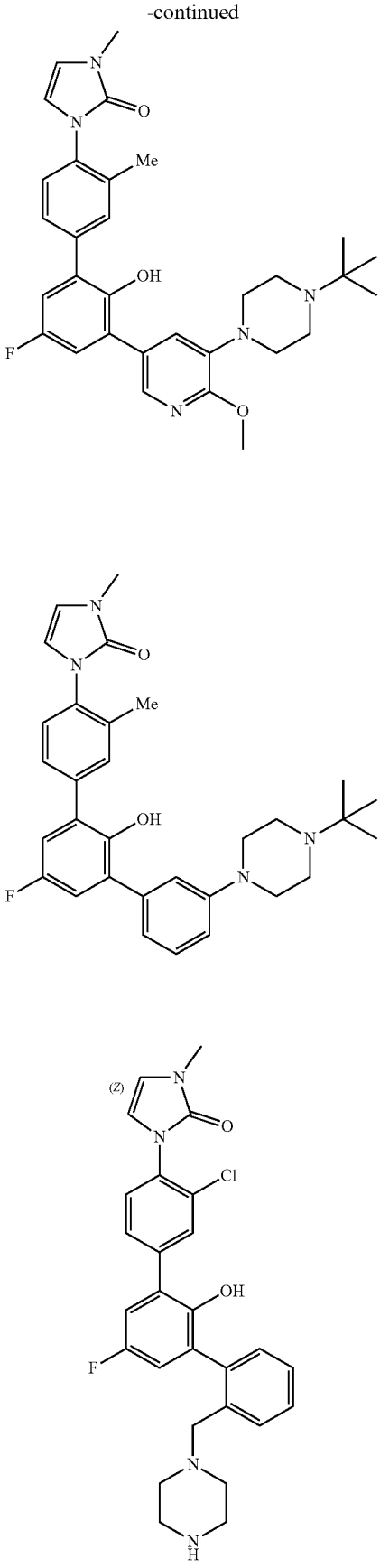

1567
-continued
1568
-continued
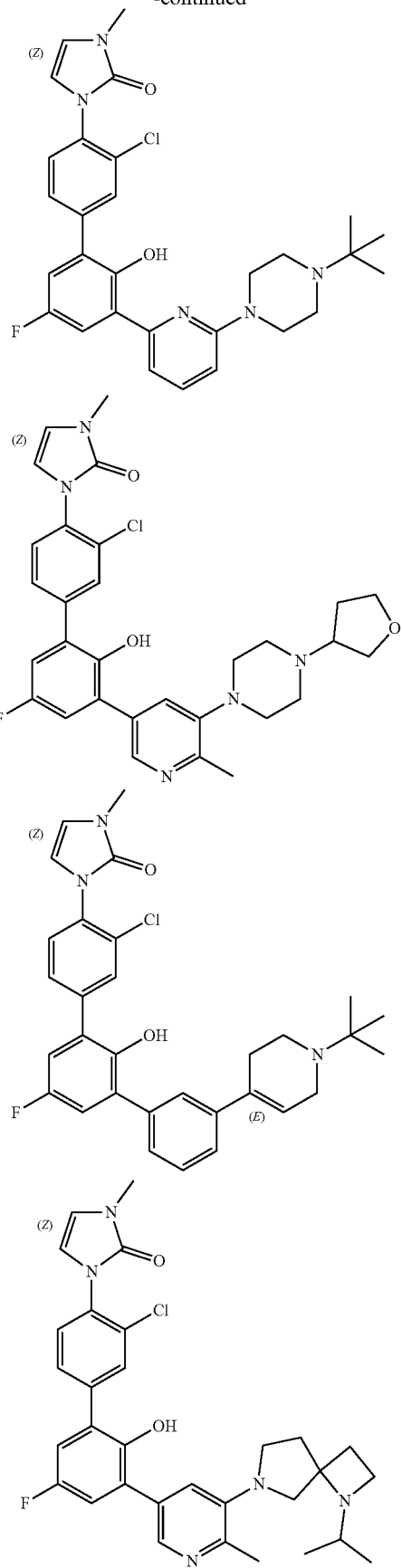
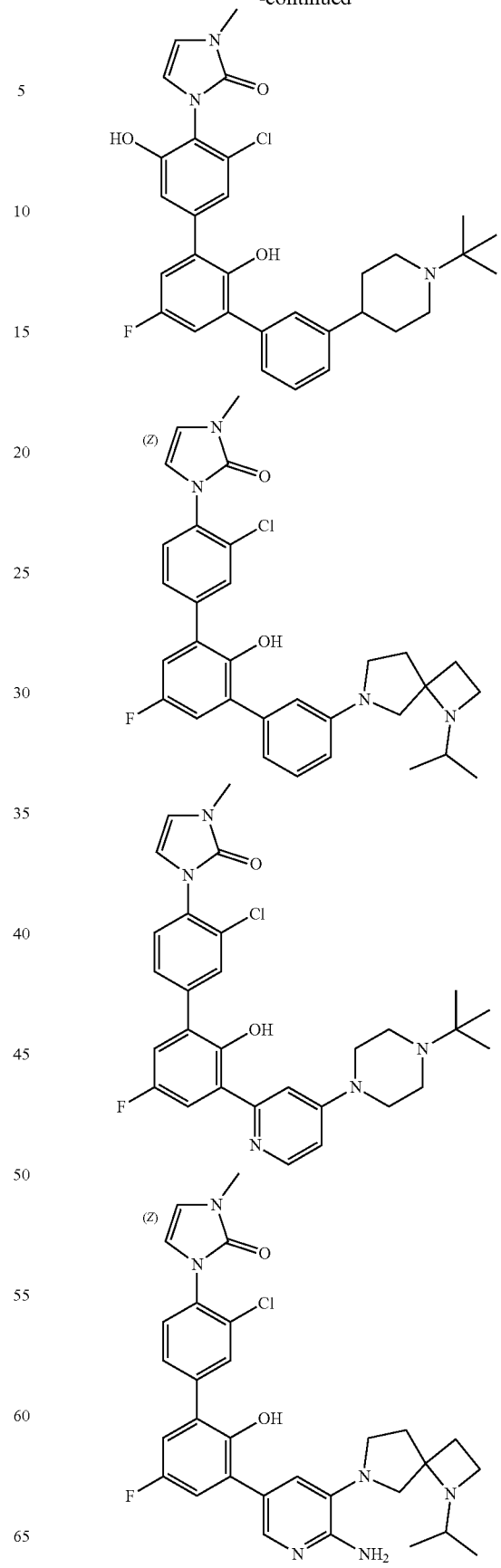

1569
-continued
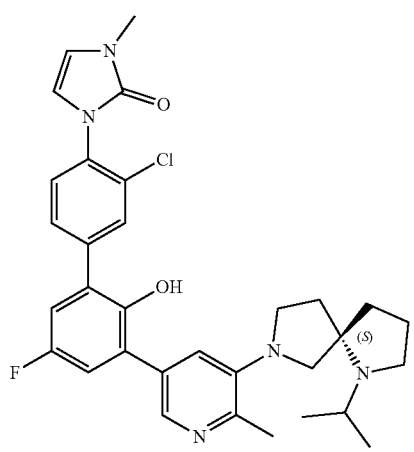
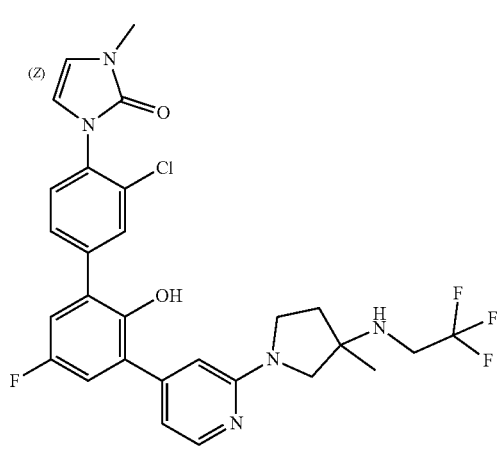
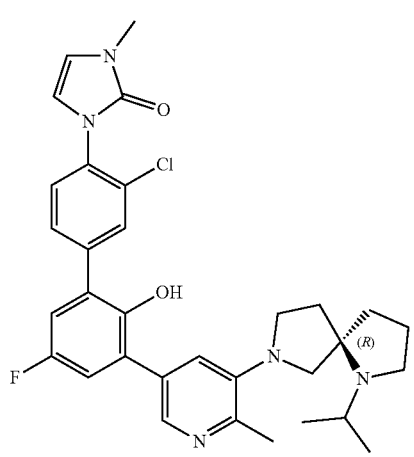
1570
-continued
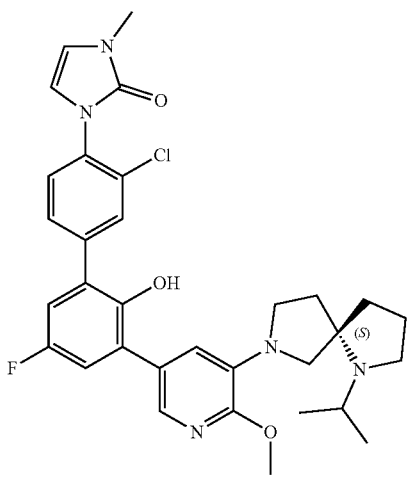

1571
-continued
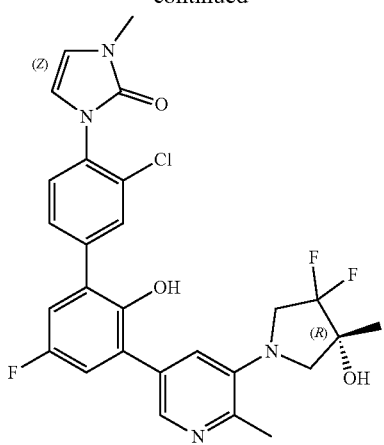
1572
-continued
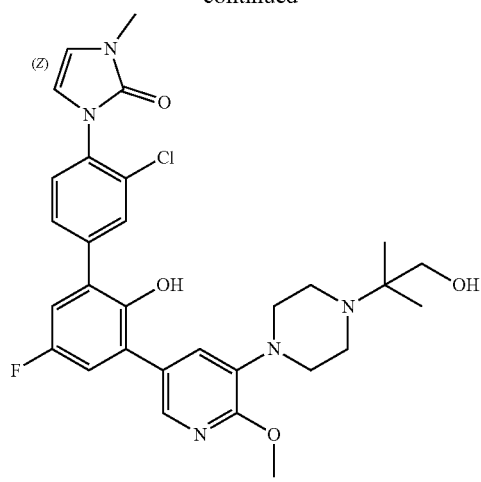
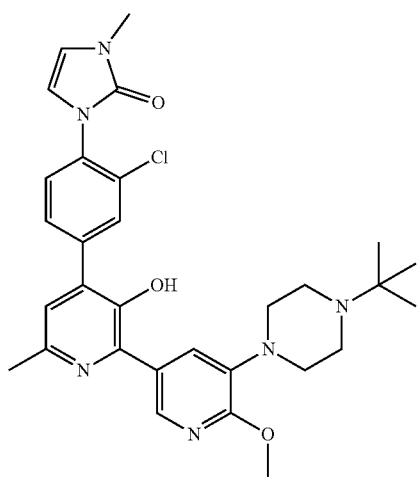
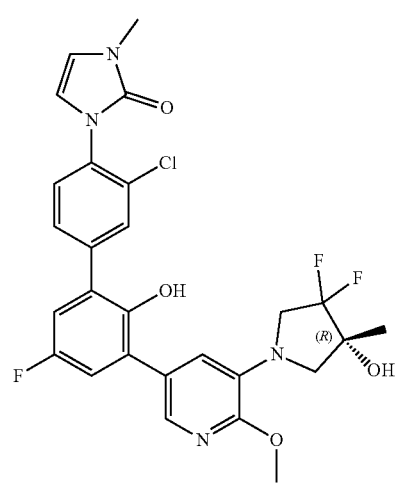
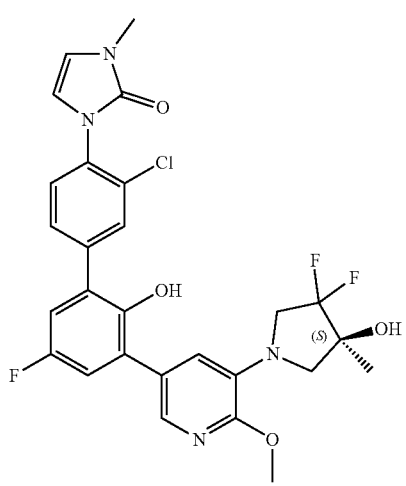

1573
-continued
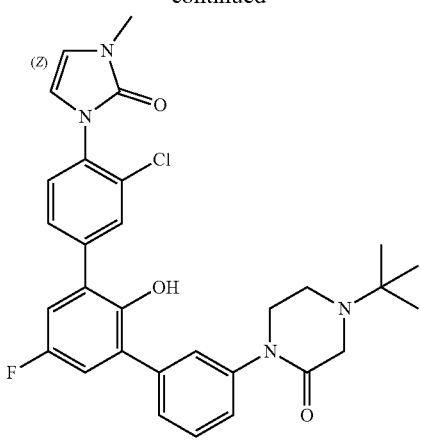
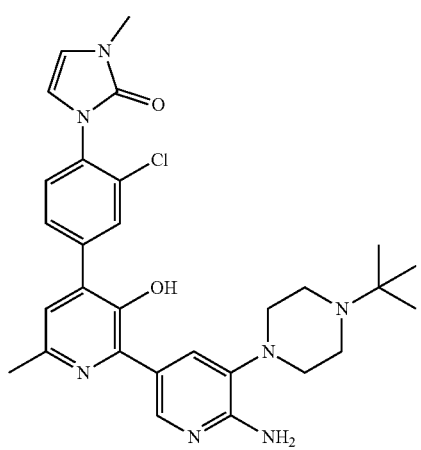
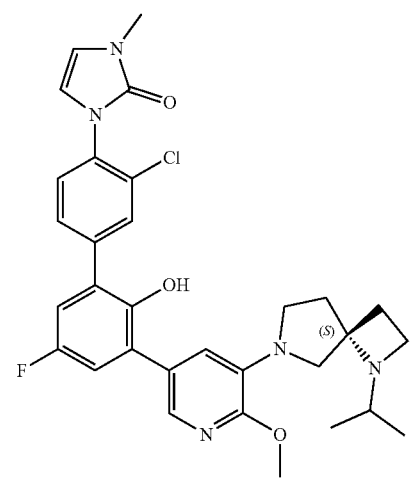
1574
-continued
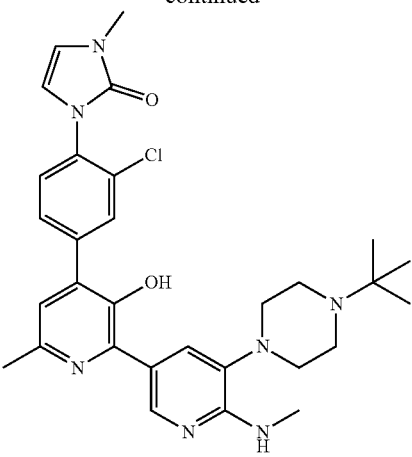
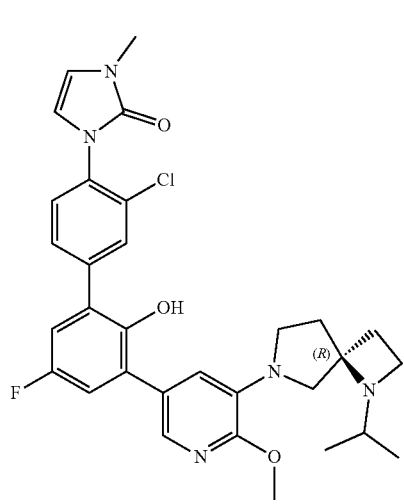
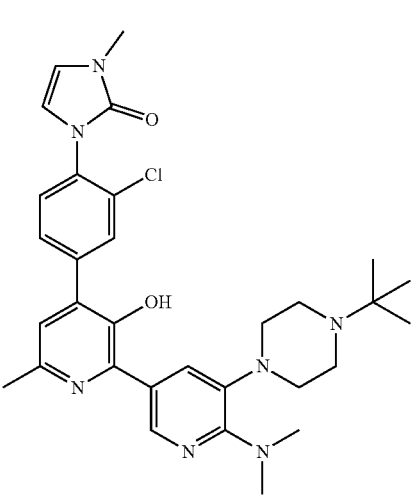

1575
-continued
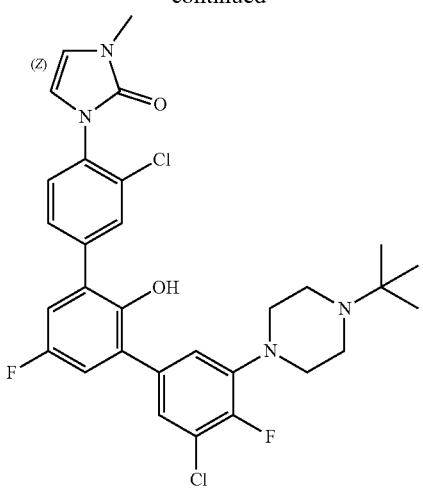
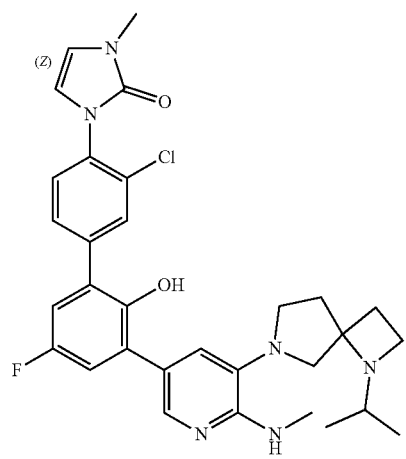
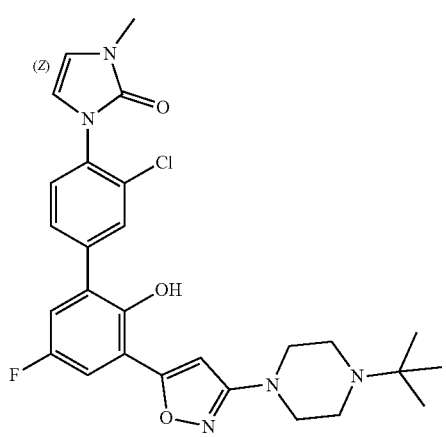
1576
-continued
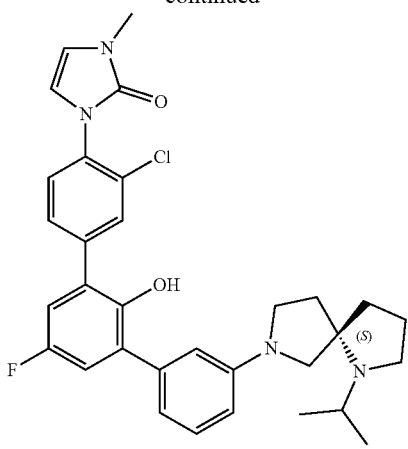
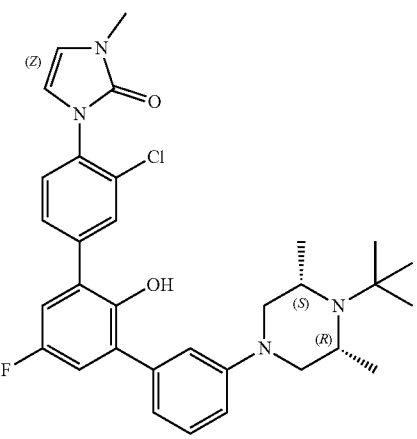
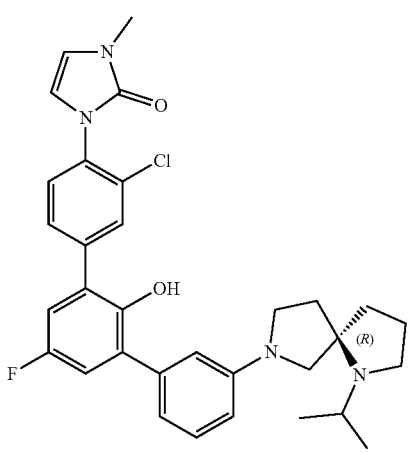

1577 -continued
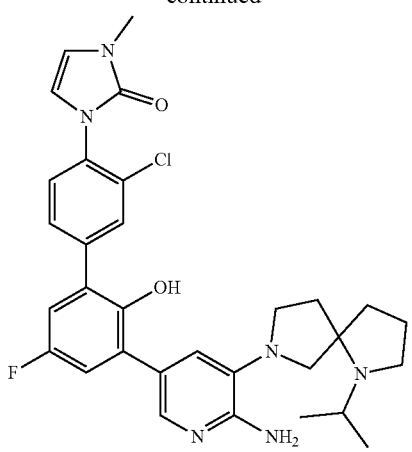
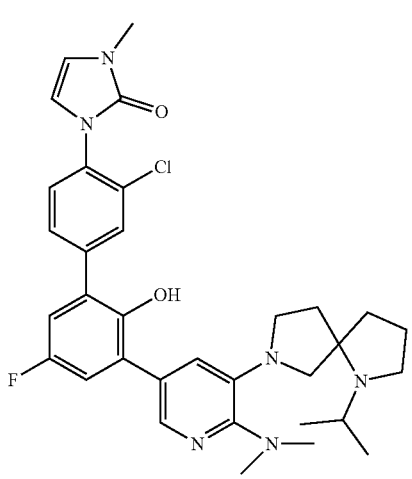
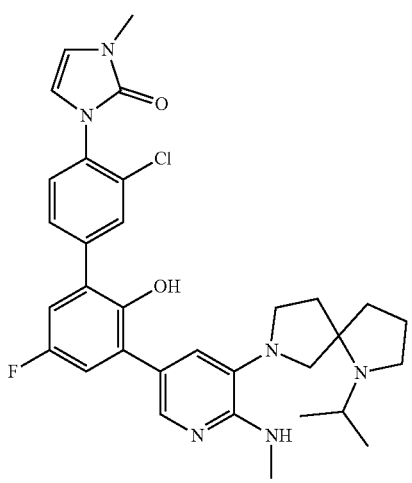
1578 -continued
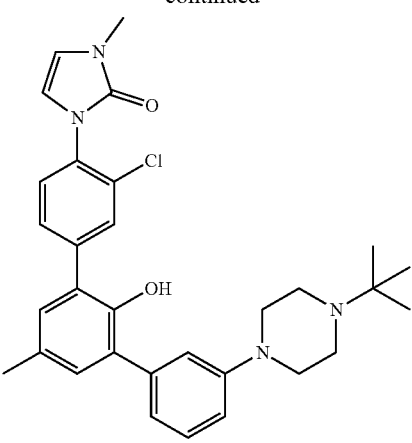
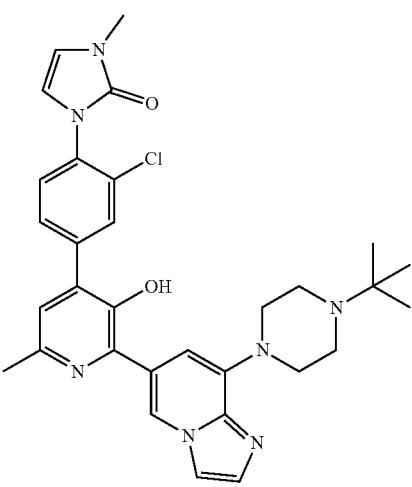
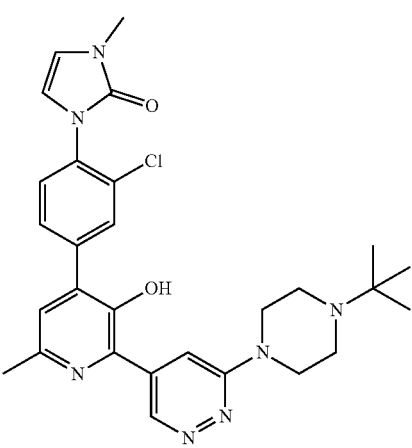

1579
-continued
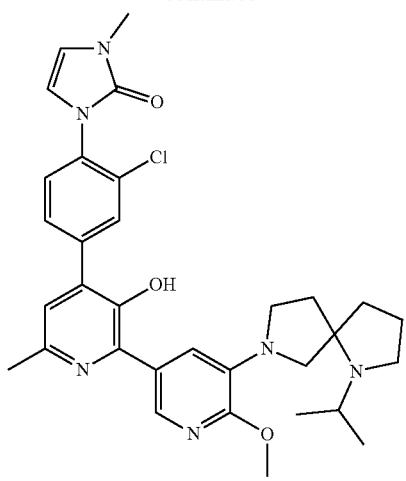
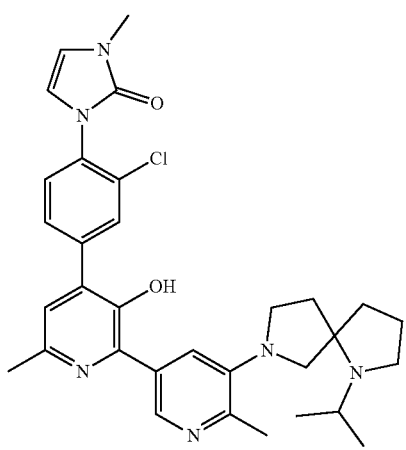
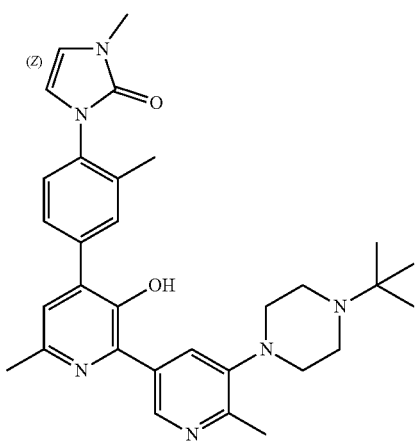
1580
-continued
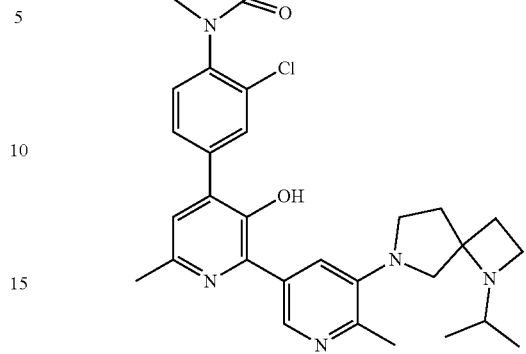
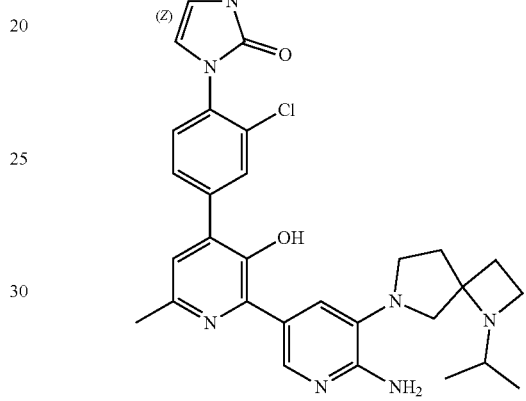
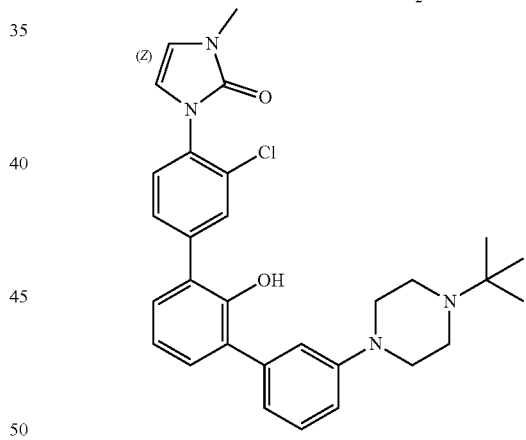
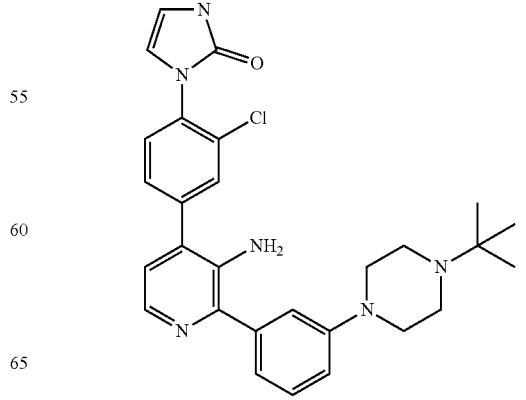

1581
-continued
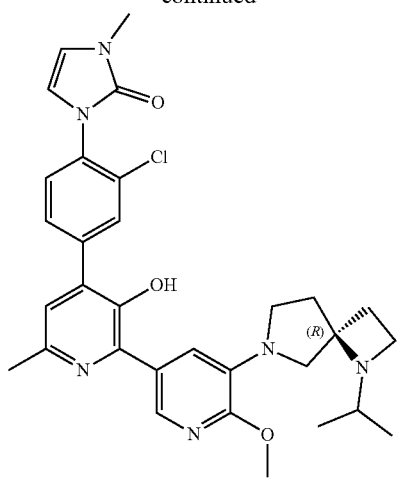
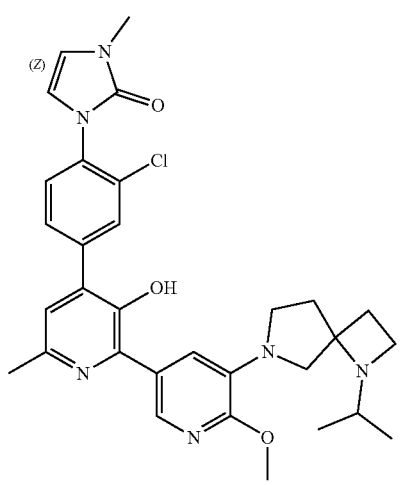
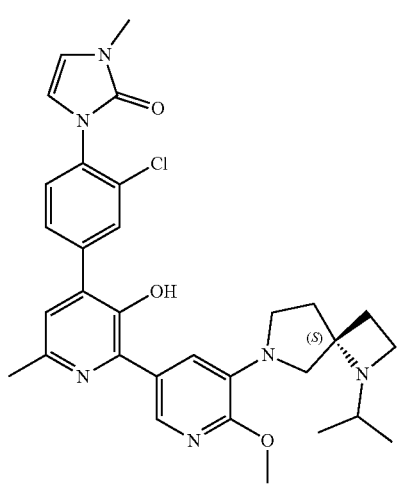
1582
-continued
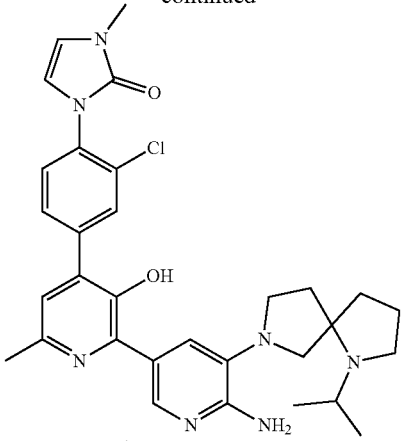
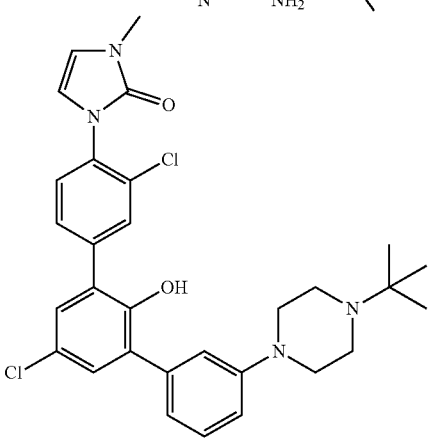
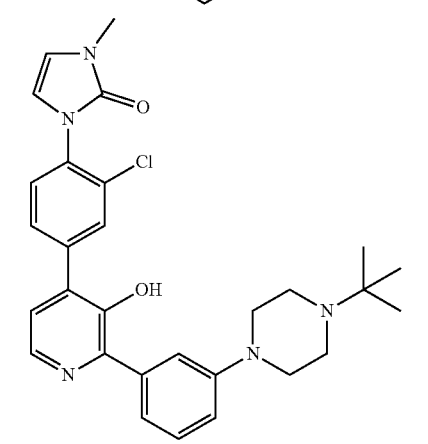
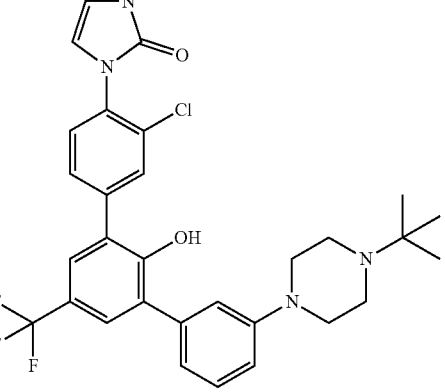

1583
-continued
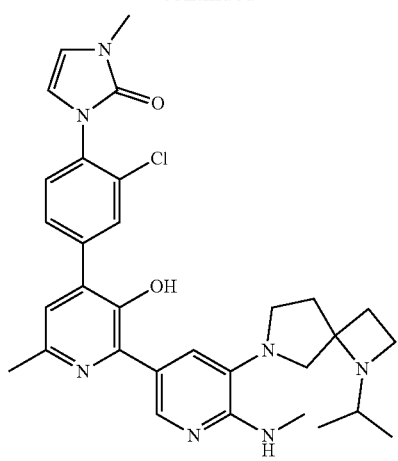
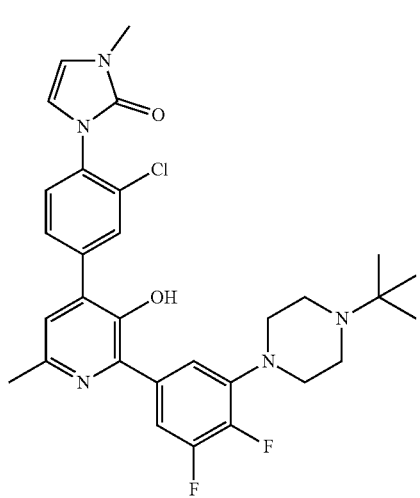
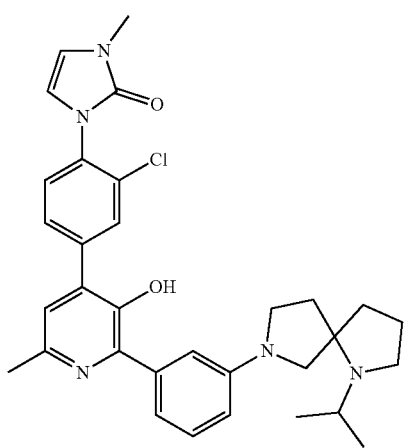
1584
-continued
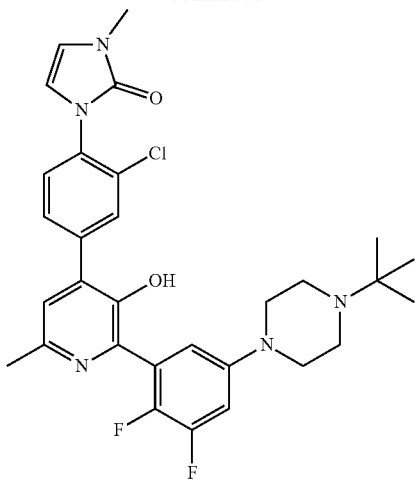
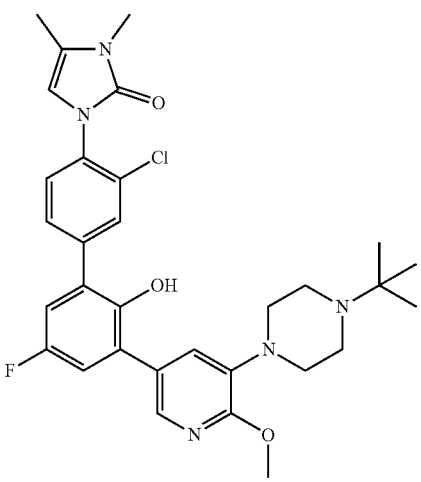
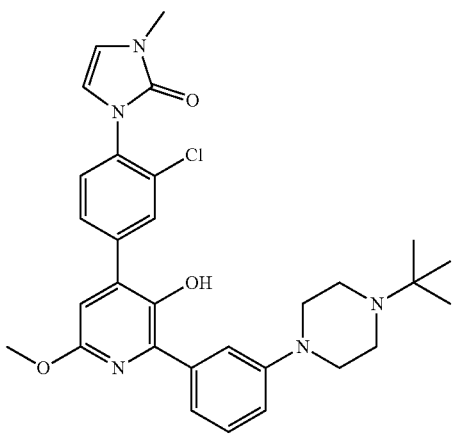

1585
-continued
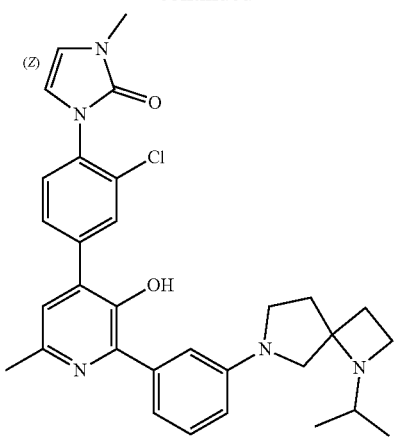
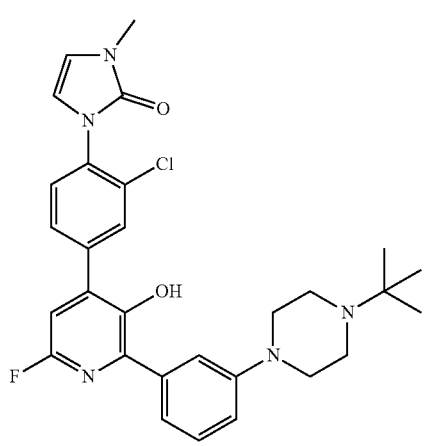
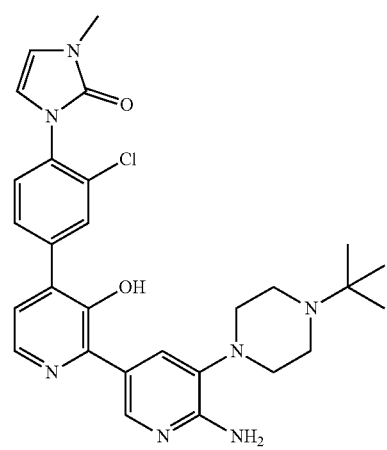
1586
-continued
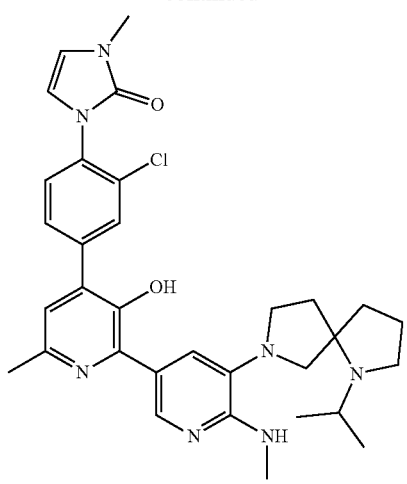
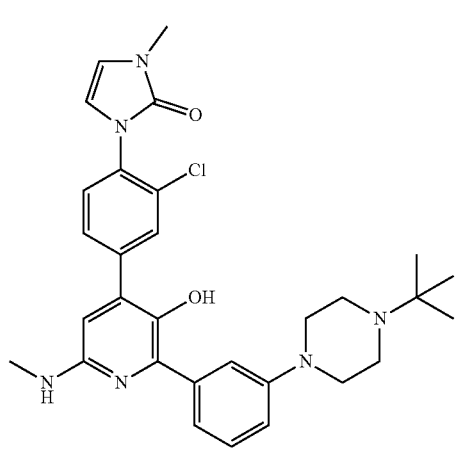
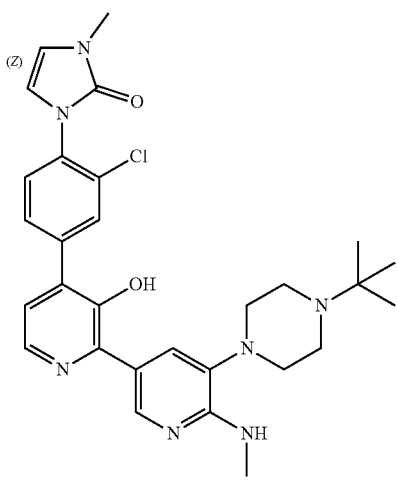

1587
-continued
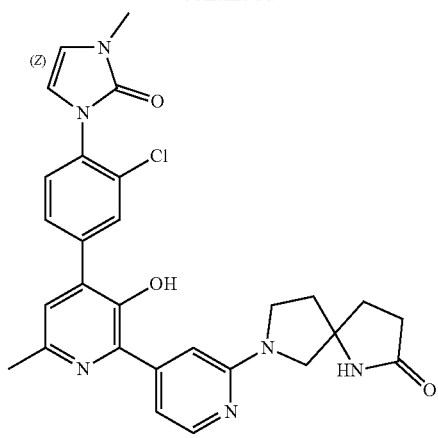
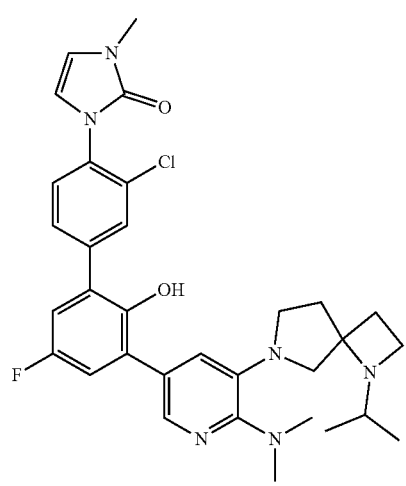
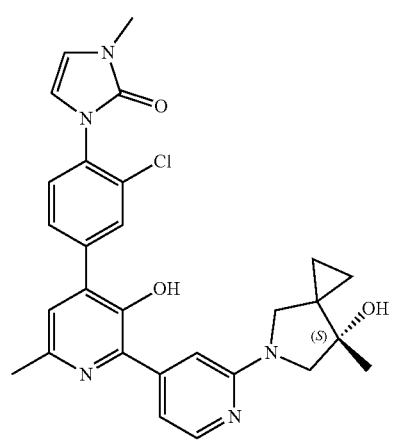
1588
-continued
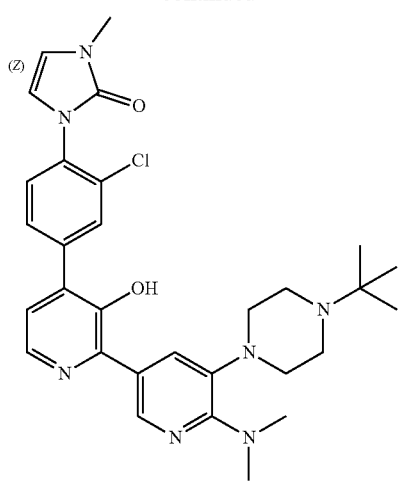
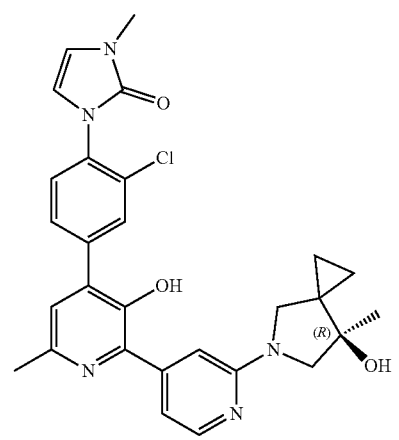
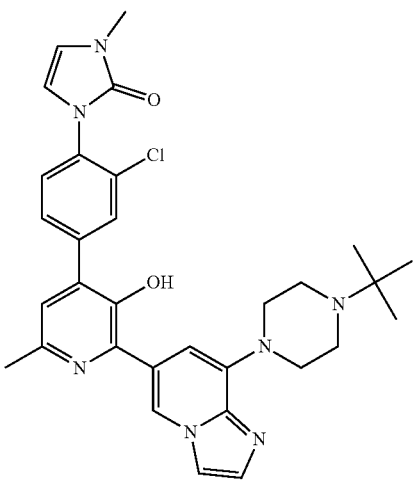

1589
-continued
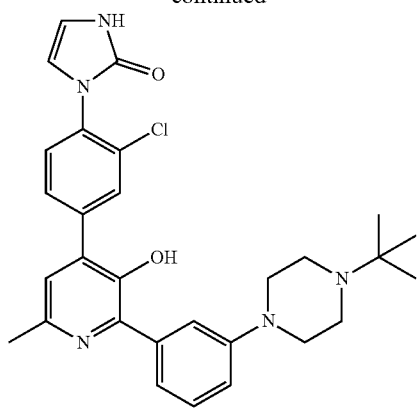
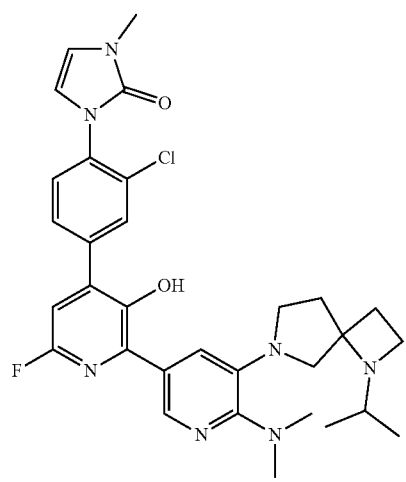
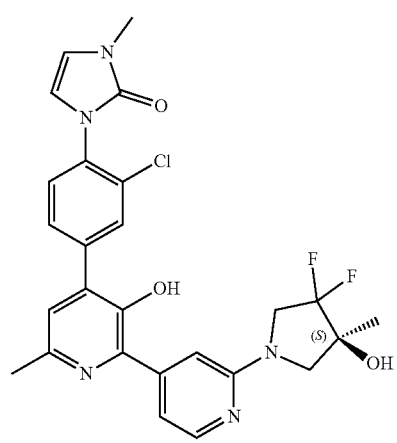
1590
-continued
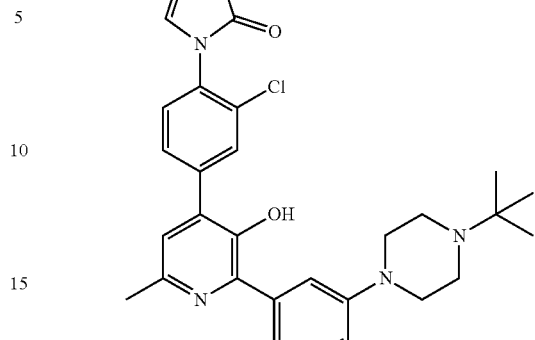
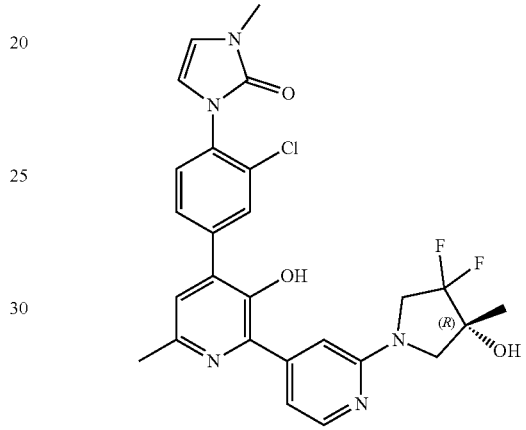
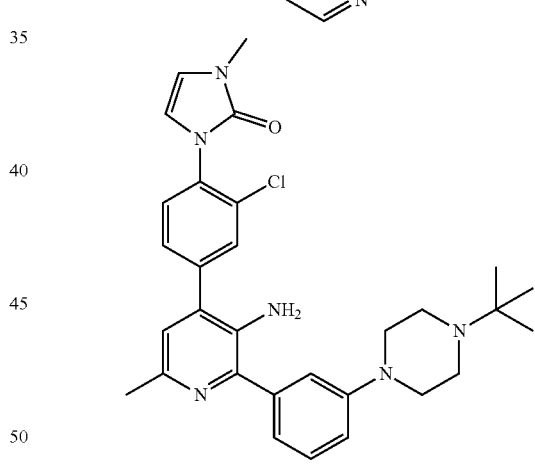
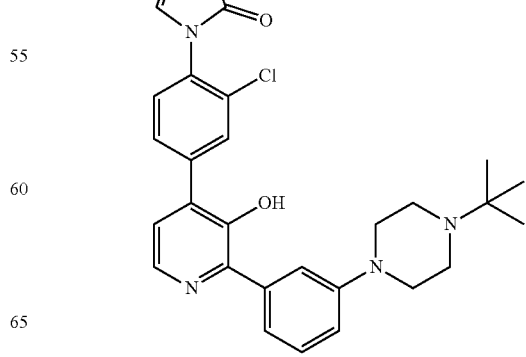

1591
-continued
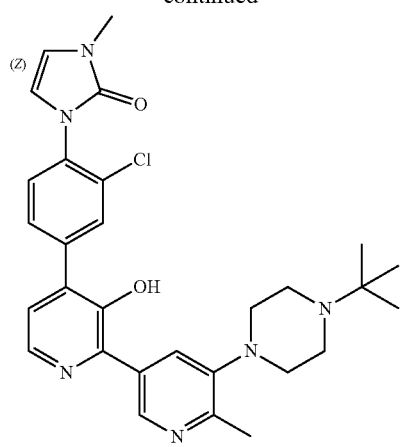
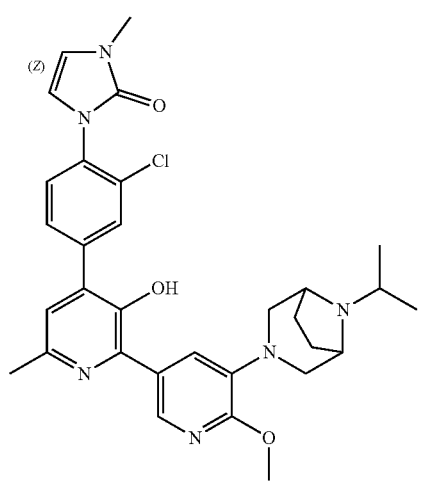
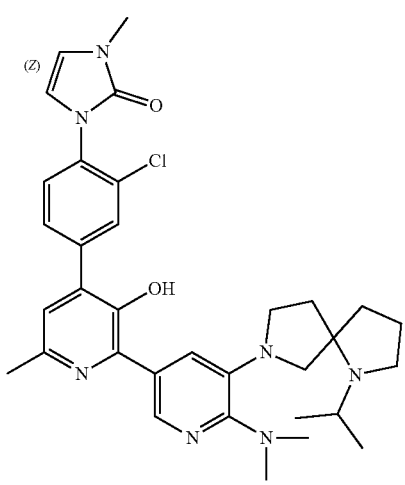
1592
-continued
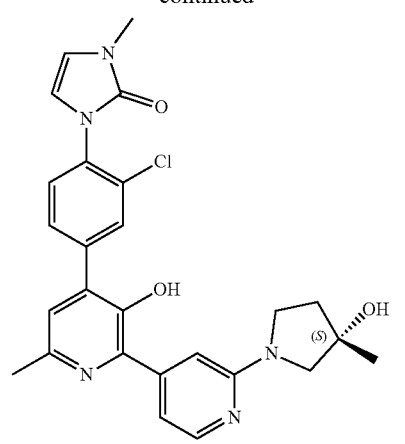
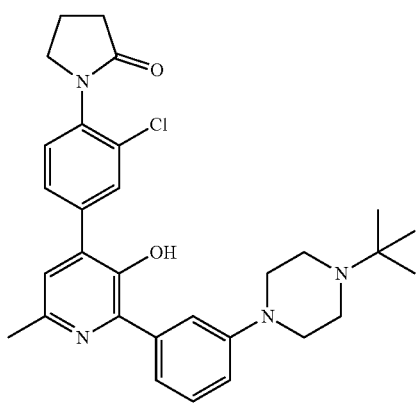
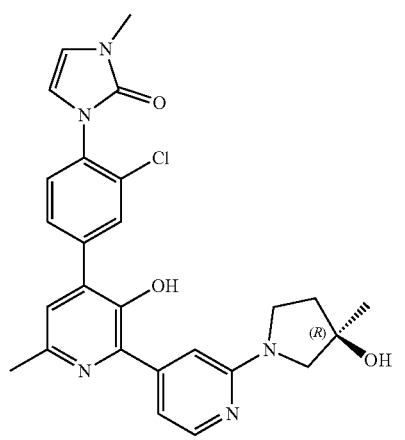
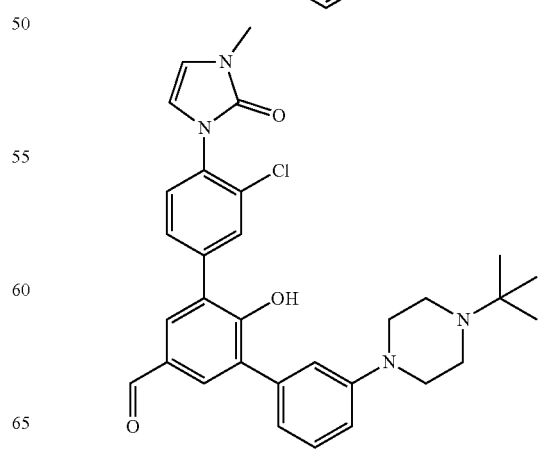

1593
-continued
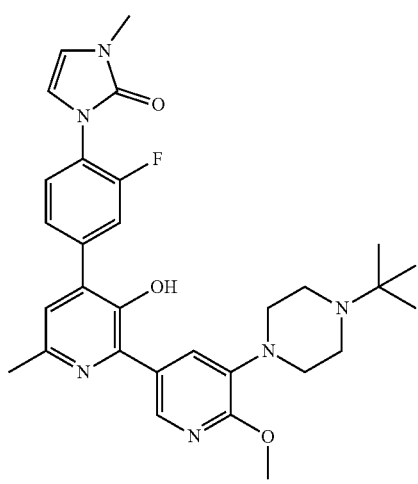
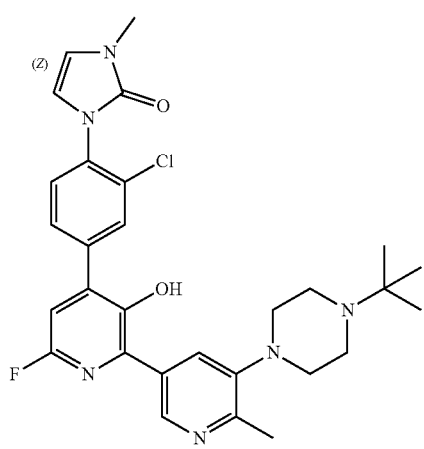
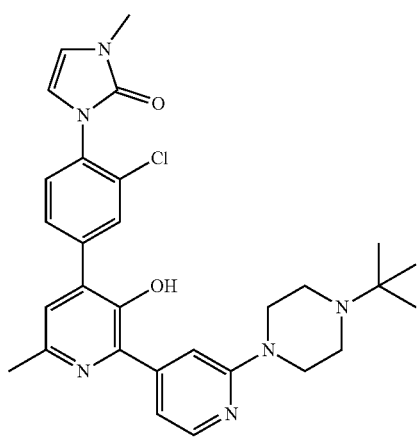
1594
-continued
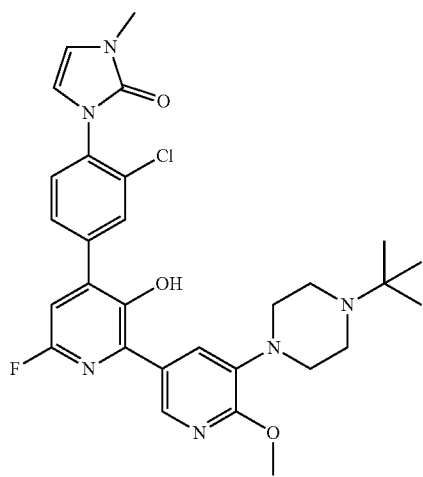
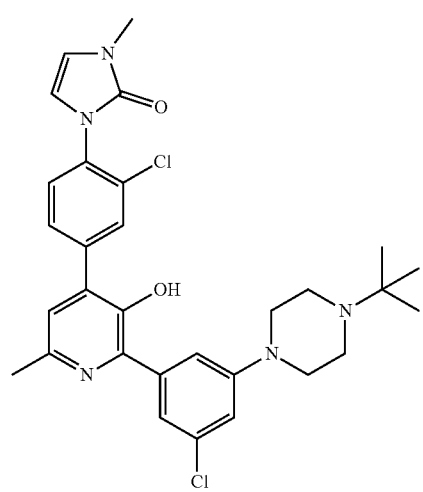

1595
-continued
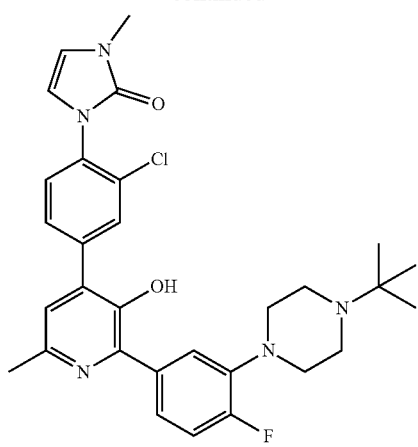
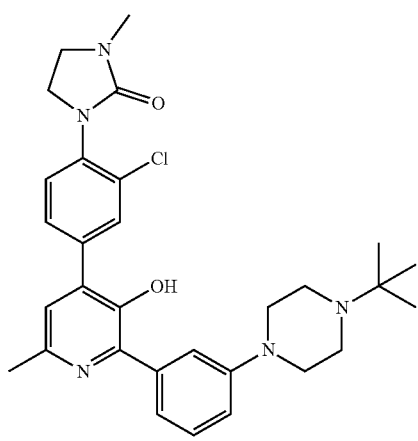
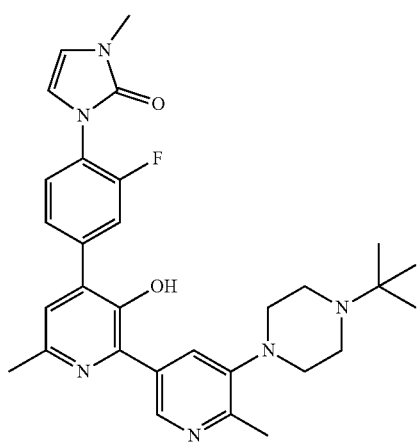
1596
-continued
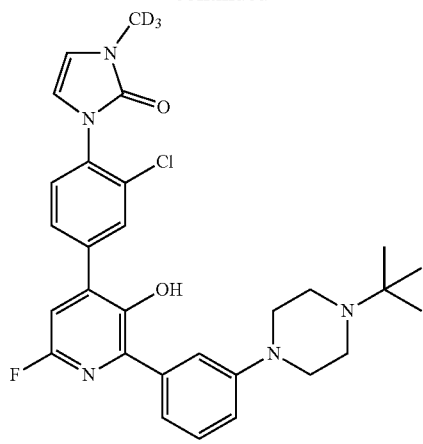
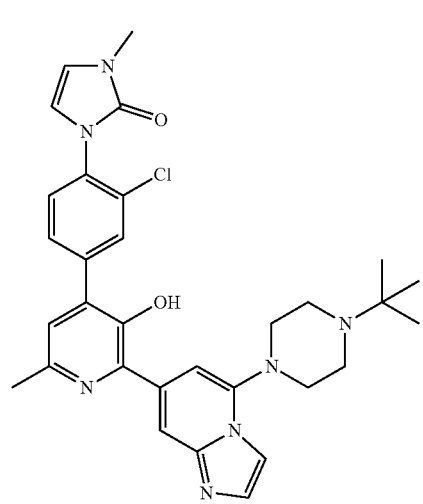
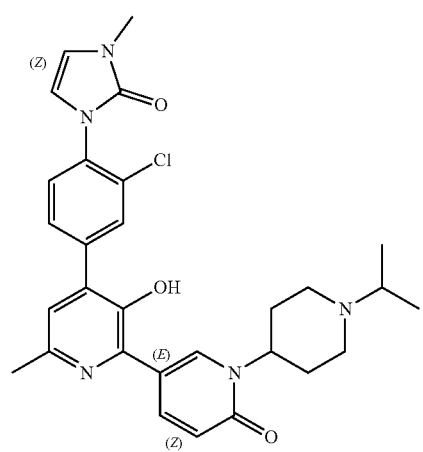

1597
-continued
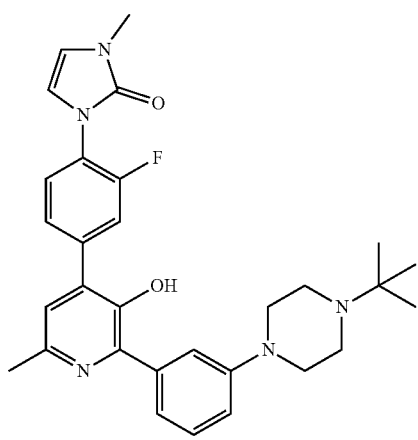
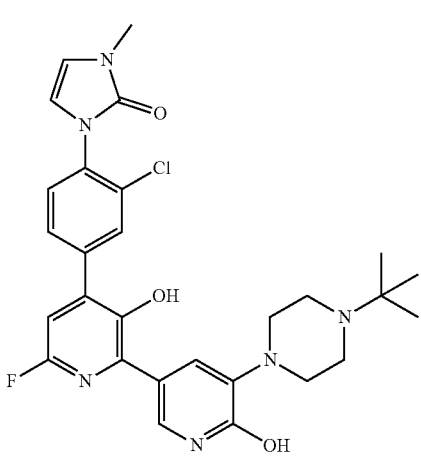
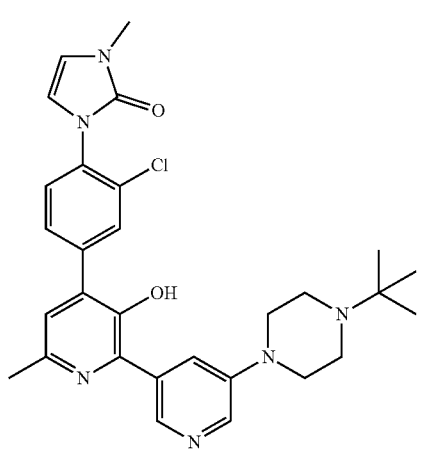
1598
-continued
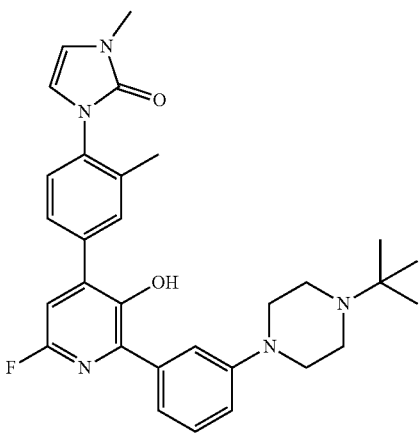
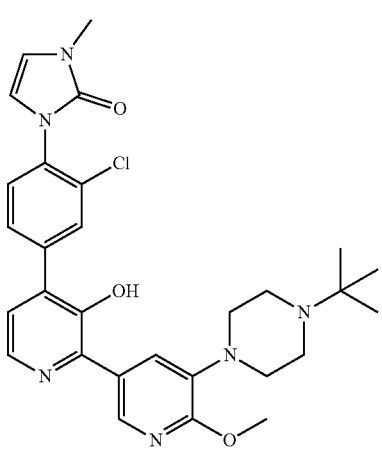
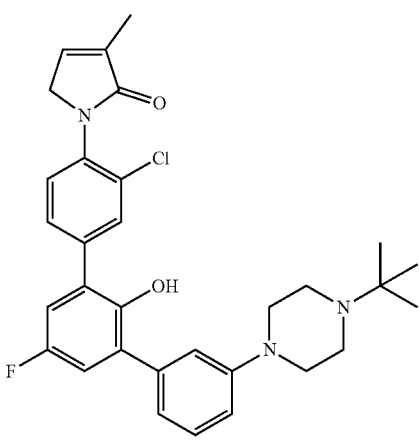

1599
-continued
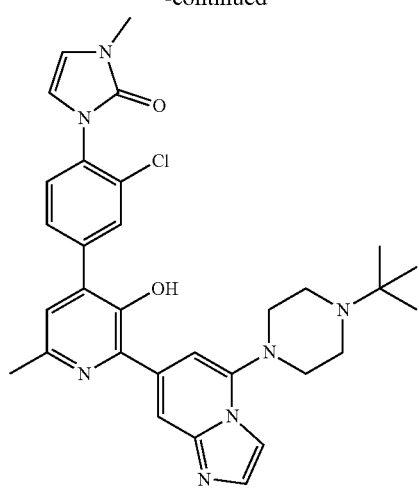
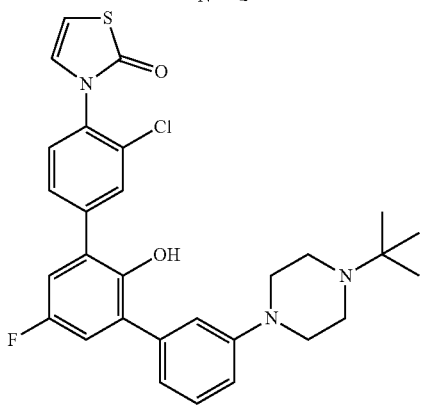
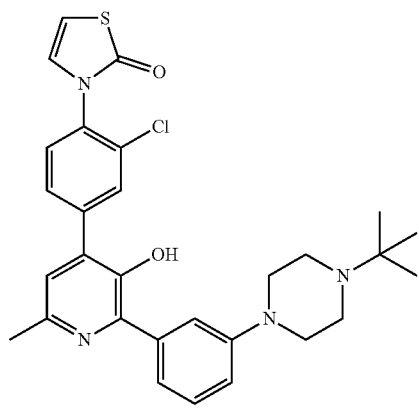
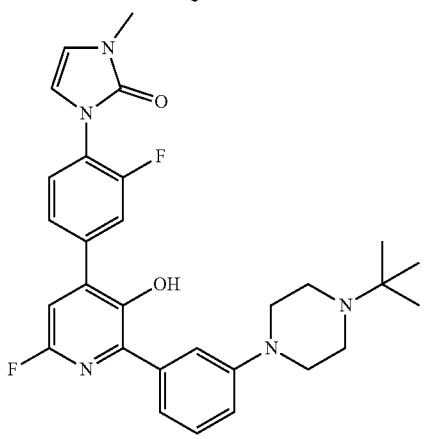
1600
-continued
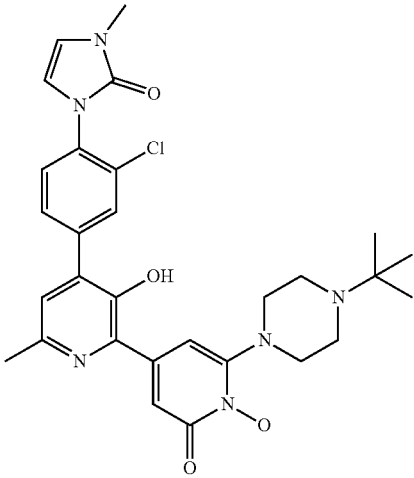
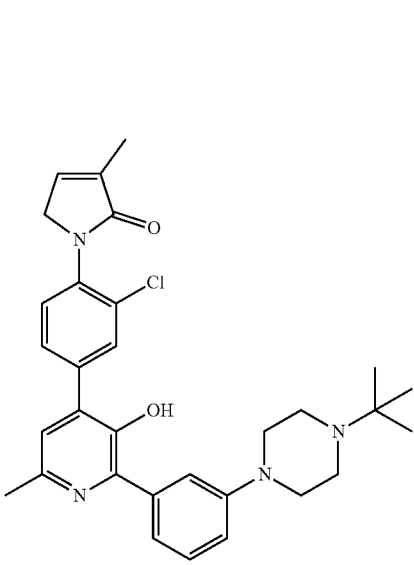
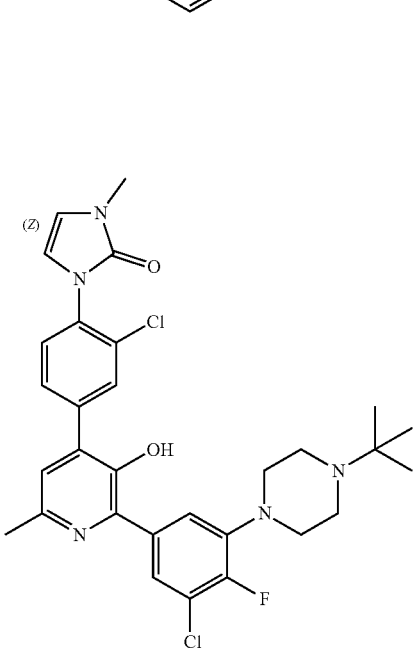

1601
-continued
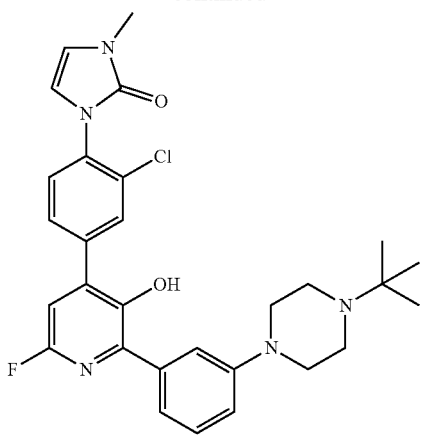
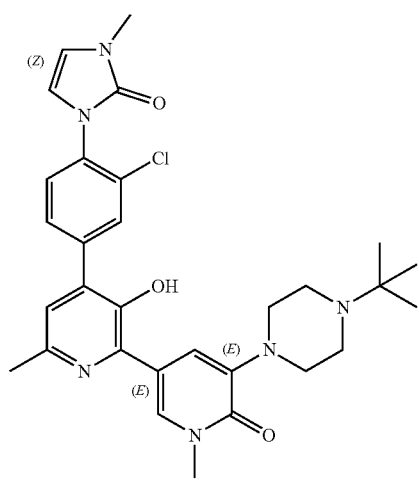
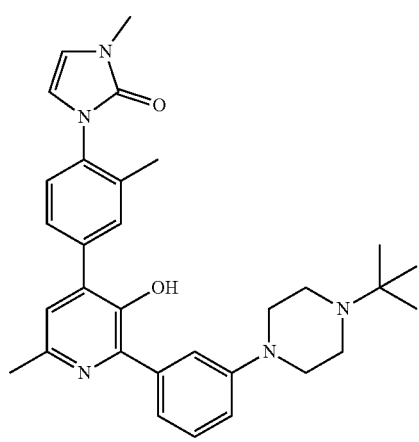
1602
-continued
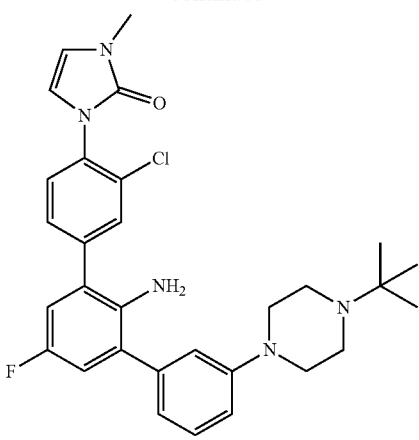
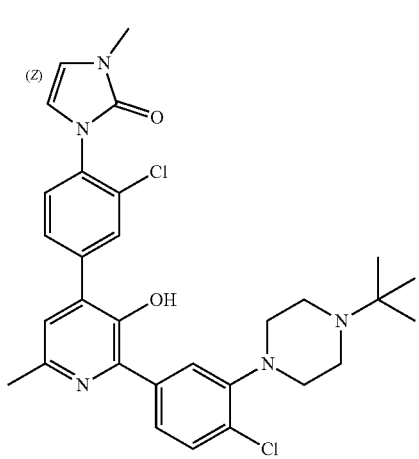
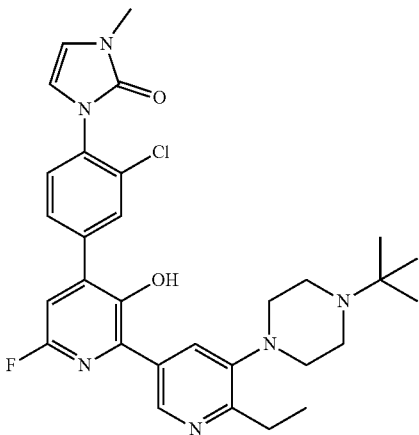

1603
-continued
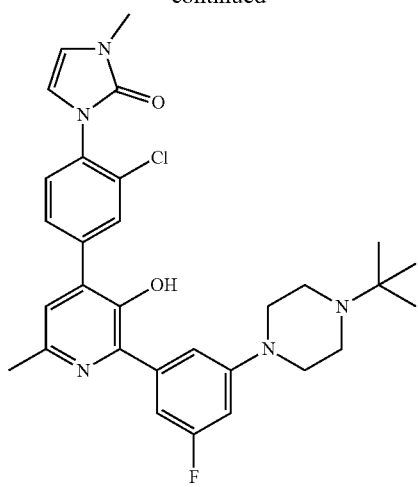
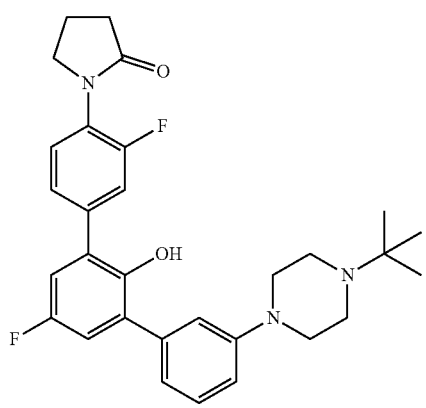
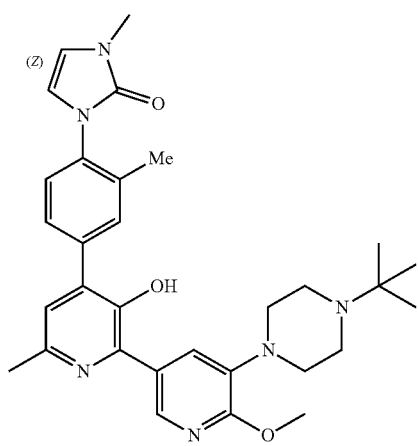
1604
-continued
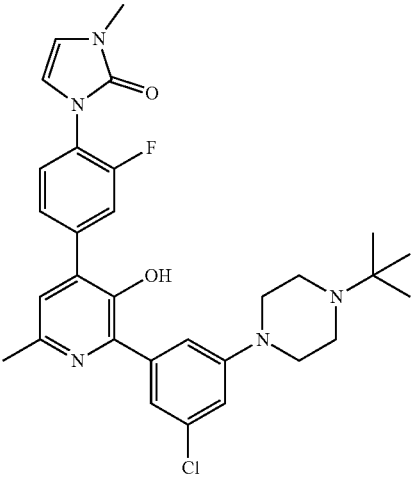
22. The compound of claim 1, wherein
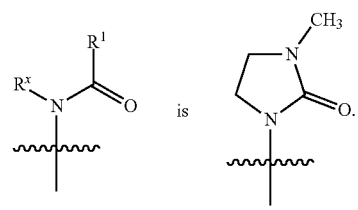
23. The compound of claim 1, wherein
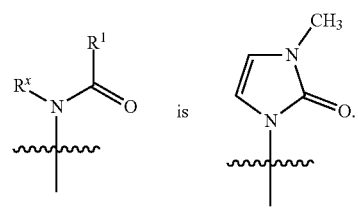
24. The compound of claim 1, wherein $R^c$ is
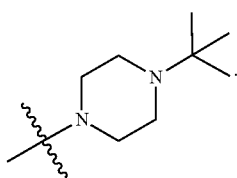 [SMILES: *N1CCN(C(C)(C)C)CC1]
25. The compound of claim 1, wherein $R^c$ is
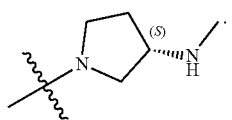

26. The compound of claim 1, wherein $R^c$ is
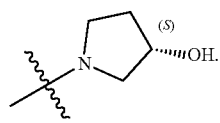
27. The compound of claim 1, wherein $R^c$ is
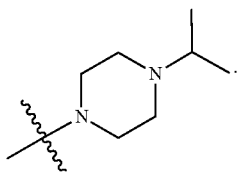 [SMILES: *N1CCN(C(C)C)CC1]
28. The compound of claim 1, wherein $R^c$ is
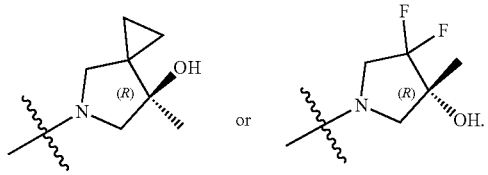
29. The compound of claim 1, wherein $R^c$ is
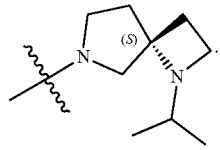
30. The compound of claim 8, wherein $R^c$ is
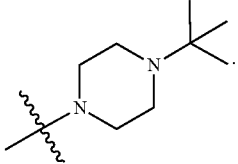 [SMILES: *N1CCN(C(C)(C)C)CC1]
31. The compound of claim 8, wherein
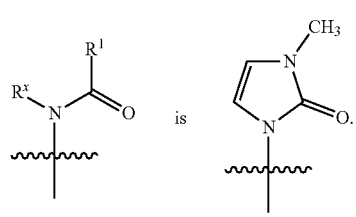
32. The compound of claim 10, wherein $R^c$ is
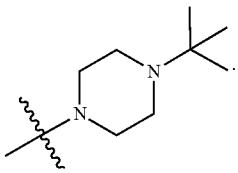 [SMILES: *N1CCN(C(C)(C)C)CC1]
33. The compound of claim 10, wherein
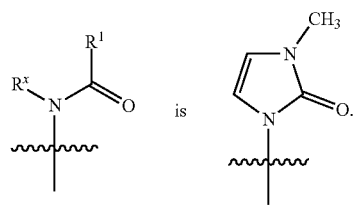
34. The compound of claim 10, wherein $R^a$ is Cl.
* * * * *